US007662581B1

(12) United States Patent
Bussiere et al.

(10) Patent No.: US 7,662,581 B1
(45) Date of Patent: Feb. 16, 2010

(54) EG5 CO-CRYSTALS

(75) Inventors: Dirksen Bussiere, Walnut Creek, CA (US); Mark Knapp, Oakland, CA (US); Vincent P. Le, San Francisco, CA (US); Eric Martin, El Cerrito, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1 day.

(21) Appl. No.: 11/018,091

(22) Filed: Dec. 20, 2004

Related U.S. Application Data

(60) Provisional application No. 60/530,561, filed on Dec. 18, 2003.

(51) Int. Cl.

| | |
|---|---|
| ***G01N 33/53*** | (2006.01) |
| ***C12Q 1/00*** | (2006.01) |
| ***G01N 33/573*** | (2006.01) |
| ***C12N 9/00*** | (2006.01) |
| ***C12N 9/14*** | (2006.01) |
| ***G01N 31/00*** | (2006.01) |
| ***G06G 7/58*** | (2006.01) |

(52) U.S. Cl. .......................... 435/7.71; 702/27; 703/11; 435/4; 435/7.4; 435/7.6; 435/183; 435/195

(58) Field of Classification Search .................. 435/7.1; 702/27

See application file for complete search history.

(56) References Cited

U.S. PATENT DOCUMENTS

| | | | | |
|---|---|---|---|---|
| 6,207,403 | B1 * | 3/2001 | Goldstein et al. | 435/21 |
| 6,472,521 | B1 | 10/2002 | Uhlmann et al. | |

FOREIGN PATENT DOCUMENTS

| | | |
|---|---|---|
| WO | WO 01/30768 | 5/2001 |
| WO | WO 01/98278 | 12/2001 |
| WO | WO 02/056880 | 7/2002 |
| WO | WO 02/057244 | 7/2002 |
| WO | WO 02/078639 | 10/2002 |
| WO | WO 03/039460 | 5/2003 |
| WO | WO 2004/004652 | 1/2004 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Turner et al., J. Biol. Chem., 2001, 276(27):25496-25502.*

Hopkins et al., Biochemistry, 2000, 39(10):2805-14.*

Witkowski et al., Biochemistry, 38, 11643-11650, 1999.*

Wishart et al., Journal of Biological Chemistry, vol. 270, No. 45, pp. 26782-26785, 1995.*

Kisselev, Structure, vol. 10, pp. 8-9, 2002.*

Branden et al., "Introduction to Protein Structure Second Edition", Garland Publishing Inc., New York, 1999.*

Drenth, "Principles of X-ray Crystallography," Springer, New York, 1995.*

Kierzek et al., Biophys Chem 91:1-20, 2001.*

U.S. Appl. No. 60/480,180, filed Jun. 20, 2003, Wang, et al.

U.S. Appl. No. 60/580,927, filed Jun. 18, 2004, Barsanti, et al.

U.S. Appl. No. 60/620,385, filed Oct. 19, 2004, Boyce, et al.

Blaney, et al., "A good ligand is hard to find: Automated docking methods", *Perspectives in Drug Discovery and Design*, 1:301-319 (1993).

Blangy, et al., "Phosphorylation by p34$^{cdc2}$ Regulates Spindle Association of Human Eg5, a Kinesin-Related Motor Essential for Bipolar Spindle Formation in Vivo", *Cell*, 83:1159-1169, (1995).

Böhm, "The computer program LUDI: A new method for the de novo design of enzyme inhibitors", *J. Comp. Aided Molec. Design*, 6:61-78, (1992).

Caflisch, et al., "Multiple copy simultaneous search and construction of ligands in binding sites: application to inhibitors of HIV-1 aspartic proteinase", *J. Med. Chem*., 36(15):2142-67, (1993).

DeBonis, et al., "Interaction of the Mitotic Inhibitor Monastrol with Human Kinesin Eg5", *Biochemistry*, 42(2):338-349, (2003).

Eisen, et al., "HOOK: A Program for Finding Novel Molecular Architectures That Satisfy the Chemical and Steric Requirements of a Macromolecule Binding Site", *Proteins: Str. Funct. Genet*., 19:199-221, (1994).

Enos, et al., "Mutation of a Gene That Encodes a Kinesin-like Protein Blocks Nuclear Division in A. nidulans", *Cell*, 60:1019-1027, (1990).

Gehlhaar, et al., "*De Novo* Design of Enzyme Inhibitors by Monte Carlo Ligand Generation", *J. Med. Chem*., 38:466-72, (1995).

Giet, et al., "The *Xenopus laevis* Aurora-related Protein Kinase pEg2 Associates with and Phosphorylates the Kinesin-related Protein XlEg5", *J. Biol. Chem*., 274(21):15005-15013, (1999).

Goodsell, et al., "Automated Docking of Substrates to Proteins by Simulated Annealing", *Proteins: Str. Funct Genet*., 8:195-202, (1990).

Hagan, et al., "Novel potential mitotic motor protein encoded by the fission yeast *cut7+* gene", *Nature*, 347:563-566, (1990).

Jones, et al., "Development and Validation of a Genetic Algorithm for Flexible Docking", *J. Mol. Biol*., 267:727-748, (1997).

Kaiser, et al., "All-*trans*-Retinoic Acid-mediated Growth Inhibition Involves Inhibition of Human Kinesin-related Protein HsEg5", *J. Biol. Chem*., 274(27):18925-18931, (1999).

Kapoor, et al., "Probing Spindle Assembly Mechanisms with Monastrol, a Small Molecule Inhibitor of the Mitotic Kinesin, Eg5", *J. Cell Biol*., 150(5):975-988, (2000).

Kuntz, et al., "A Geometric Approach to Macromolecule-Ligand Interactions", *J. Mol. Biol*., 161:269-288, (1982).

(Continued)

*Primary Examiner*—David J Steadman
*Assistant Examiner*—Jae W Lee
(74) *Attorney, Agent, or Firm*—Vinit Kathardekar; Lorna Tanner

(57) ABSTRACT

This invention provides methods of identifying an Eg5 binding ligand. The ligand is identified by using the atomic coordinates of an Eg5 crystal to generate a three dimensional structure. The three dimensional structure is used in molecular modeling techniques and docking experiments to identify ligands that bind to the binding pocket of Eg5. A novel binding pocket is identified. The invention also provides a crystallized Eg5 and ligand complex.

8 Claims, 3 Drawing Sheets

OTHER PUBLICATIONS

Lauri, et al., "CAVEAT: A program to facilitate the design of organic molecules", *J. Comp. Aided Mol. Design*, 8:51-66, (1994).

Luo, et al., "RASSE: A New Method for Structure-Based Drug Design", *J. Chem. Inf. Comput. Sci.*, 36:1187-1194, (1996).

Martin, "3D Database Searching in Drug Design", *J. Med. Chem.*, 35(12):2145-54, (1992).

Mayer, et al., "Small Molecule Inhibitor of Mitotic Spindle Bipolarity Identified in a Phenotype-Based Screen", *Science* 286:971-974, (1999).

Meyer, et al., "Backward binding and other structural surprises", *Perspectives in Drug Disc. and Design*, 3:168-95, (1995).

Moon, et al., "Computer Design of Bioactive Molecules: A Method for Receptor-Based de Novo Ligand Design", *Proteins: Str. Funct. Genet.*, 11:314-328, (1991).

Nicklaus, et al., "Conformational Changes of Small Molecules Binding to Proteins", *Bioorganic & Medicinal Chemistry*, 3(4):411-428, (1995).

Rotstein, et al., "GroupBuild: A Fragment-Based Method for *De Novo* Drug Design", J. *Med. Chem.*, 36:1700-1710, (1993).

Turner, et al., "Crystal Structure of the Mitotic Spindle Kinesin Eg5 Reveals a Novel Conformation of the Neck-linker", *J. Biol. Chem.*, 276(27):25496-25502, (2001).

* cited by examiner

SEQUENCE LISTING

<160> NUMBER OF SEQ ID NOS: 4

<210> SEQ ID NO 1
<211> LENGTH: 368
<212> TYPE: PRT
<213> ORGANISM: Homo sapiens

<400> SEQUENCE: 1

```
Met Ala Ser Gln Pro Asn Ser Ser Ala Lys Lys Lys Glu Glu Lys Gly
1               5                   10                  15

Lys Asn Ile Gln Val Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Asp Pro Arg Asn Lys Arg
            180                 185                 190

Gly Val Ile Ile Lys Gly Leu Glu Glu Ile Thr Val His Asn Lys Asp
        195                 200                 205

Glu Val Tyr Gln Ile Leu Glu Lys Gly Ala Ala Lys Arg Thr Thr Ala
    210                 215                 220

Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
            260                 265                 270

Gly Arg Ser Gly Ala Val Asp Lys Arg Ala Arg Glu Ala Gly Asn Ile
        275                 280                 285

Asn Gln Ser Leu Leu Thr Leu Gly Arg Val Ile Thr Ala Leu Val Glu
    290                 295                 300

Arg Thr Pro His Val Pro Tyr Arg Glu Ser Lys Leu Thr Arg Ile Leu
305                 310                 315                 320

Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
            340                 345                 350
```

-continued

Ala His Arg Ala Lys Asn Ile Leu Asn Lys Pro Glu Val Asn Gln Lys
355 360 365

<210> SEQ ID NO 2
<211> LENGTH: 35
<212> TYPE: DNA
<213> ORGANISM: ARTIFICIAL SEQUENCE
<220> FEATURE:
<223> OTHER INFORMATION: PRIMER

<400> SEQUENCE: 2
gagagaccat ggcgtcgcag ccaaattcgt ctgcg 35

<210> SEQ ID NO 3
<211> LENGTH: 54
<212> TYPE: DNA
<213> ORGANISM: ARTIFICIAL SEQUENCE
<220> FEATURE:
<223> OTHER INFORMATION: PRIMER

<400> SEQUENCE: 3
gagagagaat tctcatttct gattcacttc aggcttattc aatatgttct ttgc 54

<210> SEQ ID NO 4
<211> LENGTH: 1106
<212> TYPE: DNA
<213> ORGANISM: Homo sapiens

<400> SEQUENCE: 4
atggcgtcgc agccaaattc gtctgcgaag aagaaagagg agaaggggaa gaacatccag 60
gtggtggtga gatgcagacc atttaatttg gcagagcgga aagctagcgc ccattcaata 120
gtagaatgtg atcctgtacg aaaagaagtt agtgtacgaa ctggaggatt ggctgacaag 180
agctcaagga aaacatacac ttttgatatg gtgtttggag catctactaa acagattgat 240
gtttaccgaa gtgttgtttg tccaattctg gatgaagtta ttatgggcta taattgcact 300
atctttgcgt atggccaaac tggcactgga aaaactttta caatggaagg tgaaaggtca 360
cctaatgaag agtatacctg ggaagaggat ccccttggctg gtataattcc acgtaccctt 420
catcaaattt tgagaaactt actgataatg gtactgaatt ttcagtcaaa gtgtctctgt 480
tggagatcta taatgaagag ctttttgatc ttcttaatcc ctcgagcgat gtttctgaga 540
gactacagat gtttgatgat ccccgtaaca agagaggagt gataattaaa ggtttagaag 600
aaattacagt acacaacaag gatgaagtct atcaaatttt agaaaagggg gcagcaaaaa 660
ggacaactgc agctactctg atgaatgcat actctagtcg ttcccactca gttttctctg 720
ttacaataca tatgaaagaa actacgattg atggagaaga gcttgttaaa atcggaaagt 780
tgaacttggt tgatcttgca ggaagtgaaa acattggccg ttctggagct gttgataaga 840
gagctcggga agctggaaat ataaatcaat ccctgttgac tttgggaagg gtcattactg 900
cccttgtaga aagaacacct catgttcctt atcgagaatc taaactaact agaatcctcc 960
aggattctct tggagggcgt acaagaacat ctataattgc aacaatttct cctgcatctc 1020
tcaatcttga ggaaactctg agtacattgg aatatgctca tagagcaaag aacatattga 1080
ataagcctga agtgaatcag aaatga 1106

EG5 CO-CRYSTALS

This application claims benefit under 35 U.S.C. §119(e) of U.S. Provisional Application Ser. No. 60/530,561, filed Dec. 18, 2003; which is hereby incorporated by reference in its entirety.

FIELD OF THE INVENTION

This invention relates to the three-dimensional structures of the kinesin Eg5 bound to ligands; to methods for forming co-crystals of the Eg5 ligand complex; and to methods for using the three-dimensional structure of the co-crystal to identify possible therapeutic compounds for the treatment of Eg5 mediated diseases.

BACKGROUND OF THE INVENTION

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmatic reticulum. Several KRPs interact with the microtubules of the mitotic spindle or with the chromosomes directly, and appear to play a pivotal role during the mitotic stages of the cell cycle. These mitotic KRPs are of particular interest for the development of cancer therapeutics.

Eg5 (also known as HsEg5, KNSL1, or KSP) is one of several kinesin-like motor proteins that are localized to the mitotic spindle and known to be required for formation and/or function of the bipolar mitotic spindle.

In 1995, the depletion of Eg5 using an antibody directed against the C-terminus of Eg5 was shown to arrest HeLa cells in mitosis with monoastral microtubule arrays (Blangy et al., *Cell* 83:1159-1169, 1995). Mutations in bimC and cut7 genes, which are considered to be homologues of Eg5, cause failure in centrosome separation in *Aspergillus nidulans* (Enos, A. P., and N. R. Morris, *Cell* 60:1019-1027, 1990) and *Schizosaccharomyces pombe* (Hagan, I., and M. Yanagida, *Nature* 347:563-566, 1990). Treatment of cells with either ATRA (all trans-retinoic acid), which reduces HsEg5 expression on protein level, or depletion of HsEg5 using antisense oligonucleotides revealed a significant growth inhibition in DAN-G pancreatic carcinoma cells indicating that HsEg5 might be involved in the antiproliferative action of all trans-retinoic acid (Kaiser, A., et al., *J. Biol. Chem.* 274, 18925-18931, 1999). Interestingly, the *Xenopus laevis* Aurora-related protein kinase pEg2 was shown to associate and phosphorylate X1Eg5 (Giet, R., et al., *J. Biol. Chem.* 274: 15005-15013, 1999). Potential substrates of Aurora-related kinases are of particular interest for cancer drug development. For example, Aurora 1 and 2 kinases are overexpressed on protein and RNA level and the genes are amplified in colon cancer patients.

The first cell permeable small molecule inhibitor for HsEg5, "monastrol", was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry* 42:338-349, 2003; Kapoor, T. M., et al., *J. Cell Biol.* 150:975-988, 2000).

Recently, other Eg5 kinesin inhibitors have been described. WO 02/057244 and WO 02/056880 describe phenothiazine compounds and triphenylmethane compounds, respectively, for treating proliferative diseases. WO 02/078639 describes cyano-substituted dihydropyrimidine compounds for treating proliferative diseases. U.S. Pat. No. 6,472,521 describes oligonucleotides and oligonucleotide derivatives for inhibiting human Eg5 expression.

WO 01/98278, WO 01/30768, and WO 03/039460 describe quinazolinone compounds that are useful in treating cellular proliferative diseases associated with KSP kinesin activity. The compounds described in these references are 22-aminomethyl)quinazolinone derivatives. The quinazolinone compounds described in WO 01/98278 and WO 01/30768 have 2-aminomethyl substituents that are either amine, amide, or sulfonamide substituents. The quinazolinone compounds described in WO 03/039460 have the amino group of the 2-aminomethyl substituent incorporated into a 5-12 membered nitrogen-containing heterocycle.

A crystal structure of Eg5 bound to ADP-Mg was recently determined (J. Biol. Chem., Vol. 276, No. 27, pp. 25496-25502). However, this crystal structure does not provide information with respect to the manner in which inhibitors bind Eg5. Consequently, the design of Eg5 inhibitors can be greatly facilitated if a crystal structure of an inhibitor complexed to Eg5 were to be determined.

Recently, a crystal structure of Eg5 bound to Eg 5 ligands was published (WO 2004/004652. This publication identified a binding pocket of Eg5. Nevertheless, there is a need to identify an Eg5 binding pocket that differs from the binding pocket disclosed in WO 2004/004652.

SUMMARY OF THE INVENTION

This invention relates to the three-dimensional structures of the kinesin, Eg5, bound to ligands; to methods for forming co-crystals of the Eg5 ligand complex; and to methods for using the three-dimensional structure of the co-crystal to identify possible therapeutic compounds for the treatment of Eg5 mediated diseases.

The present invention provides a method of identifying an Eg5 binding ligand. The method comprises using some or all of the atomic coordinates provided in Table 4, or Table 10 to generate a three dimensional structure. The three dimensional structure is employed to design or select a ligand. The ligand may be synthesized and contacted with an Eg5 protein, and Eg5 mutant protein or a variant thereof to determine the ability of the ligand to bind to the protein. Upon binding of a ligand to an Eg5 protein, the binding of the ligand modifies Eg5 activity. Typically, the activity of Eg5 is determined by assays as described in Example 9. herein incorporated by reference. The activity of Eg5 can be determined by other methods known by one skilled in the art.

The ligand may be selected from ligand database or it may be synthesized de novo. Alternatively, the ligand may be designed by modifying a known Eg5 binding ligand.

In another embodiment the method of identifying an Eg5 binding ligand comprises the use of Eg5 amino acids listed in tables 1, 2, 3, 4, 5, 6, 7, 8, 9, or 10. Preferably, the method of identifying and Eg5 binding ligand uses the amino acids listed in tables 1, 2, 3, 5, 6, 7, 8, or 9.

In another aspect, the ligand is designed by identifying a chemical entity or a chemical fragment associating with Eg5 and assembling one or more of the identified entities or fragments into a single molecule to provide the structure of the ligand.

This invention also provides a method of crystallizing an Eg5 protein bound to a ligand. This method comprises the steps of providing an Eg5 protein, contacting the Eg5 protein with a ligand and crystallizing the Eg5 protein and ligand complex from a precipitating solution to provide a crystallized complex. The pH of the precipitating solution is between around 2 and around 7. Alternatively the pH of the precipitating solution is between 3 and 7, between 4 and 6.5. Preferably, the pH of the precipitating solution is between 5 and 6. The Eg5 protein and ligand complex can also be prepared by a hanging drop vapor diffusion method.

A crystal of Eg5 may be prepared from a precipitating solution to provide crystallized Eg5. A precipitating solution containing Eg 5 is prepared. The pH of the precipitating solution is between around 2 and around 7. Alternatively the pH of the precipitating solution is between 3 and 7, between 4 and 6.5. Preferably, the pH of the precipitating solution is between 5 and 6. The Eg5 protein and ligand complex can also be prepared by a hanging drop vapor diffusion method.

Example 8 describes the crystallization of Eg5 protein and also describes the crystallization of a ligand bound to Eg5.

Alternatively, the Eg5 and ligand complex can be prepared by soaking a ligand into an Eg5 crystal. In this method, the Eg5 crystal is prepared as described above. Next, the Eg5 crystal is placed in a solution containing between 0.5 and 100 mM ligand. The Eg5 crystal is incubated in the ligand solution for a period of time. Typically the incubation is from between 2 to 48 hours at 4° C.

The atomic coordinates of crystallized Eg5 protein bound to ligand are set forth in tables 4 and 10. These crystallized complexes have the space group P212121.

The crystallized complex of Eg5 and a ligand of this invention comprises a ligand selected from the group consisting of N-(3-aminopropyl)-N-[(3-benzyl-4-oxo-4H-pyrido[1,2-a]pyrimidin-2-yl)(cyclopropyl)methyl]-4-chlorobenzamide 1, N-(3-aminopropyl)-N-[(1R)-1-(1-benzyl-4-phenyl-1H-imidazol-2-yl)-2-methylpropyl]-4-methylbenzamide 2, N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide 3, N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide 4, N-(3-aminopropyl)-N-[(1R)-1-(1-benzyl-1H-benzimidazol-2-yl)-2-methylpropyl]-4-chlorobenzamide 5, or N-(3-aminopropyl)-N-[(1R)-1-(1-benzyl-5-bromo-1H-benzimidazol-2-yl)-2-methylpropyl]-4-methylbenzamide 6.

Another aspect of this invention provides a computer for producing a three-dimensional representation of an Eg5 and ligand complex wherein the Eg5 and ligand complex comprises a binding pocket defined by Eg5 amino acid residues provided in a table selected from the group consisting of table 1, 2, 3, 5, 6, 7, 8, and 9. The computer comprises: (a) machine-readable data storage medium comprising a data storage material encoded with machine-readable data, wherein said data comprises at least a portion of the atomic coordinates set forth in Table 4 or 10; (b) a working memory for storing instructions for processing said machine-readable data; (c) a central-processing unit coupled to said working memory and to said machine-readable data storage medium for processing said machine readable data into said three-dimensional representation; and (d) a means for displaying said three-dimensional representation.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying figures and tables, wherein.

DETAILED DESCRIPTION OF THE INVENTION

Crystallization of Eg5/Ligand Complex

Figure 1:
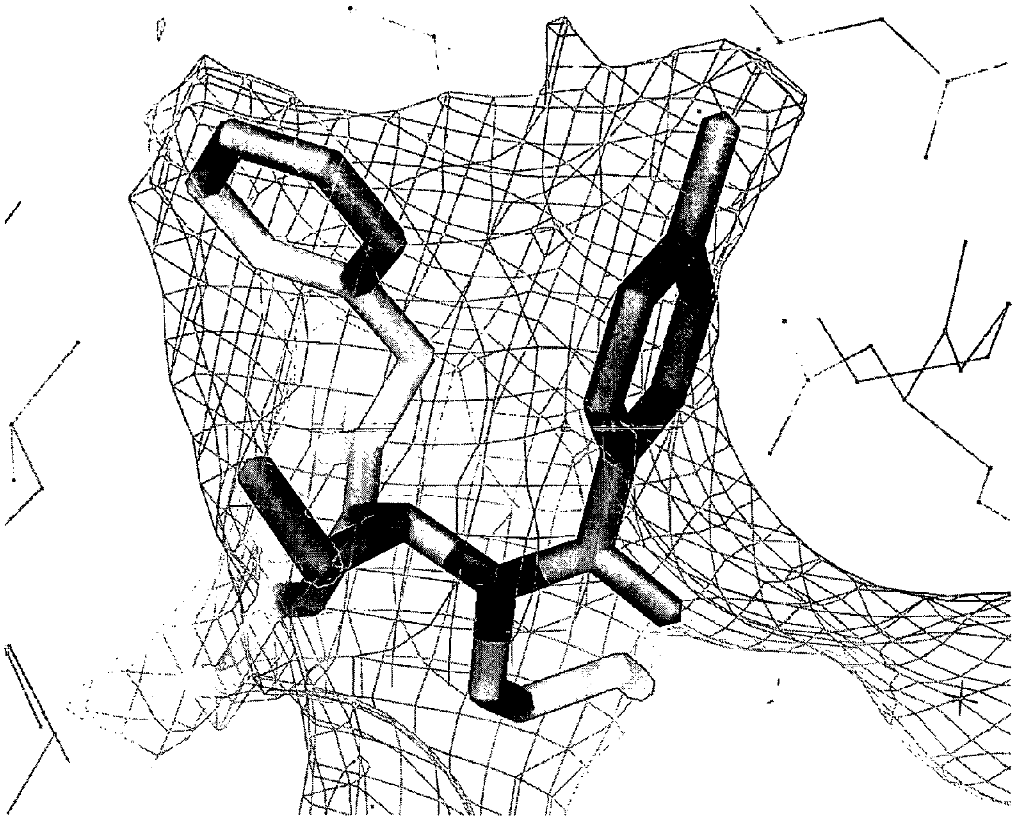
FIG. 1. Binding mode with B and Q groups in close proximity within pocket P upon ligand compound 1 binding.

N-(3-aminopropyl)-N-[(3-benzyl-4-oxo-4H-pyrido[1,2-a]pyrimidin-2-yl)(cyclopropyl)methyl]-4-chlorobenzamide shown below was synthesized as shown in Example 1. Synthesis of this compound was disclosed in U.S. 60/480,180, the contents of which are hereby incorporated by reference.

I

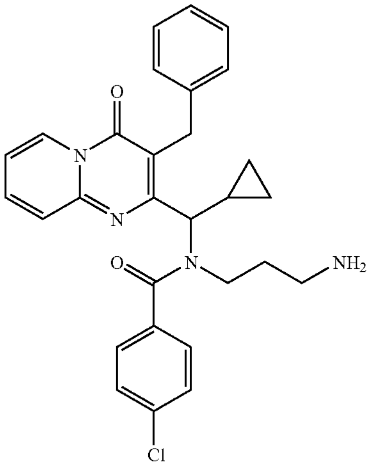

N-(3-aminopropyl)-N-[(1R)-1-(1-benzyl-4-phenyl-1H-imidazol-2-yl)-2-methylpropyl]-4-methylbenzamide shown below was synthesized as shown in Example 2. Synthesis of this compound was disclosed in U.S. 60/580,927, the contents of which are hereby incorporated by reference.

2

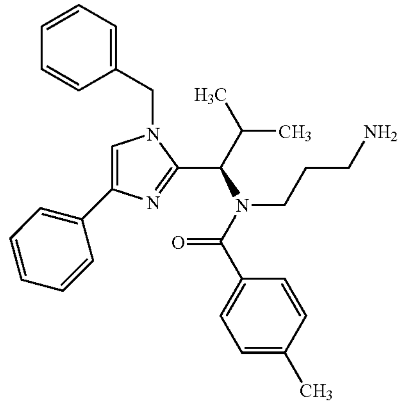

N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide shown below was synthesized as shown in Example 3. Synthesis of this compound was disclosed in U.S. 60/580,927, the contents of which are hereby incorporated by reference.

3

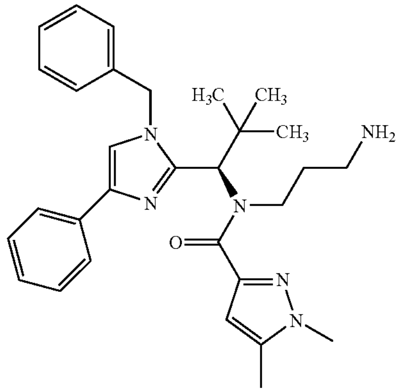

N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide shown below was synthesized as shown in Example 4. Synthesis of this compound was disclosed in U.S. 60/580,927, the contents of which are hereby incorporated by reference.

4

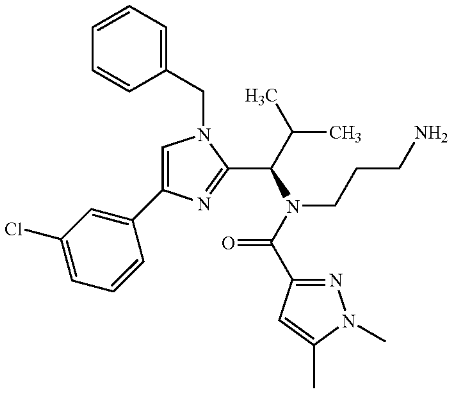

N-(3-aminopropyl)-N-[(1R)-1-(1-benzyl-1H-benzimidazol-2-yl)-2-methylpropyl]-4-chlorobenzamide shown below was synthesized as shown in Example 5. Synthesis of this compound was disclosed in U.S. 60/620,385, the contents of which are hereby incorporated by reference.

5

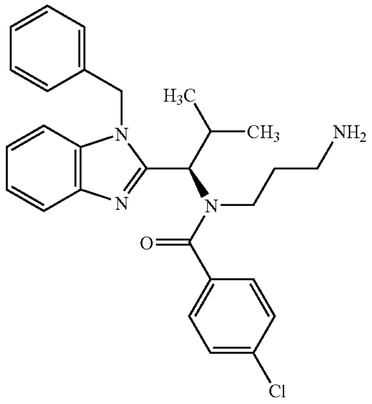

N-(3-aminopropyl)-N-[(1R)-1-(1-benzyl-5-bromo-1H-benzimidazol-2-yl)-2-methylpropyl]-4-methylbenzamide shown below was synthesized as shown in Example 6. Synthesis of this compound was disclosed in U.S. 60/620,385, the contents of which are hereby incorporated by reference.

6

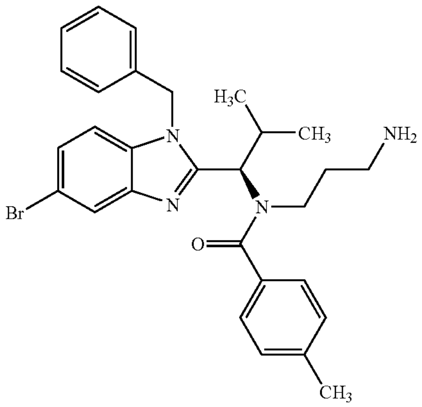

The Eg5 protein was expressed as described in Example 7. A representative method for forming suitable crystals of the Eg5/ligand complex suitable for structure determination was described in Example 8.

It will be appreciated that various crystallization methods including, for example, microcrystallization methods can be utilized to obtain three-dimensional structural information useful in identifying possible therapeutic compounds in the treatment of various disease conditions mediated by Eg5 activity.

Eg5/Ligand Structural Representation.

As noted above, in one aspect, the invention provides a method for identifying possible therapeutic compounds in the treatment of various disease conditions mediated by Eg5 activity. The method involves the use of a three-dimensional structural representation of the Eg5/ligand complex.

Variants of the atomic coordinates noted in Table 4-10 can also be used for the invention such as variants in which the RMS deviation of the x, y, and z coordinates for all heavy (i.e., not hydrogen) atoms are less than about 2.5 Å, for example, less than about 2 Å, preferably less than about 1 Å, more preferably less than about 0.5 Å, or most preferably less than about 0.1 Å compared with the atomic coordinates noted in Table 2. Coordinate transformations that retain the three-dimensional spatial relationships of atoms can also be used to give suitable variants.

The cocrystal structure of Eg5 complexed with N-(3-aminopropyl)-N-[(3-benzyl-4-oxo-4H-pyrido[1,2-a]pyrimidin-2-yl)(cyclopropyl)methyl]-4-chlorobenzamide 1, N-(3-aminopropyl)-N-[(1R)-1-(1-benzyl-4-phenyl-1H-imidazol-2-yl)-2-methylpropyl]-4-methylbenzamide 2, N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide 3, N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide 4, N-(3-aminopropyl)-N-[(1R)-1-(1-benzyl-1H-benzimidazol-2-yl)-2-methylpropyl]-4-chlorobenzamide 5, and N-(3-aminopropyl)-N-[(1R)-1-(1-benzyl-5-bromo-1H-benzimidazol-2-yl)-2-methylpropyl]-4-methylbenzamide 6 were analyzed with the program QUANTA for structural differences between the drug-bound form of the protein and the unbound form of the protein (represented by PDB accession code 1II6). Eg5 protein and ligand complexes crystallize as a dimer. The atomic coordinates shown in Tables 4 and 10 provide coordinates of both monomers. The monomers are designated in Tables 4 and 5 as "A" and "B."

The ligand-bound form of the protein shows a major structural rearrangement of the loop containing amino acid residues 119-127. In the unbound form, this loop extends away from the body of the protein structure. In the ligand-bound form, this loop flips toward the body of the protein, forming a pocket for the ligand to bind. Especially critical in this interaction are Tyr-211 and Trp-127, which form an 'aromatic' network with the ligand. The amino acid residues within an approximately 12, 14, or 17 Angstrom (Ang.) sphere of the bound ligand are listed in Tables 1-3 respectively. (Note: The A in the amino acid number indicates that the A molecule in the dimer was examined).

TABLE 1

Eg5 binding pocket residues based on an approximate 17 Ang. sphere.

| | | |
|---|---|---|
| LYS A 77 | GLN A 78 | ILE A 79 |
| VAL A 81 | TYR A 82 | VAL A 86 |
| ILE A 101 | PHE A 102 | ALA A 103 |
| GLY A 108 | THR A 109 | GLY A 110 |
| LYS A 111 | THR A 112 | PHE A 113 |
| THR A 114 | MET A 115 | GLU A 116 |
| GLY A 117 | GLU A 118 | ARG A 119 |
| SER A 120 | PRO A 121 | ASN A 122 |
| GLU A 123 | GLU A 124 | TYR A 125 |
| THR A 126 | TRP A 127 | GLU A 128 |
| GLU A 129 | ASP A 130 | PRO A 131 |
| LEU A 132 | ALA A 133 | GLY A 134 |
| ILE A 135 | ILE A 136 | PRO A 137 |
| ARG A 138 | THR A 139 | LEU A 140 |
| HIS A 141 | GLN A 142 | ILE A 143 |
| PHE A 144 | LYS A 157 | VAL A 158 |
| SER A 159 | LEU A 160 | LEU A 161 |
| GLU A 162 | LEU A 171 | LEU A 172 |
| ILE A 202 | VAL A 204 | LYS A 207 |
| ASP A 208 | GLU A 209 | VAL A 210 |
| TYR A 211 | GLN A 212 | ILE A 213 |
| LEU A 214 | GLU A 215 | LYS A 216 |
| GLY A 217 | ALA A 218 | ALA A 219 |
| LYS A 220 | ARG A 221 | THR A 222 |
| THR A 223 | SER A 232 | SER A 233 |
| HIS A 236 | SER A 237 | VAL A 238 |
| PHE A 239 | SER A 240 | VAL A 241 |

TABLE 1-continued

Eg5 binding pocket residues based on an approximate 17 Ang. sphere.

| | | |
|---|---|---|
| LEU A 261 | ASN A 262 | LEU A 263 |
| VAL A 264 | ASP A 265 | LEU A 266 |

TABLE 2

Eg5 binding pocket residues based on an approximate 14 Ang. sphere.

| | | |
|---|---|---|
| ARG A 24 | GLN A 78 | ILE A 79 |
| TYR A 82 | VAL A 86 | ALA A 103 |
| GLY A 110 | LYS A 111 | THR A 112 |
| PHE A 113 | THR A 114 | MET A 115 |
| GLU A 116 | GLY A 117 | GLU A 118 |
| ARG A 119 | SER A 120 | PRO A 121 |
| TYR A 125 | THR A 126 | TRP A 127 |
| GLU A 128 | GLU A 129 | ASP A 130 |
| PRO A 131 | LEU A 132 | ALA A 133 |
| GLY A 134 | ILE A 135 | ILE A 136 |
| PRO A 137 | ARG A 138 | THR A 139 |
| LEU A 140 | HIS A 141 | GLN A 142 |
| VAL A 158 | SER A 159 | LEU A 160 |
| GLU A 162 | LEU A 171 | LEU A 172 |
| VAL A 204 | LYS A 207 | ASP A 208 |
| GLU A 209 | VAL A 210 | TYR A 211 |
| GLN A 212 | ILE A 213 | LEU A 214 |
| GLU A 215 | LYS A 216 | GLY A 217 |
| ALA A 218 | ALA A 219 | LYS A 220 |
| ARG A 221 | THR A 222 | SER A 232 |
| SER A 237 | VAL A 238 | PHE A 239 |
| SER A 240 | VAL A 241 | LEU A 263 |
| VAL A 264 | ASP A 265 | |

TABLE 3

Eg5 binding pocket residues based on an approximate 12 Ang. sphere.

| | | |
|---|---|---|
| GLN A 78 | GLY A 110 | LYS A 111 |
| THR A 112 | PHE A 113 | THR A 114 |
| MET A 115 | GLU A 116 | GLY A 117 |
| GLU A 118 | ARG A 119 | SER A 120 |
| THR A 126 | TRP A 127 | GLU A 128 |
| ASP A 130 | PRO A 131 | LEU A 132 |
| ALA A 133 | GLY A 134 | ILE A 135 |
| ILE A 136 | PRO A 137 | ARG A 138 |
| THR A 139 | LEU A 140 | HIS A 141 |
| VAL A 158 | LEU A 160 | LEU A 172 |
| GLU A 209 | VAL A 210 | TYR A 211 |
| GLN A 212 | ILE A 213 | LEU A 214 |
| GLU A 215 | LYS A 216 | GLY A 217 |
| ALA A 218 | ALA A 219 | ARG A 221 |
| SER A 237 | PHE A 239 | LEU A 263 |
| ASP A 265 | | |

Eg5 Ligands

The term "ligand" used herein refers to compounds that bind Eg5 and modulate its activity, and does not include compounds such as adenosine diphosphate and adenosine triphophate. As used herein, "ligand" is used interchangeably with "drug," "molecule," or "compound." Upon binding or association of a ligand to Eg5, the activity of Eg5 is inhibited. Eg5 activity is determined as described in Example 9.

The term "ligand binding site" and "binding site" are used interchangeably and refer to amino acid residues of Eg5 near the ligand of the ligand and Eg5 complex. The ligand binding site encompasses the Eg5 amino acid residues that interact with the ligand. The amino acid residues of the ligand binding site are determined by identifying all of the amino acid residues within, for example, a 20 angstrom radius (shell) of the ligand in the ligand and Eg5 complex. Alternatively, the amino acid residues of the ligand binding site are the amino acid residues within 20, 19, 18, 17, 16, 15, 14, 13, 12, 11, or 10 angstrom radius from the ligand. Tables 1, 2, 3, 4, 5, 6, 7, 8, 9, and 10 identify amino acid residues of the ligand binding pockets of an Eg5 and ligand complex as described herein.

The term "variant" of a Eg5 protein refers to a polypeptide having an amino acid sequence with one or more amino acid substitutions, insertions, and/or deletions compared to the sequence of the invention receptor protein.

The term "Eg5 and ligand complex" refers to a complex of a ligand and Eg5 comprising Eg5 and a ligand bound at the ligand binding site.

Most lead compounds that initiate structure-based design cycles are identified by high-throughput screening. As a result of high throughput screening and the ligand profile and virtual screening described above, ligands are identified having the requisite conformational energies to assume a suitable shape and bind with the protein's active site. In addition to having low conformational energy and spatial compatibility with the apoprotein active site, the identified ligands are preferably synthetically accessible. The identified ligands can then be obtained (e.g., commercially obtained or synthesized) and screened for biological activity using the assay described in Example 8. The identified ligands can also be co-crystallized with the protein and the three-dimensional structure determined for the protein with bound ligand. The information obtained from structure of the protein with bound ligand can then be used to further develop the ligand profile as described above.

The method of the invention identifies ligands that can interact with Eg5. These compounds can be designed de novo, can be known compounds, or can be based on known compounds. Known Eg5 binding compounds include those described in WO 01/98278, WO 01/30768, WO 02/057244, WO 02/056880, WO 02/078639, WO03/039460, and U.S. Pat. No. 6,472,521. The compounds can be useful pharmaceuticals themselves, or can be prototypes that can be used for further pharmaceutical refinement (i.e., lead compounds) in order to improve binding affinity or other pharmacologically important features (e.g., bio-availability, toxicology, metabolism, pharmacokinetics).

Accordingly, in another aspect, the invention provides (1) a compound identified using the method of the invention; (2) a compound identified using the method of the invention for use as a pharmaceutical; (3) the use of a compound identified using the method of the invention in the manufacture of a medicament for mediating Eg5 activity; and (4) a method of treating a patient afflicted with a condition mediated by Eg5 activity that includes administering an amount of a compound identified using the method of the invention that is effective to mediate Eg5 activity.

These compounds interact with Eg5 with a binding constraint in the micromolar or, more preferably, nanomolar range or stronger.

As well as being useful compounds individually, ligands identified by the structure-based design techniques can also be used to suggest libraries of compounds for traditional in vitro or in vivo screening methods. Important pharmaceutical motifs in the ligands can be identified and mimicked in compound libraries (e.g., combinatorial libraries) for screening for Eg5-binding activity.

Identification of Eg5 Ligands

The structural information obtained from the crystallographic data can be used to develop a ligand profile useful for the rational design of compounds for mediating Eg5 activity.

The ligand profile can be primarily based on a shape interaction between the ligand and the protein ligand binding site. The evaluation of the shape interaction can include consideration of the ligand's conformational properties, ranking ligands based on their ability to achieve low energy conformations compatible with the ligand binding site. The shape interaction can also seek to maximize enthalpic interactions between the ligand and the binding site.

The process of developing a ligand profile can vary widely. For example, the profile can be developed by visual inspection of active site structures by experts. Such an inspection can include the consideration of the binding site and ligand structures and compound database searching. The development of the profile can also consider biological data and structure activity relationships (SAR) as well the consideration of known ligand binding interaction with other similar proteins.

In any event, the ligand profile is developed by considering ligand binding interactions including primary and secondary interactions and results in defining the pharmacophore. The term "pharmacophore" refers to a collection of chemical features and three-dimensional constraints that represent specific characteristics responsible for a ligand's activity. The pharmacophore includes surface-accessible features, hydrogen bond donors and acceptors, charged/ionizable groups, and/or hydrophobic patches, among other features.

In addition to the process for ligand profile development noted above, other structure-based drug design techniques can be applied to the structural representation of the Eg5 in order to identify compounds that interact with Eg5 to mediate Eg5 activity. A variety of suitable techniques are available to one of ordinary skill in the art.

Software packages for implementing molecular modeling techniques for use in structure-based drug design include SYBYL™ (available from Tripos Inc.); AMBER (available from Oxford Molecular); CERIUS$^2$ (available from Molecular Simulations Inc.); INSIGHT II (available from Molecular Simulations Inc.); CATALYST (available from Molecular Simulations Inc.); QUANTA (available from Molecular Simulations Inc.); HYPERCHEM (available from Hypercube Inc.); FIRST DISCOVERY (available from Schrodinger Inc.), MOE (available from Chemical Computing Group), and CHEMSITE (available from Pyramid Learning), among others.

The modeling software can be used to determine Eg5 binding surfaces and to reveal features such as van der Waals contacts, electrostatic interactions, and/or hydrogen bonding opportunities. These binding surfaces can be used to model docking of ligands with Eg5, to arrive at pharmacophore hypotheses, and to design possible therapeutic compounds de novo.

Eg5 Ligand Virtual Screening

The three-dimensional structure of the apoprotein, and the structure of the protein's active site in particular, allows for the determination of the fit of compounds into the active site. Utilizing a fast docking program, individual compounds from, for example, a compound database, can be evaluated for active site binding. The fit of a particular compound can be evaluated and scored. Setting a score threshold can then provide a family of compounds as a solution to the virtual screen.

At the first level, the virtual screen takes into account the three-dimensional structure of the apoprotein's active site. At the second level, the virtual screen considers the ligand profile and can utilize information obtained from the determination of the structure of protein with bound ligand. A virtual screen is possible even if there is no structural information on a bound ligand.

Information gained from the virtual screen can be considered to further develop the ligand profile. Alternatively, where the results of the virtual screen indicate a promising compound, the compound can be obtained and screened for the relevant biological activity.

Docking

Docking refers to a process in which two or more molecules are aligned based on energy considerations. Docking aligns the three-dimensional structures of two or more molecules to predict the conformation of a complex formed from the molecules (see, e.g., Blaney & Dixon (1993) Perspectives in Drug Discovery and Design 1:301). In the practice of the present invention molecules are docked with the Eg5 structure to assess their ability to interact with Eg5.

Docking can be accomplished by either geometric matching of the ligand and its receptor or by minimizing the energy of interaction. Geometric matching algorithms are preferred because of their relative speed.

Suitable docking algorithms include DOCK (Kuntz et al. (1982) J. Mol. Biol. 161:269-288, available from UCSF), the prototypical program for structure-based drug design; AUTODOCK (Goodsell & Olson (1990) Proteins: Structure, Function and Genetics 8:195-202 and available from Oxford Molecular), which docks ligands in a flexible manner to receptors using grid-based Monte Carlo simulated annealing. The flexible nature of the AUTODOCK procedure helps to avoid bias (e.g., in orientation and conformation of the ligand in the active site) introduced by the user searcher (Meyer et al. (1995) Persp. Drug Disc. 3:168-95) because, while the starting conformation in a rigid docking is normally biased towards a minimum energy conformation of the ligand, the binding conformation may be of relatively high conformational energy (Nicklaus et al (1995) Bioorganic & Medicinal Chemistry 3:411).

Other suitable docking algorithms include MOE DOCK (available from Chemical Computing Group Inc.), in which a simulated annealing search algorithm is used to flexibly dock ligands and a grid-based energy evaluation is used to score docked conformations; FLExX (available from Tripos Inc.), which docks conformationally flexible ligands into a binding site using an incremental construction algorithm that builds the ligand in the site, and scores docked conformations based on the strength of ligand-receptor interactions; GOLD (Jones et al. (1997) J. Mol. Biol. 267:727-748), a genetic algorithm for flexible ligand docking, with full ligand and partial protein flexibility, and in which energy functions are partly based on conformation and non-bonded contact information; AFFINITY (available from Molecular Simulations Inc.), which uses a two step process to dock ligands: first, initial placements of the ligand within the receptor are made using a Monte Carlo-type procedure to search both conformational and Cartesian space; and second, a simulated annealing phase optimizes the location of each ligand placement, during this phase, AFFINITY holds the "bulk" of the receptor (atoms not in the binding site) rigid, while the binding site atoms and ligand atoms are movable; $C^2$ LigandFit (available from Molecular Simulations Inc.), which uses the energy of the ligand-receptor complex to automatically find best binding modes and stochastic conformation search techniques, with the best results from the conformational sampling retained. A grid method is used to evaluate non-bonded interactions between the rigid receptor and the flexible ligand atoms. DOCKIT (available from Metaphorics LLC) uses distance geometry for fast flexible ligand docking. GLIDE (available from Schrodinger Inc.) uses a pre-computed energy grid and an efficiently pruned systematic search for flexible docking.

Preferably, the docking algorithm is used in a high-throughput mode, in which members of large structural libraries of potential ligands are screened against the receptor structure (Martin (1992) J. Med. Chem. 35:2145-54).

Suitable structural libraries include the ACD (Available Chemical Directory, form MDL Inc.), AsInEx, Bionet, ComGenex, the Derwent World Drug Index (WDI), the Contact Service Company database, LaboTest, ChemBridge Express Pick, ChemStar, BioByteMasterFile, Orion, SALOR, TRIAD, ILIAD, the National Cancer Institute database (NCI), and the Aldrich, Fluka, Sigma, and Maybridge catalogs. These are commercially available (e.g., the HTS Chemicals collection from Oxford Molecular, or the LeadQuest™ files from Tripos).

De Novo Compound Design.

The binding surface or pharmacophore of the Eg5/ligand complex can be used to map favorable interaction positions for functional groups (e.g., protons, hydroxyl groups, amine groups, acidic groups, hydrophobic groups and/or divalent cations) or small molecule fragments. Compounds can then be designed de novo in which the relevant functional groups are located in the correct spatial relationship to interact with Eg5.

Once functional groups or small molecule fragments which can interact with specific sites in the binding surface of Eg5 have been identified, they can be linked in a single compound using either bridging fragments with the correct size and geometry or frameworks which can support the functional groups at favorable orientations, thereby providing a compound according to the invention. While linking of functional groups in this way can be done manually, perhaps with the help of software such as QUANTA or SYBYL™, automated or semi-automated de novo design approaches can also be used.

Suitable de novo design software includes MCDLNG (Gehlhaar et al. (1995) J. Med. Chem. 38:466-72), which fills a receptor binding site with a close-packed array of generic atoms and uses a Monte Carlo procedure to randomly vary atom types, positions, bonding arrangements and other properties; MCSS/HOOK (Caflish et al. 1993) J. Med. Chem. 36:2142-67; Eisen et al. (1994) Proteins: Str. Funct Genet. 19:199-221; available from Molecular Simulations Inc.), which links multiple functional groups with molecular templates taken from a database; LUDI (Bohm (1992) J. Comp. Aided Molec. Design 6:61-78, available from Molecular Simulations Inc.), which computes the points of interaction that would ideally be fulfilled by a ligand, places fragments in the binding site based on their ability to interact with the receptor, and then connects them to produce a ligand; GROW (Moon and Howe (1991) Proteins: Str. Funct. Genet. 11:314-328), which starts with an initial "seed" fragment (placed manually or automatically) and grows the ligand outwards; SPROUT, which includes molecules to identify favorable hydrogen bonding and hydrophobic regions within a binding pocket (HIPPO module), selects functional groups and positions them at target sites to form starting fragments for structure generation (EleFanT), generates skeletons that satisfy the steric constraints of the binding pocket by growing spacer fragments onto the start fragments and then connecting the resulting part skeletons (SPIDeR), substitutes hetero atoms into the skeletons to generate molecules with the electrostatic properties that are complementary to those of the receptor site (MARABOU), and the solutions can be clustered and scored using the ALLigaTOR module; LEAPFROG (available from Tripos Inc.), which evaluates ligands by making small stepwise structural changes and rapidly evaluating the binding energy of the new compound, keeps or discards changes based on the altered binding energy, and evolves structures to increase the interaction energy with the receptor; GROUP-BUILD (Rorstein et al. (1993) J. Med. Chem. 36:1700), which uses a library of common organic templates and a complete empirical force field description of the non-bonding interactions between a ligand and receptor to construct ligands that have chemically reasonable structure and have steric and electrostatic properties complimentary to the receptor binding site; CAVEAT (Lauri and Bartlett (1994) Comp. Aided Mol. Design 8:51-66), which designs linking units to constrain acyclic molecules; and RASSE (Lai (1996) J. Chem. Inf. Comput. Sci. 36:1187-1194).

Eg5 Pharmacophore

Using the coordinates provided herein, an Eg5 inhibitor pharmacophore model was analyzed. The pharmacophore, a ligand comprising an amide, is shown below.

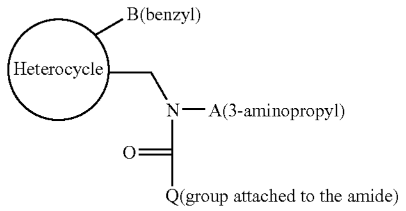

A member of this pharmacophore, N-(3-aminopropyl)-N-[(3-benzyl-4-oxo-4H-pyrido[1,2-a]pyrimidin-2-yl)(cyclopropyl)methyl]-4-chlorobenzamide 1 binds with the B and Q groups in close proximity within a single pocket "pocket P" of the binding site formed in part by Arg 119, trp 127, pro 137, ala133, glu 130, tyr 211, val 210, leu 214 (FIG. 1).

Figure 2:
FIG. 2. Binding mode with B and Q groups in close proximity within pocket P upon ligand compound 2 binding.

Phenylimidazole 2 binds similarly, with the benzyl and p-methylphenyl rings in a similar "P" pocket as shown in FIG. 2.

Figure 3:
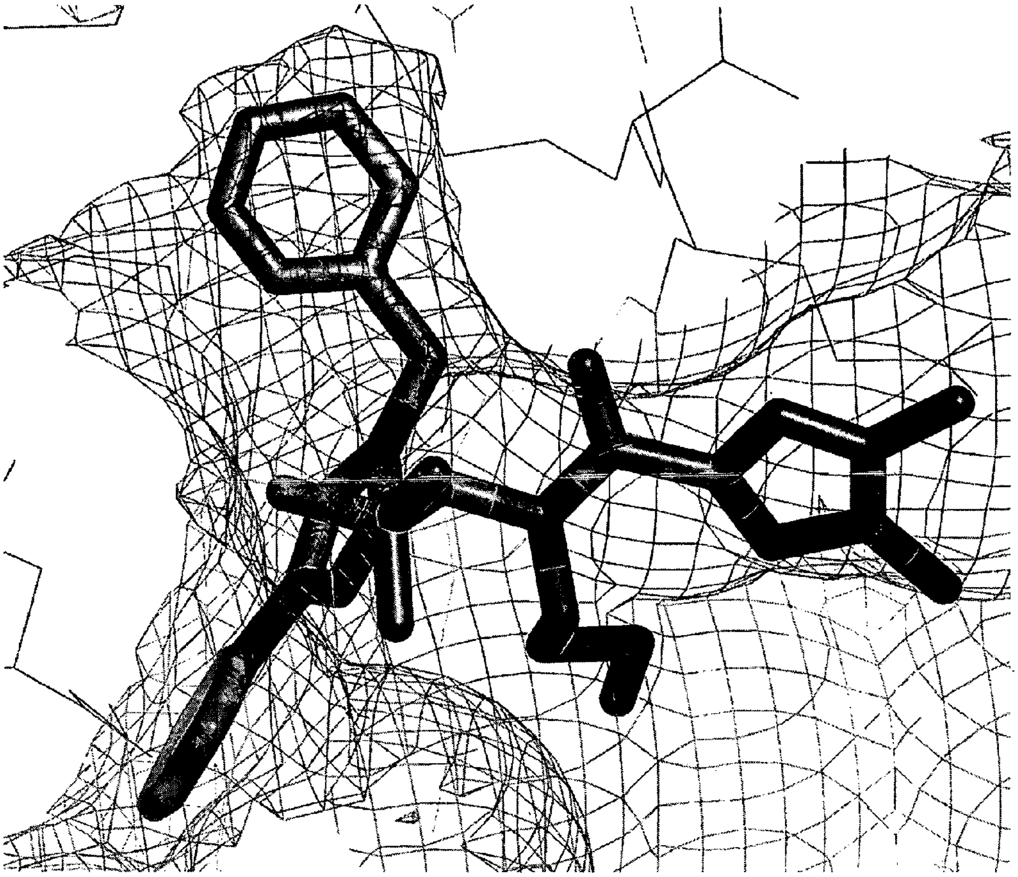
FIG. 3. Binding mode upon ligand compound 3 binding. When compound 3 binds a new pocket "P'" is formed.

Replacement of the isopropyl group with t-butyl, as in 3, causes a new binding mode, where the amide bond rotates 180 degrees. Group Q moves out of the "P" pocket to lie in a solvent exposed channel, and the pocket collapses around the remaining group B, forming a smaller pocket "P'". The phenylimidazole also slides slightly out of its heterocycle pocket in adjustment adjust for this change (FIG. 3). Compound 3 binds in a new, smaller pocket, P'.

Adding substituents to the phenyl of the phenyl imidazole may produce a similar change. For example, in 4, addition of a Cl to the phenyl ring slides it slightly out of the heterocycle pocket producing a similar conformational change.

Similar binding mode changes occur when the heterocycle is benzimidazole rather than phenylimidazole. For example, the benzimidazole 5 binds with both B and Q groups in a larger P-like pocket, but addition of a Br to the benzimidazole ring of 6 induces the conformational change so group B binds in a smaller P'-like pocket, and the Q group lies in the solvent exposed channel. Other heterocycles can be induced to use this new binding mode as well.

The coordinates of this new binding mode enables the design of new ligands. For example, since the Q group now lies in the solvent exposed channel, and can be replaced by much smaller or much larger groups. For example, the heterocycle such as long piperidyl-piperidine Q group can be accommodated in the solvent channel. Conversely, small electronegative groups, such as hydroxymethyl, can be designed to join the amide carbonyl in a bi-dentate interaction with the backbone NH of Arg 119.

Similarly, the Q and A groups, which were trans across the amide bond, are now cis. This allows the design of rigidifying cyclizations.

Eg5 Structural Representation Storage Medium

The atomic coordinates of the Eg5/ligand complex can be stored on a medium for subsequent use with a computational device, such as a computer (e.g., supercomputer, mainframe, minicomputer, or microprocessor). Typically, the coordinates are stored on a medium useful to hold large amounts of data, such as magnetic or optical media (e.g., floppy disks, hard disks, compact disks, magneto-optical media ("floptical" disks, or magnetic tape) or electronic media (e.g., random-access memory (RAM), or read-only memory (ROM). The storage medium can be local to the computer, or can be remote (e.g., a networked storage medium, including the Internet). The choice of computer, storage medium, networking, and other devices or techniques will be familiar to those of skill in the structural/computational chemistry arts. The atomic coordinates are preferably those noted in Table 4-9 or variants thereof.

The foregoing and other aspects of the invention may be better understood in connection with the following representative examples.

EXAMPLES

Compounds that were utilized in the identification and testing of the novel Eg5 binding site that is disclosed herein were prepared by the methods described in Example 1-6.

Example 1

N-(3-aminopropyl)-N-[(3-benzyl-4-oxo-4H-pyrido[1,2-a]pyrimidin-2-yl)(cyclopropyl)methyl]-4-chlorobenzamide 1

Example 1a

Synthesis of 2-(chloromethyl)-4H-pyrido[1,2-a]pyrimidin-4-one

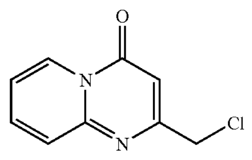

15 g (159.4 mmol) of 2-aminopyridine was combined with approximately 80 g of polyphosphoric acid and heated to 120° C. to allow stirring. To the resulting solution was added slowly 30.5 mL (223.2 mmol) of ethyl-4-chloroacetoacetate and stirred at 120° C. under nitrogen for two hours. The hot reaction mixture was then poured over 1500 mL of ice water and stirred vigorously. The aqueous layer was separated and extracted with methylene chloride (6×, approximately 6 L). The combined organic layers were washed with saturated $NaHCO_3$ and brine and dried over $MgSO_4$ and activated carbon. The solvent was removed in vacuo yielding 30.7 g (157.7 mmol, 99%) of Example 1a as a white solid.

Example 1b

Synthesis of 2-(chloromethyl)-3-iodo-4H-pyrido[1,2-a]pyrimidin-4-one

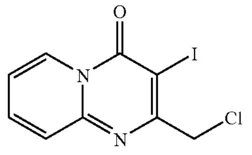

A mixture of 21.9 g (112.5 mmol) of the product from Example 1a and 38.9 g (168.8 mmol) of N-iodosuccinimide in 660 mL of acetonitrile was stirred at 80° C. under nitrogen for 16 hours. The reaction mixture was then allowed to cool to ambient temperature and the acetonitrile was removed in vacuo. The resulting solid was washed with water, saturated $Na_2O_3S_2$, saturated $NaHCO_3$, brine, and filtered. Drying under reduced pressure at 40° C. overnight yielded 29.8 g (92.9 mmol, 83%) of Example 1b as a light brown solid.

Example 1c

Synthesis of (3-iodo-4-oxo-4H-pyrido[1,2-a]pyrimidin-2-yl)methyl acetate

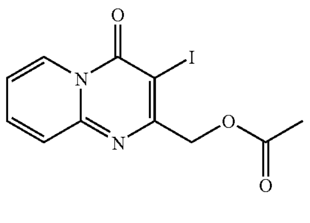

A mixture of 20.0 g (62.4 mmol) of the product from Example 1b and 9.2 g (93.6 mmol) of potassium acetate in 200 mL DMF was stirred at 40° C. under nitrogen for three hours. The reaction mixture was allowed to cool to ambient temperature and the addition of excess water to the reaction solution caused the product to precipitate out of solution. The product was filtered, washed with water (3×), and drying under reduced pressure at 40° C. overnight yielded 19.4 g (56.4 mmol, 90%) of Example 1c as a white solid.

Example 1d

Synthesis of 2-(hydroxymethyl)-3-iodo-4H-pyrido[1,2-a]pyrimidin-4-one

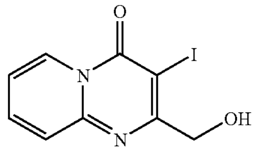

A mixture of 16.5 g (48.0 mmol) of the product from Example 1c and 13.3 g (96.0 mmol) of potassium carbonate in 300 mL methanol was stirred at ambient temperature for 3 hours. Excess water was added to the reaction mixture and the mixture was extracted using ethyl acetate (3×). The organic layers were combined, dried over $MgSO_4$ and activated carbon, and the solvent was removed in vacuo yielding 12 g (39.7 mmol, 83%) of Example 1d as a white solid.

Example 1e

Synthesis of 3-Benzyl-2-(Hydroxymethyl)-4h-Pyrido[1,2-A]Pyrimidin-4-One

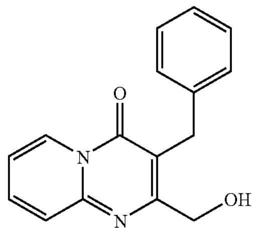

A mixture of 4.0 g (13.24 mmol) of the product from Example 1d, 1.0 g (1.32 mmol) of dichloro[1,1'-bis(diphenylphosphino)ferrocene] palladium(II) dichloromethane adduct, and 8.4 g (39.72 mmol) of $K_3PO_4$ in 30 mL of DMF was heated to 80° C. To the resulting solution was added dropwise 40 mL (19.9 mmol) of B-Benzyl-9-BBN and stirred at 80° C. under nitrogen for 12 hours. The reaction was then cooled to 0° C. and excess 1N NaOH was added to the reaction mixture. Excess 30% $H_2O_2$ was then added to the mixture at 0° C. resulting in significant gas evolution. Stirring continued for at least one additional hour or until gas ceased to evolve. The mixture was extracted with ethyl acetate (3×) and washed with saturated $Na_2O_3S_2$ and brine. The organic layers were combined, dried over $MgSO_4$ and activated carbon, and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, 50% ethyl acetate in hexanes, 57% ethyl acetate in hexanes, 67% ethyl acetate in hexanes, and 100% ethyl acetate yielded 3.2 g (12.0 mmol, 91%) of Example 1e as a pale yellow solid.

Example 1f

Synthesis of 3-benzyl-4-oxo-4H-pyrido[1,2-a]pyrimidine-2-carbaldehyde

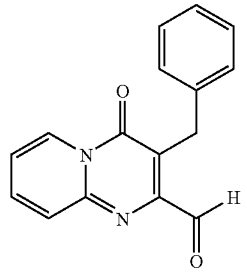

26.5 mL (53.0 mmol) of oxalyl chloride in 40 mL dichloromethane was cooled to −78° C. To the resulting solution was added a solution of 7.52 mL (105.9 mmol) of DMSO in 24 mL dichloromethane and stirred at −78° C. for one hour. Then was added a solution of 4.7 g (17.65 mmol) of the product from Example 1e in 60 mL dichloromethane and the resulting mixture was stirred at −78° C. for one hour. Then was added 24.6 mL (176.5 mmol) of triethylamine and stirred at −78° C. for one hour. The mixture was then allowed to warm to 0° C. and stirred for another hour. Finally, the mixture was allowed to warm to ambient temperature over the course of one hour. Excess water was added to the reaction mixture and the mixture was extracted (3×) using dichloromethane. The combined organic layers were dried over $MgSO_4$ and activated carbon and the solvent was removed in vacuo. The resulting material was subjected to flash chromatography on a 10 cm column. Elution with a gradient of 100% hexanes, 20% ethyl acetate in hexanes, 33% ethyl acetate in hexanes, 43% ethyl acetate in hexanes, and 50% ethyl acetate in hexanes yielded 3.1 g (11.7 mmol, 67%) of Example 1f as a yellow solid.

Example 1g

Synthesis of 3-benzyl-2-[cyclopropyl(hydroxy)methyl]-4H-pyrido[1,2-a]pyrimidin-4-one

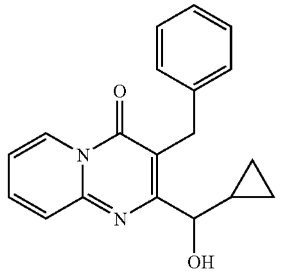

A mixture of 2.0 g (7.6 mmol) of the product from Example 1f in 40 mL anhydrous THF was cooled to −78° C. To the resulting solution was added dropwise 45.4 mL (22.7 mmol) of cyclopropylmagnesium bromide and stirred at −78° C. under nitrogen for 3 hours. The reaction was quenched with saturated $NH_4Cl$ and extracted with ethyl acetate (4×). The combined organic layers were dried over $MgSO_4$ and the solvent was removed in vacuo yielding 1.43 g (4.7 mmol, 61%) of Example 1g as a brown oil.

Example 1h

Synthesis of 1-(3-benzyl-4-oxo-4H-pyrido[1,2-a]pyrimidin-2-yl)propyl methanesulfonate

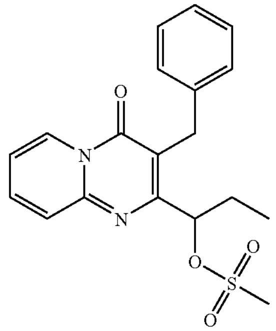

A mixture of 1.43 g (4.7 mmol) of the product from Example 1g and 1.95 mL (14.0 mmol) of triethylamine in 10 mL of anhydrous dichloromethane was cooled to 0° C. To this solution was added dropwise 0.72 mL (9.3 mmol) of methane sulfonyl chloride and the resulting solution was allowed to warm to ambient temperature. Upon completion, excess dichloromethane was added to the reaction mixture and the solution was washed with $H_2O$, saturated $NaHCO_3$, and brine. The organic layer was dried over $MgSO_4$ and the solvent was removed in vacuo yielding 1.57 g (4.1 mmol, 88%) of Example 1h as a brown oil.

Example 1i

Synthesis of 2-[azido(cyclopropyl)methyl]-3-benzyl-4H-pyrido[1,2-a]pyrimidin-4-one

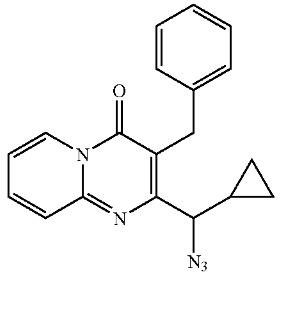

A mixture of 1.57 g (4.1 mmol) of the product from Example 1h and 0.80 g (12.3 mmol) of sodium azide in 10 mL DMF was heated to 60° C. under nitrogen for 24 hours. The reaction mixture was quenched with excess $H_2O$ and extracted with ethyl acetate (3×). The combined organic layers were washed with saturated $NaHCO_3$ and brine, dried over $MgSO_4$, and the solvent was removed in vacuo yielding 1.2 g (3.6 mmol, 88%) of Example 1i as a brown oil.

Example 1j

Synthesis of 2-[amino(cyclopropyl)methyl]-3-benzyl-4H-pyrido[1,2-a]pyrimidin-4-one

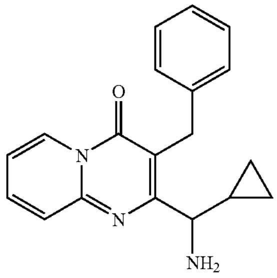

A mixture of 1.22 g (3.6 mmol) of the product from Example 1i and 1.16 g (4.4 mmol) of triphenylphosphine in a solution of 10 mL THF and 10 mL $H_2O$ was heated at 60° C. under nitrogen for 18 hours. The reaction was quenched with excess saturated $NaHCO_3$ and extracted with ethyl acetate (3×). The combined organic layers were washed with brine, dried over $MgSO_4$, and the solvent was removed in vacuo. The resulting material was subjected to flash chromatography on a 15 cm silica gel column. Elution with hexanes, 33% ethyl acetate in hexanes, 50% ethyl acetate in hexanes, ethyl acetate, and 85% dichloromethane:15% methanol:0.3% ammonia yielded 0.25 g (0.82 mmol, 22%) of Example 1j as a yellow oil.

Example 1k

Synthesis of 2-(3-{[(3-benzyl-4-oxo-4H-pyrido[1,2-a]pyrimidin-2-yl)(cyclopropyl)methyl]amino}propyl)-1H-isoindole-1,3(2H)-dione

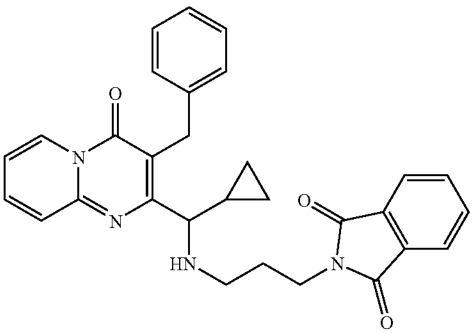

A mixture of 0.25 g (0.82 mmol) of the product from Example 1j, 0.45 g (3.3 mmol) of potassium carbonate, and 0.44 g (1.6 mmol) of N-(3-Bromopropyl)-phthalimide in 5 mL of DMF was stirred at ambient temperature under nitrogen for 30 hours. The reaction mixture was quenched with $H_2O$ and extracted with ethyl acetate (3×). The combined organic layers were washed with saturated $NaHCO_3$ and brine, dried over $MgSO_4$, and the solvent was removed in vacuo yielding 0.59 g (1.2 mmol, 150%) of Example 1k as a crude mixture.

Example 1l

Synthesis of N-[(3-benzyl-4-oxo-4H-pyrido[1,2-a]pyrimidin-2-yl)(cyclopropyl)methyl]-4-chloro-N-[3-(1,3-dioxo-1,3-dihydro-2H-isoindol-2-yl)propyl]benzamide

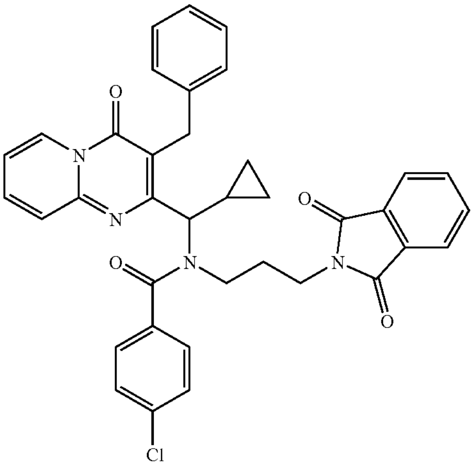

A mixture of 0.29 g (0.59 mmol) of the product from Example 1k, 0.007 g (0.06 mmol) of 4-(Dimethylamino)pyridine, and 0.25 mL (1.78 mmol) of triethylamine in 2.0 mL dichloromethane was cooled to 0° C. Then was added 0.15 mL (1.19 mmol) of 4-chlorobenzoyl chloride and slowly allowed to warm to ambient temperature. Upon completion, excess dichloromethane was added to the reaction mixture and the resulting solution was washed with saturated $NaHCO_3$ and brine, dried over $MgSO_4$, and the solvent was removed in vacuo. The resulting material was subjected to flash chromatography on a 5 cm column. Elution with a gradient of 100% hexanes, 20% ethyl acetate in hexanes, 33% ethyl acetate in hexanes, 50% ethyl acetate in hexanes, and 100% ethyl acetate yielded 0.11 g (0.17 mmol, 29%) of Example 1l as a clear oil.

Example 1m

Synthesis of N-(3-aminopropyl)-N-[(3-benzyl-4-oxo-4H-pyrido[1,2-a]pyrimidin-2-yl)(cyclopropyl) methyl]-4-chlorobenzamide

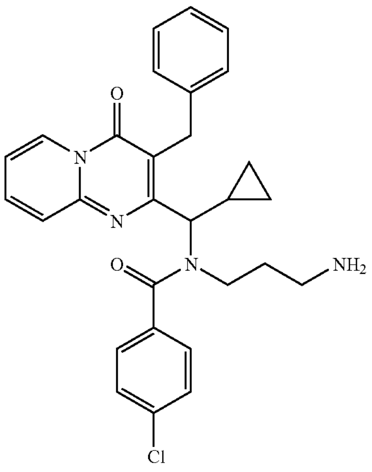

A mixture of 0.11 g (0.17 mmol) of the product from Example 1l and 0.008 mL (0.26 mmol) of hydrazine in 2 mL of ethanol was heated at 60° C. under nitrogen for 2 hours. The resulting white precipitate was filtered and washed with ethyl acetate. The filtrate was collected and the solvent was removed in vacuo. The resulting material was subjected to flash chromatography on a 5 cm column. Elution with a gradient of 100% hexanes, 33% ethyl acetate in hexanes, 100% ethyl acetate, and 97% dichloromethane:3% methanol: 0.1% ammonia yielded 0.002 g (0.004 mmol, 2.5%) of 1 as a white solid.

Example 2

N-(3-aminopropyl)-N-[(1R)-1-(1-benzyl-4-phenyl-1H-imidazol-2-yl)-2-methylpropyl]-4-methylbenzamide 2

Example 2a

Synthesis of

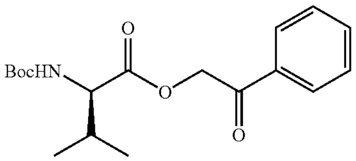

A stirred solution of D-Boc-Valine (1.0 g, 4.605 mmol) in EtOH (10 mL) was treated with $Cs_2CO_3$ (0.75 g, 2.30 mmol). After 45 min, the EtOH was removed by evaporation under reduced pressure. The residual cesium salt was re-dissolved in DMF (15 mL) and the treated with 2-bromoacetophenone (0.916 g, 4.605 mmol) and stirred at room temperature until the reaction was complete. The reaction mixture was then partitioned between EtOAc and $H_2O$, and the organics separated, then washed with $H_2O$ (×3), sat. brine (×3), then dried ($Na_2SO_4$), filtered, and evaporated under reduced pressure to give the keto-ester which was pure enough to use directly in the next step.

Example 2b

Synthesis of

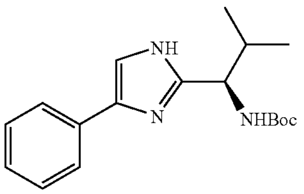

To a stirred solution of the product from Example 2a (1.589 g, 4.743 mmol) in xylenes (50 mL) was added ammonium acetate (1.82 g, 23.7 mmol). A Dean-Stark trap was added and the reaction heated to 140° C. Once the reaction was complete, the mixture was allowed to cool to room temperature, then partitioned between EtOAc and sat. aq. $NaHCO_3$. The organics were separated, then washed with sat. aq. $NaHCO_3$ (×2), $H_2O$ (×3), sat. brine (×3), then dried ($Na_2SO_4$), filtered, and evaporated under reduced pressure to give the phenyl imidazole which was pure enough to use directly in the next step.

Example 2c

Synthesis of

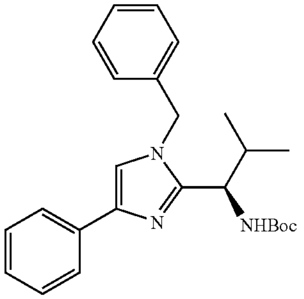

To a stirred solution/suspension of the product from Example 2b (1.00 g, 3.17 mmol) and $K_2CO_3$ (0.876 g, 6.34 mmol) in DMF (10 mL) was added benzyl bromide (0.415 mL, 3.49 mmol). Once the reaction was complete, the mixture was partitioned between EtOAc and $H_2O$. The organic layer was separated and washed with $H_2O$ (×3), sat. brine (×3), then dried ($Na_2SO_4$), filtered, and evaporated under reduced pressure to give the crude benzylated phenyl imidazole. The crude reaction material was then crystallized (EtOAc, hexanes) to give pure product. The regiochemical outcome was verified by 1H nOe NMR.

Example 2d

Synthesis of

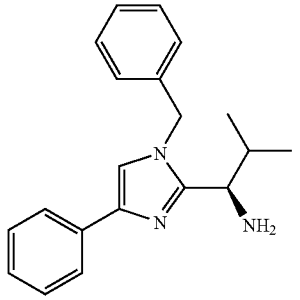

Boc-protected amine from Example 2c (0.406 g, 1.0 mmol) was treated with 10% TFA in $CH_2Cl_2$ (5 ml). Once reaction was complete, the reaction was concentrated in vacuo and then partitioned between EtOAc and sat. aq. $NaHCO_3$. The organics were separated, then washed with sat. aq. $NaHCO_3$ (×2), $H_2O$ (×2), sat. brine (×2), then dried ($Na_2SO_4$), filtered, and evaporated under reduced pressure to give the phenyl imidazole free amine which was pure enough to use directly in the next step.

Example 2e

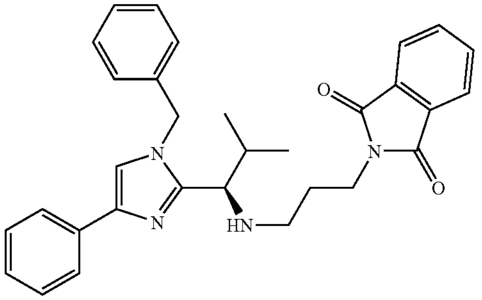

To a stirred solution of amine from Example 2d (59 mg, 0.193 mmol) and 2-(3-oxopropyl)benzo[c]azoline-1,3-dione (39 mg, 0.193 mmol) in $CH_2Cl_2$ (1.5 mL) was added AcOH (11 μL, 0.193 mmol). The mixture was allowed to stir for 5 min before the addition of sodium tris-acetoxyborohydride (45 mg, 0.212 mmol). After 1 h, the mixture was concentrated in vacuo, partitioned between EtOAc and 2 M aq. $Na_2CO_3$. The organics were separated, then washed with 2 M aq. $Na_2CO_3$ (×2), $H_2O$ (×2), sat. brine (×2), then dried ($Na_2SO_4$), filtered, and evaporated under reduced pressure to give product which was pure enough to use directly in the next step.

Example 2f

Synthesis of

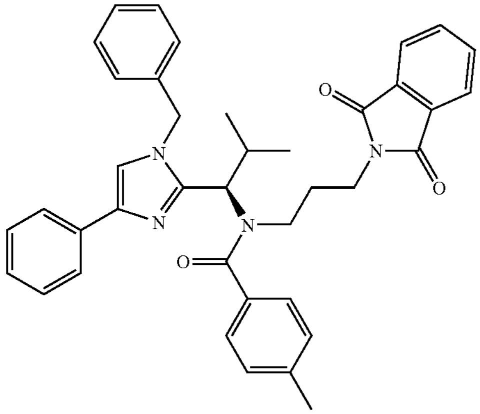

To a stirred solution of amine from Example 2e (42 mg, 0.085 mmol) in $CH_2Cl_2$ (1.2 ml) was added DIPEA (30 μL, 0.170 mmol) followed by p-toluoyl chloride (12.4 μL, 1.0 mmol). Once the reaction was complete, the mixture was partitioned between $CH_2Cl_2$ and sat. aq. $NaHCO_3$. The organics were separated and washed with $H_2O$ (×2), sat. brine (×2), then dried ($Na_2SO_4$), filtered, and evaporated under reduced pressure to give product which was pure enough to use directly in the next step.

Example 2g

Synthesis of

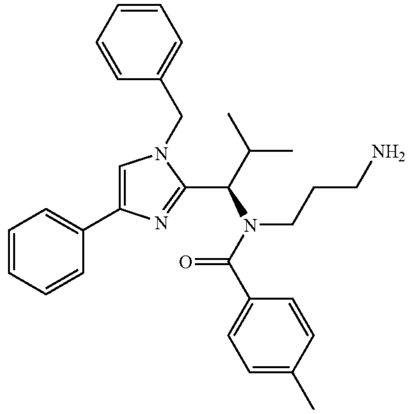

To a non-stirred solution of phthalimido compound from Example 2f (52 mg, 0.085 mmol) in EtOH (1.5 mL) was added anhydrous hydrazine (26 μL, 0.85 mmol). Once the reaction was complete, the reaction was filtered, and the filtrate evaporated under reduced pressure to give the title compound which was purified by reverse phase prep HPLC to give the pure product 2.

Example 3

N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide 3

Example 3a

Synthesis of

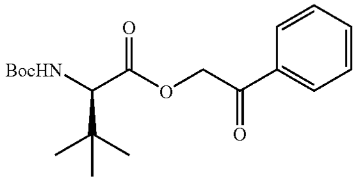

A stirred solution of the N-Boc-acid 20 (10.0 g, 43.2 mmol 1.0 equiv) in EtOH (150 mL) was treated with $Cs_2CO_3$ (7.04 g, 21.6 mmol, 0.5 equiv). After 45 min, the EtOH was removed by evaporation under reduced pressure. The residual cesium salt was re-dissolved in DMF (150 mL) and the treated with 2-bromoacetophenone 21 (8.60 g, 43.2 mmol, 1.0 equiv) and stirred at room temperature for 1 hour. The reaction mixture was then partitioned between EtOAc and $H_2O$, and the organics separated, then washed with $H_2O$ (×3), sat. brine (×3), then dried ($Na_2SO_4$), filtered, and evaporated under reduced pressure to give the keto-ester which was pure enough to use directly in the next step.

Example 3b

Synthesis of

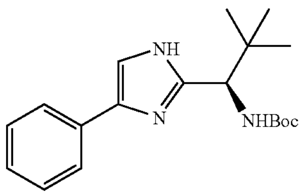

To a stirred solution of keto-ester from Example 3a (15.1 g, 43.2 mmol, 1.0 equiv) in xylenes (500 mL) was added ammonium acetate (16.6 g, 216.2 mmol, 5.0 equiv). A Dean-Stark trap was added and the reaction heated to 140° C. for 1 hour. Once the reaction was complete, the mixture was allowed to cool to room temperature, then partitioned between EtOAc and sat. aq. $NaHCO_3$. The organics were separated, then washed with sat. aq. $NaHCO_3$ (×2), $H_2O$ (×3), sat. brine (×3), then dried ($Na_2SO_4$), filtered, and evaporated under reduced pressure to give the phenyl imidazole which was pure enough to use directly in the next step.

Example 3c

Synthesis of

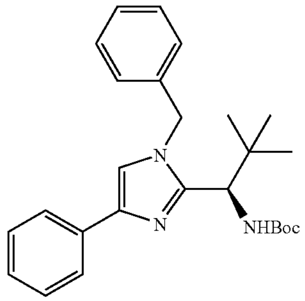

To a stirred solution/suspension of imidazole from Example 3b (14.26 g, 43.2 mmol, 1.0 equiv) and $K_2CO_3$ (12.00 g, 86.4 mmol, 2.0 equiv) in DMF (150 mL) was added the benzyl bromide (5.65 mL, 47.53 mmol, 1.1 equiv). Reaction was stirred at room temperature for 12 hours. Once the reaction was complete, the mixture was partitioned between EtOAc and $H_2O$. The organic layer was separated and washed with $H_2O$ (×3), sat. brine (×3), then dried ($Na_2SO_4$), filtered, and evaporated under reduced pressure to give the crude benzylated phenyl imidazole, which was pure enough to move directly onto the next step.

Example 3d

Synthesis of

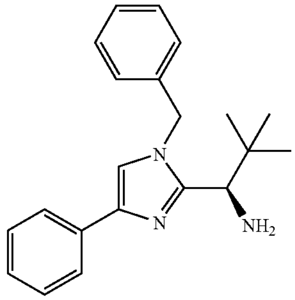

Boc-protected amine from Example 3c (5.0 g, 11.93 mmol) was treated with 15% TFA in $CH_2Cl_2$ (35 ml). Once reaction was complete, the reaction was concentrated in vacuo and then partitioned between EtOAc and sat. aq. $NaHCO_3$. The organics were separated, then washed with sat. aq. $NaHCO_3$ (×2), $H_2O$ (×2), sat. brine (×2), then dried ($Na_2SO_4$), filtered, and evaporated under reduced pressure to give the phenyl imidazole free amine which was pure enough to use directly in the next step.

Example 3e

Synthesis of

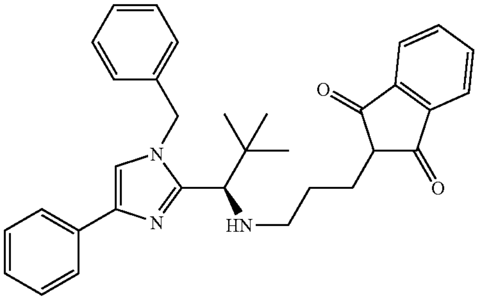

To a stirred solution of amine from Example 3d (1.00 g, 3.13 mmol, 1.0 equiv) and the 2-(3-oxopropyl)benzo[c]azoline-1,3-dione 25 (0.51 g, 2.51 mmol, 1.0 equiv) in $CH_2Cl_2$ (10 mL) was added AcOH (0.18 mL, 3.13 mmol, 1.0 equiv). The mixture was allowed to stir for 5 min before the addition of sodium tris-acetoxyborohydride (0.73 g, 3.44 mmol, 1.1 equiv). Once the reaction was complete, the mixture was concentrated in vacuo, partitioned between EtOAc and 2 M aq. $Na_2CO_3$. The organics were separated, then washed with 2 M aq. $Na_2CO_3$ (×2), $H_2O$ (×2), sat. brine (×2), then dried ($Na_2SO_4$), filtered, and evaporated under reduced pressure to give product which was pure enough to use directly in the next step.

Example 3f

Synthesis of

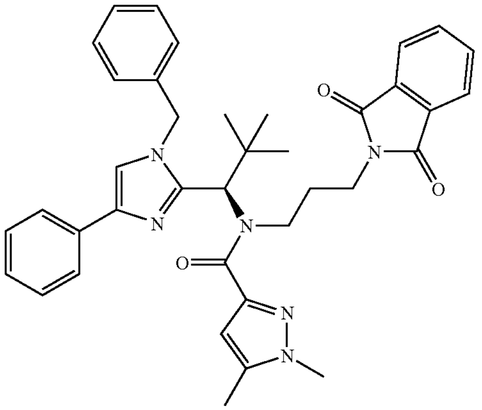

To a stirred solution of amine from Example 3e (0.04 g, 0.08 mmol, 1.0 equiv) in $CH_2Cl_2$ (0.3 ml) was added the acid (0.024 g, 0.17 mmol, 2.2 equiv), HOAT (0.24 g, 0.17 mmol, 2.2 equiv), and TEA (0.05 ml, 0.33 mmol, 4.2 equiv). After 5 minutes EDC (0.04 g, 0.18 mmol, 2.3 equiv) was added, and the reaction was heated to 55° C. for 24 hours. The mixture was then partitioned between $CH_2Cl_2$ and sat. aq. $NaHCO_3$. The organics were separated and washed with $H_2O$ (×2), sat. brine (×2), then dried ($Na_2SO_4$), filtered, and evaporated under reduced pressure to give product.

Example 3g

Synthesis of

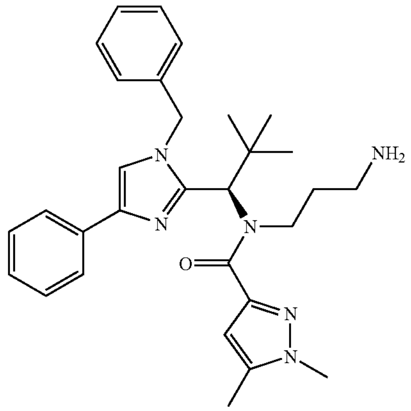

To a non-stirred solution of phthalimido compound from Example 3f (0.02 g, 0.03 mmol, 1.0 equiv) in EtOH (0.1 mL) was added anhydrous hydrazine (0.005 g, 0.15 mmol, 5.0 equiv). Once the reaction was complete, the reaction was filtered, and the filtrate evaporated under reduced pressure to give the title compound which was purified by reverse phase prep HPLC to give the pure product 3.

Example 4

N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide 4

Example 4a

Synthesis of

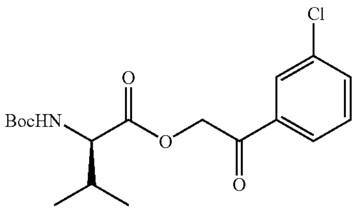

A stirred solution of the N-Boc-acid (8.0 g, 36.8 mmol 1.0 equiv) in EtOH (130 mL) was treated with $Cs_2CO_3$ (6.0 g, 18.4 mmol, 0.5 equiv). After 45 min, the EtOH was removed by evaporation under reduced pressure. The residual cesium salt was re-dissolved in DMF (130 mL) and the treated with 2-bromoacetophenone 21 (8.60 g, 36.84 mmol, 1.0 equiv) and stirred at room temperature for 1 hour. The reaction mixture was then partitioned between EtOAc and $H_2O$, and the organics separated, then washed with $H_2O$ (×3), sat. brine (×3), then dried ($Na_2SO_4$), filtered, and evaporated under reduced pressure to give the keto-ester which was pure enough to use directly in the next step.

Example 4b

Synthesis of

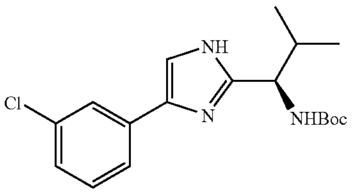

To a stirred solution of keto-ester from Example 4a (13.5 g, 36.8 mmol, 1.0 equiv) in xylenes (450 mL) was added ammonium acetate (14.2 g, 185.0 mmol, 5.0 equiv). A Dean-Stark trap was added and the reaction heated to 140° C. for 1 hour. Once the reaction was complete, the mixture was allowed to cool to room temperature, then partitioned between EtOAc and sat. aq. $NaHCO_3$. The organics were separated, then washed with sat. aq. $NaHCO_3$ (×2), $H_2O$ (×3), sat. brine (×3), then dried ($Na_2SO_4$), filtered, and evaporated under reduced pressure to give the phenyl imidazole which was pure enough to use directly in the next step.

Example 4c

Synthesis of

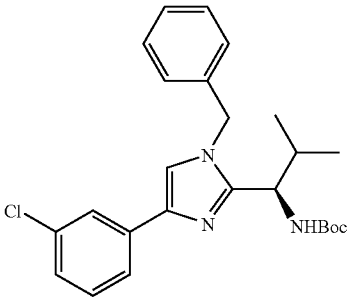

To a stirred solution/suspension of imidazole from Example 4b (12.85 g, 36.8 mmol, 1.0 equiv) and $K_2CO_3$ (10.17 g, 73.6 mmol, 2.0 equiv) in DMF (122 mL) was added the benzyl bromide (5.20 mL, 40.49 mmol, 1.1 equiv). Reaction was stirred at room temperature for 12 hours. Once the reaction was complete, the mixture was partitioned between EtOAc and $H_2O$. The organic layer was separated and washed with $H_2O$ (×3), sat. brine (×3), then dried ($Na_2SO_4$), filtered, and evaporated under reduced pressure to give the crude benzylated phenyl imidazole, which was pure enough to move directly onto the next step.

Example 4d

Synthesis of

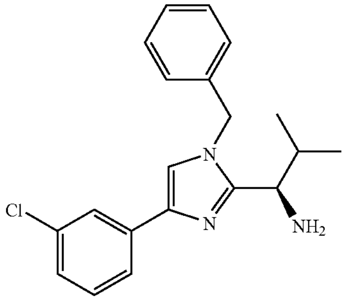

Boc-protected amine from Example 4c (5.0 g, 11.40 mmol) was treated with 15% TFA in $CH_2Cl_2$ (35 ml). Once reaction was complete, the reaction was concentrated in vacuo and then partitioned between EtOAc and sat. aq. $NaHCO_3$. The organics were separated, then washed with sat. aq. $NaHCO_3$ (×2), $H_2O$ (×2), sat. brine (×2), then dried ($Na_2SO_4$), filtered, and evaporated under reduced pressure to give the phenyl imidazole free amine which was pure enough to use directly in the next step.

Example 4e

Synthesis of

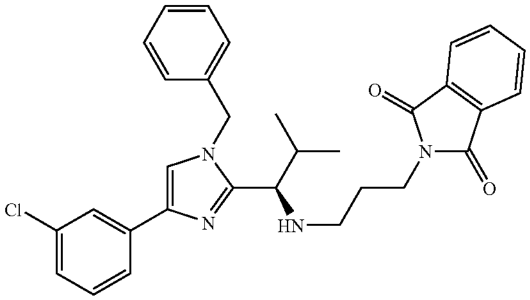

To a stirred solution of amine from Example 4d (3.86 g, 11.40 mmol, 1.0 equiv) and 2-(3-oxopropyl)benzo[c]azoline-1,3-dione (2.31 g, 11.40 mmol, 1.0 equiv) in $CH_2Cl_2$ (40 mL) was added AcOH (0.65 mL, 11.40 mmol, 1.0 equiv). The mixture was allowed to stir for 5 min before the addition of sodium tris-acetoxyborohydride (2.65 g, 12.52 mmol, 1.1 equiv). Once the reaction was complete, the mixture was concentrated in vacuo, partitioned between EtOAc and 2 M aq. $Na_2CO_3$. The organics were separated, then washed with 2 M aq. $Na_2CO_3$ (×2), $H_2O$ (×2), sat. brine (×2), then dried ($Na_2SO_4$), filtered, and evaporated under reduced pressure to give product which was pure enough to use directly in the next step.

Example 4f

Synthesis of

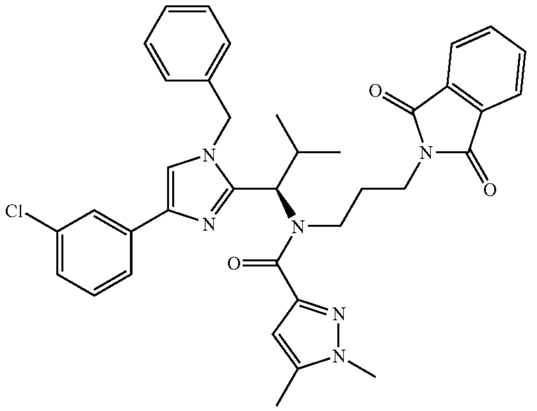

To a stirred solution of amine from Example 4e (0.05 g, 0.10 mmol, 1.0 equiv) in $CH_2Cl_2$ (0.3 ml) was added the acid (0.02 g, 0.11 mmol, 1.0 equiv), HOAT (0.15 g, 0.10 mmol, 1.0 equiv), and TEA (0.03 ml, 0.20 mmol, 2.1 equiv). After 5 minutes EDC was added (0.22 g, 0.20 mmol, 2.0 equiv), and the reaction was heated to 55° C. for 24 hours. The mixture was then partitioned between $CH_2Cl_2$ and sat. aq. $NaHCO_3$. The organics were separated and washed with $H_2O$ (×2), sat. brine (×2), then dried ($Na_2SO_4$), filtered, and evaporated under reduced pressure to give product.

Example 4g

Synthesis of

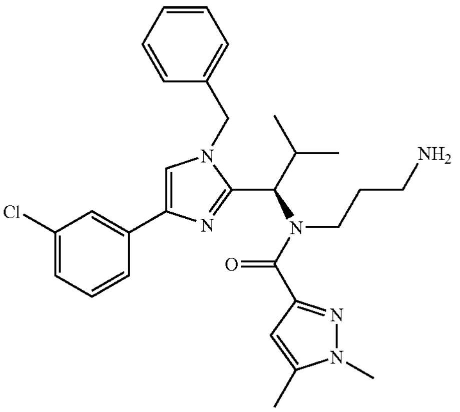

To a non-stirred solution of phthalimido compound from Example 4f (0.01 g, 0.02 mmol, 1.0 equiv) in EtOH (0.6 mL) was added anhydrous hydrazine (0.003 g, 0.10 mmol, 5.0 equiv). Once the reaction was complete, the reaction was filtered, and the filtrate evaporated under reduced pressure to give the title compound which was purified by reverse phase prep HPLC to give the pure product 4.

Example 5

N-(3-aminopropyl)-N-[(1R)-1-(1-benzyl-1H-benzimidazol-2-yl)-2-methylpropyl]-4-chlorobenzamide 5

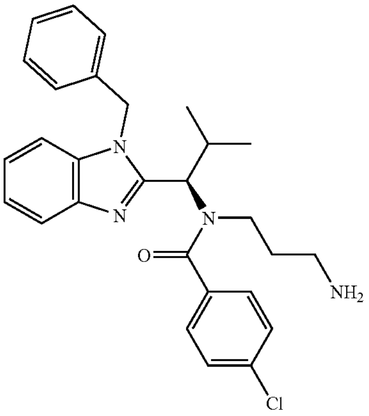

Example 5a

Synthesis of Benzyl-(2-nitro-phenyl)-amine

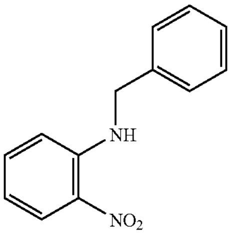

Benzylamine, (3.1 ml, 28 mmol) was added to 2-fluoronitrobenzene (3 ml, 28.5 mmol) in 20 ml dry THF and the reaction stirred overnight. The crude was diluted with ethyl acetate and washed with said. Bicarbonate and then purified by silica gel chromotography eluting with 10-50% Ethyl acetate in hexanes.

Example 5b

Synthesis of N1-Benzyl-benzene-1,2-diamine

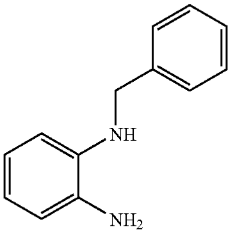

To a solution of Benzyl-(2-nitro-phenyl)-amine (230 mg, 1 mmol) in 3 ml acetic acid, was added iron (70 mg, 1.24 mmol). The reaction mixture was heated to 40° C. under argon for 2 hours. The mixture was cooled to ambient temperature and filtered through celite and the filtrate was concentrated. The resulting solid was dissolved in ethyl acetate. The organic layer was washed with saturated $NaHCO_3$, dried over $MgSO_4$, filtered and the filtrate was concentrated in vacuo to yield crude product that was used in step Example 5c.

Example 5c

Synthesis of [1-(2-Benzylaminophenylcarbamoyl)-2-methyl-propyl]-carbamic acid tert-butyl ester

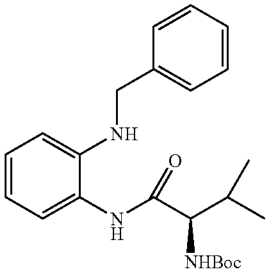

To a solution of N1-Benzyl-benzene-1,2-diamine obtained from Example 5b and triethylamine (0.19 ml, 1.35 mmol) in dry DMF (5 ml), was added Boc-D-valine (294 mg, 1.35 mmol) followed by TBTU (289 mg, 0.9 mmol). The reaction mixture was stirred at room temperature overnight. Ethyl acetate was added. The organic layer was washed with saturated $NaHCO_3$, dried over $MgSO_4$, filtered, and the filtrated was concentrated in vacuo. The crude material was purified by flash chromatography to yield [1-(2-Benzylaminophenylcarbamoyl)-2-methyl-propyl]-carbamic acid tert-butyl ester.

Example 5d

Synthesis of [1-(1-Benzyl-1H-benzimidazol-2-yl)-2-methyl-propyl]-carbamic acid tert-butyl ester

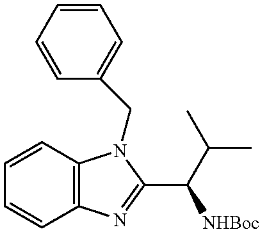

A solution of [1-(2-benzylamino-phenylcarbamoyl)-2-methyl-propyl]-carbamic acid tert-butyl ester (453 mg, 1.14 mmol) in acetic acid (4 ml) was heated at 100° C. for 2 hours. The solvent was removed in vacuo and the resulting solid was dissolved in ethyl acetate. The organic layer was washed with saturated $NaHCO_3$, dried over $MgSO_4$, filtered and the filtrate was concentrated in vacuo. The crude product was purified by flash chromatography to give of [1-(1-benzyl-5-methyl-1H-benzimidazol-2-yl)-2-methyl-propyl]-carbamic acid tert-butyl ester (389 mg, yield 90%).

Example 5e

Synthesis of 1-(1-Benzyl-1H-benzimidazol-2-yl)-2-methyl-propylamine

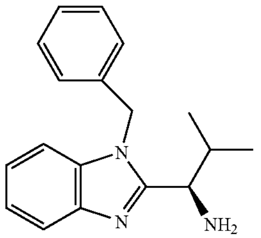

To a solution of [1-(1-Benzyl-5-bromo-1H-benzimidazol-2-yl)-2-methyl-propyl]-carbamic acid tert-butyl ester in DCM (2 ml), was added trifluoroacetic acid (0.5 ml). The reaction mixture was stirred at room temperature for 30 minutes. The solvent was removed in vacuo to give the free amine product.

Example 5f

Synthesis of 2-{3-[1-(1-Benzyl-1H-benzimidazol-2-yl)-2-methyl-propylamino]-propyl}-isoindole-1,3-dione

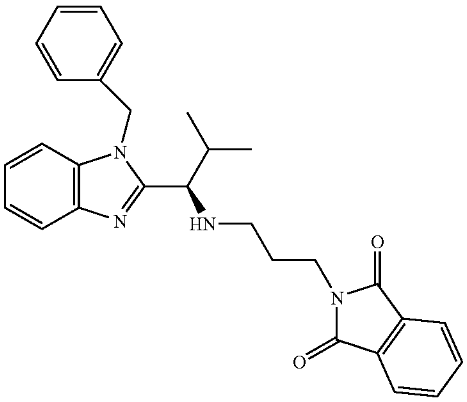

To a solution of 1-(1-benzyl-1H-benzimidazol-2-yl)-2-methyl-propylamine (160 mg, 0.56 mmol) and 3-(1,3-dioxo-1,3-dihydro-isoindol-2-yl)-propionaldehyde (114 mg, 0.56 mmol) in dry DCM (3 ml) at room temperature, was added sodium triacetoxyborohydride (119 mg, 0.56 mmol). After 10 minutes, acetic acid (34 µl, 0.56 mmol) was added to the reaction mixture. The mixture was stirred at room temperature for 1 hour. The solvent was removed in vacuo and the solid was dissolved in ethyl acetate. The organic layer was washed with saturated $NaHCO_3$, dried over $MgSO_4$, filtered and the filtrate was concentrated in vacuo. The crude product was purified by flash chromatography to give material that was used in Example 5g.

Example 5g

Synthesis of N-[1-(1-Benzyl-1H-benzimidazol-2-yl)-2-methyl-propyl]-N-[3-(1,3-dioxo-1,3-dihydro-isoindol-2-yl)-propyl]-4-chloro-benzamide

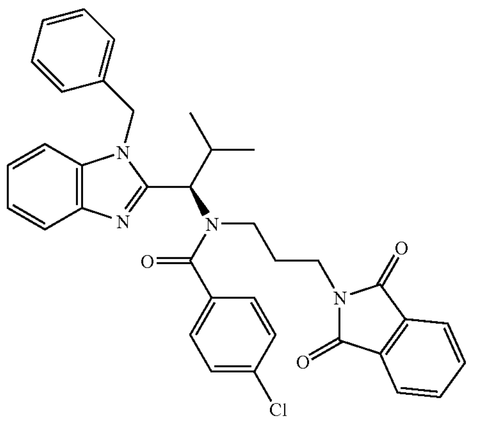

To a solution of 2-{3-[1-(1-Benzyl-5-bromo-1H-benzimidazol-2-yl)-2-methyl-propylamino]-propyl}-isoindole-1,3-dione (260 mg, 0.56 mmol) and triethylamine (0.47 ml, 3.36 mmol) in DCM (3 ml) at 0° C., was added 4-chlorobenzoylchloride (0.36 ml, 2.8 mmol, 5 eq). The reaction mixture was stirred at 0° C. for 30 minutes. Ethyl acetate and saturated sodium bicarbonate were added. The mixture was extracted with ethyl acetate. The organic layers was combined, dried over $MgSO_4$, filtered, and the filtrate was concentrated in vacuo. The crude material was purified by flash chromatography to give N-[1-(1-Benzyl-1H-benzimidazol-2-yl)-2-methyl-propyl]-N-[3-(1,3-dioxo-1,3-dihydro-isoindol-2-yl)-propyl]-4-chloro benzamide (182 mg, yield 54%)

Example 5h

Synthesis of N-(3-aminopropyl)-N-[(1R)-1-(1-benzyl-1H-benzimidazol-2-yl)-2-methylpropyl]-4-chlorobenzamide 5

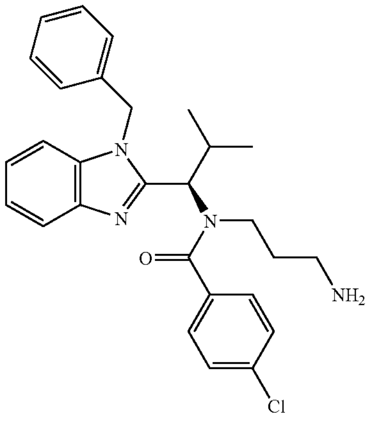

To a solution of N-[1-(1-benzyl-1H-benzimidazol-2-yl)-2-methyl-propyl]-N-[3-(1,3-dioxo-1,3-dihydro-isoindol-2-yl)-propyl]-4-chloro-benzamide (180 mg, 0.302 mmol) in ethanol at room temperature, was added hydrazine (0.19 ml, 6 mmol). The reaction was stirred at room temperature for 1 hour. The crude product was purified via reverse phase chromatography to give N-(3-aminopropyl)-N-[(1R)-1-(1-benzyl-1H-benzimidazol-2-yl)-2-methylpropyl]-4-chlorobenzamide 5 (129 mg, yield 91%).

Example 6

N-(3-aminopropyl)-N-[(1R)-1-(1-benzyl-5-bromo-1H-benzimidazol-2-yl)-2-methylpropyl]-4-methylbenzamide 6

Example 6a

Synthesis of Benzyl-(4-bromo-2-nitro-phenyl)-amine

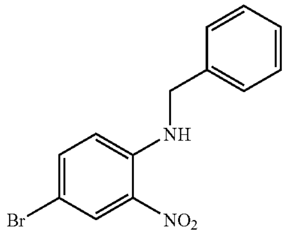

To a solution of 4-Bromo-2-nitroaniline (435 mg, 2 mmol) and benzaldehyde (0.204 ml, 2 mmol,) in 4 ml dry dichloromethane at room temperature, was added sodium triacetoxyborohydride (424 mg, 2 mmol). Then acetic acid (120 µl, 2 mmol) was added. The reaction mixture was stirred at room temperature for 8 hours. The solvent was evaporated and the solid was dissolved in ethyl acetate. The organic layer was washed with saturated $NaHCO_3$, dried over $MgSO_4$, filtered, and the solvent was removed in vacuo. The crude material was purified by flash chromatography to yield 276 mg (0.9 mmol, 45%) of benzyl-(4-bromo-2-nitrophenyl)-amine.

Example 6b

Synthesis of N1-Benzyl-4-bromo-benzene-1,2-diamine

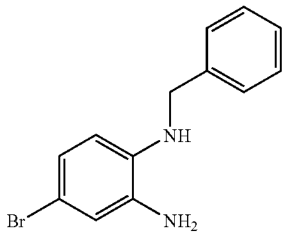

To a solution of benzyl-(4-bromo-2-nitro-phenyl)-amine (276 mg, 0.9 mmol) in 3 ml acetic acid, was added iron (70 mg, 1.2 mmol). The reaction mixture was heated to 40° C. under argon for 2 hours. The mixture was cooled to ambient temperature and filtered through celite and the filtrate was concentrated. The resulting solid was dissolved in ethyl acetate. The organic layer was washed with saturated $NaHCO_3$, dried over $MgSO_4$, filtered and the filtrate was concentrated in vacuo to yield crude product that was used in Example 6c.

Example 6c

Synthesis of [1-(2-Benzylamino-5-bromo-phenylcarbamoyl)-2-methyl-propyl]-carbamic acid tert-butyl ester

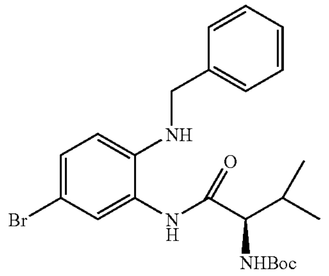

To a solution of [1-(2-benzylamino-5-bromo-phenylcarbamoyl)-2-methyl-propyl]-carbamic acid tert-butyl ester (250 mg, 0.9 mmol) and triethylamine (0.19 ml, 1.35 mmol) in dry DMF (5 ml), was added Boc-D-valine (290 mg, 1.35 mmol) followed by TBTU (290 mg, 0.9 mmol,). The reaction mixture was stirred at room temperature overnight. Ethyl acetate was added. The organic layer was washed with saturated $NaHCO_3$, dried over $MgSO_4$, filtered, and the filtrated was concentrated in vacuo. The crude material was purified by flash chromatography to yield [1-(2-Benzylamino-5-methyl-phenylcarbamoyl)-2-methyl-propyl]-carbamic acid tert-butyl ester.

Example 6d

Synthesis of [1-(1-Benzyl-5-methyl-1H-benzimidazol-2-yl)-2-methyl-propyl]-carbamic acid tert-butyl ester

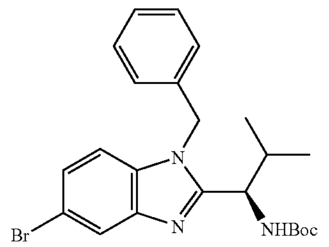

A solution of [1-(2-benzylamino-5-bromo-phenylcarbamoyl)-2-methyl-propyl]-carbamic acid tert-butyl ester (400 mg, 0.84 mmol) in acetic acid (4 ml) was heated at 100° C. for 2 hours. The solvent was removed in vacuo and the resulting solid was dissolved in ethyl acetate. The organic layer was washed with saturated $NaHCO_3$, dried over $MgSO_4$, filtered and the filtrate was concentrated in vacuo. The crude product was purified by flash chromatography to give of [1-(1-benzyl-5-methyl-1H-benzimidazol-2-yl)-2-methyl-propyl]-carbamic acid tert-butyl ester (300 mg, yield 66%).

Example 6e

Synthesis of 1-(1-Benzyl-5-bromo-1H-benzimidazol-2-yl)-2-methyl-propylamine

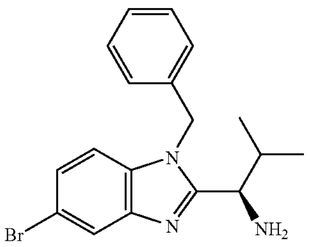

To a solution of [1-(1-Benzyl-5-bromo-1H-benzimidazol-2-yl)-2-methyl-propyl]-carbamic acid tert-butyl ester in DCM (2 ml), was added trifluoroacetic acid (0.5 ml). The reaction mixture was stirred at room temperature for 30 minutes. The solvent was removed in vacuo to give the free amine product.

Example 6f

Synthesis of 2-{3-[1-(1-Benzyl-5-bromo-1H-benzimidazol-2-yl)-2-methyl-propylamino]-propyl}-isoindole-1,3-dione

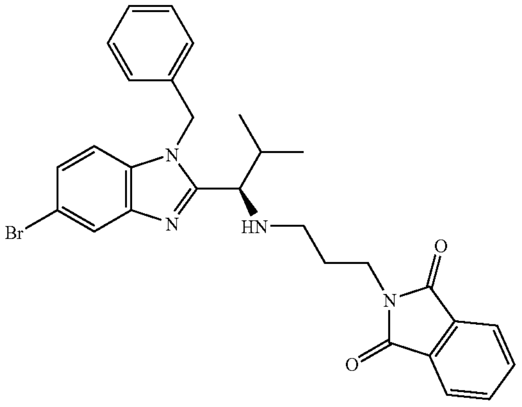

To a solution of 1-(1-benzyl-5-bromo-1H-benzimidazol-2-yl)-2-methyl-propylamine (200 mg, 0.56 mmol) and 3-(1,3-dioxo-1,3-dihydro-isoindol-2-yl)-propionaldehyde (114 mg, 0.56 mmol) in dry DCM (3 ml) at room temperature, was added sodium triacetoxyborohydride (119 mg, 0.56 mmol). After 10 minutes, acetic acid (34 μl, 0.56 mmol) was added to the reaction mixture. The mixture was stirred at room temperature for 1 hour. The solvent was removed in vacuo and the solid was dissolved in ethyl acetate. The organic layer was washed with saturated $NaHCO_3$, dried over $MgSO_4$, filtered and the filtrate was concentrated in vacuo. The crude product was purified by flash chromatography to give crude material that was used in Example 6g.

3-(1,3-Dioxo-1,3-dihydro-isoindol-2-yl)-propionaldehyde was generated using the following method.

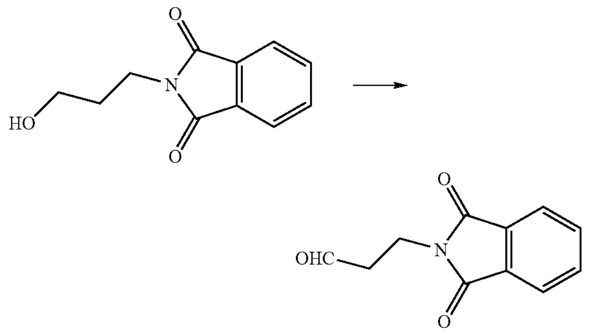

The reaction was carried out with oven dried glassware. DMSO (85 μl, 1.1 mmol) was added to oxalyl chloride solution (0.35 ml 2M solution in DCM with 5 ml dry DCM) at −78° C. The reaction mixture was stirred at −78° C. for 10 minutes. 2-(3-Hydroxy-propyl)-isoindole-1,3-dione solution (102 mg, 0.5 mmol, in 2 ml DCM) was added drop wise in 2 minutes. Then triethylamine (0.35 ml, 2.5 mmol) was added drop wise in 2 minutes. The mixture was stirred for additional 30 minutes at −78° C. and was warmed up to room temperature. The reaction mixture was extracted with ethyl acetate. The organic layer was washed with saturated sodium bicarbonate, dried over $MgSO_4$, filtered, and the filtrated was concentrated in vacuo. The crude product was purified by flash chromatography to give 3-(1,3-Dioxo-1,3-dihydro-isoindol-2-yl)-propionaldehyde.

Example 6g

Synthesis of N-[1-(1-Benzyl-5-bromo-1H-benzimidazol-2-yl)-2-methyl-propyl]-N-[3-(1,3-dioxo-1,3-dihydro-isoindol-2-yl)-propyl]-4-methyl-benzamide

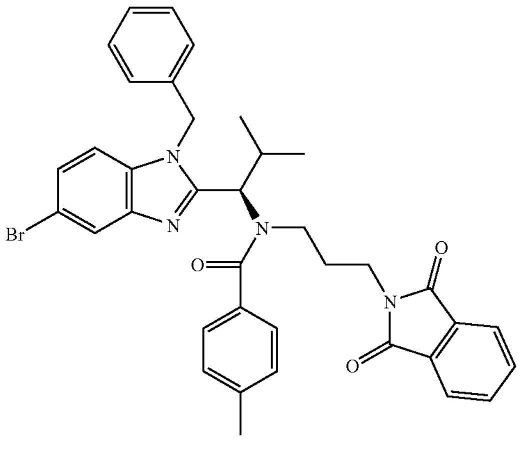

To a solution of 2-{3-[1-(1-Benzyl-5-bromo-1H-benzimidazol-2-yl)-2-methyl-propylamino]-propyl}-isoindole-1,3-dione (310 mg, 0.56 mmol) and triethylamine (0.47 ml, 3.36 mmol, 6 eq) in DCM (3 ml) at 0° C., was added p-toluoyl chloride (0.38 ml, 2.8 mmol, 5 eq). The reaction mixture was stirred at 0° C. for 30 minutes. Ethyl acetate and saturated sodium bicarbonate were added. The mixture was extracted with ethyl acetate. The organic layers was combined, dried over $MgSO_4$, filtered, and the filtrate was concentrated in vacuo. The crude material was purified by flash chromatography to give N-[1-(1-Benzyl-5-bromo-1H-benzimidazol-2-yl)-2-methyl-propyl]-N-[3-(1,3-dioxo-1,3-dihydro-isoindol-2-yl)-propyl]-4-methyl-benzamide (242 mg, yield 65%)

Example 6h

Synthesis of N-(3-Amino-propyl)-N-[1-(1-benzyl-5-bromo-1H-benzimidazol-2-yl)-2-methyl-propyl]-4-methyl-benzamide

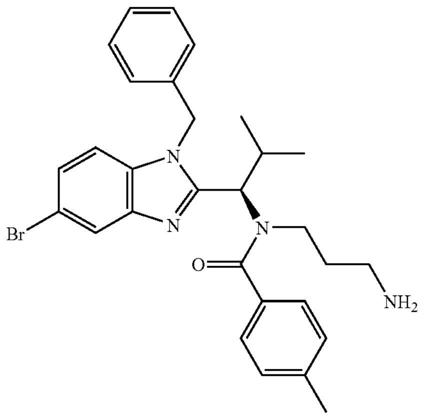

To a solution of N-[1-(1-benzyl-5-bromo-1H-benzimidazol-2-yl)-2-methyl-propyl]-N-[3-(1,3-dioxo-1,3-dihydro-isoindol-2-yl)-propyl]-4-methyl-benzamide (0.302 mmol) in ethanol at room temperature, was added hydrazine (0.19 ml, 6 mmol, 20 eq). The reaction was stirred at room temperature for 1 hour. The crude product was purified via reverse phase chromatography to give N-(3-amino-propyl)-N-[(1R)-1-(1-benzyl-5-bromo-1H-benzimidazol-2-yl)-2-methyl-propyl]-4-methyl-benzamide 6 (147 mg, yield 91%).

Example 7

Eg5 Expression and Purification

In this example, the expression and purification of an Eg5 protein construct is described.

The coding sequence for Eg5 was generated with PCR from an Eg5 containing construct and was designed to encompass amino acids 1-368. The PCR primers were designed to incorporate NcoI and EcoRI restriction sites for cloning of the fragment into Novagen's Pet28a expression vector. PCR reactions were initially sub-cloned into Invitrogens's TA cloning vector and were verified by DNA sequencing, then were moved to the final Pet28a expression vector and expressed in *E. Coli.*

The coding sequence for Eg5 was generated with PCR using the following oligos.

GAGAGACCATGGCGTCGCAGCCAAAT-TCGTCTGCG (SEQ ID NO: 2) and

GAGAGAGAATTCTCATTTCTGATTCACT-TCAGGCTTATTCAATATGT TCTTTGC (SEQ ID NO: 3)

The final sequence coding for the Eg5 construct, untagged, is as follows (SEQ ID NO: 4):

Atggcgtcgcagccaaattcgtctgcgaagaagaaagaggagaaggggaa-
gaacatccaggtggtggtgagatg cagaccatttaatttggcagagcg-
gaaagctagcgcccattcaatagtagaatgtgatcctgtacgaaaag aagttagtg-
tacgaa ctggaggattggctgacaagagctcaaggaaaacatacacttttg
atatggtgtttggagcatctactaaaca-gattgatgtttacc gaagtgttgtttgtc-
caattctggatgaagttattatgggctataattgcactatctttgcgtatgg
ccaaactggcactggaaaaacttttacaatggaag gtgaaaggtcacctaatgaa-
gagtatacctgggaagaggatcccttggctggtataattccacgtacccttcat
caaattttgagaaacttactgataatggtactgaattttcagtcaaagtgtctc tgttg-
gagatctataatgaagagctttttgatcttcttaatccctcgagc gatgtttct-
gagagactacagatgtttgatgatccccgtaacaagagaggagtgata-
attaaaggtttagaaga aattacagtacacaacaaggatgaagtc-
tatcaaattttagaaaagggggcagcaaaaaggacaactgcagctactctga-
tgaat gcatactctagtcgttcccactcagttttctctgttacaat acatatgaaa-
gaaactacgattgatggagaagagcttgttaaaatcgg aaagttgaacttggt-
tgatcttgcaggaagtgaaaacattggccgttctggagctgttgataagaga-
gctcgggaagctggaaata taaatcaatccctgttgactttgg-
gaagggtcattactgcccttgtagaaagaacacctcatgttccttatcgagaat-
ctaaactaactagaatctccaggattctcttggagggcgtacaagaacatctataatt-
gcaacaatttctcctgcatctctcaatcttgaggaaactct gagtacattggaatat-
gctcatagagcaaagaacatattgaataagcctgaagtgaatcagaaatga This expresses the following protein sequence SEQ ID 1:

MASQPNSSAKKKEEKGKNIQVVVRCR-
PFNLAERKASAHSIVECDPVRKEV SVRTGGLADKSS-
RKTYTFDMVFGASTKQIDVYRSV-
VCPILDEVIMGYNCTIFAYG
QTGTGKTFTMEGERSPNEEYTWEED-
PLAGIIPRTLHQIFEKLTDNGTEFSVKVSLL
EIYNEELFDLLNPSSDVSERLQMFD-
DPRNKRGVIIKGLEEITVHNKDEVYQILEKG AAKRT-
TAATLMNAYSSRSHSVFSVTIHMKETTI-
DGEELVKIGKLNLVDLAGSENI
GRSGAVDKRAREAGNINQSLLTLGRVI-
TALVERTPHVPYRESKLTRILQDSLGGR TRTSIIATIS-
PASLNLEETLSTLEYAHRAKNILNKPEVNQK

Eg5 Protein Purification:

| | | |
|---|---|---|
| Lysis Buffer: | 50 | mM PIPES pH 6.8 |
| | 2 | mM $MgCl_2$ |
| | 1 | mM EGTA |
| | 1 | mM ATP |
| | 1 | mM TCEP-HCl |

20 ml volume for 1 L cell culture pellet

Sonicate on ice pulsing for 3 minutes, Ultrasonics W-375 sonicator—large tip, output control 4.5, % duty cycle 60

Centrifuge JA20/19K/4° C./20 min

Buffers for all Columns:

| | | |
|---|---|---|
| A Buffer: | 50 | mM PIPES pH 6.8 |
| | 2 | mM $MgCl_2$ |
| | 1 | mM ATP |
| | 1 | mM EGTA |
| | 1 | mM TCEP-HCl |

-continued

| | | |
|---|---|---|
| B Buffer: | 50 | mM PIPES pH 6.8 |
| | 2 | mM $MgCl_2$ |
| | 1 | mM ATP |
| | 1 | mM EGTA |
| | 1 | mM TCEP-HCl |
| | 250 | mM NaCl |

SP Column

| | |
|---|---|
| Resin | SP Fast Flow (Amersham) |
| Elution | 20 CV gradient 0% to 100% B |

Pour Supernatant Over SP Column

Mono S Column

Dialyze SP pool vs. 1 L A buffer RT 1 hour before loading onto Mono S (to remove salt).

| | |
|---|---|
| Resin | Mono S (Amersham) |
| Diameter | 1.0 cm |
| Height | 10.0 cm |
| Volume | 8 ml |
| Flow Rate | 4 ml/min (max) |
| Max Pressure | 5 MPa |
| Linear Flow Rate | 305 cm/hr (max) |
| Elution | 20 CV gradient 0% to 100% B |
| Fraction Size | 5 ml |

Mono Q Column

Dialyze pool vs. 1 L A buffer RT 1 hour (to remove salt)

Load and Collect Flow Through Fractions

| | |
|---|---|
| Resin | Mono Q 10/100 GL Tricorn (Amersham) |
| Diameter | 1.0 cm |
| Height | 10.0 cm |
| Volume | 8 ml |
| Flow Rate | 4 ml/min (max) |
| Max Pressure | 5 MPa |
| Linear Flow Rate | 305 cm/hr (max) |
| Elution | Collect Flow Through Fractions |
| Fraction Size | 5 ml |

Dialysis and Concentration:

Dialyze 4° C. vs. 4×1 L changes into dialysis buffer.

Concentrate using Amicon Ultra 5K cut off 4° C. to 10+mg/ml.

0.2 filter final material

| | | |
|---|---|---|
| Dialysis Buffer: | 50 | mM PIPES pH 6.8 |
| | 2 | mM $MgCl_2$ |
| | 1 | mM ADP |
| | 1 | mM TCEP-HCl |

Example 8

Eg5 and Ligand Co-Crystallization and Resolution

In this example, the crystallization and resolution of Eg5 and ligand complex is described. After protein purification, Eg5 has a purity of greater than 95%. The protein was dialyzed into storage buffer containing: 50 mM PIPES pH 6.8, 1 mM ADP, 2 mM $MgCl_2$, and 1 mM TCEP-HCL. The protein was then concentrated to 10 mg/ml and stored at −80° C. Eg5 was crystallized in the following precipitating solution containing 100 mM MES pH 5.5, 150-300 mM $NaNO_3$, and 12-24% PEG 3350. Hanging drop vapor diffusion was used with a 1:1 ratio of protein to precipitating solution. Crystal trays were incubated at 4° C. Crystals appeared within 2448 hours. These initial crystals were then crushed into fine fragments. Then a 10-60 fold dilutions were made using the precipitating solution giving rise to the crystal seeding solutions. A new crystal tray was set up in a similar manner to the previous tray except for the addition of one extra step: after the introduction of the precipitant to the protein, a hair was ran through the seeding solution then it was brushed through the fresh protein and precipitant drop approximately three times. The crystal trays were then incubated at 4° C. Usable crystals appeared within 4-5 days.

For the co-crystal, a 1:1 molar ratio of compound was introduced to the protein solution. The mixture was incubated on ice for 1-3 hours then crystal trays were set up in similar process as previously described. Crystals were frozen using liquid nitrogen after the crystals were transferred into a cryo-solution (precipitating solution with an addition of 22.5% ethylene glycol).

Alternatively, a Eg5 and ligand complex can be obtained by soaking a ligand into an Eg5 crystal. Eg5 crystals are first prepared as described above. The ligand of interest is then soaked into the Eg5 crystal. Typically, soaking experiments was performed by preparing a solution of ligand at concentration 100 mM in the precipitating solution. If the ligand is insoluble in the precipitating solution, the ligand may solubilzed in 100% DMSO. The ligand solution was then diluted to a desired concentration with the precipitating solution, typically 0.5 to 2 mM. Six microliters of ligand (typically 0.5 to 2 mM ligand) was placed into a well. Eg5 crystals were transferred into the well containing the 6 microliters of ligand solution. Eg 5 crystal and ligand were incubated at 4° C. for 2 to 48 hours. Soaking time varied according to inhibitor potency and solubility. The crystals prepared by this soaking method were frozen using the same method as in freezing the Eg5 and ligand complex prepared by co-crystallization as described above.

Using available coordinates (PDB accession number 1II6), the structure of the co-crystal was solved using molecular replacement (and the program EPMR). The crystals were of space group P212121 with unit cell dimensions a=80.5 Ang., b=94.7 Ang., c=107.365 Ang., alpha=beta=gamma=90. This is in contrast to the available coordinates that are in space group P21. Structures were refined using standard protocols to R-factors of approximately 0.25 with appropriate free R-factors.

Eg5 crystallizes as a dimer in the asymmetric unit. Strict non-crystallographic restraints are placed upon the monomers during refinement in order to prevent over-fitting. After comparing the A monomer to the B monomer, for the six Eg5 co-structures, we determined that they differ from each other by 0.25+/−0.1 angstrom. This is within the error for the refinement protocols, so the coordinates for the two monomers should be considered equivalent for all intents and purposes.

Example 9

Assay for Determining Eg5 Activity

In this example, a representative in vitro assay for determining Eg5 activity is described.

Purified microtubules from bovine brain were purchased from Cytoskeleton Inc. The motor domain of human Eg5 (KSP, KNSL1) was cloned and purified to a purity of greater than 95%. Biomol Green was purchased from Affinity Research Products Ltd.

Microtubules and the Eg5 motor protein were diluted in assay buffer (20 mM Tris-HCl, pH 7.5, 1 mM MgCl2, 10 mM DTT and 0.25 mg/ml BSA) to a concentration of 35 ug/ml for microtubules and 45 nM for Eg5. The microtubule/Eg5 mixture was then pre-incubated at 37° C. for 10 min to promote the binding of Eg5 to microtubules. ATP was also diluted to a concentration of 300 uM in the same assay buffer. To each well of the testing plate (384 well plate) containing 1.25 uL of compounds in DMSO or DMSO only, 25 uL of ATP solution. To start the reaction, 25 uL of microtubule/Eg5 solution was added to the ATP/compound mixture. The plates were incubated at room temperature for 1 hr. At the end of incubation period, 65 uL of Biomol Green was added to each well. The plates were incubated for 5-10 min and then the absorbance at 630 nm was determined. Biomol Green reagent is a malchite green based dye that detects the release of inorganic phosphate. Developed color signal was read using a Victor II reader. The concentration of each compound for 50% inhibition (IC50) was calculated by nonlinear regression using either XLFit for Excel or Prism data analysis software by GraphPad Software Inc.

While the preferred embodiment of the invention has been illustrated and described, it will be appreciated that various changes can be made therein without departing from the spirit and scope of the invention.

Table 4. Eg5 ligand binding site compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

TABLE 4

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

REMARK coordinates from simulated annealing refinement
REMARK refinement resolution: 50.0-2.6 A
REMARK starting r = 0.2663 free_r = 0.3185
REMARK final r = 0.2589 free_r = 0.3387
REMARK rmsd bonds = 0.006847 rmsd angles = 1.34210

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

REMARK wa_initial = 4.73993 wa_dynamics = 6.09374 wa_final = 5.49958
REMARK target = mlf md-method = torsion annealing schedule = slowcool
REMARK starting temperature = 3000 total md steps = 120 * 6
REMARK sg = P2(1)2(1)2(1) a = 79.888 b = 93.745 c = 103.399 alpha = 90 beta = 90 gamma = 90
REMARK B-correction resolution: 6.0-2.6
REMARK initial B-factor correction applied to fobs:
REMARK B11 = 3.392 B22 = 6.665 B33 = −3.273
REMARK B12 = 0.000 B13 = 0.000 B23 = 0.000
REMARK B-factor correction applied to coordinate array B: 0.855
REMARK bulk solvent: (Mask) density level = 0.33466 e/A^3, B-factor = 42.7096 A^2
REMARK reflections with |Fobs|/sigma_F < 0.0 rejected
REMARK reflections with |Fobs| > 10000 * rms(Fobs) rejected
REMARK theoretical total number of refl. in resol. range: 24520 (100.0%)
REMARK number of unobserved reflections (no entry or |F| = 0): 1972 (8.0%)
REMARK number of reflections rejected: 0 (0.0%)
REMARK total number of reflections used: 22548 (92.0%)
REMARK number of reflections in working set: 21450 (87.5%)
REMARK number of reflections in test set: 1098 (4.5%)
REMARK Written by CNX VERSION: 2000

| | | | | | | | | | | | | |
|---|---|---|---|---|---|---|---|---|---|---|---|---|
| ATOM | 1 | C | GLY | A | 16 | −9.686 | 110.588 | 98.347 | 1.00 | 44.07 | A | C |
| ATOM | 2 | O | GLY | A | 16 | −8.791 | 110.022 | 98.969 | 1.00 | 43.39 | A | O |
| ATOM | 3 | N | GLY | A | 16 | −10.733 | 112.360 | 99.767 | 1.00 | 45.55 | A | N |
| ATOM | 4 | CA | GLY | A | 16 | −10.939 | 111.059 | 99.060 | 1.00 | 45.11 | A | C |
| ATOM | 5 | N | LYS | A | 17 | −9.614 | 110.815 | 97.039 | 1.00 | 43.96 | A | N |
| ATOM | 6 | CA | LYS | A | 17 | −8.440 | 110.402 | 96.285 | 1.00 | 43.60 | A | C |
| ATOM | 7 | CB | LYS | A | 17 | −8.723 | 110.406 | 94.782 | 1.00 | 43.67 | A | C |
| ATOM | 8 | CG | LYS | A | 17 | −9.713 | 109.324 | 94.350 | 1.00 | 45.04 | A | C |
| ATOM | 9 | CD | LYS | A | 17 | −9.815 | 109.160 | 92.831 | 1.00 | 44.50 | A | C |
| ATOM | 10 | CE | LYS | A | 17 | −10.310 | 110.424 | 92.139 | 1.00 | 43.83 | A | C |
| ATOM | 11 | NZ | LYS | A | 17 | −9.331 | 111.544 | 92.230 | 1.00 | 44.25 | A | N |
| ATOM | 12 | C | LYS | A | 17 | −7.262 | 111.311 | 96.598 | 1.00 | 42.58 | A | C |
| ATOM | 13 | O | LYS | A | 17 | −6.572 | 111.109 | 97.600 | 1.00 | 45.33 | A | O |
| ATOM | 14 | N | ASN | A | 18 | −7.042 | 112.319 | 95.761 | 1.00 | 37.16 | A | N |
| ATOM | 15 | CA | ASN | A | 18 | −5.925 | 113.240 | 95.959 | 1.00 | 34.09 | A | C |
| ATOM | 16 | CB | ASN | A | 18 | −6.028 | 113.960 | 97.308 | 1.00 | 33.22 | A | C |
| ATOM | 17 | CG | ASN | A | 18 | −6.395 | 115.418 | 97.158 | 1.00 | 32.01 | A | C |
| ATOM | 18 | OD1 | ASN | A | 18 | −6.247 | 116.206 | 98.089 | 1.00 | 35.49 | A | O |
| ATOM | 19 | ND2 | ASN | A | 18 | −6.885 | 115.786 | 95.985 | 1.00 | 31.48 | A | N |
| ATOM | 20 | C | ASN | A | 18 | −4.623 | 112.457 | 95.900 | 1.00 | 32.40 | A | C |
| ATOM | 21 | O | ASN | A | 18 | −3.773 | 112.713 | 95.050 | 1.00 | 32.88 | A | O |
| ATOM | 22 | N | ILE | A | 19 | −4.467 | 111.509 | 96.815 | 1.00 | 28.35 | A | N |
| ATOM | 23 | CA | ILE | A | 19 | −3.279 | 110.680 | 96.841 | 1.00 | 27.60 | A | C |
| ATOM | 24 | CB | ILE | A | 19 | −2.834 | 110.352 | 98.294 | 1.00 | 29.50 | A | C |
| ATOM | 25 | CG2 | ILE | A | 19 | −1.468 | 109.692 | 98.275 | 1.00 | 25.53 | A | C |
| ATOM | 26 | CG1 | ILE | A | 19 | −2.825 | 111.621 | 99.159 | 1.00 | 29.78 | A | C |
| ATOM | 27 | CD1 | ILE | A | 19 | −1.836 | 112.668 | 98.741 | 1.00 | 32.54 | A | C |
| ATOM | 28 | C | ILE | A | 19 | −3.666 | 109.380 | 96.145 | 1.00 | 27.45 | A | C |
| ATOM | 29 | O | ILE | A | 19 | −4.662 | 108.753 | 96.508 | 1.00 | 25.33 | A | O |
| ATOM | 30 | N | GLN | A | 20 | −2.893 | 108.974 | 95.145 | 1.00 | 26.41 | A | N |
| ATOM | 31 | CA | GLN | A | 20 | −3.206 | 107.740 | 94.441 | 1.00 | 25.53 | A | C |
| ATOM | 32 | CB | GLN | A | 20 | −3.957 | 108.038 | 93.147 | 1.00 | 26.11 | A | C |
| ATOM | 33 | CG | GLN | A | 20 | −3.056 | 108.306 | 91.975 | 1.00 | 29.47 | A | C |
| ATOM | 34 | CD | GLN | A | 20 | −3.813 | 108.319 | 90.674 | 1.00 | 34.14 | A | C |
| ATOM | 35 | OE1 | GLN | A | 20 | −3.219 | 108.368 | 89.591 | 1.00 | 31.35 | A | O |
| ATOM | 36 | NE2 | GLN | A | 20 | −5.143 | 108.274 | 90.768 | 1.00 | 37.97 | A | N |
| ATOM | 37 | C | GLN | A | 20 | −1.977 | 106.894 | 94.122 | 1.00 | 24.85 | A | C |
| ATOM | 38 | O | GLN | A | 20 | −0.903 | 107.412 | 93.777 | 1.00 | 22.03 | A | O |
| ATOM | 39 | N | VAL | A | 21 | −2.159 | 105.579 | 94.225 | 1.00 | 23.17 | A | N |
| ATOM | 40 | CA | VAL | A | 21 | −1.090 | 104.626 | 93.969 | 1.00 | 19.47 | A | C |
| ATOM | 41 | CS | VAL | A | 21 | −0.758 | 103.835 | 95.249 | 1.00 | 15.35 | A | C |
| ATOM | 42 | CG1 | VAL | A | 21 | 0.377 | 102.881 | 94.992 | 1.00 | 14.68 | A | C |
| ATOM | 43 | CG2 | VAL | A | 21 | −0.396 | 104.797 | 96.366 | 1.00 | 14.24 | A | C |
| ATOM | 44 | C | VAL | A | 21 | −1.454 | 103.659 | 92.843 | 1.00 | 18.07 | A | C |
| ATOM | 45 | O | VAL | A | 21 | −2.551 | 103.112 | 92.813 | 1.00 | 20.72 | A | O |
| ATOM | 46 | N | VAL | A | 22 | −0.524 | 103.470 | 91.912 | 1.00 | 17.46 | A | N |
| ATOM | 47 | CA | VAL | A | 22 | −0.723 | 102.573 | 90.777 | 1.00 | 14.29 | A | C |
| ATOM | 48 | CB | VAL | A | 22 | −0.963 | 103.354 | 89.486 | 1.00 | 14.92 | A | C |
| ATOM | 49 | CG1 | VAL | A | 22 | −1.965 | 104.463 | 89.748 | 1.00 | 11.20 | A | C |
| ATOM | 50 | CG2 | VAL | A | 22 | 0.352 | 103.911 | 88.957 | 1.00 | 11.06 | A | C |
| ATOM | 51 | C | VAL | A | 22 | 0.508 | 101.711 | 90.579 | 1.00 | 13.34 | A | C |
| ATOM | 52 | O | VAL | A | 22 | 1.611 | 102.070 | 90.991 | 1.00 | 13.92 | A | C |
| ATOM | 53 | N | VAL | A | 23 | 0.309 | 100.566 | 89.949 | 1.00 | 11.39 | A | N |
| ATOM | 54 | CA | VAL | A | 23 | 1.393 | 99.643 | 89.703 | 1.00 | 12.63 | A | C |
| ATOM | 55 | CB | VAL | A | 23 | 1.133 | 98.250 | 90.374 | 1.00 | 15.65 | A | C |
| ATOM | 56 | CG1 | VAL | A | 23 | 2.119 | 97.197 | 89.825 | 1.00 | 15.58 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 57 | CG2 | VAL | A | 23 | 1.281 | 98.353 | 91.884 | 1.00 | 12.07 | A | C |
| ATOM | 58 | C | VAL | A | 23 | 1.485 | 99.449 | 88.213 | 1.00 | 15.60 | A | C |
| ATOM | 59 | C | VAL | A | 23 | 0.470 | 99.437 | 87.524 | 1.00 | 17.73 | A | C |
| ATOM | 60 | N | ARG | A | 24 | 2.708 | 99.319 | 87.713 | 1.00 | 14.97 | A | N |
| ATOM | 61 | CA | ARG | A | 24 | 2.923 | 99.084 | 86.301 | 1.00 | 13.12 | A | C |
| ATOM | 62 | CB | ARG | A | 24 | 3.496 | 100.328 | 85.604 | 1.00 | 10.82 | A | C |
| ATOM | 63 | CG | ARG | A | 24 | 3.702 | 100.134 | 84.093 | 1.00 | 6.67 | A | C |
| ATOM | 64 | CD | ARG | A | 24 | 4.473 | 101.265 | 83.456 | 1.00 | 6.06 | A | C |
| ATOM | 65 | NE | ARG | A | 24 | 4.351 | 101.278 | 81.994 | 1.00 | 7.85 | A | N |
| ATOM | 66 | CZ | ARG | A | 24 | 4.966 | 102.151 | 81.192 | 1.00 | 9.23 | A | C |
| ATOM | 67 | NH1 | ARG | A | 24 | 5.762 | 103.091 | 81.696 | 1.00 | 8.02 | A | N |
| ATOM | 68 | NH2 | ARG | A | 24 | 4.774 | 102.104 | 79.881 | 1.00 | 7.40 | A | N |
| ATOM | 69 | C | ARG | A | 24 | 3.902 | 97.922 | 86.164 | 1.00 | 15.60 | A | C |
| ATOM | 70 | O | ARG | A | 24 | 5.052 | 97.998 | 86.595 | 1.00 | 15.99 | A | O |
| ATOM | 71 | N | CYS | A | 25 | 3.434 | 96.836 | 85.573 | 1.00 | 15.63 | A | N |
| ATOM | 72 | CA | CYS | A | 25 | 4.285 | 95.678 | 85.361 | 1.00 | 16.73 | A | C |
| ATOM | 73 | CB | CYS | A | 25 | 3.450 | 94.399 | 85.440 | 1.00 | 17.32 | A | C |
| ATOM | 74 | SG | CYS | A | 25 | 4.381 | 92.874 | 85.250 | 1.00 | 20.32 | A | S |
| ATOM | 75 | C | CYS | A | 25 | 4.909 | 95.818 | 83.975 | 1.00 | 17.67 | A | C |
| ATOM | 76 | O | CYS | A | 25 | 4.238 | 96.218 | 83.027 | 1.00 | 16.89 | A | O |
| ATOM | 77 | N | ARG | A | 26 | 6.195 | 95.517 | 83.858 | 1.00 | 17.78 | A | N |
| ATOM | 78 | CA | ARG | A | 26 | 6.865 | 95.604 | 82.562 | 1.00 | 17.67 | A | C |
| ATOM | 79 | CB | ARG | A | 26 | 8.302 | 96.107 | 82.716 | 1.00 | 17.15 | A | C |
| ATOM | 80 | CG | ARG | A | 26 | 9.208 | 95.199 | 83.552 | 1.00 | 18.80 | A | C |
| ATOM | 81 | CD | ARG | A | 26 | 10.676 | 95.547 | 83.338 | 1.00 | 17.93 | A | C |
| ATOM | 82 | NE | ARG | A | 26 | 11.609 | 94.771 | 84.160 | 1.00 | 20.26 | A | N |
| ATOM | 83 | CZ | ARG | A | 26 | 11.805 | 93.456 | 84.077 | 1.00 | 19.16 | A | C |
| ATOM | 84 | NH1 | ARG | A | 26 | 11.123 | 92.720 | 83.210 | 1.00 | 19.75 | A | N |
| ATOM | 85 | NH2 | ARG | A | 26 | 12.726 | 92.880 | 84.837 | 1.00 | 15.85 | A | N |
| ATOM | 86 | C | ARG | A | 26 | 6.903 | 94.216 | 81.948 | 1.00 | 16.96 | A | C |
| ATOM | 87 | O | ARG | A | 26 | 6.568 | 93.229 | 82.595 | 1.00 | 17.21 | A | O |
| ATOM | 88 | N | PRO | A | 27 | 7.265 | 94.126 | 80.671 | 1.00 | 17.24 | A | N |
| ATOM | 89 | CD | PRO | A | 27 | 7.124 | 95.145 | 79.619 | 1.00 | 17.23 | A | C |
| ATOM | 90 | CA | PRO | A | 27 | 7.312 | 92.780 | 80.102 | 1.00 | 18.54 | A | C |
| ATOM | 91 | CB | PRO | A | 27 | 7.167 | 93.033 | 78.600 | 1.00 | 17.17 | A | C |
| ATOM | 92 | CG | PRO | A | 27 | 7.633 | 94.430 | 78.415 | 1.00 | 14.65 | A | C |
| ATOM | 93 | C | PRO | A | 27 | 8.632 | 92.103 | 80.485 | 1.00 | 18.24 | A | C |
| ATOM | 94 | O | PRO | A | 27 | 9.510 | 92.739 | 81.057 | 1.00 | 17.91 | A | O |
| ATOM | 95 | N | PHE | A | 28 | 8.749 | 90.809 | 80.207 | 1.00 | 19.88 | A | N |
| ATOM | 96 | CA | PHE | A | 28 | 9.965 | 90.039 | 80.498 | 1.00 | 17.92 | A | C |
| ATOM | 97 | CB | PHE | A | 28 | 9.798 | 88.600 | 79.990 | 1.00 | 23.00 | A | C |
| ATOM | 98 | CG | PHE | A | 28 | 9.047 | 87.695 | 80.922 | 1.00 | 24.72 | A | C |
| ATOM | 99 | CD1 | PHE | A | 28 | 7.717 | 87.931 | 81.231 | 1.00 | 24.32 | A | C |
| ATOM | 100 | CD2 | PHE | A | 28 | 9.685 | 86.608 | 81.498 | 1.00 | 24.63 | A | C |
| ATOM | 101 | CE1 | PHE | A | 28 | 7.035 | 87.103 | 82.100 | 1.00 | 26.65 | A | C |
| ATOM | 102 | CE2 | PHE | A | 28 | 9.005 | 85.773 | 82.372 | 1.00 | 26.80 | A | C |
| ATOM | 103 | CZ | PHE | A | 28 | 7.676 | 86.025 | 82.673 | 1.00 | 26.28 | A | C |
| ATOM | 104 | C | PHE | A | 28 | 11.239 | 90.609 | 79.838 | 1.00 | 18.12 | A | C |
| ATOM | 105 | O | PHE | A | 28 | 11.183 | 91.183 | 78.755 | 1.00 | 14.88 | A | O |
| ATOM | 106 | N | ASN | A | 29 | 12.391 | 90.437 | 80.484 | 1.00 | 19.64 | A | N |
| ATOM | 107 | CA | ASN | A | 29 | 13.644 | 90.893 | 79.883 | 1.00 | 21.51 | A | C |
| ATOM | 108 | CB | ASN | A | 29 | 14.472 | 91.722 | 80.872 | 1.00 | 21.29 | A | C |
| ATOM | 109 | CG | ASN | A | 29 | 15.112 | 90.876 | 81.965 | 1.00 | 21.06 | A | C |
| ATOM | 110 | OD1 | ASN | A | 29 | 15.553 | 89.758 | 81.716 | 1.00 | 23.99 | A | O |
| ATOM | 111 | ND2 | ASN | A | 29 | 15.187 | 91.420 | 83.170 | 1.00 | 14.68 | A | N |
| ATOM | 112 | C | ASN | A | 29 | 14.441 | 89.668 | 79.416 | 1.00 | 20.75 | A | C |
| ATOM | 113 | O | ASN | A | 29 | 14.204 | 88.557 | 79.895 | 1.00 | 20.66 | A | O |
| ATOM | 114 | N | LEU | A | 30 | 15.379 | 89.864 | 78.493 | 1.00 | 20.80 | A | N |
| ATOM | 115 | CA | LEU | A | 30 | 16.171 | 88.748 | 77.957 | 1.00 | 24.28 | A | C |
| ATOM | 116 | CB | LEU | A | 30 | 17.282 | 89.267 | 77.044 | 1.00 | 25.77 | A | C |
| ATOM | 117 | CG | LEU | A | 30 | 16.781 | 89.819 | 75.709 | 1.00 | 31.66 | A | C |
| ATOM | 118 | CD1 | LEU | A | 30 | 17.917 | 90.527 | 74.979 | 1.00 | 34.48 | A | C |
| ATOM | 119 | CD2 | LEU | A | 30 | 16.210 | 88.678 | 74.873 | 1.00 | 30.62 | A | C |
| ATOM | 120 | C | LEU | A | 30 | 16.776 | 87.824 | 79.004 | 1.00 | 22.31 | A | C |
| ATOM | 121 | O | LEU | A | 30 | 16.641 | 86.602 | 78.919 | 1.00 | 22.70 | A | O |
| ATOM | 122 | N | ALA | A | 31 | 17.446 | 88.407 | 79.987 | 1.00 | 19.75 | A | N |
| ATOM | 123 | CA | ALA | A | 31 | 18.072 | 87.623 | 81.044 | 1.00 | 21.74 | A | C |
| ATOM | 124 | CB | ALA | A | 31 | 18.721 | 88.549 | 82.064 | 1.00 | 17.74 | A | C |
| ATOM | 125 | C | ALA | A | 31 | 17.078 | 86.700 | 81.745 | 1.00 | 22.05 | A | C |
| ATOM | 126 | O | ALA | A | 31 | 17.416 | 85.583 | 82.131 | 1.00 | 24.75 | A | O |
| ATOM | 127 | N | GLU | A | 32 | 15.852 | 87.177 | 81.915 | 1.00 | 23.73 | A | N |
| ATOM | 128 | CA | GLU | A | 32 | 14.818 | 86.393 | 82.568 | 1.00 | 24.26 | A | C |
| ATOM | 129 | CB | GLU | A | 32 | 13.580 | 87.260 | 82.828 | 1.00 | 25.44 | A | C |
| ATOM | 130 | CG | GLU | A | 32 | 13.854 | 88.430 | 83.771 | 1.00 | 27.51 | A | C |
| ATOM | 131 | CD | GLU | A | 32 | 12.666 | 89.373 | 83.930 | 1.00 | 30.32 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 132 | OE1 | GLU | A | 32 | 12.155 | 89.889 | 82.905 | 1.00 | 28.69 | A | O |
| ATOM | 133 | OE2 | GLU | A | 32 | 12.257 | 89.604 | 85.088 | 1.00 | 28.76 | A | O |
| ATOM | 134 | C | GLU | A | 32 | 14.459 | 85.166 | 81.739 | 1.00 | 25.13 | A | C |
| ATOM | 135 | O | GLU | A | 32 | 14.172 | 84.109 | 82.303 | 1.00 | 24.62 | A | O |
| ATOM | 136 | N | ARG | A | 33 | 14.461 | 85.297 | 80.412 | 1.00 | 25.04 | A | N |
| ATOM | 137 | CA | ARG | A | 33 | 14.166 | 84.149 | 79.560 | 1.00 | 26.77 | A | C |
| ATOM | 138 | CB | ARG | A | 33 | 14.007 | 84.564 | 78.094 | 1.00 | 25.27 | A | C |
| ATOM | 139 | CG | ARG | A | 33 | 12.975 | 85.631 | 77.807 | 1.00 | 24.68 | A | C |
| ATOM | 140 | CD | ARG | A | 33 | 11.565 | 85.151 | 78.050 | 1.00 | 23.25 | A | C |
| ATOM | 141 | NE | ARG | A | 33 | 10.595 | 86.049 | 77.426 | 1.00 | 24.08 | A | N |
| ATOM | 142 | CZ | ARG | A | 33 | 9.284 | 86.010 | 77.638 | 1.00 | 21.64 | A | C |
| ATOM | 143 | NH1 | ARG | A | 33 | 8.757 | 85.117 | 78.467 | 1.00 | 22.53 | A | N |
| ATOM | 144 | NH2 | ARG | A | 33 | 8.497 | 86.862 | 77.008 | 1.00 | 25.09 | A | N |
| ATOM | 145 | C | ARG | A | 33 | 15.395 | 83.250 | 79.683 | 1.00 | 27.71 | A | C |
| ATOM | 146 | O | ARG | A | 33 | 15.292 | 82.042 | 79.877 | 1.00 | 24.20 | A | O |
| ATOM | 147 | N | LYS | A | 34 | 16.562 | 83.877 | 79.579 | 1.00 | 31.56 | A | N |
| ATOM | 148 | CA | LYS | A | 34 | 17.848 | 83.190 | 79.658 | 1.00 | 35.36 | A | C |
| ATOM | 149 | CB | LYS | A | 34 | 18.988 | 84.212 | 79.582 | 1.00 | 35.79 | A | C |
| ATOM | 150 | CG | LYS | A | 34 | 20.322 | 83.612 | 79.226 | 1.00 | 39.68 | A | C |
| ATOM | 151 | CD | LYS | A | 34 | 20.272 | 82.989 | 77.836 | 1.00 | 45.68 | A | C |
| ATOM | 152 | CE | LYS | A | 34 | 20.124 | 84.054 | 76.753 | 1.00 | 47.84 | A | C |
| ATOM | 153 | NZ | LYS | A | 34 | 18.918 | 84.906 | 76.957 | 1.00 | 48.71 | A | N |
| ATOM | 154 | C | LYS | A | 34 | 17.992 | 82.343 | 80.927 | 1.00 | 36.24 | A | C |
| ATOM | 155 | O | LYS | A | 34 | 18.838 | 81.449 | 80.991 | 1.00 | 36.34 | A | O |
| ATOM | 156 | N | ALA | A | 35 | 17.177 | 82.637 | 81.934 | 1.00 | 36.35 | A | N |
| ATOM | 157 | CA | ALA | A | 35 | 17.188 | 81.881 | 83.182 | 1.00 | 35.76 | A | C |
| ATOM | 158 | CB | ALA | A | 35 | 17.323 | 82.809 | 84.357 | 1.00 | 33.44 | A | C |
| ATOM | 159 | C | ALA | A | 35 | 15.893 | 81.072 | 83.299 | 1.00 | 38.00 | A | C |
| ATOM | 160 | O | ALA | A | 35 | 15.638 | 80.436 | 84.321 | 1.00 | 39.76 | A | O |
| ATOM | 161 | N | SER | A | 36 | 15.078 | 81.113 | 82.245 | 1.00 | 38.71 | A | N |
| ATOM | 162 | CA | SER | A | 36 | 13.819 | 80.372 | 82.184 | 1.00 | 38.62 | A | C |
| ATOM | 163 | CB | SER | A | 36 | 14.085 | 78.867 | 82.358 | 1.00 | 40.39 | A | C |
| ATOM | 164 | OG | SER | A | 36 | 14.915 | 78.352 | 81.327 | 1.00 | 41.70 | A | O |
| ATOM | 165 | C | SER | A | 36 | 12.751 | 80.809 | 83.190 | 1.00 | 38.16 | A | C |
| ATOM | 166 | O | SER | A | 36 | 11.739 | 80.124 | 83.354 | 1.00 | 40.17 | A | O |
| ATOM | 167 | N | ALA | A | 37 | 12.966 | 81.944 | 83.850 | 1.00 | 34.88 | A | N |
| ATOM | 168 | CA | ALA | A | 37 | 12.017 | 82.453 | 84.841 | 1.00 | 30.25 | A | C |
| ATOM | 169 | CB | ALA | A | 37 | 12.287 | 83.939 | 85.121 | 1.00 | 29.50 | A | C |
| ATOM | 170 | C | ALA | A | 37 | 10.576 | 82.261 | 84.391 | 1.00 | 26.77 | A | C |
| ATOM | 171 | O | ALA | A | 37 | 10.299 | 82.172 | 83.203 | 1.00 | 24.81 | A | O |
| ATOM | 172 | N | HIS | A | 38 | 9.664 | 82.220 | 85.355 | 1.00 | 25.50 | A | N |
| ATOM | 173 | CA | HIS | A | 38 | 8.249 | 82.025 | 85.073 | 1.00 | 26.59 | A | C |
| ATOM | 174 | CB | HIS | A | 38 | 7.760 | 80.746 | 85.765 | 1.00 | 31.43 | A | C |
| ATOM | 175 | CG | HIS | A | 38 | 8.733 | 79.611 | 85.693 | 1.00 | 36.14 | A | C |
| ATOM | 176 | CD2 | HIS | A | 38 | 9.309 | 78.876 | 86.669 | 1.00 | 37.46 | A | C |
| ATOM | 177 | ND1 | HIS | A | 38 | 9.232 | 79.121 | 84.505 | 1.00 | 38.93 | A | N |
| ATOM | 178 | CE1 | HIS | A | 38 | 10.076 | 78.135 | 84.755 | 1.00 | 39.21 | A | C |
| ATOM | 179 | NE2 | HIS | A | 38 | 10.141 | 77.966 | 86.062 | 1.00 | 38.50 | A | N |
| ATOM | 180 | C | HIS | A | 38 | 7.395 | 83.207 | 85.541 | 1.00 | 24.15 | A | C |
| ATOM | 181 | O | HIS | A | 38 | 7.693 | 83.836 | 86.549 | 1.00 | 23.76 | A | O |
| ATOM | 182 | N | SER | A | 39 | 6.323 | 83.489 | 84.811 | 1.00 | 20.88 | A | N |
| ATOM | 183 | CA | SER | A | 39 | 5.417 | 84.574 | 85.163 | 1.00 | 22.81 | A | C |
| ATOM | 184 | CB | SER | A | 39 | 4.374 | 84.774 | 84.055 | 1.00 | 25.24 | A | C |
| ATOM | 185 | OG | SER | A | 39 | 3.417 | 85.769 | 84.397 | 1.00 | 27.59 | A | O |
| ATOM | 186 | C | SER | A | 39 | 4.699 | 84.286 | 86.473 | 1.00 | 22.04 | A | C |
| ATOM | 187 | O | SER | A | 39 | 3.999 | 83.286 | 86.599 | 1.00 | 22.64 | A | O |
| ATOM | 188 | N | ILE | A | 40 | 4.869 | 85.169 | 87.448 | 1.00 | 22.95 | A | N |
| ATOM | 189 | CA | ILE | A | 40 | 4.217 | 84.999 | 88.739 | 1.00 | 21.01 | A | C |
| ATOM | 190 | CB | ILE | A | 40 | 5.247 | 84.810 | 89.860 | 1.00 | 18.37 | A | C |
| ATOM | 191 | CG2 | ILE | A | 40 | 6.095 | 83.592 | 89.562 | 1.00 | 23.64 | A | C |
| ATOM | 192 | CG1 | ILE | A | 40 | 6.144 | 86.043 | 89.976 | 1.00 | 17.30 | A | C |
| ATOM | 193 | CD1 | ILE | A | 40 | 7.168 | 85.937 | 91.081 | 1.00 | 18.78 | A | C |
| ATOM | 194 | C | ILE | A | 40 | 3.359 | 86.219 | 89.035 | 1.00 | 22.81 | A | C |
| ATOM | 195 | O | ILE | A | 40 | 2.846 | 86.375 | 90.142 | 1.00 | 22.11 | A | O |
| ATOM | 196 | N | VAL | A | 41 | 3.197 | 87.072 | 88.024 | 1.00 | 22.07 | A | N |
| ATOM | 197 | CA | VAL | A | 41 | 2.411 | 88.288 | 88.164 | 1.00 | 24.45 | A | C |
| ATOM | 198 | CB | VAL | A | 41 | 3.286 | 89.539 | 87.930 | 1.00 | 24.79 | A | C |
| ATOM | 199 | CG1 | VAL | A | 41 | 2.436 | 90.789 | 88.032 | 1.00 | 23.69 | A | C |
| ATOM | 200 | CG2 | VAL | A | 41 | 4.416 | 89.583 | 88.953 | 1.00 | 22.06 | A | C |
| ATOM | 201 | C | VAL | A | 41 | 1.211 | 88.351 | 87.218 | 1.00 | 25.88 | A | C |
| ATOM | 202 | O | VAL | A | 41 | 1.338 | 88.205 | 86.003 | 1.00 | 24.88 | A | O |
| ATOM | 203 | N | GLU | A | 42 | 0.039 | 88.569 | 87.795 | 1.00 | 26.62 | A | N |
| ATOM | 204 | CA | GLU | A | 42 | −1.183 | 88.664 | 87.023 | 1.00 | 28.55 | A | C |
| ATOM | 205 | CB | GLU | A | 42 | −2.152 | 87.544 | 87.410 | 1.00 | 30.56 | A | C |
| ATOM | 206 | CG | GLU | A | 42 | −1.583 | 86.137 | 87.213 | 1.00 | 36.63 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 207 | CD | GLU | A | 42 | −1.000 | 85.531 | 88.491 | 1.00 | 38.85 | A | C |
| ATOM | 208 | OE1 | GLU | A | 42 | −0.316 | 84.486 | 88.392 | 1.00 | 42.00 | A | O |
| ATOM | 209 | OE2 | GLU | A | 42 | −1.231 | 86.086 | 89.590 | 1.00 | 36.65 | A | O |
| ATOM | 210 | C | GLU | A | 42 | −1.790 | 90.016 | 87.336 | 1.00 | 29.64 | A | C |
| ATOM | 211 | O | GLU | A | 42 | −2.033 | 90.329 | 88.501 | 1.00 | 32.44 | A | O |
| ATOM | 212 | N | CYS | A | 43 | −2.028 | 90.815 | 86.297 | 1.00 | 29.03 | A | N |
| ATOM | 213 | CA | CYS | A | 43 | −2.590 | 92.151 | 86.458 | 1.00 | 28.81 | A | C |
| ATOM | 214 | CB | CYS | A | 43 | −1.655 | 93.190 | 85.810 | 1.00 | 29.72 | A | C |
| ATOM | 215 | SG | CYS | A | 43 | 0.039 | 93.278 | 86.509 | 1.00 | 28.89 | A | S |
| ATOM | 216 | C | CYS | A | 43 | −3.993 | 92.275 | 85.858 | 1.00 | 27.89 | A | C |
| ATOM | 217 | O | CYS | A | 43 | −4.194 | 92.001 | 84.678 | 1.00 | 28.38 | A | O |
| ATOM | 218 | N | ASP | A | 44 | −4.957 | 92.691 | 86.676 | 1.00 | 27.50 | A | N |
| ATOM | 219 | CA | ASP | A | 44 | −6.335 | 92.863 | 86.222 | 1.00 | 26.24 | A | C |
| ATOM | 220 | CB | ASP | A | 44 | −7.281 | 91.977 | 87.035 | 1.00 | 29.87 | A | C |
| ATOM | 221 | CG | ASP | A | 44 | −8.719 | 92.090 | 86.575 | 1.00 | 32.23 | A | C |
| ATOM | 222 | OD1 | ASP | A | 44 | −9.217 | 93.231 | 86.436 | 1.00 | 34.69 | A | C |
| ATOM | 223 | OD2 | ASP | A | 44 | −9.354 | 91.037 | 86.358 | 1.00 | 34.21 | A | O |
| ATOM | 224 | C | ASP | A | 44 | −6.755 | 94.318 | 86.363 | 1.00 | 26.22 | A | C |
| ATOM | 225 | O | ASP | A | 44 | −7.210 | 94.757 | 87.415 | 1.00 | 26.81 | A | O |
| ATOM | 226 | N | PRO | A | 45 | −6.612 | 95.092 | 85.288 | 1.00 | 28.07 | A | N |
| ATOM | 227 | CD | PRO | A | 45 | −6.159 | 94.690 | 83.945 | 1.00 | 28.13 | A | C |
| ATOM | 228 | CA | PRO | A | 45 | −6.981 | 96.506 | 85.313 | 1.00 | 27.77 | A | C |
| ATOM | 229 | CB | PRO | A | 45 | −6.565 | 96.986 | 83.930 | 1.00 | 27.06 | A | C |
| ATOM | 230 | CG | PRO | A | 45 | −6.748 | 95.764 | 83.089 | 1.00 | 28.18 | A | C |
| ATOM | 231 | C | PRO | A | 45 | −8.454 | 96.773 | 85.618 | 1.00 | 28.04 | A | C |
| ATOM | 232 | O | PRO | A | 45 | −8.778 | 97.767 | 86.267 | 1.00 | 30.40 | A | O |
| ATOM | 233 | N | VAL | A | 46 | −9.342 | 95.892 | 85.166 | 1.00 | 26.99 | A | N |
| ATOM | 234 | CA | VAL | A | 46 | −10.773 | 96.080 | 85.401 | 1.00 | 28.61 | A | C |
| ATOM | 235 | CA | VAL | A | 46 | −11.624 | 95.020 | 84.644 | 1.00 | 30.12 | A | C |
| ATOM | 236 | CG1 | VAL | A | 46 | −13.105 | 95.243 | 84.918 | 1.00 | 26.52 | A | C |
| ATOM | 237 | CG2 | VAL | A | 46 | −11.356 | 95.106 | 83.145 | 1.00 | 28.25 | A | C |
| ATOM | 238 | C | VAL | A | 46 | −11.136 | 96.036 | 86.879 | 1.00 | 28.50 | A | C |
| ATOM | 239 | O | VAL | A | 46 | −12.077 | 96.694 | 87.319 | 1.00 | 27.64 | A | O |
| ATOM | 240 | N | ARG | A | 47 | −10.393 | 95.254 | 87.647 | 1.00 | 29.75 | A | N |
| ATOM | 241 | CA | ARG | A | 47 | −10.650 | 95.158 | 89.071 | 1.00 | 30.08 | A | C |
| ATOM | 242 | CB | ARG | A | 47 | −10.676 | 93.693 | 89.514 | 1.00 | 29.93 | A | C |
| ATOM | 243 | CG | ARG | A | 47 | −11.902 | 92.929 | 89.033 | 1.00 | 30.69 | A | C |
| ATOM | 244 | CD | ARG | A | 47 | −11.784 | 91.440 | 89.313 | 1.00 | 32.20 | A | C |
| ATOM | 245 | NE | ARG | A | 47 | −11.601 | 91.155 | 90.734 | 1.00 | 32.04 | A | N |
| ATOM | 246 | CZ | ARG | A | 47 | −12.531 | 91.349 | 91.664 | 1.00 | 34.54 | A | C |
| ATOM | 247 | NH1 | ARG | A | 47 | −13.723 | 91.830 | 91.327 | 1.00 | 37.36 | A | N |
| ATOM | 248 | NH2 | ARG | A | 47 | −12.267 | 91.076 | 92.937 | 1.00 | 33.04 | A | N |
| ATOM | 249 | C | ARG | A | 47 | −9.583 | 95.926 | 89.837 | 1.00 | 30.64 | A | C |
| ATOM | 250 | O | ARG | A | 47 | −9.645 | 96.046 | 91.068 | 1.00 | 30.34 | A | O |
| ATOM | 251 | N | LYS | A | 48 | −8.602 | 96.449 | 89.105 | 1.00 | 28.97 | A | N |
| ATOM | 252 | CA | LYS | A | 48 | −7.535 | 97.217 | 89.730 | 1.00 | 27.59 | A | C |
| ATOM | 253 | CB | LYS | A | 48 | −8.140 | 98.337 | 90.574 | 1.00 | 30.84 | A | C |
| ATOM | 254 | CG | LYS | A | 48 | −9.375 | 98.985 | 89.964 | 1.00 | 34.46 | A | C |
| ATOM | 255 | CD | LYS | A | 48 | −10.152 | 99.753 | 91.015 | 1.00 | 38.00 | A | C |
| ATOM | 256 | CE | LYS | A | 48 | −11.383 | 100.418 | 90.425 | 1.00 | 41.61 | A | C |
| ATOM | 257 | NZ | LYS | A | 48 | −11.041 | 101.475 | 89.424 | 1.00 | 43.60 | A | N |
| ATOM | 258 | C | LYS | A | 48 | −6.756 | 96.293 | 90.643 | 1.00 | 26.01 | A | C |
| ATOM | 259 | O | LYS | A | 48 | −6.482 | 96.644 | 91.786 | 1.00 | 26.06 | A | O |
| ATOM | 260 | N | GLU | A | 49 | −6.400 | 95.115 | 90.148 | 1.00 | 25.46 | A | N |
| ATOM | 261 | CA | GLU | A | 49 | −5.682 | 94.155 | 90.971 | 1.00 | 24.97 | A | C |
| ATOM | 262 | CB | GLU | A | 49 | −6.598 | 92.974 | 91.314 | 1.00 | 27.64 | A | C |
| ATOM | 263 | CG | GLU | A | 49 | −7.654 | 93.263 | 92.384 | 1.00 | 33.12 | A | C |
| ATOM | 264 | CD | GLU | A | 49 | −8.481 | 92.027 | 92.754 | 1.00 | 35.39 | A | C |
| ATOM | 265 | OE1 | GLU | A | 49 | −9.242 | 91.521 | 91.901 | 1.00 | 34.46 | A | O |
| ATOM | 266 | OE2 | GLU | A | 49 | −8.369 | 91.555 | 93.904 | 1.00 | 37.34 | A | O |
| ATOM | 267 | C | GLU | A | 49 | −4.384 | 93.608 | 90.403 | 1.00 | 23.37 | A | C |
| ATOM | 268 | O | GLU | A | 49 | −4.111 | 93.697 | 89.203 | 1.00 | 22.08 | A | O |
| ATOM | 269 | N | VAL | A | 50 | −3.587 | 93.043 | 91.303 | 1.00 | 21.81 | A | N |
| ATOM | 270 | CA | VAL | A | 50 | −2.318 | 92.412 | 90.968 | 1.00 | 22.02 | A | C |
| ATOM | 271 | CB | VAL | A | 50 | −1.152 | 93.440 | 90.925 | 1.00 | 19.13 | A | C |
| ATOM | 272 | CG1 | VAL | A | 50 | −1.423 | 94.562 | 91.881 | 1.00 | 18.70 | A | C |
| ATOM | 273 | CG2 | VAL | A | 50 | 0.167 | 92.747 | 91.243 | 1.00 | 14.17 | A | C |
| ATOM | 274 | C | VAL | A | 50 | −2.040 | 91.329 | 92.016 | 1.00 | 20.07 | A | C |
| ATOM | 275 | O | VAL | A | 50 | −2.004 | 91.605 | 93.212 | 1.00 | 15.87 | A | O |
| ATOM | 276 | N | SER | A | 51 | −1.879 | 90.095 | 91.546 | 1.00 | 19.78 | A | N |
| ATOM | 277 | CA | SER | A | 51 | −1.623 | 88.951 | 92.415 | 1.00 | 22.71 | A | C |
| ATOM | 278 | CB | SER | A | 51 | −2.807 | 87.979 | 92.369 | 1.00 | 21.47 | A | C |
| ATOM | 279 | OG | SER | A | 51 | −2.942 | 87.420 | 91.081 | 1.00 | 21.52 | A | O |
| ATOM | 280 | C | SER | A | 51 | −0.334 | 88.223 | 92.009 | 1.00 | 22.75 | A | C |
| ATOM | 281 | O | SER | A | 51 | 0.007 | 88.138 | 90.827 | 1.00 | 20.00 | A | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 282 | N | VAL | A | 52 | 0.371 | 87.704 | 93.008 | 1.00 | 23.62 | A | N |
| ATOM | 283 | CA | VAL | A | 52 | 1.634 | 87.010 | 92.801 | 1.00 | 25.35 | A | C |
| ATOM | 284 | CB | VAL | A | 52 | 2.784 | 87.775 | 93.497 | 1.00 | 25.17 | A | C |
| ATOM | 285 | CG1 | VAL | A | 52 | 4.128 | 87.238 | 93.036 | 1.00 | 22.61 | A | C |
| ATOM | 286 | CG2 | VAL | A | 52 | 2.661 | 89.277 | 93.228 | 1.00 | 20.90 | A | C |
| ATOM | 287 | C | VAL | A | 52 | 1.593 | 85.593 | 93.375 | 1.00 | 27.83 | A | C |
| ATOM | 288 | O | VAL | A | 52 | 0.968 | 85.352 | 94.408 | 1.00 | 29.98 | A | O |
| ATOM | 289 | N | ARG | A | 53 | 2.266 | 84.659 | 92.712 | 1.00 | 29.91 | A | N |
| ATOM | 290 | CA | ARG | A | 53 | 2.311 | 83.285 | 93.191 | 1.00 | 32.85 | A | C |
| ATOM | 291 | CB | ARG | A | 53 | 2.859 | 82.346 | 92.132 | 1.00 | 33.97 | A | C |
| ATOM | 292 | CG | ARG | A | 53 | 2.073 | 82.258 | 90.866 | 1.00 | 36.59 | A | C |
| ATOM | 293 | CD | ARG | A | 53 | 2.647 | 81.139 | 90.012 | 1.00 | 41.53 | A | C |
| ATOM | 294 | NE | ARG | A | 53 | 2.280 | 81.281 | 88.609 | 1.00 | 43.69 | A | N |
| ATOM | 295 | CZ | ARG | A | 53 | 1.032 | 81.423 | 88.175 | 1.00 | 44.49 | A | C |
| ATOM | 296 | NH1 | ARG | A | 53 | 0.021 | 81.440 | 89.036 | 1.00 | 40.69 | A | N |
| ATOM | 297 | NH2 | ARG | A | 53 | 0.798 | 81.557 | 86.877 | 1.00 | 43.14 | A | N |
| ATOM | 298 | C | ARG | A | 53 | 3.242 | 83.203 | 94.381 | 1.00 | 35.83 | A | C |
| ATOM | 299 | O | ARG | A | 53 | 4.055 | 84.086 | 94.606 | 1.00 | 38.67 | A | O |
| ATOM | 300 | N | THR | A | 54 | 3.129 | 82.122 | 95.134 | 1.00 | 41.07 | A | N |
| ATOM | 301 | CA | THR | A | 54 | 3.982 | 81.905 | 96.291 | 1.00 | 42.64 | A | C |
| ATOM | 302 | CB | THR | A | 54 | 3.141 | 81.973 | 97.598 | 1.00 | 44.25 | A | C |
| ATOM | 303 | OG1 | THR | A | 54 | 2.821 | 83.345 | 91.870 | 1.00 | 40.26 | A | O |
| ATOM | 304 | CG2 | THR | A | 54 | 3.899 | 81.383 | 98.783 | 1.00 | 46.14 | A | C |
| ATOM | 305 | C | THR | A | 54 | 4.635 | 80.540 | 96.061 | 1.00 | 43.69 | A | C |
| ATOM | 306 | O | THR | A | 54 | 5.474 | 80.082 | 96.828 | 1.00 | 43.51 | A | O |
| ATOM | 307 | N | GLY | A | 55 | 4.303 | 79.958 | 94.909 | 1.00 | 45.25 | A | N |
| ATOM | 308 | CA | GLY | A | 55 | 4.835 | 78.663 | 94.521 | 1.00 | 49.37 | A | C |
| ATOM | 309 | C | GLY | A | 55 | 6.237 | 78.331 | 95.007 | 1.00 | 50.62 | A | C |
| ATOM | 310 | O | GLY | A | 55 | 7.228 | 78.762 | 94.411 | 1.00 | 50.83 | A | O |
| ATOM | 311 | N | GLY | A | 56 | 6.312 | 77.555 | 96.092 | 1.00 | 51.54 | A | N |
| ATOM | 312 | CA | GLY | A | 56 | 7.588 | 77.138 | 96.657 | 1.00 | 49.89 | A | C |
| ATOM | 313 | C | GLY | A | 56 | 7.864 | 75.680 | 96.322 | 1.00 | 49.37 | A | C |
| ATOM | 314 | O | GLY | A | 56 | 9.006 | 75.284 | 96.082 | 1.00 | 49.16 | A | O |
| ATOM | 315 | N | LEU | A | 57 | 6.806 | 74.879 | 96.316 | 1.00 | 49.62 | A | N |
| ATOM | 316 | CA | LEU | A | 57 | 6.885 | 73.457 | 95.978 | 1.00 | 48.31 | A | C |
| ATOM | 317 | CB | LEU | A | 57 | 7.596 | 72.664 | 97.081 | 1.00 | 46.41 | A | C |
| ATOM | 318 | CG | LEU | A | 57 | 9.121 | 72.820 | 97.161 | 1.00 | 43.71 | A | C |
| ATOM | 319 | CD1 | LEU | A | 57 | 9.499 | 73.877 | 98.196 | 1.00 | 43.69 | A | C |
| ATOM | 320 | CD2 | LEU | A | 57 | 9.737 | 71.485 | 97.540 | 1.00 | 43.01 | A | C |
| ATOM | 321 | C | LEU | A | 57 | 5.463 | 72.943 | 95.775 | 1.00 | 48.54 | A | C |
| ATOM | 322 | O | LEU | A | 57 | 5.232 | 71.756 | 95.536 | 1.00 | 48.19 | A | O |
| ATOM | 323 | N | ALA | A | 58 | 4.518 | 73.875 | 95.865 | 1.00 | 49.85 | A | N |
| ATOM | 324 | CA | ALA | A | 58 | 3.099 | 73.596 | 95.695 | 1.00 | 50.62 | A | C |
| ATOM | 325 | CB | ALA | A | 58 | 2.523 | 72.981 | 96.975 | 1.00 | 50.26 | A | C |
| ATOM | 326 | C | ALA | A | 58 | 2.390 | 74.914 | 95.372 | 1.00 | 50.41 | A | C |
| ATOM | 327 | O | ALA | A | 58 | 1.614 | 75.430 | 96.181 | 1.00 | 50.22 | A | O |
| ATOM | 328 | N | ASP | A | 59 | 2.680 | 75.461 | 94.194 | 1.00 | 50.13 | A | N |
| ATOM | 329 | CA | ASP | A | 59 | 2.072 | 76.710 | 93.748 | 1.00 | 49.63 | A | C |
| ATOM | 330 | CB | ASP | A | 59 | 2.771 | 77.221 | 92.481 | 1.00 | 48.05 | A | C |
| ATOM | 331 | CG | ASP | A | 59 | 2.487 | 76.346 | 91.266 | 1.00 | 46.55 | A | C |
| ATOM | 332 | OD1 | ASP | A | 59 | 3.387 | 75.595 | 90.828 | 1.00 | 42.64 | A | O |
| ATOM | 333 | OD2 | ASP | A | 59 | 1.353 | 76.408 | 90.749 | 1.00 | 47.39 | A | O |
| ATOM | 334 | C | ASP | A | 59 | 0.597 | 76.447 | 93.439 | 1.00 | 50.19 | A | C |
| ATOM | 335 | O | ASP | A | 59 | 0.026 | 75.458 | 93.908 | 1.00 | 51.06 | A | O |
| ATOM | 336 | N | LYS | A | 60 | 0.010 | 77.333 | 92.651 | 1.00 | 48.04 | A | N |
| ATOM | 337 | CA | LYS | A | 60 | −1.411 | 77.202 | 92.249 | 1.00 | 48.04 | A | C |
| ATOM | 338 | CB | LYS | A | 60 | −1.702 | 75.780 | 91.754 | 1.00 | 49.08 | A | C |
| ATOM | 339 | CG | LYS | A | 60 | −2.160 | 74.818 | 92.840 | 1.00 | 48.13 | A | C |
| ATOM | 340 | CD | LYS | A | 60 | −2.373 | 73.411 | 92.294 | 1.00 | 49.29 | A | C |
| ATOM | 341 | CE | LYS | A | 60 | −3.409 | 73.388 | 91.177 | 1.00 | 48.17 | A | C |
| ATOM | 342 | NZ | LYS | A | 60 | −2.981 | 74.184 | 89.990 | 1.00 | 48.76 | A | N |
| ATOM | 343 | C | LYS | A | 60 | −2.376 | 77.530 | 93.376 | 1.00 | 47.62 | A | C |
| ATOM | 344 | O | LYS | A | 60 | −3.492 | 78.000 | 93.137 | 1.00 | 45.38 | A | O |
| ATOM | 345 | N | SER | A | 61 | −1.944 | 77.273 | 94.604 | 1.00 | 47.68 | A | N |
| ATOM | 346 | CA | SER | A | 61 | −2.776 | 77.538 | 95.773 | 1.00 | 46.65 | A | C |
| ATOM | 347 | CB | SER | A | 61 | −2.921 | 76.264 | 96.613 | 1.00 | 44.09 | A | C |
| ATOM | 348 | OG | SER | A | 61 | −1.668 | 75.864 | 97.137 | 1.00 | 40.76 | A | O |
| ATOM | 349 | C | SER | A | 61 | −2.177 | 78.648 | 96.635 | 1.00 | 45.80 | A | C |
| ATOM | 350 | O | SER | A | 61 | −2.791 | 79.098 | 97.607 | 1.00 | 46.98 | A | O |
| ATOM | 351 | N | SER | A | 62 | −0.979 | 79.087 | 96.268 | 1.00 | 43.45 | A | N |
| ATOM | 352 | CA | SER | A | 62 | −0.290 | 80.115 | 97.029 | 1.00 | 43.19 | A | C |
| ATOM | 353 | CB | SER | A | 62 | 1.134 | 79.642 | 97.350 | 1.00 | 42.01 | A | C |
| ATOM | 354 | OG | SER | A | 62 | 1.135 | 78.325 | 97.893 | 1.00 | 40.38 | A | O |
| ATOM | 355 | C | SER | A | 62 | −0.252 | 81.429 | 96.258 | 1.00 | 42.56 | A | C |
| ATOM | 356 | O | SER | A | 62 | 0.664 | 81.666 | 95.474 | 1.00 | 42.26 | A | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 357 | N | ARG | A | 63 | −1.251 | 82.283 | 96.466 | 1.00 | 43.27 | A | N |
| ATOM | 358 | CA | ARG | A | 63 | −1.266 | 83.557 | 95.761 | 1.00 | 43.68 | A | C |
| ATOM | 359 | CB | ARG | A | 63 | −2.201 | 83.478 | 94.557 | 1.00 | 46.35 | A | C |
| ATOM | 360 | CG | ARG | A | 63 | −1.729 | 82.520 | 93.477 | 1.00 | 52.47 | A | C |
| ATOM | 361 | CD | ARG | A | 63 | −2.838 | 82.302 | 92.482 | 1.00 | 56.80 | A | C |
| ATOM | 362 | NE | ARG | A | 63 | −3.511 | 83.562 | 92.191 | 1.00 | 60.80 | A | N |
| ATOM | 363 | Cz | ARG | A | 63 | −4.648 | 83.665 | 91.514 | 1.00 | 62.44 | A | C |
| ATOM | 364 | NH1 | ARG | A | 63 | −5.249 | 82.575 | 91.053 | 1.00 | 62.61 | A | N |
| ATOM | 365 | NH2 | ARG | A | 63 | −5.185 | 84.859 | 91.300 | 1.00 | 63.91 | A | N |
| ATOM | 366 | C | ARG | A | 63 | −1.660 | 84.728 | 96.648 | 1.00 | 41.40 | A | C |
| ATOM | 367 | O | ARG | A | 63 | −2.517 | 84.602 | 97.527 | 1.00 | 42.29 | A | O |
| ATOM | 368 | N | LYS | A | 64 | −1.025 | 85.870 | 96.408 | 1.00 | 37.81 | A | N |
| ATOM | 369 | CA | LYS | A | 64 | −1.282 | 87.073 | 97.188 | 1.00 | 33.95 | A | C |
| ATOM | 370 | CB | LYS | A | 64 | 0.018 | 87.521 | 97.865 | 1.00 | 33.42 | A | C |
| ATOM | 371 | CG | LYS | A | 64 | −0.145 | 88.633 | 98.888 | 1.00 | 39.06 | A | C |
| ATOM | 372 | CD | LYS | A | 64 | 1.038 | 88.697 | 99.862 | 1.00 | 40.25 | A | C |
| ATOM | 373 | CE | LYS | A | 64 | 1.014 | 87.532 | 100.849 | 1.00 | 42.55 | A | C |
| ATOM | 374 | NZ | LYS | A | 64 | 2.128 | 87.584 | 101.843 | 1.00 | 38.94 | A | N |
| ATOM | 375 | C | LYS | A | 64 | −1.853 | 88.173 | 96.292 | 1.00 | 31.74 | A | C |
| ATOM | 376 | O | LYS | A | 64 | −1.309 | 88.462 | 95.228 | 1.00 | 30.73 | A | O |
| ATOM | 377 | N | THR | A | 65 | −2.954 | 88.779 | 96.731 | 1.00 | 29.57 | A | N |
| ATOM | 378 | CA | THR | A | 65 | −3.628 | 89.820 | 95.965 | 1.00 | 26.74 | A | C |
| ATOM | 379 | CB | THR | A | 65 | −5.090 | 89.401 | 95.673 | 1.00 | 26.24 | A | C |
| ATOM | 380 | OG1 | THR | A | 65 | −5.094 | 88.301 | 94.755 | 1.00 | 28.04 | A | O |
| ATOM | 381 | CG2 | THR | A | 65 | −5.888 | 90.557 | 95.094 | 1.00 | 23.36 | A | C |
| ATOM | 382 | C | THR | A | 65 | −3.637 | 91.216 | 96.600 | 1.00 | 26.34 | A | C |
| ATOM | 383 | O | THR | A | 65 | −3.984 | 91.387 | 97.770 | 1.00 | 26.12 | A | O |
| ATOM | 384 | N | TYR | A | 66 | −3.254 | 92.210 | 95.803 | 1.00 | 26.09 | A | N |
| ATOM | 385 | CA | TYR | A | 66 | −3.224 | 93.600 | 96.238 | 1.00 | 24.94 | A | C |
| ATOM | 386 | CB | TYR | A | 66 | −1.810 | 94.187 | 96.156 | 1.00 | 24.97 | A | C |
| ATOM | 387 | CG | TYR | A | 66 | −0.751 | 93.465 | 96.948 | 1.00 | 23.41 | A | C |
| ATOM | 388 | CD1 | TYR | A | 66 | −0.061 | 92.387 | 96.408 | 1.00 | 23.77 | A | C |
| ATOM | 389 | CE1 | TYR | A | 66 | 0.956 | 91.764 | 97.113 | 1.00 | 23.29 | A | C |
| ATOM | 390 | CD2 | TYR | A | 66 | −0.401 | 93.896 | 98.220 | 1.00 | 25.82 | A | C |
| ATOM | 391 | CE2 | TYR | A | 66 | 0.614 | 93.280 | 98.932 | 1.00 | 25.87 | A | C |
| ATOM | 392 | CZ | TYR | A | 66 | 1.289 | 92.219 | 98.373 | 1.00 | 24.32 | A | C |
| ATOM | 393 | OH | TYR | A | 66 | 2.312 | 91.639 | 99.081 | 1.00 | 26.52 | A | O |
| ATOM | 394 | C | TYR | A | 66 | −4.133 | 94.416 | 95.330 | 1.00 | 22.86 | A | C |
| ATOM | 395 | O | TYR | A | 66 | −4.301 | 94.093 | 94.160 | 1.00 | 21.70 | A | O |
| ATOM | 396 | N | THR | A | 67 | −4.712 | 95.475 | 95.882 | 1.00 | 23.71 | A | N |
| ATOM | 397 | CA | THR | A | 67 | −5.610 | 96.356 | 95.136 | 1.00 | 22.14 | A | C |
| ATOM | 398 | CB | THR | A | 67 | −7.043 | 96.378 | 95.758 | 1.00 | 21.22 | A | C |
| ATOM | 399 | OG1 | THR | A | 67 | −7.678 | 95.107 | 95.563 | 1.00 | 22.96 | A | O |
| ATOM | 400 | CG2 | THR | A | 67 | −7.898 | 97.462 | 95.105 | 1.00 | 20.62 | A | C |
| ATOM | 401 | C | THR | A | 67 | −5.037 | 97.769 | 95.171 | 1.00 | 21.29 | A | C |
| ATOM | 402 | O | THR | A | 67 | −4.596 | 98.255 | 96.225 | 1.00 | 19.03 | A | O |
| ATOM | 403 | N | PHE | A | 68 | −5.033 | 98.424 | 94.016 | 1.00 | 20.87 | A | N |
| ATOM | 404 | CA | PHE | A | 68 | −4.513 | 99.780 | 93.927 | 1.00 | 22.94 | A | C |
| ATOM | 405 | CB | PHE | A | 68 | −3.110 | 99.771 | 93.309 | 1.00 | 20.65 | A | C |
| ATOM | 406 | CG | PHE | A | 68 | −2.120 | 98.914 | 94.064 | 1.00 | 20.68 | A | C |
| ATOM | 407 | CD1 | PHE | A | 68 | −1.871 | 97.600 | 93.673 | 1.00 | 21.47 | A | C |
| ATOM | 408 | CD2 | PHE | A | 68 | −1.465 | 99.412 | 95.185 | 1.00 | 18.10 | A | C |
| ATOM | 409 | CE1 | PHE | A | 68 | −0.988 | 96.797 | 94.388 | 1.00 | 19.48 | A | C |
| ATOM | 410 | CE2 | PHE | A | 68 | −0.584 | 98.620 | 95.903 | 1.00 | 19.24 | A | C |
| ATOM | 411 | CZ | PHE | A | 68 | −0.344 | 97.309 | 95.505 | 1.00 | 19.77 | A | C |
| ATOM | 412 | C | PHE | A | 68 | −5.454 | 100.657 | 93.115 | 1.00 | 23.66 | A | C |
| ATOM | 413 | O | PHE | A | 68 | −6.437 | 100.164 | 92.554 | 1.00 | 24.36 | A | O |
| ATOM | 414 | N | ASP | A | 69 | −5.162 | 101.956 | 93.065 | 1.00 | 23.31 | A | N |
| ATOM | 415 | CA | ASP | A | 69 | −6.002 | 102.891 | 92.327 | 1.00 | 23.07 | A | C |
| ATOM | 416 | CB | ASP | A | 69 | −5.472 | 104.314 | 92.489 | 1.00 | 23.60 | A | C |
| ATOM | 417 | CG | ASP | A | 69 | −5.705 | 104.866 | 93.885 | 1.00 | 24.40 | A | C |
| ATOM | 418 | OD1 | ASP | A | 69 | −6.879 | 104.936 | 94.306 | 1.00 | 22.51 | A | O |
| ATOM | 419 | OD2 | ASP | A | 69 | −4.717 | 105.232 | 94.560 | 1.00 | 25.44 | A | O |
| ATOM | 420 | C | ASP | A | 69 | −6.095 | 102.515 | 90.852 | 1.00 | 22.17 | A | C |
| ATOM | 421 | O | ASP | A | 69 | −7.170 | 102.573 | 90.261 | 1.00 | 22.90 | A | O |
| ATOM | 422 | N | MET | A | 70 | −4.964 | 102.137 | 90.265 | 1.00 | 21.14 | A | N |
| ATOM | 423 | CA | MET | A | 70 | −4.920 | 101.723 | 88.868 | 1.00 | 22.80 | A | C |
| ATOM | 424 | CB | MET | A | 70 | −4.621 | 102.903 | 87.953 | 1.00 | 24.58 | A | C |
| ATOM | 425 | CG | MET | A | 70 | −5.718 | 103.942 | 87.908 | 1.00 | 30.20 | A | C |
| ATOM | 426 | SD | MET | A | 70 | −5.350 | 105.250 | 86.719 | 1.00 | 30.32 | A | S |
| ATOM | 427 | CE | MET | A | 70 | −4.715 | 106.538 | 87.830 | 1.00 | 27.24 | A | C |
| ATOM | 428 | C | MET | A | 70 | −3.843 | 100.671 | 88.689 | 1.00 | 22.33 | A | C |
| ATOM | 429 | O | MET | A | 70 | −2.787 | 100.746 | 89.317 | 1.00 | 22.45 | A | O |
| ATOM | 430 | N | VAL | A | 71 | −4.125 | 99.689 | 87.837 | 1.00 | 20.80 | A | N |
| ATOM | 431 | CA | VAL | A | 71 | −3.194 | 98.600 | 87.561 | 1.00 | 19.40 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 432 | CB | VAL | A | 71 | −3.792 | 97.235 | 87.997 | 1.00 | 17.68 | A | C |
| ATOM | 433 | CG1 | VAL | A | 71 | −2.872 | 96.115 | 87.579 | 1.00 | 17.01 | A | C |
| ATOM | 434 | CG2 | VAL | A | 71 | −3.997 | 97.209 | 89.503 | 1.00 | 11.28 | A | C |
| ATOM | 435 | C | VAL | A | 71 | −2.887 | 98.565 | 86.065 | 1.00 | 18.29 | A | C |
| ATOM | 436 | O | VAL | A | 71 | −3.802 | 98.574 | 85.241 | 1.00 | 20.58 | A | O |
| ATOM | 437 | N | PHE | A | 72 | −1.605 | 98.522 | 85.716 | 1.00 | 15.09 | A | N |
| ATOM | 438 | CA | PHE | A | 72 | −1.196 | 98.510 | 84.317 | 1.00 | 14.83 | A | C |
| ATOM | 439 | CB | PHE | A | 72 | −0.339 | 99.740 | 84.004 | 1.00 | 14.11 | A | C |
| ATOM | 440 | CG | PHE | A | 72 | −1.049 | 101.055 | 84.209 | 1.00 | 13.09 | A | C |
| ATOM | 441 | CD1 | PHE | A | 72 | −2.090 | 101.435 | 83.385 | 1.00 | 9.96 | A | C |
| ATOM | 442 | CD2 | PHE | A | 72 | −0.678 | 101.900 | 85.242 | 1.00 | 10.15 | A | C |
| ATOM | 443 | CE1 | PHE | A | 72 | −2.745 | 102.624 | 83.588 | 1.00 | 11.25 | A | C |
| ATOM | 444 | CE2 | PHE | A | 72 | −1.330 | 103.086 | 85.449 | 1.00 | 8.50 | A | C |
| ATOM | 445 | CZ | PHE | A | 72 | −2.365 | 103.452 | 84.624 | 1.00 | 11.61 | A | C |
| ATOM | 446 | C | PHE | A | 72 | −0.415 | 97.257 | 83.921 | 1.00 | 19.49 | A | C |
| ATOM | 447 | O | PHE | A | 72 | 0.735 | 97.067 | 84.338 | 1.00 | 21.22 | A | O |
| ATOM | 448 | N | GLY | A | 73 | −1.034 | 96.412 | 83.101 | 1.00 | 19.25 | A | N |
| ATOM | 449 | CA | GLY | A | 73 | −0.370 | 95.200 | 82.660 | 1.00 | 20.79 | A | C |
| ATOM | 450 | C | GLY | A | 73 | 0.861 | 95.529 | 81.843 | 1.00 | 21.45 | A | C |
| ATOM | 451 | O | GLY | A | 73 | 1.093 | 96.694 | 81.528 | 1.00 | 20.06 | A | O |
| ATOM | 452 | N | ALA | A | 74 | 1.639 | 94.509 | 81.485 | 1.00 | 22.61 | A | N |
| ATOM | 453 | CA | ALA | A | 74 | 2.874 | 94.698 | 80.718 | 1.00 | 22.65 | A | C |
| ATOM | 454 | CB | ALA | A | 74 | 3.648 | 93.380 | 80.644 | 1.00 | 23.97 | A | C |
| ATOM | 455 | C | ALA | A | 74 | 2.737 | 95.283 | 79.315 | 1.00 | 23.03 | A | C |
| ATOM | 456 | O | ALA | A | 74 | 3.697 | 95.835 | 78.795 | 1.00 | 22.93 | A | O |
| ATOM | 457 | N | SER | A | 75 | 1.559 | 95.175 | 78.704 | 1.00 | 25.66 | A | N |
| ATOM | 458 | CA | SER | A | 75 | 1.367 | 95.696 | 77.345 | 1.00 | 25.20 | A | C |
| ATOM | 459 | CB | SER | A | 75 | 0.356 | 94.835 | 76.577 | 1.00 | 26.05 | A | C |
| ATOM | 460 | OG | SER | A | 75 | −0.974 | 95.132 | 76.979 | 1.00 | 25.98 | A | O |
| ATOM | 461 | C | SER | A | 75 | 0.897 | 97.147 | 77.310 | 1.00 | 23.75 | A | C |
| ATOM | 462 | O | SER | A | 75 | 0.379 | 97.610 | 76.299 | 1.00 | 25.87 | A | O |
| ATOM | 463 | N | THR | A | 76 | 1.078 | 97.859 | 78.412 | 1.00 | 22.98 | A | N |
| ATOM | 464 | CA | THR | A | 76 | 0.664 | 99.254 | 78.502 | 1.00 | 22.50 | A | C |
| ATOM | 465 | CB | THR | A | 76 | 0.636 | 99.702 | 79.979 | 1.00 | 21.97 | A | C |
| ATOM | 466 | OG1 | THR | A | 76 | −0.407 | 99.006 | 80.669 | 1.00 | 23.27 | A | O |
| ATOM | 467 | CG2 | THR | A | 76 | 0.401 | 101.187 | 80.084 | 1.00 | 25.77 | A | C |
| ATOM | 468 | C | THR | A | 76 | 1.569 | 100.208 | 77.695 | 1.00 | 22.40 | A | C |
| ATOM | 469 | O | THR | A | 76 | 2.794 | 100.103 | 77.711 | 1.00 | 21.51 | A | O |
| ATOM | 470 | N | LYS | A | 77 | 0.956 | 101.135 | 76.975 | 1.00 | 20.65 | A | N |
| ATOM | 471 | CA | LYS | A | 77 | 1.720 | 102.096 | 76.195 | 1.00 | 19.36 | A | C |
| ATOM | 472 | CB | LYS | A | 77 | 0.946 | 102.526 | 74.948 | 1.00 | 23.33 | A | C |
| ATOM | 473 | CG | LYS | A | 77 | 0.674 | 101.431 | 73.942 | 1.00 | 25.69 | A | C |
| ATOM | 474 | CD | LYS | A | 77 | 0.839 | 101.998 | 72.541 | 1.00 | 29.04 | A | C |
| ATOM | 475 | CE | LYS | A | 77 | 0.083 | 103.317 | 72.371 | 1.00 | 28.49 | A | C |
| ATOM | 476 | NZ | LYS | A | 77 | 0.631 | 104.162 | 71.258 | 1.00 | 23.31 | A | N |
| ATOM | 477 | C | LYS | A | 77 | 1.991 | 103.332 | 77.032 | 1.00 | 15.80 | A | C |
| ATOM | 478 | O | LYS | A | 77 | 1.187 | 103.688 | 77.882 | 1.00 | 15.86 | A | O |
| ATOM | 479 | N | GLN | A | 78 | 3.123 | 103.978 | 76.778 | 1.00 | 14.23 | A | N |
| ATOM | 480 | CA | GLN | A | 78 | 3.498 | 105.195 | 77.482 | 1.00 | 15.24 | A | C |
| ATOM | 481 | CB | GLN | A | 78 | 4.743 | 105.804 | 76.828 | 1.00 | 14.44 | A | C |
| ATOM | 482 | CG | GLN | A | 78 | 5.982 | 104.914 | 76.836 | 1.00 | 12.51 | A | C |
| ATOM | 483 | CD | GLN | A | 78 | 6.725 | 104.942 | 78.167 | 1.00 | 12.13 | A | C |
| ATOM | 484 | OE1 | GLN | A | 78 | 6.160 | 104.635 | 79.211 | 1.00 | 13.09 | A | O |
| ATOM | 485 | NE2 | GLN | A | 78 | 7.998 | 105.308 | 78.128 | 1.00 | 9.65 | A | N |
| ATOM | 486 | C | GLN | A | 78 | 2.340 | 106.199 | 77.410 | 1.00 | 16.69 | A | C |
| ATOM | 487 | O | GLN | A | 78 | 2.042 | 106.891 | 78.385 | 1.00 | 19.13 | A | O |
| ATOM | 488 | N | ILE | A | 79 | 1.700 | 106.257 | 76.241 | 1.00 | 18.37 | A | N |
| ATOM | 489 | CA | ILE | A | 79 | 0.571 | 107.142 | 75.966 | 1.00 | 17.11 | A | C |
| ATOM | 490 | CB | ILE | A | 79 | 0.087 | 106.973 | 74.487 | 1.00 | 17.15 | A | C |
| ATOM | 491 | CG2 | ILE | A | 79 | −0.525 | 105.612 | 74.294 | 1.00 | 19.45 | A | C |
| ATOM | 492 | CG1 | ILE | A | 79 | −0.981 | 108.007 | 74.139 | 1.00 | 19.80 | A | C |
| ATOM | 493 | CD1 | ILE | A | 79 | −0.456 | 109.408 | 73.951 | 1.00 | 21.40 | A | C |
| ATOM | 494 | C | ILE | A | 79 | −0.612 | 106.888 | 76.903 | 1.00 | 17.01 | A | C |
| ATOM | 495 | O | ILE | A | 79 | −1.358 | 107.810 | 77.228 | 1.00 | 16.82 | A | O |
| ATOM | 496 | N | ASP | A | 80 | −0.793 | 105.643 | 77.333 | 1.00 | 17.47 | A | N |
| ATOM | 497 | CA | ASP | A | 80 | −1.903 | 105.309 | 78.239 | 1.00 | 17.93 | A | C |
| ATOM | 498 | CB | ASP | A | 80 | −2.214 | 103.804 | 78.216 | 1.00 | 21.34 | A | C |
| ATOM | 499 | CG | ASP | A | 80 | −2.715 | 103.330 | 76.867 | 1.00 | 25.04 | A | C |
| ATOM | 500 | OD1 | ASP | A | 80 | −3.623 | 103.980 | 76.324 | 1.00 | 26.24 | A | O |
| ATOM | 501 | OD2 | ASP | A | 80 | −2.211 | 102.305 | 76.355 | 1.00 | 29.71 | A | O |
| ATOM | 502 | C | ASP | A | 80 | −1.564 | 105.726 | 79.664 | 1.00 | 17.34 | A | C |
| ATOM | 503 | O | ASP | A | 80 | −2.405 | 106.284 | 80.377 | 1.00 | 17.69 | A | O |
| ATOM | 504 | N | VAL | A | 81 | −0.333 | 105.443 | 80.080 | 1.00 | 15.43 | A | N |
| ATOM | 505 | CA | VAL | A | 81 | 0.114 | 105.818 | 81.410 | 1.00 | 14.62 | A | C |
| ATOM | 506 | CB | VAL | A | 81 | 1.615 | 105.568 | 81.627 | 1.00 | 14.79 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 507 | CG1 | VAL | A | 81 | 2.041 | 106.211 | 82.945 | 1.00 | 9.04 | A | C |
| ATOM | 508 | CG2 | VAL | A | 81 | 1.918 | 104.078 | 81.628 | 1.00 | 12.26 | A | C |
| ATOM | 509 | C | VAL | A | 81 | −0.091 | 107.307 | 81.533 | 1.00 | 16.19 | A | C |
| ATOM | 510 | O | VAL | A | 81 | −0.596 | 107.806 | 82.541 | 1.00 | 17.39 | A | O |
| ATOM | 511 | N | TYR | A | 82 | 0.315 | 108.025 | 80.499 | 1.00 | 15.47 | A | N |
| ATOM | 512 | CA | TYR | A | 82 | 0.179 | 109.466 | 80.524 | 1.00 | 18.43 | A | C |
| ATOM | 513 | CB | TYR | A | 82 | 0.882 | 110.086 | 79.317 | 1.00 | 20.87 | A | C |
| ATOM | 514 | CG | TYR | A | 82 | 0.808 | 111.591 | 79.310 | 1.00 | 21.23 | A | C |
| ATOM | 515 | CD1 | TYR | A | 82 | −0.168 | 112.257 | 78.575 | 1.00 | 20.34 | A | C |
| ATOM | 516 | CE1 | TYR | A | 82 | −0.300 | 113.634 | 78.652 | 1.00 | 21.98 | A | C |
| ATOM | 517 | CD2 | TYR | A | 82 | 1.656 | 112.345 | 80.113 | 1.00 | 19.43 | A | C |
| ATOM | 518 | CE2 | TYR | A | 82 | 1.526 | 113.723 | 80.193 | 1.00 | 19.86 | A | C |
| ATOM | 519 | CZ | TYR | A | 82 | 0.548 | 114.357 | 79.466 | 1.00 | 17.04 | A | C |
| ATOM | 520 | OH | TYR | A | 82 | 0.397 | 115.710 | 79.585 | 1.00 | 19.16 | A | O |
| ATOM | 521 | C | TYR | A | 82 | −1.282 | 109.920 | 80.588 | 1.00 | 21.08 | A | C |
| ATOM | 522 | O | TYR | A | 82 | −1.625 | 110.778 | 81.410 | 1.00 | 22.92 | A | O |
| ATOM | 523 | N | ARG | A | 83 | −2.142 | 109.343 | 79.747 | 1.00 | 20.03 | A | N |
| ATOM | 524 | CA | ARG | A | 83 | −3.561 | 109.722 | 79.737 | 1.00 | 22.69 | A | C |
| ATOM | 525 | CB | ARG | A | 83 | −4.327 | 109.000 | 78.611 | 1.00 | 25.53 | A | C |
| ATOM | 526 | CG | ARG | A | 83 | −4.011 | 109.450 | 77.184 | 1.00 | 30.40 | A | C |
| ATOM | 527 | CD | ARG | A | 83 | −5.044 | 108.862 | 76.211 | 1.00 | 35.89 | A | C |
| ATOM | 528 | NE | ARG | A | 83 | −4.749 | 109.100 | 74.793 | 1.00 | 38.69 | A | N |
| ATOM | 529 | CZ | ARG | A | 83 | −4.520 | 110.295 | 74.257 | 1.00 | 39.74 | A | C |
| ATOM | 530 | NH1 | ARG | A | 83 | −4.543 | 111.382 | 75.018 | 1.00 | 38.38 | A | N |
| ATOM | 531 | NH2 | ARG | A | 83 | −4.277 | 110.404 | 72.954 | 1.00 | 40.83 | A | N |
| ATOM | 532 | C | ARG | A | 83 | −4.281 | 109.438 | 81.055 | 1.00 | 21.58 | A | C |
| ATOM | 533 | O | ARG | A | 83 | −5.113 | 110.222 | 81.492 | 1.00 | 19.23 | A | O |
| ATOM | 534 | N | SER | A | 84 | −3.961 | 108.315 | 81.686 | 1.00 | 20.33 | A | N |
| ATOM | 535 | CA | SER | A | 84 | −4.617 | 107.947 | 82.933 | 1.00 | 22.28 | A | C |
| ATOM | 536 | CB | SER | A | 84 | −4.561 | 106.428 | 83.136 | 1.00 | 21.46 | A | C |
| ATOM | 537 | OG | SER | A | 84 | −5.062 | 105.724 | 82.014 | 1.00 | 26.40 | A | O |
| ATOM | 538 | C | SER | A | 84 | −4.057 | 108.614 | 84.186 | 1.00 | 21.97 | A | C |
| ATOM | 539 | O | SER | A | 84 | −4.811 | 109.046 | 85.052 | 1.00 | 22.96 | A | O |
| ATOM | 540 | N | VAL | A | 85 | −2.739 | 108.707 | 84.285 | 1.00 | 20.40 | A | N |
| ATOM | 541 | CA | VAL | A | 85 | −2.142 | 109.266 | 85.480 | 1.00 | 18.33 | A | C |
| ATOM | 542 | CB | VAL | A | 85 | −0.875 | 108.457 | 85.861 | 1.00 | 18.73 | A | C |
| ATOM | 543 | CG1 | VAL | A | 85 | −0.338 | 108.915 | 87.195 | 1.00 | 17.03 | A | C |
| ATOM | 544 | CG2 | VAL | A | 85 | −1.204 | 106.977 | 85.902 | 1.00 | 15.88 | A | C |
| ATOM | 545 | C | VAL | A | 85 | −1.805 | 110.756 | 85.456 | 1.00 | 17.77 | A | C |
| ATOM | 546 | O | VAL | A | 85 | −2.253 | 111.491 | 86.323 | 1.00 | 16.89 | A | O |
| ATOM | 547 | N | VAL | A | 86 | −1.034 | 111.203 | 84.469 | 1.00 | 18.06 | A | N |
| ATOM | 548 | CA | VAL | A | 86 | −0.633 | 112.599 | 84.392 | 1.00 | 16.44 | A | C |
| ATOM | 549 | CB | VAL | A | 86 | 0.486 | 112.787 | 83.354 | 1.00 | 15.86 | A | C |
| ATOM | 550 | CG1 | VAL | A | 86 | 1.043 | 114.204 | 83.445 | 1.00 | 14.78 | A | C |
| ATOM | 551 | CG2 | VAL | A | 86 | 1.586 | 111.770 | 83.586 | 1.00 | 14.30 | A | C |
| ATOM | 552 | C | VAL | A | 86 | −1.714 | 113.657 | 84.126 | 1.00 | 19.37 | A | C |
| ATOM | 553 | O | VAL | A | 86 | −1.857 | 114.596 | 84.915 | 1.00 | 19.31 | A | O |
| ATOM | 554 | N | CYS | A | 87 | −2.462 | 113.519 | 83.028 | 1.00 | 19.45 | A | N |
| ATOM | 555 | CA | CYS | A | 87 | −3.507 | 114.486 | 82.678 | 1.00 | 18.55 | A | C |
| ATOM | 556 | CB | CYS | A | 87 | −4.480 | 113.886 | 81.670 | 1.00 | 19.38 | A | C |
| ATOM | 557 | SG | CYS | A | 87 | −3.771 | 113.793 | 80.055 | 1.00 | 29.31 | A | S |
| ATOM | 558 | C | CYS | A | 87 | −4.299 | 115.046 | 83.846 | 1.00 | 18.40 | A | C |
| ATOM | 559 | O | CYS | A | 87 | −4.326 | 116.250 | 84.061 | 1.00 | 18.65 | A | O |
| ATOM | 560 | N | PRO | A | 88 | −4.971 | 114.181 | 84.613 | 1.00 | 17.80 | A | N |
| ATOM | 561 | CD | PRO | A | 88 | −4.976 | 112.712 | 84.650 | 1.00 | 16.35 | A | C |
| ATOM | 562 | CA | PRO | A | 88 | −5.729 | 114.740 | 85.735 | 1.00 | 20.14 | A | C |
| ATOM | 563 | CB | PRO | A | 88 | −6.146 | 113.500 | 86.532 | 1.00 | 15.24 | A | C |
| ATOM | 564 | CG | PRO | A | 88 | −6.193 | 112.432 | 85.507 | 1.00 | 16.33 | A | C |
| ATOM | 565 | C | PRO | A | 88 | −4.830 | 115.667 | 86.548 | 1.00 | 21.15 | A | C |
| ATOM | 566 | O | PRO | A | 88 | −5.183 | 116.815 | 86.813 | 1.00 | 24.60 | A | O |
| ATOM | 567 | N | ILE | A | 89 | −3.662 | 115.156 | 86.932 | 1.00 | 20.12 | A | N |
| ATOM | 568 | CA | ILE | A | 89 | −2.716 | 115.919 | 87.734 | 1.00 | 18.70 | A | C |
| ATOM | 569 | CB | ILE | A | 89 | −1.468 | 115.056 | 88.065 | 1.00 | 16.38 | A | C |
| ATOM | 570 | CG2 | ILE | A | 89 | −0.349 | 115.919 | 88.624 | 1.00 | 10.70 | A | C |
| ATOM | 571 | CG1 | ILE | A | 89 | −1.872 | 113.964 | 89.067 | 1.00 | 15.02 | A | C |
| ATOM | 572 | CD1 | ILE | A | 89 | −0.825 | 112.917 | 89.317 | 1.00 | 16.88 | A | C |
| ATOM | 573 | C | ILE | A | 89 | −2.318 | 117.223 | 87.052 | 1.00 | 18.49 | A | C |
| ATOM | 574 | O | ILE | A | 89 | −2.351 | 118.286 | 87.670 | 1.00 | 19.91 | A | O |
| ATOM | 575 | N | LEU | A | 90 | −1.969 | 117.148 | 85.773 | 1.00 | 16.78 | A | N |
| ATOM | 576 | CA | LEU | A | 90 | −1.575 | 118.339 | 85.039 | 1.00 | 16.48 | A | C |
| ATOM | 577 | CB | LEU | A | 90 | −1.243 | 117.981 | 83.585 | 1.00 | 14.46 | A | C |
| ATOM | 578 | CG | LEU | A | 90 | −0.689 | 119.135 | 82.737 | 1.00 | 18.20 | A | C |
| ATOM | 579 | CD1 | LEU | A | 90 | 0.558 | 119.722 | 83.397 | 1.00 | 13.39 | A | C |
| ATOM | 580 | CD2 | LEU | A | 90 | −0.376 | 118.644 | 81.336 | 1.00 | 19.02 | A | C |
| ATOM | 581 | C | LEU | A | 90 | −2.655 | 119.430 | 85.086 | 1.00 | 18.01 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 582 | O | LEU | A | 90 | −2.335 | 120.613 | 85.209 | 1.00 | 17.39 | A | O |
| ATOM | 583 | N | ASP | A | 91 | −3.925 | 119.036 | 84.984 | 1.00 | 20.49 | A | N |
| ATOM | 584 | CA | ASP | A | 91 | −5.021 | 120.002 | 85.031 | 1.00 | 22.60 | A | C |
| ATOM | 585 | CB | ASP | A | 91 | −6.387 | 119.309 | 84.936 | 1.00 | 21.56 | A | C |
| ATOM | 586 | CG | ASP | A | 91 | −6.635 | 118.686 | 83.578 | 1.00 | 21.91 | A | C |
| ATOM | 587 | OD1 | ASP | A | 91 | −6.274 | 119.313 | 82.564 | 1.00 | 21.46 | A | O |
| ATOM | 588 | OD2 | ASP | A | 91 | −7.209 | 117.576 | 83.518 | 1.00 | 22.88 | A | O |
| ATOM | 589 | C | ASP | A | 91 | −4.938 | 120.803 | 86.325 | 1.00 | 24.70 | A | C |
| ATOM | 590 | O | ASP | A | 91 | −5.244 | 121.999 | 86.339 | 1.00 | 25.56 | A | O |
| ATOM | 591 | N | GLU | A | 92 | −4.518 | 120.147 | 87.408 | 1.00 | 25.02 | A | N |
| ATOM | 592 | CA | GLU | A | 92 | −4.368 | 120.831 | 88.691 | 1.00 | 26.32 | A | C |
| ATOM | 593 | CB | GLU | A | 92 | −4.195 | 119.816 | 89.818 | 1.00 | 27.58 | A | C |
| ATOM | 594 | CG | GLU | A | 92 | −5.404 | 118.917 | 90.033 | 1.00 | 33.77 | A | C |
| ATOM | 595 | CD | GLU | A | 92 | −6.708 | 119.696 | 90.160 | 1.00 | 38.32 | A | C |
| ATOM | 596 | OE1 | GLU | A | 92 | −6.791 | 120.594 | 91.029 | 1.00 | 38.49 | A | O |
| ATOM | 597 | OE2 | GLU | A | 92 | −7.651 | 119.405 | 89.388 | 1.00 | 40.61 | A | O |
| ATOM | 598 | C | GLU | A | 92 | −3.184 | 121.814 | 88.687 | 1.00 | 25.65 | A | C |
| ATOM | 599 | O | GLU | A | 92 | −3.289 | 122.915 | 89.224 | 1.00 | 25.61 | A | O |
| ATOM | 600 | N | VAL | A | 93 | −2.059 | 121.424 | 88.089 | 1.00 | 24.19 | A | N |
| ATOM | 601 | CA | VAL | A | 93 | −0.900 | 122.318 | 88.024 | 1.00 | 23.00 | A | C |
| ATOM | 602 | CB | VAL | A | 93 | 0.317 | 121.657 | 87.315 | 1.00 | 21.30 | A | C |
| ATOM | 603 | CG1 | VAL | A | 93 | 1.333 | 122.712 | 86.965 | 1.00 | 20.85 | A | C |
| ATOM | 604 | CG2 | VAL | A | 93 | 0.963 | 120.613 | 88.217 | 1.00 | 20.27 | A | C |
| ATOM | 605 | C | VAL | A | 93 | −1.272 | 123.578 | 87.246 | 1.00 | 21.65 | A | C |
| ATOM | 606 | O | VAL | A | 93 | −0.960 | 124.690 | 87.661 | 1.00 | 19.35 | A | O |
| ATOM | 607 | N | ILE | A | 94 | −1.938 | 123.385 | 86.112 | 1.00 | 21.22 | A | N |
| ATOM | 608 | CA | ILE | A | 94 | −2.359 | 124.495 | 85.265 | 1.00 | 21.88 | A | C |
| ATOM | 609 | CB | ILE | A | 94 | −3.043 | 123.996 | 83.979 | 1.00 | 20.14 | A | C |
| ATOM | 610 | CG2 | ILE | A | 94 | −3.757 | 125.129 | 83.298 | 1.00 | 11.93 | A | C |
| ATOM | 611 | CG1 | ILE | A | 94 | −1.993 | 123.383 | 83.049 | 1.00 | 23.05 | A | C |
| ATOM | 612 | CD1 | ILE | A | 94 | −2.560 | 122.787 | 81.799 | 1.00 | 23.52 | A | C |
| ATOM | 613 | C | ILE | A | 94 | −3.305 | 125.433 | 85.992 | 1.00 | 23.02 | A | C |
| ATOM | 614 | O | ILE | A | 94 | −3.385 | 126.614 | 85.668 | 1.00 | 21.87 | A | O |
| ATOM | 615 | N | MET | A | 95 | −4.025 | 124.901 | 86.973 | 1.00 | 23.61 | A | N |
| ATOM | 616 | CA | MET | A | 95 | −4.942 | 125.713 | 87.749 | 1.00 | 23.95 | A | C |
| ATOM | 617 | CB | MET | A | 95 | −6.086 | 124.859 | 88.292 | 1.00 | 26.58 | A | C |
| ATOM | 618 | CG | MET | A | 95 | −7.000 | 124.307 | 87.223 | 1.00 | 30.30 | A | C |
| ATOM | 619 | SD | MET | A | 95 | −8.611 | 123.820 | 87.868 | 1.00 | 37.22 | A | S |
| ATOM | 620 | CE | MET | A | 95 | −8.351 | 122.065 | 88.177 | 1.00 | 36.22 | A | C |
| ATOM | 621 | C | MET | A | 95 | −4.182 | 126.368 | 88.898 | 1.00 | 24.61 | A | C |
| ATOM | 622 | O | MET | A | 95 | −4.778 | 126.988 | 89.776 | 1.00 | 25.12 | A | O |
| ATOM | 623 | N | GLY | A | 96 | −2.860 | 126.208 | 88.893 | 1.00 | 24.75 | A | N |
| ATOM | 624 | CA | GLY | A | 96 | −2.029 | 126.815 | 89.921 | 1.00 | 25.09 | A | C |
| ATOM | 625 | C | GLY | A | 96 | −1.727 | 126.024 | 91.183 | 1.00 | 23.36 | A | C |
| ATOM | 626 | O | GLY | A | 96 | −1.563 | 126.604 | 92.246 | 1.00 | 22.36 | A | O |
| ATOM | 627 | N | TYR | A | 97 | −1.633 | 124.707 | 91.070 | 1.00 | 24.53 | A | N |
| ATOM | 628 | CA | TYR | A | 97 | −1.352 | 123.864 | 92.224 | 1.00 | 23.07 | A | C |
| ATOM | 629 | CB | TYR | A | 97 | −2.479 | 122.844 | 92.409 | 1.00 | 24.19 | A | C |
| ATOM | 630 | CG | TYR | A | 97 | −3.775 | 123.500 | 92.844 | 1.00 | 25.51 | A | C |
| ATOM | 631 | CD1 | TYR | A | 97 | −3.842 | 124.228 | 94.030 | 1.00 | 26.10 | A | C |
| ATOM | 632 | CE1 | TYR | A | 97 | −5.000 | 124.892 | 94.401 | 1.00 | 27.03 | A | C |
| ATOM | 633 | CD2 | TYR | A | 97 | −4.911 | 123.448 | 92.042 | 1.00 | 25.21 | A | C |
| ATOM | 634 | CE2 | TYR | A | 97 | −6.070 | 124.106 | 92.404 | 1.00 | 25.24 | A | C |
| ATOM | 635 | CZ | TYR | A | 97 | −6.109 | 124.829 | 93.582 | 1.00 | 27.41 | A | C |
| ATOM | 636 | OH | TYR | A | 97 | −7.254 | 125.502 | 93.923 | 1.00 | 28.87 | A | O |
| ATOM | 637 | C | TYR | A | 97 | −0.009 | 123.168 | 92.095 | 1.00 | 23.56 | A | C |
| ATOM | 638 | O | TYR | A | 97 | 0.505 | 123.007 | 90.984 | 1.00 | 24.83 | A | O |
| ATOM | 639 | N | ASN | A | 98 | 0.555 | 122.768 | 93.235 | 1.00 | 22.86 | A | N |
| ATOM | 640 | CA | ASN | A | 98 | 1.861 | 122.103 | 93.276 | 1.00 | 22.87 | A | C |
| ATOM | 641 | CB | ASN | A | 98 | 2.688 | 122.671 | 94.430 | 1.00 | 25.39 | A | C |
| ATOM | 642 | CG | ASN | A | 98 | 4.179 | 122.536 | 94.203 | 1.00 | 28.73 | A | C |
| ATOM | 643 | OD1 | ASN | A | 98 | 4.673 | 121.467 | 93.869 | 1.00 | 33.82 | A | O |
| ATOM | 644 | ND2 | ASN | A | 98 | 4.906 | 123.625 | 94.393 | 1.00 | 28.84 | A | N |
| ATOM | 645 | C | ASN | A | 98 | 1.703 | 120.586 | 93.443 | 1.00 | 21.70 | A | C |
| ATOM | 646 | O | ASN | A | 98 | 1.276 | 120.112 | 94.500 | 1.00 | 22.72 | A | O |
| ATOM | 647 | N | CYS | A | 99 | 2.062 | 119.830 | 92.407 | 1.00 | 17.79 | A | N |
| ATOM | 648 | CA | CYS | A | 99 | 1.919 | 118.376 | 92.443 | 1.00 | 17.44 | A | C |
| ATOM | 649 | CB | CYS | A | 99 | 0.919 | 117.932 | 91.372 | 1.00 | 16.59 | A | C |
| ATOM | 650 | SG | CYS | A | 99 | −0.721 | 118.685 | 91.550 | 1.00 | 21.81 | A | S |
| ATOM | 651 | C | CYS | A | 99 | 3.213 | 117.582 | 92.288 | 1.00 | 16.36 | A | C |
| ATOM | 652 | O | CYS | A | 99 | 4.250 | 118.108 | 91.884 | 1.00 | 17.03 | A | O |
| ATOM | 653 | N | THR | A | 100 | 3.138 | 116.300 | 92.612 | 1.00 | 15.82 | A | N |
| ATOM | 654 | CA | THR | A | 100 | 4.292 | 115.424 | 92.523 | 1.00 | 16.05 | A | C |
| ATOM | 655 | CB | THR | A | 100 | 5.010 | 115.321 | 93.876 | 1.00 | 14.23 | A | C |
| ATOM | 656 | OG1 | THR | A | 100 | 5.584 | 116.585 | 94.211 | 1.00 | 19.26 | A | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 657 | CG2 | THR | A | 100 | 6.099 | 114.301 | 93.804 | 1.00 | 14.90 | A | C |
| ATOM | 658 | C | THR | A | 100 | 3.912 | 114.017 | 92.086 | 1.00 | 16.62 | A | C |
| ATOM | 659 | O | THR | A | 100 | 2.927 | 113.452 | 92.564 | 1.00 | 18.68 | A | O |
| ATOM | 660 | N | ILE | A | 101 | 4.697 | 113.461 | 91.171 | 1.00 | 14.83 | A | N |
| ATOM | 661 | CA | ILE | A | 101 | 4.478 | 112.110 | 90.671 | 1.00 | 11.43 | A | C |
| ATOM | 662 | CB | ILE | A | 101 | 4.181 | 112.106 | 89.169 | 1.00 | 8.72 | A | C |
| ATOM | 663 | CG2 | ILE | A | 101 | 4.004 | 110.700 | 88.686 | 1.00 | 5.85 | A | C |
| ATOM | 664 | CG1 | ILE | A | 101 | 2.914 | 112.899 | 88.876 | 1.00 | 11.28 | A | C |
| ATOM | 665 | CD1 | ILE | A | 101 | 2.499 | 112.860 | 87.391 | 1.00 | 7.60 | A | C |
| ATOM | 666 | C | ILE | A | 101 | 5.775 | 111.334 | 90.903 | 1.00 | 13.17 | A | C |
| ATOM | 667 | O | ILE | A | 101 | 6.857 | 111.801 | 90.532 | 1.00 | 12.82 | A | O |
| ATOM | 668 | N | PHE | A | 102 | 5.662 | 110.154 | 91.507 | 1.00 | 10.07 | A | N |
| ATOM | 669 | CA | PHE | A | 102 | 6.825 | 109.331 | 91.802 | 1.00 | 12.74 | A | C |
| ATOM | 670 | CB | PHE | A | 102 | 6.820 | 108.884 | 93.270 | 1.00 | 12.93 | A | C |
| ATOM | 671 | CG | PHE | A | 102 | 7.061 | 109.988 | 94.259 | 1.00 | 12.69 | A | C |
| ATOM | 672 | CD1 | PHE | A | 102 | 8.340 | 110.464 | 94.491 | 1.00 | 13.24 | A | C |
| ATOM | 673 | CD2 | PHE | A | 102 | 6.004 | 110.547 | 94.968 | 1.00 | 12.49 | A | C |
| ATOM | 674 | CE1 | PHE | A | 102 | 8.559 | 111.475 | 95.410 | 1.00 | 14.32 | A | C |
| ATOM | 675 | CE2 | PHE | A | 102 | 6.221 | 111.563 | 95.889 | 1.00 | 12.45 | A | C |
| ATOM | 676 | CZ | PHE | A | 102 | 7.496 | 112.027 | 96.111 | 1.00 | 10.71 | A | C |
| ATOM | 677 | C | PHE | A | 102 | 6.879 | 108.070 | 90.962 | 1.00 | 16.67 | A | C |
| ATOM | 678 | O | PHE | A | 102 | 5.860 | 107.576 | 90.489 | 1.00 | 18.68 | A | O |
| ATOM | 679 | N | ALA | A | 103 | 8.091 | 107.546 | 90.813 | 1.00 | 18.82 | A | N |
| ATOM | 680 | CA | ALA | A | 103 | 8.353 | 106.301 | 90.101 | 1.00 | 16.42 | A | C |
| ATOM | 681 | CB | ALA | A | 103 | 9.167 | 106.561 | 88.865 | 1.00 | 13.76 | A | C |
| ATOM | 682 | C | ALA | A | 103 | 9.178 | 105.555 | 91.134 | 1.00 | 17.76 | A | C |
| ATOM | 683 | O | ALA | A | 103 | 10.270 | 105.995 | 91.485 | 1.00 | 19.72 | A | O |
| ATOM | 684 | N | TYR | A | 104 | 8.652 | 104.444 | 91.638 | 1.00 | 19.24 | A | N |
| ATOM | 685 | CA | TYR | A | 104 | 9.337 | 103.678 | 92.677 | 1.00 | 18.75 | A | C |
| ATOM | 686 | CB | TYR | A | 104 | 8.640 | 103.903 | 94.020 | 1.00 | 20.29 | A | C |
| ATOM | 687 | CG | TYR | A | 104 | 9.117 | 102.973 | 95.112 | 1.00 | 22.19 | A | C |
| ATOM | 688 | CD1 | TYR | A | 104 | 9.041 | 101.597 | 94.955 | 1.00 | 20.33 | A | C |
| ATOM | 689 | CE1 | TYR | A | 104 | 9.486 | 100.747 | 95.925 | 1.00 | 20.78 | A | C |
| ATOM | 690 | CD2 | TYR | A | 104 | 9.659 | 103.471 | 96.294 | 1.00 | 22.12 | A | C |
| ATOM | 691 | CE2 | TYR | A | 104 | 10.110 | 102.616 | 97.280 | 1.00 | 19.29 | A | C |
| ATOM | 692 | CZ | TYR | A | 104 | 10.019 | 101.254 | 97.086 | 1.00 | 20.58 | A | C |
| ATOM | 693 | OH | TYR | A | 104 | 10.454 | 100.381 | 98.053 | 1.00 | 20.22 | A | O |
| ATOM | 694 | C | TYR | A | 104 | 9.389 | 102.192 | 92.394 | 1.00 | 19.64 | A | C |
| ATOM | 695 | O | TYR | A | 104 | 8.374 | 101.592 | 92.041 | 1.00 | 21.36 | A | O |
| ATOM | 696 | N | GLY | A | 105 | 10.564 | 101.591 | 92.576 | 1.00 | 20.18 | A | N |
| ATOM | 697 | CA | GLY | A | 105 | 10.705 | 100.166 | 92.328 | 1.00 | 18.67 | A | C |
| ATOM | 698 | C | GLY | A | 105 | 12.139 | 99.725 | 92.158 | 1.00 | 19.94 | A | C |
| ATOM | 699 | O | GLY | A | 105 | 13.047 | 100.548 | 92.173 | 1.00 | 20.08 | A | O |
| ATOM | 700 | N | GLN | A | 106 | 12.336 | 98.419 | 91.990 | 1.00 | 21.51 | A | N |
| ATOM | 701 | CA | GLN | A | 106 | 13.667 | 97.829 | 91.815 | 1.00 | 19.72 | A | C |
| ATOM | 702 | CB | GLN | A | 106 | 13.561 | 96.316 | 91.934 | 1.00 | 17.42 | A | C |
| ATOM | 703 | CG | GLN | A | 106 | 14.626 | 95.559 | 91.211 | 1.00 | 17.49 | A | C |
| ATOM | 704 | CD | GLN | A | 106 | 14.250 | 94.108 | 91.023 | 1.00 | 20.09 | A | C |
| ATOM | 705 | OE1 | GLN | A | 106 | 13.175 | 93.794 | 90.494 | 1.00 | 21.43 | A | O |
| ATOM | 706 | NE2 | GLN | A | 106 | 15.130 | 93.213 | 91.444 | 1.00 | 16.08 | A | N |
| ATOM | 707 | C | GLN | A | 106 | 14.335 | 98.190 | 90.495 | 1.00 | 18.70 | A | C |
| ATOM | 708 | O | GLN | A | 106 | 13.679 | 98.250 | 89.461 | 1.00 | 20.20 | A | O |
| ATOM | 709 | N | THR | A | 107 | 15.648 | 98.415 | 90.536 | 1.00 | 19.47 | A | N |
| ATOM | 710 | CA | THR | A | 107 | 16.414 | 98.779 | 89.339 | 1.00 | 18.97 | A | C |
| ATOM | 711 | CB | THR | A | 107 | 17.954 | 98.786 | 89.612 | 1.00 | 19.61 | A | C |
| ATOM | 712 | OG1 | THR | A | 107 | 18.282 | 99.830 | 90.537 | 1.00 | 24.52 | A | O |
| ATOM | 713 | CG2 | THR | A | 107 | 18.734 | 99.023 | 88.314 | 1.00 | 15.97 | A | C |
| ATOM | 714 | C | THR | A | 107 | 16.129 | 97.836 | 88.177 | 1.00 | 17.53 | A | C |
| ATOM | 715 | O | THR | A | 107 | 16.127 | 96.612 | 88.333 | 1.00 | 17.81 | A | O |
| ATOM | 716 | N | GLY | A | 108 | 15.890 | 98.418 | 87.010 | 1.00 | 16.27 | A | N |
| ATOM | 717 | CA | GLY | A | 108 | 15.605 | 97.621 | 85.837 | 1.00 | 16.82 | A | C |
| ATOM | 718 | C | GLY | A | 108 | 14.143 | 97.251 | 85.646 | 1.00 | 13.84 | A | C |
| ATOM | 719 | O | GLY | A | 108 | 13.839 | 96.486 | 84.754 | 1.00 | 13.49 | A | O |
| ATOM | 720 | N | THR | A | 109 | 13.240 | 97.770 | 86.471 | 1.00 | 13.72 | A | N |
| ATOM | 721 | CA | THR | A | 109 | 11.822 | 97.456 | 86.302 | 1.00 | 15.65 | A | C |
| ATOM | 722 | CB | THR | A | 109 | 11.121 | 97.164 | 87.657 | 1.00 | 14.36 | A | C |
| ATOM | 723 | OG1 | THR | A | 109 | 11.207 | 98.306 | 88.514 | 1.00 | 19.52 | A | O |
| ATOM | 724 | CG2 | THR | A | 109 | 11.773 | 95.987 | 88.339 | 1.00 | 15.86 | A | C |
| ATOM | 725 | C | THR | A | 109 | 11.036 | 98.553 | 85.558 | 1.00 | 15.32 | A | C |
| ATOM | 726 | O | THR | A | 109 | 9.855 | 98.379 | 85.255 | 1.00 | 17.62 | A | O |
| ATOM | 727 | N | GLY | A | 110 | 11.675 | 99.682 | 85.277 | 1.00 | 10.29 | A | N |
| ATOM | 728 | CA | GLY | A | 110 | 10.982 | 100.719 | 84.541 | 1.00 | 13.56 | A | C |
| ATOM | 729 | C | GLY | A | 110 | 10.908 | 102.143 | 85.062 | 1.00 | 12.05 | A | C |
| ATOM | 730 | O | GLY | A | 110 | 10.227 | 102.961 | 84.448 | 1.00 | 14.49 | A | O |
| ATOM | 731 | N | LYS | A | 111 | 11.584 | 102.453 | 86.165 | 1.00 | 10.25 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 732 | CA | LYS | A | 111 | 11.557 | 103.803 | 86.725 | 1.00 | 10.48 | A | C |
| ATOM | 733 | CB | LYS | A | 111 | 12.576 | 103.935 | 87.877 | 1.00 | 11.70 | A | C |
| ATOM | 734 | CG | LYS | A | 111 | 12.140 | 103.402 | 89.270 | 1.00 | 12.05 | A | C |
| ATOM | 735 | CD | LYS | A | 111 | 13.374 | 103.148 | 90.168 | 1.00 | 8.12 | A | C |
| ATOM | 736 | CE | LYS | A | 111 | 14.302 | 102.108 | 89.502 | 1.00 | 15.36 | A | C |
| ATOM | 737 | NZ | LYS | A | 111 | 15.706 | 101.994 | 90.021 | 1.00 | 9.77 | A | N |
| ATOM | 738 | C | LYS | A | 111 | 11.851 | 104.884 | 85.663 | 1.00 | 12.30 | A | C |
| ATOM | 739 | O | LYS | A | 111 | 11.005 | 105.737 | 85.379 | 1.00 | 10.39 | A | O |
| ATOM | 740 | N | THR | A | 112 | 13.037 | 104.836 | 85.060 | 1.00 | 11.75 | A | N |
| ATOM | 741 | CA | THR | A | 112 | 13.405 | 105.845 | 84.072 | 1.00 | 12.73 | A | C |
| ATOM | 742 | CB | THR | A | 112 | 14.917 | 105.848 | 83.826 | 1.00 | 11.20 | A | C |
| ATOM | 743 | OG1 | THR | A | 112 | 15.588 | 106.044 | 85.070 | 1.00 | 16.11 | A | O |
| ATOM | 744 | CG2 | THR | A | 112 | 15.308 | 106.972 | 82.882 | 1.00 | 10.18 | A | C |
| ATOM | 745 | C | THR | A | 112 | 12.674 | 105.720 | 82.740 | 1.00 | 12.67 | A | C |
| ATOM | 746 | O | THR | A | 112 | 12.424 | 106.721 | 82.064 | 1.00 | 10.95 | A | O |
| ATOM | 747 | N | PHE | A | 113 | 12.337 | 104.500 | 82.349 | 1.00 | 12.81 | A | N |
| ATOM | 748 | CA | PHE | A | 113 | 11.605 | 104.316 | 81.103 | 1.00 | 13.31 | A | C |
| ATOM | 749 | CB | PHE | A | 113 | 11.345 | 102.831 | 80.849 | 1.00 | 13.42 | A | C |
| ATOM | 750 | CG | PHE | A | 113 | 10.497 | 102.569 | 79.647 | 1.00 | 9.96 | A | C |
| ATOM | 751 | CD1 | PHE | A | 113 | 11.002 | 102.762 | 78.370 | 1.00 | 11.62 | A | C |
| ATOM | 752 | CD2 | PHE | A | 113 | 9.183 | 102.149 | 79.792 | 1.00 | 7.67 | A | C |
| ATOM | 753 | CE1 | PHE | A | 113 | 10.208 | 102.540 | 77.260 | 1.00 | 10.01 | A | C |
| ATOM | 754 | CE2 | PHE | A | 113 | 8.387 | 101.929 | 78.689 | 1.00 | 7.52 | A | C |
| ATOM | 755 | CZ | PHE | A | 113 | 8.898 | 102.123 | 77.422 | 1.00 | 8.59 | A | C |
| ATOM | 756 | C | PHE | A | 113 | 10.267 | 105.055 | 81.204 | 1.00 | 14.11 | A | C |
| ATOM | 757 | O | PHE | A | 113 | 9.842 | 105.729 | 80.269 | 1.00 | 12.94 | A | O |
| ATOM | 758 | N | THR | A | 114 | 9.611 | 104.912 | 82.354 | 1.00 | 14.23 | A | N |
| ATOM | 759 | CA | THR | A | 114 | 8.324 | 105.553 | 82.613 | 1.00 | 11.85 | A | C |
| ATOM | 760 | CB | THR | A | 114 | 7.743 | 105.094 | 83.964 | 1.00 | 10.43 | A | C |
| ATOM | 761 | OG1 | THR | A | 114 | 7.604 | 103.672 | 83.974 | 1.00 | 13.89 | A | O |
| ATOM | 762 | CG2 | THR | A | 114 | 6.390 | 105.745 | 84.225 | 1.00 | 5.85 | A | C |
| ATOM | 763 | C | THR | A | 114 | 8.473 | 107.074 | 82.681 | 1.00 | 14.01 | A | C |
| ATOM | 764 | O | THR | A | 114 | 7.765 | 107.810 | 81.993 | 1.00 | 16.39 | A | O |
| ATOM | 765 | N | MET | A | 115 | 9.401 | 107.535 | 83.513 | 1.00 | 13.06 | A | N |
| ATOM | 766 | CA | MET | A | 115 | 9.620 | 108.965 | 83.715 | 1.00 | 15.53 | A | C |
| ATOM | 767 | CB | MET | A | 115 | 10.438 | 109.196 | 84.986 | 1.00 | 14.02 | A | C |
| ATOM | 768 | CG | MET | A | 115 | 9.992 | 110.409 | 85.769 | 1.00 | 17.21 | A | C |
| ATOM | 769 | SD | MET | A | 115 | 8.260 | 110.274 | 86.340 | 1.00 | 15.14 | A | S |
| ATOM | 770 | CE | MET | A | 115 | 8.307 | 108.685 | 87.072 | 1.00 | 16.48 | A | C |
| ATOM | 771 | C | MET | A | 115 | 10.265 | 109.739 | 82.565 | 1.00 | 15.91 | A | C |
| ATOM | 772 | O | MET | A | 115 | 9.899 | 110.885 | 82.329 | 1.00 | 14.67 | A | O |
| ATOM | 773 | N | GLU | A | 116 | 11.209 | 109.124 | 81.853 | 1.00 | 16.89 | A | N |
| ATOM | 774 | CA | GLU | A | 116 | 11.876 | 109.802 | 80.748 | 1.00 | 17.69 | A | C |
| ATOM | 775 | CB | GLU | A | 116 | 13.398 | 109.758 | 80.936 | 1.00 | 17.63 | A | C |
| ATOM | 776 | CG | GLU | A | 116 | 13.877 | 110.332 | 82.259 | 1.00 | 16.03 | A | C |
| ATOM | 777 | CD | GLU | A | 116 | 15.377 | 110.507 | 82.341 | 1.00 | 13.88 | A | C |
| ATOM | 778 | OE1 | GLU | A | 116 | 15.853 | 110.903 | 83.417 | 1.00 | 16.89 | A | O |
| ATOM | 779 | OE2 | GLU | A | 116 | 16.087 | 110.262 | 81.349 | 1.00 | 15.45 | A | O |
| ATOM | 780 | C | GLU | A | 116 | 11.523 | 109.232 | 79.377 | 1.00 | 19.27 | A | C |
| ATOM | 781 | O | GLU | A | 116 | 11.171 | 109.976 | 78.465 | 1.00 | 21.50 | A | O |
| ATOM | 782 | N | GLY | A | 117 | 11.620 | 107.916 | 79.229 | 1.00 | 17.83 | A | N |
| ATOM | 783 | CA | GLY | A | 117 | 11.323 | 107.300 | 77.949 | 1.00 | 19.66 | A | C |
| ATOM | 784 | C | GLY | A | 117 | 12.575 | 107.156 | 77.098 | 1.00 | 20.75 | A | C |
| ATOM | 785 | O | GLY | A | 117 | 13.678 | 107.371 | 77.587 | 1.00 | 21.75 | A | O |
| ATOM | 786 | N | GLU | A | 118 | 12.408 | 106.800 | 75.825 | 1.00 | 22.99 | A | N |
| ATOM | 787 | CA | GLU | A | 118 | 13.539 | 106.629 | 74.904 | 1.00 | 26.12 | A | C |
| ATOM | 788 | CB | GLU | A | 118 | 14.109 | 105.211 | 75.016 | 1.00 | 25.69 | A | C |
| ATOM | 789 | CG | GLU | A | 118 | 14.018 | 104.615 | 76.394 | 1.00 | 26.96 | A | C |
| ATOM | 790 | CD | GLU | A | 118 | 14.421 | 103.167 | 76.416 | 1.00 | 26.96 | A | C |
| ATOM | 791 | OE1 | GLU | A | 118 | 14.148 | 102.485 | 75.398 | 1.00 | 27.75 | A | O |
| ATOM | 792 | OE2 | GLU | A | 118 | 14.988 | 102.717 | 77.444 | 1.00 | 20.76 | A | O |
| ATOM | 793 | C | GLU | A | 118 | 13.105 | 106.846 | 73.452 | 1.00 | 26.22 | A | C |
| ATOM | 794 | O | GLU | A | 118 | 11.912 | 106.850 | 73.146 | 1.00 | 25.09 | A | O |
| ATOM | 795 | N | ARG | A | 119 | 14.074 | 107.021 | 72.560 | 1.00 | 26.87 | A | N |
| ATOM | 796 | CA | ARG | A | 119 | 13.766 | 107.188 | 71.141 | 1.00 | 28.87 | A | C |
| ATOM | 797 | CB | ARG | A | 119 | 14.959 | 107.786 | 70.381 | 1.00 | 31.88 | A | C |
| ATOM | 798 | CG | ARG | A | 119 | 15.490 | 109.113 | 70.890 | 1.00 | 39.69 | A | C |
| ATOM | 799 | CD | ARG | A | 119 | 14.700 | 110.303 | 70.355 | 1.00 | 43.56 | A | C |
| ATOM | 800 | NE | ARG | A | 119 | 14.687 | 110.373 | 68.897 | 1.00 | 46.08 | A | N |
| ATOM | 801 | CZ | ARG | A | 119 | 14.461 | 111.490 | 68.212 | 1.00 | 46.47 | A | C |
| ATOM | 802 | NH1 | ARG | A | 119 | 14.237 | 112.630 | 68.854 | 1.00 | 46.40 | A | N |
| ATOM | 803 | NH2 | ARG | A | 119 | 14.456 | 111.467 | 66.884 | 1.00 | 46.44 | A | N |
| ATOM | 804 | C | ARG | A | 119 | 13.527 | 105.776 | 70.598 | 1.00 | 28.96 | A | C |
| ATOM | 805 | O | ARG | A | 119 | 14.157 | 104.815 | 71.061 | 1.00 | 28.33 | A | O |
| ATOM | 806 | N | SER | A | 120 | 12.623 | 105.634 | 69.633 | 1.00 | 28.30 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 807 | CA | SER | A | 120 | 12.389 | 104.318 | 69.038 | 1.00 | 29.06 | A | C |
| ATOM | 808 | CB | SER | A | 120 | 11.035 | 104.267 | 68.332 | 1.00 | 25.56 | A | C |
| ATOM | 809 | OG | SER | A | 120 | 9.990 | 104.572 | 69.219 | 1.00 | 23.87 | A | O |
| ATOM | 810 | C | SER | A | 120 | 13.485 | 104.080 | 68.001 | 1.00 | 30.08 | A | C |
| ATOM | 811 | O | SER | A | 120 | 13.881 | 105.005 | 67.287 | 1.00 | 29.09 | A | O |
| ATOM | 812 | N | PRO | A | 121 | 14.007 | 102.846 | 67.916 | 1.00 | 32.12 | A | N |
| ATOM | 813 | CD | PRO | A | 121 | 13.754 | 101.661 | 68.753 | 1.00 | 33.98 | A | C |
| ATOM | 814 | CA | PRO | A | 121 | 15.055 | 102.573 | 66.926 | 1.00 | 35.39 | A | C |
| ATOM | 815 | CB | PRO | A | 121 | 15.334 | 101.085 | 67.117 | 1.00 | 34.26 | A | C |
| ATOM | 816 | CG | PRO | A | 121 | 15.025 | 100.864 | 68.567 | 1.00 | 33.95 | A | C |
| ATOM | 817 | C | PRO | A | 121 | 14.437 | 102.856 | 65.566 | 1.00 | 37.36 | A | C |
| ATOM | 818 | O | PRO | A | 121 | 15.116 | 103.247 | 64.613 | 1.00 | 38.15 | A | O |
| ATOM | 819 | N | ASN | A | 122 | 13.122 | 102.659 | 65.513 | 1.00 | 38.79 | A | N |
| ATOM | 820 | CA | ASN | A | 122 | 12.324 | 102.864 | 64.314 | 1.00 | 40.01 | A | C |
| ATOM | 821 | CB | ASN | A | 122 | 10.870 | 102.443 | 64.577 | 1.00 | 43.53 | A | C |
| ATOM | 822 | CG | ASN | A | 122 | 10.764 | 101.187 | 65.445 | 1.00 | 43.82 | A | C |
| ATOM | 823 | OD1 | ASN | A | 122 | 9.727 | 100.515 | 65.469 | 1.00 | 43.76 | A | O |
| ATOM | 824 | ND2 | ASN | A | 122 | 11.831 | 100.877 | 66.169 | 1.00 | 43.66 | A | N |
| ATOM | 825 | C | ASN | A | 122 | 12.369 | 104.334 | 63.931 | 1.00 | 38.79 | A | C |
| ATOM | 826 | O | ASN | A | 122 | 11.422 | 104.849 | 63.349 | 1.00 | 38.16 | A | O |
| ATOM | 827 | N | GLU | A | 123 | 13.483 | 104.978 | 64.279 | 1.00 | 38.16 | A | N |
| ATOM | 828 | CA | GLU | A | 123 | 13.773 | 106.399 | 64.035 | 1.00 | 38.45 | A | C |
| ATOM | 829 | CB | GLU | A | 123 | 15.213 | 106.533 | 63.513 | 1.00 | 39.20 | A | C |
| ATOM | 830 | CG | GLU | A | 123 | 16.285 | 106.064 | 64.503 | 1.00 | 40.67 | A | C |
| ATOM | 831 | CD | GLU | A | 123 | 17.685 | 105.970 | 63.886 | 1.00 | 43.36 | A | C |
| ATOM | 832 | OE1 | GLU | A | 123 | 18.185 | 106.995 | 63.365 | 1.00 | 41.73 | A | O |
| ATOM | 833 | OE2 | GLU | A | 123 | 18.286 | 104.866 | 63.930 | 1.00 | 41.18 | A | O |
| ATOM | 834 | C | GLU | A | 123 | 12.824 | 107.180 | 63.120 | 1.00 | 36.76 | A | C |
| ATOM | 835 | O | GLU | A | 123 | 13.259 | 108.054 | 62.376 | 1.00 | 38.25 | A | O |
| ATOM | 836 | N | GLU | A | 124 | 11.530 | 106.898 | 63.206 | 1.00 | 35.31 | A | N |
| ATOM | 837 | CA | GLU | A | 124 | 10.541 | 107.558 | 62.363 | 1.00 | 36.90 | A | C |
| ATOM | 838 | CB | GLU | A | 124 | 9.691 | 106.490 | 61.636 | 1.00 | 39.26 | A | C |
| ATOM | 839 | CG | GLU | A | 124 | 8.814 | 107.015 | 60.482 | 1.00 | 43.17 | A | C |
| ATOM | 840 | CD | GLU | A | 124 | 8.896 | 106.148 | 59.218 | 1.00 | 45.74 | A | C |
| ATOM | 841 | OE1 | GLU | A | 124 | 9.961 | 106.144 | 58.559 | 1.00 | 48.70 | A | O |
| ATOM | 842 | OE2 | GLU | A | 124 | 7.898 | 105.470 | 58.882 | 1.00 | 46.19 | A | O |
| ATOM | 843 | C | GLU | A | 124 | 9.647 | 108.501 | 63.176 | 1.00 | 35.42 | A | C |
| ATOM | 844 | O | GLU | A | 124 | 8.430 | 108.555 | 62.967 | 1.00 | 35.40 | A | O |
| ATOM | 845 | N | TYR | A | 125 | 10.251 | 109.249 | 64.096 | 1.00 | 30.43 | A | N |
| ATOM | 846 | CA | TYR | A | 125 | 9.487 | 110.176 | 64.920 | 1.00 | 26.77 | A | C |
| ATOM | 847 | CB | TYR | A | 125 | 8.842 | 109.439 | 66.097 | 1.00 | 24.44 | A | C |
| ATOM | 848 | CG | TYR | A | 125 | 7.986 | 108.251 | 65.727 | 1.00 | 25.43 | A | C |
| ATOM | 849 | CD1 | TYR | A | 125 | 6.706 | 108.416 | 65.213 | 1.00 | 25.55 | A | C |
| ATOM | 850 | CE1 | TYR | A | 125 | 5.935 | 107.322 | 64.859 | 1.00 | 27.08 | A | C |
| ATOM | 851 | CD2 | TYR | A | 125 | 8.470 | 106.959 | 65.878 | 1.00 | 24.95 | A | C |
| ATOM | 852 | CE2 | TYR | A | 125 | 7.716 | 105.863 | 65.528 | 1.00 | 24.73 | A | C |
| ATOM | 853 | CZ | TYR | A | 125 | 6.448 | 106.044 | 65.016 | 1.00 | 28.47 | A | C |
| ATOM | 854 | OH | TYR | A | 125 | 5.711 | 104.939 | 64.640 | 1.00 | 25.69 | A | O |
| ATOM | 855 | C | TYR | A | 125 | 10.340 | 111.301 | 65.487 | 1.00 | 26.27 | A | C |
| ATOM | 856 | O | TYR | A | 125 | 11.504 | 111.096 | 65.817 | 1.00 | 27.28 | A | O |
| ATOM | 857 | N | THR | A | 126 | 9.769 | 112.498 | 65.566 | 1.00 | 25.19 | A | N |
| ATOM | 858 | CA | THR | A | 126 | 10.469 | 113.612 | 66.186 | 1.00 | 26.85 | A | C |
| ATOM | 859 | CB | THR | A | 126 | 9.799 | 114.975 | 65.840 | 1.00 | 28.99 | A | C |
| ATOM | 860 | OG1 | THR | A | 126 | 8.387 | 114.912 | 66.081 | 1.00 | 30.38 | A | O |
| ATOM | 861 | CG2 | THR | A | 126 | 10.015 | 115.310 | 64.382 | 1.00 | 31.91 | A | C |
| ATOM | 862 | C | THR | A | 126 | 10.200 | 113.215 | 67.638 | 1.00 | 28.05 | A | C |
| ATOM | 863 | O | THR | A | 126 | 9.457 | 112.255 | 67.868 | 1.00 | 25.55 | A | O |
| ATOM | 864 | N | TRP | A | 127 | 10.761 | 113.895 | 68.630 | 1.00 | 28.18 | A | N |
| ATOM | 865 | CA | TRP | A | 127 | 10.470 | 113.431 | 69.982 | 1.00 | 27.79 | A | C |
| ATOM | 866 | CB | TRP | A | 127 | 11.422 | 114.042 | 71.021 | 1.00 | 23.88 | A | C |
| ATOM | 867 | CG | TRP | A | 127 | 11.343 | 115.517 | 71.192 | 1.00 | 22.59 | A | C |
| ATOM | 868 | CD2 | TRP | A | 127 | 10.515 | 116.234 | 72.130 | 1.00 | 21.57 | A | C |
| ATOM | 869 | CE2 | TRP | A | 127 | 10.831 | 117.601 | 72.003 | 1.00 | 21.20 | A | C |
| ATOM | 870 | CE3 | TRP | A | 127 | 9.543 | 115.851 | 73.061 | 1.00 | 18.21 | A | C |
| ATOM | 871 | CD1 | TRP | A | 127 | 12.094 | 116.452 | 70.550 | 1.00 | 20.68 | A | C |
| ATOM | 872 | NE1 | TRP | A | 127 | 11.797 | 117.707 | 71.036 | 1.00 | 23.82 | A | N |
| ATOM | 873 | CZ2 | TRP | A | 127 | 10.210 | 118.589 | 72.774 | 1.00 | 20.83 | A | C |
| ATOM | 874 | CZ3 | TRP | A | 127 | 8.930 | 116.830 | 73.826 | 1.00 | 17.66 | A | C |
| ATOM | 875 | CH2 | TRP | A | 127 | 9.265 | 118.184 | 73.679 | 1.00 | 17.45 | A | C |
| ATOM | 876 | C | TRP | A | 127 | 9.017 | 113.625 | 70.416 | 1.00 | 27.92 | A | C |
| ATOM | 877 | O | TRP | A | 127 | 8.445 | 112.734 | 71.047 | 1.00 | 30.72 | A | O |
| ATOM | 878 | N | GLU | A | 128 | 8.412 | 114.756 | 70.062 | 1.00 | 25.61 | A | N |
| ATOM | 879 | CA | GLU | A | 128 | 7.029 | 115.027 | 70.441 | 1.00 | 24.76 | A | C |
| ATOM | 880 | CB | GLU | A | 128 | 6.609 | 116.446 | 70.034 | 1.00 | 26.91 | A | C |
| ATOM | 881 | CG | GLU | A | 128 | 7.539 | 117.552 | 70.482 | 1.00 | 29.32 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 882 | CD | GLU | A | 128 | 8.522 | 117.937 | 69.400 | 1.00 | 32.79 | A | C |
| ATOM | 883 | OE1 | GLU | A | 128 | 9.268 | 117.050 | 68.922 | 1.00 | 33.19 | A | O |
| ATOM | 884 | OE2 | GLU | A | 128 | 8.544 | 119.129 | 69.023 | 1.00 | 37.80 | A | O |
| ATOM | 885 | C | GLU | A | 128 | 6.025 | 114.049 | 69.841 | 1.00 | 24.40 | A | C |
| ATOM | 886 | O | GLU | A | 128 | 4.840 | 114.125 | 70.135 | 1.00 | 26.98 | A | O |
| ATOM | 887 | N | GLU | A | 129 | 6.472 | 113.133 | 68.996 | 1.00 | 24.46 | A | N |
| ATOM | 888 | CA | GLU | A | 129 | 5.528 | 112.195 | 68.414 | 1.00 | 24.98 | A | C |
| ATOM | 889 | CB | GLU | A | 129 | 5.321 | 112.537 | 66.935 | 1.00 | 28.90 | A | C |
| ATOM | 890 | CG | GLU | A | 129 | 4.680 | 113.930 | 66.733 | 1.00 | 34.97 | A | C |
| ATOM | 891 | CD | GLU | A | 129 | 4.514 | 114.348 | 65.263 | 1.00 | 37.45 | A | C |
| ATOM | 892 | OE1 | GLU | A | 129 | 5.534 | 114.497 | 64.548 | 1.00 | 35.56 | A | O |
| ATOM | 893 | OE2 | GLU | A | 129 | 3.352 | 114.538 | 64.831 | 1.00 | 39.16 | A | O |
| ATOM | 894 | C | GLU | A | 129 | 5.931 | 110.731 | 68.614 | 1.00 | 25.88 | A | C |
| ATOM | 895 | O | GLU | A | 129 | 5.179 | 109.817 | 68.270 | 1.00 | 23.20 | A | O |
| ATOM | 896 | N | ASP | A | 130 | 7.109 | 110.524 | 69.204 | 1.00 | 24.49 | A | N |
| ATOM | 897 | CA | ASP | A | 130 | 7.638 | 109.191 | 69.486 | 1.00 | 23.60 | A | C |
| ATOM | 898 | CB | ASP | A | 130 | 9.100 | 109.326 | 69.948 | 1.00 | 20.85 | A | C |
| ATOM | 899 | CG | ASP | A | 130 | 9.868 | 108.019 | 69.883 | 1.00 | 18.05 | A | C |
| ATOM | 900 | OD1 | ASP | A | 130 | 11.092 | 108.061 | 69.628 | 1.00 | 19.43 | A | O |
| ATOM | 901 | OD2 | ASP | A | 130 | 9.266 | 106.950 | 70.101 | 1.00 | 19.15 | A | O |
| ATOM | 902 | C | ASP | A | 130 | 6.778 | 108.494 | 70.568 | 1.00 | 24.54 | A | C |
| ATOM | 903 | O | ASP | A | 130 | 6.608 | 109.002 | 71.677 | 1.00 | 23.51 | A | O |
| ATOM | 904 | N | PRO | A | 131 | 6.225 | 107.317 | 70.246 | 1.00 | 23.90 | A | N |
| ATOM | 905 | CD | PRO | A | 131 | 6.381 | 106.612 | 68.967 | 1.00 | 21.27 | A | C |
| ATOM | 906 | CA | PRO | A | 131 | 5.382 | 106.542 | 71.161 | 1.00 | 24.51 | A | C |
| ATOM | 907 | CB | PRO | A | 131 | 4.946 | 105.352 | 70.305 | 1.00 | 23.64 | A | C |
| ATOM | 908 | CG | PRO | A | 131 | 5.116 | 105.838 | 68.898 | 1.00 | 20.98 | A | C |
| ATOM | 909 | C | PRO | A | 131 | 6.114 | 106.073 | 72.419 | 1.00 | 25.13 | A | C |
| ATOM | 910 | O | PRO | A | 131 | 5.477 | 105.693 | 73.398 | 1.00 | 25.30 | A | O |
| ATOM | 911 | N | LEU | A | 132 | 7.446 | 106.091 | 72.380 | 1.00 | 23.49 | A | N |
| ATOM | 912 | CA | LEU | A | 132 | 8.252 | 105.633 | 73.509 | 1.00 | 21.42 | A | C |
| ATOM | 913 | CB | LEU | A | 132 | 9.504 | 104.907 | 73.003 | 1.00 | 19.42 | A | C |
| ATOM | 914 | CG | LEU | A | 132 | 9.204 | 103.695 | 72.119 | 1.00 | 19.80 | A | C |
| ATOM | 915 | CD1 | LEU | A | 132 | 10.502 | 102.996 | 71.729 | 1.00 | 21.64 | A | C |
| ATOM | 916 | CD2 | LEU | A | 132 | 8.291 | 102.737 | 72.870 | 1.00 | 16.43 | A | C |
| ATOM | 917 | C | LEU | A | 132 | 8.660 | 106.732 | 74.476 | 1.00 | 19.53 | A | C |
| ATOM | 918 | O | LEU | A | 132 | 9.376 | 106.480 | 75.436 | 1.00 | 21.96 | A | O |
| ATOM | 919 | N | ALA | A | 133 | 8.208 | 107.952 | 74.226 | 1.00 | 18.19 | A | N |
| ATOM | 920 | CA | ALA | A | 133 | 8.529 | 109.070 | 75.105 | 1.00 | 16.28 | A | C |
| ATOM | 921 | CB | ALA | A | 133 | 8.092 | 110.370 | 74.467 | 1.00 | 13.92 | A | C |
| ATOM | 922 | C | ALA | A | 133 | 7.836 | 108.886 | 76.463 | 1.00 | 15.58 | A | C |
| ATOM | 923 | O | ALA | A | 133 | 6.713 | 108.395 | 76.541 | 1.00 | 15.09 | A | O |
| ATOM | 924 | N | GLY | A | 134 | 8.515 | 109.281 | 77.530 | 1.00 | 15.32 | A | N |
| ATOM | 925 | CA | GLY | A | 134 | 7.942 | 109.137 | 78.850 | 1.00 | 13.54 | A | C |
| ATOM | 926 | C | GLY | A | 134 | 7.219 | 110.388 | 79.313 | 1.00 | 15.50 | A | C |
| ATOM | 927 | O | GLY | A | 134 | 7.077 | 111.362 | 78.577 | 1.00 | 14.04 | A | O |
| ATOM | 928 | N | ILE | A | 135 | 6.769 | 110.361 | 80.559 | 1.00 | 14.50 | A | N |
| ATOM | 929 | CA | ILE | A | 135 | 6.054 | 111.469 | 81.143 | 1.00 | 13.18 | A | C |
| ATOM | 930 | CB | ILE | A | 135 | 5.795 | 111.186 | 82.605 | 1.00 | 15.26 | A | C |
| ATOM | 931 | CG2 | ILE | A | 135 | 4.944 | 112.292 | 83.210 | 1.00 | 17.34 | A | C |
| ATOM | 932 | CG1 | ILE | A | 135 | 5.125 | 109.825 | 82.735 | 1.00 | 16.12 | A | C |
| ATOM | 933 | CD1 | ILE | A | 135 | 4.980 | 109.353 | 84.159 | 1.00 | 18.86 | A | C |
| ATOM | 934 | C | ILE | A | 135 | 6.735 | 112.836 | 81.020 | 1.00 | 14.90 | A | C |
| ATOM | 935 | O | ILE | A | 135 | 6.098 | 113.802 | 80.586 | 1.00 | 15.64 | A | O |
| ATOM | 936 | N | ILE | A | 136 | 8.009 | 112.944 | 81.400 | 1.00 | 12.28 | A | N |
| ATOM | 937 | CA | ILE | A | 136 | 8.671 | 114.246 | 81.319 | 1.00 | 12.49 | A | C |
| ATOM | 938 | CB | ILE | A | 136 | 10.181 | 114.142 | 81.628 | 1.00 | 8.72 | A | C |
| ATOM | 939 | CG2 | ILE | A | 136 | 10.884 | 115.433 | 81.262 | 1.00 | 5.85 | A | C |
| ATOM | 940 | CG1 | ILE | A | 136 | 10.369 | 113.870 | 83.130 | 1.00 | 11.82 | A | C |
| ATOM | 941 | CD1 | ILE | A | 136 | 11.757 | 113.381 | 83.538 | 1.00 | 10.45 | A | C |
| ATOM | 942 | C | ILE | A | 136 | 8.439 | 114.921 | 79.966 | 1.00 | 11.50 | A | C |
| ATOM | 943 | O | ILE | A | 136 | 7.858 | 115.993 | 79.899 | 1.00 | 11.72 | A | O |
| ATOM | 944 | N | PRO | A | 137 | 8.872 | 114.287 | 78.873 | 1.00 | 13.96 | A | N |
| ATOM | 945 | CD | PRO | A | 137 | 9.586 | 112.999 | 78.866 | 1.00 | 17.39 | A | C |
| ATOM | 946 | CA | PRO | A | 137 | 8.721 | 114.802 | 77.511 | 1.00 | 13.93 | A | C |
| ATOM | 947 | CB | PRO | A | 137 | 9.275 | 113.666 | 76.651 | 1.00 | 15.54 | A | C |
| ATOM | 948 | CG | PRO | A | 137 | 10.270 | 113.024 | 77.527 | 1.00 | 15.26 | A | C |
| ATOM | 949 | C | PRO | A | 137 | 7.278 | 115.159 | 77.120 | 1.00 | 13.93 | A | C |
| ATOM | 950 | O | PRO | A | 137 | 7.029 | 116.270 | 76.645 | 1.00 | 14.92 | A | O |
| ATOM | 951 | N | ARG | A | 138 | 6.343 | 114.222 | 77.311 | 1.00 | 11.39 | A | N |
| ATOM | 952 | CA | ARG | A | 138 | 4.928 | 114.436 | 76.967 | 1.00 | 9.89 | A | C |
| ATOM | 953 | CB | ARG | A | 138 | 4.103 | 113.163 | 77.188 | 1.00 | 9.30 | A | C |
| ATOM | 954 | CG | ARG | A | 138 | 4.488 | 111.975 | 76.325 | 1.00 | 11.27 | A | C |
| ATOM | 955 | CD | ARG | A | 138 | 3.871 | 110.697 | 76.876 | 1.00 | 13.22 | A | C |
| ATOM | 956 | NE | ARG | A | 138 | 4.187 | 109.531 | 76.058 | 1.00 | 14.81 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 957 | CZ | ARG | A | 138 | 3.590 | 109.227 | 74.911 | 1.00 | 17.08 | A | C |
| ATOM | 958 | NH1 | ARG | A | 138 | 2.623 | 109.999 | 74.429 | 1.00 | 17.89 | A | N |
| ATOM | 959 | NH2 | ARG | A | 138 | 3.981 | 108.159 | 74.234 | 1.00 | 17.91 | A | N |
| ATOM | 960 | C | ARG | A | 138 | 4.301 | 115.550 | 77.796 | 1.00 | 10.60 | A | C |
| ATOM | 961 | O | ARG | A | 138 | 3.359 | 116.194 | 77.368 | 1.00 | 12.56 | A | O |
| ATOM | 962 | N | THR | A | 139 | 4.824 | 115.770 | 78.991 | 1.00 | 12.08 | A | N |
| ATOM | 963 | CA | THR | A | 139 | 4.294 | 116.801 | 79.858 | 1.00 | 13.83 | A | C |
| ATOM | 964 | CB | THR | A | 139 | 4.759 | 116.580 | 81.293 | 1.00 | 15.73 | A | C |
| ATOM | 965 | OG1 | THR | A | 139 | 4.290 | 115.300 | 81.743 | 1.00 | 15.51 | A | O |
| ATOM | 966 | CG2 | THR | A | 139 | 4.225 | 117.689 | 82.204 | 1.00 | 10.72 | A | C |
| ATOM | 967 | C | THR | A | 139 | 4.706 | 118.196 | 79.410 | 1.00 | 16.89 | A | C |
| ATOM | 968 | O | THR | A | 139 | 3.891 | 119.133 | 79.419 | 1.00 | 17.83 | A | O |
| ATOM | 969 | N | LEU | A | 140 | 5.966 | 118.347 | 79.017 | 1.00 | 17.05 | A | N |
| ATOM | 970 | CA | LEU | A | 140 | 6.459 | 119.652 | 78.579 | 1.00 | 18.83 | A | C |
| ATOM | 971 | CB | LEU | A | 140 | 7.974 | 119.616 | 78.378 | 1.00 | 17.85 | A | C |
| ATOM | 972 | CG | LEU | A | 140 | 8.763 | 119.270 | 79.639 | 1.00 | 20.58 | A | C |
| ATOM | 973 | CD1 | LEU | A | 140 | 10.250 | 119.253 | 79.326 | 1.00 | 22.51 | A | C |
| ATOM | 974 | CD2 | LEU | A | 140 | 8.449 | 120.276 | 80.729 | 1.00 | 19.56 | A | C |
| ATOM | 975 | C | LEU | A | 140 | 5.780 | 120.077 | 77.288 | 1.00 | 18.74 | A | C |
| ATOM | 976 | O | LEU | A | 140 | 5.487 | 121.249 | 77.088 | 1.00 | 19.69 | A | O |
| ATOM | 977 | N | HIS | A | 141 | 5.533 | 119.107 | 76.415 | 1.00 | 20.28 | A | N |
| ATOM | 978 | CA | HIS | A | 141 | 4.879 | 119.366 | 75.146 | 1.00 | 19.97 | A | C |
| ATOM | 979 | CB | HIS | A | 141 | 4.822 | 118.088 | 74.313 | 1.00 | 21.32 | A | C |
| ATOM | 980 | CG | HIS | A | 141 | 4.264 | 118.285 | 72.937 | 1.00 | 23.67 | A | C |
| ATOM | 981 | CD2 | HIS | A | 141 | 3.258 | 117.659 | 72.286 | 1.00 | 25.06 | A | C |
| ATOM | 982 | ND1 | HIS | A | 141 | 4.782 | 119.202 | 72.047 | 1.00 | 23.21 | A | N |
| ATOM | 983 | CE1 | HIS | A | 141 | 4.121 | 119.129 | 70.907 | 1.00 | 21.74 | A | C |
| ATOM | 984 | NE2 | HIS | A | 141 | 3.192 | 118.200 | 71.026 | 1.00 | 20.93 | A | N |
| ATOM | 985 | C | HIS | A | 141 | 3.477 | 119.860 | 75.419 | 1.00 | 18.80 | A | C |
| ATOM | 986 | O | HIS | A | 141 | 3.040 | 120.863 | 74.862 | 1.00 | 19.96 | A | O |
| ATOM | 987 | N | GLN | A | 142 | 2.774 | 119.150 | 76.289 | 1.00 | 17.40 | A | N |
| ATOM | 988 | CA | GLN | A | 142 | 1.418 | 119.528 | 76.650 | 1.00 | 19.83 | A | C |
| ATOM | 989 | CA | GLN | A | 142 | 0.843 | 118.499 | 77.622 | 1.00 | 20.70 | A | C |
| ATOM | 990 | CG | GLN | A | 142 | 0.549 | 117.159 | 76.972 | 1.00 | 25.59 | A | C |
| ATOM | 991 | CD | GLN | A | 142 | −0.494 | 117.272 | 75.874 | 1.00 | 29.46 | A | C |
| ATOM | 992 | OE1 | GLN | A | 142 | −1.592 | 117.788 | 76.102 | 1.00 | 30.45 | A | O |
| ATOM | 993 | NE2 | GLN | A | 142 | −0.161 | 116.788 | 74.676 | 1.00 | 27.67 | A | N |
| ATOM | 994 | C | GLN | A | 142 | 1.315 | 120.944 | 77.240 | 1.00 | 19.22 | A | C |
| ATOM | 995 | O | GLN | A | 142 | 0.409 | 121.694 | 76.881 | 1.00 | 17.32 | A | O |
| ATOM | 996 | N | ILE | A | 143 | 2.238 | 121.307 | 78.132 | 1.00 | 17.92 | A | N |
| ATOM | 997 | CA | ILE | A | 143 | 2.224 | 122.634 | 78.749 | 1.00 | 18.63 | A | C |
| ATOM | 998 | CB | ILE | A | 143 | 3.479 | 122.895 | 79.609 | 1.00 | 20.61 | A | C |
| ATOM | 999 | CG2 | ILE | A | 143 | 3.599 | 124.386 | 79.911 | 1.00 | 20.13 | A | C |
| ATOM | 1000 | CG1 | ILE | A | 143 | 3.402 | 122.111 | 80.921 | 1.00 | 22.18 | A | C |
| ATOM | 1001 | CD1 | ILE | A | 143 | 4.620 | 122.287 | 81.809 | 1.00 | 17.71 | A | C |
| ATOM | 1002 | C | ILE | A | 143 | 2.174 | 123.729 | 77.699 | 1.00 | 19.46 | A | C |
| ATOM | 1003 | O | ILE | A | 143 | 1.359 | 124.655 | 77.782 | 1.00 | 18.82 | A | O |
| ATOM | 1004 | N | PHE | A | 144 | 3.070 | 123.628 | 76.722 | 1.00 | 17.85 | A | N |
| ATOM | 1005 | CA | PHE | A | 144 | 3.140 | 124.602 | 75.639 | 1.00 | 18.64 | A | C |
| ATOM | 1006 | CB | PHE | A | 144 | 4.397 | 124.353 | 74.813 | 1.00 | 19.02 | A | C |
| ATOM | 1007 | CG | PHE | A | 144 | 5.654 | 124.793 | 75.501 | 1.00 | 23.65 | A | C |
| ATOM | 1008 | CD1 | PHE | A | 144 | 6.059 | 126.120 | 75.452 | 1.00 | 22.97 | A | C |
| ATOM | 1009 | CD2 | PHE | A | 144 | 6.404 | 123.893 | 76.246 | 1.00 | 25.56 | A | C |
| ATOM | 1010 | CE1 | PHE | A | 144 | 7.189 | 126.540 | 76.135 | 1.00 | 23.56 | A | C |
| ATOM | 1011 | CE2 | PHE | A | 144 | 7.534 | 124.306 | 76.932 | 1.00 | 23.99 | A | C |
| ATOM | 1012 | CZ | PHE | A | 144 | 7.927 | 125.633 | 76.877 | 1.00 | 23.53 | A | C |
| ATOM | 1013 | C | PHE | A | 144 | 1.901 | 124.544 | 74.758 | 1.00 | 18.58 | A | C |
| ATOM | 1014 | O | PHE | A | 144 | 1.306 | 125.561 | 74.437 | 1.00 | 17.12 | A | O |
| ATOM | 1015 | N | GLU | A | 145 | 1.515 | 123.337 | 74.381 | 1.00 | 19.51 | A | N |
| ATOM | 1016 | CA | GLU | A | 145 | 0.347 | 123.117 | 73.553 | 1.00 | 18.70 | A | C |
| ATOM | 1017 | CB | GLU | A | 145 | 0.214 | 121.622 | 73.298 | 1.00 | 21.25 | A | C |
| ATOM | 1018 | CG | GLU | A | 145 | 0.211 | 121.230 | 71.847 | 1.00 | 25.41 | A | C |
| ATOM | 1019 | CD | GLU | A | 145 | −1.181 | 121.226 | 71.260 | 1.00 | 27.49 | A | C |
| ATOM | 1020 | OE1 | GLU | A | 145 | −1.765 | 122.317 | 71.113 | 1.00 | 27.98 | A | O |
| ATOM | 1021 | OE2 | GLU | A | 145 | −1.686 | 120.120 | 70.958 | 1.00 | 30.13 | A | O |
| ATOM | 1022 | C | GLU | A | 145 | −0.924 | 123.649 | 74.219 | 1.00 | 19.01 | A | C |
| ATOM | 1023 | O | GLU | A | 145 | −1.698 | 124.387 | 73.616 | 1.00 | 16.70 | A | O |
| ATOM | 1024 | N | LYS | A | 146 | −1.129 | 123.275 | 75.474 | 1.00 | 20.75 | A | N |
| ATOM | 1025 | CA | LYS | A | 146 | −2.314 | 123.684 | 76.215 | 1.00 | 22.08 | A | C |
| ATOM | 1026 | CB | LYS | A | 146 | −2.337 | 122.964 | 77.566 | 1.00 | 26.10 | A | C |
| ATOM | 1027 | CG | LYS | A | 146 | −3.700 | 122.434 | 77.985 | 1.00 | 32.24 | A | C |
| ATOM | 1028 | CD | LYS | A | 146 | −3.737 | 120.906 | 77.922 | 1.00 | 34.41 | A | C |
| ATOM | 1029 | CE | LYS | A | 146 | −2.734 | 120.303 | 78.895 | 1.00 | 35.54 | A | C |
| ATOM | 1030 | NZ | LYS | A | 146 | −2.526 | 118.837 | 78.687 | 1.00 | 39.31 | A | N |
| ATOM | 1031 | C | LYS | A | 146 | −2.425 | 125.202 | 76.443 | 1.00 | 23.07 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1032 | O | LYS | A | 146 | −3.438 | 125.822 | 76.104 | 1.00 | 23.12 | A | O |
| ATOM | 1033 | N | LEU | A | 147 | −1.384 | 125.797 | 77.017 | 1.00 | 22.75 | A | N |
| ATOM | 1034 | CA | LEU | A | 147 | −1.388 | 127.220 | 77.319 | 1.00 | 22.42 | A | C |
| ATOM | 1035 | CB | LEU | A | 147 | −0.211 | 127.545 | 78.232 | 1.00 | 20.98 | A | C |
| ATOM | 1036 | CG | LEU | A | 147 | −0.200 | 126.705 | 79.511 | 1.00 | 23.78 | A | C |
| ATOM | 1037 | CD1 | LEU | A | 147 | 1.025 | 127.057 | 80.342 | 1.00 | 24.50 | A | C |
| ATOM | 1038 | CD2 | LEU | A | 147 | −1.483 | 126.933 | 80.308 | 1.00 | 21.54 | A | C |
| ATOM | 1039 | C | LEU | A | 147 | −1.375 | 128.124 | 76.086 | 1.00 | 24.45 | A | C |
| ATOM | 1040 | O | LEU | A | 147 | −1.995 | 129.192 | 76.078 | 1.00 | 27.97 | A | O |
| ATOM | 1041 | N | THR | A | 148 | −0.661 | 127.713 | 75.048 | 1.00 | 23.76 | A | N |
| ATOM | 1042 | CA | THR | A | 148 | −0.617 | 128.490 | 73.817 | 1.00 | 23.05 | A | C |
| ATOM | 1043 | CB | THR | A | 148 | 0.442 | 127.920 | 72.831 | 1.00 | 23.51 | A | C |
| ATOM | 1044 | OG1 | THR | A | 148 | 1.758 | 128.137 | 73.360 | 1.00 | 25.68 | A | O |
| ATOM | 1045 | CG2 | THR | A | 148 | 0.330 | 128.585 | 71.470 | 1.00 | 20.45 | A | C |
| ATOM | 1046 | C | THR | A | 148 | −1.995 | 128.429 | 73.151 | 1.00 | 22.63 | A | C |
| ATOM | 1047 | O | THR | A | 148 | −2.445 | 129.392 | 72.550 | 1.00 | 20.03 | A | O |
| ATOM | 1048 | N | ASP | A | 149 | −2.664 | 127.290 | 73.278 | 1.00 | 25.44 | A | N |
| ATOM | 1049 | CA | ASP | A | 149 | −3.975 | 127.104 | 72.672 | 1.00 | 27.30 | A | C |
| ATOM | 1050 | CB | ASP | A | 149 | −4.416 | 125.641 | 72.792 | 1.00 | 30.81 | A | C |
| ATOM | 1051 | CG | ASP | A | 149 | −5.586 | 125.311 | 71.882 | 1.00 | 34.97 | A | C |
| ATOM | 1052 | OD1 | ASP | A | 149 | −5.457 | 125.524 | 70.651 | 1.00 | 33.93 | A | O |
| ATOM | 1053 | OD2 | ASP | A | 149 | −6.628 | 124.842 | 72.399 | 1.00 | 35.40 | A | O |
| ATOM | 1054 | C | ASP | A | 149 | −5.047 | 128.013 | 73.260 | 1.00 | 26.60 | A | C |
| ATOM | 1055 | O | ASP | A | 149 | −5.883 | 128.534 | 72.522 | 1.00 | 24.42 | A | O |
| ATOM | 1056 | N | ASN | A | 150 | −5.040 | 128.204 | 74.579 | 1.00 | 27.01 | A | N |
| ATOM | 1057 | CA | ASN | A | 150 | −6.046 | 129.071 | 75.186 | 1.00 | 27.37 | A | C |
| ATOM | 1058 | CB | ASN | A | 150 | −6.477 | 128.556 | 76.577 | 1.00 | 26.89 | A | C |
| ATOM | 1059 | CG | ASN | A | 150 | −5.323 | 128.413 | 77.553 | 1.00 | 27.79 | A | C |
| ATOM | 1060 | OD1 | ASN | A | 150 | −4.434 | 129.265 | 77.636 | 1.00 | 28.17 | A | O |
| ATOM | 1061 | ND2 | ASN | A | 150 | −5.347 | 127.338 | 78.320 | 1.00 | 29.92 | A | N |
| ATOM | 1062 | C | ASN | A | 150 | −5.577 | 130.521 | 75.263 | 1.00 | 27.18 | A | C |
| ATOM | 1063 | O | ASN | A | 150 | −6.288 | 131.388 | 75.767 | 1.00 | 25.16 | A | O |
| ATOM | 1064 | N | GLY | A | 151 | −4.376 | 130.773 | 74.751 | 1.00 | 28.69 | A | N |
| ATOM | 1065 | CA | GLY | A | 151 | −3.822 | 132.116 | 74.738 | 1.00 | 28.79 | A | C |
| ATOM | 1066 | C | GLY | A | 151 | −3.390 | 132.701 | 76.070 | 1.00 | 29.13 | A | C |
| ATOM | 1067 | O | GLY | A | 151 | −3.459 | 133.909 | 76.261 | 1.00 | 28.25 | A | O |
| ATOM | 1068 | N | THR | A | 152 | −2.931 | 131.860 | 76.989 | 1.00 | 30.47 | A | N |
| ATOM | 1069 | CA | THR | A | 152 | −2.492 | 132.332 | 78.303 | 1.00 | 30.84 | A | C |
| ATOM | 1070 | CB | THR | A | 152 | −2.490 | 131.175 | 79.347 | 1.00 | 31.96 | A | C |
| ATOM | 1071 | OG1 | THR | A | 152 | −3.792 | 130.583 | 79.428 | 1.00 | 32.43 | A | O |
| ATOM | 1072 | CG2 | THR | A | 152 | −2.105 | 131.698 | 80.716 | 1.00 | 33.65 | A | C |
| ATOM | 1073 | C | THR | A | 152 | −1.076 | 132.916 | 78.255 | 1.00 | 30.02 | A | C |
| ATOM | 1074 | O | THR | A | 152 | −0.216 | 132.418 | 77.524 | 1.00 | 29.69 | A | O |
| ATOM | 1075 | N | GLU | A | 153 | −0.840 | 133.979 | 79.025 | 1.00 | 29.60 | A | N |
| ATOM | 1076 | CA | GLU | A | 153 | 0.489 | 134.591 | 79.101 | 1.00 | 27.76 | A | C |
| ATOM | 1077 | CB | GLU | A | 153 | 0.404 | 136.042 | 79.601 | 1.00 | 27.20 | A | C |
| ATOM | 1078 | CG | GLU | A | 153 | 1.742 | 136.793 | 79.577 | 1.00 | 29.51 | A | C |
| ATOM | 1079 | CD | GLU | A | 153 | 1.628 | 138.272 | 79.981 | 1.00 | 31.77 | A | C |
| ATOM | 1080 | OE1 | GLU | A | 153 | 0.874 | 139.023 | 79.327 | 1.00 | 32.79 | A | O |
| ATOM | 1081 | OE2 | GLU | A | 153 | 2.299 | 138.688 | 80.950 | 1.00 | 30.00 | A | O |
| ATOM | 1082 | C | GLU | A | 153 | 1.227 | 133.726 | 80.118 | 1.00 | 25.69 | A | C |
| ATOM | 1083 | O | GLU | A | 153 | 0.823 | 133.639 | 81.279 | 1.00 | 27.36 | A | O |
| ATOM | 1084 | N | PHE | A | 154 | 2.303 | 133.080 | 79.690 | 1.00 | 24.41 | A | N |
| ATOM | 1085 | CA | PHE | A | 154 | 3.018 | 132.193 | 80.594 | 1.00 | 22.37 | A | C |
| ATOM | 1086 | CB | PHE | A | 154 | 2.418 | 130.789 | 80.494 | 1.00 | 20.69 | A | C |
| ATOM | 1087 | CG | PHE | A | 154 | 2.701 | 130.112 | 79.184 | 1.00 | 18.84 | A | C |
| ATOM | 1088 | CD1 | PHE | A | 154 | 3.768 | 129.234 | 79.054 | 1.00 | 19.30 | A | C |
| ATOM | 1089 | CD2 | PHE | A | 154 | 1.913 | 130.369 | 78.071 | 1.00 | 18.45 | A | C |
| ATOM | 1090 | CE1 | PHE | A | 154 | 4.043 | 128.620 | 77.836 | 1.00 | 19.75 | A | C |
| ATOM | 1091 | CE2 | PHE | A | 154 | 2.181 | 129.761 | 76.849 | 1.00 | 17.04 | A | C |
| ATOM | 1092 | CZ | PHE | A | 154 | 3.248 | 128.885 | 76.733 | 1.00 | 17.90 | A | C |
| ATOM | 1093 | C | PHE | A | 154 | 4.498 | 132.094 | 80.302 | 1.00 | 20.68 | A | C |
| ATOM | 1094 | O | PHE | A | 154 | 4.929 | 132.302 | 79.168 | 1.00 | 20.73 | A | O |
| ATOM | 1095 | N | SER | A | 155 | 5.267 | 131.768 | 81.337 | 1.00 | 17.88 | A | N |
| ATOM | 1096 | CA | SER | A | 155 | 6.699 | 131.572 | 81.200 | 1.00 | 17.73 | A | C |
| ATOM | 1097 | CB | SER | A | 155 | 7.483 | 132.692 | 81.892 | 1.00 | 20.69 | A | C |
| ATOM | 1098 | OG | SER | A | 155 | 7.341 | 132.653 | 83.302 | 1.00 | 25.15 | A | O |
| ATOM | 1099 | C | SER | A | 155 | 6.997 | 130.231 | 81.851 | 1.00 | 17.38 | A | C |
| ATOM | 1100 | O | SER | A | 155 | 6.400 | 129.890 | 82.864 | 1.00 | 19.12 | A | O |
| ATOM | 1101 | N | VAL | A | 156 | 7.913 | 129.471 | 81.260 | 1.00 | 19.18 | A | N |
| ATOM | 1102 | CA | VAL | A | 156 | 8.290 | 128.150 | 81.766 | 1.00 | 16.97 | A | C |
| ATOM | 1103 | CB | VAL | A | 156 | 7.989 | 127.053 | 80.723 | 1.00 | 15.20 | A | C |
| ATOM | 1104 | CG1 | VAL | A | 156 | 8.583 | 125.723 | 81.167 | 1.00 | 13.57 | A | C |
| ATOM | 1105 | CG2 | VAL | A | 156 | 6.492 | 126.922 | 80.525 | 1.00 | 15.31 | A | C |
| ATOM | 1106 | C | VAL | A | 156 | 9.768 | 128.033 | 82.124 | 1.00 | 19.33 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1107 | O | VAL | A | 156 | 10.647 | 128.436 | 81.351 | 1.00 | 19.06 | A | O |
| ATOM | 1108 | N | LYS | A | 157 | 10.044 | 127.478 | 83.300 | 1.00 | 20.71 | A | N |
| ATOM | 1109 | CA | LYS | A | 157 | 11.420 | 127.264 | 83.723 | 1.00 | 22.37 | A | C |
| ATOM | 1110 | CB | LYS | A | 157 | 11.889 | 128.388 | 84.662 | 1.00 | 22.07 | A | C |
| ATOM | 1111 | CG | LYS | A | 157 | 11.021 | 128.644 | 85.874 | 1.00 | 26.35 | A | C |
| ATOM | 1112 | CD | LYS | A | 157 | 11.486 | 129.918 | 86.592 | 1.00 | 28.09 | A | C |
| ATOM | 1113 | CE | LYS | A | 157 | 10.547 | 130.291 | 87.734 | 1.00 | 30.50 | A | C |
| ATOM | 1114 | NZ | LYS | A | 157 | 10.934 | 131.579 | 88.370 | 1.00 | 35.72 | A | N |
| ATOM | 1115 | C | LYS | A | 157 | 11.540 | 125.889 | 84.379 | 1.00 | 20.35 | A | C |
| ATOM | 1116 | O | LYS | A | 157 | 10.592 | 125.402 | 84.994 | 1.00 | 20.92 | A | O |
| ATOM | 1117 | N | VAL | A | 158 | 12.702 | 125.262 | 84.219 | 1.00 | 17.92 | A | N |
| ATOM | 1118 | CA | VAL | A | 158 | 12.947 | 123.929 | 84.767 | 1.00 | 19.39 | A | C |
| ATOM | 1119 | CB | VAL | A | 158 | 13.127 | 122.889 | 83.655 | 1.00 | 19.65 | A | C |
| ATOM | 1120 | CG1 | VAL | A | 158 | 11.881 | 122.827 | 82.770 | 1.00 | 21.76 | A | C |
| ATOM | 1121 | CG2 | VAL | A | 158 | 14.356 | 123.237 | 82.833 | 1.00 | 17.06 | A | C |
| ATOM | 1122 | C | VAL | A | 158 | 14.194 | 123.845 | 85.628 | 1.00 | 20.80 | A | C |
| ATOM | 1123 | O | VAL | A | 158 | 15.015 | 124.765 | 85.663 | 1.00 | 24.80 | A | O |
| ATOM | 1124 | N | SER | A | 159 | 14.335 | 122.715 | 86.312 | 1.00 | 19.14 | A | N |
| ATOM | 1125 | CA | SER | A | 159 | 15.482 | 122.462 | 87.172 | 1.00 | 18.25 | A | C |
| ATOM | 1126 | CB | SER | A | 159 | 15.309 | 123.151 | 88.524 | 1.00 | 18.04 | A | C |
| ATOM | 1127 | OG | SER | A | 159 | 14.263 | 122.553 | 89.257 | 1.00 | 21.67 | A | O |
| ATOM | 1128 | C | SER | A | 159 | 15.589 | 120.961 | 87.373 | 1.00 | 18.18 | A | C |
| ATOM | 1129 | O | SER | A | 159 | 14.592 | 120.243 | 87.326 | 1.00 | 17.13 | A | O |
| ATOM | 1130 | N | LEU | A | 160 | 16.806 | 120.484 | 87.591 | 1.00 | 20.17 | A | N |
| ATOM | 1131 | CA | LEU | A | 160 | 17.029 | 119.067 | 87.788 | 1.00 | 21.04 | A | C |
| ATOM | 1132 | CB | LEU | A | 160 | 17.285 | 118.368 | 86.446 | 1.00 | 23.34 | A | C |
| ATOM | 1133 | CG | LEU | A | 160 | 17.450 | 116.843 | 86.539 | 1.00 | 25.79 | A | C |
| ATOM | 1134 | CD1 | LEU | A | 160 | 16.146 | 116.224 | 87.032 | 1.00 | 26.24 | A | C |
| ATOM | 1135 | CD2 | LEU | A | 160 | 17.829 | 116.257 | 85.182 | 1.00 | 25.56 | A | C |
| ATOM | 1136 | C | LEU | A | 160 | 18.214 | 118.833 | 88.696 | 1.00 | 21.71 | A | C |
| ATOM | 1137 | O | LEU | A | 160 | 19.349 | 119.140 | 88.350 | 1.00 | 22.07 | A | O |
| ATOM | 1138 | N | LEU | A | 161 | 17.955 | 118.300 | 89.877 | 1.00 | 23.63 | A | N |
| ATOM | 1139 | CA | LEU | A | 161 | 19.057 | 118.005 | 90.776 | 1.00 | 25.12 | A | C |
| ATOM | 1140 | CB | LEU | A | 161 | 18.957 | 118.807 | 92.078 | 1.00 | 26.26 | A | C |
| ATOM | 1141 | CG | LEU | A | 161 | 17.760 | 118.647 | 93.004 | 1.00 | 22.98 | A | C |
| ATOM | 1142 | CD1 | LEU | A | 161 | 17.385 | 117.195 | 93.160 | 1.00 | 23.81 | A | C |
| ATOM | 1143 | CD2 | LEU | A | 161 | 18.140 | 119.255 | 94.340 | 1.00 | 24.49 | A | C |
| ATOM | 1144 | C | LEU | A | 161 | 19.079 | 116.519 | 91.078 | 1.00 | 24.19 | A | C |
| ATOM | 1145 | O | LEU | A | 161 | 18.122 | 115.799 | 90.813 | 1.00 | 23.98 | A | O |
| ATOM | 1146 | N | GLU | A | 162 | 20.183 | 116.056 | 91.630 | 1.00 | 24.57 | A | N |
| ATOM | 1147 | CA | GLU | A | 162 | 20.302 | 114.650 | 91.937 | 1.00 | 27.14 | A | C |
| ATOM | 1148 | CB | GLU | A | 162 | 21.299 | 114.006 | 90.977 | 1.00 | 28.32 | A | C |
| ATOM | 1149 | CG | GLU | A | 162 | 21.656 | 112.574 | 91.305 | 1.00 | 32.54 | A | C |
| ATOM | 1150 | CD | GLU | A | 162 | 22.767 | 112.044 | 90.411 | 1.00 | 34.31 | A | C |
| ATOM | 1151 | OE1 | GLU | A | 162 | 22.555 | 111.944 | 89.181 | 1.00 | 34.91 | A | O |
| ATOM | 1152 | OE2 | GLU | A | 162 | 23.853 | 111.733 | 90.941 | 1.00 | 36.54 | A | O |
| ATOM | 1153 | C | GLU | A | 162 | 20.758 | 114.466 | 93.369 | 1.00 | 25.84 | A | C |
| ATOM | 1154 | O | GLU | A | 162 | 21.796 | 114.997 | 93.764 | 1.00 | 25.10 | A | O |
| ATOM | 1155 | N | ILE | A | 163 | 19.960 | 113.747 | 94.153 | 1.00 | 22.59 | A | N |
| ATOM | 1156 | CA | ILE | A | 163 | 20.319 | 113.469 | 95.532 | 1.00 | 22.22 | A | C |
| ATOM | 1157 | CB | ILE | A | 163 | 19.078 | 113.238 | 96.428 | 1.00 | 20.01 | A | C |
| ATOM | 1158 | CG2 | ILE | A | 163 | 19.494 | 113.141 | 97.891 | 1.00 | 18.67 | A | C |
| ATOM | 1159 | CG1 | ILE | A | 163 | 18.102 | 114.400 | 96.291 | 1.00 | 19.31 | A | C |
| ATOM | 1160 | CD1 | ILE | A | 163 | 16.878 | 114.242 | 97.141 | 1.00 | 14.94 | A | C |
| ATOM | 1161 | C | ILE | A | 163 | 21.132 | 112.179 | 95.521 | 1.00 | 22.25 | A | C |
| ATOM | 1162 | O | ILE | A | 163 | 20.718 | 111.186 | 94.939 | 1.00 | 20.14 | A | O |
| ATOM | 1163 | N | TYR | A | 164 | 22.298 | 112.192 | 96.147 | 1.00 | 23.63 | A | N |
| ATOM | 1164 | CA | TYR | A | 164 | 23.104 | 110.983 | 96.197 | 1.00 | 26.96 | A | C |
| ATOM | 1165 | CB | TYR | A | 164 | 24.060 | 110.912 | 95.009 | 1.00 | 27.69 | A | C |
| ATOM | 1166 | CG | TYR | A | 164 | 25.012 | 109.753 | 95.124 | 1.00 | 30.07 | A | C |
| ATOM | 1167 | CD1 | TYR | A | 164 | 26.339 | 109.951 | 95.481 | 1.00 | 30.15 | A | C |
| ATOM | 1168 | CE1 | TYR | A | 164 | 27.191 | 108.876 | 95.684 | 1.00 | 29.28 | A | C |
| ATOM | 1169 | CD2 | TYR | A | 164 | 24.563 | 108.446 | 94.965 | 1.00 | 30.80 | A | C |
| ATOM | 1170 | CE2 | TYR | A | 164 | 25.408 | 107.369 | 95.173 | 1.00 | 29.59 | A | C |
| ATOM | 1171 | CZ | TYR | A | 164 | 26.719 | 107.592 | 95.535 | 1.00 | 28.75 | A | C |
| ATOM | 1172 | OH | TYR | A | 164 | 27.554 | 106.526 | 95.788 | 1.00 | 32.05 | A | O |
| ATOM | 1173 | C | TYR | A | 164 | 23.882 | 110.896 | 97.499 | 1.00 | 28.14 | A | C |
| ATOM | 1174 | O | TYR | A | 164 | 24.785 | 111.686 | 97.750 | 1.00 | 28.73 | A | O |
| ATOM | 1175 | N | ASN | A | 165 | 23.517 | 109.926 | 98.329 | 1.00 | 30.67 | A | N |
| ATOM | 1176 | CA | ASN | A | 165 | 24.163 | 109.741 | 99.617 | 1.00 | 30.48 | A | C |
| ATOM | 1177 | CB | ASN | A | 165 | 25.650 | 109.441 | 99.428 | 1.00 | 33.85 | A | C |
| ATOM | 1178 | CG | ASN | A | 165 | 26.343 | 109.109 | 100.729 | 1.00 | 37.24 | A | C |
| ATOM | 1179 | OD1 | ASN | A | 165 | 25.842 | 108.305 | 101.519 | 1.00 | 38.47 | A | O |
| ATOM | 1180 | ND2 | ASN | A | 165 | 27.505 | 109.721 | 100.963 | 1.00 | 39.69 | A | N |
| ATOM | 1181 | C | ASN | A | 165 | 23.990 | 110.988 | 100.470 | 1.00 | 30.06 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1182 | O | ASN | A | 165 | 24.945 | 111.460 | 101.080 | 1.00 | 30.17 | A | O |
| ATOM | 1183 | N | GLU | A | 166 | 22.771 | 111.521 | 100.500 | 1.00 | 29.22 | A | N |
| ATOM | 1184 | CA | GLU | A | 166 | 22.468 | 112.716 | 101.285 | 1.00 | 29.02 | A | C |
| ATOM | 1185 | CB | GLU | A | 166 | 23.046 | 112.581 | 102.699 | 1.00 | 32.29 | A | C |
| ATOM | 1186 | CG | GLU | A | 166 | 22.194 | 111.751 | 103.633 | 1.00 | 36.91 | A | C |
| ATOM | 1187 | CD | GLU | A | 166 | 20.819 | 112.352 | 103.833 | 1.00 | 40.07 | A | C |
| ATOM | 1188 | OE1 | GLU | A | 166 | 20.109 | 112.584 | 102.822 | 1.00 | 42.45 | A | O |
| ATOM | 1189 | OE2 | GLU | A | 166 | 20.451 | 112.591 | 105.002 | 1.00 | 42.27 | A | O |
| ATOM | 1190 | C | GLU | A | 166 | 22.942 | 114.045 | 100.685 | 1.00 | 28.70 | A | C |
| ATOM | 1191 | O | GLU | A | 166 | 22.670 | 115.111 | 101.237 | 1.00 | 26.71 | A | O |
| ATOM | 1192 | N | GLU | A | 167 | 23.656 | 113.997 | 99.568 | 1.00 | 26.15 | A | N |
| ATOM | 1193 | CA | GLU | A | 167 | 24.111 | 115.237 | 98.967 | 1.00 | 27.09 | A | C |
| ATOM | 1194 | CB | GLU | A | 167 | 25.579 | 115.134 | 98.573 | 1.00 | 29.46 | A | C |
| ATOM | 1195 | CG | GLU | A | 167 | 26.485 | 114.790 | 99.737 | 1.00 | 34.97 | A | C |
| ATOM | 1196 | CD | GLU | A | 167 | 27.923 | 115.200 | 99.498 | 1.00 | 35.62 | A | C |
| ATOM | 1197 | OE1 | GLU | A | 167 | 28.292 | 116.319 | 99.912 | 1.00 | 37.83 | A | O |
| ATOM | 1198 | OE2 | GLU | A | 167 | 28.678 | 114.412 | 98.890 | 1.00 | 35.27 | A | O |
| ATOM | 1199 | C | GLU | A | 167 | 23.280 | 115.639 | 97.757 | 1.00 | 25.73 | A | C |
| ATOM | 1200 | O | GLU | A | 167 | 22.611 | 114.808 | 97.137 | 1.00 | 25.91 | A | O |
| ATOM | 1201 | N | LEU | A | 168 | 23.326 | 116.928 | 97.442 | 1.00 | 22.78 | A | N |
| ATOM | 1202 | CA | LEU | A | 168 | 22.585 | 117.482 | 96.322 | 1.00 | 20.85 | A | C |
| ATOM | 1203 | CB | LEU | A | 168 | 21.706 | 118.630 | 96.812 | 1.00 | 19.02 | A | C |
| ATOM | 1204 | CG | LEU | A | 168 | 20.413 | 118.272 | 97.548 | 1.00 | 18.07 | A | C |
| ATOM | 1205 | CD1 | LEU | A | 168 | 20.536 | 116.965 | 98.279 | 1.00 | 18.28 | A | C |
| ATOM | 1206 | CD2 | LEU | A | 168 | 20.081 | 119.382 | 98.505 | 1.00 | 17.66 | A | C |
| ATOM | 1207 | C | LEU | A | 168 | 23.539 | 117.983 | 95.251 | 1.00 | 20.17 | A | C |
| ATOM | 1208 | O | LEU | A | 168 | 24.521 | 118.639 | 95.561 | 1.00 | 19.33 | A | O |
| ATOM | 1209 | N | PHE | A | 169 | 23.255 | 117.659 | 93.993 | 1.00 | 22.06 | A | N |
| ATOM | 1210 | CA | PHE | A | 169 | 24.094 | 118.098 | 92.885 | 1.00 | 22.40 | A | C |
| ATOM | 1211 | CB | PHE | A | 169 | 24.929 | 116.925 | 92.366 | 1.00 | 21.26 | A | C |
| ATOM | 1212 | CG | PHE | A | 169 | 25.814 | 116.304 | 93.419 | 1.00 | 24.53 | A | C |
| ATOM | 1213 | CD1 | PHE | A | 169 | 25.294 | 115.425 | 94.359 | 1.00 | 26.05 | A | C |
| ATOM | 1214 | CD2 | PHE | A | 169 | 27.167 | 116.603 | 93.475 | 1.00 | 26.36 | A | C |
| ATOM | 1215 | CE1 | PHE | A | 169 | 26.106 | 114.856 | 95.331 | 1.00 | 26.65 | A | C |
| ATOM | 1216 | CE2 | PHE | A | 169 | 27.986 | 116.035 | 94.449 | 1.00 | 26.78 | A | C |
| ATOM | 1217 | CZ | PHE | A | 169 | 27.455 | 115.164 | 95.374 | 1.00 | 25.81 | A | C |
| ATOM | 1218 | C | PHE | A | 169 | 23.208 | 118.694 | 91.782 | 1.00 | 22.64 | A | C |
| ATOM | 1219 | O | PHE | A | 169 | 22.064 | 118.271 | 91.608 | 1.00 | 20.82 | A | O |
| ATOM | 1220 | N | ASP | A | 170 | 23.735 | 119.679 | 91.051 | 1.00 | 22.66 | A | N |
| ATOM | 1221 | CA | ASP | A | 170 | 22.981 | 120.366 | 89.998 | 1.00 | 22.30 | A | C |
| ATOM | 1222 | CB | ASP | A | 170 | 23.187 | 121.875 | 90.098 | 1.00 | 19.61 | A | C |
| ATOM | 1223 | CG | ASP | A | 170 | 22.123 | 122.650 | 89.361 | 1.00 | 21.03 | A | C |
| ATOM | 1224 | OD1 | ASP | A | 170 | 21.613 | 122.131 | 88.343 | 1.00 | 19.22 | A | O |
| ATOM | 1225 | OD2 | ASP | A | 170 | 21.804 | 123.777 | 89.795 | 1.00 | 21.48 | A | O |
| ATOM | 1226 | C | ASP | A | 170 | 23.349 | 119.922 | 88.595 | 1.00 | 23.44 | A | C |
| ATOM | 1227 | O | ASP | A | 170 | 24.380 | 120.331 | 88.054 | 1.00 | 25.75 | A | O |
| ATOM | 1228 | N | LEU | A | 171 | 22.480 | 119.117 | 87.990 | 1.00 | 23.27 | A | N |
| ATOM | 1229 | CA | LEU | A | 171 | 22.725 | 118.586 | 86.660 | 1.00 | 20.25 | A | C |
| ATOM | 1230 | CB | LEU | A | 171 | 21.837 | 117.360 | 86.443 | 1.00 | 19.63 | A | C |
| ATOM | 1231 | CG | LEU | A | 171 | 22.077 | 116.275 | 87.505 | 1.00 | 18.88 | A | C |
| ATOM | 1232 | CD1 | LEU | A | 171 | 21.170 | 115.081 | 87.279 | 1.00 | 20.14 | A | C |
| ATOM | 1233 | CD2 | LEU | A | 171 | 23.517 | 115.846 | 87.456 | 1.00 | 17.29 | A | C |
| ATOM | 1234 | C | LEU | A | 171 | 22.546 | 119.583 | 85.525 | 1.00 | 21.57 | A | C |
| ATOM | 1235 | O | LEU | A | 171 | 23.077 | 119.384 | 84.437 | 1.00 | 25.13 | A | O |
| ATOM | 1236 | N | LEU | A | 172 | 21.814 | 120.661 | 85.772 | 1.00 | 23.25 | A | N |
| ATOM | 1237 | CA | LEU | A | 172 | 21.590 | 121.678 | 84.742 | 1.00 | 25.15 | A | C |
| ATOM | 1238 | CB | LEU | A | 172 | 20.135 | 122.161 | 84.798 | 1.00 | 22.50 | A | C |
| ATOM | 1239 | CG | LEU | A | 172 | 19.126 | 121.376 | 83.956 | 1.00 | 19.56 | A | C |
| ATOM | 1240 | CD1 | LEU | A | 172 | 19.487 | 119.926 | 83.982 | 1.00 | 16.35 | A | C |
| ATOM | 1241 | CD2 | LEU | A | 172 | 17.712 | 121.613 | 84.453 | 1.00 | 16.56 | A | C |
| ATOM | 1242 | C | LEU | A | 172 | 22.526 | 122.886 | 84.833 | 1.00 | 27.89 | A | C |
| ATOM | 1243 | O | LEU | A | 172 | 22.196 | 123.963 | 84.340 | 1.00 | 30.34 | A | O |
| ATOM | 1244 | N | ASN | A | 173 | 23.688 | 122.712 | 85.457 | 1.00 | 30.10 | A | N |
| ATOM | 1245 | CA | ASN | A | 173 | 24.646 | 123.802 | 85.605 | 1.00 | 32.86 | A | C |
| ATOM | 1246 | CB | ASN | A | 173 | 25.097 | 123.913 | 87.064 | 1.00 | 34.33 | A | C |
| ATOM | 1247 | CG | ASN | A | 173 | 26.016 | 125.102 | 87.306 | 1.00 | 37.08 | A | C |
| ATOM | 1248 | OD1 | ASN | A | 173 | 26.881 | 125.411 | 86.483 | 1.00 | 37.63 | A | O |
| ATOM | 1249 | ND2 | ASN | A | 173 | 25.845 | 125.763 | 88.449 | 1.00 | 36.61 | A | N |
| ATOM | 1250 | C | ASN | A | 173 | 25.863 | 123.578 | 84.713 | 1.00 | 36.05 | A | C |
| ATOM | 1251 | O | ASN | A | 173 | 26.563 | 122.570 | 84.833 | 1.00 | 37.05 | A | O |
| ATOM | 1252 | N | PRO | A | 174 | 26.138 | 124.527 | 83.808 | 1.00 | 38.71 | A | N |
| ATOM | 1253 | CD | PRO | A | 174 | 25.341 | 125.741 | 83.568 | 1.00 | 38.63 | A | C |
| ATOM | 1254 | CA | PRO | A | 174 | 27.272 | 124.454 | 82.878 | 1.00 | 39.37 | A | C |
| ATOM | 1255 | CB | PRO | A | 174 | 27.192 | 125.784 | 82.134 | 1.00 | 38.93 | A | C |
| ATOM | 1256 | CG | PRO | A | 174 | 25.721 | 126.083 | 82.144 | 1.00 | 39.67 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1257 | C | PRO | A | 174 | 28.619 | 124.270 | 83.582 | 1.00 | 40.68 | A | C |
| ATOM | 1258 | O | PRO | A | 174 | 29.129 | 123.152 | 83.684 | 1.00 | 41.07 | A | O |
| ATOM | 1259 | N | SER | A | 175 | 29.190 | 125.371 | 84.062 | 1.00 | 41.76 | A | N |
| ATOM | 1260 | CA | SER | A | 175 | 30.477 | 125.335 | 84.757 | 1.00 | 44.13 | A | C |
| ATOM | 1261 | CB | SER | A | 175 | 30.926 | 126.756 | 85.108 | 1.00 | 47.05 | A | C |
| ATOM | 1262 | OG | SER | A | 175 | 30.087 | 127.335 | 86.098 | 1.00 | 47.60 | A | O |
| ATOM | 1263 | C | SER | A | 175 | 30.373 | 124.524 | 86.038 | 1.00 | 44.79 | A | C |
| ATOM | 1264 | O | SER | A | 175 | 29.948 | 123.370 | 86.027 | 1.00 | 46.17 | A | O |
| ATOM | 1265 | N | SER | A | 176 | 30.764 | 125.154 | 87.142 | 1.00 | 46.33 | A | N |
| ATOM | 1266 | CA | SER | A | 176 | 30.706 | 124.559 | 88.476 | 1.00 | 47.41 | A | C |
| ATOM | 1267 | CB | SER | A | 176 | 29.253 | 124.195 | 88.820 | 1.00 | 47.21 | A | C |
| ATOM | 1268 | OG | SER | A | 176 | 28.727 | 123.229 | 87.928 | 1.00 | 47.29 | A | O |
| ATOM | 1269 | C | SER | A | 176 | 31.613 | 123.356 | 88.755 | 1.00 | 47.00 | A | C |
| ATOM | 1270 | O | SER | A | 176 | 32.492 | 123.438 | 89.622 | 1.00 | 48.12 | A | O |
| ATOM | 1271 | N | ASP | A | 177 | 31.392 | 122.251 | 88.037 | 1.00 | 44.30 | A | N |
| ATOM | 1272 | CA | ASP | A | 177 | 32.169 | 121.021 | 88.215 | 1.00 | 43.49 | A | C |
| ATOM | 1273 | CB | ASP | A | 177 | 33.472 | 121.301 | 88.976 | 1.00 | 44.02 | A | C |
| ATOM | 1274 | CG | ASP | A | 177 | 34.311 | 120.054 | 89.186 | 1.00 | 45.03 | A | C |
| ATOM | 1275 | OD1 | ASP | A | 177 | 33.829 | 119.099 | 89.833 | 1.00 | 45.25 | A | O |
| ATOM | 1276 | OD2 | ASP | A | 177 | 35.460 | 120.031 | 88.705 | 1.00 | 45.93 | A | O |
| ATOM | 1277 | C | ASP | A | 177 | 31.316 | 120.016 | 88.989 | 1.00 | 42.24 | A | C |
| ATOM | 1278 | O | ASP | A | 177 | 30.846 | 120.300 | 90.088 | 1.00 | 41.58 | A | O |
| ATOM | 1279 | N | VAL | A | 178 | 31.133 | 118.834 | 88.413 | 1.00 | 41.29 | A | N |
| ATOM | 1280 | CA | VAL | A | 178 | 30.306 | 117.791 | 89.012 | 1.00 | 42.33 | A | C |
| ATOM | 1281 | CB | VAL | A | 178 | 30.346 | 116.513 | 88.138 | 1.00 | 42.40 | A | C |
| ATOM | 1282 | CG1 | VAL | A | 178 | 30.197 | 116.899 | 86.672 | 1.00 | 42.78 | A | C |
| ATOM | 1283 | CG2 | VAL | A | 178 | 31.639 | 115.742 | 88.372 | 1.00 | 40.61 | A | C |
| ATOM | 1284 | C | VAL | A | 178 | 30.564 | 117.393 | 90.476 | 1.00 | 42.21 | A | C |
| ATOM | 1285 | O | VAL | A | 178 | 29.751 | 116.680 | 91.068 | 1.00 | 42.47 | A | O |
| ATOM | 1286 | N | SER | A | 179 | 31.668 | 117.844 | 91.068 | 1.00 | 41.58 | A | N |
| ATOM | 1287 | CA | SER | A | 179 | 31.964 | 117.484 | 92.457 | 1.00 | 40.78 | A | C |
| ATOM | 1288 | CB | SER | A | 179 | 33.456 | 117.181 | 92.622 | 1.00 | 41.71 | A | C |
| ATOM | 1289 | OG | SER | A | 179 | 34.246 | 118.335 | 92.384 | 1.00 | 41.80 | A | O |
| ATOM | 1290 | C | SER | A | 179 | 31.564 | 118.555 | 93.472 | 1.00 | 40.05 | A | C |
| ATOM | 1291 | O | SER | A | 179 | 32.048 | 118.547 | 94.603 | 1.00 | 39.37 | A | O |
| ATOM | 1292 | N | GLU | A | 180 | 30.677 | 119.464 | 93.074 | 1.00 | 39.55 | A | N |
| ATOM | 1293 | CA | GLU | A | 180 | 30.230 | 120.548 | 93.947 | 1.00 | 41.07 | A | C |
| ATOM | 1294 | CB | GLU | A | 180 | 30.265 | 121.865 | 93.162 | 1.00 | 42.35 | A | C |
| ATOM | 1295 | CG | GLU | A | 180 | 29.547 | 123.026 | 93.829 | 1.00 | 44.57 | A | C |
| ATOM | 1296 | CD | GLU | A | 180 | 29.599 | 124.305 | 93.000 | 1.00 | 47.29 | A | C |
| ATOM | 1297 | OE1 | GLU | A | 180 | 28.809 | 125.232 | 93.286 | 1.00 | 49.44 | A | O |
| ATOM | 1298 | OE2 | GLU | A | 180 | 30.434 | 124.390 | 92.072 | 1.00 | 46.48 | A | O |
| ATOM | 1299 | C | GLU | A | 180 | 28.828 | 120.307 | 94.523 | 1.00 | 39.19 | A | C |
| ATOM | 1300 | O | GLU | A | 180 | 27.881 | 120.095 | 93.773 | 1.00 | 39.05 | A | O |
| ATOM | 1301 | N | ARG | A | 181 | 28.689 | 120.347 | 95.849 | 1.00 | 36.90 | A | N |
| ATOM | 1302 | CA | ARG | A | 181 | 27.384 | 120.118 | 96.468 | 1.00 | 35.39 | A | C |
| ATOM | 1303 | CB | ARG | A | 181 | 27.521 | 119.268 | 97.735 | 1.00 | 35.60 | A | C |
| ATOM | 1304 | CG | ARG | A | 181 | 28.176 | 117.925 | 97.500 | 1.00 | 38.66 | A | C |
| ATOM | 1305 | CD | ARG | A | 181 | 29.696 | 118.017 | 97.609 | 1.00 | 40.98 | A | C |
| ATOM | 1306 | NE | ARG | A | 181 | 30.149 | 117.923 | 98.997 | 1.00 | 40.75 | A | N |
| ATOM | 1307 | CZ | ARG | A | 181 | 31.420 | 118.003 | 99.378 | 1.00 | 41.29 | A | C |
| ATOM | 1308 | NH1 | ARG | A | 181 | 32.378 | 118.186 | 98.475 | 1.00 | 41.03 | A | N |
| ATOM | 1309 | NH2 | ARG | A | 181 | 31.737 | 117.889 | 100.662 | 1.00 | 40.35 | A | N |
| ATOM | 1310 | C | ARG | A | 181 | 26.630 | 121.398 | 96.806 | 1.00 | 34.19 | A | C |
| ATOM | 1311 | O | ARG | A | 181 | 27.231 | 122.437 | 97.070 | 1.00 | 32.33 | A | O |
| ATOM | 1312 | N | LEU | A | 182 | 25.305 | 121.308 | 96.806 | 1.00 | 32.32 | A | N |
| ATOM | 1313 | CA | LEU | A | 182 | 24.474 | 122.462 | 97.103 | 1.00 | 32.86 | A | C |
| ATOM | 1314 | CB | LEU | A | 182 | 23.227 | 122.466 | 96.216 | 1.00 | 31.46 | A | C |
| ATOM | 1315 | CG | LEU | A | 182 | 23.514 | 122.602 | 94.723 | 1.00 | 29.64 | A | C |
| ATOM | 1316 | CD1 | LEU | A | 182 | 22.217 | 122.916 | 93.989 | 1.00 | 29.22 | A | C |
| ATOM | 1317 | CD2 | LEU | A | 182 | 24.527 | 123.712 | 94.504 | 1.00 | 25.26 | A | C |
| ATOM | 1318 | C | LEU | A | 182 | 24.063 | 122.526 | 98.563 | 1.00 | 33.11 | A | C |
| ATOM | 1319 | O | LEU | A | 182 | 23.963 | 121.516 | 99.248 | 1.00 | 34.30 | A | O |
| ATOM | 1320 | N | GLN | A | 183 | 23.822 | 123.737 | 99.032 | 1.00 | 35.07 | A | N |
| ATOM | 1321 | CA | GLN | A | 183 | 23.421 | 123.938 | 100.406 | 1.00 | 36.11 | A | C |
| ATOM | 1322 | CB | GLN | A | 183 | 24.218 | 125.103 | 101.003 | 1.00 | 41.67 | A | C |
| ATOM | 1323 | CG | GLN | A | 183 | 25.733 | 124.971 | 100.780 | 1.00 | 45.42 | A | C |
| ATOM | 1324 | CD | GLN | A | 183 | 26.539 | 126.094 | 101.419 | 1.00 | 47.48 | A | C |
| ATOM | 1325 | OE1 | GLN | A | 183 | 27.748 | 126.212 | 101.193 | 1.00 | 46.58 | A | O |
| ATOM | 1326 | NE2 | GLN | A | 183 | 25.874 | 126.920 | 102.227 | 1.00 | 47.08 | A | N |
| ATOM | 1327 | C | GLN | A | 183 | 21.925 | 124.218 | 100.434 | 1.00 | 35.14 | A | C |
| ATOM | 1328 | O | GLN | A | 183 | 21.393 | 124.943 | 99.585 | 1.00 | 31.37 | A | O |
| ATOM | 1329 | N | MET | A | 184 | 21.253 | 123.633 | 101.416 | 1.00 | 34.56 | A | N |
| ATOM | 1330 | CA | MET | A | 184 | 19.819 | 123.790 | 101.552 | 1.00 | 35.32 | A | C |
| ATOM | 1331 | CB | MET | A | 184 | 19.144 | 122.449 | 101.276 | 1.00 | 37.15 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1332 | CG | MET | A | 184 | 17.702 | 122.376 | 101.724 | 1.00 | 39.29 | A | C |
| ATOM | 1333 | SD | MET | A | 184 | 17.026 | 120.749 | 101.406 | 1.00 | 46.67 | A | S |
| ATOM | 1334 | CE | MET | A | 184 | 17.652 | 119.805 | 102.807 | 1.00 | 37.41 | A | C |
| ATOM | 1335 | C | MET | A | 184 | 19.424 | 124.284 | 102.931 | 1.00 | 34.27 | A | C |
| ATOM | 1336 | O | MET | A | 184 | 20.049 | 123.922 | 103.915 | 1.00 | 35.08 | A | O |
| ATOM | 1337 | N | PHE | A | 185 | 18.385 | 125.114 | 102.995 | 1.00 | 34.93 | A | N |
| ATOM | 1338 | CA | PHE | A | 185 | 17.894 | 125.628 | 104.272 | 1.00 | 35.00 | A | C |
| ATOM | 1339 | CB | PHE | A | 185 | 18.895 | 126.620 | 104.877 | 1.00 | 36.50 | A | C |
| ATOM | 1340 | CG | PHE | A | 185 | 19.457 | 127.606 | 103.894 | 1.00 | 38.47 | A | C |
| ATOM | 1341 | CD1 | PHE | A | 185 | 18.654 | 128.580 | 103.324 | 1.00 | 39.19 | A | C |
| ATOM | 1342 | CD2 | PHE | A | 185 | 20.801 | 127.565 | 103.554 | 1.00 | 39.21 | A | C |
| ATOM | 1343 | CE1 | PHE | A | 185 | 19.182 | 129.498 | 102.433 | 1.00 | 39.76 | A | C |
| ATOM | 1344 | CE2 | PHE | A | 185 | 21.336 | 128.474 | 102.667 | 1.00 | 39.34 | A | C |
| ATOM | 1345 | CZ | PHE | A | 185 | 20.525 | 129.445 | 102.105 | 1.00 | 41.47 | A | C |
| ATOM | 1346 | C | PHE | A | 185 | 16.503 | 126.247 | 104.220 | 1.00 | 33.87 | A | C |
| ATOM | 1347 | O | PHE | A | 185 | 16.067 | 126.748 | 103.189 | 1.00 | 33.92 | A | O |
| ATOM | 1348 | N | ASP | A | 186 | 15.820 | 126.188 | 105.359 | 1.00 | 34.25 | A | N |
| ATOM | 1349 | CA | ASP | A | 186 | 14.464 | 126.708 | 105.537 | 1.00 | 34.70 | A | C |
| ATOM | 1350 | CB | ASP | A | 186 | 14.134 | 126.745 | 107.024 | 1.00 | 33.45 | A | C |
| ATOM | 1351 | CG | ASP | A | 186 | 14.151 | 125.373 | 107.655 | 1.00 | 33.81 | A | C |
| ATOM | 1352 | OD1 | ASP | A | 186 | 14.134 | 125.300 | 108.900 | 1.00 | 33.45 | A | O |
| ATOM | 1353 | OD2 | ASP | A | 186 | 14.170 | 124.366 | 106.914 | 1.00 | 30.88 | A | O |
| ATOM | 1354 | C | ASP | A | 186 | 14.186 | 128.081 | 104.940 | 1.00 | 35.60 | A | C |
| ATOM | 1355 | O | ASP | A | 186 | 14.975 | 129.017 | 105.098 | 1.00 | 33.00 | A | O |
| ATOM | 1356 | N | ASP | A | 187 | 13.035 | 128.191 | 104.283 | 1.00 | 36.69 | A | N |
| ATOM | 1357 | CA | ASP | A | 187 | 12.618 | 129.438 | 103.650 | 1.00 | 39.53 | A | C |
| ATOM | 1358 | CB | ASP | A | 187 | 11.891 | 129.134 | 102.340 | 1.00 | 39.55 | A | C |
| ATOM | 1359 | CG | ASP | A | 187 | 11.460 | 130.387 | 101.614 | 1.00 | 40.96 | A | C |
| ATOM | 1360 | OD1 | ASP | A | 187 | 10.651 | 130.267 | 100.664 | 1.00 | 41.44 | A | O |
| ATOM | 1361 | OD2 | ASP | A | 187 | 11.935 | 131.488 | 101.992 | 1.00 | 40.46 | A | O |
| ATOM | 1362 | C | ASP | A | 187 | 11.709 | 130.284 | 104.543 | 1.00 | 39.91 | A | C |
| ATOM | 1363 | O | ASP | A | 187 | 10.694 | 129.807 | 105.046 | 1.00 | 41.26 | A | O |
| ATOM | 1364 | N | PRO | A | 188 | 12.065 | 131.558 | 104.744 | 1.00 | 42.01 | A | N |
| ATOM | 1365 | CD | PRO | A | 188 | 13.339 | 132.149 | 104.301 | 1.00 | 43.41 | A | C |
| ATOM | 1366 | CA | PRO | A | 188 | 11.308 | 132.509 | 105.567 | 1.00 | 44.15 | A | C |
| ATOM | 1367 | CB | PRO | A | 188 | 12.152 | 133.781 | 105.485 | 1.00 | 43.77 | A | C |
| ATOM | 1368 | CG | PRO | A | 188 | 13.547 | 133.251 | 105.315 | 1.00 | 44.44 | A | C |
| ATOM | 1369 | C | PRO | A | 188 | 9.880 | 132.743 | 105.057 | 1.00 | 47.21 | A | C |
| ATOM | 1370 | O | PRO | A | 188 | 9.638 | 132.801 | 103.842 | 1.00 | 46.47 | A | O |
| ATOM | 1371 | N | ARG | A | 189 | 8.939 | 132.889 | 105.987 | 1.00 | 48.80 | A | N |
| ATOM | 1372 | CA | ARG | A | 189 | 7.544 | 133.125 | 105.628 | 1.00 | 50.89 | A | C |
| ATOM | 1373 | CB | ARG | A | 189 | 7.460 | 134.142 | 104.483 | 1.00 | 53.43 | A | C |
| ATOM | 1374 | CG | ARG | A | 189 | 7.857 | 135.568 | 104.846 | 1.00 | 55.35 | A | C |
| ATOM | 1375 | CD | ARG | A | 189 | 7.857 | 136.471 | 103.617 | 1.00 | 56.93 | A | C |
| ATOM | 1376 | NE | ARG | A | 189 | 6.704 | 136.223 | 102.753 | 1.00 | 59.39 | A | N |
| ATOM | 1377 | CZ | ARG | A | 189 | 6.558 | 135.141 | 101.990 | 1.00 | 59.94 | A | C |
| ATOM | 1378 | NH1 | ARG | A | 189 | 7.497 | 134.200 | 101.976 | 1.00 | 58.44 | A | N |
| ATOM | 1379 | NH2 | ARG | A | 189 | 5.471 | 134.992 | 101.242 | 1.00 | 59.57 | A | N |
| ATOM | 1380 | C | ARG | A | 189 | 6.858 | 131.827 | 105.200 | 1.00 | 51.44 | A | C |
| ATOM | 1381 | O | ARG | A | 189 | 6.009 | 131.293 | 105.915 | 1.00 | 50.73 | A | O |
| ATOM | 1382 | N | ASN | A | 190 | 7.224 | 131.327 | 104.022 | 1.00 | 51.35 | A | N |
| ATOM | 1383 | CA | ASN | A | 190 | 6.635 | 130.095 | 103.524 | 1.00 | 50.74 | A | C |
| ATOM | 1384 | CB | ASN | A | 190 | 6.777 | 129.989 | 102.009 | 1.00 | 51.34 | A | C |
| ATOM | 1385 | CG | ASN | A | 190 | 6.326 | 128.635 | 101.476 | 1.00 | 52.20 | A | C |
| ATOM | 1386 | OD1 | ASN | A | 190 | 6.409 | 128.367 | 100.280 | 1.00 | 54.49 | A | O |
| ATOM | 1387 | ND2 | ASN | A | 190 | 5.845 | 127.778 | 102.367 | 1.00 | 50.92 | A | N |
| ATOM | 1388 | C | ASN | A | 190 | 7.288 | 128.884 | 104.157 | 1.00 | 50.41 | A | C |
| ATOM | 1389 | O | ASN | A | 190 | 8.149 | 128.247 | 103.554 | 1.00 | 50.91 | A | O |
| ATOM | 1390 | N | LYS | A | 191 | 6.883 | 128.572 | 105.379 | 1.00 | 50.02 | A | N |
| ATOM | 1391 | CA | LYS | A | 191 | 7.418 | 127.413 | 106.067 | 1.00 | 49.63 | A | C |
| ATOM | 1392 | CB | LYS | A | 191 | 6.701 | 127.243 | 107.406 | 1.00 | 50.22 | A | C |
| ATOM | 1393 | CG | LYS | A | 191 | 7.209 | 126.101 | 108.273 | 1.00 | 50.50 | A | C |
| ATOM | 1394 | CD | LYS | A | 191 | 6.644 | 126.212 | 109.681 | 1.00 | 51.57 | A | C |
| ATOM | 1395 | CE | LYS | A | 191 | 7.159 | 127.463 | 110.401 | 1.00 | 52.88 | A | C |
| ATOM | 1396 | NZ | LYS | A | 191 | 6.852 | 128.740 | 109.686 | 1.00 | 53.10 | A | N |
| ATOM | 1397 | C | LYS | A | 191 | 7.127 | 126.236 | 105.142 | 1.00 | 48.85 | A | C |
| ATOM | 1398 | O | LYS | A | 191 | 6.679 | 126.428 | 104.009 | 1.00 | 49.68 | A | O |
| ATOM | 1399 | N | ARG | A | 192 | 7.378 | 125.018 | 105.599 | 1.00 | 46.67 | A | N |
| ATOM | 1400 | CA | ARG | A | 192 | 7.105 | 123.868 | 104.748 | 1.00 | 44.80 | A | C |
| ATOM | 1401 | CB | ARG | A | 192 | 5.608 | 123.784 | 104.458 | 1.00 | 47.22 | A | C |
| ATOM | 1402 | CG | ARG | A | 192 | 4.742 | 123.527 | 105.685 | 1.00 | 50.78 | A | C |
| ATOM | 1403 | CD | ARG | A | 192 | 3.260 | 123.434 | 105.318 | 1.00 | 52.19 | A | C |
| ATOM | 1404 | NE | ARG | A | 192 | 3.009 | 122.488 | 104.230 | 1.00 | 54.56 | A | N |
| ATOM | 1405 | CZ | ARG | A | 192 | 3.234 | 122.745 | 102.942 | 1.00 | 57.14 | A | C |
| ATOM | 1406 | NH1 | ARG | A | 192 | 3.715 | 123.927 | 102.569 | 1.00 | 57.70 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1407 | NH2 | ARG | A | 192 | 2.984 | 121.820 | 102.019 | 1.00 | 56.71 | A | N |
| ATOM | 1408 | C | ARG | A | 192 | 7.865 | 123.980 | 103.431 | 1.00 | 41.35 | A | C |
| ATOM | 1409 | O | ARG | A | 192 | 7.735 | 123.123 | 102.558 | 1.00 | 39.56 | A | O |
| ATOM | 1410 | N | GLY | A | 193 | 8.645 | 125.048 | 103.293 | 1.00 | 38.55 | A | N |
| ATOM | 1411 | CA | GLY | A | 193 | 9.423 | 125.257 | 102.085 | 1.00 | 35.30 | A | C |
| ATOM | 1412 | C | GLY | A | 193 | 10.913 | 125.231 | 102.374 | 1.00 | 32.57 | A | C |
| ATOM | 1413 | O | GLY | A | 193 | 11.332 | 125.335 | 103.522 | 1.00 | 34.21 | A | O |
| ATOM | 1414 | N | VAL | A | 194 | 11.720 | 125.087 | 101.333 | 1.00 | 30.19 | A | N |
| ATOM | 1415 | CA | VAL | A | 194 | 13.168 | 125.054 | 101.495 | 1.00 | 29.01 | A | C |
| ATOM | 1416 | CB | VAL | A | 194 | 13.700 | 123.614 | 101.512 | 1.00 | 29.20 | A | C |
| ATOM | 1417 | CG1 | VAL | A | 194 | 12.953 | 122.796 | 102.550 | 1.00 | 28.70 | A | C |
| ATOM | 1418 | CG2 | VAL | A | 194 | 13.560 | 122.993 | 100.125 | 1.00 | 26.36 | A | C |
| ATOM | 1419 | C | VAL | A | 194 | 13.822 | 125.785 | 100.329 | 1.00 | 29.43 | A | C |
| ATOM | 1420 | O | VAL | A | 194 | 13.216 | 125.950 | 99.265 | 1.00 | 26.23 | A | O |
| ATOM | 1421 | N | ILE | A | 195 | 15.058 | 126.225 | 100.537 | 1.00 | 28.93 | A | N |
| ATOM | 1422 | CA | ILE | A | 195 | 15.800 | 126.936 | 99.505 | 1.00 | 30.00 | A | C |
| ATOM | 1423 | CB | ILE | A | 195 | 16.087 | 128.385 | 99.899 | 1.00 | 29.05 | A | C |
| ATOM | 1424 | CG2 | ILE | A | 195 | 17.153 | 128.962 | 98.982 | 1.00 | 29.77 | A | C |
| ATOM | 1425 | CG1 | ILE | A | 195 | 14.802 | 129.211 | 99.812 | 1.00 | 32.93 | A | C |
| ATOM | 1426 | CD1 | ILE | A | 195 | 14.968 | 130.648 | 100.281 | 1.00 | 35.45 | A | C |
| ATOM | 1427 | C | ILE | A | 195 | 17.126 | 126.257 | 99.224 | 1.00 | 31.80 | A | C |
| ATOM | 1428 | O | ILE | A | 195 | 17.949 | 126.077 | 100.114 | 1.00 | 32.60 | A | O |
| ATOM | 1429 | N | ILE | A | 196 | 17.323 | 125.875 | 97.971 | 1.00 | 32.82 | A | N |
| ATOM | 1430 | CA | ILE | A | 196 | 18.543 | 125.211 | 97.556 | 1.00 | 31.27 | A | C |
| ATOM | 1431 | CB | ILE | A | 196 | 18.205 | 124.010 | 96.655 | 1.00 | 30.68 | A | C |
| ATOM | 1432 | CG2 | ILE | A | 196 | 19.449 | 123.197 | 96.363 | 1.00 | 32.58 | A | C |
| ATOM | 1433 | CG1 | ILE | A | 196 | 17.180 | 123.125 | 97.362 | 1.00 | 31.63 | A | C |
| ATOM | 1434 | CD1 | ILE | A | 196 | 16.686 | 121.978 | 96.530 | 1.00 | 29.62 | A | C |
| ATOM | 1435 | C | ILE | A | 196 | 19.315 | 126.262 | 96.783 | 1.00 | 30.09 | A | C |
| ATOM | 1436 | O | ILE | A | 196 | 19.117 | 126.432 | 95.587 | 1.00 | 30.53 | A | O |
| ATOM | 1437 | N | LYS | A | 197 | 20.189 | 126.981 | 97.473 | 1.00 | 30.85 | A | N |
| ATOM | 1438 | CA | LYS | A | 197 | 20.949 | 128.038 | 96.820 | 1.00 | 31.10 | A | C |
| ATOM | 1439 | CB | LYS | A | 197 | 21.740 | 128.862 | 97.831 | 1.00 | 29.66 | A | C |
| ATOM | 1440 | CG | LYS | A | 197 | 22.799 | 128.094 | 98.566 | 1.00 | 32.42 | A | C |
| ATOM | 1441 | CD | LYS | A | 197 | 23.844 | 129.041 | 99.151 | 1.00 | 33.86 | A | C |
| ATOM | 1442 | CE | LYS | A | 197 | 23.205 | 130.239 | 99.831 | 1.00 | 34.54 | A | C |
| ATOM | 1443 | NZ | LYS | A | 197 | 22.547 | 131.143 | 98.845 | 1.00 | 38.02 | A | N |
| ATOM | 1444 | C | LYS | A | 197 | 21.891 | 127.535 | 95.749 | 1.00 | 29.14 | A | C |
| ATOM | 1445 | O | LYS | A | 197 | 22.534 | 126.498 | 95.901 | 1.00 | 28.56 | A | O |
| ATOM | 1446 | N | GLY | A | 198 | 21.959 | 128.296 | 94.661 | 1.00 | 29.04 | A | N |
| ATOM | 1447 | CA | GLY | A | 198 | 22.817 | 127.941 | 93.554 | 1.00 | 27.12 | A | C |
| ATOM | 1448 | C | GLY | A | 198 | 22.082 | 127.115 | 92.525 | 1.00 | 28.06 | A | C |
| ATOM | 1449 | O | GLY | A | 198 | 22.507 | 127.053 | 91.371 | 1.00 | 29.31 | A | O |
| ATOM | 1450 | N | LEU | A | 199 | 20.978 | 126.487 | 92.925 | 1.00 | 27.38 | A | N |
| ATOM | 1451 | CA | LEU | A | 199 | 20.233 | 125.660 | 91.991 | 1.00 | 27.34 | A | C |
| ATOM | 1452 | CB | LEU | A | 199 | 18.913 | 125.167 | 92.594 | 1.00 | 26.95 | A | C |
| ATOM | 1453 | CG | LEU | A | 199 | 18.255 | 124.079 | 91.732 | 1.00 | 23.86 | A | C |
| ATOM | 1454 | CD1 | LEU | A | 199 | 19.221 | 122.907 | 91.603 | 1.00 | 23.14 | A | C |
| ATOM | 1455 | CD2 | LEU | A | 199 | 16.944 | 123.620 | 92.335 | 1.00 | 20.24 | A | C |
| ATOM | 1456 | C | LEU | A | 199 | 19.939 | 126.445 | 90.733 | 1.00 | 27.62 | A | C |
| ATOM | 1457 | O | LEU | A | 199 | 19.464 | 127.576 | 90.792 | 1.00 | 30.54 | A | O |
| ATOM | 1458 | N | GLU | A | 200 | 20.232 | 125.828 | 89.598 | 1.00 | 26.74 | A | N |
| ATOM | 1459 | CA | GLU | A | 200 | 20.021 | 126.427 | 88.292 | 1.00 | 27.77 | A | C |
| ATOM | 1460 | CB | GLU | A | 200 | 20.920 | 125.714 | 87.275 | 1.00 | 28.86 | A | C |
| ATOM | 1461 | CG | GLU | A | 200 | 21.067 | 126.400 | 85.939 | 1.00 | 33.25 | A | C |
| ATOM | 1462 | CD | GLU | A | 200 | 21.961 | 127.631 | 85.996 | 1.00 | 33.33 | A | C |
| ATOM | 1463 | OE1 | GLU | A | 200 | 21.605 | 128.605 | 86.697 | 1.00 | 35.24 | A | O |
| ATOM | 1464 | OE2 | GLU | A | 200 | 23.019 | 127.620 | 85.332 | 1.00 | 31.62 | A | O |
| ATOM | 1465 | C | GLU | A | 200 | 18.545 | 126.268 | 87.900 | 1.00 | 27.25 | A | C |
| ATOM | 1466 | O | GLU | A | 200 | 17.969 | 125.188 | 88.029 | 1.00 | 27.74 | A | O |
| ATOM | 1467 | N | GLU | A | 201 | 17.929 | 127.347 | 87.438 | 1.00 | 27.08 | A | N |
| ATOM | 1468 | CA | GLU | A | 201 | 16.537 | 127.300 | 87.018 | 1.00 | 25.87 | A | C |
| ATOM | 1469 | CB | GLU | A | 201 | 15.665 | 128.085 | 87.990 | 1.00 | 25.25 | A | C |
| ATOM | 1470 | CG | GLU | A | 201 | 15.710 | 127.505 | 89.398 | 1.00 | 30.83 | A | C |
| ATOM | 1471 | CD | GLU | A | 201 | 14.539 | 127.927 | 90.266 | 1.00 | 30.45 | A | C |
| ATOM | 1472 | OE1 | GLU | A | 201 | 14.430 | 129.127 | 90.604 | 1.00 | 31.33 | A | O |
| ATOM | 1473 | OE2 | GLU | A | 201 | 13.727 | 127.042 | 90.608 | 1.00 | 33.74 | A | O |
| ATOM | 1474 | C | GLU | A | 201 | 16.392 | 127.859 | 85.609 | 1.00 | 25.65 | A | C |
| ATOM | 1475 | O | GLU | A | 201 | 15.987 | 129.001 | 85.423 | 1.00 | 25.32 | A | O |
| ATOM | 1476 | N | ILE | A | 202 | 16.735 | 127.028 | 84.626 | 1.00 | 26.55 | A | N |
| ATOM | 1477 | CA | ILE | A | 202 | 16.683 | 127.378 | 83.211 | 1.00 | 25.58 | A | C |
| ATOM | 1478 | CB | ILE | A | 202 | 17.137 | 126.190 | 82.325 | 1.00 | 24.62 | A | C |
| ATOM | 1479 | CG2 | ILE | A | 202 | 17.315 | 126.647 | 80.902 | 1.00 | 21.69 | A | C |
| ATOM | 1480 | CG1 | ILE | A | 202 | 18.451 | 125.598 | 82.848 | 1.00 | 26.45 | A | C |
| ATOM | 1481 | CD1 | ILE | A | 202 | 19.610 | 126.564 | 82.862 | 1.00 | 21.84 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1482 | C | ILE | A | 202 | 15.290 | 127.770 | 82.760 | 1.00 | 26.15 | A | C |
| ATOM | 1483 | O | ILE | A | 202 | 14.314 | 127.121 | 83.116 | 1.00 | 27.71 | A | O |
| ATOM | 1484 | N | THR | A | 203 | 15.208 | 128.840 | 81.976 | 1.00 | 27.89 | A | N |
| ATOM | 1485 | CA | THR | A | 203 | 13.942 | 129.313 | 81.437 | 1.00 | 28.95 | A | C |
| ATOM | 1486 | CB | THR | A | 203 | 13.939 | 130.841 | 81.280 | 1.00 | 29.78 | A | C |
| ATOM | 1487 | OG1 | THR | A | 203 | 14.135 | 131.451 | 82.558 | 1.00 | 31.82 | A | O |
| ATOM | 1488 | CG2 | THR | A | 203 | 12.616 | 131.323 | 80.701 | 1.00 | 31.36 | A | C |
| ATOM | 1489 | C | THR | A | 203 | 13.796 | 128.682 | 80.058 | 1.00 | 30.82 | A | C |
| ATOM | 1490 | O | THR | A | 203 | 14.721 | 128.738 | 79.247 | 1.00 | 32.61 | A | O |
| ATOM | 1491 | N | VAL | A | 204 | 12.644 | 128.070 | 79.800 | 1.00 | 31.47 | A | N |
| ATOM | 1492 | CA | VAL | A | 204 | 12.376 | 127.423 | 78.512 | 1.00 | 30.94 | A | C |
| ATOM | 1493 | CB | VAL | A | 204 | 11.719 | 126.021 | 78.713 | 1.00 | 30.83 | A | C |
| ATOM | 1494 | CG1 | VAL | A | 204 | 11.725 | 125.235 | 77.411 | 1.00 | 29.45 | A | C |
| ATOM | 1495 | CG2 | VAL | A | 204 | 12.454 | 125.251 | 79.806 | 1.00 | 30.28 | A | C |
| ATOM | 1496 | C | VAL | A | 204 | 11.416 | 128.316 | 77.737 | 1.00 | 30.13 | A | C |
| ATOM | 1497 | O | VAL | A | 204 | 10.255 | 128.458 | 78.109 | 1.00 | 30.73 | A | O |
| ATOM | 1498 | N | HIS | A | 205 | 11.899 | 128.914 | 76.658 | 1.00 | 30.14 | A | N |
| ATOM | 1499 | CA | HIS | A | 205 | 11.075 | 129.818 | 75.862 | 1.00 | 29.71 | A | C |
| ATOM | 1500 | CB | HIS | A | 205 | 11.961 | 130.839 | 75.139 | 1.00 | 29.33 | A | C |
| ATOM | 1501 | CG | HIS | A | 205 | 13.018 | 131.444 | 76.009 | 1.00 | 29.66 | A | C |
| ATOM | 1502 | CD2 | HIS | A | 205 | 13.060 | 132.628 | 76.665 | 1.00 | 27.43 | A | C |
| ATOM | 1503 | ND1 | HIS | A | 205 | 14.194 | 130.791 | 76.318 | 1.00 | 29.40 | A | N |
| ATOM | 1504 | CE1 | HIS | A | 205 | 14.913 | 131.547 | 77.129 | 1.00 | 29.25 | A | C |
| ATOM | 1505 | NE2 | HIS | A | 205 | 14.247 | 132.667 | 77.356 | 1.00 | 28.09 | A | N |
| ATOM | 1506 | C | HIS | A | 205 | 10.169 | 129.130 | 74.845 | 1.00 | 30.17 | A | C |
| ATOM | 1507 | O | HIS | A | 205 | 9.086 | 129.636 | 74.539 | 1.00 | 29.29 | A | O |
| ATOM | 1508 | N | ASN | A | 206 | 10.600 | 127.986 | 74.319 | 1.00 | 31.72 | A | N |
| ATOM | 1509 | CA | ASN | A | 206 | 9.793 | 127.282 | 73.334 | 1.00 | 32.43 | A | C |
| ATOM | 1510 | CB | ASN | A | 206 | 10.255 | 127.661 | 71.933 | 1.00 | 33.10 | A | C |
| ATOM | 1511 | CG | ASN | A | 206 | 11.633 | 127.151 | 71.624 | 1.00 | 33.52 | A | C |
| ATOM | 1512 | OD1 | ASN | A | 206 | 11.854 | 125.940 | 71.546 | 1.00 | 38.65 | A | O |
| ATOM | 1513 | ND2 | ASN | A | 206 | 12.576 | 128.067 | 71.445 | 1.00 | 32.20 | A | N |
| ATOM | 1514 | C | ASN | A | 206 | 9.760 | 125.760 | 73.469 | 1.00 | 33.08 | A | C |
| ATOM | 1515 | O | ASN | A | 206 | 10.724 | 125.133 | 73.899 | 1.00 | 30.00 | A | O |
| ATOM | 1516 | N | LYS | A | 207 | 8.629 | 125.186 | 73.073 | 1.00 | 35.89 | A | N |
| ATOM | 1517 | CA | LYS | A | 207 | 8.387 | 123.750 | 73.134 | 1.00 | 38.20 | A | C |
| ATOM | 1518 | CB | LYS | A | 207 | 7.003 | 123.434 | 72.555 | 1.00 | 40.57 | A | C |
| ATOM | 1519 | CG | LYS | A | 207 | 6.653 | 121.949 | 72.512 | 1.00 | 41.21 | A | C |
| ATOM | 1520 | CD | LYS | A | 207 | 5.679 | 121.650 | 71.381 | 1.00 | 42.79 | A | C |
| ATOM | 1521 | CE | LYS | A | 207 | 6.289 | 121.993 | 70.028 | 1.00 | 45.17 | A | C |
| ATOM | 1522 | NZ | LYS | A | 207 | 5.453 | 121.530 | 68.891 | 1.00 | 43.79 | A | N |
| ATOM | 1523 | C | LYS | A | 207 | 9.428 | 122.896 | 72.417 | 1.00 | 39.32 | A | C |
| ATOM | 1524 | O | LYS | A | 207 | 9.083 | 121.867 | 71.830 | 1.00 | 41.12 | A | O |
| ATOM | 1525 | N | ASP | A | 208 | 10.691 | 123.310 | 72.443 | 1.00 | 38.23 | A | N |
| ATOM | 1526 | CA | ASP | A | 208 | 11.731 | 122.510 | 71.804 | 1.00 | 39.89 | A | C |
| ATOM | 1527 | CB | ASP | A | 208 | 11.584 | 122.552 | 70.280 | 1.00 | 41.78 | A | C |
| ATOM | 1528 | CG | ASP | A | 208 | 11.414 | 121.156 | 69.676 | 1.00 | 43.58 | A | C |
| ATOM | 1529 | OD1 | ASP | A | 208 | 12.375 | 120.355 | 69.748 | 1.00 | 45.57 | A | O |
| ATOM | 1530 | OD2 | ASP | A | 208 | 10.323 | 120.855 | 69.142 | 1.00 | 38.46 | A | O |
| ATOM | 1531 | C | ASP | A | 208 | 13.137 | 122.913 | 72.217 | 1.00 | 39.63 | A | C |
| ATOM | 1532 | O | ASP | A | 208 | 14.130 | 122.444 | 71.659 | 1.00 | 39.93 | A | O |
| ATOM | 1533 | N | GLU | A | 209 | 13.208 | 123.785 | 73.214 | 1.00 | 39.09 | A | N |
| ATOM | 1534 | CA | GLU | A | 209 | 14.478 | 124.244 | 73.746 | 1.00 | 35.35 | A | C |
| ATOM | 1535 | CB | GLU | A | 209 | 14.330 | 125.669 | 74.282 | 1.00 | 35.77 | A | C |
| ATOM | 1536 | CG | GLU | A | 209 | 15.642 | 126.391 | 74.554 | 1.00 | 37.17 | A | C |
| ATOM | 1537 | CD | GLU | A | 209 | 15.430 | 127.798 | 75.088 | 1.00 | 38.27 | A | C |
| ATOM | 1538 | OE1 | GLU | A | 209 | 14.736 | 128.603 | 74.425 | 1.00 | 35.17 | A | O |
| ATOM | 1539 | OE2 | GLU | A | 209 | 15.960 | 128.097 | 76.177 | 1.00 | 40.07 | A | O |
| ATOM | 1540 | C | GLU | A | 209 | 14.747 | 123.279 | 74.885 | 1.00 | 34.21 | A | C |
| ATOM | 1541 | O | GLU | A | 209 | 15.863 | 123.169 | 75.390 | 1.00 | 35.45 | A | O |
| ATOM | 1542 | N | VAL | A | 210 | 13.693 | 122.571 | 75.270 | 1.00 | 32.75 | A | N |
| ATOM | 1543 | CA | VAL | A | 210 | 13.754 | 121.598 | 76.351 | 1.00 | 32.75 | A | C |
| ATOM | 1544 | CB | VAL | A | 210 | 12.346 | 120.965 | 76.614 | 1.00 | 35.46 | A | C |
| ATOM | 1545 | CG1 | VAL | A | 210 | 11.287 | 122.049 | 76.676 | 1.00 | 36.80 | A | C |
| ATOM | 1546 | CG2 | VAL | A | 210 | 12.002 | 119.969 | 75.525 | 1.00 | 36.70 | A | C |
| ATOM | 1547 | C | VAL | A | 210 | 14.744 | 120.478 | 76.031 | 1.00 | 29.94 | A | C |
| ATOM | 1548 | O | VAL | A | 210 | 15.580 | 120.116 | 76.858 | 1.00 | 30.76 | A | O |
| ATOM | 1549 | N | TYR | A | 211 | 14.650 | 119.945 | 74.820 | 1.00 | 26.77 | A | N |
| ATOM | 1550 | CA | TYR | A | 211 | 15.510 | 118.852 | 74.397 | 1.00 | 27.14 | A | C |
| ATOM | 1551 | CB | TYR | A | 211 | 15.312 | 118.581 | 72.907 | 1.00 | 24.99 | A | C |
| ATOM | 1552 | CG | TYR | A | 211 | 16.045 | 117.358 | 72.418 | 1.00 | 21.82 | A | C |
| ATOM | 1553 | CD1 | TYR | A | 211 | 17.412 | 117.391 | 72.170 | 1.00 | 21.81 | A | C |
| ATOM | 1554 | CE1 | TYR | A | 211 | 18.093 | 116.258 | 71.751 | 1.00 | 23.80 | A | C |
| ATOM | 1555 | CD2 | TYR | A | 211 | 15.372 | 116.160 | 72.233 | 1.00 | 21.14 | A | C |
| ATOM | 1556 | CE2 | TYR | A | 211 | 16.038 | 115.019 | 71.813 | 1.00 | 24.24 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1557 | CZ | TYR | A | 211 | 17.400 | 115.071 | 71.574 | 1.00 | 26.17 | A | C |
| ATOM | 1558 | OH | TYR | A | 211 | 18.066 | 113.930 | 71.177 | 1.00 | 27.08 | A | O |
| ATOM | 1559 | C | TYR | A | 211 | 16.995 | 119.034 | 74.680 | 1.00 | 27.92 | A | C |
| ATOM | 1560 | O | TYR | A | 211 | 17.643 | 118.136 | 75.202 | 1.00 | 25.50 | A | O |
| ATOM | 1561 | N | GLN | A | 212 | 17.541 | 120.191 | 74.332 | 1.00 | 30.90 | A | N |
| ATOM | 1562 | CA | GLN | A | 212 | 18.958 | 120.411 | 74.549 | 1.00 | 32.93 | A | C |
| ATOM | 1563 | CB | GLN | A | 212 | 19.454 | 121.572 | 73.683 | 1.00 | 35.09 | A | C |
| ATOM | 1564 | CG | GLN | A | 212 | 19.102 | 122.946 | 74.191 | 1.00 | 39.70 | A | C |
| ATOM | 1565 | CD | GLN | A | 212 | 19.239 | 123.999 | 73.108 | 1.00 | 42.59 | A | C |
| ATOM | 1566 | OE1 | GLN | A | 212 | 19.405 | 125.185 | 73.394 | 1.00 | 45.65 | A | O |
| ATOM | 1567 | NE2 | GLN | A | 212 | 19.154 | 123.571 | 71.853 | 1.00 | 43.32 | A | N |
| ATOM | 1568 | C | GLN | A | 212 | 19.272 | 120.656 | 76.013 | 1.00 | 31.57 | A | C |
| ATOM | 1569 | O | GLN | A | 212 | 20.348 | 120.290 | 76.491 | 1.00 | 31.33 | A | O |
| ATOM | 1570 | N | ILE | A | 213 | 18.337 | 121.263 | 76.734 | 1.00 | 30.80 | A | N |
| ATOM | 1571 | CA | ILE | A | 213 | 18.561 | 121.514 | 78.151 | 1.00 | 30.91 | A | C |
| ATOM | 1572 | CB | ILE | A | 213 | 17.411 | 122.336 | 78.755 | 1.00 | 30.52 | A | C |
| ATOM | 1573 | CG2 | ILE | A | 213 | 17.623 | 122.514 | 80.259 | 1.00 | 28.20 | A | C |
| ATOM | 1574 | CG1 | ILE | A | 213 | 17.355 | 123.706 | 78.080 | 1.00 | 31.84 | A | C |
| ATOM | 1575 | CD1 | ILE | A | 213 | 16.252 | 124.599 | 78.604 | 1.00 | 31.68 | A | C |
| ATOM | 1576 | C | ILE | A | 213 | 18.710 | 120.184 | 78.907 | 1.00 | 30.16 | A | C |
| ATOM | 1577 | O | ILE | A | 213 | 19.578 | 120.042 | 79.767 | 1.00 | 29.32 | A | O |
| ATOM | 1578 | N | LEU | A | 214 | 17.866 | 119.212 | 78.574 | 1.00 | 27.33 | A | N |
| ATOM | 1579 | CA | LEU | A | 214 | 17.923 | 117.910 | 79.216 | 1.00 | 24.78 | A | C |
| ATOM | 1580 | CB | LEU | A | 214 | 16.588 | 117.182 | 79.040 | 1.00 | 22.50 | A | C |
| ATOM | 1581 | CG | LEU | A | 214 | 15.484 | 117.761 | 79.932 | 1.00 | 23.55 | A | C |
| ATOM | 1582 | CD1 | LEU | A | 214 | 14.152 | 117.188 | 79.576 | 1.00 | 21.76 | A | C |
| ATOM | 1583 | CD2 | LEU | A | 214 | 15.809 | 117.458 | 81.385 | 1.00 | 25.65 | A | C |
| ATOM | 1584 | C | LEU | A | 214 | 19.069 | 117.069 | 78.669 | 1.00 | 26.61 | A | C |
| ATOM | 1585 | O | LEU | A | 214 | 19.738 | 116.357 | 79.421 | 1.00 | 25.92 | A | O |
| ATOM | 1586 | N | GLU | A | 215 | 19.307 | 117.152 | 77.362 | 1.00 | 28.15 | A | N |
| ATOM | 1587 | CA | GLU | A | 215 | 20.392 | 116.397 | 76.755 | 1.00 | 28.53 | A | C |
| ATOM | 1588 | CB | GLU | A | 215 | 20.514 | 116.721 | 75.269 | 1.00 | 30.78 | A | C |
| ATOM | 1589 | CG | GLU | A | 215 | 21.633 | 115.962 | 74.563 | 1.00 | 34.88 | A | C |
| ATOM | 1590 | CD | GLU | A | 215 | 21.744 | 116.314 | 73.079 | 1.00 | 38.61 | A | C |
| ATOM | 1591 | OE1 | GLU | A | 215 | 21.873 | 117.519 | 72.763 | 1.00 | 40.88 | A | O |
| ATOM | 1592 | OE2 | GLU | A | 215 | 21.709 | 115.393 | 72.228 | 1.00 | 39.22 | A | O |
| ATOM | 1593 | C | GLU | A | 215 | 21.689 | 116.742 | 77.480 | 1.00 | 29.70 | A | C |
| ATOM | 1594 | O | GLU | A | 215 | 22.495 | 115.861 | 77.765 | 1.00 | 30.75 | A | O |
| ATOM | 1595 | N | LYS | A | 216 | 21.891 | 118.023 | 77.775 | 1.00 | 27.92 | A | N |
| ATOM | 1596 | CA | LYS | A | 216 | 23.081 | 118.446 | 78.508 | 1.00 | 27.16 | A | C |
| ATOM | 1597 | CB | LYS | A | 216 | 23.142 | 119.974 | 78.607 | 1.00 | 29.06 | A | C |
| ATOM | 1598 | CG | LYS | A | 216 | 24.283 | 120.596 | 77.820 | 1.00 | 29.49 | A | C |
| ATOM | 1599 | CD | LYS | A | 216 | 24.393 | 122.092 | 78.081 | 1.00 | 29.95 | A | C |
| ATOM | 1600 | CE | LYS | A | 216 | 23.254 | 122.860 | 77.425 | 1.00 | 33.41 | A | C |
| ATOM | 1601 | NZ | LYS | A | 216 | 23.352 | 122.837 | 75.936 | 1.00 | 32.43 | A | N |
| ATOM | 1602 | C | LYS | A | 216 | 22.982 | 117.854 | 79.912 | 1.00 | 28.86 | A | C |
| ATOM | 1603 | O | LYS | A | 216 | 23.991 | 117.516 | 80.541 | 1.00 | 28.11 | A | O |
| ATOM | 1604 | N | GLY | A | 217 | 21.748 | 117.732 | 80.393 | 1.00 | 27.55 | A | N |
| ATOM | 1605 | CA | GLY | A | 217 | 21.519 | 117.179 | 81.714 | 1.00 | 29.42 | A | C |
| ATOM | 1606 | C | GLY | A | 217 | 21.948 | 115.729 | 81.803 | 1.00 | 29.42 | A | C |
| ATOM | 1607 | O | GLY | A | 217 | 22.536 | 115.301 | 82.794 | 1.00 | 28.79 | A | O |
| ATOM | 1608 | N | ALA | A | 218 | 21.657 | 114.961 | 80.764 | 1.00 | 28.40 | A | N |
| ATOM | 1609 | CA | ALA | A | 218 | 22.037 | 113.557 | 80.763 | 1.00 | 28.80 | A | C |
| ATOM | 1610 | CB | ALA | A | 218 | 21.437 | 112.850 | 79.549 | 1.00 | 26.40 | A | C |
| ATOM | 1611 | C | ALA | A | 218 | 23.557 | 113.467 | 80.735 | 1.00 | 28.12 | A | C |
| ATOM | 1612 | O | ALA | A | 218 | 24.152 | 112.618 | 81.397 | 1.00 | 29.94 | A | O |
| ATOM | 1613 | N | ALA | A | 219 | 24.177 | 114.356 | 79.971 | 1.00 | 26.15 | A | N |
| ATOM | 1614 | CA | ALA | A | 219 | 25.626 | 114.376 | 79.855 | 1.00 | 27.24 | A | C |
| ATOM | 1615 | CB | ALA | A | 219 | 26.059 | 115.536 | 78.950 | 1.00 | 28.52 | A | C |
| ATOM | 1616 | C | ALA | A | 219 | 26.244 | 114.527 | 81.238 | 1.00 | 26.66 | A | C |
| ATOM | 1617 | O | ALA | A | 219 | 26.948 | 113.636 | 81.722 | 1.00 | 24.78 | A | O |
| ATOM | 1618 | N | LYS | A | 220 | 25.966 | 115.667 | 81.859 | 1.00 | 27.28 | A | N |
| ATOM | 1619 | CA | LYS | A | 220 | 26.466 | 115.980 | 83.189 | 1.00 | 29.86 | A | C |
| ATOM | 1620 | CB | LYS | A | 220 | 25.784 | 117.253 | 83.701 | 1.00 | 30.55 | A | C |
| ATOM | 1621 | CG | LYS | A | 220 | 26.375 | 117.827 | 84.971 | 1.00 | 32.34 | A | C |
| ATOM | 1622 | CD | LYS | A | 220 | 26.857 | 119.263 | 84.760 | 1.00 | 35.00 | A | C |
| ATOM | 1623 | CE | LYS | A | 220 | 27.994 | 119.311 | 83.738 | 1.00 | 36.11 | A | C |
| ATOM | 1624 | NZ | LYS | A | 220 | 28.667 | 120.642 | 83.666 | 1.00 | 35.23 | A | N |
| ATOM | 1625 | C | LYS | A | 220 | 26.190 | 114.812 | 84.136 | 1.00 | 30.03 | A | C |
| ATOM | 1626 | O | LYS | A | 220 | 27.020 | 114.481 | 84.987 | 1.00 | 29.70 | A | O |
| ATOM | 1627 | N | ARG | A | 221 | 25.027 | 114.184 | 83.968 | 1.00 | 30.12 | A | N |
| ATOM | 1628 | CA | ARG | A | 221 | 24.616 | 113.055 | 84.800 | 1.00 | 30.72 | A | C |
| ATOM | 1629 | CB | ARG | A | 221 | 23.258 | 112.526 | 84.338 | 1.00 | 32.37 | A | C |
| ATOM | 1630 | CG | ARG | A | 221 | 22.339 | 112.072 | 85.462 | 1.00 | 31.69 | A | C |
| ATOM | 1631 | CD | ARG | A | 221 | 21.534 | 110.831 | 85.085 | 1.00 | 32.65 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1632 | NE | ARG | A | 221 | 20.881 | 110.900 | 83.774 | 1.00 | 32.33 | A | N |
| ATOM | 1633 | CZ | ARG | A | 221 | 19.571 | 111.044 | 83.580 | 1.00 | 29.17 | A | C |
| ATOM | 1634 | NH1 | ARG | A | 221 | 18.739 | 111.153 | 84.610 | 1.00 | 28.36 | A | N |
| ATOM | 1635 | NH2 | ARG | A | 221 | 19.084 | 111.030 | 82.348 | 1.00 | 30.01 | A | N |
| ATOM | 1636 | C | ARG | A | 221 | 25.642 | 111.934 | 84.696 | 1.00 | 30.44 | A | C |
| ATOM | 1637 | O | ARG | A | 221 | 26.089 | 111.383 | 85.698 | 1.00 | 32.26 | A | O |
| ATOM | 1638 | N | THR | A | 222 | 26.006 | 111.598 | 83.468 | 1.00 | 28.92 | A | N |
| ATOM | 1639 | CA | THR | A | 222 | 26.976 | 110.547 | 83.217 | 1.00 | 29.35 | A | C |
| ATOM | 1640 | CB | THR | A | 222 | 27.051 | 110.232 | 81.717 | 1.00 | 30.01 | A | C |
| ATOM | 1641 | OG1 | THR | A | 222 | 25.762 | 109.821 | 81.249 | 1.00 | 28.86 | A | O |
| ATOM | 1642 | CG2 | THR | A | 222 | 28.061 | 109.128 | 81.457 | 1.00 | 31.28 | A | C |
| ATOM | 1643 | C | THR | A | 222 | 28.381 | 110.911 | 83.712 | 1.00 | 30.02 | A | C |
| ATOM | 1644 | O | THR | A | 222 | 29.111 | 110.050 | 84.205 | 1.00 | 29.31 | A | O |
| ATOM | 1645 | N | THR | A | 223 | 28.765 | 112.179 | 83.566 | 1.00 | 29.42 | A | N |
| ATOM | 1646 | CA | THR | A | 223 | 30.083 | 112.620 | 84.014 | 1.00 | 27.38 | A | C |
| ATOM | 1647 | CB | THR | A | 223 | 30.305 | 114.120 | 83.708 | 1.00 | 27.25 | A | C |
| ATOM | 1648 | OG1 | THR | A | 223 | 30.682 | 114.271 | 82.335 | 1.00 | 26.60 | A | O |
| ATOM | 1649 | CG2 | THR | A | 223 | 31.388 | 114.707 | 84.613 | 1.00 | 23.64 | A | C |
| ATOM | 1650 | C | THR | A | 223 | 30.268 | 112.380 | 85.513 | 1.00 | 28.17 | A | C |
| ATOM | 1651 | O | THR | A | 223 | 31.259 | 111.772 | 85.933 | 1.00 | 25.99 | A | O |
| ATOM | 1652 | N | ALA | A | 224 | 29.307 | 112.845 | 86.309 | 1.00 | 28.70 | A | N |
| ATOM | 1653 | CA | ALA | A | 224 | 29.358 | 112.695 | 87.761 | 1.00 | 30.60 | A | C |
| ATOM | 1654 | CB | ALA | A | 224 | 28.086 | 113.266 | 88.394 | 1.00 | 31.95 | A | C |
| ATOM | 1655 | C | ALA | A | 224 | 29.537 | 111.249 | 88.196 | 1.00 | 31.70 | A | C |
| ATOM | 1656 | O | ALA | A | 224 | 30.357 | 110.953 | 89.069 | 1.00 | 32.44 | A | O |
| ATOM | 1657 | N | ALA | A | 225 | 28.765 | 110.356 | 87.583 | 1.00 | 30.73 | A | N |
| ATOM | 1658 | CA | ALA | A | 225 | 28.799 | 108.935 | 87.908 | 1.00 | 33.05 | A | C |
| ATOM | 1659 | CB | ALA | A | 225 | 27.715 | 108.209 | 87.134 | 1.00 | 31.51 | A | C |
| ATOM | 1660 | C | ALA | A | 225 | 30.140 | 108.267 | 87.643 | 1.00 | 35.18 | A | C |
| ATOM | 1661 | O | ALA | A | 225 | 30.499 | 107.285 | 88.298 | 1.00 | 35.77 | A | O |
| ATOM | 1662 | N | THR | A | 226 | 30.878 | 108.798 | 86.679 | 1.00 | 37.95 | A | N |
| ATOM | 1663 | CA | THR | A | 226 | 32.169 | 108.240 | 86.306 | 1.00 | 39.61 | A | C |
| ATOM | 1664 | CB | THR | A | 226 | 32.421 | 108.435 | 84.803 | 1.00 | 41.90 | A | C |
| ATOM | 1665 | OG1 | THR | A | 226 | 31.359 | 107.830 | 84.054 | 1.00 | 43.04 | A | O |
| ATOM | 1666 | CG2 | THR | A | 226 | 33.746 | 107.804 | 84.400 | 1.00 | 44.15 | A | C |
| ATOM | 1667 | C | THR | A | 226 | 33.352 | 108.836 | 87.056 | 1.00 | 40.54 | A | C |
| ATOM | 1668 | O | THR | A | 226 | 34.487 | 108.408 | 86.855 | 1.00 | 41.78 | A | O |
| ATOM | 1669 | N | LEU | A | 227 | 33.094 | 109.814 | 87.919 | 1.00 | 39.16 | A | N |
| ATOM | 1670 | CA | LEU | A | 227 | 34.167 | 110.463 | 88.659 | 1.00 | 37.24 | A | C |
| ATOM | 1671 | CB | LEU | A | 227 | 34.281 | 111.925 | 88.229 | 1.00 | 34.76 | A | C |
| ATOM | 1672 | CG | LEU | A | 227 | 34.587 | 112.123 | 86.746 | 1.00 | 34.11 | A | C |
| ATOM | 1673 | CD1 | LEU | A | 227 | 34.610 | 113.606 | 86.417 | 1.00 | 33.56 | A | C |
| ATOM | 1674 | CD2 | LEU | A | 227 | 35.923 | 111.471 | 86.413 | 1.00 | 32.19 | A | C |
| ATOM | 1675 | C | LEU | A | 227 | 33.985 | 110.395 | 90.159 | 1.00 | 37.94 | A | C |
| ATOM | 1676 | O | LEU | A | 227 | 34.953 | 110.476 | 90.910 | 1.00 | 40.67 | A | O |
| ATOM | 1677 | N | MET | A | 228 | 32.744 | 110.261 | 90.601 | 1.00 | 36.96 | A | N |
| ATOM | 1678 | CA | MET | A | 228 | 32.484 | 110.191 | 92.022 | 1.00 | 38.41 | A | C |
| ATOM | 1679 | CB | MET | A | 228 | 31.760 | 111.454 | 92.472 | 1.00 | 39.99 | A | C |
| ATOM | 1680 | CG | MET | A | 228 | 32.477 | 112.716 | 92.038 | 1.00 | 43.21 | A | C |
| ATOM | 1681 | SD | MET | A | 228 | 31.764 | 114.182 | 92.774 | 1.00 | 49.04 | A | S |
| ATOM | 1682 | CE | MET | A | 228 | 30.157 | 114.212 | 91.908 | 1.00 | 44.42 | A | C |
| ATOM | 1683 | C | MET | A | 228 | 31.656 | 108.961 | 92.326 | 1.00 | 37.56 | A | C |
| ATOM | 1684 | O | MET | A | 228 | 31.098 | 108.812 | 93.415 | 1.00 | 36.47 | A | O |
| ATOM | 1685 | N | ASN | A | 229 | 31.595 | 108.068 | 91.352 | 1.00 | 37.61 | A | N |
| ATOM | 1686 | CA | ASN | A | 229 | 30.815 | 106.858 | 91.504 | 1.00 | 38.54 | A | C |
| ATOM | 1687 | CB | ASN | A | 229 | 31.559 | 105.864 | 92.397 | 1.00 | 42.24 | A | C |
| ATOM | 1688 | CG | ASN | A | 229 | 32.769 | 105.259 | 91.699 | 1.00 | 44.82 | A | C |
| ATOM | 1689 | OD1 | ASN | A | 229 | 33.349 | 104.276 | 92.161 | 1.00 | 47.89 | A | O |
| ATOM | 1690 | ND2 | ASN | A | 229 | 33.152 | 105.847 | 90.574 | 1.00 | 44.26 | A | N |
| ATOM | 1691 | C | ASN | A | 229 | 29.444 | 107.194 | 92.076 | 1.00 | 36.19 | A | C |
| ATOM | 1692 | O | ASN | A | 229 | 29.080 | 106.756 | 93.168 | 1.00 | 36.92 | A | O |
| ATOM | 1693 | N | ALA | A | 230 | 28.705 | 108.008 | 91.326 | 1.00 | 33.71 | A | N |
| ATOM | 1694 | CA | ALA | A | 230 | 27.356 | 108.421 | 91.700 | 1.00 | 32.58 | A | C |
| ATOM | 1695 | CB | ALA | A | 230 | 27.203 | 109.938 | 91.576 | 1.00 | 27.65 | A | C |
| ATOM | 1696 | C | ALA | A | 230 | 26.435 | 107.714 | 90.713 | 1.00 | 30.61 | A | C |
| ATOM | 1697 | O | ALA | A | 230 | 25.859 | 108.334 | 89.819 | 1.00 | 30.46 | A | O |
| ATOM | 1698 | N | TYR | A | 231 | 26.316 | 106.404 | 90.884 | 1.00 | 27.03 | A | N |
| ATOM | 1699 | CA | TYR | A | 231 | 25.504 | 105.577 | 90.011 | 1.00 | 26.46 | A | C |
| ATOM | 1700 | CB | TYR | A | 231 | 25.722 | 104.113 | 90.380 | 1.00 | 26.44 | A | C |
| ATOM | 1701 | CG | TYR | A | 231 | 27.192 | 103.766 | 90.453 | 1.00 | 28.60 | A | C |
| ATOM | 1702 | CD1 | TYR | A | 231 | 28.101 | 104.400 | 89.624 | 1.00 | 31.69 | A | C |
| ATOM | 1703 | CE1 | TYR | A | 231 | 29.447 | 104.081 | 89.643 | 1.00 | 31.27 | A | C |
| ATOM | 1704 | CD2 | TYR | A | 231 | 27.669 | 102.793 | 91.320 | 1.00 | 30.41 | A | C |
| ATOM | 1705 | CE2 | TYR | A | 231 | 29.021 | 102.460 | 91.348 | 1.00 | 33.03 | A | C |
| ATOM | 1706 | CZ | TYR | A | 231 | 29.905 | 103.109 | 90.498 | 1.00 | 32.08 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1707 | OH | TYR | A | 231 | 31.241 | 102.768 | 90.460 | 1.00 | 32.59 | A | O |
| ATOM | 1708 | C | TYR | A | 231 | 24.030 | 105.950 | 90.058 | 1.00 | 27.23 | A | C |
| ATOM | 1709 | O | TYR | A | 231 | 23.442 | 106.055 | 91.135 | 1.00 | 29.24 | A | O |
| ATOM | 1710 | N | SER | A | 232 | 23.441 | 106.159 | 88.880 | 1.00 | 26.97 | A | N |
| ATOM | 1711 | CA | SER | A | 232 | 22.033 | 106.552 | 88.768 | 1.00 | 26.72 | A | C |
| ATOM | 1712 | CB | SER | A | 232 | 21.628 | 106.708 | 87.292 | 1.00 | 26.52 | A | C |
| ATOM | 1713 | OG | SER | A | 232 | 21.159 | 105.486 | 86.736 | 1.00 | 29.15 | A | O |
| ATOM | 1714 | C | SER | A | 232 | 21.075 | 105.577 | 89.456 | 1.00 | 25.94 | A | C |
| ATOM | 1715 | O | SER | A | 232 | 20.007 | 105.967 | 89.916 | 1.00 | 25.71 | A | O |
| ATOM | 1716 | N | SER | A | 233 | 21.450 | 104.308 | 89.521 | 1.00 | 23.82 | A | N |
| ATOM | 1717 | CA | SER | A | 233 | 20.599 | 103.337 | 90.182 | 1.00 | 25.88 | A | C |
| ATOM | 1718 | CB | SER | A | 233 | 21.093 | 101.913 | 89.910 | 1.00 | 25.58 | A | C |
| ATOM | 1719 | OG | SER | A | 233 | 21.025 | 101.596 | 88.533 | 1.00 | 31.72 | A | O |
| ATOM | 1720 | C | SER | A | 233 | 20.592 | 103.588 | 91.689 | 1.00 | 26.72 | A | C |
| ATOM | 1721 | O | SER | A | 233 | 19.712 | 103.102 | 92.400 | 1.00 | 27.71 | A | O |
| ATOM | 1722 | N | ARG | A | 234 | 21.562 | 104.358 | 92.175 | 1.00 | 26.10 | A | N |
| ATOM | 1723 | CA | ARG | A | 234 | 21.663 | 104.637 | 93.607 | 1.00 | 26.33 | A | C |
| ATOM | 1724 | CB | ARG | A | 234 | 23.078 | 104.334 | 94.080 | 1.00 | 27.67 | A | C |
| ATOM | 1725 | CG | ARG | A | 234 | 23.441 | 102.883 | 93.942 | 1.00 | 30.93 | A | C |
| ATOM | 1726 | CD | ARG | A | 234 | 24.930 | 102.718 | 93.835 | 1.00 | 36.40 | A | C |
| ATOM | 1727 | NE | ARG | A | 234 | 25.289 | 101.345 | 93.508 | 1.00 | 40.22 | A | N |
| ATOM | 1728 | CZ | ARG | A | 234 | 25.106 | 100.313 | 94.323 | 1.00 | 42.20 | A | C |
| ATOM | 1729 | NH1 | ARG | A | 234 | 24.570 | 100.498 | 95.528 | 1.00 | 39.48 | A | N |
| ATOM | 1730 | NH2 | ARG | A | 234 | 25.449 | 99.096 | 93.921 | 1.00 | 43.21 | A | N |
| ATOM | 1731 | C | ARG | A | 234 | 21.287 | 106.047 | 94.043 | 1.00 | 25.77 | A | C |
| ATOM | 1732 | O | ARG | A | 234 | 21.615 | 106.461 | 95.154 | 1.00 | 26.15 | A | O |
| ATOM | 1733 | N | SER | A | 235 | 20.584 | 106.783 | 93.192 | 1.00 | 23.67 | A | N |
| ATOM | 1734 | CA | SER | A | 235 | 20.213 | 108.136 | 93.552 | 1.00 | 22.26 | A | C |
| ATOM | 1735 | CB | SER | A | 235 | 21.250 | 109.119 | 92.991 | 1.00 | 25.16 | A | C |
| ATOM | 1736 | OG | SER | A | 235 | 21.596 | 108.819 | 91.648 | 1.00 | 26.07 | A | O |
| ATOM | 1737 | C | SER | A | 235 | 18.809 | 108.540 | 93.126 | 1.00 | 21.95 | A | C |
| ATOM | 1738 | O | SER | A | 235 | 18.156 | 107.848 | 92.348 | 1.00 | 22.75 | A | O |
| ATOM | 1739 | N | HIS | A | 236 | 18.346 | 109.665 | 93.664 | 1.00 | 19.10 | A | N |
| ATOM | 1740 | CA | HIS | A | 236 | 17.026 | 110.177 | 93.346 | 1.00 | 17.01 | A | C |
| ATOM | 1741 | CB | HIS | A | 236 | 16.337 | 110.710 | 94.592 | 1.00 | 18.70 | A | C |
| ATOM | 1742 | CG | HIS | A | 236 | 16.318 | 109.741 | 95.728 | 1.00 | 19.39 | A | C |
| ATOM | 1743 | CD2 | HIS | A | 236 | 16.743 | 109.862 | 97.007 | 1.00 | 16.18 | A | C |
| ATOM | 1744 | ND1 | HIS | A | 236 | 15.798 | 108.470 | 95.611 | 1.00 | 20.72 | A | N |
| ATOM | 1745 | CE1 | HIS | A | 236 | 15.903 | 107.850 | 96.773 | 1.00 | 22.96 | A | C |
| ATOM | 1746 | NE2 | HIS | A | 236 | 16.472 | 108.673 | 97.637 | 1.00 | 20.14 | A | N |
| ATOM | 1747 | C | HIS | A | 236 | 17.157 | 111.301 | 92.358 | 1.00 | 15.47 | A | C |
| ATOM | 1748 | O | HIS | A | 236 | 18.020 | 112.159 | 92.503 | 1.00 | 15.19 | A | O |
| ATOM | 1749 | N | SER | A | 237 | 16.290 | 111.290 | 91.356 | 1.00 | 15.61 | A | N |
| ATOM | 1750 | CA | SER | A | 237 | 16.295 | 112.311 | 90.325 | 1.00 | 15.74 | A | C |
| ATOM | 1751 | CB | SER | A | 237 | 16.264 | 111.666 | 88.937 | 1.00 | 13.08 | A | C |
| ATOM | 1752 | OG | SER | A | 237 | 16.201 | 112.652 | 87.924 | 1.00 | 16.54 | A | O |
| ATOM | 1753 | C | SER | A | 237 | 15.057 | 113.159 | 90.518 | 1.00 | 16.12 | A | C |
| ATOM | 1754 | O | SER | A | 237 | 13.945 | 112.669 | 90.382 | 1.00 | 18.10 | A | O |
| ATOM | 1755 | N | VAL | A | 238 | 15.239 | 114.427 | 90.848 | 1.00 | 14.96 | A | N |
| ATOM | 1756 | CA | VAL | A | 238 | 14.092 | 115.290 | 91.025 | 1.00 | 15.04 | A | C |
| ATOM | 1757 | CB | VAL | A | 238 | 14.091 | 115.971 | 92.400 | 1.00 | 15.58 | A | C |
| ATOM | 1758 | CG1 | VAL | A | 238 | 12.785 | 116.708 | 92.596 | 1.00 | 13.91 | A | C |
| ATOM | 1759 | CG2 | VAL | A | 238 | 14.267 | 114.936 | 93.494 | 1.00 | 17.63 | A | C |
| ATOM | 1760 | C | VAL | A | 238 | 14.038 | 116.359 | 89.952 | 1.00 | 15.21 | A | C |
| ATOM | 1761 | O | VAL | A | 238 | 14.821 | 117.312 | 89.956 | 1.00 | 15.94 | A | O |
| ATOM | 1762 | N | PHE | A | 239 | 13.109 | 116.183 | 89.023 | 1.00 | 14.87 | A | N |
| ATOM | 1763 | CA | PHE | A | 239 | 12.933 | 117.133 | 87.943 | 1.00 | 14.99 | A | C |
| ATOM | 1764 | CB | PHE | A | 239 | 12.700 | 116.385 | 86.627 | 1.00 | 15.79 | A | C |
| ATOM | 1765 | CG | PHE | A | 239 | 12.272 | 117.271 | 85.495 | 1.00 | 15.79 | A | C |
| ATOM | 1766 | CD1 | PHE | A | 239 | 10.932 | 117.422 | 85.185 | 1.00 | 17.37 | A | C |
| ATOM | 1767 | CD2 | PHE | A | 239 | 13.205 | 117.969 | 84.756 | 1.00 | 14.09 | A | C |
| ATOM | 1768 | CE1 | PHE | A | 239 | 10.538 | 118.249 | 84.157 | 1.00 | 18.65 | A | C |
| ATOM | 1769 | CE2 | PHE | A | 239 | 12.811 | 118.799 | 83.727 | 1.00 | 15.93 | A | C |
| ATOM | 1770 | CZ | PHE | A | 239 | 11.479 | 118.938 | 83.427 | 1.00 | 17.94 | A | C |
| ATOM | 1771 | C | PHE | A | 239 | 11.747 | 118.020 | 88.291 | 1.00 | 14.16 | A | C |
| ATOM | 1772 | O | PHE | A | 239 | 10.709 | 117.525 | 88.706 | 1.00 | 14.72 | A | O |
| ATOM | 1773 | N | SER | A | 240 | 11.908 | 119.332 | 88.142 | 1.00 | 13.96 | A | N |
| ATOM | 1774 | CA | SER | A | 240 | 10.833 | 120.275 | 88.456 | 1.00 | 14.01 | A | C |
| ATOM | 1775 | CB | SER | A | 240 | 11.152 | 121.086 | 89.710 | 1.00 | 11.50 | A | C |
| ATOM | 1776 | OG | SER | A | 240 | 11.035 | 120.291 | 90.875 | 1.00 | 17.82 | A | O |
| ATOM | 1777 | C | SER | A | 240 | 10.557 | 121.254 | 87.346 | 1.00 | 15.41 | A | C |
| ATOM | 1778 | O | SER | A | 240 | 11.477 | 121.733 | 86.679 | 1.00 | 15.50 | A | O |
| ATOM | 1779 | N | VAL | A | 241 | 9.281 | 121.556 | 87.151 | 1.00 | 15.51 | A | N |
| ATOM | 1780 | CA | VAL | A | 241 | 8.882 | 122.520 | 86.141 | 1.00 | 16.16 | A | C |
| ATOM | 1781 | CB | VAL | A | 241 | 8.306 | 121.837 | 84.854 | 1.00 | 18.46 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1782 | CG1 | VAL | A | 241 | 7.094 | 120.975 | 85.191 | 1.00 | 13.75 | A | C |
| ATOM | 1783 | CG2 | VAL | A | 241 | 7.944 | 122.917 | 83.811 | 1.00 | 15.59 | A | C |
| ATOM | 1784 | C | VAL | A | 241 | 7.838 | 123.416 | 86.787 | 1.00 | 17.11 | A | C |
| ATOM | 1785 | O | VAL | A | 241 | 6.861 | 122.943 | 87.376 | 1.00 | 15.68 | A | O |
| ATOM | 1786 | N | THR | A | 242 | 8.069 | 124.719 | 86.711 | 1.00 | 18.24 | A | N |
| ATOM | 1787 | CA | THR | A | 242 | 7.155 | 125.677 | 87.304 | 1.00 | 16.90 | A | C |
| ATOM | 1788 | CB | THR | A | 242 | 7.899 | 126.605 | 88.261 | 1.00 | 16.43 | A | C |
| ATOM | 1789 | OG1 | THR | A | 242 | 8.643 | 125.822 | 89.203 | 1.00 | 18.82 | A | O |
| ATOM | 1790 | CG2 | THR | A | 242 | 6.920 | 127.485 | 89.010 | 1.00 | 14.69 | A | C |
| ATOM | 1791 | C | THR | A | 242 | 6.541 | 126.498 | 86.191 | 1.00 | 19.46 | A | C |
| ATOM | 1792 | O | THR | A | 242 | 7.209 | 126.809 | 85.215 | 1.00 | 21.09 | A | O |
| ATOM | 1793 | N | ILE | A | 243 | 5.263 | 126.830 | 86.311 | 1.00 | 21.17 | A | N |
| ATOM | 1794 | CA | ILE | A | 243 | 4.631 | 127.635 | 85.276 | 1.00 | 23.58 | A | C |
| ATOM | 1795 | CB | ILE | A | 243 | 3.504 | 126.874 | 84.527 | 1.00 | 23.68 | A | C |
| ATOM | 1796 | CG2 | ILE | A | 243 | 2.917 | 127.767 | 83.457 | 1.00 | 22.82 | A | C |
| ATOM | 1797 | CG1 | ILE | A | 243 | 4.039 | 125.600 | 83.876 | 1.00 | 22.88 | A | C |
| ATOM | 1798 | CD1 | ILE | A | 243 | 4.382 | 124.515 | 84.854 | 1.00 | 25.25 | A | C |
| ATOM | 1799 | C | ILE | A | 243 | 4.009 | 128.910 | 85.846 | 1.00 | 24.77 | A | C |
| ATOM | 1800 | O | ILE | A | 243 | 3.166 | 128.839 | 86.742 | 1.00 | 26.46 | A | O |
| ATOM | 1801 | N | HIS | A | 244 | 4.441 | 130.068 | 85.339 | 1.00 | 21.90 | A | N |
| ATOM | 1802 | CA | HIS | A | 244 | 3.870 | 131.350 | 85.752 | 1.00 | 20.71 | A | C |
| ATOM | 1803 | CB | HIS | A | 244 | 4.941 | 132.451 | 85.796 | 1.00 | 18.58 | A | C |
| ATOM | 1804 | CG | HIS | A | 244 | 5.689 | 132.512 | 87.097 | 1.00 | 22.27 | A | C |
| ATOM | 1805 | CD2 | HIS | A | 244 | 5.629 | 133.402 | 88.116 | 1.00 | 21.19 | A | C |
| ATOM | 1806 | ND1 | HIS | A | 244 | 6.592 | 131.545 | 87.489 | 1.00 | 19.71 | A | N |
| ATOM | 1807 | CE1 | HIS | A | 244 | 7.053 | 131.836 | 88.690 | 1.00 | 20.45 | A | C |
| ATOM | 1808 | NE2 | HIS | A | 244 | 6.484 | 132.958 | 89.094 | 1.00 | 22.26 | A | N |
| ATOM | 1809 | C | HIS | A | 244 | 2.823 | 131.652 | 84.686 | 1.00 | 20.47 | A | C |
| ATOM | 1810 | O | HIS | A | 244 | 3.152 | 131.779 | 83.503 | 1.00 | 18.52 | A | O |
| ATOM | 1811 | N | MET | A | 245 | 1.562 | 131.736 | 85.101 | 1.00 | 20.37 | A | N |
| ATOM | 1812 | CA | MET | A | 245 | 0.466 | 131.971 | 84.164 | 1.00 | 21.36 | A | C |
| ATOM | 1813 | CB | MET | A | 245 | −0.408 | 130.724 | 84.056 | 1.00 | 21.01 | A | C |
| ATOM | 1814 | CG | MET | A | 245 | 0.354 | 129.421 | 83.902 | 1.00 | 20.47 | A | C |
| ATOM | 1815 | SD | MET | A | 245 | −0.750 | 128.022 | 84.008 | 1.00 | 20.90 | A | S |
| ATOM | 1816 | CE | MET | A | 245 | −1.016 | 127.915 | 85.794 | 1.00 | 18.88 | A | C |
| ATOM | 1817 | C | MET | A | 245 | −0.438 | 133.135 | 84.525 | 1.00 | 23.52 | A | C |
| ATOM | 1818 | O | MET | A | 245 | −0.691 | 133.415 | 85.701 | 1.00 | 23.49 | A | O |
| ATOM | 1819 | N | LYS | A | 246 | −0.943 | 133.798 | 83.494 | 1.00 | 25.78 | A | N |
| ATOM | 1820 | CA | LYS | A | 246 | −1.846 | 134.922 | 83.674 | 1.00 | 28.15 | A | C |
| ATOM | 1821 | CB | LYS | A | 246 | −1.074 | 136.237 | 83.617 | 1.00 | 28.85 | A | C |
| ATOM | 1822 | CG | LYS | A | 246 | −1.935 | 137.443 | 83.910 | 1.00 | 34.09 | A | C |
| ATOM | 1823 | CD | LYS | A | 246 | −1.122 | 138.723 | 84.053 | 1.00 | 36.39 | A | C |
| ATOM | 1824 | CE | LYS | A | 246 | −2.028 | 139.896 | 84.424 | 1.00 | 39.16 | A | C |
| ATOM | 1825 | NZ | LYS | A | 246 | −1.284 | 141.167 | 84.653 | 1.00 | 42.33 | A | N |
| ATOM | 1826 | C | LYS | A | 246 | −2.878 | 134.875 | 82.561 | 1.00 | 28.82 | A | C |
| ATOM | 1827 | O | LYS | A | 246 | −2.519 | 134.913 | 81.392 | 1.00 | 29.37 | A | O |
| ATOM | 1828 | N | GLU | A | 247 | −4.153 | 134.760 | 82.917 | 1.00 | 30.75 | A | N |
| ATOM | 1829 | CA | GLU | A | 247 | −5.205 | 134.717 | 81.907 | 1.00 | 34.53 | A | C |
| ATOM | 1830 | CB | GLU | A | 247 | −5.917 | 133.364 | 81.916 | 1.00 | 36.13 | A | C |
| ATOM | 1831 | CG | GLU | A | 247 | −6.111 | 132.750 | 83.271 | 1.00 | 42.21 | A | C |
| ATOM | 1832 | CD | GLU | A | 247 | −6.843 | 131.423 | 83.190 | 1.00 | 46.41 | A | C |
| ATOM | 1833 | OE1 | GLU | A | 247 | −6.857 | 130.679 | 84.199 | 1.00 | 48.67 | A | O |
| ATOM | 1834 | OE2 | GLU | A | 247 | −7.410 | 131.126 | 82.115 | 1.00 | 46.87 | A | O |
| ATOM | 1835 | C | GLU | A | 247 | −6.227 | 135.846 | 82.019 | 1.00 | 34.64 | A | C |
| ATOM | 1836 | O | GLU | A | 247 | −6.791 | 136.102 | 83.092 | 1.00 | 35.01 | A | O |
| ATOM | 1837 | N | THR | A | 248 | −6.456 | 136.510 | 80.887 | 1.00 | 32.54 | A | N |
| ATOM | 1838 | CA | THR | A | 248 | −7.376 | 137.630 | 80.814 | 1.00 | 31.54 | A | C |
| ATOM | 1839 | CB | THR | A | 248 | −6.650 | 138.901 | 80.318 | 1.00 | 29.94 | A | C |
| ATOM | 1840 | OG1 | THR | A | 248 | −5.604 | 139.239 | 81.231 | 1.00 | 34.62 | A | O |
| ATOM | 1841 | CG2 | THR | A | 248 | −7.610 | 140.064 | 80.225 | 1.00 | 29.47 | A | C |
| ATOM | 1842 | C | THR | A | 248 | −8.561 | 137.361 | 79.890 | 1.00 | 29.77 | A | C |
| ATOM | 1843 | O | THR | A | 248 | −8.403 | 136.876 | 78.773 | 1.00 | 27.61 | A | O |
| ATOM | 1844 | N | THR | A | 249 | −9.752 | 137.689 | 80.375 | 1.00 | 30.47 | A | N |
| ATOM | 1845 | CA | THR | A | 249 | −10.984 | 137.532 | 79.612 | 1.00 | 29.88 | A | C |
| ATOM | 1846 | CB | THR | A | 249 | −11.822 | 136.359 | 80.144 | 1.00 | 32.48 | A | C |
| ATOM | 1847 | OG1 | THR | A | 249 | −11.220 | 135.111 | 79.756 | 1.00 | 28.17 | A | O |
| ATOM | 1848 | CG2 | THR | A | 249 | −13.238 | 136.444 | 79.608 | 1.00 | 31.65 | A | C |
| ATOM | 1849 | C | THR | A | 249 | −11.790 | 138.815 | 79.768 | 1.00 | 28.83 | A | C |
| ATOM | 1850 | O | THR | A | 249 | −12.242 | 139.118 | 80.866 | 1.00 | 28.63 | A | O |
| ATOM | 1851 | N | ILE | A | 250 | −11.962 | 139.569 | 78.682 | 1.00 | 29.45 | A | N |
| ATOM | 1852 | CA | ILE | A | 250 | −12.704 | 140.833 | 78.736 | 1.00 | 28.63 | A | C |
| ATOM | 1853 | CB | ILE | A | 250 | −12.959 | 141.390 | 77.325 | 1.00 | 24.01 | A | C |
| ATOM | 1854 | CG2 | ILE | A | 250 | −13.851 | 142.613 | 77.401 | 1.00 | 22.31 | A | C |
| ATOM | 1855 | CG1 | ILE | A | 250 | −11.623 | 141.740 | 76.666 | 1.00 | 24.23 | A | C |
| ATOM | 1856 | CD1 | ILE | A | 250 | −11.732 | 142.164 | 75.214 | 1.00 | 21.04 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1857 | C | ILE | A | 250 | −14.036 | 140.663 | 79.464 | 1.00 | 30.12 | A | C |
| ATOM | 1858 | O | ILE | A | 250 | −14.771 | 139.712 | 79.207 | 1.00 | 29.47 | A | O |
| ATOM | 1859 | N | ASP | A | 251 | −14.343 | 141.588 | 80.371 | 1.00 | 33.65 | A | N |
| ATOM | 1860 | CA | ASP | A | 251 | −15.583 | 141.511 | 81.143 | 1.00 | 38.67 | A | C |
| ATOM | 1861 | CB | ASP | A | 251 | −16.822 | 141.655 | 80.242 | 1.00 | 40.02 | A | C |
| ATOM | 1862 | CG | ASP | A | 251 | −16.937 | 143.027 | 79.611 | 1.00 | 40.05 | A | C |
| ATOM | 1863 | OD1 | ASP | A | 251 | −16.547 | 144.018 | 80.284 | 1.00 | 35.35 | A | O |
| ATOM | 1864 | OD2 | ASP | A | 251 | −17.432 | 143.102 | 78.454 | 1.00 | 36.62 | A | O |
| ATOM | 1865 | C | ASP | A | 251 | −15.610 | 140.138 | 81.798 | 1.00 | 40.74 | A | C |
| ATOM | 1866 | O | ASP | A | 251 | −16.626 | 139.432 | 81.765 | 1.00 | 39.70 | A | O |
| ATOM | 1867 | N | GLY | A | 252 | −14.475 | 139.762 | 82.380 | 1.00 | 42.03 | A | N |
| ATOM | 1868 | CA | GLY | A | 252 | −14.355 | 138.469 | 83.024 | 1.00 | 41.14 | A | C |
| ATOM | 1869 | C | GLY | A | 252 | −13.340 | 138.555 | 84.135 | 1.00 | 42.68 | A | C |
| ATOM | 1870 | O | GLY | A | 252 | −12.788 | 139.629 | 84.396 | 1.00 | 43.97 | A | O |
| ATOM | 1871 | N | GLU | A | 253 | −13.086 | 137.433 | 84.794 | 1.00 | 43.59 | A | N |
| ATOM | 1872 | CA | GLU | A | 253 | −12.134 | 137.410 | 85.895 | 1.00 | 43.80 | A | C |
| ATOM | 1873 | CB | GLU | A | 253 | −12.486 | 136.264 | 86.854 | 1.00 | 45.42 | A | C |
| ATOM | 1874 | CG | GLU | A | 253 | −11.663 | 136.196 | 88.144 | 1.00 | 47.63 | A | C |
| ATOM | 1875 | CD | GLU | A | 253 | −11.848 | 137.408 | 89.044 | 1.00 | 48.73 | A | C |
| ATOM | 1876 | OE1 | GLU | A | 253 | −11.637 | 137.273 | 90.273 | 1.00 | 46.79 | A | O |
| ATOM | 1877 | OE2 | GLU | A | 253 | −12.191 | 138.495 | 88.525 | 1.00 | 48.20 | A | O |
| ATOM | 1878 | C | GLU | A | 253 | −10.720 | 137.236 | 85.355 | 1.00 | 42.32 | A | C |
| ATOM | 1879 | O | GLU | A | 253 | −10.479 | 136.382 | 84.500 | 1.00 | 42.16 | A | O |
| ATOM | 1880 | N | GLU | A | 254 | −9.798 | 138.069 | 85.833 | 1.00 | 40.24 | A | N |
| ATOM | 1881 | CA | GLU | A | 254 | −8.401 | 137.978 | 85.421 | 1.00 | 37.96 | A | C |
| ATOM | 1882 | CB | GLU | A | 254 | −7.723 | 139.345 | 85.508 | 1.00 | 39.14 | A | C |
| ATOM | 1883 | CG | GLU | A | 254 | −6.290 | 139.356 | 85.001 | 1.00 | 42.21 | A | C |
| ATOM | 1884 | CD | GLU | A | 254 | −5.605 | 140.698 | 85.188 | 1.00 | 42.84 | A | C |
| ATOM | 1885 | OE1 | GLU | A | 254 | −5.360 | 141.090 | 86.353 | 1.00 | 41.37 | A | O |
| ATOM | 1886 | OE2 | GLU | A | 254 | −5.314 | 141.359 | 84.168 | 1.00 | 42.71 | A | O |
| ATOM | 1887 | C | GLU | A | 254 | −7.731 | 137.001 | 86.388 | 1.00 | 35.66 | A | C |
| ATOM | 1888 | O | GLU | A | 254 | −7.862 | 137.137 | 87.604 | 1.00 | 34.06 | A | O |
| ATOM | 1889 | N | LEU | A | 255 | −7.027 | 136.010 | 85.855 | 1.00 | 33.72 | A | N |
| ATOM | 1890 | CA | LEU | A | 255 | −6.375 | 135.030 | 86.717 | 1.00 | 32.37 | A | C |
| ATOM | 1891 | CB | LEU | A | 255 | −6.935 | 133.634 | 86.449 | 1.00 | 33.03 | A | C |
| ATOM | 1892 | CG | LEU | A | 255 | −8.315 | 133.360 | 87.049 | 1.00 | 35.25 | A | C |
| ATOM | 1893 | CD1 | LEU | A | 255 | −8.853 | 132.048 | 86.529 | 1.00 | 34.56 | A | C |
| ATOM | 1894 | CD2 | LEU | A | 255 | −8.208 | 133.340 | 88.566 | 1.00 | 33.73 | A | C |
| ATOM | 1895 | C | LEU | A | 255 | −4.862 | 134.975 | 86.649 | 1.00 | 30.72 | A | C |
| ATOM | 1896 | O | LEU | A | 255 | −4.271 | 134.840 | 85.578 | 1.00 | 30.27 | A | O |
| ATOM | 1897 | N | VAL | A | 256 | −4.242 | 135.085 | 87.817 | 1.00 | 28.80 | A | N |
| ATOM | 1898 | CA | VAL | A | 256 | −2.798 | 135.014 | 87.923 | 1.00 | 26.10 | A | C |
| ATOM | 1899 | CB | VAL | A | 256 | −2.218 | 136.286 | 88.538 | 1.00 | 24.57 | A | C |
| ATOM | 1900 | CG1 | VAL | A | 256 | −0.767 | 136.053 | 88.941 | 1.00 | 24.95 | A | C |
| ATOM | 1901 | CG2 | VAL | A | 256 | −2.301 | 137.410 | 87.531 | 1.00 | 25.62 | A | C |
| ATOM | 1902 | C | VAL | A | 256 | −2.467 | 133.833 | 88.811 | 1.00 | 24.50 | A | C |
| ATOM | 1903 | O | VAL | A | 256 | −2.852 | 133.802 | 89.978 | 1.00 | 25.95 | A | O |
| ATOM | 1904 | N | LYS | A | 257 | −1.766 | 132.850 | 88.257 | 1.00 | 22.30 | A | N |
| ATOM | 1905 | CA | LYS | A | 257 | −1.414 | 131.680 | 89.037 | 1.00 | 19.36 | A | C |
| ATOM | 1906 | CB | LYS | A | 257 | −2.491 | 130.599 | 88.884 | 1.00 | 20.07 | A | C |
| ATOM | 1907 | CG | LYS | A | 257 | −3.139 | 130.523 | 87.524 | 1.00 | 20.37 | A | C |
| ATOM | 1908 | CD | LYS | A | 257 | −4.296 | 129.527 | 87.543 | 1.00 | 20.61 | A | C |
| ATOM | 1909 | CE | LYS | A | 257 | −5.106 | 129.535 | 86.247 | 1.00 | 22.75 | A | C |
| ATOM | 1910 | NZ | LYS | A | 257 | −4.313 | 129.239 | 85.012 | 1.00 | 21.12 | A | N |
| ATOM | 1911 | C | LYS | A | 257 | −0.057 | 131.100 | 88.724 | 1.00 | 16.79 | A | C |
| ATOM | 1912 | O | LYS | A | 257 | 0.501 | 131.345 | 87.669 | 1.00 | 16.48 | A | O |
| ATOM | 1913 | N | ILE | A | 258 | 0.471 | 130.348 | 89.679 | 1.00 | 16.81 | A | N |
| ATOM | 1914 | CA | ILE | A | 258 | 1.753 | 129.694 | 89.540 | 1.00 | 18.04 | A | C |
| ATOM | 1915 | CB | ILE | A | 258 | 2.760 | 130.203 | 90.589 | 1.00 | 18.13 | A | C |
| ATOM | 1916 | CG2 | ILE | A | 258 | 4.027 | 129.377 | 90.523 | 1.00 | 18.02 | A | C |
| ATOM | 1917 | CG1 | ILE | A | 258 | 3.068 | 131.684 | 90.343 | 1.00 | 19.96 | A | C |
| ATOM | 1918 | CD1 | ILE | A | 258 | 3.856 | 132.342 | 91.441 | 1.00 | 16.99 | A | C |
| ATOM | 1919 | C | ILE | A | 258 | 1.537 | 128.195 | 89.744 | 1.00 | 19.48 | A | C |
| ATOM | 1920 | O | ILE | A | 258 | 1.011 | 127.771 | 90.776 | 1.00 | 20.41 | A | O |
| ATOM | 1921 | N | GLY | A | 259 | 1.931 | 127.401 | 88.751 | 1.00 | 19.30 | A | N |
| ATOM | 1922 | CA | GLY | A | 259 | 1.779 | 125.961 | 88.839 | 1.00 | 20.91 | A | C |
| ATOM | 1923 | C | GLY | A | 259 | 3.133 | 125.291 | 88.942 | 1.00 | 21.01 | A | C |
| ATOM | 1924 | O | GLY | A | 259 | 4.148 | 125.899 | 88.604 | 1.00 | 22.90 | A | O |
| ATOM | 1925 | N | LYS | A | 260 | 3.164 | 124.046 | 89.407 | 1.00 | 21.18 | A | N |
| ATOM | 1926 | CA | LYS | A | 260 | 4.434 | 123.339 | 89.527 | 1.00 | 21.85 | A | C |
| ATOM | 1927 | CB | LYS | A | 260 | 5.204 | 123.871 | 90.741 | 1.00 | 22.05 | A | C |
| ATOM | 1928 | CG | LYS | A | 260 | 6.561 | 123.229 | 90.940 | 1.00 | 23.53 | A | C |
| ATOM | 1929 | CD | LYS | A | 260 | 7.401 | 124.052 | 91.897 | 1.00 | 26.59 | A | C |
| ATOM | 1930 | CE | LYS | A | 260 | 8.848 | 123.587 | 91.909 | 1.00 | 25.81 | A | C |
| ATOM | 1931 | NZ | LYS | A | 260 | 9.701 | 124.546 | 92.681 | 1.00 | 31.32 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 1932 | C | LYS | A | 260 | 4.298 | 121.820 | 89.630 | 1.00 | 18.84 | A | C |
| ATOM | 1933 | O | LYS | A | 260 | 3.479 | 121.316 | 90.391 | 1.00 | 20.04 | A | O |
| ATOM | 1934 | N | LEU | A | 261 | 5.109 | 121.098 | 88.863 | 1.00 | 16.74 | A | N |
| ATOM | 1935 | CA | LEU | A | 261 | 5.090 | 119.641 | 88.904 | 1.00 | 16.51 | A | C |
| ATOM | 1936 | CB | LEU | A | 261 | 4.532 | 119.060 | 87.603 | 1.00 | 16.37 | A | C |
| ATOM | 1937 | CG | LEU | A | 261 | 4.377 | 117.528 | 87.623 | 1.00 | 19.84 | A | C |
| ATOM | 1938 | CD1 | LEU | A | 261 | 3.491 | 117.125 | 88.795 | 1.00 | 16.92 | A | C |
| ATOM | 1939 | CD2 | LEU | A | 261 | 3.770 | 117.025 | 86.319 | 1.00 | 18.98 | A | C |
| ATOM | 1940 | C | LEU | A | 261 | 6.475 | 119.039 | 89.144 | 1.00 | 15.87 | A | C |
| ATOM | 1941 | O | LEU | A | 261 | 7.435 | 119.370 | 88.446 | 1.00 | 13.76 | A | O |
| ATOM | 1942 | N | ASN | A | 262 | 6.565 | 118.155 | 90.137 | 1.00 | 15.48 | A | N |
| ATOM | 1943 | CA | ASN | A | 262 | 7.815 | 117.475 | 90.450 | 1.00 | 13.77 | A | C |
| ATOM | 1944 | CB | ASN | A | 262 | 8.058 | 117.430 | 91.960 | 1.00 | 15.24 | A | C |
| ATOM | 1945 | CG | ASN | A | 262 | 7.859 | 118.776 | 92.626 | 1.00 | 19.57 | A | C |
| ATOM | 1946 | OD1 | ASN | A | 262 | 6.818 | 119.026 | 93.235 | 1.00 | 18.30 | A | O |
| ATOM | 1947 | ND2 | ASN | A | 262 | 8.855 | 119.653 | 92.511 | 1.00 | 17.38 | A | N |
| ATOM | 1948 | C | ASN | A | 262 | 7.723 | 116.050 | 89.924 | 1.00 | 11.89 | A | C |
| ATOM | 1949 | O | ASN | A | 262 | 6.774 | 115.328 | 90.208 | 1.00 | 14.14 | A | O |
| ATOM | 1950 | N | LEU | A | 263 | 8.708 | 115.650 | 89.145 | 1.00 | 9.74 | A | N |
| ATOM | 1951 | CA | LEU | A | 263 | 8.731 | 114.314 | 88.588 | 1.00 | 13.15 | A | C |
| ATOM | 1952 | CB | LEU | A | 263 | 8.743 | 114.411 | 87.066 | 1.00 | 13.63 | A | C |
| ATOM | 1953 | CG | LEU | A | 263 | 7.520 | 115.185 | 86.560 | 1.00 | 13.69 | A | C |
| ATOM | 1954 | CD1 | LEU | A | 263 | 7.543 | 115.308 | 85.050 | 1.00 | 14.90 | A | C |
| ATOM | 1955 | CD2 | LEU | A | 263 | 6.258 | 114.464 | 86.989 | 1.00 | 13.22 | A | C |
| ATOM | 1956 | C | LEU | A | 263 | 9.973 | 113.611 | 89.139 | 1.00 | 15.26 | A | C |
| ATOM | 1957 | O | LEU | A | 263 | 11.106 | 113.881 | 88.723 | 1.00 | 15.88 | A | O |
| ATOM | 1958 | N | VAL | A | 264 | 9.735 | 112.703 | 90.079 | 1.00 | 14.34 | A | N |
| ATOM | 1959 | CA | VAL | A | 264 | 10.796 | 111.993 | 90.774 | 1.00 | 14.18 | A | C |
| ATOM | 1960 | CB | VAL | A | 264 | 10.503 | 112.025 | 92.301 | 1.00 | 15.35 | A | C |
| ATOM | 1961 | CG1 | VAL | A | 264 | 11.718 | 111.539 | 93.098 | 1.00 | 15.90 | A | C |
| ATOM | 1962 | CG2 | VAL | A | 264 | 10.102 | 113.431 | 92.712 | 1.00 | 12.44 | A | C |
| ATOM | 1963 | C | VAL | A | 264 | 11.096 | 110.545 | 90.374 | 1.00 | 12.44 | A | C |
| ATOM | 1964 | O | VAL | A | 264 | 10.238 | 109.675 | 90.503 | 1.00 | 14.19 | A | O |
| ATOM | 1965 | N | ASP | A | 265 | 12.326 | 110.306 | 89.913 | 1.00 | 10.90 | A | N |
| ATOM | 1966 | CA | ASP | A | 265 | 12.812 | 108.970 | 89.533 | 1.00 | 13.92 | A | C |
| ATOM | 1967 | CB | ASP | A | 265 | 13.710 | 109.073 | 88.290 | 1.00 | 16.81 | A | C |
| ATOM | 1968 | CG | ASP | A | 265 | 14.022 | 107.724 | 87.666 | 1.00 | 18.55 | A | C |
| ATOM | 1969 | OD1 | ASP | A | 265 | 14.153 | 106.733 | 88.417 | 1.00 | 23.49 | A | O |
| ATOM | 1970 | OD2 | ASP | A | 265 | 14.155 | 107.660 | 86.421 | 1.00 | 18.09 | A | O |
| ATOM | 1971 | C | ASP | A | 265 | 13.643 | 108.524 | 90.755 | 1.00 | 15.06 | A | C |
| ATOM | 1972 | O | ASP | A | 265 | 14.777 | 108.972 | 90.946 | 1.00 | 15.27 | A | O |
| ATOM | 1973 | N | LEU | A | 266 | 13.077 | 107.656 | 91.589 | 1.00 | 14.01 | A | N |
| ATOM | 1974 | CA | LEU | A | 266 | 13.758 | 107.226 | 92.807 | 1.00 | 12.91 | A | C |
| ATOM | 1975 | CB | LEU | A | 266 | 12.738 | 106.693 | 93.819 | 1.00 | 9.20 | A | C |
| ATOM | 1976 | CG | LEU | A | 266 | 11.638 | 107.646 | 94.301 | 1.00 | 11.27 | A | C |
| ATOM | 1977 | CD1 | LEU | A | 266 | 10.557 | 106.849 | 94.996 | 1.00 | 9.83 | A | C |
| ATOM | 1978 | CD2 | LEU | A | 266 | 12.208 | 108.705 | 95.232 | 1.00 | 10.15 | A | C |
| ATOM | 1979 | C | LEU | A | 266 | 14.855 | 106.194 | 92.630 | 1.00 | 13.98 | A | C |
| ATOM | 1980 | O | LEU | A | 266 | 14.883 | 105.441 | 91.658 | 1.00 | 13.37 | A | O |
| ATOM | 1981 | N | ALA | A | 267 | 15.772 | 106.176 | 93.588 | 1.00 | 15.98 | A | N |
| ATOM | 1982 | CA | ALA | A | 267 | 16.856 | 105.210 | 93.571 | 1.00 | 17.01 | A | C |
| ATOM | 1983 | CB | ALA | A | 267 | 17.780 | 105.438 | 94.757 | 1.00 | 17.18 | A | C |
| ATOM | 1984 | C | ALA | A | 267 | 16.190 | 103.843 | 93.674 | 1.00 | 16.42 | A | C |
| ATOM | 1985 | O | ALA | A | 267 | 15.180 | 103.697 | 94.356 | 1.00 | 15.23 | A | O |
| ATOM | 1986 | N | GLY | A | 268 | 16.747 | 102.850 | 92.989 | 1.00 | 17.27 | A | N |
| ATOM | 1987 | CA | GLY | A | 268 | 16.174 | 101.525 | 93.024 | 1.00 | 16.05 | A | C |
| ATOM | 1988 | C | GLY | A | 268 | 15.909 | 101.082 | 94.443 | 1.00 | 20.14 | A | C |
| ATOM | 1989 | O | GLY | A | 268 | 16.594 | 101.495 | 95.380 | 1.00 | 18.77 | A | O |
| ATOM | 1990 | N | SER | A | 269 | 14.901 | 100.238 | 94.609 | 1.00 | 24.02 | A | N |
| ATOM | 1991 | CA | SER | A | 269 | 14.546 | 99.728 | 95.924 | 1.00 | 27.58 | A | C |
| ATOM | 1992 | CB | SER | A | 269 | 13.048 | 99.403 | 95.937 | 1.00 | 25.56 | A | C |
| ATOM | 1993 | OG | SER | A | 269 | 12.617 | 98.988 | 94.652 | 1.00 | 20.75 | A | O |
| ATOM | 1994 | C | SER | A | 269 | 15.401 | 98.494 | 96.270 | 1.00 | 30.90 | A | C |
| ATOM | 1995 | O | SER | A | 269 | 15.026 | 97.367 | 95.959 | 1.00 | 31.03 | A | O |
| ATOM | 1996 | N | GLU | A | 270 | 16.565 | 98.722 | 96.886 | 1.00 | 37.21 | A | N |
| ATOM | 1997 | CA | GLU | A | 270 | 17.490 | 97.640 | 97.273 | 1.00 | 41.67 | A | C |
| ATOM | 1998 | CB | GLU | A | 270 | 18.356 | 97.213 | 96.074 | 1.00 | 42.09 | A | C |
| ATOM | 1999 | CG | GLU | A | 270 | 17.604 | 96.767 | 94.818 | 1.00 | 37.67 | A | C |
| ATOM | 2000 | CD | GLU | A | 270 | 17.838 | 97.701 | 93.634 | 1.00 | 38.24 | A | C |
| ATOM | 2001 | OE1 | GLU | A | 270 | 16.846 | 98.253 | 93.117 | 1.00 | 39.37 | A | O |
| ATOM | 2002 | OE2 | GLU | A | 270 | 19.004 | 97.886 | 93.215 | 1.00 | 33.91 | A | O |
| ATOM | 2003 | C | GLU | A | 270 | 18.424 | 98.049 | 98.431 | 1.00 | 45.77 | A | C |
| ATOM | 2004 | O | GLU | A | 270 | 18.380 | 99.192 | 98.899 | 1.00 | 45.98 | A | O |
| ATOM | 2005 | N | ARG | A | 281 | 19.265 | 97.104 | 98.873 | 1.00 | 49.43 | A | N |
| ATOM | 2006 | CA | ARG | A | 281 | 20.251 | 97.284 | 99.966 | 1.00 | 52.26 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2007 | CB | ARG | A | 281 | 21.413 | 98.173 | 99.492 | 1.00 | 52.62 | A | C |
| ATOM | 2008 | CG | ARG | A | 281 | 22.608 | 98.256 | 100.464 | 1.00 | 53.59 | A | C |
| ATOM | 2009 | CD | ARG | A | 281 | 23.494 | 96.996 | 100.458 | 1.00 | 52.55 | A | C |
| ATOM | 2010 | NE | ARG | A | 281 | 24.706 | 97.158 | 101.273 | 1.00 | 50.60 | A | N |
| ATOM | 2011 | CZ | ARG | A | 281 | 24.739 | 97.109 | 102.606 | 1.00 | 50.83 | A | C |
| ATOM | 2012 | NH1 | ARG | A | 281 | 23.627 | 96.893 | 103.300 | 1.00 | 49.19 | A | N |
| ATOM | 2013 | NH2 | ARG | A | 281 | 25.887 | 97.290 | 103.254 | 1.00 | 47.03 | A | N |
| ATOM | 2014 | C | ARG | A | 281 | 19.691 | 97.826 | 101.299 | 1.00 | 53.26 | A | C |
| ATOM | 2015 | O | ARG | A | 281 | 18.507 | 98.167 | 101.383 | 1.00 | 52.74 | A | O |
| ATOM | 2016 | N | ALA | A | 282 | 20.538 | 97.908 | 102.334 | 1.00 | 55.03 | A | N |
| ATOM | 2017 | CA | ALA | A | 282 | 20.081 | 98.390 | 103.646 | 1.00 | 55.45 | A | C |
| ATOM | 2018 | CB | ALA | A | 282 | 19.308 | 97.261 | 104.343 | 1.00 | 55.34 | A | C |
| ATOM | 2019 | C | ALA | A | 282 | 21.066 | 99.031 | 104.666 | 1.00 | 55.95 | A | C |
| ATOM | 2020 | O | ALA | A | 282 | 20.601 | 99.625 | 105.649 | 1.00 | 56.31 | A | O |
| ATOM | 2021 | N | ARG | A | 283 | 22.388 | 98.931 | 104.471 | 1.00 | 54.87 | A | N |
| ATOM | 2022 | CA | ARG | A | 283 | 23.335 | 99.516 | 105.448 | 1.00 | 53.34 | A | C |
| ATOM | 2023 | CB | ARG | A | 283 | 24.535 | 98.582 | 105.675 | 1.00 | 54.32 | A | C |
| ATOM | 2024 | CG | ARG | A | 283 | 25.230 | 98.757 | 107.042 | 1.00 | 53.78 | A | C |
| ATOM | 2025 | CD | ARG | A | 283 | 25.762 | 100.180 | 107.272 | 1.00 | 56.35 | A | C |
| ATOM | 2026 | NE | ARG | A | 283 | 24.703 | 101.165 | 107.518 | 1.00 | 57.31 | A | N |
| ATOM | 2027 | CZ | ARG | A | 283 | 24.905 | 102.478 | 107.642 | 1.00 | 57.79 | A | C |
| ATOM | 2028 | NH1 | ARG | A | 283 | 26.130 | 102.981 | 107.543 | 1.00 | 57.84 | A | N |
| ATOM | 2029 | NH2 | ARG | A | 283 | 23.881 | 103.295 | 107.864 | 1.00 | 56.89 | A | N |
| ATOM | 2030 | C | ARG | A | 283 | 23.839 | 100.938 | 105.137 | 1.00 | 50.69 | A | C |
| ATOM | 2031 | O | ARG | A | 283 | 23.107 | 101.897 | 105.352 | 1.00 | 50.33 | A | O |
| ATOM | 2032 | N | GLU | A | 284 | 25.084 | 101.091 | 104.677 | 1.00 | 48.43 | A | N |
| ATOM | 2033 | CA | GLU | A | 284 | 25.586 | 102.433 | 104.367 | 1.00 | 46.98 | A | C |
| ATOM | 2034 | CB | GLU | A | 284 | 27.001 | 102.390 | 103.786 | 1.00 | 47.64 | A | C |
| ATOM | 2035 | CG | GLU | A | 284 | 27.682 | 103.770 | 103.702 | 1.00 | 48.53 | A | C |
| ATOM | 2036 | CD | GLU | A | 284 | 27.322 | 104.570 | 102.446 | 1.00 | 48.59 | A | C |
| ATOM | 2037 | OE1 | GLU | A | 284 | 26.120 | 104.740 | 102.153 | 1.00 | 48.86 | A | O |
| ATOM | 2038 | OE2 | GLU | A | 284 | 28.249 | 105.045 | 101.752 | 1.00 | 46.24 | A | O |
| ATOM | 2039 | C | GLU | A | 284 | 24.616 | 102.981 | 103.339 | 1.00 | 47.59 | A | C |
| ATOM | 2040 | O | GLU | A | 284 | 24.297 | 104.176 | 103.324 | 1.00 | 46.98 | A | O |
| ATOM | 2041 | N | ALA | A | 285 | 24.151 | 102.085 | 102.469 | 1.00 | 46.09 | A | N |
| ATOM | 2042 | CA | ALA | A | 285 | 23.165 | 102.438 | 101.460 | 1.00 | 40.81 | A | C |
| ATOM | 2043 | CB | ALA | A | 285 | 23.035 | 101.323 | 100.433 | 1.00 | 42.35 | A | C |
| ATOM | 2044 | C | ALA | A | 285 | 21.895 | 102.565 | 102.292 | 1.00 | 36.94 | A | C |
| ATOM | 2045 | O | ALA | A | 285 | 20.779 | 102.424 | 101.800 | 1.00 | 34.30 | A | O |
| ATOM | 2046 | N | GLY | A | 286 | 22.115 | 102.812 | 103.583 | 1.00 | 35.53 | A | N |
| ATOM | 2047 | CA | GLY | A | 286 | 21.039 | 102.986 | 104.538 | 1.00 | 33.89 | A | C |
| ATOM | 2048 | C | GLY | A | 286 | 20.465 | 104.369 | 104.355 | 1.00 | 33.21 | A | C |
| ATOM | 2049 | O | GLY | A | 286 | 19.421 | 104.703 | 104.918 | 1.00 | 34.48 | A | O |
| ATOM | 2050 | N | ASN | A | 287 | 21.168 | 105.180 | 103.568 | 1.00 | 30.99 | A | N |
| ATOM | 2051 | CA | ASN | A | 287 | 20.719 | 106.524 | 103.262 | 1.00 | 29.41 | A | C |
| ATOM | 2052 | CB | ASN | A | 287 | 21.908 | 107.389 | 102.841 | 1.00 | 31.73 | A | C |
| ATOM | 2053 | CG | ASN | A | 287 | 22.924 | 107.552 | 103.957 | 1.00 | 36.29 | A | C |
| ATOM | 2054 | OD1 | ASN | A | 287 | 23.911 | 108.274 | 103.820 | 1.00 | 37.00 | A | 0 |
| ATOM | 2055 | ND2 | ASN | A | 287 | 22.686 | 106.871 | 105.075 | 1.00 | 38.51 | A | N |
| ATOM | 2056 | C | ASN | A | 287 | 19.680 | 106.400 | 102.138 | 1.00 | 27.62 | A | C |
| ATOM | 2057 | O | ASN | A | 287 | 18.757 | 107.220 | 102.021 | 1.00 | 24.70 | A | O |
| ATOM | 2058 | N | ILE | A | 288 | 19.830 | 105.364 | 101.318 | 1.00 | 24.42 | A | N |
| ATOM | 2059 | CA | ILE | A | 288 | 18.870 | 105.120 | 100.254 | 1.00 | 24.40 | A | C |
| ATOM | 2060 | CB | ILE | A | 288 | 19.421 | 104.165 | 99.181 | 1.00 | 23.82 | A | C |
| ATOM | 2061 | CG2 | ILE | A | 288 | 18.329 | 103.843 | 98.174 | 1.00 | 24.22 | A | C |
| ATOM | 2062 | CG1 | ILE | A | 288 | 20.604 | 104.805 | 98.451 | 1.00 | 22.05 | A | C |
| ATOM | 2063 | CD1 | ILE | A | 288 | 21.236 | 103.902 | 97.392 | 1.00 | 19.49 | A | C |
| ATOM | 2064 | C | ILE | A | 288 | 17.650 | 104.470 | 100.910 | 1.00 | 24.04 | A | C |
| ATOM | 2065 | O | ILE | A | 288 | 16.525 | 104.935 | 100.745 | 1.00 | 24.34 | A | O |
| ATOM | 2066 | N | ASN | A | 289 | 17.890 | 103.407 | 101.675 | 1.00 | 24.06 | A | N |
| ATOM | 2067 | CA | ASN | A | 289 | 16.834 | 102.680 | 102.377 | 1.00 | 26.62 | A | C |
| ATOM | 2068 | CB | ASN | A | 289 | 17.433 | 101.466 | 103.100 | 1.00 | 26.94 | A | C |
| ATOM | 2069 | CG | ASN | A | 289 | 16.454 | 100.809 | 104.079 | 1.00 | 28.88 | A | C |
| ATOM | 2070 | OD1 | ASN | A | 289 | 15.406 | 100.306 | 103.685 | 1.00 | 30.75 | A | O |
| ATOM | 2071 | ND2 | ASN | A | 289 | 16.806 | 100.811 | 105.361 | 1.00 | 30.67 | A | N |
| ATOM | 2072 | C | ASN | A | 289 | 16.077 | 103.551 | 103.384 | 1.00 | 28.71 | A | C |
| ATOM | 2073 | O | ASN | A | 289 | 14.850 | 103.452 | 103.513 | 1.00 | 28.33 | A | O |
| ATOM | 2074 | N | GLN | A | 290 | 16.808 | 104.402 | 104.094 | 1.00 | 30.82 | A | N |
| ATOM | 2075 | CA | GLN | A | 290 | 16.198 | 105.265 | 105.095 | 1.00 | 31.98 | A | C |
| ATOM | 2076 | CB | GLN | A | 290 | 17.276 | 105.877 | 105.993 | 1.00 | 37.48 | A | C |
| ATOM | 2077 | CG | GLN | A | 290 | 16.805 | 106.239 | 107.408 | 1.00 | 44.03 | A | C |
| ATOM | 2078 | CD | GLN | A | 290 | 16.024 | 107.539 | 107.475 | 1.00 | 46.39 | A | C |
| ATOM | 2079 | OE1 | GLN | A | 290 | 15.644 | 107.989 | 108.558 | 1.00 | 45.52 | A | O |
| ATOM | 2080 | NE2 | GLN | A | 290 | 15.783 | 108.153 | 106.316 | 1.00 | 50.34 | A | N |
| ATOM | 2081 | C | GLN | A | 290 | 15.375 | 106.363 | 104.439 | 1.00 | 29.92 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2082 | O | GLN | A | 290 | 14.275 | 106.662 | 104.899 | 1.00 | 29.08 | A | O |
| ATOM | 2083 | N | SER | A | 291 | 15.904 | 106.956 | 103.367 | 1.00 | 26.49 | A | N |
| ATOM | 2084 | CA | SER | A | 291 | 15.183 | 108.013 | 102.661 | 1.00 | 24.85 | A | C |
| ATOM | 2085 | CB | SER | A | 291 | 16.071 | 108.699 | 101.604 | 1.00 | 25.47 | A | C |
| ATOM | 2086 | OG | SER | A | 291 | 16.548 | 107.800 | 100.615 | 1.00 | 29.15 | A | O |
| ATOM | 2087 | C | SER | A | 291 | 13.913 | 107.461 | 102.022 | 1.00 | 22.60 | A | C |
| ATOM | 2088 | O | SER | A | 291 | 12.857 | 108.076 | 102.129 | 1.00 | 23.20 | A | O |
| ATOM | 2089 | N | LEU | A | 292 | 14.000 | 106.299 | 101.375 | 1.00 | 22.23 | A | N |
| ATOM | 2090 | CA | LEU | A | 292 | 12.808 | 105.696 | 100.773 | 1.00 | 23.08 | A | C |
| ATOM | 2091 | CB | LEU | A | 292 | 13.164 | 104.440 | 99.974 | 1.00 | 20.29 | A | C |
| ATOM | 2092 | CG | LEU | A | 292 | 13.898 | 104.641 | 98.639 | 1.00 | 19.85 | A | C |
| ATOM | 2093 | CD1 | LEU | A | 292 | 14.277 | 103.285 | 98.049 | 1.00 | 17.14 | A | C |
| ATOM | 2094 | CD2 | LEU | A | 292 | 13.017 | 105.417 | 97.676 | 1.00 | 15.17 | A | C |
| ATOM | 2095 | C | LEU | A | 292 | 11.805 | 105.335 | 101.876 | 1.00 | 23.69 | A | C |
| ATOM | 2096 | O | LEU | A | 292 | 10.596 | 105.484 | 101.697 | 1.00 | 21.99 | A | O |
| ATOM | 2097 | N | LEU | A | 293 | 12.312 | 104.866 | 103.015 | 1.00 | 23.39 | A | N |
| ATOM | 2098 | CA | LEU | A | 293 | 11.454 | 104.513 | 104.143 | 1.00 | 23.23 | A | C |
| ATOM | 2099 | CB | LEU | A | 293 | 12.261 | 103.867 | 105.270 | 1.00 | 25.74 | A | C |
| ATOM | 2100 | CG | LEU | A | 293 | 12.255 | 102.345 | 105.446 | 1.00 | 28.66 | A | C |
| ATOM | 2101 | CD1 | LEU | A | 293 | 10.944 | 101.770 | 104.908 | 1.00 | 27.54 | A | C |
| ATOM | 2102 | CD2 | LEU | A | 293 | 13.439 | 101.738 | 104.740 | 1.00 | 24.58 | A | C |
| ATOM | 2103 | C | LEU | A | 293 | 10.755 | 105.756 | 104.693 | 1.00 | 23.54 | A | C |
| ATOM | 2104 | O | LEU | A | 293 | 9.566 | 105.714 | 105.015 | 1.00 | 23.12 | A | O |
| ATOM | 2105 | N | THR | A | 294 | 11.493 | 106.858 | 104.823 | 1.00 | 21.46 | A | N |
| ATOM | 2106 | CA | THR | A | 294 | 10.891 | 108.096 | 105.320 | 1.00 | 22.48 | A | C |
| ATOM | 2107 | CB | THR | A | 294 | 11.907 | 109.265 | 105.334 | 1.00 | 19.41 | A | C |
| ATOM | 2108 | OG1 | THR | A | 294 | 12.996 | 108.942 | 106.205 | 1.00 | 17.00 | A | O |
| ATOM | 2109 | CG2 | THR | A | 294 | 11.246 | 110.539 | 105.831 | 1.00 | 17.41 | A | C |
| ATOM | 2110 | C | THR | A | 294 | 9.733 | 108.455 | 104.379 | 1.00 | 22.53 | A | C |
| ATOM | 2111 | O | THR | A | 294 | 8.586 | 108.600 | 104.796 | 1.00 | 21.39 | A | O |
| ATOM | 2112 | N | LEU | A | 295 | 10.054 | 108.582 | 103.099 | 1.00 | 20.92 | A | N |
| ATOM | 2113 | CA | LEU | A | 295 | 9.059 | 108.895 | 102.089 | 1.00 | 18.95 | A | C |
| ATOM | 2114 | CB | LEU | A | 295 | 9.609 | 108.594 | 100.696 | 1.00 | 18.65 | A | C |
| ATOM | 2115 | CG | LEU | A | 295 | 8.604 | 108.854 | 99.577 | 1.00 | 19.48 | A | C |
| ATOM | 2116 | CD1 | LEU | A | 295 | 8.233 | 110.330 | 99.581 | 1.00 | 21.00 | A | C |
| ATOM | 2117 | CD2 | LEU | A | 295 | 9.188 | 108.457 | 98.233 | 1.00 | 16.04 | A | C |
| ATOM | 2118 | C | LEU | A | 295 | 7.793 | 108.079 | 102.314 | 1.00 | 20.21 | A | C |
| ATOM | 2119 | O | LEU | A | 295 | 6.689 | 108.628 | 102.367 | 1.00 | 22.51 | A | O |
| ATOM | 2120 | N | GLY | A | 296 | 7.959 | 106.768 | 102.449 | 1.00 | 17.15 | A | N |
| ATOM | 2121 | CA | GLY | A | 296 | 6.823 | 105.900 | 102.654 | 1.00 | 16.20 | A | C |
| ATOM | 2122 | C | GLY | A | 296 | 6.019 | 106.289 | 103.870 | 1.00 | 18.28 | A | C |
| ATOM | 2123 | O | GLY | A | 296 | 4.795 | 106.260 | 103.853 | 1.00 | 19.82 | A | O |
| ATOM | 2124 | N | ARG | A | 297 | 6.704 | 106.656 | 104.939 | 1.00 | 19.06 | A | N |
| ATOM | 2125 | CA | ARG | A | 297 | 6.015 | 107.037 | 106.151 | 1.00 | 21.37 | A | C |
| ATOM | 2126 | CB | ARG | A | 297 | 7.014 | 107.084 | 107.312 | 1.00 | 21.67 | A | C |
| ATOM | 2127 | CG | ARG | A | 297 | 7.389 | 105.684 | 107.817 | 1.00 | 23.94 | A | C |
| ATOM | 2128 | CD | ARG | A | 297 | 8.781 | 105.627 | 108.433 | 1.00 | 23.49 | A | C |
| ATOM | 2129 | NE | ARG | A | 297 | 8.994 | 106.733 | 109.356 | 1.00 | 29.09 | A | N |
| ATOM | 2130 | CZ | ARG | A | 297 | 8.226 | 106.978 | 110.410 | 1.00 | 31.22 | A | C |
| ATOM | 2131 | NH1 | ARG | A | 297 | 7.196 | 106.185 | 110.677 | 1.00 | 32.38 | A | N |
| ATOM | 2132 | NH2 | ARG | A | 297 | 8.474 | 108.031 | 111.183 | 1.00 | 34.15 | A | N |
| ATOM | 2133 | C | ARG | A | 297 | 5.281 | 108.370 | 105.973 | 1.00 | 23.73 | A | C |
| ATOM | 2134 | O | ARG | A | 297 | 4.204 | 108.581 | 106.546 | 1.00 | 23.97 | A | O |
| ATOM | 2135 | N | VAL | A | 298 | 5.846 | 109.261 | 105.164 | 1.00 | 24.34 | A | N |
| ATOM | 2136 | CA | VAL | A | 298 | 5.214 | 110.554 | 104.926 | 1.00 | 25.89 | A | C |
| ATOM | 2137 | CB | VAL | A | 298 | 6.147 | 111.518 | 104.173 | 1.00 | 25.99 | A | C |
| ATOM | 2138 | CG1 | VAL | A | 298 | 5.418 | 112.819 | 103.901 | 1.00 | 22.68 | A | C |
| ATOM | 2139 | CG2 | VAL | A | 298 | 7.409 | 111.776 | 104.988 | 1.00 | 25.99 | A | C |
| ATOM | 2140 | C | VAL | A | 298 | 3.934 | 110.390 | 104.104 | 1.00 | 25.86 | A | C |
| ATOM | 2141 | O | VAL | A | 298 | 2.926 | 111.060 | 104.362 | 1.00 | 25.23 | A | O |
| ATOM | 2142 | N | ILE | A | 299 | 3.979 | 109.496 | 103.118 | 1.00 | 25.01 | A | N |
| ATOM | 2143 | CA | ILE | A | 299 | 2.828 | 109.240 | 102.263 | 1.00 | 25.07 | A | C |
| ATOM | 2144 | CB | ILE | A | 299 | 3.198 | 108.355 | 101.060 | 1.00 | 25.46 | A | C |
| ATOM | 2145 | CG2 | ILE | A | 299 | 1.956 | 108.060 | 100.235 | 1.00 | 23.42 | A | C |
| ATOM | 2146 | CG1 | ILE | A | 299 | 4.234 | 109.061 | 100.188 | 1.00 | 24.53 | A | C |
| ATOM | 2147 | CD1 | ILE | A | 299 | 3.776 | 110.408 | 99.696 | 1.00 | 26.78 | A | C |
| ATOM | 2148 | C | ILE | A | 299 | 1.705 | 108.553 | 103.029 | 1.00 | 25.91 | A | C |
| ATOM | 2149 | O | ILE | A | 299 | 0.540 | 108.894 | 102.859 | 1.00 | 25.57 | A | O |
| ATOM | 2150 | N | THR | A | 300 | 2.060 | 107.583 | 103.866 | 1.00 | 28.05 | A | N |
| ATOM | 2151 | CA | THR | A | 300 | 1.074 | 106.863 | 104.665 | 1.00 | 29.44 | A | C |
| ATOM | 2152 | CB | THR | A | 300 | 1.729 | 105.740 | 105.492 | 1.00 | 29.48 | A | C |
| ATOM | 2153 | OG1 | THR | A | 300 | 2.480 | 104.872 | 104.630 | 1.00 | 29.73 | A | O |
| ATOM | 2154 | CG2 | THR | A | 300 | 0.660 | 104.938 | 106.212 | 1.00 | 28.92 | A | C |
| ATOM | 2155 | C | THR | A | 300 | 0.386 | 107.840 | 105.619 | 1.00 | 30.05 | A | C |
| ATOM | 2156 | O | THR | A | 300 | −0.836 | 107.838 | 105.749 | 1.00 | 28.54 | A | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2157 | N | ALA | A | 301 | 1.181 | 108.679 | 106.277 | 1.00 | 30.13 | A | N |
| ATOM | 2158 | CA | ALA | A | 301 | 0.649 | 109.673 | 107.204 | 1.00 | 29.43 | A | C |
| ATOM | 2159 | CB | ALA | A | 301 | 1.784 | 110.501 | 107.797 | 1.00 | 29.37 | A | C |
| ATOM | 2160 | C | ALA | A | 301 | −0.350 | 110.590 | 106.512 | 1.00 | 28.95 | A | C |
| ATOM | 2161 | O | ALA | A | 301 | −1.332 | 111.001 | 107.115 | 1.00 | 27.60 | A | O |
| ATOM | 2162 | N | LEU | A | 302 | −0.096 | 110.923 | 105.250 | 1.00 | 30.01 | A | N |
| ATOM | 2163 | CA | LEU | A | 302 | −1.008 | 111.798 | 104.509 | 1.00 | 29.64 | A | C |
| ATOM | 2164 | CB | LEU | A | 302 | −0.351 | 112.315 | 103.228 | 1.00 | 27.90 | A | C |
| ATOM | 2165 | CG | LEU | A | 302 | 0.938 | 113.128 | 103.336 | 1.00 | 28.21 | A | C |
| ATOM | 2166 | CD1 | LEU | A | 302 | 1.424 | 113.479 | 101.940 | 1.00 | 25.97 | A | C |
| ATOM | 2167 | CD2 | LEU | A | 302 | 0.706 | 114.379 | 104.142 | 1.00 | 26.07 | A | C |
| ATOM | 2168 | C | LEU | A | 302 | −2.293 | 111.063 | 104.141 | 1.00 | 31.03 | A | C |
| ATOM | 2169 | O | LEU | A | 302 | −3.342 | 111.679 | 103.973 | 1.00 | 30.51 | A | O |
| ATOM | 2170 | N | VAL | A | 303 | −2.208 | 109.746 | 104.003 | 1.00 | 32.07 | A | N |
| ATOM | 2171 | CA | VAL | A | 303 | −3.385 | 108.960 | 103.666 | 1.00 | 34.56 | A | C |
| ATOM | 2172 | CB | VAL | A | 303 | −3.008 | 107.604 | 103.046 | 1.00 | 32.84 | A | C |
| ATOM | 2173 | CG1 | VAL | A | 303 | −4.212 | 106.685 | 103.043 | 1.00 | 30.78 | A | C |
| ATOM | 2174 | CG2 | VAL | A | 303 | −2.510 | 107.811 | 101.632 | 1.00 | 33.37 | A | C |
| ATOM | 2115 | C | VAL | A | 303 | −4.220 | 108.710 | 104.910 | 1.00 | 36.11 | A | C |
| ATOM | 2176 | O | VAL | A | 303 | −5.430 | 108.898 | 104.892 | 1.00 | 34.14 | A | O |
| ATOM | 2177 | N | GLU | A | 304 | −3.557 | 108.290 | 105.985 | 1.00 | 39.50 | A | N |
| ATOM | 2178 | CA | GLU | A | 304 | −4.218 | 107.998 | 107.256 | 1.00 | 40.92 | A | C |
| ATOM | 2179 | CB | GLU | A | 304 | −3.282 | 107.195 | 108.175 | 1.00 | 40.69 | A | C |
| ATOM | 2180 | CG | GLU | A | 304 | −2.416 | 106.154 | 107.476 | 1.00 | 43.68 | A | C |
| ATOM | 2181 | CD | GLU | A | 304 | −3.169 | 104.894 | 107.090 | 1.00 | 47.88 | A | C |
| ATOM | 2182 | OE1 | GLU | A | 304 | −4.253 | 105.008 | 106.475 | 1.00 | 48.09 | A | O |
| ATOM | 2183 | OE2 | GLU | A | 304 | −2.669 | 103.784 | 107.392 | 1.00 | 48.97 | A | O |
| ATOM | 2184 | C | GLU | A | 304 | −4.569 | 109.324 | 107.930 | 1.00 | 41.19 | A | C |
| ATOM | 2185 | O | GLU | A | 304 | −5.263 | 109.358 | 108.944 | 1.00 | 41.12 | A | O |
| ATOM | 2186 | N | ARG | A | 305 | −4.081 | 110.415 | 107.356 | 1.00 | 41.75 | A | N |
| ATOM | 2187 | CA | ARG | A | 305 | −4.320 | 111.745 | 107.905 | 1.00 | 43.87 | A | C |
| ATOM | 2188 | CB | ARG | A | 305 | −5.818 | 112.054 | 107.942 | 1.00 | 44.73 | A | C |
| ATOM | 2189 | CG | ARG | A | 305 | −6.520 | 111.852 | 106.622 | 1.00 | 47.77 | A | C |
| ATOM | 2190 | CD | ARG | A | 305 | −7.947 | 112.373 | 106.659 | 1.00 | 51.10 | A | C |
| ATOM | 2191 | NE | ARG | A | 305 | −8.708 | 111.932 | 105.491 | 1.00 | 53.86 | A | N |
| ATOM | 2192 | CZ | ARG | A | 305 | −9.944 | 112.329 | 105.202 | 1.00 | 53.16 | A | C |
| ATOM | 2193 | NH1 | ARG | A | 305 | −10.575 | 113.186 | 105.998 | 1.00 | 50.24 | A | N |
| ATOM | 2194 | NH2 | ARG | A | 305 | −10.546 | 111.868 | 104.111 | 1.00 | 51.96 | A | N |
| ATOM | 2195 | C | ARG | A | 305 | −3.732 | 111.898 | 109.311 | 1.00 | 43.55 | A | C |
| ATOM | 2196 | O | ARG | A | 305 | −4.339 | 112.522 | 110.184 | 1.00 | 43.87 | A | O |
| ATOM | 2197 | N | THR | A | 306 | −2.558 | 111.315 | 109.533 | 1.00 | 42.57 | A | N |
| ATOM | 2198 | CA | THR | A | 306 | −1.894 | 111.426 | 110.824 | 1.00 | 40.98 | A | C |
| ATOM | 2199 | CB | THR | A | 306 | −0.609 | 110.577 | 110.863 | 1.00 | 42.49 | A | C |
| ATOM | 2200 | OG1 | THR | A | 306 | −0.936 | 109.199 | 110.634 | 1.00 | 45.16 | A | O |
| ATOM | 2201 | CG2 | THR | A | 306 | 0.086 | 110.717 | 112.215 | 1.00 | 42.39 | A | C |
| ATOM | 2202 | C | THR | A | 306 | −1.529 | 112.903 | 110.962 | 1.00 | 40.47 | A | C |
| ATOM | 2203 | O | THR | A | 306 | −1.006 | 113.513 | 110.021 | 1.00 | 39.21 | A | O |
| ATOM | 2204 | N | PRO | A | 307 | −1.816 | 113.508 | 112.127 | 1.00 | 39.70 | A | N |
| ATOM | 2205 | CD | PRO | A | 307 | −2.465 | 112.946 | 113.324 | 1.00 | 38.02 | A | C |
| ATOM | 2206 | CA | PRO | A | 307 | −1.494 | 114.926 | 112.325 | 1.00 | 36.42 | A | C |
| ATOM | 2207 | CB | PRO | A | 307 | −2.081 | 115.225 | 113.707 | 1.00 | 33.83 | A | C |
| ATOM | 2208 | CG | PRO | A | 307 | −2.033 | 113.918 | 114.396 | 1.00 | 36.00 | A | C |
| ATOM | 2209 | C | PRO | A | 307 | 0.003 | 115.219 | 112.222 | 1.00 | 34.10 | A | C |
| ATOM | 2210 | O | PRO | A | 307 | 0.416 | 116.349 | 111.964 | 1.00 | 33.44 | A | O |
| ATOM | 2211 | N | HIS | A | 308 | 0.810 | 114.185 | 112.413 | 1.00 | 33.11 | A | N |
| ATOM | 2212 | CA | HIS | A | 308 | 2.257 | 114.327 | 112.328 | 1.00 | 33.49 | A | C |
| ATOM | 2213 | CB | HIS | A | 308 | 2.915 | 113.820 | 113.611 | 1.00 | 31.56 | A | C |
| ATOM | 2214 | CG | HIS | A | 308 | 4.380 | 113.549 | 113.470 | 1.00 | 30.69 | A | C |
| ATOM | 2215 | CD2 | HIS | A | 308 | 5.457 | 114.354 | 113.639 | 1.00 | 29.53 | A | C |
| ATOM | 2216 | ND1 | HIS | A | 308 | 4.875 | 112.318 | 113.091 | 1.00 | 29.45 | A | N |
| ATOM | 2217 | CE1 | HIS | A | 308 | 6.195 | 112.378 | 113.036 | 1.00 | 28.82 | A | C |
| ATOM | 2218 | NE2 | HIS | A | 308 | 6.573 | 113.601 | 113.365 | 1.00 | 25.66 | A | N |
| ATOM | 2219 | C | HIS | A | 308 | 2.851 | 113.593 | 111.119 | 1.00 | 31.85 | A | C |
| ATOM | 2220 | O | HIS | A | 308 | 2.812 | 112.362 | 111.033 | 1.00 | 29.92 | A | O |
| ATOM | 2221 | N | VAL | A | 309 | 3.395 | 114.377 | 110.191 | 1.00 | 29.01 | A | N |
| ATOM | 2222 | CA | VAL | A | 309 | 4.024 | 113.867 | 108.982 | 1.00 | 25.55 | A | C |
| ATOM | 2223 | CB | VAL | A | 309 | 3.328 | 114.457 | 107.722 | 1.00 | 26.58 | A | C |
| ATOM | 2224 | CG1 | VAL | A | 309 | 1.901 | 113.960 | 107.644 | 1.00 | 27.82 | A | C |
| ATOM | 2225 | CG2 | VAL | A | 309 | 3.291 | 115.951 | 107.797 | 1.00 | 23.68 | A | C |
| ATOM | 2226 | C | VAL | A | 309 | 5.507 | 114.257 | 109.027 | 1.00 | 21.21 | A | C |
| ATOM | 2227 | O | VAL | A | 309 | 5.865 | 115.430 | 108.995 | 1.00 | 18.92 | A | O |
| ATOM | 2228 | N | PRO | A | 310 | 6.384 | 113.257 | 109.120 | 1.00 | 19.50 | A | N |
| ATOM | 2229 | CD | PRO | A | 310 | 5.910 | 111.864 | 109.178 | 1.00 | 18.98 | A | C |
| ATOM | 2230 | CA | PRO | A | 310 | 7.853 | 113.310 | 109.192 | 1.00 | 20.04 | A | C |
| ATOM | 2231 | CS | PRO | A | 310 | 8.221 | 111.858 | 109.486 | 1.00 | 20.21 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2232 | CG | PRO | A | 310 | 7.138 | 111.100 | 108.766 | 1.00 | 18.39 | A | C |
| ATOM | 2233 | C | PRO | A | 310 | 8.700 | 113.885 | 108.034 | 1.00 | 20.35 | A | C |
| ATOM | 2234 | O | PRO | A | 310 | 9.741 | 113.326 | 107.700 | 1.00 | 17.58 | A | O |
| ATOM | 2235 | N | TYR | A | 311 | 8.298 | 115.009 | 107.454 | 1.00 | 21.00 | A | N |
| ATOM | 2236 | CA | TYR | A | 311 | 9.061 | 115.588 | 106.353 | 1.00 | 24.03 | A | C |
| ATOM | 2237 | CB | TYR | A | 311 | 8.459 | 116.926 | 105.926 | 1.00 | 23.91 | A | C |
| ATOM | 2238 | CG | TYR | A | 311 | 7.030 | 116.861 | 105.474 | 1.00 | 21.57 | A | C |
| ATOM | 2239 | CD1 | TYR | A | 311 | 6.013 | 117.307 | 106.295 | 1.00 | 18.21 | A | C |
| ATOM | 2240 | CE1 | TYR | A | 311 | 4.712 | 117.298 | 105.879 | 1.00 | 21.21 | A | C |
| ATOM | 2241 | CD2 | TYR | A | 311 | 6.699 | 116.389 | 104.209 | 1.00 | 21.84 | A | C |
| ATOM | 2242 | CE2 | TYR | A | 311 | 5.387 | 116.370 | 103.781 | 1.00 | 22.50 | A | C |
| ATOM | 2243 | CZ | TYR | A | 311 | 4.398 | 116.832 | 104.625 | 1.00 | 21.08 | A | C |
| ATOM | 2244 | OH | TYR | A | 311 | 3.089 | 116.841 | 104.222 | 1.00 | 21.48 | A | O |
| ATOM | 2245 | C | TYR | A | 311 | 10.542 | 115.821 | 106.654 | 1.00 | 26.06 | A | C |
| ATOM | 2246 | O | TYR | A | 311 | 11.405 | 115.548 | 105.815 | 1.00 | 27.37 | A | O |
| ATOM | 2247 | N | ARG | A | 312 | 10.820 | 116.349 | 107.845 | 1.00 | 28.01 | A | N |
| ATOM | 2248 | CA | ARG | A | 312 | 12.181 | 116.674 | 108.287 | 1.00 | 26.29 | A | C |
| ATOM | 2249 | CB | ARG | A | 312 | 12.137 | 117.314 | 109.682 | 1.00 | 27.90 | A | C |
| ATOM | 2250 | CG | ARG | A | 312 | 12.177 | 118.837 | 109.704 | 1.00 | 30.12 | A | C |
| ATOM | 2251 | CD | ARG | A | 312 | 13.395 | 119.359 | 108.958 | 1.00 | 34.76 | A | C |
| ATOM | 2252 | NE | ARG | A | 312 | 13.668 | 120.772 | 109.216 | 1.00 | 38.62 | A | N |
| ATOM | 2253 | CZ | ARG | A | 312 | 12.743 | 121.728 | 109.250 | 1.00 | 39.68 | A | C |
| ATOM | 2254 | NH1 | ARG | A | 312 | 11.462 | 121.430 | 109.053 | 1.00 | 39.68 | A | N |
| ATOM | 2255 | NH2 | ARG | A | 312 | 13.106 | 122.991 | 109.453 | 1.00 | 37.13 | A | N |
| ATOM | 2256 | C | ARG | A | 312 | 13.185 | 115.525 | 108.320 | 1.00 | 24.62 | A | C |
| ATOM | 2257 | O | ARG | A | 312 | 14.395 | 115.750 | 108.247 | 1.00 | 22.44 | A | O |
| ATOM | 2258 | N | GLU | A | 313 | 12.696 | 114.297 | 108.422 | 1.00 | 23.10 | A | N |
| ATOM | 2259 | CA | GLU | A | 313 | 13.594 | 113.156 | 108.515 | 1.00 | 23.22 | A | C |
| ATOM | 2260 | CB | GLU | A | 313 | 12.809 | 111.913 | 108.955 | 1.00 | 25.98 | A | C |
| ATOM | 2261 | CG | GLU | A | 313 | 12.313 | 111.976 | 110.395 | 1.00 | 29.78 | A | C |
| ATOM | 2262 | CD | GLU | A | 313 | 11.504 | 110.747 | 110.796 | 1.00 | 33.60 | A | C |
| ATOM | 2263 | OE1 | GLU | A | 313 | 12.029 | 109.623 | 110.675 | 1.00 | 35.73 | A | O |
| ATOM | 2264 | OE2 | GLU | A | 313 | 10.344 | 110.899 | 111.235 | 1.00 | 36.47 | A | O |
| ATOM | 2265 | C | GLU | A | 313 | 14.473 | 112.824 | 107.306 | 1.00 | 20.57 | A | C |
| ATOM | 2266 | O | GLU | A | 313 | 15.378 | 112.004 | 107.417 | 1.00 | 22.05 | A | O |
| ATOM | 2267 | N | SER | A | 314 | 14.230 | 113.433 | 106.153 | 1.00 | 18.44 | A | N |
| ATOM | 2268 | CA | SER | A | 314 | 15.087 | 113.158 | 104.997 | 1.00 | 17.77 | A | C |
| ATOM | 2269 | CB | SER | A | 314 | 14.591 | 111.933 | 104.200 | 1.00 | 15.35 | A | C |
| ATOM | 2270 | OG | SER | A | 314 | 13.661 | 112.282 | 103.186 | 1.00 | 17.77 | A | O |
| ATOM | 2271 | C | SER | A | 314 | 15.163 | 114.368 | 104.086 | 1.00 | 16.09 | A | C |
| ATOM | 2272 | O | SER | A | 314 | 14.306 | 115.238 | 104.136 | 1.00 | 16.39 | A | O |
| ATOM | 2273 | N | LYS | A | 315 | 16.199 | 114.421 | 103.262 | 1.00 | 17.91 | A | N |
| ATOM | 2274 | CA | LYS | A | 315 | 16.382 | 115.527 | 102.332 | 1.00 | 18.85 | A | C |
| ATOM | 2275 | CB | LYS | A | 315 | 17.712 | 115.387 | 101.604 | 1.00 | 18.36 | A | C |
| ATOM | 2276 | CG | LYS | A | 315 | 18.867 | 115.143 | 102.530 | 1.00 | 20.17 | A | C |
| ATOM | 2277 | CD | LYS | A | 315 | 19.260 | 116.411 | 103.243 | 1.00 | 21.74 | A | C |
| ATOM | 2278 | CE | LYS | A | 315 | 19.868 | 117.383 | 102.257 | 1.00 | 23.54 | A | C |
| ATOM | 2279 | NZ | LYS | A | 315 | 21.054 | 116.769 | 101.606 | 1.00 | 21.59 | A | N |
| ATOM | 2280 | C | LYS | A | 315 | 15.265 | 115.486 | 101.313 | 1.00 | 19.31 | A | C |
| ATOM | 2281 | O | LYS | A | 315 | 14.637 | 116.504 | 101.030 | 1.00 | 22.38 | A | O |
| ATOM | 2282 | N | LEU | A | 316 | 15.034 | 114.296 | 100.764 | 1.00 | 17.67 | A | N |
| ATOM | 2283 | CA | LEU | A | 316 | 14.000 | 114.085 | 99.762 | 1.00 | 17.31 | A | C |
| ATOM | 2284 | CB | LEU | A | 316 | 13.896 | 112.595 | 99.432 | 1.00 | 15.58 | A | C |
| ATOM | 2285 | CG | LEU | A | 316 | 12.774 | 112.194 | 98.477 | 1.00 | 13.65 | A | C |
| ATOM | 2286 | CD1 | LEU | A | 316 | 12.950 | 112.848 | 97.150 | 1.00 | 16.57 | A | C |
| ATOM | 2287 | CD2 | LEU | A | 316 | 12.763 | 110.694 | 98.316 | 1.00 | 20.85 | A | C |
| ATOM | 2288 | C | LEU | A | 316 | 12.632 | 114.618 | 100.178 | 1.00 | 18.49 | A | C |
| ATOM | 2289 | O | LEU | A | 316 | 12.038 | 115.414 | 99.464 | 1.00 | 18.39 | A | O |
| ATOM | 2290 | N | THR | A | 317 | 12.134 | 114.188 | 101.336 | 1.00 | 20.98 | A | N |
| ATOM | 2291 | CA | THR | A | 317 | 10.823 | 114.639 | 101.804 | 1.00 | 21.96 | A | C |
| ATOM | 2292 | CB | THR | A | 317 | 10.306 | 113.773 | 102.971 | 1.00 | 23.27 | A | C |
| ATOM | 2293 | OG1 | THR | A | 317 | 11.338 | 113.608 | 103.956 | 1.00 | 16.25 | A | O |
| ATOM | 2294 | CG2 | THR | A | 317 | 9.850 | 112.424 | 102.448 | 1.00 | 21.46 | A | C |
| ATOM | 2295 | C | THR | A | 317 | 10.765 | 116.092 | 102.238 | 1.00 | 22.24 | A | C |
| ATOM | 2296 | O | THR | A | 317 | 9.729 | 116.728 | 102.133 | 1.00 | 25.01 | A | O |
| ATOM | 2297 | N | ARG | A | 318 | 11.874 | 116.615 | 102.736 | 1.00 | 24.90 | A | N |
| ATOM | 2298 | CA | ARG | A | 318 | 11.920 | 118.000 | 103.177 | 1.00 | 25.69 | A | C |
| ATOM | 2299 | CB | ARG | A | 318 | 13.197 | 118.227 | 103.993 | 1.00 | 26.64 | A | C |
| ATOM | 2300 | CG | ARG | A | 318 | 13.667 | 119.667 | 104.086 | 1.00 | 33.10 | A | C |
| ATOM | 2301 | CD | ARG | A | 318 | 13.050 | 120.445 | 105.255 | 1.00 | 37.25 | A | C |
| ATOM | 2302 | NE | ARG | A | 318 | 13.831 | 121.655 | 105.513 | 1.00 | 39.52 | A | N |
| ATOM | 2303 | CZ | ARG | A | 318 | 15.136 | 121.647 | 105.783 | 1.00 | 39.40 | A | C |
| ATOM | 2304 | NH1 | ARG | A | 318 | 15.797 | 120.497 | 105.841 | 1.00 | 37.12 | A | N |
| ATOM | 2305 | NH2 | ARG | A | 318 | 15.790 | 122.787 | 105.967 | 1.00 | 40.07 | A | N |
| ATOM | 2306 | C | ARG | A | 318 | 11.892 | 118.893 | 101.943 | 1.00 | 24.83 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2307 | O | ARG | A | 318 | 11.359 | 120.005 | 101.967 | 1.00 | 26.37 | A | O |
| ATOM | 2308 | N | ILE | A | 319 | 12.461 | 118.387 | 100.857 | 1.00 | 22.88 | A | N |
| ATOM | 2309 | CA | ILE | A | 319 | 12.512 | 119.122 | 99.601 | 1.00 | 21.25 | A | C |
| ATOM | 2310 | CB | ILE | A | 319 | 13.609 | 118.545 | 98.679 | 1.00 | 17.21 | A | C |
| ATOM | 2311 | CG2 | ILE | A | 319 | 13.554 | 119.204 | 97.331 | 1.00 | 14.91 | A | C |
| ATOM | 2312 | CG1 | ILE | A | 319 | 14.976 | 118.741 | 99.323 | 1.00 | 15.46 | A | C |
| ATOM | 2313 | CD1 | ILE | A | 319 | 16.137 | 118.257 | 98.490 | 1.00 | 12.72 | A | C |
| ATOM | 2314 | C | ILE | A | 319 | 11.172 | 119.097 | 98.859 | 1.00 | 20.97 | A | C |
| ATOM | 2315 | O | ILE | A | 319 | 10.809 | 120.061 | 98.187 | 1.00 | 19.08 | A | O |
| ATOM | 2316 | N | LEU | A | 320 | 10.433 | 117.999 | 98.988 | 1.00 | 21.43 | A | N |
| ATOM | 2317 | CA | LEU | A | 320 | 9.145 | 117.879 | 98.305 | 1.00 | 21.89 | A | C |
| ATOM | 2318 | CB | LEU | A | 320 | 9.003 | 116.475 | 97.716 | 1.00 | 18.57 | A | C |
| ATOM | 2319 | CG | LEU | A | 320 | 10.048 | 116.091 | 96.674 | 1.00 | 17.04 | A | C |
| ATOM | 2320 | CD1 | LEU | A | 320 | 9.806 | 114.653 | 96.262 | 1.00 | 21.97 | A | C |
| ATOM | 2321 | CD2 | LEU | A | 320 | 9.956 | 117.011 | 95.450 | 1.00 | 17.89 | A | C |
| ATOM | 2322 | C | LEU | A | 320 | 7.945 | 118.187 | 99.199 | 1.00 | 22.03 | A | C |
| ATOM | 2323 | O | LEU | A | 320 | 6.787 | 118.025 | 98.784 | 1.00 | 20.52 | A | O |
| ATOM | 2324 | N | GLN | A | 321 | 8.233 | 118.649 | 100.412 | 1.00 | 22.32 | A | N |
| ATOM | 2325 | CA | GLN | A | 321 | 7.203 | 118.974 | 101.392 | 1.00 | 23.68 | A | C |
| ATOM | 2326 | CB | GLN | A | 321 | 7.852 | 119.399 | 102.705 | 1.00 | 22.86 | A | C |
| ATOM | 2327 | CG | GLN | A | 321 | 6.853 | 119.793 | 103.775 | 1.00 | 27.39 | A | C |
| ATOM | 2328 | CD | GLN | A | 321 | 7.511 | 120.294 | 105.050 | 1.00 | 28.62 | A | C |
| ATOM | 2329 | OE1 | GLN | A | 321 | 6.836 | 120.569 | 106.038 | 1.00 | 32.79 | A | O |
| ATOM | 2330 | NE2 | GLN | A | 321 | 8.832 | 120.420 | 105.031 | 1.00 | 28.69 | A | N |
| ATOM | 2331 | C | GLN | A | 321 | 6.229 | 120.063 | 100.938 | 1.00 | 25.41 | A | C |
| ATOM | 2332 | O | GLN | A | 321 | 5.019 | 119.965 | 101.162 | 1.00 | 24.42 | A | O |
| ATOM | 2333 | N | ASP | A | 322 | 6.747 | 121.102 | 100.297 | 1.00 | 28.40 | A | N |
| ATOM | 2334 | CA | ASP | A | 322 | 5.870 | 122.174 | 99.867 | 1.00 | 28.69 | A | C |
| ATOM | 2335 | CB | ASP | A | 322 | 6.616 | 123.207 | 99.044 | 1.00 | 31.53 | A | C |
| ATOM | 2336 | CG | ASP | A | 322 | 5.880 | 124.520 | 98.987 | 1.00 | 33.80 | A | C |
| ATOM | 2337 | OD1 | ASP | A | 322 | 4.632 | 124.506 | 99.027 | 1.00 | 34.46 | A | O |
| ATOM | 2338 | OD2 | ASP | A | 322 | 6.544 | 125.568 | 98.900 | 1.00 | 38.65 | A | O |
| ATOM | 2339 | C | ASP | A | 322 | 4.727 | 121.620 | 99.047 | 1.00 | 28.09 | A | C |
| ATOM | 2340 | O | ASP | A | 322 | 3.574 | 121.992 | 99.248 | 1.00 | 27.83 | A | O |
| ATOM | 2341 | N | SER | A | 323 | 5.055 | 120.718 | 98.132 | 1.00 | 29.10 | A | N |
| ATOM | 2342 | CA | SER | A | 323 | 4.056 | 120.104 | 97.271 | 1.00 | 28.53 | A | C |
| ATOM | 2343 | CB | SER | A | 323 | 4.725 | 119.422 | 96.084 | 1.00 | 28.77 | A | C |
| ATOM | 2344 | OG | SER | A | 323 | 3.876 | 118.419 | 95.556 | 1.00 | 36.72 | A | O |
| ATOM | 2345 | C | SER | A | 323 | 3.211 | 119.087 | 98.008 | 1.00 | 26.14 | A | C |
| ATOM | 2346 | O | SER | A | 323 | 1.992 | 119.128 | 97.944 | 1.00 | 30.11 | A | O |
| ATOM | 2347 | N | LEU | A | 324 | 3.864 | 118.181 | 98.717 | 1.00 | 25.18 | A | N |
| ATOM | 2348 | CA | LEU | A | 324 | 3.161 | 117.129 | 99.440 | 1.00 | 26.64 | A | C |
| ATOM | 2349 | CB | LEU | A | 324 | 4.170 | 116.142 | 100.037 | 1.00 | 21.87 | A | C |
| ATOM | 2350 | CG | LEU | A | 324 | 5.016 | 115.383 | 99.018 | 1.00 | 20.05 | A | C |
| ATOM | 2351 | CD1 | LEU | A | 324 | 6.101 | 114.583 | 99.731 | 1.00 | 16.27 | A | C |
| ATOM | 2352 | CD2 | LEU | A | 324 | 4.104 | 114.479 | 98.185 | 1.00 | 14.62 | A | C |
| ATOM | 2353 | C | LEU | A | 324 | 2.244 | 117.630 | 100.543 | 1.00 | 26.89 | A | C |
| ATOM | 2354 | O | LEU | A | 324 | 1.123 | 117.149 | 100.694 | 1.00 | 24.05 | A | O |
| ATOM | 2355 | N | GLY | A | 325 | 2.730 | 118.603 | 101.308 | 1.00 | 30.50 | A | N |
| ATOM | 2356 | CA | GLY | A | 325 | 1.969 | 119.142 | 102.421 | 1.00 | 33.07 | A | C |
| ATOM | 2357 | C | GLN | A | 325 | 0.749 | 119.988 | 102.124 | 1.00 | 34.55 | A | C |
| ATOM | 2358 | O | GLY | A | 325 | −0.145 | 120.093 | 102.958 | 1.00 | 34.47 | A | O |
| ATOM | 2359 | N | GLY | A | 326 | 0.705 | 120.605 | 100.949 | 1.00 | 36.32 | A | N |
| ATOM | 2360 | CA | GLY | A | 326 | −0.437 | 121.430 | 100.607 | 1.00 | 37.56 | A | C |
| ATOM | 2361 | C | GLY | A | 326 | −1.549 | 120.598 | 100.009 | 1.00 | 39.35 | A | C |
| ATOM | 2362 | O | GLY | A | 326 | −1.399 | 119.388 | 99.840 | 1.00 | 41.28 | A | O |
| ATOM | 2363 | N | ARG | A | 327 | −2.677 | 121.234 | 99.709 | 1.00 | 41.06 | A | N |
| ATOM | 2364 | CA | ARG | A | 327 | −3.790 | 120.519 | 99.106 | 1.00 | 42.73 | A | C |
| ATOM | 2365 | CB | ARG | A | 327 | −5.103 | 121.314 | 99.258 | 1.00 | 46.65 | A | C |
| ATOM | 2366 | CG | ARG | A | 327 | −5.198 | 122.652 | 98.526 | 1.00 | 45.98 | A | C |
| ATOM | 2367 | CD | ARG | A | 327 | −5.513 | 122.444 | 97.050 | 1.00 | 51.51 | A | C |
| ATOM | 2368 | NE | ARG | A | 327 | −6.527 | 121.410 | 96.839 | 1.00 | 53.63 | A | N |
| ATOM | 2369 | CZ | ARG | A | 327 | −6.852 | 120.910 | 95.647 | 1.00 | 54.18 | A | C |
| ATOM | 2370 | NH1 | ARG | A | 327 | −6.245 | 121.351 | 94.551 | 1.00 | 54.22 | A | N |
| ATOM | 2371 | NH2 | ARG | A | 327 | −7.772 | 119.954 | 95.551 | 1.00 | 52.47 | A | N |
| ATOM | 2372 | C | ARG | A | 327 | −3.395 | 120.354 | 97.646 | 1.00 | 41.37 | A | C |
| ATOM | 2373 | O | ARG | A | 327 | −3.318 | 121.325 | 96.893 | 1.00 | 39.81 | A | O |
| ATOM | 2374 | N | THR | A | 328 | −3.098 | 119.123 | 97.255 | 1.00 | 38.53 | A | N |
| ATOM | 2375 | CA | THR | A | 328 | −2.681 | 118.882 | 95.889 | 1.00 | 37.66 | A | C |
| ATOM | 2376 | CB | THR | A | 328 | −1.180 | 119.185 | 95.705 | 1.00 | 39.08 | A | C |
| ATOM | 2377 | OG1 | THR | A | 328 | −0.406 | 118.110 | 96.250 | 1.00 | 39.80 | A | O |
| ATOM | 2378 | CG2 | THR | A | 328 | −0.802 | 120.469 | 96.432 | 1.00 | 41.76 | A | C |
| ATOM | 2379 | C | THR | A | 328 | −2.900 | 117.434 | 95.524 | 1.00 | 34.11 | A | C |
| ATOM | 2380 | O | THR | A | 328 | −3.533 | 116.685 | 96.255 | 1.00 | 33.80 | A | O |
| ATOM | 2381 | N | ARG | A | 329 | −2.370 | 117.049 | 94.377 | 1.00 | 30.76 | A | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2382 | CA | ARG | A | 329 | −2.477 | 115.681 | 93.937 | 1.00 | 29.59 | A | C |
| ATOM | 2383 | CB | ARG | A | 329 | −3.132 | 115.602 | 92.559 | 1.00 | 29.94 | A | C |
| ATOM | 2384 | CG | ARG | A | 329 | −4.589 | 116.032 | 92.558 | 1.00 | 31.02 | A | C |
| ATOM | 2385 | CD | ARG | A | 329 | −5.326 | 115.372 | 91.416 | 1.00 | 34.76 | A | C |
| ATOM | 2386 | NE | ARG | A | 329 | −6.710 | 115.819 | 91.285 | 1.00 | 37.54 | A | N |
| ATOM | 2387 | CZ | ARG | A | 329 | −7.635 | 115.167 | 90.586 | 1.00 | 39.36 | A | C |
| ATOM | 2388 | NH1 | ARG | A | 329 | −7.325 | 114.038 | 89.961 | 1.00 | 37.86 | A | N |
| ATOM | 2389 | NH2 | ARG | A | 329 | −8.869 | 115.645 | 90.503 | 1.00 | 40.91 | A | N |
| ATOM | 2390 | C | ARG | A | 329 | −1.082 | 115.094 | 93.909 | 1.00 | 27.34 | A | C |
| ATOM | 2391 | O | ARG | A | 329 | −0.135 | 115.726 | 93.435 | 1.00 | 24.25 | A | O |
| ATOM | 2392 | N | THR | A | 330 | −0.961 | 113.893 | 94.455 | 1.00 | 25.53 | A | N |
| ATOM | 2393 | CA | THR | A | 330 | 0.311 | 113.201 | 94.513 | 1.00 | 25.50 | A | C |
| ATOM | 2394 | CB | THR | A | 330 | 0.872 | 113.188 | 95.936 | 1.00 | 22.47 | A | C |
| ATOM | 2395 | OG1 | THR | A | 330 | 1.180 | 114.524 | 96.343 | 1.00 | 23.74 | A | O |
| ATOM | 2396 | CG2 | THR | A | 330 | 2.121 | 112.359 | 95.988 | 1.00 | 26.51 | A | C |
| ATOM | 2397 | C | THR | A | 330 | 0.115 | 111.771 | 94.057 | 1.00 | 26.09 | A | C |
| ATOM | 2398 | O | THR | A | 330 | −0.766 | 111.062 | 94.551 | 1.00 | 25.82 | A | O |
| ATOM | 2399 | N | SER | A | 331 | 0.936 | 111.345 | 93.107 | 1.00 | 26.48 | A | N |
| ATOM | 2400 | CA | SER | A | 331 | 0.830 | 109.993 | 92.590 | 1.00 | 22.95 | A | C |
| ATOM | 2401 | CB | SER | A | 331 | 0.272 | 110.040 | 91.170 | 1.00 | 21.46 | A | C |
| ATOM | 2402 | OG | SER | A | 331 | 0.609 | 108.858 | 90.462 | 1.00 | 26.96 | A | O |
| ATOM | 2403 | C | SER | A | 331 | 2.149 | 109.231 | 92.605 | 1.00 | 22.11 | A | C |
| ATOM | 2404 | O | SER | A | 331 | 3.209 | 109.790 | 92.332 | 1.00 | 23.54 | A | O |
| ATOM | 2405 | N | ILE | A | 332 | 2.071 | 107.946 | 92.935 | 1.00 | 21.48 | A | N |
| ATOM | 2406 | CA | ILE | A | 332 | 3.244 | 107.082 | 92.955 | 1.00 | 19.76 | A | C |
| ATOM | 2407 | CB | ILE | A | 332 | 3.466 | 106.440 | 94.326 | 1.00 | 19.73 | A | C |
| ATOM | 2408 | CG2 | ILE | A | 332 | 4.556 | 105.379 | 94.238 | 1.00 | 17.71 | A | C |
| ATOM | 2409 | CG1 | ILE | A | 332 | 3.864 | 107.500 | 95.339 | 1.00 | 24.96 | A | C |
| ATOM | 2410 | CD1 | ILE | A | 332 | 4.020 | 106.944 | 96.748 | 1.00 | 28.41 | A | C |
| ATOM | 2411 | C | ILE | A | 332 | 3.033 | 105.946 | 91.967 | 1.00 | 20.33 | A | C |
| ATOM | 2412 | O | ILE | A | 332 | 1.999 | 105.268 | 91.990 | 1.00 | 18.12 | A | O |
| ATOM | 2413 | N | ILE | A | 333 | 4.011 | 105.744 | 91.096 | 1.00 | 17.54 | A | N |
| ATOM | 2414 | CA | ILE | A | 333 | 3.937 | 104.659 | 90.137 | 1.00 | 15.95 | A | C |
| ATOM | 2415 | CB | ILE | A | 333 | 4.254 | 105.149 | 88.715 | 1.00 | 14.96 | A | C |
| ATOM | 2416 | CG2 | ILE | A | 333 | 3.984 | 104.041 | 87.721 | 1.00 | 15.60 | A | C |
| ATOM | 2417 | CG1 | ILE | A | 333 | 3.383 | 106.363 | 88.389 | 1.00 | 15.12 | A | C |
| ATOM | 2418 | CD1 | ILE | A | 333 | 3.367 | 106.764 | 86.937 | 1.00 | 7.12 | A | C |
| ATOM | 2419 | C | ILE | A | 333 | 4.946 | 103.582 | 90.552 | 1.00 | 15.57 | A | C |
| ATOM | 2420 | O | ILE | A | 333 | 6.156 | 103.753 | 90.400 | 1.00 | 15.65 | A | O |
| ATOM | 2421 | N | ALA | A | 334 | 4.432 | 102.486 | 91.100 | 1.00 | 15.20 | A | N |
| ATOM | 2422 | CA | ALA | A | 334 | 5.258 | 101.375 | 91.545 | 1.00 | 15.26 | A | C |
| ATOM | 2423 | CB | ALA | A | 334 | 4.593 | 100.688 | 92.732 | 1.00 | 11.42 | A | C |
| ATOM | 2424 | C | ALA | A | 334 | 5.480 | 100.376 | 90.404 | 1.00 | 16.40 | A | C |
| ATOM | 2425 | O | ALA | A | 334 | 4.561 | 99.651 | 90.017 | 1.00 | 16.89 | A | O |
| ATOM | 2426 | N | THR | A | 335 | 6.704 | 100.345 | 89.876 | 1.00 | 16.49 | A | N |
| ATOM | 2427 | CA | THR | A | 335 | 7.078 | 99.447 | 88.782 | 1.00 | 15.33 | A | C |
| ATOM | 2428 | CB | THR | A | 335 | 8.231 | 100.054 | 87.916 | 1.00 | 14.44 | A | C |
| ATOM | 2429 | OG1 | THR | A | 335 | 9.390 | 100.261 | 88.727 | 1.00 | 12.66 | A | O |
| ATOM | 2430 | CG2 | THR | A | 335 | 7.816 | 101.372 | 87.320 | 1.00 | 12.87 | A | C |
| ATOM | 2431 | C | THR | A | 335 | 7.539 | 98.074 | 89.271 | 1.00 | 16.21 | A | C |
| ATOM | 2432 | O | THR | A | 335 | 8.295 | 97.973 | 90.240 | 1.00 | 16.59 | A | O |
| ATOM | 2433 | N | ILE | A | 336 | 7.097 | 97.016 | 88.596 | 1.00 | 15.86 | A | N |
| ATOM | 2434 | CA | ILE | A | 336 | 7.500 | 95.662 | 88.980 | 1.00 | 14.00 | A | C |
| ATOM | 2435 | CB | ILE | A | 336 | 6.413 | 94.949 | 89.813 | 1.00 | 12.00 | A | C |
| ATOM | 2436 | CG2 | ILE | A | 336 | 6.138 | 95.719 | 91.083 | 1.00 | 15.32 | A | C |
| ATOM | 2437 | CG1 | ILE | A | 336 | 5.129 | 94.811 | 89.001 | 1.00 | 13.53 | A | C |
| ATOM | 2438 | CD1 | ILE | A | 336 | 4.011 | 94.116 | 89.762 | 1.00 | 12.40 | A | C |
| ATOM | 2439 | C | ILE | A | 336 | 7.815 | 94.767 | 87.783 | 1.00 | 17.40 | A | C |
| ATOM | 2440 | O | ILE | A | 336 | 7.469 | 95.080 | 86.635 | 1.00 | 19.20 | A | O |
| ATOM | 2441 | N | SER | A | 337 | 8.478 | 93.651 | 88.076 | 1.00 | 18.37 | A | N |
| ATOM | 2442 | CA | SER | A | 337 | 8.849 | 92.641 | 87.087 | 1.00 | 20.79 | A | C |
| ATOM | 2443 | CB | SER | A | 337 | 10.239 | 92.072 | 87.428 | 1.00 | 21.56 | A | C |
| ATOM | 2444 | OG | SER | A | 337 | 10.507 | 90.849 | 86.759 | 1.00 | 17.90 | A | O |
| ATOM | 2445 | C | SER | A | 337 | 7.805 | 91.513 | 87.140 | 1.00 | 20.59 | A | C |
| ATOM | 2446 | O | SER | A | 337 | 7.156 | 91.304 | 88.166 | 1.00 | 19.58 | A | O |
| ATOM | 2447 | N | PRO | A | 338 | 7.616 | 90.786 | 86.029 | 1.00 | 19.44 | A | N |
| ATOM | 2448 | CD | PRO | A | 338 | 7.930 | 91.171 | 84.640 | 1.00 | 13.27 | A | C |
| ATOM | 2449 | CA | PRO | A | 338 | 6.631 | 89.700 | 86.069 | 1.00 | 18.52 | A | C |
| ATOM | 2450 | CB | PRO | A | 338 | 5.974 | 89.808 | 84.707 | 1.00 | 18.29 | A | C |
| ATOM | 2451 | CG | PRO | A | 338 | 7.154 | 90.144 | 83.828 | 1.00 | 15.69 | A | C |
| ATOM | 2452 | C | PRO | A | 338 | 7.292 | 88.330 | 86.281 | 1.00 | 20.08 | A | C |
| ATOM | 2453 | O | PRO | A | 338 | 6.607 | 87.315 | 86.411 | 1.00 | 18.70 | A | O |
| ATOM | 2454 | N | ALA | A | 339 | 8.624 | 88.306 | 86.330 | 1.00 | 21.76 | A | N |
| ATOM | 2455 | CA | ALA | A | 339 | 9.370 | 87.052 | 86.472 | 1.00 | 21.99 | A | C |
| ATOM | 2456 | CB | ALA | A | 339 | 10.678 | 87.145 | 85.677 | 1.00 | 21.69 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2457 | C | ALA | A | 339 | 9.671 | 86.576 | 87.893 | 1.00 | 21.09 | A | C |
| ATOM | 2458 | O | ALA | A | 339 | 9.873 | 87.372 | 88.806 | 1.00 | 21.05 | A | O |
| ATOM | 2459 | N | SER | A | 340 | 9.717 | 85.257 | 88.049 | 1.00 | 21.58 | A | N |
| ATOM | 2460 | CA | SER | A | 340 | 10.007 | 84.597 | 89.318 | 1.00 | 21.65 | A | C |
| ATOM | 2461 | CB | SER | A | 340 | 9.928 | 83.076 | 89.141 | 1.00 | 24.02 | A | C |
| ATOM | 2462 | OG | SER | A | 340 | 10.956 | 82.585 | 88.280 | 1.00 | 20.18 | A | O |
| ATOM | 2463 | C | SER | A | 340 | 11.393 | 84.954 | 89.838 | 1.00 | 23.29 | A | C |
| ATOM | 2464 | O | SER | A | 340 | 11.633 | 84.957 | 91.047 | 1.00 | 23.73 | A | O |
| ATOM | 2465 | N | LEU | A | 341 | 12.299 | 85.246 | 88.913 | 1.00 | 25.12 | A | N |
| ATOM | 2466 | CA | LEU | A | 341 | 13.678 | 85.602 | 89.223 | 1.00 | 25.89 | A | C |
| ATOM | 2467 | CA | LEU | A | 341 | 14.411 | 85.933 | 87.917 | 1.00 | 25.96 | A | C |
| ATOM | 2468 | CG | LEU | A | 341 | 15.932 | 85.811 | 87.883 | 1.00 | 28.23 | A | C |
| ATOM | 2469 | CD1 | LEU | A | 341 | 16.313 | 84.386 | 88.245 | 1.00 | 29.50 | A | C |
| ATOM | 2470 | CD2 | LEU | A | 341 | 16.462 | 86.182 | 86.490 | 1.00 | 30.33 | A | C |
| ATOM | 2471 | C | LEU | A | 341 | 13.785 | 86.786 | 90.194 | 1.00 | 27.55 | A | C |
| ATOM | 2472 | O | LEU | A | 341 | 14.725 | 86.862 | 90.996 | 1.00 | 26.77 | A | O |
| ATOM | 2473 | N | ASN | A | 342 | 12.815 | 87.700 | 90.130 | 1.00 | 26.83 | A | N |
| ATOM | 2474 | CA | ASN | A | 342 | 12.827 | 88.887 | 90.979 | 1.00 | 27.51 | A | C |
| ATOM | 2475 | CB | ASN | A | 342 | 12.913 | 90.141 | 90.104 | 1.00 | 26.16 | A | C |
| ATOM | 2476 | CG | ASN | A | 342 | 14.168 | 90.177 | 89.278 | 1.00 | 24.91 | A | C |
| ATOM | 2477 | OD1 | ASN | A | 342 | 14.123 | 90.358 | 88.063 | 1.00 | 26.80 | A | O |
| ATOM | 2478 | ND2 | ASN | A | 342 | 15.306 | 90.005 | 89.935 | 1.00 | 26.71 | A | N |
| ATOM | 2479 | C | ASN | A | 342 | 11.614 | 88.985 | 91.888 | 1.00 | 29.21 | A | C |
| ATOM | 2480 | O | ASN | A | 342 | 11.143 | 90.084 | 92.209 | 1.00 | 29.32 | A | O |
| ATOM | 2481 | N | LEU | A | 343 | 11.117 | 87.836 | 92.320 | 1.00 | 30.92 | A | N |
| ATOM | 2482 | CA | LEU | A | 343 | 9.942 | 87.802 | 93.182 | 1.00 | 33.47 | A | C |
| ATOM | 2483 | CB | LEU | A | 343 | 9.566 | 86.348 | 93.486 | 1.00 | 34.69 | A | C |
| ATOM | 2484 | CG | LEU | A | 343 | 8.374 | 86.101 | 94.412 | 1.00 | 35.05 | A | C |
| ATOM | 2485 | CD1 | LEU | A | 343 | 8.015 | 84.634 | 94.425 | 1.00 | 38.29 | A | C |
| ATOM | 2486 | CD2 | LEU | A | 343 | 8.724 | 86.567 | 95.808 | 1.00 | 36.54 | A | C |
| ATOM | 2487 | C | LEU | A | 343 | 10.074 | 88.605 | 94.489 | 1.00 | 34.82 | A | C |
| ATOM | 2488 | O | LEU | A | 343 | 9.168 | 89.370 | 94.835 | 1.00 | 32.42 | A | O |
| ATOM | 2489 | N | GLU | A | 344 | 11.180 | 88.434 | 95.220 | 1.00 | 36.12 | A | N |
| ATOM | 2490 | CA | GLU | A | 344 | 11.374 | 89.173 | 96.480 | 1.00 | 34.96 | A | C |
| ATOM | 2491 | CB | GLU | A | 344 | 12.709 | 88.837 | 97.145 | 1.00 | 36.44 | A | C |
| ATOM | 2492 | CG | GLU | A | 344 | 12.676 | 87.688 | 98.118 | 1.00 | 41.07 | A | C |
| ATOM | 2493 | CD | GLU | A | 344 | 12.720 | 86.340 | 97.425 | 1.00 | 45.75 | A | C |
| ATOM | 2494 | OE1 | GLU | A | 344 | 13.656 | 86.108 | 96.623 | 1.00 | 44.68 | A | O |
| ATOM | 2495 | OE2 | GLU | A | 344 | 11.821 | 85.511 | 97.687 | 1.00 | 49.64 | A | O |
| ATOM | 2496 | C | GLU | A | 344 | 11.310 | 90.687 | 96.325 | 1.00 | 32.36 | A | C |
| ATOM | 2497 | O | GLU | A | 344 | 10.689 | 91.368 | 97.135 | 1.00 | 31.60 | A | O |
| ATOM | 2498 | N | GLU | A | 345 | 11.975 | 91.221 | 95.308 | 1.00 | 29.69 | A | N |
| ATOM | 2499 | CA | GLU | A | 345 | 11.950 | 92.658 | 95.105 | 1.00 | 27.75 | A | C |
| ATOM | 2500 | CB | GLU | A | 345 | 12.974 | 93.064 | 94.044 | 1.00 | 29.30 | A | C |
| ATOM | 2501 | CG | GLU | A | 345 | 14.387 | 93.107 | 94.571 | 1.00 | 30.84 | A | C |
| ATOM | 2502 | CD | GLU | A | 345 | 14.458 | 93.744 | 95.950 | 1.00 | 36.62 | A | C |
| ATOM | 2503 | OE1 | GLU | A | 345 | 13.695 | 94.704 | 96.217 | 1.00 | 39.10 | A | O |
| ATOM | 2504 | OE2 | GLU | A | 345 | 15.284 | 93.290 | 96.771 | 1.00 | 40.15 | A | O |
| ATOM | 2505 | C | GLU | A | 345 | 10.549 | 93.122 | 94.701 | 1.00 | 26.54 | A | C |
| ATOM | 2506 | O | GLU | A | 345 | 10.130 | 94.231 | 95.048 | 1.00 | 22.08 | A | O |
| ATOM | 2507 | N | THR | A | 346 | 9.831 | 92.258 | 93.982 | 1.00 | 24.85 | A | N |
| ATOM | 2508 | CA | THR | A | 346 | 8.483 | 92.562 | 93.529 | 1.00 | 22.50 | A | C |
| ATOM | 2509 | CB | THR | A | 346 | 7.990 | 91.529 | 92.489 | 1.00 | 21.62 | A | C |
| ATOM | 2510 | OG1 | THR | A | 346 | 8.590 | 91.808 | 91.214 | 1.00 | 25.37 | A | O |
| ATOM | 2511 | CG2 | THR | A | 346 | 6.480 | 91.571 | 92.364 | 1.00 | 13.54 | A | C |
| ATOM | 2512 | C | THR | A | 346 | 7.530 | 92.583 | 94.711 | 1.00 | 23.61 | A | C |
| ATOM | 2513 | O | THR | A | 346 | 6.673 | 93.464 | 94.826 | 1.00 | 26.57 | A | O |
| ATOM | 2514 | N | LEU | A | 347 | 7.680 | 91.623 | 95.608 | 1.00 | 23.22 | A | N |
| ATOM | 2515 | CA | LEU | A | 347 | 6.812 | 91.574 | 96.771 | 1.00 | 22.61 | A | C |
| ATOM | 2516 | CB | LEU | A | 347 | 6.960 | 90.233 | 97.485 | 1.00 | 25.92 | A | C |
| ATOM | 2517 | CG | LEU | A | 347 | 6.275 | 89.101 | 96.725 | 1.00 | 27.59 | A | C |
| ATOM | 2518 | CD1 | LEU | A | 347 | 6.518 | 87.788 | 97.426 | 1.00 | 28.76 | A | C |
| ATOM | 2519 | CD2 | LEU | A | 347 | 4.786 | 89.400 | 96.632 | 1.00 | 23.91 | A | C |
| ATOM | 2520 | C | LEU | A | 347 | 7.105 | 92.716 | 97.720 | 1.00 | 22.49 | A | C |
| ATOM | 2521 | O | LEU | A | 347 | 6.199 | 93.245 | 98.361 | 1.00 | 24.59 | A | O |
| ATOM | 2522 | N | SER | A | 348 | 8.373 | 93.097 | 97.814 | 1.00 | 22.25 | A | N |
| ATOM | 2523 | CA | SER | A | 348 | 8.761 | 94.204 | 98.675 | 1.00 | 21.61 | A | C |
| ATOM | 2524 | CB | SER | A | 348 | 10.287 | 94.303 | 98.754 | 1.00 | 23.30 | A | C |
| ATOM | 2525 | OG | SER | A | 348 | 10.684 | 95.416 | 99.536 | 1.00 | 23.88 | A | O |
| ATOM | 2526 | C | SER | A | 348 | 8.168 | 95.506 | 98.120 | 1.00 | 19.44 | A | C |
| ATOM | 2527 | O | SER | A | 348 | 7.703 | 96.360 | 98.872 | 1.00 | 20.27 | A | O |
| ATOM | 2528 | N | THR | A | 349 | 8.165 | 95.650 | 96.801 | 1.00 | 19.29 | A | N |
| ATOM | 2529 | CA | THR | A | 349 | 7.599 | 96.849 | 96.184 | 1.00 | 20.42 | A | C |
| ATOM | 2530 | CB | THR | A | 349 | 7.906 | 96.889 | 94.689 | 1.00 | 20.74 | A | C |
| ATOM | 2531 | OG1 | THR | A | 349 | 9.308 | 97.088 | 94.509 | 1.00 | 20.60 | A | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2532 | CG2 | THR | A | 349 | 7.135 | 98.009 | 94.011 | 1.00 | 20.52 | A | C |
| ATOM | 2533 | C | THR | A | 349 | 6.087 | 96.924 | 96.394 | 1.00 | 18.84 | A | C |
| ATOM | 2534 | O | THR | A | 349 | 5.561 | 97.958 | 96.806 | 1.00 | 15.49 | A | O |
| ATOM | 2535 | N | LEU | A | 350 | 5.391 | 95.826 | 96.111 | 1.00 | 18.86 | A | N |
| ATOM | 2536 | CA | LEU | A | 350 | 3.944 | 95.779 | 96.299 | 1.00 | 19.58 | A | C |
| ATOM | 2537 | CB | LEU | A | 350 | 3.383 | 94.410 | 95.884 | 1.00 | 20.18 | A | C |
| ATOM | 2538 | CG | LEU | A | 350 | 3.437 | 94.073 | 94.386 | 1.00 | 18.70 | A | C |
| ATOM | 2539 | CD1 | LEU | A | 350 | 3.093 | 92.630 | 94.183 | 1.00 | 18.11 | A | C |
| ATOM | 2540 | CD2 | LEU | A | 350 | 2.479 | 94.967 | 93.611 | 1.00 | 17.09 | A | C |
| ATOM | 2541 | C | LEU | A | 350 | 3.630 | 96.040 | 97.763 | 1.00 | 21.01 | A | C |
| ATOM | 2542 | O | LEU | A | 350 | 2.694 | 96.768 | 98.093 | 1.00 | 23.90 | A | O |
| ATOM | 2543 | N | GLU | A | 351 | 4.410 | 95.444 | 98.654 | 1.00 | 20.61 | A | N |
| ATOM | 2544 | CA | GLU | A | 351 | 4.186 | 95.661 | 100.077 | 1.00 | 20.06 | A | C |
| ATOM | 2545 | CB | GLU | A | 351 | 5.177 | 94.843 | 100.900 | 1.00 | 21.85 | A | C |
| ATOM | 2546 | CG | GLU | A | 351 | 4.743 | 93.401 | 101.124 | 1.00 | 25.50 | A | C |
| ATOM | 2547 | CD | GLU | A | 351 | 3.442 | 93.318 | 101.909 | 1.00 | 26.93 | A | C |
| ATOM | 2548 | OE1 | GLU | A | 351 | 3.372 | 93.946 | 102.985 | 1.00 | 28.15 | A | O |
| ATOM | 2549 | OE2 | GLU | A | 351 | 2.496 | 92.634 | 101.458 | 1.00 | 22.45 | A | O |
| ATOM | 2550 | C | GLU | A | 351 | 4.315 | 97.144 | 100.412 | 1.00 | 18.99 | A | C |
| ATOM | 2551 | O | GLU | A | 351 | 3.437 | 97.724 | 101.051 | 1.00 | 17.51 | A | O |
| ATOM | 2552 | N | TYR | A | 352 | 5.413 | 97.755 | 99.977 | 1.00 | 18.91 | A | N |
| ATOM | 2553 | CA | TYR | A | 352 | 5.655 | 99.181 | 100.214 | 1.00 | 17.47 | A | C |
| ATOM | 2554 | CB | TYR | A | 352 | 6.958 | 99.588 | 99.533 | 1.00 | 16.44 | A | C |
| ATOM | 2555 | CG | TYR | A | 352 | 7.335 | 101.046 | 99.656 | 1.00 | 15.71 | A | C |
| ATOM | 2556 | CD1 | TYR | A | 352 | 6.714 | 102.012 | 98.878 | 1.00 | 13.89 | A | C |
| ATOM | 2557 | CE1 | TYR | A | 352 | 7.104 | 103.334 | 98.938 | 1.00 | 16.73 | A | C |
| ATOM | 2558 | CD2 | TYR | A | 352 | 8.360 | 101.448 | 100.512 | 1.00 | 17.54 | A | C |
| ATOM | 2559 | CE2 | TYR | A | 352 | 8.760 | 102.766 | 100.584 | 1.00 | 14.56 | A | C |
| ATOM | 2560 | CZ | TYR | A | 352 | 8.132 | 103.712 | 99.791 | 1.00 | 18.75 | A | C |
| ATOM | 2561 | OH | TYR | A | 352 | 8.542 | 105.030 | 99.828 | 1.00 | 11.90 | A | O |
| ATOM | 2562 | C | TYR | A | 352 | 4.488 | 100.000 | 99.660 | 1.00 | 18.50 | A | C |
| ATOM | 2563 | O | TYR | A | 352 | 3.928 | 100.871 | 100.338 | 1.00 | 15.65 | A | O |
| ATOM | 2564 | N | ALA | A | 353 | 4.115 | 99.709 | 98.419 | 1.00 | 19.21 | A | N |
| ATOM | 2565 | CA | ALA | A | 353 | 3.006 | 100.409 | 97.798 | 1.00 | 20.47 | A | C |
| ATOM | 2566 | CB | ALA | A | 353 | 2.744 | 99.849 | 96.424 | 1.00 | 18.38 | A | C |
| ATOM | 2567 | C | ALA | A | 353 | 1.761 | 100.265 | 98.668 | 1.00 | 22.31 | A | C |
| ATOM | 2568 | O | ALA | A | 353 | 1.107 | 101.249 | 98.983 | 1.00 | 24.35 | A | O |
| ATOM | 2569 | N | HIS | A | 354 | 1.450 | 99.033 | 99.057 | 1.00 | 23.63 | A | N |
| ATOM | 2570 | CA | HIS | A | 354 | 0.283 | 98.726 | 99.886 | 1.00 | 24.89 | A | C |
| ATOM | 2571 | CB | HIS | A | 354 | 0.191 | 97.216 | 100.090 | 1.00 | 27.75 | A | C |
| ATOM | 2572 | CG | HIS | A | 354 | −1.011 | 96.782 | 100.865 | 1.00 | 28.91 | A | C |
| ATOM | 2573 | CD2 | HIS | A | 354 | −1.124 | 96.117 | 102.038 | 1.00 | 29.49 | A | C |
| ATOM | 2574 | ND1 | HIS | A | 354 | −2.298 | 97.002 | 100.425 | 1.00 | 28.46 | A | N |
| ATOM | 2575 | CE1 | HIS | A | 354 | −3.152 | 96.490 | 101.292 | 1.00 | 26.86 | A | C |
| ATOM | 2576 | NE2 | HIS | A | 354 | −2.466 | 95.947 | 102.280 | 1.00 | 27.73 | A | N |
| ATOM | 2577 | C | HIS | A | 354 | 0.296 | 99.414 | 101.250 | 1.00 | 25.78 | A | C |
| ATOM | 2578 | O | HIS | A | 354 | −0.753 | 99.742 | 101.800 | 1.00 | 24.26 | A | O |
| ATOM | 2579 | N | ARG | A | 355 | 1.486 | 99.625 | 101.796 | 1.00 | 25.92 | A | N |
| ATOM | 2580 | CA | ARG | A | 355 | 1.627 | 100.268 | 103.094 | 1.00 | 26.30 | A | C |
| ATOM | 2581 | CB | ARG | A | 355 | 3.001 | 99.917 | 103.700 | 1.00 | 25.37 | A | C |
| ATOM | 2582 | CG | ARG | A | 355 | 3.427 | 100.766 | 104.886 | 1.00 | 27.80 | A | C |
| ATOM | 2583 | CD | ARG | A | 355 | 4.497 | 100.066 | 105.728 | 1.00 | 30.16 | A | C |
| ATOM | 2584 | NE | ARG | A | 355 | 5.511 | 99.394 | 104.920 | 1.00 | 33.82 | A | N |
| ATOM | 2585 | CZ | ARG | A | 355 | 6.496 | 100.009 | 104.272 | 1.00 | 35.44 | A | C |
| ATOM | 2586 | NH1 | ARG | A | 355 | 6.619 | 101.329 | 104.331 | 1.00 | 35.76 | A | N |
| ATOM | 2587 | NH2 | ARG | A | 355 | 7.362 | 99.297 | 103.561 | 1.00 | 32.3S | A | N |
| ATOM | 2588 | C | ARG | A | 355 | 1.455 | 101.778 | 102.973 | 1.00 | 26.89 | A | C |
| ATOM | 2589 | O | ARG | A | 355 | 1.068 | 102.449 | 103.931 | 1.00 | 26.62 | A | O |
| ATOM | 2590 | N | ALA | A | 356 | 1.738 | 102.315 | 101.792 | 1.00 | 26.46 | A | N |
| ATOM | 2591 | CA | ALA | A | 356 | 1.615 | 103.750 | 101.577 | 1.00 | 25.71 | A | C |
| ATOM | 2592 | CB | ALA | A | 356 | 2.261 | 104.140 | 100.260 | 1.00 | 24.56 | A | C |
| ATOM | 2593 | C | ALA | A | 356 | 0.151 | 104.162 | 101.594 | 1.00 | 26.79 | A | C |
| ATOM | 2594 | O | ALA | A | 356 | −0.215 | 105.159 | 102.207 | 1.00 | 28.94 | A | O |
| ATOM | 2595 | N | LYS | A | 357 | −0.691 | 103.405 | 100.910 | 1.00 | 26.89 | A | N |
| ATOM | 2596 | CA | LYS | A | 357 | −2.116 | 103.705 | 100.884 | 1.00 | 29.29 | A | C |
| ATOM | 2597 | CB | LYS | A | 357 | −2.489 | 104.569 | 99.677 | 1.00 | 29.14 | A | C |
| ATOM | 2598 | CG | LYS | A | 357 | −3.969 | 104.920 | 99.656 | 1.00 | 30.62 | A | C |
| ATOM | 2599 | CD | LYS | A | 357 | −4.419 | 105.560 | 98.347 | 1.00 | 28.56 | A | C |
| ATOM | 2600 | CE | LYS | A | 357 | −5.929 | 105.765 | 98.353 | 1.00 | 25.99 | A | C |
| ATOM | 2601 | NZ | LYS | A | 357 | −6.426 | 106.373 | 97.096 | 1.00 | 24.25 | A | N |
| ATOM | 2602 | C | LYS | A | 357 | −2.858 | 102.378 | 100.828 | 1.00 | 31.42 | A | C |
| ATOM | 2603 | O | LYS | A | 357 | −2.932 | 101.722 | 99.781 | 1.00 | 29.34 | A | O |
| ATOM | 2604 | N | ASN | A | 358 | −3.401 | 101.996 | 101.976 | 1.00 | 33.42 | A | N |
| ATOM | 2605 | CA | ASN | A | 358 | −4.111 | 100.738 | 102.134 | 1.00 | 32.74 | A | C |
| ATOM | 2606 | CB | ASN | A | 358 | −4.341 | 100.473 | 103.614 | 1.00 | 35.19 | A | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2607 | CG | ASN | A | 358 | −4.391 | 99.011 | 103.931 | 1.00 | 40.36 | A | C |
| ATOM | 2608 | OD1 | ASN | A | 358 | −4.662 | 98.622 | 105.061 | 1.00 | 44.63 | A | O |
| ATOM | 2609 | ND2 | ASN | A | 358 | −4.118 | 98.182 | 102.933 | 1.00 | 42.20 | A | N |
| ATOM | 2610 | C | ASN | A | 358 | −5.440 | 100.677 | 101.403 | 1.00 | 31.26 | A | C |
| ATOM | 2611 | O | ASN | A | 358 | −6.337 | 101.467 | 101.664 | 1.00 | 29.98 | A | O |
| ATOM | 2612 | N | ILE | A | 359 | −5.562 | 99.720 | 100.492 | 1.00 | 31.56 | A | N |
| ATOM | 2613 | CA | ILE | A | 359 | −6.787 | 99.547 | 99.730 | 1.00 | 29.76 | A | C |
| ATOM | 2614 | CB | ILE | A | 359 | −6.582 | 99.878 | 98.243 | 1.00 | 27.50 | A | C |
| ATOM | 2615 | CG2 | ILE | A | 359 | −7.888 | 99.738 | 97.494 | 1.00 | 25.03 | A | C |
| ATOM | 2616 | CG1 | ILE | A | 359 | −6.083 | 101.310 | 98.098 | 1.00 | 27.66 | A | C |
| ATOM | 2617 | CD1 | ILE | A | 359 | −5.960 | 101.761 | 96.677 | 1.00 | 27.21 | A | C |
| ATOM | 2618 | C | ILE | A | 359 | −7.267 | 98.114 | 99.848 | 1.00 | 29.44 | A | C |
| ATOM | 2619 | O | ILE | A | 359 | −6.728 | 97.216 | 99.215 | 1.00 | 31.45 | A | O |
| ATOM | 2620 | N | LEU | A | 360 | −8.289 | 97.907 | 100.665 | 1.00 | 27.56 | A | N |
| ATOM | 2621 | CA | LEU | A | 360 | −8.853 | 96.582 | 100.878 | 1.00 | 2S.68 | A | C |
| ATOM | 2622 | CB | LEU | A | 360 | −10.122 | 96.711 | 101.707 | 1.00 | 26.66 | A | C |
| ATOM | 2623 | CG | LEU | A | 360 | −9.900 | 97.488 | 102.998 | 1.00 | 30.63 | A | C |
| ATOM | 2624 | CD1 | LEU | A | 360 | −11.237 | 97.879 | 103.607 | 1.00 | 33.32 | A | C |
| ATOM | 2625 | CD2 | LEU | A | 360 | −9.072 | 96.643 | 103.951 | 1.00 | 30.58 | A | C |
| ATOM | 2626 | C | LEU | A | 360 | −9.184 | 95.852 | 99.583 | 1.00 | 23.54 | A | C |
| ATOM | 2627 | O | LEU | A | 360 | −9.543 | 96.477 | 98.587 | 1.00 | 21.41 | A | O |
| ATOM | 2628 | N | ASN | A | 361 | −9.054 | 94.529 | 99.593 | 1.00 | 23.09 | A | N |
| ATOM | 2629 | CA | ASN | A | 361 | −9.417 | 93.756 | 98.415 | 1.00 | 25.98 | A | C |
| ATOM | 2630 | CB | ASN | A | 361 | −8.783 | 92.360 | 98.434 | 1.00 | 20.78 | A | C |
| ATOM | 2631 | CG | ASN | A | 361 | −7.279 | 92.403 | 98.218 | 1.00 | 25.04 | A | C |
| ATOM | 2632 | OD1 | ASN | A | 361 | −6.733 | 93.427 | 97.805 | 1.00 | 25.79 | A | O |
| ATOM | 2633 | ND2 | ASN | A | 361 | −6.602 | 91.290 | 98.487 | 1.00 | 23.55 | A | N |
| ATOM | 2634 | C | ASN | A | 361 | −10.939 | 93.634 | 98.450 | 1.00 | 28.66 | A | C |
| ATOM | 2635 | O | ASN | A | 361 | −11.522 | 93.406 | 99.510 | 1.00 | 31.02 | A | O |
| ATOM | 2636 | N | LYS | A | 362 | −11.585 | 93.816 | 97.305 | 1.00 | 29.94 | A | N |
| ATOM | 2637 | CA | LYS | A | 362 | −13.035 | 93.703 | 97.250 | 1.00 | 30.96 | A | C |
| ATOM | 2638 | CB | LYS | A | 362 | −13.587 | 94.526 | 96.092 | 1.00 | 30.98 | A | C |
| ATOM | 2639 | CG | LYS | A | 362 | −13.192 | 95.984 | 96.134 | 1.00 | 32.66 | A | C |
| ATOM | 2640 | CD | LYS | A | 362 | −13.630 | 96.652 | 94.854 | 1.00 | 35.83 | A | C |
| ATOM | 2641 | CE | LYS | A | 362 | −13.124 | 95.881 | 93.633 | 1.00 | 36.12 | A | C |
| ATOM | 2642 | NZ | LYS | A | 362 | −11.638 | 95.884 | 93.533 | 1.00 | 33.66 | A | N |
| ATOM | 2643 | C | LYS | A | 362 | −13.348 | 92.237 | 97.038 | 1.00 | 32.39 | A | C |
| ATOM | 2644 | O | LYS | A | 362 | −12.545 | 91.513 | 96.457 | 1.00 | 34.80 | A | O |
| ATOM | 2645 | N | PRO | A | 363 | −14.507 | 91.765 | 97.521 | 1.00 | 34.04 | A | N |
| ATOM | 2646 | CD | PRO | A | 363 | −15.545 | 92.400 | 98.355 | 1.00 | 35.56 | A | C |
| ATOM | 2647 | CA | PRO | A | 363 | −14.805 | 90.347 | 97.314 | 1.00 | 34.66 | A | C |
| ATOM | 2648 | CB | PRO | A | 363 | −16.270 | 90.247 | 97.724 | 1.00 | 32.94 | A | C |
| ATOM | 2649 | CG | PRO | A | 363 | −16.333 | 91.194 | 98.871 | 1.00 | 32.97 | A | C |
| ATOM | 2650 | C | PRO | A | 363 | −14.549 | 89.893 | 95.878 | 1.00 | 36.06 | A | C |
| ATOM | 2651 | O | PRO | A | 363 | −14.654 | 90.669 | 94.930 | 1.00 | 35.20 | A | O |
| ATOM | 2652 | N | GLU | A | 364 | −14.203 | 88.620 | 95.747 | 1.00 | 39.61 | A | N |
| ATOM | 2653 | CA | GLU | A | 364 | −13.907 | 87.986 | 94.470 | 1.00 | 42.65 | A | C |
| ATOM | 2654 | CB | GLU | A | 364 | −13.621 | 86.502 | 94.705 | 1.00 | 43.78 | A | C |
| ATOM | 2655 | CG | GLU | A | 364 | −14.698 | 85.818 | 95.541 | 1.00 | 45.70 | A | C |
| ATOM | 2656 | CD | GLU | A | 364 | −14.766 | 86.351 | 96.967 | 1.00 | 48.37 | A | C |
| ATOM | 2657 | OE1 | GLU | A | 364 | −15.823 | 86.183 | 97.616 | 1.00 | 51.54 | A | O |
| ATOM | 2658 | OE2 | GLU | A | 364 | −13.763 | 86.929 | 97.445 | 1.00 | 47.95 | A | O |
| ATOM | 2659 | C | GLU | A | 364 | −15.002 | 88.127 | 93.412 | 1.00 | 44.24 | A | C |
| ATOM | 2660 | O | GLU | A | 364 | −15.906 | 88.961 | 93.531 | 1.00 | 43.77 | A | O |
| ATOM | 2661 | N | VAL | A | 365 | −14.901 | 87.278 | 92.388 | 1.00 | 45.43 | A | N |
| ATOM | 2662 | CA | VAL | A | 365 | −15.812 | 87.257 | 91.244 | 1.00 | 45.75 | A | C |
| ATOM | 2663 | CB | VAL | A | 365 | −17.125 | 88.044 | 91.513 | 1.00 | 47.19 | A | C |
| ATOM | 2664 | CG1 | VAL | A | 365 | −17.818 | 88.366 | 90.203 | 1.00 | 44.82 | A | C |
| ATOM | 2665 | CG2 | VAL | A | 365 | −18.060 | 87.216 | 92.391 | 1.00 | 46.88 | A | C |
| ATOM | 2666 | C | VAL | A | 365 | −15.096 | 87.876 | 90.047 | 1.00 | 44.82 | A | C |
| ATOM | 2667 | OXT | VAL | A | 365 | −14.510 | 88.965 | 90.234 | 1.00 | 43.94 | A | O |
| ATOM | 2668 | C | GLY | B | 16 | 49.139 | 73.725 | 98.255 | 1.00 | 45.54 | B | C |
| ATOM | 2669 | O | GLY | B | 16 | 48.209 | 74.266 | 98.861 | 1.00 | 45.24 | B | O |
| ATOM | 2670 | N | GLY | B | 16 | 50.225 | 72.065 | 99.751 | 1.00 | 45.31 | B | N |
| ATOM | 2671 | CA | GLY | B | 16 | 50.410 | 73.327 | 98.979 | 1.00 | 46.04 | B | C |
| ATOM | 2672 | N | LYS | B | 17 | 49.092 | 73.464 | 96.953 | 1.00 | 44.72 | B | N |
| ATOM | 2673 | CA | LYS | B | 17 | 47.906 | 73.797 | 96.178 | 1.00 | 43.40 | B | C |
| ATOM | 2674 | CB | LYS | B | 17 | 48.202 | 73.732 | 94.677 | 1.00 | 43.73 | B | C |
| ATOM | 2675 | CG | LYS | B | 17 | 49.174 | 74.807 | 94.204 | 1.00 | 44.76 | B | C |
| ATOM | 2676 | CD | LYS | B | 17 | 49.283 | 74.881 | 92.677 | 1.00 | 46.41 | B | C |
| ATOM | 2677 | CE | LYS | B | 17 | 49.822 | 73.589 | 92.059 | 1.00 | 45.65 | B | C |
| ATOM | 2678 | NZ | LYS | B | 17 | 48.881 | 72.444 | 92.174 | 1.00 | 39.85 | B | N |
| ATOM | 2679 | C | LYS | B | 17 | 46.754 | 72.859 | 96.531 | 1.00 | 42.78 | B | C |
| ATOM | 2680 | O | LYS | B | 17 | 46.056 | 73.080 | 97.524 | 1.00 | 44.01 | B | O |
| ATOM | 2681 | N | ASN | B | 18 | 46.569 | 71.805 | 95.740 | 1.00 | 38.46 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2682 | CA | ASN | B | 18 | 45.477 | 70.866 | 95.983 | 1.00 | 36.04 | B | C |
| ATOM | 2683 | CB | ASN | B | 18 | 45.597 | 70.221 | 97.366 | 1.00 | 34.61 | B | C |
| ATOM | 2684 | CG | ASN | B | 18 | 46.017 | 68.761 | 97.293 | 1.00 | 34.87 | B | C |
| ATOM | 2685 | OD1 | ASN | B | 18 | 45.899 | 68.018 | 98.274 | 1.00 | 34.60 | B | O |
| ATOM | 2686 | ND2 | ASN | B | 18 | 46.515 | 68.342 | 96.129 | 1.00 | 31.72 | B | N |
| ATOM | 2687 | C | ASN | B | 18 | 44.151 | 71.607 | 95.884 | 1.00 | 33.96 | B | C |
| ATOM | 2688 | O | ASN | B | 18 | 43.311 | 71.286 | 95.049 | 1.00 | 35.77 | B | O |
| ATOM | 2689 | N | ILE | B | 19 | 43.962 | 72.590 | 96.751 | 1.00 | 30.25 | B | N |
| ATOM | 2690 | CA | ILE | B | 19 | 42.751 | 73.389 | 96.723 | 1.00 | 31.08 | B | C |
| ATOM | 2691 | CB | ILE | B | 19 | 42.289 | 73.781 | 98.135 | 1.00 | 32.10 | B | C |
| ATOM | 2692 | CG2 | ILE | B | 19 | 40.898 | 74.381 | 98.054 | 1.00 | 32.73 | B | C |
| ATOM | 2693 | CG1 | ILE | B | 19 | 42.300 | 72.564 | 99.068 | 1.00 | 31.96 | B | C |
| ATOM | 2694 | CD1 | ILE | B | 19 | 41.341 | 71.475 | 98.687 | 1.00 | 35.66 | B | C |
| ATOM | 2695 | C | ILE | B | 19 | 43.081 | 74.677 | 95.957 | 1.00 | 30.05 | B | C |
| ATOM | 2696 | O | ILE | B | 19 | 44.028 | 75.387 | 96.299 | 1.00 | 28.62 | B | O |
| ATOM | 2697 | N | GLN | B | 20 | 42.318 | 74.979 | 94.915 | 1.00 | 28.61 | B | N |
| ATOM | 2698 | CA | GLN | B | 20 | 42.595 | 76.187 | 94.160 | 1.00 | 27.81 | B | C |
| ATOM | 2699 | CB | GLN | B | 20 | 43.372 | 75.847 | 92.889 | 1.00 | 29.10 | B | C |
| ATOM | 2700 | CG | GLN | B | 20 | 42.495 | 75.487 | 91.717 | 1.00 | 31.41 | B | C |
| ATOM | 2701 | CD | GLN | B | 20 | 43.277 | 75.443 | 90.427 | 1.00 | 34.34 | B | C |
| ATOM | 2702 | OE1 | GLN | B | 20 | 42.704 | 75.330 | 89.333 | 1.00 | 32.64 | B | O |
| ATOM | 2703 | NE2 | GLN | B | 20 | 44.601 | 75.532 | 90.544 | 1.00 | 34.95 | B | N |
| ATOM | 2704 | C | GLN | B | 20 | 41.336 | 76.982 | 93.806 | 1.00 | 25.85 | B | C |
| ATOM | 2705 | O | GLN | B | 20 | 40.275 | 76.418 | 93.527 | 1.00 | 24.40 | B | O |
| ATOM | 2706 | N | VAL | B | 21 | 41.481 | 78.303 | 93.812 | 1.00 | 23.00 | B | N |
| ATOM | 2707 | CA | VAL | B | 21 | 40.383 | 79.208 | 93.516 | 1.00 | 20.19 | B | C |
| ATOM | 2708 | CB | VAL | B | 21 | 40.042 | 80.056 | 94.756 | 1.00 | 16.86 | B | C |
| ATOM | 2709 | CG1 | VAL | B | 21 | 38.898 | 80.980 | 94.451 | 1.00 | 15.56 | B | C |
| ATOM | 2710 | CG2 | VAL | B | 21 | 39.694 | 79.148 | 95.918 | 1.00 | 15.24 | B | C |
| ATOM | 2711 | C | VAL | B | 21 | 40.721 | 80.136 | 92.351 | 1.00 | 20.21 | B | C |
| ATOM | 2712 | O | VAL | B | 21 | 41.797 | 80.739 | 92.311 | 1.00 | 22.27 | B | O |
| ATOM | 2713 | N | VAL | B | 22 | 39.799 | 80.241 | 91.400 | 1.00 | 17.52 | B | N |
| ATOM | 2714 | CA | VAL | B | 22 | 40.000 | 81.097 | 90.241 | 1.00 | 15.51 | B | C |
| ATOM | 2715 | CB | VAL | B | 22 | 40.289 | 80.275 | 88.979 | 1.00 | 14.57 | B | C |
| ATOM | 2716 | CG1 | VAL | B | 22 | 41.341 | 79.233 | 89.270 | 1.00 | 9.73 | B | C |
| ATOM | 2717 | CG2 | VAL | B | 22 | 39.004 | 79.632 | 88.475 | 1.00 | 15.06 | B | C |
| ATOM | 2718 | C | VAL | B | 22 | 38.745 | 81.914 | 89.990 | 1.00 | 14.82 | B | C |
| ATOM | 2719 | O | VAL | B | 22 | 37.651 | 81.540 | 90.403 | 1.00 | 16.22 | B | O |
| ATOM | 2720 | N | VAL | B | 23 | 38.915 | 83.033 | 89.308 | 1.00 | 13.78 | B | N |
| ATOM | 2721 | CA | VAL | B | 23 | 37.804 | 83.908 | 88.987 | 1.00 | 14.50 | B | C |
| ATOM | 2722 | CB | VAL | B | 23 | 38.002 | 85.336 | 89.597 | 1.00 | 15.33 | B | C |
| ATOM | 2723 | CG1 | VAL | B | 23 | 37.009 | 86.331 | 89.002 | 1.00 | 13.94 | B | C |
| ATOM | 2724 | CG2 | VAL | B | 23 | 37.820 | 85.280 | 91.098 | 1.00 | 15.34 | B | C |
| ATOM | 2725 | C | VAL | B | 23 | 37.727 | 84.007 | 87.472 | 1.00 | 14.62 | B | C |
| ATOM | 2726 | O | VAL | B | 23 | 38.749 | 83.965 | 86.776 | 1.00 | 15.16 | B | O |
| ATOM | 2727 | N | ARG | B | 24 | 36.506 | 84.095 | 86.968 | 1.00 | 11.00 | B | N |
| ATOM | 2728 | CA | ARG | B | 24 | 36.290 | 84.229 | 85.542 | 1.00 | 14.68 | B | C |
| ATOM | 2729 | CB | ARG | B | 24 | 35.743 | 82.937 | 84.931 | 1.00 | 10.66 | B | C |
| ATOM | 2730 | CG | ARG | B | 24 | 35.562 | 83.034 | 83.416 | 1.00 | 9.90 | B | C |
| ATOM | 2731 | CD | ARG | B | 24 | 34.837 | 81.840 | 82.816 | 1.00 | 10.82 | B | C |
| ATOM | 2732 | NE | ARG | B | 24 | 34.962 | 81.797 | 81.360 | 1.00 | 11.63 | B | N |
| ATOM | 2733 | CZ | ARG | B | 24 | 34.394 | 80.868 | 80.598 | 1.00 | 12.56 | B | C |
| ATOM | 2734 | NH1 | ARG | B | 24 | 33.661 | 79.918 | 81.160 | 1.00 | 12.98 | B | N |
| ATOM | 2735 | NH2 | ARG | B | 24 | 34.572 | 80.874 | 79.287 | 1.00 | 12.38 | B | N |
| ATOM | 2736 | C | ARG | B | 24 | 35.286 | 85.345 | 85.321 | 1.00 | 14.70 | B | C |
| ATOM | 2737 | O | ARG | B | 24 | 34.136 | 85.230 | 85.727 | 1.00 | 14.99 | B | O |
| ATOM | 2738 | N | CYS | B | 25 | 35.727 | 86.424 | 84.689 | 1.00 | 15.32 | B | N |
| ATOM | 2739 | CA | CYS | B | 25 | 34.854 | 87.554 | 84.403 | 1.00 | 17.45 | B | C |
| ATOM | 2740 | CB | CYS | B | 25 | 35.658 | 88.859 | 84.426 | 1.00 | 17.46 | B | C |
| ATOM | 2741 | SG | CYS | B | 25 | 34.671 | 90.353 | 84.163 | 1.00 | 22.87 | B | S |
| ATOM | 2742 | C | CYS | B | 25 | 34.246 | 87.330 | 83.019 | 1.00 | 18.91 | B | C |
| ATOM | 2743 | O | CYS | B | 25 | 34.938 | 86.909 | 82.097 | 1.00 | 17.81 | B | O |
| ATOM | 2744 | N | ARG | B | 26 | 32.948 | 87.578 | 82.877 | 1.00 | 18.90 | B | N |
| ATOM | 2745 | CA | ARG | B | 26 | 32.296 | 87.400 | 81.587 | 1.00 | 17.65 | B | C |
| ATOM | 2746 | CB | ARG | B | 26 | 30.873 | 86.866 | 81.758 | 1.00 | 15.72 | B | C |
| ATOM | 2747 | CG | ARG | B | 26 | 29.921 | 87.805 | 82.519 | 1.00 | 18.39 | B | C |
| ATOM | 2748 | CD | ARG | B | 26 | 28.463 | 87.413 | 82.280 | 1.00 | 18.97 | B | C |
| ATOM | 2749 | NE | ARG | B | 26 | 27.496 | 88.183 | 83.063 | 1.00 | 23.45 | B | N |
| ATOM | 2750 | CZ | ARG | B | 26 | 27.265 | 89.487 | 82.927 | 1.00 | 23.62 | B | C |
| ATOM | 2751 | NH1 | ARG | B | 26 | 27.942 | 90.190 | 82.029 | 1.00 | 26.18 | B | N |
| ATOM | 2752 | NH2 | ARG | B | 26 | 26.347 | 90.091 | 83.674 | 1.00 | 18.85 | B | N |
| ATOM | 2753 | C | ARG | B | 26 | 32.233 | 88.750 | 80.900 | 1.00 | 18.53 | B | C |
| ATOM | 2754 | O | ARG | B | 26 | 32.564 | 89.776 | 81.493 | 1.00 | 19.43 | B | O |
| ATOM | 2755 | N | PRO | B | 27 | 31.866 | 88.767 | 79.617 | 1.00 | 18.76 | B | N |
| ATOM | 2756 | CD | PRO | B | 27 | 32.069 | 87.702 | 78.624 | 1.00 | 17.49 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2757 | CA | PRO | B | 27 | 31.794 | 90.077 | 78.971 | 1.00 | 19.70 | B | C |
| ATOM | 2758 | CB | PRO | B | 27 | 31.976 | 89.748 | 77.489 | 1.00 | 18.44 | B | C |
| ATOM | 2759 | CG | PRO | B | 27 | 31.549 | 88.335 | 77.378 | 1.00 | 17.05 | B | C |
| ATOM | 2760 | C | PRO | B | 27 | 30.448 | 90.724 | 79.291 | 1.00 | 21.17 | B | C |
| ATOM | 2761 | O | PRO | B | 27 | 29.573 | 90.064 | 79.859 | 1.00 | 18.12 | B | O |
| ATOM | 2762 | N | PHE | B | 28 | 30.305 | 92.009 | 78.952 | 1.00 | 21.04 | B | N |
| ATOM | 2763 | CA | PHE | B | 28 | 29.076 | 92.776 | 79.188 | 1.00 | 21.06 | B | C |
| ATOM | 2764 | CB | PHE | B | 28 | 29.224 | 94.185 | 78.607 | 1.00 | 23.05 | B | C |
| ATOM | 2765 | CG | PHE | B | 28 | 29.928 | 95.158 | 79.506 | 1.00 | 24.69 | B | C |
| ATOM | 2766 | CD1 | PHE | B | 28 | 31.252 | 94.970 | 79.858 | 1.00 | 26.80 | B | C |
| ATOM | 2767 | CD2 | PHE | B | 28 | 29.258 | 96.266 | 79.998 | 1.00 | 25.05 | B | C |
| ATOM | 2768 | CE1 | PHE | B | 28 | 31.907 | 95.867 | 80.690 | 1.00 | 27.43 | B | C |
| ATOM | 2769 | CE2 | PHE | B | 28 | 29.899 | 97.170 | 80.831 | 1.00 | 30.75 | B | C |
| ATOM | 2770 | CZ | PHE | B | 28 | 31.233 | 96.968 | 81.179 | 1.00 | 30.68 | B | C |
| ATOM | 2771 | C | PHE | B | 28 | 27.830 | 92.148 | 78.553 | 1.00 | 21.07 | B | C |
| ATOM | 2772 | O | PHE | B | 28 | 27.935 | 91.511 | 77.507 | 1.00 | 21.35 | B | O |
| ATOM | 2773 | N | ASN | B | 29 | 26.660 | 92.324 | 79.172 | 1.00 | 19.74 | B | N |
| ATOM | 2774 | CA | ASN | B | 29 | 25.419 | 91.803 | 78.583 | 1.00 | 20.63 | B | C |
| ATOM | 2775 | CB | ASN | B | 29 | 24.583 | 90.990 | 79.600 | 1.00 | 19.37 | B | C |
| ATOM | 2776 | CG | ASN | B | 29 | 23.905 | 91.853 | 80.647 | 1.00 | 20.88 | B | C |
| ATOM | 2777 | OD1 | ASN | B | 29 | 23.445 | 92.957 | 80.358 | 1.00 | 23.30 | B | O |
| ATOM | 2778 | ND2 | ASN | B | 29 | 23.821 | 91.340 | 81.877 | 1.00 | 21.32 | B | N |
| ATOM | 2779 | C | ASN | B | 29 | 24.603 | 92.988 | 78.056 | 1.00 | 21.50 | B | C |
| ATOM | 2780 | O | ASN | B | 29 | 24.796 | 94.128 | 78.495 | 1.00 | 22.04 | B | O |
| ATOM | 2781 | N | LEU | B | 30 | 23.701 | 92.727 | 77.115 | 1.00 | 21.23 | B | N |
| ATOM | 2782 | CA | LEU | B | 30 | 22.867 | 93.777 | 76.532 | 1.00 | 22.61 | B | C |
| ATOM | 2783 | CB | LEU | B | 30 | 21.787 | 93.155 | 75.658 | 1.00 | 25.40 | B | C |
| ATOM | 2784 | CG | LEU | B | 30 | 22.295 | 92.533 | 74.355 | 1.00 | 28.35 | B | C |
| ATOM | 2785 | CD1 | LEU | B | 30 | 21.160 | 91.773 | 73.676 | 1.00 | 27.19 | B | C |
| ATOM | 2786 | CD2 | LEU | B | 30 | 22.855 | 93.631 | 73.444 | 1.00 | 22.90 | B | C |
| ATOM | 2787 | C | LEU | B | 30 | 22.206 | 94.730 | 77.527 | 1.00 | 22.55 | B | C |
| ATOM | 2788 | O | LEU | B | 30 | 22.286 | 95.949 | 77.367 | 1.00 | 21.50 | B | O |
| ATOM | 2789 | N | ALA | B | 31 | 21.537 | 94.182 | 78.536 | 1.00 | 23.21 | B | N |
| ATOM | 2790 | CA | ALA | B | 31 | 20.870 | 95.006 | 79.534 | 1.00 | 22.80 | B | C |
| ATOM | 2791 | CB | ALA | B | 31 | 20.246 | 94.134 | 80.619 | 1.00 | 18.20 | B | C |
| ATOM | 2792 | C | ALA | B | 31 | 21.851 | 95.981 | 80.162 | 1.00 | 25.03 | B | C |
| ATOM | 2793 | O | ALA | B | 31 | 21.506 | 97.142 | 80.423 | 1.00 | 25.66 | B | O |
| ATOM | 2794 | N | GLU | B | 32 | 23.073 | 95.516 | 80.400 | 1.00 | 25.52 | B | N |
| ATOM | 2795 | CA | GLU | B | 32 | 24.089 | 96.358 | 81.029 | 1.00 | 28.24 | B | C |
| ATOM | 2796 | CB | GLU | B | 32 | 25.345 | 95.530 | 81.351 | 1.00 | 28.44 | B | C |
| ATOM | 2797 | CG | GLU | B | 32 | 25.087 | 94.398 | 82.353 | 1.00 | 28.26 | B | C |
| ATOM | 2798 | CD | GLU | B | 32 | 26.301 | 93.506 | 82.587 | 1.00 | 30.85 | B | C |
| ATOM | 2799 | OE1 | GLU | B | 32 | 26.855 | 92.957 | 81.601 | 1.00 | 27.87 | B | O |
| ATOM | 2800 | OE2 | GLU | B | 32 | 26.696 | 93.351 | 83.763 | 1.00 | 30.58 | B | O |
| ATOM | 2801 | C | GLU | B | 32 | 24.428 | 97.558 | 80.149 | 1.00 | 27.81 | B | C |
| ATOM | 2802 | O | GLU | B | 32 | 24.677 | 98.650 | 80.652 | 1.00 | 27.90 | B | 0 |
| ATOM | 2803 | N | ARG | B | 33 | 24.442 | 97.358 | 78.838 | 1.00 | 28.16 | B | N |
| ATOM | 2804 | CA | ARG | B | 33 | 24.698 | 98.469 | 77.924 | 1.00 | 30.97 | B | C |
| ATOM | 2805 | CB | ARG | B | 33 | 24.870 | 97.975 | 76.491 | 1.00 | 28.54 | B | C |
| ATOM | 2806 | CG | ARG | B | 33 | 25.940 | 96.926 | 76.288 | 1.00 | 28.22 | B | C |
| ATOM | 2807 | CD | ARG | B | 33 | 27.340 | 97.465 | 76.521 | 1.00 | 25.16 | B | C |
| ATOM | 2808 | NE | ARG | B | 33 | 28.345 | 96.602 | 75.895 | 1.00 | 23.79 | B | N |
| ATOM | 2809 | CZ | ARG | B | 33 | 29.663 | 96.719 | 76.061 | 1.00 | 21.88 | B | C |
| ATOM | 2810 | NH1 | ARG | B | 33 | 30.169 | 97.666 | 76.839 | 1.00 | 24.68 | B | N |
| ATOM | 2811 | NH2 | ARG | B | 33 | 30.483 | 95.879 | 75.453 | 1.00 | 19.99 | B | N |
| ATOM | 2812 | C | ARG | B | 33 | 23.447 | 99.350 | 77.972 | 1.00 | 34.08 | B | C |
| ATOM | 2813 | O | ARG | B | 33 | 23.528 | 100.577 | 78.055 | 1.00 | 33.32 | B | O |
| ATOM | 2814 | N | LYS | B | 34 | 22.290 | 98.692 | 77.918 | 1.00 | 37.50 | B | N |
| ATOM | 2815 | CA | LYS | B | 34 | 20.990 | 99.357 | 77.950 | 1.00 | 40.38 | B | C |
| ATOM | 2816 | CB | LYS | B | 34 | 19.870 | 98.310 | 77.955 | 1.00 | 41.64 | B | C |
| ATOM | 2817 | CG | LYS | B | 34 | 18.513 | 98.861 | 77.557 | 1.00 | 43.99 | B | C |
| ATOM | 2818 | CD | LYS | B | 34 | 18.554 | 99.405 | 76.144 | 1.00 | 45.47 | B | C |
| ATOM | 2819 | CE | LYS | B | 34 | 18.798 | 98.296 | 75.119 | 1.00 | 49.66 | B | C |
| ATOM | 2820 | NZ | LYS | B | 34 | 20.029 | 97.484 | 75.369 | 1.00 | 51.80 | B | N |
| ATOM | 2821 | C | LYS | B | 34 | 20.833 | 100.273 | 79.168 | 1.00 | 41.63 | B | C |
| ATOM | 2822 | O | LYS | B | 34 | 19.988 | 101.176 | 79.171 | 1.00 | 41.88 | B | O |
| ATOM | 2823 | N | ALA | B | 35 | 21.636 | 100.037 | 80.202 | 1.00 | 40.00 | B | N |
| ATOM | 2824 | CA | ALA | B | 35 | 21.575 | 100.858 | 81.406 | 1.00 | 39.62 | B | C |
| ATOM | 2825 | CB | ALA | B | 35 | 21.454 | 99.975 | 82.652 | 1.00 | 38.27 | B | C |
| ATOM | 2826 | C | ALA | B | 35 | 22.837 | 101.710 | 81.479 | 1.00 | 40.56 | B | C |
| ATOM | 2827 | O | ALA | B | 35 | 23.061 | 102.433 | 82.458 | 1.00 | 41.25 | B | O |
| ATOM | 2828 | N | SER | B | 36 | 23.661 | 101.609 | 80.437 | 1.00 | 39.16 | B | N |
| ATOM | 2829 | CA | SER | B | 36 | 24.904 | 102.366 | 80.341 | 1.00 | 39.18 | B | C |
| ATOM | 2830 | CB | SER | B | 36 | 24.594 | 103.865 | 80.426 | 1.00 | 43.21 | B | C |
| ATOM | 2831 | OG | SER | B | 36 | 23.750 | 104.277 | 79.356 | 1.00 | 46.42 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2832 | C | SER | B | 36 | 25.973 | 102.011 | 81.381 | 1.00 | 38.31 | B | C |
| ATOM | 2833 | O | SER | B | 36 | 26.959 | 102.738 | 81.535 | 1.00 | 38.27 | B | O |
| ATOM | 2834 | N | ALA | B | 37 | 25.788 | 100.897 | 82.086 | 1.00 | 36.63 | B | N |
| ATOM | 2835 | CA | ALA | B | 37 | 26.738 | 100.478 | 83.112 | 1.00 | 32.97 | B | C |
| ATOM | 2836 | CB | ALA | B | 37 | 26.523 | 99.006 | 83.451 | 1.00 | 30.86 | B | C |
| ATOM | 2837 | C | ALA | B | 37 | 28.188 | 100.715 | 82.680 | 1.00 | 30.60 | B | C |
| ATOM | 2838 | O | ALA | B | 37 | 28.484 | 100.764 | 81.487 | 1.00 | 29.21 | B | O |
| ATOM | 2839 | N | HIS | B | 38 | 29.080 | 100.850 | 83.660 | 1.00 | 28.72 | B | N |
| ATOM | 2840 | CA | HIS | B | 38 | 30.500 | 101.081 | 83.407 | 1.00 | 29.34 | B | C |
| ATOM | 2841 | CB | HIS | B | 38 | 30.925 | 102.391 | 84.068 | 1.00 | 33.95 | B | C |
| ATOM | 2842 | CG | HIS | B | 38 | 29.910 | 103.486 | 83.945 | 1.00 | 37.23 | B | C |
| ATOM | 2843 | CD2 | HIS | B | 38 | 29.321 | 104.263 | 84.882 | 1.00 | 35.52 | B | C |
| ATOM | 2844 | ND1 | HIS | B | 38 | 29.386 | 103.885 | 82.732 | 1.00 | 40.35 | B | N |
| ATOM | 2845 | CE1 | HIS | B | 38 | 28.518 | 104.862 | 82.929 | 1.00 | 37.80 | B | C |
| ATOM | 2846 | NE2 | HIS | B | 38 | 28.461 | 105.110 | 84.224 | 1.00 | 37.06 | B | N |
| ATOM | 2847 | C | HIS | B | 38 | 31.380 | 99.944 | 83.943 | 1.00 | 28.92 | B | C |
| ATOM | 2848 | O | HIS | B | 38 | 31.074 | 99.344 | 84.975 | 1.00 | 30.21 | B | O |
| ATOM | 2849 | N | SER | B | 39 | 32.479 | 99.661 | 83.248 | 1.00 | 26.88 | B | N |
| ATOM | 2850 | CA | SER | B | 39 | 33.397 | 98.601 | 83.660 | 1.00 | 25.05 | B | C |
| ATOM | 2851 | CB | SER | B | 39 | 34.450 | 98.354 | 82.575 | 1.00 | 26.54 | B | C |
| ATOM | 2852 | OG | SER | B | 39 | 35.413 | 97.393 | 82.996 | 1.00 | 27.32 | B | O |
| ATOM | 2853 | C | SER | B | 39 | 34.099 | 98.955 | 84.962 | 1.00 | 24.58 | B | C |
| ATOM | 2854 | O | SER | B | 39 | 34.785 | 99.962 | 85.050 | 1.00 | 28.38 | B | O |
| ATOM | 2855 | N | ILE | B | 40 | 33.934 | 98.125 | 85.977 | 1.00 | 23.85 | B | N |
| ATOM | 2856 | CA | ILE | B | 40 | 34.570 | 98.385 | 87.254 | 1.00 | 24.65 | B | C |
| ATOM | 2857 | CB | ILE | B | 40 | 33.516 | 98.601 | 88.361 | 1.00 | 24.57 | B | C |
| ATOM | 2858 | CG2 | ILE | B | 40 | 32.615 | 99.755 | 87.989 | 1.00 | 24.89 | B | C |
| ATOM | 2859 | CG1 | ILE | B | 40 | 32.656 | 97.345 | 88.520 | 1.00 | 25.10 | B | C |
| ATOM | 2860 | CD1 | ILE | B | 40 | 31.597 | 97.469 | 89.584 | 1.00 | 27.45 | B | C |
| ATOM | 2861 | C | ILE | B | 40 | 35.454 | 97.200 | 87.615 | 1.00 | 24.14 | B | C |
| ATOM | 2862 | O | ILE | B | 40 | 35.954 | 97.100 | 88.733 | 1.00 | 25.03 | B | O |
| ATOM | 2863 | N | VAL | B | 41 | 35.651 | 96.310 | 86.652 | 1.00 | 23.02 | B | N |
| ATOM | 2864 | CA | VAL | B | 41 | 36.469 | 95.125 | 86.869 | 1.00 | 26.01 | B | C |
| ATOM | 2865 | CB | VAL | B | 41 | 35.640 | 93.844 | 86.675 | 1.00 | 25.81 | B | C |
| ATOM | 2866 | CG1 | VAL | B | 41 | 36.521 | 92.632 | 86.892 | 1.00 | 26.25 | B | C |
| ATOM | 2867 | CG2 | VAL | B | 41 | 34.460 | 93.835 | 87.635 | 1.00 | 25.45 | B | C |
| ATOM | 2868 | C | VAL | B | 41 | 37.681 | 95.053 | 85.941 | 1.00 | 27.37 | B | C |
| ATOM | 2869 | O | VAL | B | 41 | 37.560 | 95.139 | 84.718 | 1.00 | 28.32 | B | O |
| ATOM | 2870 | N | GLU | B | 42 | 38.853 | 94.899 | 86.538 | 1.00 | 28.49 | B | N |
| ATOM | 2871 | CA | GLU | B | 42 | 40.087 | 94.800 | 85.780 | 1.00 | 29.62 | B | C |
| ATOM | 2872 | CB | GLU | B | 42 | 41.010 | 95.973 | 86.111 | 1.00 | 32.09 | B | C |
| ATOM | 2873 | CG | GLU | B | 42 | 40.396 | 97.341 | 85.829 | 1.00 | 35.61 | B | C |
| ATOM | 2874 | CD | GLU | B | 42 | 39.804 | 98.008 | 87.069 | 1.00 | 37.64 | B | C |
| ATOM | 2875 | OE1 | GLU | B | 42 | 39.073 | 99.006 | 86.902 | 1.00 | 39.80 | B | O |
| ATOM | 2876 | OE2 | GLU | B | 42 | 40.076 | 97.554 | 88.208 | 1.00 | 38.54 | B | O |
| ATOM | 2877 | C | GLU | B | 42 | 40.748 | 93.480 | 86.163 | 1.00 | 30.33 | B | C |
| ATOM | 2878 | O | GLU | B | 42 | 41.017 | 93.237 | 87.337 | 1.00 | 30.81 | B | O |
| ATOM | 2879 | N | CYS | B | 43 | 40.993 | 92.627 | 85.170 | 1.00 | 30.26 | B | N |
| ATOM | 2880 | CA | CYS | B | 43 | 41.602 | 91.325 | 85.409 | 1.00 | 30.60 | B | C |
| ATOM | 2881 | CB | CYS | B | 43 | 40.724 | 90.221 | 84.809 | 1.00 | 29.47 | B | C |
| ATOM | 2882 | SG | CYS | B | 43 | 39.031 | 90.127 | 85.489 | 1.00 | 36.31 | B | S |
| ATOM | 2883 | C | CYS | B | 43 | 43.013 | 91.221 | 84.835 | 1.00 | 31.77 | B | C |
| ATOM | 2884 | O | CYS | B | 43 | 43.226 | 91.434 | 83.643 | 1.00 | 35.17 | B | O |
| ATOM | 2885 | N | ASP | B | 44 | 43.978 | 90.900 | 85.691 | 1.00 | 31.33 | B | N |
| ATOM | 2886 | CA | ASP | B | 44 | 45.367 | 90.741 | 85.258 | 1.00 | 31.13 | B | C |
| ATOM | 2887 | CB | ASP | B | 44 | 46.289 | 91.682 | 86.035 | 1.00 | 31.81 | B | C |
| ATOM | 2888 | CG | ASP | B | 44 | 47.728 | 91.597 | 85.569 | 1.00 | 32.14 | B | C |
| ATOM | 2889 | OD1 | ASP | B | 44 | 48.260 | 90.475 | 85.490 | 1.00 | 34.89 | B | O |
| ATOM | 2890 | OD2 | ASP | B | 44 | 48.333 | 92.649 | 85.283 | 1.00 | 37.47 | B | O |
| ATOM | 2891 | C | ASP | B | 44 | 45.823 | 89.296 | 85.471 | 1.00 | 29.29 | B | C |
| ATOM | 2892 | O | ASP | B | 44 | 46.246 | 88.912 | 86.570 | 1.00 | 26.17 | B | O |
| ATOM | 2893 | N | PRO | B | 45 | 45.737 | 88.475 | 84.418 | 1.00 | 28.37 | B | N |
| ATOM | 2894 | CD | PRO | B | 45 | 45.288 | 88.810 | 83.054 | 1.00 | 29.07 | B | C |
| ATOM | 2895 | CA | PRO | B | 45 | 46.144 | 87.070 | 84.512 | 1.00 | 28.75 | B | C |
| ATOM | 2896 | CB | PRO | B | 45 | 45.761 | 86.507 | 83.142 | 1.00 | 28.30 | B | C |
| ATOM | 2897 | CG | PRO | B | 45 | 45.909 | 87.694 | 82.230 | 1.00 | 28.78 | B | C |
| ATOM | 2898 | C | PRO | B | 45 | 47.624 | 86.867 | 84.852 | 1.00 | 29.05 | B | C |
| ATOM | 2899 | O | PRO | B | 45 | 47.971 | 85.949 | 85.595 | 1.00 | 30.05 | B | O |
| ATOM | 2900 | N | VAL | B | 46 | 48.492 | 87.730 | 84.329 | 1.00 | 28.13 | B | N |
| ATOM | 2901 | CA | VAL | B | 46 | 49.922 | 87.609 | 84.592 | 1.00 | 29.81 | B | C |
| ATOM | 2902 | CB | VAL | B | 46 | 50.740 | 88.659 | 83.800 | 1.00 | 30.47 | B | C |
| ATOM | 2903 | CG1 | VAL | B | 46 | 52.227 | 88.492 | 84.110 | 1.00 | 29.40 | B | C |
| ATOM | 2904 | CG2 | VAL | B | 46 | 50.486 | 88.514 | 82.309 | 1.00 | 27.34 | B | C |
| ATOM | 2905 | C | VAL | B | 46 | 50.263 | 87.746 | 86.080 | 1.00 | 31.01 | B | C |
| ATOM | 2906 | O | VAL | B | 46 | 51.226 | 87.150 | 86.566 | 1.00 | 34.14 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2907 | N | ARG | B | 47 | 49.483 | 88.537 | 86.804 | 1.00 | 30.24 | B | N |
| ATOM | 2908 | CA | ARG | B | 47 | 49.729 | 88.716 | 88.223 | 1.00 | 30.09 | B | C |
| ATOM | 2909 | CB | ARG | B | 47 | 49.712 | 90.198 | 88.583 | 1.00 | 30.53 | B | C |
| ATOM | 2910 | CG | ARG | B | 47 | 50.913 | 90.971 | 88.050 | 1.00 | 31.88 | B | C |
| ATOM | 2911 | CD | ARG | B | 47 | 50.757 | 92.468 | 88.269 | 1.00 | 31.56 | B | C |
| ATOM | 2912 | NE | ARG | B | 47 | 50.536 | 92.794 | 89.677 | 1.00 | 33.34 | B | N |
| ATOM | 2913 | CZ | ARG | B | 47 | 51.454 | 92.675 | 90.631 | 1.00 | 33.85 | B | C |
| ATOM | 2914 | NH1 | ARG | B | 47 | 52.669 | 92.236 | 90.335 | 1.00 | 35.84 | B | N |
| ATOM | 2915 | NH2 | ARG | B | 47 | 51.155 | 92.996 | 91.884 | 1.00 | 33.08 | B | N |
| ATOM | 2916 | C | ARG | B | 47 | 48.673 | 87.970 | 89.013 | 1.00 | 31.73 | B | C |
| ATOM | 2917 | O | ARG | B | 47 | 48.709 | 87.940 | 90.231 | 1.00 | 32.39 | B | O |
| ATOM | 2918 | N | LYS | B | 48 | 47.722 | 87.368 | 88.305 | 1.00 | 31.16 | B | N |
| ATOM | 2919 | CA | LYS | B | 48 | 46.670 | 86.610 | 88.964 | 1.00 | 29.16 | B | C |
| ATOM | 2920 | CB | LYS | B | 48 | 47.300 | 85.557 | 89.868 | 1.00 | 30.92 | B | C |
| ATOM | 2921 | CG | LYS | B | 48 | 48.568 | 84.919 | 89.302 | 1.00 | 36.24 | B | C |
| ATOM | 2922 | CD | LYS | B | 48 | 49.345 | 84.206 | 90.406 | 1.00 | 38.79 | B | C |
| ATOM | 2923 | CE | LYS | B | 48 | 50.603 | 83.532 | 89.887 | 1.00 | 41.88 | B | C |
| ATOM | 2924 | NZ | LYS | B | 48 | 50.307 | 82.429 | 88.926 | 1.00 | 42.96 | B | N |
| ATOM | 2925 | C | LYS | B | 48 | 45.833 | 87.560 | 89.812 | 1.00 | 29.07 | B | C |
| ATOM | 2926 | O | LYS | B | 48 | 45.505 | 87.256 | 90.959 | 1.00 | 30.49 | B | O |
| ATOM | 2927 | N | GLU | B | 49 | 45.471 | 88.708 | 89.257 | 1.00 | 27.75 | B | N |
| ATOM | 2928 | CA | GLU | B | 49 | 44.701 | 89.666 | 90.037 | 1.00 | 26.69 | B | C |
| ATOM | 2929 | CB | GLU | B | 49 | 45.563 | 90.890 | 90.363 | 1.00 | 29.03 | B | C |
| ATOM | 2930 | CG | GLU | B | 49 | 46.645 | 90.666 | 91.407 | 1.00 | 34.87 | B | C |
| ATOM | 2931 | CD | GLU | B | 49 | 47.425 | 91.941 | 91.720 | 1.00 | 38.38 | B | C |
| ATOM | 2932 | OE1 | GLU | B | 49 | 48.176 | 92.428 | 90.839 | 1.00 | 37.79 | B | O |
| ATOM | 2933 | OE2 | GLU | B | 49 | 47.277 | 92.462 | 92.849 | 1.00 | 39.50 | B | O |
| ATOM | 2934 | C | GLU | B | 49 | 43.397 | 90.150 | 89.420 | 1.00 | 25.01 | B | C |
| ATOM | 2935 | O | GLU | B | 49 | 43.150 | 90.006 | 88.227 | 1.00 | 22.36 | B | O |
| ATOM | 2936 | N | VAL | B | 50 | 42.568 | 90.732 | 90.276 | 1.00 | 23.14 | B | N |
| ATOM | 2937 | CA | VAL | B | 50 | 41.289 | 91.306 | 89.889 | 1.00 | 21.92 | B | C |
| ATOM | 2938 | CB | VAL | B | 50 | 40.149 | 90.243 | 89.890 | 1.00 | 20.53 | B | C |
| ATOM | 2939 | CG1 | VAL | B | 50 | 40.438 | 89.166 | 90.910 | 1.00 | 20.07 | B | C |
| ATOM | 2940 | CG2 | VAL | B | 50 | 38.808 | 90.916 | 90.188 | 1.00 | 15.24 | B | C |
| ATOM | 2941 | C | VAL | B | 50 | 40.974 | 92.425 | 90.882 | 1.00 | 22.18 | B | C |
| ATOM | 2942 | O | VAL | B | 50 | 40.927 | 92.198 | 92.094 | 1.00 | 24.54 | B | O |
| ATOM | 2943 | N | SER | B | 51 | 40.794 | 93.635 | 90.362 | 1.00 | 21.71 | B | N |
| ATOM | 2944 | CA | SER | B | 51 | 40.499 | 94.812 | 91.187 | 1.00 | 22.96 | B | C |
| ATOM | 2945 | CB | SER | B | 51 | 41.639 | 95.837 | 91.096 | 1.00 | 23.67 | B | C |
| ATOM | 2946 | OG | SER | B | 51 | 41.758 | 96.347 | 89.773 | 1.00 | 25.65 | B | O |
| ATOM | 2947 | C | SER | B | 51 | 39.200 | 95.472 | 90.741 | 1.00 | 22.82 | B | C |
| ATOM | 2948 | O | SER | B | 51 | 38.875 | 95.493 | 89.548 | 1.00 | 19.21 | B | O |
| ATOM | 2949 | N | VAL | B | 52 | 38.476 | 96.022 | 91.711 | 1.00 | 24.45 | B | N |
| ATOM | 2950 | CA | VAL | B | 52 | 37.193 | 96.664 | 91.455 | 1.00 | 27.31 | B | C |
| ATOM | 2951 | CB | VAL | B | 52 | 36.045 | 95.903 | 92.182 | 1.00 | 27.01 | B | C |
| ATOM | 2952 | CG1 | VAL | B | 52 | 34.689 | 96.392 | 91.678 | 1.00 | 27.10 | B | C |
| ATOM | 2953 | CG2 | VAL | B | 52 | 36.200 | 94.400 | 91.980 | 1.00 | 25.29 | B | C |
| ATOM | 2954 | C | VAL | B | 52 | 37.186 | 98.099 | 91.955 | 1.00 | 28.46 | B | C |
| ATOM | 2955 | O | VAL | B | 52 | 37.800 | 98.398 | 92.979 | 1.00 | 27.54 | B | O |
| ATOM | 2956 | N | ARG | B | 53 | 36.486 | 98.979 | 91.241 | 1.00 | 32.17 | B | N |
| ATOM | 2957 | CA | ARG | B | 53 | 36.393 | 100.379 | 91.651 | 1.00 | 35.31 | B | C |
| ATOM | 2958 | CB | ARG | B | 53 | 35.822 | 101.260 | 90.543 | 1.00 | 35.96 | B | C |
| ATOM | 2959 | CG | ARG | B | 53 | 36.602 | 101.299 | 89.261 | 1.00 | 38.71 | B | C |
| ATOM | 2960 | CD | ARG | B | 53 | 36.010 | 102.352 | 88.346 | 1.00 | 40.50 | B | C |
| ATOM | 2961 | NE | ARG | B | 53 | 36.398 | 102.135 | 86.960 | 1.00 | 43.72 | B | N |
| ATOM | 2962 | CZ | ARG | B | 53 | 37.653 | 102.026 | 86.542 | 1.00 | 43.67 | B | C |
| ATOM | 2963 | NH1 | ARG | B | 53 | 38.660 | 102.113 | 87.409 | 1.00 | 41.33 | B | N |
| ATOM | 2964 | NH2 | ARG | B | 53 | 37.897 | 101.826 | 85.254 | 1.00 | 41.91 | B | N |
| ATOM | 2965 | C | ARG | B | 53 | 35.457 | 100.491 | 92.843 | 1.00 | 38.21 | B | C |
| ATOM | 2966 | O | ARG | B | 53 | 34.688 | 99.577 | 93.141 | 1.00 | 37.48 | B | O |
| ATOM | 2967 | N | THR | B | 54 | 35.517 | 101.638 | 93.507 | 1.00 | 41.41 | B | N |
| ATOM | 2968 | CA | THR | B | 54 | 34.674 | 101.917 | 94.662 | 1.00 | 43.37 | B | C |
| ATOM | 2969 | CB | THR | B | 54 | 35.473 | 101.861 | 95.974 | 1.00 | 42.57 | B | C |
| ATOM | 2970 | OG1 | THR | B | 54 | 35.795 | 100.500 | 96.285 | 1.00 | 39.71 | B | O |
| ATOM | 2971 | CG2 | THR | B | 54 | 34.674 | 102.492 | 97.114 | 1.00 | 41.99 | B | C |
| ATOM | 2972 | C | THR | B | 54 | 34.108 | 103.326 | 94.540 | 1.00 | 45.18 | B | C |
| ATOM | 2973 | O | THR | B | 54 | 32.986 | 103.601 | 94.973 | 1.00 | 45.79 | B | O |
| ATOM | 2974 | N | GLY | B | 55 | 34.928 | 104.231 | 94.007 | 1.00 | 45.54 | B | N |
| ATOM | 2975 | CA | GLY | B | 55 | 34.516 | 105.615 | 93.844 | 1.00 | 47.49 | B | C |
| ATOM | 2976 | C | GLY | B | 55 | 34.095 | 106.313 | 95.128 | 1.00 | 49.19 | B | C |
| ATOM | 2977 | O | GLY | B | 55 | 34.368 | 107.501 | 95.300 | 1.00 | 50.22 | B | O |
| ATOM | 2978 | N | GLY | B | 56 | 33.436 | 105.582 | 96.027 | 1.00 | 49.81 | B | N |
| ATOM | 2979 | CA | GLY | B | 56 | 32.986 | 106.156 | 97.286 | 1.00 | 51.53 | B | C |
| ATOM | 2980 | C | GLY | B | 56 | 32.100 | 107.374 | 97.081 | 1.00 | 52.97 | B | C |
| ATOM | 2981 | O | GLY | B | 56 | 30.868 | 107.285 | 97.123 | 1.00 | 52.12 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 2982 | N | LEU | B | 57 | 32.743 | 108.519 | 96.864 | 1.00 | 54.16 | B | N |
| ATOM | 2983 | CA | LEU | B | 57 | 32.053 | 109.785 | 96.626 | 1.00 | 54.22 | B | C |
| ATOM | 2984 | CB | LEU | B | 57 | 31.033 | 110.056 | 97.746 | 1.00 | 55.14 | B | C |
| ATOM | 2985 | CG | LEU | B | 57 | 29.648 | 110.577 | 97.328 | 1.00 | 54.88 | B | C |
| ATOM | 2986 | CD1 | LEU | B | 57 | 28.743 | 110.694 | 98.557 | 1.00 | 54.48 | B | C |
| ATOM | 2987 | CD2 | LEU | B | 57 | 29.782 | 111.929 | 96.628 | 1.00 | 53.58 | B | C |
| ATOM | 2988 | C | LEU | B | 57 | 33.102 | 110.906 | 96.561 | 1.00 | 52.17 | B | C |
| ATOM | 2989 | O | LEU | B | 57 | 33.470 | 111.482 | 97.585 | 1.00 | 49.98 | B | O |
| ATOM | 2990 | N | ALA | B | 58 | 33.583 | 111.182 | 95.347 | 1.00 | 50.86 | B | N |
| ATOM | 2991 | CA | ALA | B | 58 | 34.594 | 112.214 | 95.084 | 1.00 | 51.31 | B | C |
| ATOM | 2992 | CB | ALA | B | 58 | 34.914 | 112.998 | 96.360 | 1.00 | 52.35 | B | C |
| ATOM | 2993 | C | ALA | B | 58 | 35.879 | 111.611 | 94.514 | 1.00 | 50.63 | B | C |
| ATOM | 2994 | O | ALA | B | 58 | 36.379 | 112.050 | 93.472 | 1.00 | 47.35 | B | O |
| ATOM | 2995 | N | ASP | B | 59 | 36.403 | 110.604 | 95.210 | 1.00 | 50.38 | B | N |
| ATOM | 2996 | CA | ASP | B | 59 | 37.624 | 109.921 | 94.799 | 1.00 | 49.36 | B | C |
| ATOM | 2997 | CB | ASP | B | 59 | 38.575 | 109.769 | 96.001 | 1.00 | 50.79 | B | C |
| ATOM | 2998 | CG | ASP | B | 59 | 37.932 | 109.038 | 97.180 | 1.00 | 51.94 | B | C |
| ATOM | 2999 | OD1 | ASP | B | 59 | 37.695 | 107.812 | 97.076 | 1.00 | 51.71 | B | O |
| ATOM | 3000 | OD2 | ASP | B | 59 | 37.664 | 109.696 | 98.212 | 1.00 | 49.04 | B | O |
| ATOM | 3001 | C | ASP | B | 59 | 37.337 | 108.551 | 94.188 | 1.00 | 47.52 | B | C |
| ATOM | 3002 | O | ASP | B | 59 | 37.393 | 107.532 | 94.880 | 1.00 | 45.95 | B | O |
| ATOM | 3003 | N | LYS | B | 60 | 37.025 | 108.531 | 92.892 | 1.00 | 46.49 | B | N |
| ATOM | 3004 | CA | LYS | B | 60 | 36.748 | 107.278 | 92.196 | 1.00 | 46.09 | B | C |
| ATOM | 3005 | CB | LYS | B | 60 | 36.282 | 107.536 | 90.760 | 1.00 | 46.80 | B | C |
| ATOM | 3006 | CG | LYS | B | 60 | 36.028 | 106.256 | 89.975 | 1.00 | 45.00 | B | C |
| ATOM | 3007 | CD | LYS | B | 60 | 35.237 | 106.523 | 88.713 | 1.00 | 45.07 | B | C |
| ATOM | 3008 | CE | LYS | B | 60 | 34.965 | 105.229 | 87.952 | 1.00 | 49.40 | B | C |
| ATOM | 3009 | NZ | LYS | B | 60 | 34.171 | 104.252 | 88.749 | 1.00 | 51.86 | B | N |
| ATOM | 3010 | C | LYS | B | 60 | 38.034 | 106.467 | 92.174 | 1.00 | 46.58 | B | C |
| ATOM | 3011 | O | LYS | B | 60 | 38.054 | 105.295 | 91.782 | 1.00 | 44.22 | B | O |
| ATOM | 3012 | N | SER | B | 61 | 39.109 | 107.116 | 92.605 | 1.00 | 47.03 | B | N |
| ATOM | 3013 | CA | SER | B | 61 | 40.411 | 106.483 | 92.656 | 1.00 | 48.54 | B | C |
| ATOM | 3014 | CB | SER | B | 61 | 41.404 | 107.413 | 93.360 | 1.00 | 47.77 | B | C |
| ATOM | 3015 | OG | SER | B | 61 | 42.714 | 106.875 | 93.329 | 1.00 | 46.07 | B | O |
| ATOM | 3016 | C | SER | B | 61 | 40.325 | 105.136 | 93.392 | 1.00 | 49.15 | B | C |
| ATOM | 3017 | O | SER | B | 61 | 40.618 | 104.083 | 92.814 | 1.00 | 49.36 | B | O |
| ATOM | 3018 | N | SER | B | 62 | 39.912 | 105.179 | 94.660 | 1.00 | 48.09 | B | N |
| ATOM | 3019 | CA | SER | B | 62 | 39.796 | 103.981 | 95.492 | 1.00 | 45.55 | B | C |
| ATOM | 3020 | CB | SER | B | 62 | 38.797 | 104.223 | 96.628 | 1.00 | 44.57 | B | C |
| ATOM | 3021 | OG | SER | B | 62 | 39.269 | 103.668 | 97.843 | 1.00 | 38.91 | B | O |
| ATOM | 3022 | C | SER | B | 62 | 39.395 | 102.743 | 94.681 | 1.00 | 45.14 | B | C |
| ATOM | 3023 | O | SER | B | 62 | 38.469 | 102.769 | 93.864 | 1.00 | 44.37 | B | O |
| ATOM | 3024 | N | ARG | B | 63 | 40.110 | 101.657 | 94.941 | 1.00 | 45.10 | B | N |
| ATOM | 3025 | CA | ARG | B | 63 | 39.942 | 100.380 | 94.262 | 1.00 | 44.92 | B | C |
| ATOM | 3026 | CB | ARG | B | 63 | 40.835 | 100.350 | 93.023 | 1.00 | 47.34 | B | C |
| ATOM | 3027 | CG | ARG | B | 63 | 40.388 | 101.288 | 91.915 | 1.00 | 52.54 | B | C |
| ATOM | 3028 | CD | ARG | B | 63 | 41.510 | 101.477 | 90.921 | 1.00 | 57.13 | B | C |
| ATOM | 3029 | NE | ARG | B | 63 | 42.213 | 100.220 | 90.687 | 1.00 | 60.47 | B | N |
| ATOM | 3030 | CZ | ARG | B | 63 | 43.357 | 100.118 | 90.019 | 1.00 | 61.81 | B | C |
| ATOM | 3031 | NH1 | ARG | B | 63 | 43.930 | 101.204 | 89.515 | 1.00 | 62.05 | B | N |
| ATOM | 3032 | NH2 | ARG | B | 63 | 43.931 | 98.932 | 89.861 | 1.00 | 61.92 | B | N |
| ATOM | 3033 | C | ARG | B | 63 | 40.343 | 99.249 | 95.206 | 1.00 | 42.15 | B | C |
| ATOM | 3034 | O | ARG | B | 63 | 41.182 | 99.434 | 96.093 | 1.00 | 41.77 | B | O |
| ATOM | 3035 | N | LYS | B | 64 | 39.748 | 98.078 | 95.007 | 1.00 | 39.77 | B | N |
| ATOM | 3036 | CA | LYS | B | 64 | 40.043 | 96.926 | 95.849 | 1.00 | 37.52 | B | C |
| ATOM | 3037 | CB | LYS | B | 64 | 38.748 | 96.470 | 96.543 | 1.00 | 37.50 | B | C |
| ATOM | 3038 | CG | LYS | B | 64 | 38.936 | 95.398 | 97.613 | 1.00 | 42.88 | B | C |
| ATOM | 3039 | CD | LYS | B | 64 | 37.753 | 95.342 | 98.585 | 1.00 | 43.29 | B | C |
| ATOM | 3040 | CE | LYS | B | 64 | 37.725 | 96.579 | 99.491 | 1.00 | 44.91 | B | C |
| ATOM | 3041 | NZ | LYS | B | 64 | 36.612 | 96.550 | 100.484 | 1.00 | 43.02 | B | N |
| ATOM | 3042 | C | LYS | B | 64 | 40.672 | 95.797 | 95.009 | 1.00 | 35.90 | B | C |
| ATOM | 3043 | O | LYS | B | 64 | 40.169 | 95.443 | 93.932 | 1.00 | 34.30 | B | O |
| ATOM | 3044 | N | THR | B | 65 | 41.777 | 95.242 | 95.503 | 1.00 | 32.44 | B | N |
| ATOM | 3045 | CA | THR | B | 65 | 42.490 | 94.184 | 94.788 | 1.00 | 30.41 | B | C |
| ATOM | 3046 | CB | THR | B | 65 | 43.951 | 94.618 | 94.490 | 1.00 | 29.46 | B | C |
| ATOM | 3047 | OG1 | THR | B | 65 | 43.949 | 95.637 | 93.483 | 1.00 | 29.64 | B | O |
| ATOM | 3048 | CG2 | THR | B | 65 | 44.780 | 93.441 | 94.010 | 1.00 | 25.82 | B | C |
| ATOM | 3049 | C | THR | B | 65 | 42.532 | 92.827 | 95.483 | 1.00 | 29.54 | B | C |
| ATOM | 3050 | O | THR | B | 65 | 42.883 | 92.730 | 96.659 | 1.00 | 30.96 | B | O |
| ATOM | 3051 | N | TYR | B | 66 | 42.178 | 91.783 | 94.738 | 1.00 | 28.39 | B | N |
| ATOM | 3052 | CA | TYR | B | 66 | 42.199 | 90.421 | 95.256 | 1.00 | 27.17 | B | C |
| ATOM | 3053 | CB | TYR | B | 66 | 40.808 | 89.785 | 95.206 | 1.00 | 26.17 | B | C |
| ATOM | 3054 | CG | TYR | B | 66 | 39.716 | 90.522 | 95.944 | 1.00 | 26.44 | B | C |
| ATOM | 3055 | CD1 | TYR | B | 66 | 39.000 | 91.541 | 95.335 | 1.00 | 26.42 | B | C |
| ATOM | 3056 | CE1 | TYR | B | 66 | 37.948 | 92.159 | 95.989 | 1.00 | 26.02 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3057 | CD2 | TYR | B | 66 | 39.355 | 90.151 | 97.234 | 1.00 | 26.87 | B | C |
| ATOM | 3058 | CE2 | TYR | B | 66 | 38.311 | 90.762 | 97.890 | 1.00 | 24.27 | B | C |
| ATOM | 3059 | CZ | TYR | B | 66 | 37.607 | 91.760 | 97.265 | 1.00 | 26.69 | B | C |
| ATOM | 3060 | OH | TYR | B | 66 | 36.534 | 92.342 | 97.904 | 1.00 | 26.29 | B | O |
| ATOM | 3061 | C | TYR | B | 66 | 43.142 | 89.587 | 94.384 | 1.00 | 26.81 | B | C |
| ATOM | 3062 | O | TYR | B | 66 | 43.292 | 89.855 | 93.184 | 1.00 | 26.04 | B | O |
| ATOM | 3063 | N | THR | B | 67 | 43.764 | 88.580 | 94.994 | 1.00 | 24.59 | B | N |
| ATOM | 3064 | CA | THR | B | 67 | 44.682 | 87.680 | 94.296 | 1.00 | 23.72 | B | C |
| ATOM | 3065 | CB | THR | B | 67 | 46.105 | 87.711 | 94.920 | 1.00 | 23.99 | B | C |
| ATOM | 3066 | OG1 | THR | B | 67 | 46.719 | 88.985 | 94.675 | 1.00 | 28.16 | B | O |
| ATOM | 3067 | CG2 | THR | B | 67 | 46.969 | 86.625 | 94.331 | 1.00 | 21.26 | B | C |
| ATOM | 3068 | C | THR | B | 67 | 44.135 | 86.261 | 94.405 | 1.00 | 23.72 | B | C |
| ATOM | 3069 | O | THR | B | 67 | 43.658 | 85.851 | 95.469 | 1.00 | 22.42 | B | O |
| ATOM | 3070 | N | PHE | B | 68 | 44.188 | 85.522 | 93.301 | 1.00 | 24.48 | B | N |
| ATOM | 3071 | CA | PHE | B | 68 | 43.698 | 84.148 | 93.277 | 1.00 | 24.84 | B | C |
| ATOM | 3072 | CB | PHE | B | 68 | 42.298 | 84.084 | 92.649 | 1.00 | 24.07 | B | C |
| ATOM | 3073 | CG | PHE | B | 68 | 41.274 | 84.946 | 93.351 | 1.00 | 23.15 | B | C |
| ATOM | 3074 | CD1 | PHE | B | 68 | 40.987 | 86.225 | 92.894 | 1.00 | 24.49 | B | C |
| ATOM | 3075 | CD2 | PHE | B | 68 | 40.616 | 84.485 | 94.478 | 1.00 | 21.36 | B | C |
| ATOM | 3076 | CE1 | PHE | B | 68 | 40.059 | 87.030 | 93.552 | 1.00 | 23.89 | B | C |
| ATOM | 3077 | CE2 | PHE | B | 68 | 39.688 | 85.285 | 95.142 | 1.00 | 22.79 | B | C |
| ATOM | 3078 | CZ | PHE | B | 68 | 39.410 | 86.557 | 94.678 | 1.00 | 21.00 | B | C |
| ATOM | 3079 | C | PHE | B | 68 | 44.673 | 83.265 | 92.505 | 1.00 | 25.10 | B | C |
| ATOM | 3080 | O | PHE | B | 68 | 45.647 | 83.762 | 91.924 | 1.00 | 23.59 | B | O |
| ATOM | 3081 | N | ASP | B | 69 | 44.420 | 81.959 | 92.512 | 1.00 | 24.68 | B | N |
| ATOM | 3082 | CA | ASP | B | 69 | 45.289 | 81.015 | 91.825 | 1.00 | 23.10 | B | C |
| ATOM | 3083 | CB | ASP | B | 69 | 44.797 | 79.591 | 92.051 | 1.00 | 25.41 | B | C |
| ATOM | 3084 | CG | ASP | B | 69 | 45.020 | 79.121 | 93.479 | 1.00 | 27.32 | B | C |
| ATOM | 3085 | OD1 | ASP | B | 69 | 46.193 | 79.095 | 93.924 | 1.00 | 29.74 | B | O |
| ATOM | 3086 | OD2 | ASP | B | 69 | 44.028 | 78.779 | 94.155 | 1.00 | 26.85 | B | O |
| ATOM | 3087 | C | ASP | B | 69 | 45.382 | 81.323 | 90.347 | 1.00 | 23.14 | B | C |
| ATOM | 3088 | O | ASP | B | 69 | 46.472 | 81.297 | 89.778 | 1.00 | 25.16 | B | O |
| ATOM | 3089 | N | MET | B | 70 | 44.241 | 81.612 | 89.726 | 1.00 | 23.50 | B | N |
| ATOM | 3090 | CA | MET | B | 70 | 44.195 | 81.973 | 88.303 | 1.00 | 22.46 | B | C |
| ATOM | 3091 | CB | MET | B | 70 | 43.957 | 80.747 | 87.427 | 1.00 | 24.03 | B | C |
| ATOM | 3092 | CG | MET | B | 70 | 45.079 | 79.736 | 87.473 | 1.00 | 28.86 | B | C |
| ATOM | 3093 | SD | MET | B | 70 | 44.767 | 78.341 | 86.392 | 1.00 | 33.19 | B | S |
| ATOM | 3094 | CE | MET | B | 70 | 44.191 | 77.115 | 87.538 | 1.00 | 30.50 | B | C |
| ATOM | 3095 | C | MET | B | 70 | 43.089 | 82.995 | 88.055 | 1.00 | 22.41 | B | C |
| ATOM | 3096 | O | MET | B | 70 | 42.024 | 82.933 | 88.667 | 1.00 | 20.76 | B | O |
| ATOM | 3097 | N | VAL | B | 71 | 43.361 | 83.943 | 87.162 | 1.00 | 22.85 | B | N |
| ATOM | 3098 | CA | VAL | B | 71 | 42.406 | 84.993 | 86.824 | 1.00 | 21.35 | B | C |
| ATOM | 3099 | CB | VAL | B | 71 | 42.966 | 86.377 | 87.190 | 1.00 | 19.69 | B | C |
| ATOM | 3100 | CG1 | VAL | B | 71 | 42.014 | 87.464 | 86.711 | 1.00 | 20.42 | B | C |
| ATOM | 3101 | CG2 | VAL | B | 71 | 43.165 | 86.469 | 88.690 | 1.00 | 15.52 | B | C |
| ATOM | 3102 | C | VAL | B | 71 | 42.113 | 84.959 | 85.329 | 1.00 | 21.29 | B | C |
| ATOM | 3103 | O | VAL | B | 71 | 43.033 | 84.972 | 84.514 | 1.00 | 24.15 | B | O |
| ATOM | 3104 | N | PHE | B | 72 | 40.835 | 84.922 | 84.968 | 1.00 | 19.32 | B | N |
| ATOM | 3105 | CA | PHE | B | 72 | 40.447 | 84.853 | 83.561 | 1.00 | 18.98 | B | C |
| ATOM | 3106 | CB | PHE | B | 72 | 39.633 | 83.578 | 83.306 | 1.00 | 16.84 | B | C |
| ATOM | 3107 | CG | PHE | B | 72 | 40.377 | 82.302 | 83.592 | 1.00 | 14.90 | B | C |
| ATOM | 3108 | CD1 | PHE | B | 72 | 41.414 | 81.883 | 82.767 | 1.00 | 11.52 | B | C |
| ATOM | 3109 | CD2 | PHE | B | 72 | 40.028 | 81.506 | 84.680 | 1.00 | 13.39 | B | C |
| ATOM | 3110 | CE1 | PHE | B | 72 | 42.087 | 80.700 | 83.020 | 1.00 | 8.15 | B | C |
| ATOM | 3111 | CE2 | PHE | B | 72 | 40.701 | 80.319 | 84.937 | 1.00 | 7.47 | B | C |
| ATOM | 3112 | CZ | PHE | B | 72 | 41.727 | 79.922 | 84.107 | 1.00 | 12.50 | B | C |
| ATOM | 3113 | C | PHE | B | 72 | 39.623 | 86.051 | 83.107 | 1.00 | 20.59 | B | C |
| ATOM | 3114 | O | PHE | B | 72 | 38.463 | 86.192 | 83.491 | 1.00 | 21.66 | B | O |
| ATOM | 3115 | N | GLY | B | 73 | 40.218 | 86.900 | 82.275 | 1.00 | 21.28 | B | N |
| ATOM | 3116 | CA | GLY | B | 73 | 39.506 | 88.061 | 81.769 | 1.00 | 20.44 | B | C |
| ATOM | 3117 | C | GLY | B | 73 | 38.293 | 87.634 | 80.957 | 1.00 | 22.36 | B | C |
| ATOM | 3118 | O | GLY | B | 73 | 38.090 | 86.437 | 80.719 | 1.00 | 22.17 | B | O |
| ATOM | 3119 | N | ALA | B | 74 | 37.502 | 88.608 | 80.511 | 1.00 | 21.87 | B | N |
| ATOM | 3120 | CA | ALA | B | 74 | 36.290 | 88.331 | 79.748 | 1.00 | 23.94 | B | C |
| ATOM | 3121 | CB | ALA | B | 74 | 35.475 | 89.609 | 79.602 | 1.00 | 25.87 | B | C |
| ATOM | 3122 | C | ALA | B | 74 | 36.474 | 87.682 | 78.376 | 1.00 | 26.37 | B | C |
| ATOM | 3123 | O | ALA | B | 74 | 35.541 | 87.066 | 77.861 | 1.00 | 29.60 | B | O |
| ATOM | 3124 | N | SER | B | 75 | 37.658 | 87.803 | 77.781 | 1.00 | 25.89 | B | N |
| ATOM | 3125 | CA | SER | B | 75 | 37.887 | 87.225 | 76.458 | 1.00 | 25.77 | B | C |
| ATOM | 3126 | CB | SER | B | 75 | 38.865 | 88.091 | 75.664 | 1.00 | 27.59 | B | C |
| ATOM | 3127 | OG | SER | B | 75 | 40.193 | 87.870 | 76.106 | 1.00 | 31.12 | B | O |
| ATOM | 3128 | C | SER | B | 75 | 38.419 | 85.795 | 76.502 | 1.00 | 24.50 | B | C |
| ATOM | 3129 | O | SER | B | 75 | 39.010 | 85.315 | 75.532 | 1.00 | 26.35 | B | O |
| ATOM | 3130 | N | THR | B | 76 | 38.200 | 85.117 | 77.623 | 1.00 | 22.05 | B | N |
| ATOM | 3131 | CA | THR | B | 76 | 38.653 | 83.746 | 77.796 | 1.00 | 19.71 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3132 | CB | THR | B | 76 | 38.664 | 83.385 | 79.289 | 1.00 | 22.60 | B | C |
| ATOM | 3133 | OG1 | THR | B | 76 | 39.672 | 84.156 | 79.956 | 1.00 | 21.73 | B | O |
| ATOM | 3134 | CG2 | THR | B | 76 | 38.927 | 81.896 | 79.491 | 1.00 | 26.24 | B | C |
| ATOM | 3135 | C | THR | B | 76 | 37.778 | 82.741 | 77.037 | 1.00 | 21.11 | B | C |
| ATOM | 3136 | O | THR | B | 76 | 36.554 | 82.832 | 77.035 | 1.00 | 20.25 | B | O |
| ATOM | 3137 | N | LYS | B | 77 | 38.416 | 81.783 | 76.374 | 1.00 | 22.76 | B | N |
| ATOM | 3138 | CA | LYS | B | 77 | 37.677 | 80.772 | 75.630 | 1.00 | 21.76 | B | C |
| ATOM | 3139 | CB | LYS | B | 77 | 38.467 | 80.306 | 74.409 | 1.00 | 24.32 | B | C |
| ATOM | 3140 | CG | LYS | B | 77 | 38.709 | 81.362 | 73.342 | 1.00 | 27.40 | B | C |
| ATOM | 3141 | CD | LYS | B | 77 | 38.606 | 80.709 | 71.955 | 1.00 | 30.85 | B | C |
| ATOM | 3142 | CE | LYS | B | 77 | 39.423 | 79.417 | 71.858 | 1.00 | 29.67 | B | C |
| ATOM | 3143 | NZ | LYS | B | 77 | 38.911 | 78.494 | 70.799 | 1.00 | 25.42 | B | N |
| ATOM | 3144 | C | LYS | B | 77 | 37.430 | 79.582 | 76.539 | 1.00 | 18.69 | B | C |
| ATOM | 3145 | O | LYS | B | 77 | 38.203 | 79.341 | 77.465 | 1.00 | 19.36 | B | O |
| ATOM | 3146 | N | GLN | B | 78 | 36.350 | 78.853 | 76.274 | 1.00 | 14.49 | B | N |
| ATOM | 3147 | CA | GLN | B | 78 | 36.002 | 77.671 | 77.050 | 1.00 | 13.74 | B | C |
| ATOM | 3148 | CB | GLN | B | 78 | 34.781 | 76.993 | 76.445 | 1.00 | 13.87 | B | C |
| ATOM | 3149 | CG | GLN | B | 78 | 33.533 | 77.870 | 76.388 | 1.00 | 13.92 | B | C |
| ATOM | 3150 | CD | GLN | B | 78 | 32.767 | 77.880 | 77.693 | 1.00 | 14.70 | B | C |
| ATOM | 3151 | OE1 | GLN | B | 78 | 33.292 | 78.279 | 78.738 | 1.00 | 15.07 | B | O |
| ATOM | 3152 | NE2 | GLN | B | 78 | 31.517 | 77.431 | 77.642 | 1.00 | 12.19 | B | N |
| ATOM | 3153 | C | GLN | B | 78 | 37.185 | 76.704 | 77.030 | 1.00 | 16.13 | B | C |
| ATOM | 3154 | O | GLN | B | 78 | 37.505 | 76.085 | 78.043 | 1.00 | 16.93 | B | O |
| ATOM | 3155 | N | ILE | B | 79 | 37.830 | 76.605 | 75.867 | 1.00 | 17.26 | B | N |
| ATOM | 3156 | CA | ILE | B | 79 | 38.988 | 75.739 | 75.642 | 1.00 | 17.92 | B | C |
| ATOM | 3157 | CB | ILE | B | 79 | 39.479 | 75.844 | 74.155 | 1.00 | 19.33 | B | C |
| ATOM | 3158 | CG2 | ILE | B | 79 | 40.025 | 77.232 | 73.882 | 1.00 | 20.49 | B | C |
| ATOM | 3159 | CG1 | ILE | B | 79 | 40.596 | 74.839 | 73.874 | 1.00 | 17.62 | B | C |
| ATOM | 3160 | CD1 | ILE | B | 79 | 40.132 | 73.427 | 73.739 | 1.00 | 21.00 | B | C |
| ATOM | 3161 | C | ILE | B | 79 | 40.160 | 76.069 | 76.573 | 1.00 | 17.01 | B | C |
| ATOM | 3162 | O | ILE | B | 79 | 40.929 | 75.183 | 76.942 | 1.00 | 16.33 | B | O |
| ATOM | 3163 | N | ASP | B | 80 | 40.305 | 77.343 | 76.935 | 1.00 | 18.44 | B | N |
| ATOM | 3164 | CA | ASP | B | 80 | 41.386 | 77.772 | 77.837 | 1.00 | 19.44 | B | C |
| ATOM | 3165 | CB | ASP | B | 80 | 41.638 | 79.283 | 77.734 | 1.00 | 23.02 | B | C |
| ATOM | 3166 | CG | ASP | B | 80 | 42.149 | 79.696 | 76.366 | 1.00 | 27.19 | B | C |
| ATOM | 3167 | OD1 | ASP | B | 80 | 43.082 | 79.033 | 75.869 | 1.00 | 26.80 | B | O |
| ATOM | 3168 | OD2 | ASP | B | 80 | 41.626 | 80.680 | 75.793 | 1.00 | 31.79 | B | O |
| ATOM | 3169 | C | ASP | B | 80 | 41.043 | 77.432 | 79.277 | 1.00 | 18.17 | B | C |
| ATOM | 3170 | O | ASP | B | 80 | 41.901 | 76.960 | 80.032 | 1.00 | 19.63 | B | O |
| ATOM | 3171 | N | VAL | B | 81 | 39.794 | 77.687 | 79.659 | 1.00 | 14.90 | B | N |
| ATOM | 3172 | CA | VAL | B | 81 | 39.350 | 77.373 | 81.008 | 1.00 | 14.10 | B | C |
| ATOM | 3173 | CB | VAL | B | 81 | 37.831 | 77.596 | 81.206 | 1.00 | 16.41 | B | C |
| ATOM | 3174 | CG1 | VAL | B | 81 | 37.403 | 77.025 | 82.549 | 1.00 | 8.37 | B | C |
| ATOM | 3175 | CG2 | VAL | B | 81 | 37.499 | 79.067 | 81.129 | 1.00 | 15.46 | B | C |
| ATOM | 3176 | C | VAL | B | 81 | 39.603 | 75.901 | 81.223 | 1.00 | 14.02 | B | C |
| ATOM | 3177 | O | VAL | B | 81 | 40.102 | 75.481 | 82.271 | 1.00 | 14.92 | B | O |
| ATOM | 3178 | N | TYR | B | 82 | 39.246 | 75.116 | 80.218 | 1.00 | 11.61 | B | N |
| ATOM | 3179 | CA | TYR | B | 82 | 39.427 | 73.683 | 80.318 | 1.00 | 18.44 | B | C |
| ATOM | 3180 | CB | TYR | B | 82 | 38.761 | 72.973 | 79.134 | 1.00 | 20.03 | B | C |
| ATOM | 3181 | CG | TYR | B | 82 | 38.879 | 71.478 | 79.211 | 1.00 | 23.03 | B | C |
| ATOM | 3182 | CD1 | TYR | B | 82 | 39.868 | 70.803 | 78.502 | 1.00 | 25.76 | B | C |
| ATOM | 3183 | CE1 | TYR | B | 82 | 40.034 | 69.429 | 78.635 | 1.00 | 27.61 | B | C |
| ATOM | 3184 | CD2 | TYR | B | 82 | 38.049 | 70.738 | 80.055 | 1.00 | 23.15 | B | C |
| ATOM | 3185 | CE2 | TYR | B | 82 | 38.206 | 69.363 | 80.197 | 1.00 | 23.62 | B | C |
| ATOM | 3186 | CZ | TYR | B | 82 | 39.204 | 68.716 | 79.487 | 1.00 | 25.18 | B | C |
| ATOM | 3187 | OH | TYR | B | 82 | 39.409 | 67.370 | 79.652 | 1.00 | 23.89 | B | O |
| ATOM | 3188 | C | TYR | B | 82 | 40.895 | 73.282 | 80.426 | 1.00 | 21.58 | B | C |
| ATOM | 3189 | O | TYR | B | 82 | 41.255 | 72.491 | 81.307 | 1.00 | 24.48 | B | O |
| ATOM | 3190 | N | ARG | B | 83 | 41.746 | 73.829 | 79.560 | 1.00 | 20.69 | B | N |
| ATOM | 3191 | CA | ARG | B | 83 | 43.171 | 73.486 | 79.584 | 1.00 | 22.43 | B | C |
| ATOM | 3192 | CB | ARG | B | 83 | 43.924 | 74.164 | 78.427 | 1.00 | 27.52 | B | C |
| ATOM | 3193 | CG | ARG | B | 83 | 43.621 | 73.639 | 77.010 | 1.00 | 31.08 | B | C |
| ATOM | 3194 | CD | ARG | B | 83 | 44.637 | 74.216 | 76.018 | 1.00 | 34.04 | B | C |
| ATOM | 3195 | NE | ARG | B | 83 | 44.362 | 73.903 | 74.614 | 1.00 | 37.11 | B | N |
| ATOM | 3196 | CZ | ARG | B | 83 | 44.179 | 72.677 | 74.126 | 1.00 | 38.20 | B | C |
| ATOM | 3197 | NH1 | ARG | B | 83 | 44.232 | 71.618 | 74.926 | 1.00 | 37.92 | B | N |
| ATOM | 3198 | NH2 | ARG | B | 83 | 43.951 | 72.509 | 72.829 | 1.00 | 34.28 | B | N |
| ATOM | 3199 | C | ARG | B | 83 | 43.865 | 73.863 | 80.887 | 1.00 | 23.47 | B | C |
| ATOM | 3200 | O | ARG | B | 83 | 44.735 | 73.135 | 81.369 | 1.00 | 24.11 | B | O |
| ATOM | 3201 | N | SER | B | 84 | 43.488 | 75.002 | 81.459 | 1.00 | 23.15 | B | N |
| ATOM | 3202 | CA | SER | B | 84 | 44.120 | 75.472 | 82.689 | 1.00 | 22.69 | B | C |
| ATOM | 3203 | CB | SER | B | 84 | 43.995 | 76.996 | 82.786 | 1.00 | 24.24 | B | C |
| ATOM | 3204 | OG | SER | B | 84 | 44.501 | 77.631 | 81.624 | 1.00 | 26.32 | B | O |
| ATOM | 3205 | C | SER | B | 84 | 43.587 | 74.852 | 83.974 | 1.00 | 21.94 | B | C |
| ATOM | 3206 | O | SER | B | 84 | 44.351 | 74.477 | 84.851 | 1.00 | 21.03 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3207 | N | VAL | B | 85 | 42.272 | 74.737 | 84.083 | 1.00 | 21.77 | B | N |
| ATOM | 3208 | CA | VAL | B | 85 | 41.669 | 74.202 | 85.289 | 1.00 | 18.41 | B | C |
| ATOM | 3209 | CB | VAL | B | 85 | 40.384 | 74.962 | 85.597 | 1.00 | 20.44 | B | C |
| ATOM | 3210 | CG1 | VAL | B | 85 | 39.856 | 74.566 | 86.960 | 1.00 | 22.21 | B | C |
| ATOM | 3211 | CG2 | VAL | B | 85 | 40.661 | 76.462 | 85.541 | 1.00 | 22.80 | B | C |
| ATOM | 3212 | C | VAL | B | 85 | 41.379 | 72.708 | 85.331 | 1.00 | 17.43 | B | C |
| ATOM | 3213 | O | VAL | B | 85 | 41.829 | 72.028 | 86.239 | 1.00 | 18.15 | B | O |
| ATOM | 3214 | N | VAL | B | 86 | 40.647 | 72.188 | 84.349 | 1.00 | 19.14 | B | N |
| ATOM | 3215 | CA | VAL | B | 86 | 40.294 | 70.766 | 84.337 | 1.00 | 18.32 | B | C |
| ATOM | 3216 | CB | VAL | B | 86 | 39.195 | 70.489 | 83.306 | 1.00 | 18.69 | B | C |
| ATOM | 3217 | CG1 | VAL | B | 86 | 38.696 | 69.053 | 83.444 | 1.00 | 13.34 | B | C |
| ATOM | 3218 | CG2 | VAL | B | 86 | 38.054 | 71.473 | 83.505 | 1.00 | 18.08 | B | C |
| ATOM | 3219 | C | VAL | B | 86 | 41.412 | 69.731 | 84.134 | 1.00 | 20.17 | B | C |
| ATOM | 3220 | O | VAL | B | 86 | 41.576 | 68.835 | 84.968 | 1.00 | 18.33 | B | O |
| ATOM | 3221 | N | CYS | B | 87 | 42.170 | 69.843 | 83.041 | 1.00 | 19.64 | B | N |
| ATOM | 3222 | CA | CYS | B | 87 | 43.246 | 68.888 | 82.754 | 1.00 | 18.72 | B | C |
| ATOM | 3223 | CB | CYS | B | 87 | 44.224 | 69.467 | 81.741 | 1.00 | 20.68 | B | C |
| ATOM | 3224 | SG | CYS | B | 87 | 43.585 | 69.465 | 80.086 | 1.00 | 28.68 | B | S |
| ATOM | 3225 | C | CYS | B | 87 | 44.028 | 68.402 | 83.965 | 1.00 | 17.76 | B | C |
| ATOM | 3226 | O | CYS | B | 87 | 44.053 | 67.214 | 84.257 | 1.00 | 17.82 | B | O |
| ATOM | 3227 | N | PRO | B | 88 | 44.689 | 69.312 | 84.685 | 1.00 | 17.93 | B | N |
| ATOM | 3228 | CD | PRO | B | 88 | 44.603 | 70.780 | 84.688 | 1.00 | 17.63 | B | C |
| ATOM | 3229 | CA | PRO | B | 88 | 45.439 | 68.831 | 85.849 | 1.00 | 19.51 | B | C |
| ATOM | 3230 | CB | PRO | B | 88 | 45.801 | 70.122 | 86.591 | 1.00 | 16.31 | B | C |
| ATOM | 3231 | CG | PRO | B | 88 | 45.802 | 71.155 | 85.518 | 1.00 | 17.74 | B | C |
| ATOM | 3232 | C | PRO | B | 88 | 44.557 | 67.910 | 86.701 | 1.00 | 19.54 | B | C |
| ATOM | 3233 | O | PRO | B | 88 | 44.924 | 66.783 | 87.014 | 1.00 | 21.57 | B | O |
| ATOM | 3234 | N | ILE | B | 89 | 43.385 | 68.412 | 87.071 | 1.00 | 20.80 | B | N |
| ATOM | 3235 | CA | ILE | B | 89 | 42.440 | 67.663 | 87.890 | 1.00 | 19.05 | B | C |
| ATOM | 3236 | CB | ILE | B | 89 | 41.164 | 68.511 | 88.137 | 1.00 | 19.18 | B | C |
| ATOM | 3237 | CG2 | ILE | B | 89 | 40.051 | 67.648 | 88.701 | 1.00 | 12.57 | B | C |
| ATOM | 3238 | CG1 | ILE | B | 89 | 41.527 | 69.675 | 89.074 | 1.00 | 18.47 | B | C |
| ATOM | 3239 | CD1 | ILE | B | 89 | 40.436 | 70.706 | 89.281 | 1.00 | 18.42 | B | C |
| ATOM | 3240 | C | ILE | B | 89 | 42.073 | 66.318 | 87.275 | 1.00 | 17.01 | B | C |
| ATOM | 3241 | O | ILE | B | 89 | 42.091 | 65.303 | 87.952 | 1.00 | 16.89 | B | O |
| ATOM | 3242 | N | LEU | B | 90 | 41.764 | 66.312 | 85.985 | 1.00 | 16.50 | B | N |
| ATOM | 3243 | CA | LEU | B | 90 | 41.395 | 65.085 | 85.309 | 1.00 | 15.39 | B | C |
| ATOM | 3244 | CB | LEU | B | 90 | 41.043 | 65.361 | 83.842 | 1.00 | 15.87 | B | C |
| ATOM | 3245 | CG | LEU | B | 90 | 40.566 | 64.139 | 83.044 | 1.00 | 19.09 | B | C |
| ATOM | 3246 | CD1 | LEU | B | 90 | 39.333 | 63.542 | 83.701 | 1.00 | 12.34 | B | C |
| ATOM | 3247 | CD2 | LEU | B | 90 | 40.261 | 64.541 | 81.607 | 1.00 | 20.59 | B | C |
| ATOM | 3248 | C | LEU | B | 90 | 42.506 | 64.052 | 85.398 | 1.00 | 16.69 | B | C |
| ATOM | 3249 | O | LEU | B | 90 | 42.225 | 62.867 | 85.547 | 1.00 | 18.80 | B | O |
| ATOM | 3250 | N | ASP | B | 91 | 43.761 | 64.487 | 85.307 | 1.00 | 17.26 | B | N |
| ATOM | 3251 | CA | ASP | B | 91 | 44.877 | 63.556 | 85.397 | 1.00 | 19.52 | B | C |
| ATOM | 3252 | CB | ASP | B | 91 | 46.221 | 64.283 | 85.281 | 1.00 | 19.85 | B | C |
| ATOM | 3253 | CG | ASP | B | 91 | 46.491 | 64.814 | 83.877 | 1.00 | 19.70 | B | C |
| ATOM | 3254 | OD1 | ASP | B | 91 | 46.183 | 64.106 | 82.895 | 1.00 | 19.03 | B | O |
| ATOM | 3255 | OD2 | ASP | B | 91 | 47.030 | 65.936 | 83.754 | 1.00 | 19.14 | B | O |
| ATOM | 3256 | C | ASP | B | 91 | 44.796 | 62.812 | 86.728 | 1.00 | 23.78 | B | C |
| ATOM | 3257 | O | ASP | B | 91 | 45.111 | 61.617 | 86.804 | 1.00 | 26.24 | B | O |
| ATOM | 3258 | N | GLU | B | 92 | 44.362 | 63.510 | 87.776 | 1.00 | 25.23 | B | N |
| ATOM | 3259 | CA | GLU | B | 92 | 44.217 | 62.879 | 89.085 | 1.00 | 27.26 | B | C |
| ATOM | 3260 | CB | GLU | B | 92 | 44.004 | 63.932 | 90.174 | 1.00 | 28.41 | B | C |
| ATOM | 3261 | CG | GLU | B | 92 | 45.187 | 64.877 | 90.357 | 1.00 | 35.04 | B | C |
| ATOM | 3262 | CD | GLU | B | 92 | 46.516 | 64.145 | 90.515 | 1.00 | 39.26 | B | C |
| ATOM | 3263 | OE1 | GLU | B | 92 | 46.616 | 63.280 | 91.419 | 1.00 | 37.62 | B | O |
| ATOM | 3264 | OE2 | GLU | B | 92 | 47.458 | 64.441 | 89.736 | 1.00 | 38.63 | B | O |
| ATOM | 3265 | C | GLU | B | 92 | 43.065 | 61.855 | 89.108 | 1.00 | 26.56 | B | C |
| ATOM | 3266 | O | GLU | B | 92 | 43.214 | 60.762 | 89.661 | 1.00 | 29.51 | B | O |
| ATOM | 3267 | N | VAL | B | 93 | 41.923 | 62.193 | 88.521 | 1.00 | 22.63 | B | N |
| ATOM | 3268 | CA | VAL | B | 93 | 40.803 | 61.249 | 88.493 | 1.00 | 22.22 | B | C |
| ATOM | 3269 | CB | VAL | B | 93 | 39.561 | 61.823 | 87.749 | 1.00 | 19.89 | B | C |
| ATOM | 3270 | CG1 | VAL | B | 93 | 38.587 | 60.723 | 87.455 | 1.00 | 16.96 | B | C |
| ATOM | 3271 | CG2 | VAL | B | 93 | 38.887 | 62.892 | 88.589 | 1.00 | 20.59 | B | C |
| ATOM | 3272 | C | VAL | B | 93 | 41.223 | 59.970 | 87.781 | 1.00 | 22.63 | B | C |
| ATOM | 3273 | O | VAL | B | 93 | 40.951 | 58.875 | 88.257 | 1.00 | 22.32 | B | O |
| ATOM | 3274 | N | ILE | B | 94 | 41.882 | 60.120 | 86.634 | 1.00 | 24.76 | B | N |
| ATOM | 3275 | CA | ILE | B | 94 | 42.337 | 58.978 | 85.841 | 1.00 | 24.09 | B | C |
| ATOM | 3276 | CB | ILE | B | 94 | 43.011 | 59.435 | 84.536 | 1.00 | 22.70 | B | C |
| ATOM | 3277 | CG2 | ILE | B | 94 | 43.775 | 58.277 | 83.905 | 1.00 | 17.36 | B | C |
| ATOM | 3278 | CG1 | ILE | B | 94 | 41.952 | 59.982 | 83.580 | 1.00 | 21.24 | B | C |
| ATOM | 3279 | CD1 | ILE | B | 94 | 42.522 | 60.497 | 82.285 | 1.00 | 23.67 | B | C |
| ATOM | 3280 | C | ILE | B | 94 | 43.313 | 58.107 | 86.619 | 1.00 | 25.00 | B | C |
| ATOM | 3281 | O | ILE | B | 94 | 43.440 | 56.918 | 86.350 | 1.00 | 23.32 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3282 | N | MET | B | 95 | 44.009 | 58.709 | 87.576 | 1.00 | 26.13 | B | N |
| ATOM | 3283 | CA | MET | B | 95 | 44.950 | 57.965 | 88.401 | 1.00 | 28.16 | B | C |
| ATOM | 3284 | CB | MET | B | 95 | 46.072 | 58.874 | 88.914 | 1.00 | 29.92 | B | C |
| ATOM | 3285 | CG | MET | B | 95 | 46.982 | 59.407 | 87.825 | 1.00 | 33.76 | B | C |
| ATOM | 3286 | SD | MET | B | 95 | 48.561 | 59.992 | 88.474 | 1.00 | 39.06 | B | S |
| ATOM | 3287 | CE | MET | B | 95 | 48.256 | 61.732 | 88.639 | 1.00 | 37.02 | B | C |
| ATOM | 3288 | C | MET | B | 95 | 44.202 | 57.358 | 89.580 | 1.00 | 28.27 | B | C |
| ATOM | 3289 | O | MET | B | 95 | 44.817 | 56.837 | 90.509 | 1.00 | 29.72 | B | O |
| ATOM | 3290 | N | GLY | B | 96 | 42.874 | 57.452 | 89.544 | 1.00 | 27.43 | B | N |
| ATOM | 3291 | CA | GLY | B | 96 | 42.052 | 56.873 | 90.596 | 1.00 | 24.78 | B | C |
| ATOM | 3292 | C | GLY | B | 96 | 41.714 | 57.718 | 91.805 | 1.00 | 24.85 | B | C |
| ATOM | 3293 | O | GLY | B | 96 | 41.561 | 57.185 | 92.901 | 1.00 | 23.65 | B | O |
| ATOM | 3294 | N | TYR | B | 97 | 41.580 | 59.026 | 91.619 | 1.00 | 25.98 | B | N |
| ATOM | 3295 | CA | TYR | B | 97 | 41.257 | 59.926 | 92.727 | 1.00 | 24.49 | B | C |
| ATOM | 3296 | CB | TYR | B | 97 | 42.356 | 60.985 | 92.875 | 1.00 | 24.17 | B | C |
| ATOM | 3297 | CG | TYR | B | 97 | 43.665 | 60.388 | 93.352 | 1.00 | 28.86 | B | C |
| ATOM | 3298 | CD1 | TYR | B | 97 | 43.749 | 59.738 | 94.585 | 1.00 | 31.63 | B | C |
| ATOM | 3299 | CE1 | TYR | B | 97 | 44.928 | 59.142 | 95.007 | 1.00 | 31.31 | B | C |
| ATOM | 3300 | CD2 | TYR | B | 97 | 44.803 | 60.428 | 92.561 | 1.00 | 30.09 | B | C |
| ATOM | 3301 | CE2 | TYR | B | 97 | 45.990 | 59.830 | 92.980 | 1.00 | 29.58 | B | C |
| ATOM | 3302 | CZ | TYR | B | 97 | 46.042 | 59.189 | 94.196 | 1.00 | 30.72 | B | C |
| ATOM | 3303 | OH | TYR | B | 97 | 47.201 | 58.558 | 94.586 | 1.00 | 36.08 | B | O |
| ATOM | 3304 | C | TYR | B | 97 | 39.893 | 60.582 | 92.551 | 1.00 | 23.86 | B | C |
| ATOM | 3305 | O | TYR | B | 97 | 39.392 | 60.686 | 91.432 | 1.00 | 25.48 | B | O |
| ATOM | 3306 | N | ASN | B | 98 | 39.301 | 61.012 | 93.664 | 1.00 | 23.05 | B | N |
| ATOM | 3307 | CA | ASN | B | 98 | 37.979 | 61.643 | 93.675 | 1.00 | 21.50 | B | C |
| ATOM | 3308 | CB | ASN | B | 98 | 37.173 | 61.123 | 94.865 | 1.00 | 22.93 | B | C |
| ATOM | 3309 | CG | ASN | B | 98 | 35.689 | 61.185 | 94.631 | 1.00 | 27.58 | B | C |
| ATOM | 3310 | OD1 | ASN | B | 98 | 35.150 | 62.217 | 94.239 | 1.00 | 33.76 | B | O |
| ATOM | 3311 | ND2 | ASN | B | 98 | 35.010 | 60.075 | 94.873 | 1.00 | 31.49 | B | N |
| ATOM | 3312 | C | ASN | B | 98 | 38.100 | 63.167 | 93.769 | 1.00 | 21.45 | B | C |
| ATOM | 3313 | O | ASN | B | 98 | 38.491 | 63.702 | 94.806 | 1.00 | 22.92 | B | O |
| ATOM | 3314 | N | CYS | B | 99 | 37.742 | 63.863 | 92.692 | 1.00 | 19.80 | B | N |
| ATOM | 3315 | CA | CYS | B | 99 | 37.841 | 65.318 | 92.650 | 1.00 | 17.59 | B | C |
| ATOM | 3316 | CB | CYS | B | 99 | 38.851 | 65.719 | 91.571 | 1.00 | 18.03 | B | C |
| ATOM | 3317 | SG | CYS | B | 99 | 40.532 | 65.034 | 91.864 | 1.00 | 19.68 | B | S |
| ATOM | 3318 | C | CYS | B | 99 | 36.519 | 66.056 | 92.441 | 1.00 | 16.38 | B | C |
| ATOM | 3319 | O | CYS | B | 99 | 35.509 | 65.469 | 92.072 | 1.00 | 17.60 | B | O |
| ATOM | 3320 | N | THR | B | 100 | 36.535 | 67.359 | 92.686 | 1.00 | 18.30 | B | N |
| ATOM | 3321 | CA | THR | B | 100 | 35.343 | 68.181 | 92.548 | 1.00 | 16.11 | B | C |
| ATOM | 3322 | CB | THR | B | 100 | 34.622 | 68.328 | 93.894 | 1.00 | 17.96 | B | C |
| ATOM | 3323 | OG1 | THR | B | 100 | 34.092 | 67.059 | 94.295 | 1.00 | 21.94 | B | O |
| ATOM | 3324 | CG2 | THR | B | 100 | 33.490 | 69.339 | 93.789 | 1.00 | 18.30 | B | C |
| ATOM | 3325 | C | THR | B | 100 | 35.692 | 69.568 | 92.054 | 1.00 | 18.40 | B | C |
| ATOM | 3326 | O | THR | B | 100 | 36.657 | 70.183 | 92.524 | 1.00 | 20.25 | B | O |
| ATOM | 3327 | N | ILE | B | 101 | 34.908 | 70.054 | 91.099 | 1.00 | 15.95 | B | N |
| ATOM | 3328 | CA | ILE | B | 101 | 35.096 | 71.383 | 90.548 | 1.00 | 13.69 | B | C |
| ATOM | 3329 | CB | ILE | B | 101 | 35.413 | 71.330 | 89.045 | 1.00 | 10.90 | B | C |
| ATOM | 3330 | CG2 | ILE | B | 101 | 35.555 | 72.731 | 88.501 | 1.00 | 11.54 | B | C |
| ATOM | 3331 | CG1 | ILE | B | 101 | 36.702 | 70.554 | 88.810 | 1.00 | 12.71 | B | C |
| ATOM | 3332 | CD1 | ILE | B | 101 | 37.155 | 70.519 | 87.342 | 1.00 | 10.76 | B | C |
| ATOM | 3333 | C | ILE | B | 101 | 33.772 | 72.126 | 90.755 | 1.00 | 15.49 | B | C |
| ATOM | 3334 | O | ILE | B | 101 | 32.702 | 71.582 | 90.467 | 1.00 | 15.47 | B | O |
| ATOM | 3335 | N | PHE | B | 102 | 33.849 | 73.358 | 91.254 | 1.00 | 13.02 | B | N |
| ATOM | 3336 | CA | PHE | B | 102 | 32.662 | 74.157 | 91.504 | 1.00 | 12.35 | B | C |
| ATOM | 3337 | CB | PHE | B | 102 | 32.656 | 74.661 | 92.948 | 1.00 | 12.49 | B | C |
| ATOM | 3338 | CG | PHE | B | 102 | 32.436 | 73.602 | 93.975 | 1.00 | 13.47 | B | C |
| ATOM | 3339 | CD1 | PHE | B | 102 | 31.161 | 73.130 | 94.247 | 1.00 | 12.88 | B | C |
| ATOM | 3340 | CD2 | PHE | B | 102 | 33.507 | 73.111 | 94.722 | 1.00 | 14.87 | B | C |
| ATOM | 3341 | CE1 | PHE | B | 102 | 30.950 | 72.189 | 95.249 | 1.00 | 10.33 | B | C |
| ATOM | 3342 | CE2 | PHE | B | 102 | 33.304 | 72.166 | 95.724 | 1.00 | 12.33 | B | C |
| ATOM | 3343 | CZ | PHE | B | 102 | 32.022 | 71.708 | 95.986 | 1.00 | 10.21 | B | C |
| ATOM | 3344 | C | PHE | B | 102 | 32.564 | 75.384 | 90.605 | 1.00 | 13.86 | B | C |
| ATOM | 3345 | O | PHE | B | 102 | 33.563 | 75.909 | 90.122 | 1.00 | 15.56 | B | O |
| ATOM | 3346 | N | ALA | B | 103 | 31.336 | 75.850 | 90.420 | 1.00 | 14.81 | B | N |
| ATOM | 3347 | CA | ALA | B | 103 | 31.044 | 77.050 | 89.655 | 1.00 | 14.96 | B | C |
| ATOM | 3348 | CB | ALA | B | 103 | 30.242 | 76.714 | 88.443 | 1.00 | 12.80 | B | C |
| ATOM | 3349 | C | ALA | B | 103 | 30.200 | 77.847 | 90.637 | 1.00 | 17.03 | B | C |
| ATOM | 3350 | O | ALA | B | 103 | 29.102 | 77.426 | 90.991 | 1.00 | 18.47 | B | O |
| ATOM | 3351 | N | TYR | B | 104 | 30.716 | 78.981 | 91.098 | 1.00 | 17.79 | B | N |
| ATOM | 3352 | CA | TYR | B | 104 | 30.000 | 79.793 | 92.073 | 1.00 | 20.19 | B | C |
| ATOM | 3353 | CB | TYR | B | 104 | 30.686 | 79.673 | 93.435 | 1.00 | 16.64 | B | C |
| ATOM | 3354 | CG | TYR | B | 104 | 30.151 | 80.630 | 94.471 | 1.00 | 19.32 | B | C |
| ATOM | 3355 | CD1 | TYR | B | 104 | 30.148 | 81.998 | 94.234 | 1.00 | 20.71 | B | C |
| ATOM | 3356 | CE1 | TYR | B | 104 | 29.647 | 82.890 | 95.161 | 1.00 | 19.37 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3357 | CD2 | TYR | B | 104 | 29.638 | 80.174 | 95.683 | 1.00 | 21.29 | B | C |
| ATOM | 3358 | CE2 | TYR | B | 104 | 29.133 | 81.063 | 96.624 | 1.00 | 18.86 | B | C |
| ATOM | 3359 | CZ | TYR | B | 104 | 29.140 | 82.421 | 96.348 | 1.00 | 20.87 | B | C |
| ATOM | 3360 | OH | TYR | B | 104 | 28.608 | 83.328 | 97.239 | 1.00 | 20.77 | B | O |
| ATOM | 3361 | C | TYR | B | 104 | 29.884 | 81.272 | 91.685 | 1.00 | 22.84 | B | C |
| ATOM | 3362 | O | TYR | B | 104 | 30.875 | 81.902 | 91.301 | 1.00 | 24.83 | B | O |
| ATOM | 3363 | N | GLY | B | 105 | 28.678 | 81.827 | 91.805 | 1.00 | 20.41 | B | N |
| ATOM | 3364 | CA | GLY | B | 105 | 28.481 | 83.227 | 91.478 | 1.00 | 19.88 | B | C |
| ATOM | 3365 | C | GLY | B | 105 | 27.029 | 83.624 | 91.288 | 1.00 | 19.78 | B | C |
| ATOM | 3366 | O | GLY | B | 105 | 26.132 | 82.785 | 91.322 | 1.00 | 20.42 | B | O |
| ATOM | 3367 | N | GLN | B | 106 | 26.801 | 84.913 | 91.072 | 1.00 | 17.99 | B | N |
| ATOM | 3368 | CA | GLN | B | 106 | 25.461 | 85.452 | 90.885 | 1.00 | 17.43 | B | C |
| ATOM | 3369 | CB | GLN | B | 106 | 25.519 | 86.971 | 90.955 | 1.00 | 17.38 | B | C |
| ATOM | 3370 | CG | GLN | B | 106 | 24.473 | 87.666 | 90.129 | 1.00 | 20.22 | B | C |
| ATOM | 3371 | CD | GLN | B | 106 | 24.815 | 89.123 | 89.893 | 1.00 | 21.50 | B | C |
| ATOM | 3372 | OE1 | GLN | B | 106 | 25.881 | 89.440 | 89.376 | 1.00 | 21.28 | B | O |
| ATOM | 3373 | NE2 | GLN | B | 106 | 23.908 | 90.016 | 90.269 | 1.00 | 22.52 | B | N |
| ATOM | 3374 | C | GLN | B | 106 | 24.816 | 85.023 | 89.571 | 1.00 | 18.15 | B | C |
| ATOM | 3375 | O | GLN | B | 106 | 25.479 | 84.968 | 88.546 | 1.00 | 19.29 | B | O |
| ATOM | 3376 | N | THR | B | 107 | 23.515 | 84.732 | 89.609 | 1.00 | 18.01 | B | N |
| ATOM | 3377 | CA | THR | B | 107 | 22.778 | 84.290 | 88.427 | 1.00 | 17.43 | B | C |
| ATOM | 3378 | CB | THR | B | 107 | 21.246 | 84.225 | 88.689 | 1.00 | 16.84 | B | C |
| ATOM | 3379 | OG1 | THR | B | 107 | 20.951 | 83.165 | 89.612 | 1.00 | 21.76 | B | O |
| ATOM | 3380 | CG2 | THR | B | 107 | 20.490 | 83.971 | 87.402 | 1.00 | 13.79 | B | C |
| ATOM | 3381 | C | THR | B | 107 | 23.030 | 85.184 | 87.220 | 1.00 | 20.24 | B | C |
| ATOM | 3382 | O | THR | B | 107 | 22.978 | 86.417 | 87.308 | 1.00 | 23.03 | B | O |
| ATOM | 3383 | N | GLY | B | 108 | 23.308 | 84.551 | 86.085 | 1.00 | 20.39 | B | N |
| ATOM | 3384 | CA | GLY | B | 108 | 23.579 | 85.290 | 84.871 | 1.00 | 16.88 | B | C |
| ATOM | 3385 | C | GLY | B | 108 | 25.036 | 85.685 | 84.671 | 1.00 | 15.01 | B | C |
| ATOM | 3386 | O | GLY | B | 108 | 25.342 | 86.397 | 83.719 | 1.00 | 10.83 | B | O |
| ATOM | 3387 | N | THR | B | 109 | 25.938 | 85.237 | 85.544 | 1.00 | 15.65 | B | N |
| ATOM | 3388 | CA | THR | B | 109 | 27.350 | 85.589 | 85.384 | 1.00 | 17.09 | B | C |
| ATOM | 3389 | CB | THR | B | 109 | 28.014 | 85.942 | 86.738 | 1.00 | 17.23 | B | C |
| ATOM | 3390 | OG1 | THR | B | 109 | 27.932 | 84.819 | 87.624 | 1.00 | 21.47 | B | O |
| ATOM | 3391 | CG2 | THR | B | 109 | 27.331 | 87.145 | 87.369 | 1.00 | 15.34 | B | C |
| ATOM | 3392 | C | THR | B | 109 | 28.181 | 84.504 | 84.689 | 1.00 | 15.73 | B | C |
| ATOM | 3393 | O | THR | B | 109 | 29.354 | 84.723 | 84.372 | 1.00 | 12.53 | B | O |
| ATOM | 3394 | N | GLY | B | 110 | 27.581 | 83.336 | 84.463 | 1.00 | 14.41 | B | N |
| ATOM | 3395 | CA | GLY | B | 110 | 28.308 | 82.284 | 83.776 | 1.00 | 15.72 | B | C |
| ATOM | 3396 | C | GLY | B | 110 | 28.423 | 80.894 | 84.377 | 1.00 | 16.16 | B | C |
| ATOM | 3397 | O | GLY | B | 110 | 29.123 | 80.060 | 83.801 | 1.00 | 18.25 | B | O |
| ATOM | 3398 | N | LYS | B | 111 | 27.758 | 80.630 | 85.502 | 1.00 | 14.84 | B | N |
| ATOM | 3399 | CA | LYS | B | 111 | 27.819 | 79.316 | 86.128 | 1.00 | 13.48 | B | C |
| ATOM | 3400 | CB | LYS | B | 111 | 26.791 | 79.214 | 87.268 | 1.00 | 16.16 | B | C |
| ATOM | 3401 | CG | LYS | B | 111 | 27.188 | 79.843 | 88.614 | 1.00 | 12.15 | B | C |
| ATOM | 3402 | CD | LYS | B | 111 | 25.937 | 80.084 | 89.477 | 1.00 | 12.05 | B | C |
| ATOM | 3403 | CE | LYS | B | 111 | 25.009 | 81.084 | 88.776 | 1.00 | 15.90 | B | C |
| ATOM | 3404 | NZ | LYS | B | 111 | 23.608 | 81.161 | 89.269 | 1.00 | 15.34 | B | N |
| ATOM | 3405 | C | LYS | B | 111 | 27.576 | 78.190 | 85.111 | 1.00 | 14.05 | B | C |
| ATOM | 3406 | O | LYS | B | 111 | 28.468 | 77.385 | 84.842 | 1.00 | 13.79 | B | O |
| ATOM | 3407 | N | THR | B | 112 | 26.381 | 78.145 | 84.527 | 1.00 | 13.45 | B | N |
| ATOM | 3408 | CA | THR | B | 112 | 26.056 | 77.075 | 83.582 | 1.00 | 14.11 | B | C |
| ATOM | 3409 | CB | THR | B | 112 | 24.541 | 76.993 | 83.333 | 1.00 | 13.35 | B | C |
| ATOM | 3410 | OG1 | THR | B | 112 | 23.870 | 76.818 | 84.584 | 1.00 | 15.11 | B | O |
| ATOM | 3411 | CG2 | THR | B | 112 | 24.210 | 75.801 | 82.453 | 1.00 | 10.97 | B | C |
| ATOM | 3412 | C | THR | B | 112 | 26.783 | 77.155 | 82.242 | 1.00 | 13.78 | B | C |
| ATOM | 3413 | O | THR | B | 112 | 27.037 | 76.132 | 81.612 | 1.00 | 10.37 | B | O |
| ATOM | 3414 | N | PHE | B | 113 | 27.105 | 78.364 | 81.796 | 1.00 | 14.04 | B | N |
| ATOM | 3415 | CA | PHE | B | 113 | 27.835 | 78.501 | 80.543 | 1.00 | 14.11 | B | C |
| ATOM | 3416 | CB | PHE | B | 113 | 28.042 | 79.968 | 80.209 | 1.00 | 12.24 | B | C |
| ATOM | 3417 | CG | PHE | B | 113 | 28.906 | 80.190 | 79.008 | 1.00 | 13.18 | B | C |
| ATOM | 3418 | CD1 | PHE | B | 113 | 28.427 | 79.930 | 77.740 | 1.00 | 15.18 | B | C |
| ATOM | 3419 | CD2 | PHE | B | 113 | 30.201 | 80.660 | 79.145 | 1.00 | 13.33 | B | C |
| ATOM | 3420 | CE1 | PHE | B | 113 | 29.221 | 80.138 | 76.622 | 1.00 | 12.82 | B | C |
| ATOM | 3421 | CE2 | PHE | B | 113 | 31.001 | 80.869 | 78.036 | 1.00 | 12.65 | B | C |
| ATOM | 3422 | CZ | PHE | B | 113 | 30.507 | 80.608 | 76.770 | 1.00 | 10.98 | B | C |
| ATOM | 3423 | C | PHE | B | 113 | 29.200 | 77.811 | 80.697 | 1.00 | 14.52 | B | C |
| ATOM | 3424 | O | PHE | B | 113 | 29.656 | 77.090 | 79.808 | 1.00 | 13.74 | B | O |
| ATOM | 3425 | N | THR | B | 114 | 29.839 | 78.037 | 81.841 | 1.00 | 13.89 | B | N |
| ATOM | 3426 | CA | THR | B | 114 | 31.137 | 77.438 | 82.146 | 1.00 | 12.29 | B | C |
| ATOM | 3427 | CB | THR | B | 114 | 31.695 | 77.972 | 83.472 | 1.00 | 9.97 | B | C |
| ATOM | 3428 | OG1 | THR | B | 114 | 31.756 | 79.393 | 83.421 | 1.00 | 15.41 | B | O |
| ATOM | 3429 | CG2 | THR | B | 114 | 33.069 | 77.414 | 83.744 | 1.00 | 5.85 | B | C |
| ATOM | 3430 | C | THR | B | 114 | 31.035 | 75.925 | 82.292 | 1.00 | 13.04 | B | C |
| ATOM | 3431 | O | THR | B | 114 | 31.780 | 75.183 | 81.662 | 1.00 | 17.27 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 3432 | N | MET | B | 115 | 30.102 | 75.479 | 83.120 | 1.00 | 10.95 | B | N |
| ATOM | 3433 | CA | MET | B | 115 | 29.924 | 74.059 | 83.393 | 1.00 | 13.39 | B | C |
| ATOM | 3434 | CB | MET | B | 115 | 29.095 | 73.877 | 84.669 | 1.00 | 14.53 | B | C |
| ATOM | 3435 | CG | MET | B | 115 | 29.537 | 72.698 | 85.516 | 1.00 | 17.01 | B | C |
| ATOM | 3436 | SD | MET | B | 115 | 31.219 | 72.876 | 86.164 | 1.00 | 18.74 | B | S |
| ATOM | 3437 | CE | MET | B | 115 | 31.189 | 74.548 | 86.694 | 1.00 | 14.42 | B | C |
| ATOM | 3438 | C | MET | B | 115 | 29.315 | 73.211 | 82.278 | 1.00 | 13.36 | B | C |
| ATOM | 3439 | O | MET | B | 115 | 29.710 | 72.060 | 82.088 | 1.00 | 10.96 | B | O |
| ATOM | 3440 | N | GLU | B | 116 | 28.357 | 73.763 | 81.544 | 1.00 | 14.51 | B | N |
| ATOM | 3441 | CA | GLU | B | 116 | 27.721 | 73.006 | 80.476 | 1.00 | 16.02 | B | C |
| ATOM | 3442 | CB | GLU | B | 116 | 26.199 | 73.028 | 80.640 | 1.00 | 12.94 | B | C |
| ATOM | 3443 | CG | GLU | B | 116 | 25.726 | 72.492 | 81.974 | 1.00 | 17.29 | B | C |
| ATOM | 3444 | CD | GLU | B | 116 | 24.210 | 72.279 | 82.059 | 1.00 | 19.14 | B | C |
| ATOM | 3445 | OE1 | GLU | B | 116 | 23.751 | 71.871 | 83.148 | 1.00 | 20.48 | B | O |
| ATOM | 3446 | OE2 | GLU | B | 116 | 23.479 | 72.503 | 81.065 | 1.00 | 14.72 | B | O |
| ATOM | 3447 | C | GLU | B | 116 | 28.085 | 73.498 | 79.082 | 1.00 | 18.01 | B | C |
| ATOM | 3448 | O | GLU | B | 116 | 28.487 | 72.709 | 78.234 | 1.00 | 17.29 | B | O |
| ATOM | 3449 | N | GLY | B | 117 | 27.931 | 74.801 | 78.855 | 1.00 | 19.87 | B | N |
| ATOM | 3450 | CA | GLY | B | 117 | 28.216 | 75.381 | 77.555 | 1.00 | 20.30 | B | C |
| ATOM | 3451 | C | GLY | B | 117 | 26.973 | 75.443 | 76.688 | 1.00 | 20.61 | B | C |
| ATOM | 3452 | O | GLY | B | 117 | 25.879 | 75.206 | 77.181 | 1.00 | 21.51 | B | O |
| ATOM | 3453 | N | GLU | B | 118 | 27.140 | 75.750 | 75.399 | 1.00 | 23.23 | B | N |
| ATOM | 3454 | CA | GLU | B | 118 | 26.022 | 75.840 | 74.456 | 1.00 | 24.83 | B | C |
| ATOM | 3455 | CB | GLU | B | 118 | 25.426 | 77.242 | 74.490 | 1.00 | 24.26 | B | C |
| ATOM | 3456 | CG | GLU | B | 118 | 25.511 | 77.902 | 75.833 | 1.00 | 26.72 | B | C |
| ATOM | 3457 | CD | GLU | B | 118 | 25.037 | 79.331 | 75.800 | 1.00 | 27.97 | B | C |
| ATOM | 3458 | OE1 | GLU | B | 118 | 25.253 | 79.991 | 74.761 | 1.00 | 30.60 | B | O |
| ATOM | 3459 | OE2 | GLU | B | 118 | 24.466 | 79.793 | 76.811 | 1.00 | 24.41 | B | O |
| ATOM | 3460 | C | GLU | B | 118 | 26.474 | 75.541 | 73.021 | 1.00 | 25.87 | B | C |
| ATOM | 3461 | O | GLU | B | 118 | 27.672 | 75.510 | 72.733 | 1.00 | 26.38 | B | O |
| ATOM | 3462 | N | ARG | B | 119 | 25.514 | 75.324 | 72.125 | 1.00 | 25.19 | B | N |
| ATOM | 3463 | CA | ARG | B | 119 | 25.839 | 75.059 | 70.730 | 1.00 | 28.27 | B | C |
| ATOM | 3464 | CB | ARG | B | 119 | 24.673 | 74.391 | 69.990 | 1.00 | 32.54 | B | C |
| ATOM | 3465 | CG | ARG | B | 119 | 24.189 | 73.077 | 70.555 | 1.00 | 38.99 | B | C |
| ATOM | 3466 | CD | ARG | B | 119 | 25.029 | 71.887 | 70.089 | 1.00 | 42.89 | B | C |
| ATOM | 3467 | NE | ARG | B | 119 | 25.062 | 71.737 | 68.638 | 1.00 | 44.87 | B | N |
| ATOM | 3468 | CZ | ARG | B | 119 | 25.324 | 70.591 | 68.018 | 1.00 | 46.20 | B | C |
| ATOM | 3469 | NH1 | ARG | B | 119 | 25.568 | 69.498 | 68.731 | 1.00 | 45.67 | B | N |
| ATOM | 3470 | NH2 | ARG | B | 119 | 25.355 | 70.538 | 66.689 | 1.00 | 45.96 | B | N |
| ATOM | 3471 | C | ARG | B | 119 | 26.054 | 76.417 | 70.104 | 1.00 | 28.13 | B | C |
| ATOM | 3472 | O | ARG | B | 119 | 25.426 | 77.395 | 70.517 | 1.00 | 29.25 | B | O |
| ATOM | 3473 | N | SER | B | 120 | 26.925 | 76.483 | 69.105 | 1.00 | 27.55 | B | N |
| ATOM | 3474 | CA | SER | B | 120 | 27.160 | 77.748 | 68.423 | 1.00 | 28.94 | B | C |
| ATOM | 3475 | CB | SER | B | 120 | 28.442 | 77.670 | 67.609 | 1.00 | 25.53 | B | C |
| ATOM | 3476 | OG | SER | B | 120 | 29.528 | 77.469 | 68.483 | 1.00 | 26.89 | B | O |
| ATOM | 3477 | C | SER | B | 120 | 25.970 | 78.060 | 67.516 | 1.00 | 30.08 | B | C |
| ATOM | 3478 | O | SER | B | 120 | 25.635 | 77.284 | 66.625 | 1.00 | 28.34 | B | O |
| ATOM | 3479 | N | PRO | B | 121 | 25.317 | 79.210 | 67.746 | 1.00 | 32.61 | B | N |
| ATOM | 3480 | CD | PRO | B | 121 | 25.796 | 80.236 | 68.690 | 1.00 | 32.55 | B | C |
| ATOM | 3481 | CA | PRO | B | 121 | 24.150 | 79.704 | 67.003 | 1.00 | 35.01 | B | C |
| ATOM | 3482 | CB | PRO | B | 121 | 24.262 | 81.214 | 67.179 | 1.00 | 32.75 | B | C |
| ATOM | 3483 | CG | PRO | B | 121 | 24.698 | 81.305 | 68.606 | 1.00 | 32.24 | B | C |
| ATOM | 3484 | C | PRO | B | 121 | 24.029 | 79.275 | 65.532 | 1.00 | 36.85 | B | C |
| ATOM | 3485 | O | PRO | B | 121 | 24.287 | 80.055 | 64.610 | 1.00 | 36.78 | B | O |
| ATOM | 3486 | N | ASN | B | 122 | 23.623 | 78.023 | 65.335 | 1.00 | 39.14 | B | N |
| ATOM | 3487 | CA | ASN | B | 122 | 23.431 | 77.439 | 64.013 | 1.00 | 40.78 | B | C |
| ATOM | 3488 | CB | ASN | B | 122 | 22.337 | 78.197 | 63.258 | 1.00 | 44.36 | B | C |
| ATOM | 3489 | CG | ASN | B | 122 | 20.950 | 77.943 | 63.825 | 1.00 | 46.49 | B | C |
| ATOM | 3490 | OD1 | ASN | B | 122 | 20.608 | 76.806 | 64.169 | 1.00 | 48.52 | B | O |
| ATOM | 3491 | ND2 | ASN | B | 122 | 20.134 | 78.997 | 63.904 | 1.00 | 45.64 | B | N |
| ATOM | 3492 | C | ASN | B | 122 | 24.659 | 77.310 | 63.112 | 1.00 | 40.24 | B | C |
| ATOM | 3493 | O | ASN | B | 122 | 24.516 | 77.029 | 61.915 | 1.00 | 38.39 | B | O |
| ATOM | 3494 | N | GLU | B | 123 | 25.858 | 77.509 | 63.660 | 1.00 | 38.55 | B | N |
| ATOM | 3495 | CA | GLU | B | 123 | 27.069 | 77.369 | 62.850 | 1.00 | 37.57 | B | C |
| ATOM | 3496 | CB | GLU | B | 123 | 28.032 | 78.552 | 63.056 | 1.00 | 37.27 | B | C |
| ATOM | 3497 | CG | GLU | B | 123 | 28.459 | 78.830 | 64.485 | 1.00 | 39.05 | B | C |
| ATOM | 3498 | CD | GLU | B | 123 | 27.967 | 80.182 | 64.977 | 1.00 | 38.17 | B | C |
| ATOM | 3499 | OE1 | GLU | B | 123 | 26.741 | 80.347 | 65.117 | 1.00 | 37.68 | B | O |
| ATOM | 3500 | OE2 | GLU | B | 123 | 28.802 | 81.082 | 65.220 | 1.00 | 40.75 | B | O |
| ATOM | 3501 | C | GLU | B | 123 | 27.750 | 76.048 | 63.182 | 1.00 | 34.54 | B | C |
| ATOM | 3502 | O | GLU | B | 123 | 28.919 | 76.004 | 63.549 | 1.00 | 34.43 | B | O |
| ATOM | 3503 | N | GLU | B | 124 | 26.977 | 74.978 | 63.032 | 1.00 | 32.35 | B | N |
| ATOM | 3504 | CA | GLU | B | 124 | 27.379 | 73.599 | 63.292 | 1.00 | 34.24 | B | C |
| ATOM | 3505 | CB | GLU | B | 124 | 27.085 | 72.733 | 62.063 | 1.00 | 34.60 | B | C |
| ATOM | 3506 | CG | GLU | B | 124 | 25.702 | 72.937 | 61.460 | 1.00 | 39.99 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3507 | CD | GLU | B | 124 | 24.617 | 73.228 | 62.502 | 1.00 | 43.71 | B | C |
| ATOM | 3508 | OE1 | GLU | B | 124 | 23.435 | 72.937 | 62.199 | 1.00 | 44.44 | B | O |
| ATOM | 3509 | OE2 | GLU | B | 124 | 24.935 | 73.757 | 63.605 | 1.00 | 39.76 | B | O |
| ATOM | 3510 | C | GLU | B | 124 | 28.795 | 73.292 | 63.780 | 1.00 | 33.99 | B | C |
| ATOM | 3511 | O | GLU | B | 124 | 29.779 | 73.908 | 63.366 | 1.00 | 37.04 | B | O |
| ATOM | 3512 | N | TYR | B | 125 | 28.853 | 72.293 | 64.657 | 1.00 | 31.73 | B | N |
| ATOM | 3513 | CA | TYR | B | 125 | 30.060 | 71.778 | 65.288 | 1.00 | 28.89 | B | C |
| ATOM | 3514 | CB | TYR | B | 125 | 30.683 | 72.794 | 66.247 | 1.00 | 25.95 | B | C |
| ATOM | 3515 | CG | TYR | B | 125 | 31.550 | 73.896 | 65.681 | 1.00 | 24.24 | B | C |
| ATOM | 3516 | CD1 | TYR | B | 125 | 31.074 | 75.200 | 65.586 | 1.00 | 22.46 | B | C |
| ATOM | 3517 | CE1 | TYR | B | 125 | 31.903 | 76.235 | 65.223 | 1.00 | 22.42 | B | C |
| ATOM | 3518 | CD2 | TYR | B | 125 | 32.887 | 73.669 | 65.380 | 1.00 | 22.47 | B | C |
| ATOM | 3519 | CE2 | TYR | B | 125 | 33.730 | 74.709 | 65.015 | 1.00 | 20.44 | B | C |
| ATOM | 3520 | CZ | TYR | B | 125 | 33.233 | 75.988 | 64.942 | 1.00 | 24.51 | B | C |
| ATOM | 3521 | OH | TYR | B | 125 | 34.073 | 77.035 | 64.615 | 1.00 | 26.65 | B | O |
| ATOM | 3522 | C | TYR | B | 125 | 29.560 | 70.636 | 66.163 | 1.00 | 29.35 | B | C |
| ATOM | 3523 | O | TYR | B | 125 | 28.969 | 70.904 | 67.208 | 1.00 | 31.83 | B | O |
| ATOM | 3524 | N | THR | B | 126 | 29.760 | 69.380 | 65.782 | 1.00 | 31.04 | B | N |
| ATOM | 3525 | CA | THR | B | 126 | 29.301 | 68.308 | 66.670 | 1.00 | 31.82 | B | C |
| ATOM | 3526 | CB | THR | B | 126 | 29.968 | 66.964 | 66.343 | 1.00 | 33.45 | B | C |
| ATOM | 3527 | OG1 | THR | B | 126 | 31.393 | 67.099 | 66.434 | 1.00 | 36.76 | B | O |
| ATOM | 3528 | CG2 | THR | B | 126 | 29.581 | 66.511 | 64.950 | 1.00 | 33.07 | B | C |
| ATOM | 3529 | C | THR | B | 126 | 29.756 | 68.762 | 68.056 | 1.00 | 30.11 | B | C |
| ATOM | 3530 | O | THR | B | 126 | 30.823 | 69.361 | 68.177 | 1.00 | 29.09 | B | O |
| ATOM | 3531 | N | TRP | B | 127 | 28.966 | 68.493 | 69.096 | 1.00 | 29.92 | B | N |
| ATOM | 3532 | CA | TRP | B | 127 | 29.331 | 68.948 | 70.443 | 1.00 | 27.38 | B | C |
| ATOM | 3533 | CB | TRP | B | 127 | 28.400 | 68.347 | 71.503 | 1.00 | 22.99 | B | C |
| ATOM | 3534 | CG | TRP | B | 127 | 28.502 | 66.868 | 71.711 | 1.00 | 20.52 | B | C |
| ATOM | 3535 | CD2 | TRP | B | 127 | 29.356 | 66.189 | 72.642 | 1.00 | 19.37 | B | C |
| ATOM | 3536 | CE2 | TRP | B | 127 | 29.039 | 64.814 | 72.577 | 1.00 | 19.08 | B | C |
| ATOM | 3537 | CE3 | TRP | B | 127 | 30.355 | 66.609 | 73.526 | 1.00 | 20.00 | B | C |
| ATOM | 3538 | CD1 | TRP | B | 127 | 27.730 | 65.897 | 71.124 | 1.00 | 22.04 | B | C |
| ATOM | 3539 | NE1 | TRP | B | 127 | 28.045 | 64.663 | 71.646 | 1.00 | 18.75 | B | N |
| ATOM | 3540 | CZ2 | TRP | B | 127 | 29.685 | 63.861 | 73.364 | 1.00 | 18.36 | B | C |
| ATOM | 3541 | CZ3 | TRP | B | 127 | 30.996 | 65.662 | 74.305 | 1.00 | 18.13 | B | C |
| ATOM | 3542 | CH2 | TRP | B | 127 | 30.658 | 64.302 | 74.219 | 1.00 | 18.64 | B | C |
| ATOM | 3543 | C | TRP | B | 127 | 30.787 | 68.724 | 70.856 | 1.00 | 27.11 | B | C |
| ATOM | 3544 | O | TRP | B | 127 | 31.261 | 69.348 | 71.805 | 1.00 | 25.48 | B | O |
| ATOM | 3545 | N | GLU | B | 128 | 31.495 | 67.847 | 70.147 | 1.00 | 26.94 | B | N |
| ATOM | 3546 | CA | GLU | B | 128 | 32.893 | 67.582 | 70.456 | 1.00 | 28.14 | B | C |
| ATOM | 3547 | CB | GLU | B | 128 | 33.342 | 66.242 | 69.870 | 1.00 | 32.58 | B | C |
| ATOM | 3548 | CG | GLU | B | 128 | 32.878 | 65.011 | 70.624 | 1.00 | 33.69 | B | C |
| ATOM | 3549 | CD | GLU | B | 128 | 31.611 | 64.419 | 70.059 | 1.00 | 35.90 | B | C |
| ATOM | 3550 | OE1 | GLU | B | 128 | 31.188 | 63.354 | 70.561 | 1.00 | 40.13 | B | O |
| ATOM | 3551 | OE2 | GLU | B | 128 | 31.038 | 65.010 | 69.115 | 1.00 | 37.58 | B | O |
| ATOM | 3552 | C | GLU | B | 128 | 33.832 | 68.668 | 69.943 | 1.00 | 28.98 | B | C |
| ATOM | 3553 | O | GLU | B | 128 | 34.853 | 68.953 | 70.563 | 1.00 | 31.28 | B | O |
| ATOM | 3554 | N | GLU | B | 129 | 33.495 | 69.272 | 68.810 | 1.00 | 29.63 | B | N |
| ATOM | 3555 | CA | GLU | B | 129 | 34.338 | 70.312 | 68.231 | 1.00 | 28.86 | B | C |
| ATOM | 3556 | CB | GLU | B | 129 | 34.387 | 70.178 | 66.698 | 1.00 | 31.73 | B | C |
| ATOM | 3557 | CG | GLU | B | 129 | 35.071 | 68.915 | 66.160 | 1.00 | 36.15 | B | C |
| ATOM | 3558 | CD | GLU | B | 129 | 35.301 | 68.944 | 64.639 | 1.00 | 39.21 | B | C |
| ATOM | 3559 | OE1 | GLU | B | 129 | 35.717 | 67.904 | 64.088 | 1.00 | 41.42 | B | O |
| ATOM | 3560 | OE2 | GLU | B | 129 | 35.080 | 69.996 | 63.992 | 1.00 | 39.83 | B | O |
| ATOM | 3561 | C | GLU | B | 129 | 33.882 | 71.722 | 68.581 | 1.00 | 28.21 | B | C |
| ATOM | 3562 | O | GLU | B | 129 | 34.677 | 72.666 | 68.531 | 1.00 | 30.14 | B | O |
| ATOM | 3563 | N | ASP | B | 130 | 32.608 | 71.867 | 68.939 | 1.00 | 26.28 | B | N |
| ATOM | 3564 | CA | ASP | B | 130 | 32.041 | 73.183 | 69.252 | 1.00 | 22.99 | B | C |
| ATOM | 3565 | CB | ASP | B | 130 | 30.590 | 73.008 | 69.720 | 1.00 | 18.97 | B | C |
| ATOM | 3566 | CG | ASP | B | 130 | 29.762 | 74.283 | 69.598 | 1.00 | 16.27 | B | C |
| ATOM | 3567 | OD1 | ASP | B | 130 | 28.543 | 74.174 | 69.362 | 1.00 | 14.99 | B | O |
| ATOM | 3568 | OD2 | ASP | B | 130 | 30.310 | 75.390 | 69.752 | 1.00 | 12.61 | B | O |
| ATOM | 3569 | C | ASP | B | 130 | 32.864 | 73.950 | 70.295 | 1.00 | 23.11 | B | C |
| ATOM | 3570 | O | ASP | B | 130 | 33.038 | 73.506 | 71.428 | 1.00 | 23.70 | B | O |
| ATOM | 3571 | N | PRO | B | 131 | 33.388 | 75.119 | 69.912 | 1.00 | 23.86 | B | N |
| ATOM | 3572 | CD | PRO | B | 131 | 33.249 | 75.712 | 68.573 | 1.00 | 24.14 | B | C |
| ATOM | 3573 | CA | PRO | B | 131 | 34.202 | 75.981 | 70.776 | 1.00 | 24.27 | B | C |
| ATOM | 3574 | CB | PRO | B | 131 | 34.589 | 77.140 | 69.856 | 1.00 | 22.37 | B | C |
| ATOM | 3575 | CG | PRO | B | 131 | 34.477 | 76.569 | 68.495 | 1.00 | 23.73 | B | C |
| ATOM | 3576 | C | PRO | B | 131 | 33.454 | 76.491 | 72.002 | 1.00 | 22.06 | B | C |
| ATOM | 3577 | O | PRO | B | 131 | 34.070 | 76.941 | 72.971 | 1.00 | 20.25 | B | O |
| ATOM | 3578 | N | LEU | B | 132 | 32.126 | 76.435 | 71.949 | 1.00 | 22.76 | B | N |
| ATOM | 3579 | CA | LEU | B | 132 | 31.296 | 76.919 | 73.050 | 1.00 | 21.73 | B | C |
| ATOM | 3580 | CB | LEU | B | 132 | 30.028 | 77.581 | 72.508 | 1.00 | 18.93 | B | C |
| ATOM | 3581 | CG | LEU | B | 132 | 30.290 | 78.747 | 71.553 | 1.00 | 18.36 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3582 | CD1 | LEU | B | 132 | 28.963 | 79.361 | 71.116 | 1.00 | 16.68 | B | C |
| ATOM | 3583 | CD2 | LEU | B | 132 | 31.164 | 79.781 | 72.238 | 1.00 | 12.83 | B | C |
| ATOM | 3584 | C | LEU | B | 132 | 30.910 | 75.856 | 74.060 | 1.00 | 21.26 | B | C |
| ATOM | 3585 | O | LEU | B | 132 | 30.175 | 76.141 | 74.996 | 1.00 | 24.67 | B | O |
| ATOM | 3586 | N | ALA | B | 133 | 31.399 | 74.634 | 73.876 | 1.00 | 21.14 | B | N |
| ATOM | 3587 | CA | ALA | B | 133 | 31.098 | 73.551 | 74.809 | 1.00 | 19.34 | B | C |
| ATOM | 3588 | CB | ALA | B | 133 | 31.598 | 72.226 | 74.250 | 1.00 | 17.93 | B | C |
| ATOM | 3589 | C | ALA | B | 133 | 31.758 | 73.830 | 76.161 | 1.00 | 17.85 | B | C |
| ATOM | 3590 | O | ALA | B | 133 | 32.871 | 74.373 | 76.221 | 1.00 | 17.39 | B | O |
| ATOM | 3591 | N | GLY | B | 134 | 31.068 | 73.452 | 77.236 | 1.00 | 15.35 | B | N |
| ATOM | 3592 | CA | GLY | B | 134 | 31.589 | 73.671 | 78.573 | 1.00 | 14.42 | B | C |
| ATOM | 3593 | C | GLY | B | 134 | 32.380 | 72.501 | 79.100 | 1.00 | 12.81 | B | C |
| ATOM | 3594 | O | GLY | B | 134 | 32.624 | 71.534 | 78.398 | 1.00 | 14.63 | B | O |
| ATOM | 3595 | N | ILE | B | 135 | 32.761 | 72.584 | 80.362 | 1.00 | 13.28 | B | N |
| ATOM | 3596 | CA | ILE | B | 135 | 33.550 | 71.537 | 80.994 | 1.00 | 15.88 | B | C |
| ATOM | 3597 | CB | ILE | B | 135 | 33.816 | 71.898 | 82.451 | 1.00 | 17.26 | B | C |
| ATOM | 3598 | CG2 | ILE | B | 135 | 34.730 | 70.869 | 83.087 | 1.00 | 19.11 | B | C |
| ATOM | 3599 | CG1 | ILE | B | 135 | 34.435 | 73.292 | 82.511 | 1.00 | 19.66 | B | C |
| ATOM | 3600 | CD1 | ILE | B | 135 | 34.579 | 73.833 | 83.909 | 1.00 | 23.20 | B | C |
| ATOM | 3601 | C | ILE | B | 135 | 32.958 | 70.134 | 80.932 | 1.00 | 16.69 | B | C |
| ATOM | 3602 | O | ILE | B | 135 | 33.649 | 69.191 | 80.551 | 1.00 | 20.13 | B | O |
| ATOM | 3603 | N | ILE | B | 136 | 31.689 | 69.983 | 81.301 | 1.00 | 15.13 | B | N |
| ATOM | 3604 | CA | ILE | B | 136 | 31.072 | 68.666 | 81.289 | 1.00 | 11.64 | B | C |
| ATOM | 3605 | CB | ILE | B | 136 | 29.548 | 68.745 | 81.576 | 1.00 | 10.42 | B | C |
| ATOM | 3606 | CG2 | ILE | B | 136 | 28.883 | 67.396 | 81.304 | 1.00 | 6.78 | B | C |
| ATOM | 3607 | CG1 | ILE | B | 136 | 29.333 | 69.135 | 83.043 | 1.00 | 11.27 | B | C |
| ATOM | 3608 | CD1 | ILE | B | 136 | 27.926 | 69.598 | 83.376 | 1.00 | 12.66 | B | C |
| ATOM | 3609 | C | ILE | B | 136 | 31.330 | 67.940 | 79.981 | 1.00 | 10.93 | B | C |
| ATOM | 3610 | O | ILE | B | 136 | 31.922 | 66.869 | 79.980 | 1.00 | 11.23 | B | O |
| ATOM | 3611 | N | PRO | B | 137 | 30.907 | 68.523 | 78.847 | 1.00 | 14.85 | B | N |
| ATOM | 3612 | CD | PRO | B | 137 | 30.170 | 69.794 | 78.775 | 1.00 | 16.19 | B | C |
| ATOM | 3613 | CA | PRO | B | 137 | 31.081 | 67.955 | 77.503 | 1.00 | 14.86 | B | C |
| ATOM | 3614 | CB | PRO | B | 137 | 30.522 | 69.048 | 76.596 | 1.00 | 14.73 | B | C |
| ATOM | 3615 | CG | PRO | B | 137 | 29.505 | 69.702 | 77.437 | 1.00 | 15.60 | B | C |
| ATOM | 3616 | C | PRO | B | 137 | 32.539 | 67.621 | 77.149 | 1.00 | 14.64 | B | C |
| ATOM | 3617 | O | PRO | B | 137 | 32.840 | 66.504 | 76.729 | 1.00 | 16.40 | B | O |
| ATOM | 3618 | N | ARG | B | 138 | 33.432 | 68.595 | 77.316 | 1.00 | 10.50 | B | N |
| ATOM | 3619 | CA | ARG | B | 138 | 34.850 | 68.415 | 77.008 | 1.00 | 12.94 | B | C |
| ATOM | 3620 | CB | ARG | B | 138 | 35.609 | 69.727 | 77.190 | 1.00 | 9.46 | B | C |
| ATOM | 3621 | CG | ARG | B | 138 | 35.199 | 70.826 | 76.240 | 1.00 | 9.32 | B | C |
| ATOM | 3622 | CD | ARG | B | 138 | 35.800 | 72.139 | 76.690 | 1.00 | 14.52 | B | C |
| ATOM | 3623 | NE | ARG | B | 138 | 35.453 | 73.242 | 75.810 | 1.00 | 16.04 | B | N |
| ATOM | 3624 | CZ | ARG | B | 138 | 36.063 | 73.496 | 74.659 | 1.00 | 19.17 | B | C |
| ATOM | 3625 | NH1 | ARG | B | 138 | 37.056 | 72.719 | 74.253 | 1.00 | 16.45 | B | N |
| ATOM | 3626 | NH2 | ARG | B | 138 | 35.680 | 74.529 | 73.914 | 1.00 | 22.10 | B | N |
| ATOM | 3627 | C | ARG | B | 138 | 35.505 | 67.350 | 77.880 | 1.00 | 15.14 | B | C |
| ATOM | 3628 | O | ARG | B | 138 | 36.464 | 66.697 | 77.470 | 1.00 | 17.25 | B | O |
| ATOM | 3629 | N | THR | B | 139 | 34.984 | 67.180 | 79.085 | 1.00 | 16.70 | B | N |
| ATOM | 3630 | CA | THR | B | 139 | 35.528 | 66.200 | 80.013 | 1.00 | 17.41 | B | C |
| ATOM | 3631 | CB | THR | B | 139 | 35.023 | 66.469 | 81.441 | 1.00 | 15.52 | B | C |
| ATOM | 3632 | OG1 | THR | B | 139 | 35.452 | 67.773 | 81.841 | 1.00 | 18.68 | B | O |
| ATOM | 3633 | CG2 | THR | B | 139 | 35.578 | 65.443 | 82.421 | 1.00 | 12.34 | B | C |
| ATOM | 3634 | C | THR | B | 139 | 35.179 | 64.773 | 79.630 | 1.00 | 17.92 | B | C |
| ATOM | 3635 | O | THR | B | 139 | 36.029 | 63.890 | 79.672 | 1.00 | 17.76 | B | O |
| ATOM | 3636 | N | LEU | B | 140 | 33.924 | 64.550 | 79.263 | 1.00 | 20.04 | B | N |
| ATOM | 3637 | CA | LEU | B | 140 | 33.471 | 63.219 | 78.879 | 1.00 | 21.48 | B | C |
| ATOM | 3638 | CB | LEU | B | 140 | 31.957 | 63.221 | 78.663 | 1.00 | 22.65 | B | C |
| ATOM | 3639 | CG | LEU | B | 140 | 31.141 | 63.605 | 79.901 | 1.00 | 21.83 | B | C |
| ATOM | 3640 | CD1 | LEU | B | 140 | 29.662 | 63.532 | 79.588 | 1.00 | 22.80 | B | C |
| ATOM | 3641 | CD2 | LEU | B | 140 | 31.488 | 62.693 | 81.041 | 1.00 | 18.53 | B | C |
| ATOM | 3642 | C | LEU | B | 140 | 34.174 | 62.750 | 77.612 | 1.00 | 22.42 | B | C |
| ATOM | 3643 | O | LEU | B | 140 | 34.506 | 61.571 | 77.483 | 1.00 | 20.68 | B | O |
| ATOM | 3644 | N | HIS | B | 141 | 34.395 | 63.682 | 76.684 | 1.00 | 22.02 | B | N |
| ATOM | 3645 | CA | HIS | B | 141 | 35.070 | 63.371 | 75.429 | 1.00 | 21.49 | B | C |
| ATOM | 3646 | CB | HIS | B | 141 | 35.104 | 64.610 | 74.531 | 1.00 | 23.02 | B | C |
| ATOM | 3647 | CG | HIS | B | 141 | 35.681 | 64.363 | 73.172 | 1.00 | 24.94 | B | C |
| ATOM | 3648 | CD2 | HIS | B | 141 | 36.659 | 65.003 | 72.491 | 1.00 | 25.57 | B | C |
| ATOM | 3649 | ND1 | HIS | B | 141 | 35.204 | 63.386 | 72.327 | 1.00 | 28.32 | B | N |
| ATOM | 3650 | CE1 | HIS | B | 141 | 35.859 | 63.439 | 71.181 | 1.00 | 26.04 | B | C |
| ATOM | 3651 | NE2 | HIS | B | 141 | 36.747 | 64.413 | 71.255 | 1.00 | 21.76 | B | N |
| ATOM | 3652 | C | HIS | B | 141 | 36.487 | 62.921 | 75.738 | 1.00 | 20.63 | B | C |
| ATOM | 3653 | O | HIS | B | 141 | 36.951 | 61.897 | 75.241 | 1.00 | 21.86 | B | O |
| ATOM | 3654 | N | GLN | B | 142 | 37.162 | 63.690 | 76.583 | 1.00 | 19.17 | B | N |
| ATOM | 3655 | CA | GLN | B | 142 | 38.527 | 63.385 | 76.965 | 1.00 | 19.12 | B | C |
| ATOM | 3656 | CB | GLN | B | 142 | 39.066 | 64.483 | 77.881 | 1.00 | 18.74 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3657 | CG | GLN | B | 142 | 39.304 | 65.810 | 77.175 | 1.00 | 21.72 | B | C |
| ATOM | 3658 | CD | GLN | B | 142 | 40.349 | 65.692 | 76.066 | 1.00 | 27.32 | B | C |
| ATOM | 3659 | OE1 | GLN | B | 142 | 41.475 | 65.242 | 76.306 | 1.00 | 27.45 | B | O |
| ATOM | 3660 | NE2 | GLN | B | 142 | 39.981 | 66.097 | 74.849 | 1.00 | 22.68 | B | N |
| ATOM | 3661 | C | GLN | B | 142 | 38.672 | 62.020 | 77.630 | 1.00 | 20.10 | B | C |
| ATOM | 3662 | O | GLN | B | 142 | 39.618 | 61.290 | 77.339 | 1.00 | 20.60 | B | O |
| ATOM | 3663 | N | ILE | B | 143 | 37.736 | 61.671 | 78.513 | 1.00 | 21.45 | B | N |
| ATOM | 3664 | CA | ILE | B | 143 | 37.786 | 60.382 | 79.205 | 1.00 | 19.48 | B | C |
| ATOM | 3665 | CB | ILE | B | 143 | 36.541 | 60.128 | 80.065 | 1.00 | 18.76 | B | C |
| ATOM | 3666 | CG2 | ILE | B | 143 | 36.488 | 58.676 | 80.466 | 1.00 | 21.05 | B | C |
| ATOM | 3667 | CG1 | ILE | B | 143 | 36.573 | 60.979 | 81.327 | 1.00 | 20.98 | B | C |
| ATOM | 3668 | CD1 | ILE | B | 143 | 35.318 | 60.799 | 82.197 | 1.00 | 16.97 | B | C |
| ATOM | 3669 | C | ILE | B | 143 | 37.876 | 59.237 | 78.213 | 1.00 | 18.61 | B | C |
| ATOM | 3670 | O | ILE | B | 143 | 38.709 | 58.347 | 78.361 | 1.00 | 17.15 | B | O |
| ATOM | 3671 | N | PHE | B | 144 | 37.001 | 59.261 | 77.215 | 1.00 | 18.47 | B | N |
| ATOM | 3672 | CA | PHE | B | 144 | 36.971 | 58.226 | 76.195 | 1.00 | 19.05 | B | C |
| ATOM | 3673 | CB | PHE | B | 144 | 35.710 | 58.380 | 75.345 | 1.00 | 17.56 | B | C |
| ATOM | 3674 | CG | PHE | B | 144 | 34.463 | 57.944 | 76.051 | 1.00 | 21.75 | B | C |
| ATOM | 3675 | CD1 | PHE | B | 144 | 34.088 | 56.611 | 76.057 | 1.00 | 23.21 | B | C |
| ATOM | 3676 | CD2 | PHE | B | 144 | 33.677 | 58.861 | 76.737 | 1.00 | 24.23 | B | C |
| ATOM | 3677 | CE1 | PHE | B | 144 | 32.953 | 56.198 | 76.732 | 1.00 | 23.39 | B | C |
| ATOM | 3678 | CE2 | PHE | B | 144 | 32.543 | 58.457 | 77.413 | 1.00 | 23.12 | B | C |
| ATOM | 3679 | CZ | PHE | B | 144 | 32.178 | 57.126 | 77.412 | 1.00 | 24.11 | B | C |
| ATOM | 3680 | C | PHE | B | 144 | 38.209 | 58.276 | 75.326 | 1.00 | 19.37 | B | C |
| ATOM | 3681 | O | PHE | B | 144 | 38.830 | 57.256 | 75.060 | 1.00 | 20.27 | B | O |
| ATOM | 3682 | N | GLU | B | 145 | 38.566 | 59.475 | 74.893 | 1.00 | 19.70 | B | N |
| ATOM | 3683 | CA | GLU | B | 145 | 39.728 | 59.676 | 74.050 | 1.00 | 19.14 | B | C |
| ATOM | 3684 | CB | GLU | B | 145 | 39.839 | 61.159 | 73.712 | 1.00 | 23.32 | B | C |
| ATOM | 3685 | CG | GLU | B | 145 | 39.835 | 61.484 | 72.232 | 1.00 | 30.02 | B | C |
| ATOM | 3686 | CD | GLU | B | 145 | 41.232 | 61.511 | 71.644 | 1.00 | 32.94 | B | C |
| ATOM | 3687 | OE1 | GLU | B | 145 | 41.856 | 60.435 | 71.552 | 1.00 | 34.33 | B | O |
| ATOM | 3688 | OE2 | GLU | B | 145 | 41.711 | 62.612 | 71.284 | 1.00 | 34.33 | B | O |
| ATOM | 3689 | C | GLU | B | 145 | 41.002 | 59.213 | 74.754 | 1.00 | 20.48 | B | C |
| ATOM | 3690 | O | GLU | B | 145 | 41.789 | 58.449 | 74.202 | 1.00 | 20.86 | B | O |
| ATOM | 3691 | N | LYS | B | 146 | 41.197 | 59.675 | 75.982 | 1.00 | 20.59 | B | N |
| ATOM | 3692 | CA | LYS | B | 146 | 42.383 | 59.345 | 76.751 | 1.00 | 20.94 | B | C |
| ATOM | 3693 | CB | LYS | B | 146 | 42.367 | 60.123 | 78.065 | 1.00 | 23.43 | B | C |
| ATOM | 3694 | CG | LYS | B | 146 | 43.701 | 60.718 | 78.470 | 1.00 | 30.29 | B | C |
| ATOM | 3695 | CD | LYS | B | 146 | 43.686 | 62.235 | 78.315 | 1.00 | 32.85 | B | C |
| ATOM | 3696 | CE | LYS | B | 146 | 42.668 | 62.857 | 79.252 | 1.00 | 34.01 | B | C |
| ATOM | 3697 | NZ | LYS | B | 146 | 42.431 | 64.309 | 78.981 | 1.00 | 37.35 | B | N |
| ATOM | 3698 | C | LYS | B | 146 | 42.545 | 57.855 | 77.048 | 1.00 | 22.12 | B | C |
| ATOM | 3699 | O | LYS | B | 146 | 43.571 | 57.259 | 76.736 | 1.00 | 24.37 | B | O |
| ATOM | 3700 | N | LEU | B | 147 | 41.529 | 57.256 | 77.653 | 1.00 | 22.43 | B | N |
| ATOM | 3701 | CA | LEU | B | 147 | 41.574 | 55.850 | 78.021 | 1.00 | 21.91 | B | C |
| ATOM | 3702 | CB | LEU | B | 147 | 40.395 | 55.532 | 78.946 | 1.00 | 21.24 | B | C |
| ATOM | 3703 | CG | LEU | B | 147 | 40.331 | 56.431 | 80.188 | 1.00 | 22.12 | B | C |
| ATOM | 3704 | CD1 | LEU | B | 147 | 39.105 | 56.069 | 81.007 | 1.00 | 25.32 | B | C |
| ATOM | 3705 | CD2 | LEU | B | 147 | 41.607 | 56.287 | 81.023 | 1.00 | 17.26 | B | C |
| ATOM | 3706 | C | LEU | B | 147 | 41.592 | 54.889 | 76.837 | 1.00 | 23.93 | B | C |
| ATOM | 3707 | O | LEU | B | 147 | 42.230 | 53.840 | 76.899 | 1.00 | 26.66 | B | O |
| ATOM | 3708 | N | THR | B | 148 | 40.886 | 55.232 | 75.767 | 1.00 | 22.66 | B | N |
| ATOM | 3709 | CA | THR | B | 148 | 40.861 | 54.388 | 74.591 | 1.00 | 22.70 | B | C |
| ATOM | 3710 | CB | THR | B | 148 | 39.798 | 54.877 | 73.569 | 1.00 | 24.37 | B | C |
| ATOM | 3711 | OG1 | THR | B | 148 | 38.481 | 54.639 | 74.081 | 1.00 | 27.07 | B | O |
| ATOM | 3712 | CG2 | THR | B | 148 | 39.954 | 54.155 | 72.251 | 1.00 | 23.55 | B | C |
| ATOM | 3713 | C | THR | B | 148 | 42.241 | 54.460 | 73.942 | 1.00 | 25.07 | B | C |
| ATOM | 3714 | O | THR | B | 148 | 42.728 | 53.479 | 73.382 | 1.00 | 25.67 | B | 0 |
| ATOM | 3715 | N | ASP | B | 149 | 42.877 | 55.625 | 74.033 | 1.00 | 24.97 | B | N |
| ATOM | 3716 | CA | ASP | B | 149 | 44.183 | 55.822 | 73.425 | 1.00 | 25.79 | B | C |
| ATOM | 3717 | CB | ASP | B | 149 | 44.578 | 57.295 | 73.471 | 1.00 | 30.12 | B | C |
| ATOM | 3718 | CG | ASP | B | 149 | 45.744 | 57.616 | 72.544 | 1.00 | 35.63 | B | C |
| ATOM | 3719 | OD1 | ASP | B | 149 | 45.623 | 57.345 | 71.325 | 1.00 | 37.02 | B | O |
| ATOM | 3720 | OD2 | ASP | B | 149 | 46.776 | 58.138 | 73.027 | 1.00 | 35.21 | B | O |
| ATOM | 3721 | C | ASP | B | 149 | 45.277 | 54.980 | 74.060 | 1.00 | 27.85 | B | C |
| ATOM | 3722 | O | ASP | B | 149 | 46.141 | 54.452 | 73.357 | 1.00 | 31.19 | B | O |
| ATOM | 3723 | N | ASN | B | 150 | 45.264 | 54.852 | 75.381 | 1.00 | 27.11 | B | N |
| ATOM | 3724 | CA | ASN | B | 150 | 46.277 | 54.043 | 76.031 | 1.00 | 27.67 | B | C |
| ATOM | 372S | CB | ASN | B | 150 | 46.673 | 54.639 | 77.394 | 1.00 | 26.27 | B | C |
| ATOM | 3726 | CG | ASN | B | 150 | 45.502 | 54.779 | 78.348 | 1.00 | 25.85 | B | C |
| ATOM | 3727 | OD1 | ASN | B | 150 | 44.654 | 53.894 | 78.448 | 1.00 | 27.23 | B | O |
| ATOM | 3728 | ND2 | ASN | B | 150 | 45.463 | 55.888 | 79.074 | 1.00 | 25.93 | B | N |
| ATOM | 3729 | C | ASN | B | 150 | 45.817 | 52.593 | 76.189 | 1.00 | 29.73 | B | C |
| ATOM | 3730 | O | ASN | B | 150 | 46.507 | 51.781 | 76.801 | 1.00 | 31.84 | B | O |
| ATOM | 3731 | N | GLY | B | 151 | 44.648 | 52.279 | 75.634 | 1.00 | 30.76 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3732 | CA | GLY | B | 151 | 44.115 | 50.925 | 75.695 | 1.00 | 31.11 | B | C |
| ATOM | 3733 | C | GLY | B | 151 | 43.700 | 50.378 | 77.050 | 1.00 | 33.33 | B | C |
| ATOM | 3734 | O | GLY | B | 151 | 43.784 | 49.169 | 77.276 | 1.00 | 35.22 | B | O |
| ATOM | 3735 | N | THR | B | 152 | 43.238 | 51.247 | 77.948 | 1.00 | 34.09 | B | N |
| ATOM | 3736 | CA | THR | B | 152 | 42.803 | 50.820 | 79.279 | 1.00 | 31.78 | B | C |
| ATOM | 3737 | CB | THR | B | 152 | 42.744 | 52.015 | 80.262 | 1.00 | 31.96 | B | C |
| ATOM | 3738 | OG1 | THR | B | 152 | 44.021 | 52.660 | 80.325 | 1.00 | 31.34 | B | O |
| ATOM | 3739 | CG2 | THR | B | 152 | 42.359 | 51.538 | 81.658 | 1.00 | 31.59 | B | C |
| ATOM | 3740 | C | THR | B | 152 | 41.410 | 50.185 | 79.243 | 1.00 | 31.33 | B | C |
| ATOM | 3741 | O | THR | B | 152 | 40.552 | 50.606 | 78.473 | 1.00 | 33.47 | B | O |
| ATOM | 3742 | N | GLU | B | 153 | 41.194 | 49.165 | 80.066 | 1.00 | 30.61 | B | N |
| ATOM | 3743 | CA | GLU | B | 153 | 39.886 | 48.521 | 80.149 | 1.00 | 28.90 | B | C |
| ATOM | 3744 | CB | GLU | B | 153 | 40.010 | 47.098 | 80.714 | 1.00 | 27.86 | B | C |
| ATOM | 3745 | CG | GLU | B | 153 | 38.701 | 46.302 | 80.718 | 1.00 | 30.70 | B | C |
| ATOM | 3746 | CD | GLU | B | 153 | 38.867 | 44.859 | 81.198 | 1.00 | 33.07 | B | C |
| ATOM | 3747 | OE1 | GLU | B | 153 | 39.699 | 44.128 | 80.615 | 1.00 | 34.44 | B | O |
| ATOM | 3748 | OE2 | GLU | B | 153 | 38.160 | 44.448 | 82.147 | 1.00 | 31.30 | B | O |
| ATOM | 3749 | C | GLU | B | 153 | 39.127 | 49.416 | 81.119 | 1.00 | 26.91 | B | C |
| ATOM | 3750 | O | GLU | B | 153 | 39.533 | 49.566 | 82.268 | 1.00 | 27.21 | B | O |
| ATOM | 3751 | N | PHE | B | 154 | 38.034 | 50.016 | 80.661 | 1.00 | 26.38 | B | N |
| ATOM | 3752 | CA | PHE | B | 154 | 37.266 | 50.928 | 81.516 | 1.00 | 13.54 | B | C |
| ATOM | 3753 | CB | PHE | B | 154 | 37.820 | 52.347 | 81.365 | 1.00 | 21.73 | B | C |
| ATOM | 3754 | CG | PHE | B | 154 | 37.542 | 52.956 | 80.016 | 1.00 | 19.24 | B | C |
| ATOM | 3755 | CD1 | PHE | B | 154 | 36.434 | 53.770 | 79.821 | 1.00 | 19.90 | B | C |
| ATOM | 3756 | CD2 | PHE | B | 154 | 38.348 | 52.665 | 78.929 | 1.00 | 18.83 | B | C |
| ATOM | 3757 | CE1 | PHE | B | 154 | 36.131 | 54.283 | 78.565 | 1.00 | 19.50 | B | C |
| ATOM | 3758 | CE2 | PHE | B | 154 | 38.054 | 53.171 | 77.667 | 1.00 | 19.32 | B | C |
| ATOM | 3759 | CZ | PHE | B | 154 | 36.945 | 53.981 | 77.484 | 1.00 | 18.95 | B | C |
| ATOM | 3760 | C | PHE | B | 154 | 35.782 | 50.959 | 81.189 | 1.00 | 21.47 | B | C |
| ATOM | 3761 | O | PHE | B | 154 | 35.369 | 50.676 | 80.071 | 1.00 | 21.81 | B | O |
| ATOM | 3762 | N | SER | B | 155 | 34.983 | 51.319 | 82.183 | 1.00 | 23.10 | B | N |
| ATOM | 3763 | CA | SER | B | 155 | 33.537 | 51.443 | 82.015 | 1.00 | 20.67 | B | C |
| ATOM | 3764 | CB | SER | B | 155 | 32.789 | 50.333 | 82.761 | 1.00 | 19.80 | B | C |
| ATOM | 3765 | OG | SER | B | 155 | 32.961 | 50.444 | 84.158 | 1.00 | 23.37 | B | O |
| ATOM | 3766 | C | SER | B | 155 | 33.206 | 52.792 | 82.616 | 1.00 | 16.89 | B | C |
| ATOM | 3767 | O | SER | B | 155 | 33.793 | 53.178 | 83.620 | 1.00 | 17.26 | B | O |
| ATOM | 3768 | N | VAL | B | 156 | 32.284 | 53.505 | 81.980 | 1.00 | 16.25 | B | N |
| ATOM | 3769 | CA | VAL | B | 156 | 31.861 | 54.829 | 82.419 | 1.00 | 15.99 | B | C |
| ATOM | 3770 | CB | VAL | B | 156 | 32.112 | 55.892 | 81.323 | 1.00 | 13.77 | B | C |
| ATOM | 3771 | CG1 | VAL | B | 156 | 31.472 | 57.198 | 81.721 | 1.00 | 12.35 | B | C |
| ATOM | 3772 | CG2 | VAL | B | 156 | 33.594 | 56.093 | 81.108 | 1.00 | 12.87 | B | C |
| ATOM | 3773 | C | VAL | B | 156 | 30.384 | 54.914 | 82.779 | 1.00 | 17.74 | B | C |
| ATOM | 3774 | O | VAL | B | 156 | 29.526 | 54.431 | 82.040 | 1.00 | 18.43 | B | O |
| ATOM | 3775 | N | LYS | B | 157 | 30.091 | 55.528 | 83.922 | 1.00 | 17.78 | B | N |
| ATOM | 3776 | CA | LYS | B | 157 | 28.708 | 55.726 | 84.334 | 1.00 | 20.16 | B | C |
| ATOM | 3777 | CB | LYS | B | 157 | 28.264 | 54.638 | 85.322 | 1.00 | 20.30 | B | C |
| ATOM | 3778 | CG | LYS | B | 157 | 29.127 | 54.458 | 86.533 | 1.00 | 21.75 | B | C |
| ATOM | 3779 | CD | LYS | B | 157 | 28.682 | 53.220 | 87.292 | 1.00 | 26.88 | B | C |
| ATOM | 3780 | CE | LYS | B | 157 | 29.607 | 52.921 | 88.468 | 1.00 | 32.38 | B | C |
| ATOM | 3781 | NZ | LYS | B | 157 | 29.225 | 51.658 | 89.180 | 1.00 | 35.18 | B | N |
| ATOM | 3782 | C | LYS | B | 157 | 28.532 | 57.133 | 84.924 | 1.00 | 19.15 | B | C |
| ATOM | 3783 | O | LYS | B | 157 | 29.448 | 57.675 | 85.537 | 1.00 | 19.06 | B | O |
| ATOM | 3784 | N | VAL | B | 158 | 27.358 | 57.721 | 84.707 | 1.00 | 18.32 | B | N |
| ATOM | 3785 | CA | VAL | B | 158 | 27.058 | 59.063 | 85.196 | 1.00 | 17.90 | B | C |
| ATOM | 3786 | CB | VAL | B | 158 | 26.859 | 60.052 | 84.035 | 1.00 | 17.79 | B | C |
| ATOM | 3787 | CG1 | VAL | B | 158 | 28.105 | 60.092 | 83.156 | 1.00 | 21.47 | B | C |
| ATOM | 3788 | CG2 | VAL | B | 158 | 25.627 | 59.649 | 83.220 | 1.00 | 17.20 | B | C |
| ATOM | 3789 | C | VAL | B | 158 | 25.791 | 59.137 | 86.034 | 1.00 | 18.73 | B | C |
| ATOM | 3790 | O | VAL | B | 158 | 24.990 | 58.206 | 86.078 | 1.00 | 20.65 | B | O |
| ATOM | 3791 | N | SER | B | 159 | 25.615 | 60.278 | 86.682 | 1.00 | 17.87 | B | N |
| ATOM | 3792 | CA | SER | B | 159 | 24.442 | 60.537 | 87.498 | 1.00 | 17.50 | B | C |
| ATOM | 3793 | CB | SER | B | 159 | 24.610 | 59.927 | 88.897 | 1.00 | 17.71 | B | C |
| ATOM | 3794 | OG | SER | B | 159 | 25.616 | 60.593 | 89.640 | 1.00 | 23.82 | B | O |
| ATOM | 3795 | C | SER | B | 159 | 24.283 | 62.055 | 87.590 | 1.00 | 17.36 | B | C |
| ATOM | 3796 | O | SER | B | 159 | 25.254 | 62.799 | 87.454 | 1.00 | 16.96 | B | O |
| ATOM | 3797 | N | LEU | B | 160 | 23.055 | 62.512 | 87.802 | 1.00 | 19.16 | B | N |
| ATOM | 3798 | CA | LEU | B | 160 | 22.787 | 63.939 | 87.914 | 1.00 | 20.16 | B | C |
| ATOM | 3799 | CB | LEU | B | 160 | 22.526 | 64.561 | 86.539 | 1.00 | 24.37 | B | C |
| ATOM | 3800 | CG | LEU | B | 160 | 22.311 | 66.082 | 86.580 | 1.00 | 25.91 | B | C |
| ATOM | 3801 | CD1 | LEU | B | 160 | 23.595 | 66.749 | 87.047 | 1.00 | 27.41 | B | C |
| ATOM | 3802 | CD2 | LEU | B | 160 | 21.910 | 66.616 | 85.215 | 1.00 | 26.05 | B | C |
| ATOM | 3803 | C | LEU | B | 160 | 21.584 | 64.205 | 88.784 | 1.00 | 20.60 | B | C |
| ATOM | 3804 | O | LEU | B | 160 | 20.454 | 63.894 | 88.407 | 1.00 | 19.72 | B | O |
| ATOM | 3805 | N | LEU | B | 161 | 21.816 | 64.770 | 89.958 | 1.00 | 21.44 | B | N |
| ATOM | 3806 | CA | LEU | B | 161 | 20.699 | 65.089 | 90.822 | 1.00 | 22.44 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3807 | CB | LEU | B | 161 | 20.806 | 64.377 | 92.168 | 1.00 | 22.40 | B | C |
| ATOM | 3808 | CG | LEU | B | 161 | 21.989 | 64.598 | 93.104 | 1.00 | 21.76 | B | C |
| ATOM | 3809 | CD1 | LEU | B | 161 | 22.330 | 66.054 | 93.206 | 1.00 | 20.10 | B | C |
| ATOM | 3810 | CD2 | LEU | B | 161 | 21.624 | 64.030 | 94.477 | 1.00 | 22.51 | B | C |
| ATOM | 3811 | C | LEU | B | 161 | 20.631 | 66.587 | 91.031 | 1.00 | 24.39 | B | C |
| ATOM | 3812 | O | LEU | B | 161 | 21.567 | 67.328 | 90.718 | 1.00 | 23.37 | B | O |
| ATOM | 3813 | N | GLU | B | 162 | 19.508 | 67.038 | 91.557 | 1.00 | 25.76 | B | N |
| ATOM | 3814 | CA | GLU | B | 162 | 19.345 | 68.450 | 91.805 | 1.00 | 26.24 | B | C |
| ATOM | 3815 | CB | GLU | B | 162 | 18.337 | 69.018 | 90.819 | 1.00 | 28.54 | B | C |
| ATOM | 3816 | CG | GLU | B | 162 | 17.957 | 70.463 | 91.065 | 1.00 | 32.16 | B | C |
| ATOM | 3817 | CD | GLU | B | 162 | 16.839 | 70.920 | 90.147 | 1.00 | 30.55 | B | C |
| ATOM | 3818 | OE1 | GLU | B | 162 | 17.048 | 70.954 | 88.917 | 1.00 | 31.49 | B | O |
| ATOM | 3819 | OE2 | GLU | B | 162 | 15.752 | 71.233 | 90.660 | 1.00 | 29.76 | B | O |
| ATOM | 3820 | C | GLU | B | 162 | 18.869 | 68.678 | 93.229 | 1.00 | 25.59 | B | C |
| ATOM | 3821 | O | GLU | B | 162 | 17.844 | 68.124 | 93.645 | 1.00 | 24.17 | B | O |
| ATOM | 3822 | N | ILE | B | 163 | 19.635 | 69.462 | 93.985 | 1.00 | 22.67 | B | N |
| ATOM | 3823 | CA | ILE | B | 163 | 19.252 | 69.798 | 95.347 | 1.00 | 22.12 | B | C |
| ATOM | 3824 | CB | ILE | B | 163 | 20.484 | 70.106 | 96.247 | 1.00 | 20.37 | B | C |
| ATOM | 3825 | CG2 | ILE | B | 163 | 20.047 | 70.255 | 97.703 | 1.00 | 19.02 | B | C |
| ATOM | 3826 | CG1 | ILE | B | 163 | 21.504 | 68.977 | 96.168 | 1.00 | 19.13 | B | C |
| ATOM | 3827 | CD1 | ILE | B | 163 | 22.721 | 69.219 | 97.026 | 1.00 | 15.38 | B | C |
| ATOM | 3828 | C | ILE | B | 163 | 18.408 | 71.074 | 95.253 | 1.00 | 22.77 | B | C |
| ATOM | 3829 | O | ILE | B | 163 | 18.799 | 72.041 | 94.611 | 1.00 | 22.19 | B | O |
| ATOM | 3830 | N | TYR | B | 164 | 17.246 | 71.076 | 95.880 | 1.00 | 23.71 | B | N |
| ATOM | 3831 | CA | TYR | B | 164 | 16.404 | 72.261 | 95.863 | 1.00 | 25.10 | B | C |
| ATOM | 3832 | CB | TYR | B | 164 | 15.444 | 72.232 | 94.673 | 1.00 | 25.51 | B | C |
| ATOM | 3833 | CG | TYR | B | 164 | 14.463 | 73.370 | 94.725 | 1.00 | 27.98 | B | C |
| ATOM | 3834 | CD1 | TYR | B | 164 | 13.141 | 73.157 | 95.107 | 1.00 | 28.70 | B | C |
| ATOM | 3835 | CE1 | TYR | B | 164 | 12.265 | 74.213 | 95.260 | 1.00 | 29.81 | B | C |
| ATOM | 3836 | CD2 | TYR | B | 164 | 14.878 | 74.678 | 94.490 | 1.00 | 27.98 | B | C |
| ATOM | 3837 | CE2 | TYR | B | 164 | 14.009 | 75.742 | 94.644 | 1.00 | 28.54 | B | C |
| ATOM | 3838 | CZ | TYR | B | 164 | 12.705 | 75.503 | 95.031 | 1.00 | 29.87 | B | C |
| ATOM | 3839 | OH | TYR | B | 164 | 11.843 | 76.559 | 95.205 | 1.00 | 32.97 | B | O |
| ATOM | 3840 | C | TYR | B | 164 | 15.623 | 72.375 | 97.165 | 1.00 | 25.79 | B | C |
| ATOM | 3841 | O | TYR | B | 164 | 14.773 | 71.540 | 97.474 | 1.00 | 25.92 | B | O |
| ATOM | 3842 | N | ASN | B | 165 | 15.930 | 73.412 | 97.934 | 1.00 | 28.14 | B | N |
| ATOM | 3843 | CA | ASN | B | 165 | 15.277 | 73.638 | 99.213 | 1.00 | 29.81 | B | C |
| ATOM | 3844 | CB | ASN | B | 165 | 13.783 | 73.902 | 99.008 | 1.00 | 33.30 | B | C |
| ATOM | 3845 | CG | ASN | B | 165 | 13.057 | 74.222 | 100.316 | 1.00 | 38.14 | B | C |
| ATOM | 3846 | OD1 | ASN | B | 165 | 13.532 | 75.032 | 101.122 | 1.00 | 37.15 | B | O |
| ATOM | 3847 | NO2 | ASN | B | 165 | 11.896 | 73.593 | 100.528 | 1.00 | 37.72 | B | N |
| ATOM | 3848 | C | ASN | B | 165 | 15.470 | 72.438 | 100.130 | 1.00 | 30.32 | B | C |
| ATOM | 3849 | O | ASN | B | 165 | 14.518 | 71.972 | 100.752 | 1.00 | 33.01 | B | O |
| ATOM | 3850 | N | GLU | B | 166 | 16.703 | 71.939 | 100.200 | 1.00 | 30.55 | B | N |
| ATOM | 3851 | CA | GLU | B | 166 | 17.042 | 70.796 | 101.039 | 1.00 | 27.26 | B | C |
| ATOM | 3852 | CB | GLU | B | 166 | 16.454 | 70.976 | 102.436 | 1.00 | 30.85 | B | C |
| ATOM | 3853 | CG | GLU | B | 166 | 17.272 | 71.881 | 103.324 | 1.00 | 36.91 | B | C |
| ATOM | 3854 | CD | GLU | B | 166 | 18.659 | 71.321 | 103.566 | 1.00 | 41.36 | B | C |
| ATOM | 3855 | OE1 | GLU | B | 166 | 19.375 | 71.049 | 102.568 | 1.00 | 43.05 | B | O |
| ATOM | 3856 | OE2 | GLU | B | 166 | 19.031 | 71.150 | 104.750 | 1.00 | 41.36 | B | O |
| ATOM | 3857 | C | GLU | B | 166 | 16.615 | 69.440 | 100.498 | 1.00 | 26.94 | B | C |
| ATOM | 3858 | O | GLU | B | 166 | 16.907 | 68.412 | 101.105 | 1.00 | 25.10 | B | O |
| ATOM | 3859 | N | GLU | B | 167 | 15.920 | 69.413 | 99.368 | 1.00 | 25.49 | B | N |
| ATOM | 3860 | CA | GLU | B | 167 | 15.510 | 68.124 | 98.834 | 1.00 | 25.73 | B | C |
| ATOM | 3861 | CB | GLU | B | 167 | 14.046 | 68.153 | 98.437 | 1.00 | 25.91 | B | C |
| ATOM | 3862 | CG | GLU | B | 167 | 13.125 | 68.509 | 99.576 | 1.00 | 30.91 | B | C |
| ATOM | 3863 | CD | GLU | B | 167 | 11.712 | 68.033 | 99.333 | 1.00 | 36.44 | B | C |
| ATOM | 3864 | OE1 | GLU | B | 167 | 11.386 | 66.910 | 99.776 | 1.00 | 38.31 | B | O |
| ATOM | 3865 | OE2 | GLU | B | 167 | 10.931 | 68.773 | 98.688 | 1.00 | 39.64 | B | O |
| ATOM | 3866 | C | GLU | B | 167 | 16.365 | 67.687 | 97.652 | 1.00 | 25.32 | B | C |
| ATOM | 3867 | O | GLU | B | 167 | 17.021 | 68.506 | 97.002 | 1.00 | 27.05 | B | O |
| ATOM | 3868 | N | LEU | B | 168 | 16.364 | 66.385 | 97.392 | 1.00 | 22.49 | B | N |
| ATOM | 3869 | CA | LEU | B | 168 | 17.130 | 65.797 | 96.303 | 1.00 | 19.66 | B | C |
| ATOM | 3870 | CB | LEU | B | 168 | 18.041 | 64.700 | 96.848 | 1.00 | 17.24 | B | C |
| ATOM | 3871 | CG | LEU | B | 168 | 19.317 | 65.126 | 97.578 | 1.00 | 16.09 | B | C |
| ATOM | 3872 | CD1 | LEU | B | 168 | 19.163 | 66.472 | 98.248 | 1.00 | 12.39 | B | C |
| ATOM | 3873 | CD2 | LEU | B | 168 | 19.657 | 64.053 | 98.592 | 1.00 | 15.51 | B | C |
| ATOM | 3874 | C | LEU | B | 168 | 16.197 | 65.209 | 95.260 | 1.00 | 20.41 | B | C |
| ATOM | 3875 | O | LEU | B | 168 | 15.244 | 64.521 | 95.601 | 1.00 | 21.20 | B | O |
| ATOM | 3876 | N | PHE | B | 169 | 16.471 | 65.482 | 93.988 | 1.00 | 22.13 | B | N |
| ATOM | 3877 | CA | PHE | B | 169 | 15.652 | 64.961 | 92.900 | 1.00 | 21.34 | B | C |
| ATOM | 3878 | CB | PHE | B | 169 | 14.790 | 66.078 | 92.317 | 1.00 | 22.97 | B | C |
| ATOM | 3879 | CG | PHE | B | 169 | 13.876 | 66.729 | 93.329 | 1.00 | 24.76 | B | C |
| ATOM | 3880 | CD1 | PHE | B | 169 | 14.365 | 67.653 | 94.237 | 1.00 | 26.07 | B | C |
| ATOM | 3881 | CD2 | PHE | B | 169 | 12.531 | 66.403 | 93.381 | 1.00 | 27.75 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3882 | CE1 | PHE | B | 169 | 13.531 | 68.241 | 95.180 | 1.00 | 28.08 | B | C |
| ATOM | 3883 | CE2 | PHE | B | 169 | 11.689 | 66.984 | 94.319 | 1.00 | 29.95 | B | C |
| ATOM | 3884 | CZ | PHE | B | 169 | 12.188 | 67.905 | 95.221 | 1.00 | 28.91 | B | C |
| ATOM | 3885 | C | PHE | B | 169 | 16.564 | 64.349 | 91.830 | 1.00 | 24.15 | B | C |
| ATOM | 3886 | O | PHE | B | 169 | 17.684 | 64.825 | 91.616 | 1.00 | 24.30 | B | O |
| ATOM | 3887 | N | ASP | B | 170 | 16.087 | 63.288 | 91.171 | 1.00 | 24.59 | B | N |
| ATOM | 3888 | CA | ASP | B | 170 | 16.868 | 62.578 | 90.154 | 1.00 | 22.04 | B | C |
| ATOM | 3889 | CB | ASP | B | 170 | 16.702 | 61.068 | 90.331 | 1.00 | 17.80 | B | C |
| ATOM | 3890 | CG | ASP | B | 170 | 17.795 | 60.275 | 89.647 | 1.00 | 16.75 | B | C |
| ATOM | 3891 | OD1 | ASP | B | 170 | 18.312 | 60.714 | 88.600 | 1.00 | 20.88 | B | O |
| ATOM | 3892 | OD2 | ASP | B | 170 | 18.130 | 59.195 | 90.152 | 1.00 | 17.72 | B | O |
| ATOM | 3893 | C | ASP | B | 170 | 16.486 | 62.951 | 88.728 | 1.00 | 22.24 | B | C |
| ATOM | 3894 | O | ASP | B | 170 | 15.463 | 62.499 | 88.211 | 1.00 | 23.78 | B | O |
| ATOM | 3895 | N | LEU | B | 171 | 17.340 | 63.734 | 88.081 | 1.00 | 21.24 | B | N |
| ATOM | 3896 | CA | LEU | B | 171 | 17.086 | 64.188 | 86.722 | 1.00 | 20.72 | B | C |
| ATOM | 3897 | CB | LEU | B | 171 | 17.939 | 65.422 | 86.437 | 1.00 | 18.70 | B | C |
| ATOM | 3898 | CG | LEU | B | 171 | 17.653 | 66.533 | 87.455 | 1.00 | 19.59 | B | C |
| ATOM | 3899 | CD1 | LEU | B | 171 | 18.536 | 67.742 | 87.206 | 1.00 | 20.77 | B | C |
| ATOM | 3900 | CD2 | LEU | B | 171 | 16.190 | 66.916 | 87.363 | 1.00 | 18.14 | B | C |
| ATOM | 3901 | C | LEU | B | 171 | 17.304 | 63.140 | 85.637 | 1.00 | 21.60 | B | C |
| ATOM | 3902 | O | LEU | B | 171 | 16.784 | 63.277 | 84.528 | 1.00 | 22.73 | B | O |
| ATOM | 3903 | N | LEU | B | 172 | 18.057 | 62.091 | 85.949 | 1.00 | 21.94 | B | N |
| ATOM | 3904 | CA | LEU | B | 172 | 18.335 | 61.038 | 84.975 | 1.00 | 23.20 | B | C |
| ATOM | 3905 | CB | LEU | B | 172 | 19.797 | 60.608 | 85.083 | 1.00 | 19.60 | B | C |
| ATOM | 3906 | CG | LEU | B | 172 | 20.786 | 61.363 | 84.204 | 1.00 | 18.49 | B | C |
| ATOM | 3907 | CD1 | LEU | B | 172 | 20.397 | 62.815 | 84.153 | 1.00 | 14.93 | B | C |
| ATOM | 3908 | CD2 | LEU | B | 172 | 22.210 | 61.170 | 84.721 | 1.00 | 16.62 | B | C |
| ATOM | 3909 | C | LEU | B | 172 | 17.434 | 59.814 | 85.120 | 1.00 | 26.93 | B | C |
| ATOM | 3910 | O | LEU | B | 172 | 17.787 | 58.728 | 84.671 | 1.00 | 28.48 | B | O |
| ATOM | 3911 | N | ASN | B | 173 | 16.274 | 59.986 | 85.746 | 1.00 | 30.19 | B | N |
| ATOM | 3912 | CA | ASN | B | 173 | 15.341 | 58.879 | 85.936 | 1.00 | 33.52 | B | C |
| ATOM | 3913 | CB | ASN | B | 173 | 14.864 | 58.833 | 87.390 | 1.00 | 33.76 | B | C |
| ATOM | 3914 | CG | ASN | B | 173 | 13.976 | 57.631 | 87.676 | 1.00 | 36.85 | B | C |
| ATOM | 3915 | OD1 | ASN | B | 173 | 13.142 | 57.244 | 86.850 | 1.00 | 39.76 | B | O |
| ATOM | 3916 | ND2 | ASN | B | 173 | 14.141 | 57.042 | 88.856 | 1.00 | 35.42 | B | N |
| ATOM | 3917 | C | ASN | B | 173 | 14.131 | 59.012 | 85.020 | 1.00 | 35.87 | B | C |
| ATOM | 3918 | O | ASN | B | 173 | 13.393 | 59.989 | 85.087 | 1.00 | 37.15 | B | O |
| ATOM | 3919 | N | PRO | B | 174 | 13.905 | 58.016 | 84.157 | 1.00 | 38.19 | B | N |
| ATOM | 3920 | CD | PRO | B | 174 | 14.743 | 56.822 | 83.978 | 1.00 | 39.37 | B | C |
| ATOM | 3921 | CA | PRO | B | 174 | 12.777 | 58.011 | 83.217 | 1.00 | 40.63 | B | C |
| ATOM | 3922 | CB | PRO | B | 174 | 12.900 | 56.648 | 82.538 | 1.00 | 39.50 | B | C |
| ATOM | 3923 | CG | PRO | B | 174 | 14.377 | 56.393 | 82.578 | 1.00 | 40.77 | B | C |
| ATOM | 3924 | C | PRO | B | 174 | 11.418 | 58.188 | 83.901 | 1.00 | 42.23 | B | C |
| ATOM | 3925 | O | PRO | B | 174 | 10.875 | 59.293 | 83.943 | 1.00 | 42.09 | B | O |
| ATOM | 3926 | N | SER | B | 175 | 10.881 | 57.094 | 84.437 | 1.00 | 43.47 | B | N |
| ATOM | 3927 | CA | SER | B | 175 | 9.584 | 57.116 | 85.103 | 1.00 | 45.82 | B | C |
| ATOM | 3928 | CB | SER | B | 175 | 9.172 | 55.704 | 85.525 | 1.00 | 47.53 | B | C |
| ATOM | 3929 | OG | SER | B | 175 | 10.027 | 55.194 | 86.535 | 1.00 | 48.69 | B | O |
| ATOM | 3930 | C | SER | B | 175 | 9.551 | 58.034 | 86.314 | 1.00 | 47.52 | B | C |
| ATOM | 3931 | O | SER | B | 175 | 10.075 | 59.148 | 86.278 | 1.00 | 49.25 | B | O |
| ATOM | 3932 | N | SER | B | 176 | 8.919 | 57.566 | 87.385 | 1.00 | 49.97 | B | N |
| ATOM | 3933 | CA | SER | B | 176 | 8.788 | 58.363 | 88.598 | 1.00 | 52.55 | B | C |
| ATOM | 3934 | CB | SER | B | 176 | 10.143 | 58.937 | 89.013 | 1.00 | 51.43 | B | C |
| ATOM | 3935 | OG | SER | B | 176 | 11.108 | 57.912 | 89.143 | 1.00 | 52.63 | B | O |
| ATOM | 3936 | C | SER | B | 176 | 7.819 | 59.498 | 88.277 | 1.00 | 54.47 | B | C |
| ATOM | 3937 | O | SER | B | 176 | 6.610 | 59.267 | 88.144 | 1.00 | 53.97 | B | O |
| ATOM | 3938 | N | ASP | B | 177 | 8.369 | 60.709 | 88.148 | 1.00 | 56.02 | B | N |
| ATOM | 3939 | CA | ASP | B | 177 | 7.616 | 61.929 | 87.821 | 1.00 | 57.92 | B | C |
| ATOM | 3940 | CB | ASP | B | 177 | 6.104 | 61.713 | 87.950 | 1.00 | 56.58 | B | C |
| ATOM | 3941 | CG | ASP | B | 177 | 5.626 | 61.775 | 89.392 | 1.00 | 55.26 | B | C |
| ATOM | 3942 | OD1 | ASP | B | 177 | 4.412 | 61.978 | 89.602 | 1.00 | 56.06 | B | O |
| ATOM | 3943 | OD2 | ASP | B | 177 | 6.462 | 61.618 | 90.312 | 1.00 | 53.12 | B | O |
| ATOM | 3944 | C | ASP | B | 177 | 8.004 | 63.092 | 88.733 | 1.00 | 57.79 | B | C |
| ATOM | 3945 | O | ASP | B | 177 | 7.138 | 63.692 | 89.375 | 1.00 | 58.89 | B | O |
| ATOM | 3946 | N | VAL | B | 178 | 9.291 | 63.425 | 88.779 | 1.00 | 58.49 | B | N |
| ATOM | 3947 | CA | VAL | B | 178 | 9.758 | 64.508 | 89.643 | 1.00 | 57.05 | B | C |
| ATOM | 3948 | CB | VAL | B | 178 | 9.459 | 65.912 | 89.023 | 1.00 | 57.50 | B | C |
| ATOM | 3949 | CG1 | VAL | B | 178 | 9.878 | 65.933 | 87.561 | 1.00 | 54.90 | B | C |
| ATOM | 3950 | CG2 | VAL | B | 178 | 7.981 | 66.268 | 89.165 | 1.00 | 57.65 | B | C |
| ATOM | 3951 | C | VAL | B | 178 | 9.031 | 64.360 | 90.981 | 1.00 | 56.49 | B | C |
| ATOM | 3952 | O | VAL | B | 178 | 8.579 | 63.263 | 91.320 | 1.00 | 57.55 | B | O |
| ATOM | 3953 | N | SER | B | 179 | 8.919 | 65.452 | 91.734 | 1.00 | 54.12 | B | N |
| ATOM | 3954 | CA | SER | B | 179 | 8.244 | 65.451 | 93.036 | 1.00 | 50.93 | B | C |
| ATOM | 3955 | CB | SER | B | 179 | 6.728 | 65.347 | 92.847 | 1.00 | 49.45 | B | C |
| ATOM | 3956 | OG | SER | B | 179 | 6.353 | 64.051 | 92.420 | 1.00 | 47.99 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 3957 | C | SER | B | 179 | 8.713 | 64.351 | 94.003 | 1.00 | 48.65 | B | C |
| ATOM | 3958 | O | SER | B | 179 | 8.776 | 64.570 | 95.213 | 1.00 | 47.56 | B | O |
| ATOM | 3959 | N | GLU | B | 180 | 9.025 | 63.173 | 93.469 | 1.00 | 46.26 | B | N |
| ATOM | 3960 | CA | GLU | B | 180 | 9.494 | 62.048 | 94.276 | 1.00 | 44.62 | B | C |
| ATOM | 3961 | CB | GLU | B | 180 | 9.413 | 60.758 | 93.455 | 1.00 | 44.66 | B | C |
| ATOM | 3962 | CG | GLU | B | 180 | 9.830 | 59.504 | 94.195 | 1.00 | 46.68 | B | C |
| ATOM | 3963 | CD | GLU | B | 180 | 9.717 | 58.249 | 93.336 | 1.00 | 48.34 | B | C |
| ATOM | 3964 | OE1 | GLU | B | 180 | 10.319 | 58.216 | 92.236 | 1.00 | 47.31 | B | O |
| ATOM | 3965 | OE2 | GLU | B | 180 | 9.028 | 57.295 | 93.765 | 1.00 | 46.45 | B | O |
| ATOM | 3966 | C | GLU | B | 180 | 10.937 | 62.300 | 94.727 | 1.00 | 42.64 | B | C |
| ATOM | 3967 | O | GLU | B | 180 | 11.880 | 62.137 | 93.949 | 1.00 | 44.21 | B | O |
| ATOM | 3968 | N | ARG | B | 181 | 11.096 | 62.703 | 95.985 | 1.00 | 38.57 | B | N |
| ATOM | 3969 | CA | ARG | B | 181 | 12.408 | 63.005 | 96.551 | 1.00 | 35.41 | B | C |
| ATOM | 3970 | CB | ARG | B | 181 | 12.259 | 63.924 | 97.768 | 1.00 | 34.13 | B | C |
| ATOM | 3971 | CG | ARG | B | 181 | 11.538 | 65.231 | 97.477 | 1.00 | 36.13 | B | C |
| ATOM | 3972 | CD | ARG | B | 181 | 10.021 | 65.097 | 97.584 | 1.00 | 37.35 | B | C |
| ATOM | 3973 | NE | ARG | B | 181 | 9.554 | 65.246 | 98.960 | 1.00 | 38.48 | B | N |
| ATOM | 3974 | CZ | ARG | B | 181 | 8.281 | 65.155 | 99.340 | 1.00 | 41.00 | B | C |
| ATOM | 3975 | NH1 | ARG | B | 181 | 7.328 | 64.908 | 98.448 | 1.00 | 41.40 | B | N |
| ATOM | 3976 | NH2 | ARG | B | 181 | 7.960 | 65.318 | 100.618 | 1.00 | 41.22 | B | N |
| ATOM | 3977 | C | ARG | B | 181 | 13.199 | 61.764 | 96.955 | 1.00 | 35.04 | B | C |
| ATOM | 3978 | O | ARG | B | 181 | 12.633 | 60.716 | 97.266 | 1.00 | 34.00 | B | O |
| ATOM | 3979 | N | LEU | B | 182 | 14.519 | 61.895 | 96.962 | 1.00 | 33.59 | B | N |
| ATOM | 3980 | CA | LEU | B | 182 | 15.379 | 60.783 | 97.322 | 1.00 | 32.60 | B | C |
| ATOM | 3981 | CB | LEU | B | 182 | 16.634 | 60.781 | 96.451 | 1.00 | 30.04 | B | C |
| ATOM | 3982 | CG | LEU | B | 182 | 16.364 | 60.566 | 94.972 | 1.00 | 27.16 | B | C |
| ATOM | 3983 | CD1 | LEU | B | 182 | 17.665 | 60.252 | 94.263 | 1.00 | 28.31 | B | C |
| ATOM | 3984 | CD2 | LEU | B | 182 | 15.392 | 59.426 | 94.806 | 1.00 | 26.58 | B | C |
| ATOM | 3985 | C | LEU | B | 182 | 15.780 | 60.801 | 98.784 | 1.00 | 32.42 | B | C |
| ATOM | 3986 | O | LEU | B | 182 | 15.866 | 61.853 | 99.408 | 1.00 | 33.21 | B | O |
| ATOM | 3987 | N | GLN | B | 183 | 16.036 | 59.619 | 99.321 | 1.00 | 33.99 | B | N |
| ATOM | 3988 | CA | GLN | B | 183 | 16.433 | 59.486 | 100.712 | 1.00 | 35.98 | B | C |
| ATOM | 3989 | CB | GLN | B | 183 | 15.669 | 58.323 | 101.353 | 1.00 | 40.69 | B | C |
| ATOM | 3990 | CG | GLN | B | 183 | 14.158 | 58.402 | 101.117 | 1.00 | 43.90 | B | C |
| ATOM | 3991 | CD | GLN | B | 183 | 13.384 | 57.297 | 101.809 | 1.00 | 45.84 | B | C |
| ATOM | 3992 | OE1 | GLN | B | 183 | 12.180 | 57.132 | 101.591 | 1.00 | 47.38 | B | O |
| ATOM | 3993 | NE2 | GLN | B | 183 | 14.069 | 56.537 | 102.654 | 1.00 | 44.55 | B | N |
| ATOM | 3994 | C | GLN | B | 183 | 17.938 | 59.261 | 100.784 | 1.00 | 34.46 | B | C |
| ATOM | 3995 | O | GLN | B | 183 | 18.510 | 58.502 | 99.996 | 1.00 | 32.17 | B | O |
| ATOM | 3996 | N | MET | B | 184 | 18.576 | 59.934 | 101.731 | 1.00 | 33.83 | B | N |
| ATOM | 3997 | CA | MET | B | 184 | 20.014 | 59.833 | 101.888 | 1.00 | 35.19 | B | C |
| ATOM | 3998 | CB | MET | B | 184 | 20.643 | 61.185 | 101.557 | 1.00 | 36.07 | B | C |
| ATOM | 3999 | CG | MET | B | 184 | 22.087 | 61.330 | 101.988 | 1.00 | 39.02 | B | C |
| ATOM | 4000 | SD | MET | B | 184 | 22.738 | 62.964 | 101.592 | 1.00 | 41.97 | B | S |
| ATOM | 4001 | CE | MET | B | 184 | 22.101 | 63.937 | 102.936 | 1.00 | 37.14 | B | C |
| ATOM | 4002 | C | MET | B | 184 | 20.426 | 59.402 | 103.288 | 1.00 | 35.44 | B | C |
| ATOM | 4003 | O | MET | B | 184 | 19.787 | 59.778 | 104.270 | 1.00 | 37.48 | B | O |
| ATOM | 4004 | N | PHE | B | 185 | 21.486 | 58.603 | 103.378 | 1.00 | 34.49 | B | N |
| ATOM | 4005 | CA | PHE | B | 185 | 21.989 | 58.165 | 104.681 | 1.00 | 35.54 | B | C |
| ATOM | 4006 | CB | PHE | B | 185 | 21.012 | 57.182 | 105.344 | 1.00 | 38.08 | B | C |
| ATOM | 4007 | CG | PHE | B | 185 | 20.478 | 56.133 | 104.419 | 1.00 | 39.17 | B | C |
| ATOM | 4008 | CD1 | PHE | B | 185 | 21.312 | 55.172 | 103.887 | 1.00 | 39.69 | B | C |
| ATOM | 4009 | CD2 | PHE | B | 185 | 19.131 | 56.107 | 104.089 | 1.00 | 39.72 | B | C |
| ATOM | 4010 | CE1 | PHE | B | 185 | 20.814 | 54.199 | 103.040 | 1.00 | 41.82 | B | C |
| ATOM | 4011 | CE2 | PHE | B | 185 | 18.628 | 55.143 | 103.245 | 1.00 | 39.84 | B | C |
| ATOM | 4012 | CZ | PHE | B | 185 | 19.473 | 54.184 | 102.719 | 1.00 | 40.56 | B | C |
| ATOM | 4013 | C | PHE | B | 185 | 23.405 | 57.584 | 104.681 | 1.00 | 33.28 | B | C |
| ATOM | 4014 | O | PHE | B | 185 | 23.876 | 57.053 | 103.682 | 1.00 | 31.52 | B | O |
| ATOM | 4015 | N | ASP | B | 186 | 24.072 | 57.720 | 105.823 | 1.00 | 33.11 | B | N |
| ATOM | 4016 | CA | ASP | B | 186 | 25.442 | 57.254 | 106.041 | 1.00 | 33.57 | B | C |
| ATOM | 4017 | CB | ASP | B | 186 | 25.764 | 57.303 | 107.534 | 1.00 | 34.22 | B | C |
| ATOM | 4018 | CG | ASP | B | 186 | 25.679 | 58.696 | 108.094 | 1.00 | 35.72 | B | C |
| ATOM | 4019 | OD1 | ASP | B | 186 | 25.710 | 58.846 | 109.332 | 1.00 | 36.35 | B | O |
| ATOM | 4020 | OD2 | ASP | B | 186 | 25.588 | 59.647 | 107.290 | 1.00 | 39.04 | B | O |
| ATOM | 4021 | C | ASP | B | 186 | 25.770 | 55.861 | 105.509 | 1.00 | 32.65 | B | C |
| ATOM | 4022 | O | ASP | B | 186 | 25.011 | 54.903 | 105.679 | 1.00 | 29.34 | B | O |
| ATOM | 4023 | N | ASP | B | 187 | 26.933 | 55.758 | 104.882 | 1.00 | 32.38 | B | N |
| ATOM | 4024 | CA | ASP | B | 187 | 27.380 | 54.502 | 104.307 | 1.00 | 35.63 | B | C |
| ATOM | 4025 | CB | ASP | B | 187 | 28.089 | 54.764 | 102.984 | 1.00 | 36.02 | B | C |
| ATOM | 4026 | CG | ASP | B | 187 | 28.559 | 53.487 | 102.319 | 1.00 | 35.64 | B | C |
| ATOM | 4027 | OD1 | ASP | B | 187 | 29.369 | 53.574 | 101.376 | 1.00 | 35.80 | B | O |
| ATOM | 4028 | OD2 | ASP | B | 187 | 28.116 | 52.395 | 102.737 | 1.00 | 34.78 | B | O |
| ATOM | 4029 | C | ASP | B | 187 | 28.317 | 53.726 | 105.230 | 1.00 | 37.07 | B | C |
| ATOM | 4030 | O | ASP | B | 187 | 29.341 | 54.243 | 105.674 | 1.00 | 36.16 | B | O |
| ATOM | 4031 | N | PRO | B | 188 | 27.979 | 52.460 | 105.514 | 1.00 | 39.09 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4032 | CD | PRO | B | 188 | 26.718 | 51.818 | 105.107 | 1.00 | 39.89 | B | C |
| ATOM | 4033 | CA | PRO | B | 188 | 28.757 | 51.568 | 106.380 | 1.00 | 41.61 | B | C |
| ATOM | 4034 | CB | PRO | B | 188 | 27.948 | 50.274 | 106.354 | 1.00 | 40.56 | B | C |
| ATOM | 4035 | CG | PRO | B | 188 | 26.548 | 50.764 | 106.172 | 1.00 | 42.27 | B | C |
| ATOM | 4036 | C | PRO | B | 188 | 30.192 | 51.359 | 105.902 | 1.00 | 44.03 | B | C |
| ATOM | 4037 | O | PRO | B | 188 | 30.452 | 51.264 | 104.704 | 1.00 | 43.71 | B | O |
| ATOM | 4038 | N | ARG | B | 189 | 31.122 | 51.279 | 106.845 | 1.00 | 47.41 | B | N |
| ATOM | 4039 | CA | ARG | B | 189 | 32.529 | 51.078 | 106.506 | 1.00 | 51.65 | B | C |
| ATOM | 4040 | CB | ARG | B | 189 | 32.661 | 50.016 | 105.410 | 1.00 | 52.67 | B | C |
| ATOM | 4041 | CG | ARG | B | 189 | 32.314 | 48.598 | 105.842 | 1.00 | 55.70 | B | C |
| ATOM | 4042 | CD | ARG | B | 189 | 32.344 | 47.621 | 104.676 | 1.00 | 55.65 | B | C |
| ATOM | 4043 | NE | ARG | B | 189 | 33.486 | 47.861 | 103.802 | 1.00 | 58.25 | B | N |
| ATOM | 4044 | CZ | ARG | B | 189 | 33.594 | 48.904 | 102.978 | 1.00 | 60.43 | B | C |
| ATOM | 4045 | NH1 | ARG | B | 189 | 32.622 | 49.815 | 102.906 | 1.00 | 57.93 | B | N |
| ATOM | 4046 | NH2 | ARG | B | 189 | 34.681 | 49.043 | 102.226 | 1.00 | 59.76 | B | N |
| ATOM | 4047 | C | ARG | B | 189 | 33.178 | 52.380 | 106.033 | 1.00 | 52.71 | B | C |
| ATOM | 4048 | O | ARG | B | 189 | 33.987 | 52.987 | 106.749 | 1.00 | 52.95 | B | O |
| ATOM | 4049 | N | ASN | B | 190 | 32.827 | 52.799 | 104.821 | 1.00 | 51.71 | B | N |
| ATOM | 4050 | CA | ASN | B | 190 | 33.370 | 54.030 | 104.274 | 1.00 | 50.25 | B | C |
| ATOM | 4051 | CB | ASN | B | 190 | 33.241 | 54.054 | 102.755 | 1.00 | 50.97 | B | C |
| ATOM | 4052 | CG | ASN | B | 190 | 33.640 | 55.392 | 102.161 | 1.00 | 51.16 | B | C |
| ATOM | 4053 | OD1 | ASN | B | 190 | 33.553 | 55.594 | 100.955 | 1.00 | 55.22 | B | O |
| ATOM | 4054 | ND2 | ASN | B | 190 | 34.081 | 56.311 | 103.008 | 1.00 | 49.87 | B | N |
| ATOM | 4055 | C | ASN | B | 190 | 32.664 | 55.249 | 104.842 | 1.00 | 48.53 | B | C |
| ATOM | 4056 | O | ASN | B | 190 | 31.780 | 55.817 | 104.204 | 1.00 | 47.07 | B | O |
| ATOM | 4057 | N | LYS | B | 191 | 33.055 | 55.644 | 106.046 | 1.00 | 48.31 | B | N |
| ATOM | 4058 | CA | LYS | B | 191 | 32.476 | 56.818 | 106.680 | 1.00 | 47.75 | B | C |
| ATOM | 4059 | CB | LYS | B | 191 | 33.183 | 57.074 | 108.015 | 1.00 | 48.17 | B | C |
| ATOM | 4060 | CG | LYS | B | 191 | 32.644 | 58.237 | 108.827 | 1.00 | 50.02 | B | C |
| ATOM | 4061 | CD | LYS | B | 191 | 33.201 | 58.214 | 110.244 | 1.00 | 52.02 | B | C |
| ATOM | 4062 | CE | LYS | B | 191 | 32.710 | 56.989 | 111.019 | 1.00 | 52.64 | B | C |
| ATOM | 4063 | NZ | LYS | B | 191 | 33.067 | 55.686 | 110.369 | 1.00 | 51.34 | B | N |
| ATOM | 4064 | C | LYS | B | 191 | 32.735 | 57.957 | 105.694 | 1.00 | 47.46 | B | C |
| ATOM | 4065 | O | LYS | B | 191 | 33.196 | 57.712 | 104.577 | 1.00 | 49.47 | B | O |
| ATOM | 4066 | N | ARG | B | 192 | 32.442 | 59.192 | 106.077 | 1.00 | 45.16 | B | N |
| ATOM | 4067 | CA | ARG | B | 192 | 32.688 | 60.302 | 105.166 | 1.00 | 44.21 | B | C |
| ATOM | 4068 | CB | ARG | B | 192 | 34.191 | 60.431 | 104.895 | 1.00 | 46.45 | B | C |
| ATOM | 4069 | CG | ARG | B | 192 | 35.034 | 60.756 | 106.115 | 1.00 | 49.93 | B | C |
| ATOM | 4070 | CD | ARG | B | 192 | 36.516 | 60.883 | 105.764 | 1.00 | 52.87 | B | C |
| ATOM | 4071 | NE | ARG | B | 192 | 36.757 | 61.776 | 104.632 | 1.00 | 54.52 | B | N |
| ATOM | 4072 | CZ | ARG | B | 192 | 36.564 | 61.441 | 103.358 | 1.00 | 55.51 | B | C |
| ATOM | 4073 | NH1 | ARG | B | 192 | 36.128 | 60.227 | 103.046 | 1.00 | 56.13 | B | N |
| ATOM | 4074 | NH2 | ARG | B | 192 | 36.804 | 62.319 | 102.391 | 1.00 | 55.91 | B | N |
| ATOM | 4075 | C | ARG | B | 192 | 31.957 | 60.085 | 103.839 | 1.00 | 41.97 | B | C |
| ATOM | 4076 | O | ARG | B | 192 | 32.081 | 60.888 | 102.911 | 1.00 | 42.23 | B | O |
| ATOM | 4077 | N | GLY | B | 193 | 31.210 | 58.988 | 103.751 | 1.00 | 38.68 | B | N |
| ATOM | 4078 | CA | GLY | B | 193 | 30.470 | 58.685 | 102.541 | 1.00 | 33.43 | B | C |
| ATOM | 4079 | C | GLY | B | 193 | 28.983 | 58.678 | 102.822 | 1.00 | 30.94 | B | C |
| ATOM | 4080 | O | GLY | B | 193 | 28.575 | 58.611 | 103.984 | 1.00 | 30.25 | B | O |
| ATOM | 4081 | N | VAL | B | 194 | 28.174 | 58.757 | 101.769 | 1.00 | 27.84 | B | N |
| ATOM | 4082 | CA | VAL | B | 194 | 26.724 | 58.757 | 101.921 | 1.00 | 28.35 | B | C |
| ATOM | 4083 | CB | VAL | B | 194 | 26.139 | 60.176 | 101.867 | 1.00 | 27.02 | B | C |
| ATOM | 4084 | CG1 | VAL | B | 194 | 26.841 | 61.066 | 102.886 | 1.00 | 28.40 | B | C |
| ATOM | 4085 | CG2 | VAL | B | 194 | 26.279 | 60.744 | 100.458 | 1.00 | 26.38 | B | C |
| ATOM | 4086 | C | VAL | B | 194 | 26.103 | 57.960 | 100.795 | 1.00 | 28.61 | B | C |
| ATOM | 4087 | O | VAL | B | 194 | 26.720 | 57.781 | 99.747 | 1.00 | 26.90 | B | O |
| ATOM | 4088 | N | ILE | B | 195 | 24.888 | 57.472 | 101.020 | 1.00 | 29.05 | B | N |
| ATOM | 4089 | CA | ILE | B | 195 | 24.170 | 56.701 | 100.012 | 1.00 | 29.20 | B | C |
| ATOM | 4090 | CB | ILE | B | 195 | 23.916 | 55.258 | 100.473 | 1.00 | 30.08 | B | C |
| ATOM | 4091 | CG2 | ILE | B | 195 | 22.853 | 54.609 | 99.594 | 1.00 | 26.30 | B | C |
| ATOM | 4092 | CG1 | ILE | B | 195 | 25.227 | 54.467 | 100.430 | 1.00 | 30.79 | B | C |
| ATOM | 4093 | CD1 | ILE | B | 195 | 25.109 | 53.075 | 101.011 | 1.00 | 33.69 | B | C |
| ATOM | 4094 | C | ILE | B | 195 | 22.830 | 57.340 | 99.692 | 1.00 | 30.03 | B | C |
| ATOM | 4095 | O | ILE | B | 195 | 22.002 | 57.568 | 100.571 | 1.00 | 30.60 | B | O |
| ATOM | 4096 | N | ILE | B | 196 | 22.630 | 57.638 | 98.420 | 1.00 | 30.50 | B | N |
| ATOM | 4097 | CA | ILE | B | 196 | 21.397 | 58.247 | 97.974 | 1.00 | 29.89 | B | C |
| ATOM | 4098 | CB | ILE | B | 196 | 21.702 | 59.412 | 97.016 | 1.00 | 29.79 | B | C |
| ATOM | 4099 | CG2 | ILE | B | 196 | 20.429 | 60.170 | 96.674 | 1.00 | 32.53 | B | C |
| ATOM | 4100 | CG1 | ILE | B | 196 | 22.717 | 60.345 | 97.677 | 1.00 | 28.19 | B | C |
| ATOM | 4101 | CD1 | ILE | B | 196 | 23.188 | 61.468 | 96.792 | 1.00 | 28.00 | B | C |
| ATOM | 4102 | C | ILE | B | 196 | 20.664 | 57.142 | 97.251 | 1.00 | 26.77 | B | C |
| ATOM | 4103 | O | ILE | B | 196 | 20.874 | 56.935 | 96.065 | 1.00 | 28.13 | B | O |
| ATOM | 4104 | N | LYS | B | 197 | 19.813 | 56.422 | 97.970 | 1.00 | 26.61 | B | N |
| ATOM | 4105 | CA | LYS | B | 197 | 19.084 | 55.314 | 97.363 | 1.00 | 27.53 | B | C |
| ATOM | 4106 | CB | LYS | B | 197 | 18.300 | 54.527 | 98.414 | 1.00 | 28.97 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4107 | CG | LYS | B | 197 | 17.197 | 55.311 | 99.090 | 1.00 | 31.44 | B | C |
| ATOM | 4108 | CD | LYS | B | 197 | 16.186 | 54.371 | 99.734 | 1.00 | 33.94 | B | C |
| ATOM | 4109 | CE | LYS | B | 197 | 16.864 | 53.214 | 100.472 | 1.00 | 33.82 | B | C |
| ATOM | 4110 | NZ | LYS | B | 197 | 17.565 | 52.283 | 99.530 | 1.00 | 36.39 | B | N |
| ATOM | 4111 | C | LYS | B | 197 | 18.134 | 55.734 | 96.256 | 1.00 | 25.32 | B | C |
| ATOM | 4112 | O | LYS | B | 197 | 17.458 | 56.754 | 96.348 | 1.00 | 24.77 | B | O |
| ATOM | 4113 | N | GLY | B | 198 | 18.100 | 54.918 | 95.210 | 1.00 | 25.51 | B | N |
| ATOM | 4114 | CA | GLY | B | 198 | 17.240 | 55.171 | 94.080 | 1.00 | 25.05 | B | C |
| ATOM | 4115 | C | GLY | B | 198 | 17.952 | 55.972 | 93.023 | 1.00 | 28.10 | B | C |
| ATOM | 4116 | O | GLY | B | 198 | 17.534 | 55.980 | 91.868 | 1.00 | 30.84 | B | O |
| ATOM | 4117 | N | LEU | B | 199 | 19.033 | 56.647 | 93.400 | 1.00 | 28.44 | B | N |
| ATOM | 4118 | CA | LEU | B | 199 | 19.750 | 57.463 | 92.430 | 1.00 | 27.25 | B | C |
| ATOM | 4119 | CB | LEU | B | 199 | 21.045 | 58.032 | 93.017 | 1.00 | 28.13 | B | C |
| ATOM | 4120 | CG | LEU | B | 199 | 21.701 | 59.069 | 92.093 | 1.00 | 24.35 | B | C |
| ATOM | 4121 | CD1 | LEU | B | 199 | 20.725 | 60.221 | 91.851 | 1.00 | 25.05 | B | C |
| ATOM | 4122 | CD2 | LEU | B | 199 | 22.980 | 59.579 | 92.710 | 1.00 | 19.45 | B | C |
| ATOM | 4123 | C | LEU | B | 199 | 20.073 | 56.635 | 91.211 | 1.00 | 26.49 | B | C |
| ATOM | 4124 | O | LEU | B | 199 | 20.580 | 55.523 | 91.323 | 1.00 | 29.59 | B | O |
| ATOM | 4125 | N | GLU | B | 200 | 19.766 | 57.188 | 90.049 | 1.00 | 25.84 | B | N |
| ATOM | 4126 | CA | GLU | B | 200 | 20.011 | 56.535 | 88.772 | 1.00 | 25.41 | B | C |
| ATOM | 4127 | CB | GLU | B | 200 | 19.097 | 57.161 | 87.714 | 1.00 | 28.35 | B | C |
| ATOM | 4128 | CG | GLU | B | 200 | 18.998 | 56.400 | 86.403 | 1.00 | 32.13 | B | C |
| ATOM | 4129 | CD | GLU | B | 200 | 18.134 | 55.147 | 86.501 | 1.00 | 32.95 | B | C |
| ATOM | 4130 | OE1 | GLU | B | 200 | 18.518 | 54.187 | 87.208 | 1.00 | 31.60 | B | O |
| ATOM | 4131 | OE2 | GLU | B | 200 | 17.062 | 55.126 | 85.861 | 1.00 | 34.68 | B | O |
| ATOM | 4132 | C | GLU | B | 200 | 21.480 | 56.717 | 88.369 | 1.00 | 24.85 | B | C |
| ATOM | 4133 | O | GLU | B | 200 | 22.017 | 57.823 | 88.421 | 1.00 | 22.95 | B | O |
| ATOM | 4134 | N | GLU | B | 201 | 22.130 | 55.628 | 87.976 | 1.00 | 25.07 | B | N |
| ATOM | 4135 | CA | GLU | B | 201 | 23.523 | 55.700 | 87.564 | 1.00 | 26.11 | B | C |
| ATOM | 4136 | CB | GLU | B | 201 | 24.425 | 55.012 | 88.592 | 1.00 | 26.95 | B | C |
| ATOM | 4137 | CG | GLU | B | 201 | 24.350 | 55.659 | 89.968 | 1.00 | 30.54 | B | C |
| ATOM | 4138 | CD | GLU | B | 201 | 25.533 | 55.322 | 90.858 | 1.00 | 32.96 | B | C |
| ATOM | 4139 | OE1 | GLU | B | 201 | 25.672 | 54.150 | 91.273 | 1.00 | 33.33 | B | O |
| ATOM | 4140 | OE2 | GLU | B | 201 | 26.330 | 56.241 | 91.141 | 1.00 | 35.54 | B | O |
| ATOM | 4141 | C | GLU | B | 201 | 23.706 | 55.074 | 86.191 | 1.00 | 25.37 | B | C |
| ATOM | 4142 | O | GLU | B | 201 | 24.161 | 53.941 | 86.067 | 1.00 | 27.40 | B | O |
| ATOM | 4143 | N | ILE | B | 202 | 23.348 | 55.844 | 85.168 | 1.00 | 26.01 | B | N |
| ATOM | 4144 | CA | ILE | B | 202 | 23.433 | 55.425 | 83.776 | 1.00 | 25.82 | B | C |
| ATOM | 4145 | CB | ILE | B | 202 | 22.950 | 56.545 | 82.819 | 1.00 | 25.86 | B | C |
| ATOM | 4146 | CG2 | ILE | B | 202 | 22.804 | 55.996 | 81.423 | 1.00 | 24.46 | B | C |
| ATOM | 4147 | CG1 | ILE | B | 202 | 21.615 | 57.129 | 83.294 | 1.00 | 27.29 | B | C |
| ATOM | 4148 | CD1 | ILE | B | 202 | 20.490 | 56.138 | 83.330 | 1.00 | 28.37 | B | C |
| ATOM | 4149 | C | ILE | B | 202 | 24.846 | 55.055 | 83.347 | 1.00 | 27.62 | B | C |
| ATOM | 4150 | O | ILE | B | 202 | 25.805 | 55.762 | 83.656 | 1.00 | 27.29 | B | O |
| ATOM | 4151 | N | THR | B | 203 | 24.961 | 53.947 | 82.621 | 1.00 | 28.32 | B | N |
| ATOM | 4152 | CA | THR | B | 203 | 26.240 | 53.486 | 82.114 | 1.00 | 28.76 | B | C |
| ATOM | 4153 | CB | THR | B | 203 | 26.291 | 51.945 | 82.035 | 1.00 | 29.56 | B | C |
| ATOM | 4154 | OG1 | THR | B | 203 | 26.109 | 51.392 | 83.346 | 1.00 | 34.00 | B | O |
| ATOM | 4155 | CG2 | THR | B | 203 | 27.637 | 51.480 | 81.487 | 1.00 | 31.47 | B | C |
| ATOM | 4156 | C | THR | B | 203 | 26.384 | 54.063 | 80.710 | 1.00 | 29.64 | B | C |
| ATOM | 4157 | O | THR | B | 203 | 25.464 | 53.964 | 79.904 | 1.00 | 31.95 | B | O |
| ATOM | 4158 | N | VAL | B | 204 | 27.527 | 54.684 | 80.432 | 1.00 | 29.58 | B | N |
| ATOM | 4159 | CA | VAL | B | 204 | 27.790 | 55.274 | 79.124 | 1.00 | 29.71 | B | C |
| ATOM | 4160 | CB | VAL | B | 204 | 28.407 | 56.684 | 79.266 | 1.00 | 29.97 | B | C |
| ATOM | 4161 | CG1 | VAL | B | 204 | 28.397 | 57.408 | 77.923 | 1.00 | 29.69 | B | C |
| ATOM | 4162 | CG2 | VAL | B | 204 | 27.647 | 57.474 | 80.313 | 1.00 | 32.05 | B | C |
| ATOM | 4163 | C | VAL | B | 204 | 28.778 | 54.370 | 78.393 | 1.00 | 30.37 | B | C |
| ATOM | 4164 | O | VAL | B | 204 | 29.941 | 54.268 | 78.780 | 1.00 | 29.52 | B | O |
| ATOM | 4165 | N | HIS | B | 205 | 28.316 | 53.723 | 77.329 | 1.00 | 30.25 | B | N |
| ATOM | 4166 | CA | HIS | B | 205 | 29.169 | 52.805 | 76.580 | 1.00 | 31.14 | B | C |
| ATOM | 4167 | CB | HIS | B | 205 | 28.317 | 51.725 | 75.897 | 1.00 | 28.36 | B | C |
| ATOM | 4168 | CG | HIS | B | 205 | 27.278 | 51.121 | 76.793 | 1.00 | 28.60 | B | C |
| ATOM | 4169 | CD2 | HIS | B | 205 | 27.268 | 49.962 | 77.494 | 1.00 | 26.10 | B | C |
| ATOM | 4170 | ND1 | HIS | B | 205 | 26.091 | 51.758 | 77.089 | 1.00 | 26.93 | B | N |
| ATOM | 4171 | CE1 | HIS | B | 205 | 25.395 | 51.017 | 77.932 | 1.00 | 26.36 | B | C |
| ATOM | 4172 | NE2 | HIS | B | 205 | 26.088 | 49.923 | 78.195 | 1.00 | 26.42 | B | N |
| ATOM | 4173 | C | HIS | B | 205 | 30.060 | 53.468 | 75.544 | 1.00 | 32.00 | B | C |
| ATOM | 4174 | O | HIS | B | 205 | 31.155 | 52.980 | 75.263 | 1.00 | 32.84 | B | O |
| ATOM | 4175 | N | ASN | B | 206 | 29.612 | 54.579 | 74.974 | 1.00 | 33.21 | B | N |
| ATOM | 4176 | CA | ASN | B | 206 | 30.424 | 55.235 | 73.960 | 1.00 | 34.84 | B | C |
| ATOM | 4177 | CB | ASN | B | 206 | 29.986 | 54.772 | 72.573 | 1.00 | 34.66 | B | C |
| ATOM | 4178 | CG | ASN | B | 206 | 28.593 | 55.227 | 72.225 | 1.00 | 33.97 | B | C |
| ATOM | 4179 | OD1 | ASN | B | 206 | 28.344 | 56.419 | 72.058 | 1.00 | 36.78 | B | O |
| ATOM | 4180 | ND2 | ASN | B | 206 | 27.669 | 54.277 | 72.114 | 1.00 | 35.18 | B | N |
| ATOM | 4181 | C | ASN | B | 206 | 30.417 | 56.753 | 74.013 | 1.00 | 35.69 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4182 | O | ASN | B | 206 | 29.429 | 57.370 | 74.408 | 1.00 | 37.73 | B | O |
| ATOM | 4183 | N | LYS | B | 207 | 31.530 | 57.342 | 73.589 | 1.00 | 36.51 | B | N |
| ATOM | 4184 | CA | LYS | B | 207 | 31.720 | 58.790 | 73.581 | 1.00 | 37.68 | B | C |
| ATOM | 4185 | CB | LYS | B | 207 | 33.101 | 59.113 | 73.003 | 1.00 | 38.80 | B | C |
| ATOM | 4186 | CG | LYS | B | 207 | 33.421 | 60.596 | 72.913 | 1.00 | 41.20 | B | C |
| ATOM | 4187 | CD | LYS | B | 207 | 34.384 | 60.878 | 71.769 | 1.00 | 43.48 | B | C |
| ATOM | 4188 | CE | LYS | B | 207 | 33.781 | 60.469 | 70.428 | 1.00 | 47.33 | B | C |
| ATOM | 4189 | NZ | LYS | B | 207 | 34.619 | 60.892 | 69.261 | 1.00 | 47.34 | B | N |
| ATOM | 4190 | C | LYS | B | 207 | 30.653 | 59.585 | 72.818 | 1.00 | 37.55 | B | C |
| ATOM | 4191 | O | LYS | B | 207 | 30.963 | 60.593 | 72.178 | 1.00 | 37.73 | B | O |
| ATOM | 4192 | N | ASP | B | 208 | 29.404 | 59.142 | 72.867 | 1.00 | 37.36 | B | N |
| ATOM | 4193 | CA | ASP | B | 208 | 28.352 | 59.877 | 72.183 | 1.00 | 38.86 | B | C |
| ATOM | 4194 | CB | ASP | B | 208 | 28.516 | 59.758 | 70.667 | 1.00 | 41.88 | B | C |
| ATOM | 4195 | CG | ASP | B | 208 | 28.632 | 61.122 | 69.988 | 1.00 | 43.54 | B | C |
| ATOM | 4196 | OD1 | ASP | B | 208 | 27.640 | 61.882 | 70.013 | 1.00 | 46.59 | B | O |
| ATOM | 4197 | OD2 | ASP | B | 208 | 29.714 | 61.438 | 69.442 | 1.00 | 40.73 | B | O |
| ATOM | 4198 | C | ASP | B | 208 | 26.959 | 59.447 | 72.604 | 1.00 | 38.64 | B | C |
| ATOM | 4199 | O | ASP | B | 208 | 25.961 | 59.857 | 72.009 | 1.00 | 39.61 | B | O |
| ATOM | 4200 | N | GLU | B | 209 | 26.903 | 58.614 | 73.637 | 1.00 | 37.55 | B | N |
| ATOM | 4201 | CA | GLU | B | 209 | 25.637 | 58.143 | 74.184 | 1.00 | 35.16 | B | C |
| ATOM | 4202 | CB | GLU | B | 209 | 25.814 | 56.745 | 74.786 | 1.00 | 34.97 | B | C |
| ATOM | 4203 | CG | GLU | B | 209 | 24.514 | 56.020 | 75.115 | 1.00 | 36.53 | B | C |
| ATOM | 4204 | CD | GLU | B | 209 | 24.753 | 54.632 | 75.690 | 1.00 | 39.10 | B | C |
| ATOM | 4205 | OE1 | GLU | B | 209 | 25.468 | 53.833 | 75.044 | 1.00 | 38.05 | B | O |
| ATOM | 4206 | OE2 | GLU | B | 209 | 24.225 | 54.336 | 76.784 | 1.00 | 38.30 | B | O |
| ATOM | 4207 | C | GLU | B | 209 | 25.332 | 59.158 | 75.283 | 1.00 | 34.21 | B | C |
| ATOM | 4208 | O | GLU | B | 209 | 24.211 | 59.250 | 75.797 | 1.00 | 32.86 | B | O |
| ATOM | 4209 | N | VAL | B | 210 | 26.363 | 59.928 | 75.622 | 1.00 | 31.40 | B | N |
| ATOM | 4210 | CA | VAL | B | 210 | 26.266 | 60.949 | 76.648 | 1.00 | 31.45 | B | C |
| ATOM | 4211 | CB | VAL | B | 210 | 27.644 | 61.635 | 76.879 | 1.00 | 33.07 | B | C |
| ATOM | 4212 | CG1 | VAL | B | 210 | 28.737 | 60.580 | 77.005 | 1.00 | 35.64 | B | C |
| ATOM | 4213 | CG2 | VAL | B | 210 | 27.965 | 62.575 | 75.743 | 1.00 | 32.36 | B | C |
| ATOM | 4214 | C | VAL | B | 210 | 25.239 | 62.011 | 76.271 | 1.00 | 29.51 | B | C |
| ATOM | 4215 | O | VAL | B | 210 | 24.387 | 62.377 | 77.074 | 1.00 | 30.57 | B | O |
| ATOM | 4216 | N | TYR | B | 211 | 25.317 | 62.489 | 75.037 | 1.00 | 27.68 | B | N |
| ATOM | 4217 | CA | TYR | B | 211 | 24.424 | 63.525 | 74.557 | 1.00 | 26.69 | B | C |
| ATOM | 4218 | CB | TYR | B | 211 | 24.607 | 63.712 | 73.056 | 1.00 | 25.77 | B | C |
| ATOM | 4219 | CG | TYR | B | 211 | 23.846 | 64.897 | 72.509 | 1.00 | 23.15 | B | C |
| ATOM | 4220 | CD1 | TYR | B | 211 | 22.485 | 64.812 | 72.226 | 1.00 | 22.04 | B | C |
| ATOM | 4221 | CE1 | TYR | B | 211 | 21.779 | 65.916 | 71.761 | 1.00 | 21.37 | B | C |
| ATOM | 4222 | CD2 | TYR | B | 211 | 24.482 | 66.115 | 72.309 | 1.00 | 20.57 | B | C |
| ATOM | 4223 | CE2 | TYR | B | 211 | 23.790 | 67.217 | 71.841 | 1.00 | 22.33 | B | C |
| ATOM | 4224 | CZ | TYR | B | 211 | 22.443 | 67.117 | 71.570 | 1.00 | 23.40 | B | C |
| ATOM | 4225 | OH | TYR | B | 211 | 21.774 | 68.231 | 71.111 | 1.00 | 27.17 | B | O |
| ATOM | 4226 | C | TYR | B | 211 | 22.944 | 63.310 | 74.847 | 1.00 | 29.11 | B | C |
| ATOM | 4227 | O | TYR | B | 211 | 22.260 | 64.209 | 75.344 | 1.00 | 26.74 | B | O |
| ATOM | 4228 | N | GLN | B | 212 | 22.437 | 62.126 | 74.529 | 1.00 | 32.31 | B | N |
| ATOM | 4229 | CA | GLN | B | 212 | 21.024 | 61.859 | 74.749 | 1.00 | 34.13 | B | C |
| ATOM | 4230 | CB | GLN | B | 212 | 20.585 | 60.649 | 73.931 | 1.00 | 36.57 | B | C |
| ATOM | 4231 | CG | GLN | B | 212 | 20.939 | 59.316 | 74.536 | 1.00 | 42.06 | B | C |
| ATOM | 4232 | CD | GLN | B | 212 | 20.859 | 58.203 | 73.513 | 1.00 | 43.87 | B | C |
| ATOM | 4233 | OE1 | GLN | B | 212 | 20.749 | 57.031 | 73.867 | 1.00 | 44.53 | B | O |
| ATOM | 4234 | NE2 | GLN | B | 212 | 20.931 | 58.567 | 72.231 | 1.00 | 42.63 | B | N |
| ATOM | 4235 | C | GLN | B | 212 | 20.697 | 61.657 | 76.223 | 1.00 | 32.71 | B | C |
| ATOM | 4236 | O | GLN | B | 212 | 19.589 | 61.960 | 76.671 | 1.00 | 32.43 | B | O |
| ATOM | 4237 | N | ILE | 8 | 213 | 21.655 | 61.148 | 76.984 | 1.00 | 31.21 | B | N |
| ATOM | 4238 | CA | ILE | B | 213 | 21.414 | 60.962 | 78.408 | 1.00 | 30.83 | B | C |
| ATOM | 4239 | CB | ILE | B | 213 | 22.581 | 60.208 | 79.074 | 1.00 | 29.85 | B | C |
| ATOM | 4240 | CG2 | ILE | B | 213 | 22.359 | 60.120 | 80.575 | 1.00 | 25.89 | B | C |
| ATOM | 4241 | CG1 | ILE | B | 213 | 22.686 | 58.806 | 78.478 | 1.00 | 32.17 | B | C |
| ATOM | 4242 | CD1 | ILE | B | 213 | 23.816 | 57.977 | 79.058 | 1.00 | 35.82 | B | C |
| ATOM | 4243 | C | ILE | B | 213 | 21.222 | 62.325 | 79.093 | 1.00 | 30.08 | B | C |
| ATOM | 4244 | O | ILE | B | 213 | 20.342 | 62.488 | 79.942 | 1.00 | 28.99 | B | O |
| ATOM | 4245 | N | LEU | B | 214 | 22.039 | 63.304 | 78.709 | 1.00 | 26.87 | B | N |
| ATOM | 4246 | CA | LEU | B | 214 | 21.950 | 64.634 | 79.288 | 1.00 | 25.28 | B | C |
| ATOM | 4247 | CB | LEU | B | 214 | 23.266 | 65.377 | 79.090 | 1.00 | 23.79 | B | C |
| ATOM | 4248 | CG | LEU | B | 214 | 24.371 | 64.886 | 80.022 | 1.00 | 26.94 | B | C |
| ATOM | 4249 | CD1 | LEU | B | 214 | 25.690 | 65.490 | 79.615 | 1.00 | 27.61 | B | C |
| ATOM | 4250 | CD2 | LEU | B | 214 | 24.032 | 65.251 | 81.461 | 1.00 | 25.91 | B | C |
| ATOM | 4251 | C | LEU | B | 214 | 20.793 | 65.434 | 78.698 | 1.00 | 25.90 | B | C |
| ATOM | 4252 | O | LEU | B | 214 | 20.143 | 66.212 | 79.402 | 1.00 | 20.34 | B | O |
| ATOM | 4253 | N | GLU | B | 215 | 20.537 | 65.243 | 77.408 | 1.00 | 26.54 | B | N |
| ATOM | 4254 | CA | GLU | B | 215 | 19.439 | 65.943 | 76.757 | 1.00 | 28.21 | B | C |
| ATOM | 4255 | CB | GLU | B | 215 | 19.323 | 65.526 | 75.293 | 1.00 | 31.04 | B | C |
| ATOM | 4256 | CG | GLU | B | 215 | 18.204 | 66.231 | 74.540 | 1.00 | 34.94 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4257 | CD | GLU | B | 215 | 18.127 | 65.807 | 73.085 | 1.00 | 38.91 | B | C |
| ATOM | 4258 | OE1 | GLU | B | 215 | 18.009 | 64.582 | 72.838 | 1.00 | 40.02 | B | O |
| ATOM | 4259 | OE2 | GLU | B | 215 | 18.185 | 66.693 | 72.196 | 1.00 | 39.04 | B | O |
| ATOM | 4260 | C | GLU | B | 215 | 18.157 | 65.593 | 77.498 | 1.00 | 27.93 | B | C |
| ATOM | 4261 | O | GLU | B | 215 | 17.321 | 66.455 | 77.751 | 1.00 | 27.90 | B | O |
| ATOM | 4262 | N | LYS | B | 216 | 18.006 | 64.323 | 77.852 | 1.00 | 27.64 | B | N |
| ATOM | 4263 | CA | LYS | B | 216 | 16.825 | 63.894 | 78.591 | 1.00 | 28.80 | B | C |
| ATOM | 4264 | CB | LYS | B | 216 | 16.811 | 62.372 | 78.764 | 1.00 | 27.39 | B | C |
| ATOM | 4265 | CG | LYS | B | 216 | 15.709 | 61.684 | 77.984 | 1.00 | 28.84 | B | C |
| ATOM | 4266 | CD | LYS | B | 216 | 15.631 | 60.204 | 78.310 | 1.00 | 29.98 | B | C |
| ATOM | 4267 | CE | LYS | B | 216 | 16.793 | 59.432 | 77.705 | 1.00 | 31.07 | B | C |
| ATOM | 4268 | NZ | LYS | B | 216 | 16.728 | 59.390 | 76.217 | 1.00 | 31.81 | B | N |
| ATOM | 4269 | C | LYS | B | 216 | 16.885 | 64.567 | 79.955 | 1.00 | 29.26 | B | C |
| ATOM | 4270 | O | LYS | B | 216 | 15.858 | 64.934 | 80.539 | 1.00 | 29.34 | B | O |
| ATOM | 4271 | N | GLY | B | 217 | 18.106 | 64.734 | 80.453 | 1.00 | 28.04 | B | N |
| ATOM | 4272 | CA | GLY | B | 217 | 18.296 | 65.377 | 81.740 | 1.00 | 27.73 | B | C |
| ATOM | 4273 | C | GLY | B | 217 | 17.817 | 66.818 | 81.742 | 1.00 | 27.09 | B | C |
| ATOM | 4274 | O | GLY | B | 217 | 17.209 | 67.277 | 82.707 | 1.00 | 24.49 | B | O |
| ATOM | 4275 | N | ALA | B | 218 | 18.095 | 67.543 | 80.663 | 1.00 | 25.94 | B | N |
| ATOM | 4276 | CA | ALA | B | 218 | 17.668 | 68.929 | 80.579 | 1.00 | 26.01 | B | C |
| ATOM | 4277 | CB | ALA | B | 218 | 18.251 | 69.584 | 79.338 | 1.00 | 23.70 | B | C |
| ATOM | 4278 | C | ALA | B | 218 | 16.146 | 68.966 | 80.541 | 1.00 | 26.18 | B | C |
| ATOM | 4279 | O | ALA | B | 218 | 15.511 | 69.811 | 81.168 | 1.00 | 27.26 | B | O |
| ATOM | 4280 | N | ALA | B | 219 | 15.562 | 68.028 | 79.811 | 1.00 | 25.01 | B | N |
| ATOM | 4281 | CA | ALA | B | 219 | 14.116 | 67.958 | 79.697 | 1.00 | 26.18 | B | C |
| ATOM | 4282 | CB | ALA | B | 219 | 13.718 | 66.754 | 78.860 | 1.00 | 25.30 | B | C |
| ATOM | 4283 | C | ALA | B | 219 | 13.507 | 67.852 | 81.084 | 1.00 | 27.86 | B | C |
| ATOM | 4284 | O | ALA | B | 219 | 12.782 | 68.742 | 81.531 | 1.00 | 27.67 | B | O |
| ATOM | 4285 | N | LYS | B | 220 | 13.811 | 66.749 | 81.760 | 1.00 | 28.18 | B | N |
| ATOM | 4286 | CA | LYS | B | 220 | 13.314 | 66.495 | 83.102 | 1.00 | 29.65 | B | C |
| ATOM | 4287 | CB | LYS | B | 220 | 14.035 | 65.274 | 83.679 | 1.00 | 31.09 | B | C |
| ATOM | 4288 | CG | LYS | B | 220 | 13.458 | 64.755 | 84.981 | 1.00 | 34.84 | B | C |
| ATOM | 4289 | CD | LYS | B | 220 | 12.980 | 63.312 | 84.842 | 1.00 | 37.10 | B | C |
| ATOM | 4290 | CE | LYS | B | 220 | 11.864 | 63.176 | 83.799 | 1.00 | 37.37 | B | C |
| ATOM | 4291 | NZ | LYS | B | 220 | 11.228 | 61.814 | 83.800 | 1.00 | 36.27 | B | N |
| ATOM | 4292 | C | LYS | B | 220 | 13.533 | 67.716 | 84.002 | 1.00 | 29.23 | B | C |
| ATOM | 4293 | O | LYS | B | 220 | 12.676 | 68.064 | 84.827 | 1.00 | 26.26 | B | O |
| ATOM | 4294 | N | ARG | B | 221 | 14.685 | 68.361 | 83.825 | 1.00 | 30.30 | B | N |
| ATOM | 4295 | CA | ARG | B | 221 | 15.057 | 69.545 | 84.597 | 1.00 | 30.85 | B | C |
| ATOM | 4296 | CB | ARG | B | 221 | 16.402 | 70.097 | 84.102 | 1.00 | 33.27 | B | C |
| ATOM | 4297 | CG | ARG | B | 221 | 17.313 | 70.641 | 85.205 | 1.00 | 31.91 | B | C |
| ATOM | 4298 | CD | ARG | B | 221 | 18.084 | 71.893 | 84.780 | 1.00 | 30.28 | B | C |
| ATOM | 4299 | NE | ARG | B | 221 | 18.746 | 71.797 | 83.476 | 1.00 | 27.97 | B | N |
| ATOM | 4300 | CZ | ARG | B | 221 | 20.059 | 71.667 | 83.296 | 1.00 | 25.03 | B | C |
| ATOM | 4301 | NH1 | ARG | B | 221 | 20.879 | 71.605 | 84.329 | 1.00 | 24.30 | B | N |
| ATOM | 4302 | NH2 | ARG | B | 221 | 20.560 | 71.625 | 82.072 | 1.00 | 27.37 | B | N |
| ATOM | 4303 | C | ARG | B | 221 | 13.997 | 70.626 | 84.433 | 1.00 | 29.51 | B | C |
| ATOM | 4304 | O | ARG | B | 221 | 13.548 | 71.225 | 85.400 | 1.00 | 28.25 | B | O |
| ATOM | 4305 | N | THR | B | 222 | 13.610 | 70.869 | 83.186 | 1.00 | 29.13 | B | N |
| ATOM | 4306 | CA | THR | B | 222 | 12.622 | 71.882 | 82.871 | 1.00 | 28.92 | B | C |
| ATOM | 4307 | CB | THR | B | 222 | 12.570 | 72.136 | 81.345 | 1.00 | 30.71 | B | C |
| ATOM | 4308 | OG1 | THR | B | 222 | 13.858 | 72.578 | 80.882 | 1.00 | 28.81 | B | O |
| ATOM | 4309 | CG2 | THR | B | 222 | 11.528 | 73.202 | 81.021 | 1.00 | 32.15 | B | C |
| ATOM | 4310 | C | THR | B | 222 | 11.232 | 71.496 | 83.377 | 1.00 | 28.78 | B | C |
| ATOM | 4311 | O | THR | B | 222 | 10.474 | 72.348 | 83.852 | 1.00 | 29.45 | B | O |
| ATOM | 4312 | N | THR | B | 223 | 10.895 | 70.214 | 83.285 | 1.00 | 27.18 | B | N |
| ATOM | 4313 | CA | THR | B | 223 | 9.595 | 69.752 | 83.747 | 1.00 | 27.05 | B | C |
| ATOM | 4314 | CB | THR | B | 223 | 9.419 | 68.240 | 83.502 | 1.00 | 28.22 | B | C |
| ATOM | 4315 | OG1 | THR | B | 223 | 9.041 | 68.018 | 82.136 | 1.00 | 30.04 | B | O |
| ATOM | 4316 | CG2 | THR | B | 223 | 8.356 | 67.662 | 84.428 | 1.00 | 24.59 | B | C |
| ATOM | 4317 | C | THR | B | 223 | 9.390 | 70.045 | 85.230 | 1.00 | 28.40 | B | C |
| ATOM | 4318 | O | THR | B | 223 | 8.358 | 70.596 | 85.630 | 1.00 | 28.85 | B | O |
| ATOM | 4319 | N | ALA | B | 224 | 10.373 | 69.679 | 86.044 | 1.00 | 27.97 | B | N |
| ATOM | 4320 | CA | ALA | B | 224 | 10.308 | 69.896 | 87.486 | 1.00 | 29.11 | B | C |
| ATOM | 4321 | CB | ALA | B | 224 | 11.593 | 69.393 | 88.135 | 1.00 | 30.29 | B | C |
| ATOM | 4322 | C | ALA | B | 224 | 10.074 | 71.357 | 87.874 | 1.00 | 30.20 | B | C |
| ATOM | 4323 | O | ALA | B | 224 | 9.239 | 71.656 | 88.736 | 1.00 | 29.06 | B | O |
| ATOM | 4324 | N | ALA | B | 225 | 10.827 | 72.253 | 87.239 | 1.00 | 31.17 | B | N |
| ATOM | 4325 | CA | ALA | B | 225 | 10.737 | 73.689 | 87.489 | 1.00 | 32.99 | B | C |
| ATOM | 4326 | CB | ALA | B | 225 | 11.804 | 74.415 | 86.681 | 1.00 | 29.49 | B | C |
| ATOM | 4327 | C | ALA | B | 225 | 9.364 | 74.289 | 87.171 | 1.00 | 36.04 | B | C |
| ATOM | 4328 | O | ALA | B | 225 | 8.959 | 75.276 | 87.781 | 1.00 | 36.32 | B | O |
| ATOM | 4329 | N | THR | B | 226 | 8.657 | 73.693 | 86.216 | 1.00 | 37.97 | B | N |
| ATOM | 4330 | CA | THR | B | 226 | 7.351 | 74.194 | 85.799 | 1.00 | 40.38 | B | C |
| ATOM | 4331 | CB | THR | B | 226 | 7.125 | 73.922 | 84.290 | 1.00 | 41.69 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4332 | OG1 | THR | B | 226 | 8.156 | 74.563 | 83.522 | 1.00 | 43.89 | B | O |
| ATOM | 4333 | CG2 | THR | B | 226 | 5.771 | 74.457 | 83.846 | 1.00 | 43.14 | B | C |
| ATOM | 4334 | C | THR | B | 226 | 6.173 | 73.604 | 86.576 | 1.00 | 40.97 | B | C |
| ATOM | 4335 | O | THR | B | 226 | 5.025 | 73.988 | 86.358 | 1.00 | 42.25 | B | O |
| ATOM | 4336 | N | LEU | B | 227 | 6.453 | 72.686 | 87.493 | 1.00 | 39.99 | B | N |
| ATOM | 4337 | CA | LEU | B | 227 | 5.394 | 72.038 | 88.247 | 1.00 | 37.62 | B | C |
| ATOM | 4338 | CB | LEU | B | 227 | 5.340 | 70.556 | 87.883 | 1.00 | 35.54 | B | C |
| ATOM | 4339 | CG | LEU | B | 227 | 5.024 | 70.275 | 86.415 | 1.00 | 33.04 | B | C |
| ATOM | 4340 | CD1 | LEU | B | 227 | 5.075 | 68.781 | 86.157 | 1.00 | 33.61 | B | C |
| ATOM | 4341 | CD2 | LEU | B | 227 | 3.656 | 70.841 | 86.071 | 1.00 | 29.64 | B | C |
| ATOM | 4342 | C | LEU | B | 227 | 5.550 | 72.177 | 89.744 | 1.00 | 39.00 | B | C |
| ATOM | 4343 | O | LEU | B | 227 | 4.572 | 72.088 | 90.493 | 1.00 | 37.85 | B | O |
| ATOM | 4344 | N | MET | B | 228 | 6.782 | 72.379 | 90.191 | 1.00 | 39.08 | B | N |
| ATOM | 4345 | CA | MET | B | 228 | 7.035 | 72.527 | 91.612 | 1.00 | 36.77 | B | C |
| ATOM | 4346 | CB | MET | B | 228 | 7.801 | 71.324 | 92.124 | 1.00 | 36.29 | B | C |
| ATOM | 4347 | CG | MET | B | 228 | 7.127 | 70.032 | 91.755 | 1.00 | 40.56 | B | C |
| ATOM | 4348 | SD | MET | B | 228 | 7.885 | 68.650 | 92.576 | 1.00 | 43.69 | B | S |
| ATOM | 4349 | CE | MET | B | 228 | 9.478 | 68.578 | 91.666 | 1.00 | 41.78 | B | C |
| ATOM | 4350 | C | MET | B | 228 | 7.825 | 73.785 | 91.853 | 1.00 | 35.66 | B | C |
| ATOM | 4351 | O | MET | B | 228 | 8.379 | 73.994 | 92.921 | 1.00 | 36.56 | B | O |
| ATOM | 4352 | N | ASN | B | 229 | 7.868 | 74.635 | 90.844 | 1.00 | 36.58 | B | N |
| ATOM | 4353 | CA | ASN | B | 229 | 8.608 | 75.871 | 90.967 | 1.00 | 37.73 | B | C |
| ATOM | 4354 | CB | ASN | B | 229 | 7.818 | 76.882 | 91.808 | 1.00 | 40.79 | B | C |
| ATOM | 4355 | CG | ASN | B | 229 | 6.596 | 77.422 | 91.073 | 1.00 | 45.26 | B | C |
| ATOM | 4356 | OD1 | ASN | B | 229 | 5.996 | 78.416 | 91.492 | 1.00 | 48.06 | B | O |
| ATOM | 4357 | ND2 | ASN | B | 229 | 6.221 | 76.769 | 89.971 | 1.00 | 46.34 | B | N |
| ATOM | 4358 | C | ASN | B | 229 | 9.982 | 75.602 | 91.579 | 1.00 | 35.72 | B | C |
| ATOM | 4359 | O | ASN | B | 229 | 10.320 | 76.115 | 92.643 | 1.00 | 34.31 | B | O |
| ATOM | 4360 | N | ALA | B | 230 | 10.756 | 74.766 | 90.889 | 1.00 | 33.50 | B | N |
| ATOM | 4361 | CA | ALA | B | 230 | 12.118 | 74.424 | 91.284 | 1.00 | 29.78 | B | C |
| ATOM | 4362 | CB | ALA | B | 230 | 12.317 | 72.925 | 91.252 | 1.00 | 27.89 | B | C |
| ATOM | 4363 | C | ALA | B | 230 | 13.035 | 75.100 | 90.262 | 1.00 | 28.58 | B | C |
| ATOM | 4364 | O | ALA | B | 230 | 13.665 | 74.447 | 89.439 | 1.00 | 29.02 | B | O |
| ATOM | 4365 | N | TYR | B | 231 | 13.086 | 76.423 | 90.332 | 1.00 | 28.05 | B | N |
| ATOM | 4366 | CA | TYR | B | 231 | 13.881 | 77.242 | 89.433 | 1.00 | 29.75 | B | C |
| ATOM | 4367 | CB | TYR | B | 231 | 13.616 | 78.710 | 89.772 | 1.00 | 29.12 | B | C |
| ATOM | 4368 | CG | TYR | B | 231 | 12.135 | 79.001 | 89.820 | 1.00 | 30.63 | B | C |
| ATOM | 4369 | CD1 | TYR | B | 231 | 11.248 | 78.257 | 89.059 | 1.00 | 30.83 | B | C |
| ATOM | 4370 | CE1 | TYR | B | 231 | 9.902 | 78.535 | 89.055 | 1.00 | 29.72 | B | C |
| ATOM | 4371 | CD2 | TYR | B | 231 | 11.622 | 80.041 | 90.584 | 1.00 | 31.95 | B | C |
| ATOM | 4372 | CE2 | TYR | B | 231 | 10.258 | 80.333 | 90.574 | 1.00 | 30.26 | B | C |
| ATOM | 4373 | CZ | TYR | B | 231 | 9.409 | 79.572 | 89.800 | 1.00 | 30.16 | B | C |
| ATOM | 4374 | OH | TYR | B | 231 | 8.064 | 79.860 | 89.733 | 1.00 | 34.30 | B | O |
| ATOM | 4375 | C | TYR | B | 231 | 15.374 | 76.920 | 89.491 | 1.00 | 29.64 | B | C |
| ATOM | 4376 | O | TYR | B | 231 | 15.968 | 76.907 | 90.569 | 1.00 | 30.34 | B | O |
| ATOM | 4377 | N | SER | B | 232 | 15.967 | 76.672 | 88.323 | 1.00 | 27.96 | B | N |
| ATOM | 4378 | CA | SER | B | 232 | 17.380 | 76.320 | 88.228 | 1.00 | 26.90 | B | C |
| ATOM | 4379 | CB | SER | B | 232 | 17.792 | 76.128 | 86.756 | 1.00 | 23.60 | B | C |
| ATOM | 4380 | OG | SER | B | 232 | 18.225 | 77.341 | 86.158 | 1.00 | 25.66 | B | O |
| ATOM | 4381 | C | SER | B | 232 | 18.289 | 77.350 | 88.890 | 1.00 | 27.27 | B | C |
| ATOM | 4382 | O | SER | B | 232 | 19.355 | 77.005 | 89.413 | 1.00 | 26.77 | B | O |
| ATOM | 4383 | N | SER | B | 233 | 17.874 | 78.611 | 88.880 | 1.00 | 24.64 | B | N |
| ATOM | 4384 | CA | SER | B | 233 | 18.700 | 79.638 | 89.488 | 1.00 | 25.20 | B | C |
| ATOM | 4385 | CB | SER | B | 233 | 18.188 | 81.031 | 89.110 | 1.00 | 27.81 | B | C |
| ATOM | 4386 | OG | SER | B | 233 | 18.254 | 81.246 | 87.709 | 1.00 | 26.86 | B | O |
| ATOM | 4387 | C | SER | B | 233 | 18.718 | 79.481 | 91.003 | 1.00 | 22.37 | B | C |
| ATOM | 4388 | O | SER | B | 233 | 19.580 | 80.030 | 91.677 | 1.00 | 21.96 | B | O |
| ATOM | 4389 | N | ARG | B | 234 | 17.776 | 78.709 | 91.531 | 1.00 | 21.88 | B | N |
| ATOM | 4390 | CA | ARG | B | 234 | 17.679 | 78.500 | 92.977 | 1.00 | 23.55 | B | C |
| ATOM | 4391 | CB | ARG | B | 234 | 16.250 | 78.783 | 93.431 | 1.00 | 24.44 | B | C |
| ATOM | 4392 | CG | ARG | B | 234 | 15.846 | 80.230 | 93.231 | 1.00 | 28.77 | B | C |
| ATOM | 4393 | CD | ARG | B | 234 | 14.351 | 80.360 | 93.079 | 1.00 | 33.33 | B | C |
| ATOM | 4394 | NE | ARG | B | 234 | 13.970 | 81.710 | 92.678 | 1.00 | 36.63 | B | N |
| ATOM | 4395 | CZ | ARG | B | 234 | 14.102 | 82.785 | 93.451 | 1.00 | 37.20 | B | C |
| ATOM | 4396 | NH1 | ARG | B | 234 | 14.604 | 82.676 | 94.677 | 1.00 | 33.90 | B | N |
| ATOM | 4397 | NH2 | ARG | B | 234 | 13.736 | 83.974 | 92.993 | 1.00 | 38.33 | B | N |
| ATOM | 4398 | C | ARG | B | 234 | 18.106 | 77.123 | 93.483 | 1.00 | 22.75 | B | C |
| ATOM | 4399 | O | ARG | B | 234 | 17.827 | 76.764 | 94.621 | 1.00 | 21.42 | B | O |
| ATOM | 4400 | N | SER | B | 235 | 18.796 | 76.356 | 92.649 | 1.00 | 23.02 | B | N |
| ATOM | 4401 | CA | SER | B | 235 | 19.214 | 75.032 | 93.069 | 1.00 | 24.50 | B | C |
| ATOM | 4402 | CB | SER | B | 235 | 18.220 | 73.987 | 92.545 | 1.00 | 26.40 | B | C |
| ATOM | 4403 | OG | SER | B | 235 | 17.852 | 74.245 | 91.205 | 1.00 | 27.30 | B | O |
| ATOM | 4404 | C | SER | B | 235 | 20.634 | 74.654 | 92.679 | 1.00 | 22.43 | B | C |
| ATOM | 4405 | O | SER | B | 235 | 21.269 | 75.331 | 91.872 | 1.00 | 22.90 | B | O |
| ATOM | 4406 | N | HIS | B | 236 | 21.134 | 73.576 | 93.281 | 1.00 | 21.12 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4407 | CA | HIS | B | 236 | 22.485 | 73.098 | 93.002 | 1.00 | 17.07 | B | C |
| ATOM | 4408 | CB | HIS | B | 236 | 23.193 | 72.642 | 94.276 | 1.00 | 17.18 | B | C |
| ATOM | 4409 | CG | HIS | B | 236 | 23.173 | 73.653 | 95.378 | 1.00 | 18.53 | B | C |
| ATOM | 4410 | CD2 | HIS | B | 236 | 22.730 | 73.574 | 96.655 | 1.00 | 18.08 | B | C |
| ATOM | 4411 | ND1 | HIS | B | 236 | 23.648 | 74.934 | 95.217 | 1.00 | 20.67 | B | N |
| ATOM | 4412 | CE1 | HIS | B | 236 | 23.498 | 75.601 | 96.346 | 1.00 | 20.76 | B | C |
| ATOM | 4413 | NE2 | HIS | B | 236 | 22.943 | 74.799 | 97.235 | 1.00 | 19.64 | B | N |
| ATOM | 4414 | C | HIS | B | 236 | 22.384 | 71.932 | 92.059 | 1.00 | 14.58 | B | C |
| ATOM | 4415 | O | HIS | B | 236 | 21.533 | 71.073 | 92.217 | 1.00 | 17.52 | B | O |
| ATOM | 4416 | N | SER | B | 237 | 23.255 | 71.915 | 91.066 | 1.00 | 14.10 | B | N |
| ATOM | 4417 | CA | SER | B | 237 | 23.282 | 70.846 | 90.093 | 1.00 | 13.25 | B | C |
| ATOM | 4418 | CB | SER | B | 237 | 23.305 | 71.427 | 88.679 | 1.00 | 12.04 | B | C |
| ATOM | 4419 | OG | SER | B | 237 | 23.483 | 70.406 | 87.712 | 1.00 | 17.19 | B | O |
| ATOM | 4420 | C | SER | B | 237 | 24.549 | 70.049 | 90.346 | 1.00 | 15.78 | B | C |
| ATOM | 4421 | O | SER | B | 237 | 25.649 | 70.568 | 90.208 | 1.00 | 17.33 | B | O |
| ATOM | 4422 | N | VAL | B | 238 | 24.408 | 68.793 | 90.741 | 1.00 | 16.91 | B | N |
| ATOM | 4423 | CA | VAL | B | 238 | 25.596 | 67.987 | 90.977 | 1.00 | 16.55 | B | C |
| ATOM | 4424 | CB | VAL | B | 238 | 25.603 | 67.371 | 92.381 | 1.00 | 17.15 | B | C |
| ATOM | 4425 | CG1 | VAL | B | 238 | 26.920 | 66.663 | 92.625 | 1.00 | 16.52 | B | C |
| ATOM | 4426 | CG2 | VAL | B | 238 | 25.386 | 68.454 | 93.419 | 1.00 | 19.91 | B | C |
| ATOM | 4427 | C | VAL | B | 238 | 25.699 | 66.873 | 89.955 | 1.00 | 17.16 | B | C |
| ATOM | 4428 | O | VAL | B | 238 | 24.946 | 65.890 | 89.994 | 1.00 | 19.90 | B | O |
| ATOM | 4429 | N | PHE | B | 239 | 26.627 | 67.042 | 89.022 | 1.00 | 14.72 | B | N |
| ATOM | 4430 | CA | PHE | B | 239 | 26.850 | 66.038 | 87.990 | 1.00 | 15.04 | B | C |
| ATOM | 4431 | CB | PHE | B | 239 | 27.086 | 66.724 | 86.638 | 1.00 | 16.44 | B | C |
| ATOM | 4432 | CG | PHE | B | 239 | 27.547 | 65.789 | 85.555 | 1.00 | 16.89 | B | C |
| ATOM | 4433 | CD1 | PHE | B | 239 | 28.895 | 65.635 | 85.283 | 1.00 | 14.81 | B | C |
| ATOM | 4434 | CD2 | PHE | B | 239 | 26.635 | 65.025 | 84.841 | 1.00 | 16.05 | B | C |
| ATOM | 4435 | CE1 | PHE | B | 239 | 29.322 | 64.741 | 84.325 | 1.00 | 11.47 | B | C |
| ATOM | 4436 | CE2 | PHE | B | 239 | 27.064 | 64.127 | 83.882 | 1.00 | 13.44 | B | C |
| ATOM | 4437 | CZ | PHE | B | 239 | 28.404 | 63.988 | 83.627 | 1.00 | 13.26 | B | C |
| ATOM | 4438 | C | PHE | B | 239 | 28.061 | 65.192 | 88.396 | 1.00 | 13.42 | B | C |
| ATOM | 4439 | O | PHE | B | 239 | 29.091 | 65.736 | 88.792 | 1.00 | 9.48 | B | O |
| ATOM | 4440 | N | SER | B | 240 | 27.926 | 63.870 | 88.319 | 1.00 | 11.51 | B | N |
| ATOM | 4441 | CA | SER | B | 240 | 29.020 | 62.978 | 88.686 | 1.00 | 12.08 | B | C |
| ATOM | 4442 | CB | SER | B | 240 | 28.707 | 62.224 | 89.979 | 1.00 | 12.25 | B | C |
| ATOM | 4443 | OG | SER | B | 240 | 28.822 | 63.055 | 91.111 | 1.00 | 13.21 | B | O |
| ATOM | 4444 | C | SER | B | 240 | 29.339 | 61.955 | 87.630 | 1.00 | 12.08 | B | C |
| ATOM | 4445 | O | SER | B | 240 | 28.452 | 61.404 | 87.005 | 1.00 | 12.57 | B | O |
| ATOM | 4446 | N | VAL | B | 241 | 30.623 | 61.710 | 87.433 | 1.00 | 12.24 | B | N |
| ATOM | 4447 | CA | VAL | B | 241 | 31.055 | 60.692 | 86.495 | 1.00 | 14.05 | B | C |
| ATOM | 4448 | CB | VAL | B | 241 | 31.620 | 61.309 | 85.185 | 1.00 | 14.57 | B | C |
| ATOM | 4449 | CG1 | VAL | B | 241 | 32.830 | 62.172 | 85.477 | 1.00 | 14.92 | B | C |
| ATOM | 4450 | CG2 | VAL | B | 241 | 31.971 | 60.203 | 84.195 | 1.00 | 14.37 | B | C |
| ATOM | 4451 | C | VAL | B | 241 | 32.119 | 59.851 | 87.214 | 1.00 | 16.04 | B | C |
| ATOM | 4452 | O | VAL | B | 241 | 33.062 | 60.382 | 87.803 | 1.00 | 11.15 | B | O |
| ATOM | 4453 | N | THR | B | 242 | 31.930 | 58.537 | 87.200 | 1.00 | 17.42 | B | N |
| ATOM | 4454 | CA | THR | B | 242 | 32.866 | 57.629 | 87.844 | 1.00 | 18.97 | B | C |
| ATOM | 4455 | CB | THR | B | 242 | 32.138 | 56.732 | 88.849 | 1.00 | 18.82 | B | C |
| ATOM | 4456 | OG1 | THR | B | 242 | 31.413 | 57.554 | 89.773 | 1.00 | 20.40 | B | O |
| ATOM | 4457 | CG2 | THR | B | 242 | 33.131 | 55.876 | 89.619 | 1.00 | 16.85 | B | C |
| ATOM | 4458 | C | THR | B | 242 | 33.523 | 56.758 | 86.788 | 1.00 | 20.54 | B | C |
| ATOM | 4459 | O | THR | B | 242 | 32.877 | 56.328 | 85.840 | 1.00 | 21.64 | B | O |
| ATOM | 4460 | N | ILE | B | 243 | 34.814 | 56.508 | 86.926 | 1.00 | 22.60 | B | N |
| ATOM | 4461 | CA | ILE | B | 243 | 35.485 | 55.658 | 85.951 | 1.00 | 24.57 | B | C |
| ATOM | 4462 | CB | ILE | B | 243 | 36.599 | 56.414 | 85.185 | 1.00 | 25.78 | B | C |
| ATOM | 4463 | CG2 | ILE | B | 243 | 37.236 | 55.488 | 84.166 | 1.00 | 26.85 | B | C |
| ATOM | 4464 | CG1 | ILE | B | 243 | 36.029 | 57.633 | 84.459 | 1.00 | 24.91 | B | C |
| ATOM | 4465 | CD1 | ILE | B | 243 | 35.649 | 58.757 | 85.371 | 1.00 | 25.90 | B | C |
| ATOM | 4466 | C | ILE | B | 243 | 36.126 | 54.423 | 86.588 | 1.00 | 23.38 | B | C |
| ATOM | 4467 | O | ILE | B | 243 | 36.932 | 54.553 | 87.503 | 1.00 | 24.57 | B | O |
| ATOM | 4468 | N | HIS | B | 244 | 35.746 | 53.237 | 86.116 | 1.00 | 21.59 | B | N |
| ATOM | 4469 | CA | HIS | B | 244 | 36.341 | 51.989 | 86.596 | 1.00 | 21.09 | B | C |
| ATOM | 4470 | CB | HIS | B | 244 | 35.297 | 50.864 | 86.687 | 1.00 | 19.77 | B | C |
| ATOM | 4471 | CG | HIS | B | 244 | 34.542 | 50.842 | 87.983 | 1.00 | 22.90 | B | C |
| ATOM | 4472 | CD2 | HIS | B | 244 | 34.620 | 50.004 | 89.045 | 1.00 | 23.38 | B | C |
| ATOM | 4473 | ND1 | HIS | B | 244 | 33.605 | 51.795 | 88.319 | 1.00 | 22.93 | B | N |
| ATOM | 4474 | CE1 | HIS | B | 244 | 33.141 | 51.549 | 89.531 | 1.00 | 21.38 | B | C |
| ATOM | 4475 | NE2 | HIS | B | 244 | 33.742 | 50.467 | 89.993 | 1.00 | 24.74 | B | N |
| ATOM | 4476 | C | HIS | B | 244 | 37.409 | 51.652 | 85.554 | 1.00 | 20.81 | B | C |
| ATOM | 4477 | O | HIS | B | 244 | 37.102 | 51.404 | 84.379 | 1.00 | 21.04 | B | O |
| ATOM | 4478 | N | MET | B | 245 | 38.667 | 51.666 | 85.980 | 1.00 | 20.58 | B | N |
| ATOM | 4479 | CA | MET | B | 245 | 39.778 | 51.403 | 85.069 | 1.00 | 22.28 | B | C |
| ATOM | 4480 | CB | MET | B | 245 | 40.631 | 52.661 | 84.912 | 1.00 | 21.44 | B | C |
| ATOM | 4481 | CG | MET | B | 245 | 39.850 | 53.931 | 84.667 | 1.00 | 22.16 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4482 | SD | MET | B | 245 | 40.919 | 55.395 | 84.754 | 1.00 | 23.62 | B | S |
| ATOM | 4483 | CE | MET | B | 245 | 41.066 | 55.594 | 86.531 | 1.00 | 20.34 | B | C |
| ATOM | 4484 | C | MET | B | 245 | 40.693 | 50.274 | 85.505 | 1.00 | 23.45 | B | C |
| ATOM | 4485 | O | MET | B | 245 | 40.895 | 50.042 | 86.697 | 1.00 | 25.99 | B | O |
| ATOM | 4486 | N | LYS | B | 246 | 41.256 | 49.587 | 84.520 | 1.00 | 26.51 | B | N |
| ATOM | 4487 | CA | LYS | B | 246 | 42.184 | 48.491 | 84.268 | 1.00 | 29.07 | B | C |
| ATOM | 4488 | CB | LYS | B | 246 | 41.449 | 47.148 | 84.767 | 1.00 | 29.28 | B | C |
| ATOM | 4489 | CG | LYS | B | 246 | 42.349 | 45.974 | 85.098 | 1.00 | 34.15 | B | C |
| ATOM | 4490 | CD | LYS | B | 246 | 41.568 | 44.678 | 85.276 | 1.00 | 35.85 | B | C |
| ATOM | 4491 | CE | LYS | B | 246 | 42.498 | 43.555 | 85.732 | 1.00 | 40.03 | B | C |
| ATOM | 4492 | NZ | LYS | B | 246 | 41.787 | 42.272 | 86.012 | 1.00 | 41.21 | B | N |
| ATOM | 4493 | C | LYS | B | 246 | 43.230 | 48.498 | 83.664 | 1.00 | 30.47 | B | C |
| ATOM | 4494 | O | LYS | B | 246 | 42.890 | 48.365 | 82.491 | 1.00 | 30.14 | B | O |
| ATOM | 4495 | N | GLU | B | 247 | 44.496 | 48.673 | 84.027 | 1.00 | 30.62 | B | N |
| ATOM | 4496 | CA | GLU | B | 247 | 45.549 | 48.673 | 83.022 | 1.00 | 34.02 | B | C |
| ATOM | 4497 | CB | GLU | B | 247 | 46.247 | 50.032 | 82.958 | 1.00 | 36.35 | B | C |
| ATOM | 4498 | CG | GLU | B | 247 | 46.387 | 50.741 | 84.280 | 1.00 | 44.18 | B | C |
| ATOM | 4499 | CD | GLU | B | 247 | 47.059 | 52.091 | 84.126 | 1.00 | 48.18 | B | C |
| ATOM | 4500 | OE1 | GLU | B | 247 | 47.046 | 52.878 | 85.102 | 1.00 | 49.92 | B | O |
| ATOM | 4501 | OE2 | GLU | B | 247 | 47.604 | 52.358 | 83.029 | 1.00 | 47.92 | B | O |
| ATOM | 4502 | C | GLU | B | 247 | 46.577 | 47.563 | 83.205 | 1.00 | 33.62 | B | C |
| ATOM | 4503 | O | GLU | B | 247 | 47.112 | 47.357 | 84.294 | 1.00 | 32.66 | B | O |
| ATOM | 4504 | N | THR | B | 248 | 46.841 | 46.852 | 82.109 | 1.00 | 33.51 | B | N |
| ATOM | 4505 | CA | THR | B | 248 | 47.783 | 45.741 | 82.094 | 1.00 | 32.18 | B | C |
| ATOM | 4506 | CB | THR | B | 248 | 47.089 | 44.441 | 81.639 | 1.00 | 33.50 | B | C |
| ATOM | 4507 | OG1 | THR | B | 248 | 46.031 | 44.110 | 82.545 | 1.00 | 35.14 | B | O |
| ATOM | 4508 | CG2 | THR | B | 248 | 48.074 | 43.297 | 81.614 | 1.00 | 34.79 | B | C |
| ATOM | 4509 | C | THR | B | 248 | 48.966 | 45.986 | 81.164 | 1.00 | 31.51 | B | C |
| ATOM | 4510 | O | THR | B | 248 | 48.794 | 46.390 | 80.015 | 1.00 | 32.35 | B | O |
| ATOM | 4511 | N | THR | B | 249 | 50.163 | 45.724 | 81.674 | 1.00 | 32.97 | B | N |
| ATOM | 4512 | CA | THR | B | 249 | 51.404 | 45.894 | 80.920 | 1.00 | 33.74 | B | C |
| ATOM | 4513 | CB | THR | B | 249 | 52.210 | 47.123 | 81.422 | 1.00 | 32.82 | B | C |
| ATOM | 4514 | OG1 | THR | B | 249 | 51.558 | 48.336 | 81.015 | 1.00 | 34.38 | B | O |
| ATOM | 4515 | CG2 | THR | B | 249 | 53.623 | 47.089 | 80.867 | 1.00 | 32.80 | B | C |
| ATOM | 4516 | C | THR | B | 249 | 52.241 | 44.640 | 81.150 | 1.00 | 33.28 | B | C |
| ATOM | 4517 | O | THR | B | 249 | 52.682 | 44.398 | 82.270 | 1.00 | 35.85 | B | O |
| ATOM | 4518 | N | ILE | B | 250 | 52.455 | 43.842 | 80.105 | 1.00 | 31.41 | B | N |
| ATOM | 4519 | CA | ILE | B | 250 | 53.237 | 42.609 | 80.238 | 1.00 | 29.74 | B | C |
| ATOM | 4520 | CB | ILE | B | 250 | 53.523 | 41.980 | 78.866 | 1.00 | 27.04 | B | C |
| ATOM | 4521 | CG2 | ILE | B | 250 | 54.435 | 40.782 | 79.017 | 1.00 | 24.00 | B | C |
| ATOM | 4522 | CG1 | ILE | B | 250 | 52.210 | 41.538 | 78.220 | 1.00 | 25.44 | B | C |
| ATOM | 4523 | CD1 | ILE | B | 250 | 52.352 | 41.061 | 76.791 | 1.00 | 24.26 | B | C |
| ATOM | 4524 | C | ILE | B | 250 | 54.557 | 42.857 | 80.957 | 1.00 | 32.83 | B | C |
| ATOM | 4525 | O | ILE | B | 250 | 55.272 | 43.808 | 80.648 | 1.00 | 34.21 | B | O |
| ATOM | 4526 | N | ASP | B | 251 | 54.881 | 41.993 | 81.917 | 1.00 | 37.23 | B | N |
| ATOM | 4527 | CA | ASP | B | 251 | 56.110 | 42.142 | 82.702 | 1.00 | 39.56 | B | C |
| ATOM | 4528 | CB | ASP | B | 251 | 57.366 | 41.997 | 81.822 | 1.00 | 39.28 | B | C |
| ATOM | 4529 | CG | ASP | B | 251 | 57.523 | 40.602 | 81.240 | 1.00 | 37.22 | B | C |
| ATOM | 4530 | OD1 | ASP | B | 251 | 57.180 | 39.627 | 81.935 | 1.00 | 34.38 | B | O |
| ATOM | 4531 | OD2 | ASP | B | 251 | 58.003 | 40.482 | 80.093 | 1.00 | 37.59 | B | O |
| ATOM | 4532 | C | ASP | B | 251 | 56.084 | 43.539 | 83.303 | 1.00 | 41.43 | B | C |
| ATOM | 4533 | O | ASP | B | 251 | 57.086 | 44.256 | 83.282 | 1.00 | 43.84 | B | O |
| ATOM | 4534 | N | GLY | B | 252 | 54.922 | 43.920 | 83.821 | 1.00 | 40.90 | B | N |
| ATOM | 4535 | CA | GLY | B | 252 | 54.763 | 45.238 | 84.407 | 1.00 | 42.54 | B | C |
| ATOM | 4536 | C | GLY | B | 252 | 53.724 | 45.202 | 85.505 | 1.00 | 43.38 | B | C |
| ATOM | 4537 | O | GLY | B | 252 | 53.161 | 44.143 | 85.797 | 1.00 | 42.27 | B | O |
| ATOM | 4538 | N | GLU | B | 253 | 53.464 | 46.353 | 86.116 | 1.00 | 43.55 | B | N |
| ATOM | 4539 | CA | GLU | B | 253 | 52.494 | 46.428 | 87.199 | 1.00 | 43.75 | B | C |
| ATOM | 4540 | CB | GLU | B | 253 | 52.804 | 47.636 | 88.090 | 1.00 | 45.15 | B | C |
| ATOM | 4541 | CG | GLU | B | 253 | 51.977 | 47.735 | 89.374 | 1.00 | 47.37 | B | C |
| ATOM | 4542 | CD | GLU | B | 253 | 52.209 | 46.574 | 90.332 | 1.00 | 47.00 | B | C |
| ATOM | 4543 | OE1 | GLU | B | 253 | 51.986 | 46.756 | 91.549 | 1.00 | 46.13 | B | O |
| ATOM | 4544 | OE2 | GLU | B | 253 | 52.603 | 45.480 | 89.869 | 1.00 | 47.02 | B | O |
| ATOM | 4545 | C | GLU | B | 253 | 51.074 | 46.529 | 86.652 | 1.00 | 42.76 | B | C |
| ATOM | 4546 | O | GLU | B | 253 | 50.799 | 47.335 | 85.761 | 1.00 | 44.02 | B | O |
| ATOM | 4547 | N | GLU | B | 254 | 50.181 | 45.689 | 87.170 | 1.00 | 41.06 | B | N |
| ATOM | 4548 | CA | GLU | B | 254 | 48.783 | 45.707 | 86.750 | 1.00 | 39.43 | B | C |
| ATOM | 4549 | CB | GLU | B | 254 | 48.152 | 44.324 | 86.902 | 1.00 | 38.86 | B | C |
| ATOM | 4550 | CG | GLU | B | 254 | 46.722 | 44.266 | 86.395 | 1.00 | 41.79 | B | C |
| ATOM | 4551 | CD | GLU | B | 254 | 46.065 | 42.924 | 86.630 | 1.00 | 41.81 | B | C |
| ATOM | 4552 | OE1 | GLU | B | 254 | 45.818 | 42.584 | 87.804 | 1.00 | 39.08 | B | O |
| ATOM | 4553 | OE2 | GLU | B | 254 | 45.795 | 42.210 | 85.640 | 1.00 | 45.15 | B | O |
| ATOM | 4554 | C | GLU | B | 254 | 48.060 | 46.707 | 87.651 | 1.00 | 38.26 | B | C |
| ATOM | 4555 | O | GLU | B | 254 | 48.156 | 46.634 | 88.881 | 1.00 | 35.57 | B | O |
| ATOM | 4556 | N | LEU | B | 255 | 47.341 | 47.646 | 87.050 | 1.00 | 36.72 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4557 | CA | LEU | B | 255 | 46.659 | 48.652 | 87.845 | 1.00 | 34.06 | B | C |
| ATOM | 4558 | CB | LEU | B | 255 | 47.194 | 50.044 | 87.495 | 1.00 | 35.43 | B | C |
| ATOM | 4559 | CG | LEU | B | 255 | 48.560 | 50.386 | 88.100 | 1.00 | 37.99 | B | C |
| ATOM | 4560 | CD1 | LEU | B | 255 | 49.065 | 51.697 | 87.533 | 1.00 | 37.38 | B | C |
| ATOM | 4561 | CD2 | LEU | B | 255 | 48.432 | 50.468 | 89.619 | 1.00 | 39.23 | B | C |
| ATOM | 4562 | C | LEU | B | 255 | 45.150 | 48.653 | 87.748 | 1.00 | 31.87 | B | C |
| ATOM | 4563 | O | LEU | B | 255 | 44.578 | 48.698 | 86.662 | 1.00 | 31.89 | B | O |
| ATOM | 4564 | N | VAL | B | 256 | 44.513 | 48.598 | 88.911 | 1.00 | 29.69 | B | N |
| ATOM | 4565 | CA | VAL | B | 256 | 43.064 | 48.628 | 89.008 | 1.00 | 26.19 | B | C |
| ATOM | 4566 | CB | VAL | B | 256 | 42.519 | 47.370 | 89.681 | 1.00 | 23.99 | B | C |
| ATOM | 4567 | CG1 | VAL | B | 256 | 41.071 | 47.570 | 90.057 | 1.00 | 21.69 | B | C |
| ATOM | 4568 | CG2 | VAL | B | 256 | 42.651 | 46.199 | 88.736 | 1.00 | 26.53 | B | C |
| ATOM | 4569 | C | VAL | B | 256 | 42.697 | 49.840 | 89.847 | 1.00 | 25.61 | B | C |
| ATOM | 4570 | O | VAL | B | 256 | 43.069 | 49.936 | 91.015 | 1.00 | 24.53 | B | O |
| ATOM | 4571 | N | LYS | B | 257 | 41.976 | 50.777 | 89.246 | 1.00 | 23.95 | B | N |
| ATOM | 4572 | CA | LYS | B | 257 | 41.596 | 51.973 | 89.974 | 1.00 | 21.48 | B | C |
| ATOM | 4573 | CB | LYS | B | 257 | 42.652 | 53.067 | 89.774 | 1.00 | 21.75 | B | C |
| ATOM | 4574 | CG | LYS | B | 257 | 43.283 | 53.120 | 88.390 | 1.00 | 19.65 | B | C |
| ATOM | 4575 | CD | LYS | B | 257 | 44.386 | 54.172 | 88.364 | 1.00 | 18.78 | B | C |
| ATOM | 4576 | CE | LYS | B | 257 | 45.255 | 54.091 | 87.104 | 1.00 | 20.78 | B | C |
| ATOM | 4577 | NZ | LYS | B | 257 | 44.511 | 54.272 | 85.830 | 1.00 | 19.03 | B | N |
| ATOM | 4578 | C | LYS | B | 257 | 40.227 | 52.499 | 89.618 | 1.00 | 19.15 | B | C |
| ATOM | 4579 | O | LYS | B | 257 | 39.690 | 52.196 | 88.560 | 1.00 | 19.08 | B | O |
| ATOM | 4580 | N | ILE | B | 258 | 39.664 | 53.281 | 90.529 | 1.00 | 18.25 | B | N |
| ATOM | 4581 | CA | ILE | B | 258 | 38.354 | 53.884 | 90.334 | 1.00 | 19.93 | B | C |
| ATOM | 4582 | CB | ILE | B | 258 | 37.352 | 53.396 | 91.396 | 1.00 | 19.62 | B | C |
| ATOM | 4583 | CG2 | ILE | B | 258 | 36.063 | 54.186 | 91.303 | 1.00 | 19.26 | B | C |
| ATOM | 4584 | CG1 | ILE | B | 258 | 37.082 | 51.904 | 91.203 | 1.00 | 21.90 | B | C |
| ATOM | 4585 | CD1 | ILE | B | 258 | 36.293 | 51.267 | 92.349 | 1.00 | 18.05 | B | C |
| ATOM | 4586 | C | ILE | B | 258 | 38.505 | 55.395 | 90.453 | 1.00 | 19.64 | B | C |
| ATOM | 4587 | O | ILE | B | 258 | 38.990 | 55.892 | 91.472 | 1.00 | 21.57 | B | O |
| ATOM | 4588 | N | GLY | B | 259 | 38.106 | 56.116 | 89.408 | 1.00 | 18.14 | B | N |
| ATOM | 4589 | CA | GLY | B | 259 | 38.209 | 57.567 | 89.423 | 1.00 | 18.61 | B | C |
| ATOM | 4590 | C | GLY | B | 259 | 36.837 | 58.210 | 89.487 | 1.00 | 17.76 | B | C |
| ATOM | 4591 | O | GLY | B | 259 | 35.833 | 57.568 | 89.168 | 1.00 | 18.67 | B | O |
| ATOM | 4592 | N | LYS | B | 260 | 36.776 | 59.472 | 89.892 | 1.00 | 16.34 | B | N |
| ATOM | 4593 | CA | LYS | B | 260 | 35.491 | 60.145 | 89.985 | 1.00 | 18.12 | B | C |
| ATOM | 4594 | CB | LYS | B | 260 | 34.730 | 59.638 | 91.211 | 1.00 | 19.03 | B | C |
| ATOM | 4595 | CG | LYS | B | 260 | 33.361 | 60.256 | 91.367 | 1.00 | 22.50 | B | C |
| ATOM | 4596 | CD | LYS | B | 260 | 32.526 | 59.445 | 92.335 | 1.00 | 26.15 | B | C |
| ATOM | 4597 | CE | LYS | B | 260 | 31.064 | 59.879 | 92.330 | 1.00 | 24.70 | B | C |
| ATOM | 4598 | NZ | LYS | B | 260 | 30.225 | 58.922 | 93.124 | 1.00 | 26.07 | B | N |
| ATOM | 4599 | C | LYS | B | 260 | 35.575 | 61.664 | 90.040 | 1.00 | 16.87 | B | C |
| ATOM | 4600 | O | LYS | B | 260 | 36.340 | 62.213 | 90.820 | 1.00 | 16.21 | B | O |
| ATOM | 4601 | N | LEU | B | 261 | 34.775 | 62.330 | 89.211 | 1.00 | 17.10 | B | N |
| ATOM | 4602 | CA | LEU | B | 261 | 34.738 | 63.787 | 89.169 | 1.00 | 14.79 | B | C |
| ATOM | 4603 | CB | LEU | B | 261 | 35.294 | 64.307 | 87.837 | 1.00 | 15.10 | B | C |
| ATOM | 4604 | CG | LEU | B | 261 | 35.417 | 65.844 | 87.754 | 1.00 | 19.62 | B | C |
| ATOM | 4605 | CD1 | LEU | B | 261 | 36.253 | 66.355 | 88.919 | 1.00 | 19.09 | B | C |
| ATOM | 4606 | CD2 | LEU | B | 261 | 36.053 | 66.270 | 86.454 | 1.00 | 14.62 | B | C |
| ATOM | 4607 | C | LEU | B | 261 | 33.319 | 64.347 | 89.369 | 1.00 | 14.72 | B | C |
| ATOM | 4608 | O | LEU | B | 261 | 32.364 | 63.931 | 88.702 | 1.00 | 10.69 | B | O |
| ATOM | 4609 | N | ASN | B | 262 | 33.193 | 65.290 | 90.299 | 1.00 | 14.37 | B | N |
| ATOM | 4610 | CA | ASN | B | 262 | 31.911 | 65.936 | 90.569 | 1.00 | 14.42 | B | C |
| ATOM | 4611 | CB | ASN | B | 262 | 31.648 | 66.047 | 92.067 | 1.00 | 15.45 | B | C |
| ATOM | 4612 | CG | ASN | B | 262 | 31.879 | 64.754 | 92.786 | 1.00 | 17.34 | B | C |
| ATOM | 4613 | OD1 | ASN | B | 262 | 32.938 | 64.541 | 93.376 | 1.00 | 23.50 | B | O |
| ATOM | 4614 | ND2 | ASN | B | 262 | 30.897 | 63.866 | 92.731 | 1.00 | 12.33 | B | N |
| ATOM | 4615 | C | ASN | B | 262 | 31.962 | 67.337 | 89.986 | 1.00 | 13.98 | B | C |
| ATOM | 4616 | O | ASN | B | 262 | 32.875 | 68.101 | 90.278 | 1.00 | 15.43 | B | O |
| ATOM | 4617 | N | LEU | B | 263 | 30.983 | 67.668 | 89.157 | 1.00 | 13.50 | B | N |
| ATOM | 4618 | CA | LEU | B | 263 | 30.934 | 68.981 | 88.545 | 1.00 | 13.87 | B | C |
| ATOM | 4619 | CB | LEU | B | 263 | 30.965 | 68.818 | 87.029 | 1.00 | 15.01 | B | C |
| ATOM | 4620 | CG | LEU | B | 263 | 32.204 | 68.018 | 86.584 | 1.00 | 9.60 | B | C |
| ATOM | 4621 | CD1 | LEU | B | 263 | 32.187 | 67.808 | 85.095 | 1.00 | 13.20 | B | C |
| ATOM | 4622 | CD2 | LEU | B | 263 | 33.451 | 68.761 | 86.973 | 1.00 | 10.27 | B | C |
| ATOM | 4623 | C | LEU | B | 263 | 29.662 | 69.657 | 89.048 | 1.00 | 14.94 | B | C |
| ATOM | 4624 | O | LEU | B | 263 | 28.554 | 69.308 | 88.652 | 1.00 | 17.32 | B | O |
| ATOM | 4625 | N | VAL | B | 264 | 29.849 | 70.629 | 89.937 | 1.00 | 14.36 | B | N |
| ATOM | 4626 | CA | VAL | B | 264 | 28.759 | 71.337 | 90.585 | 1.00 | 15.08 | B | C |
| ATOM | 4627 | CB | VAL | B | 264 | 29.041 | 71.399 | 92.103 | 1.00 | 15.92 | B | C |
| ATOM | 4628 | CG1 | VAL | B | 264 | 27.804 | 71.848 | 92.860 | 1.00 | 15.03 | B | C |
| ATOM | 4629 | CG2 | VAL | B | 264 | 29.512 | 70.034 | 92.589 | 1.00 | 15.10 | B | C |
| ATOM | 4630 | C | VAL | B | 264 | 28.436 | 72.755 | 90.097 | 1.00 | 15.33 | B | C |
| ATOM | 4631 | O | VAL | B | 264 | 29.280 | 73.646 | 90.150 | 1.00 | 14.33 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4632 | N | ASP | B | 265 | 27.199 | 72.945 | 89.635 | 1.00 | 14.75 | B | N |
| ATOM | 4633 | CA | ASP | B | 265 | 26.677 | 74.238 | 89.173 | 1.00 | 14.11 | B | C |
| ATOM | 4634 | CB | ASP | B | 265 | 25.779 | 74.048 | 87.937 | 1.00 | 15.44 | B | C |
| ATOM | 4635 | CG | ASP | B | 265 | 25.442 | 75.373 | 87.233 | 1.00 | 20.13 | B | C |
| ATOM | 4636 | OD1 | ASP | B | 265 | 25.299 | 76.415 | 87.916 | 1.00 | 23.16 | B | O |
| ATOM | 4637 | OD2 | ASP | B | 265 | 25.306 | 75.381 | 85.993 | 1.00 | 18.29 | B | O |
| ATOM | 4638 | C | ASP | B | 265 | 25.823 | 74.719 | 90.364 | 1.00 | 13.70 | B | C |
| ATOM | 4639 | O | ASP | B | 265 | 24.699 | 74.258 | 90.556 | 1.00 | 12.68 | B | O |
| ATOM | 4640 | N | LEU | B | 266 | 26.359 | 75.633 | 91.165 | 1.00 | 12.40 | B | N |
| ATOM | 4641 | CA | LEU | B | 266 | 25.660 | 76.108 | 92.355 | 1.00 | 13.14 | B | C |
| ATOM | 4642 | CB | LEU | B | 266 | 26.663 | 76.717 | 93.330 | 1.00 | 9.43 | B | C |
| ATOM | 4643 | CG | LEU | B | 266 | 27.781 | 75.825 | 93.859 | 1.00 | 11.81 | B | C |
| ATOM | 4644 | CD1 | LEU | B | 266 | 28.831 | 76.703 | 94.536 | 1.00 | 10.63 | B | C |
| ATOM | 4645 | CD2 | LEU | B | 266 | 27.218 | 74.782 | 94.833 | 1.00 | 11.01 | B | C |
| ATOM | 4646 | C | LEU | B | 266 | 24.538 | 77.116 | 92.130 | 1.00 | 15.82 | B | C |
| ATOM | 4647 | O | LEU | B | 266 | 24.543 | 77.883 | 91.150 | 1.00 | 17.45 | B | O |
| ATOM | 4648 | N | ALA | B | 267 | 23.578 | 77.120 | 93.054 | 1.00 | 14.80 | B | N |
| ATOM | 4649 | CA | ALA | B | 267 | 22.472 | 78.071 | 92.987 | 1.00 | 15.90 | B | C |
| ATOM | 4650 | CB | ALA | B | 267 | 21.530 | 77.874 | 94.161 | 1.00 | 15.23 | B | C |
| ATOM | 4651 | C | ALA | B | 267 | 23.086 | 79.466 | 93.037 | 1.00 | 15.60 | B | C |
| ATOM | 4652 | O | ALA | B | 267 | 24.054 | 79.694 | 93.754 | 1.00 | 16.32 | B | O |
| ATOM | 4653 | N | GLY | B | 268 | 22.531 | 80.394 | 92.269 | 1.00 | 18.41 | B | N |
| ATOM | 4654 | CA | GLY | B | 268 | 23.062 | 81.745 | 92.253 | 1.00 | 18.72 | B | C |
| ATOM | 4655 | C | GLY | B | 268 | 23.311 | 82.263 | 93.653 | 1.00 | 20.65 | B | C |
| ATOM | 4656 | O | GLY | B | 268 | 22.626 | 81.869 | 94.597 | 1.00 | 20.05 | B | O |
| ATOM | 4657 | N | SER | B | 269 | 24.296 | 83.143 | 93.788 | 1.00 | 23.42 | B | N |
| ATOM | 4658 | CA | SER | B | 269 | 24.645 | 83.714 | 95.081 | 1.00 | 27.09 | B | C |
| ATOM | 4659 | CB | SER | B | 269 | 26.124 | 84.087 | 95.073 | 1.00 | 23.34 | B | C |
| ATOM | 4660 | OG | SER | B | 269 | 26.534 | 84.475 | 93.775 | 1.00 | 15.79 | B | O |
| ATOM | 4661 | C | SER | B | 269 | 23.768 | 84.925 | 95.398 | 1.00 | 30.96 | B | C |
| ATOM | 4662 | O | SER | B | 269 | 24.034 | 86.039 | 94.953 | 1.00 | 30.66 | B | O |
| ATOM | 4663 | N | GLU | B | 270 | 22.720 | 84.688 | 96.185 | 1.00 | 38.56 | B | N |
| ATOM | 4664 | CA | GLU | B | 270 | 21.766 | 85.736 | 96.554 | 1.00 | 45.56 | B | C |
| ATOM | 4665 | CB | GLU | B | 270 | 21.045 | 86.197 | 95.287 | 1.00 | 43.73 | B | C |
| ATOM | 4666 | CG | GLU | B | 270 | 20.739 | 85.031 | 94.341 | 1.00 | 46.18 | B | C |
| ATOM | 4667 | CD | GLU | B | 270 | 20.742 | 85.418 | 92.866 | 1.00 | 44.02 | B | C |
| ATOM | 4668 | OE1 | GLU | B | 270 | 19.843 | 86.176 | 92.442 | 1.00 | 43.06 | B | O |
| ATOM | 4669 | OE2 | GLU | B | 270 | 21.647 | 84.957 | 92.137 | 1.00 | 39.18 | B | O |
| ATOM | 4670 | C | GLU | B | 270 | 20.759 | 85.241 | 97.603 | 1.00 | 49.77 | B | C |
| ATOM | 4671 | O | GLU | B | 270 | 20.997 | 84.230 | 98.271 | 1.00 | 49.02 | B | O |
| ATOM | 4672 | N | ARG | B | 281 | 19.652 | 85.972 | 97.754 | 1.00 | 54.80 | B | N |
| ATOM | 4673 | CA | ARG | B | 281 | 18.578 | 85.631 | 98.703 | 1.00 | 59.48 | B | C |
| ATOM | 4674 | CB | ARG | B | 281 | 18.132 | 84.172 | 98.479 | 1.00 | 58.54 | B | C |
| ATOM | 4675 | CG | ARG | B | 281 | 16.621 | 83.986 | 98.255 | 1.00 | 55.90 | B | C |
| ATOM | 4676 | CD | ARG | B | 281 | 15.819 | 84.086 | 99.558 | 1.00 | 55.86 | B | C |
| ATOM | 4677 | NE | ARG | B | 281 | 14.373 | 83.968 | 99.343 | 1.00 | 56.44 | B | N |
| ATOM | 4678 | CZ | ARG | B | 281 | 13.460 | 83.945 | 100.316 | 1.00 | 55.68 | B | C |
| ATOM | 4679 | NH1 | ARG | B | 281 | 13.830 | 84.029 | 101.587 | 1.00 | 55.50 | B | N |
| ATOM | 4680 | NH2 | ARG | B | 281 | 12.170 | 83.844 | 100.019 | 1.00 | 54.89 | B | N |
| ATOM | 4681 | C | ARG | B | 281 | 18.923 | 85.873 | 100.193 | 1.00 | 62.67 | B | C |
| ATOM | 4682 | O | ARG | B | 281 | 20.071 | 85.693 | 100.616 | 1.00 | 62.71 | B | O |
| ATOM | 4683 | N | ALA | B | 282 | 17.914 | 86.273 | 100.975 | 1.00 | 65.54 | B | N |
| ATOM | 4684 | CA | ALA | B | 282 | 18.080 | 86.584 | 102.401 | 1.00 | 67.98 | B | C |
| ATOM | 4685 | CB | ALA | B | 282 | 17.362 | 87.893 | 102.720 | 1.00 | 66.69 | B | C |
| ATOM | 4686 | C | ALA | B | 282 | 17.664 | 85.512 | 103.424 | 1.00 | 69.99 | B | C |
| ATOM | 4687 | O | ALA | B | 282 | 18.528 | 84.836 | 103.991 | 1.00 | 70.15 | B | O |
| ATOM | 4688 | N | ARG | B | 283 | 16.358 | 85.367 | 103.677 | 1.00 | 71.34 | B | N |
| ATOM | 4689 | CA | ARG | B | 283 | 15.873 | 84.383 | 104.659 | 1.00 | 72.73 | B | C |
| ATOM | 4690 | CB | ARG | B | 283 | 14.620 | 84.910 | 105.376 | 1.00 | 73.04 | B | C |
| ATOM | 4691 | CG | ARG | B | 283 | 13.969 | 83.888 | 106.320 | 1.00 | 72.71 | B | C |
| ATOM | 4692 | CD | ARG | B | 283 | 15.013 | 83.167 | 107.180 | 1.00 | 71.94 | B | C |
| ATOM | 4693 | NE | ARG | B | 283 | 14.479 | 81.983 | 107.855 | 1.00 | 69.52 | B | N |
| ATOM | 4694 | CZ | ARG | B | 283 | 15.232 | 81.035 | 108.410 | 1.00 | 69.25 | B | C |
| ATOM | 4695 | NH1 | ARG | B | 283 | 16.556 | 81.125 | 108.371 | 1.00 | 67.04 | B | N |
| ATOM | 4696 | NH2 | ARG | B | 283 | 14.665 | 79.994 | 109.008 | 1.00 | 68.70 | B | N |
| ATOM | 4697 | C | ARG | B | 283 | 15.608 | 82.950 | 104.166 | 1.00 | 73.38 | B | C |
| ATOM | 4698 | O | ARG | B | 283 | 15.070 | 82.123 | 104.908 | 1.00 | 73.65 | B | O |
| ATOM | 4699 | N | GLU | B | 284 | 15.970 | 82.654 | 102.920 | 1.00 | 74.27 | B | N |
| ATOM | 4700 | CA | GLU | B | 284 | 15.803 | 81.301 | 102.388 | 1.00 | 74.16 | B | C |
| ATOM | 4701 | CB | GLU | B | 284 | 15.694 | 81.321 | 100.859 | 1.00 | 73.94 | B | C |
| ATOM | 4702 | CG | GLU | B | 284 | 15.477 | 79.948 | 100.231 | 1.00 | 75.90 | B | C |
| ATOM | 4703 | CD | GLU | B | 284 | 15.437 | 79.989 | 98.704 | 1.00 | 76.96 | B | C |
| ATOM | 4704 | OE1 | GLU | B | 284 | 15.163 | 78.935 | 98.085 | 1.00 | 76.44 | B | O |
| ATOM | 4705 | OE2 | GLU | B | 284 | 15.682 | 81.070 | 98.121 | 1.00 | 76.44 | B | O |
| ATOM | 4706 | C | GLU | B | 284 | 17.075 | 80.565 | 102.800 | 1.00 | 74.27 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4707 | O | GLU | B | 284 | 17.183 | 79.346 | 102.673 | 1.00 | 74.02 | B | O |
| ATOM | 4708 | N | ALA | B | 285 | 18.031 | 81.345 | 103.301 | 1.00 | 73.99 | B | N |
| ATOM | 4709 | CA | ALA | B | 285 | 19.332 | 80.857 | 103.748 | 1.00 | 72.81 | B | C |
| ATOM | 4710 | CB | ALA | B | 285 | 19.933 | 81.835 | 104.770 | 1.00 | 74.63 | B | C |
| ATOM | 4711 | C | ALA | B | 285 | 19.255 | 79.462 | 104.343 | 1.00 | 71.13 | B | C |
| ATOM | 4712 | O | ALA | B | 285 | 19.852 | 78.526 | 103.810 | 1.00 | 70.58 | B | O |
| ATOM | 4713 | N | GLY | B | 286 | 18.528 | 79.332 | 105.452 | 1.00 | 70.47 | B | N |
| ATOM | 4714 | CA | GLY | B | 286 | 18.382 | 78.037 | 106.094 | 1.00 | 68.38 | B | C |
| ATOM | 4715 | C | GLY | B | 286 | 18.057 | 76.983 | 105.054 | 1.00 | 66.36 | B | C |
| ATOM | 4716 | O | GLY | B | 286 | 17.960 | 75.791 | 105.363 | 1.00 | 65.92 | B | O |
| ATOM | 4717 | N | ASN | B | 287 | 17.893 | 77.439 | 103.812 | 1.00 | 63.20 | B | N |
| ATOM | 4718 | CA | ASN | B | 287 | 17.576 | 76.575 | 102.684 | 1.00 | 59.06 | B | C |
| ATOM | 4719 | CB | ASN | B | 287 | 16.056 | 76.437 | 102.538 | 1.00 | 60.31 | B | C |
| ATOM | 4720 | CG | ASN | B | 287 | 15.325 | 76.514 | 103.873 | 1.00 | 60.82 | B | C |
| ATOM | 4721 | OD1 | ASN | B | 287 | 15.343 | 77.549 | 104.546 | 1.00 | 60.20 | B | O |
| ATOM | 4722 | ND2 | ASN | B | 287 | 14.674 | 75.418 | 104.260 | 1.00 | 61.57 | B | N |
| ATOM | 4723 | C | ASN | B | 287 | 18.149 | 77.166 | 101.394 | 1.00 | 55.99 | B | C |
| ATOM | 4724 | O | ASN | B | 287 | 17.436 | 77.280 | 100.396 | 1.00 | 55.75 | B | O |
| ATOM | 4725 | N | ILE | B | 288 | 19.424 | 77.552 | 101.420 | 1.00 | 52.70 | B | N |
| ATOM | 4726 | CA | ILE | B | 288 | 20.087 | 78.124 | 100.245 | 1.00 | 50.33 | B | C |
| ATOM | 4727 | CB | ILE | B | 288 | 19.170 | 79.105 | 99.485 | 1.00 | 52.23 | B | C |
| ATOM | 4728 | CG2 | ILE | B | 288 | 18.711 | 80.224 | 100.409 | 1.00 | 52.30 | B | C |
| ATOM | 4729 | CG1 | ILE | B | 288 | 19.924 | 79.697 | 98.290 | 1.00 | 53.57 | B | C |
| ATOM | 4730 | CD1 | ILE | B | 288 | 20.513 | 78.662 | 97.360 | 1.00 | 53.55 | B | C |
| ATOM | 4731 | C | ILE | B | 288 | 21.379 | 78.852 | 100.590 | 1.00 | 49.17 | B | C |
| ATOM | 4732 | O | ILE | B | 288 | 22.466 | 78.320 | 100.381 | 1.00 | 50.37 | B | O |
| ATOM | 4733 | N | ASN | B | 289 | 21.278 | 80.073 | 101.108 | 1.00 | 47.01 | B | N |
| ATOM | 4734 | CA | ASN | B | 289 | 22.489 | 80.800 | 101.463 | 1.00 | 43.90 | B | C |
| ATOM | 4735 | CB | ASN | B | 289 | 22.179 | 82.241 | 101.902 | 1.00 | 46.81 | B | C |
| ATOM | 4736 | CG | ASN | B | 289 | 22.777 | 83.295 | 100.948 | 1.00 | 50.12 | B | C |
| ATOM | 4737 | OD1 | ASN | B | 289 | 23.869 | 83.106 | 100.401 | 1.00 | 49.87 | B | O |
| ATOM | 4738 | ND2 | ASN | B | 289 | 22.068 | 84.411 | 100.766 | 1.00 | 48.06 | B | N |
| ATOM | 4739 | C | ASN | B | 289 | 23.193 | 80.050 | 102.585 | 1.00 | 41.52 | B | C |
| ATOM | 4740 | O | ASN | B | 289 | 24.417 | 80.080 | 102.690 | 1.00 | 42.73 | B | O |
| ATOM | 4741 | N | GLN | B | 290 | 22.425 | 79.362 | 103.421 | 1.00 | 36.75 | B | N |
| ATOM | 4742 | CA | GLN | B | 290 | 23.036 | 78.615 | 104.506 | 1.00 | 35.31 | B | C |
| ATOM | 4743 | CB | GLN | B | 290 | 21.971 | 78.015 | 105.427 | 1.00 | 40.36 | B | C |
| ATOM | 4744 | CG | GLN | B | 290 | 22.448 | 77.736 | 106.862 | 1.00 | 45.77 | B | C |
| ATOM | 4745 | CD | GLN | B | 290 | 23.274 | 76.465 | 106.999 | 1.00 | 49.06 | B | C |
| ATOM | 4746 | OE1 | GLN | B | 290 | 23.652 | 76.071 | 108.109 | 1.00 | 48.63 | B | O |
| ATOM | 4747 | NE2 | GLN | B | 290 | 23.554 | 75.812 | 105.874 | 1.00 | 51.35 | B | N |
| ATOM | 4748 | C | GLN | B | 290 | 23.894 | 77.515 | 103.913 | 1.00 | 31.00 | B | C |
| ATOM | 4749 | O | GLN | B | 290 | 25.000 | 77.263 | 104.389 | 1.00 | 29.79 | B | O |
| ATOM | 4750 | N | SER | B | 291 | 23.393 | 76.862 | 102.869 | 1.00 | 28.12 | B | N |
| ATOM | 4751 | CA | SER | B | 291 | 24.162 | 75.793 | 102.239 | 1.00 | 26.03 | B | C |
| ATOM | 4752 | CB | SER | B | 291 | 23.312 | 75.023 | 101.215 | 1.00 | 22.16 | B | C |
| ATOM | 4753 | OG | SER | B | 291 | 22.779 | 75.868 | 100.220 | 1.00 | 21.59 | B | O |
| ATOM | 4754 | C | SER | B | 291 | 25.428 | 76.353 | 101.591 | 1.00 | 24.06 | B | C |
| ATOM | 4755 | O | SER | B | 291 | 26.510 | 75.792 | 101.769 | 1.00 | 25.15 | B | O |
| ATOM | 4756 | N | LEU | B | 292 | 25.309 | 77.458 | 100.856 | 1.00 | 22.28 | B | N |
| ATOM | 4757 | CA | LEU | B | 292 | 26.486 | 78.060 | 100.235 | 1.00 | 23.33 | B | C |
| ATOM | 4758 | CB | LEU | B | 292 | 26.100 | 79.270 | 99.384 | 1.00 | 21.79 | B | C |
| ATOM | 4759 | CG | LEU | B | 292 | 25.395 | 79.002 | 98.050 | 1.00 | 22.99 | B | C |
| ATOM | 4760 | CD1 | LEU | B | 292 | 25.000 | 80.322 | 97.411 | 1.00 | 21.70 | B | C |
| ATOM | 4761 | CD2 | LEU | B | 292 | 26.306 | 78.206 | 97.127 | 1.00 | 19.57 | B | C |
| ATOM | 4762 | C | LEU | B | 292 | 27.467 | 78.496 | 101.317 | 1.00 | 26.21 | B | C |
| ATOM | 4763 | O | LEU | B | 292 | 28.680 | 78.367 | 101.138 | 1.00 | 28.29 | B | O |
| ATOM | 4764 | N | LEU | B | 293 | 26.942 | 79.018 | 102.432 | 1.00 | 26.17 | B | N |
| ATOM | 4765 | CA | LEU | B | 293 | 27.770 | 79.451 | 103.556 | 1.00 | 23.99 | B | C |
| ATOM | 4766 | CB | LEU | B | 293 | 26.920 | 80.117 | 104.643 | 1.00 | 27.99 | B | C |
| ATOM | 4767 | CG | LEU | B | 293 | 26.900 | 81.649 | 104.771 | 1.00 | 30.69 | B | C |
| ATOM | 4768 | CD1 | LEU | B | 293 | 28.216 | 82.233 | 104.258 | 1.00 | 30.43 | B | C |
| ATOM | 4769 | CD2 | LEU | B | 293 | 25.717 | 82.215 | 103.994 | 1.00 | 30.19 | B | C |
| ATOM | 4770 | C | LEU | B | 293 | 28.508 | 78.263 | 104.164 | 1.00 | 22.11 | B | C |
| ATOM | 4771 | O | LEU | B | 293 | 29.700 | 78.343 | 104.437 | 1.00 | 24.60 | B | O |
| ATOM | 4772 | N | THR | B | 294 | 27.797 | 77.162 | 104.393 | 1.00 | 22.72 | B | N |
| ATOM | 4773 | CA | THR | B | 294 | 28.426 | 75.963 | 104.945 | 1.00 | 23.03 | B | C |
| ATOM | 4774 | CB | THR | B | 294 | 27.448 | 74.765 | 104.986 | 1.00 | 20.18 | B | C |
| ATOM | 4775 | OG1 | THR | B | 294 | 26.321 | 75.082 | 105.812 | 1.00 | 18.94 | B | O |
| ATOM | 4776 | CG2 | THR | B | 294 | 28.146 | 73.539 | 105.541 | 1.00 | 17.49 | B | C |
| ATOM | 4777 | C | THR | B | 294 | 29.593 | 75.587 | 104.030 | 1.00 | 22.98 | B | C |
| ATOM | 4778 | O | THR | B | 294 | 30.740 | 75.475 | 104.472 | 1.00 | 23.56 | B | O |
| ATOM | 4779 | N | LEU | B | 295 | 29.290 | 75.411 | 102.748 | 1.00 | 19.28 | B | N |
| ATOM | 4780 | CA | LEU | B | 295 | 30.304 | 75.061 | 101.768 | 1.00 | 19.89 | B | C |
| ATOM | 4781 | CB | LEU | B | 295 | 29.764 | 75.258 | 100.353 | 1.00 | 18.96 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4782 | CG | LEU | B | 295 | 30.795 | 74.981 | 99.263 | 1.00 | 17.85 | B | C |
| ATOM | 4783 | CD1 | LEU | B | 295 | 31.209 | 73.511 | 99.330 | 1.00 | 22.07 | B | C |
| ATOM | 4784 | CD2 | LEU | B | 295 | 30.215 | 75.330 | 97.894 | 1.00 | 17.74 | B | C |
| ATOM | 4785 | C | LEU | B | 295 | 31.548 | 75.916 | 101.955 | 1.00 | 21.33 | B | C |
| ATOM | 4786 | O | LEU | B | 295 | 32.670 | 75.398 | 102.046 | 1.00 | 18.27 | B | O |
| ATOM | 4787 | N | GLY | B | 296 | 31.340 | 77.232 | 102.011 | 1.00 | 20.60 | B | N |
| ATOM | 4788 | CA | GLY | B | 296 | 32.450 | 78.148 | 102.182 | 1.00 | 19.66 | B | C |
| ATOM | 4789 | C | GLY | B | 296 | 33.243 | 77.844 | 103.433 | 1.00 | 20.75 | B | C |
| ATOM | 4790 | O | GLY | B | 296 | 34.474 | 77.905 | 103.437 | 1.00 | 22.93 | B | O |
| ATOM | 4791 | N | ARG | B | 297 | 32.546 | 77.507 | 104.506 | 1.00 | 20.08 | B | N |
| ATOM | 4792 | CA | ARG | B | 297 | 33.237 | 77.206 | 105.746 | 1.00 | 23.65 | B | C |
| ATOM | 4793 | CB | ARG | B | 297 | 32.228 | 77.185 | 106.893 | 1.00 | 24.72 | B | C |
| ATOM | 4794 | CG | ARG | B | 297 | 31.802 | 78.590 | 107.310 | 1.00 | 24.91 | B | C |
| ATOM | 4795 | CD | ARG | B | 297 | 30.418 | 78.618 | 107.910 | 1.00 | 24.80 | B | C |
| ATOM | 4796 | NE | ARG | B | 297 | 30.240 | 77.566 | 108.906 | 1.00 | 29.88 | B | N |
| ATOM | 4797 | CZ | ARG | B | 297 | 31.023 | 77.399 | 109.970 | 1.00 | 31.41 | B | C |
| ATOM | 4798 | NH1 | ARG | B | 297 | 32.048 | 78.219 | 110.180 | 1.00 | 31.30 | B | N |
| ATOM | 4799 | NH2 | ARG | B | 297 | 30.783 | 76.411 | 110.824 | 1.00 | 30.91 | B | N |
| ATOM | 4800 | C | ARG | B | 297 | 34.018 | 75.900 | 105.658 | 1.00 | 24.89 | B | C |
| ATOM | 4801 | O | ARG | B | 297 | 35.084 | 75.763 | 106.260 | 1.00 | 25.19 | B | O |
| ATOM | 4802 | N | VAL | B | 298 | 33.495 | 74.943 | 104.897 | 1.00 | 25.36 | B | N |
| ATOM | 4803 | CA | VAL | B | 298 | 34.179 | 73.668 | 104.722 | 1.00 | 25.90 | B | C |
| ATOM | 4804 | CB | VAL | B | 298 | 33.277 | 72.634 | 104.004 | 1.00 | 26.72 | B | C |
| ATOM | 4805 | CG1 | VAL | B | 298 | 34.046 | 71.350 | 103.781 | 1.00 | 22.92 | B | C |
| ATOM | 4806 | CG2 | VAL | B | 298 | 32.029 | 72.361 | 104.831 | 1.00 | 27.29 | B | C |
| ATOM | 4807 | C | VAL | B | 298 | 35.459 | 73.847 | 103.897 | 1.00 | 25.99 | B | C |
| ATOM | 4808 | O | VAL | B | 298 | 36.485 | 73.231 | 104.179 | 1.00 | 27.75 | B | O |
| ATOM | 4809 | N | ILE | B | 299 | 35.393 | 74.697 | 102.879 | 1.00 | 26.60 | B | N |
| ATOM | 4810 | CA | ILE | B | 299 | 36.545 | 74.941 | 102.014 | 1.00 | 27.49 | B | C |
| ATOM | 4811 | CB | ILE | B | 299 | 36.155 | 75.740 | 100.758 | 1.00 | 27.45 | B | C |
| ATOM | 4812 | CG2 | ILE | B | 299 | 37.398 | 76.035 | 99.935 | 1.00 | 29.46 | B | C |
| ATOM | 4813 | CG1 | ILE | B | 299 | 35.161 | 74.938 | 99.915 | 1.00 | 25.99 | B | C |
| ATOM | 4814 | CD1 | ILE | B | 299 | 35.687 | 73.580 | 99.491 | 1.00 | 25.02 | B | C |
| ATOM | 4815 | C | ILE | B | 299 | 37.645 | 75.701 | 102.732 | 1.00 | 28.82 | B | C |
| ATOM | 4816 | O | ILE | B | 299 | 38.834 | 75.418 | 102.551 | 1.00 | 27.67 | B | O |
| ATOM | 4817 | N | THR | B | 300 | 37.248 | 76.681 | 103.534 | 1.00 | 30.45 | B | N |
| ATOM | 4818 | CA | THR | B | 300 | 38.212 | 77.468 | 104.288 | 1.00 | 31.31 | B | C |
| ATOM | 4819 | CB | THR | B | 300 | 37.521 | 78.627 | 105.030 | 1.00 | 33.48 | B | C |
| ATOM | 4820 | OG1 | THR | B | 300 | 36.772 | 79.415 | 104.095 | 1.00 | 33.01 | B | O |
| ATOM | 4821 | CG2 | THR | B | 300 | 38.554 | 79.510 | 105.719 | 1.00 | 31.98 | B | C |
| ATOM | 4822 | C | THR | B | 300 | 38.909 | 76.557 | 105.304 | 1.00 | 31.60 | B | C |
| ATOM | 4823 | O | THR | B | 300 | 40.131 | 76.603 | 105.454 | 1.00 | 33.56 | B | O |
| ATOM | 4824 | N | ALA | B | 301 | 38.131 | 75.726 | 105.992 | 1.00 | 30.19 | B | N |
| ATOM | 4825 | CA | ALA | B | 301 | 38.692 | 74.800 | 106.967 | 1.00 | 31.24 | B | C |
| ATOM | 4826 | CB | ALA | B | 301 | 37.587 | 73.969 | 107.591 | 1.00 | 32.43 | B | C |
| ATOM | 4827 | C | ALA | B | 301 | 39.732 | 73.884 | 106.321 | 1.00 | 31.84 | B | C |
| ATOM | 4828 | O | ALA | B | 301 | 40.735 | 73.553 | 106.941 | 1.00 | 33.31 | B | O |
| ATOM | 4829 | N | LEU | B | 302 | 39.496 | 73.475 | 105.078 | 1.00 | 30.99 | B | N |
| ATOM | 4830 | CA | LEU | B | 302 | 40.440 | 72.600 | 104.385 | 1.00 | 30.61 | B | C |
| ATOM | 4831 | CB | LEU | B | 302 | 39.810 | 72.011 | 103.128 | 1.00 | 27.52 | B | C |
| ATOM | 4832 | CG | LEU | B | 302 | 38.546 | 71.174 | 103.280 | 1.00 | 30.79 | B | C |
| ATOM | 4833 | CD1 | LEU | B | 302 | 38.093 | 70.726 | 101.889 | 1.00 | 28.89 | B | C |
| ATOM | 4834 | CD2 | LEU | B | 302 | 38.813 | 69.968 | 104.178 | 1.00 | 29.51 | B | C |
| ATOM | 4835 | C | LEU | B | 302 | 41.702 | 73.349 | 103.987 | 1.00 | 32.21 | B | C |
| ATOM | 4836 | O | LEU | B | 302 | 42.766 | 72.750 | 103.818 | 1.00 | 32.80 | B | O |
| ATOM | 4837 | N | VAL | B | 303 | 41.581 | 74.662 | 103.807 | 1.00 | 35.09 | B | N |
| ATOM | 4838 | CA | VAL | B | 303 | 42.733 | 75.477 | 103.435 | 1.00 | 37.35 | B | C |
| ATOM | 4839 | CB | VAL | B | 303 | 42.313 | 76.784 | 102.748 | 1.00 | 37.61 | B | C |
| ATOM | 4840 | CG1 | VAL | B | 303 | 43.500 | 77.740 | 102.687 | 1.00 | 36.16 | B | C |
| ATOM | 4841 | CG2 | VAL | B | 303 | 41.811 | 76.491 | 101.346 | 1.00 | 38.43 | B | C |
| ATOM | 4842 | C | VAL | B | 303 | 43.547 | 75.834 | 104.667 | 1.00 | 38.44 | B | C |
| ATOM | 4843 | O | VAL | B | 303 | 44.772 | 75.729 | 104.663 | 1.00 | 37.69 | B | O |
| ATOM | 4844 | N | GLU | B | 304 | 42.852 | 76.258 | 105.718 | 1.00 | 39.31 | B | N |
| ATOM | 4845 | CA | GLU | B | 304 | 43.496 | 76.628 | 106.973 | 1.00 | 42.03 | B | C |
| ATOM | 4846 | CB | GLU | B | 304 | 42.529 | 77.442 | 107.834 | 1.00 | 43.25 | B | C |
| ATOM | 4847 | CG | GLU | B | 304 | 41.641 | 78.409 | 107.055 | 1.00 | 44.22 | B | C |
| ATOM | 4848 | CD | GLU | B | 304 | 42.359 | 79.674 | 106.627 | 1.00 | 46.94 | B | C |
| ATOM | 4849 | OE1 | GLU | B | 304 | 43.465 | 79.558 | 106.058 | 1.00 | 48.45 | B | O |
| ATOM | 4850 | OE2 | GLU | B | 304 | 41.813 | 80.782 | 106.852 | 1.00 | 45.01 | B | O |
| ATOM | 4851 | C | GLU | B | 304 | 43.888 | 75.352 | 107.723 | 1.00 | 43.14 | B | C |
| ATOM | 4852 | O | GLU | B | 304 | 44.574 | 75.399 | 108.743 | 1.00 | 44.25 | B | O |
| ATOM | 4853 | N | ARG | B | 305 | 43.439 | 74.213 | 107.209 | 1.00 | 43.56 | B | N |
| ATOM | 4854 | CA | ARG | B | 305 | 43.720 | 72.928 | 107.823 | 1.00 | 44.20 | B | C |
| ATOM | 4855 | CB | ARG | B | 305 | 45.226 | 72.674 | 107.885 | 1.00 | 45.46 | B | C |
| ATOM | 4856 | CG | ARG | B | 305 | 45.924 | 72.792 | 106.550 | 1.00 | 48.05 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4857 | CD | ARG | B | 305 | 47.359 | 72.301 | 106.623 | 1.00 | 50.93 | B | C |
| ATOM | 4858 | NE | ARG | B | 305 | 48.120 | 72.712 | 105.446 | 1.00 | 53.39 | B | N |
| ATOM | 4859 | CZ | ARG | B | 305 | 49.357 | 72.310 | 105.171 | 1.00 | 53.81 | B | C |
| ATOM | 4860 | NH1 | ARG | B | 305 | 49.982 | 71.476 | 105.990 | 1.00 | 51.90 | B | N |
| ATOM | 4861 | NH2 | ARG | B | 305 | 49.971 | 72.748 | 104.077 | 1.00 | 55.11 | B | N |
| ATOM | 4862 | C | ARG | B | 305 | 43.132 | 72.848 | 109.224 | 1.00 | 44.24 | B | C |
| ATOM | 4863 | O | ARG | B | 305 | 43.765 | 72.327 | 110.141 | 1.00 | 45.62 | B | O |
| ATOM | 4864 | N | THR | B | 306 | 41.928 | 73.381 | 109.394 | 1.00 | 43.64 | B | N |
| ATOM | 4865 | CA | THR | B | 306 | 41.262 | 73.317 | 110.686 | 1.00 | 43.21 | B | C |
| ATOM | 4866 | CB | THR | B | 306 | 39.943 | 74.125 | 110.675 | 1.00 | 44.25 | B | C |
| ATOM | 4867 | OG1 | THR | B | 306 | 40.228 | 75.502 | 110.396 | 1.00 | 45.12 | B | O |
| ATOM | 4868 | CG2 | THR | B | 306 | 39.235 | 74.019 | 112.021 | 1.00 | 43.62 | B | C |
| ATOM | 4869 | C | THR | B | 306 | 40.951 | 71.835 | 110.895 | 1.00 | 43.12 | B | C |
| ATOM | 4870 | O | THR | B | 306 | 40.479 | 71.162 | 109.978 | 1.00 | 43.22 | B | O |
| ATOM | 4871 | N | PRO | B | 307 | 41.239 | 71.298 | 112.092 | 1.00 | 41.84 | B | N |
| ATOM | 4872 | CD | PRO | B | 307 | 41.847 | 71.938 | 113.271 | 1.00 | 38.68 | B | C |
| ATOM | 4873 | CA | PRO | B | 307 | 40.962 | 69.879 | 112.348 | 1.00 | 40.14 | B | C |
| ATOM | 4874 | CB | PRO | B | 307 | 41.523 | 69.665 | 113.754 | 1.00 | 39.05 | B | C |
| ATOM | 4875 | CG | PRO | B | 307 | 41.412 | 71.024 | 114.378 | 1.00 | 38.62 | B | C |
| ATOM | 4876 | C | PRO | B | 307 | 39.481 | 69.525 | 112.235 | 1.00 | 38.93 | B | C |
| ATOM | 4877 | O | PRO | B | 307 | 39.125 | 68.369 | 111.988 | 1.00 | 39.42 | B | O |
| ATOM | 4878 | N | HIS | B | 308 | 38.624 | 70.529 | 112.401 | 1.00 | 37.67 | B | N |
| ATOM | 4879 | CA | HIS | B | 308 | 37.180 | 70.327 | 112.317 | 1.00 | 36.93 | B | C |
| ATOM | 4880 | CB | HIS | B | 308 | 36.495 | 70.864 | 113.573 | 1.00 | 33.85 | B | C |
| ATOM | 4881 | CG | HIS | B | 308 | 35.025 | 71.092 | 113.403 | 1.00 | 35.42 | B | C |
| ATOM | 4882 | CD2 | HIS | B | 308 | 33.963 | 70.285 | 113.643 | 1.00 | 34.13 | B | C |
| ATOM | 4883 | ND1 | HIS | B | 308 | 34.507 | 72.272 | 112.910 | 1.00 | 37.98 | B | N |
| ATOM | 4884 | CE1 | HIS | B | 308 | 33.188 | 72.183 | 112.858 | 1.00 | 37.41 | B | C |
| ATOM | 4885 | NE2 | HIS | B | 308 | 32.832 | 70.987 | 113.297 | 1.00 | 33.17 | B | N |
| ATOM | 4886 | C | HIS | B | 308 | 36.556 | 70.976 | 111.088 | 1.00 | 35.46 | B | C |
| ATOM | 4887 | O | HIS | B | 308 | 36.513 | 72.203 | 110.975 | 1.00 | 38.95 | B | O |
| ATOM | 4888 | N | VAL | B | 309 | 36.073 | 70.135 | 110.177 | 1.00 | 32.41 | B | N |
| ATOM | 4889 | CA | VAL | B | 309 | 35.429 | 70.574 | 108.942 | 1.00 | 28.19 | B | C |
| ATOM | 4890 | CB | VAL | B | 309 | 36.135 | 69.956 | 107.723 | 1.00 | 27.83 | B | C |
| ATOM | 4891 | CG1 | VAL | B | 309 | 37.549 | 70.503 | 107.610 | 1.00 | 29.22 | B | C |
| ATOM | 4892 | CG2 | VAL | B | 309 | 36.207 | 68.457 | 107.878 | 1.00 | 27.93 | B | C |
| ATOM | 4893 | C | VAL | B | 309 | 33.958 | 70.139 | 108.995 | 1.00 | 26.22 | B | C |
| ATOM | 4894 | O | VAL | B | 309 | 33.643 | 68.951 | 109.025 | 1.00 | 24.85 | B | O |
| ATOM | 4895 | N | PRO | B | 310 | 33.041 | 71.115 | 109.026 | 1.00 | 24.04 | B | N |
| ATOM | 4896 | CD | PRO | B | 310 | 33.469 | 72.528 | 109.010 | 1.00 | 24.94 | B | C |
| ATOM | 4897 | CA | PRO | B | 310 | 31.576 | 71.014 | 109.090 | 1.00 | 23.48 | B | C |
| ATOM | 4898 | CB | PRO | B | 310 | 31.152 | 72.466 | 109.314 | 1.00 | 24.69 | B | C |
| ATOM | 4899 | CG | PRO | B | 310 | 32.210 | 73.242 | 108.586 | 1.00 | 24.77 | B | C |
| ATOM | 4900 | C | PRO | B | 310 | 30.771 | 70.361 | 107.951 | 1.00 | 25.12 | B | C |
| ATOM | 4901 | O | PRO | B | 310 | 29.725 | 70.884 | 107.564 | 1.00 | 26.41 | B | O |
| ATOM | 4902 | N | TYR | B | 311 | 31.209 | 69.216 | 107.441 | 1.00 | 24.37 | B | N |
| ATOM | 4903 | CA | TYR | B | 311 | 30.478 | 68.563 | 106.352 | 1.00 | 24.77 | B | C |
| ATOM | 4904 | CB | TYR | B | 311 | 31.117 | 67.228 | 105.990 | 1.00 | 23.65 | B | C |
| ATOM | 4905 | CG | TYR | B | 311 | 32.552 | 67.310 | 105.549 | 1.00 | 22.56 | B | C |
| ATOM | 4906 | CD1 | TYR | B | 311 | 33.576 | 66.964 | 106.414 | 1.00 | 23.19 | B | C |
| ATOM | 4907 | CE1 | TYR | B | 311 | 34.889 | 67.010 | 106.016 | 1.00 | 22.82 | B | C |
| ATOM | 4908 | CD2 | TYR | B | 311 | 32.885 | 67.713 | 104.264 | 1.00 | 22.00 | B | C |
| ATOM | 4909 | CE2 | TYR | B | 311 | 34.203 | 67.764 | 103.854 | 1.00 | 22.18 | B | C |
| ATOM | 4910 | CZ | TYR | B | 311 | 35.201 | 67.410 | 104.740 | 1.00 | 24.23 | B | C |
| ATOM | 4911 | OH | TYR | B | 311 | 36.523 | 67.451 | 104.366 | 1.00 | 25.23 | B | O |
| ATOM | 4912 | C | TYR | B | 311 | 29.007 | 68.299 | 106.645 | 1.00 | 26.63 | B | C |
| ATOM | 4913 | O | TYR | B | 311 | 28.151 | 68.508 | 105.788 | 1.00 | 29.19 | B | O |
| ATOM | 4914 | N | ARG | B | 312 | 28.726 | 67.811 | 107.849 | 1.00 | 27.88 | B | N |
| ATOM | 4915 | CA | ARG | B | 312 | 27.371 | 67.477 | 108.281 | 1.00 | 26.70 | B | C |
| ATOM | 4916 | CB | ARG | B | 312 | 27.405 | 66.916 | 109.705 | 1.00 | 30.55 | B | C |
| ATOM | 4917 | CG | ARG | B | 312 | 27.423 | 65.405 | 109.810 | 1.00 | 32.17 | B | C |
| ATOM | 4918 | CD | ARG | B | 312 | 26.220 | 64.809 | 109.099 | 1.00 | 33.70 | B | C |
| ATOM | 4919 | NE | ARG | B | 312 | 25.998 | 63.399 | 109.432 | 1.00 | 36.50 | B | N |
| ATOM | 4920 | CZ | ARG | B | 312 | 26.960 | 62.480 | 109.539 | 1.00 | 35.56 | B | C |
| ATOM | 4921 | NH1 | ARG | B | 312 | 28.235 | 62.812 | 109.350 | 1.00 | 34.20 | B | N |
| ATOM | 4922 | NH2 | ARG | B | 312 | 26.644 | 61.218 | 109.806 | 1.00 | 29.51 | B | N |
| ATOM | 4923 | C | ARG | B | 312 | 26.345 | 68.603 | 108.256 | 1.00 | 26.41 | B | C |
| ATOM | 4924 | O | ARG | B | 312 | 25.142 | 68.345 | 108.186 | 1.00 | 25.90 | B | O |
| ATOM | 4925 | N | GLU | B | 313 | 26.800 | 69.849 | 108.314 | 1.00 | 25.53 | B | N |
| ATOM | 4926 | CA | GLU | B | 313 | 25.859 | 70.962 | 108.353 | 1.00 | 24.52 | B | C |
| ATOM | 4927 | CB | GLU | B | 313 | 26.595 | 72.252 | 108.731 | 1.00 | 27.17 | B | C |
| ATOM | 4928 | CG | GLU | B | 313 | 27.058 | 72.278 | 110.175 | 1.00 | 29.55 | B | C |
| ATOM | 4929 | CD | GLU | B | 313 | 27.840 | 73.531 | 110.517 | 1.00 | 36.42 | B | C |
| ATOM | 4930 | OE1 | GLU | B | 313 | 27.286 | 74.642 | 110.341 | 1.00 | 37.85 | B | O |
| ATOM | 4931 | OE2 | GLU | B | 313 | 29.006 | 73.403 | 110.966 | 1.00 | 38.92 | B | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 4932 | C | GLU | B | 313 | 24.975 | 71.199 | 107.133 | 1.00 | 21.30 | B | C |
| ATOM | 4933 | O | GLU | B | 313 | 24.042 | 71.979 | 107.213 | 1.00 | 24.22 | B | O |
| ATOM | 4934 | N | SER | B | 314 | 25.245 | 70.549 | 106.011 | 1.00 | 19.20 | B | N |
| ATOM | 4935 | CA | SER | B | 314 | 24.395 | 70.743 | 104.834 | 1.00 | 18.29 | B | C |
| ATOM | 4936 | CB | SER | B | 314 | 24.875 | 71.942 | 103.997 | 1.00 | 18.56 | B | C |
| ATOM | 4937 | OG | SER | B | 314 | 25.887 | 71.587 | 103.068 | 1.00 | 17.95 | B | O |
| ATOM | 4938 | C | SER | B | 314 | 24.369 | 69.483 | 103.976 | 1.00 | 17.91 | B | C |
| ATOM | 4939 | O | SER | B | 314 | 25.251 | 68.627 | 104.082 | 1.00 | 17.71 | B | O |
| ATOM | 4940 | N | LYS | B | 315 | 23.348 | 69.364 | 103.142 | 1.00 | 16.72 | B | N |
| ATOM | 4941 | CA | LYS | B | 315 | 23.208 | 68.204 | 102.272 | 1.00 | 18.10 | B | C |
| ATOM | 4942 | CB | LYS | B | 315 | 21.875 | 68.254 | 101.535 | 1.00 | 17.88 | B | C |
| ATOM | 4943 | CG | LYS | B | 315 | 20.700 | 68.514 | 102.437 | 1.00 | 22.11 | B | C |
| ATOM | 4944 | CD | LYS | B | 315 | 20.357 | 67.271 | 103.211 | 1.00 | 23.03 | B | C |
| ATOM | 4945 | CE | LYS | B | 315 | 19.771 | 66.243 | 102.278 | 1.00 | 26.01 | B | C |
| ATOM | 4946 | NZ | LYS | B | 315 | 18.572 | 66.792 | 101.591 | 1.00 | 25.27 | B | N |
| ATOM | 4947 | C | LYS | B | 315 | 24.328 | 68.224 | 101.244 | 1.00 | 19.37 | B | C |
| ATOM | 4948 | O | LYS | B | 315 | 24.961 | 67.206 | 100.975 | 1.00 | 19.90 | B | O |
| ATOM | 4949 | N | LEU | B | 316 | 24.555 | 69.400 | 100.671 | 1.00 | 19.13 | B | N |
| ATOM | 4950 | CA | LEU | B | 316 | 25.581 | 69.587 | 99.659 | 1.00 | 19.00 | B | C |
| ATOM | 4951 | CB | LEU | B | 316 | 25.664 | 71.065 | 99.266 | 1.00 | 16.76 | B | C |
| ATOM | 4952 | CG | LEU | B | 316 | 26.776 | 71.451 | 98.291 | 1.00 | 17.33 | B | C |
| ATOM | 4953 | CD1 | LEU | B | 316 | 26.596 | 70.720 | 96.994 | 1.00 | 18.63 | B | C |
| ATOM | 4954 | CD2 | LEU | B | 316 | 26.749 | 72.945 | 98.049 | 1.00 | 21.38 | B | C |
| ATOM | 4955 | C | LEU | B | 316 | 26.955 | 69.106 | 100.102 | 1.00 | 21.24 | B | C |
| ATOM | 4956 | O | LEU | B | 316 | 27.573 | 68.295 | 99.427 | 1.00 | 24.93 | B | O |
| ATOM | 4957 | N | THR | B | 317 | 27.436 | 69.603 | 101.235 | 1.00 | 22.17 | B | N |
| ATOM | 4958 | CA | THR | B | 317 | 28.756 | 69.231 | 101.724 | 1.00 | 21.92 | B | C |
| ATOM | 4959 | CB | THR | B | 317 | 29.221 | 70.185 | 102.846 | 1.00 | 23.22 | B | C |
| ATOM | 4960 | OG1 | THR | B | 317 | 28.171 | 70.341 | 103.813 | 1.00 | 21.70 | B | O |
| ATOM | 4961 | CG2 | THR | B | 317 | 29.595 | 71.542 | 102.264 | 1.00 | 21.66 | B | C |
| ATOM | 4962 | C | THR | B | 317 | 28.844 | 67.797 | 102.234 | 1.00 | 22.94 | B | C |
| ATOM | 4963 | O | THR | B | 317 | 29.899 | 67.165 | 102.158 | 1.00 | 21.47 | B | O |
| ATOM | 4964 | N | ARG | B | 318 | 27.743 | 67.287 | 102.767 | 1.00 | 24.14 | B | N |
| ATOM | 4965 | CA | ARG | B | 318 | 27.726 | 65.920 | 103.279 | 1.00 | 25.44 | B | C |
| ATOM | 4966 | CB | ARG | B | 318 | 26.445 | 65.694 | 104.095 | 1.00 | 26.56 | B | C |
| ATOM | 4967 | CG | ARG | B | 318 | 26.015 | 64.251 | 104.244 | 1.00 | 27.63 | B | C |
| ATOM | 4968 | CD | ARG | B | 318 | 26.653 | 63.545 | 105.411 | 1.00 | 30.64 | B | C |
| ATOM | 4969 | NE | ARG | B | 318 | 25.895 | 62.334 | 105.725 | 1.00 | 34.42 | B | N |
| ATOM | 4970 | CZ | ARG | B | 318 | 24.595 | 62.322 | 106.026 | 1.00 | 35.76 | B | C |
| ATOM | 4971 | NH1 | ARG | B | 318 | 23.906 | 63.458 | 106.059 | 1.00 | 33.17 | B | N |
| ATOM | 4972 | NH2 | ARG | B | 318 | 23.976 | 61.173 | 106.280 | 1.00 | 35.70 | B | N |
| ATOM | 4973 | C | ARG | B | 318 | 27.795 | 64.968 | 102.084 | 1.00 | 23.24 | B | C |
| ATOM | 4974 | O | ARG | B | 318 | 28.379 | 63.886 | 102.153 | 1.00 | 25.34 | B | O |
| ATOM | 4975 | N | ILE | B | 319 | 27.205 | 65.395 | 100.978 | 1.00 | 21.76 | B | N |
| ATOM | 4976 | CA | ILE | B | 319 | 27.197 | 64.602 | 99.760 | 1.00 | 19.72 | B | C |
| ATOM | 4977 | CB | ILE | B | 319 | 26.096 | 65.088 | 98.815 | 1.00 | 14.42 | B | C |
| ATOM | 4978 | CG2 | ILE | B | 319 | 26.195 | 64.363 | 97.490 | 1.00 | 12.55 | B | C |
| ATOM | 4979 | CG1 | ILE | B | 319 | 24.730 | 64.870 | 99.470 | 1.00 | 13.14 | B | C |
| ATOM | 4980 | CD1 | ILE | B | 319 | 23.549 | 65.270 | 98.615 | 1.00 | 10.82 | B | C |
| ATOM | 4981 | C | ILE | B | 319 | 28.551 | 64.630 | 99.027 | 1.00 | 19.56 | B | C |
| ATOM | 4982 | O | ILE | B | 319 | 28.960 | 63.628 | 98.431 | 1.00 | 17.68 | B | O |
| ATOM | 4983 | N | LEU | B | 320 | 29.248 | 65.765 | 99.082 | 1.00 | 17.95 | B | N |
| ATOM | 4984 | CA | LEU | B | 320 | 30.545 | 65.888 | 98.411 | 1.00 | 20.97 | B | C |
| ATOM | 4985 | CB | LEU | B | 320 | 30.669 | 67.264 | 97.755 | 1.00 | 19.20 | B | C |
| ATOM | 4986 | CG | LEU | B | 320 | 29.618 | 67.569 | 96.692 | 1.00 | 19.80 | B | C |
| ATOM | 4987 | CD1 | LEU | B | 320 | 29.801 | 68.985 | 96.195 | 1.00 | 19.89 | B | C |
| ATOM | 4988 | CD2 | LEU | B | 320 | 29.737 | 66.576 | 95.549 | 1.00 | 17.14 | B | C |
| ATOM | 4989 | C | LEU | B | 320 | 31.747 | 65.656 | 99.331 | 1.00 | 22.94 | B | C |
| ATOM | 4990 | O | LEU | B | 320 | 32.905 | 65.823 | 98.916 | 1.00 | 18.99 | B | O |
| ATOM | 4991 | N | GLN | B | 321 | 31.460 | 65.261 | 100.570 | 1.00 | 25.33 | B | N |
| ATOM | 4992 | CA | GLN | B | 321 | 32.487 | 65.007 | 101.581 | 1.00 | 27.51 | B | C |
| ATOM | 4993 | CB | GLN | B | 321 | 31.835 | 64.619 | 102.907 | 1.00 | 27.61 | B | C |
| ATOM | 4994 | CG | GLN | B | 321 | 32.839 | 64.342 | 104.004 | 1.00 | 29.44 | B | C |
| ATOM | 4995 | CD | GLN | B | 321 | 32.187 | 63.911 | 105.296 | 1.00 | 29.87 | B | C |
| ATOM | 4996 | OE1 | GLN | B | 321 | 32.859 | 63.742 | 106.307 | 1.00 | 31.96 | B | O |
| ATOM | 4997 | NE2 | GLN | B | 321 | 30.873 | 63.724 | 105.269 | 1.00 | 29.69 | B | N |
| ATOM | 4998 | C | GLN | B | 321 | 33.494 | 63.928 | 101.197 | 1.00 | 28.32 | B | C |
| ATOM | 4999 | O | GLN | B | 321 | 34.693 | 64.059 | 101.447 | 1.00 | 25.77 | B | O |
| ATOM | 5000 | N | ASP | B | 322 | 33.015 | 62.855 | 100.590 | 1.00 | 30.09 | B | N |
| ATOM | 5001 | CA | ASP | B | 322 | 33.927 | 61.792 | 100.209 | 1.00 | 30.34 | B | C |
| ATOM | 5002 | CB | ASP | B | 322 | 33.219 | 60.714 | 99.403 | 1.00 | 32.26 | B | C |
| ATOM | 5003 | CG | ASP | B | 322 | 33.980 | 59.418 | 99.412 | 1.00 | 34.90 | B | C |
| ATOM | 5004 | OD1 | ASP | B | 322 | 35.230 | 59.478 | 99.450 | 1.00 | 36.79 | B | O |
| ATOM | 5005 | OD2 | ASP | B | 322 | 33.335 | 58.348 | 99.379 | 1.00 | 37.65 | B | O |
| ATOM | 5006 | C | ASP | B | 322 | 35.054 | 62.354 | 99.373 | 1.00 | 28.09 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 5007 | O | ASP | B | 322 | 36.214 | 62.046 | 99.589 | 1.00 | 30.48 | B | O |
| ATOM | 5008 | N | SER | B | 323 | 34.703 | 63.181 | 98.404 | 1.00 | 28.37 | B | N |
| ATOM | 5009 | CA | SER | B | 323 | 35.698 | 63.780 | 97.530 | 1.00 | 28.03 | B | C |
| ATOM | 5010 | CB | SER | B | 323 | 35.029 | 64.388 | 96.310 | 1.00 | 29.61 | B | C |
| ATOM | 5011 | OG | SER | B | 323 | 35.866 | 65.388 | 95.756 | 1.00 | 32.98 | B | O |
| ATOM | 5012 | C | SER | B | 323 | 36.507 | 64.860 | 98.216 | 1.00 | 28.54 | B | C |
| ATOM | 5013 | O | SER | B | 323 | 37.729 | 64.855 | 98.156 | 1.00 | 33.73 | B | O |
| ATOM | 5014 | N | LEU | B | 324 | 35.819 | 65.790 | 98.866 | 1.00 | 28.38 | B | N |
| ATOM | 5015 | CA | LEU | B | 324 | 36.478 | 66.894 | 99.548 | 1.00 | 28.81 | B | C |
| ATOM | 5016 | CB | LEU | B | 324 | 35.428 | 67.863 | 100.088 | 1.00 | 26.02 | B | C |
| ATOM | 5017 | CG | LEU | B | 324 | 34.576 | 68.570 | 99.036 | 1.00 | 24.27 | B | C |
| ATOM | 5018 | CD1 | LEU | B | 324 | 33.498 | 69.417 | 99.717 | 1.00 | 19.70 | B | C |
| ATOM | 5019 | CD2 | LEU | B | 324 | 35.477 | 69.438 | 98.163 | 1.00 | 20.24 | B | C |
| ATOM | 5020 | C | LEU | B | 324 | 37.399 | 66.482 | 100.691 | 1.00 | 30.48 | B | C |
| ATOM | 5021 | O | LEU | B | 324 | 38.497 | 67.020 | 100.832 | 1.00 | 30.13 | B | O |
| ATOM | 5022 | N | GLY | B | 325 | 36.944 | 65.530 | 101.499 | 1.00 | 32.90 | B | N |
| ATOM | 5023 | CA | GLY | B | 325 | 37.710 | 65.086 | 102.652 | 1.00 | 35.69 | B | C |
| ATOM | 5024 | C | GLY | B | 325 | 38.957 | 64.259 | 102.413 | 1.00 | 38.91 | B | C |
| ATOM | 5025 | O | GLY | B | 325 | 39.846 | 64.228 | 103.270 | 1.00 | 40.28 | B | O |
| ATOM | 5026 | N | GLY | B | 326 | 39.034 | 63.581 | 101.271 | 1.00 | 39.79 | B | N |
| ATOM | 5027 | CA | GLY | B | 326 | 40.205 | 62.771 | 100.991 | 1.00 | 40.75 | B | C |
| ATOM | 5028 | C | GLY | B | 326 | 41.306 | 63.605 | 100.368 | 1.00 | 41.76 | B | C |
| ATOM | 5029 | O | GLY | B | 326 | 41.130 | 64.804 | 100.145 | 1.00 | 42.11 | B | O |
| ATOM | 5030 | N | ARG | B | 327 | 42.452 | 62.986 | 100.102 | 1.00 | 42.72 | B | N |
| ATOM | 5031 | CA | ARG | B | 327 | 43.551 | 63.704 | 99.471 | 1.00 | 43.72 | B | C |
| ATOM | 5032 | CB | ARG | B | 327 | 44.882 | 62.954 | 99.673 | 1.00 | 48.10 | B | C |
| ATOM | 5033 | CG | ARG | B | 327 | 45.019 | 61.580 | 98.995 | 1.00 | 48.37 | B | C |
| ATOM | 5034 | CD | ARG | B | 327 | 45.338 | 61.721 | 97.516 | 1.00 | 50.26 | B | C |
| ATOM | 5035 | NE | ARG | B | 327 | 46.323 | 62.774 | 97.266 | 1.00 | 53.39 | B | N |
| ATOM | 5036 | CZ | ARG | B | 327 | 46.659 | 63.216 | 96.054 | 1.00 | 55.41 | B | C |
| ATOM | 5037 | NH1 | ARG | B | 327 | 46.092 | 62.699 | 94.970 | 1.00 | 55.09 | B | N |
| ATOM | 5038 | NH2 | ARG | B | 327 | 47.558 | 64.183 | 95.924 | 1.00 | 53.46 | B | N |
| ATOM | 5039 | C | ARG | B | 327 | 43.171 | 63.773 | 97.999 | 1.00 | 43.31 | B | C |
| ATOM | 5040 | O | ARG | B | 327 | 43.157 | 62.759 | 97.296 | 1.00 | 44.10 | B | O |
| ATOM | 5041 | N | THR | B | 328 | 42.827 | 64.968 | 97.535 | 1.00 | 40.18 | B | N |
| ATOM | 5042 | CA | THR | B | 328 | 42.416 | 65.124 | 96.150 | 1.00 | 38.03 | B | C |
| ATOM | 5043 | CB | THR | B | 328 | 40.924 | 64.769 | 95.966 | 1.00 | 38.46 | B | C |
| ATOM | 5044 | OG1 | THR | B | 328 | 40.117 | 65.861 | 96.422 | 1.00 | 39.24 | B | O |
| ATOM | 5045 | CG2 | THR | B | 328 | 40.559 | 63.524 | 96.776 | 1.00 | 38.85 | B | C |
| ATOM | 5046 | C | THR | B | 328 | 42.585 | 66.560 | 95.724 | 1.00 | 36.49 | B | C |
| ATOM | 5047 | O | THR | B | 328 | 43.166 | 67.371 | 96.440 | 1.00 | 38.63 | B | O |
| ATOM | 5048 | N | ARG | B | 329 | 42.070 | 66.870 | 94.546 | 1.00 | 33.71 | B | N |
| ATOM | 5049 | CA | ARG | B | 329 | 42.125 | 68.224 | 94.041 | 1.00 | 30.91 | B | C |
| ATOM | 5050 | CB | ARG | B | 329 | 42.799 | 68.257 | 92.676 | 1.00 | 30.74 | B | C |
| ATOM | 5051 | CG | ARG | B | 329 | 44.270 | 67.882 | 92.727 | 1.00 | 30.94 | B | C |
| ATOM | 5052 | CD | ARG | B | 329 | 44.997 | 68.493 | 91.551 | 1.00 | 35.33 | B | C |
| ATOM | 5053 | NE | ARG | B | 329 | 46.393 | 68.082 | 91.451 | 1.00 | 38.67 | B | N |
| ATOM | 5054 | CZ | ARG | B | 329 | 47.306 | 68.736 | 90.738 | 1.00 | 40.81 | B | C |
| ATOM | 5055 | NH1 | ARG | B | 329 | 46.966 | 69.835 | 90.071 | 1.00 | 37.70 | B | N |
| ATOM | 5056 | NH2 | ARG | B | 329 | 48.555 | 68.290 | 90.683 | 1.00 | 41.86 | B | N |
| ATOM | 5057 | C | ARG | B | 329 | 40.702 | 68.775 | 93.966 | 1.00 | 28.76 | B | C |
| ATOM | 5058 | O | ARG | B | 329 | 39.774 | 68.102 | 93.506 | 1.00 | 26.88 | B | O |
| ATOM | 5059 | N | THR | B | 330 | 40.538 | 69.995 | 94.457 | 1.00 | 25.63 | B | N |
| ATOM | 5060 | CA | THR | B | 330 | 39.244 | 70.651 | 94.474 | 1.00 | 24.77 | B | C |
| ATOM | 5061 | CB | THR | B | 330 | 38.679 | 70.718 | 95.894 | 1.00 | 24.32 | B | C |
| ATOM | 5062 | OG1 | THR | B | 330 | 38.410 | 69.391 | 96.361 | 1.00 | 26.75 | B | O |
| ATOM | 5063 | CG2 | THR | B | 330 | 37.405 | 71.528 | 95.920 | 1.00 | 25.45 | B | C |
| ATOM | 5064 | C | THR | B | 330 | 39.397 | 72.061 | 93.952 | 1.00 | 24.41 | B | C |
| ATOM | 5065 | O | THR | B | 330 | 40.249 | 72.821 | 94.420 | 1.00 | 24.97 | B | O |
| ATOM | 5066 | N | SER | B | 331 | 38.569 | 72.415 | 92.980 | 1.00 | 23.57 | B | N |
| ATOM | 5067 | CA | SER | B | 331 | 38.646 | 73.739 | 92.398 | 1.00 | 21.81 | B | C |
| ATOM | 5068 | CB | SER | B | 331 | 39.234 | 73.637 | 90.998 | 1.00 | 18.84 | B | C |
| ATOM | 5069 | OG | SER | B | 331 | 38.889 | 74.769 | 90.238 | 1.00 | 21.28 | B | O |
| ATOM | 5070 | C | SER | B | 331 | 37.304 | 74.465 | 92.350 | 1.00 | 21.14 | B | C |
| ATOM | 5071 | O | SER | B | 331 | 36.256 | 73.863 | 92.086 | 1.00 | 21.51 | B | O |
| ATOM | 5072 | N | ILE | B | 332 | 37.347 | 75.763 | 92.624 | 1.00 | 18.30 | B | N |
| ATOM | 5073 | CA | ILE | B | 332 | 36.158 | 76.594 | 92.589 | 1.00 | 17.64 | B | C |
| ATOM | 5074 | CB | ILE | B | 332 | 35.893 | 77.282 | 93.920 | 1.00 | 20.57 | B | C |
| ATOM | 5075 | CG2 | ILE | B | 332 | 34.765 | 78.287 | 93.760 | 1.00 | 18.44 | B | C |
| ATOM | 5076 | CG1 | ILE | B | 332 | 35.514 | 76.253 | 94.978 | 1.00 | 24.27 | B | C |
| ATOM | 5077 | CD1 | ILE | B | 332 | 35.345 | 76.858 | 96.347 | 1.00 | 28.70 | B | C |
| ATOM | 5078 | C | ILE | B | 332 | 36.330 | 77.699 | 91.570 | 1.00 | 19.46 | B | C |
| ATOM | 5079 | O | ILE | B | 332 | 37.312 | 78.443 | 91.601 | 1.00 | 18.27 | B | O |
| ATOM | 5080 | N | ILE | B | 333 | 35.366 | 77.811 | 90.663 | 1.00 | 19.49 | B | N |
| ATOM | 5081 | CA | ILE | B | 333 | 35.415 | 78.853 | 89.656 | 1.00 | 17.70 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 5082 | CB | ILE | B | 333 | 35.128 | 78.279 | 88.267 | 1.00 | 15.23 | B | C |
| ATOM | 5083 | CG2 | ILE | B | 333 | 35.372 | 79.334 | 87.214 | 1.00 | 14.43 | B | C |
| ATOM | 5084 | CG1 | ILE | B | 333 | 36.055 | 77.093 | 88.014 | 1.00 | 15.53 | B | C |
| ATOM | 5085 | CD1 | ILE | B | 333 | 36.060 | 76.610 | 86.576 | 1.00 | 18.45 | B | C |
| ATOM | 5086 | C | ILE | B | 333 | 34.387 | 79.922 | 90.011 | 1.00 | 16.96 | B | C |
| ATOM | 5087 | O | ILE | B | 333 | 33.177 | 79.718 | 89.875 | 1.00 | 18.17 | B | O |
| ATOM | 5088 | N | ALA | B | 334 | 34.875 | 81.057 | 90.499 | 1.00 | 15.71 | B | N |
| ATOM | 5089 | CA | ALA | B | 334 | 33.998 | 82.160 | 90.880 | 1.00 | 15.64 | B | C |
| ATOM | 5090 | CB | ALA | B | 334 | 34.612 | 82.921 | 92.017 | 1.00 | 11.70 | B | C |
| ATOM | 5091 | C | ALA | B | 334 | 33.738 | 83.099 | 89.695 | 1.00 | 17.92 | B | C |
| ATOM | 5092 | O | ALA | B | 334 | 34.618 | 83.860 | 89.291 | 1.00 | 17.95 | B | O |
| ATOM | 5093 | N | THR | B | 335 | 32.527 | 83.036 | 89.138 | 1.00 | 17.87 | B | N |
| ATOM | 5094 | CA | THR | B | 335 | 32.146 | 83.878 | 88.003 | 1.00 | 17.25 | B | C |
| ATOM | 5095 | CB | THR | B | 335 | 31.040 | 83.211 | 87.159 | 1.00 | 16.88 | B | C |
| ATOM | 5096 | OG1 | THR | B | 335 | 29.862 | 83.074 | 87.954 | 1.00 | 13.01 | B | O |
| ATOM | 5097 | CG2 | THR | B | 335 | 31.486 | 81.853 | 86.658 | 1.00 | 14.76 | B | C |
| ATOM | 5098 | C | THR | B | 335 | 31.623 | 85.263 | 88.421 | 1.00 | 18.02 | B | C |
| ATOM | 5099 | O | THR | B | 335 | 30.830 | 85.388 | 89.360 | 1.00 | 18.39 | B | O |
| ATOM | 5100 | N | ILE | B | 336 | 32.046 | 86.299 | 87.703 | 1.00 | 17.25 | B | N |
| ATOM | 5101 | CA | ILE | B | 336 | 31.609 | 87.659 | 88.005 | 1.00 | 15.54 | B | C |
| ATOM | 5102 | CB | ILE | B | 336 | 32.677 | 88.422 | 88.817 | 1.00 | 13.31 | B | C |
| ATOM | 5103 | CG2 | ILE | B | 336 | 32.955 | 87.709 | 90.116 | 1.00 | 14.05 | B | C |
| ATOM | 5104 | CG1 | ILE | B | 336 | 33.967 | 88.535 | 88.006 | 1.00 | 16.05 | B | C |
| ATOM | 5105 | CD1 | ILE | B | 336 | 35.070 | 89.277 | 88.722 | 1.00 | 16.78 | B | C |
| ATOM | 5106 | C | ILE | B | 336 | 31.281 | 88.488 | 86.759 | 1.00 | 16.04 | B | C |
| ATOM | 5107 | O | ILE | B | 336 | 31.648 | 88.125 | 85.633 | 1.00 | 16.85 | B | O |
| ATOM | 5108 | N | SER | B | 337 | 30.582 | 89.599 | 86.983 | 1.00 | 16.19 | B | N |
| ATOM | 5109 | CA | SER | B | 337 | 30.195 | 90.540 | 85.930 | 1.00 | 17.82 | B | C |
| ATOM | 5110 | CB | SER | B | 337 | 28.774 | 91.070 | 86.189 | 1.00 | 21.09 | B | C |
| ATOM | 5111 | OG | SER | B | 337 | 28.483 | 92.234 | 85.427 | 1.00 | 18.40 | B | O |
| ATOM | 5112 | C | SER | B | 337 | 31.182 | 91.710 | 85.941 | 1.00 | 19.15 | B | C |
| ATOM | 5113 | O | SER | B | 337 | 31.795 | 92.014 | 86.960 | 1.00 | 21.66 | B | O |
| ATOM | 5114 | N | PRO | B | 338 | 31.363 | 92.375 | 84.800 | 1.00 | 19.49 | B | N |
| ATOM | 5115 | CD | PRO | B | 338 | 31.106 | 91.894 | 83.430 | 1.00 | 18.07 | B | C |
| ATOM | 5116 | CA | PRO | B | 338 | 32.302 | 93.498 | 84.798 | 1.00 | 20.09 | B | C |
| ATOM | 5117 | CB | PRO | B | 338 | 32.993 | 93.347 | 83.452 | 1.00 | 21.24 | B | C |
| ATOM | 5118 | CG | PRO | B | 338 | 31.864 | 92.907 | 82.565 | 1.00 | 17.67 | B | C |
| ATOM | 5119 | C | PRO | B | 338 | 31.605 | 94.852 | 84.936 | 1.00 | 22.24 | B | C |
| ATOM | 5120 | O | PRO | B | 338 | 32.268 | 95.880 | 85.070 | 1.00 | 21.58 | B | O |
| ATOM | 5121 | N | ALA | B | 339 | 30.271 | 94.846 | 84.924 | 1.00 | 23.10 | B | N |
| ATOM | 5122 | CA | ALA | B | 339 | 29.490 | 96.088 | 85.008 | 1.00 | 23.31 | B | C |
| ATOM | 5123 | CB | ALA | B | 339 | 28.198 | 95.938 | 84.223 | 1.00 | 24.55 | B | C |
| ATOM | 5124 | C | ALA | B | 339 | 29.164 | 96.598 | 86.402 | 1.00 | 23.72 | B | C |
| ATOM | 5125 | O | ALA | B | 339 | 28.998 | 95.820 | 87.346 | 1.00 | 23.75 | B | O |
| ATOM | 5126 | N | SER | B | 340 | 29.047 | 97.923 | 86.496 | 1.00 | 24.02 | B | N |
| ATOM | 5127 | CA | SER | B | 340 | 28.736 | 98.629 | 87.745 | 1.00 | 24.88 | B | C |
| ATOM | 5128 | CB | SER | B | 340 | 28.783 | 100.146 | 87.518 | 1.00 | 23.66 | B | C |
| ATOM | 5129 | OG | SER | B | 340 | 27.738 | 100.573 | 86.663 | 1.00 | 16.47 | B | O |
| ATOM | 5130 | C | SER | B | 340 | 27.351 | 98.250 | 88.269 | 1.00 | 25.29 | B | C |
| ATOM | 5131 | O | SER | B | 340 | 27.085 | 98.291 | 89.468 | 1.00 | 25.56 | B | O |
| ATOM | 5132 | N | LEU | B | 341 | 26.477 | 97.879 | 87.344 | 1.00 | 28.17 | B | N |
| ATOM | 5133 | CA | LEU | B | 341 | 25.105 | 97.494 | 87.650 | 1.00 | 29.85 | B | C |
| ATOM | 5134 | CB | LEU | B | 341 | 24.401 | 97.091 | 86.346 | 1.00 | 29.04 | B | C |
| ATOM | 5135 | CG | LEU | B | 341 | 22.876 | 97.180 | 86.299 | 1.00 | 31.99 | B | C |
| ATOM | 5136 | CD1 | LEU | B | 341 | 22.458 | 98.624 | 86.569 | 1.00 | 34.29 | B | C |
| ATOM | 5137 | CD2 | LEU | B | 341 | 22.358 | 96.723 | 84.942 | 1.00 | 30.64 | B | C |
| ATOM | 5138 | C | LEU | B | 341 | 25.015 | 96.350 | 88.667 | 1.00 | 31.50 | B | C |
| ATOM | 5139 | O | LEU | B | 341 | 24.051 | 96.270 | 89.429 | 1.00 | 32.89 | B | O |
| ATOM | 5140 | N | ASN | B | 342 | 26.019 | 95.471 | 88.682 | 1.00 | 31.28 | B | N |
| ATOM | 5141 | CA | ASN | B | 342 | 26.027 | 94.334 | 89.596 | 1.00 | 29.88 | B | C |
| ATOM | 5142 | CB | ASN | B | 342 | 25.986 | 93.039 | 88.792 | 1.00 | 29.20 | B | C |
| ATOM | 5143 | CG | ASN | B | 342 | 24.715 | 92.915 | 87.943 | 1.00 | 31.51 | B | C |
| ATOM | 5144 | OD1 | ASN | B | 342 | 24.775 | 92.676 | 86.734 | 1.00 | 30.57 | B | O |
| ATOM | 5145 | ND2 | ASN | B | 342 | 23.561 | 93.071 | 88.581 | 1.00 | 29.58 | B | N |
| ATOM | 5146 | C | ASN | B | 342 | 27.238 | 94.329 | 90.513 | 1.00 | 31.57 | B | C |
| ATOM | 5147 | O | ASN | B | 342 | 27.738 | 93.264 | 90.885 | 1.00 | 34.20 | B | O |
| ATOM | 5148 | N | LEU | B | 343 | 27.701 | 95.515 | 90.891 | 1.00 | 31.36 | B | N |
| ATOM | 5149 | CA | LEU | B | 343 | 28.865 | 95.622 | 91.754 | 1.00 | 33.51 | B | C |
| ATOM | 5150 | CB | LEU | B | 343 | 29.205 | 97.103 | 92.000 | 1.00 | 34.51 | B | C |
| ATOM | 5151 | CG | LEU | B | 343 | 30.380 | 97.438 | 92.933 | 1.00 | 36.51 | B | C |
| ATOM | 5152 | CD1 | LEU | B | 343 | 30.684 | 98.934 | 92.879 | 1.00 | 38.44 | B | C |
| ATOM | 5153 | CD2 | LEU | B | 343 | 30.039 | 97.023 | 94.361 | 1.00 | 35.51 | B | C |
| ATOM | 5154 | C | LEU | B | 343 | 28.728 | 94.872 | 93.085 | 1.00 | 34.52 | B | C |
| ATOM | 5155 | O | LEU | B | 343 | 29.629 | 94.118 | 93.451 | 1.00 | 36.71 | B | O |
| ATOM | 5156 | N | GLU | B | 344 | 27.620 | 95.065 | 93.805 | 1.00 | 34.05 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 5157 | CA | GLU | B | 344 | 27.437 | 94.393 | 95.098 | 1.00 | 35.49 | B | C |
| ATOM | 5158 | CB | GLU | B | 344 | 26.084 | 94.729 | 95.734 | 1.00 | 39.36 | B | C |
| ATOM | 5159 | CG | GLU | B | 344 | 26.108 | 95.897 | 96.704 | 1.00 | 42.32 | B | C |
| ATOM | 5160 | CD | GLU | B | 344 | 26.052 | 97.214 | 95.988 | 1.00 | 46.69 | B | C |
| ATOM | 5161 | OE1 | GLU | B | 344 | 25.106 | 97.393 | 95.188 | 1.00 | 50.64 | B | O |
| ATOM | 5162 | OE2 | GLU | B | 344 | 26.942 | 98.061 | 96.219 | 1.00 | 48.60 | B | O |
| ATOM | 5163 | C | GLU | B | 344 | 27.554 | 92.885 | 95.028 | 1.00 | 33.18 | B | C |
| ATOM | 5164 | O | GLU | B | 344 | 28.196 | 92.271 | 95.877 | 1.00 | 34.73 | B | O |
| ATOM | 5165 | N | GLU | B | 345 | 26.915 | 92.282 | 94.033 | 1.00 | 30.70 | B | N |
| ATOM | 5166 | CA | GLU | B | 345 | 26.980 | 90.838 | 93.893 | 1.00 | 29.23 | B | C |
| ATOM | 5167 | CB | GLU | B | 345 | 25.978 | 90.358 | 92.846 | 1.00 | 31.49 | B | C |
| ATOM | 5168 | CG | GLU | B | 345 | 24.559 | 90.288 | 93.370 | 1.00 | 30.74 | B | C |
| ATOM | 5169 | CD | GLU | B | 345 | 24.496 | 89.713 | 94.777 | 1.00 | 34.86 | B | C |
| ATOM | 5170 | OE1 | GLU | B | 345 | 25.289 | 88.796 | 95.098 | 1.00 | 40.04 | B | O |
| ATOM | 5171 | OE2 | GLU | B | 345 | 23.647 | 90.175 | 95.565 | 1.00 | 36.01 | B | O |
| ATOM | 5172 | C | GLU | B | 345 | 28.390 | 90.390 | 93.531 | 1.00 | 26.40 | B | C |
| ATOM | 5173 | O | GLU | B | 345 | 28.830 | 89.323 | 93.962 | 1.00 | 21.99 | B | O |
| ATOM | 5174 | N | THR | B | 346 | 29.089 | 91.221 | 92.755 | 1.00 | 24.57 | B | N |
| ATOM | 5175 | CA | THR | B | 346 | 30.468 | 90.933 | 92.348 | 1.00 | 24.25 | B | C |
| ATOM | 5176 | CB | THR | B | 346 | 30.949 | 91.921 | 91.252 | 1.00 | 23.94 | B | C |
| ATOM | 5177 | OG1 | THR | B | 346 | 30.369 | 91.562 | 89.991 | 1.00 | 22.74 | B | O |
| ATOM | 5178 | CG2 | THR | B | 346 | 32.451 | 91.903 | 91.126 | 1.00 | 19.92 | B | C |
| ATOM | 5179 | C | THR | B | 346 | 31.414 | 91.013 | 93.546 | 1.00 | 22.72 | B | C |
| ATOM | 5180 | O | THR | B | 346 | 32.303 | 90.176 | 93.707 | 1.00 | 23.79 | B | O |
| ATOM | 5181 | N | LEU | B | 347 | 31.212 | 92.012 | 94.395 | 1.00 | 20.93 | B | N |
| ATOM | 5182 | CA | LEU | B | 347 | 32.060 | 92.160 | 95.563 | 1.00 | 24.01 | B | C |
| ATOM | 5183 | CB | LEU | B | 347 | 31.849 | 93.535 | 96.189 | 1.00 | 26.79 | B | C |
| ATOM | 5184 | CG | LEU | B | 347 | 32.521 | 94.638 | 95.372 | 1.00 | 24.89 | B | C |
| ATOM | 5185 | CD1 | LEU | B | 347 | 32.225 | 95.969 | 95.988 | 1.00 | 27.93 | B | C |
| ATOM | 5186 | CD2 | LEU | B | 347 | 34.019 | 94.398 | 95.331 | 1.00 | 24.44 | B | C |
| ATOM | 5187 | C | LEU | B | 347 | 31.805 | 91.058 | 96.573 | 1.00 | 22.76 | B | C |
| ATOM | 5188 | O | LEU | B | 347 | 32.729 | 90.581 | 97.239 | 1.00 | 20.73 | B | O |
| ATOM | 5189 | N | SER | B | 348 | 30.549 | 90.640 | 96.675 | 1.00 | 22.96 | B | N |
| ATOM | 5190 | CA | SER | B | 348 | 30.195 | 89.566 | 97.594 | 1.00 | 22.76 | B | C |
| ATOM | 5191 | CB | SER | B | 348 | 28.680 | 89.410 | 97.669 | 1.00 | 23.54 | B | C |
| ATOM | 5192 | OG | SER | B | 348 | 28.345 | 88.299 | 98.483 | 1.00 | 25.45 | B | O |
| ATOM | 5193 | C | SER | B | 348 | 30.830 | 88.251 | 97.127 | 1.00 | 22.13 | B | C |
| ATOM | 5194 | O | SER | B | 348 | 31.282 | 87.449 | 97.943 | 1.00 | 24.60 | B | O |
| ATOM | 5195 | N | THR | B | 349 | 30.859 | 88.035 | 95.813 | 1.00 | 18.79 | B | N |
| ATOM | 5196 | CA | THR | B | 349 | 31.453 | 86.833 | 95.257 | 1.00 | 19.94 | B | C |
| ATOM | 5197 | CB | THR | B | 349 | 31.152 | 86.717 | 93.762 | 1.00 | 22.31 | B | C |
| ATOM | 5198 | OG1 | THR | B | 349 | 29.767 | 86.396 | 93.590 | 1.00 | 21.92 | B | O |
| ATOM | 5199 | CG2 | THR | B | 349 | 32.010 | 85.622 | 93.117 | 1.00 | 22.94 | B | C |
| ATOM | 5200 | C | THR | B | 349 | 32.969 | 86.816 | 95.474 | 1.00 | 20.38 | B | C |
| ATOM | 5201 | O | THR | B | 349 | 33.528 | 85.816 | 95.932 | 1.00 | 20.12 | B | O |
| ATOM | 5202 | N | LEU | B | 350 | 33.629 | 87.923 | 95.152 | 1.00 | 19.98 | B | N |
| ATOM | 5203 | CA | LEU | B | 350 | 35.071 | 88.023 | 95.339 | 1.00 | 19.98 | B | C |
| ATOM | 5204 | CB | LEU | B | 350 | 35.579 | 89.395 | 94.866 | 1.00 | 20.36 | B | C |
| ATOM | 5205 | CG | LEU | B | 350 | 35.548 | 89.636 | 93.354 | 1.00 | 18.89 | B | C |
| ATOM | 5206 | CD1 | LEU | B | 350 | 35.873 | 91.067 | 93.044 | 1.00 | 17.46 | B | C |
| ATOM | 5207 | CD2 | LEU | B | 350 | 36.532 | 88.701 | 92.678 | 1.00 | 20.88 | B | C |
| ATOM | 5208 | C | LEU | B | 350 | 35.394 | 87.832 | 96.813 | 1.00 | 20.58 | B | C |
| ATOM | 5209 | O | LEU | B | 350 | 36.348 | 87.150 | 97.169 | 1.00 | 21.69 | B | O |
| ATOM | 5210 | N | GLU | B | 351 | 34.597 | 88.452 | 97.672 | 1.00 | 21.70 | B | N |
| ATOM | 5211 | CA | GLU | B | 351 | 34.803 | 88.330 | 99.104 | 1.00 | 21.33 | B | C |
| ATOM | 5212 | CB | GLU | B | 351 | 33.764 | 89.166 | 99.851 | 1.00 | 23.46 | B | C |
| ATOM | 5213 | CG | GLU | B | 351 | 34.168 | 90.619 | 100.013 | 1.00 | 23.61 | B | C |
| ATOM | 5214 | CD | GLU | B | 351 | 35.457 | 90.761 | 100.806 | 1.00 | 27.23 | B | C |
| ATOM | 5215 | OE1 | GLU | B | 351 | 35.534 | 90.194 | 101.923 | 1.00 | 29.00 | B | O |
| ATOM | 5216 | OE2 | GLU | B | 351 | 36.390 | 91.432 | 100.317 | 1.00 | 23.25 | B | O |
| ATOM | 5217 | C | GLU | B | 351 | 34.711 | 86.872 | 99.518 | 1.00 | 20.35 | B | C |
| ATOM | 5218 | O | GLU | B | 351 | 35.602 | 86.361 | 100.197 | 1.00 | 20.89 | B | O |
| ATOM | 5219 | N | TYR | B | 352 | 33.632 | 86.208 | 99.099 | 1.00 | 20.73 | B | N |
| ATOM | 5220 | CA | TYR | B | 352 | 33.410 | 84.791 | 99.409 | 1.00 | 21.78 | B | C |
| ATOM | 5221 | CB | TYR | B | 352 | 32.118 | 84.310 | 98.738 | 1.00 | 21.30 | B | C |
| ATOM | 5222 | CG | TYR | B | 352 | 31.786 | 82.838 | 98.939 | 1.00 | 22.97 | B | C |
| ATOM | 5223 | CD1 | TYR | B | 352 | 32.473 | 81.845 | 98.252 | 1.00 | 21.67 | B | C |
| ATOM | 5224 | CE1 | TYR | B | 352 | 32.132 | 80.510 | 98.389 | 1.00 | 23.62 | B | C |
| ATOM | 5225 | CD2 | TYR | B | 352 | 30.751 | 82.451 | 99.781 | 1.00 | 23.14 | B | C |
| ATOM | 5226 | CE2 | TYR | B | 352 | 30.402 | 81.120 | 99.926 | 1.00 | 22.93 | B | C |
| ATOM | 5227 | CZ | TYR | B | 352 | 31.091 | 80.148 | 99.224 | 1.00 | 24.78 | B | C |
| ATOM | 5228 | OH | TYR | B | 352 | 30.710 | 78.822 | 99.336 | 1.00 | 16.14 | B | O |
| ATOM | 5229 | C | TYR | B | 352 | 34.598 | 83.974 | 98.924 | 1.00 | 21.40 | B | C |
| ATOM | 5230 | O | TYR | B | 352 | 35.155 | 83.164 | 99.670 | 1.00 | 22.25 | B | O |
| ATOM | 5231 | N | ALA | B | 353 | 34.990 | 84.205 | 97.675 | 1.00 | 20.79 | B | N |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 5232 | CA | ALA | B | 353 | 36.127 | 83.508 | 97.095 | 1.00 | 23.10 | B | C |
| ATOM | 5233 | CB | ALA | B | 353 | 36.385 | 84.024 | 95.686 | 1.00 | 20.51 | B | C |
| ATOM | 5234 | C | ALA | B | 353 | 37.366 | 83.713 | 97.978 | 1.00 | 22.75 | B | C |
| ATOM | 5235 | O | ALA | B | 353 | 38.019 | 82.748 | 98.382 | 1.00 | 22.74 | B | O |
| ATOM | 5236 | N | HIS | B | 354 | 37.657 | 84.977 | 98.281 | 1.00 | 25.59 | B | N |
| ATOM | 5237 | CA | HIS | B | 354 | 38.802 | 85.380 | 99.109 | 1.00 | 26.84 | B | C |
| ATOM | 5238 | CB | HIS | B | 354 | 38.828 | 86.907 | 99.244 | 1.00 | 27.71 | B | C |
| ATOM | 5239 | CG | HIS | B | 354 | 40.009 | 87.430 | 100.000 | 1.00 | 30.87 | B | C |
| ATOM | 5240 | CD2 | HIS | B | 354 | 40.087 | 88.157 | 101.141 | 1.00 | 30.25 | B | C |
| ATOM | 5241 | ND1 | HIS | B | 354 | 41.308 | 87.247 | 99.573 | 1.00 | 31.55 | B | N |
| ATOM | 5242 | CE1 | HIS | B | 354 | 42.133 | 87.843 | 100.414 | 1.00 | 31.60 | B | C |
| ATOM | 5243 | NE2 | HIS | B | 354 | 41.418 | 88.403 | 101.374 | 1.00 | 31.73 | B | N |
| ATOM | 5244 | C | HIS | B | 354 | 38.793 | 84.757 | 100.501 | 1.00 | 26.40 | B | C |
| ATOM | 5245 | O | HIS | B | 354 | 39.848 | 84.464 | 101.061 | 1.00 | 25.94 | B | O |
| ATOM | 5246 | N | ARG | B | 355 | 37.600 | 84.569 | 101.056 | 1.00 | 28.55 | B | N |
| ATOM | 5247 | CA | ARG | B | 355 | 37.450 | 83.973 | 102.378 | 1.00 | 29.51 | B | C |
| ATOM | 5248 | CB | ARG | B | 355 | 36.062 | 84.305 | 102.949 | 1.00 | 29.02 | B | C |
| ATOM | 5249 | CG | ARG | B | 355 | 35.654 | 83.484 | 104.174 | 1.00 | 31.42 | B | C |
| ATOM | 5250 | CO | ARG | B | 355 | 34.580 | 84.208 | 104.976 | 1.00 | 30.54 | B | C |
| ATOM | 5251 | NE | ARG | B | 355 | 33.556 | 84.800 | 104.118 | 1.00 | 33.28 | B | N |
| ATOM | 5252 | CZ | ARG | B | 355 | 32.591 | 84.117 | 103.509 | 1.00 | 35.28 | B | C |
| ATOM | 5253 | NH1 | ARG | B | 355 | 32.498 | 82.801 | 103.660 | 1.00 | 37.73 | B | N |
| ATOM | 5254 | NH2 | ARG | B | 355 | 31.723 | 84.754 | 102.734 | 1.00 | 33.42 | B | N |
| ATOM | 5255 | C | ARG | B | 355 | 37.655 | 82.462 | 102.337 | 1.00 | 28.53 | B | C |
| ATOM | 5256 | O | ARG | B | 355 | 38.029 | 81.852 | 103.344 | 1.00 | 29.01 | B | O |
| ATOM | 5257 | N | ALA | B | 356 | 37.414 | 81.862 | 101.175 | 1.00 | 27.02 | B | N |
| ATOM | 5258 | CA | ALA | B | 356 | 37.579 | 80.423 | 101.036 | 1.00 | 29.85 | B | C |
| ATOM | 5259 | CB | ALA | B | 356 | 36.968 | 79.954 | 99.730 | 1.00 | 28.71 | B | C |
| ATOM | 5260 | C | ALA | B | 356 | 39.060 | 80.044 | 101.104 | 1.00 | 30.15 | B | C |
| ATOM | 5261 | O | ALA | B | 356 | 39.438 | 79.109 | 101.809 | 1.00 | 32.84 | B | O |
| ATOM | 5262 | N | LYS | B | 357 | 39.892 | 80.766 | 100.365 | 1.00 | 30.08 | B | N |
| ATOM | 5263 | CA | LYS | B | 357 | 41.330 | 80.520 | 100.367 | 1.00 | 32.33 | B | C |
| ATOM | 5264 | CB | LYS | B | 357 | 41.754 | 79.627 | 99.195 | 1.00 | 32.12 | B | C |
| ATOM | 5265 | CG | LYS | B | 357 | 43.247 | 79.318 | 99.205 | 1.00 | 31.36 | B | C |
| ATOM | 5266 | CD | LYS | B | 357 | 43.729 | 78.640 | 97.935 | 1.00 | 28.79 | B | C |
| ATOM | 5267 | CE | LYS | B | 357 | 45.245 | 78.476 | 97.975 | 1.00 | 26.81 | B | C |
| ATOM | 5268 | NZ | LYS | B | 357 | 45.792 | 77.806 | 96.772 | 1.00 | 24.78 | B | N |
| ATOM | 5269 | C | LYS | B | 357 | 42.031 | 81.868 | 100.264 | 1.00 | 34.04 | B | C |
| ATOM | 5270 | O | LYS | B | 357 | 42.097 | 82.475 | 99.187 | 1.00 | 31.55 | B | O |
| ATOM | 5271 | N | ASN | B | 358 | 42.550 | 82.322 | 101.402 | 1.00 | 35.14 | B | N |
| ATOM | 5272 | CA | ASN | B | 358 | 43.227 | 83.605 | 101.502 | 1.00 | 35.84 | B | C |
| ATOM | 5273 | CB | ASN | B | 358 | 43.443 | 83.948 | 102.968 | 1.00 | 37.99 | B | C |
| ATOM | 5274 | CG | ASN | B | 358 | 43.425 | 85.427 | 103.208 | 1.00 | 42.46 | B | C |
| ATOM | 5275 | OD1 | ASN | B | 358 | 43.631 | 85.889 | 104.327 | 1.00 | 47.10 | B | O |
| ATOM | 5276 | ND2 | ASN | B | 358 | 43.168 | 86.191 | 102.152 | 1.00 | 42.80 | B | N |
| ATOM | 5277 | C | ASN | B | 358 | 44.562 | 83.673 | 100.773 | 1.00 | 35.91 | B | C |
| ATOM | 5278 | O | ASN | B | 358 | 45.489 | 82.915 | 101.082 | 1.00 | 35.86 | B | O |
| ATOM | 5279 | N | ILE | B | 359 | 44.660 | 84.589 | 99.813 | 1.00 | 34.02 | B | N |
| ATOM | 5280 | CA | ILE | B | 359 | 45.888 | 84.759 | 99.047 | 1.00 | 34.17 | B | C |
| ATOM | 5281 | CB | ILE | B | 359 | 45.707 | 84.348 | 97.580 | 1.00 | 31.12 | B | C |
| ATOM | 5282 | CG2 | ILE | B | 359 | 47.029 | 84.488 | 96.847 | 1.00 | 30.92 | B | C |
| ATOM | 5283 | CG1 | ILE | B | 359 | 45.231 | 82.895 | 97.505 | 1.00 | 28.79 | B | C |
| ATOM | 5284 | CD1 | ILE | B | 359 | 45.111 | 82.360 | 96.117 | 1.00 | 25.40 | B | C |
| ATOM | 5285 | C | ILE | B | 359 | 46.374 | 86.201 | 99.102 | 1.00 | 37.27 | B | C |
| ATOM | 5286 | O | ILE | B | 359 | 45.844 | 87.088 | 98.420 | 1.00 | 38.31 | B | O |
| ATOM | 5287 | N | LEU | B | 360 | 47.400 | 86.402 | 99.927 | 1.00 | 39.26 | B | N |
| ATOM | 5288 | CA | LEU | B | 360 | 48.036 | 87.691 | 100.176 | 1.00 | 39.18 | B | C |
| ATOM | 5289 | CB | LEU | B | 360 | 49.294 | 87.475 | 101.027 | 1.00 | 37.17 | B | C |
| ATOM | 5290 | CG | LEU | B | 360 | 49.224 | 86.513 | 102.221 | 1.00 | 36.23 | B | C |
| ATOM | 5291 | CD1 | LEU | B | 360 | 48.594 | 85.186 | 101.813 | 1.00 | 35.82 | B | C |
| ATOM | 5292 | CD2 | LEU | B | 360 | 50.629 | 86.269 | 102.739 | 1.00 | 36.36 | B | C |
| ATOM | 5293 | C | LEU | B | 360 | 48.423 | 88.435 | 98.902 | 1.00 | 38.73 | B | C |
| ATOM | 5294 | O | LEU | B | 360 | 49.086 | 87.871 | 98.033 | 1.00 | 38.39 | B | O |
| ATOM | 5295 | N | ASN | B | 361 | 48.023 | 89.703 | 98.807 | 1.00 | 38.66 | B | N |
| ATOM | 5296 | CA | ASN | B | 361 | 48.346 | 90.537 | 97.646 | 1.00 | 40.66 | B | C |
| ATOM | 5297 | CB | ASN | B | 361 | 47.811 | 91.968 | 97.821 | 1.00 | 37.91 | B | C |
| ATOM | 5298 | CG | ASN | B | 361 | 46.331 | 92.020 | 98.136 | 1.00 | 36.57 | B | C |
| ATOM | 5299 | OD1 | ASN | B | 361 | 45.485 | 91.674 | 97.306 | 1.00 | 35.63 | B | O |
| ATOM | 5300 | ND2 | ASN | B | 361 | 46.008 | 92.467 | 99.347 | 1.00 | 37.46 | B | N |
| ATOM | 5301 | C | ASN | B | 361 | 49.865 | 90.639 | 97.466 | 1.00 | 42.13 | B | C |
| ATOM | 5302 | O | ASN | B | 361 | 50.529 | 91.376 | 98.199 | 1.00 | 40.72 | B | O |
| ATOM | 5303 | N | LYS | B | 362 | 50.413 | 89.912 | 96.496 | 1.00 | 44.23 | B | N |
| ATOM | 5304 | CA | LYS | B | 362 | 51.852 | 89.967 | 96.237 | 1.00 | 47.00 | B | C |
| ATOM | 5305 | CB | LYS | B | 362 | 52.157 | 89.345 | 94.876 | 1.00 | 47.08 | B | C |
| ATOM | 5306 | CG | LYS | B | 362 | 51.897 | 87.857 | 94.814 | 1.00 | 49.53 | B | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | | |
|---|---|---|---|---|---|---|---|---|---|---|---|---|
| ATOM | 5307 | CD | LYS | B | 362 | 51.701 | 87.391 | 93.378 | 1.00 | 50.61 | B | C |
| ATOM | 5308 | CE | LYS | B | 362 | 50.289 | 87.680 | 92.884 | 1.00 | 49.24 | B | C |
| ATOM | 5309 | NZ | LYS | B | 362 | 49.935 | 89.122 | 92.950 | 1.00 | 49.26 | B | N |
| ATOM | 5310 | C | LYS | B | 362 | 52.320 | 91.427 | 96.256 | 1.00 | 48.70 | B | C |
| ATOM | 5311 | Q | LYS | B | 362 | 51.740 | 92.278 | 95.577 | 1.00 | 46.71 | B | O |
| ATOM | 5312 | N | PRO | B | 363 | 53.388 | 91.731 | 91.021 | 1.00 | 51.10 | B | N |
| ATOM | 5313 | CD | PRO | B | 363 | 54.376 | 90.794 | 97.589 | 1.00 | 51.01 | B | C |
| ATOM | 5314 | CA | PRO | B | 363 | 53.884 | 93.110 | 97.089 | 1.00 | 53.07 | B | C |
| ATOM | 5315 | CB | PRO | B | 363 | 55.362 | 92.922 | 97.406 | 1.00 | 53.55 | B | C |
| ATOM | 5316 | CG | PRO | B | 363 | 55.339 | 91.728 | 98.308 | 1.00 | 52.93 | B | C |
| ATOM | 5317 | C | PRO | B | 363 | 53.646 | 93.834 | 95.770 | 1.00 | 54.59 | B | C |
| ATOM | 5318 | O | PRO | B | 363 | 54.038 | 93.349 | 94.711 | 1.00 | 55.28 | B | O |
| ATOM | 5319 | N | GLU | B | 364 | 52.989 | 94.986 | 95.847 | 1.00 | 55.52 | B | N |
| ATOM | 5320 | CA | GLU | B | 364 | 52.663 | 95.781 | 94.669 | 1.00 | 56.91 | B | C |
| ATOM | 5321 | CB | GLU | B | 364 | 52.411 | 97.237 | 95.075 | 1.00 | 57.32 | B | C |
| ATOM | 5322 | CG | GLU | B | 364 | 53.439 | 97.815 | 96.042 | 1.00 | 58.31 | B | C |
| ATOM | 5323 | CD | GLU | B | 364 | 53.032 | 97.653 | 97.496 | 1.00 | 58.07 | B | C |
| ATOM | 5324 | OE1 | GLU | B | 364 | 51.955 | 98.176 | 97.865 | 1.00 | 55.07 | B | O |
| ATOM | 5325 | OE2 | GLU | B | 364 | 53.786 | 97.011 | 98.265 | 1.00 | 59.16 | B | O |
| ATOM | 5326 | C | GLU | B | 364 | 53.692 | 95.735 | 93.539 | 1.00 | 58.77 | B | C |
| ATOM | 5327 | O | GLU | B | 364 | 54.772 | 95.159 | 93.682 | 1.00 | 58.08 | B | O |
| ATOM | 5328 | N | VAL | B | 365 | 53.333 | 96.355 | 92.413 | 1.00 | 60.32 | B | N |
| ATOM | 5329 | CA | VAL | B | 365 | 54.176 | 96.417 | 91.216 | 1.00 | 60.11 | B | C |
| ATOM | 5330 | CB | VAL | B | 365 | 53.843 | 97.685 | 90.377 | 1.00 | 60.39 | B | C |
| ATOM | 5331 | CG1 | VAL | B | 365 | 53.796 | 98.917 | 91.280 | 1.00 | 59.25 | B | C |
| ATOM | 5332 | CG2 | VAL | B | 365 | 54.881 | 97.873 | 89.273 | 1.00 | 60.03 | B | C |
| ATOM | 5333 | C | VAL | B | 365 | 55.677 | 96.389 | 91.503 | 1.00 | 59.64 | B | C |
| ATOM | 5334 | OXT | VAL | B | 365 | 56.158 | 97.331 | 92.168 | 1.00 | 59.90 | B | O |
| ATOM | 5335 | N | NO3 | | 2000 | 18.595 | 75.024 | 97.565 | 1.00 | 52.56 | | N |
| ATOM | 5336 | O1 | NO3 | | 2000 | 18.863 | 74.109 | 98.403 | 1.00 | 51.01 | | O |
| ATOM | 5337 | O2 | NO3 | | 2000 | 18.165 | 74.683 | 96.501 | 1.00 | 51.29 | | O |
| ATOM | 5338 | O3 | NO3 | | 2000 | 18.790 | 76.182 | 97.890 | 1.00 | 52.44 | | O |
| ATOM | 5339 | N | NO3 | | 2001 | 23.963 | 104.765 | 99.974 | 1.00 | 66.74 | | N |
| ATOM | 5340 | O1 | NO3 | | 2001 | 23.741 | 105.308 | 98.863 | 1.00 | 68.45 | | O |
| ATOM | 5341 | O2 | NO3 | | 2001 | 24.847 | 103.956 | 100.014 | 1.00 | 66.51 | | O |
| ATOM | 5342 | O3 | NO3 | | 2001 | 23.273 | 105.099 | 100.924 | 1.00 | 65.15 | | O |
| TER | 5343 | | NO3 | | 2001 | | | | | | | |
| ATOM | 5344 | MG | MG | | 2602 | 22.424 | 78.120 | 85.762 | 1.00 | 25.11 | | MG |
| TER | 5345 | | MG | | 2602 | | | | | | | |
| ATOM | 5346 | MG | MG | | 2603 | 17.096 | 104.976 | 86.459 | 1.00 | 37.15 | | MG |
| TER | 5347 | | MG | | 2603 | | | | | | | |
| ATOM | 5348 | PB | ADP | | 2601 | 15.476 | 101.502 | 86.036 | 1.00 | 17.57 | | P |
| ATOM | 5349 | O1B | ADP | | 2601 | 15.970 | 100.754 | 87.192 | 1.00 | 22.84 | | O |
| ATOM | 5350 | O2B | ADP | | 2601 | 13.913 | 101.303 | 85.861 | 1.00 | 21.81 | | O |
| ATOM | 5351 | O3B | ADP | | 2601 | 15.835 | 103.081 | 86.153 | 1.00 | 21.03 | | O |
| ATOM | 5352 | PA | ADP | | 2601 | 16.003 | 101.554 | 83.255 | 1.00 | 26.70 | | P |
| ATOM | 5353 | O1A | ADP | | 2601 | 16.277 | 103.015 | 83.352 | 1.00 | 33.51 | | O |
| ATOM | 5354 | O2A | ADP | | 2601 | 16.955 | 100.793 | 82.195 | 1.00 | 28.63 | | O |
| ATOM | 5355 | O3A | ADP | | 2601 | 16.230 | 100.946 | 84.725 | 1.00 | 26.63 | | O |
| ATOM | 5356 | O5* | ADP | | 2601 | 14.518 | 101.298 | 82.783 | 1.00 | 17.16 | | O |
| ATOM | 5357 | C5* | ADP | | 2601 | 13.978 | 100.020 | 82.537 | 1.00 | 24.19 | | C |
| ATOM | 5358 | C4* | ADP | | 2601 | 14.701 | 99.215 | 81.407 | 1.00 | 25.68 | | C |
| ATOM | 5359 | O4* | ADP | | 2601 | 13.971 | 98.025 | 81.267 | 1.00 | 24.47 | | O |
| ATOM | 5360 | C3* | ADP | | 2601 | 14.663 | 99.948 | 80.064 | 1.00 | 28.76 | | C |
| ATOM | 5361 | O3* | ADP | | 2601 | 16.004 | 100.303 | 79.741 | 1.00 | 34.63 | | O |
| ATOM | 5362 | C2* | ADP | | 2601 | 14.155 | 98.934 | 79.095 | 1.00 | 25.45 | | C |
| ATOM | 5363 | O2* | ADP | | 2601 | 15.227 | 98.337 | 78.400 | 1.00 | 32.03 | | O |
| ATOM | 5364 | C1* | ADP | | 2601 | 13.378 | 97.981 | 79.978 | 1.00 | 21.50 | | C |
| ATOM | 5365 | N9 | ADP | | 2601 | 11.947 | 98.385 | 80.128 | 1.00 | 22.10 | | N |
| ATOM | 5366 | C8 | ADP | | 2601 | 11.346 | 98.947 | 81.229 | 1.00 | 20.57 | | C |
| ATOM | 5367 | N7 | ADP | | 2601 | 10.086 | 99.187 | 81.102 | 1.00 | 18.74 | | N |
| ATOM | 5368 | C5 | ADP | | 2601 | 9.797 | 98.762 | 79.828 | 1.00 | 19.52 | | C |
| ATOM | 5369 | C6 | ADP | | 2601 | 8.600 | 98.738 | 79.080 | 1.00 | 21.62 | | C |
| ATOM | 5370 | N6 | ADP | | 2601 | 7.426 | 99.178 | 79.567 | 1.00 | 24.17 | | N |
| ATOM | 5371 | N1 | ADP | | 2601 | 8.639 | 98.249 | 77.823 | 1.00 | 24.80 | | N |
| ATOM | 5372 | C2 | ADP | | 2601 | 9.802 | 97.805 | 77.332 | 1.00 | 28.07 | | C |
| ATOM | 5373 | N3 | ADP | | 2601 | 10.995 | 97.771 | 77.939 | 1.00 | 27.92 | | N |
| ATOM | 5374 | C4 | ADP | | 2601 | 10.926 | 98.272 | 79.209 | 1.00 | 21.63 | | C |
| TER | 5375 | | ADP | | 2601 | | | | | | | |
| ATOM | 5376 | PB | ADP | | 2602 | 23.795 | 81.438 | 85.171 | 1.00 | 15.66 | | P |
| ATOM | 5377 | O1B | ADP | | 2602 | 23.046 | 82.173 | 86.196 | 1.00 | 16.94 | | O |
| ATOM | 5378 | O2B | ADP | | 2602 | 25.360 | 81.755 | 85.294 | 1.00 | 15.07 | | O |
| ATOM | 5379 | O3B | ADP | | 2602 | 23.546 | 79.852 | 85.283 | 1.00 | 14.57 | | O |
| ATOM | 5380 | PA | ADP | | 2602 | 23.723 | 81.344 | 82.309 | 1.00 | 17.95 | | P |
| ATOM | 5381 | O1A | ADP | | 2602 | 23.580 | 79.883 | 82.311 | 1.00 | 25.41 | | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5382 | O2A | ADP | 2602 | 22.868 | 82.063 | 81.162 | 1.00 | 27.54 | | O |
| ATOM | 5383 | O3A | ADP | 2602 | 23.231 | 81.911 | 83.734 | 1.00 | 19.95 | | O |
| ATOM | 5384 | O5* | ADP | 2602 | 25.228 | 81.714 | 82.050 | 1.00 | 16.67 | | O |
| ATOM | 5385 | C5* | ADP | 2602 | 25.655 | 83.028 | 81.896 | 1.00 | 26.38 | | C |
| ATOM | 5386 | C4* | ADP | 2602 | 25.076 | 83.611 | 80.572 | 1.00 | 29.57 | | C |
| ATOM | 5387 | O4* | ADP | 2602 | 25.562 | 84.936 | 80.379 | 1.00 | 24.61 | | O |
| ATOM | 5388 | C3* | ADP | 2602 | 25.499 | 82.806 | 79.326 | 1.00 | 33.25 | | C |
| ATOM | 5389 | O3* | ADP | 2602 | 24.515 | 81.838 | 79.016 | 1.00 | 38.37 | | O |
| ATOM | 5390 | C2* | ADP | 2602 | 25.583 | 83.897 | 78.311 | 1.00 | 29.90 | | C |
| ATOM | 5391 | O2* | ADP | 2602 | 24.291 | 84.249 | 77.835 | 1.00 | 32.26 | | O |
| ATOM | 5392 | C1* | ADP | 2602 | 26.274 | 84.943 | 79.150 | 1.00 | 24.63 | | C |
| ATOM | 5393 | N9 | ADP | 2602 | 27.706 | 84.579 | 79.399 | 1.00 | 23.86 | | N |
| ATOM | 5394 | C8 | ADP | 2602 | 28.314 | 84.190 | 80.587 | 1.00 | 24.21 | | C |
| ATOM | 5395 | N7 | ADP | 2602 | 29.592 | 83.947 | 80.494 | 1.00 | 23.45 | | N |
| ATOM | 5396 | C5 | ADP | 2602 | 29.872 | 84.186 | 79.157 | 1.00 | 22.91 | | C |
| ATOM | 5397 | C6 | ADP | 2602 | 31.060 | 84.118 | 78.396 | 1.00 | 22.94 | | C |
| ATOM | 5398 | N6 | ADP | 2602 | 32.245 | 83.774 | 78.916 | 1.00 | 22.81 | | N |
| ATOM | 5399 | N1 | ADP | 2602 | 30.992 | 84.421 | 77.078 | 1.00 | 24.38 | | N |
| ATOM | 5400 | C2 | ADP | 2602 | 29.815 | 84.771 | 76.542 | 1.00 | 22.03 | | C |
| ATOM | 5401 | N3 | ADP | 2602 | 28.635 | 84.875 | 77.146 | 1.00 | 21.04 | | N |
| ATOM | 5402 | C4 | ADP | 2602 | 28.725 | 84.567 | 78.473 | 1.00 | 23.71 | | C |
| TER | 5403 | | ADP | 2602 | | | | | | | |
| ATOM | 5404 | C1 | 258 | 1 | 17.749 | 114.057 | 82.698 | 1.00 | 15.85 | ADRU | C |
| ATOM | 5405 | C2 | 258 | 1 | 17.994 | 113.776 | 81.383 | 1.00 | 15.85 | ADRU | C |
| ATOM | 5406 | C3 | 258 | 1 | 16.885 | 113.508 | 80.496 | 1.00 | 15.85 | ADRU | C |
| ATOM | 5407 | N1 | 258 | 1 | 15.594 | 113.545 | 80.998 | 1.00 | 15.85 | ADRU | N |
| ATOM | 5408 | CS | 258 | 1 | 15.415 | 113.835 | 82.342 | 1.00 | 15.85 | ADRU | C |
| ATOM | 5409 | C6 | 258 | 1 | 16.469 | 114.086 | 83.175 | 1.00 | 15.85 | ADRU | C |
| ATOM | 5410 | N10 | 258 | 1 | 17.118 | 113.222 | 79.174 | 1.00 | 15.85 | ADRU | N |
| ATOM | 5411 | C11 | 258 | 1 | 16.105 | 112.960 | 78.288 | 1.00 | 15.85 | ADRU | C |
| ATOM | 5412 | C8 | 258 | 1 | 14.806 | 112.987 | 78.728 | 1.00 | 15.85 | ADRU | C |
| ATOM | 5413 | C13 | 258 | 1 | 14.512 | 113.288 | 80.134 | 1.00 | 15.85 | ADRU | C |
| ATOM | 5414 | C14 | 258 | 1 | 13.654 | 112.713 | 77.790 | 1.00 | 15.85 | ADRU | C |
| ATOM | 5415 | C15 | 258 | 1 | 13.206 | 113.956 | 77.029 | 1.00 | 15.85 | ADRU | C |
| ATOM | 5416 | C18 | 258 | 1 | 12.857 | 115.153 | 77.689 | 1.00 | 15.85 | ADRU | C |
| ATOM | 5417 | C19 | 258 | 1 | 12.447 | 116.266 | 76.953 | 1.00 | 15.85 | ADRU | C |
| ATOM | 5418 | C20 | 258 | 1 | 12.381 | 116.196 | 75.549 | 1.00 | 15.85 | ADRU | C |
| ATOM | 5419 | C21 | 258 | 1 | 12.730 | 115.008 | 74.883 | 1.00 | 15.85 | ADRU | C |
| ATOM | 5420 | C22 | 258 | 1 | 13.141 | 113.891 | 75.620 | 1.00 | 15.85 | ADRU | C |
| ATOM | 5421 | C28 | 258 | 1 | 13.354 | 113.324 | 80.578 | 1.00 | 15.85 | ADRU | O |
| ATOM | 5422 | C30 | 258 | 1 | 16.462 | 112.656 | 76.828 | 1.00 | 15.85 | ADRU | C |
| ATOM | 5423 | C31 | 258 | 1 | 17.489 | 113.706 | 76.348 | 1.00 | 15.85 | ADRU | C |
| ATOM | 5424 | C32 | 258 | 1 | 16.801 | 114.895 | 75.612 | 1.00 | 15.85 | ADRU | C |
| ATOM | 5425 | N38 | 258 | 1 | 17.060 | 111.303 | 76.625 | 1.00 | 15.85 | ADRU | N |
| ATOM | 5426 | C40 | 258 | 1 | 18.289 | 110.972 | 77.401 | 1.00 | 15.85 | ADRU | C |
| ATOM | 5427 | C41 | 258 | 1 | 18.010 | 110.102 | 78.672 | 1.00 | 15.85 | ADRU | C |
| ATOM | 5428 | C44 | 258 | 1 | 17.186 | 108.805 | 78.457 | 1.00 | 15.85 | ADRU | C |
| ATOM | 5429 | N47 | 258 | 1 | 16.952 | 108.061 | 79.707 | 1.00 | 15.85 | ADRU | N |
| ATOM | 5430 | C52 | 258 | 1 | 16.566 | 110.339 | 75.775 | 1.00 | 15.85 | ADRU | C |
| ATOM | 5431 | O53 | 258 | 1 | 17.137 | 109.251 | 75.661 | 1.00 | 15.85 | ADRU | O |
| ATOM | 5432 | C54 | 258 | 1 | 15.412 | 110.449 | 74.982 | 1.00 | 15.85 | ADRU | C |
| ATOM | 5433 | C55 | 258 | 1 | 14.230 | 109.792 | 75.428 | 1.00 | 15.85 | ADRU | C |
| ATOM | 5434 | C56 | 258 | 1 | 13.040 | 109.848 | 74.675 | 1.00 | 15.85 | ADRU | C |
| ATOM | 5435 | C57 | 258 | 1 | 13.001 | 110.556 | 73.463 | 1.00 | 15.85 | ADRU | C |
| ATOM | 5436 | C58 | 258 | 1 | 14.181 | 111.217 | 73.005 | 1.00 | 15.85 | ADRU | C |
| ATOM | 5437 | C59 | 258 | 1 | 15.385 | 111.164 | 73.762 | 1.00 | 15.85 | ADRU | C |
| ATOM | 5438 | CL1 | 258 | 1 | 11.714 | 110.610 | 72.656 | 1.00 | 15.85 | ADRU | C |
| ATOM | 5439 | C7 | 258 | 1 | 17.996 | 113.972 | 74.962 | 1.00 | 15.85 | ADRU | C |
| TER | 5440 | | 258 | 1 | | | | | | ADRU | |
| ATOM | 5441 | C1 | 258 | 2 | 21.750 | 68.720 | 82.459 | 1.00 | 15.85 | 2 | C |
| ATOM | 5442 | C2 | 258 | 2 | 21.547 | 68.914 | 81.119 | 1.00 | 15.85 | 2 | C |
| ATOM | 5443 | C3 | 258 | 2 | 22.684 | 69.204 | 80.273 | 1.00 | 15.85 | 2 | C |
| ATOM | 5444 | N1 | 258 | 2 | 23.950 | 69.280 | 80.846 | 1.00 | 15.85 | 2 | N |
| ATOM | 5445 | C5 | 258 | 2 | 24.084 | 69.072 | 82.223 | 1.00 | 15.85 | 2 | C |
| ATOM | 5446 | C6 | 258 | 2 | 23.010 | 68.799 | 83.010 | 1.00 | 15.85 | 2 | C |
| ATOM | 5447 | N10 | 258 | 2 | 22.510 | 69.401 | 78.926 | 1.00 | 15.85 | 2 | N |
| ATOM | 5448 | C11 | 258 | 2 | 23.552 | 69.678 | 78.085 | 1.00 | 15.85 | 2 | C |
| ATOM | 5449 | C8 | 258 | 2 | 24.819 | 69.760 | 78.593 | 1.00 | 15.85 | 2 | C |
| ATOM | 5450 | C13 | 258 | 2 | 25.049 | 69.557 | 80.030 | 1.00 | 15.85 | 2 | C |
| ATOM | 5451 | C14 | 258 | 2 | 26.006 | 70.057 | 77.696 | 1.00 | 15.85 | 2 | C |
| ATOM | 5452 | C15 | 258 | 2 | 26.593 | 68.795 | 77.080 | 1.00 | 15.85 | 2 | C |
| ATOM | 5453 | C18 | 258 | 2 | 27.018 | 67.700 | 77.872 | 1.00 | 15.85 | 2 | C |
| ATOM | 5454 | C19 | 258 | 2 | 27.557 | 66.548 | 77.255 | 1.00 | 15.85 | 2 | C |
| ATOM | 5455 | C20 | 258 | 2 | 27.674 | 66.490 | 75.840 | 1.00 | 15.85 | 2 | C |
| ATOM | 5456 | C21 | 258 | 2 | 27.248 | 67.583 | 75.056 | 1.00 | 15.85 | 2 | C |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5457 | C22 | 258 | 2 | 26.710 | 68.730 | 75.680 | 1.00 | 15.85 | 2 | C |
| ATOM | 5458 | O28 | 258 | 2 | 26.167 | 69.620 | 80.546 | 1.00 | 15.85 | 2 | O |
| ATOM | 5459 | C30 | 258 | 2 | 23.260 | 69.882 | 76.593 | 1.00 | 15.85 | 2 | C |
| ATOM | 5460 | C31 | 258 | 2 | 22.284 | 68.795 | 76.128 | 1.00 | 15.85 | 2 | C |
| ATOM | 5461 | C32 | 258 | 2 | 23.007 | 67.437 | 75.885 | 1.00 | 15.85 | 2 | C |
| ATOM | 5462 | N38 | 258 | 2 | 22.650 | 71.217 | 76.300 | 1.00 | 15.85 | 2 | N |
| ATOM | 5463 | C40 | 258 | 2 | 21.377 | 71.535 | 76.989 | 1.00 | 15.85 | 2 | C |
| ATOM | 5464 | C41 | 258 | 2 | 21.553 | 72.343 | 78.297 | 1.00 | 15.85 | 2 | C |
| ATOM | 5465 | C44 | 258 | 2 | 21.997 | 73.792 | 78.113 | 1.00 | 15.85 | 2 | C |
| ATOM | 5466 | N47 | 258 | 2 | 22.143 | 74.485 | 79.398 | 1.00 | 15.85 | 2 | N |
| ATOM | 5467 | C52 | 258 | 2 | 23.182 | 72.156 | 75.438 | 1.00 | 15.85 | 2 | C |
| ATOM | 5468 | O53 | 258 | 2 | 22.610 | 73.234 | 75.244 | 1.00 | 15.85 | 2 | O |
| ATOM | 5469 | C54 | 258 | 2 | 24.391 | 71.997 | 74.716 | 1.00 | 15.85 | 2 | C |
| ATOM | 5470 | C55 | 258 | 2 | 25.578 | 72.578 | 75.225 | 1.00 | 15.85 | 2 | C |
| ATOM | 5471 | C56 | 258 | 2 | 26.801 | 72.453 | 74.539 | 1.00 | 15.85 | 2 | C |
| ATOM | 5472 | C57 | 258 | 2 | 26.864 | 71.743 | 73.326 | 1.00 | 15.85 | 2 | C |
| ATOM | 5473 | C58 | 258 | 2 | 25.677 | 71.158 | 72.806 | 1.00 | 15.85 | 2 | C |
| ATOM | 5474 | C59 | 258 | 2 | 24.445 | 71.286 | 73.499 | 1.00 | 15.85 | 2 | C |
| ATOM | 5475 | CL1 | 258 | 2 | 28.192 | 71.606 | 72.585 | 1.00 | 15.85 | 2 | C |
| ATOM | 5476 | C7 | 258 | 2 | 22.104 | 68.217 | 74.768 | 1.00 | 15.85 | 2 | C |
| TER | 5477 | | 258 | 2 | | | | | | 2 | |
| ATOM | 5478 | OH2 | TIP | 1 | 13.316 | 112.771 | 86.782 | 1.00 | 27.72 | S | O |
| ATOM | 5479 | OH2 | TIP | 2 | 21.291 | 108.165 | 97.704 | 1.00 | 26.46 | S | O |
| ATOM | 5480 | OH2 | TIP | 3 | −7.702 | 127.503 | 85.435 | 1.00 | 26.36 | S | O |
| ATOM | 5481 | OH2 | TIP | 4 | 17.950 | 116.600 | 105.999 | 1.00 | 21.62 | S | O |
| ATOM | 5482 | OH2 | TIP | 5 | 13.129 | 121.252 | 93.302 | 1.00 | 34.16 | S | O |
| ATOM | 5483 | OH2 | TIP | 6 | 17.948 | 111.384 | 100.889 | 1.00 | 23.31 | S | O |
| ATOM | 5484 | OH2 | TIP | 7 | 5.531 | 101.208 | 75.528 | 1.00 | 15.26 | S | O |
| ATOM | 5485 | OH2 | TIP | 8 | −4.547 | 135.702 | 74.016 | 1.00 | 25.89 | S | O |
| ATOM | 5486 | OH2 | TIP | 9 | 13.546 | 81.951 | 89.702 | 1.00 | 21.05 | S | O |
| ATOM | 5487 | OH2 | TIP | 10 | 30.991 | 49.800 | 87.857 | 1.00 | 28.41 | S | O |
| ATOM | 5488 | OH2 | TIP | 11 | 21.808 | 71.979 | 100.560 | 1.00 | 18.92 | S | O |
| ATOM | 5489 | OH2 | TIP | 12 | 28.819 | 58.634 | 88.996 | 1.00 | 28.36 | S | O |
| ATOM | 5490 | OH2 | TIP | 13 | −6.812 | 100.347 | 85.996 | 1.00 | 23.83 | S | O |
| ATOM | 5491 | OH2 | TIP | 14 | 21.587 | 79.185 | 83.595 | 1.00 | 12.53 | S | O |
| ATOM | 5492 | OH2 | TIP | 15 | 12.125 | 102.911 | 93.996 | 1.00 | 22.31 | S | O |
| ATOM | 5493 | OH2 | TIP | 16 | 38.995 | 70.036 | 75.058 | 1.00 | 15.09 | S | O |
| ATOM | 5494 | OH2 | TIP | 17 | 23.786 | 93.573 | 92.022 | 1.00 | 21.56 | S | O |
| ATOM | 5495 | OH2 | TIP | 18 | 28.594 | 86.145 | 96.752 | 1.00 | 11.99 | S | O |
| ATOM | 5496 | OH2 | TIP | 19 | 4.088 | 108.526 | 79.214 | 1.00 | 19.72 | S | O |
| ATOM | 5497 | OH2 | TIP | 20 | 36.912 | 77.621 | 73.468 | 1.00 | 11.10 | S | O |
| ATOM | 5498 | OH2 | TIP | 21 | 25.778 | 70.023 | 86.567 | 1.00 | 26.24 | S | O |
| ATOM | 5499 | OH2 | TIP | 22 | 36.946 | 72.760 | 70.766 | 1.00 | 40.00 | S | O |
| ATOM | 5500 | OH2 | TIP | 23 | 24.882 | 56.827 | 95.690 | 1.00 | 24.44 | S | O |
| ATOM | 5501 | OH2 | TIP | 24 | 33.461 | 82.110 | 74.084 | 1.00 | 29.20 | S | O |
| ATOM | 5502 | OH2 | TIP | 25 | 49.659 | 40.223 | 81.945 | 1.00 | 34.88 | S | O |
| ATOM | 5503 | OH2 | TIP | 26 | 3.110 | 134.177 | −76.485 | 1.00 | 27.79 | S | O |
| ATOM | 5504 | OH2 | TIP | 27 | 18.243 | 83.011 | 92.634 | 1.00 | 22.85 | S | O |
| ATOM | 5505 | OH2 | TIP | 28 | −5.213 | 80.220 | 97.203 | 1.00 | 35.44 | S | O |
| ATOM | 5506 | OH2 | TIP | 29 | 23.079 | 116.450 | 69.093 | 1.00 | 33.10 | S | O |
| ATOM | 5507 | OH2 | TIP | 30 | 19.318 | 135.139 | 97.597 | 1.00 | 28.63 | S | O |
| ATOM | 5508 | OH2 | TIP | 31 | 35.183 | 74.977 | 79.135 | 1.00 | 40.06 | S | O |
| ATOM | 5509 | OH2 | TIP | 32 | 48.405 | 69.712 | 83.784 | 1.00 | 39.55 | S | O |
| ATOM | 5510 | OH2 | TIP | 33 | 6.497 | 132.223 | 71.168 | 1.00 | 15.15 | S | O |
| ATOM | 5511 | OH2 | TIP | 34 | 28.552 | 100.514 | 101.935 | 1.00 | 38.44 | S | O |
| ATOM | 5512 | OH2 | TIP | 35 | 51.524 | 80.885 | 94.924 | 1.00 | 29.19 | S | O |
| ATOM | 5513 | OH2 | TIP | 36 | 26.848 | 80.580 | 93.555 | 1.00 | 24.78 | S | O |
| ATOM | 5514 | OH2 | TIP | 37 | 9.012 | 130.325 | 91.285 | 1.00 | 24.42 | S | O |
| ATOM | 5515 | OH2 | TIP | 38 | −8.596 | 126.861 | 73.815 | 1.00 | 27.90 | S | O |
| ATOM | 5516 | OH2 | TIP | 39 | 10.315 | 96.602 | 91.913 | 1.00 | 17.61 | S | O |
| ATOM | 5517 | OH2 | TIP | 40 | 34.781 | 57.047 | 94.773 | 1.00 | 26.21 | S | O |
| ATOM | 5518 | OH2 | TIP | 41 | 3.003 | 134.606 | 88.439 | 1.00 | 38.84 | S | O |
| ATOM | 5519 | OH2 | TIP | 42 | 27.882 | 60.121 | 93.316 | 1.00 | 24.35 | S | O |
| ATOM | 5520 | OH2 | TIP | 43 | 19.100 | 109.097 | 72.071 | 1.00 | 33.28 | S | O |
| ATOM | 5521 | OH2 | TIP | 44 | 9.579 | 59.047 | 80.746 | 1.00 | 31.50 | S | O |
| ATOM | 5522 | OH2 | TIP | 45 | 5.781 | 56.343 | 84.585 | 1.00 | 34.80 | S | O |
| ATOM | 5523 | OH2 | TIP | 46 | 16.272 | 95.117 | 98.422 | 1.00 | 37.95 | S | O |
| ATOM | 5524 | OH2 | TIP | 47 | 51.946 | 59.099 | 86.131 | 1.00 | 22.79 | S | O |
| ATOM | 5525 | OH2 | TIP | 48 | 8.125 | 117.055 | 110.390 | 1.00 | 31.70 | S | O |
| ATOM | 5526 | OH2 | TIP | 49 | −4.806 | 118.907 | 74.337 | 1.00 | 52.99 | S | O |
| ATOM | 5527 | OH2 | TIP | 50 | 11.865 | 98.771 | 95.211 | 1.00 | 43.08 | S | O |
| ATOM | 5528 | OH2 | TIP | 51 | 12.646 | 103.181 | 94.982 | 1.00 | 30.05 | S | O |
| ATOM | 5529 | OH2 | TIP | 52 | 13.151 | 71.655 | 103.790 | 1.00 | 25.08 | S | O |
| ATOM | 5530 | OH2 | TIP | 53 | 49.361 | 80.398 | 97.965 | 1.00 | 31.34 | S | O |
| ATOM | 5531 | OH2 | TIP | 54 | 19.317 | 89.253 | 71.438 | 1.00 | 29.32 | S | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5532 | OH2 | TIP | 55 | 8.109 | 86.901 | 105.626 | 1.00 | 22.15 | S | O |
| ATOM | 5533 | OH2 | TIP | 56 | 18.403 | 93.592 | 77.183 | 1.00 | 44.60 | S | O |
| ATOM | 5534 | OH2 | TIP | 57 | 30.889 | 83.352 | 105.753 | 1.00 | 48.70 | S | O |
| ATOM | 5535 | OH2 | TIP | 58 | 24.848 | 120.073 | 82.455 | 1.00 | 46.18 | S | O |
| ATOM | 5536 | OH2 | TIP | 59 | 9.564 | 48.922 | 87.375 | 1.00 | 26.01 | S | O |
| ATOM | 5537 | OH2 | TIP | 60 | 11.389 | 65.234 | 80.414 | 1.00 | 24.69 | S | O |
| ATOM | 5538 | OH2 | TIP | 61 | 61.999 | 37.245 | 84.871 | 1.00 | 33.08 | S | O |
| ATOM | 5539 | OH2 | TIP | 62 | 22.027 | 136.786 | 98.876 | 1.00 | 35.47 | S | O |
| ATOM | 5540 | OH2 | TIP | 63 | 19.999 | 87.197 | 85.649 | 1.00 | 30.49 | S | O |
| ATOM | 5541 | OH2 | TIP | 64 | 8.658 | 101.459 | 107.138 | 1.00 | 48.11 | S | O |
| ATOM | 5542 | OH2 | TIP | 65 | 31.090 | 53.202 | 92.988 | 1.00 | 33.52 | S | O |
| ATOM | 5543 | OH2 | TIP | 66 | 2.798 | 108.528 | 70.894 | 1.00 | 24.40 | S | O |
| ATOM | 5544 | OH2 | TIP | 67 | 15.036 | 61.784 | 82.610 | 1.00 | 52.77 | S | O |
| ATOM | 5545 | OH2 | TIP | 68 | 8.855 | 96.326 | 101.819 | 1.00 | 29.67 | S | O |
| ATOM | 5546 | OH2 | TIP | 69 | 25.551 | 66.370 | 67.590 | 1.00 | 32.13 | S | O |
| ATOM | 5547 | OH2 | TIP | 70 | 0.936 | 91.897 | 83.237 | 1.00 | 41.45 | S | O |
| ATOM | 5548 | OH2 | TIP | 71 | 30.477 | 69.920 | 113.145 | 1.00 | 17.87 | S | O |
| ATOM | 5549 | OH2 | TIP | 72 | 34.684 | 117.446 | 86.205 | 1.00 | 35.87 | S | O |
| ATOM | 5550 | OH2 | TIP | 73 | 41.397 | 112.406 | 96.985 | 1.00 | 35.92 | S | O |
| ATOM | 5551 | OH2 | TIP | 74 | 10.590 | 123.951 | 106.268 | 1.00 | 56.16 | S | O |
| ATOM | 5552 | OH2 | TIP | 75 | 58.450 | 99.184 | 90.773 | 1.00 | 37.33 | S | O |
| ATOM | 5553 | OH2 | TIP | 76 | 23.550 | 72.114 | 111.942 | 1.00 | 36.14 | S | O |
| ATOM | 5554 | OH2 | TIP | 77 | −1.429 | 94.908 | 79.584 | 1.00 | 31.07 | S | O |
| ATOM | 5555 | OH2 | TIP | 78 | −3.563 | 140.411 | 88.982 | 1.00 | 37.05 | S | O |
| ATOM | 5556 | OH2 | TIP | 79 | 47.533 | 55.966 | 86.211 | 1.00 | 32.05 | S | O |
| ATOM | 5557 | OH2 | TIP | 80 | 60.873 | 39.356 | 82.366 | 1.00 | 31.86 | S | O |
| ATOM | 5558 | OH2 | TIP | 81 | 1.351 | 144.301 | 86.522 | 1.00 | 42.45 | S | O |
| ATOM | 5559 | OH2 | TIP | 82 | 43.625 | 80.260 | 73.121 | 1.00 | 32.58 | S | O |
| ATOM | 5560 | OH2 | TIP | 83 | −9.854 | 100.785 | 93.708 | 1.00 | 61.86 | S | O |
| ATOM | 5561 | OH2 | TIP | 84 | 9.334 | 133.381 | 86.533 | 1.00 | 51.67 | S | O |
| ATOM | 5562 | OH2 | TIP | 85 | 48.221 | 77.700 | 90.691 | 1.00 | 33.81 | S | O |
| ATOM | 5563 | OH2 | TIP | 86 | 21.340 | 97.274 | 91.150 | 1.00 | 32.30 | S | O |
| ATOM | 5564 | OH2 | TIP | 87 | 17.041 | 90.569 | 86.172 | 1.00 | 32.11 | S | O |
| ATOM | 5565 | OH2 | TIP | 88 | 8.585 | 127.118 | 68.776 | 1.00 | 39.30 | S | O |
| ATOM | 5566 | OH2 | TIP | 89 | −8.423 | 113.539 | 82.687 | 1.00 | 39.89 | S | O |
| ATOM | 5567 | OH2 | TIP | 90 | 32.951 | 49.351 | 79.656 | 1.00 | 46.33 | S | O |
| ATOM | 5568 | OH2 | TIP | 91 | 4.730 | 123.041 | 108.929 | 1.00 | 52.91 | S | O |
| ATOM | 5569 | OH2 | TIP | 92 | 26.440 | 118.493 | 101.594 | 1.00 | 36.04 | S | O |
| ATOM | 5570 | OH2 | TIP | 93 | 35.388 | 127.513 | 91.957 | 1.00 | 32.51 | S | O |
| ATOM | 5571 | OH2 | TIP | 94 | 19.256 | 104.455 | 83.135 | 1.00 | 28.22 | S | O |
| ATOM | 5572 | OH2 | TIP | 95 | 9.913 | 133.213 | 77.324 | 1.00 | 41.60 | S | O |
| ATOM | 5573 | OH2 | TIP | 96 | 35.661 | 45.932 | 79.237 | 1.00 | 52.97 | S | O |
| ATOM | 5574 | OH2 | TIP | 97 | −11.050 | 120.500 | 91.863 | 1.00 | 29.06 | S | O |
| ATOM | 5575 | OH2 | TIP | 98 | −0.241 | 137.855 | 75.064 | 1.00 | 42.73 | S | O |
| ATOM | 5576 | OH2 | TIP | 99 | 3.111 | 134.945 | 83.369 | 1.00 | 38.57 | S | O |
| ATOM | 5577 | OH2 | TIP | 100 | 23.007 | 74.844 | 73.135 | 1.00 | 47.84 | S | O |
| ATOM | 5578 | OH2 | TIP | 101 | 45.424 | 93.581 | 79.125 | 1.00 | 46.41 | S | O |
| ATOM | 5579 | OH2 | TIP | 102 | 35.324 | 56.156 | 71.691 | 1.00 | 32.19 | S | O |
| ATOM | 5580 | OH2 | TIP | 103 | 20.430 | 65.732 | 68.478 | 1.00 | 33.39 | S | O |
| ATOM | 5581 | OH2 | TIP | 104 | 5.189 | 104.660 | 111.621 | 1.00 | 26.22 | S | O |
| ATOM | 5582 | OH2 | TIP | 105 | 37.497 | 48.010 | 84.102 | 1.00 | 26.17 | S | O |
| ATOM | 5583 | OH2 | TIP | 106 | 28.548 | 131.775 | 99.724 | 1.00 | 34.04 | S | O |
| ATOM | 5584 | OH2 | TIP | 107 | 20.485 | 100.216 | 59.368 | 1.00 | 27.32 | S | O |
| ATOM | 5585 | OH2 | TIP | 108 | 40.673 | 79.977 | 108.936 | 1.00 | 33.78 | S | O |
| ATOM | 5586 | OH2 | TIP | 109 | 15.077 | 74.745 | 84.145 | 1.00 | 29.18 | S | O |
| ATOM | 5587 | OH2 | TIP | 110 | 32.243 | 69.272 | 64.195 | 1.00 | 25.89 | S | O |
| ATOM | 5588 | OH2 | TIP | 111 | 22.002 | 66.970 | 106.333 | 1.00 | 44.15 | S | O |
| ATOM | 5589 | OH2 | TIP | 112 | 19.821 | 56.842 | 68.918 | 1.00 | 43.46 | S | O |
| ATOM | 5590 | OH2 | TIP | 113 | 1.202 | 122.726 | 97.426 | 1.00 | 24.98 | S | O |
| ATOM | 5591 | OH2 | TIP | 114 | −4.361 | 128.981 | 82.232 | 1.00 | 13.64 | S | O |
| ATOM | 5592 | OH2 | TIP | 115 | 22.440 | 120.452 | 74.476 | 1.00 | 37.68 | S | O |
| ATOM | 5593 | OH2 | TIP | 116 | 6.883 | 60.686 | 85.013 | 1.00 | 30.52 | S | O |
| ATOM | 5594 | OH2 | TIP | 117 | 12.798 | 130.102 | 93.128 | 1.00 | 41.32 | S | O |
| ATOM | 5595 | OH2 | TIP | 118 | 39.203 | 65.630 | 64.256 | 1.00 | 35.27 | S | O |
| ATOM | 5596 | OH2 | TIP | 119 | −21.318 | 82.189 | 94.772 | 1.00 | 36.85 | S | O |
| ATOM | 5597 | OH2 | TIP | 120 | 34.122 | 67.507 | 60.367 | 1.00 | 44.98 | S | O |
| ATOM | 5598 | OH2 | TIP | 121 | 29.538 | 59.352 | 98.831 | 1.00 | 27.70 | S | O |
| ATOM | 5599 | OH2 | TIP | 122 | 13.385 | 134.037 | 86.009 | 1.00 | 24.31 | S | O |
| ATOM | 5600 | OH2 | TIP | 123 | 40.397 | 60.807 | 96.501 | 1.00 | 11.63 | S | O |
| ATOM | 5601 | OH2 | TIP | 124 | 14.329 | 62.283 | 74.399 | 1.00 | 37.38 | S | O |
| ATOM | 5602 | OH2 | TIP | 125 | 6.940 | 90.271 | 83.111 | 1.00 | 62.86 | S | O |
| ATOM | 5603 | OH2 | TIP | 126 | 49.193 | 44.365 | 84.132 | 1.00 | 37.97 | S | O |
| ATOM | 5604 | OH2 | TIP | 127 | −10.492 | 125.624 | 83.884 | 1.00 | 41.94 | S | O |
| ATOM | 5605 | OH2 | TIP | 128 | −1.113 | 97.433 | 74.105 | 1.00 | 34.43 | S | O |
| ATOM | 5606 | OH2 | TIP | 129 | 6.626 | 116.156 | 78.287 | 1.00 | 32.76 | S | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5607 | OH2 | TIP | 130 | 25.088 | 101.400 | 86.723 | 1.00 | 26.15 | S | O |
| ATOM | 5608 | OH2 | TIP | 131 | 43.290 | 63.242 | 73.567 | 1.00 | 35.06 | S | O |
| ATOM | 5609 | OH2 | TIP | 132 | 3.638 | 103.059 | 107.513 | 1.00 | 70.98 | S | O |
| ATOM | 5610 | OH2 | TIP | 133 | 11.446 | 97.435 | 105.122 | 1.00 | 37.25 | S | O |
| ATOM | 5611 | OH2 | TIP | 134 | 3.495 | 101.372 | 71.864 | 1.00 | 59.36 | S | O |
| ATOM | 5612 | OH2 | TIP | 135 | 7.875 | 129.839 | 85.398 | 1.00 | 37.98 | S | O |
| ATOM | 5613 | OH2 | TIP | 136 | 39.397 | 92.011 | 101.491 | 1.00 | 33.94 | S | O |
| ATOM | 5614 | OH2 | TIP | 137 | 18.493 | 99.688 | 85.049 | 1.00 | 37.85 | S | O |
| ATOM | 5615 | OH2 | TIP | 138 | 14.714 | 68.832 | 104.507 | 1.00 | 29.31 | S | O |
| ATOM | 5616 | OH2 | TIP | 139 | 20.718 | 77.382 | 80.373 | 1.00 | 14.87 | S | O |
| ATOM | 5617 | OH2 | TIP | 140 | 6.294 | 90.083 | 78.832 | 1.00 | 16.62 | S | O |
| ATOM | 5618 | OH2 | TIP | 141 | 42.474 | 54.170 | 92.745 | 1.00 | 11.80 | S | O |
| ATOM | 5619 | OH2 | TIP | 142 | −2.148 | 115.176 | 106.930 | 1.00 | 38.53 | S | O |
| ATOM | 5620 | OH2 | TIP | 143 | −8.521 | 117.470 | 87.466 | 1.00 | 39.42 | S | O |
| ATOM | 5621 | OH2 | TIP | 144 | 1.965 | 140.041 | 85.253 | 1.00 | 46.25 | S | O |
| ATOM | 5622 | OH2 | TIP | 145 | 51.445 | 53.655 | 89.752 | 1.00 | 42.21 | S | O |
| ATOM | 5623 | OH2 | TIP | 146 | 9.314 | 102.530 | 111.836 | 1.00 | 29.92 | S | O |
| ATOM | 5624 | OH2 | TIP | 147 | 23.519 | 82.150 | 75.473 | 1.00 | 50.78 | S | O |
| ATOM | 5625 | OH2 | TIP | 148 | 11.156 | 69.577 | 78.817 | 1.00 | 31.47 | S | O |
| ATOM | 5626 | OH2 | TIP | 149 | 39.650 | 112.019 | 95.147 | 1.00 | 45.98 | S | O |
| ATOM | 5627 | OH2 | TIP | 150 | 13.771 | 59.189 | 91.812 | 1.00 | 24.38 | S | O |
| ATOM | 5628 | OH2 | TIP | 151 | 21.891 | 77.594 | 76.292 | 1.00 | 23.90 | S | O |
| ATOM | 5629 | OH2 | TIP | 152 | −5.860 | 97.854 | 80.242 | 1.00 | 30.84 | S | O |
| ATOM | 5630 | OH2 | TIP | 153 | 31.038 | 114.616 | 103.657 | 1.00 | 33.54 | S | O |
| ATOM | 5631 | OH2 | TIP | 154 | 16.925 | 121.280 | 111.509 | 1.00 | 41.36 | S | O |
| ATOM | 5632 | OH2 | TIP | 155 | 3.391 | 109.067 | 63.689 | 1.00 | 40.25 | S | O |
| ATOM | 5633 | OH2 | TIP | 156 | 19.278 | 117.745 | 68.461 | 1.00 | 37.06 | S | O |
| ATOM | 5634 | OH2 | TIP | 157 | 0.995 | 138.618 | 90.654 | 1.00 | 32.41 | S | O |
| ATOM | 5635 | OH2 | TIP | 158 | −6.927 | 123.416 | 83.995 | 1.00 | 30.57 | S | O |
| ATOM | 5636 | OH2 | TIP | 159 | 17.736 | 108.291 | 89.320 | 1.00 | 39.48 | S | O |
| ATOM | 5637 | OH2 | TIP | 160 | −5.647 | 82.386 | 87.960 | 1.00 | 21.22 | S | O |
| ATOM | 5638 | OH2 | TIP | 161 | −9.087 | 93.967 | 81.732 | 1.00 | 35.10 | S | O |
| ATOM | 5639 | OH2 | TIP | 162 | 50.126 | 53.476 | 79.227 | 1.00 | 42.49 | S | O |
| ATOM | 5640 | OH2 | TIP | 163 | 7.331 | 103.313 | 84.853 | 1.00 | 23.00 | S | O |
| ATOM | 5641 | OH2 | TIP | 164 | 20.949 | 70.781 | 63.452 | 1.00 | 26.28 | S | O |
| ATOM | 5642 | OH2 | TIP | 165 | 7.928 | 100.014 | 83.055 | 1.00 | 46.75 | S | O |
| ATOM | 5643 | OH2 | TIP | 166 | 12.641 | 73.146 | 108.626 | 1.00 | 22.35 | S | O |
| ATOM | 5644 | OH2 | TIP | 167 | 35.412 | 106.758 | 102.980 | 1.00 | 19.91 | S | O |
| ATOM | 5645 | OH2 | TIP | 168 | 47.124 | 90.158 | 80.292 | 1.00 | 35.80 | S | O |
| ATOM | 5646 | OH2 | TIP | 169 | 15.475 | 99.144 | 63.960 | 1.00 | 23.18 | S | O |
| ATOM | 5647 | OH2 | TIP | 170 | 18.901 | 94.293 | 92.040 | 1.00 | 27.41 | S | O |
| ATOM | 5648 | OH2 | TIP | 171 | 47.769 | 67.686 | 88.062 | 1.00 | 49.51 | S | O |
| ATOM | 5649 | OH2 | TIP | 172 | 26.145 | 120.673 | 91.489 | 1.00 | 31.46 | S | O |
| ATOM | 5650 | OH2 | TIP | 173 | 15.200 | 97.478 | 69.637 | 1.00 | 28.11 | S | O |
| ATOM | 5651 | OH2 | TIP | 174 | 49.244 | 67.973 | 96.940 | 1.00 | 25.47 | S | O |
| ATOM | 5652 | OH2 | TIP | 175 | 7.670 | 54.262 | 95.127 | 1.00 | 30.80 | S | O |
| ATOM | 5653 | OH2 | TIP | 176 | −15.404 | 133.724 | 90.351 | 1.00 | 32.90 | S | O |
| ATOM | 5654 | OH2 | TIP | 177 | 30.535 | 103.639 | 79.835 | 1.00 | 39.25 | S | O |
| ATOM | 5655 | OH2 | TIP | 178 | 18.592 | 68.506 | 61.157 | 1.00 | 51.48 | S | O |
| ATOM | 5656 | OH2 | TIP | 179 | 32.263 | 83.170 | 65.127 | 1.00 | 27.65 | S | O |
| ATOM | 5657 | OH2 | TIP | 180 | 21.006 | 88.983 | 78.768 | 1.00 | 38.20 | S | O |
| ATOM | 5658 | OH2 | TIP | 181 | 21.613 | 130.280 | 71.104 | 1.00 | 29.62 | S | O |
| ATOM | 5659 | OH2 | TIP | 182 | 16.989 | 70.224 | 66.062 | 1.00 | 34.66 | S | O |
| ATOM | 5660 | OH2 | TIP | 183 | 16.250 | 46.600 | 102.162 | 1.00 | 31.40 | S | O |
| ATOM | 5661 | OH2 | TIP | 184 | −12.520 | 127.320 | 93.239 | 1.00 | 24.74 | S | O |
| ATOM | 5662 | OH2 | TIP | 185 | 22.209 | 133.850 | 102.438 | 1.00 | 36.16 | S | O |
| ATOM | 5663 | OH2 | TIP | 186 | 34.060 | 51.593 | 77.332 | 1.00 | 41.78 | S | O |
| ATOM | 5664 | OH2 | TIP | 187 | 57.002 | 103.420 | 90.870 | 1.00 | 31.72 | S | O |
| ATOM | 5665 | OH2 | TIP | 188 | 31.104 | 57.133 | 69.505 | 1.00 | 26.27 | S | O |
| ATOM | 5666 | OH2 | TIP | 189 | 42.460 | 106.314 | 96.356 | 1.00 | 59.36 | S | O |
| ATOM | 5667 | OH2 | TIP | 190 | 17.403 | 105.184 | 75.238 | 1.00 | 61.69 | S | O |
| ATOM | 5668 | OH2 | TIP | 191 | 57.524 | 51.414 | 94.161 | 1.00 | 25.81 | S | O |
| ATOM | 5669 | OH2 | TIP | 192 | 44.246 | 74.719 | 101.319 | 1.00 | 42.18 | S | O |
| ATOM | 5670 | OH2 | TIP | 193 | 52.087 | 39.177 | 83.001 | 1.00 | 46.43 | S | O |
| ATOM | 5671 | OH2 | TIP | 194 | −1.903 | 130.390 | 95.926 | 1.00 | 26.70 | S | O |
| ATOM | 5672 | OH2 | TIP | 195 | 18.794 | 103.776 | 76.951 | 1.00 | 33.89 | S | O |
| ATOM | 5673 | OH2 | TIP | 196 | 0.817 | 118.362 | 105.307 | 1.00 | 17.32 | S | O |
| ATOM | 5674 | OH2 | TIP | 197 | 41.699 | 86.192 | 77.278 | 1.00 | 32.70 | S | O |
| ATOM | 5675 | OH2 | TIP | 198 | −1.577 | 102.497 | 110.054 | 1.00 | 27.44 | S | O |
| ATOM | 5676 | OH2 | TIP | 199 | 26.971 | 132.460 | 83.963 | 1.00 | 43.16 | S | O |
| ATOM | 5677 | OH2 | TIP | 200 | 20.240 | 86.360 | 95.434 | 1.00 | 49.90 | S | O |
| ATOM | 5678 | OH2 | TIP | 201 | 9.386 | 63.776 | 82.506 | 1.00 | 38.45 | S | O |
| ATOM | 5679 | OH2 | TIP | 202 | −5.616 | 110.474 | 88.632 | 1.00 | 39.13 | S | O |
| ATOM | 5680 | OH2 | TIP | 203 | 22.281 | 120.447 | 101.722 | 1.00 | 38.39 | S | O |
| ATOM | 5681 | OH2 | TIP | 204 | 55.906 | 47.833 | 85.061 | 1.00 | 38.63 | S | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5682 | OH2 | TIP | 205 | −4.219 | 117.132 | 99.965 | 1.00 | 37.16 | S | O |
| ATOM | 5683 | OH2 | TIP | 206 | 1.500 | 111.742 | 72.190 | 1.00 | 69.64 | S | O |
| ATOM | 5684 | OH2 | TIP | 207 | 6.486 | 140.249 | 98.320 | 1.00 | 29.05 | S | O |
| ATOM | 5685 | OH2 | TIP | 208 | 10.812 | 136.991 | 77.889 | 1.00 | 46.77 | S | O |
| ATOM | 5686 | OH2 | TIP | 209 | 4.761 | 134.801 | 95.240 | 1.00 | 42.80 | S | O |
| ATOM | 5687 | OH2 | TIP | 210 | 5.776 | 71.902 | 99.147 | 1.00 | 27.28 | S | O |
| ATOM | 5688 | OH2 | TIP | 211 | 17.965 | 57.068 | 73.867 | 1.00 | 47.81 | S | O |
| ATOM | 5689 | OH2 | TIP | 212 | 32.947 | 121.893 | 85.288 | 1.00 | 51.82 | S | O |
| ATOM | 5690 | OH2 | TIP | 213 | 20.028 | 132.134 | 101.611 | 1.00 | 31.84 | S | O |
| ATOM | 5691 | OH2 | TIP | 214 | 6.934 | 139.543 | 84.417 | 1.00 | 40.36 | S | O |
| ATOM | 5692 | OH2 | TIP | 215 | 30.249 | 133.725 | 85.816 | 1.00 | 38.48 | S | O |
| ATOM | 5693 | OH2 | TIP | 216 | 12.651 | 123.840 | 90.947 | 1.00 | 22.61 | S | O |
| ATOM | 5694 | OH2 | TIP | 217 | 29.398 | 86.098 | 101.372 | 1.00 | 45.88 | S | O |
| ATOM | 5695 | OH2 | TIP | 218 | 18.295 | 128.096 | 92.729 | 1.00 | 40.28 | S | O |
| ATOM | 5696 | OH2 | TIP | 219 | 21.509 | 52.543 | 88.212 | 1.00 | 31.93 | S | O |
| ATOM | 5697 | OH2 | TIP | 220 | 29.554 | 48.745 | 95.592 | 1.00 | 36.56 | S | O |
| ATOM | 5698 | OH2 | TIP | 221 | 2.091 | 114.471 | 74.818 | 1.00 | 48.68 | S | O |
| ATOM | 5699 | OH2 | TIP | 222 | 38.498 | 91.150 | 104.410 | 1.00 | 31.36 | S | O |
| ATOM | 5700 | OH2 | TIP | 223 | 32.720 | 46.532 | 95.582 | 1.00 | 27.83 | S | O |
| ATOM | 5701 | OH2 | TIP | 224 | 7.159 | 85.271 | 101.088 | 1.00 | 30.36 | S | O |
| ATOM | 5702 | OH2 | TIP | 225 | 49.651 | 62.679 | 82.167 | 1.00 | 34.64 | S | O |
| ATOM | 5703 | OH2 | TIP | 226 | 48.285 | 84.670 | 82.686 | 1.00 | 56.51 | S | O |
| ATOM | 5704 | OH2 | TIP | 227 | −18.862 | 92.994 | 90.302 | 1.00 | 34.68 | S | O |
| ATOM | 5705 | OH2 | TIP | 228 | 1.905 | 135.655 | 85.883 | 1.00 | 46.58 | S | O |
| ATOM | 5706 | OH2 | TIP | 229 | 48.318 | 82.744 | 84.515 | 1.00 | 56.63 | S | O |
| ATOM | 5707 | OH2 | TIP | 230 | 9.739 | 136.432 | 106.604 | 1.00 | 39.12 | S | O |
| ATOM | 5708 | OH2 | TIP | 231 | 12.648 | 79.439 | 103.305 | 1.00 | 52.60 | S | O |
| ATOM | 5709 | OH2 | TIP | 232 | 10.768 | 107.055 | 94.897 | 1.00 | 51.49 | S | O |
| ATOM | 5710 | OH2 | TIP | 233 | 28.527 | 112.470 | 79.066 | 1.00 | 31.88 | S | O |
| ATOM | 5711 | OH2 | TIP | 234 | 2.679 | 126.350 | 100.967 | 1.00 | 18.07 | S | O |
| ATOM | 5712 | OH2 | TIP | 235 | 20.522 | 103.319 | 61.810 | 1.00 | 41.17 | S | O |
| ATOM | 5713 | OH2 | TIP | 236 | −12.540 | 100.845 | 87.248 | 1.00 | 40.05 | S | O |
| ATOM | 5714 | OH2 | TIP | 237 | −3.133 | 116.871 | 110.413 | 1.00 | 28.99 | S | O |
| ATOM | 5715 | OH2 | TIP | 238 | −2.128 | 97.225 | 78.268 | 1.00 | 41.45 | S | O |
| ATOM | 5716 | OH2 | TIP | 239 | 45.424 | 90.620 | 101.521 | 1.00 | 38.02 | S | O |
| ATOM | 5717 | OH2 | TIP | 240 | 36.362 | 80.091 | 69.550 | 1.00 | 41.55 | S | O |
| ATOM | 5718 | OH2 | TIP | 241 | 49.524 | 53.309 | 92.117 | 1.00 | 43.04 | S | O |
| ATOM | 5719 | OH2 | TIP | 242 | 23.505 | 114.188 | 68.143 | 1.00 | 44.45 | S | O |
| ATOM | 5720 | OH2 | TIP | 243 | 19.387 | 58.050 | 77.819 | 1.00 | 25.71 | S | O |
| ATOM | 5721 | OH2 | TIP | 244 | 15.229 | 53.305 | 91.943 | 1.00 | 41.08 | S | O |
| ATOM | 5722 | OH2 | TIP | 245 | 1.128 | 119.125 | 69.204 | 1.00 | 38.57 | S | O |
| ATOM | 5723 | OH2 | TIP | 246 | 26.228 | 78.389 | 108.064 | 1.00 | 30.19 | S | O |
| ATOM | 5724 | OH2 | TIP | 247 | −0.152 | 115.653 | 98.488 | 1.00 | 40.88 | S | O |
| ATOM | 5725 | OH2 | TIP | 248 | 22.718 | 131.704 | 85.123 | 1.00 | 39.13 | S | O |
| ATOM | 5726 | OH2 | TIP | 249 | 0.977 | 71.121 | 99.636 | 1.00 | 53.25 | S | O |
| ATOM | 5727 | OH2 | TIP | 250 | 43.294 | 42.394 | 89.593 | 1.00 | 35.06 | S | O |
| ATOM | 5728 | OH2 | TIP | 251 | 36.837 | 88.073 | 106.367 | 1.00 | 61.49 | S | O |
| ATOM | 5729 | OH2 | TIP | 252 | 45.545 | 58.920 | 80.160 | 1.00 | 34.86 | S | O |
| ATOM | 5730 | OH2 | TIP | 253 | 18.572 | 121.349 | 105.076 | 1.00 | 88.40 | S | O |
| ATOM | 5731 | OH2 | TIP | 254 | 49.862 | 65.494 | 93.542 | 1.00 | 36.42 | S | O |
| ATOM | 5732 | OH2 | TIP | 255 | 3.228 | 72.336 | 100.783 | 1.00 | 25.67 | S | O |
| ATOM | 5733 | OH2 | TIP | 256 | 45.472 | 55.276 | 82.859 | 1.00 | 27.91 | S | O |
| ATOM | 5734 | OH2 | TIP | 257 | 36.832 | 82.448 | 63.323 | 1.00 | 37.26 | S | O |
| ATOM | 5735 | OH2 | TIP | 258 | −0.443 | 76.793 | 88.968 | 1.00 | 43.02 | S | O |
| ATOM | 5736 | OH2 | TIP | 259 | 4.176 | 106.750 | 109.320 | 1.00 | 35.06 | S | O |
| ATOM | 5737 | OH2 | TIP | 260 | 30.733 | 67.359 | 110.337 | 1.00 | 31.19 | S | O |
| ATOM | 5738 | OH2 | TIP | 261 | 10.503 | 105.193 | 112.435 | 1.00 | 33.96 | S | O |
| ATOM | 5739 | OH2 | TIP | 262 | 26.050 | 106.942 | 83.528 | 1.00 | 31.92 | S | O |
| ATOM | 5740 | OH2 | TIP | 263 | −5.727 | 137.015 | 94.218 | 1.00 | 62.53 | S | O |
| ATOM | 5741 | OH2 | TIP | 264 | 50.426 | 63.418 | 94.717 | 1.00 | 36.63 | S | O |
| ATOM | 5742 | OH2 | TIP | 265 | −14.909 | 135.616 | 88.320 | 1.00 | 77.78 | S | O |
| ATOM | 5743 | OH2 | TIP | 266 | 37.862 | 48.517 | 87.981 | 1.00 | 34.98 | S | O |
| ATOM | 5744 | OH2 | TIP | 267 | 45.717 | 82.856 | 74.286 | 1.00 | 38.84 | S | O |
| ATOM | 5745 | OH2 | TIP | 268 | 37.349 | 49.689 | 78.157 | 1.00 | 51.60 | S | O |
| ATOM | 5746 | OH2 | TIP | 269 | 2.893 | 138.822 | 76.974 | 1.00 | 37.65 | S | O |
| ATOM | 5747 | OH2 | TIP | 270 | 23.807 | 88.816 | 85.629 | 1.00 | 31.45 | S | O |
| ATOM | 5748 | OH2 | TIP | 271 | 59.824 | 100.962 | 97.341 | 1.00 | 25.89 | S | O |
| ATOM | 5749 | OH2 | TIP | 272 | −8.343 | 139.810 | 94.131 | 1.00 | 30.31 | S | O |
| ATOM | 5750 | OH2 | TIP | 273 | 19.818 | 68.876 | 67.875 | 1.00 | 33.63 | S | O |
| ATOM | 5751 | OH2 | TIP | 274 | 3.744 | 125.780 | 92.748 | 1.00 | 49.89 | S | O |
| ATOM | 5752 | OH2 | TIP | 275 | 1.301 | 112.892 | 68.017 | 1.00 | 28.31 | S | O |
| ATOM | 5753 | OH2 | TIP | 276 | −9.764 | 100.654 | 84.713 | 1.00 | 35.44 | S | O |
| ATOM | 5754 | OH2 | TIP | 277 | 52.419 | 75.492 | 96.377 | 1.00 | 37.16 | S | O |
| ATOM | 5755 | OH2 | TIP | 278 | 46.322 | 67.055 | 78.101 | 1.00 | 49.48 | S | O |
| ATOM | 5756 | OH2 | TIP | 279 | 15.827 | 98.296 | 101.509 | 1.00 | 44.28 | S | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5757 | OH2 | TIP | 280 | 19.661 | 70.297 | 73.317 | 1.00 | 38.53 | S | O |
| ATOM | 5758 | OH2 | TIP | 281 | 9.404 | 121.945 | 100.319 | 1.00 | 32.52 | S | O |
| ATOM | 5759 | OH2 | TIP | 282 | 18.159 | 91.560 | 80.307 | 1.00 | 19.68 | S | O |
| ATOM | 5760 | OH2 | TIP | 283 | 4.569 | 111.545 | 72.682 | 1.00 | 42.50 | S | O |
| ATOM | 5761 | OH2 | TIP | 284 | 14.597 | 63.038 | 69.922 | 1.00 | 40.45 | S | O |
| ATOM | 5762 | OH2 | TIP | 285 | −13.961 | 94.174 | 101.055 | 1.00 | 34.94 | S | O |
| ATOM | 5763 | OH2 | TIP | 286 | −5.487 | 104.979 | 110.804 | 1.00 | 35.26 | S | O |
| ATOM | 5764 | OH2 | TIP | 287 | 2.737 | 97.635 | 108.052 | 1.00 | 33.16 | S | O |
| ATOM | 5765 | OH2 | TIP | 288 | −11.433 | 132.305 | 86.282 | 1.00 | 58.09 | S | O |
| ATOM | 5766 | OH2 | TIP | 289 | −12.697 | 91.810 | 85.991 | 1.00 | 51.64 | S | O |
| ATOM | 5767 | OH2 | TIP | 290 | 55.201 | 74.370 | 96.472 | 1.00 | 58.25 | S | O |
| ATOM | 5768 | OH2 | TIP | 291 | −4.467 | 73.484 | 96.164 | 1.00 | 58.87 | S | O |
| ATOM | 5769 | OH2 | TIP | 292 | −4.483 | 119.058 | 102.769 | 1.00 | 38.57 | S | O |
| ATOM | 5770 | OH2 | TIP | 293 | 23.558 | 47.336 | 93.946 | 1.00 | 43.44 | S | O |
| ATOM | 5771 | OH2 | TIP | 294 | 31.510 | 98.840 | 104.945 | 1.00 | 54.84 | S | O |
| ATOM | 5772 | OH2 | TIP | 295 | 34.260 | 132.703 | 88.750 | 1.00 | 31.45 | S | O |
| ATOM | 5773 | OH2 | TIP | 296 | 21.096 | 130.519 | 93.490 | 1.00 | 33.64 | S | O |
| ATOM | 5774 | OH2 | TIP | 297 | 21.211 | 76.051 | 67.898 | 1.00 | 35.31 | S | O |
| ATOM | 5775 | OH2 | TIP | 298 | −3.012 | 112.373 | 92.805 | 1.00 | 32.59 | S | O |
| ATOM | 5776 | OH2 | TIP | 299 | 23.071 | 131.953 | 94.354 | 1.00 | 38.39 | S | O |
| ATOM | 5777 | OH2 | TIP | 300 | −0.430 | 96.926 | 105.362 | 1.00 | 42.41 | S | O |
| ATOM | 5778 | OH2 | TIP | 301 | 17.544 | 75.910 | 69.621 | 1.00 | 28.68 | S | O |
| ATOM | 5779 | OH2 | TIP | 302 | 24.813 | 109.173 | 75.768 | 1.00 | 37.55 | S | O |
| ATOM | 5780 | OH2 | TIP | 303 | 6.283 | 113.420 | 73.594 | 1.00 | 45.97 | S | O |
| ATOM | 5781 | OH2 | TIP | 304 | 19.733 | 106.364 | 76.662 | 1.00 | 48.24 | S | O |
| ATOM | 5782 | OH2 | TIP | 305 | 53.823 | 67.763 | 87.755 | 1.00 | 44.19 | S | O |
| ATOM | 5783 | OH2 | TIP | 306 | 42.599 | 49.370 | 94.201 | 1.00 | 44.96 | S | O |
| ATOM | 5784 | OH2 | TIP | 307 | 36.094 | 55.801 | 106.625 | 1.00 | 29.87 | S | O |
| ATOM | 5785 | OH2 | TIP | 308 | 19.452 | 93.449 | 95.713 | 1.00 | 29.73 | S | O |
| ATOM | 5786 | OH2 | TIP | 309 | 40.536 | 45.937 | 93.402 | 1.00 | 45.30 | S | O |
| ATOM | 5787 | OH2 | TIP | 310 | 34.533 | 92.513 | 107.446 | 1.00 | 42.42 | S | O |
| ATOM | 5788 | OH2 | TIP | 311 | 45.415 | 78.582 | 110.954 | 1.00 | 40.65 | S | O |
| ATOM | 5789 | OH2 | TIP | 312 | 30.562 | 93.938 | 103.825 | 1.00 | 43.48 | S | O |
| ATOM | 5790 | OH2 | TIP | 313 | 24.881 | 118.778 | 99.720 | 1.00 | 40.09 | S | O |
| ATOM | 5791 | OH2 | TIP | 314 | 12.549 | 63.959 | 101.525 | 1.00 | 66.25 | S | O |
| ATOM | 5792 | OH2 | TIP | 315 | 2.233 | 61.989 | 93.273 | 1.00 | 27.29 | S | O |
| ATOM | 5793 | OH2 | TIP | 316 | 28.221 | 114.802 | 76.373 | 1.00 | 46.45 | S | O |
| ATOM | 5794 | OH2 | TIP | 317 | 19.771 | 115.046 | 67.872 | 1.00 | 35.88 | S | O |
| ATOM | 5795 | OH2 | TIP | 318 | 27.593 | 117.801 | 80.377 | 1.00 | 45.21 | S | O |
| ATOM | 5796 | OH2 | TIP | 319 | 14.571 | 131.770 | 89.347 | 1.00 | 49.06 | S | O |
| ATOM | 5797 | OH2 | TIP | 320 | 57.503 | 45.191 | 86.464 | 1.00 | 46.59 | S | O |
| ATOM | 5798 | OH2 | TIP | 321 | 38.367 | 97.325 | 82.834 | 1.00 | 38.48 | S | O |
| ATOM | 5799 | OH2 | TIP | 322 | 40.065 | 86.711 | 104.841 | 1.00 | 43.33 | S | O |
| ATOM | 5800 | OH2 | TIP | 323 | 1.121 | 93.359 | 106.084 | 1.00 | 40.45 | S | O |
| ATOM | 5801 | OH2 | TIP | 324 | 56.166 | 97.830 | 100.532 | 1.00 | 36.80 | S | O |
| ATOM | 5802 | OH2 | TIP | 325 | 26.751 | 49.033 | 74.004 | 1.00 | 37.09 | S | O |
| ATOM | 5803 | OH2 | TIP | 326 | 20.057 | 110.302 | 88.627 | 1.00 | 43.74 | S | O |
| ATOM | 5804 | OH2 | TIP | 327 | 27.611 | 60.414 | 65.999 | 1.00 | 37.95 | S | O |
| ATOM | 5805 | OH2 | TIP | 328 | 29.381 | 98.811 | 107.329 | 1.00 | 40.90 | S | O |
| ATOM | 5806 | OH2 | TIP | 329 | 39.047 | 82.543 | 69.250 | 1.00 | 35.37 | S | O |
| ATOM | 5807 | OH2 | TIP | 330 | −5.421 | 142.869 | 79.829 | 1.00 | 28.74 | S | O |
| ATOM | 5808 | OH2 | TIP | 331 | 8.705 | 135.925 | 74.014 | 1.00 | 30.66 | S | O |
| ATOM | 5809 | OH2 | TIP | 332 | −1.388 | 130.211 | 92.499 | 1.00 | 30.02 | S | O |
| ATOM | 5810 | OH2 | TIP | 333 | 4.980 | 117.479 | 111.161 | 1.00 | 31.68 | S | O |
| ATOM | 5811 | OH2 | TIP | 334 | 4.119 | 59.553 | 91.639 | 1.00 | 35.25 | S | O |
| ATOM | 5812 | OH2 | TIP | 335 | 41.983 | 101.902 | 98.172 | 1.00 | 26.16 | S | O |
| ATOM | 5813 | OH2 | TIP | 336 | 5.654 | 135.953 | 86.008 | 1.00 | 29.65 | S | O |
| ATOM | 5814 | OH2 | TIP | 337 | 42.974 | 95.415 | 84.128 | 1.00 | 25.96 | S | O |
| ATOM | 5815 | OH2 | TIP | 338 | −9.960 | 104.266 | 85.461 | 1.00 | 34.54 | S | O |
| ATOM | 5816 | OH2 | TIP | 339 | 0.445 | 112.538 | 75.000 | 1.00 | 19.89 | S | O |
| ATOM | 5817 | OH2 | TIP | 340 | 48.930 | 83.242 | 92.801 | 1.00 | 39.28 | S | O |
| ATOM | 5818 | OH2 | TIP | 341 | −9.256 | 86.186 | 90.252 | 1.00 | 31.11 | S | O |
| ATOM | 5819 | OH2 | TIP | 342 | 0.872 | 82.024 | 100.610 | 1.00 | 48.25 | S | O |
| ATOM | 5820 | OH2 | TIP | 343 | 13.452 | 93.009 | 100.653 | 1.00 | 34.69 | S | O |
| ATOM | 5821 | OH2 | TIP | 344 | −7.347 | 112.124 | 80.603 | 1.00 | 30.30 | S | O |
| ATOM | 5822 | OH2 | TIP | 345 | 20.904 | 130.018 | 76.592 | 1.00 | 21.44 | S | O |
| ATOM | 5823 | OH2 | TIP | 346 | −7.019 | 121.374 | 101.984 | 1.00 | 53.07 | S | O |
| ATOM | 5824 | OH2 | TIP | 347 | 8.736 | 91.595 | 101.156 | 1.00 | 41.62 | S | O |
| ATOM | 5825 | OH2 | TIP | 348 | 51.203 | 62.213 | 90.296 | 1.00 | 43.99 | S | O |
| ATOM | 5826 | OH2 | TIP | 349 | 40.456 | 46.770 | 76.175 | 1.00 | 63.64 | S | O |
| ATOM | 5827 | OH2 | TIP | 350 | 53.411 | 83.328 | 98.211 | 1.00 | 44.44 | S | O |
| ATOM | 5828 | OH2 | TIP | 351 | 51.254 | 60.054 | 93.683 | 1.00 | 32.60 | S | O |
| ATOM | 5829 | OH2 | TIP | 352 | 29.513 | 93.601 | 99.923 | 1.00 | 44.46 | S | O |
| ATOM | 5830 | OH2 | TIP | 353 | 21.902 | 125.455 | 66.342 | 1.00 | 53.61 | S | O |
| ATOM | 5831 | OH2 | TIP | 354 | −10.119 | 128.281 | 93.773 | 1.00 | 55.82 | S | O |

TABLE 4-continued

Eg5 ligand binding site/compound 1 X-ray coordinates. Complete coordinates of the entire motor domain of Eg5. Table 4 discloses residues 16-270, 281-365, 16-270 and 281-365 of SEQ ID NO: 1, respectively, in order of appearance.

| | | | | | | | | | | | |
|---|---|---|---|---|---|---|---|---|---|---|---|
| ATOM | 5832 | OH2 | TIP | 355 | 51.887 | 94.144 | 101.702 | 1.00 | 44.26 | S | O |
| ATOM | 5833 | OH2 | TIP | 356 | 4.798 | 131.273 | 109.905 | 1.00 | 32.80 | S | O |
| ATOM | 5834 | OH2 | TIP | 357 | 50.783 | 48.949 | 94.610 | 1.00 | 24.54 | S | O |
| ATOM | 5835 | OH2 | TIP | 358 | 30.963 | 127.045 | 82.358 | 1.00 | 22.12 | S | O |
| ATOM | 5836 | OH2 | TIP | 359 | 28.149 | 60.606 | 106.368 | 1.00 | 44.38 | S | O |
| ATOM | 5837 | OH2 | TIP | 360 | 3.996 | 136.867 | 104.297 | 1.00 | 46.84 | S | O |
| ATOM | 5838 | OH2 | TIP | 361 | −3.461 | 107.627 | 71.713 | 1.00 | 41.58 | S | O |
| ATOM | 5839 | OH2 | TIP | 362 | 51.927 | 55.289 | 93.165 | 1.00 | 34.37 | S | O |
| ATOM | 5840 | OH2 | TIP | 363 | 11.662 | 114.001 | 61.828 | 1.00 | 46.84 | S | O |
| ATOM | 5841 | OH2 | TIP | 364 | 20.034 | 134.881 | 92.136 | 1.00 | 43.39 | S | O |
| ATOM | 5842 | OH2 | TIP | 365 | 8.625 | 118.688 | 65.788 | 1.00 | 68.06 | S | O |
| ATOM | 5843 | OH2 | TIP | 366 | 26.652 | 56.024 | 67.883 | 1.00 | 35.76 | S | O |
| ATOM | 5844 | OH2 | TIP | 367 | 7.449 | 137.012 | 95.122 | 1.00 | 34.24 | S | O |
| ATOM | 5845 | OH2 | TIP | 368 | 17.818 | 49.539 | 101.911 | 1.00 | 23.94 | S | O |
| ATOM | 5846 | OH2 | TIP | 369 | 20.960 | 130.888 | 89.807 | 1.00 | 37.77 | S | O |
| ATOM | 5847 | OH2 | TIP | 370 | 22.532 | 66.087 | 115.734 | 1.00 | 31.96 | S | O |
| ATOM | 5848 | OH2 | TIP | 371 | 46.285 | 54.299 | 93.532 | 1.00 | 42.79 | S | O |
| ATOM | 5849 | OH2 | TIP | 372 | 27.611 | 63.238 | 64.798 | 1.00 | 53.87 | S | O |
| ATOM | 5850 | OH2 | TIP | 373 | −21.930 | 85.697 | 87.889 | 1.00 | 44.63 | S | O |
| ATOM | 5851 | OH2 | TIP | 374 | 6.611 | 126.845 | 93.403 | 1.00 | 43.76 | S | O |
| ATOM | 5852 | OH2 | TIP | 375 | 20.018 | 49.231 | 72.385 | 1.00 | 44.58 | S | O |
| ATOM | 5853 | OH2 | TIP | 376 | 32.888 | 103.089 | 86.983 | 1.00 | 89.08 | S | O |
| ATOM | 5854 | OH2 | TIP | 377 | 16.544 | 83.681 | 75.807 | 1.00 | 38.12 | S | O |
| ATOM | 5855 | OH2 | TIP | 378 | 25.390 | 104.149 | 110.093 | 1.00 | 43.02 | S | O |
| ATOM | 5856 | OH2 | TIP | 379 | 6.595 | 136.610 | 81.397 | 1.00 | 26.37 | S | O |
| ATOM | 5857 | OH2 | TIP | 380 | 54.563 | 87.457 | 87.663 | 1.00 | 57.73 | S | O |
| ATOM | 5858 | OH2 | TIP | 381 | 16.909 | 79.616 | 77.107 | 1.00 | 39.63 | S | O |
| ATOM | 5859 | OH2 | TIP | 382 | 14.580 | 99.107 | 108.256 | 1.00 | 28.38 | S | O |
| ATOM | 5860 | OH2 | TIP | 383 | −11.878 | 113.136 | 92.437 | 1.00 | 42.07 | S | O |
| ATOM | 5861 | OH2 | TIP | 384 | 1.175 | 106.349 | 112.241 | 1.00 | 55.22 | S | O |
| ATOM | 5862 | OH2 | TIP | 385 | −17.189 | 138.348 | 86.736 | 1.00 | 49.96 | S | O |
| ATOM | 5863 | OH2 | TIP | 386 | 26.821 | 112.950 | 103.186 | 1.00 | 39.63 | S | O |
| ATOM | 5864 | OH2 | TIP | 387 | 13.325 | 109.205 | 96.279 | 1.00 | 38.56 | S | O |
| ATOM | 5865 | OH2 | TIP | 388 | 45.781 | 38.572 | 86.710 | 1.00 | 37.13 | S | O |
| ATOM | 5866 | OH2 | TIP | 389 | 6.138 | 124.848 | 111.718 | 1.00 | 41.73 | S | O |
| ATOM | 5867 | OH2 | TIP | 390 | 25.714 | 48.031 | 81.474 | 1.00 | 46.93 | S | O |
| ATOM | 5868 | OH2 | TIP | 391 | 30.229 | 104.292 | 99.777 | 1.00 | 25.10 | S | O |
| ATOM | 5869 | OH2 | TIP | 392 | 21.240 | 64.832 | 108.231 | 1.00 | 41.16 | S | O |
| ATOM | 5870 | OH2 | TIP | 393 | 19.047 | 88.063 | 90.101 | 1.00 | 40.04 | S | O |
| ATOM | 5871 | OH2 | TIP | 394 | −10.386 | 126.744 | 95.848 | 1.00 | 35.65 | S | O |
| ATOM | 5872 | OH2 | TIP | 395 | 24.125 | 87.089 | 104.767 | 1.00 | 44.40 | S | O |
| ATOM | 5873 | OH2 | TIP | 396 | −9.972 | 113.933 | 97.127 | 1.00 | 21.56 | S | O |
| ATOM | 5874 | OH2 | TIP | 397 | 20.992 | 80.440 | 86.380 | 1.00 | 27.03 | S | O |
| ATOM | 5875 | OH2 | TIP | 398 | 17.132 | 73.728 | 78.362 | 1.00 | 22.99 | S | O |
| ATOM | 5876 | OH2 | TIP | 399 | 40.506 | 88.217 | 78.612 | 1.00 | 29.97 | S | O |
| ATOM | 5877 | OH2 | TIP | 400 | 19.832 | 109.946 | 61.763 | 1.00 | 31.99 | S | O |
| ATOM | 5878 | OH2 | TIP | 401 | −15.475 | 96.740 | 98.578 | 1.00 | 37.30 | S | O |
| ATOM | 5879 | OH2 | TIP | 402 | −11.241 | 123.692 | 85.356 | 1.00 | 48.33 | S | O |
| ATOM | 5880 | OH2 | TIP | 403 | 2.745 | 87.641 | 82.864 | 1.00 | 45.50 | S | O |
| ATOM | 5881 | OH2 | TIP | 404 | 21.142 | 100.149 | 111.460 | 1.00 | 40.96 | S | O |
| ATOM | 5882 | OH2 | TIP | 405 | 13.667 | 126.808 | 66.888 | 1.00 | 36.96 | S | O |
| ATOM | 5883 | OH2 | TIP | 406 | 23.180 | 108.651 | 84.435 | 1.00 | 42.00 | S | O |
| ATOM | 5884 | OH2 | TIP | 407 | 23.032 | 62.207 | 68.547 | 1.00 | 25.26 | S | O |
| ATOM | 5885 | OH2 | TIP | 408 | −16.777 | 111.092 | 92.202 | 1.00 | 40.25 | S | O |
| ATOM | 5886 | OH2 | TIP | 409 | 11.842 | 101.374 | 100.083 | 1.00 | 44.74 | S | O |
| ATOM | 5887 | OH2 | TIP | 410 | 29.590 | 109.714 | 76.751 | 1.00 | 31.48 | S | O |
| ATOM | 5888 | OH2 | TIP | 411 | 36.320 | 86.142 | 108.034 | 1.00 | 36.38 | S | O |
| ATOM | 5889 | OH2 | TIP | 412 | 20.217 | 124.611 | 110.828 | 1.00 | 72.85 | S | O |
| ATOM | 5890 | OH2 | TIP | 413 | 22.124 | 102.789 | 75.865 | 1.00 | 38.10 | S | O |
| ATOM | 5891 | OH2 | TIP | 414 | 49.245 | 56.531 | 96.399 | 1.00 | 48.41 | S | O |
| ATOM | 5892 | OH2 | TIP | 415 | 0.080 | 134.595 | 92.067 | 1.00 | 38.72 | S | O |
| ATOM | 5893 | OH2 | TIP | 416 | 49.475 | 93.483 | 100.252 | 1.00 | 40.82 | S | O |
| ATOM | 5894 | OH2 | TIP | 417 | 31.599 | 62.479 | 96.043 | 1.00 | 60.27 | S | O |
| ATOM | 5895 | OH2 | TIP | 418 | −13.179 | 123.988 | 88.268 | 1.00 | 38.76 | S | O |
| END | | | | | | | | | | | |

Table 5. Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

TABLE 5

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | |
|---|---|---|---|---|---|---|---|---|---|---|
| ATOM | 1 | MG | MG | A3001 | 18.025 | 15.455 | 34.795 | 1.00 | 58.63 | COFAMG |
| TER | 2 | | MG | A3001 | | | | | | |
| ATOM | 3 | N1 | ADP | A4001 | 8.772 | 9.801 | 26.422 | 1.00 | 35.28 | COFA N |
| ATOM | 4 | C2 | ADP | A4001 | 9.963 | 9.533 | 25.779 | 1.00 | 36.55 | COFA C |
| ATOM | 5 | N3 | ADP | A4001 | 11.205 | 9.450 | 26.355 | 1.00 | 35.70 | COFA N |
| ATOM | 6 | C1* | ADP | A4001 | 13.652 | 9.405 | 28.369 | 1.00 | 35.41 | COFA C |
| ATOM | 7 | C4 | ADP | A4001 | 11.164 | 9.690 | 27.720 | 1.00 | 32.74 | COFA C |
| ATOM | 8 | C5 | ADP | A4001 | 10.012 | 9.969 | 28.491 | 1.00 | 32.95 | COFA C |
| ATOM | 9 | C6 | ADP | A4001 | 8.777 | 10.027 | 27.783 | 1.00 | 34.10 | COFA C |
| ATOM | 10 | N6 | ADP | A4001 | 7.628 | 10.282 | 28.401 | 1.00 | 31.01 | COFA N |
| ATOM | 11 | N7 | ADP | A4001 | 10.322 | 10.142 | 29.801 | 1.00 | 34.31 | COFA N |
| ATOM | 12 | C8 | ADP | A4001 | 11.600 | 9.955 | 29.832 | 1.00 | 34.86 | COFA C |
| ATOM | 13 | N9 | ADP | A4001 | 12.213 | 9.662 | 28.615 | 1.00 | 34.69 | COFA N |
| ATOM | 14 | C2* | ADP | A4001 | 14.203 | 10.678 | 27.681 | 1.00 | 37.68 | COFA C |
| ATOM | 15 | O2* | ADP | A4001 | 14.081 | 10.755 | 26.289 | 1.00 | 38.72 | COFA O |
| ATOM | 16 | C3* | ADP | A4001 | 15.597 | 10.733 | 28.190 | 1.00 | 39.03 | COFA C |
| ATOM | 17 | O3* | ADP | A4001 | 16.440 | 9.795 | 27.497 | 1.00 | 36.14 | COFA O |
| ATOM | 18 | O1A | ADP | A4001 | 17.221 | 14.201 | 31.959 | 1.00 | 50.75 | COFA O |
| ATOM | 19 | O1B | ADP | A4001 | 15.700 | 12.029 | 35.584 | 1.00 | 48.30 | COFA O |
| ATOM | 20 | C4* | ADP | A4001 | 15.503 | 10.260 | 29.642 | 1.00 | 38.39 | COFA C |
| ATOM | 21 | O4* | ADP | A4001 | 14.359 | 9.433 | 29.669 | 1.00 | 37.03 | COFA O |
| ATOM | 22 | O2A | ADP | A4001 | 18.059 | 11.955 | 30.951 | 1.00 | 50.92 | COFA O |
| ATOM | 23 | O2B | ADP | A4001 | 14.305 | 12.418 | 33.581 | 1.00 | 49.70 | COFA O |
| ATOM | 24 | C5* | ADP | A4001 | 14.882 | 11.376 | 30.675 | 1.00 | 38.79 | COFA C |
| ATOM | 25 | O5* | ADP | A4001 | 15.520 | 12.547 | 31.032 | 1.00 | 36.50 | COFA O |
| ATOM | 26 | O3A | ADP | A4001 | 16.759 | 12.094 | 33.321 | 1.00 | 49.32 | COFA O |
| ATOM | 27 | O3B | ADP | A4001 | 15.913 | 14.263 | 34.459 | 1.00 | 47.17 | COFA O |
| ATOM | 28 | PA | ADP | A4001 | 16.885 | 12.722 | 31.809 | 1.00 | 54.35 | COFA P |
| ATOM | 29 | PB | ADP | A4001 | 15.659 | 12.676 | 34.305 | 1.00 | 43.94 | COFA P |
| TER | 30 | | ADP | A4001 | | | | | | |
| ATOM | 31 | C1 | LIG | A1001 | 17.364 | 24.527 | 29.621 | 1.00 | 48.97 | LIGA C |
| ATOM | 32 | C2 | LIG | A1001 | 16.889 | 24.218 | 28.279 | 1.00 | 48.55 | LIGA C |
| ATOM | 33 | C3 | LIG | A1001 | 16.473 | 24.591 | 30.750 | 1.00 | 50.33 | LIGA C |
| ATOM | 34 | C4 | LIG | A1001 | 16.969 | 24.885 | 32.052 | 1.00 | 50.68 | LIGA C |
| ATOM | 35 | C5 | LIG | A1001 | 18.360 | 25.127 | 32.252 | 1.00 | 51.58 | LIGA C |
| ATOM | 36 | C6 | LIG | A1001 | 19.255 | 25.076 | 31.148 | 1.00 | 50.97 | LIGA C |
| ATOM | 37 | C7 | LIG | A1001 | 18.761 | 24.773 | 29.839 | 1.00 | 50.69 | LIGA C |
| ATOM | 38 | N8 | LIG | A1001 | 17.709 | 23.977 | 27.208 | 1.00 | 48.34 | LIGA N |
| ATOM | 39 | C9 | LIG | A1001 | 16.904 | 23.719 | 26.138 | 1.00 | 46.52 | LIGA C |
| ATOM | 40 | C10 | LIG | A1001 | 17.381 | 23.394 | 24.738 | 1.00 | 46.69 | LIGA C |
| ATOM | 41 | N11 | LIG | A1001 | 17.957 | 21.994 | 24.694 | 1.00 | 46.52 | LIGA N |
| ATOM | 42 | C12 | LIG | A1001 | 17.388 | 21.017 | 23.887 | 1.00 | 47.03 | LIGA C |
| ATOM | 43 | O13 | LIG | A1001 | 17.922 | 19.912 | 23.753 | 1.00 | 46.63 | LIGA O |
| ATOM | 44 | C14 | LIG | A1001 | 16.169 | 21.172 | 23.163 | 1.00 | 48.57 | LIGA C |
| ATOM | 45 | C15 | LIG | A1001 | 19.237 | 21.687 | 25.434 | 1.00 | 44.80 | LIGA C |
| ATOM | 46 | C16 | LIG | A1001 | 19.074 | 21.022 | 26.829 | 1.00 | 44.30 | LIGA C |
| ATOM | 47 | C17 | LIG | A1001 | 18.812 | 19.503 | 26.847 | 1.00 | 46.82 | LIGA C |
| ATOM | 48 | N18 | LIG | A1001 | 18.059 | 19.103 | 28.056 | 1.00 | 46.84 | LIGA N |
| ATOM | 49 | C19 | LIG | A1001 | 18.378 | 24.494 | 24.266 | 1.00 | 46.80 | LIGA C |
| ATOM | 50 | C20 | LIG | A1001 | 17.771 | 25.916 | 24.262 | 1.00 | 47.54 | LIGA C |
| ATOM | 51 | C21 | LIG | A1001 | 18.916 | 24.249 | 22.844 | 1.00 | 47.74 | LIGA C |
| ATOM | 52 | N22 | LIG | A1001 | 15.619 | 23.817 | 26.561 | 1.00 | 47.65 | LIGA N |
| ATOM | 53 | C23 | LIG | A1001 | 14.385 | 23.635 | 25.755 | 1.00 | 48.29 | LIGA C |
| ATOM | 54 | C24 | LIG | A1001 | 14.048 | 24.870 | 24.908 | 1.00 | 47.10 | LIGA C |
| ATOM | 55 | C25 | LIG | A1001 | 15.641 | 24.117 | 27.884 | 1.00 | 47.59 | LIGA C |
| ATOM | 56 | C26 | LIG | A1001 | 13.849 | 24.725 | 23.506 | 1.00 | 46.06 | LIGA C |
| ATOM | 57 | C27 | LIG | A1001 | 13.521 | 25.856 | 22.710 | 1.00 | 46.57 | LIGA C |
| ATOM | 58 | C28 | LIG | A1001 | 13.388 | 27.146 | 23.319 | 1.00 | 46.61 | LIGA C |
| ATOM | 59 | C29 | LIG | A1001 | 13.589 | 27.292 | 24.723 | 1.00 | 47.26 | LIGA C |
| ATOM | 60 | C30 | LIG | A1001 | 13.915 | 26.160 | 25.510 | 1.00 | 45.90 | LIGA C |
| ATOM | 61 | C31 | LIG | A1001 | 16.132 | 21.719 | 21.824 | 1.00 | 49.21 | LIGA C |
| ATOM | 62 | C32 | LIG | A1001 | 14.883 | 21.848 | 21.133 | 1.00 | 49.32 | LIGA C |
| ATOM | 63 | C33 | LIG | A1001 | 13.656 | 21.431 | 21.768 | 1.00 | 49.37 | LIGA C |
| ATOM | 64 | C34 | LIG | A1001 | 12.338 | 21.567 | 21.041 | 1.00 | 48.83 | LIGA C |
| ATOM | 65 | C35 | LIG | A1001 | 13.687 | 20.892 | 23.088 | 1.00 | 48.92 | LIGA C |
| ATOM | 66 | C36 | LIG | A1001 | 14.930 | 20.761 | 23.780 | 1.00 | 48.76 | LIGA C |
| TER | 67 | | LIG | A1001 | | | | | | |
| ATOM | 68 | N | GLN | A 78 | 3.935 | 15.358 | 25.259 | 1.00 | 30.53 | MOLA N |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 69 | CA | GLN | A | 78 | 4.287 | 16.634 | 25.890 | 1.00 | 28.43 | MOLA C |
| ATOM | 70 | C | GLN | A | 78 | 3.146 | 17.658 | 25.849 | 1.00 | 28.91 | MOLA C |
| ATOM | 71 | O | GLN | A | 78 | 2.826 | 18.287 | 26.866 | 1.00 | 29.77 | MOLA O |
| ATOM | 72 | CB | GLN | A | 78 | 5.502 | 17.252 | 25.197 | 1.00 | 26.32 | MOLA C |
| ATOM | 73 | CG | GLN | A | 78 | 6.744 | 16.369 | 25.139 | 1.00 | 22.54 | MOLA C |
| ATOM | 74 | CD | GLN | A | 78 | 7.467 | 16.315 | 26.457 | 1.00 | 22.44 | MOLA C |
| ATOM | 75 | NE2 | GLN | A | 78 | 8.725 | 16.756 | 26.468 | 1.00 | 21.32 | MOLA N |
| ATOM | 76 | OE1 | GLN | A | 78 | 6.904 | 15.887 | 27.462 | 1.00 | 23.63 | MOLA O |
| TER | 77 | | GLN | A | 78 | | | | | | |
| ATOM | 78 | N | LYS | A | 111 | 12.171 | 13.708 | 34.415 | 1.00 | 23.51 | MOLA N |
| ATOM | 79 | CA | LYS | A | 111 | 12.213 | 15.070 | 34.917 | 1.00 | 22.07 | MOLA C |
| ATOM | 80 | C | LYS | A | 111 | 12.579 | 16.088 | 33.858 | 1.00 | 23.88 | MOLA C |
| ATOM | 81 | O | LYS | A | 111 | 11.798 | 17.008 | 33.578 | 1.00 | 22.73 | MOLA O |
| ATOM | 82 | CB | LYS | A | 111 | 13.193 | 15.176 | 36.079 | 1.00 | 23.46 | MOLA C |
| ATOM | 83 | CG | LYS | A | 111 | 12.531 | 15.237 | 37.438 | 1.00 | 24.81 | MOLA C |
| ATOM | 84 | CD | LYS | A | 111 | 12.996 | 14.146 | 38.385 | 1.00 | 26.27 | MOLA C |
| ATOM | 85 | CE | LYS | A | 111 | 14.496 | 14.201 | 38.633 | 1.00 | 27.85 | MOLA C |
| ATOM | 86 | NZ | LYS | A | 111 | 15.181 | 13.043 | 37.991 | 1.00 | 25.91 | MOLA N |
| ATOM | 87 | N | THR | A | 112 | 13.752 | 15.921 | 33.249 | 1.00 | 24.45 | MOLA N |
| ATOM | 88 | CA | THR | A | 112 | 14.195 | 16.872 | 32.225 | 1.00 | 25.33 | MOLA C |
| ATOM | 89 | C | THR | A | 112 | 13.386 | 16.800 | 30.932 | 1.00 | 23.67 | MOLA C |
| ATOM | 90 | O | THR | A | 112 | 13.140 | 17.819 | 30.282 | 1.00 | 19.71 | MOLA O |
| ATOM | 91 | CB | THR | A | 112 | 15.661 | 16.679 | 31.881 | 1.00 | 24.94 | MOLA C |
| ATOM | 92 | CG2 | THR | A | 112 | 16.156 | 17.836 | 30.994 | 1.00 | 24.69 | MOLA C |
| ATOM | 93 | OG1 | THR | A | 112 | 16.418 | 16.654 | 33.092 | 1.00 | 30.07 | MOLA O |
| ATOM | 94 | N | PHE | A | 113 | 12.988 | 15.591 | 30.554 | 1.00 | 22.57 | MOLA N |
| ATOM | 95 | CA | PHE | A | 113 | 12.191 | 15.425 | 29.351 | 1.00 | 22.32 | MOLA C |
| ATOM | 96 | C | PHE | A | 113 | 10.887 | 16.212 | 29.503 | 1.00 | 22.95 | MOLA C |
| ATOM | 97 | O | PHE | A | 113 | 10.408 | 16.837 | 28.561 | 1.00 | 20.59 | MOLA O |
| ATOM | 98 | CB | PHE | A | 113 | 11.858 | 13.950 | 29.128 | 1.00 | 20.62 | MOLA C |
| ATOM | 99 | CG | PHE | A | 113 | 11.007 | 13.714 | 27.927 | 1.00 | 21.47 | MOLA C |
| ATOM | 100 | CD1 | PHE | A | 113 | 11.558 | 13.770 | 26.651 | 1.00 | 21.89 | MOLA C |
| ATOM | 101 | CD2 | PHE | A | 113 | 9.648 | 13.491 | 28.059 | 1.00 | 20.48 | MOLA C |
| ATOM | 102 | CE1 | PHE | A | 113 | 10.769 | 13.608 | 25.541 | 1.00 | 21.91 | MOLA C |
| ATOM | 103 | CE2 | PHE | A | 113 | 8.854 | 13.330 | 26.952 | 1.00 | 20.99 | MOLA C |
| ATOM | 104 | CZ | PHE | A | 113 | 9.413 | 13.388 | 25.689 | 1.00 | 19.96 | MOLA C |
| ATOM | 105 | N | THR | A | 114 | 10.314 | 16.148 | 30.702 | 1.00 | 23.95 | MOLA N |
| ATOM | 106 | CA | THR | A | 114 | 9.077 | 16.841 | 31.013 | 1.00 | 25.38 | MOLA C |
| ATOM | 107 | C | THR | A | 114 | 9.272 | 18.359 | 31.102 | 1.00 | 26.64 | MOLA C |
| ATOM | 108 | O | THR | A | 114 | 8.527 | 19.134 | 30.503 | 1.00 | 27.81 | MOLA O |
| ATOM | 109 | CB | THR | A | 114 | 8.508 | 16.352 | 32.353 | 1.00 | 23.89 | MOLA C |
| ATOM | 110 | CG2 | THR | A | 114 | 7.343 | 17.227 | 32.796 | 1.00 | 23.72 | MOLA C |
| ATOM | 111 | OG1 | THR | A | 114 | 8.059 | 15.002 | 32.213 | 1.00 | 27.14 | MOLA O |
| ATOM | 112 | N | MET | A | 115 | 10.289 | 18.774 | 31.844 | 1.00 | 27.38 | MOLA N |
| ATOM | 113 | CA | MET | A | 115 | 10.548 | 20.192 | 32.043 | 1.00 | 28.73 | MOLA C |
| ATOM | 114 | C | MET | A | 115 | 11.138 | 20.922 | 30.843 | 1.00 | 29.72 | MOLA C |
| ATOM | 115 | O | MET | A | 115 | 10.773 | 22.068 | 30.567 | 1.00 | 29.54 | MOLA O |
| ATOM | 116 | CB | MET | A | 115 | 11.455 | 20.380 | 33.261 | 1.00 | 27.73 | MOLA C |
| ATOM | 117 | CG | MET | A | 115 | 10.937 | 21.434 | 34.216 | 1.00 | 32.69 | MOLA C |
| ATOM | 118 | SD | MET | A | 115 | 9.226 | 21.133 | 34.707 | 1.00 | 30.88 | MOLA S |
| ATOM | 119 | CE | MET | A | 115 | 8.992 | 22.360 | 35.955 | 1.00 | 33.70 | MOLA C |
| ATOM | 120 | N | GLU | A | 116 | 12.027 | 20.250 | 30.118 | 1.00 | 30.43 | MOLA N |
| ATOM | 121 | CA | GLU | A | 116 | 12.690 | 20.856 | 28.979 | 1.00 | 31.16 | MOLA C |
| ATOM | 122 | C | GLU | A | 116 | 12.310 | 20.290 | 27.619 | 1.00 | 31.67 | MOLA C |
| ATOM | 123 | O | GLU | A | 116 | 12.063 | 21.045 | 26.677 | 1.00 | 31.91 | MOLA O |
| ATOM | 124 | CB | GLU | A | 116 | 14.199 | 20.754 | 29.180 | 1.00 | 32.39 | MOLA C |
| ATOM | 125 | CG | GLU | A | 116 | 14.629 | 21.186 | 30.563 | 1.00 | 33.59 | MOLA C |
| ATOM | 126 | CD | GLU | A | 116 | 16.128 | 21.299 | 30.707 | 1.00 | 34.86 | MOLA C |
| ATOM | 127 | OE1 | GLU | A | 116 | 16.569 | 21.806 | 31.760 | 1.00 | 37.55 | MOLA O |
| ATOM | 128 | OE2 | GLU | A | 116 | 16.858 | 20.885 | 29.783 | 1.00 | 31.10 | MOLA O |
| ATOM | 129 | N | GLY | A | 117 | 12.276 | 18.971 | 27.505 | 1.00 | 30.88 | MOLA N |
| ATOM | 130 | CA | GLY | A | 117 | 11.931 | 18.379 | 26.235 | 1.00 | 32.99 | MOLA C |
| ATOM | 131 | C | GLY | A | 117 | 13.185 | 18.148 | 25.426 | 1.00 | 35.24 | MOLA C |
| ATOM | 132 | O | GLY | A | 117 | 14.279 | 18.434 | 25.882 | 1.00 | 34.98 | MOLA O |
| ATOM | 133 | N | GLU | A | 118 | 13.022 | 17.639 | 24.214 | 1.00 | 38.49 | MOLA N |
| ATOM | 134 | CA | GLU | A | 118 | 14.147 | 17.346 | 23.329 | 1.00 | 42.88 | MOLA C |
| ATOM | 135 | C | GLU | A | 118 | 13.827 | 17.787 | 21.900 | 1.00 | 45.13 | MOLA C |
| ATOM | 136 | O | GLU | A | 118 | 12.680 | 18.111 | 21.572 | 1.00 | 43.43 | MOLA O |
| ATOM | 137 | CB | GLU | A | 118 | 14.440 | 15.834 | 23.323 | 1.00 | 43.61 | MOLA C |
| ATOM | 138 | CG | GLU | A | 118 | 15.329 | 15.337 | 24.440 | 1.00 | 46.66 | MOLA C |
| ATOM | 139 | CD | GLU | A | 118 | 15.155 | 13.851 | 24.717 | 1.00 | 48.14 | MOLA C |
| ATOM | 140 | OE1 | GLU | A | 118 | 14.899 | 13.090 | 23.754 | 1.00 | 50.02 | MOLA O |
| ATOM | 141 | OE2 | GLU | A | 118 | 15.284 | 13.449 | 25.898 | 1.00 | 47.70 | MOLA O |
| ATOM | 142 | N | ARG | A | 119 | 14.846 | 17.813 | 21.048 | 1.00 | 47.27 | MOLA N |
| ATOM | 143 | CA | ARG | A | 119 | 14.608 | 18.177 | 19.666 | 1.00 | 50.08 | MOLA C |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | | |
|---|---|---|---|---|---|---|---|---|---|---|---|---|
| ATOM | 144 | C | ARG | A | 119 | 14.208 | 16.859 | 19.017 | 1.00 | 50.67 | MOLA | C |
| ATOM | 145 | O | ARG | A | 119 | 14.739 | 15.788 | 19.360 | 1.00 | 49.62 | MOLA | O |
| ATOM | 146 | CB | ARG | A | 119 | 15.873 | 18.757 | 19.021 | 1.00 | 52.71 | MOLA | C |
| ATOM | 147 | CG | ARG | A | 119 | 15.585 | 19.714 | 17.856 | 1.00 | 55.78 | MOLA | C |
| ATOM | 148 | CD | ARG | A | 119 | 14.315 | 20.548 | 18.129 | 1.00 | 58.04 | MOLA | C |
| ATOM | 149 | NE | ARG | A | 119 | 14.166 | 21.711 | 17.249 | 1.00 | 60.04 | MOLA | N |
| ATOM | 150 | CZ | ARG | A | 119 | 14.949 | 22.791 | 17.290 | 1.00 | 61.75 | MOLA | C |
| ATOM | 151 | NH1 | ARG | A | 119 | 15.941 | 22.865 | 18.172 | 1.00 | 60.87 | MOLA | N |
| ATOM | 152 | NH2 | ARG | A | 119 | 14.749 | 23.798 | 16.443 | 1.00 | 61.40 | MOLA | N |
| ATOM | 153 | N | SER | A | 120 | 13.255 | 16.928 | 18.101 | 1.00 | 50.63 | MOLA | N |
| ATOM | 154 | CA | SER | A | 120 | 12.781 | 15.731 | 17.437 | 1.00 | 51.64 | MOLA | C |
| ATOM | 155 | C | SER | A | 120 | 13.791 | 15.268 | 16.383 | 1.00 | 54.06 | MOLA | C |
| ATOM | 156 | O | SER | A | 120 | 14.311 | 16.082 | 15.609 | 1.00 | 53.36 | MOLA | O |
| ATOM | 157 | CB | SER | A | 120 | 11.427 | 16.015 | 16.793 | 1.00 | 49.74 | MOLA | C |
| ATOM | 158 | OG | SER | A | 120 | 10.589 | 14.880 | 16.844 | 1.00 | 49.07 | MOLA | O |
| ATOM | 159 | N | PRO | A | 121 | 14.102 | 13.956 | 16.363 | 1.00 | 55.58 | MOLA | N |
| ATOM | 160 | CA | PRO | A | 121 | 15.046 | 13.365 | 15.410 | 1.00 | 57.86 | MOLA | C |
| ATOM | 161 | C | PRO | A | 121 | 14.560 | 13.612 | 13.985 | 1.00 | 60.14 | MOLA | C |
| ATOM | 162 | O | PRO | A | 121 | 15.355 | 13.651 | 13.044 | 1.00 | 60.42 | MOLA | O |
| ATOM | 163 | CB | PRO | A | 121 | 15.031 | 11.886 | 15.786 | 1.00 | 57.08 | MOLA | C |
| ATOM | 164 | CG | PRO | A | 121 | 14.809 | 11.932 | 17.260 | 1.00 | 55.62 | MOLA | C |
| ATOM | 165 | CD | PRO | A | 121 | 13.705 | 12.962 | 17.376 | 1.00 | 56.17 | MOLA | C |
| TER | 166 | | PRO | A | 121 | | | | | | | |
| ATOM | 167 | N | GLU | A | 123 | 13.960 | 16.062 | 12.773 | 1.00 | 64.44 | MOLA | N |
| ATOM | 168 | CA | GLU | A | 123 | 14.769 | 17.203 | 12.349 | 1.00 | 64.82 | MOLA | C |
| ATOM | 169 | C | GLU | A | 123 | 13.980 | 18.290 | 11.623 | 1.00 | 64.56 | MOLA | C |
| ATOM | 170 | O | GLU | A | 123 | 14.456 | 19.416 | 11.481 | 1.00 | 65.54 | MOLA | O |
| ATOM | 171 | CB | GLU | A | 123 | 15.923 | 16.709 | 11.469 | 1.00 | 65.57 | MOLA | C |
| ATOM | 172 | CG | GLU | A | 123 | 16.701 | 17.785 | 10.721 | 1.00 | 68.11 | MOLA | C |
| ATOM | 173 | CD | GLU | A | 123 | 17.410 | 18.769 | 11.636 | 1.00 | 69.60 | MOLA | C |
| ATOM | 174 | OE1 | GLU | A | 123 | 16.781 | 19.778 | 12.031 | 1.00 | 71.08 | MOLA | O |
| ATOM | 175 | OE2 | GLU | A | 123 | 18.598 | 18.531 | 11.959 | 1.00 | 68.54 | MOLA | O |
| ATOM | 176 | N | GLU | A | 124 | 12.766 | 17.968 | 11.191 | 1.00 | 63.07 | MOLA | N |
| ATOM | 177 | CA | GLU | A | 124 | 11.964 | 18.939 | 10.464 | 1.00 | 62.36 | MOLA | C |
| ATOM | 178 | C | GLU | A | 124 | 10.959 | 19.679 | 11.351 | 1.00 | 60.55 | MOLA | C |
| ATOM | 179 | O | GLU | A | 124 | 9.743 | 19.620 | 11.115 | 1.00 | 61.29 | MOLA | O |
| ATOM | 180 | CB | GLU | A | 124 | 11.224 | 18.250 | 9.303 | 1.00 | 65.13 | MOLA | C |
| ATOM | 181 | CG | GLU | A | 124 | 11.977 | 17.069 | 8.645 | 1.00 | 67.64 | MOLA | C |
| ATOM | 182 | CD | GLU | A | 124 | 13.236 | 17.471 | 7.873 | 1.00 | 68.37 | MOLA | C |
| ATOM | 183 | OE1 | GLU | A | 124 | 14.108 | 18.170 | 8.440 | 1.00 | 66.90 | MOLA | O |
| ATOM | 184 | OE2 | GLU | A | 124 | 13.353 | 17.066 | 6.693 | 1.00 | 68.66 | MOLA | O |
| ATOM | 185 | N | TYR | A | 125 | 11.459 | 20.380 | 12.364 | 1.00 | 55.92 | MOLA | N |
| ATOM | 186 | CA | TYR | A | 125 | 10.588 | 21.143 | 13.255 | 1.00 | 51.40 | MOLA | C |
| ATOM | 187 | C | TYR | A | 125 | 11.306 | 22.329 | 13.873 | 1.00 | 50.33 | MOLA | C |
| ATOM | 188 | O | TYR | A | 125 | 12.468 | 22.226 | 14.254 | 1.00 | 50.06 | MOLA | O |
| ATOM | 189 | CB | TYR | A | 125 | 10.083 | 20.282 | 14.410 | 1.00 | 49.05 | MOLA | C |
| ATOM | 190 | CG | TYR | A | 125 | 9.081 | 19.204 | 14.074 | 1.00 | 46.58 | MOLA | C |
| ATOM | 191 | CD1 | TYR | A | 125 | 7.801 | 19.523 | 13.662 | 1.00 | 44.96 | MOLA | C |
| ATOM | 192 | CD2 | TYR | A | 125 | 9.406 | 17.859 | 14.233 | 1.00 | 45.04 | MOLA | C |
| ATOM | 193 | CE1 | TYR | A | 125 | 6.869 | 18.535 | 13.424 | 1.00 | 45.11 | MOLA | C |
| ATOM | 194 | CE2 | TYR | A | 125 | 8.485 | 16.867 | 13.997 | 1.00 | 44.42 | MOLA | C |
| ATOM | 195 | CZ | TYR | A | 125 | 7.216 | 17.208 | 13.596 | 1.00 | 44.88 | MOLA | C |
| ATOM | 196 | OH | TYR | A | 125 | 6.287 | 16.222 | 13.377 | 1.00 | 45.06 | MOLA | O |
| ATOM | 197 | N | THR | A | 126 | 10.617 | 23.461 | 13.959 | 1.00 | 49.56 | MOLA | N |
| ATOM | 198 | CA | THR | A | 126 | 11.187 | 24.625 | 14.614 | 1.00 | 49.43 | MOLA | C |
| ATOM | 199 | C | THR | A | 126 | 10.832 | 24.349 | 16.079 | 1.00 | 49.91 | MOLA | C |
| ATOM | 200 | O | THR | A | 126 | 9.820 | 23.693 | 16.352 | 1.00 | 48.32 | MOLA | O |
| ATOM | 201 | CB | THR | A | 126 | 10.527 | 25.930 | 14.136 | 1.00 | 49.99 | MOLA | C |
| ATOM | 202 | CG2 | THR | A | 126 | 11.079 | 26.334 | 12.791 | 1.00 | 50.07 | MOLA | C |
| ATOM | 203 | OG1 | THR | A | 126 | 9.108 | 25.748 | 14.030 | 1.00 | 53.03 | MOLA | O |
| ATOM | 204 | N | TRP | A | 127 | 11.645 | 24.827 | 17.022 | 1.00 | 50.21 | MOLA | N |
| ATOM | 205 | CA | TRP | A | 127 | 11.369 | 24.550 | 18.426 | 1.00 | 48.63 | MOLA | C |
| ATOM | 206 | C | TRP | A | 127 | 9.964 | 24.896 | 18.887 | 1.00 | 48.83 | MOLA | C |
| ATOM | 207 | O | TRP | A | 127 | 9.405 | 24.196 | 19.732 | 1.00 | 48.83 | MOLA | O |
| ATOM | 208 | CB | TRP | A | 127 | 12.385 | 25.231 | 19.339 | 1.00 | 46.54 | MOLA | C |
| ATOM | 209 | CG | TRP | A | 127 | 12.316 | 26.721 | 19.389 | 1.00 | 43.87 | MOLA | C |
| ATOM | 210 | CD1 | TRP | A | 127 | 13.053 | 27.594 | 18.653 | 1.00 | 42.03 | MOLA | C |
| ATOM | 211 | CD2 | TRP | A | 127 | 11.531 | 27.517 | 20.296 | 1.00 | 42.26 | MOLA | C |
| ATOM | 212 | CE2 | TRP | A | 127 | 11.860 | 28.868 | 20.053 | 1.00 | 41.96 | MOLA | C |
| ATOM | 213 | CE3 | TRP | A | 127 | 10.589 | 27.216 | 21.291 | 1.00 | 40.05 | MOLA | C |
| ATOM | 214 | NE1 | TRP | A | 127 | 12.789 | 28.885 | 19.047 | 1.00 | 42.75 | MOLA | N |
| ATOM | 215 | CZ2 | TRP | A | 127 | 11.284 | 29.922 | 20.770 | 1.00 | 40.66 | MOLA | C |
| ATOM | 216 | CZ3 | TRP | A | 127 | 10.020 | 28.261 | 22.005 | 1.00 | 40.13 | MOLA | C |
| ATOM | 217 | CH2 | TRP | A | 127 | 10.372 | 29.601 | 21.739 | 1.00 | 40.15 | MOLA | C |
| ATOM | 218 | N | GLU | A | 128 | 9.379 | 25.953 | 18.338 | 1.00 | 48.03 | MOLA | N |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 219 | CA | GLU | A | 128 | 8.037 | 26.332 | 18.744 | 1.00 | 48.42 | MOLA C |
| ATOM | 220 | C | GLU | A | 128 | 6.992 | 25.333 | 18.267 | 1.00 | 48.05 | MOLA C |
| ATOM | 221 | O | GLU | A | 128 | 5.866 | 25.339 | 18.740 | 1.00 | 47.91 | MOLA O |
| ATOM | 222 | CB | GLU | A | 128 | 7.669 | 27.717 | 18.213 | 1.00 | 50.74 | MOLA C |
| ATOM | 223 | CG | GLU | A | 128 | 8.674 | 28.810 | 18.509 | 1.00 | 54.06 | MOLA C |
| ATOM | 224 | CD | GLU | A | 128 | 9.639 | 29.015 | 17.361 | 1.00 | 57.42 | MOLA C |
| ATOM | 225 | OE1 | GLU | A | 128 | 10.357 | 28.051 | 16.999 | 1.00 | 57.54 | MOLA O |
| ATOM | 226 | OE2 | GLU | A | 128 | 9.666 | 30.143 | 16.816 | 1.00 | 59.51 | MOLA O |
| ATOM | 227 | N | GLU | A | 129 | 7.357 | 24.459 | 17.343 | 1.00 | 48.69 | MOLA N |
| ATOM | 228 | CA | GLU | A | 129 | 6.394 | 23.493 | 16.833 | 1.00 | 48.78 | MOLA C |
| ATOM | 229 | C | GLU | A | 129 | 6.796 | 22.049 | 17.103 | 1.00 | 48.18 | MOLA C |
| ATOM | 230 | O | GLU | A | 129 | 6.061 | 21.116 | 16.774 | 1.00 | 47.94 | MOLA O |
| ATOM | 231 | CB | GLU | A | 129 | 6.213 | 23.703 | 15.328 | 1.00 | 51.98 | MOLA C |
| ATOM | 232 | CG | GLU | A | 129 | 5.665 | 25.083 | 14.948 | 1.00 | 56.61 | MOLA C |
| ATOM | 233 | CD | GLU | A | 129 | 5.846 | 25.426 | 13.464 | 1.00 | 59.78 | MOLA C |
| ATOM | 234 | OE1 | GLU | A | 129 | 5.451 | 26.545 | 13.068 | 1.00 | 61.92 | MOLA O |
| ATOM | 235 | OE2 | GLU | A | 129 | 6.382 | 24.592 | 12.697 | 1.00 | 60.67 | MOLA O |
| ATOM | 236 | N | ASP | A | 130 | 7.958 | 21.858 | 17.714 | 1.00 | 45.89 | MOLA N |
| ATOM | 237 | CA | ASP | A | 130 | 8.435 | 20.515 | 17.980 | 1.00 | 43.97 | MOLA C |
| ATOM | 238 | C | ASP | A | 130 | 7.583 | 19.758 | 19.007 | 1.00 | 42.85 | MOLA C |
| ATOM | 239 | O | ASP | A | 130 | 7.404 | 20.181 | 20.149 | 1.00 | 41.54 | MOLA O |
| ATOM | 240 | CB | ASP | A | 130 | 9.905 | 20.562 | 18.415 | 1.00 | 43.29 | MOLA C |
| ATOM | 241 | CG | ASP | A | 130 | 10.629 | 19.247 | 18.173 | 1.00 | 42.49 | MOLA C |
| ATOM | 242 | OD1 | ASP | A | 130 | 11.818 | 19.291 | 17.771 | 1.00 | 42.14 | MOLA O |
| ATOM | 243 | OD2 | ASP | A | 130 | 10.011 | 18.175 | 18.387 | 1.00 | 41.45 | MOLA O |
| ATOM | 244 | N | PRO | A | 131 | 7.042 | 18.613 | 18.591 | 1.00 | 41.35 | MOLA N |
| ATOM | 245 | CA | PRO | A | 131 | 6.203 | 17.759 | 19.429 | 1.00 | 41.00 | MOLA C |
| ATOM | 246 | C | PRO | A | 131 | 6.893 | 17.274 | 20.698 | 1.00 | 39.33 | MOLA C |
| ATOM | 247 | O | PRO | A | 131 | 6.231 | 16.936 | 21.669 | 1.00 | 41.64 | MOLA O |
| ATOM | 248 | CB | PRO | A | 131 | 5.854 | 16.599 | 18.498 | 1.00 | 40.29 | MOLA C |
| ATOM | 249 | CG | PRO | A | 131 | 5.876 | 17.228 | 17.150 | 1.00 | 40.33 | MOLA C |
| ATOM | 250 | CD | PRO | A | 131 | 7.105 | 18.098 | 17.215 | 1.00 | 40.58 | MOLA C |
| ATOM | 251 | N | LEU | A | 132 | 8.219 | 17.235 | 20.693 | 1.00 | 37.41 | MOLA N |
| ATOM | 252 | CA | LEU | A | 132 | 8.960 | 16.757 | 21.855 | 1.00 | 33.88 | MOLA C |
| ATOM | 253 | C | LEU | A | 132 | 9.354 | 17.848 | 22.842 | 1.00 | 31.79 | MOLA C |
| ATOM | 254 | O | LEU | A | 132 | 9.998 | 17.574 | 23.851 | 1.00 | 32.48 | MOLA O |
| ATOM | 255 | CB | LEU | A | 132 | 10.209 | 15.991 | 21.393 | 1.00 | 33.03 | MOLA C |
| ATOM | 256 | CG | LEU | A | 132 | 9.902 | 14.668 | 20.684 | 1.00 | 33.61 | MOLA C |
| ATOM | 257 | CD1 | LEU | A | 132 | 11.203 | 13.972 | 20.334 | 1.00 | 31.78 | MOLA C |
| ATOM | 258 | CD2 | LEU | A | 132 | 9.022 | 13.779 | 21.574 | 1.00 | 30.59 | MOLA C |
| ATOM | 259 | N | ALA | A | 133 | 8.978 | 19.086 | 22.546 | 1.00 | 30.22 | MOLA N |
| ATOM | 260 | CA | ALA | A | 133 | 9.283 | 20.205 | 23.427 | 1.00 | 29.13 | MOLA C |
| ATOM | 261 | C | ALA | A | 133 | 8.625 | 20.049 | 24.814 | 1.00 | 29.42 | MOLA C |
| ATOM | 262 | O | ALA | A | 133 | 7.477 | 19.600 | 24.941 | 1.00 | 26.92 | MOLA O |
| ATOM | 263 | CB | ALA | A | 133 | 8.833 | 21.496 | 22.783 | 1.00 | 27.97 | MOLA C |
| ATOM | 264 | N | GLY | A | 134 | 9.363 | 20.426 | 25.851 | 1.00 | 28.80 | MOLA N |
| ATOM | 265 | CA | GLY | A | 134 | 8.845 | 20.314 | 27.201 | 1.00 | 29.81 | MOLA C |
| ATOM | 266 | C | GLY | A | 134 | 8.166 | 21.584 | 27.685 | 1.00 | 30.21 | MOLA C |
| ATOM | 267 | O | GLY | A | 134 | 7.986 | 22.543 | 26.925 | 1.00 | 31.59 | MOLA O |
| ATOM | 268 | N | ILE | A | 135 | 7.799 | 21.596 | 28.959 | 1.00 | 26.84 | MOLA N |
| ATOM | 269 | CA | ILE | A | 135 | 7.117 | 22.738 | 29.538 | 1.00 | 25.65 | MOLA C |
| ATOM | 270 | C | ILE | A | 135 | 7.808 | 24.095 | 29.363 | 1.00 | 25.68 | MOLA C |
| ATOM | 271 | O | ILE | A | 135 | 7.192 | 25.054 | 28.914 | 1.00 | 25.73 | MOLA O |
| ATOM | 272 | CB | ILE | A | 135 | 6.888 | 22.505 | 31.025 | 1.00 | 24.80 | MOLA C |
| ATOM | 273 | CG1 | ILE | A | 135 | 6.108 | 21.212 | 31.209 | 1.00 | 21.39 | MOLA C |
| ATOM | 274 | CG2 | ILE | A | 135 | 6.180 | 23.702 | 31.637 | 1.00 | 22.91 | MOLA C |
| ATOM | 275 | CD1 | ILE | A | 135 | 6.104 | 20.722 | 32.607 | 1.00 | 22.61 | MOLA C |
| ATOM | 276 | N | ILE | A | 136 | 9.081 | 24.183 | 29.725 | 1.00 | 26.13 | MOLA N |
| ATOM | 277 | CA | ILE | A | 136 | 9.794 | 25.456 | 29.624 | 1.00 | 26.33 | MOLA C |
| ATOM | 278 | C | ILE | A | 136 | 9.589 | 26.194 | 28.296 | 1.00 | 27.04 | MOLA C |
| ATOM | 279 | O | ILE | A | 136 | 9.016 | 27.289 | 28.269 | 1.00 | 26.55 | MOLA O |
| ATOM | 280 | CB | ILE | A | 136 | 11.298 | 25.264 | 29.933 | 1.00 | 24.26 | MOLA C |
| ATOM | 281 | CG1 | ILE | A | 136 | 11.468 | 25.039 | 31.443 | 1.00 | 24.14 | MOLA C |
| ATOM | 282 | CG2 | ILE | A | 136 | 12.082 | 26.485 | 29.521 | 1.00 | 23.25 | MOLA C |
| ATOM | 283 | CD1 | ILE | A | 136 | 12.685 | 24.214 | 31.841 | 1.00 | 23.01 | MOLA C |
| ATOM | 284 | N | PRO | A | 137 | 10.016 | 25.593 | 27.180 | 1.00 | 27.44 | MOLA N |
| ATOM | 285 | CA | PRO | A | 137 | 9.868 | 26.216 | 25.856 | 1.00 | 27.12 | MOLA C |
| ATOM | 286 | C | PRO | A | 137 | 8.417 | 26.581 | 25.501 | 1.00 | 27.08 | MOLA C |
| ATOM | 287 | O | PRO | A | 137 | 8.150 | 27.710 | 25.070 | 1.00 | 28.33 | MOLA O |
| ATOM | 288 | CB | PRO | A | 137 | 10.431 | 25.167 | 24.893 | 1.00 | 25.22 | MOLA C |
| ATOM | 289 | CG | PRO | A | 137 | 11.108 | 24.172 | 25.762 | 1.00 | 25.48 | MOLA C |
| ATOM | 290 | CD | PRO | A | 137 | 10.439 | 24.188 | 27.067 | 1.00 | 27.63 | MOLA C |
| ATOM | 291 | N | ARG | A | 138 | 7.494 | 25.627 | 25.653 | 1.00 | 25.47 | MOLA N |
| ATOM | 292 | CA | ARG | A | 138 | 6.091 | 25.875 | 25.336 | 1.00 | 25.58 | MOLA C |
| ATOM | 293 | C | ARG | A | 138 | 5.516 | 27.020 | 26.164 | 1.00 | 26.48 | MOLA C |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 294 | O | ARG | A | 138 | 4.605 | 27.711 | 25.736 | 1.00 | 28.23 | MOLA O |
| ATOM | 295 | CB | ARG | A | 138 | 5.237 | 24.642 | 25.591 | 1.00 | 24.49 | MOLA C |
| ATOM | 296 | CG | ARG | A | 138 | 5.626 | 23.426 | 24.805 | 1.00 | 25.67 | MOLA C |
| ATOM | 297 | CD | ARG | A | 138 | 4.781 | 22.249 | 25.238 | 1.00 | 25.39 | MOLA C |
| ATOM | 298 | NE | ARG | A | 138 | 5.209 | 21.042 | 24.567 | 1.00 | 26.84 | MOLA N |
| ATOM | 299 | CZ | ARG | A | 138 | 4.704 | 20.604 | 23.425 | 1.00 | 29.15 | MOLA C |
| ATOM | 300 | NH1 | ARG | A | 138 | 3.729 | 21.279 | 22.832 | 1.00 | 28.31 | MOLA N |
| ATOM | 301 | NH2 | ARG | A | 138 | 5.199 | 19.505 | 22.861 | 1.00 | 28.81 | MOLA N |
| ATOM | 302 | N | THR | A | 139 | 6.042 | 27.220 | 27.356 | 1.00 | 26.24 | MOLA N |
| ATOM | 303 | CA | THR | A | 139 | 5.538 | 28.275 | 28.202 | 1.00 | 26.93 | MOLA C |
| ATOM | 304 | C | THR | A | 139 | 6.029 | 29.630 | 27.717 | 1.00 | 27.45 | MOLA C |
| ATOM | 305 | O | THR | A | 139 | 5.261 | 30.591 | 27.632 | 1.00 | 26.68 | MOLA O |
| ATOM | 306 | CB | THR | A | 139 | 5.974 | 28.051 | 29.660 | 1.00 | 26.74 | MOLA C |
| ATOM | 307 | CG2 | THR | A | 139 | 5.464 | 29.181 | 30.562 | 1.00 | 26.06 | MOLA C |
| ATOM | 308 | OG1 | THR | A | 139 | 5.456 | 26.800 | 30.111 | 1.00 | 23.80 | MOLA O |
| ATOM | 309 | N | LEU | A | 140 | 7.310 | 29.714 | 27.399 | 1.00 | 28.37 | MOLA N |
| ATOM | 310 | CA | LEU | A | 140 | 7.859 | 30.974 | 26.929 | 1.00 | 30.71 | MOLA C |
| ATOM | 311 | C | LEU | A | 140 | 7.161 | 31.390 | 25.640 | 1.00 | 31.42 | MOLA C |
| ATOM | 312 | O | LEU | A | 140 | 6.940 | 32.579 | 25.401 | 1.00 | 29.98 | MOLA O |
| ATOM | 313 | CB | LEU | A | 140 | 9.372 | 30.843 | 26.732 | 1.00 | 29.55 | MOLA C |
| ATOM | 314 | CG | LEU | A | 140 | 10.061 | 30.710 | 28.100 | 1.00 | 31.11 | MOLA C |
| ATOM | 315 | CD1 | LEU | A | 140 | 11.522 | 30.306 | 27.932 | 1.00 | 31.08 | MOLA C |
| ATOM | 316 | CD2 | LEU | A | 140 | 9.941 | 32.028 | 28.849 | 1.00 | 29.53 | MOLA C |
| ATOM | 317 | N | HIS | A | 141 | 6.790 | 30.398 | 24.836 | 1.00 | 32.39 | MOLA N |
| ATOM | 318 | CA | HIS | A | 141 | 6.106 | 30.642 | 23.576 | 1.00 | 34.39 | MOLA C |
| ATOM | 319 | C | HIS | A | 141 | 4.705 | 31.186 | 23.830 | 1.00 | 34.09 | MOLA C |
| ATOM | 320 | O | HIS | A | 141 | 4.278 | 32.161 | 23.208 | 1.00 | 31.66 | MOLA O |
| ATOM | 321 | CB | HIS | A | 141 | 6.014 | 29.349 | 22.774 | 1.00 | 38.62 | MOLA C |
| ATOM | 322 | CG | HIS | A | 141 | 5.321 | 29.503 | 21.455 | 1.00 | 43.11 | MOLA C |
| ATOM | 323 | CD2 | HIS | A | 141 | 4.120 | 29.051 | 21.020 | 1.00 | 44.46 | MOLA C |
| ATOM | 324 | ND1 | HIS | A | 141 | 5.884 | 30.176 | 20.389 | 1.00 | 44.25 | MOLA N |
| ATOM | 325 | CE1 | HIS | A | 141 | 5.062 | 30.127 | 19.356 | 1.00 | 43.32 | MOLA C |
| ATOM | 326 | NE2 | HIS | A | 141 | 3.986 | 29.450 | 19.711 | 1.00 | 44.64 | MOLA N |
| TER | 327 | | HIS | A | 141 | | | | | | |
| ATOM | 328 | N | PHE | A | 144 | 4.471 | 34.877 | 25.186 | 1.00 | 35.92 | MOLA N |
| ATOM | 329 | CA | PHE | A | 144 | 4.614 | 35.809 | 24.080 | 1.00 | 36.63 | MOLA C |
| ATOM | 330 | C | PHE | A | 144 | 3.402 | 35.832 | 23.152 | 1.00 | 36.61 | MOLA C |
| ATOM | 331 | O | PHE | A | 144 | 2.923 | 36.902 | 22.767 | 1.00 | 35.66 | MOLA O |
| ATOM | 332 | CB | PHE | A | 144 | 5.876 | 35.484 | 23.297 | 1.00 | 35.75 | MOLA C |
| ATOM | 333 | CG | PHE | A | 144 | 7.120 | 36.005 | 23.947 | 1.00 | 37.27 | MOLA C |
| ATOM | 334 | CD1 | PHE | A | 144 | 7.431 | 37.357 | 23.895 | 1.00 | 36.45 | MOLA C |
| ATOM | 335 | CD2 | PHE | A | 144 | 7.961 | 35.156 | 24.644 | 1.00 | 37.35 | MOLA C |
| ATOM | 336 | CE1 | PHE | A | 144 | 8.553 | 37.840 | 24.527 | 1.00 | 36.66 | MOLA C |
| ATOM | 337 | CE2 | PHE | A | 144 | 9.089 | 35.638 | 25.280 | 1.00 | 36.43 | MOLA C |
| ATOM | 338 | CZ | PHE | A | 144 | 9.386 | 36.977 | 25.224 | 1.00 | 36.20 | MOLA C |
| TER | 339 | | PHE | A | 144 | | | | | | |
| ATOM | 340 | N | VAL | A | 158 | 14.054 | 36.335 | 32.438 | 1.00 | 32.93 | MOLA N |
| ATOM | 341 | CA | VAL | A | 158 | 14.247 | 34.994 | 32.974 | 1.00 | 32.88 | MOLA C |
| ATOM | 342 | C | VAL | A | 158 | 15.494 | 34.896 | 33.840 | 1.00 | 34.27 | MOLA C |
| ATOM | 343 | O | VAL | A | 158 | 16.397 | 35.734 | 33.769 | 1.00 | 35.45 | MOLA O |
| ATOM | 344 | CB | VAL | A | 158 | 14.401 | 33.946 | 31.850 | 1.00 | 32.12 | MOLA C |
| ATOM | 345 | CG1 | VAL | A | 158 | 13.109 | 33.840 | 31.028 | 1.00 | 31.77 | MOLA C |
| ATOM | 346 | CG2 | VAL | A | 158 | 15.580 | 34.314 | 30.970 | 1.00 | 29.49 | MOLA C |
| ATOM | 347 | N | SER | A | 159 | 15.539 | 33.861 | 34.665 | 1.00 | 33.35 | MOLA N |
| ATOM | 348 | CA | SER | A | 159 | 16.678 | 33.623 | 35.526 | 1.00 | 32.63 | MOLA C |
| ATOM | 349 | C | SER | A | 159 | 16.812 | 32.122 | 35.643 | 1.00 | 31.30 | MOLA C |
| ATOM | 350 | O | SER | A | 159 | 15.836 | 31.386 | 35.577 | 1.00 | 29.96 | MOLA O |
| ATOM | 351 | CB | SER | A | 159 | 16.467 | 34.256 | 36.900 | 1.00 | 33.14 | MOLA C |
| ATOM | 352 | OG | SER | A | 159 | 15.317 | 33.717 | 37.528 | 1.00 | 38.45 | MOLA O |
| ATOM | 353 | N | LEU | A | 160 | 18.034 | 31.660 | 35.805 | 1.00 | 33.35 | MOLA N |
| ATOM | 354 | CA | LEU | A | 160 | 18.264 | 30.233 | 35.904 | 1.00 | 33.68 | MOLA C |
| ATOM | 355 | C | LEU | A | 160 | 19.333 | 29.964 | 36.930 | 1.00 | 33.78 | MOLA C |
| ATOM | 356 | O | LEU | A | 160 | 20.492 | 30.313 | 36.734 | 1.00 | 34.26 | MOLA O |
| ATOM | 357 | CB | LEU | A | 160 | 18.711 | 29.702 | 34.554 | 1.00 | 34.55 | MOLA C |
| ATOM | 358 | CG | LEU | A | 160 | 19.030 | 28.217 | 34.494 | 1.00 | 35.04 | MOLA C |
| ATOM | 359 | CD1 | LEU | A | 160 | 17.796 | 27.389 | 34.837 | 1.00 | 33.75 | MOLA C |
| ATOM | 360 | CD2 | LEU | A | 160 | 19.545 | 27.912 | 33.094 | 1.00 | 35.95 | MOLA C |
| ATOM | 361 | N | LEU | A | 161 | 18.946 | 29.354 | 38.035 | 1.00 | 34.16 | MOLA N |
| ATOM | 362 | CA | LEU | A | 161 | 19.924 | 29.050 | 39.060 | 1.00 | 36.08 | MOLA C |
| ATOM | 363 | C | LEU | A | 161 | 19.965 | 27.550 | 39.333 | 1.00 | 36.63 | MOLA C |
| ATOM | 364 | O | LEU | A | 161 | 18.972 | 26.843 | 39.179 | 1.00 | 35.64 | MOLA O |
| ATOM | 365 | CB | LEU | A | 161 | 19.607 | 29.829 | 40.346 | 1.00 | 34.42 | MOLA C |
| ATOM | 366 | CG | LEU | A | 161 | 18.485 | 29.316 | 41.238 | 1.00 | 32.57 | MOLA C |
| ATOM | 367 | CD1 | LEU | A | 161 | 18.991 | 28.161 | 42.079 | 1.00 | 33.34 | MOLA C |
| ATOM | 368 | CD2 | LEU | A | 161 | 18.023 | 30.424 | 42.135 | 1.00 | 33.60 | MOLA C |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 369 | N | GLU | A | 162 | 21.133 | 27.070 | 39.729 | 1.00 | 39.03 | MOLA N |
| ATOM | 370 | CA | GLU | A | 162 | 21.290 | 25.662 | 40.034 | 1.00 | 41.79 | MOLA C |
| ATOM | 371 | C | GLU | A | 162 | 21.716 | 25.525 | 41.484 | 1.00 | 41.84 | MOLA C |
| ATOM | 372 | O | GLU | A | 162 | 22.695 | 26.144 | 41.905 | 1.00 | 42.02 | MOLA O |
| ATOM | 373 | CB | GLU | A | 162 | 22.348 | 25.047 | 39.135 | 1.00 | 44.04 | MOLA C |
| ATOM | 374 | CG | GLU | A | 162 | 22.634 | 23.601 | 39.448 | 1.00 | 50.66 | MOLA C |
| ATOM | 375 | CD | GLU | A | 162 | 23.956 | 23.137 | 38.858 | 1.00 | 53.98 | MOLA C |
| ATOM | 376 | OE1 | GLU | A | 162 | 24.083 | 23.074 | 37.610 | 1.00 | 54.84 | MOLA O |
| ATOM | 377 | OE2 | GLU | A | 162 | 24.872 | 22.844 | 39.659 | 1.00 | 56.25 | MOLA O |
| TER | 378 | | GLU | A | 162 | | | | | | |
| ATOM | 379 | N | PHE | A | 169 | 24.366 | 28.577 | 42.316 | 1.00 | 41.39 | MOLA N |
| ATOM | 380 | CA | PHE | A | 169 | 25.154 | 28.947 | 41.145 | 1.00 | 41.07 | MOLA C |
| ATOM | 381 | C | PHE | A | 169 | 24.269 | 29.571 | 40.062 | 1.00 | 39.87 | MOLA C |
| ATOM | 382 | O | PHE | A | 169 | 23.155 | 29.108 | 39.805 | 1.00 | 39.12 | MOLA O |
| ATOM | 383 | CB | PHE | A | 169 | 25.901 | 27.732 | 40.592 | 1.00 | 41.16 | MOLA C |
| ATOM | 384 | CG | PHE | A | 169 | 26.739 | 27.033 | 41.611 | 1.00 | 44.56 | MOLA C |
| ATOM | 385 | CD1 | PHE | A | 169 | 26.194 | 26.038 | 42.416 | 1.00 | 44.90 | MOLA C |
| ATOM | 386 | CD2 | PHE | A | 169 | 28.072 | 27.383 | 41.792 | 1.00 | 45.82 | MOLA C |
| ATOM | 387 | CE1 | PHE | A | 169 | 26.964 | 25.400 | 43.384 | 1.00 | 44.77 | MOLA C |
| ATOM | 388 | CE2 | PHE | A | 169 | 28.853 | 26.747 | 42.763 | 1.00 | 45.48 | MOLA C |
| ATOM | 389 | CZ | PHE | A | 169 | 28.294 | 25.753 | 43.559 | 1.00 | 44.78 | MOLA C |
| ATOM | 390 | N | ASP | A | 170 | 24.775 | 30.630 | 39.437 | 1.00 | 40.16 | MOLA N |
| ATOM | 391 | CA | ASP | A | 170 | 24.046 | 31.348 | 38.395 | 1.00 | 40.22 | MOLA C |
| ATOM | 392 | C | ASP | A | 170 | 24.380 | 30.769 | 37.039 | 1.00 | 40.27 | MOLA C |
| ATOM | 393 | O | ASP | A | 170 | 25.506 | 30.905 | 36.571 | 1.00 | 40.41 | MOLA O |
| ATOM | 394 | CB | ASP | A | 170 | 24.425 | 32.824 | 38.419 | 1.00 | 39.14 | MOLA C |
| ATOM | 395 | CG | ASP | A | 170 | 23.505 | 33.670 | 37.572 | 1.00 | 41.31 | MOLA C |
| ATOM | 396 | OD1 | ASP | A | 170 | 22.934 | 33.133 | 36.592 | 1.00 | 40.76 | MOLA O |
| ATOM | 397 | OD2 | ASP | A | 170 | 23.361 | 34.877 | 37.880 | 1.00 | 42.03 | MOLA O |
| ATOM | 398 | N | LEU | A | 171 | 23.403 | 30.131 | 36.401 | 1.00 | 41.12 | MOLA N |
| ATOM | 399 | CA | LEU | A | 171 | 23.631 | 29.526 | 35.093 | 1.00 | 41.67 | MOLA C |
| ATOM | 400 | C | LEU | A | 171 | 23.473 | 30.500 | 33.938 | 1.00 | 43.14 | MOLA C |
| ATOM | 401 | O | LEU | A | 171 | 23.863 | 30.202 | 32.814 | 1.00 | 43.43 | MOLA O |
| ATOM | 402 | CB | LEU | A | 171 | 22.694 | 28.334 | 34.887 | 1.00 | 40.76 | MOLA C |
| ATOM | 403 | CG | LEU | A | 171 | 23.015 | 27.087 | 35.717 | 1.00 | 39.98 | MOLA C |
| ATOM | 404 | CD1 | LEU | A | 171 | 22.040 | 25.966 | 35.374 | 1.00 | 40.11 | MOLA C |
| ATOM | 405 | CD2 | LEU | A | 171 | 24.424 | 26.642 | 35.435 | 1.00 | 38.40 | MOLA C |
| ATOM | 406 | N | LEU | A | 172 | 22.915 | 31.673 | 34.198 | 1.00 | 45.88 | MOLA N |
| ATOM | 407 | CA | LEU | A | 172 | 22.744 | 32.646 | 33.125 | 1.00 | 49.92 | MOLA C |
| ATOM | 408 | C | LEU | A | 172 | 23.721 | 33.812 | 33.176 | 1.00 | 53.22 | MOLA C |
| ATOM | 409 | O | LEU | A | 172 | 23.470 | 34.853 | 32.575 | 1.00 | 54.57 | MOLA O |
| ATOM | 410 | CB | LEU | A | 172 | 21.308 | 33.178 | 33.105 | 1.00 | 48.10 | MOLA C |
| ATOM | 411 | CG | LEU | A | 172 | 20.354 | 32.420 | 32.176 | 1.00 | 47.12 | MOLA C |
| ATOM | 412 | CD1 | LEU | A | 172 | 20.726 | 30.967 | 32.142 | 1.00 | 45.79 | MOLA C |
| ATOM | 413 | CD2 | LEU | A | 172 | 18.920 | 32.594 | 32.641 | 1.00 | 46.60 | MOLA C |
| TER | 414 | | LEU | A | 172 | | | | | | |
| ATOM | 415 | N | VAL | A | 204 | 14.135 | 39.055 | 27.911 | 1.00 | 51.02 | MOLA N |
| ATOM | 416 | CA | VAL | A | 204 | 13.759 | 38.438 | 26.643 | 1.00 | 51.45 | MOLA C |
| ATOM | 417 | C | VAL | A | 204 | 12.833 | 39.406 | 25.907 | 1.00 | 52.25 | MOLA C |
| ATOM | 418 | O | VAL | A | 204 | 11.733 | 39.703 | 26.383 | 1.00 | 51.24 | MOLA O |
| ATOM | 419 | CB | VAL | A | 204 | 13.002 | 37.099 | 26.884 | 1.00 | 51.30 | MOLA C |
| ATOM | 420 | CG1 | VAL | A | 204 | 12.888 | 36.316 | 25.585 | 1.00 | 51.03 | MOLA C |
| ATOM | 421 | CG2 | VAL | A | 204 | 13.714 | 36.277 | 27.951 | 1.00 | 49.87 | MOLA C |
| TER | 422 | | VAL | A | 204 | | | | | | |
| ATOM | 423 | N | ASN | A | 206 | 11.893 | 39.057 | 22.432 | 1.00 | 58.62 | MOLA N |
| ATOM | 424 | CA | ASN | A | 206 | 11.044 | 38.361 | 21.472 | 1.00 | 61.28 | MOLA C |
| ATOM | 425 | C | ASN | A | 206 | 10.972 | 36.875 | 21.784 | 1.00 | 62.28 | MOLA C |
| ATOM | 426 | O | ASN | A | 206 | 11.893 | 36.306 | 22.358 | 1.00 | 61.51 | MOLA O |
| ATOM | 427 | CB | ASN | A | 206 | 11.563 | 38.567 | 20.047 | 1.00 | 62.35 | MOLA C |
| ATOM | 428 | CG | ASN | A | 206 | 12.836 | 37.786 | 19.762 | 1.00 | 64.37 | MOLA C |
| ATOM | 429 | ND2 | ASN | A | 206 | 13.938 | 38.503 | 19.568 | 1.00 | 63.66 | MOLA N |
| ATOM | 430 | OD1 | ASN | A | 206 | 12.830 | 36.550 | 19.714 | 1.00 | 66.42 | MOLA O |
| ATOM | 431 | N | LYS | A | 207 | 9.874 | 36.247 | 21.382 | 1.00 | 64.56 | MOLA N |
| ATOM | 432 | CA | LYS | A | 207 | 9.665 | 34.835 | 21.650 | 1.00 | 67.76 | MOLA C |
| ATOM | 433 | C | LYS | A | 207 | 10.820 | 33.916 | 21.265 | 1.00 | 69.11 | MOLA C |
| ATOM | 434 | O | LYS | A | 207 | 11.114 | 32.961 | 21.980 | 1.00 | 70.16 | MOLA O |
| ATOM | 435 | CB | LYS | A | 207 | 8.383 | 34.345 | 20.964 | 1.00 | 69.17 | MOLA C |
| ATOM | 436 | CG | LYS | A | 207 | 8.459 | 34.292 | 19.448 | 1.00 | 71.04 | MOLA C |
| ATOM | 437 | CD | LYS | A | 207 | 7.342 | 33.438 | 18.855 | 1.00 | 71.83 | MOLA C |
| ATOM | 438 | CE | LYS | A | 207 | 7.503 | 33.315 | 17.342 | 1.00 | 72.12 | MOLA C |
| ATOM | 439 | NZ | LYS | A | 207 | 6.622 | 32.280 | 16.741 | 1.00 | 71.59 | MOLA N |
| ATOM | 440 | N | ASP | A | 208 | 11.490 | 34.191 | 20.153 | 1.00 | 69.96 | MOLA N |
| ATOM | 441 | CA | ASP | A | 208 | 12.578 | 33.311 | 19.736 | 1.00 | 71.00 | MOLA C |
| ATOM | 442 | C | ASP | A | 208 | 13.963 | 33.593 | 20.305 | 1.00 | 70.04 | MOLA C |
| ATOM | 443 | O | ASP | A | 208 | 14.865 | 32.765 | 20.176 | 1.00 | 70.71 | MOLA O |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 444 | CB | ASP | A | 208 | 12.649 | 33.241 | 18.207 | 1.00 | 72.93 | MOLA C |
| ATOM | 445 | CG | ASP | A | 208 | 11.652 | 32.244 | 17.622 | 1.00 | 74.34 | MOLA C |
| ATOM | 446 | OD1 | ASP | A | 208 | 10.427 | 32.488 | 17.718 | 1.00 | 75.62 | MOLA O |
| ATOM | 447 | OD2 | ASP | A | 208 | 12.099 | 31.210 | 17.075 | 1.00 | 74.01 | MOLA O |
| ATOM | 448 | N | GLU | A | 209 | 14.142 | 34.743 | 20.943 | 1.00 | 68.24 | MOLA N |
| ATOM | 449 | CA | GLU | A | 209 | 15.439 | 35.069 | 21.524 | 1.00 | 66.39 | MOLA C |
| ATOM | 450 | C | GLU | A | 209 | 15.704 | 34.181 | 22.738 | 1.00 | 64.12 | MOLA C |
| ATOM | 451 | O | GLU | A | 209 | 16.810 | 34.144 | 23.264 | 1.00 | 63.41 | MOLA O |
| ATOM | 452 | CB | GLU | A | 209 | 15.480 | 36.533 | 21.961 | 1.00 | 68.62 | MOLA C |
| ATOM | 453 | CG | GLU | A | 209 | 16.885 | 37.051 | 22.262 | 1.00 | 70.98 | MOLA C |
| ATOM | 454 | CD | GLU | A | 209 | 16.885 | 38.328 | 23.087 | 1.00 | 72.67 | MOLA C |
| ATOM | 455 | OE1 | GLU | A | 209 | 16.075 | 39.235 | 22.784 | 1.00 | 73.94 | MOLA O |
| ATOM | 456 | OE2 | GLU | A | 209 | 17.703 | 38.422 | 24.032 | 1.00 | 72.27 | MOLA O |
| ATOM | 457 | N | VAL | A | 210 | 14.678 | 33.468 | 23.187 | 1.00 | 62.12 | MOLA N |
| ATOM | 458 | CA | VAL | A | 210 | 14.827 | 32.599 | 24.344 | 1.00 | 60.12 | MOLA C |
| ATOM | 459 | C | VAL | A | 210 | 15.748 | 31.421 | 24.030 | 1.00 | 58.02 | MOLA C |
| ATOM | 460 | O | VAL | A | 210 | 16.470 | 30.932 | 24.904 | 1.00 | 57.88 | MOLA O |
| ATOM | 461 | CB | VAL | A | 210 | 13.447 | 32.054 | 24.834 | 1.00 | 60.55 | MOLA C |
| ATOM | 462 | CG1 | VAL | A | 210 | 12.452 | 33.195 | 24.951 | 1.00 | 59.76 | MOLA C |
| ATOM | 463 | CG2 | VAL | A | 210 | 12.929 | 30.974 | 23.895 | 1.00 | 58.85 | MOLA C |
| ATOM | 464 | N | TYR | A | 211 | 15.731 | 30.975 | 22.780 | 1.00 | 55.45 | MOLA N |
| ATOM | 465 | CA | TYR | A | 211 | 16.552 | 29.848 | 22.376 | 1.00 | 54.57 | MOLA C |
| ATOM | 466 | C | TYR | A | 211 | 18.035 | 30.082 | 22.643 | 1.00 | 55.54 | MOLA C |
| ATOM | 467 | O | TYR | A | 211 | 18.725 | 29.207 | 23.167 | 1.00 | 55.45 | MOLA O |
| ATOM | 468 | CB | TYR | A | 211 | 16.324 | 29.534 | 20.896 | 1.00 | 52.19 | MOLA C |
| ATOM | 469 | CG | TYR | A | 211 | 16.888 | 28.197 | 20.475 | 1.00 | 50.94 | MOLA C |
| ATOM | 470 | CD1 | TYR | A | 211 | 18.249 | 28.030 | 20.238 | 1.00 | 50.65 | MOLA C |
| ATOM | 471 | CD2 | TYR | A | 211 | 16.059 | 27.091 | 20.339 | 1.00 | 50.08 | MOLA C |
| ATOM | 472 | CE1 | TYR | A | 211 | 18.762 | 26.801 | 19.879 | 1.00 | 50.18 | MOLA C |
| ATOM | 473 | CE2 | TYR | A | 211 | 16.562 | 25.862 | 19.981 | 1.00 | 49.81 | MOLA C |
| ATOM | 474 | CZ | TYR | A | 211 | 17.909 | 25.717 | 19.751 | 1.00 | 50.22 | MOLA C |
| ATOM | 475 | OH | TYR | A | 211 | 18.396 | 24.476 | 19.394 | 1.00 | 50.86 | MOLA O |
| ATOM | 476 | N | GLN | A | 212 | 18.530 | 31.260 | 22.286 | 1.00 | 56.74 | MOLA N |
| ATOM | 477 | CA | GLN | A | 212 | 19.936 | 31.559 | 22.514 | 1.00 | 58.30 | MOLA C |
| ATOM | 478 | C | GLN | A | 212 | 20.189 | 31.624 | 24.012 | 1.00 | 57.37 | MOLA C |
| ATOM | 479 | O | GLN | A | 212 | 21.207 | 31.136 | 24.499 | 1.00 | 57.22 | MOLA O |
| ATOM | 480 | CB | GLN | A | 212 | 20.324 | 32.895 | 21.875 | 1.00 | 59.84 | MOLA C |
| ATOM | 481 | CG | GLN | A | 212 | 19.611 | 34.087 | 22.477 | 1.00 | 65.07 | MOLA C |
| ATOM | 482 | CD | GLN | A | 212 | 20.324 | 35.406 | 22.212 | 1.00 | 68.60 | MOLA C |
| ATOM | 483 | NE2 | GLN | A | 212 | 21.486 | 35.334 | 21.555 | 1.00 | 70.00 | MOLA N |
| ATOM | 484 | OE1 | GLN | A | 212 | 19.840 | 36.476 | 22.601 | 1.00 | 68.76 | MOLA O |
| ATOM | 485 | N | ILE | A | 213 | 19.252 | 32.220 | 24.741 | 1.00 | 56.40 | MOLA N |
| ATOM | 486 | CA | ILE | A | 213 | 19.391 | 32.362 | 26.182 | 1.00 | 55.48 | MOLA C |
| ATOM | 487 | C | ILE | A | 213 | 19.522 | 31.018 | 26.897 | 1.00 | 54.83 | MOLA C |
| ATOM | 488 | O | ILE | A | 213 | 20.467 | 30.806 | 27.651 | 1.00 | 54.25 | MOLA O |
| ATOM | 489 | CB | ILE | A | 213 | 18.206 | 33.141 | 26.771 | 1.00 | 55.06 | MOLA C |
| ATOM | 490 | CG1 | ILE | A | 213 | 18.096 | 34.496 | 26.074 | 1.00 | 56.77 | MOLA C |
| ATOM | 491 | CG2 | ILE | A | 213 | 18.403 | 33.345 | 28.263 | 1.00 | 53.71 | MOLA C |
| ATOM | 492 | CD1 | ILE | A | 213 | 16.877 | 35.310 | 26.476 | 1.00 | 57.11 | MOLA C |
| ATOM | 493 | N | LEU | A | 214 | 18.586 | 30.109 | 26.660 | 1.00 | 53.16 | MOLA N |
| ATOM | 494 | CA | LEU | A | 214 | 18.653 | 28.815 | 27.312 | 1.00 | 52.88 | MOLA C |
| ATOM | 495 | C | LEU | A | 214 | 19.796 | 27.949 | 26.810 | 1.00 | 52.21 | MOLA C |
| ATOM | 496 | O | LEU | A | 214 | 20.373 | 27.172 | 27.570 | 1.00 | 52.35 | MOLA O |
| ATOM | 497 | CB | LEU | A | 214 | 17.314 | 28.085 | 27.172 | 1.00 | 53.39 | MOLA C |
| ATOM | 498 | CG | LEU | A | 214 | 16.302 | 28.649 | 28.174 | 1.00 | 53.49 | MOLA C |
| ATOM | 499 | CD1 | LEU | A | 214 | 14.970 | 27.984 | 28.031 | 1.00 | 52.96 | MOLA C |
| ATOM | 500 | CD2 | LEU | A | 214 | 16.839 | 28.444 | 29.579 | 1.00 | 53.39 | MOLA C |
| ATOM | 501 | N | GLU | A | 215 | 20.132 | 28.091 | 25.533 | 1.00 | 52.22 | MOLA N |
| ATOM | 502 | CA | GLU | A | 215 | 21.221 | 27.321 | 24.948 | 1.00 | 51.97 | MOLA C |
| ATOM | 503 | C | GLU | A | 215 | 22.525 | 27.607 | 25.704 | 1.00 | 51.01 | MOLA C |
| ATOM | 504 | O | GLU | A | 215 | 23.251 | 26.680 | 26.071 | 1.00 | 49.85 | MOLA O |
| ATOM | 505 | CB | GLU | A | 215 | 21.361 | 27.665 | 23.465 | 1.00 | 53.98 | MOLA C |
| ATOM | 506 | CG | GLU | A | 215 | 22.478 | 26.933 | 22.744 | 1.00 | 56.54 | MOLA C |
| ATOM | 507 | CD | GLU | A | 215 | 22.425 | 27.148 | 21.241 | 1.00 | 58.68 | MOLA C |
| ATOM | 508 | OE1 | GLU | A | 215 | 22.336 | 28.320 | 20.811 | 1.00 | 59.72 | MOLA O |
| ATOM | 509 | OE2 | GLU | A | 215 | 22.470 | 26.147 | 20.488 | 1.00 | 59.50 | MOLA O |
| ATOM | 510 | N | LYS | A | 216 | 22.812 | 28.884 | 25.946 | 1.00 | 49.66 | MOLA N |
| ATOM | 511 | CA | LYS | A | 216 | 24.011 | 29.255 | 26.692 | 1.00 | 50.44 | MOLA C |
| ATOM | 512 | C | LYS | A | 216 | 23.900 | 28.639 | 28.080 | 1.00 | 49.50 | MOLA C |
| ATOM | 513 | O | LYS | A | 216 | 24.868 | 28.102 | 28.618 | 1.00 | 48.36 | MOLA O |
| ATOM | 514 | CB | LYS | A | 216 | 24.115 | 30.777 | 26.830 | 1.00 | 52.72 | MOLA C |
| ATOM | 515 | CG | LYS | A | 216 | 24.268 | 31.517 | 25.508 | 1.00 | 55.91 | MOLA C |
| ATOM | 516 | CD | LYS | A | 216 | 24.451 | 33.016 | 25.724 | 1.00 | 57.56 | MOLA C |
| ATOM | 517 | CE | LYS | A | 216 | 24.585 | 33.750 | 24.390 | 1.00 | 58.92 | MOLA C |
| ATOM | 518 | NZ | LYS | A | 216 | 24.860 | 35.209 | 24.557 | 1.00 | 59.48 | MOLA N |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 519 | N | GLY | A | 217 | 22.701 | 28.724 | 28.648 | 1.00 | 48.30 | MOLA N |
| ATOM | 520 | CA | GLY | A | 217 | 22.459 | 28.173 | 29.965 | 1.00 | 49.00 | MOLA C |
| ATOM | 521 | C | GLY | A | 217 | 22.757 | 26.688 | 30.033 | 1.00 | 49.19 | MOLA C |
| ATOM | 522 | O | GLY | A | 217 | 23.328 | 26.198 | 31.010 | 1.00 | 48.36 | MOLA O |
| ATOM | 523 | N | ALA | A | 218 | 22.371 | 25.963 | 28.992 | 1.00 | 48.74 | MOLA N |
| ATOM | 524 | CA | ALA | A | 218 | 22.609 | 24.530 | 28.959 | 1.00 | 49.55 | MOLA C |
| ATOM | 525 | C | ALA | A | 218 | 24.104 | 24.231 | 28.943 | 1.00 | 50.19 | MOLA C |
| ATOM | 526 | O | ALA | A | 218 | 24.558 | 23.235 | 29.508 | 1.00 | 50.15 | MOLA O |
| ATOM | 527 | CB | ALA | A | 218 | 21.938 | 23.923 | 27.738 | 1.00 | 48.51 | MOLA C |
| ATOM | 528 | N | ALA | A | 219 | 24.867 | 25.104 | 28.294 | 1.00 | 50.75 | MOLA N |
| ATOM | 529 | CA | ALA | A | 219 | 26.311 | 24.936 | 28.193 | 1.00 | 51.93 | MOLA C |
| ATOM | 530 | C | ALA | A | 219 | 26.962 | 25.182 | 29.538 | 1.00 | 53.20 | MOLA C |
| ATOM | 531 | O | ALA | A | 219 | 27.771 | 24.381 | 30.009 | 1.00 | 53.31 | MOLA O |
| ATOM | 532 | CB | ALA | A | 219 | 26.872 | 25.901 | 27.164 | 1.00 | 52.56 | MOLA C |
| ATOM | 533 | N | LYS | A | 220 | 26.600 | 26.307 | 30.142 | 1.00 | 54.19 | MOLA N |
| ATOM | 534 | CA | LYS | A | 220 | 27.114 | 26.699 | 31.444 | 1.00 | 56.74 | MOLA C |
| ATOM | 535 | C | LYS | A | 220 | 26.836 | 25.566 | 32.434 | 1.00 | 57.57 | MOLA C |
| ATOM | 536 | O | LYS | A | 220 | 27.625 | 25.300 | 33.344 | 1.00 | 57.68 | MOLA O |
| ATOM | 537 | CB | LYS | A | 220 | 26.401 | 27.970 | 31.909 | 1.00 | 57.36 | MOLA C |
| ATOM | 538 | CG | LYS | A | 220 | 27.021 | 28.654 | 33.107 | 1.00 | 58.80 | MOLA C |
| ATOM | 539 | CD | LYS | A | 220 | 28.061 | 29.673 | 32.675 | 1.00 | 60.73 | MOLA C |
| ATOM | 540 | CE | LYS | A | 220 | 28.434 | 30.582 | 33.835 | 1.00 | 63.29 | MOLA C |
| ATOM | 541 | NZ | LYS | A | 220 | 29.493 | 31.564 | 33.465 | 1.00 | 65.69 | MOLA N |
| ATOM | 542 | N | ARG | A | 221 | 25.703 | 24.899 | 32.242 | 1.00 | 57.65 | MOLA N |
| ATOM | 543 | CA | ARG | A | 221 | 25.303 | 23.810 | 33.118 | 1.00 | 57.64 | MOLA C |
| ATOM | 544 | C | ARG | A | 221 | 26.253 | 22.637 | 32.903 | 1.00 | 57.30 | MOLA C |
| ATOM | 545 | O | ARG | A | 221 | 26.650 | 21.956 | 33.849 | 1.00 | 56.30 | MOLA O |
| ATOM | 546 | CB | ARG | A | 221 | 23.865 | 23.401 | 32.798 | 1.00 | 58.58 | MOLA C |
| ATOM | 547 | CG | ARG | A | 221 | 23.150 | 22.642 | 33.907 | 1.00 | 60.55 | MOLA C |
| ATOM | 548 | CD | ARG | A | 221 | 22.705 | 21.276 | 33.422 | 1.00 | 63.89 | MOLA C |
| ATOM | 549 | NE | ARG | A | 221 | 21.868 | 21.338 | 32.221 | 1.00 | 65.54 | MOLA N |
| ATOM | 550 | CZ | ARG | A | 221 | 20.587 | 21.704 | 32.203 | 1.00 | 65.15 | MOLA C |
| ATOM | 551 | NH1 | ARG | A | 221 | 19.964 | 22.051 | 33.326 | 1.00 | 65.24 | MOLA N |
| ATOM | 552 | NH2 | ARG | A | 221 | 19.921 | 21.694 | 31.057 | 1.00 | 63.89 | MOLA N |
| ATOM | 553 | N | THR | A | 222 | 26.624 | 22.418 | 31.645 | 1.00 | 55.86 | MOLA N |
| ATOM | 554 | CA | THR | A | 222 | 27.524 | 21.333 | 31.292 | 1.00 | 55.16 | MOLA C |
| ATOM | 555 | C | THR | A | 222 | 28.954 | 21.589 | 31.763 | 1.00 | 54.26 | MOLA C |
| ATOM | 556 | O | THR | A | 222 | 29.639 | 20.669 | 32.202 | 1.00 | 52.91 | MOLA O |
| ATOM | 557 | CB | THR | A | 222 | 27.542 | 21.115 | 29.777 | 1.00 | 56.10 | MOLA C |
| ATOM | 558 | CG2 | THR | A | 222 | 28.538 | 20.033 | 29.419 | 1.00 | 56.10 | MOLA C |
| ATOM | 559 | OG1 | THR | A | 222 | 26.236 | 20.733 | 29.330 | 1.00 | 56.64 | MOLA O |
| TER | 560 | | THR | A | 222 | | | | | | |
| ATOM | 561 | N | SER | A | 232 | 23.884 | 17.136 | 37.017 | 1.00 | 52.74 | MOLA N |
| ATOM | 562 | CA | SER | A | 232 | 22.457 | 17.462 | 37.017 | 1.00 | 51.30 | MOLA C |
| ATOM | 563 | C | SER | A | 232 | 21.596 | 16.518 | 37.855 | 1.00 | 49.34 | MOLA C |
| ATOM | 564 | O | SER | A | 232 | 20.612 | 16.943 | 38.456 | 1.00 | 48.92 | MOLA O |
| ATOM | 565 | CB | SER | A | 232 | 21.920 | 17.487 | 35.588 | 1.00 | 52.92 | MOLA C |
| ATOM | 566 | OG | SER | A | 232 | 22.405 | 18.624 | 34.888 | 1.00 | 57.03 | MOLA O |
| TER | 567 | | SER | A | 232 | | | | | | |
| ATOM | 568 | N | HIS | A | 236 | 19.259 | 20.716 | 42.084 | 1.00 | 37.46 | MOLA N |
| ATOM | 569 | CA | HIS | A | 236 | 17.986 | 21.318 | 41.761 | 1.00 | 34.56 | MOLA C |
| ATOM | 570 | C | HIS | A | 236 | 18.201 | 22.396 | 40.734 | 1.00 | 33.33 | MOLA C |
| ATOM | 571 | O | HIS | A | 236 | 19.085 | 23.234 | 40.870 | 1.00 | 32.33 | MOLA O |
| ATOM | 572 | CB | HIS | A | 236 | 17.341 | 21.932 | 43.001 | 1.00 | 34.14 | MOLA C |
| ATOM | 573 | CG | HIS | A | 236 | 17.243 | 20.990 | 44.156 | 1.00 | 32.77 | MOLA C |
| ATOM | 574 | CD2 | HIS | A | 236 | 17.415 | 21.188 | 45.482 | 1.00 | 30.39 | MOLA C |
| ATOM | 575 | ND1 | HIS | A | 236 | 16.927 | 19.657 | 44.001 | 1.00 | 32.74 | MOLA N |
| ATOM | 576 | CE1 | HIS | A | 236 | 16.908 | 19.074 | 45.187 | 1.00 | 32.19 | MOLA C |
| ATOM | 577 | NE2 | HIS | A | 236 | 17.201 | 19.981 | 46.102 | 1.00 | 31.95 | MOLA N |
| ATOM | 578 | N | SER | A | 237 | 17.373 | 22.360 | 39.697 | 1.00 | 33.27 | MOLA N |
| ATOM | 579 | CA | SER | A | 237 | 17.432 | 23.331 | 38.620 | 1.00 | 31.69 | MOLA C |
| ATOM | 580 | C | SER | A | 237 | 16.202 | 24.224 | 38.795 | 1.00 | 31.63 | MOLA C |
| ATOM | 581 | O | SER | A | 237 | 15.064 | 23.762 | 38.712 | 1.00 | 31.60 | MOLA O |
| ATOM | 582 | CB | SER | A | 237 | 17.387 | 22.603 | 37.278 | 1.00 | 31.26 | MOLA C |
| ATOM | 583 | OG | SER | A | 237 | 17.830 | 23.432 | 36.222 | 1.00 | 36.95 | MOLA O |
| ATOM | 584 | N | VAL | A | 238 | 16.424 | 25.500 | 39.072 | 1.00 | 30.04 | MOLA N |
| ATOM | 585 | CA | VAL | A | 238 | 15.302 | 26.398 | 39.244 | 1.00 | 29.67 | MOLA C |
| ATOM | 586 | C | VAL | A | 238 | 15.266 | 27.461 | 38.166 | 1.00 | 28.92 | MOLA C |
| ATOM | 587 | O | VAL | A | 238 | 16.093 | 28.374 | 38.149 | 1.00 | 27.20 | MOLA O |
| ATOM | 588 | CB | VAL | A | 238 | 15.330 | 27.073 | 40.624 | 1.00 | 30.72 | MOLA C |
| ATOM | 589 | CG1 | VAL | A | 238 | 14.262 | 28.123 | 40.701 | 1.00 | 29.20 | MOLA C |
| ATOM | 590 | CG2 | VAL | A | 238 | 15.082 | 26.035 | 41.716 | 1.00 | 33.25 | MOLA C |
| ATOM | 591 | N | PHE | A | 239 | 14.313 | 27.318 | 37.250 | 1.00 | 28.37 | MOLA N |
| ATOM | 592 | CA | PHE | A | 239 | 14.156 | 28.279 | 36.171 | 1.00 | 29.26 | MOLA C |
| ATOM | 593 | C | PHE | A | 239 | 12.991 | 29.192 | 36.535 | 1.00 | 30.00 | MOLA C |

TABLE 5-continued

Eg5 ligand binding site/compound 2 X-ray coordinates. 10 Angstrom shell of the binding pocket. Table 5 discloses residues 111-121, 123-141, 158-162, 169-172, 206-222 and 236-241 of SEQ ID NO: 1, respectively, in order of appearance.

| | | | | | | | | | | | |
|---|---|---|---|---|---|---|---|---|---|---|---|
| ATOM | 594 | O | PHE | A | 239 | 11.929 | 28.723 | 36.959 | 1.00 | 29.92 | MOLA O |
| ATOM | 595 | CB | PHE | A | 239 | 13.885 | 27.554 | 34.852 | 1.00 | 29.39 | MOLA C |
| ATOM | 596 | CG | PHE | A | 239 | 13.558 | 28.477 | 33.705 | 1.00 | 29.30 | MOLA C |
| ATOM | 597 | CD1 | PHE | A | 239 | 12.251 | 28.863 | 33.456 | 1.00 | 28.28 | MOLA C |
| ATOM | 598 | CD2 | PHE | A | 239 | 14.565 | 28.960 | 32.883 | 1.00 | 29.29 | MOLA C |
| ATOM | 599 | CE1 | PHE | A | 239 | 11.955 | 29.714 | 32.404 | 1.00 | 30.73 | MOLA C |
| ATOM | 600 | CE2 | PHE | A | 239 | 14.269 | 29.817 | 31.825 | 1.00 | 30.36 | MOLA C |
| ATOM | 601 | CZ | PHE | A | 239 | 12.967 | 30.192 | 31.587 | 1.00 | 29.26 | MOLA C |
| ATOM | 602 | N | SER | A | 240 | 13.186 | 30.493 | 36.373 | 1.00 | 30.04 | MOLA N |
| ATOM | 603 | CA | SER | A | 240 | 12.134 | 31.442 | 36.719 | 1.00 | 32.55 | MOLA C |
| ATOM | 604 | C | SER | A | 240 | 11.845 | 32.435 | 35.621 | 1.00 | 33.23 | MOLA C |
| ATOM | 605 | O | SER | A | 240 | 12.759 | 32.939 | 34.963 | 1.00 | 32.98 | MOLA O |
| ATOM | 606 | CB | SER | A | 240 | 12.495 | 32.215 | 37.995 | 1.00 | 32.81 | MOLA C |
| ATOM | 607 | OG | SER | A | 240 | 12.594 | 31.343 | 39.118 | 1.00 | 36.21 | MOLA O |
| ATOM | 608 | N | VAL | A | 241 | 10.559 | 32.701 | 35.430 | 1.00 | 33.54 | MOLA N |
| ATOM | 609 | CA | VAL | A | 241 | 10.092 | 33.661 | 34.442 | 1.00 | 34.61 | MOLA C |
| ATOM | 610 | C | VAL | A | 241 | 9.218 | 34.694 | 35.149 | 1.00 | 32.42 | MOLA C |
| ATOM | 611 | O | VAL | A | 241 | 8.264 | 34.361 | 35.854 | 1.00 | 30.59 | MOLA O |
| ATOM | 612 | CB | VAL | A | 241 | 9.284 | 32.967 | 33.303 | 1.00 | 37.08 | MOLA C |
| ATOM | 613 | CG1 | VAL | A | 241 | 8.213 | 33.894 | 32.777 | 1.00 | 40.17 | MOLA C |
| ATOM | 614 | CG2 | VAL | A | 241 | 10.203 | 32.638 | 32.160 | 1.00 | 41.42 | MOLA C |
| TER | 615 | | VAL | A | 241 | | | | | | |
| ATOM | 616 | N | LEU | A | 263 | 9.872 | 27.044 | 37.505 | 1.00 | 24.68 | MOLA N |
| ATOM | 617 | CA | LEU | A | 263 | 9.876 | 25.681 | 36.989 | 1.00 | 24.88 | MOLA C |
| ATOM | 618 | C | LEU | A | 263 | 11.102 | 24.945 | 37.546 | 1.00 | 26.25 | MOLA C |
| ATOM | 619 | O | LEU | A | 263 | 12.254 | 25.216 | 37.160 | 1.00 | 27.13 | MOLA O |
| ATOM | 620 | CB | LEU | A | 263 | 9.874 | 25.722 | 35.455 | 1.00 | 22.93 | MOLA C |
| ATOM | 621 | CG | LEU | A | 263 | 8.618 | 26.429 | 34.943 | 1.00 | 21.90 | MOLA C |
| ATOM | 622 | CD1 | LEU | A | 263 | 8.659 | 26.654 | 33.443 | 1.00 | 23.86 | MOLA C |
| ATOM | 623 | CD2 | LEU | A | 263 | 7.426 | 25.577 | 35.295 | 1.00 | 22.48 | MOLA C |
| ATOM | 624 | N | VAL | A | 264 | 10.829 | 24.009 | 38.449 | 1.00 | 25.37 | MOLA N |
| ATOM | 625 | CA | VAL | A | 264 | 11.856 | 23.255 | 39.157 | 1.00 | 26.39 | MOLA C |
| ATOM | 626 | C | VAL | A | 264 | 12.139 | 21.803 | 38.769 | 1.00 | 27.16 | MOLA C |
| ATOM | 627 | O | VAL | A | 264 | 11.270 | 20.939 | 38.908 | 1.00 | 28.14 | MOLA O |
| ATOM | 628 | CB | VAL | A | 264 | 11.536 | 23.251 | 40.666 | 1.00 | 25.95 | MOLA C |
| ATOM | 629 | CG1 | VAL | A | 264 | 12.727 | 22.740 | 41.458 | 1.00 | 26.55 | MOLA C |
| ATOM | 630 | CG2 | VAL | A | 264 | 11.143 | 24.643 | 41.104 | 1.00 | 26.08 | MOLA C |
| ATOM | 631 | N | ASP | A | 265 | 13.365 | 21.539 | 38.317 | 1.00 | 27.15 | MOLA N |
| ATOM | 632 | CA | ASP | A | 265 | 13.799 | 20.184 | 37.968 | 1.00 | 29.33 | MOLA C |
| ATOM | 633 | C | ASP | A | 265 | 14.607 | 19.729 | 39.195 | 1.00 | 29.00 | MOLA C |
| ATOM | 634 | O | ASP | A | 265 | 15.745 | 20.155 | 39.367 | 1.00 | 31.12 | MOLA O |
| ATOM | 635 | CB | ASP | A | 265 | 14.716 | 20.208 | 36.737 | 1.00 | 30.79 | MOLA C |
| ATOM | 636 | CG | ASP | A | 265 | 14.992 | 18.812 | 36.186 | 1.00 | 33.53 | MOLA C |
| ATOM | 637 | OD1 | ASP | A | 265 | 14.814 | 17.844 | 36.948 | 1.00 | 35.30 | MOLA O |
| ATOM | 638 | OD2 | ASP | A | 265 | 15.389 | 18.677 | 35.001 | 1.00 | 34.83 | MOLA O |
| END | | | | | | | | | | | |

Table 6. Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

TABLE 6

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | |
|---|---|---|---|---|---|---|---|---|---|---|
| ATOM | 1 | MG | MG | A3001 | 17.558 | 15.429 | 33.763 | 1.00 | 39.37 | COFAMG |
| TER | 2 | | MG | A3001 | | | | | | |
| ATOM | 3 | N1 | ADP | A4001 | 8.641 | 10.214 | 25.832 | 1.00 | 19.63 | COFA N |
| ATOM | 4 | C2 | ADP | A4001 | 9.672 | 10.143 | 24.964 | 1.00 | 29.43 | COFA C |
| ATOM | 5 | N3 | ADP | A4001 | 10.998 | 10.110 | 25.294 | 1.00 | 21.72 | COFA N |
| ATOM | 6 | C1* | ADP | A4001 | 13.807 | 10.054 | 26.640 | 1.00 | 24.67 | COFA C |
| ATOM | 7 | C4 | ADP | A4001 | 11.340 | 10.155 | 26.588 | 1.00 | 25.15 | COFA C |
| ATOM | 8 | C5 | ADP | A4001 | 10.292 | 10.242 | 27.617 | 1.00 | 31.74 | COFA C |
| ATOM | 9 | C6 | ADP | A4001 | 8.882 | 10.261 | 27.162 | 1.00 | 29.55 | COFA C |
| ATOM | 10 | N6 | ADP | A4001 | 7.899 | 10.350 | 28.082 | 1.00 | 27.36 | COFA N |
| ATOM | 11 | N7 | ADP | A4001 | 10.916 | 10.287 | 28.817 | 1.00 | 33.08 | COFA N |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | |
|---|---|---|---|---|---|---|---|---|---|---|
| ATOM | 12 | C8 | ADP | A4001 | 12.250 | 10.200 | 28.571 | 1.00 | 29.19 | COFA C |
| ATOM | 13 | N9 | ADP | A4001 | 12.484 | 10.129 | 27.245 | 1.00 | 33.30 | COFA N |
| ATOM | 14 | C2* | ADP | A4001 | 14.393 | 11.436 | 26.495 | 1.00 | 20.15 | COFA C |
| ATOM | 15 | O2* | ADP | A4001 | 13.957 | 12.124 | 25.310 | 1.00 | 34.17 | COFA O |
| ATOM | 16 | C3* | ADP | A4001 | 15.882 | 11.172 | 26.631 | 1.00 | 23.23 | COFA C |
| ATOM | 17 | O3* | ADP | A4001 | 16.482 | 10.695 | 25.427 | 1.00 | 26.55 | COFA O |
| ATOM | 18 | O1A | ADP | A4001 | 14.112 | 13.443 | 30.782 | 1.00 | 41.83 | COFA O |
| ATOM | 19 | O1B | ADP | A4001 | 14.600 | 12.362 | 34.049 | 1.00 | 25.36 | COFA O |
| ATOM | 20 | C4* | ADP | A4001 | 15.892 | 10.070 | 27.666 | 1.00 | 21.34 | COFA C |
| ATOM | 21 | O4* | ADP | A4001 | 14.595 | 9.474 | 27.667 | 1.00 | 23.81 | COFA O |
| ATOM | 22 | O2A | ADP | A4001 | 16.541 | 13.381 | 29.888 | 1.00 | 37.09 | COFA O |
| ATOM | 23 | O2B | ADP | A4001 | 15.639 | 14.355 | 32.961 | 1.00 | 35.57 | COFA O |
| ATOM | 24 | C5* | ADP | A4001 | 16.110 | 10.640 | 29.062 | 1.00 | 38.19 | COFA C |
| ATOM | 25 | O5* | ADP | A4001 | 15.013 | 11.440 | 29.522 | 1.00 | 38.09 | COFA O |
| ATOM | 26 | O3A | ADP | A4001 | 15.766 | 12.018 | 31.927 | 1.00 | 23.99 | COFA O |
| ATOM | 27 | O3B | ADP | A4001 | 17.085 | 12.523 | 33.921 | 1.00 | 34.66 | COFA O |
| ATOM | 28 | PA | ADP | A4001 | 15.361 | 12.676 | 30.501 | 1.00 | 36.53 | COFA P |
| ATOM | 29 | PB | ADP | A4001 | 15.766 | 12.874 | 33.291 | 1.00 | 28.78 | COFA P |
| TER | 30 | | ADP | A4001 | | | | | | |
| ATOM | 31 | C | LIG | A1001 | 19.225 | 23.970 | 23.276 | 1.00 | 33.65 | LIGA C |
| ATOM | 32 | C1 | LIG | A1001 | 16.017 | 25.035 | 27.391 | 1.00 | 32.60 | LIGA C |
| ATOM | 33 | C2 | LIG | A1001 | 15.848 | 24.282 | 26.110 | 1.00 | 41.53 | LIGA C |
| ATOM | 34 | C3 | LIG | A1001 | 15.161 | 24.866 | 28.416 | 1.00 | 34.30 | LIGA C |
| ATOM | 35 | C4 | LIG | A1001 | 15.424 | 25.466 | 29.587 | 1.00 | 29.32 | LIGA C |
| ATOM | 36 | C5 | LIG | A1001 | 16.538 | 26.195 | 29.677 | 1.00 | 22.03 | LIGA C |
| ATOM | 37 | C6 | LIG | A1001 | 17.286 | 26.269 | 28.652 | 1.00 | 42.31 | LIGA C |
| ATOM | 38 | C7 | LIG | A1001 | 17.052 | 25.730 | 27.601 | 1.00 | 43.54 | LIGA C |
| ATOM | 39 | N8 | LIG | A1001 | 16.820 | 24.067 | 25.195 | 1.00 | 48.45 | LIGA N |
| ATOM | 40 | C9 | LIG | A1001 | 16.294 | 23.337 | 24.179 | 1.00 | 49.51 | LIGA C |
| ATOM | 41 | C10 | LIG | A1001 | 17.013 | 22.847 | 22.971 | 1.00 | 37.95 | LIGA C |
| ATOM | 42 | N11 | LIG | A1001 | 17.567 | 21.498 | 23.203 | 1.00 | 46.47 | LIGA N |
| ATOM | 43 | C12 | LIG | A1001 | 17.064 | 20.485 | 22.504 | 1.00 | 53.25 | LIGA C |
| ATOM | 44 | O13 | LIG | A1001 | 16.160 | 20.711 | 21.719 | 1.00 | 65.10 | LIGA O |
| ATOM | 45 | C14 | LIG | A1001 | 17.582 | 19.078 | 22.664 | 1.00 | 58.39 | LIGA C |
| ATOM | 46 | C15 | LIG | A1001 | 18.625 | 21.389 | 24.203 | 1.00 | 46.94 | LIGA C |
| ATOM | 47 | C16 | LIG | A1001 | 17.927 | 21.351 | 25.558 | 1.00 | 33.87 | LIGA C |
| ATOM | 48 | C17 | LIG | A1001 | 17.651 | 19.935 | 26.024 | 1.00 | 27.45 | LIGA C |
| ATOM | 49 | N18 | LIG | A1001 | 17.422 | 20.013 | 27.452 | 1.00 | 30.80 | LIGA N |
| ATOM | 50 | C19 | LIG | A1001 | 18.024 | 23.869 | 22.453 | 1.00 | 33.41 | LIGA C |
| ATOM | 51 | C20 | LIG | A1001 | 17.309 | 25.214 | 22.415 | 1.00 | 33.08 | LIGA C |
| ATOM | 52 | C21 | LIG | A1001 | 18.438 | 23.469 | 21.045 | 1.00 | 32.59 | LIGA C |
| ATOM | 53 | N22 | LIG | A1001 | 14.992 | 23.098 | 24.435 | 1.00 | 56.25 | LIGA N |
| ATOM | 54 | C23 | LIG | A1001 | 14.100 | 22.294 | 23.573 | 1.00 | 39.37 | LIGA C |
| ATOM | 55 | C24 | LIG | A1001 | 13.066 | 23.055 | 22.783 | 1.00 | 50.24 | LIGA C |
| ATOM | 56 | C25 | LIG | A1001 | 14.694 | 23.662 | 25.628 | 1.00 | 49.02 | LIGA C |
| ATOM | 57 | C26 | LIG | A1001 | 12.065 | 22.368 | 22.199 | 1.00 | 50.24 | LIGA C |
| ATOM | 58 | C27 | LIG | A1001 | 11.166 | 23.076 | 21.509 | 1.00 | 49.99 | LIGA C |
| ATOM | 59 | C28 | LIG | A1001 | 11.319 | 24.404 | 21.445 | 1.00 | 40.15 | LIGA C |
| ATOM | 60 | C29 | LIG | A1001 | 12.306 | 24.944 | 22.022 | 1.00 | 40.43 | LIGA C |
| ATOM | 61 | C30 | LIG | A1001 | 13.121 | 24.318 | 22.646 | 1.00 | 50.70 | LIGA C |
| ATOM | 62 | N31 | LIG | A1001 | 18.081 | 18.343 | 23.701 | 1.00 | 59.53 | LIGA N |
| ATOM | 63 | N33 | LIG | A1001 | 18.386 | 17.082 | 23.143 | 1.00 | 45.65 | LIGA N |
| ATOM | 64 | C35 | LIG | A1001 | 18.067 | 17.126 | 21.873 | 1.00 | 43.92 | LIGA C |
| ATOM | 65 | C36 | LIG | A1001 | 17.578 | 18.316 | 21.567 | 1.00 | 54.47 | LIGA C |
| ATOM | 66 | C37 | LIG | A1001 | 18.933 | 16.045 | 24.039 | 1.00 | 32.46 | LIGA C |
| ATOM | 67 | C38 | LIG | A1001 | 18.241 | 15.997 | 20.936 | 1.00 | 50.09 | LIGA C |
| TER | 68 | | LIG | A1001 | | | | | | |
| ATOM | 69 | N | GLN | A 78 | 3.579 | 15.600 | 24.673 | 1.00 | 30.73 | MOLA N |
| ATOM | 70 | CA | GLN | A 78 | 4.010 | 16.816 | 25.381 | 1.00 | 29.06 | MOLA C |
| ATOM | 71 | C | GLN | A 78 | 2.797 | 17.689 | 25.595 | 1.00 | 31.71 | MOLA C |
| ATOM | 72 | O | GLN | A 78 | 2.366 | 17.920 | 26.711 | 1.00 | 34.94 | MOLA O |
| ATOM | 73 | CB | GLN | A 78 | 5.056 | 17.566 | 24.572 | 1.00 | 27.93 | MOLA C |
| ATOM | 74 | CG | GLN | A 78 | 6.397 | 16.834 | 24.441 | 1.00 | 22.53 | MOLA C |
| ATOM | 75 | CD | GLN | A 78 | 7.059 | 16.657 | 25.807 | 1.00 | 35.07 | MOLA C |
| ATOM | 76 | NE2 | GLN | A 78 | 8.399 | 16.645 | 25.836 | 1.00 | 12.74 | MOLA N |
| ATOM | 77 | OE1 | GLN | A 78 | 6.368 | 16.555 | 26.831 | 1.00 | 41.40 | MOLA O |
| TER | 78 | | GLN | A 78 | | | | | | |
| ATOM | 79 | N | LYS | A 111 | 12.457 | 13.714 | 33.391 | 1.00 | 32.09 | MOLA N |
| ATOM | 80 | CA | LYS | A 111 | 12.298 | 15.005 | 34.049 | 1.00 | 30.94 | MOLA C |
| ATOM | 81 | C | LYS | A 111 | 12.537 | 16.105 | 33.046 | 1.00 | 31.61 | MOLA C |
| ATOM | 82 | O | LYS | A 111 | 11.621 | 16.870 | 32.705 | 1.00 | 32.58 | MOLA O |
| ATOM | 83 | CB | LYS | A 111 | 13.329 | 15.165 | 35.150 | 1.00 | 31.09 | MOLA C |
| ATOM | 84 | CG | LYS | A 111 | 12.935 | 14.598 | 36.492 | 1.00 | 29.98 | MOLA C |
| ATOM | 85 | CD | LYS | A 111 | 14.153 | 14.611 | 37.370 | 1.00 | 27.11 | MOLA C |
| ATOM | 86 | CE | LYS | A 111 | 14.973 | 13.358 | 37.257 | 1.00 | 32.97 | MOLA C |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 87 | NZ | LYS | A | 111 | 14.598 | 12.490 | 38.407 | 1.00 | 32.09 | MOLA N |
| ATOM | 88 | N | THR | A | 112 | 13.783 | 16.178 | 32.570 | 1.00 | 29.46 | MOLA N |
| ATOM | 89 | CA | THR | A | 112 | 14.159 | 17.238 | 31.653 | 1.00 | 25.95 | MOLA C |
| ATOM | 90 | C | THR | A | 112 | 13.357 | 17.122 | 30.359 | 1.00 | 29.83 | MOLA C |
| ATOM | 91 | O | THR | A | 112 | 12.987 | 18.151 | 29.755 | 1.00 | 35.34 | MOLA O |
| ATOM | 92 | CB | THR | A | 112 | 15.698 | 17.329 | 31.431 | 1.00 | 24.53 | MOLA C |
| ATOM | 93 | CG2 | THR | A | 112 | 16.084 | 18.495 | 30.543 | 1.00 | 2.00 | MOLA C |
| ATOM | 94 | OG1 | THR | A | 112 | 16.350 | 17.496 | 32.702 | 1.00 | 32.58 | MOLA O |
| ATOM | 95 | N | PHE | A | 113 | 13.064 | 15.897 | 29.929 | 1.00 | 27.54 | MOLA N |
| ATOM | 96 | CA | PHE | A | 113 | 12.241 | 15.740 | 28.739 | 1.00 | 27.65 | MOLA C |
| ATOM | 97 | C | PHE | A | 113 | 10.956 | 16.566 | 28.924 | 1.00 | 30.23 | MOLA C |
| ATOM | 98 | O | PHE | A | 113 | 10.586 | 17.381 | 28.073 | 1.00 | 29.41 | MOLA O |
| ATOM | 99 | CB | PHE | A | 113 | 11.870 | 14.285 | 28.513 | 1.00 | 24.75 | MOLA C |
| ATOM | 100 | CG | PHE | A | 113 | 11.004 | 14.065 | 27.318 | 1.00 | 22.45 | MOLA C |
| ATOM | 101 | CD1 | PHE | A | 113 | 11.564 | 13.999 | 26.042 | 1.00 | 24.43 | MOLA C |
| ATOM | 102 | CD2 | PHE | A | 113 | 9.622 | 13.930 | 27.458 | 1.00 | 20.05 | MOLA C |
| ATOM | 103 | CE1 | PHE | A | 113 | 10.749 | 13.810 | 24.911 | 1.00 | 27.65 | MOLA C |
| ATOM | 104 | CE2 | PHE | A | 113 | 8.805 | 13.713 | 26.350 | 1.00 | 12.49 | MOLA C |
| ATOM | 105 | CZ | PHE | A | 113 | 9.361 | 13.660 | 25.074 | 1.00 | 17.35 | MOLA C |
| ATOM | 106 | N | THR | A | 114 | 10.290 | 16.345 | 30.056 | 1.00 | 31.57 | MOLA N |
| ATOM | 107 | CA | THR | A | 114 | 9.024 | 16.984 | 30.336 | 1.00 | 30.22 | MOLA C |
| ATOM | 108 | C | THR | A | 114 | 9.201 | 18.467 | 30.406 | 1.00 | 32.12 | MOLA C |
| ATOM | 109 | O | THR | A | 114 | 8.387 | 19.238 | 29.870 | 1.00 | 35.90 | MOLA O |
| ATOM | 110 | CB | THR | A | 114 | 8.479 | 16.573 | 31.696 | 1.00 | 26.87 | MOLA C |
| ATOM | 111 | CG2 | THR | A | 114 | 7.142 | 17.237 | 31.925 | 1.00 | 24.43 | MOLA C |
| ATOM | 112 | OG1 | THR | A | 114 | 8.299 | 15.160 | 31.706 | 1.00 | 28.52 | MOLA O |
| ATOM | 113 | N | MET | A | 115 | 10.259 | 18.881 | 31.085 | 1.00 | 29.83 | MOLA N |
| ATOM | 114 | CA | MET | A | 115 | 10.325 | 20.267 | 31.417 | 1.00 | 26.52 | MOLA C |
| ATOM | 115 | C | MET | A | 115 | 10.905 | 21.105 | 30.305 | 1.00 | 27.47 | MOLA C |
| ATOM | 116 | O | MET | A | 115 | 10.616 | 22.287 | 30.226 | 1.00 | 29.77 | MOLA O |
| ATOM | 117 | CB | MET | A | 115 | 11.073 | 20.472 | 32.695 | 1.00 | 24.20 | MOLA C |
| ATOM | 118 | CG | MET | A | 115 | 10.499 | 21.594 | 33.452 | 1.00 | 21.17 | MOLA C |
| ATOM | 119 | SD | MET | A | 115 | 9.093 | 20.913 | 34.306 | 1.00 | 50.71 | MOLA S |
| ATOM | 120 | CE | MET | A | 115 | 8.768 | 22.028 | 35.678 | 1.00 | 35.67 | MOLA C |
| ATOM | 121 | N | GLU | A | 116 | 11.694 | 20.506 | 29.425 | 1.00 | 26.76 | MOLA N |
| ATOM | 122 | CA | GLU | A | 116 | 12.299 | 21.287 | 28.352 | 1.00 | 26.47 | MOLA C |
| ATOM | 123 | C | GLU | A | 116 | 11.997 | 20.699 | 26.955 | 1.00 | 26.80 | MOLA C |
| ATOM | 124 | O | GLU | A | 116 | 11.935 | 21.424 | 25.968 | 1.00 | 23.64 | MOLA O |
| ATOM | 125 | CB | GLU | A | 116 | 13.816 | 21.407 | 28.590 | 1.00 | 25.94 | MOLA C |
| ATOM | 126 | CG | GLU | A | 116 | 14.237 | 21.619 | 30.072 | 1.00 | 23.10 | MOLA C |
| ATOM | 127 | CD | GLU | A | 116 | 15.762 | 21.782 | 30.251 | 1.00 | 29.16 | MOLA C |
| ATOM | 128 | OE1 | GLU | A | 116 | 16.206 | 22.013 | 31.408 | 1.00 | 50.08 | MOLA O |
| ATOM | 129 | OE2 | GLU | A | 116 | 16.525 | 21.648 | 29.257 | 1.00 | 15.18 | MOLA O |
| ATOM | 130 | N | GLY | A | 117 | 11.847 | 19.372 | 26.882 | 1.00 | 27.97 | MOLA N |
| ATOM | 131 | CA | GLY | A | 117 | 11.560 | 18.684 | 25.633 | 1.00 | 28.38 | MOLA C |
| ATOM | 132 | C | GLY | A | 117 | 12.744 | 18.679 | 24.700 | 1.00 | 30.59 | MOLA C |
| ATOM | 133 | O | GLY | A | 117 | 13.872 | 18.848 | 25.141 | 1.00 | 29.46 | MOLA O |
| ATOM | 134 | N | GLU | A | 118 | 12.499 | 18.453 | 23.410 | 1.00 | 35.46 | MOLA N |
| ATOM | 135 | CA | GLU | A | 118 | 13.582 | 18.496 | 22.450 | 1.00 | 41.18 | MOLA C |
| ATOM | 136 | C | GLU | A | 118 | 13.167 | 19.000 | 21.114 | 1.00 | 45.41 | MOLA C |
| ATOM | 137 | O | GLU | A | 118 | 11.984 | 19.076 | 20.802 | 1.00 | 46.63 | MOLA O |
| ATOM | 138 | CB | GLU | A | 118 | 14.229 | 17.145 | 22.283 | 1.00 | 41.50 | MOLA C |
| ATOM | 139 | CG | GLU | A | 118 | 15.001 | 16.725 | 23.489 | 1.00 | 42.95 | MOLA C |
| ATOM | 140 | CD | GLU | A | 118 | 15.189 | 15.254 | 23.507 | 1.00 | 37.17 | MOLA C |
| ATOM | 141 | OE1 | GLU | A | 118 | 15.534 | 14.752 | 22.417 | 1.00 | 27.25 | MOLA O |
| ATOM | 142 | OE2 | GLU | A | 118 | 14.985 | 14.618 | 24.576 | 1.00 | 37.36 | MOLA O |
| ATOM | 143 | N | ARG | A | 119 | 14.196 | 19.339 | 20.348 | 1.00 | 51.78 | MOLA N |
| ATOM | 144 | CA | ARG | A | 119 | 14.106 | 19.834 | 18.991 | 1.00 | 57.16 | MOLA C |
| ATOM | 145 | C | ARG | A | 119 | 13.871 | 18.584 | 18.159 | 1.00 | 61.53 | MOLA C |
| ATOM | 146 | O | ARG | A | 119 | 14.769 | 17.726 | 18.089 | 1.00 | 62.56 | MOLA O |
| ATOM | 147 | CB | ARG | A | 119 | 15.468 | 20.416 | 18.617 | 1.00 | 55.94 | MOLA C |
| ATOM | 148 | CG | ARG | A | 119 | 15.474 | 21.506 | 17.615 | 1.00 | 54.14 | MOLA C |
| ATOM | 149 | CD | ARG | A | 119 | 15.014 | 22.785 | 18.260 | 1.00 | 54.59 | MOLA C |
| ATOM | 150 | NE | ARG | A | 119 | 13.642 | 23.068 | 17.887 | 1.00 | 63.36 | MOLA N |
| ATOM | 151 | CZ | ARG | A | 119 | 13.307 | 23.693 | 16.764 | 1.00 | 65.54 | MOLA C |
| ATOM | 152 | NH1 | ARG | A | 119 | 12.039 | 23.910 | 16.482 | 1.00 | 58.78 | MOLA N |
| ATOM | 153 | NH2 | ARG | A | 119 | 14.249 | 24.091 | 15.916 | 1.00 | 72.78 | MOLA N |
| ATOM | 154 | N | SER | A | 120 | 12.689 | 18.460 | 17.547 | 1.00 | 65.13 | MOLA N |
| ATOM | 155 | CA | SER | A | 120 | 12.403 | 17.302 | 16.686 | 1.00 | 68.37 | MOLA C |
| ATOM | 156 | C | SER | A | 120 | 13.575 | 16.988 | 15.749 | 1.00 | 72.26 | MOLA C |
| ATOM | 157 | O | SER | A | 120 | 14.034 | 17.843 | 14.979 | 1.00 | 73.37 | MOLA O |
| ATOM | 158 | CB | SER | A | 120 | 11.086 | 17.450 | 15.930 | 1.00 | 67.48 | MOLA C |
| ATOM | 159 | OG | SER | A | 120 | 10.014 | 17.281 | 16.832 | 1.00 | 64.35 | MOLA O |
| ATOM | 160 | N | PRO | A | 121 | 14.064 | 15.744 | 15.830 | 1.00 | 75.66 | MOLA N |
| ATOM | 161 | CA | PRO | A | 121 | 15.306 | 15.273 | 15.207 | 1.00 | 76.09 | MOLA C |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | | |
|---|---|---|---|---|---|---|---|---|---|---|---|---|
| ATOM | 162 | C | PRO | A | 121 | 15.234 | 15.187 | 13.700 | 1.00 | 76.02 | MOLA | C |
| ATOM | 163 | O | PRO | A | 121 | 14.848 | 14.137 | 13.190 | 1.00 | 76.23 | MOLA | O |
| ATOM | 164 | CB | PRO | A | 121 | 15.445 | 13.854 | 15.767 | 1.00 | 77.22 | MOLA | C |
| ATOM | 165 | CG | PRO | A | 121 | 14.005 | 13.424 | 16.054 | 1.00 | 77.56 | MOLA | C |
| ATOM | 166 | CD | PRO | A | 121 | 13.257 | 14.670 | 16.564 | 1.00 | 75.47 | MOLA | C |
| ATOM | 167 | N | ASN | A | 122 | 15.608 | 16.260 | 13.002 | 1.00 | 76.21 | MOLA | N |
| ATOM | 168 | CA | ASN | A | 122 | 15.642 | 16.279 | 11.512 | 1.00 | 78.16 | MOLA | C |
| ATOM | 169 | C | ASN | A | 122 | 14.368 | 16.830 | 10.822 | 1.00 | 77.82 | MOLA | C |
| ATOM | 170 | O | ASN | A | 122 | 14.451 | 17.451 | 9.740 | 1.00 | 77.49 | MOLA | O |
| ATOM | 171 | CB | ASN | A | 122 | 16.074 | 14.915 | 10.904 | 1.00 | 78.34 | MOLA | C |
| ATOM | 172 | CG | ASN | A | 122 | 17.587 | 14.630 | 11.066 | 1.00 | 80.48 | MOLA | C |
| ATOM | 173 | ND2 | ASN | A | 122 | 17.910 | 13.624 | 11.878 | 1.00 | 78.33 | MOLA | N |
| ATOM | 174 | OD1 | ASN | A | 122 | 18.442 | 15.290 | 10.451 | 1.00 | 73.49 | MOLA | O |
| TER | 175 | | ASN | A | 122 | | | | | | | |
| ATOM | 176 | N | TYR | A | 125 | 10.137 | 21.690 | 12.150 | 1.00 | 64.93 | MOLA | N |
| ATOM | 177 | CA | TYR | A | 125 | 9.156 | 22.700 | 12.500 | 1.00 | 61.98 | MOLA | C |
| ATOM | 178 | C | TYR | A | 125 | 9.933 | 23.811 | 13.174 | 1.00 | 61.48 | MOLA | C |
| ATOM | 179 | O | TYR | A | 125 | 11.087 | 23.599 | 13.559 | 1.00 | 61.50 | MOLA | O |
| ATOM | 180 | CB | TYR | A | 125 | 8.173 | 22.168 | 13.518 | 1.00 | 60.05 | MOLA | C |
| ATOM | 181 | CG | TYR | A | 125 | 7.826 | 20.712 | 13.394 | 1.00 | 56.90 | MOLA | C |
| ATOM | 182 | CD1 | TYR | A | 125 | 6.496 | 20.289 | 13.504 | 1.00 | 40.52 | MOLA | C |
| ATOM | 183 | CD2 | TYR | A | 125 | 8.815 | 19.752 | 13.183 | 1.00 | 54.54 | MOLA | C |
| ATOM | 184 | CE1 | TYR | A | 125 | 6.155 | 18.947 | 13.435 | 1.00 | 25.84 | MOLA | C |
| ATOM | 185 | CE2 | TYR | A | 125 | 8.493 | 18.404 | 13.099 | 1.00 | 49.97 | MOLA | C |
| ATOM | 186 | CZ | TYR | A | 125 | 7.153 | 17.998 | 13.229 | 1.00 | 50.92 | MOLA | C |
| ATOM | 187 | OH | TYR | A | 125 | 6.809 | 16.646 | 13.132 | 1.00 | 53.78 | MOLA | O |
| ATOM | 188 | N | THR | A | 126 | 9.328 | 24.988 | 13.328 | 1.00 | 61.27 | MOLA | N |
| ATOM | 189 | CA | THR | A | 126 | 9.948 | 26.026 | 14.167 | 1.00 | 63.03 | MOLA | C |
| ATOM | 190 | C | THR | A | 126 | 9.962 | 25.558 | 15.612 | 1.00 | 63.76 | MOLA | C |
| ATOM | 191 | O | THR | A | 126 | 9.439 | 24.489 | 15.934 | 1.00 | 65.75 | MOLA | O |
| ATOM | 192 | CB | THR | A | 126 | 9.194 | 27.361 | 14.140 | 1.00 | 63.25 | MOLA | C |
| ATOM | 193 | CG2 | THR | A | 126 | 10.026 | 28.445 | 13.447 | 1.00 | 59.84 | MOLA | C |
| ATOM | 194 | OG1 | THR | A | 126 | 7.934 | 27.183 | 13.476 | 1.00 | 64.86 | MOLA | O |
| ATOM | 195 | N | TRP | A | 127 | 10.549 | 26.341 | 16.502 | 1.00 | 62.83 | MOLA | N |
| ATOM | 196 | CA | TRP | A | 127 | 10.511 | 25.925 | 17.882 | 1.00 | 62.57 | MOLA | C |
| ATOM | 197 | C | TRP | A | 127 | 9.084 | 26.075 | 18.430 | 1.00 | 61.10 | MOLA | C |
| ATOM | 198 | O | TRP | A | 127 | 8.616 | 25.198 | 19.153 | 1.00 | 60.89 | MOLA | O |
| ATOM | 199 | CB | TRP | A | 127 | 11.570 | 26.645 | 18.705 | 1.00 | 63.96 | MOLA | C |
| ATOM | 200 | CG | TRP | A | 127 | 11.436 | 28.119 | 18.675 | 1.00 | 66.44 | MOLA | C |
| ATOM | 201 | CD1 | TRP | A | 127 | 12.019 | 28.974 | 17.789 | 1.00 | 65.78 | MOLA | C |
| ATOM | 202 | CD2 | TRP | A | 127 | 10.667 | 28.928 | 19.579 | 1.00 | 68.49 | MOLA | C |
| ATOM | 203 | CE2 | TRP | A | 127 | 10.833 | 30.266 | 19.181 | 1.00 | 75.72 | MOLA | C |
| ATOM | 204 | CE3 | TRP | A | 127 | 9.852 | 28.648 | 20.686 | 1.00 | 70.43 | MOLA | C |
| ATOM | 205 | NE1 | TRP | A | 127 | 11.664 | 30.266 | 18.087 | 1.00 | 78.27 | MOLA | N |
| ATOM | 206 | CZ2 | TRP | A | 127 | 10.206 | 31.331 | 19.846 | 1.00 | 71.27 | MOLA | C |
| ATOM | 207 | CZ3 | TRP | A | 127 | 9.232 | 29.703 | 21.348 | 1.00 | 69.09 | MOLA | C |
| ATOM | 208 | CH2 | TRP | A | 127 | 9.410 | 31.027 | 20.922 | 1.00 | 65.53 | MOLA | C |
| ATOM | 209 | N | GLU | A | 128 | 8.386 | 27.148 | 18.038 | 1.00 | 61.13 | MOLA | N |
| ATOM | 210 | CA | GLU | A | 128 | 6.980 | 27.407 | 18.442 | 1.00 | 60.92 | MOLA | C |
| ATOM | 211 | C | GLU | A | 128 | 6.126 | 26.199 | 18.111 | 1.00 | 60.60 | MOLA | C |
| ATOM | 212 | O | GLU | A | 128 | 5.118 | 25.898 | 18.749 | 1.00 | 61.80 | MOLA | O |
| ATOM | 213 | CB | GLU | A | 128 | 6.365 | 28.565 | 17.630 | 1.00 | 60.09 | MOLA | C |
| ATOM | 214 | CG | GLU | A | 128 | 6.940 | 29.959 | 17.825 | 1.00 | 63.61 | MOLA | C |
| ATOM | 215 | CD | GLU | A | 128 | 8.030 | 30.322 | 16.822 | 1.00 | 77.42 | MOLA | C |
| ATOM | 216 | OE1 | GLU | A | 128 | 8.475 | 31.490 | 16.840 | 1.00 | 85.03 | MOLA | O |
| ATOM | 217 | OE2 | GLU | A | 128 | 8.449 | 29.458 | 16.018 | 1.00 | 83.23 | MOLA | O |
| ATOM | 218 | N | GLU | A | 129 | 6.583 | 25.515 | 17.084 | 1.00 | 58.52 | MOLA | N |
| ATOM | 219 | CA | GLU | A | 129 | 5.818 | 24.588 | 16.319 | 1.00 | 56.41 | MOLA | C |
| ATOM | 220 | C | GLU | A | 129 | 6.080 | 23.123 | 16.730 | 1.00 | 55.46 | MOLA | C |
| ATOM | 221 | O | GLU | A | 129 | 5.259 | 22.230 | 16.472 | 1.00 | 55.07 | MOLA | O |
| ATOM | 222 | CB | GLU | A | 129 | 6.312 | 24.819 | 14.884 | 1.00 | 56.87 | MOLA | C |
| ATOM | 223 | CG | GLU | A | 129 | 5.299 | 24.706 | 13.785 | 1.00 | 64.29 | MOLA | C |
| ATOM | 224 | CD | GLU | A | 129 | 4.138 | 25.633 | 13.995 | 1.00 | 70.41 | MOLA | C |
| ATOM | 225 | OE1 | GLU | A | 129 | 3.578 | 26.102 | 12.981 | 1.00 | 69.77 | MOLA | O |
| ATOM | 226 | OE2 | GLU | A | 129 | 3.800 | 25.890 | 15.175 | 1.00 | 76.60 | MOLA | O |
| ATOM | 227 | N | ASP | A | 130 | 7.216 | 22.882 | 17.381 | 1.00 | 51.56 | MOLA | N |
| ATOM | 228 | CA | ASP | A | 130 | 7.730 | 21.530 | 17.547 | 1.00 | 48.19 | MOLA | C |
| ATOM | 229 | C | ASP | A | 130 | 6.896 | 20.749 | 18.508 | 1.00 | 47.68 | MOLA | C |
| ATOM | 230 | O | ASP | A | 130 | 6.603 | 21.244 | 19.577 | 1.00 | 51.23 | MOLA | O |
| ATOM | 231 | CB | ASP | A | 130 | 9.156 | 21.619 | 18.053 | 1.00 | 48.24 | MOLA | C |
| ATOM | 232 | CG | ASP | A | 130 | 9.907 | 20.347 | 17.887 | 1.00 | 43.77 | MOLA | C |
| ATOM | 233 | OD1 | ASP | A | 130 | 11.010 | 20.405 | 17.317 | 1.00 | 49.48 | MOLA | O |
| ATOM | 234 | OD2 | ASP | A | 130 | 9.410 | 19.302 | 18.327 | 1.00 | 46.43 | MOLA | O |
| ATOM | 235 | N | PRO | A | 131 | 6.466 | 19.536 | 18.121 | 1.00 | 47.74 | MOLA | N |
| ATOM | 236 | CA | PRO | A | 131 | 5.620 | 18.637 | 18.953 | 1.00 | 46.17 | MOLA | C |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 237 | C | PRO | A | 131 | 6.316 | 18.068 | 20.194 | 1.00 | 45.47 | MOLA C |
| ATOM | 238 | O | PRO | A | 131 | 5.662 | 17.941 | 21.245 | 1.00 | 45.60 | MOLA O |
| ATOM | 239 | CB | PRO | A | 131 | 5.259 | 17.505 | 17.993 | 1.00 | 45.49 | MOLA C |
| ATOM | 240 | CG | PRO | A | 131 | 5.534 | 18.064 | 16.610 | 1.00 | 45.28 | MOLA C |
| ATOM | 241 | CD | PRO | A | 131 | 6.721 | 18.959 | 16.794 | 1.00 | 46.78 | MOLA C |
| ATOM | 242 | N | LEU | A | 132 | 7.607 | 17.714 | 20.054 | 1.00 | 43.25 | MOLA N |
| ATOM | 243 | CA | LEU | A | 132 | 8.485 | 17.286 | 21.174 | 1.00 | 40.91 | MOLA C |
| ATOM | 244 | C | LEU | A | 132 | 8.815 | 18.414 | 22.212 | 1.00 | 43.37 | MOLA C |
| ATOM | 245 | O | LEU | A | 132 | 9.320 | 18.149 | 23.322 | 1.00 | 43.09 | MOLA O |
| ATOM | 246 | CB | LEU | A | 132 | 9.786 | 16.719 | 20.633 | 1.00 | 37.25 | MOLA C |
| ATOM | 247 | CG | LEU | A | 132 | 9.853 | 15.345 | 19.977 | 1.00 | 35.16 | MOLA C |
| ATOM | 248 | CD1 | LEU | A | 132 | 11.304 | 15.080 | 19.628 | 1.00 | 24.85 | MOLA C |
| ATOM | 249 | CD2 | LEU | A | 132 | 9.312 | 14.216 | 20.875 | 1.00 | 16.69 | MOLA C |
| ATOM | 250 | N | ALA | A | 133 | 8.527 | 19.665 | 21.841 | 1.00 | 42.08 | MOLA N |
| ATOM | 251 | CA | ALA | A | 133 | 8.669 | 20.812 | 22.735 | 1.00 | 38.53 | MOLA C |
| ATOM | 252 | C | ALA | A | 133 | 8.178 | 20.514 | 24.113 | 1.00 | 36.19 | MOLA C |
| ATOM | 253 | O | ALA | A | 133 | 7.030 | 20.154 | 24.274 | 1.00 | 35.70 | MOLA O |
| ATOM | 254 | CB | ALA | A | 133 | 7.859 | 21.975 | 22.201 | 1.00 | 37.88 | MOLA C |
| ATOM | 255 | N | GLY | A | 134 | 9.022 | 20.722 | 25.113 | 1.00 | 36.21 | MOLA N |
| ATOM | 256 | CA | GLY | A | 134 | 8.573 | 20.643 | 26.524 | 1.00 | 35.75 | MOLA C |
| ATOM | 257 | C | GLY | A | 134 | 7.820 | 21.868 | 27.061 | 1.00 | 33.83 | MOLA C |
| ATOM | 258 | O | GLY | A | 134 | 7.604 | 22.880 | 26.359 | 1.00 | 30.19 | MOLA O |
| ATOM | 259 | N | ILE | A | 135 | 7.442 | 21.768 | 28.332 | 1.00 | 32.53 | MOLA N |
| ATOM | 260 | CA | ILE | A | 135 | 6.730 | 22.818 | 29.048 | 1.00 | 29.60 | MOLA C |
| ATOM | 261 | C | ILE | A | 135 | 7.381 | 24.177 | 29.016 | 1.00 | 31.72 | MOLA C |
| ATOM | 262 | O | ILE | A | 135 | 6.741 | 25.153 | 28.569 | 1.00 | 34.54 | MOLA O |
| ATOM | 263 | CB | ILE | A | 135 | 6.606 | 22.482 | 30.499 | 1.00 | 30.81 | MOLA C |
| ATOM | 264 | CG1 | ILE | A | 135 | 5.609 | 21.345 | 30.679 | 1.00 | 27.10 | MOLA C |
| ATOM | 265 | CG2 | ILE | A | 135 | 6.161 | 23.725 | 31.294 | 1.00 | 25.97 | MOLA C |
| ATOM | 266 | CD1 | ILE | A | 135 | 5.613 | 20.812 | 32.061 | 1.00 | 13.72 | MOLA C |
| ATOM | 267 | N | ILE | A | 136 | 8.610 | 24.275 | 29.537 | 1.00 | 28.56 | MOLA N |
| ATOM | 268 | CA | ILE | A | 136 | 9.349 | 25.559 | 29.483 | 1.00 | 28.11 | MOLA C |
| ATOM | 269 | C | ILE | A | 136 | 9.127 | 26.391 | 28.186 | 1.00 | 28.33 | MOLA C |
| ATOM | 270 | O | ILE | A | 136 | 8.559 | 27.489 | 28.251 | 1.00 | 30.44 | MOLA O |
| ATOM | 271 | CB | ILE | A | 136 | 10.863 | 25.434 | 29.830 | 1.00 | 27.26 | MOLA C |
| ATOM | 272 | CG1 | ILE | A | 136 | 11.009 | 25.175 | 31.324 | 1.00 | 27.40 | MOLA C |
| ATOM | 273 | CG2 | ILE | A | 136 | 11.604 | 26.731 | 29.517 | 1.00 | 24.90 | MOLA C |
| ATOM | 274 | CD1 | ILE | A | 136 | 12.416 | 25.196 | 31.822 | 1.00 | 25.50 | MOLA C |
| ATOM | 275 | N | PRO | A | 137 | 9.532 | 25.881 | 27.011 | 1.00 | 26.84 | MOLA N |
| ATOM | 276 | CA | PRO | A | 137 | 9.321 | 26.747 | 25.845 | 1.00 | 27.34 | MOLA C |
| ATOM | 277 | C | PRO | A | 137 | 7.830 | 26.855 | 25.440 | 1.00 | 28.24 | MOLA C |
| ATOM | 278 | O | PRO | A | 137 | 7.410 | 27.882 | 24.906 | 1.00 | 27.64 | MOLA O |
| ATOM | 279 | CB | PRO | A | 137 | 10.096 | 26.025 | 24.742 | 1.00 | 28.18 | MOLA C |
| ATOM | 280 | CG | PRO | A | 137 | 9.952 | 24.568 | 25.072 | 1.00 | 23.64 | MOLA C |
| ATOM | 281 | CD | PRO | A | 137 | 10.092 | 24.577 | 26.623 | 1.00 | 27.65 | MOLA C |
| ATOM | 282 | N | ARG | A | 138 | 7.028 | 25.813 | 25.663 | 1.00 | 27.95 | MOLA N |
| ATOM | 283 | CA | ARG | A | 138 | 5.618 | 25.951 | 25.321 | 1.00 | 30.50 | MOLA C |
| ATOM | 284 | C | ARG | A | 138 | 5.022 | 27.152 | 26.073 | 1.00 | 33.14 | MOLA C |
| ATOM | 285 | O | ARG | A | 138 | 4.293 | 27.988 | 25.524 | 1.00 | 34.12 | MOLA O |
| ATOM | 286 | CB | ARG | A | 138 | 4.860 | 24.683 | 25.642 | 1.00 | 28.36 | MOLA C |
| ATOM | 287 | CG | ARG | A | 138 | 5.026 | 23.677 | 24.566 | 1.00 | 26.19 | MOLA C |
| ATOM | 288 | CD | ARG | A | 138 | 4.409 | 22.367 | 24.930 | 1.00 | 28.71 | MOLA C |
| ATOM | 289 | NE | ARG | A | 138 | 4.787 | 21.406 | 23.918 | 1.00 | 29.74 | MOLA N |
| ATOM | 290 | CZ | ARG | A | 138 | 4.000 | 20.978 | 22.939 | 1.00 | 29.03 | MOLA C |
| ATOM | 291 | NH1 | ARG | A | 138 | 2.742 | 21.395 | 22.834 | 1.00 | 36.95 | MOLA N |
| ATOM | 292 | NH2 | ARG | A | 138 | 4.477 | 20.093 | 22.066 | 1.00 | 51.01 | MOLA N |
| ATOM | 293 | N | THR | A | 139 | 5.386 | 27.239 | 27.334 | 1.00 | 33.02 | MOLA N |
| ATOM | 294 | CA | THR | A | 139 | 4.876 | 28.254 | 28.183 | 1.00 | 34.19 | MOLA C |
| ATOM | 295 | C | THR | A | 139 | 5.328 | 29.645 | 27.757 | 1.00 | 38.01 | MOLA C |
| ATOM | 296 | O | THR | A | 139 | 4.545 | 30.584 | 27.791 | 1.00 | 40.83 | MOLA O |
| ATOM | 297 | CB | THR | A | 139 | 5.307 | 27.944 | 29.586 | 1.00 | 32.20 | MOLA C |
| ATOM | 298 | CG2 | THR | A | 139 | 5.256 | 29.178 | 30.446 | 1.00 | 24.60 | MOLA C |
| ATOM | 299 | OG1 | THR | A | 139 | 4.410 | 26.961 | 30.099 | 1.00 | 35.50 | MOLA O |
| ATOM | 300 | N | LEU | A | 140 | 6.579 | 29.799 | 27.345 | 1.00 | 39.26 | MOLA N |
| ATOM | 301 | CA | LEU | A | 140 | 7.029 | 31.129 | 26.976 | 1.00 | 38.03 | MOLA C |
| ATOM | 302 | C | LEU | A | 140 | 6.132 | 31.619 | 25.859 | 1.00 | 39.51 | MOLA C |
| ATOM | 303 | O | LEU | A | 140 | 5.550 | 32.709 | 25.960 | 1.00 | 38.40 | MOLA O |
| ATOM | 304 | CB | LEU | A | 140 | 8.524 | 31.139 | 26.617 | 1.00 | 39.04 | MOLA C |
| ATOM | 305 | CG | LEU | A | 140 | 9.472 | 31.453 | 27.787 | 1.00 | 26.91 | MOLA C |
| ATOM | 306 | CD1 | LEU | A | 140 | 8.843 | 31.154 | 29.096 | 1.00 | 25.82 | MOLA C |
| ATOM | 307 | CD2 | LEU | A | 140 | 10.683 | 30.644 | 27.642 | 1.00 | 27.88 | MOLA C |
| ATOM | 308 | N | HIS | A | 141 | 5.980 | 30.776 | 24.831 | 1.00 | 41.16 | MOLA N |
| ATOM | 309 | CA | HIS | A | 141 | 5.055 | 31.021 | 23.710 | 1.00 | 42.59 | MOLA C |
| ATOM | 310 | C | HIS | A | 141 | 3.693 | 31.537 | 24.231 | 1.00 | 43.82 | MOLA C |
| ATOM | 311 | O | HIS | A | 141 | 3.410 | 32.749 | 24.156 | 1.00 | 44.22 | MOLA O |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 312 | CB | HIS | A | 141 | 4.891 | 29.747 | 22.864 | 1.00 | 40.91 | MOLA C |
| ATOM | 313 | CG | HIS | A | 141 | 4.452 | 29.988 | 21.447 | 1.00 | 43.27 | MOLA C |
| ATOM | 314 | CD2 | HIS | A | 141 | 5.100 | 30.544 | 20.393 | 1.00 | 53.75 | MOLA C |
| ATOM | 315 | ND1 | HIS | A | 141 | 3.213 | 29.609 | 20.972 | 1.00 | 42.50 | MOLA N |
| ATOM | 316 | CE1 | HIS | A | 141 | 3.115 | 29.926 | 19.692 | 1.00 | 36.73 | MOLA C |
| ATOM | 317 | NE2 | HIS | A | 141 | 4.247 | 30.493 | 19.313 | 1.00 | 35.42 | MOLA N |
| TER | 318 | | HIS | A | 141 | | | | | | |
| ATOM | 319 | N | VAL | A | 158 | 13.305 | 36.852 | 32.285 | 1.00 | 38.05 | MOLA N |
| ATOM | 320 | CA | VAL | A | 158 | 13.582 | 35.476 | 32.813 | 1.00 | 38.44 | MOLA C |
| ATOM | 321 | C | VAL | A | 158 | 14.977 | 35.126 | 33.415 | 1.00 | 40.53 | MOLA C |
| ATOM | 322 | O | VAL | A | 158 | 16.009 | 35.559 | 32.908 | 1.00 | 42.08 | MOLA O |
| ATOM | 323 | CB | VAL | A | 158 | 13.315 | 34.466 | 31.743 | 1.00 | 35.61 | MOLA C |
| ATOM | 324 | CG1 | VAL | A | 158 | 11.932 | 34.669 | 31.217 | 1.00 | 38.26 | MOLA C |
| ATOM | 325 | CG2 | VAL | A | 158 | 14.304 | 34.654 | 30.645 | 1.00 | 31.90 | MOLA C |
| ATOM | 326 | N | SER | A | 159 | 15.005 | 34.315 | 34.473 | 1.00 | 40.72 | MOLA N |
| ATOM | 327 | CA | SER | A | 159 | 16.279 | 33.920 | 35.088 | 1.00 | 43.10 | MOLA C |
| ATOM | 328 | C | SER | A | 159 | 16.421 | 32.411 | 35.188 | 1.00 | 43.20 | MOLA C |
| ATOM | 329 | O | SER | A | 159 | 15.529 | 31.752 | 35.678 | 1.00 | 45.99 | MOLA O |
| ATOM | 330 | CB | SER | A | 159 | 16.318 | 34.438 | 36.504 | 1.00 | 43.43 | MOLA C |
| ATOM | 331 | OG | SER | A | 159 | 15.131 | 33.993 | 37.148 | 1.00 | 46.97 | MOLA O |
| ATOM | 332 | N | LEU | A | 160 | 17.542 | 31.860 | 34.767 | 1.00 | 42.19 | MOLA N |
| ATOM | 333 | CA | LEU | A | 160 | 17.766 | 30.441 | 34.953 | 1.00 | 44.35 | MOLA C |
| ATOM | 334 | C | LEU | A | 160 | 19.023 | 30.140 | 35.757 | 1.00 | 46.06 | MOLA C |
| ATOM | 335 | O | LEU | A | 160 | 20.147 | 30.499 | 35.371 | 1.00 | 46.39 | MOLA O |
| ATOM | 336 | CB | LEU | A | 160 | 17.873 | 29.714 | 33.624 | 1.00 | 46.01 | MOLA C |
| ATOM | 337 | CG | LEU | A | 160 | 18.458 | 28.319 | 33.817 | 1.00 | 46.96 | MOLA C |
| ATOM | 338 | CD1 | LEU | A | 160 | 17.432 | 27.424 | 34.491 | 1.00 | 45.08 | MOLA C |
| ATOM | 339 | CD2 | LEU | A | 160 | 18.885 | 27.752 | 32.502 | 1.00 | 45.00 | MOLA C |
| ATOM | 340 | N | LEU | A | 161 | 18.828 | 29.448 | 36.866 | 1.00 | 44.74 | MOLA N |
| ATOM | 341 | CA | LEU | A | 161 | 19.927 | 29.143 | 37.721 | 1.00 | 45.55 | MOLA C |
| ATOM | 342 | C | LEU | A | 161 | 19.884 | 27.675 | 38.076 | 1.00 | 49.54 | MOLA C |
| ATOM | 343 | O | LEU | A | 161 | 18.943 | 26.955 | 37.739 | 1.00 | 52.44 | MOLA O |
| ATOM | 344 | CB | LEU | A | 161 | 19.862 | 29.986 | 38.982 | 1.00 | 44.78 | MOLA C |
| ATOM | 345 | CG | LEU | A | 161 | 18.860 | 29.524 | 40.036 | 1.00 | 40.96 | MOLA C |
| ATOM | 346 | CD1 | LEU | A | 161 | 19.354 | 28.302 | 40.752 | 1.00 | 42.59 | MOLA C |
| ATOM | 347 | CD2 | LEU | A | 161 | 18.668 | 30.621 | 41.006 | 1.00 | 29.68 | MOLA C |
| TER | 348 | | LEU | A | 161 | | | | | | |
| ATOM | 349 | N | LEU | A | 171 | 22.868 | 30.758 | 35.209 | 1.00 | 51.69 | MOLA N |
| ATOM | 350 | CA | LEU | A | 171 | 23.189 | 30.172 | 33.916 | 1.00 | 52.06 | MOLA C |
| ATOM | 351 | C | LEU | A | 171 | 22.999 | 31.140 | 32.792 | 1.00 | 52.86 | MOLA C |
| ATOM | 352 | O | LEU | A | 171 | 23.473 | 30.898 | 31.690 | 1.00 | 54.73 | MOLA O |
| ATOM | 353 | CB | LEU | A | 171 | 22.383 | 28.910 | 33.682 | 1.00 | 50.87 | MOLA C |
| ATOM | 354 | CG | LEU | A | 171 | 23.052 | 27.898 | 34.591 | 1.00 | 48.90 | MOLA C |
| ATOM | 355 | CD1 | LEU | A | 171 | 22.235 | 26.648 | 34.732 | 1.00 | 47.88 | MOLA C |
| ATOM | 356 | CD2 | LEU | A | 171 | 24.444 | 27.615 | 34.041 | 1.00 | 39.76 | MOLA C |
| ATOM | 357 | N | LEU | A | 172 | 22.334 | 32.252 | 33.080 | 1.00 | 53.67 | MOLA N |
| ATOM | 358 | CA | LEU | A | 172 | 22.047 | 33.235 | 32.049 | 1.00 | 53.56 | MOLA C |
| ATOM | 359 | C | LEU | A | 172 | 23.036 | 34.375 | 31.953 | 1.00 | 56.18 | MOLA C |
| ATOM | 360 | O | LEU | A | 172 | 22.756 | 35.333 | 31.243 | 1.00 | 55.95 | MOLA O |
| ATOM | 361 | CB | LEU | A | 172 | 20.654 | 33.825 | 32.245 | 1.00 | 54.21 | MOLA C |
| ATOM | 362 | CG | LEU | A | 172 | 19.473 | 33.153 | 31.553 | 1.00 | 40.42 | MOLA C |
| ATOM | 363 | CD1 | LEU | A | 172 | 19.896 | 32.682 | 30.204 | 1.00 | 44.11 | MOLA C |
| ATOM | 364 | CD2 | LEU | A | 172 | 19.024 | 32.021 | 32.362 | 1.00 | 47.51 | MOLA C |
| TER | 365 | | LEU | A | 172 | | | | | | |
| ATOM | 366 | N | ASP | A | 208 | 10.947 | 34.541 | 19.893 | 1.00 | 69.31 | MOLA N |
| ATOM | 367 | CA | ASP | A | 208 | 12.087 | 34.535 | 18.948 | 1.00 | 71.07 | MOLA C |
| ATOM | 368 | C | ASP | A | 208 | 13.383 | 34.968 | 19.579 | 1.00 | 70.75 | MOLA C |
| ATOM | 369 | O | ASP | A | 208 | 14.454 | 34.481 | 19.222 | 1.00 | 72.29 | MOLA O |
| ATOM | 370 | CB | ASP | A | 208 | 11.835 | 35.443 | 17.746 | 1.00 | 71.90 | MOLA C |
| ATOM | 371 | CG | ASP | A | 208 | 10.755 | 34.920 | 16.844 | 1.00 | 79.56 | MOLA C |
| ATOM | 372 | OD1 | ASP | A | 208 | 9.779 | 35.671 | 16.622 | 1.00 | 82.68 | MOLA O |
| ATOM | 373 | OD2 | ASP | A | 208 | 10.872 | 33.759 | 16.378 | 1.00 | 88.98 | MOLA O |
| ATOM | 374 | N | GLU | A | 209 | 13.289 | 35.941 | 20.470 | 1.00 | 69.71 | MOLA N |
| ATOM | 375 | CA | GLU | A | 209 | 14.427 | 36.328 | 21.264 | 1.00 | 67.75 | MOLA C |
| ATOM | 376 | C | GLU | A | 209 | 14.533 | 35.260 | 22.367 | 1.00 | 63.94 | MOLA C |
| ATOM | 377 | O | GLU | A | 209 | 15.609 | 35.048 | 22.952 | 1.00 | 63.72 | MOLA O |
| ATOM | 378 | CB | GLU | A | 209 | 14.218 | 37.736 | 21.818 | 1.00 | 68.26 | MOLA C |
| ATOM | 379 | CG | GLU | A | 209 | 15.390 | 38.284 | 22.603 | 1.00 | 75.22 | MOLA C |
| ATOM | 380 | CD | GLU | A | 209 | 15.036 | 39.555 | 23.346 | 1.00 | 84.21 | MOLA C |
| ATOM | 381 | OE1 | GLU | A | 209 | 14.194 | 40.328 | 22.827 | 1.00 | 75.22 | MOLA O |
| ATOM | 382 | OE2 | GLU | A | 209 | 15.605 | 39.773 | 24.444 | 1.00 | 94.29 | MOLA O |
| ATOM | 383 | N | VAL | A | 210 | 13.405 | 34.584 | 22.619 | 1.00 | 58.87 | MOLA N |
| ATOM | 384 | CA | VAL | A | 210 | 13.349 | 33.458 | 23.559 | 1.00 | 54.30 | MOLA C |
| ATOM | 385 | C | VAL | A | 210 | 14.266 | 32.336 | 23.121 | 1.00 | 52.18 | MOLA C |
| ATOM | 386 | O | VAL | A | 210 | 15.200 | 31.974 | 23.831 | 1.00 | 50.81 | MOLA O |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 387 | CB | VAL | A | 210 | 11.916 | 32.912 | 23.771 | 1.00 | 52.71 | MOLA C |
| ATOM | 388 | CG1 | VAL | A | 210 | 11.030 | 33.340 | 22.654 | 1.00 | 55.14 | MOLA C |
| ATOM | 389 | CG2 | VAL | A | 210 | 11.928 | 31.384 | 23.935 | 1.00 | 45.57 | MOLA C |
| ATOM | 390 | N | TYR | A | 211 | 14.022 | 31.798 | 21.941 | 1.00 | 51.26 | MOLA N |
| ATOM | 391 | CA | TYR | A | 211 | 14.861 | 30.716 | 21.491 | 1.00 | 50.18 | MOLA C |
| ATOM | 392 | C | TYR | A | 211 | 16.374 | 30.928 | 21.774 | 1.00 | 51.58 | MOLA C |
| ATOM | 393 | O | TYR | A | 211 | 17.044 | 29.970 | 22.178 | 1.00 | 52.38 | MOLA O |
| ATOM | 394 | CB | TYR | A | 211 | 14.584 | 30.363 | 20.040 | 1.00 | 48.21 | MOLA C |
| ATOM | 395 | CG | TYR | A | 211 | 15.377 | 29.175 | 19.582 | 1.00 | 46.75 | MOLA C |
| ATOM | 396 | CD1 | TYR | A | 211 | 16.662 | 29.341 | 19.035 | 1.00 | 49.00 | MOLA C |
| ATOM | 397 | CD2 | TYR | A | 211 | 14.864 | 27.873 | 19.700 | 1.00 | 41.83 | MOLA C |
| ATOM | 398 | CE1 | TYR | A | 211 | 17.420 | 28.237 | 18.607 | 1.00 | 53.26 | MOLA C |
| ATOM | 399 | CE2 | TYR | A | 211 | 15.619 | 26.755 | 19.278 | 1.00 | 48.74 | MOLA C |
| ATOM | 400 | CZ | TYR | A | 211 | 16.897 | 26.948 | 18.736 | 1.00 | 53.12 | MOLA C |
| ATOM | 401 | OH | TYR | A | 211 | 17.664 | 25.871 | 18.325 | 1.00 | 53.01 | MOLA O |
| ATOM | 402 | N | GLN | A | 212 | 16.930 | 32.139 | 21.625 | 1.00 | 51.92 | MOLA N |
| ATOM | 403 | CA | GLN | A | 212 | 18.376 | 32.276 | 21.919 | 1.00 | 51.34 | MOLA C |
| ATOM | 404 | C | GLN | A | 212 | 18.661 | 31.930 | 23.341 | 1.00 | 52.52 | MOLA C |
| ATOM | 405 | O | GLN | A | 212 | 19.446 | 31.041 | 23.624 | 1.00 | 55.89 | MOLA O |
| ATOM | 406 | CB | GLN | A | 212 | 18.931 | 33.662 | 21.709 | 1.00 | 50.64 | MOLA C |
| ATOM | 407 | CG | GLN | A | 212 | 19.341 | 33.943 | 20.332 | 1.00 | 51.72 | MOLA C |
| ATOM | 408 | CD | GLN | A | 212 | 18.201 | 34.505 | 19.610 | 1.00 | 62.20 | MOLA C |
| ATOM | 409 | NE2 | GLN | A | 212 | 18.459 | 35.102 | 18.448 | 1.00 | 74.08 | MOLA N |
| ATOM | 410 | OE1 | GLN | A | 212 | 17.067 | 34.436 | 20.099 | 1.00 | 72.97 | MOLA O |
| ATOM | 411 | N | ILE | A | 213 | 18.047 | 32.673 | 24.245 | 1.00 | 52.40 | MOLA N |
| ATOM | 412 | CA | ILE | A | 213 | 18.164 | 32.391 | 25.662 | 1.00 | 51.15 | MOLA C |
| ATOM | 413 | C | ILE | A | 213 | 18.237 | 30.888 | 25.918 | 1.00 | 47.80 | MOLA C |
| ATOM | 414 | O | ILE | A | 213 | 19.219 | 30.404 | 26.471 | 1.00 | 46.00 | MOLA O |
| ATOM | 415 | CB | ILE | A | 213 | 16.990 | 33.032 | 26.410 | 1.00 | 52.30 | MOLA C |
| ATOM | 416 | CG1 | ILE | A | 213 | 17.462 | 34.315 | 27.096 | 1.00 | 58.58 | MOLA C |
| ATOM | 417 | CG2 | ILE | A | 213 | 16.393 | 32.076 | 27.422 | 1.00 | 55.87 | MOLA C |
| ATOM | 418 | CD1 | ILE | A | 213 | 16.351 | 35.356 | 27.325 | 1.00 | 75.32 | MOLA C |
| ATOM | 419 | N | LEU | A | 214 | 17.215 | 30.154 | 25.480 | 1.00 | 45.71 | MOLA N |
| ATOM | 420 | CA | LEU | A | 214 | 17.157 | 28.713 | 25.720 | 1.00 | 42.79 | MOLA C |
| ATOM | 421 | C | LEU | A | 214 | 18.437 | 28.033 | 25.272 | 1.00 | 42.75 | MOLA C |
| ATOM | 422 | O | LEU | A | 214 | 18.900 | 27.119 | 25.946 | 1.00 | 42.76 | MOLA O |
| ATOM | 423 | CB | LEU | A | 214 | 15.894 | 28.080 | 25.121 | 1.00 | 41.71 | MOLA C |
| ATOM | 424 | CG | LEU | A | 214 | 14.639 | 28.685 | 25.788 | 1.00 | 37.56 | MOLA C |
| ATOM | 425 | CD1 | LEU | A | 214 | 13.381 | 27.846 | 25.652 | 1.00 | 15.00 | MOLA C |
| ATOM | 426 | CD2 | LEU | A | 214 | 14.909 | 28.899 | 27.245 | 1.00 | 28.22 | MOLA C |
| ATOM | 427 | N | GLU | A | 215 | 19.032 | 28.495 | 24.169 | 1.00 | 42.10 | MOLA N |
| ATOM | 428 | CA | GLU | A | 215 | 20.367 | 28.012 | 23.768 | 1.00 | 42.47 | MOLA C |
| ATOM | 429 | C | GLU | A | 215 | 21.428 | 28.443 | 24.750 | 1.00 | 43.21 | MOLA C |
| ATOM | 430 | O | GLU | A | 215 | 21.986 | 27.618 | 25.448 | 1.00 | 43.70 | MOLA O |
| ATOM | 431 | CB | GLU | A | 215 | 20.760 | 28.532 | 22.415 | 1.00 | 40.29 | MOLA C |
| ATOM | 432 | CG | GLU | A | 215 | 20.485 | 27.587 | 21.302 | 1.00 | 48.53 | MOLA C |
| ATOM | 433 | CD | GLU | A | 215 | 20.799 | 28.214 | 19.976 | 1.00 | 62.44 | MOLA C |
| ATOM | 434 | OE1 | GLU | A | 215 | 20.386 | 29.388 | 19.782 | 1.00 | 71.58 | MOLA O |
| ATOM | 435 | OE2 | GLU | A | 215 | 21.455 | 27.542 | 19.143 | 1.00 | 65.51 | MOLA O |
| ATOM | 436 | N | LYS | A | 216 | 21.686 | 29.746 | 24.800 | 1.00 | 45.78 | MOLA N |
| ATOM | 437 | CA | LYS | A | 216 | 22.623 | 30.345 | 25.754 | 1.00 | 49.55 | MOLA C |
| ATOM | 438 | C | LYS | A | 216 | 22.701 | 29.540 | 27.055 | 1.00 | 48.38 | MOLA C |
| ATOM | 439 | O | LYS | A | 216 | 23.800 | 29.127 | 27.488 | 1.00 | 48.55 | MOLA O |
| ATOM | 440 | CB | LYS | A | 216 | 22.211 | 31.790 | 26.101 | 1.00 | 51.47 | MOLA C |
| ATOM | 441 | CG | LYS | A | 216 | 22.550 | 32.912 | 25.085 | 1.00 | 56.78 | MOLA C |
| ATOM | 442 | CD | LYS | A | 216 | 22.395 | 34.316 | 25.760 | 1.00 | 55.05 | MOLA C |
| ATOM | 443 | CE | LYS | A | 216 | 22.915 | 35.476 | 24.881 | 1.00 | 61.58 | MOLA C |
| ATOM | 444 | NZ | LYS | A | 216 | 22.176 | 35.685 | 23.585 | 1.00 | 71.01 | MOLA N |
| ATOM | 445 | N | GLY | A | 217 | 21.527 | 29.346 | 27.671 | 1.00 | 46.21 | MOLA N |
| ATOM | 446 | CA | GLY | A | 217 | 21.388 | 28.597 | 28.917 | 1.00 | 43.66 | MOLA C |
| ATOM | 447 | C | GLY | A | 217 | 22.008 | 27.227 | 28.764 | 1.00 | 43.18 | MOLA C |
| ATOM | 448 | O | GLY | A | 217 | 23.059 | 26.939 | 29.344 | 1.00 | 40.67 | MOLA O |
| ATOM | 449 | N | ALA | A | 218 | 21.374 | 26.401 | 27.937 | 1.00 | 43.23 | MOLA N |
| ATOM | 450 | CA | ALA | A | 218 | 21.852 | 25.058 | 27.689 | 1.00 | 43.19 | MOLA C |
| ATOM | 451 | C | ALA | A | 218 | 23.357 | 25.090 | 27.570 | 1.00 | 43.73 | MOLA C |
| ATOM | 452 | O | ALA | A | 218 | 24.040 | 24.294 | 28.204 | 1.00 | 46.28 | MOLA O |
| ATOM | 453 | CB | ALA | A | 218 | 21.235 | 24.492 | 26.434 | 1.00 | 43.91 | MOLA C |
| ATOM | 454 | N | ALA | A | 219 | 23.876 | 26.018 | 26.774 | 1.00 | 42.36 | MOLA N |
| ATOM | 455 | CA | ALA | A | 219 | 25.316 | 26.141 | 26.581 | 1.00 | 41.91 | MOLA C |
| ATOM | 456 | C | ALA | A | 219 | 26.010 | 26.351 | 27.917 | 1.00 | 43.49 | MOLA C |
| ATOM | 457 | O | ALA | A | 219 | 26.871 | 25.557 | 28.308 | 1.00 | 44.41 | MOLA O |
| ATOM | 458 | CB | ALA | A | 219 | 25.639 | 27.268 | 25.639 | 1.00 | 40.46 | MOLA C |
| ATOM | 459 | N | LYS | A | 220 | 25.633 | 27.398 | 28.639 | 1.00 | 44.19 | MOLA N |
| ATOM | 460 | CA | LYS | A | 220 | 26.309 | 27.654 | 29.897 | 1.00 | 45.36 | MOLA C |
| ATOM | 461 | C | LYS | A | 220 | 26.156 | 26.447 | 30.833 | 1.00 | 42.25 | MOLA C |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 462 | O | LYS | A | 220 | 27.050 | 26.120 | 31.605 | 1.00 | 40.39 | MOLA O |
| ATOM | 463 | CB | LYS | A | 220 | 25.838 | 28.975 | 30.526 | 1.00 | 46.26 | MOLA C |
| ATOM | 464 | CG | LYS | A | 220 | 26.829 | 29.515 | 31.581 | 1.00 | 57.07 | MOLA C |
| ATOM | 465 | CD | LYS | A | 220 | 26.805 | 31.039 | 31.813 | 1.00 | 51.86 | MOLA C |
| ATOM | 466 | CE | LYS | A | 220 | 27.352 | 31.347 | 33.232 | 1.00 | 64.64 | MOLA C |
| ATOM | 467 | NZ | LYS | A | 220 | 27.574 | 32.795 | 33.575 | 1.00 | 59.41 | MOLA N |
| ATOM | 468 | N | ARG | A | 221 | 25.026 | 25.762 | 30.717 | 1.00 | 42.67 | MOLA N |
| ATOM | 469 | CA | ARG | A | 221 | 24.742 | 24.545 | 31.476 | 1.00 | 43.12 | MOLA C |
| ATOM | 470 | C | ARG | A | 221 | 25.847 | 23.528 | 31.299 | 1.00 | 44.97 | MOLA C |
| ATOM | 471 | O | ARG | A | 221 | 26.387 | 22.989 | 32.261 | 1.00 | 43.68 | MOLA O |
| ATOM | 472 | CB | ARG | A | 221 | 23.486 | 23.903 | 30.912 | 1.00 | 42.23 | MOLA C |
| ATOM | 473 | CG | ARG | A | 221 | 23.086 | 22.641 | 31.627 | 1.00 | 48.01 | MOLA C |
| ATOM | 474 | CD | ARG | A | 221 | 21.879 | 22.921 | 32.447 | 1.00 | 44.15 | MOLA C |
| ATOM | 475 | NE | ARG | A | 221 | 20.799 | 23.240 | 31.523 | 1.00 | 52.54 | MOLA N |
| ATOM | 476 | CZ | ARG | A | 221 | 19.556 | 23.465 | 31.899 | 1.00 | 46.98 | MOLA C |
| ATOM | 477 | NH1 | ARG | A | 221 | 19.242 | 23.414 | 33.190 | 1.00 | 45.06 | MOLA N |
| ATOM | 478 | NH2 | ARG | A | 221 | 18.642 | 23.728 | 30.985 | 1.00 | 51.88 | MOLA N |
| ATOM | 479 | N | THR | A | 222 | 26.110 | 23.244 | 30.022 | 1.00 | 47.71 | MOLA N |
| ATOM | 480 | CA | THR | A | 222 | 27.150 | 22.354 | 29.565 | 1.00 | 48.26 | MOLA C |
| ATOM | 481 | C | THR | A | 222 | 28.427 | 22.783 | 30.212 | 1.00 | 50.20 | MOLA C |
| ATOM | 482 | O | THR | A | 222 | 28.943 | 22.071 | 31.069 | 1.00 | 51.35 | MOLA O |
| ATOM | 483 | CB | THR | A | 222 | 27.259 | 22.426 | 28.049 | 1.00 | 47.88 | MOLA C |
| ATOM | 484 | CG2 | THR | A | 222 | 28.485 | 21.681 | 27.549 | 1.00 | 48.98 | MOLA C |
| ATOM | 485 | OG1 | THR | A | 222 | 26.083 | 21.830 | 27.490 | 1.00 | 47.71 | MOLA O |
| TER | 486 | | THR | A | 222 | | | | | | |
| ATOM | 487 | N | SER | A | 232 | 24.391 | 17.439 | 35.355 | 1.00 | 39.34 | MOLA N |
| ATOM | 488 | CA | SER | A | 232 | 22.965 | 17.656 | 35.321 | 1.00 | 38.72 | MOLA C |
| ATOM | 489 | C | SER | A | 232 | 22.222 | 16.707 | 36.252 | 1.00 | 36.89 | MOLA C |
| ATOM | 490 | O | SER | A | 232 | 21.475 | 17.145 | 37.118 | 1.00 | 39.02 | MOLA O |
| ATOM | 491 | CB | SER | A | 232 | 22.433 | 17.563 | 33.898 | 1.00 | 38.02 | MOLA C |
| ATOM | 492 | OG | SER | A | 232 | 23.438 | 17.068 | 33.038 | 1.00 | 45.94 | MOLA O |
| TER | 493 | | SER | A | 232 | | | | | | |
| ATOM | 494 | N | SER | A | 237 | 17.541 | 22.473 | 38.494 | 1.00 | 43.48 | MOLA N |
| ATOM | 495 | CA | SER | A | 237 | 17.411 | 23.516 | 37.501 | 1.00 | 43.56 | MOLA C |
| ATOM | 496 | C | SER | A | 237 | 16.127 | 24.289 | 37.733 | 1.00 | 43.86 | MOLA C |
| ATOM | 497 | O | SER | A | 237 | 15.017 | 23.705 | 37.733 | 1.00 | 45.28 | MOLA O |
| ATOM | 498 | CB | SER | A | 237 | 17.469 | 22.977 | 36.093 | 1.00 | 42.41 | MOLA C |
| ATOM | 499 | OG | SER | A | 237 | 17.627 | 24.079 | 35.222 | 1.00 | 46.38 | MOLA O |
| ATOM | 500 | N | VAL | A | 238 | 16.299 | 25.600 | 37.954 | 1.00 | 40.56 | MOLA N |
| ATOM | 501 | CA | VAL | A | 238 | 15.194 | 26.469 | 38.310 | 1.00 | 36.80 | MOLA C |
| ATOM | 502 | C | VAL | A | 238 | 15.086 | 27.561 | 37.319 | 1.00 | 35.49 | MOLA C |
| ATOM | 503 | O | VAL | A | 238 | 15.845 | 28.528 | 37.365 | 1.00 | 36.32 | MOLA O |
| ATOM | 504 | CB | VAL | A | 238 | 15.399 | 27.122 | 39.635 | 1.00 | 36.20 | MOLA C |
| ATOM | 505 | CG1 | VAL | A | 238 | 14.055 | 27.313 | 40.281 | 1.00 | 32.63 | MOLA C |
| ATOM | 506 | CG2 | VAL | A | 238 | 16.238 | 26.235 | 40.504 | 1.00 | 40.18 | MOLA C |
| ATOM | 507 | N | PHE | A | 239 | 14.138 | 27.383 | 36.414 | 1.00 | 33.53 | MOLA N |
| ATOM | 508 | CA | PHE | A | 239 | 13.878 | 28.348 | 35.393 | 1.00 | 34.51 | MOLA C |
| ATOM | 509 | C | PHE | A | 239 | 12.694 | 29.225 | 35.799 | 1.00 | 37.17 | MOLA C |
| ATOM | 510 | O | PHE | A | 239 | 11.560 | 28.720 | 35.946 | 1.00 | 38.32 | MOLA O |
| ATOM | 511 | CB | PHE | A | 239 | 13.568 | 27.657 | 34.080 | 1.00 | 32.29 | MOLA C |
| ATOM | 512 | CG | PHE | A | 239 | 13.399 | 28.621 | 32.948 | 1.00 | 36.81 | MOLA C |
| ATOM | 513 | CD1 | PHE | A | 239 | 12.216 | 29.379 | 32.834 | 1.00 | 31.95 | MOLA C |
| ATOM | 514 | CD2 | PHE | A | 239 | 14.444 | 28.830 | 32.028 | 1.00 | 20.56 | MOLA C |
| ATOM | 515 | CE1 | PHE | A | 239 | 12.058 | 30.299 | 31.783 | 1.00 | 42.09 | MOLA C |
| ATOM | 516 | CE2 | PHE | A | 239 | 14.314 | 29.754 | 30.970 | 1.00 | 22.92 | MOLA C |
| ATOM | 517 | CZ | PHE | A | 239 | 13.123 | 30.500 | 30.841 | 1.00 | 38.40 | MOLA C |
| ATOM | 518 | N | SER | A | 240 | 12.949 | 30.526 | 35.963 | 1.00 | 36.63 | MOLA N |
| ATOM | 519 | CA | SER | A | 240 | 11.916 | 31.446 | 36.474 | 1.00 | 38.69 | MOLA C |
| ATOM | 520 | C | SER | A | 240 | 11.507 | 32.533 | 35.512 | 1.00 | 37.76 | MOLA C |
| ATOM | 521 | O | SER | A | 240 | 12.349 | 33.231 | 34.929 | 1.00 | 40.65 | MOLA O |
| ATOM | 522 | CB | SER | A | 240 | 12.322 | 32.066 | 37.814 | 1.00 | 37.90 | MOLA C |
| ATOM | 523 | OG | SER | A | 240 | 11.795 | 31.309 | 38.895 | 1.00 | 40.95 | MOLA O |
| TER | 524 | | SER | A | 240 | | | | | | |
| ATOM | 525 | N | LEU | A | 263 | 9.437 | 26.953 | 37.036 | 1.00 | 36.80 | MOLA N |
| ATOM | 526 | CA | LEU | A | 263 | 9.377 | 25.574 | 36.634 | 1.00 | 33.68 | MOLA C |
| ATOM | 527 | C | LEU | A | 263 | 10.660 | 24.874 | 37.127 | 1.00 | 33.64 | MOLA C |
| ATOM | 528 | O | LEU | A | 263 | 11.767 | 25.311 | 36.817 | 1.00 | 33.67 | MOLA O |
| ATOM | 529 | CB | LEU | A | 263 | 9.322 | 25.582 | 35.131 | 1.00 | 33.93 | MOLA C |
| ATOM | 530 | CG | LEU | A | 263 | 8.346 | 26.666 | 34.698 | 1.00 | 24.47 | MOLA C |
| ATOM | 531 | CD1 | LEU | A | 263 | 8.796 | 27.394 | 33.423 | 1.00 | 13.99 | MOLA C |
| ATOM | 532 | CD2 | LEU | A | 263 | 7.043 | 26.014 | 34.461 | 1.00 | 21.52 | MOLA C |
| ATOM | 533 | N | VAL | A | 264 | 10.527 | 23.784 | 37.881 | 1.00 | 34.38 | MOLA N |
| ATOM | 534 | CA | VAL | A | 264 | 11.715 | 23.175 | 38.518 | 1.00 | 33.24 | MOLA C |
| ATOM | 535 | C | VAL | A | 264 | 12.006 | 21.695 | 38.223 | 1.00 | 33.21 | MOLA C |
| ATOM | 536 | O | VAL | A | 264 | 11.204 | 20.810 | 38.542 | 1.00 | 31.44 | MOLA O |

TABLE 6-continued

Novel Eg5 ligand binding site/compound 3 X-ray coordinates. 10 Angstrom shell of the binding pocket. Table 6 discloses residues 111-122, 125-141, 158-161, 208-222 and 237-240 of SEQ ID NO: 1, respectively, in order of appearance.

| | | | | | | | | | | | |
|---|---|---|---|---|---|---|---|---|---|---|---|
| ATOM | 537 | CB | VAL | A | 264 | 11.680 | 23.388 | 40.040 | 1.00 | 32.52 | MOLA C |
| ATOM | 538 | CG1 | VAL | A | 264 | 12.944 | 22.884 | 40.649 | 1.00 | 29.22 | MOLA C |
| ATOM | 539 | CG2 | VAL | A | 264 | 11.519 | 24.846 | 40.343 | 1.00 | 28.08 | MOLA C |
| ATOM | 540 | N | ASP | A | 265 | 13.183 | 21.475 | 37.627 | 1.00 | 34.60 | MOLA N |
| ATOM | 541 | CA | ASP | A | 265 | 13.764 | 20.166 | 37.280 | 1.00 | 32.76 | MOLA C |
| ATOM | 542 | C | ASP | A | 265 | 14.640 | 19.710 | 38.407 | 1.00 | 34.10 | MOLA C |
| ATOM | 543 | O | ASP | A | 265 | 15.757 | 20.190 | 38.561 | 1.00 | 33.83 | MOLA O |
| ATOM | 544 | CB | ASP | A | 265 | 14.686 | 20.347 | 36.091 | 1.00 | 33.82 | MOLA C |
| ATOM | 545 | CG | ASP | A | 265 | 14.775 | 19.117 | 35.200 | 1.00 | 36.48 | MOLA C |
| ATOM | 546 | OD1 | ASP | A | 265 | 14.742 | 17.974 | 35.710 | 1.00 | 53.03 | MOLA O |
| ATOM | 547 | OD2 | ASP | A | 265 | 14.883 | 19.314 | 33.971 | 1.00 | 31.07 | MOLA O |
| END | | | | | | | | | | | |

Table 7. Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

TABLE 7

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | |
|---|---|---|---|---|---|---|---|---|---|---|
| ATOM | 1 | MG | MG | A3001 | 16.254 | 14.044 | 34.685 | 1.00 | 31.64 | COFAMG |
| TER | 2 | | MG | A3001 | | | | | | |
| ATOM | 3 | N1 | ADP | A4001 | 8.020 | 8.695 | 25.933 | 1.00 | 33.27 | COFA N |
| ATOM | 4 | C2 | ADP | A4001 | 9.098 | 8.204 | 25.271 | 1.00 | 31.44 | COFA C |
| ATOM | 5 | N3 | ADP | A4001 | 10.276 | 8.086 | 25.934 | 1.00 | 32.37 | COFA N |
| ATOM | 6 | C1* | ADP | A4001 | 12.777 | 8.136 | 27.921 | 1.00 | 35.82 | COFA C |
| ATOM | 7 | C4 | ADP | A4001 | 10.429 | 8.497 | 27.239 | 1.00 | 35.47 | COFA C |
| ATOM | 8 | C5 | ADP | A4001 | 9.283 | 9.042 | 27.976 | 1.00 | 31.50 | COFA C |
| ATOM | 9 | C6 | ADP | A4001 | 8.047 | 9.104 | 27.258 | 1.00 | 41.54 | COFA C |
| ATOM | 10 | N6 | ADP | A4001 | 7.048 | 9.596 | 28.003 | 1.00 | 44.03 | COFA N |
| ATOM | 11 | N7 | ADP | A4001 | 9.645 | 9.393 | 29.217 | 1.00 | 35.06 | COFA N |
| ATOM | 12 | C8 | ADP | A4001 | 10.962 | 9.080 | 29.305 | 1.00 | 36.03 | COFA C |
| ATOM | 13 | N9 | ADP | A4001 | 11.399 | 8.552 | 28.137 | 1.00 | 39.01 | COFA N |
| ATOM | 14 | C2* | ADP | A4001 | 13.522 | 9.417 | 27.620 | 1.00 | 33.12 | COFA C |
| ATOM | 15 | O2* | ADP | A4001 | 13.402 | 9.625 | 26.218 | 1.00 | 46.91 | COFA O |
| ATOM | 16 | C3* | ADP | A4001 | 14.855 | 8.984 | 27.995 | 1.00 | 30.92 | COFA C |
| ATOM | 17 | O3* | ADP | A4001 | 14.969 | 8.274 | 26.771 | 1.00 | 31.71 | COFA O |
| ATOM | 18 | O1A | ADP | A4001 | 13.745 | 12.107 | 31.077 | 1.00 | 36.01 | COFA O |
| ATOM | 19 | O1B | ADP | A4001 | 13.645 | 10.969 | 35.131 | 1.00 | 26.12 | COFA O |
| ATOM | 20 | C4* | ADP | A4001 | 14.710 | 7.995 | 29.143 | 1.00 | 27.55 | COFA C |
| ATOM | 21 | O4* | ADP | A4001 | 13.362 | 7.526 | 29.093 | 1.00 | 28.27 | COFA O |
| ATOM | 22 | O2A | ADP | A4001 | 16.217 | 11.089 | 31.226 | 1.00 | 32.93 | COFA O |
| ATOM | 23 | O2B | ADP | A4001 | 15.046 | 12.649 | 33.743 | 1.00 | 28.81 | COFA O |
| ATOM | 24 | C5* | ADP | A4001 | 14.885 | 8.620 | 30.494 | 1.00 | 24.37 | COFA C |
| ATOM | 25 | O5* | ADP | A4001 | 14.207 | 9.863 | 30.418 | 1.00 | 32.93 | COFA O |
| ATOM | 26 | O3A | ADP | A4001 | 14.426 | 10.464 | 32.833 | 1.00 | 46.64 | COFA O |
| ATOM | 27 | O3B | ADP | A4001 | 16.019 | 10.366 | 34.735 | 1.00 | 18.87 | COFA O |
| ATOM | 28 | PA | ADP | A4001 | 14.703 | 11.012 | 31.380 | 1.00 | 24.94 | COFA P |
| ATOM | 29 | PB | ADP | A4001 | 14.838 | 11.215 | 34.207 | 1.00 | 26.65 | COFA P |
| TER | 30 | | ADP | A4001 | | | | | | |
| ATOM | 31 | CL | LIG | A1001 | 19.992 | 24.104 | 29.182 | 1.00 | 38.92 | LIGACL |
| ATOM | 32 | C1 | LIG | A1001 | 16.809 | 22.622 | 27.339 | 1.00 | 37.64 | LIGA C |
| ATOM | 33 | C2 | LIG | A1001 | 16.526 | 21.878 | 26.184 | 1.00 | 30.16 | LIGA C |
| ATOM | 34 | C3 | LIG | A1001 | 15.762 | 22.889 | 28.245 | 1.00 | 33.59 | LIGA C |
| ATOM | 35 | C4 | LIG | A1001 | 16.033 | 23.561 | 29.427 | 1.00 | 25.90 | LIGA C |
| ATOM | 36 | C5 | LIG | A1001 | 17.363 | 23.937 | 29.671 | 1.00 | 15.37 | LIGA C |
| ATOM | 37 | C6 | LIG | A1001 | 18.331 | 23.609 | 28.733 | 1.00 | 31.39 | LIGA C |
| ATOM | 38 | C7 | LIG | A1001 | 18.041 | 22.960 | 27.622 | 1.00 | 23.90 | LIGA C |
| ATOM | 39 | N8 | LIG | A1001 | 17.451 | 21.520 | 25.252 | 1.00 | 27.11 | LIGA N |
| ATOM | 40 | C9 | LIG | A1001 | 16.860 | 20.756 | 24.322 | 1.00 | 31.28 | LIGA C |
| ATOM | 41 | C10 | LIG | A1001 | 17.574 | 20.163 | 23.141 | 1.00 | 39.64 | LIGA C |
| ATOM | 42 | N11 | LIG | A1001 | 17.942 | 18.781 | 23.414 | 1.00 | 37.27 | LIGA N |
| ATOM | 43 | C12 | LIG | A1001 | 17.627 | 17.781 | 22.605 | 1.00 | 40.73 | LIGA C |
| ATOM | 44 | O13 | LIG | A1001 | 17.102 | 17.994 | 21.564 | 1.00 | 44.25 | LIGA O |
| ATOM | 45 | C14 | LIG | A1001 | 17.925 | 16.383 | 23.037 | 1.00 | 37.87 | LIGA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | |
|---|---|---|---|---|---|---|---|---|---|---|
| ATOM | 46 | C15 | LIG | A1001 | 18.871 | 18.686 | 24.515 | 1.00 | 34.48 | LIGA C |
| ATOM | 47 | C16 | LIG | A1001 | 17.945 | 18.225 | 25.632 | 1.00 | 29.70 | LIGA C |
| ATOM | 48 | C17 | LIG | A1001 | 18.783 | 17.746 | 26.821 | 1.00 | 29.02 | LIGA C |
| ATOM | 49 | N18 | LIG | A1001 | 17.989 | 17.407 | 27.988 | 1.00 | 18.77 | LIGA N |
| ATOM | 50 | C19 | LIG | A1001 | 18.845 | 20.930 | 22.943 | 1.00 | 41.69 | LIGA C |
| ATOM | 51 | C20 | LIG | A1001 | 18.496 | 22.254 | 22.275 | 1.00 | 25.34 | LIGA C |
| ATOM | 52 | C21 | LIG | A1001 | 19.828 | 20.111 | 22.167 | 1.00 | 26.42 | LIGA C |
| ATOM | 53 | N22 | LIG | A1001 | 15.563 | 20.651 | 24.653 | 1.00 | 28.15 | LIGA N |
| ATOM | 54 | C23 | LIG | A1001 | 14.659 | 19.849 | 23.909 | 1.00 | 40.14 | LIGA C |
| ATOM | 55 | C24 | LIG | A1001 | 14.056 | 20.556 | 22.769 | 1.00 | 30.91 | LIGA C |
| ATOM | 56 | C25 | LIG | A1001 | 15.312 | 21.287 | 25.794 | 1.00 | 36.74 | LIGA C |
| ATOM | 57 | C26 | LIG | A1001 | 13.245 | 19.766 | 21.945 | 1.00 | 34.81 | LIGA C |
| ATOM | 58 | C27 | LIG | A1001 | 12.634 | 20.395 | 20.921 | 1.00 | 33.90 | LIGA C |
| ATOM | 59 | C28 | LIG | A1001 | 12.873 | 21.788 | 20.803 | 1.00 | 30.57 | LIGA C |
| ATOM | 60 | C29 | LIG | A1001 | 13.708 | 22.484 | 21.673 | 1.00 | 30.94 | LIGA C |
| ATOM | 61 | C30 | LIG | A1001 | 14.279 | 21.818 | 22.628 | 1.00 | 20.64 | LIGA C |
| ATOM | 62 | N31 | LIG | A1001 | 18.106 | 15.880 | 24.298 | 1.00 | 31.91 | LIGA N |
| ATOM | 63 | N33 | LIG | A1001 | 18.310 | 14.509 | 24.106 | 1.00 | 43.25 | LIGA N |
| ATOM | 64 | C35 | LIG | A1001 | 18.199 | 14.252 | 22.787 | 1.00 | 38.36 | LIGA C |
| ATOM | 65 | C36 | LIG | A1001 | 17.945 | 15.401 | 22.141 | 1.00 | 39.56 | LIGA C |
| ATOM | 66 | C37 | LIG | A1001 | 18.516 | 13.561 | 25.159 | 1.00 | 36.12 | LIGA C |
| ATOM | 67 | C38 | LIG | A1001 | 18.268 | 12.933 | 22.191 | 1.00 | 33.56 | LIGA C |
| TER | 68 | | LIG | A1001 | | | | | | |
| ATOM | 69 | N | GLN | A 78 | 3.675 | 14.611 | 24.614 | 1.00 | 19.08 | MOLA N |
| ATOM | 70 | CA | GLN | A 78 | 4.193 | 15.813 | 25.271 | 1.00 | 18.06 | MOLA C |
| ATOM | 71 | C | GLN | A 78 | 3.122 | 16.883 | 25.204 | 1.00 | 28.18 | MOLA C |
| ATOM | 72 | O | GLN | A 78 | 2.800 | 17.552 | 26.267 | 1.00 | 25.87 | MOLA O |
| ATOM | 73 | CB | GLN | A 78 | 5.351 | 16.374 | 24.530 | 1.00 | 17.34 | MOLA C |
| ATOM | 74 | CG | GLN | A 78 | 6.636 | 15.517 | 24.456 | 1.00 | 25.45 | MOLA C |
| ATOM | 75 | CD | GLN | A 78 | 7.343 | 15.547 | 25.728 | 1.00 | 25.40 | MOLA C |
| ATOM | 76 | NE2 | GLN | A 78 | 8.519 | 16.154 | 25.720 | 1.00 | 28.27 | MOLA N |
| ATOM | 77 | OE1 | GLN | A 78 | 6.798 | 15.115 | 26.761 | 1.00 | 21.67 | MOLA O |
| TER | 78 | | GLN | A 78 | | | | | | |
| ATOM | 79 | N | LYS | A 111 | 11.500 | 12.716 | 33.923 | 1.00 | 32.84 | MOLA N |
| ATOM | 80 | CA | LYS | A 111 | 11.415 | 14.064 | 34.420 | 1.00 | 29.77 | MOLA C |
| ATOM | 81 | C | LYS | A 111 | 12.066 | 15.051 | 33.422 | 1.00 | 30.25 | MOLA C |
| ATOM | 82 | O | LYS | A 111 | 11.490 | 16.101 | 33.051 | 1.00 | 28.66 | MOLA O |
| ATOM | 83 | CB | LYS | A 111 | 12.132 | 14.121 | 35.733 | 1.00 | 31.25 | MOLA C |
| ATOM | 84 | CG | LYS | A 111 | 11.580 | 13.184 | 36.789 | 1.00 | 25.89 | MOLA C |
| ATOM | 85 | CD | LYS | A 111 | 12.290 | 13.426 | 38.130 | 1.00 | 14.88 | MOLA C |
| ATOM | 86 | CE | LYS | A 111 | 13.814 | 12.995 | 38.162 | 1.00 | 25.46 | MOLA C |
| ATOM | 87 | NZ | LYS | A 111 | 13.941 | 11.546 | 38.316 | 1.00 | 20.49 | MOLA N |
| ATOM | 88 | N | THR | A 112 | 13.277 | 14.728 | 32.962 | 1.00 | 30.08 | MOLA N |
| ATOM | 89 | CA | THR | A 112 | 13.885 | 15.633 | 32.021 | 1.00 | 28.05 | MOLA C |
| ATOM | 90 | C | THR | A 112 | 13.073 | 15.605 | 30.704 | 1.00 | 25.93 | MOLA C |
| ATOM | 91 | O | THR | A 112 | 12.841 | 16.624 | 30.112 | 1.00 | 27.44 | MOLA O |
| ATOM | 92 | CB | THR | A 112 | 15.386 | 15.366 | 31.810 | 1.00 | 30.35 | MOLA C |
| ATOM | 93 | CG2 | THR | A 112 | 15.988 | 16.499 | 31.086 | 1.00 | 26.22 | MOLA C |
| ATOM | 94 | OG1 | THR | A 112 | 16.049 | 15.245 | 33.048 | 1.00 | 26.36 | MOLA O |
| ATOM | 95 | N | PHE | A 113 | 12.651 | 14.430 | 30.265 | 1.00 | 22.48 | MOLA N |
| ATOM | 96 | CA | PHE | A 113 | 11.816 | 14.291 | 29.088 | 1.00 | 23.89 | MOLA C |
| ATOM | 97 | C | PHE | A 113 | 10.602 | 15.210 | 29.159 | 1.00 | 24.98 | MOLA C |
| ATOM | 98 | O | PHE | A 113 | 10.286 | 15.981 | 28.248 | 1.00 | 22.65 | MOLA O |
| ATOM | 99 | CB | PHE | A 113 | 11.300 | 12.843 | 28.921 | 1.00 | 23.38 | MOLA C |
| ATOM | 100 | CG | PHE | A 113 | 10.557 | 12.638 | 27.630 | 1.00 | 35.93 | MOLA C |
| ATOM | 101 | CD1 | PHE | A 113 | 11.195 | 12.875 | 26.393 | 1.00 | 53.28 | MOLA C |
| ATOM | 102 | CD2 | PHE | A 113 | 9.223 | 12.277 | 27.619 | 1.00 | 43.21 | MOLA C |
| ATOM | 103 | CE1 | PHE | A 113 | 10.517 | 12.733 | 25.189 | 1.00 | 33.41 | MOLA C |
| ATOM | 104 | CE2 | PHE | A 113 | 8.541 | 12.115 | 26.424 | 1.00 | 24.70 | MOLA C |
| ATOM | 105 | CZ | PHE | A 113 | 9.189 | 12.336 | 25.195 | 1.00 | 38.47 | MOLA C |
| ATOM | 106 | N | THR | A 114 | 9.928 | 15.165 | 30.283 | 1.00 | 24.58 | MOLA N |
| ATOM | 107 | CA | THR | A 114 | 8.723 | 15.890 | 30.395 | 1.00 | 24.38 | MOLA C |
| ATOM | 108 | C | THR | A 114 | 8.981 | 17.355 | 30.411 | 1.00 | 26.54 | MOLA C |
| ATOM | 109 | O | THR | A 114 | 8.221 | 18.118 | 29.816 | 1.00 | 35.31 | MOLA O |
| ATOM | 110 | CB | THR | A 114 | 7.993 | 15.462 | 31.626 | 1.00 | 22.83 | MOLA C |
| ATOM | 111 | CG2 | THR | A 114 | 6.818 | 16.301 | 31.852 | 1.00 | 30.38 | MOLA C |
| ATOM | 112 | OG1 | THR | A 114 | 7.519 | 14.139 | 31.408 | 1.00 | 26.36 | MOLA O |
| ATOM | 113 | N | MET | A 115 | 10.055 | 17.771 | 31.051 | 1.00 | 27.93 | MOLA N |
| ATOM | 114 | CA | MET | A 115 | 10.290 | 19.223 | 31.273 | 1.00 | 27.35 | MOLA C |
| ATOM | 115 | C | MET | A 115 | 11.023 | 19.929 | 30.155 | 1.00 | 24.33 | MOLA C |
| ATOM | 116 | O | MET | A 115 | 10.689 | 21.039 | 29.837 | 1.00 | 24.39 | MOLA O |
| ATOM | 117 | CB | MET | A 115 | 11.015 | 19.422 | 32.584 | 1.00 | 29.60 | MOLA C |
| ATOM | 118 | CG | MET | A 115 | 10.158 | 19.002 | 33.761 | 1.00 | 37.05 | MOLA C |
| ATOM | 119 | SD | MET | A 115 | 9.218 | 20.194 | 34.759 | 1.00 | 41.45 | MOLA S |
| ATOM | 120 | CE | MET | A 115 | 8.743 | 21.414 | 33.824 | 1.00 | 56.91 | MOLA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 121 | N | GLU | A | 116 | 11.993 | 19.251 | 29.549 | 1.00 | 28.79 | MOLA N |
| ATOM | 122 | CA | GLU | A | 116 | 12.762 | 19.768 | 28.387 | 1.00 | 31.95 | MOLA C |
| ATOM | 123 | C | GLU | A | 116 | 12.476 | 18.982 | 27.129 | 1.00 | 30.92 | MOLA C |
| ATOM | 124 | O | GLU | A | 116 | 12.181 | 19.523 | 26.074 | 1.00 | 32.41 | MOLA O |
| ATOM | 125 | CB | GLU | A | 116 | 14.250 | 19.652 | 28.673 | 1.00 | 30.36 | MOLA C |
| ATOM | 126 | CG | GLU | A | 116 | 14.697 | 20.141 | 30.048 | 1.00 | 35.58 | MOLA C |
| ATOM | 127 | CD | GLU | A | 116 | 16.208 | 19.918 | 30.259 | 1.00 | 44.94 | MOLA C |
| ATOM | 128 | OE1 | GLU | A | 116 | 16.697 | 20.132 | 31.387 | 1.00 | 32.12 | MOLA O |
| ATOM | 129 | OE2 | GLU | A | 116 | 16.906 | 19.511 | 29.296 | 1.00 | 32.94 | MOLA O |
| ATOM | 130 | N | GLY | A | 117 | 12.556 | 17.680 | 27.246 | 1.00 | 30.29 | MOLA N |
| ATOM | 131 | CA | GLY | A | 117 | 12.329 | 16.833 | 26.094 | 1.00 | 36.30 | MOLA C |
| ATOM | 132 | C | GLY | A | 117 | 13.457 | 16.769 | 25.089 | 1.00 | 39.46 | MOLA C |
| ATOM | 133 | O | GLY | A | 117 | 14.600 | 16.946 | 25.413 | 1.00 | 41.61 | MOLA O |
| ATOM | 134 | N | GLU | A | 118 | 13.106 | 16.513 | 23.845 | 1.00 | 40.90 | MOLA N |
| ATOM | 135 | CA | GLU | A | 118 | 14.090 | 16.116 | 22.885 | 1.00 | 42.84 | MOLA C |
| ATOM | 136 | C | GLU | A | 118 | 13.732 | 16.511 | 21.533 | 1.00 | 40.32 | MOLA C |
| ATOM | 137 | O | GLU | A | 118 | 12.557 | 16.705 | 21.214 | 1.00 | 39.49 | MOLA O |
| ATOM | 138 | CB | GLU | A | 118 | 14.227 | 14.594 | 22.866 | 1.00 | 39.45 | MOLA C |
| ATOM | 139 | CG | GLU | A | 118 | 14.351 | 13.955 | 24.224 | 1.00 | 34.66 | MOLA C |
| ATOM | 140 | CD | GLU | A | 118 | 14.738 | 12.473 | 24.145 | 1.00 | 45.04 | MOLA C |
| ATOM | 141 | OE1 | GLU | A | 118 | 15.004 | 11.982 | 22.999 | 1.00 | 40.72 | MOLA O |
| ATOM | 142 | OE2 | GLU | A | 118 | 14.771 | 11.813 | 25.232 | 1.00 | 36.80 | MOLA O |
| ATOM | 143 | N | ARG | A | 119 | 14.780 | 16.618 | 20.729 | 1.00 | 42.17 | MOLA N |
| ATOM | 144 | CA | ARG | A | 119 | 14.605 | 16.853 | 19.333 | 1.00 | 46.44 | MOLA C |
| ATOM | 145 | C | ARG | A | 119 | 14.479 | 15.524 | 18.685 | 1.00 | 45.22 | MOLA C |
| ATOM | 146 | O | ARG | A | 119 | 15.121 | 14.568 | 19.115 | 1.00 | 39.75 | MOLA O |
| ATOM | 147 | CB | ARG | A | 119 | 15.712 | 17.687 | 18.723 | 1.00 | 42.34 | MOLA C |
| ATOM | 148 | CG | ARG | A | 119 | 14.965 | 18.562 | 17.864 | 1.00 | 58.04 | MOLA C |
| ATOM | 149 | CD | ARG | A | 119 | 15.215 | 19.921 | 17.470 | 1.00 | 57.38 | MOLA C |
| ATOM | 150 | NE | ARG | A | 119 | 15.453 | 19.974 | 16.019 | 1.00 | 59.53 | MOLA N |
| ATOM | 151 | CZ | ARG | A | 119 | 14.983 | 20.950 | 15.230 | 1.00 | 82.71 | MOLA C |
| ATOM | 152 | NH1 | ARG | A | 119 | 14.206 | 21.902 | 15.730 | 1.00 | 89.97 | MOLA N |
| ATOM | 153 | NH2 | ARG | A | 119 | 15.220 | 20.954 | 13.929 | 1.00 | 79.90 | MOLA N |
| ATOM | 154 | N | SER | A | 120 | 13.580 | 15.444 | 17.711 | 1.00 | 49.95 | MOLA N |
| ATOM | 155 | CA | SER | A | 120 | 13.253 | 14.174 | 17.058 | 1.00 | 54.89 | MOLA C |
| ATOM | 156 | CS | ER | A | 120 | 14.412 | 13.674 | 16.155 | 1.00 | 57.07 | MOLA C |
| ATOM | 157 | O | SER | A | 120 | 15.005 | 14.464 | 15.429 | 1.00 | 53.62 | MOLA O |
| ATOM | 158 | CB | SER | A | 120 | 11.921 | 14.362 | 16.306 | 1.00 | 55.53 | MOLA C |
| ATOM | 159 | OG | SER | A | 120 | 10.979 | 15.087 | 17.118 | 1.00 | 60.69 | MOLA O |
| ATOM | 160 | N | PRO | A | 121 | 14.750 | 12.362 | 16.225 | 1.00 | 60.88 | MOLA N |
| ATOM | 161 | CA | PRO | A | 121 | 15.912 | 11.835 | 15.484 | 1.00 | 62.93 | MOLA C |
| ATOM | 162 | C | PRO | A | 121 | 15.877 | 12.324 | 14.075 | 1.00 | 67.08 | MOLA C |
| ATOM | 163 | O | PRO | A | 121 | 14.920 | 12.086 | 13.358 | 1.00 | 67.41 | MOLA O |
| ATOM | 164 | CB | PRO | A | 121 | 15.723 | 10.325 | 15.471 | 1.00 | 61.44 | MOLA C |
| ATOM | 165 | CG | PRO | A | 121 | 14.525 | 10.034 | 16.265 | 1.00 | 61.39 | MOLA C |
| ATOM | 166 | CD | PRO | A | 121 | 14.044 | 11.293 | 16.952 | 1.00 | 62.04 | MOLA C |
| ATOM | 167 | N | ASN | A | 122 | 16.962 | 12.970 | 13.705 | 1.00 | 70.27 | MOLA N |
| ATOM | 168 | CA | ASN | A | 122 | 17.129 | 13.788 | 12.492 | 1.00 | 70.95 | MOLA C |
| ATOM | 169 | C | ASN | A | 122 | 16.083 | 14.762 | 11.991 | 1.00 | 71.69 | MOLA C |
| ATOM | 170 | O | ASN | A | 122 | 16.498 | 15.764 | 11.441 | 1.00 | 70.23 | MOLA O |
| ATOM | 171 | CB | ASN | A | 122 | 17.691 | 13.070 | 11.265 | 1.00 | 70.88 | MOLA C |
| ATOM | 172 | CG | ASN | A | 122 | 18.568 | 11.905 | 11.612 | 1.00 | 68.36 | MOLA C |
| ATOM | 173 | ND2 | ASN | A | 122 | 18.085 | 11.041 | 12.459 | 1.00 | 63.57 | MOLA N |
| ATOM | 174 | OD1 | ASN | A | 122 | 19.682 | 11.807 | 11.148 | 1.00 | 69.66 | MOLA O |
| TER | 175 | | ASN | A | 122 | | | | | | |
| ATOM | 176 | N | TYR | A | 125 | 11.376 | 17.773 | 11.727 | 1.00 | 56.33 | MOLA N |
| ATOM | 177 | CA | TYR | A | 125 | 10.561 | 18.891 | 12.288 | 1.00 | 56.16 | MOLA C |
| ATOM | 178 | C | TYR | A | 125 | 11.453 | 20.047 | 12.651 | 1.00 | 53.99 | MOLA C |
| ATOM | 179 | O | TYR | A | 125 | 12.584 | 19.845 | 12.996 | 1.00 | 57.11 | MOLA O |
| ATOM | 180 | CB | TYR | A | 125 | 9.808 | 18.474 | 13.570 | 1.00 | 52.63 | MOLA C |
| ATOM | 181 | CG | TYR | A | 125 | 8.821 | 17.358 | 13.398 | 1.00 | 49.44 | MOLA C |
| ATOM | 182 | CD1 | TYR | A | 125 | 7.506 | 17.606 | 13.025 | 1.00 | 39.90 | MOLA C |
| ATOM | 183 | CD2 | TYR | A | 125 | 9.189 | 16.033 | 13.637 | 1.00 | 39.63 | MOLA C |
| ATOM | 184 | CE1 | TYR | A | 125 | 6.599 | 16.541 | 12.900 | 1.00 | 43.96 | MOLA C |
| ATOM | 185 | CE2 | TYR | A | 125 | 8.270 | 14.970 | 13.511 | 1.00 | 38.40 | MOLA C |
| ATOM | 186 | CZ | TYR | A | 125 | 7.012 | 15.222 | 13.145 | 1.00 | 35.88 | MOLA C |
| ATOM | 187 | OH | TYR | A | 125 | 6.155 | 14.159 | 13.079 | 1.00 | 49.81 | MOLA O |
| ATOM | 188 | N | THR | A | 126 | 10.941 | 21.257 | 12.603 | 1.00 | 53.17 | MOLA N |
| ATOM | 189 | CA | THR | A | 126 | 11.672 | 22.377 | 13.224 | 1.00 | 57.70 | MOLA C |
| ATOM | 190 | C | THR | A | 126 | 11.417 | 22.329 | 14.734 | 1.00 | 58.39 | MOLA C |
| ATOM | 191 | O | THR | A | 126 | 10.713 | 21.457 | 15.222 | 1.00 | 61.85 | MOLA O |
| ATOM | 192 | CB | THR | A | 126 | 11.248 | 23.746 | 12.736 | 1.00 | 57.89 | MOLA C |
| ATOM | 193 | CG2 | THR | A | 126 | 11.356 | 23.761 | 11.261 | 1.00 | 61.23 | MOLA C |
| ATOM | 194 | OG1 | THR | A | 126 | 9.919 | 24.039 | 13.229 | 1.00 | 59.38 | MOLA O |
| ATOM | 195 | N | TRP | A | 127 | 11.946 | 23.285 | 15.483 | 1.00 | 56.54 | MOLA N |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 196 | CA | TRP | A | 127 | 11.971 | 23.126 | 16.923 | 1.00 | 51.26 | MOLA C |
| ATOM | 197 | C | TRP | A | 127 | 10.691 | 23.496 | 17.553 | 1.00 | 52.25 | MOLA C |
| ATOM | 198 | O | TRP | A | 127 | 10.449 | 23.003 | 18.662 | 1.00 | 46.65 | MOLA O |
| ATOM | 199 | CB | TRP | A | 127 | 13.135 | 23.919 | 17.596 | 1.00 | 47.91 | MOLA C |
| ATOM | 200 | CG | TRP | A | 127 | 13.019 | 25.407 | 17.596 | 1.00 | 35.37 | MOLA C |
| ATOM | 201 | CD1 | TRP | A | 127 | 13.492 | 26.245 | 16.645 | 1.00 | 43.94 | MOLA C |
| ATOM | 202 | CD2 | TRP | A | 127 | 12.374 | 26.231 | 18.576 | 1.00 | 33.67 | MOLA C |
| ATOM | 203 | CE2 | TRP | A | 127 | 12.493 | 27.574 | 18.125 | 1.00 | 43.91 | MOLA C |
| ATOM | 204 | CE3 | TRP | A | 127 | 11.657 | 25.972 | 19.764 | 1.00 | 44.32 | MOLA C |
| ATOM | 205 | NE1 | TRP | A | 127 | 13.187 | 27.540 | 16.950 | 1.00 | 37.69 | MOLA N |
| ATOM | 206 | CZ2 | TRP | A | 127 | 11.983 | 28.680 | 18.855 | 1.00 | 37.78 | MOLA C |
| ATOM | 207 | CZ3 | TRP | A | 127 | 11.095 | 27.096 | 20.505 | 1.00 | 39.59 | MOLA C |
| ATOM | 208 | CH2 | TRP | A | 127 | 11.275 | 28.415 | 20.038 | 1.00 | 46.66 | MOLA C |
| ATOM | 209 | N | GLU | A | 128 | 9.884 | 24.340 | 16.874 | 1.00 | 52.47 | MOLA N |
| ATOM | 210 | CA | GLU | A | 128 | 8.632 | 24.831 | 17.481 | 1.00 | 51.45 | MOLA C |
| ATOM | 211 | C | GLU | A | 128 | 7.393 | 24.010 | 17.030 | 1.00 | 49.91 | MOLA C |
| ATOM | 212 | O | GLU | A | 128 | 6.243 | 24.347 | 17.309 | 1.00 | 52.14 | MOLA O |
| ATOM | 213 | CB | GLU | A | 128 | 8.492 | 26.330 | 17.277 | 1.00 | 48.29 | MOLA C |
| ATOM | 214 | CG | GLU | A | 128 | 8.760 | 26.791 | 15.877 | 1.00 | 54.22 | MOLA C |
| ATOM | 215 | CD | GLU | A | 128 | 9.023 | 28.293 | 15.778 | 1.00 | 55.05 | MOLA C |
| ATOM | 216 | OE1 | GLU | A | 128 | 10.077 | 28.634 | 15.205 | 1.00 | 63.55 | MOLA O |
| ATOM | 217 | OE2 | GLU | A | 128 | 8.163 | 29.124 | 16.229 | 1.00 | 44.73 | MOLA O |
| ATOM | 218 | N | GLU | A | 129 | 7.663 | 22.883 | 16.386 | 1.00 | 49.10 | MOLA N |
| ATOM | 219 | CA | GLU | A | 129 | 6.630 | 21.960 | 15.905 | 1.00 | 50.36 | MOLA C |
| ATOM | 220 | C | GLU | A | 129 | 6.903 | 20.576 | 16.411 | 1.00 | 46.20 | MOLA C |
| ATOM | 221 | O | GLU | A | 129 | 6.125 | 19.665 | 16.217 | 1.00 | 45.26 | MOLA O |
| ATOM | 222 | CB | GLU | A | 129 | 6.774 | 21.779 | 14.398 | 1.00 | 52.68 | MOLA C |
| ATOM | 223 | CG | GLU | A | 129 | 5.802 | 22.532 | 13.419 | 1.00 | 61.49 | MOLA C |
| ATOM | 224 | CD | GLU | A | 129 | 5.707 | 24.049 | 13.777 | 1.00 | 62.78 | MOLA C |
| ATOM | 225 | OE1 | GLU | A | 129 | 6.357 | 24.909 | 13.129 | 1.00 | 45.45 | MOLA O |
| ATOM | 226 | OE2 | GLU | A | 129 | 4.931 | 24.395 | 14.716 | 1.00 | 59.05 | MOLA O |
| ATOM | 227 | N | ASP | A | 130 | 8.045 | 20.398 | 17.022 | 1.00 | 43.74 | MOLA N |
| ATOM | 228 | CA | ASP | A | 130 | 8.513 | 19.067 | 17.330 | 1.00 | 41.73 | MOLA C |
| ATOM | 229 | C | ASP | A | 130 | 7.764 | 18.453 | 18.467 | 1.00 | 39.12 | MOLA C |
| ATOM | 230 | O | ASP | A | 130 | 7.828 | 18.967 | 19.552 | 1.00 | 44.27 | MOLA O |
| ATOM | 231 | CB | ASP | A | 130 | 9.963 | 19.114 | 17.731 | 1.00 | 37.08 | MOLA C |
| ATOM | 232 | CG | ASP | A | 130 | 10.560 | 17.739 | 17.756 | 1.00 | 48.19 | MOLA C |
| ATOM | 233 | OD1 | ASP | A | 130 | 11.778 | 17.572 | 17.516 | 1.00 | 35.03 | MOLA O |
| ATOM | 234 | OD2 | ASP | A | 130 | 9.772 | 16.791 | 17.972 | 1.00 | 40.03 | MOLA O |
| ATOM | 235 | N | PRO | A | 131 | 7.002 | 17.394 | 18.211 | 1.00 | 37.74 | MOLA N |
| ATOM | 236 | CA | PRO | A | 131 | 6.222 | 16.665 | 19.197 | 1.00 | 36.34 | MOLA C |
| ATOM | 237 | C | PRO | A | 131 | 6.980 | 16.188 | 20.454 | 1.00 | 38.07 | MOLA C |
| ATOM | 238 | O | PRO | A | 131 | 6.409 | 16.008 | 21.558 | 1.00 | 37.70 | MOLA O |
| ATOM | 239 | CB | PRO | A | 131 | 5.711 | 15.436 | 18.399 | 1.00 | 33.03 | MOLA C |
| ATOM | 240 | CG | PRO | A | 131 | 6.432 | 15.409 | 17.215 | 1.00 | 37.62 | MOLA C |
| ATOM | 241 | CD | PRO | A | 131 | 6.766 | 16.837 | 16.873 | 1.00 | 37.65 | MOLA C |
| ATOM | 242 | N | LEU | A | 132 | 8.249 | 15.891 | 20.294 | 1.00 | 40.42 | MOLA N |
| ATOM | 243 | CA | LEU | A | 132 | 9.024 | 15.464 | 21.471 | 1.00 | 40.49 | MOLA C |
| ATOM | 244 | C | LEU | A | 132 | 9.530 | 16.680 | 22.311 | 1.00 | 36.73 | MOLA C |
| ATOM | 245 | O | LEU | A | 132 | 10.265 | 16.514 | 23.265 | 1.00 | 33.82 | MOLA O |
| ATOM | 246 | CB | LEU | A | 132 | 10.207 | 14.614 | 21.032 | 1.00 | 41.62 | MOLA C |
| ATOM | 247 | CG | LEU | A | 132 | 9.901 | 13.268 | 20.414 | 1.00 | 34.30 | MOLA C |
| ATOM | 248 | CD1 | LEU | A | 132 | 11.224 | 12.537 | 20.182 | 1.00 | 28.89 | MOLA C |
| ATOM | 249 | CD2 | LEU | A | 132 | 9.013 | 12.435 | 21.240 | 1.00 | 27.42 | MOLA C |
| ATOM | 250 | N | ALA | A | 133 | 9.136 | 17.886 | 21.957 | 1.00 | 32.85 | MOLA N |
| ATOM | 251 | CA | ALA | A | 133 | 9.523 | 19.023 | 22.758 | 1.00 | 35.74 | MOLA C |
| ATOM | 252 | C | ALA | A | 133 | 8.847 | 18.897 | 24.106 | 1.00 | 35.93 | MOLA C |
| ATOM | 253 | O | ALA | A | 133 | 7.738 | 18.372 | 24.157 | 1.00 | 30.95 | MOLA O |
| ATOM | 254 | CB | ALA | A | 133 | 9.124 | 20.310 | 22.099 | 1.00 | 36.70 | MOLA C |
| ATOM | 255 | N | GLY | A | 134 | 9.540 | 19.375 | 25.165 | 1.00 | 33.37 | MOLA N |
| ATOM | 256 | CA | GLY | A | 134 | 9.023 | 19.363 | 26.516 | 1.00 | 33.29 | MOLA C |
| ATOM | 257 | C | GLY | A | 134 | 8.407 | 20.665 | 26.986 | 1.00 | 32.18 | MOLA C |
| ATOM | 258 | O | GLY | A | 134 | 8.129 | 21.536 | 26.219 | 1.00 | 31.63 | MOLA O |
| ATOM | 259 | N | ILE | A | 135 | 8.178 | 20.812 | 28.290 | 1.00 | 30.60 | MOLA N |
| ATOM | 260 | CA | ILE | A | 135 | 7.459 | 21.986 | 28.790 | 1.00 | 27.00 | MOLA C |
| ATOM | 261 | C | ILE | A | 135 | 8.202 | 23.276 | 28.512 | 1.00 | 26.01 | MOLA C |
| ATOM | 262 | O | ILE | A | 135 | 7.665 | 24.255 | 28.070 | 1.00 | 26.20 | MOLA O |
| ATOM | 263 | CB | ILE | A | 135 | 7.215 | 21.784 | 30.263 | 1.00 | 29.22 | MOLA C |
| ATOM | 264 | CG1 | ILE | A | 135 | 6.231 | 20.620 | 30.473 | 1.00 | 28.60 | MOLA C |
| ATOM | 265 | CG2 | ILE | A | 135 | 6.720 | 23.037 | 30.916 | 1.00 | 36.81 | MOLA C |
| ATOM | 266 | CD1 | ILE | A | 135 | 5.782 | 20.354 | 31.954 | 1.00 | 30.82 | MOLA C |
| ATOM | 267 | N | ILE | A | 136 | 9.461 | 23.297 | 28.809 | 1.00 | 29.92 | MOLA N |
| ATOM | 268 | CA | ILE | A | 136 | 10.226 | 24.568 | 28.684 | 1.00 | 29.21 | MOLA C |
| ATOM | 269 | C | ILE | A | 136 | 10.223 | 25.234 | 27.282 | 1.00 | 30.19 | MOLA C |
| ATOM | 270 | O | ILE | A | 136 | 9.844 | 26.390 | 27.116 | 1.00 | 28.56 | MOLA O |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 271 | CB | ILE | A | 136 | 11.678 | 24.341 | 29.172 | 1.00 | 26.07 | MOLA C |
| ATOM | 272 | CG1 | ILE | A | 136 | 11.655 | 24.234 | 30.669 | 1.00 | 19.35 | MOLA C |
| ATOM | 273 | CG2 | ILE | A | 136 | 12.602 | 25.420 | 28.723 | 1.00 | 19.77 | MOLA C |
| ATOM | 274 | CD1 | ILE | A | 136 | 12.794 | 23.551 | 31.249 | 1.00 | 21.35 | MOLA C |
| ATOM | 275 | N | PRO | A | 137 | 10.659 | 24.500 | 26.277 | 1.00 | 31.30 | MOLA N |
| ATOM | 276 | CA | PRO | A | 137 | 10.666 | 25.053 | 24.921 | 1.00 | 31.51 | MOLA C |
| ATOM | 277 | C | PRO | A | 137 | 9.248 | 25.432 | 24.472 | 1.00 | 30.49 | MOLA C |
| ATOM | 278 | O | PRO | A | 137 | 9.055 | 26.424 | 23.823 | 1.00 | 34.14 | MOLA O |
| ATOM | 279 | CB | PRO | A | 137 | 11.191 | 23.887 | 24.053 | 1.00 | 30.90 | MOLA C |
| ATOM | 280 | CG | PRO | A | 137 | 11.021 | 22.644 | 24.871 | 1.00 | 31.62 | MOLA C |
| ATOM | 281 | CD | PRO | A | 137 | 11.092 | 23.093 | 26.340 | 1.00 | 31.42 | MOLA C |
| ATOM | 282 | N | ARG | A | 138 | 8.258 | 24.633 | 24.804 | 1.00 | 30.91 | MOLA N |
| ATOM | 283 | CA | ARG | A | 138 | 6.890 | 24.947 | 24.425 | 1.00 | 30.78 | MOLA C |
| ATOM | 284 | C | ARG | A | 138 | 6.429 | 26.159 | 25.166 | 1.00 | 29.55 | MOLA C |
| ATOM | 285 | O | ARG | A | 138 | 5.743 | 26.991 | 24.603 | 1.00 | 34.99 | MOLA O |
| ATOM | 286 | CB | ARG | A | 138 | 5.945 | 23.790 | 24.754 | 1.00 | 28.23 | MOLA C |
| ATOM | 287 | CG | ARG | A | 138 | 6.030 | 22.684 | 23.778 | 1.00 | 25.72 | MOLA C |
| ATOM | 288 | CD | ARG | A | 138 | 5.223 | 21.441 | 24.188 | 1.00 | 29.72 | MOLA C |
| ATOM | 289 | NE | ARG | A | 138 | 5.670 | 20.291 | 23.389 | 1.00 | 37.37 | MOLA N |
| ATOM | 290 | CZ | ARG | A | 138 | 5.054 | 19.787 | 22.313 | 1.00 | 44.68 | MOLA C |
| ATOM | 291 | NH1 | ARG | A | 138 | 3.894 | 20.281 | 21.867 | 1.00 | 26.49 | MOLA N |
| ATOM | 292 | NH2 | ARG | A | 138 | 5.605 | 18.756 | 21.692 | 1.00 | 39.36 | MOLA N |
| ATOM | 293 | N | THR | A | 139 | 6.762 | 26.251 | 26.449 | 1.00 | 26.54 | MOLA N |
| ATOM | 294 | CA | THR | A | 139 | 6.269 | 27.373 | 27.218 | 1.00 | 28.59 | MOLA C |
| ATOM | 295 | C | THR | A | 139 | 6.859 | 28.680 | 26.716 | 1.00 | 28.09 | MOLA C |
| ATOM | 296 | O | THR | A | 139 | 6.187 | 29.656 | 26.538 | 1.00 | 26.50 | MOLA O |
| ATOM | 297 | CB | THR | A | 139 | 6.536 | 27.190 | 28.660 | 1.00 | 30.10 | MOLA C |
| ATOM | 298 | CG2 | THR | A | 139 | 6.107 | 28.421 | 29.365 | 1.00 | 29.94 | MOLA C |
| ATOM | 299 | OG1 | THR | A | 139 | 5.791 | 26.050 | 29.133 | 1.00 | 23.80 | MOLA O |
| ATOM | 300 | N | LEU | A | 140 | 8.119 | 28.644 | 26.385 | 1.00 | 32.17 | MOLA N |
| ATOM | 301 | CA | LEU | A | 140 | 8.778 | 29.800 | 25.830 | 1.00 | 33.69 | MOLA C |
| ATOM | 302 | C | LEU | A | 140 | 8.196 | 30.258 | 24.518 | 1.00 | 36.42 | MOLA C |
| ATOM | 303 | O | LEU | A | 140 | 7.984 | 31.443 | 24.319 | 1.00 | 36.16 | MOLA O |
| ATOM | 304 | CB | LEU | A | 140 | 10.241 | 29.492 | 25.616 | 1.00 | 34.03 | MOLA C |
| ATOM | 305 | CG | LEU | A | 140 | 11.058 | 29.549 | 26.915 | 1.00 | 42.16 | MOLA C |
| ATOM | 306 | CD1 | LEU | A | 140 | 12.551 | 29.292 | 26.687 | 1.00 | 44.26 | MOLA C |
| ATOM | 307 | CD2 | LEU | A | 140 | 10.856 | 30.882 | 27.719 | 1.00 | 32.25 | MOLA C |
| ATOM | 308 | N | HIS | A | 141 | 7.954 | 29.334 | 23.617 | 1.00 | 35.29 | MOLA N |
| ATOM | 309 | CA | HIS | A | 141 | 7.336 | 29.691 | 22.369 | 1.00 | 36.22 | MOLA C |
| ATOM | 310 | C | HIS | A | 141 | 5.955 | 30.332 | 22.560 | 1.00 | 36.58 | MOLA C |
| ATOM | 311 | O | HIS | A | 141 | 5.637 | 31.324 | 21.918 | 1.00 | 35.28 | MOLA O |
| ATOM | 312 | CB | HIS | A | 141 | 7.265 | 28.431 | 21.504 | 1.00 | 38.92 | MOLA C |
| ATOM | 313 | CG | HIS | A | 141 | 6.787 | 28.659 | 20.097 | 1.00 | 46.28 | MOLA C |
| ATOM | 314 | CD2 | HIS | A | 141 | 7.439 | 29.087 | 18.988 | 1.00 | 59.13 | MOLA C |
| ATOM | 315 | ND1 | HIS | A | 141 | 5.489 | 28.404 | 19.706 | 1.00 | 53.80 | MOLA N |
| ATOM | 316 | CE1 | HIS | A | 141 | 5.359 | 28.666 | 18.421 | 1.00 | 53.06 | MOLA C |
| ATOM | 317 | NE2 | HIS | A | 141 | 6.524 | 29.089 | 17.961 | 1.00 | 58.70 | MOLA N |
| TER | 318 | | HIS | A | 141 | | | | | | |
| ATOM | 319 | N | VAL | A | 158 | 15.470 | 34.388 | 31.165 | 1.00 | 35.84 | MOLA N |
| ATOM | 320 | CA | VAL | A | 158 | 15.494 | 33.062 | 31.747 | 1.00 | 32.10 | MOLA C |
| ATOM | 321 | C | VAL | A | 158 | 16.685 | 32.857 | 32.648 | 1.00 | 32.79 | MOLA C |
| ATOM | 322 | O | VAL | A | 158 | 17.699 | 33.546 | 32.572 | 1.00 | 37.06 | MOLA O |
| ATOM | 323 | CB | VAL | A | 158 | 15.553 | 32.051 | 30.634 | 1.00 | 34.98 | MOLA C |
| ATOM | 324 | CG1 | VAL | A | 158 | 14.278 | 32.150 | 29.770 | 1.00 | 28.33 | MOLA C |
| ATOM | 325 | CG2 | VAL | A | 158 | 16.762 | 32.282 | 29.788 | 1.00 | 38.81 | MOLA C |
| ATOM | 326 | N | SER | A | 159 | 16.567 | 31.921 | 33.558 | 1.00 | 33.87 | MOLA N |
| ATOM | 327 | CA | SER | A | 159 | 17.764 | 31.527 | 34.331 | 1.00 | 32.32 | MOLA C |
| ATOM | 328 | C | SER | A | 159 | 17.802 | 29.988 | 34.537 | 1.00 | 30.43 | MOLA C |
| ATOM | 329 | O | SER | A | 159 | 16.736 | 29.295 | 34.487 | 1.00 | 35.25 | MOLA O |
| ATOM | 330 | CB | SER | A | 159 | 17.862 | 32.325 | 35.637 | 1.00 | 31.46 | MOLA C |
| ATOM | 331 | OG | SER | A | 159 | 16.714 | 32.130 | 36.410 | 1.00 | 39.39 | MOLA O |
| ATOM | 332 | N | LEU | A | 160 | 18.987 | 29.418 | 34.686 | 1.00 | 25.85 | MOLA N |
| ATOM | 333 | CA | LEU | A | 160 | 19.049 | 27.995 | 34.982 | 1.00 | 27.49 | MOLA C |
| ATOM | 334 | C | LEU | A | 160 | 19.983 | 27.798 | 36.168 | 1.00 | 26.15 | MOLA C |
| ATOM | 335 | O | LEU | A | 160 | 21.147 | 28.176 | 36.113 | 1.00 | 26.68 | MOLA O |
| ATOM | 336 | CB | LEU | A | 160 | 19.479 | 27.154 | 33.729 | 1.00 | 29.02 | MOLA C |
| ATOM | 337 | CG | LEU | A | 160 | 19.559 | 25.622 | 33.857 | 1.00 | 34.07 | MOLA C |
| ATOM | 338 | CD1 | LEU | A | 160 | 18.255 | 25.023 | 34.393 | 1.00 | 22.04 | MOLA C |
| ATOM | 339 | CD2 | LEU | A | 160 | 19.904 | 24.918 | 32.589 | 1.00 | 30.36 | MOLA C |
| ATOM | 340 | N | LEU | A | 161 | 19.476 | 27.225 | 37.252 | 1.00 | 24.69 | MOLA N |
| ATOM | 341 | CA | LEU | A | 161 | 20.332 | 26.901 | 38.355 | 1.00 | 25.67 | MOLA C |
| ATOM | 342 | C | LEU | A | 161 | 20.144 | 25.471 | 38.730 | 1.00 | 27.76 | MOLA C |
| ATOM | 343 | O | LEU | A | 161 | 19.228 | 24.813 | 38.193 | 1.00 | 32.71 | MOLA O |
| ATOM | 344 | CB | LEU | A | 161 | 20.124 | 27.825 | 39.518 | 1.00 | 22.36 | MOLA C |
| ATOM | 345 | CG | LEU | A | 161 | 18.876 | 27.727 | 40.355 | 1.00 | 21.18 | MOLA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 346 | CD1 | LEU | A | 161 | 19.008 | 26.713 | 41.465 | 1.00 | 28.78 | MOLA C |
| ATOM | 347 | CD2 | LEU | A | 161 | 18.668 | 29.098 | 41.030 | 1.00 | 22.60 | MOLA C |
| ATOM | 348 | N | GLU | A | 162 | 21.041 | 24.941 | 39.578 | 1.00 | 25.99 | MOLA N |
| ATOM | 349 | CA | GLU | A | 162 | 20.900 | 23.601 | 40.070 | 1.00 | 23.57 | MOLA C |
| ATOM | 350 | C | GLU | A | 162 | 21.164 | 23.616 | 41.526 | 1.00 | 27.46 | MOLA C |
| ATOM | 351 | O | GLU | A | 162 | 21.865 | 24.502 | 42.036 | 1.00 | 27.31 | MOLA O |
| ATOM | 352 | CB | GLU | A | 162 | 21.935 | 22.785 | 39.443 | 1.00 | 24.81 | MOLA C |
| ATOM | 353 | CG | GLU | A | 162 | 21.411 | 21.960 | 38.328 | 1.00 | 29.19 | MOLA C |
| ATOM | 354 | CD | GLU | A | 162 | 22.485 | 21.112 | 37.669 | 1.00 | 45.23 | MOLA C |
| ATOM | 355 | OE1 | GLU | A | 162 | 22.391 | 20.902 | 36.432 | 1.00 | 30.52 | MOLA O |
| ATOM | 356 | OE2 | GLU | A | 162 | 23.393 | 20.651 | 38.419 | 1.00 | 45.86 | MOLA O |
| TER | 357 | | GLU | A | 162 | | | | | | |
| ATOM | 358 | N | ASP | A | 170 | 25.055 | 28.148 | 39.187 | 1.00 | 31.07 | MOLA N |
| ATOM | 359 | CA | ASP | A | 170 | 24.498 | 28.804 | 38.023 | 1.00 | 31.71 | MOLA C |
| ATOM | 360 | CA | SP | A | 170 | 24.907 | 27.978 | 36.869 | 1.00 | 31.16 | MOLA C |
| ATOM | 361 | O | ASP | A | 170 | 25.999 | 27.568 | 36.858 | 1.00 | 33.22 | MOLA O |
| ATOM | 362 | CB | ASP | A | 170 | 25.135 | 30.188 | 37.894 | 1.00 | 31.72 | MOLA C |
| ATOM | 363 | CG | ASP | A | 170 | 24.472 | 31.013 | 36.878 | 1.00 | 35.54 | MOLA C |
| ATOM | 364 | OD1 | ASP | A | 170 | 23.861 | 30.412 | 35.962 | 1.00 | 23.42 | MOLA O |
| ATOM | 365 | OD2 | ASP | A | 170 | 24.544 | 32.246 | 37.013 | 1.00 | 42.79 | MOLA O |
| ATOM | 366 | N | LEU | A | 171 | 24.103 | 27.741 | 35.873 | 1.00 | 34.95 | MOLA N |
| ATOM | 367 | CA | LEU | A | 171 | 24.610 | 26.975 | 34.716 | 1.00 | 38.50 | MOLA C |
| ATOM | 368 | C | LEU | A | 171 | 24.706 | 27.747 | 33.386 | 1.00 | 38.97 | MOLA C |
| ATOM | 369 | O | LEU | A | 171 | 25.164 | 27.203 | 32.345 | 1.00 | 39.55 | MOLA O |
| ATOM | 370 | CB | LEU | A | 171 | 23.732 | 25.762 | 34.515 | 1.00 | 39.03 | MOLA C |
| ATOM | 371 | CG | LEU | A | 171 | 24.051 | 24.683 | 35.528 | 1.00 | 35.66 | MOLA C |
| ATOM | 372 | CD1 | LEU | A | 171 | 23.021 | 24.563 | 36.526 | 1.00 | 35.70 | MOLA C |
| ATOM | 373 | CD2 | LEU | A | 171 | 24.079 | 23.369 | 34.718 | 1.00 | 42.72 | MOLA C |
| ATOM | 374 | N | LEU | A | 172 | 24.260 | 28.998 | 33.415 | 1.00 | 35.63 | MOLA N |
| ATOM | 375 | CA | LEU | A | 172 | 24.206 | 29.784 | 32.205 | 1.00 | 38.62 | MOLA C |
| ATOM | 376 | C | LEU | A | 172 | 25.256 | 30.855 | 32.239 | 1.00 | 40.33 | MOLA C |
| ATOM | 377 | O | LEU | A | 172 | 25.446 | 31.602 | 31.261 | 1.00 | 49.47 | MOLA O |
| ATOM | 378 | CB | LEU | A | 172 | 22.823 | 30.406 | 32.023 | 1.00 | 40.33 | MOLA C |
| ATOM | 379 | CG | LEU | A | 172 | 21.811 | 29.508 | 31.299 | 1.00 | 35.66 | MOLA C |
| ATOM | 380 | CD1 | LEU | A | 172 | 21.861 | 28.047 | 31.662 | 1.00 | 52.98 | MOLA C |
| ATOM | 381 | CD2 | LEU | A | 172 | 20.475 | 30.098 | 31.529 | 1.00 | 18.42 | MOLA C |
| ATOM | 382 | N | ASN | A | 173 | 25.975 | 30.945 | 33.344 | 1.00 | 43.84 | MOLA N |
| ATOM | 383 | CA | ASN | A | 173 | 27.103 | 31.883 | 33.391 | 1.00 | 45.56 | MOLA C |
| ATOM | 384 | C | ASN | A | 173 | 28.314 | 31.533 | 32.497 | 1.00 | 46.22 | MOLA C |
| ATOM | 385 | O | ASN | A | 173 | 28.885 | 30.475 | 32.653 | 1.00 | 45.01 | MOLA O |
| ATOM | 386 | CB | ASN | A | 173 | 27.635 | 32.010 | 34.802 | 1.00 | 44.11 | MOLA C |
| ATOM | 387 | CG | ASN | A | 173 | 28.817 | 33.058 | 34.898 | 1.00 | 48.63 | MOLA C |
| ATOM | 388 | ND2 | ASN | A | 173 | 28.791 | 33.885 | 35.952 | 1.00 | 28.03 | MOLA N |
| ATOM | 389 | OD1 | ASN | A | 173 | 29.698 | 33.131 | 34.015 | 1.00 | 47.59 | MOLA O |
| TER | 390 | | ASN | A | 173 | | | | | | |
| ATOM | 391 | N | ILE | A | 202 | 19.407 | 35.525 | 31.150 | 1.00 | 39.51 | MOLA N |
| ATOM | 392 | CA | ILE | A | 202 | 19.557 | 35.726 | 29.723 | 1.00 | 40.20 | MOLA C |
| ATOM | 393 | C | ILE | A | 202 | 18.263 | 36.215 | 29.133 | 1.00 | 39.54 | MOLA C |
| ATOM | 394 | O | ILE | A | 202 | 17.216 | 35.541 | 29.262 | 1.00 | 38.09 | MOLA O |
| ATOM | 395 | CB | ILE | A | 202 | 19.978 | 34.419 | 29.016 | 1.00 | 40.41 | MOLA C |
| ATOM | 396 | CG1 | ILE | A | 202 | 21.416 | 34.116 | 29.443 | 1.00 | 36.04 | MOLA C |
| ATOM | 397 | CG2 | ILE | A | 202 | 19.906 | 34.558 | 27.496 | 1.00 | 35.29 | MOLA C |
| ATOM | 398 | CD1 | ILE | A | 202 | 21.937 | 32.781 | 28.914 | 1.00 | 46.74 | MOLA C |
| TER | 399 | | ILE | A | 202 | | | | | | |
| ATOM | 400 | N | GLU | A | 209 | 15.361 | 33.152 | 19.120 | 1.00 | 51.98 | MOLA N |
| ATOM | 401 | CA | GLU | A | 209 | 16.516 | 33.181 | 20.001 | 1.00 | 48.60 | MOLA C |
| ATOM | 402 | C | GLU | A | 209 | 16.406 | 32.099 | 21.076 | 1.00 | 44.55 | MOLA C |
| ATOM | 403 | O | GLU | A | 209 | 17.359 | 31.790 | 21.741 | 1.00 | 46.63 | MOLA O |
| ATOM | 404 | CB | GLU | A | 209 | 16.647 | 34.550 | 20.622 | 1.00 | 47.15 | MOLA C |
| ATOM | 405 | CG | GLU | A | 209 | 18.050 | 34.856 | 21.074 | 1.00 | 54.94 | MOLA C |
| ATOM | 406 | CD | GLU | A | 209 | 18.174 | 36.269 | 21.656 | 1.00 | 65.61 | MOLA C |
| ATOM | 407 | OE1 | GLU | A | 209 | 18.155 | 36.462 | 22.883 | 1.00 | 79.56 | MOLA O |
| ATOM | 408 | OE2 | GLU | A | 209 | 18.255 | 37.219 | 20.885 | 1.00 | 73.23 | MOLA O |
| ATOM | 409 | N | VAL | A | 210 | 15.236 | 31.484 | 21.201 | 1.00 | 43.35 | MOLA N |
| ATOM | 410 | CA | VAL | A | 210 | 15.004 | 30.475 | 22.222 | 1.00 | 42.64 | MOLA C |
| ATOM | 411 | C | VAL | A | 210 | 15.854 | 29.279 | 21.923 | 1.00 | 44.94 | MOLA C |
| ATOM | 412 | O | VAL | A | 210 | 16.570 | 28.772 | 22.793 | 1.00 | 48.25 | MOLA O |
| ATOM | 413 | CB | VAL | A | 210 | 13.568 | 29.941 | 22.296 | 1.00 | 39.05 | MOLA C |
| ATOM | 414 | CG1 | VAL | A | 210 | 13.094 | 30.008 | 23.611 | 1.00 | 44.35 | MOLA C |
| ATOM | 415 | CG2 | VAL | A | 210 | 12.615 | 30.862 | 21.616 | 1.00 | 39.63 | MOLA C |
| ATOM | 416 | N | TYR | A | 211 | 15.786 | 28.813 | 20.684 | 1.00 | 44.83 | MOLA N |
| ATOM | 417 | CA | TYR | A | 211 | 16.539 | 27.624 | 20.384 | 1.00 | 42.50 | MOLA C |
| ATOM | 418 | C | TYR | A | 211 | 18.010 | 27.821 | 20.725 | 1.00 | 44.62 | MOLA C |
| ATOM | 419 | O | TYR | A | 211 | 18.588 | 27.104 | 21.527 | 1.00 | 46.32 | MOLA O |
| ATOM | 420 | CB | TYR | A | 211 | 16.354 | 27.177 | 18.962 | 1.00 | 36.60 | MOLA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 421 | CG | TYR | A | 211 | 16.766 | 25.724 | 18.808 | 1.00 | 41.62 | MOLA C |
| ATOM | 422 | CD1 | TYR | A | 211 | 15.995 | 24.665 | 19.377 | 1.00 | 51.90 | MOLA C |
| ATOM | 423 | CD2 | TYR | A | 211 | 17.908 | 25.388 | 18.129 | 1.00 | 32.38 | MOLA C |
| ATOM | 424 | CE1 | TYR | A | 211 | 16.370 | 23.330 | 19.246 | 1.00 | 40.57 | MOLA C |
| ATOM | 425 | CE2 | TYR | A | 211 | 18.290 | 24.066 | 18.022 | 1.00 | 43.32 | MOLA C |
| ATOM | 426 | CZ | TYR | A | 211 | 17.507 | 23.057 | 18.568 | 1.00 | 38.83 | MOLA C |
| ATOM | 427 | OH | TYR | A | 211 | 17.886 | 21.794 | 18.431 | 1.00 | 31.99 | MOLA O |
| ATOM | 428 | N | GLN | A | 212 | 18.594 | 28.839 | 20.144 | 1.00 | 47.41 | MOLA N |
| ATOM | 429 | CA | GLN | A | 212 | 20.013 | 29.075 | 20.307 | 1.00 | 47.52 | MOLA C |
| ATOM | 430 | C | GLN | A | 212 | 20.324 | 29.053 | 21.807 | 1.00 | 43.97 | MOLA C |
| ATOM | 431 | O | GLN | A | 212 | 21.317 | 28.484 | 22.238 | 1.00 | 38.47 | MOLA O |
| ATOM | 432 | CS | GLN | A | 212 | 20.415 | 30.443 | 19.667 | 1.00 | 47.95 | MOLA C |
| ATOM | 433 | CG | GLN | A | 212 | 19.927 | 30.695 | 18.170 | 1.00 | 45.88 | MOLA C |
| ATOM | 434 | CD | GLN | A | 212 | 19.697 | 32.200 | 17.816 | 1.00 | 56.45 | MOLA C |
| ATOM | 435 | NE2 | GLN | A | 212 | 20.431 | 33.074 | 18.472 | 1.00 | 67.14 | MOLA N |
| ATOM | 436 | OE1 | GLN | A | 212 | 18.860 | 32.555 | 16.980 | 1.00 | 72.99 | MOLA O |
| ATOM | 437 | N | ILE | A | 213 | 19.482 | 29.706 | 22.605 | 1.00 | 44.51 | MOLA N |
| ATOM | 438 | CA | ILE | A | 213 | 19.751 | 29.825 | 24.038 | 1.00 | 44.13 | MOLA C |
| ATOM | 439 | C | ILE | A | 213 | 19.814 | 28.444 | 24.728 | 1.00 | 45.10 | MOLA C |
| ATOM | 440 | O | ILE | A | 213 | 20.770 | 28.126 | 25.444 | 1.00 | 44.95 | MOLA O |
| ATOM | 441 | CB | ILE | A | 213 | 18.699 | 30.700 | 24.678 | 1.00 | 43.99 | MOLA C |
| ATOM | 442 | CG1 | ILE | A | 213 | 18.981 | 32.142 | 24.286 | 1.00 | 42.97 | MOLA C |
| ATOM | 443 | CG2 | ILE | A | 213 | 18.686 | 30.504 | 26.201 | 1.00 | 38.42 | MOLA C |
| ATOM | 444 | CD1 | ILE | A | 213 | 17.930 | 33.144 | 24.724 | 1.00 | 54.63 | MOLA C |
| ATOM | 445 | N | LEU | A | 214 | 18.832 | 27.601 | 24.431 | 1.00 | 43.17 | MOLA N |
| ATOM | 446 | CA | LEU | A | 214 | 18.790 | 26.232 | 24.921 | 1.00 | 45.83 | MOLA C |
| ATOM | 447 | C | LEU | A | 214 | 19.926 | 25.316 | 24.427 | 1.00 | 47.44 | MOLA C |
| ATOM | 448 | O | LEU | A | 214 | 20.459 | 24.536 | 25.197 | 1.00 | 51.80 | MOLA O |
| ATOM | 449 | CB | LEU | A | 214 | 17.433 | 25.616 | 24.596 | 1.00 | 45.89 | MOLA C |
| ATOM | 450 | CG | LEU | A | 214 | 16.336 | 26.526 | 25.184 | 1.00 | 48.79 | MOLA C |
| ATOM | 451 | CD1 | LEU | A | 214 | 14.992 | 26.028 | 24.752 | 1.00 | 43.79 | MOLA C |
| ATOM | 452 | CD2 | LEU | A | 214 | 16.459 | 26.612 | 26.700 | 1.00 | 48.71 | MOLA C |
| ATOM | 453 | N | GLU | A | 215 | 20.314 | 25.375 | 23.169 | 1.00 | 49.53 | MOLA N |
| ATOM | 454 | CA | GLU | A | 215 | 21.507 | 24.630 | 22.690 | 1.00 | 49.94 | MOLA C |
| ATOM | 455 | C | GLU | A | 215 | 22.697 | 24.850 | 23.586 | 1.00 | 48.94 | MOLA C |
| ATOM | 456 | O | GLU | A | 215 | 23.251 | 23.920 | 24.165 | 1.00 | 51.22 | MOLA O |
| ATOM | 457 | CB | GLU | A | 215 | 21.936 | 25.143 | 21.318 | 1.00 | 51.55 | MOLA C |
| ATOM | 458 | CG | GLU | A | 215 | 22.550 | 24.116 | 20.435 | 1.00 | 49.34 | MOLA C |
| ATOM | 459 | CD | GLU | A | 215 | 22.382 | 24.526 | 19.009 | 1.00 | 51.60 | MOLA C |
| ATOM | 460 | OE1 | GLU | A | 215 | 22.118 | 23.647 | 18.183 | 1.00 | 59.66 | MOLA O |
| ATOM | 461 | OE2 | GLU | A | 215 | 22.445 | 25.736 | 18.704 | 1.00 | 32.86 | MOLA O |
| ATOM | 462 | N | LYS | A | 216 | 23.105 | 26.106 | 23.617 | 1.00 | 47.42 | MOLA N |
| ATOM | 463 | CA | LYS | A | 216 | 24.114 | 26.584 | 24.489 | 1.00 | 47.67 | MOLA C |
| ATOM | 464 | C | LYS | A | 216 | 24.046 | 25.895 | 25.817 | 1.00 | 44.04 | MOLA C |
| ATOM | 465 | O | LYS | A | 216 | 24.937 | 25.061 | 26.110 | 1.00 | 47.37 | MOLA O |
| ATOM | 466 | CB | LYS | A | 216 | 23.889 | 28.058 | 24.696 | 1.00 | 47.76 | MOLA C |
| ATOM | 467 | CG | LYS | A | 216 | 25.144 | 28.840 | 24.570 | 1.00 | 56.16 | MOLA C |
| ATOM | 468 | CD | LYS | A | 216 | 25.031 | 30.302 | 25.025 | 1.00 | 56.30 | MOLA C |
| ATOM | 469 | CE | LYS | A | 216 | 26.449 | 30.938 | 24.854 | 1.00 | 63.07 | MOLA C |
| ATOM | 470 | NZ | LYS | A | 216 | 26.439 | 32.381 | 24.374 | 1.00 | 59.00 | MOLA N |
| ATOM | 471 | N | GLY | A | 217 | 22.991 | 26.190 | 26.596 | 1.00 | 37.38 | MOLA N |
| ATOM | 472 | CA | GLY | A | 217 | 22.882 | 25.651 | 27.964 | 1.00 | 37.42 | MOLA C |
| ATOM | 473 | C | GLY | A | 217 | 23.371 | 24.207 | 28.061 | 1.00 | 38.18 | MOLA C |
| ATOM | 474 | O | GLY | A | 217 | 24.135 | 23.835 | 28.982 | 1.00 | 37.32 | MOLA O |
| ATOM | 475 | N | ALA | A | 218 | 22.953 | 23.397 | 27.082 | 1.00 | 35.55 | MOLA N |
| ATOM | 476 | CA | ALA | A | 218 | 23.165 | 21.978 | 27.163 | 1.00 | 37.44 | MOLA C |
| ATOM | 477 | C | ALA | A | 218 | 24.624 | 21.569 | 27.061 | 1.00 | 39.67 | MOLA C |
| ATOM | 478 | O | ALA | A | 218 | 25.065 | 20.653 | 27.776 | 1.00 | 38.88 | MOLA O |
| ATOM | 479 | CB | ALA | A | 218 | 22.403 | 21.318 | 26.079 | 1.00 | 37.86 | MOLA C |
| ATOM | 480 | N | ALA | A | 219 | 25.329 | 22.227 | 26.128 | 1.00 | 42.38 | MOLA N |
| ATOM | 481 | CA | ALA | A | 219 | 26.767 | 22.109 | 25.922 | 1.00 | 41.37 | MOLA C |
| ATOM | 482 | C | ALA | A | 219 | 27.435 | 22.557 | 27.196 | 1.00 | 42.35 | MOLA C |
| ATOM | 483 | O | ALA | A | 219 | 28.275 | 21.865 | 27.744 | 1.00 | 43.93 | MOLA O |
| ATOM | 484 | CB | ALA | A | 219 | 27.184 | 23.009 | 24.844 | 1.00 | 41.31 | MOLA C |
| ATOM | 485 | N | LYS | A | 220 | 27.042 | 23.714 | 27.678 | 1.00 | 37.89 | MOLA N |
| ATOM | 486 | CA | LYS | A | 220 | 27.600 | 24.136 | 28.889 | 1.00 | 36.26 | MOLA C |
| ATOM | 487 | C | LYS | A | 220 | 27.266 | 23.085 | 29.920 | 1.00 | 39.39 | MOLA C |
| ATOM | 488 | O | LYS | A | 220 | 28.154 | 22.597 | 30.642 | 1.00 | 43.65 | MOLA O |
| ATOM | 489 | CB | LYS | A | 220 | 27.001 | 25.459 | 29.297 | 1.00 | 35.22 | MOLA C |
| ATOM | 490 | CG | LYS | A | 220 | 27.999 | 26.428 | 29.216 | 1.00 | 30.27 | MOLA C |
| ATOM | 491 | CD | LYS | A | 220 | 27.703 | 27.580 | 30.133 | 1.00 | 49.97 | MOLA C |
| ATOM | 492 | CE | LYS | A | 220 | 28.863 | 28.555 | 29.884 | 1.00 | 56.37 | MOLA C |
| ATOM | 493 | NZ | LYS | A | 220 | 29.135 | 28.978 | 31.358 | 1.00 | 68.28 | MOLA N |
| ATOM | 494 | N | ARG | A | 221 | 25.983 | 22.734 | 30.002 | 1.00 | 36.86 | MOLA N |
| ATOM | 495 | CA | ARG | A | 221 | 25.563 | 22.004 | 31.189 | 1.00 | 36.32 | MOLA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 496 | C | ARG | A | 221 | 26.407 | 20.767 | 31.203 | 1.00 | 33.60 | MOLA C |
| ATOM | 497 | O | ARG | A | 221 | 26.941 | 20.401 | 32.229 | 1.00 | 30.61 | MOLA O |
| ATOM | 498 | CB | ARG | A | 221 | 24.053 | 21.740 | 31.210 | 1.00 | 40.80 | MOLA C |
| ATOM | 499 | CG | ARG | A | 221 | 23.590 | 20.921 | 32.351 | 1.00 | 33.93 | MOLA C |
| ATOM | 500 | CD | ARG | A | 221 | 22.087 | 20.923 | 32.464 | 1.00 | 29.82 | MOLA C |
| ATOM | 501 | NE | ARG | A | 221 | 21.465 | 20.530 | 31.223 | 1.00 | 39.42 | MOLA N |
| ATOM | 502 | CZ | ARG | A | 221 | 20.202 | 20.694 | 30.954 | 1.00 | 27.72 | MOLA C |
| ATOM | 503 | NH1 | ARG | A | 221 | 19.435 | 21.280 | 31.803 | 1.00 | 29.59 | MOLA N |
| ATOM | 504 | NH2 | ARG | A | 221 | 19.736 | 20.337 | 29.784 | 1.00 | 43.17 | MOLA N |
| ATOM | 505 | N | THR | A | 222 | 26.624 | 20.227 | 30.014 | 1.00 | 34.51 | MOLA N |
| ATOM | 506 | CA | THR | A | 222 | 27.398 | 18.995 | 29.833 | 1.00 | 34.65 | MOLA C |
| ATOM | 507 | C | THR | A | 222 | 28.868 | 19.134 | 30.152 | 1.00 | 34.96 | MOLA C |
| ATOM | 508 | O | THR | A | 222 | 29.473 | 18.242 | 30.732 | 1.00 | 35.19 | MOLA O |
| ATOM | 509 | CB | THR | A | 222 | 27.296 | 18.501 | 28.401 | 1.00 | 36.34 | MOLA C |
| ATOM | 510 | CG2 | THR | A | 222 | 28.420 | 17.520 | 28.061 | 1.00 | 34.55 | MOLA C |
| ATOM | 511 | OG1 | THR | A | 222 | 26.044 | 17.822 | 28.226 | 1.00 | 32.56 | MOLA O |
| TER | 512 | | THR | A | 222 | | | | | | |
| ATOM | 513 | N | SER | A | 232 | 23.513 | 14.530 | 37.314 | 1.00 | 31.51 | MOLA N |
| ATOM | 514 | CA | SER | A | 232 | 22.285 | 15.283 | 37.143 | 1.00 | 32.40 | MOLA C |
| ATOM | 515 | C | SER | A | 232 | 21.100 | 14.656 | 37.972 | 1.00 | 32.63 | MOLA C |
| ATOM | 516 | O | SER | A | 232 | 20.111 | 15.359 | 38.349 | 1.00 | 34.39 | MOLA O |
| ATOM | 517 | CB | SER | A | 232 | 22.012 | 15.391 | 35.662 | 1.00 | 31.42 | MOLA C |
| ATOM | 518 | OG | SER | A | 232 | 21.010 | 14.496 | 35.339 | 1.00 | 35.99 | MOLA O |
| TER | 519 | | SER | A | 232 | | | | | | |
| ATOM | 520 | N | SER | A | 237 | 17.074 | 20.779 | 39.363 | 1.00 | 24.70 | MOLA N |
| ATOM | 521 | CA | SER | A | 237 | 17.299 | 21.771 | 38.325 | 1.00 | 23.59 | MOLA C |
| ATOM | 522 | C | SER | A | 237 | 16.167 | 22.811 | 38.355 | 1.00 | 26.19 | MOLA C |
| ATOM | 523 | O | SER | A | 237 | 15.024 | 22.450 | 38.335 | 1.00 | 26.71 | MOLA O |
| ATOM | 524 | CB | SER | A | 237 | 17.370 | 21.109 | 36.958 | 1.00 | 24.16 | MOLA C |
| ATOM | 525 | OG | SER | A | 237 | 17.663 | 22.047 | 35.956 | 1.00 | 31.24 | MOLA O |
| ATOM | 526 | N | VAL | A | 238 | 16.478 | 24.096 | 38.446 | 1.00 | 25.17 | MOLA N |
| ATOM | 527 | CA | VAL | A | 238 | 15.404 | 25.054 | 38.512 | 1.00 | 27.76 | MOLA C |
| ATOM | 528 | C | VAL | A | 238 | 15.548 | 25.887 | 37.257 | 1.00 | 28.33 | MOLA C |
| ATOM | 529 | O | VAL | A | 238 | 16.593 | 26.433 | 37.050 | 1.00 | 25.53 | MOLA O |
| ATOM | 530 | CB | VAL | A | 238 | 15.451 | 25.933 | 39.781 | 1.00 | 28.84 | MOLA C |
| ATOM | 531 | CG1 | VAL | A | 238 | 14.368 | 26.948 | 39.774 | 1.00 | 28.71 | MOLA C |
| ATOM | 532 | CG2 | VAL | A | 238 | 15.289 | 25.098 | 41.041 | 1.00 | 20.88 | MOLA C |
| ATOM | 533 | N | PHE | A | 239 | 14.526 | 25.929 | 36.381 | 1.00 | 29.59 | MOLA N |
| ATOM | 534 | CA | PHE | A | 239 | 14.589 | 26.759 | 35.165 | 1.00 | 29.03 | MOLA C |
| ATOM | 535 | C | PHE | A | 239 | 13.528 | 27.839 | 35.240 | 1.00 | 27.62 | MOLA C |
| ATOM | 536 | O | PHE | A | 239 | 12.358 | 27.575 | 35.042 | 1.00 | 28.47 | MOLA O |
| ATOM | 537 | CB | PHE | A | 239 | 14.403 | 25.921 | 33.898 | 1.00 | 28.66 | MOLA C |
| ATOM | 538 | CG | PHE | A | 239 | 14.606 | 26.701 | 32.626 | 1.00 | 25.64 | MOLA C |
| ATOM | 539 | CD1 | PHE | A | 239 | 13.686 | 27.522 | 32.144 | 1.00 | 17.52 | MOLA C |
| ATOM | 540 | CD2 | PHE | A | 239 | 15.722 | 26.633 | 31.927 | 1.00 | 38.58 | MOLA C |
| ATOM | 541 | CE1 | PHE | A | 239 | 13.929 | 28.289 | 30.967 | 1.00 | 32.14 | MOLA C |
| ATOM | 542 | CE2 | PHE | A | 239 | 15.889 | 27.397 | 30.700 | 1.00 | 40.60 | MOLA C |
| ATOM | 543 | CZ | PHE | A | 239 | 14.995 | 28.174 | 30.273 | 1.00 | 34.31 | MOLA C |
| ATOM | 544 | N | SER | A | 240 | 13.937 | 29.072 | 35.495 | 1.00 | 29.19 | MOLA N |
| ATOM | 545 | CA | SER | A | 240 | 12.976 | 30.185 | 35.781 | 1.00 | 28.96 | MOLA C |
| ATOM | 546 | C | SER | A | 240 | 12.890 | 31.109 | 34.632 | 1.00 | 29.06 | MOLA C |
| ATOM | 547 | O | SER | A | 240 | 13.906 | 31.699 | 34.272 | 1.00 | 34.55 | MOLA O |
| ATOM | 548 | CB | SER | A | 240 | 13.390 | 30.992 | 37.036 | 1.00 | 20.52 | MOLA C |
| ATOM | 549 | OG | SER | A | 240 | 12.898 | 30.388 | 38.196 | 1.00 | 24.32 | MOLA O |
| ATOM | 550 | N | VAL | A | 241 | 11.693 | 31.249 | 34.086 | 1.00 | 29.99 | MOLA N |
| ATOM | 551 | CA | VAL | A | 241 | 11.407 | 32.265 | 33.062 | 1.00 | 32.96 | MOLA C |
| ATOM | 552 | C | VAL | A | 241 | 10.617 | 33.414 | 33.728 | 1.00 | 35.76 | MOLA C |
| ATOM | 553 | O | VAL | A | 241 | 9.640 | 33.201 | 34.398 | 1.00 | 38.39 | MOLA O |
| ATOM | 554 | CB | VAL | A | 241 | 10.704 | 31.657 | 31.767 | 1.00 | 34.94 | MOLA C |
| ATOM | 555 | CG1 | VAL | A | 241 | 9.705 | 30.527 | 32.132 | 1.00 | 41.40 | MOLA C |
| ATOM | 556 | CG2 | VAL | A | 241 | 9.994 | 32.726 | 30.940 | 1.00 | 25.05 | MOLA C |
| TER | 557 | | VAL | A | 241 | | | | | | |
| ATOM | 558 | N | LEU | A | 263 | 10.261 | 26.018 | 36.556 | 1.00 | 26.45 | MOLA N |
| ATOM | 559 | CA | LEU | A | 263 | 10.135 | 24.659 | 36.067 | 1.00 | 28.33 | MOLA C |
| ATOM | 560 | C | LEU | A | 263 | 11.207 | 23.844 | 36.728 | 1.00 | 25.69 | MOLA C |
| ATOM | 561 | O | LEU | A | 263 | 12.381 | 23.988 | 36.413 | 1.00 | 21.56 | MOLA O |
| ATOM | 562 | CB | LEU | A | 263 | 10.264 | 24.628 | 34.543 | 1.00 | 30.73 | MOLA C |
| ATOM | 563 | CG | LEU | A | 263 | 9.150 | 25.512 | 33.969 | 1.00 | 32.32 | MOLA C |
| ATOM | 564 | CD1 | LEU | A | 263 | 9.538 | 25.951 | 32.582 | 1.00 | 36.47 | MOLA C |
| ATOM | 565 | CD2 | LEU | A | 263 | 7.748 | 24.822 | 34.042 | 1.00 | 22.02 | MOLA C |
| ATOM | 566 | N | VAL | A | 264 | 10.775 | 22.989 | 37.653 | 1.00 | 23.75 | MOLA N |
| ATOM | 567 | CA | VAL | A | 264 | 11.661 | 22.228 | 38.483 | 1.00 | 24.66 | MOLA C |
| ATOM | 568 | C | VAL | A | 264 | 11.725 | 20.760 | 38.119 | 1.00 | 26.92 | MOLA C |
| ATOM | 569 | O | VAL | A | 264 | 10.693 | 20.059 | 38.103 | 1.00 | 32.37 | MOLA O |
| ATOM | 570 | CB | VAL | A | 264 | 11.244 | 22.365 | 39.895 | 1.00 | 25.18 | MOLA C |

TABLE 7-continued

Novel Eg5 ligand binding site/compound 4 X-ray coordinates. 10 Angstrom shell of the binding pocket. Table 7 discloses residues 111-122, 125-141, 158-162, 170-173, 209-222 and 237-241 of SEQ ID NO: 1, respectively, in order of appearance.

| | | | | | | | | | | | |
|---|---|---|---|---|---|---|---|---|---|---|---|
| ATOM | 571 | CG1 | VAL | A | 264 | 12.325 | 21.855 | 40.755 | 1.00 | 27.26 | MOLA C |
| ATOM | 572 | CG2 | VAL | A | 264 | 11.069 | 23.784 | 40.220 | 1.00 | 30.60 | MOLA C |
| ATOM | 573 | N | ASP | A | 265 | 12.950 | 20.304 | 37.808 | 1.00 | 25.30 | MOLA N |
| ATOM | 574 | CA | ASP | A | 265 | 13.252 | 18.911 | 37.436 | 1.00 | 20.74 | MOLA C |
| ATOM | 575 | C | ASP | A | 265 | 14.027 | 18.339 | 38.592 | 1.00 | 24.63 | MOLA C |
| ATOM | 576 | O | ASP | A | 265 | 15.245 | 18.499 | 38.719 | 1.00 | 29.78 | MOLA O |
| ATOM | 577 | CB | ASP | A | 265 | 14.030 | 18.893 | 36.152 | 1.00 | 20.01 | MOLA C |
| ATOM | 578 | CG | ASP | A | 265 | 14.370 | 17.534 | 35.713 | 1.00 | 23.17 | MOLA C |
| ATOM | 579 | OD1 | ASP | A | 265 | 14.074 | 16.650 | 36.493 | 1.00 | 22.66 | MOLA O |
| ATOM | 580 | OD2 | ASP | A | 265 | 14.941 | 17.344 | 34.595 | 1.00 | 24.80 | MOLA O |
| END | | | | | | | | | | | |

Table 8. Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

TABLE 8

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | |
|---|---|---|---|---|---|---|---|---|---|---|
| ATOM | 1 | N1 | ADP | A4001 | 8.705 | 9.889 | 25.640 | 1.00 | 33.28 | COFA N |
| ATOM | 2 | C2 | ADP | A4001 | 9.848 | 9.673 | 24.943 | 1.00 | 35.03 | COFA C |
| ATOM | 3 | N3 | ADP | A4001 | 11.062 | 9.691 | 25.507 | 1.00 | 32.17 | COFA N |
| ATOM | 4 | C1* | ADP | A4001 | 13.511 | 9.790 | 27.144 | 1.00 | 30.57 | COFA C |
| ATOM | 5 | C4 | ADP | A4001 | 11.125 | 9.881 | 26.833 | 1.00 | 31.72 | COFA C |
| ATOM | 6 | C5 | ADP | A4001 | 9.916 | 10.097 | 27.646 | 1.00 | 28.45 | COFA C |
| ATOM | 7 | C6 | ADP | A4001 | 8.673 | 10.106 | 26.958 | 1.00 | 33.89 | COFA C |
| ATOM | 8 | N6 | ADP | A4001 | 7.559 | 10.309 | 27.675 | 1.00 | 37.80 | COFA N |
| ATOM | 9 | N7 | ADP | A4001 | 10.241 | 10.281 | 28.896 | 1.00 | 29.68 | COFA N |
| ATOM | 10 | C8 | ADP | A4001 | 11.619 | 10.203 | 28.896 | 1.00 | 35.05 | COFA C |
| ATOM | 11 | N9 | ADP | A4001 | 12.139 | 9.980 | 27.651 | 1.00 | 32.92 | COFA N |
| ATOM | 12 | C2* | ADP | A4001 | 14.108 | 11.053 | 26.541 | 1.00 | 32.21 | COFA C |
| ATOM | 13 | O2* | ADP | A4001 | 14.114 | 11.198 | 25.140 | 1.00 | 34.68 | COFA O |
| ATOM | 14 | C3* | ADP | A4001 | 15.552 | 10.842 | 27.007 | 1.00 | 35.73 | COFA C |
| ATOM | 15 | O3* | ADP | A4001 | 16.133 | 9.698 | 26.304 | 1.00 | 28.83 | COFA O |
| ATOM | 16 | O1A | ADP | A4001 | 17.087 | 13.820 | 31.217 | 1.00 | 41.64 | COFA O |
| ATOM | 17 | O1B | ADP | A4001 | 17.165 | 12.217 | 33.596 | 1.00 | 22.18 | COFA O |
| ATOM | 18 | C4* | ADP | A4001 | 15.355 | 10.511 | 28.486 | 1.00 | 33.22 | COFA C |
| ATOM | 19 | O4* | ADP | A4001 | 14.461 | 9.401 | 28.154 | 1.00 | 35.08 | COFA O |
| ATOM | 20 | O2A | ADP | A4001 | 16.602 | 11.454 | 30.270 | 1.00 | 36.64 | COFA O |
| ATOM | 21 | O2B | ADP | A4001 | 14.810 | 12.481 | 34.643 | 1.00 | 21.26 | COFA O |
| ATOM | 22 | C5* | ADP | A4001 | 14.633 | 11.587 | 29.433 | 1.00 | 29.64 | COFA C |
| ATOM | 23 | O5* | ADP | A4001 | 15.179 | 12.928 | 29.765 | 1.00 | 14.42 | COFA O |
| ATOM | 24 | O3A | ADP | A4001 | 15.109 | 12.246 | 32.164 | 1.00 | 21.78 | COFA O |
| ATOM | 25 | O3B | ADP | A4001 | 16.021 | 14.203 | 33.199 | 1.00 | 16.99 | COFA O |
| ATOM | 26 | PA | ADP | A4001 | 16.070 | 12.716 | 30.913 | 1.00 | 34.78 | COFA P |
| ATOM | 27 | PB | ADP | A4001 | 15.800 | 12.721 | 33.517 | 1.00 | 21.35 | COFA P |
| TER | 28 | | ADP | A4001 | | | | | | |
| ATOM | 29 | MG | MG | A3001 | 17.706 | 15.248 | 33.600 | 1.00 | 59.88 | COFBMG |
| TER | 30 | | MG | A3001 | | | | | | |
| ATOM | 31 | CL | LIG | A1001 | 11.667 | 22.175 | 20.502 | 1.00 | 38.34 | LIGACL |
| ATOM | 32 | C1 | LIG | A1001 | 15.962 | 24.803 | 27.285 | 1.00 | 50.62 | LIGA C |
| ATOM | 33 | N1 | LIG | A1001 | 17.911 | 24.786 | 26.258 | 1.00 | 54.67 | LIGA N |
| ATOM | 34 | O1 | LIG | A1001 | 17.570 | 20.675 | 22.656 | 1.00 | 52.02 | LIGA O |
| ATOM | 35 | C2 | LIG | A1001 | 15.087 | 24.981 | 28.357 | 1.00 | 51.01 | LIGA C |
| ATOM | 36 | N2 | LIG | A1001 | 17.772 | 22.595 | 23.859 | 1.00 | 48.70 | LIGA N |
| ATOM | 37 | C3 | LIG | A1001 | 15.563 | 25.413 | 29.592 | 1.00 | 50.41 | LIGA C |
| ATOM | 38 | N3 | LIG | A1001 | 15.759 | 24.404 | 26.035 | 1.00 | 50.71 | LIGA N |
| ATOM | 39 | C4 | LIG | A1001 | 16.944 | 25.648 | 29.728 | 1.00 | 54.40 | LIGA C |
| ATOM | 40 | M4 | LIG | A1001 | 17.972 | 19.353 | 27.051 | 1.00 | 35.49 | LIGA N |
| ATOM | 41 | C5 | LIG | A1001 | 17.851 | 25.467 | 28.657 | 1.00 | 53.59 | LIGA C |
| ATOM | 42 | C6 | LIG | A1001 | 17.333 | 25.035 | 27.437 | 1.00 | 54.07 | LIGA C |
| ATOM | 43 | C7 | LIG | A1001 | 16.951 | 24.363 | 25.407 | 1.00 | 52.29 | LIGA C |
| ATOM | 44 | C8 | LIG | A1001 | 17.251 | 23.985 | 24.004 | 1.00 | 52.87 | LIGA C |
| ATOM | 45 | C9 | LIG | A1001 | 18.305 | 24.972 | 23.476 | 1.00 | 55.08 | LIGA C |
| ATOM | 46 | C10 | LIG | A1001 | 19.057 | 24.442 | 22.243 | 1.00 | 55.44 | LIGA C |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | |
|---|---|---|---|---|---|---|---|---|---|---|
| ATOM | 47 | C11 | LIG | A1001 | 17.658 | 26.354 | 23.261 | 1.00 | 54.47 | LIGA C |
| ATOM | 48 | C12 | LIG | A1001 | 14.441 | 24.059 | 25.477 | 1.00 | 51.67 | LIGA C |
| ATOM | 49 | C13 | LIG | A1001 | 13.865 | 25.264 | 24.752 | 1.00 | 51.56 | LIGA C |
| ATOM | 50 | C14 | LIG | A1001 | 13.780 | 25.258 | 23.353 | 1.00 | 50.61 | LIGA C |
| ATOM | 51 | C15 | LIG | A1001 | 13.264 | 26.347 | 22.651 | 1.00 | 47.35 | LIGA C |
| ATOM | 52 | C16 | LIG | A1001 | 12.837 | 27.454 | 23.345 | 1.00 | 49.06 | LIGA C |
| ATOM | 53 | C17 | LIG | A1001 | 12.952 | 27.485 | 24.749 | 1.00 | 52.62 | LIGA C |
| ATOM | 54 | C18 | LIG | A1001 | 13.458 | 26.395 | 25.461 | 1.00 | 50.74 | LIGA C |
| ATOM | 55 | C19 | LIG | A1001 | 17.037 | 21.724 | 23.006 | 1.00 | 49.16 | LIGA C |
| ATOM | 56 | C20 | LIG | A1001 | 15.662 | 21.901 | 22.440 | 1.00 | 45.77 | LIGA C |
| ATOM | 57 | C21 | LIG | A1001 | 14.526 | 21.566 | 23.150 | 1.00 | 44.40 | LIGA C |
| ATOM | 58 | C22 | LIG | A1001 | 13.261 | 21.641 | 22.568 | 1.00 | 45.58 | LIGA C |
| ATOM | 59 | C23 | LIG | A1001 | 13.119 | 22.048 | 21.224 | 1.00 | 46.87 | LIGA C |
| ATOM | 60 | C25 | LIG | A1001 | 14.286 | 22.362 | 20.522 | 1.00 | 44.84 | LIGA C |
| ATOM | 61 | C26 | LIG | A1001 | 15.538 | 22.286 | 21.122 | 1.00 | 46.01 | LIGA C |
| ATOM | 62 | C27 | LIG | A1001 | 18.802 | 21.961 | 24.758 | 1.00 | 47.68 | LIGA C |
| ATOM | 63 | C28 | LIG | A1001 | 18.364 | 21.639 | 26.209 | 1.00 | 45.69 | LIGA C |
| ATOM | 64 | C29 | LIG | A1001 | 19.002 | 20.383 | 26.824 | 1.00 | 43.67 | LIGA C |
| TER | 65 | | LIG | A1001 | | | | | | |
| ATOM | 66 | N | GLN | A 78 | 3.899 | 15.363 | 24.691 | 1.00 | 34.20 | MOLA N |
| ATOM | 67 | CA | GLN | A 78 | 4.199 | 16.595 | 25.363 | 1.00 | 32.63 | MOLA C |
| ATOM | 68 | C | GLN | A 78 | 3.011 | 17.560 | 25.389 | 1.00 | 32.39 | MOLA C |
| ATOM | 69 | O | GLN | A 78 | 2.547 | 17.930 | 26.448 | 1.00 | 32.24 | MOLA O |
| ATOM | 70 | CB | GLN | A 78 | 5.381 | 17.269 | 24.755 | 1.00 | 32.48 | MOLA C |
| ATOM | 71 | CG | GLN | A 78 | 6.608 | 16.430 | 24.681 | 1.00 | 32.41 | MOLA C |
| ATOM | 72 | CD | GLN | A 78 | 7.332 | 16.377 | 25.986 | 1.00 | 36.75 | MOLA C |
| ATOM | 73 | NE2 | GLN | A 78 | 8.605 | 16.852 | 25.983 | 1.00 | 25.36 | MOLA N |
| ATOM | 74 | OE1 | GLN | A 78 | 6.770 | 15.874 | 27.009 | 1.00 | 41.64 | MOLA O |
| TER | 75 | | GLN | A 78 | | | | | | |
| ATOM | 76 | N | GLY | A 110 | 12.577 | 11.269 | 32.801 | 1.00 | 34.98 | MOLA N |
| ATOM | 77 | CA | GLY | A 110 | 12.163 | 12.343 | 31.939 | 1.00 | 35.12 | MOLA C |
| ATOM | 78 | C | GLY | A 110 | 11.915 | 13.670 | 32.623 | 1.00 | 34.90 | MOLA C |
| ATOM | 79 | O | GLY | A 110 | 11.109 | 14.431 | 32.111 | 1.00 | 34.93 | MOLA O |
| ATOM | 80 | N | LYS | A 111 | 12.578 | 13.980 | 33.749 | 1.00 | 34.27 | MOLA N |
| ATOM | 81 | CA | LYS | A 111 | 12.305 | 15.275 | 34.339 | 1.00 | 34.21 | MOLA C |
| ATOM | 82 | C | LYS | A 111 | 12.617 | 16.302 | 33.229 | 1.00 | 33.86 | MOLA C |
| ATOM | 83 | O | LYS | A 111 | 11.827 | 17.212 | 32.917 | 1.00 | 34.24 | MOLA O |
| ATOM | 84 | CB | LYS | A 111 | 13.080 | 15.536 | 35.632 | 1.00 | 33.66 | MOLA C |
| ATOM | 85 | CG | LYS | A 111 | 12.576 | 14.886 | 36.927 | 1.00 | 33.62 | MOLA C |
| ATOM | 86 | CD | LYS | A 111 | 13.516 | 13.677 | 37.452 | 1.00 | 31.88 | MOLA C |
| ATOM | 87 | CE | LYS | A 111 | 15.085 | 13.972 | 37.492 | 1.00 | 30.10 | MOLA C |
| ATOM | 88 | NZ | LYS | A 111 | 16.036 | 12.913 | 36.946 | 1.00 | 23.99 | MOLA N |
| ATOM | 89 | N | THR | A 112 | 13.734 | 16.092 | 32.566 | 1.00 | 33.63 | MOLA N |
| ATOM | 90 | CA | THR | A 112 | 14.170 | 17.069 | 31.574 | 1.00 | 33.61 | MOLA C |
| ATOM | 91 | C | THR | A 112 | 13.368 | 16.972 | 30.265 | 1.00 | 33.01 | MOLA C |
| ATOM | 92 | O | THR | A 112 | 13.194 | 18.020 | 29.587 | 1.00 | 32.38 | MOLA O |
| ATOM | 93 | CB | THR | A 112 | 15.701 | 16.977 | 31.320 | 1.00 | 32.58 | MOLA C |
| ATOM | 94 | CG2 | THR | A 112 | 16.205 | 18.151 | 30.517 | 1.00 | 30.79 | MOLA C |
| ATOM | 95 | OG1 | THR | A 112 | 16.372 | 17.097 | 32.579 | 1.00 | 36.63 | MOLA O |
| ATOM | 96 | N | PHE | A 113 | 12.926 | 15.753 | 29.905 | 1.00 | 31.75 | MOLA N |
| ATOM | 97 | CA | PHE | A 113 | 12.033 | 15.590 | 28.743 | 1.00 | 31.89 | MOLA C |
| ATOM | 98 | C | PHE | A 113 | 10.694 | 16.429 | 28.893 | 1.00 | 33.26 | MOLA C |
| ATOM | 99 | O | PHE | A 113 | 10.302 | 17.341 | 28.027 | 1.00 | 33.33 | MOLA O |
| ATOM | 100 | CB | PHE | A 113 | 11.706 | 14.132 | 28.544 | 1.00 | 30.33 | MOLA C |
| ATOM | 101 | CG | PHE | A 113 | 11.043 | 13.892 | 27.285 | 1.00 | 29.15 | MOLA C |
| ATOM | 102 | CD1 | PHE | A 113 | 11.748 | 13.967 | 26.125 | 1.00 | 28.76 | MOLA C |
| ATOM | 103 | CD2 | PHE | A 113 | 9.680 | 13.726 | 27.226 | 1.00 | 33.49 | MOLA C |
| ATOM | 104 | CE1 | PHE | A 113 | 11.118 | 13.752 | 24.901 | 1.00 | 32.21 | MOLA C |
| ATOM | 105 | CE2 | PHE | A 113 | 9.037 | 13.505 | 26.036 | 1.00 | 35.01 | MOLA C |
| ATOM | 106 | CZ | PHE | A 113 | 9.759 | 13.520 | 24.848 | 1.00 | 31.16 | MOLA C |
| ATOM | 107 | N | THR | A 114 | 10.034 | 16.148 | 30.020 | 1.00 | 32.99 | MOLA N |
| ATOM | 108 | CA | THR | A 114 | 8.832 | 16.862 | 30.402 | 1.00 | 33.13 | MOLA C |
| ATOM | 109 | C | THR | A 114 | 9.143 | 18.348 | 30.327 | 1.00 | 34.43 | MOLA C |
| ATOM | 110 | O | THR | A 114 | 8.587 | 19.063 | 29.499 | 1.00 | 37.23 | MOLA O |
| ATOM | 111 | CB | THR | A 114 | 8.383 | 16.463 | 31.824 | 1.00 | 32.82 | MOLA C |
| ATOM | 112 | CG2 | THR | A 114 | 7.046 | 17.130 | 32.198 | 1.00 | 32.38 | MOLA C |
| ATOM | 113 | OG1 | THR | A 114 | 8.109 | 15.047 | 31.871 | 1.00 | 25.25 | MOLA O |
| ATOM | 114 | N | MET | A 115 | 10.117 | 18.753 | 31.090 | 1.00 | 33.64 | MOLA N |
| ATOM | 115 | CA | MET | A 115 | 10.356 | 20.154 | 31.343 | 1.00 | 34.42 | MOLA C |
| ATOM | 116 | C | MET | A 115 | 11.016 | 20.971 | 30.226 | 1.00 | 34.25 | MOLA C |
| ATOM | 117 | O | MET | A 115 | 10.720 | 22.124 | 30.105 | 1.00 | 35.21 | MOLA O |
| ATOM | 118 | CB | MET | A 115 | 11.253 | 20.285 | 32.598 | 1.00 | 34.36 | MOLA C |
| ATOM | 119 | CG | MET | A 115 | 10.865 | 21.392 | 33.451 | 1.00 | 37.00 | MOLA C |
| ATOM | 120 | SD | MET | A 115 | 9.366 | 20.961 | 34.335 | 1.00 | 44.81 | MOLA S |
| ATOM | 121 | CE | MET | A 115 | 8.963 | 22.508 | 35.009 | 1.00 | 40.78 | MOLA C |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | | |
|---|---|---|---|---|---|---|---|---|---|---|---|---|
| ATOM | 122 | N | GLU | A | 116 | 11.935 | 20.432 | 29.449 | 1.00 | 33.84 | MOLA | N |
| ATOM | 123 | CA | GLU | A | 116 | 12.536 | 21.207 | 28.344 | 1.00 | 34.39 | MOLA | C |
| ATOM | 124 | C | GLU | A | 116 | 12.090 | 20.689 | 26.967 | 1.00 | 35.31 | MOLA | C |
| ATOM | 125 | O | GLU | A | 116 | 11.848 | 21.462 | 26.075 | 1.00 | 33.87 | MOLA | O |
| ATOM | 126 | CB | GLU | A | 116 | 14.078 | 21.197 | 28.418 | 1.00 | 33.80 | MOLA | C |
| ATOM | 127 | CG | GLU | A | 116 | 14.638 | 21.633 | 29.768 | 1.00 | 35.08 | MOLA | C |
| ATOM | 128 | CD | GLU | A | 116 | 16.167 | 21.814 | 29.799 | 1.00 | 35.17 | MOLA | C |
| ATOM | 129 | OE1 | GLU | A | 116 | 16.878 | 21.427 | 28.866 | 1.00 | 31.77 | MOLA | O |
| ATOM | 130 | OE2 | GLU | A | 116 | 16.677 | 22.383 | 30.793 | 1.00 | 40.74 | MOLA | O |
| ATOM | 131 | N | GLY | A | 117 | 11.980 | 19.366 | 26.852 | 1.00 | 37.18 | MOLA | N |
| ATOM | 132 | CA | GLY | A | 117 | 11.773 | 18.687 | 25.622 | 1.00 | 40.02 | MOLA | C |
| ATOM | 133 | C | GLY | A | 117 | 13.016 | 18.607 | 24.742 | 1.00 | 42.51 | MOLA | C |
| ATOM | 134 | O | GLY | A | 117 | 14.034 | 19.129 | 25.086 | 1.00 | 42.24 | MOLA | O |
| ATOM | 135 | N | GLU | A | 118 | 12.885 | 17.971 | 23.578 | 1.00 | 45.75 | MOLA | N |
| ATOM | 136 | CA | GLU | A | 118 | 13.981 | 17.759 | 22.637 | 1.00 | 48.22 | MOLA | C |
| ATOM | 137 | C | GLU | A | 118 | 13.534 | 18.368 | 21.323 | 1.00 | 50.71 | MOLA | C |
| ATOM | 138 | O | GLU | A | 118 | 12.345 | 18.739 | 21.167 | 1.00 | 51.56 | MOLA | O |
| ATOM | 139 | CB | GLU | A | 118 | 14.317 | 16.229 | 22.515 | 1.00 | 48.24 | MOLA | C |
| ATOM | 140 | CG | GLU | A | 118 | 14.976 | 15.648 | 23.788 | 1.00 | 48.01 | MOLA | C |
| ATOM | 141 | CD | GLU | A | 118 | 14.897 | 14.133 | 23.970 | 1.00 | 50.88 | MOLA | C |
| ATOM | 142 | OE1 | GLU | A | 118 | 14.704 | 13.393 | 22.924 | 1.00 | 56.13 | MOLA | O |
| ATOM | 143 | OE2 | GLU | A | 118 | 15.023 | 13.689 | 25.189 | 1.00 | 43.70 | MOLA | O |
| ATOM | 144 | N | ARG | A | 119 | 14.471 | 18.535 | 20.391 | 1.00 | 53.34 | MOLA | N |
| ATOM | 145 | CA | ARG | A | 119 | 14.059 | 18.863 | 19.021 | 1.00 | 55.36 | MOLA | C |
| ATOM | 146 | C | ARG | A | 119 | 13.835 | 17.567 | 18.310 | 1.00 | 54.96 | MOLA | C |
| ATOM | 147 | O | ARG | A | 119 | 14.551 | 16.599 | 18.578 | 1.00 | 53.96 | MOLA | O |
| ATOM | 148 | CB | ARG | A | 119 | 15.113 | 19.663 | 18.270 | 1.00 | 56.48 | MOLA | C |
| ATOM | 149 | CG | ARG | A | 119 | 14.486 | 20.519 | 17.112 | 1.00 | 62.32 | MOLA | C |
| ATOM | 150 | CD | ARG | A | 119 | 15.026 | 20.302 | 15.656 | 1.00 | 67.53 | MOLA | C |
| ATOM | 151 | NE | ARG | A | 119 | 16.425 | 19.913 | 15.633 | 1.00 | 72.94 | MOLA | N |
| ATOM | 152 | CZ | ARG | A | 119 | 17.415 | 20.547 | 16.279 | 1.00 | 78.85 | MOLA | C |
| ATOM | 153 | NH1 | ARG | A | 119 | 17.182 | 21.616 | 17.055 | 1.00 | 80.84 | MOLA | N |
| ATOM | 154 | NH2 | ARG | A | 119 | 18.663 | 20.089 | 16.168 | 1.00 | 80.52 | MOLA | N |
| ATOM | 155 | N | SER | A | 120 | 12.851 | 17.522 | 17.421 | 1.00 | 56.19 | MOLA | N |
| ATOM | 156 | CA | SER | A | 120 | 12.642 | 16.282 | 16.651 | 1.00 | 57.60 | MOLA | C |
| ATOM | 157 | C | SER | A | 120 | 13.915 | 16.022 | 15.753 | 1.00 | 59.86 | MOLA | C |
| ATOM | 158 | O | SER | A | 120 | 14.365 | 16.919 | 15.010 | 1.00 | 58.09 | MOLA | O |
| ATOM | 159 | CB | SER | A | 120 | 11.290 | 16.231 | 15.879 | 1.00 | 56.99 | MOLA | C |
| ATOM | 160 | OG | SER | A | 120 | 10.177 | 15.877 | 16.691 | 1.00 | 53.41 | MOLA | O |
| ATOM | 161 | N | PRO | A | 121 | 14.505 | 14.813 | 15.877 | 1.00 | 63.76 | MOLA | N |
| ATOM | 162 | CA | PRO | A | 121 | 15.660 | 14.377 | 15.029 | 1.00 | 66.07 | MOLA | C |
| ATOM | 163 | C | PRO | A | 121 | 15.313 | 14.541 | 13.534 | 1.00 | 68.32 | MOLA | C |
| ATOM | 164 | O | PRO | A | 121 | 14.408 | 15.303 | 13.265 | 1.00 | 68.87 | MOLA | O |
| ATOM | 165 | CB | PRO | A | 121 | 15.863 | 12.886 | 15.426 | 1.00 | 66.27 | MOLA | C |
| ATOM | 166 | CG | PRO | A | 121 | 14.604 | 12.461 | 16.253 | 1.00 | 65.22 | MOLA | C |
| ATOM | 167 | CD | PRO | A | 121 | 14.061 | 13.740 | 16.807 | 1.00 | 64.10 | MOLA | C |
| TER | 168 | | PRO | A | 121 | | | | | | | |
| ATOM | 169 | N | GLU | A | 123 | 14.723 | 16.185 | 11.571 | 1.00 | 72.44 | MOLA | N |
| ATOM | 170 | CA | GLU | A | 123 | 13.572 | 17.092 | 11.312 | 1.00 | 72.75 | MOLA | C |
| ATOM | 171 | C | GLU | A | 123 | 13.832 | 18.576 | 11.168 | 1.00 | 71.11 | MOLA | C |
| ATOM | 172 | O | GLU | A | 123 | 14.994 | 19.064 | 11.078 | 1.00 | 70.82 | MOLA | O |
| ATOM | 173 | CB | GLU | A | 123 | 12.365 | 16.868 | 12.293 | 1.00 | 73.38 | MOLA | C |
| ATOM | 174 | CG | GLU | A | 123 | 11.703 | 15.490 | 12.189 | 1.00 | 76.69 | MOLA | C |
| ATOM | 175 | CD | GLU | A | 123 | 10.340 | 15.411 | 11.468 | 1.00 | 81.65 | MOLA | C |
| ATOM | 176 | OE1 | GLU | A | 123 | 9.641 | 14.384 | 11.736 | 1.00 | 82.98 | MOLA | O |
| ATOM | 177 | OE2 | GLU | A | 123 | 9.970 | 16.304 | 10.633 | 1.00 | 83.84 | MOLA | O |
| ATOM | 178 | N | GLU | A | 124 | 12.695 | 19.260 | 11.053 | 1.00 | 68.90 | MOLA | N |
| ATOM | 179 | CA | GLU | A | 124 | 12.738 | 20.657 | 10.753 | 1.00 | 67.83 | MOLA | C |
| ATOM | 180 | C | GLU | A | 124 | 11.477 | 21.395 | 11.259 | 1.00 | 65.90 | MOLA | C |
| ATOM | 181 | O | GLU | A | 124 | 11.020 | 22.318 | 10.587 | 1.00 | 66.21 | MOLA | O |
| ATOM | 182 | CB | GLU | A | 124 | 12.990 | 20.866 | 9.228 | 1.00 | 68.24 | MOLA | C |
| ATOM | 183 | CG | GLU | A | 124 | 14.165 | 20.092 | 8.546 | 1.00 | 68.96 | MOLA | C |
| ATOM | 184 | CD | GLU | A | 124 | 15.631 | 20.524 | 8.845 | 1.00 | 69.98 | MOLA | C |
| ATOM | 185 | OE1 | GLU | A | 124 | 15.936 | 21.409 | 9.694 | 1.00 | 69.48 | MOLA | O |
| ATOM | 186 | OE2 | GLU | A | 124 | 16.542 | 19.945 | 8.187 | 1.00 | 68.65 | MOLA | O |
| ATOM | 187 | N | TYR | A | 125 | 10.980 | 21.065 | 12.463 | 1.00 | 63.06 | MOLA | N |
| ATOM | 188 | CA | TYR | A | 125 | 9.780 | 21.732 | 13.044 | 1.00 | 60.91 | MOLA | C |
| ATOM | 189 | C | TYR | A | 125 | 9.796 | 23.185 | 13.642 | 1.00 | 59.58 | MOLA | C |
| ATOM | 190 | O | TYR | A | 125 | 8.715 | 23.662 | 14.078 | 1.00 | 61.85 | MOLA | O |
| ATOM | 191 | CB | TYR | A | 125 | 9.196 | 20.866 | 14.134 | 1.00 | 59.72 | MOLA | C |
| ATOM | 192 | CG | TYR | A | 125 | 8.364 | 19.733 | 13.654 | 1.00 | 58.35 | MOLA | C |
| ATOM | 193 | CD1 | TYR | A | 125 | 7.021 | 19.914 | 13.275 | 1.00 | 55.38 | MOLA | C |
| ATOM | 194 | CD2 | TYR | A | 125 | 8.881 | 18.450 | 13.660 | 1.00 | 55.15 | MOLA | C |
| ATOM | 195 | CE1 | TYR | A | 125 | 6.250 | 18.836 | 12.885 | 1.00 | 53.57 | MOLA | C |
| ATOM | 196 | CE2 | TYR | A | 125 | 8.133 | 17.397 | 13.279 | 1.00 | 54.50 | MOLA | C |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| ATOM | 197 | CZ | TYR | A | 125 | 6.823 | 17.573 | 12.881 | 1.00 | 54.37 | MOLA C |
| ATOM | 198 | OH | TYR | A | 125 | 6.134 | 16.434 | 12.484 | 1.00 | 54.46 | MOLA O |
| ATOM | 199 | N | THR | A | 126 | 10.906 | 23.918 | 13.622 | 1.00 | 56.67 | MOLA N |
| ATOM | 200 | CA | THR | A | 126 | 11.051 | 25.140 | 14.472 | 1.00 | 54.54 | MOLA C |
| ATOM | 201 | C | THR | A | 126 | 10.534 | 24.878 | 15.877 | 1.00 | 53.52 | MOLA C |
| ATOM | 202 | O | THR | A | 126 | 9.541 | 24.180 | 16.105 | 1.00 | 51.93 | MOLA O |
| ATOM | 203 | CB | THR | A | 126 | 10.362 | 26.500 | 13.966 | 1.00 | 54.11 | MOLA C |
| ATOM | 204 | CG2 | THR | A | 126 | 10.666 | 26.809 | 12.520 | 1.00 | 53.57 | MOLA C |
| ATOM | 205 | OG1 | THR | A | 126 | 8.926 | 26.430 | 14.099 | 1.00 | 49.94 | MOLA O |
| ATOM | 206 | N | TRP | A | 127 | 11.191 | 25.521 | 16.830 | 1.00 | 52.53 | MOLA N |
| ATOM | 207 | CA | TRP | A | 127 | 11.084 | 25.046 | 18.192 | 1.00 | 51.27 | MOLA C |
| ATOM | 208 | C | TRP | A | 127 | 9.680 | 25.184 | 18.679 | 1.00 | 50.31 | MOLA C |
| ATOM | 209 | O | TRP | A | 127 | 9.218 | 24.333 | 19.450 | 1.00 | 48.87 | MOLA O |
| ATOM | 210 | CB | TRP | A | 127 | 12.116 | 25.726 | 19.117 | 1.00 | 51.57 | MOLA C |
| ATOM | 211 | CG | TRP | A | 127 | 11.969 | 27.209 | 19.414 | 1.00 | 47.63 | MOLA C |
| ATOM | 212 | CD1 | TRP | A | 127 | 12.733 | 28.215 | 18.893 | 1.00 | 47.25 | MOLA C |
| ATOM | 213 | CD2 | TRP | A | 127 | 11.080 | 27.836 | 20.371 | 1.00 | 46.46 | MOLA C |
| ATOM | 214 | CE2 | TRP | A | 127 | 11.367 | 29.231 | 20.358 | 1.00 | 45.53 | MOLA C |
| ATOM | 215 | CE3 | TRP | A | 127 | 10.059 | 27.367 | 21.246 | 1.00 | 48.23 | MOLA C |
| ATOM | 216 | NE1 | TRP | A | 127 | 12.377 | 29.426 | 19.444 | 1.00 | 47.30 | MOLA N |
| ATOM | 217 | CZ2 | TRP | A | 127 | 10.671 | 30.163 | 21.161 | 1.00 | 44.49 | MOLA C |
| ATOM | 218 | CZ3 | TRP | A | 127 | 9.359 | 28.306 | 22.042 | 1.00 | 48.23 | MOLA C |
| ATOM | 219 | CH2 | TRP | A | 127 | 9.678 | 29.696 | 21.981 | 1.00 | 46.00 | MOLA C |
| ATOM | 220 | N | GLU | A | 128 | 9.015 | 26.243 | 18.180 | 1.00 | 49.83 | MOLA N |
| ATOM | 221 | CA | GLU | A | 128 | 7.622 | 26.595 | 18.547 | 1.00 | 49.75 | MOLA C |
| ATOM | 222 | C | GLU | A | 128 | 6.540 | 25.656 | 18.001 | 1.00 | 49.54 | MOLA C |
| ATOM | 223 | O | GLU | A | 128 | 5.397 | 25.746 | 18.412 | 1.00 | 50.63 | MOLA O |
| ATOM | 224 | CB | GLU | A | 128 | 7.227 | 28.005 | 18.093 | 1.00 | 50.31 | MOLA C |
| ATOM | 225 | CG | GLU | A | 128 | 8.287 | 29.107 | 17.970 | 1.00 | 54.07 | MOLA C |
| ATOM | 226 | CD | GLU | A | 128 | 8.848 | 29.281 | 16.544 | 1.00 | 58.71 | MOLA C |
| ATOM | 227 | OE1 | GLU | A | 128 | 10.029 | 29.695 | 16.432 | 1.00 | 65.49 | MOLA O |
| ATOM | 228 | OE2 | GLU | A | 128 | 8.142 | 29.019 | 15.529 | 1.00 | 57.68 | MOLA O |
| ATOM | 229 | N | GLU | A | 129 | 6.865 | 24.794 | 17.057 | 1.00 | 49.41 | MOLA N |
| ATOM | 230 | CA | GLU | A | 129 | 5.864 | 23.871 | 16.547 | 1.00 | 49.85 | MOLA C |
| ATOM | 231 | C | GLU | A | 129 | 6.250 | 22.397 | 16.836 | 1.00 | 48.26 | MOLA C |
| ATOM | 232 | O | GLU | A | 129 | 5.435 | 21.462 | 16.574 | 1.00 | 48.98 | MOLA O |
| ATOM | 233 | CB | GLU | A | 129 | 5.567 | 24.142 | 15.035 | 1.00 | 51.03 | MOLA C |
| ATOM | 234 | CG | GLU | A | 129 | 4.061 | 24.018 | 14.595 | 1.00 | 55.16 | MOLA C |
| ATOM | 235 | CD | GLU | A | 129 | 2.984 | 24.514 | 15.635 | 1.00 | 61.40 | MOLA C |
| ATOM | 236 | OE1 | GLU | A | 129 | 3.176 | 25.607 | 16.255 | 1.00 | 63.85 | MOLA O |
| ATOM | 237 | OE2 | GLU | A | 129 | 1.924 | 23.819 | 15.843 | 1.00 | 61.85 | MOLA O |
| ATOM | 238 | N | ASP | A | 130 | 7.431 | 22.201 | 17.439 | 1.00 | 45.03 | MOLA N |
| ATOM | 239 | CA | ASP | A | 130 | 8.016 | 20.865 | 17.509 | 1.00 | 42.70 | MOLA C |
| ATOM | 240 | C | ASP | A | 130 | 7.278 | 20.061 | 18.577 | 1.00 | 41.65 | MOLA C |
| ATOM | 241 | O | ASP | A | 130 | 7.214 | 20.415 | 19.744 | 1.00 | 40.14 | MOLA O |
| ATOM | 242 | CB | ASP | A | 130 | 9.536 | 20.912 | 17.733 | 1.00 | 42.10 | MOLA C |
| ATOM | 243 | CG | ASP | A | 130 | 10.165 | 19.548 | 17.748 | 1.00 | 39.87 | MOLA C |
| ATOM | 244 | OD1 | ASP | A | 130 | 11.400 | 19.432 | 17.538 | 1.00 | 35.98 | MOLA O |
| ATOM | 245 | OD2 | ASP | A | 130 | 9.502 | 18.524 | 17.963 | 1.00 | 38.25 | MOLA O |
| ATOM | 246 | N | PRO | A | 131 | 6.634 | 18.994 | 18.136 | 1.00 | 41.03 | MOLA N |
| ATOM | 247 | CA | PRO | A | 131 | 5.828 | 18.180 | 19.038 | 1.00 | 39.86 | MOLA C |
| ATOM | 248 | C | PRO | A | 131 | 6.571 | 17.663 | 20.321 | 1.00 | 38.73 | MOLA C |
| ATOM | 249 | O | PRO | A | 131 | 5.903 | 17.275 | 21.298 | 1.00 | 37.47 | MOLA O |
| ATOM | 250 | CB | PRO | A | 131 | 5.385 | 17.011 | 18.129 | 1.00 | 39.27 | MOLA C |
| ATOM | 251 | CG | PRO | A | 131 | 6.269 | 17.076 | 16.954 | 1.00 | 39.49 | MOLA C |
| ATOM | 252 | CD | PRO | A | 131 | 6.594 | 18.490 | 16.743 | 1.00 | 40.45 | MOLA C |
| ATOM | 253 | N | LEU | A | 132 | 7.911 | 17.648 | 20.286 | 1.00 | 37.39 | MOLA N |
| ATOM | 254 | CA | LEU | A | 132 | 8.767 | 17.105 | 21.358 | 1.00 | 35.97 | MOLA C |
| ATOM | 255 | C | LEU | A | 132 | 9.146 | 18.170 | 22.389 | 1.00 | 35.40 | MOLA C |
| ATOM | 256 | O | LEU | A | 132 | 9.653 | 17.915 | 23.497 | 1.00 | 34.82 | MOLA O |
| ATOM | 257 | CB | LEU | A | 132 | 10.037 | 16.553 | 20.725 | 1.00 | 35.19 | MOLA C |
| ATOM | 258 | CG | LEU | A | 132 | 9.826 | 15.251 | 19.959 | 1.00 | 34.85 | MOLA C |
| ATOM | 259 | CD1 | LEU | A | 132 | 11.196 | 14.695 | 19.614 | 1.00 | 33.22 | MOLA C |
| ATOM | 260 | CD2 | LEU | A | 132 | 8.984 | 14.134 | 20.729 | 1.00 | 29.91 | MOLA C |
| ATOM | 261 | N | ALA | A | 133 | 8.929 | 19.390 | 21.977 | 1.00 | 35.14 | MOLA N |
| ATOM | 262 | CA | ALA | A | 133 | 9.034 | 20.521 | 22.851 | 1.00 | 36.16 | MOLA C |
| ATOM | 263 | C | ALA | A | 133 | 8.416 | 20.243 | 24.182 | 1.00 | 35.01 | MOLA C |
| ATOM | 264 | O | ALA | A | 133 | 7.325 | 19.744 | 24.195 | 1.00 | 36.24 | MOLA O |
| ATOM | 265 | CB | ALA | A | 133 | 8.324 | 21.721 | 22.230 | 1.00 | 36.29 | MOLA C |
| ATOM | 266 | N | GLY | A | 134 | 9.097 | 20.584 | 25.274 | 1.00 | 34.40 | MOLA N |
| ATOM | 267 | CA | GLY | A | 134 | 8.556 | 20.339 | 26.637 | 1.00 | 34.47 | MOLA C |
| ATOM | 268 | C | GLY | A | 134 | 7.781 | 21.554 | 27.150 | 1.00 | 33.71 | MOLA C |
| ATOM | 269 | O | GLY | A | 134 | 7.403 | 22.472 | 26.423 | 1.00 | 33.24 | MOLA O |
| ATOM | 270 | N | ILE | A | 135 | 7.585 | 21.574 | 28.443 | 1.00 | 33.30 | MOLA N |
| ATOM | 271 | CA | ILE | A | 135 | 6.778 | 22.591 | 29.081 | 1.00 | 32.43 | MOLA C |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| ATOM | 272 | C | ILE | A | 135 | 7.337 | 23.993 | 28.985 | 1.00 | 32.04 | MOLA C |
| ATOM | 273 | O | ILE | A | 135 | 6.581 | 24.917 | 28.783 | 1.00 | 32.10 | MOLA O |
| ATOM | 274 | CB | ILE | A | 135 | 6.614 | 22.224 | 30.536 | 1.00 | 32.35 | MOLA C |
| ATOM | 275 | CG1 | ILE | A | 135 | 5.494 | 21.221 | 30.672 | 1.00 | 32.30 | MOLA C |
| ATOM | 276 | CG2 | ILE | A | 135 | 6.326 | 23.435 | 31.395 | 1.00 | 30.68 | MOLA C |
| ATOM | 277 | CD1 | ILE | A | 135 | 5.447 | 20.709 | 32.109 | 1.00 | 33.17 | MOLA C |
| ATOM | 278 | N | ILE | A | 136 | 8.639 | 24.148 | 29.199 | 1.00 | 32.06 | MOLA N |
| ATOM | 279 | CA | ILE | A | 136 | 9.284 | 25.477 | 29.265 | 1.00 | 31.85 | MOLA C |
| ATOM | 280 | C | ILE | A | 136 | 9.155 | 26.228 | 27.933 | 1.00 | 31.59 | MOLA C |
| ATOM | 281 | O | ILE | A | 136 | 8.591 | 27.333 | 27.949 | 1.00 | 33.15 | MOLA O |
| ATOM | 282 | CB | ILE | A | 136 | 10.720 | 25.315 | 29.677 | 1.00 | 32.27 | MOLA C |
| ATOM | 283 | CG1 | ILE | A | 136 | 10.824 | 25.231 | 31.192 | 1.00 | 32.57 | MOLA C |
| ATOM | 284 | CG2 | ILE | A | 136 | 11.620 | 26.430 | 29.142 | 1.00 | 34.92 | MOLA C |
| ATOM | 285 | CD1 | ILE | A | 136 | 12.183 | 24.536 | 31.648 | 1.00 | 32.32 | MOLA C |
| ATOM | 286 | N | PRO | A | 137 | 9.644 | 25.717 | 26.798 | 1.00 | 29.71 | MOLA N |
| ATOM | 287 | CA | PRO | A | 137 | 9.380 | 26.363 | 25.487 | 1.00 | 30.18 | MOLA C |
| ATOM | 288 | C | PRO | A | 137 | 7.903 | 26.556 | 25.121 | 1.00 | 29.79 | MOLA C |
| ATOM | 289 | O | PRO | A | 137 | 7.526 | 27.631 | 24.695 | 1.00 | 30.55 | MOLA O |
| ATOM | 290 | CB | PRO | A | 137 | 10.089 | 25.437 | 24.476 | 1.00 | 28.66 | MOLA C |
| ATOM | 291 | CG | PRO | A | 137 | 10.229 | 24.209 | 25.182 | 1.00 | 28.52 | MOLA C |
| ATOM | 292 | CD | PRO | A | 137 | 10.520 | 24.576 | 26.615 | 1.00 | 29.79 | MOLA C |
| ATOM | 293 | N | ARG | A | 138 | 7.078 | 25.552 | 25.293 | 1.00 | 30.44 | MOLA N |
| ATOM | 294 | CA | ARG | A | 138 | 5.661 | 25.745 | 25.043 | 1.00 | 32.91 | MOLA C |
| ATOM | 295 | C | ARG | A | 138 | 5.067 | 26.928 | 25.864 | 1.00 | 34.03 | MOLA C |
| ATOM | 296 | O | ARG | A | 138 | 4.296 | 27.742 | 25.312 | 1.00 | 34.65 | MOLA O |
| ATOM | 297 | CB | ARG | A | 138 | 4.839 | 24.478 | 25.387 | 1.00 | 33.30 | MOLA C |
| ATOM | 298 | CG | ARG | A | 138 | 5.149 | 23.321 | 24.571 | 1.00 | 30.29 | MOLA C |
| ATOM | 299 | CD | ARG | A | 138 | 4.387 | 22.130 | 24.947 | 1.00 | 32.19 | MOLA C |
| ATOM | 300 | NE | ARG | A | 138 | 4.921 | 21.106 | 24.072 | 1.00 | 35.12 | MOLA N |
| ATOM | 301 | CZ | ARG | A | 138 | 4.446 | 20.796 | 22.870 | 1.00 | 37.97 | MOLA C |
| ATOM | 302 | NH1 | ARG | A | 138 | 3.343 | 21.360 | 22.413 | 1.00 | 41.74 | MOLA N |
| ATOM | 303 | NH2 | ARG | A | 138 | 5.049 | 19.876 | 22.139 | 1.00 | 35.02 | MOLA N |
| ATOM | 304 | N | THR | A | 139 | 5.419 | 26.996 | 27.161 | 1.00 | 34.82 | MOLA N |
| ATOM | 305 | CA | THR | A | 139 | 4.969 | 28.081 | 28.083 | 1.00 | 35.31 | MOLA C |
| ATOM | 306 | C | THR | A | 139 | 5.452 | 29.451 | 27.647 | 1.00 | 36.60 | MOLA C |
| ATOM | 307 | O | THR | A | 139 | 4.719 | 30.381 | 27.730 | 1.00 | 37.16 | MOLA O |
| ATOM | 308 | CB | THR | A | 139 | 5.474 | 27.869 | 29.508 | 1.00 | 35.07 | MOLA C |
| ATOM | 309 | CG2 | THR | A | 139 | 4.699 | 28.692 | 30.530 | 1.00 | 35.15 | MOLA C |
| ATOM | 310 | OG1 | THR | A | 139 | 5.236 | 26.534 | 29.911 | 1.00 | 31.85 | MOLA O |
| ATOM | 311 | N | LEU | A | 140 | 6.692 | 29.606 | 27.238 | 1.00 | 37.98 | MOLA N |
| ATOM | 312 | CA | LEU | A | 140 | 7.103 | 30.940 | 26.815 | 1.00 | 39.27 | MOLA C |
| ATOM | 313 | C | LEU | A | 140 | 6.396 | 31.252 | 25.497 | 1.00 | 40.57 | MOLA C |
| ATOM | 314 | O | LEU | A | 140 | 5.945 | 32.371 | 25.321 | 1.00 | 40.62 | MOLA O |
| ATOM | 315 | CB | LEU | A | 140 | 8.611 | 31.075 | 26.684 | 1.00 | 38.59 | MOLA C |
| ATOM | 316 | CG | LEU | A | 140 | 9.343 | 30.833 | 27.981 | 1.00 | 39.51 | MOLA C |
| ATOM | 317 | CD1 | LEU | A | 140 | 10.836 | 30.716 | 27.642 | 1.00 | 42.85 | MOLA C |
| ATOM | 318 | CD2 | LEU | A | 140 | 9.076 | 31.921 | 28.942 | 1.00 | 36.00 | MOLA C |
| ATOM | 319 | N | HIS | A | 141 | 6.264 | 30.278 | 24.586 | 1.00 | 41.30 | MOLA N |
| ATOM | 320 | CA | HIS | A | 141 | 5.447 | 30.535 | 23.416 | 1.00 | 42.47 | MOLA C |
| ATOM | 321 | C | HIS | A | 141 | 3.984 | 30.993 | 23.813 | 1.00 | 41.75 | MOLA C |
| ATOM | 322 | O | HIS | A | 141 | 3.463 | 31.955 | 23.252 | 1.00 | 40.89 | MOLA O |
| ATOM | 323 | CB | HIS | A | 141 | 5.473 | 29.336 | 22.442 | 1.00 | 43.81 | MOLA C |
| ATOM | 324 | CG | HIS | A | 141 | 4.689 | 29.562 | 21.164 | 1.00 | 48.13 | MOLA C |
| ATOM | 325 | CD2 | HIS | A | 141 | 3.351 | 29.568 | 20.924 | 1.00 | 52.64 | MOLA C |
| ATOM | 326 | ND1 | HIS | A | 141 | 5.287 | 29.838 | 19.950 | 1.00 | 52.95 | MOLA N |
| ATOM | 327 | CE1 | HIS | A | 141 | 4.360 | 29.996 | 19.020 | 1.00 | 53.75 | MOLA C |
| ATOM | 328 | NE2 | HIS | A | 141 | 3.173 | 29.853 | 19.590 | 1.00 | 53.84 | MOLA N |
| TER | 329 | | HIS | A | 141 | | | | | | |
| ATOM | 330 | N | PHE | A | 144 | 3.858 | 34.789 | 24.924 | 1.00 | 43.68 | MOLA N |
| ATOM | 331 | CA | PHE | A | 144 | 3.888 | 35.731 | 23.837 | 1.00 | 43.81 | MOLA C |
| ATOM | 332 | C | PHE | A | 144 | 2.598 | 35.739 | 23.061 | 1.00 | 43.62 | MOLA C |
| ATOM | 333 | O | PHE | A | 144 | 2.008 | 36.761 | 22.878 | 1.00 | 41.34 | MOLA O |
| ATOM | 334 | CB | PHE | A | 144 | 5.074 | 35.468 | 22.932 | 1.00 | 44.09 | MOLA C |
| ATOM | 335 | CG | PHE | A | 144 | 6.312 | 36.005 | 23.503 | 1.00 | 44.80 | MOLA C |
| ATOM | 336 | CD1 | PHE | A | 144 | 6.479 | 37.354 | 23.590 | 1.00 | 42.15 | MOLA C |
| ATOM | 337 | CD2 | PHE | A | 144 | 7.259 | 35.166 | 24.074 | 1.00 | 45.52 | MOLA C |
| ATOM | 338 | CE1 | PHE | A | 144 | 7.600 | 37.845 | 24.184 | 1.00 | 44.09 | MOLA C |
| ATOM | 339 | CE2 | PHE | A | 144 | 8.384 | 35.663 | 24.669 | 1.00 | 43.29 | MOLA C |
| ATOM | 340 | CZ | PHE | A | 144 | 8.566 | 36.977 | 24.726 | 1.00 | 41.30 | MOLA C |
| TER | 341 | | PHE | A | 144 | | | | | | |
| ATOM | 342 | N | VAL | A | 158 | 13.533 | 36.398 | 32.134 | 1.00 | 37.72 | MOLA N |
| ATOM | 343 | CA | VAL | A | 158 | 13.817 | 35.080 | 32.685 | 1.00 | 37.75 | MOLA C |
| ATOM | 344 | C | VAL | A | 158 | 15.115 | 34.983 | 33.503 | 1.00 | 37.86 | MOLA C |
| ATOM | 345 | O | VAL | A | 158 | 15.985 | 35.849 | 33.415 | 1.00 | 38.53 | MOLA O |
| ATOM | 346 | CB | VAL | A | 158 | 13.897 | 34.040 | 31.567 | 1.00 | 37.81 | MOLA C |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| ATOM | 347 | CG1 | VAL | A | 158 | 12.472 | 33.793 | 30.955 | 1.00 | 38.92 | MOLA C |
| ATOM | 348 | CG2 | VAL | A | 158 | 14.930 | 34.445 | 30.529 | 1.00 | 34.87 | MOLA C |
| ATOM | 349 | N | SER | A | 159 | 15.197 | 33.895 | 34.283 | 1.00 | 38.76 | MOLA N |
| ATOM | 350 | CA | SER | A | 159 | 16.317 | 33.467 | 35.199 | 1.00 | 38.03 | MOLA C |
| ATOM | 351 | C | SER | A | 159 | 16.523 | 31.983 | 34.989 | 1.00 | 38.25 | MOLA C |
| ATOM | 352 | O | SER | A | 159 | 15.583 | 31.241 | 34.707 | 1.00 | 38.15 | MOLA O |
| ATOM | 353 | CB | SER | A | 159 | 15.944 | 33.592 | 36.706 | 1.00 | 38.14 | MOLA C |
| ATOM | 354 | OG | SER | A | 159 | 15.797 | 34.937 | 37.134 | 1.00 | 39.02 | MOLA O |
| ATOM | 355 | N | LEU | A | 160 | 17.730 | 31.515 | 35.156 | 1.00 | 38.91 | MOLA N |
| ATOM | 356 | CA | LEU | A | 160 | 17.929 | 30.093 | 35.210 | 1.00 | 39.60 | MOLA C |
| ATOM | 357 | C | LEU | A | 160 | 19.082 | 29.879 | 36.143 | 1.00 | 40.39 | MOLA C |
| ATOM | 358 | O | LEU | A | 160 | 20.195 | 30.350 | 35.893 | 1.00 | 40.81 | MOLA O |
| ATOM | 359 | CB | LEU | A | 160 | 18.251 | 29.558 | 33.828 | 1.00 | 39.84 | MOLA C |
| ATOM | 360 | CG | LEU | A | 160 | 18.603 | 28.065 | 33.689 | 1.00 | 38.77 | MOLA C |
| ATOM | 361 | CD1 | LEU | A | 160 | 17.364 | 27.125 | 33.866 | 1.00 | 38.56 | MOLA C |
| ATOM | 362 | CD2 | LEU | A | 160 | 19.313 | 27.855 | 32.295 | 1.00 | 38.16 | MOLA C |
| ATOM | 363 | N | LEU | A | 161 | 18.825 | 29.247 | 37.258 | 1.00 | 40.58 | MOLA N |
| ATOM | 364 | CA | LEU | A | 161 | 19.894 | 29.018 | 38.126 | 1.00 | 41.43 | MOLA C |
| ATOM | 365 | C | LEU | A | 161 | 19.873 | 27.585 | 38.529 | 1.00 | 42.33 | MOLA C |
| ATOM | 366 | O | LEU | A | 161 | 18.852 | 26.900 | 38.412 | 1.00 | 42.87 | MOLA O |
| ATOM | 367 | CB | LEU | A | 161 | 19.796 | 29.934 | 39.314 | 1.00 | 41.27 | MOLA C |
| ATOM | 368 | CG | LEU | A | 161 | 18.744 | 29.523 | 40.342 | 1.00 | 42.78 | MOLA C |
| ATOM | 369 | CD1 | LEU | A | 161 | 19.095 | 28.331 | 41.172 | 1.00 | 40.63 | MOLA C |
| ATOM | 370 | CD2 | LEU | A | 161 | 18.602 | 30.649 | 41.295 | 1.00 | 46.49 | MOLA C |
| TER | 371 | | LEU | A | 161 | | | | | | |
| ATOM | 372 | N | LEU | A | 171 | 23.125 | 30.466 | 35.528 | 1.00 | 43.00 | MOLA N |
| ATOM | 373 | CA | LEU | A | 171 | 23.525 | 29.806 | 34.285 | 1.00 | 43.57 | MOLA C |
| ATOM | 374 | C | LEU | A | 171 | 23.555 | 30.740 | 33.178 | 1.00 | 44.57 | MOLA C |
| ATOM | 375 | O | LEU | A | 171 | 24.091 | 30.477 | 32.123 | 1.00 | 43.77 | MOLA O |
| ATOM | 376 | CB | LEU | A | 171 | 22.542 | 28.697 | 33.982 | 1.00 | 42.70 | MOLA C |
| ATOM | 377 | CG | LEU | A | 171 | 22.808 | 27.588 | 35.007 | 1.00 | 43.69 | MOLA C |
| ATOM | 378 | CD1 | LEU | A | 171 | 21.933 | 26.341 | 34.850 | 1.00 | 44.17 | MOLA C |
| ATOM | 379 | CD2 | LEU | A | 171 | 24.319 | 27.172 | 34.980 | 1.00 | 43.32 | MOLA C |
| ATOM | 380 | N | LEU | A | 172 | 22.924 | 31.846 | 33.463 | 1.00 | 46.40 | MOLA N |
| ATOM | 381 | CA | LEU | A | 172 | 22.491 | 32.750 | 32.492 | 1.00 | 47.97 | MOLA C |
| ATOM | 382 | C | LEU | A | 172 | 23.458 | 33.918 | 32.566 | 1.00 | 49.84 | MOLA C |
| ATOM | 383 | O | LEU | A | 172 | 23.271 | 34.950 | 31.902 | 1.00 | 49.25 | MOLA O |
| ATOM | 384 | CB | LEU | A | 172 | 21.073 | 33.133 | 32.875 | 1.00 | 47.58 | MOLA C |
| ATOM | 385 | CG | LEU | A | 172 | 20.144 | 33.093 | 31.715 | 1.00 | 48.18 | MOLA C |
| ATOM | 386 | CD1 | LEU | A | 172 | 20.063 | 31.658 | 31.151 | 1.00 | 46.63 | MOLA C |
| ATOM | 387 | CD2 | LEU | A | 172 | 18.770 | 33.673 | 32.174 | 1.00 | 50.42 | MOLA C |
| TER | 388 | | LEU | A | 172 | | | | | | |
| ATOM | 389 | N | VAL | A | 204 | 13.421 | 39.475 | 27.754 | 1.00 | 58.11 | MOLA N |
| ATOM | 390 | CA | VAL | A | 204 | 13.191 | 38.683 | 26.569 | 1.00 | 59.41 | MOLA C |
| ATOM | 391 | C | VAL | A | 204 | 12.111 | 39.296 | 25.695 | 1.00 | 60.36 | MOLA C |
| ATOM | 392 | O | VAL | A | 204 | 10.915 | 39.300 | 26.041 | 1.00 | 58.90 | MOLA O |
| ATOM | 393 | CB | VAL | A | 204 | 12.870 | 37.294 | 26.959 | 1.00 | 59.52 | MOLA C |
| ATOM | 394 | CG1 | VAL | A | 204 | 12.272 | 36.551 | 25.803 | 1.00 | 59.74 | MOLA C |
| ATOM | 395 | CG2 | VAL | A | 204 | 14.194 | 36.634 | 27.432 | 1.00 | 61.34 | MOLA C |
| TER | 396 | | VAL | A | 204 | | | | | | |
| ATOM | 397 | N | ASN | A | 206 | 11.094 | 39.283 | 22.328 | 1.00 | 62.45 | MOLA N |
| ATOM | 398 | CA | ASN | A | 206 | 10.108 | 38.754 | 21.392 | 1.00 | 63.18 | MOLA C |
| ATOM | 399 | C | ASN | A | 206 | 10.138 | 37.270 | 21.504 | 1.00 | 65.10 | MOLA C |
| ATOM | 400 | O | ASN | A | 206 | 11.047 | 36.749 | 22.130 | 1.00 | 65.19 | MOLA O |
| ATOM | 401 | CB | ASN | A | 206 | 10.514 | 39.105 | 19.990 | 1.00 | 62.37 | MOLA C |
| ATOM | 402 | CG | ASN | A | 206 | 11.909 | 38.608 | 19.677 | 1.00 | 60.69 | MOLA C |
| ATOM | 403 | ND2 | ASN | A | 206 | 12.939 | 39.412 | 20.035 | 1.00 | 60.07 | MOLA N |
| ATOM | 404 | OD1 | ASN | A | 206 | 12.076 | 37.486 | 19.181 | 1.00 | 53.06 | MOLA O |
| ATOM | 405 | N | LYS | A | 207 | 9.194 | 36.574 | 20.869 | 1.00 | 67.47 | MOLA N |
| ATOM | 406 | CA | LYS | A | 207 | 9.121 | 35.092 | 21.053 | 1.00 | 69.23 | MOLA C |
| ATOM | 407 | C | LYS | A | 207 | 10.404 | 34.337 | 20.750 | 1.00 | 69.55 | MOLA C |
| ATOM | 408 | O | LYS | A | 207 | 10.631 | 33.316 | 21.365 | 1.00 | 69.86 | MOLA O |
| ATOM | 409 | CB | LYS | A | 207 | 7.881 | 34.377 | 20.396 | 1.00 | 69.94 | MOLA C |
| ATOM | 410 | CG | LYS | A | 207 | 7.244 | 34.970 | 19.096 | 1.00 | 71.68 | MOLA C |
| ATOM | 411 | CD | LYS | A | 207 | 5.680 | 34.931 | 19.120 | 1.00 | 73.27 | MOLA C |
| ATOM | 412 | CE | LYS | A | 207 | 5.088 | 36.365 | 19.295 | 1.00 | 73.70 | MOLA C |
| ATOM | 413 | NZ | LYS | A | 207 | 3.595 | 36.378 | 19.457 | 1.00 | 73.78 | MOLA N |
| ATOM | 414 | N | ASP | A | 208 | 11.246 | 34.806 | 19.836 | 1.00 | 70.46 | MOLA N |
| ATOM | 415 | CA | ASP | A | 208 | 12.280 | 33.892 | 19.325 | 1.00 | 70.97 | MOLA C |
| ATOM | 416 | C | ASP | A | 208 | 13.667 | 34.113 | 19.919 | 1.00 | 70.14 | MOLA C |
| ATOM | 417 | O | ASP | A | 208 | 14.370 | 33.127 | 20.073 | 1.00 | 70.30 | MOLA O |
| ATOM | 418 | CB | ASP | A | 208 | 12.213 | 33.777 | 17.786 | 1.00 | 71.87 | MOLA C |
| ATOM | 419 | CG | ASP | A | 208 | 10.841 | 33.150 | 17.288 | 1.00 | 74.48 | MOLA C |
| ATOM | 420 | OD1 | ASP | A | 208 | 10.222 | 33.686 | 16.335 | 1.00 | 79.14 | MOLA O |
| ATOM | 421 | OD2 | ASP | A | 208 | 10.283 | 32.145 | 17.805 | 1.00 | 76.39 | MOLA O |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| ATOM | 422 | N | GLU | A | 209 | 13.996 | 35.369 | 20.305 | 1.00 | 69.49 | MOLA N |
| ATOM | 423 | CA | GLU | A | 209 | 15.144 | 35.790 | 21.232 | 1.00 | 68.43 | MOLA C |
| ATOM | 424 | C | GLU | A | 209 | 15.360 | 34.836 | 22.459 | 1.00 | 67.69 | MOLA C |
| ATOM | 425 | O | GLU | A | 209 | 16.498 | 34.647 | 22.949 | 1.00 | 67.68 | MOLA O |
| ATOM | 426 | CB | GLU | A | 209 | 14.891 | 37.242 | 21.738 | 1.00 | 68.37 | MOLA C |
| ATOM | 427 | CG | GLU | A | 209 | 16.061 | 38.025 | 22.327 | 1.00 | 67.99 | MOLA C |
| ATOM | 428 | CD | GLU | A | 209 | 15.668 | 39.445 | 22.780 | 1.00 | 69.06 | MOLA C |
| ATOM | 429 | OE1 | GLU | A | 209 | 15.015 | 39.603 | 23.830 | 1.00 | 70.62 | MOLA O |
| ATOM | 430 | OE2 | GLU | A | 209 | 16.011 | 40.436 | 22.106 | 1.00 | 69.30 | MOLA O |
| ATOM | 431 | N | VAL | A | 210 | 14.231 | 34.290 | 22.948 | 1.00 | 65.81 | MOLA N |
| ATOM | 432 | CA | VAL | A | 210 | 14.115 | 33.172 | 23.919 | 1.00 | 63.84 | MOLA C |
| ATOM | 433 | C | VAL | A | 210 | 15.030 | 31.950 | 23.685 | 1.00 | 62.34 | MOLA C |
| ATOM | 434 | O | VAL | A | 210 | 15.557 | 31.336 | 24.598 | 1.00 | 62.19 | MOLA O |
| ATOM | 435 | CB | VAL | A | 210 | 12.654 | 32.587 | 23.851 | 1.00 | 63.58 | MOLA C |
| ATOM | 436 | CG1 | VAL | A | 210 | 12.526 | 31.255 | 24.630 | 1.00 | 63.47 | MOLA C |
| ATOM | 437 | CG2 | VAL | A | 210 | 11.601 | 33.589 | 24.315 | 1.00 | 62.89 | MOLA C |
| ATOM | 438 | N | TYR | A | 211 | 15.140 | 31.531 | 22.451 | 1.00 | 60.58 | MOLA N |
| ATOM | 439 | CA | TYR | A | 211 | 15.850 | 30.315 | 22.187 | 1.00 | 59.58 | MOLA C |
| ATOM | 440 | C | TYR | A | 211 | 17.326 | 30.577 | 22.426 | 1.00 | 60.39 | MOLA C |
| ATOM | 441 | O | TYR | A | 211 | 18.009 | 29.811 | 23.126 | 1.00 | 59.66 | MOLA O |
| ATOM | 442 | CB | TYR | A | 211 | 15.580 | 29.889 | 20.743 | 1.00 | 59.01 | MOLA C |
| ATOM | 443 | CG | TYR | A | 211 | 16.390 | 28.727 | 20.246 | 1.00 | 53.98 | MOLA C |
| ATOM | 444 | CD1 | TYR | A | 211 | 17.701 | 28.904 | 19.817 | 1.00 | 48.78 | MOLA C |
| ATOM | 445 | CD2 | TYR | A | 211 | 15.823 | 27.444 | 20.151 | 1.00 | 49.61 | MOLA C |
| ATOM | 446 | CE1 | TYR | A | 211 | 18.442 | 27.823 | 19.327 | 1.00 | 49.86 | MOLA C |
| ATOM | 447 | CE2 | TYR | A | 211 | 16.569 | 26.341 | 19.635 | 1.00 | 46.65 | MOLA C |
| ATOM | 448 | CZ | TYR | A | 211 | 17.861 | 26.548 | 19.253 | 1.00 | 48.47 | MOLA C |
| ATOM | 449 | OH | TYR | A | 211 | 18.608 | 25.481 | 18.815 | 1.00 | 53.11 | MOLA O |
| ATOM | 450 | N | GLN | A | 212 | 17.829 | 31.670 | 21.845 | 1.00 | 61.45 | MOLA N |
| ATOM | 451 | CA | GLN | A | 212 | 19.283 | 31.857 | 21.829 | 1.00 | 62.24 | MOLA C |
| ATOM | 452 | C | GLN | A | 212 | 19.807 | 32.117 | 23.240 | 1.00 | 61.47 | MOLA C |
| ATOM | 453 | O | GLN | A | 212 | 20.952 | 31.810 | 23.516 | 1.00 | 61.51 | MOLA O |
| ATOM | 454 | CB | GLN | A | 212 | 19.805 | 32.904 | 20.817 | 1.00 | 63.06 | MOLA C |
| ATOM | 455 | CG | GLN | A | 212 | 19.265 | 34.307 | 20.911 | 1.00 | 64.92 | MOLA C |
| ATOM | 456 | CD | GLN | A | 212 | 18.310 | 34.538 | 19.806 | 1.00 | 67.37 | MOLA C |
| ATOM | 457 | NE2 | GLN | A | 212 | 17.153 | 33.884 | 19.867 | 1.00 | 62.51 | MOLA N |
| ATOM | 458 | OE1 | GLN | A | 212 | 18.631 | 35.251 | 18.866 | 1.00 | 70.85 | MOLA O |
| ATOM | 459 | N | ILE | A | 213 | 18.954 | 32.635 | 24.126 | 1.00 | 60.48 | MOLA N |
| ATOM | 460 | CA | ILE | A | 213 | 19.312 | 32.857 | 25.550 | 1.00 | 59.26 | MOLA C |
| ATOM | 461 | C | ILE | A | 213 | 19.379 | 31.572 | 26.385 | 1.00 | 56.83 | MOLA C |
| ATOM | 462 | O | ILE | A | 213 | 20.245 | 31.445 | 27.244 | 1.00 | 55.35 | MOLA O |
| ATOM | 463 | CB | ILE | A | 213 | 18.315 | 33.887 | 26.211 | 1.00 | 59.85 | MOLA C |
| ATOM | 464 | CG1 | ILE | A | 213 | 18.525 | 35.304 | 25.626 | 1.00 | 62.11 | MOLA C |
| ATOM | 465 | CG2 | ILE | A | 213 | 18.453 | 33.913 | 27.762 | 1.00 | 59.48 | MOLA C |
| ATOM | 466 | CD1 | ILE | A | 213 | 19.976 | 35.895 | 25.818 | 1.00 | 64.64 | MOLA C |
| ATOM | 467 | N | LEU | A | 214 | 18.413 | 30.683 | 26.173 | 1.00 | 54.38 | MOLA N |
| ATOM | 468 | CA | LEU | A | 214 | 18.412 | 29.422 | 26.837 | 1.00 | 53.15 | MOLA C |
| ATOM | 469 | C | LEU | A | 214 | 19.310 | 28.455 | 26.156 | 1.00 | 52.18 | MOLA C |
| ATOM | 470 | O | LEU | A | 214 | 19.629 | 27.441 | 26.729 | 1.00 | 51.74 | MOLA O |
| ATOM | 471 | CB | LEU | A | 214 | 17.039 | 28.832 | 26.850 | 1.00 | 52.75 | MOLA C |
| ATOM | 472 | CG | LEU | A | 214 | 16.051 | 29.671 | 27.642 | 1.00 | 54.02 | MOLA C |
| ATOM | 473 | CD1 | LEU | A | 214 | 14.622 | 28.976 | 27.690 | 1.00 | 55.45 | MOLA C |
| ATOM | 474 | CD2 | LEU | A | 214 | 16.550 | 30.003 | 29.052 | 1.00 | 52.10 | MOLA C |
| ATOM | 475 | N | GLU | A | 215 | 19.697 | 28.723 | 24.920 | 1.00 | 51.15 | MOLA N |
| ATOM | 476 | CA | GLU | A | 215 | 20.708 | 27.865 | 24.326 | 1.00 | 50.79 | MOLA C |
| ATOM | 477 | C | GLU | A | 215 | 22.014 | 28.021 | 25.130 | 1.00 | 49.92 | MOLA C |
| ATOM | 478 | O | GLU | A | 215 | 22.661 | 27.027 | 25.491 | 1.00 | 48.28 | MOLA O |
| ATOM | 479 | CB | GLU | A | 215 | 20.920 | 28.211 | 22.866 | 1.00 | 50.80 | MOLA C |
| ATOM | 480 | CG | GLU | A | 215 | 21.898 | 27.290 | 22.140 | 1.00 | 51.69 | MOLA C |
| ATOM | 481 | CD | GLU | A | 215 | 22.082 | 27.688 | 20.650 | 1.00 | 53.44 | MOLA C |
| ATOM | 482 | OE1 | GLU | A | 215 | 21.850 | 26.838 | 19.744 | 1.00 | 53.04 | MOLA O |
| ATOM | 483 | OE2 | GLU | A | 215 | 22.429 | 28.871 | 20.379 | 1.00 | 51.87 | MOLA O |
| ATOM | 484 | N | LYS | A | 216 | 22.353 | 29.289 | 25.402 | 1.00 | 49.70 | MOLA N |
| ATOM | 485 | CA | LYS | A | 216 | 23.632 | 29.715 | 26.022 | 1.00 | 50.06 | MOLA C |
| ATOM | 486 | C | LYS | A | 216 | 23.751 | 29.136 | 27.426 | 1.00 | 50.23 | MOLA C |
| ATOM | 487 | O | LYS | A | 216 | 24.666 | 28.351 | 27.701 | 1.00 | 50.11 | MOLA O |
| ATOM | 488 | CB | LYS | A | 216 | 23.764 | 31.257 | 26.079 | 1.00 | 49.82 | MOLA C |
| ATOM | 489 | CG | LYS | A | 216 | 23.967 | 31.964 | 24.733 | 1.00 | 50.39 | MOLA C |
| ATOM | 490 | CD | LYS | A | 216 | 24.386 | 33.431 | 24.904 | 1.00 | 49.84 | MOLA C |
| ATOM | 491 | CE | LYS | A | 216 | 23.934 | 34.287 | 23.724 | 1.00 | 48.98 | MOLA C |
| ATOM | 492 | NZ | LYS | A | 216 | 22.589 | 34.920 | 24.020 | 1.00 | 51.28 | MOLA N |
| ATOM | 493 | N | GLY | A | 217 | 22.755 | 29.465 | 28.263 | 1.00 | 50.29 | MOLA N |
| ATOM | 494 | CA | GLY | A | 217 | 22.603 | 28.912 | 29.590 | 1.00 | 50.04 | MOLA C |
| ATOM | 495 | C | GLY | A | 217 | 22.758 | 27.401 | 29.659 | 1.00 | 50.20 | MOLA C |
| ATOM | 496 | O | GLY | A | 217 | 23.391 | 26.892 | 30.585 | 1.00 | 49.80 | MOLA O |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| ATOM | 497 | N | ALA | A | 218 | 22.198 | 26.667 | 28.706 | 1.00 | 50.83 | MOLA N |
| ATOM | 498 | CA | ALA | A | 218 | 22.452 | 25.196 | 28.675 | 1.00 | 52.27 | MOLA C |
| ATOM | 499 | C | ALA | A | 218 | 23.959 | 24.846 | 28.448 | 1.00 | 52.16 | MOLA C |
| ATOM | 500 | O | ALA | A | 218 | 24.439 | 23.802 | 28.923 | 1.00 | 53.18 | MOLA O |
| ATOM | 501 | CB | ALA | A | 218 | 21.543 | 24.451 | 27.636 | 1.00 | 52.11 | MOLA C |
| ATOM | 502 | N | ALA | A | 219 | 24.675 | 25.717 | 27.739 | 1.00 | 51.34 | MOLA N |
| ATOM | 503 | CA | ALA | A | 219 | 26.098 | 25.543 | 27.509 | 1.00 | 51.20 | MOLA C |
| ATOM | 504 | C | ALA | A | 219 | 26.826 | 25.722 | 28.798 | 1.00 | 52.01 | MOLA C |
| ATOM | 505 | O | ALA | A | 219 | 27.560 | 24.833 | 29.212 | 1.00 | 53.63 | MOLA O |
| ATOM | 506 | CB | ALA | A | 219 | 26.631 | 26.562 | 26.468 | 1.00 | 50.98 | MOLA C |
| ATOM | 507 | N | LYS | A | 220 | 26.625 | 26.868 | 29.455 | 1.00 | 52.30 | MOLA N |
| ATOM | 508 | CA | LYS | A | 220 | 27.231 | 27.132 | 30.793 | 1.00 | 52.38 | MOLA C |
| ATOM | 509 | C | LYS | A | 220 | 27.029 | 26.001 | 31.827 | 1.00 | 50.99 | MOLA C |
| ATOM | 510 | O | LYS | A | 220 | 27.838 | 25.833 | 32.727 | 1.00 | 49.66 | MOLA O |
| ATOM | 511 | CB | LYS | A | 220 | 26.710 | 28.472 | 31.399 | 1.00 | 53.01 | MOLA C |
| ATOM | 512 | CG | LYS | A | 220 | 27.750 | 29.592 | 31.570 | 1.00 | 56.70 | MOLA C |
| ATOM | 513 | CD | LYS | A | 220 | 27.886 | 30.500 | 30.261 | 1.00 | 61.35 | MOLA C |
| ATOM | 514 | CE | LYS | A | 220 | 29.372 | 30.907 | 29.893 | 1.00 | 61.49 | MOLA C |
| ATOM | 515 | NZ | LYS | A | 220 | 30.231 | 31.371 | 31.048 | 1.00 | 60.27 | MOLA N |
| ATOM | 516 | N | ARG | A | 221 | 25.924 | 25.274 | 31.713 | 1.00 | 50.87 | MOLA N |
| ATOM | 517 | CA | ARG | A | 221 | 25.603 | 24.181 | 32.646 | 1.00 | 51.89 | MOLA C |
| ATOM | 518 | C | ARG | A | 221 | 26.442 | 22.994 | 32.288 | 1.00 | 53.36 | MOLA C |
| ATOM | 519 | O | ARG | A | 221 | 26.871 | 22.231 | 33.144 | 1.00 | 54.73 | MOLA O |
| ATOM | 520 | CB | ARG | A | 221 | 24.147 | 23.760 | 32.523 | 1.00 | 51.26 | MOLA C |
| ATOM | 521 | CG | ARG | A | 221 | 23.802 | 22.488 | 33.200 | 1.00 | 48.99 | MOLA C |
| ATOM | 522 | CD | ARG | A | 221 | 22.294 | 22.433 | 33.507 | 1.00 | 49.19 | MOLA C |
| ATOM | 523 | NE | ARG | A | 221 | 21.494 | 22.543 | 32.283 | 1.00 | 46.17 | MOLA N |
| ATOM | 524 | CZ | ARG | A | 221 | 20.236 | 22.964 | 32.180 | 1.00 | 45.72 | MOLA C |
| ATOM | 525 | NH1 | ARG | A | 221 | 19.547 | 23.432 | 33.233 | 1.00 | 47.76 | MOLA N |
| ATOM | 526 | NH2 | ARG | A | 221 | 19.680 | 22.933 | 30.971 | 1.00 | 45.26 | MOLA N |
| ATOM | 527 | N | THR | A | 222 | 26.642 | 22.839 | 30.988 | 1.00 | 53.77 | MOLA N |
| ATOM | 528 | CA | THR | A | 222 | 27.530 | 21.843 | 30.481 | 1.00 | 53.52 | MOLA C |
| ATOM | 529 | C | THR | A | 222 | 28.931 | 22.097 | 31.024 | 1.00 | 52.48 | MOLA C |
| ATOM | 530 | O | THR | A | 222 | 29.558 | 21.223 | 31.669 | 1.00 | 51.05 | MOLA O |
| ATOM | 531 | CB | THR | A | 222 | 27.478 | 21.934 | 28.966 | 1.00 | 54.20 | MOLA C |
| ATOM | 532 | CG2 | THR | A | 222 | 28.321 | 20.730 | 28.287 | 1.00 | 54.18 | MOLA C |
| ATOM | 533 | OG1 | THR | A | 222 | 26.086 | 21.844 | 28.560 | 1.00 | 53.25 | MOLA O |
| TER | 534 | | THR | A | 222 | | | | | | |
| ATOM | 535 | N | SER | A | 232 | 24.401 | 17.572 | 36.402 | 1.00 | 48.63 | MOLA N |
| ATOM | 536 | CA | SER | A | 232 | 23.044 | 18.091 | 36.410 | 1.00 | 47.89 | MOLA C |
| ATOM | 537 | C | SER | A | 232 | 22.031 | 17.079 | 36.860 | 1.00 | 46.26 | MOLA C |
| ATOM | 538 | O | SER | A | 232 | 20.888 | 17.489 | 37.228 | 1.00 | 46.87 | MOLA O |
| ATOM | 539 | CB | SER | A | 232 | 22.692 | 18.594 | 35.024 | 1.00 | 48.39 | MOLA C |
| ATOM | 540 | OG | SER | A | 232 | 22.897 | 17.533 | 34.122 | 1.00 | 49.46 | MOLA O |
| TER | 541 | | SER | A | 232 | | | | | | |
| ATOM | 542 | N | SER | A | 237 | 17.566 | 22.368 | 38.806 | 1.00 | 37.09 | MOLA N |
| ATOM | 543 | CA | SER | A | 237 | 17.649 | 23.446 | 37.823 | 1.00 | 37.18 | MOLA C |
| ATOM | 544 | C | SER | A | 237 | 16.362 | 24.188 | 38.063 | 1.00 | 36.58 | MOLA C |
| ATOM | 545 | O | SER | A | 237 | 15.340 | 23.571 | 38.215 | 1.00 | 35.86 | MOLA O |
| ATOM | 546 | CB | SER | A | 237 | 17.818 | 22.881 | 36.392 | 1.00 | 37.48 | MOLA C |
| ATOM | 547 | OG | SER | A | 237 | 17.106 | 23.610 | 35.415 | 1.00 | 40.71 | MOLA O |
| ATOM | 548 | N | VAL | A | 238 | 16.455 | 25.511 | 38.266 | 1.00 | 37.34 | MOLA N |
| ATOM | 549 | CA | VAL | A | 238 | 15.293 | 26.371 | 38.530 | 1.00 | 36.03 | MOLA C |
| ATOM | 550 | C | VAL | A | 238 | 15.146 | 27.406 | 37.456 | 1.00 | 36.03 | MOLA C |
| ATOM | 551 | O | VAL | A | 238 | 15.911 | 28.320 | 37.403 | 1.00 | 37.21 | MOLA O |
| ATOM | 552 | CB | VAL | A | 238 | 15.442 | 27.064 | 39.815 | 1.00 | 35.17 | MOLA C |
| ATOM | 553 | CG1 | VAL | A | 238 | 14.139 | 27.724 | 40.198 | 1.00 | 33.17 | MOLA C |
| ATOM | 554 | CG2 | VAL | A | 238 | 15.788 | 26.026 | 40.862 | 1.00 | 38.36 | MOLA C |
| ATOM | 555 | N | PHE | A | 239 | 14.177 | 27.234 | 36.582 | 1.00 | 35.86 | MOLA N |
| ATOM | 556 | CA | PHE | A | 239 | 13.862 | 28.247 | 35.629 | 1.00 | 36.49 | MOLA C |
| ATOM | 557 | C | PHE | A | 239 | 12.700 | 29.062 | 36.145 | 1.00 | 35.76 | MOLA C |
| ATOM | 558 | O | PHE | A | 239 | 11.687 | 28.479 | 36.525 | 1.00 | 34.96 | MOLA O |
| ATOM | 559 | CB | PHE | A | 239 | 13.534 | 27.584 | 34.264 | 1.00 | 37.55 | MOLA C |
| ATOM | 560 | CG | PHE | A | 239 | 12.959 | 28.532 | 33.244 | 1.00 | 37.46 | MOLA C |
| ATOM | 561 | CD1 | PHE | A | 239 | 11.612 | 28.734 | 33.169 | 1.00 | 40.61 | MOLA C |
| ATOM | 562 | CD2 | PHE | A | 239 | 13.766 | 29.218 | 32.376 | 1.00 | 38.85 | MOLA C |
| ATOM | 563 | CE1 | PHE | A | 239 | 11.072 | 29.625 | 32.244 | 1.00 | 41.92 | MOLA C |
| ATOM | 564 | CE2 | PHE | A | 239 | 13.236 | 30.132 | 31.435 | 1.00 | 38.14 | MOLA C |
| ATOM | 565 | CZ | PHE | A | 239 | 11.889 | 30.316 | 31.363 | 1.00 | 40.32 | MOLA C |
| ATOM | 566 | N | SER | A | 240 | 12.821 | 30.397 | 36.112 | 1.00 | 36.11 | MOLA N |
| ATOM | 567 | CA | SER | A | 240 | 11.710 | 31.320 | 36.466 | 1.00 | 35.79 | MOLA C |
| ATOM | 568 | C | SER | A | 240 | 11.415 | 32.196 | 35.316 | 1.00 | 34.95 | MOLA C |
| ATOM | 569 | O | SER | A | 240 | 12.336 | 32.715 | 34.703 | 1.00 | 31.71 | MOLA O |
| ATOM | 570 | CB | SER | A | 240 | 12.071 | 32.256 | 37.609 | 1.00 | 36.48 | MOLA C |
| ATOM | 571 | OG | SER | A | 240 | 12.029 | 31.596 | 38.868 | 1.00 | 36.86 | MOLA O |

TABLE 8-continued

Novel Eg5 ligand binding site/compound 5 X-ray coordinates. 10 Angstrom shell of the binding pocket. Table 8 discloses residues 110-121, 123-141, 158-161, 206-222 and 237-240 of SEQ ID NO: 1, respectively, in order of appearance.

| | | | | | | | | | | | |
|---|---|---|---|---|---|---|---|---|---|---|---|
| TER | 572 | | SER | A | 240 | | | | | | |
| ATOM | 573 | N | LEU | A | 263 | 9.755 | 26.710 | 37.366 | 1.00 | 34.56 | MOLA N |
| ATOM | 574 | CA | LEU | A | 263 | 9.732 | 25.486 | 36.575 | 1.00 | 34.38 | MOLA C |
| ATOM | 575 | C | LEU | A | 263 | 11.049 | 24.772 | 36.872 | 1.00 | 35.65 | MOLA C |
| ATOM | 576 | O | LEU | A | 263 | 12.119 | 25.077 | 36.315 | 1.00 | 35.56 | MOLA O |
| ATOM | 577 | CB | LEU | A | 263 | 9.635 | 25.838 | 35.091 | 1.00 | 34.84 | MOLA C |
| ATOM | 578 | CG | LEU | A | 263 | 8.415 | 26.631 | 34.621 | 1.00 | 30.32 | MOLA C |
| ATOM | 579 | CD1 | LEU | A | 263 | 8.540 | 26.768 | 33.168 | 1.00 | 34.83 | MOLA C |
| ATOM | 580 | CD2 | LEU | A | 263 | 7.222 | 25.883 | 34.884 | 1.00 | 22.29 | MOLA C |
| ATOM | 581 | N | VAL | A | 264 | 10.932 | 23.833 | 37.786 | 1.00 | 36.68 | MOLA N |
| ATOM | 582 | CA | VAL | A | 264 | 12.028 | 23.233 | 38.437 | 1.00 | 37.21 | MOLA C |
| ATOM | 583 | C | VAL | A | 264 | 12.234 | 21.846 | 37.914 | 1.00 | 37.93 | MOLA C |
| ATOM | 584 | O | VAL | A | 264 | 11.332 | 21.004 | 38.000 | 1.00 | 39.99 | MOLA O |
| ATOM | 585 | CB | VAL | A | 264 | 11.678 | 23.078 | 39.908 | 1.00 | 37.98 | MOLA C |
| ATOM | 586 | CG1 | VAL | A | 264 | 12.921 | 22.519 | 40.722 | 1.00 | 39.03 | MOLA C |
| ATOM | 587 | CG2 | VAL | A | 264 | 11.183 | 24.454 | 40.461 | 1.00 | 37.85 | MOLA C |
| ATOM | 588 | N | ASP | A | 265 | 13.438 | 21.591 | 37.449 | 1.00 | 37.42 | MOLA N |
| ATOM | 589 | CA | ASP | A | 265 | 13.889 | 20.283 | 37.095 | 1.00 | 37.48 | MOLA C |
| ATOM | 590 | C | ASP | A | 265 | 14.737 | 19.697 | 38.266 | 1.00 | 37.98 | MOLA C |
| ATOM | 591 | O | ASP | A | 265 | 15.919 | 19.927 | 38.354 | 1.00 | 38.53 | MOLA O |
| ATOM | 592 | CB | ASP | A | 265 | 14.704 | 20.390 | 35.781 | 1.00 | 36.26 | MOLA C |
| ATOM | 593 | CG | ASP | A | 265 | 14.998 | 19.038 | 35.193 | 1.00 | 34.99 | MOLA C |
| ATOM | 594 | OD1 | ASP | A | 265 | 15.078 | 18.086 | 36.004 | 1.00 | 33.15 | MOLA O |
| ATOM | 595 | OD2 | ASP | A | 265 | 15.161 | 18.823 | 33.973 | 1.00 | 28.45 | MOLA O |
| END | | | | | | | | | | | |

Table 9. Novel Eg5 ligand binding site/compound 6 X-ray coordinates. 10 Angstrom shell of the binding pocket. Table 9 discloses residues 110-141, 158-162, 209-222 and 237-240 of SEQ ID NO: 1, respectively, in order of appearance.

TABLE 9

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 1 | C1 | LIG | A1001 | 15.926 | 23.499 | 26.907 | 1.00 | 40.93 | LIGA C |
| ATOM | 2 | C2 | LIG | A1001 | 14.841 | 23.688 | 27.761 | 1.00 | 47.94 | LIGA C |
| ATOM | 3 | C3 | LIG | A1001 | 15.030 | 24.423 | 28.922 | 1.00 | 43.73 | LIGA C |
| ATOM | 4 | C4 | LIG | A1001 | 16.278 | 24.996 | 29.202 | 1.00 | 41.47 | LIGA C |
| ATOM | 5 | C6 | LIG | A1001 | 17.363 | 24.787 | 28.365 | 1.00 | 43.01 | LIGA C |
| ATOM | 6 | C7 | LIG | A1001 | 17.162 | 24.039 | 27.209 | 1.00 | 36.47 | LIGA C |
| ATOM | 7 | N8 | LIG | A1001 | 17.979 | 23.709 | 26.214 | 1.00 | 42.80 | LIGA N |
| ATOM | 8 | C9 | LIG | A1001 | 17.313 | 22.956 | 25.333 | 1.00 | 39.22 | LIGA C |
| ATOM | 9 | C10 | LIG | A1001 | 17.901 | 22.377 | 24.103 | 1.00 | 46.28 | LIGA C |
| ATOM | 10 | C11 | LIG | A1001 | 19.054 | 23.243 | 23.568 | 1.00 | 51.39 | LIGA C |
| ATOM | 11 | C12 | LIG | A1001 | 18.587 | 24.664 | 23.300 | 1.00 | 47.52 | LIGA C |
| ATOM | 12 | C13 | LIG | A1001 | 19.678 | 22.626 | 22.327 | 1.00 | 51.00 | LIGA C |
| ATOM | 13 | N14 | LIG | A1001 | 18.432 | 21.033 | 24.391 | 1.00 | 44.36 | LIGA N |
| ATOM | 14 | C15 | LIG | A1001 | 17.945 | 19.982 | 23.728 | 1.00 | 47.64 | LIGA C |
| ATOM | 15 | C16 | LIG | A1001 | 18.546 | 18.634 | 23.955 | 1.00 | 57.22 | LIGA C |
| ATOM | 16 | O17 | LIG | A1001 | 16.936 | 20.085 | 23.054 | 1.00 | 53.79 | LIGA O |
| ATOM | 17 | C18 | LIG | A1001 | 19.384 | 20.971 | 25.513 | 1.00 | 52.79 | LIGA C |
| ATOM | 18 | C19 | LIG | A1001 | 18.808 | 19.924 | 26.468 | 1.00 | 56.29 | LIGA C |
| ATOM | 19 | C20 | LIG | A1001 | 18.677 | 20.322 | 27.920 | 1.00 | 61.47 | LIGA C |
| ATOM | 20 | N21 | LIG | A1001 | 17.889 | 19.282 | 28.575 | 1.00 | 46.03 | LIGA N |
| ATOM | 21 | N22 | LIG | A1001 | 16.047 | 22.861 | 25.753 | 1.00 | 46.02 | LIGA N |
| ATOM | 22 | C23 | LIG | A1001 | 14.993 | 22.060 | 25.143 | 1.00 | 48.14 | LIGA C |
| ATOM | 23 | C24 | LIG | A1001 | 14.182 | 22.695 | 24.082 | 1.00 | 52.72 | LIGA C |
| ATOM | 24 | C25 | LIG | A1001 | 19.852 | 18.316 | 23.581 | 1.00 | 69.39 | LIGA C |
| ATOM | 25 | C26 | LIG | A1001 | 20.354 | 17.039 | 23.852 | 1.00 | 67.24 | LIGA C |
| ATOM | 26 | C27 | LIG | A1001 | 19.558 | 16.092 | 24.507 | 1.00 | 62.12 | LIGA C |
| ATOM | 27 | C28 | LIG | A1001 | 20.061 | 14.710 | 24.824 | 1.00 | 63.39 | LIGA C |
| ATOM | 28 | C29 | LIG | A1001 | 18.286 | 16.419 | 24.900 | 1.00 | 57.20 | LIGA C |
| ATOM | 29 | C30 | LIG | A1001 | 17.782 | 17.685 | 24.627 | 1.00 | 64.39 | LIGA C |
| ATOM | 30 | C31 | LIG | A1001 | 14.244 | 24.078 | 23.862 | 1.00 | 44.02 | LIGA C |
| ATOM | 31 | C32 | LIG | A1001 | 13.471 | 24.622 | 22.863 | 1.00 | 42.46 | LIGA C |
| ATOM | 32 | C33 | LIG | A1001 | 12.643 | 23.763 | 22.119 | 1.00 | 51.06 | LIGA C |
| ATOM | 33 | C34 | LIG | A1001 | 12.610 | 22.375 | 22.337 | 1.00 | 53.32 | LIGA C |
| ATOM | 34 | C35 | LIG | A1001 | 13.379 | 21.821 | 23.344 | 1.00 | 49.53 | LIGA C |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 35 | BR | LIG | A1001 | 16.530 | 25.923 | 30.831 | 1.00 | 62.66 | LIGA BR |
| TER | 36 | | LIG | A1001 | | | | | | |
| ATOM | 37 | MG | MG | A3001 | 17.368 | 15.442 | 34.621 | 1.00 | 28.23 | COFAMG |
| TER | 38 | | MG | A3001 | | | | | | |
| ATOM | 39 | N1 | ADP | A4001 | 8.619 | 9.785 | 26.794 | 1.00 | 33.38 | COFA N |
| ATOM | 40 | C2 | ADP | A4001 | 9.690 | 9.535 | 26.012 | 1.00 | 38.57 | COFA C |
| ATOM | 41 | N3 | ADP | A4001 | 10.938 | 9.583 | 26.446 | 1.00 | 36.28 | COFA N |
| ATOM | 42 | C1* | ADP | A4001 | 13.644 | 9.758 | 28.042 | 1.00 | 38.01 | COFA C |
| ATOM | 43 | C4 | ADP | A4001 | 11.183 | 9.871 | 27.736 | 1.00 | 29.60 | COFA C |
| ATOM | 44 | C5 | ADP | A4001 | 10.079 | 10.182 | 28.639 | 1.00 | 25.18 | COFA C |
| ATOM | 45 | C6 | ADP | A4001 | 8.724 | 10.094 | 28.079 | 1.00 | 35.82 | COFA C |
| ATOM | 46 | N6 | ADP | A4001 | 7.633 | 10.321 | 28.804 | 1.00 | 30.85 | COFA N |
| ATOM | 47 | N7 | ADP | A4001 | 10.610 | 10.412 | 29.842 | 1.00 | 32.37 | COFA N |
| ATOM | 48 | C8 | ADP | A4001 | 11.941 | 10.328 | 29.722 | 1.00 | 33.11 | COFA C |
| ATOM | 49 | N9 | ADP | A4001 | 12.274 | 10.026 | 28.464 | 1.00 | 32.61 | COFA N |
| ATOM | 50 | C2* | ADP | A4001 | 14.478 | 10.972 | 27.835 | 1.00 | 35.97 | COFA C |
| ATOM | 51 | O2* | ADP | A4001 | 14.384 | 11.380 | 26.480 | 1.00 | 39.00 | COFA O |
| ATOM | 52 | C3* | ADP | A4001 | 15.843 | 10.430 | 28.167 | 1.00 | 38.32 | COFA C |
| ATOM | 53 | O3* | ADP | A4001 | 16.312 | 9.691 | 27.032 | 1.00 | 46.40 | COFA O |
| ATOM | 54 | O1A | ADP | A4001 | 14.263 | 13.443 | 31.581 | 1.00 | 44.12 | COFA O |
| ATOM | 55 | O1B | ADP | A4001 | 14.484 | 12.195 | 35.420 | 1.00 | 31.01 | COFA O |
| ATOM | 56 | C4* | ADP | A4001 | 15.597 | 9.462 | 29.305 | 1.00 | 34.41 | COFA C |
| ATOM | 57 | O4* | ADP | A4001 | 14.256 | 9.017 | 29.137 | 1.00 | 33.39 | COFA O |
| ATOM | 58 | O2A | ADP | A4001 | 16.830 | 12.802 | 31.283 | 1.00 | 48.40 | COFA O |
| ATOM | 59 | O2B | ADP | A4001 | 15.748 | 14.172 | 34.421 | 1.00 | 29.52 | COFA O |
| ATOM | 60 | C5* | ADP | A4001 | 15.789 | 10.072 | 30.699 | 1.00 | 38.60 | COFA C |
| ATOM | 61 | O5* | ADP | A4001 | 14.874 | 11.157 | 30.958 | 1.00 | 29.78 | COFA O |
| ATOM | 62 | O3A | ADP | A4001 | 15.422 | 11.922 | 33.172 | 1.00 | 29.66 | COFA O |
| ATOM | 63 | O3B | ADP | A4001 | 16.973 | 12.085 | 34.991 | 1.00 | 28.69 | COFA O |
| ATOM | 64 | PA | ADP | A4001 | 15.426 | 12.490 | 31.654 | 1.00 | 32.92 | COFA P |
| ATOM | 65 | PB | ADP | A4001 | 15.634 | 12.683 | 34.588 | 1.00 | 29.09 | COFA P |
| TER | 66 | | ADP | A4001 | | | | | | |
| ATOM | 67 | N | GLN | A 78 | 3.974 | 15.272 | 25.244 | 1.00 | 28.66 | MOLA N |
| ATOM | 68 | CA | GLN | A 78 | 4.323 | 16.539 | 25.815 | 1.00 | 31.19 | MOLA C |
| ATOM | 69 | C | GLN | A 78 | 3.203 | 17.580 | 25.771 | 1.00 | 32.20 | MOLA C |
| ATOM | 70 | O | GLN | A 78 | 3.026 | 18.335 | 26.731 | 1.00 | 30.06 | MOLA O |
| ATOM | 71 | CB | GLN | A 78 | 5.549 | 17.102 | 25.123 | 1.00 | 27.84 | MOLA C |
| ATOM | 72 | CG | GLN | A 78 | 6.845 | 16.303 | 25.233 | 1.00 | 32.63 | MOLA C |
| ATOM | 73 | CD | GLN | A 78 | 7.532 | 16.451 | 26.572 | 1.00 | 28.59 | MOLA C |
| ATOM | 74 | NE2 | GLN | A 78 | 8.824 | 16.853 | 26.578 | 1.00 | 31.70 | MOLA N |
| ATOM | 75 | OE1 | GLN | A 78 | 6.946 | 16.086 | 27.571 | 1.00 | 27.98 | MOLA O |
| TER | 76 | | GLN | A 78 | | | | | | |
| ATOM | 77 | N | GLY | A 110 | 12.246 | 10.975 | 33.807 | 1.00 | 30.23 | MOLA N |
| ATOM | 78 | CA | GLY | A 110 | 11.708 | 11.945 | 32.914 | 1.00 | 29.79 | MOLA C |
| ATOM | 79 | C | GLY | A 110 | 11.459 | 13.324 | 33.470 | 1.00 | 29.32 | MOLA C |
| ATOM | 80 | O | GLY | A 110 | 10.661 | 14.042 | 32.889 | 1.00 | 30.22 | MOLA O |
| ATOM | 81 | N | LYS | A 111 | 12.207 | 13.745 | 34.491 | 1.00 | 27.17 | MOLA N |
| ATOM | 82 | CA | LYS | A 111 | 12.061 | 15.085 | 35.031 | 1.00 | 28.75 | MOLA C |
| ATOM | 83 | C | LYS | A 111 | 12.492 | 16.164 | 34.030 | 1.00 | 32.48 | MOLA C |
| ATOM | 84 | O | LYS | A 111 | 11.795 | 17.180 | 33.823 | 1.00 | 28.94 | MOLA O |
| ATOM | 85 | CB | LYS | A 111 | 12.860 | 15.232 | 36.303 | 1.00 | 28.01 | MOLA C |
| ATOM | 86 | CG | LYS | A 111 | 12.400 | 14.319 | 37.471 | 1.00 | 26.11 | MOLA C |
| ATOM | 87 | CD | LYS | A 111 | 13.222 | 14.688 | 38.716 | 1.00 | 28.12 | MOLA C |
| ATOM | 88 | CE | LYS | A 111 | 14.727 | 14.232 | 38.544 | 1.00 | 29.52 | MOLA C |
| ATOM | 89 | NZ | LYS | A 111 | 14.811 | 12.763 | 38.391 | 1.00 | 30.72 | MOLA N |
| ATOM | 90 | N | THR | A 112 | 13.667 | 15.960 | 33.446 | 1.00 | 31.14 | MOLA N |
| ATOM | 91 | CA | THR | A 112 | 14.185 | 16.872 | 32.431 | 1.00 | 29.78 | MOLA C |
| ATOM | 92 | C | THR | A 112 | 13.437 | 16.793 | 31.124 | 1.00 | 29.05 | MOLA C |
| ATOM | 93 | O | THR | A 112 | 13.156 | 17.828 | 30.480 | 1.00 | 30.90 | MOLA O |
| ATOM | 94 | CB | THR | A 112 | 15.661 | 16.635 | 32.195 | 1.00 | 32.31 | MOLA C |
| ATOM | 95 | CG2 | THR | A 112 | 16.219 | 17.714 | 31.243 | 1.00 | 29.98 | MOLA C |
| ATOM | 96 | OG1 | THR | A 112 | 16.348 | 16.846 | 33.422 | 1.00 | 34.66 | MOLA O |
| ATOM | 97 | N | PHE | A 113 | 13.076 | 15.584 | 30.725 | 1.00 | 27.11 | MOLA N |
| ATOM | 98 | CA | PHE | A 113 | 12.262 | 15.442 | 29.540 | 1.00 | 27.93 | MOLA C |
| ATOM | 99 | C | PHE | A 113 | 10.971 | 16.265 | 29.705 | 1.00 | 28.01 | MOLA C |
| ATOM | 100 | O | PHE | A 113 | 10.475 | 16.877 | 28.752 | 1.00 | 27.07 | MOLA O |
| ATOM | 101 | CB | PHE | A 113 | 11.977 | 13.990 | 29.259 | 1.00 | 28.46 | MOLA C |
| ATOM | 102 | CG | PHE | A 113 | 11.157 | 13.757 | 28.013 | 1.00 | 26.58 | MOLA C |
| ATOM | 103 | CD1 | PHE | A 113 | 11.739 | 13.825 | 26.763 | 1.00 | 30.97 | MOLA C |
| ATOM | 104 | CD2 | PHE | A 113 | 9.798 | 13.482 | 28.113 | 1.00 | 26.60 | MOLA C |
| ATOM | 105 | CE1 | PHE | A 113 | 10.983 | 13.663 | 25.613 | 1.00 | 32.56 | MOLA C |
| ATOM | 106 | CE2 | PHE | A 113 | 9.019 | 13.321 | 26.954 | 1.00 | 27.77 | MOLA C |
| ATOM | 107 | CZ | PHE | A 113 | 9.607 | 13.375 | 25.714 | 1.00 | 28.95 | MOLA C |
| ATOM | 108 | N | THR | A 114 | 10.421 | 16.262 | 30.914 | 1.00 | 28.03 | MOLA N |
| ATOM | 109 | CA | THR | A 114 | 9.150 | 16.894 | 31.153 | 1.00 | 26.78 | MOLA C |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 110 | C | THR | A 114 | 9.330 | 18.420 | 31.196 | 1.00 | 30.01 | MOLA C |
| ATOM | 111 | O | THR | A 114 | 8.582 | 19.170 | 30.558 | 1.00 | 28.45 | MOLA O |
| ATOM | 112 | CB | THR | A 114 | 8.544 | 16.380 | 32.464 | 1.00 | 29.85 | MOLA C |
| ATOM | 113 | CG2 | THR | A 114 | 7.276 | 17.197 | 32.838 | 1.00 | 28.03 | MOLA C |
| ATOM | 114 | OG1 | THR | A 114 | 8.091 | 15.016 | 32.340 | 1.00 | 25.56 | MOLA O |
| ATOM | 115 | N | MET | A 115 | 10.331 | 18.880 | 31.943 | 1.00 | 29.12 | MOLA N |
| ATOM | 116 | CA | MET | A 115 | 10.526 | 20.312 | 32.157 | 1.00 | 31.81 | MOLA C |
| ATOM | 117 | C | MET | A 115 | 11.117 | 21.035 | 30.939 | 1.00 | 30.99 | MOLA C |
| ATOM | 118 | O | MET | A 115 | 10.744 | 22.163 | 30.643 | 1.00 | 31.58 | MOLA O |
| ATOM | 119 | CB | MET | A 115 | 11.380 | 20.543 | 33.418 | 1.00 | 31.97 | MOLA C |
| ATOM | 120 | CG | MET | A 115 | 10.885 | 21.654 | 34.316 | 1.00 | 41.53 | MOLA C |
| ATOM | 121 | SD | MET | A 115 | 9.145 | 21.641 | 34.784 | 1.00 | 41.38 | MOLA S |
| ATOM | 122 | CE | MET | A 115 | 9.107 | 21.104 | 36.458 | 1.00 | 46.50 | MOLA C |
| ATOM | 123 | N | GLU | A 116 | 12.004 | 20.379 | 30.223 | 1.00 | 30.32 | MOLA N |
| ATOM | 124 | CA | GLU | A 116 | 12.707 | 21.005 | 29.134 | 1.00 | 34.27 | MOLA C |
| ATOM | 125 | C | GLU | A 116 | 12.365 | 20.374 | 27.800 | 1.00 | 34.76 | MOLA C |
| ATOM | 126 | O | GLU | A 116 | 12.079 | 21.062 | 26.836 | 1.00 | 38.25 | MOLA O |
| ATOM | 127 | CB | GLU | A 116 | 14.213 | 20.908 | 29.380 | 1.00 | 36.60 | MOLA C |
| ATOM | 128 | CG | GLU | A 116 | 14.664 | 21.403 | 30.745 | 1.00 | 37.25 | MOLA C |
| ATOM | 129 | CD | GLU | A 116 | 16.187 | 21.523 | 30.857 | 1.00 | 41.48 | MOLA C |
| ATOM | 130 | OE1 | GLU | A 116 | 16.665 | 21.815 | 31.962 | 1.00 | 48.91 | MOLA O |
| ATOM | 131 | OE2 | GLU | A 116 | 16.897 | 21.324 | 29.853 | 1.00 | 39.60 | MOLA O |
| ATOM | 132 | N | GLY | A 117 | 12.399 | 19.052 | 27.766 | 1.00 | 37.01 | MOLA N |
| ATOM | 133 | CA | GLY | A 117 | 12.106 | 18.275 | 26.569 | 1.00 | 37.82 | MOLA C |
| ATOM | 134 | C | GLY | A 117 | 13.286 | 18.255 | 25.631 | 1.00 | 36.85 | MOLA C |
| ATOM | 135 | O | GLY | A 117 | 14.374 | 18.669 | 25.983 | 1.00 | 36.95 | MOLA O |
| ATOM | 136 | N | GLU | A 118 | 13.031 | 17.855 | 24.401 | 1.00 | 39.42 | MOLA N |
| ATOM | 137 | CA | GLU | A 118 | 14.089 | 17.632 | 23.433 | 1.00 | 44.34 | MOLA C |
| ATOM | 138 | C | GLU | A 118 | 13.661 | 18.054 | 22.034 | 1.00 | 44.63 | MOLA C |
| ATOM | 139 | O | GLU | A 118 | 12.492 | 18.342 | 21.753 | 1.00 | 45.11 | MOLA O |
| ATOM | 140 | CB | GLU | A 118 | 14.518 | 16.126 | 23.411 | 1.00 | 42.03 | MOLA C |
| ATOM | 141 | CG | GLU | A 118 | 14.949 | 15.585 | 24.765 | 1.00 | 49.98 | MOLA C |
| ATOM | 142 | CD | GLU | A 118 | 15.140 | 14.082 | 24.816 | 1.00 | 45.86 | MOLA C |
| ATOM | 143 | OE1 | GLU | A 118 | 15.090 | 13.424 | 23.747 | 1.00 | 35.68 | MOLA O |
| ATOM | 144 | OE2 | GLU | A 118 | 15.311 | 13.557 | 25.952 | 1.00 | 42.63 | MOLA O |
| ATOM | 145 | N | ARG | A 119 | 14.647 | 18.038 | 21.155 | 1.00 | 49.70 | MOLA N |
| ATOM | 146 | CA | ARG | A 119 | 14.501 | 18.412 | 19.759 | 1.00 | 53.41 | MOLA C |
| ATOM | 147 | C | ARG | A 119 | 14.185 | 17.153 | 18.944 | 1.00 | 55.16 | MOLA C |
| ATOM | 148 | O | ARG | A 119 | 14.866 | 16.134 | 19.073 | 1.00 | 57.29 | MOLA O |
| ATOM | 149 | CB | ARG | A 119 | 15.830 | 19.014 | 19.305 | 1.00 | 54.19 | MOLA C |
| ATOM | 150 | CG | ARG | A 119 | 15.718 | 20.258 | 18.487 | 1.00 | 63.53 | MOLA C |
| ATOM | 151 | CD | ARG | A 119 | 15.223 | 21.487 | 19.248 | 1.00 | 71.72 | MOLA C |
| ATOM | 152 | NE | ARG | A 119 | 15.345 | 22.682 | 18.403 | 1.00 | 72.55 | MOLA N |
| ATOM | 153 | CZ | ARG | A 119 | 14.567 | 22.955 | 17.357 | 1.00 | 72.68 | MOLA C |
| ATOM | 154 | NH1 | ARG | A 119 | 14.774 | 24.057 | 16.643 | 1.00 | 79.51 | MOLA N |
| ATOM | 155 | NH2 | ARG | A 119 | 13.585 | 22.129 | 17.011 | 1.00 | 70.71 | MOLA N |
| ATOM | 156 | N | SER | A 120 | 13.152 | 17.196 | 18.115 | 1.00 | 57.38 | MOLA N |
| ATOM | 157 | CA | SER | A 120 | 12.840 | 16.038 | 17.291 | 1.00 | 61.26 | MOLA C |
| ATOM | 158 | C | SER | A 120 | 14.064 | 15.745 | 16.397 | 1.00 | 65.44 | MOLA C |
| ATOM | 159 | O | SER | A 120 | 14.808 | 16.661 | 16.061 | 1.00 | 65.08 | MOLA O |
| ATOM | 160 | CB | SER | A 120 | 11.545 | 16.243 | 16.512 | 1.00 | 60.04 | MOLA C |
| ATOM | 161 | OG | SER | A 120 | 10.429 | 15.788 | 17.272 | 1.00 | 57.87 | MOLA O |
| ATOM | 162 | N | PRO | A 121 | 14.213 | 14.496 | 15.955 | 1.00 | 70.20 | MOLA N |
| ATOM | 163 | CA | PRO | A 121 | 15.516 | 13.926 | 15.628 | 1.00 | 72.33 | MOLA C |
| ATOM | 164 | C | PRO | A 121 | 16.575 | 14.971 | 15.278 | 1.00 | 76.15 | MOLA C |
| ATOM | 165 | O | PRO | A 121 | 17.458 | 15.271 | 16.096 | 1.00 | 76.30 | MOLA O |
| ATOM | 166 | CB | PRO | A 121 | 15.207 | 13.025 | 14.419 | 1.00 | 73.20 | MOLA C |
| ATOM | 167 | CG | PRO | A 121 | 13.764 | 12.633 | 14.565 | 1.00 | 70.37 | MOLA C |
| ATOM | 168 | CD | PRO | A 121 | 13.115 | 13.618 | 15.507 | 1.00 | 72.01 | MOLA C |
| ATOM | 169 | N | ASN | A 122 | 16.472 | 15.512 | 14.066 | 1.00 | 78.78 | MOLA N |
| ATOM | 170 | CA | ASN | A 122 | 17.360 | 16.562 | 13.590 | 1.00 | 78.82 | MOLA C |
| ATOM | 171 | C | ASN | A 122 | 16.533 | 17.452 | 12.663 | 1.00 | 80.53 | MOLA C |
| ATOM | 172 | O | ASN | A 122 | 15.325 | 17.215 | 12.481 | 1.00 | 79.52 | MOLA O |
| ATOM | 173 | CB | ASN | A 122 | 18.583 | 15.962 | 12.872 | 1.00 | 80.31 | MOLA C |
| ATOM | 174 | CG | ASN | A 122 | 19.838 | 16.836 | 12.992 | 1.00 | 81.72 | MOLA C |
| ATOM | 175 | ND2 | ASN | A 122 | 20.111 | 17.322 | 14.203 | 1.00 | 88.02 | MOLA N |
| ATOM | 176 | OD1 | ASN | A 122 | 20.557 | 17.056 | 12.006 | 1.00 | 93.43 | MOLA O |
| ATOM | 177 | N | GLU | A 123 | 17.180 | 18.452 | 12.061 | 1.00 | 80.57 | MOLA N |
| ATOM | 178 | CA | GLU | A 123 | 16.471 | 19.560 | 11.411 | 1.00 | 79.28 | MOLA C |
| ATOM | 179 | C | GLU | A 123 | 15.115 | 19.162 | 10.820 | 1.00 | 79.58 | MOLA C |
| ATOM | 180 | O | GLU | A 123 | 14.932 | 19.056 | 9.598 | 1.00 | 81.43 | MOLA O |
| ATOM | 181 | CB | GLU | A 123 | 17.361 | 20.275 | 10.383 | 1.00 | 80.71 | MOLA C |
| ATOM | 182 | CG | GLU | A 123 | 18.509 | 21.076 | 11.005 | 1.00 | 84.17 | MOLA C |
| ATOM | 183 | CD | GLU | A 123 | 18.048 | 22.208 | 11.920 | 1.00 | 90.08 | MOLA C |
| ATOM | 184 | OE1 | GLU | A 123 | 16.818 | 22.420 | 12.082 | 1.00 | 96.04 | MOLA O |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 185 | OE2 | GLU | A 123 | 18.928 | 22.897 | 12.481 | 1.00 | 88.70 | MOLA O |
| ATOM | 186 | N | GLU | A 124 | 14.188 | 18.930 | 11.748 | 1.00 | 76.38 | MOLA N |
| ATOM | 187 | CA | GLU | A 124 | 12.769 | 18.742 | 11.493 | 1.00 | 73.29 | MOLA C |
| ATOM | 188 | C | GLU | A 124 | 12.109 | 19.578 | 12.596 | 1.00 | 71.07 | MOLA C |
| ATOM | 189 | O | GLU | A 124 | 12.607 | 19.603 | 13.741 | 1.00 | 74.45 | MOLA O |
| ATOM | 190 | CB | GLU | A 124 | 12.409 | 17.261 | 11.643 | 1.00 | 73.51 | MOLA C |
| ATOM | 191 | CG | GLU | A 124 | 10.938 | 16.910 | 11.451 | 1.00 | 75.73 | MOLA C |
| ATOM | 192 | CD | GLU | A 124 | 10.626 | 15.474 | 11.880 | 1.00 | 75.92 | MOLA C |
| ATOM | 193 | OE1 | GLU | A 124 | 9.525 | 14.975 | 11.530 | 1.00 | 77.68 | MOLA O |
| ATOM | 194 | OE2 | GLU | A 124 | 11.484 | 14.840 | 12.567 | 1.00 | 66.18 | MOLA O |
| ATOM | 195 | N | TYR | A 125 | 11.026 | 20.277 | 12.271 | 1.00 | 64.54 | MOLA N |
| ATOM | 196 | CA | TYR | A 125 | 10.316 | 21.121 | 13.255 | 1.00 | 60.89 | MOLA C |
| ATOM | 197 | C | TYR | A 125 | 11.117 | 22.325 | 13.759 | 1.00 | 57.20 | MOLA C |
| ATOM | 198 | O | TYR | A 125 | 12.285 | 22.223 | 14.105 | 1.00 | 56.80 | MOLA O |
| ATOM | 199 | CB | TYR | A 125 | 9.871 | 20.310 | 14.478 | 1.00 | 57.62 | MOLA C |
| ATOM | 200 | CG | TYR | A 125 | 8.822 | 19.252 | 14.219 | 1.00 | 54.91 | MOLA C |
| ATOM | 201 | CD1 | TYR | A 125 | 9.140 | 17.900 | 14.292 | 1.00 | 43.17 | MOLA C |
| ATOM | 202 | CD2 | TYR | A 125 | 7.511 | 19.600 | 13.954 | 1.00 | 49.88 | MOLA C |
| ATOM | 203 | CE1 | TYR | A 125 | 8.185 | 16.920 | 14.061 | 1.00 | 48.43 | MOLA C |
| ATOM | 204 | CE2 | TYR | A 125 | 6.543 | 18.635 | 13.756 | 1.00 | 52.60 | MOLA C |
| ATOM | 205 | CZ | TYR | A 125 | 6.890 | 17.293 | 13.810 | 1.00 | 52.43 | MOLA C |
| ATOM | 206 | OH | TYR | A 125 | 5.933 | 16.328 | 13.620 | 1.00 | 55.44 | MOLA O |
| ATOM | 207 | N | THR | A 126 | 10.478 | 23.477 | 13.813 | 1.00 | 53.95 | MOLA N |
| ATOM | 208 | CA | THR | A 126 | 11.074 | 24.596 | 14.513 | 1.00 | 53.69 | MOLA C |
| ATOM | 209 | C | THR | A 126 | 10.836 | 24.375 | 16.041 | 1.00 | 52.14 | MOLA C |
| ATOM | 210 | O | THR | A 126 | 9.942 | 23.596 | 16.444 | 1.00 | 44.71 | MOLA O |
| ATOM | 211 | CB | THR | A 126 | 10.488 | 25.942 | 13.997 | 1.00 | 53.49 | MOLA C |
| ATOM | 212 | CG2 | THR | A 126 | 9.027 | 26.130 | 14.391 | 1.00 | 52.96 | MOLA C |
| ATOM | 213 | OG1 | THR | A 126 | 11.159 | 27.039 | 14.619 | 1.00 | 60.99 | MOLA O |
| ATOM | 214 | N | TRP | A 127 | 11.632 | 25.047 | 16.877 | 1.00 | 50.44 | MOLA N |
| ATOM | 215 | CA | TRP | A 127 | 11.591 | 24.797 | 18.330 | 1.00 | 50.29 | MOLA C |
| ATOM | 216 | C | TRP | A 127 | 10.176 | 25.010 | 18.872 | 1.00 | 49.58 | MOLA C |
| ATOM | 217 | O | TRP | A 127 | 9.682 | 24.177 | 19.650 | 1.00 | 48.73 | MOLA O |
| ATOM | 218 | CB | TRP | A 127 | 12.661 | 25.612 | 19.082 | 1.00 | 48.28 | MOLA C |
| ATOM | 219 | CG | TRP | A 127 | 12.413 | 27.078 | 19.235 | 1.00 | 48.07 | MOLA C |
| ATOM | 220 | CD1 | TRP | A 127 | 12.925 | 28.090 | 18.461 | 1.00 | 48.86 | MOLA C |
| ATOM | 221 | CD2 | TRP | A 127 | 11.666 | 27.721 | 20.283 | 1.00 | 52.74 | MOLA C |
| ATOM | 222 | CE2 | TRP | A 127 | 11.732 | 29.114 | 20.055 | 1.00 | 54.59 | MOLA C |
| ATOM | 223 | CE3 | TRP | A 127 | 10.897 | 27.256 | 21.365 | 1.00 | 52.49 | MOLA C |
| ATOM | 224 | NE1 | TRP | A 127 | 12.500 | 29.312 | 18.935 | 1.00 | 45.79 | MOLA N |
| ATOM | 225 | CZ2 | TRP | A 127 | 11.079 | 30.042 | 20.878 | 1.00 | 53.36 | MOLA C |
| ATOM | 226 | CZ3 | TRP | A 127 | 10.264 | 28.185 | 22.197 | 1.00 | 49.33 | MOLA C |
| ATOM | 227 | CH2 | TRP | A 127 | 10.349 | 29.556 | 21.938 | 1.00 | 50.68 | MOLA C |
| ATOM | 228 | N | GLU | A 128 | 9.489 | 26.034 | 18.353 | 1.00 | 49.29 | MOLA N |
| ATOM | 229 | CA | GLU | A 128 | 8.126 | 26.373 | 18.807 | 1.00 | 48.91 | MOLA C |
| ATOM | 230 | C | GLU | A 128 | 7.049 | 25.364 | 18.440 | 1.00 | 48.55 | MOLA C |
| ATOM | 231 | O | GLU | A 128 | 5.978 | 25.363 | 19.047 | 1.00 | 46.95 | MOLA O |
| ATOM | 232 | CB | GLU | A 128 | 7.656 | 27.710 | 18.252 | 1.00 | 51.35 | MOLA C |
| ATOM | 233 | CG | GLU | A 128 | 8.505 | 28.906 | 18.599 | 1.00 | 50.33 | MOLA C |
| ATOM | 234 | CD | GLU | A 128 | 9.276 | 29.391 | 17.401 | 1.00 | 65.73 | MOLA C |
| ATOM | 235 | OE1 | GLU | A 128 | 9.824 | 28.530 | 16.691 | 1.00 | 65.31 | MOLA O |
| ATOM | 236 | OE2 | GLU | A 128 | 9.302 | 30.622 | 17.157 | 1.00 | 74.67 | MOLA O |
| ATOM | 237 | N | GLU | A 129 | 7.289 | 24.533 | 17.438 | 1.00 | 47.74 | MOLA N |
| ATOM | 238 | CA | GLU | A 129 | 6.278 | 23.571 | 17.033 | 1.00 | 46.74 | MOLA C |
| ATOM | 239 | C | GLU | A 129 | 6.726 | 22.131 | 17.262 | 1.00 | 47.21 | MOLA C |
| ATOM | 240 | O | GLU | A 129 | 6.061 | 21.175 | 16.815 | 1.00 | 47.92 | MOLA O |
| ATOM | 241 | CB | GLU | A 129 | 5.941 | 23.771 | 15.553 | 1.00 | 49.67 | MOLA C |
| ATOM | 242 | CG | GLU | A 129 | 5.081 | 24.990 | 15.243 | 1.00 | 50.96 | MOLA C |
| ATOM | 243 | CD | GLU | A 129 | 3.709 | 24.978 | 15.939 | 1.00 | 68.78 | MOLA C |
| ATOM | 244 | OE1 | GLU | A 129 | 3.312 | 26.047 | 16.448 | 1.00 | 79.04 | MOLA O |
| ATOM | 245 | OE2 | GLU | A 129 | 3.016 | 23.923 | 15.978 | 1.00 | 64.98 | MOLA O |
| ATOM | 246 | N | ASP | A 130 | 7.847 | 21.956 | 17.956 | 1.00 | 42.93 | MOLA N |
| ATOM | 247 | CA | ASP | A 130 | 8.423 | 20.626 | 18.111 | 1.00 | 41.94 | MOLA C |
| ATOM | 248 | C | ASP | A 130 | 7.630 | 19.862 | 19.171 | 1.00 | 39.68 | MOLA C |
| ATOM | 249 | O | ASP | A 130 | 7.458 | 20.335 | 20.266 | 1.00 | 40.43 | MOLA O |
| ATOM | 250 | CB | ASP | A 130 | 9.893 | 20.753 | 18.487 | 1.00 | 41.86 | MOLA C |
| ATOM | 251 | CG | ASP | A 130 | 10.669 | 19.468 | 18.292 | 1.00 | 43.26 | MOLA C |
| ATOM | 252 | OD1 | ASP | A 130 | 11.875 | 19.555 | 17.946 | 1.00 | 47.40 | MOLA O |
| ATOM | 253 | OD2 | ASP | A 130 | 10.189 | 18.343 | 18.527 | 1.00 | 50.95 | MOLA O |
| ATOM | 254 | N | PRO | A 131 | 7.074 | 18.721 | 18.800 | 1.00 | 39.00 | MOLA N |
| ATOM | 255 | CA | PRO | A 131 | 6.273 | 17.921 | 19.718 | 1.00 | 38.78 | MOLA C |
| ATOM | 256 | C | PRO | A 131 | 6.998 | 17.343 | 20.936 | 1.00 | 37.75 | MOLA C |
| ATOM | 257 | O | PRO | A 131 | 6.318 | 16.854 | 21.832 | 1.00 | 38.44 | MOLA O |
| ATOM | 258 | CB | PRO | A 131 | 5.740 | 16.779 | 18.839 | 1.00 | 39.04 | MOLA C |
| ATOM | 259 | CG | PRO | A 131 | 6.584 | 16.805 | 17.581 | 1.00 | 39.99 | MOLA C |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 260 | CD | PRO | A 131 | 7.099 | 18.168 | 17.432 | 1.00 | 41.02 | MOLA C |
| ATOM | 261 | N | LEU | A 132 | 8.337 | 17.406 | 20.957 | 1.00 | 35.90 | MOLA N |
| ATOM | 262 | CA | LEU | A 132 | 9.145 | 16.862 | 22.033 | 1.00 | 33.52 | MOLA C |
| ATOM | 263 | C | LEU | A 132 | 9.612 | 17.972 | 22.971 | 1.00 | 31.18 | MOLA C |
| ATOM | 264 | O | LEU | A 132 | 10.148 | 17.710 | 24.046 | 1.00 | 32.31 | MOLA O |
| ATOM | 265 | CB | LEU | A 132 | 10.332 | 16.066 | 21.493 | 1.00 | 34.32 | MOLA C |
| ATOM | 266 | CG | LEU | A 132 | 10.065 | 14.815 | 20.644 | 1.00 | 36.24 | MOLA C |
| ATOM | 267 | CD1 | LEU | A 132 | 11.364 | 14.063 | 20.373 | 1.00 | 42.96 | MOLA C |
| ATOM | 268 | CD2 | LEU | A 132 | 9.040 | 13.874 | 21.297 | 1.00 | 44.74 | MOLA C |
| ATOM | 269 | N | ALA | A 133 | 9.297 | 19.215 | 22.631 | 1.00 | 32.05 | MOLA N |
| ATOM | 270 | CA | ALA | A 133 | 9.554 | 20.327 | 23.536 | 1.00 | 31.34 | MOLA C |
| ATOM | 271 | C | ALA | A 133 | 8.807 | 20.129 | 24.877 | 1.00 | 28.61 | MOLA C |
| ATOM | 272 | O | ALA | A 133 | 7.692 | 19.599 | 24.918 | 1.00 | 30.25 | MOLA O |
| ATOM | 273 | CB | ALA | A 133 | 9.152 | 21.615 | 22.902 | 1.00 | 33.31 | MOLA C |
| ATOM | 274 | N | GLY | A 134 | 9.379 | 20.612 | 25.959 | 1.00 | 29.98 | MOLA N |
| ATOM | 275 | CA | GLY | A 134 | 8.761 | 20.395 | 27.286 | 1.00 | 32.01 | MOLA C |
| ATOM | 276 | C | GLY | A 134 | 8.119 | 21.660 | 27.784 | 1.00 | 32.57 | MOLA C |
| ATOM | 277 | O | GLY | A 134 | 7.971 | 22.602 | 27.052 | 1.00 | 35.19 | MOLA O |
| ATOM | 278 | N | ILE | A 135 | 7.805 | 21.700 | 29.069 | 1.00 | 32.29 | MOLA N |
| ATOM | 279 | CA | ILE | A 135 | 7.114 | 22.812 | 29.666 | 1.00 | 31.19 | MOLA C |
| ATOM | 280 | C | ILE | A 135 | 7.799 | 24.172 | 29.493 | 1.00 | 33.39 | MOLA C |
| ATOM | 281 | O | ILE | A 135 | 7.137 | 25.171 | 29.171 | 1.00 | 32.23 | MOLA O |
| ATOM | 282 | CB | ILE | A 135 | 6.913 | 22.506 | 31.173 | 1.00 | 30.40 | MOLA C |
| ATOM | 283 | CG1 | ILE | A 135 | 5.922 | 21.338 | 31.345 | 1.00 | 30.82 | MOLA C |
| ATOM | 284 | CG2 | ILE | A 135 | 6.466 | 23.754 | 31.917 | 1.00 | 30.67 | MOLA C |
| ATOM | 285 | CD1 | ILE | A 135 | 5.808 | 20.799 | 32.783 | 1.00 | 27.96 | MOLA C |
| ATOM | 286 | N | ILE | A 136 | 9.097 | 24.254 | 29.747 | 1.00 | 31.04 | MOLA N |
| ATOM | 287 | CA | ILE | A 136 | 9.759 | 25.571 | 29.685 | 1.00 | 32.05 | MOLA C |
| ATOM | 288 | C | ILE | A 136 | 9.623 | 26.298 | 28.290 | 1.00 | 32.36 | MOLA C |
| ATOM | 289 | O | ILE | A 136 | 9.169 | 27.442 | 28.219 | 1.00 | 28.17 | MOLA O |
| ATOM | 290 | CB | ILE | A 136 | 11.251 | 25.491 | 30.161 | 1.00 | 31.12 | MOLA C |
| ATOM | 291 | CG1 | ILE | A 136 | 11.324 | 25.312 | 31.686 | 1.00 | 32.46 | MOLA C |
| ATOM | 292 | CG2 | ILE | A 136 | 12.050 | 26.777 | 29.757 | 1.00 | 32.12 | MOLA C |
| ATOM | 293 | CD1 | ILE | A 136 | 12.714 | 24.899 | 32.210 | 1.00 | 34.49 | MOLA C |
| ATOM | 294 | N | PRO | A 137 | 10.085 | 25.683 | 27.210 | 1.00 | 35.73 | MOLA N |
| ATOM | 295 | CA | PRO | A 137 | 9.940 | 26.307 | 25.889 | 1.00 | 34.56 | MOLA C |
| ATOM | 296 | C | PRO | A 137 | 8.478 | 26.597 | 25.495 | 1.00 | 35.39 | MOLA C |
| ATOM | 297 | O | PRO | A 137 | 8.208 | 27.676 | 24.936 | 1.00 | 35.24 | MOLA O |
| ATOM | 298 | CB | PRO | A 137 | 10.620 | 25.310 | 24.946 | 1.00 | 36.29 | MOLA C |
| ATOM | 299 | CG | PRO | A 137 | 10.825 | 24.085 | 25.741 | 1.00 | 37.35 | MOLA C |
| ATOM | 300 | CD | PRO | A 137 | 10.905 | 24.464 | 27.164 | 1.00 | 33.20 | MOLA C |
| ATOM | 301 | N | ARG | A 138 | 7.556 | 25.653 | 25.748 | 1.00 | 33.93 | MOLA N |
| ATOM | 302 | CA | ARG | A 138 | 6.139 | 25.864 | 25.442 | 1.00 | 31.15 | MOLA C |
| ATOM | 303 | C | ARG | A 138 | 5.585 | 27.025 | 26.255 | 1.00 | 32.50 | MOLA C |
| ATOM | 304 | O | ARG | A 138 | 4.793 | 27.803 | 25.748 | 1.00 | 31.64 | MOLA O |
| ATOM | 305 | CB | ARG | A 138 | 5.276 | 24.629 | 25.749 | 1.00 | 33.83 | MOLA C |
| ATOM | 306 | CG | ARG | A 138 | 5.476 | 23.447 | 24.835 | 1.00 | 29.48 | MOLA C |
| ATOM | 307 | CD | ARG | A 138 | 4.825 | 22.163 | 25.283 | 1.00 | 31.41 | MOLA C |
| ATOM | 308 | NE | ARG | A 138 | 5.265 | 21.020 | 24.474 | 1.00 | 31.55 | MOLA N |
| ATOM | 309 | CZ | ARG | A 138 | 4.668 | 20.649 | 23.355 | 1.00 | 33.07 | MOLA C |
| ATOM | 310 | NH1 | ARG | A 138 | 3.652 | 21.356 | 22.888 | 1.00 | 28.72 | MOLA N |
| ATOM | 311 | NH2 | ARG | A 138 | 5.103 | 19.608 | 22.677 | 1.00 | 29.40 | MOLA N |
| ATOM | 312 | N | THR | A 139 | 5.981 | 27.140 | 27.523 | 1.00 | 31.35 | MOLA N |
| ATOM | 313 | CA | THR | A 139 | 5.555 | 28.238 | 28.356 | 1.00 | 30.47 | MOLA C |
| ATOM | 314 | C | THR | A 139 | 6.034 | 29.606 | 27.831 | 1.00 | 33.17 | MOLA C |
| ATOM | 315 | O | THR | A 139 | 5.286 | 30.608 | 27.818 | 1.00 | 31.11 | MOLA O |
| ATOM | 316 | CB | THR | A 139 | 6.010 | 28.019 | 29.839 | 1.00 | 30.43 | MOLA C |
| ATOM | 317 | CG2 | THR | A 139 | 5.436 | 29.080 | 30.715 | 1.00 | 36.29 | MOLA C |
| ATOM | 318 | OG1 | THR | A 139 | 5.456 | 26.817 | 30.378 | 1.00 | 28.90 | MOLA O |
| ATOM | 319 | N | LEU | A 140 | 7.300 | 29.701 | 27.474 | 1.00 | 31.53 | MOLA N |
| ATOM | 320 | CA | LEU | A 140 | 7.814 | 30.970 | 26.975 | 1.00 | 32.94 | MOLA C |
| ATOM | 321 | C | LEU | A 140 | 7.149 | 31.352 | 25.646 | 1.00 | 35.04 | MOLA C |
| ATOM | 322 | O | LEU | A 140 | 6.816 | 32.517 | 25.420 | 1.00 | 35.49 | MOLA O |
| ATOM | 323 | CB | LEU | A 140 | 9.342 | 30.941 | 26.838 | 1.00 | 31.62 | MOLA C |
| ATOM | 324 | CG | LEU | A 140 | 10.222 | 31.060 | 28.111 | 1.00 | 42.04 | MOLA C |
| ATOM | 325 | CD1 | LEU | A 140 | 9.821 | 32.217 | 29.050 | 1.00 | 36.69 | MOLA C |
| ATOM | 326 | CD2 | LEU | A 140 | 10.193 | 29.815 | 28.899 | 1.00 | 59.28 | MOLA C |
| ATOM | 327 | N | HIS | A 141 | 6.865 | 30.372 | 24.801 | 1.00 | 34.93 | MOLA N |
| ATOM | 328 | CA | HIS | A 141 | 6.256 | 30.683 | 23.512 | 1.00 | 35.29 | MOLA C |
| ATOM | 329 | C | HIS | A 141 | 4.821 | 31.207 | 23.703 | 1.00 | 37.46 | MOLA C |
| ATOM | 330 | O | HIS | A 141 | 4.415 | 32.200 | 23.090 | 1.00 | 34.04 | MOLA O |
| ATOM | 331 | CB | HIS | A 141 | 6.250 | 29.465 | 22.632 | 1.00 | 34.20 | MOLA C |
| ATOM | 332 | CG | HIS | A 141 | 5.601 | 29.683 | 21.298 | 1.00 | 41.74 | MOLA C |
| ATOM | 333 | CD2 | HIS | A 141 | 4.505 | 29.116 | 20.733 | 1.00 | 46.44 | MOLA C |
| ATOM | 334 | ND1 | HIS | A 141 | 6.102 | 30.562 | 20.361 | 1.00 | 44.79 | MOLA N |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 335 | CE1 | HIS | A 141 | 5.339 | 30.532 | 19.282 | 1.00 | 46.00 | MOLA C |
| ATOM | 336 | NE2 | HIS | A 141 | 4.368 | 29.656 | 19.478 | 1.00 | 48.00 | MOLA N |
| TER | 337 | | HIS | A 141 | | | | | | |
| ATOM | 338 | N | VAL | A 158 | 13.999 | 36.249 | 32.507 | 1.00 | 40.84 | MOLA N |
| ATOM | 339 | CA | VAL | A 158 | 14.212 | 34.887 | 32.958 | 1.00 | 41.83 | MOLA C |
| ATOM | 340 | C | VAL | A 158 | 15.505 | 34.774 | 33.749 | 1.00 | 43.19 | MOLA C |
| ATOM | 341 | O | VAL | A 158 | 16.458 | 35.553 | 33.533 | 1.00 | 44.11 | MOLA O |
| ATOM | 342 | CB | VAL | A 158 | 14.273 | 33.883 | 31.780 | 1.00 | 41.70 | MOLA C |
| ATOM | 343 | CG1 | VAL | A 158 | 12.978 | 33.882 | 31.005 | 1.00 | 46.06 | MOLA C |
| ATOM | 344 | CG2 | VAL | A 158 | 15.435 | 34.177 | 30.861 | 1.00 | 45.52 | MOLA C |
| ATOM | 345 | N | SER | A 159 | 15.523 | 33.811 | 34.669 | 1.00 | 40.51 | MOLA N |
| ATOM | 346 | CA | SER | A 159 | 16.748 | 33.417 | 35.366 | 1.00 | 40.20 | MOLA C |
| ATOM | 347 | C | SER | A 159 | 16.779 | 31.894 | 35.504 | 1.00 | 37.84 | MOLA C |
| ATOM | 348 | O | SER | A 159 | 15.752 | 31.242 | 35.430 | 1.00 | 39.12 | MOLA O |
| ATOM | 349 | CB | SER | A 159 | 16.823 | 34.069 | 36.730 | 1.00 | 41.31 | MOLA C |
| ATOM | 350 | OG | SER | A 159 | 15.811 | 33.567 | 37.584 | 1.00 | 53.35 | MOLA O |
| ATOM | 351 | N | LEU | A 160 | 17.975 | 31.352 | 35.678 | 1.00 | 34.08 | MOLA N |
| ATOM | 352 | CA | LEU | A 160 | 18.207 | 29.933 | 35.816 | 1.00 | 35.57 | MOLA C |
| ATOM | 353 | C | LEU | A 160 | 19.298 | 29.766 | 36.852 | 1.00 | 38.34 | MOLA C |
| ATOM | 354 | O | LEU | A 160 | 20.393 | 30.305 | 36.725 | 1.00 | 39.98 | MOLA O |
| ATOM | 355 | CB | LEU | A 160 | 18.638 | 29.309 | 34.494 | 1.00 | 30.91 | MOLA C |
| ATOM | 356 | CG | LEU | A 160 | 18.885 | 27.805 | 34.429 | 1.00 | 35.11 | MOLA C |
| ATOM | 357 | CD1 | LEU | A 160 | 17.621 | 26.962 | 34.795 | 1.00 | 35.53 | MOLA C |
| ATOM | 358 | CD2 | LEU | A 160 | 19.358 | 27.450 | 33.037 | 1.00 | 37.28 | MOLA C |
| ATOM | 359 | N | LEU | A 161 | 18.983 | 29.037 | 37.896 | 1.00 | 38.89 | MOLA N |
| ATOM | 360 | CA | LEU | A 161 | 19.910 | 28.832 | 38.965 | 1.00 | 41.64 | MOLA C |
| ATOM | 361 | C | LEU | A 161 | 19.948 | 27.354 | 39.267 | 1.00 | 40.30 | MOLA C |
| ATOM | 362 | O | LEU | A 161 | 18.913 | 26.674 | 39.179 | 1.00 | 36.67 | MOLA O |
| ATOM | 363 | CB | LEU | A 161 | 19.478 | 29.658 | 40.185 | 1.00 | 42.48 | MOLA C |
| ATOM | 364 | CG | LEU | A 161 | 18.689 | 29.044 | 41.332 | 1.00 | 46.46 | MOLA C |
| ATOM | 365 | CD1 | LEU | A 161 | 19.551 | 28.185 | 42.239 | 1.00 | 55.01 | MOLA C |
| ATOM | 366 | CD2 | LEU | A 161 | 18.097 | 30.118 | 42.128 | 1.00 | 48.36 | MOLA C |
| ATOM | 367 | N | GLU | A 162 | 21.145 | 26.836 | 39.521 | 1.00 | 40.56 | MOLA N |
| ATOM | 368 | CA | GLU | A 162 | 21.298 | 25.485 | 40.044 | 1.00 | 44.78 | MOLA C |
| ATOM | 369 | C | GLU | A 162 | 21.656 | 25.535 | 41.526 | 1.00 | 42.83 | MOLA C |
| ATOM | 370 | O | GLU | A 162 | 22.388 | 26.417 | 41.979 | 1.00 | 44.24 | MOLA O |
| ATOM | 371 | CB | GLU | A 162 | 22.339 | 24.690 | 39.273 | 1.00 | 45.00 | MOLA C |
| ATOM | 372 | CG | GLU | A 162 | 21.745 | 23.760 | 38.226 | 1.00 | 61.58 | MOLA C |
| ATOM | 373 | CD | GLU | A 162 | 22.640 | 22.558 | 37.902 | 1.00 | 56.26 | MOLA C |
| ATOM | 374 | OE1 | GLU | A 162 | 22.111 | 21.583 | 37.289 | 1.00 | 77.39 | MOLA O |
| ATOM | 375 | OE2 | GLU | A 162 | 23.858 | 22.609 | 38.232 | 1.00 | 71.01 | MOLA O |
| TER | 376 | | GLU | A 162 | | | | | | |
| ATOM | 377 | N | LEU | A 171 | 23.316 | 30.003 | 36.110 | 1.00 | 44.89 | MOLA N |
| ATOM | 378 | CA | LEU | A 171 | 23.668 | 29.393 | 34.833 | 1.00 | 43.75 | MOLA C |
| ATOM | 379 | C | LEU | A 171 | 23.473 | 30.330 | 33.647 | 1.00 | 43.35 | MOLA C |
| ATOM | 380 | O | LEU | A 171 | 23.665 | 29.923 | 32.517 | 1.00 | 43.56 | MOLA O |
| ATOM | 381 | CB | LEU | A 171 | 22.852 | 28.104 | 34.627 | 1.00 | 44.22 | MOLA C |
| ATOM | 382 | CG | LEU | A 171 | 23.055 | 26.935 | 35.619 | 1.00 | 40.93 | MOLA C |
| ATOM | 383 | CD1 | LEU | A 171 | 22.152 | 25.765 | 35.227 | 1.00 | 44.28 | MOLA C |
| ATOM | 384 | CD2 | LEU | A 171 | 24.501 | 26.465 | 35.662 | 1.00 | 38.69 | MOLA C |
| ATOM | 385 | N | LEU | A 172 | 23.032 | 31.563 | 33.894 | 1.00 | 46.50 | MOLA N |
| ATOM | 386 | CA | LEU | A 172 | 22.867 | 32.561 | 32.827 | 1.00 | 48.70 | MOLA C |
| ATOM | 387 | C | LEU | A 172 | 23.874 | 33.721 | 32.872 | 1.00 | 51.31 | MOLA C |
| ATOM | 388 | O | LEU | A 172 | 23.764 | 34.670 | 32.095 | 1.00 | 52.31 | MOLA O |
| ATOM | 389 | CB | LEU | A 172 | 21.452 | 33.144 | 32.845 | 1.00 | 45.93 | MOLA C |
| ATOM | 390 | CG | LEU | A 172 | 20.330 | 32.131 | 32.606 | 1.00 | 46.97 | MOLA C |
| ATOM | 391 | CD1 | LEU | A 172 | 19.064 | 32.839 | 32.206 | 1.00 | 48.26 | MOLA C |
| ATOM | 392 | CD2 | LEU | A 172 | 20.701 | 31.150 | 31.530 | 1.00 | 45.13 | MOLA C |
| TER | 393 | | LEU | A 172 | | | | | | |
| ATOM | 394 | N | LYS | A 207 | 10.323 | 36.206 | 21.024 | 1.00 | 60.48 | MOLA N |
| ATOM | 395 | CA | LYS | A 207 | 10.486 | 34.782 | 21.227 | 1.00 | 64.75 | MOLA C |
| ATOM | 396 | C | LYS | A 207 | 11.656 | 34.196 | 20.397 | 1.00 | 64.10 | MOLA C |
| ATOM | 397 | O | LYS | A 207 | 12.092 | 33.076 | 20.649 | 1.00 | 64.45 | MOLA O |
| ATOM | 398 | CB | LYS | A 207 | 9.152 | 34.036 | 21.029 | 1.00 | 64.99 | MOLA C |
| ATOM | 399 | CG | LYS | A 207 | 8.573 | 34.141 | 19.653 | 1.00 | 70.32 | MOLA C |
| ATOM | 400 | CD | LYS | A 207 | 7.153 | 33.615 | 19.620 | 1.00 | 68.39 | MOLA C |
| ATOM | 401 | CE | LYS | A 207 | 6.584 | 33.739 | 18.209 | 1.00 | 70.20 | MOLA C |
| ATOM | 402 | NZ | LYS | A 207 | 7.474 | 33.118 | 17.165 | 1.00 | 74.37 | MOLA N |
| TER | 403 | | LYS | A 207 | | | | | | |
| ATOM | 404 | N | GLU | A 209 | 14.604 | 35.278 | 20.578 | 1.00 | 61.45 | MOLA N |
| ATOM | 405 | CA | GLU | A 209 | 15.727 | 35.392 | 21.508 | 1.00 | 60.19 | MOLA C |
| ATOM | 406 | C | GLU | A 209 | 15.687 | 34.244 | 22.542 | 1.00 | 56.92 | MOLA C |
| ATOM | 407 | O | GLU | A 209 | 16.665 | 33.947 | 23.237 | 1.00 | 54.33 | MOLA O |
| ATOM | 408 | CB | GLU | A 209 | 15.584 | 36.720 | 22.247 | 1.00 | 60.79 | MOLA C |
| ATOM | 409 | CG | GLU | A 209 | 16.851 | 37.541 | 22.380 | 1.00 | 65.43 | MOLA C |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 410 | CD | GLU | A 209 | 16.575 | 38.833 | 23.106 | 1.00 | 66.99 | MOLA C |
| ATOM | 411 | OE1 | GLU | A 209 | 15.523 | 39.457 | 22.825 | 1.00 | 70.59 | MOLA O |
| ATOM | 412 | OE2 | GLU | A 209 | 17.396 | 39.207 | 23.974 | 1.00 | 92.21 | MOLA O |
| ATOM | 413 | N | VAL | A 210 | 14.534 | 33.599 | 22.640 | 1.00 | 53.09 | MOLA N |
| ATOM | 414 | CA | VAL | A 210 | 14.329 | 32.576 | 23.642 | 1.00 | 52.17 | MOLA C |
| ATOM | 415 | C | VAL | A 210 | 15.300 | 31.422 | 23.515 | 1.00 | 50.45 | MOLA C |
| ATOM | 416 | O | VAL | A 210 | 15.858 | 30.973 | 24.527 | 1.00 | 44.80 | MOLA O |
| ATOM | 417 | CB | VAL | A 210 | 12.911 | 31.999 | 23.567 | 1.00 | 50.64 | MOLA C |
| ATOM | 418 | CG1 | VAL | A 210 | 12.777 | 30.759 | 24.448 | 1.00 | 50.67 | MOLA C |
| ATOM | 419 | CG2 | VAL | A 210 | 11.902 | 33.056 | 23.958 | 1.00 | 48.32 | MOLA C |
| ATOM | 420 | N | TYR | A 211 | 15.415 | 30.903 | 22.290 | 1.00 | 49.84 | MOLA N |
| ATOM | 421 | CA | TYR | A 211 | 16.204 | 29.716 | 22.026 | 1.00 | 51.89 | MOLA C |
| ATOM | 422 | C | TYR | A 211 | 17.657 | 29.916 | 22.418 | 1.00 | 50.39 | MOLA C |
| ATOM | 423 | O | TYR | A 211 | 18.251 | 29.060 | 23.049 | 1.00 | 47.14 | MOLA O |
| ATOM | 424 | CB | TYR | A 211 | 16.118 | 29.343 | 20.554 | 1.00 | 52.77 | MOLA O |
| ATOM | 425 | CG | TYR | A 211 | 16.686 | 27.981 | 20.266 | 1.00 | 52.73 | MOLA C |
| ATOM | 426 | CD1 | TYR | A 211 | 18.004 | 27.824 | 19.872 | 1.00 | 56.05 | MOLA C |
| ATOM | 427 | CD2 | TYR | A 211 | 15.898 | 26.840 | 20.407 | 1.00 | 56.90 | MOLA C |
| ATOM | 428 | CE1 | TYR | A 211 | 18.526 | 26.568 | 19.614 | 1.00 | 54.85 | MOLA C |
| ATOM | 429 | CE2 | TYR | A 211 | 16.401 | 25.595 | 20.137 | 1.00 | 59.28 | MOLA C |
| ATOM | 430 | CZ | TYR | A 211 | 17.717 | 25.462 | 19.727 | 1.00 | 58.41 | MOLA C |
| ATOM | 431 | OH | TYR | A 211 | 18.226 | 24.203 | 19.484 | 1.00 | 62.34 | MOLA O |
| ATOM | 432 | N | GLN | A 212 | 18.200 | 31.064 | 22.032 | 1.00 | 51.78 | MOLA N |
| ATOM | 433 | CA | GLN | A 212 | 19.583 | 31.443 | 22.321 | 1.00 | 52.14 | MOLA C |
| ATOM | 434 | C | GLN | A 212 | 19.851 | 31.490 | 23.814 | 1.00 | 51.41 | MOLA C |
| ATOM | 435 | O | GLN | A 212 | 20.896 | 31.042 | 24.280 | 1.00 | 51.97 | MOLA O |
| ATOM | 436 | CB | GLN | A 212 | 19.879 | 32.799 | 21.644 | 1.00 | 53.28 | MOLA C |
| ATOM | 437 | CG | GLN | A 212 | 20.997 | 33.653 | 22.246 | 1.00 | 58.44 | MOLA C |
| ATOM | 438 | CD | GLN | A 212 | 20.456 | 34.862 | 23.022 | 1.00 | 79.00 | MOLA C |
| ATOM | 439 | NE2 | GLN | A 212 | 21.068 | 35.152 | 24.177 | 1.00 | 75.58 | MOLA N |
| ATOM | 440 | OE1 | GLN | A 212 | 19.506 | 35.532 | 22.569 | 1.00 | 82.34 | MOLA O |
| ATOM | 441 | N | ILE | A 213 | 18.888 | 31.975 | 24.579 | 1.00 | 51.84 | MOLA N |
| ATOM | 442 | CA | ILE | A 213 | 19.053 | 32.054 | 26.027 | 1.00 | 52.44 | MOLA C |
| ATOM | 443 | C | ILE | A 213 | 19.043 | 30.665 | 26.677 | 1.00 | 51.93 | MOLA C |
| ATOM | 444 | O | ILE | A 213 | 19.870 | 30.354 | 27.541 | 1.00 | 49.09 | MOLA O |
| ATOM | 445 | CB | ILE | A 213 | 17.985 | 32.961 | 26.643 | 1.00 | 54.01 | MOLA C |
| ATOM | 446 | CG1 | ILE | A 213 | 18.097 | 34.380 | 26.045 | 1.00 | 52.23 | MOLA C |
| ATOM | 447 | CG2 | ILE | A 213 | 18.171 | 33.024 | 28.165 | 1.00 | 53.32 | MOLA C |
| ATOM | 448 | CD1 | ILE | A 213 | 16.875 | 35.283 | 26.288 | 1.00 | 53.64 | MOLA C |
| ATOM | 449 | N | LEU | A 214 | 18.117 | 29.826 | 26.246 | 1.00 | 52.24 | MOLA N |
| ATOM | 450 | CA | LEU | A 214 | 18.058 | 28.443 | 26.721 | 1.00 | 53.71 | MOLA C |
| ATOM | 451 | C | LEU | A 214 | 19.360 | 27.703 | 26.400 | 1.00 | 52.77 | MOLA C |
| ATOM | 452 | O | LEU | A 214 | 19.861 | 26.907 | 27.195 | 1.00 | 49.50 | MOLA O |
| ATOM | 453 | CB | LEU | A 214 | 16.881 | 27.720 | 26.061 | 1.00 | 52.85 | MOLA C |
| ATOM | 454 | CG | LEU | A 214 | 15.509 | 27.719 | 26.761 | 1.00 | 59.95 | MOLA C |
| ATOM | 455 | CD1 | LEU | A 214 | 15.336 | 28.827 | 27.784 | 1.00 | 50.58 | MOLA C |
| ATOM | 456 | CD2 | LEU | A 214 | 14.373 | 27.723 | 25.727 | 1.00 | 56.64 | MOLA C |
| ATOM | 457 | N | GLU | A 215 | 19.894 | 27.991 | 25.220 | 1.00 | 53.24 | MOLA N |
| ATOM | 458 | CA | GLU | A 215 | 21.121 | 27.372 | 24.729 | 1.00 | 53.91 | MOLA C |
| ATOM | 459 | C | GLU | A 215 | 22.315 | 27.659 | 25.626 | 1.00 | 50.22 | MOLA C |
| ATOM | 460 | O | GLU | A 215 | 23.019 | 26.735 | 26.057 | 1.00 | 46.58 | MOLA O |
| ATOM | 461 | CB | GLU | A 215 | 21.393 | 27.877 | 23.324 | 1.00 | 54.28 | MOLA C |
| ATOM | 462 | CG | GLU | A 215 | 22.225 | 26.953 | 22.464 | 1.00 | 60.75 | MOLA C |
| ATOM | 463 | CD | GLU | A 215 | 21.956 | 27.199 | 20.995 | 1.00 | 59.08 | MOLA C |
| ATOM | 464 | OE1 | GLU | A 215 | 21.755 | 28.384 | 20.640 | 1.00 | 68.20 | MOLA O |
| ATOM | 465 | OE2 | GLU | A 215 | 21.873 | 26.212 | 20.221 | 1.00 | 74.56 | MOLA O |
| ATOM | 466 | N | LYS | A 216 | 22.531 | 28.929 | 25.938 | 1.00 | 50.85 | MOLA N |
| ATOM | 467 | CA | LYS | A 216 | 23.649 | 29.312 | 26.822 | 1.00 | 53.41 | MOLA C |
| ATOM | 468 | C | LYS | A 216 | 23.488 | 28.630 | 28.185 | 1.00 | 51.89 | MOLA C |
| ATOM | 469 | O | LYS | A 216 | 24.461 | 28.149 | 28.775 | 1.00 | 49.85 | MOLA O |
| ATOM | 470 | CB | LYS | A 216 | 23.721 | 30.836 | 27.014 | 1.00 | 54.46 | MOLA C |
| ATOM | 471 | CG | LYS | A 216 | 23.835 | 31.676 | 25.711 | 1.00 | 61.78 | MOLA C |
| ATOM | 472 | CD | LYS | A 216 | 23.717 | 33.219 | 25.964 | 1.00 | 59.15 | MOLA C |
| ATOM | 473 | CE | LYS | A 216 | 2S.092 | 33.922 | 26.121 | 1.00 | 70.04 | MOLA C |
| ATOM | 474 | NZ | LYS | A 216 | 24.984 | 35.392 | 26.478 | 1.00 | 61.11 | MOLA N |
| ATOM | 475 | N | GLY | A 217 | 22.249 | 28.551 | 28.666 | 1.00 | 50.87 | MOLA N |
| ATOM | 476 | CA | GLY | A 217 | 21.988 | 27.933 | 29.966 | 1.00 | 50.86 | MOLA C |
| ATOM | 477 | C | GLY | A 217 | 22.456 | 26.491 | 29.976 | 1.00 | 49.21 | MOLA C |
| ATOM | 478 | O | GLY | A 217 | 23.229 | 26.056 | 30.842 | 1.00 | 46.38 | MOLA O |
| ATOM | 479 | N | ALA | A 218 | 21.993 | 25.743 | 28.993 | 1.00 | 49.07 | MOLA N |
| ATOM | 480 | CA | ALA | A 218 | 22.351 | 24.341 | 28.891 | 1.00 | 50.64 | MOLA C |
| ATOM | 481 | C | ALA | A 218 | 23.867 | 24.160 | 28.758 | 1.00 | 50.06 | MOLA C |
| ATOM | 482 | O | ALA | A 218 | 24.434 | 23.214 | 29.298 | 1.00 | 51.02 | MOLA O |
| ATOM | 483 | CB | ALA | A 218 | 21.603 | 23.678 | 27.698 | 1.00 | 49.35 | MOLA C |
| ATOM | 484 | N | ALA | A 219 | 24.509 | 25.045 | 28.000 | 1.00 | 50.06 | MOLA N |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 485 | CA | ALA | A 219 | 25.952 | 24.964 | 27.791 | 1.00 | 51.23 | MOLA C |
| ATOM | 486 | C | ALA | A 219 | 26.648 | 25.096 | 29.130 | 1.00 | 51.11 | MOLA C |
| ATOM | 487 | O | ALA | A 219 | 27.511 | 24.302 | 29.475 | 1.00 | 50.29 | MOLA O |
| ATOM | 488 | CB | ALA | A 219 | 26.418 | 26.073 | 26.837 | 1.00 | 52.36 | MOLA C |
| ATOM | 489 | N | LYS | A 220 | 26.195 | 26.069 | 29.909 | 1.00 | 51.11 | MOLA N |
| ATOM | 490 | CA | LYS | A 220 | 26.807 | 26.383 | 31.186 | 1.00 | 51.30 | MOLA C |
| ATOM | 491 | C | LYS | A 220 | 26.543 | 25.285 | 32.234 | 1.00 | 51.73 | MOLA C |
| ATOM | 492 | O | LYS | A 220 | 27.381 | 25.004 | 33.101 | 1.00 | 52.28 | MOLA O |
| ATOM | 493 | CB | LYS | A 220 | 26.273 | 27.729 | 31.660 | 1.00 | 53.37 | MOLA C |
| ATOM | 494 | CG | LYS | A 220 | 27.035 | 28.372 | 32.798 | 1.00 | 55.07 | MOLA C |
| ATOM | 495 | CD | LYS | A 220 | 28.112 | 29.313 | 32.283 | 1.00 | 62.88 | MOLA C |
| ATOM | 496 | CE | LYS | A 220 | 27.915 | 30.744 | 32.783 | 1.00 | 72.33 | MOLA C |
| ATOM | 497 | NZ | LYS | A 220 | 27.913 | 30.932 | 34.276 | 1.00 | 72.63 | MOLA N |
| ATOM | 498 | N | ARG | A 221 | 25.375 | 24.667 | 32.178 | 1.00 | 49.24 | MOLA N |
| ATOM | 499 | CA | ARG | A 221 | 25.097 | 23.570 | 33.076 | 1.00 | 50.11 | MOLA C |
| ATOM | 500 | C | ARG | A 221 | 26.095 | 22.418 | 32.827 | 1.00 | 48.63 | MOLA C |
| ATOM | 501 | O | ARG | A 221 | 26.567 | 21.788 | 33.758 | 1.00 | 45.88 | MOLA O |
| ATOM | 502 | CB | ARG | A 221 | 23.646 | 23.113 | 32.885 | 1.00 | 49.01 | MOLA C |
| ATOM | 503 | CG | ARG | A 221 | 23.130 | 22.045 | 33.875 | 1.00 | 52.14 | MOLA C |
| ATOM | 504 | CD | ARG | A 221 | 21.590 | 21.935 | 33.870 | 1.00 | 51.56 | MOLA C |
| ATOM | 505 | NE | ARG | A 221 | 21.100 | 22.224 | 32.524 | 1.00 | 61.41 | MOLA N |
| ATOM | 506 | CZ | ARG | A 221 | 19.931 | 22.784 | 32.219 | 1.00 | 58.92 | MOLA C |
| ATOM | 507 | NH1 | ARG | A 221 | 19.060 | 23.127 | 33.176 | 1.00 | 56.45 | MOLA N |
| ATOM | 508 | NH2 | ARG | A 221 | 19.644 | 23.004 | 30.936 | 1.00 | 53.43 | MOLA N |
| ATOM | 509 | N | THR | A 222 | 26.417 | 22.174 | 31.562 | 1.00 | 50.61 | MOLA N |
| ATOM | 510 | CA | THR | A 222 | 27.329 | 21.110 | 31.165 | 1.00 | 51.68 | MOLA C |
| ATOM | 511 | C | THR | A 222 | 28.777 | 21.359 | 31.630 | 1.00 | 51.68 | MOLA C |
| ATOM | 512 | O | THR | A 222 | 29.463 | 20.429 | 32.036 | 1.00 | 52.32 | MOLA O |
| ATOM | 513 | CB | THR | A 222 | 27.300 | 20.935 | 29.631 | 1.00 | 51.77 | MOLA C |
| ATOM | 514 | CG2 | THR | A 222 | 28.202 | 19.768 | 29.212 | 1.00 | 54.07 | MOLA C |
| ATOM | 515 | OG1 | THR | A 222 | 25.995 | 20.521 | 29.200 | 1.00 | 53.79 | MOLA O |
| TER | 516 | | THR | A 222 | | | | | | |
| ATOM | 517 | N | SER | A 232 | 23.735 | 17.286 | 37.098 | 1.00 | 46.54 | MOLA N |
| ATOM | 518 | CA | SER | A 232 | 22.377 | 17.812 | 37.156 | 1.00 | 45.63 | MOLA C |
| ATOM | 519 | C | SER | A 232 | 21.446 | 16.887 | 37.907 | 1.00 | 43.70 | MOLA C |
| ATOM | 520 | O | SER | A 232 | 20.498 | 17.348 | 38.549 | 1.00 | 43.91 | MOLA O |
| ATOM | 521 | CB | SER | A 232 | 21.864 | 18.062 | 35.749 | 1.00 | 47.49 | MOLA C |
| ATOM | 522 | OG | SER | A 232 | 21.781 | 16.845 | 35.027 | 1.00 | 49.04 | MOLA O |
| TER | 523 | | SER | A 232 | | | | | | |
| ATOM | 524 | N | SER | A 237 | 17.393 | 22.416 | 39.722 | 1.00 | 35.65 | MOLA N |
| ATOM | 525 | CA | SER | A 237 | 17.396 | 23.503 | 38.744 | 1.00 | 35.10 | MOLA C |
| ATOM | 526 | C | SER | A 237 | 16.126 | 24.348 | 38.892 | 1.00 | 36.19 | MOLA C |
| ATOM | 527 | O | SER | A 237 | 14.990 | 23.815 | 38.957 | 1.00 | 32.72 | MOLA O |
| ATOM | 528 | CB | SER | A 237 | 17.465 | 22.898 | 37.352 | 1.00 | 35.72 | MOLA C |
| ATOM | 529 | OG | SER | A 237 | 17.477 | 23.902 | 36.348 | 1.00 | 48.22 | MOLA O |
| ATOM | 530 | N | VAL | A 238 | 16.312 | 25.652 | 39.044 | 1.00 | 34.78 | MOLA N |
| ATOM | 531 | CA | VAL | A 238 | 15.198 | 26.551 | 39.149 | 1.00 | 35.39 | MOLA C |
| ATOM | 532 | C | VAL | A 238 | 15.189 | 27.565 | 38.026 | 1.00 | 33.00 | MOLA C |
| ATOM | 533 | O | VAL | A 238 | 15.975 | 28.514 | 38.002 | 1.00 | 31.05 | MOLA O |
| ATOM | 534 | CB | VAL | A 238 | 15.179 | 27.322 | 40.456 | 1.00 | 35.99 | MOLA C |
| ATOM | 535 | CG1 | VAL | A 238 | 13.919 | 28.102 | 40.510 | 1.00 | 31.83 | MOLA C |
| ATOM | 536 | CG2 | VAL | A 238 | 15.278 | 26.406 | 41.634 | 1.00 | 38.12 | MOLA C |
| ATOM | 537 | N | PHE | A 239 | 14.270 | 27.366 | 37.096 | 1.00 | 31.84 | MOLA N |
| ATOM | 538 | CA | PHE | A 239 | 14.082 | 28.320 | 36.041 | 1.00 | 34.07 | MOLA C |
| ATOM | 539 | C | PHE | A 239 | 12.915 | 29.231 | 36.446 | 1.00 | 34.92 | MOLA C |
| ATOM | 540 | O | PHE | A 239 | 11.845 | 28.761 | 36.807 | 1.00 | 36.29 | MOLA O |
| ATOM | 541 | CB | PHE | A 239 | 13.785 | 27.600 | 34.730 | 1.00 | 33.42 | MOLA C |
| ATOM | 542 | CG | PHE | A 239 | 13.627 | 28.524 | 33.579 | 1.00 | 32.00 | MOLA C |
| ATOM | 543 | CD1 | PHE | A 239 | 12.369 | 29.016 | 33.236 | 1.00 | 41.98 | MOLA C |
| ATOM | 544 | CD2 | PHE | A 239 | 14.724 | 28.874 | 32.805 | 1.00 | 45.78 | MOLA C |
| ATOM | 545 | CE1 | PHE | A 239 | 12.223 | 29.875 | 32.165 | 1.00 | 41.34 | MOLA C |
| ATOM | 546 | CE2 | PHE | A 239 | 14.580 | 29.746 | 31.734 | 1.00 | 43.27 | MOLA C |
| ATOM | 547 | CZ | PHE | A 239 | 13.334 | 30.248 | 31.424 | 1.00 | 38.95 | MOLA C |
| ATOM | 548 | N | SER | A 240 | 13.127 | 30.528 | 36.417 | 1.00 | 35.91 | MOLA N |
| ATOM | 549 | CA | SER | A 240 | 12.075 | 31.472 | 36.752 | 1.00 | 36.72 | MOLA C |
| ATOM | 550 | C | SER | A 240 | 11.823 | 32.411 | 35.571 | 1.00 | 38.46 | MOLA C |
| ATOM | 551 | O | SER | A 240 | 12.775 | 32.824 | 34.893 | 1.00 | 34.30 | MOLA O |
| ATOM | 552 | CB | SER | A 240 | 12.481 | 32.290 | 37.989 | 1.00 | 39.28 | MOLA C |
| ATOM | 553 | OG | SER | A 240 | 12.582 | 31.452 | 39.143 | 1.00 | 41.14 | MOLA O |
| TER | 554 | | SER | A 240 | | | | | | |
| ATOM | 555 | N | LEU | A 263 | 9.883 | 26.977 | 37.462 | 1.00 | 29.70 | MOLA N |
| ATOM | 556 | CA | LEU | A 263 | 9.826 | 25.654 | 36.894 | 1.00 | 31.71 | MOLA C |
| ATOM | 557 | C | LEU | A 263 | 11.032 | 24.937 | 37.443 | 1.00 | 29.65 | MOLA C |
| ATOM | 558 | O | LEU | A 263 | 12.171 | 25.283 | 37.129 | 1.00 | 31.11 | MOLA O |
| ATOM | 559 | CB | LEU | A 263 | 9.874 | 25.768 | 35.362 | 1.00 | 31.71 | MOLA C |

TABLE 9-continued

Novel Eg5 ligand binding site/compound 6 X-ray coordinates. 10 Angstrom shell of the binding pocket. Table 9 discloses residues 110-141, 158-162, 209-222 and 237-240 of SEQ ID NO:1, respectively, in order of appearance.

| | | | | | | | | | | |
|---|---|---|---|---|---|---|---|---|---|---|
| ATOM | 560 | CG | LEU | A 263 | 8.699 | 26.606 | 34.850 | 1.00 | 35.64 | MOLA C |
| ATOM | 561 | CD1 | LEU | A 263 | 8.870 | 27.042 | 33.429 | 1.00 | 40.37 | MOLA C |
| ATOM | 562 | CD2 | LEU | A 263 | 7.436 | 25.809 | 34.990 | 1.00 | 36.52 | MOLA C |
| ATOM | 563 | N | VAL | A 264 | 10.764 | 23.996 | 38.334 | 1.00 | 30.40 | MOLA N |
| ATOM | 564 | CA | VAL | A 264 | 11.788 | 23.356 | 39.137 | 1.00 | 29.81 | MOLA C |
| ATOM | 565 | C | VAL | A 264 | 11.961 | 21.867 | 38.804 | 1.00 | 29.20 | MOLA C |
| ATOM | 566 | O | VAL | A 264 | 11.031 | 21.073 | 38.899 | 1.00 | 29.03 | MOLA O |
| ATOM | 567 | CB | VAL | A 264 | 11.435 | 23.459 | 40.625 | 1.00 | 30.73 | MOLA C |
| ATOM | 568 | CG1 | VAL | A 264 | 12.555 | 22.911 | 41.471 | 1.00 | 33.67 | MOLA C |
| ATOM | 569 | CG2 | VAL | A 264 | 11.102 | 24.836 | 40.993 | 1.00 | 29.78 | MOLA C |
| ATOM | 570 | N | ASP | A 265 | 13.172 | 21.523 | 38.410 | 1.00 | 27.03 | MOLA N |
| ATOM | 571 | CA | ASP | A 265 | 13.591 | 20.184 | 38.074 | 1.00 | 29.09 | MOLA C |
| ATOM | 572 | C | ASP | A 265 | 14.499 | 19.662 | 39.224 | 1.00 | 30.39 | MOLA C |
| ATOM | 573 | O | ASP | A 265 | 15.625 | 20.090 | 39.365 | 1.00 | 33.95 | MOLA O |
| ATOM | 574 | CB | ASP | A 265 | 14.323 | 20.295 | 36.737 | 1.00 | 30.56 | MOLA C |
| ATOM | 575 | CG | ASP | A 265 | 14.853 | 18.981 | 36.246 | 1.00 | 38.02 | MOLA C |
| ATOM | 576 | OD1 | ASP | A 265 | 14.758 | 17.981 | 37.003 | 1.00 | 40.28 | MOLA O |
| ATOM | 577 | OD2 | ASP | A 265 | 15.421 | 18.865 | 35.130 | 1.00 | 50.10 | MOLA O |
| TER | 578 | | ASP | A 265 | | | | | | |
| END | | | | | | | | | | |

Table 10. Novel Eg5 ligand binding site/compound 3 X-ray coordinates. Complete coordinates of the entire motor domain of Eg5. Table 10 discloses residues 16-55, 61-270, 285-365, 16-55, 61-270 and 285-365 of SEQ ID NO: 1, respectively, in order of appearance.

TABLE 10

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1 | N | GLY | A 16 | −8.471 | 21.615 | 49.182 | 1.00 | 77.82 | MOLA N |
| ATOM | 2 | CA | GLY | A 16 | −7.567 | 20.521 | 48.716 | 1.00 | 76.09 | MOLA C |
| ATOM | 3 | C | GLY | A 16 | −6.658 | 20.937 | 47.577 | 1.00 | 75.50 | MOLA C |
| ATOM | 4 | O | GLY | A 16 | −5.531 | 21.406 | 47.801 | 1.00 | 74.88 | MOLA O |
| ATOM | 5 | N | LYS | A 17 | −7.180 | 20.787 | 46.361 | 1.00 | 74.32 | MOLA N |
| ATOM | 6 | CA | LYS | A 17 | −6.444 | 20.986 | 45.105 | 1.00 | 72.36 | MOLA C |
| ATOM | 7 | CB | LYS | A 17 | −7.329 | 20.566 | 43.920 | 1.00 | 72.22 | MOLA C |
| ATOM | 8 | CG | LYS | A 17 | −8.657 | 21.320 | 43.801 | 1.00 | 72.93 | MOLA C |
| ATOM | 9 | CD | LYS | A 17 | −8.554 | 22.600 | 42.962 | 1.00 | 67.69 | MOLA C |
| ATOM | 10 | CE | LYS | A 17 | −8.619 | 22.306 | 41.458 | 1.00 | 64.89 | MOLA C |
| ATOM | 11 | NZ | LYS | A 17 | −7.589 | 21.326 | 41.025 | 1.00 | 51.00 | MOLA N |
| ATOM | 12 | C | LYS | A 17 | −5.842 | 22.374 | 44.841 | 1.00 | 71.34 | MOLA C |
| ATOM | 13 | O | LYS | A 17 | −5.897 | 22.872 | 43.723 | 1.00 | 72.49 | MOLA O |
| ATOM | 14 | N | ASN | A 18 | −5.265 | 23.000 | 45.856 | 1.00 | 68.95 | MOLA N |
| ATOM | 15 | CA | ASN | A 18 | −4.524 | 24.218 | 45.629 | 1.00 | 67.26 | MOLA C |
| ATOM | 16 | CB | ASN | A 18 | −4.423 | 25.023 | 46.919 | 1.00 | 68.03 | MOLA C |
| ATOM | 17 | CG | ASN | A 18 | −4.110 | 26.487 | 46.669 | 1.00 | 72.15 | MOLA C |
| ATOM | 18 | OD1 | ASN | A 18 | −3.610 | 27.186 | 47.548 | 1.00 | 75.80 | MOLA O |
| ATOM | 19 | ND2 | ASN | A 18 | −4.410 | 26.961 | 45.463 | 1.00 | 83.36 | MOLA N |
| ATOM | 20 | C | ASN | A 18 | −3.147 | 23.768 | 45.182 | 1.00 | 66.05 | MOLA C |
| ATOM | 21 | O | ASN | A 18 | −2.274 | 24.564 | 44.818 | 1.00 | 66.62 | MOLA O |
| ATOM | 22 | N | ILE | A 19 | −2.982 | 22.450 | 45.217 | 1.00 | 64.39 | MOLA N |
| ATOM | 23 | CA | ILE | A 19 | −1.723 | 21.767 | 44.972 | 1.00 | 61.50 | MOLA C |
| ATOM | 24 | CB | ILE | A 19 | −1.061 | 21.360 | 46.305 | 1.00 | 61.41 | MOLA C |
| ATOM | 25 | CG1 | ILE | A 19 | −0.850 | 22.587 | 47.226 | 1.00 | 61.94 | MOLA C |
| ATOM | 26 | CD1 | ILE | A 19 | −2.110 | 23.013 | 48.140 | 1.00 | 38.19 | MOLA C |
| ATOM | 27 | CG2 | ILE | A 19 | 0.235 | 20.573 | 46.063 | 1.00 | 64.61 | MOLA C |
| ATOM | 28 | C | ILE | A 19 | −2.091 | 20.509 | 44.219 | 1.00 | 59.05 | MOLA C |
| ATOM | 29 | O | ILE | A 19 | −3.062 | 19.839 | 44.573 | 1.00 | 58.25 | MOLA O |
| ATOM | 30 | N | GLN | A 20 | −1.347 | 20.196 | 43.169 | 1.00 | 57.28 | MOLA N |
| ATOM | 31 | CA | GLN | A 20 | −1.667 | 19.025 | 42.355 | 1.00 | 56.60 | MOLA C |
| ATOM | 32 | CB | GLN | A 20 | −2.276 | 19.449 | 41.015 | 1.00 | 57.33 | MOLA C |
| ATOM | 33 | CG | GLN | A 20 | −3.714 | 19.958 | 41.107 | 1.00 | 58.31 | MOLA C |
| ATOM | 34 | CD | GLN | A 20 | −4.731 | 18.873 | 40.823 | 1.00 | 63.31 | MOLA C |
| ATOM | 35 | OE1 | GLN | A 20 | −4.942 | 18.500 | 39.671 | 1.00 | 70.90 | MOLA O |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 36 | NE2 | GLN | A 20 | −5.380 | 18.370 | 41.867 | 1.00 | 66.67 | MOLA N |
| ATOM | 37 | C | GLN | A 20 | −0.461 | 18.120 | 42.138 | 1.00 | 55.48 | MOLA C |
| ATOM | 38 | O | GLN | A 20 | 0.639 | 18.594 | 41.812 | 1.00 | 56.18 | MOLA O |
| ATOM | 39 | N | VAL | A 21 | −0.673 | 16.816 | 42.328 | 1.00 | 52.76 | MOLA N |
| ATOM | 40 | CA | VAL | A 21 | 0.388 | 15.822 | 42.171 | 1.00 | 48.69 | MOLA C |
| ATOM | 41 | CB | VAL | A 21 | 0.547 | 14.947 | 43.407 | 1.00 | 47.76 | MOLA C |
| ATOM | 42 | CG1 | VAL | A 21 | 1.618 | 13.895 | 43.157 | 1.00 | 46.50 | MOLA C |
| ATOM | 43 | CG2 | VAL | A 21 | 0.905 | 15.776 | 44.613 | 1.00 | 46.37 | MOLA C |
| ATOM | 44 | C | VAL | A 21 | 0.056 | 14.872 | 41.054 | 1.00 | 46.83 | MOLA C |
| ATOM | 45 | O | VAL | A 21 | −0.999 | 14.251 | 41.051 | 1.00 | 48.81 | MOLA O |
| ATOM | 46 | N | VAL | A 22 | 0.963 | 14.735 | 40.109 | 1.00 | 44.40 | MOLA N |
| ATOM | 47 | CA | VAL | A 22 | 0.730 | 13.787 | 39.049 | 1.00 | 42.13 | MOLA C |
| ATOM | 48 | CB | VAL | A 22 | 0.348 | 14.471 | 37.770 | 1.00 | 42.26 | MOLA C |
| ATOM | 49 | CG1 | VAL | A 22 | −0.989 | 15.140 | 37.949 | 1.00 | 39.66 | MOLA C |
| ATOM | 50 | CG2 | VAL | A 22 | 1.469 | 15.458 | 37.375 | 1.00 | 37.67 | MOLA C |
| ATOM | 51 | C | VAL | A 22 | 1.958 | 12.963 | 38.762 | 1.00 | 42.29 | MOLA C |
| ATOM | 52 | O | VAL | A 22 | 3.079 | 13.291 | 39.147 | 1.00 | 41.62 | MOLA O |
| ATOM | 53 | N | VAL | A 23 | 1.722 | 11.881 | 38.053 | 1.00 | 41.93 | MOLA N |
| ATOM | 54 | CA | VAL | A 23 | 2.764 | 10.996 | 37.698 | 1.00 | 41.48 | MOLA C |
| ATOM | 55 | CB | VAL | A 23 | 2.606 | 9.658 | 38.435 | 1.00 | 42.90 | MOLA C |
| ATOM | 56 | CG1 | VAL | A 23 | 3.565 | 8.579 | 37.887 | 1.00 | 40.60 | MOLA C |
| ATOM | 57 | CG2 | VAL | A 23 | 2.828 | 9.877 | 39.911 | 1.00 | 43.27 | MOLA C |
| ATOM | 58 | C | VAL | A 23 | 2.629 | 10.809 | 36.219 | 1.00 | 41.72 | MOLA C |
| ATOM | 59 | O | VAL | A 23 | 1.517 | 10.660 | 35.692 | 1.00 | 42.44 | MOLA O |
| ATOM | 60 | N | ARG | A 24 | 3.779 | 10.884 | 35.554 | 1.00 | 41.45 | MOLA N |
| ATOM | 61 | CA | ARG | A 24 | 3.925 | 10.556 | 34.144 | 1.00 | 39.24 | MOLA C |
| ATOM | 62 | CB | ARG | A 24 | 4.674 | 11.651 | 33.404 | 1.00 | 34.62 | MOLA C |
| ATOM | 63 | CG | ARG | A 24 | 4.838 | 11.385 | 31.937 | 1.00 | 36.57 | MOLA C |
| ATOM | 64 | CD | ARG | A 24 | 5.390 | 12.618 | 31.272 | 1.00 | 28.99 | MOLA C |
| ATOM | 65 | NE | ARG | A 24 | 5.350 | 12.611 | 29.822 | 1.00 | 15.29 | MOLA N |
| ATOM | 66 | CZ | ARG | A 24 | 5.857 | 13.611 | 29.118 | 1.00 | 22.21 | MOLA C |
| ATOM | 67 | NH1 | ARG | A 24 | 6.409 | 14.615 | 29.766 | 1.00 | 33.59 | MOLA N |
| ATOM | 68 | NH2 | ARG | A 24 | 5.813 | 13.636 | 27.794 | 1.00 | 17.49 | MOLA N |
| ATOM | 69 | C | ARG | A 24 | 4.796 | 9.345 | 34.220 | 1.00 | 39.66 | MOLA C |
| ATOM | 70 | O | ARG | A 24 | 5.578 | 9.223 | 35.185 | 1.00 | 39.26 | MOLA O |
| ATOM | 71 | N | CYS | A 25 | 4.637 | 8.445 | 33.250 | 1.00 | 38.37 | MOLA N |
| ATOM | 72 | CA | CYS | A 25 | 5.471 | 7.256 | 33.149 | 1.00 | 39.02 | MOLA C |
| ATOM | 73 | CB | CYS | A 25 | 4.679 | 5.997 | 33.497 | 1.00 | 37.76 | MOLA C |
| ATOM | 74 | SG | CYS | A 25 | 5.521 | 4.466 | 33.019 | 1.00 | 39.40 | MOLA S |
| ATOM | 75 | C | CYS | A 25 | 6.018 | 7.161 | 31.735 | 1.00 | 40.56 | MOLA C |
| ATOM | 76 | O | CYS | A 25 | 5.255 | 7.148 | 30.761 | 1.00 | 41.64 | MOLA O |
| ATOM | 77 | N | ARG | A 26 | 7.334 | 7.101 | 31.602 | 1.00 | 40.83 | MOLA N |
| ATOM | 78 | CA | ARG | A 26 | 7.877 | 7.097 | 30.257 | 1.00 | 43.11 | MOLA C |
| ATOM | 79 | CB | ARG | A 26 | 9.334 | 7.554 | 30.207 | 1.00 | 41.68 | MOLA C |
| ATOM | 80 | CG | ARG | A 26 | 10.330 | 6.637 | 30.913 | 1.00 | 38.20 | MOLA C |
| ATOM | 81 | CD | ARG | A 26 | 11.762 | 6.897 | 30.405 | 1.00 | 37.93 | MOLA C |
| ATOM | 82 | NE | ARG | A 26 | 12.771 | 6.120 | 31.125 | 1.00 | 38.00 | MOLA N |
| ATOM | 83 | CZ | ARG | A 26 | 12.783 | 4.789 | 31.208 | 1.00 | 47.53 | MOLA C |
| ATOM | 84 | NH1 | ARG | A 26 | 11.827 | 4.069 | 30.631 | 1.00 | 56.89 | MOLA N |
| ATOM | 85 | NH2 | ARG | A 26 | 13.737 | 4.168 | 31.887 | 1.00 | 34.54 | MOLA N |
| ATOM | 86 | C | ARG | A 26 | 7.742 | 5.687 | 29.718 | 1.00 | 48.09 | MOLA C |
| ATOM | 87 | O | ARG | A 26 | 7.370 | 4.768 | 30.472 | 1.00 | 50.71 | MOLA O |
| ATOM | 88 | N | PRO | A 27 | 7.971 | 5.533 | 28.400 | 1.00 | 47.89 | MOLA N |
| ATOM | 89 | CA | PRO | A 27 | 8.103 | 4.306 | 27.631 | 1.00 | 46.49 | MOLA C |
| ATOM | 90 | CB | PRO | A 27 | 8.080 | 4.821 | 26.184 | 1.00 | 47.23 | MOLA C |
| ATOM | 91 | CG | PRO | A 27 | 7.454 | 6.222 | 26.263 | 1.00 | 47.67 | MOLA C |
| ATOM | 92 | CD | PRO | A 27 | 8.008 | 6.730 | 27.537 | 1.00 | 49.34 | MOLA C |
| ATOM | 93 | C | PRO | A 27 | 9.438 | 3.618 | 27.868 | 1.00 | 46.83 | MOLA C |
| ATOM | 94 | O | PRO | A 27 | 10.387 | 4.260 | 28.288 | 1.00 | 48.19 | MOLA O |
| ATOM | 95 | N | PHE | A 28 | 9.524 | 2.325 | 27.576 | 1.00 | 46.87 | MOLA N |
| ATOM | 96 | CA | PHE | A 28 | 10.814 | 1.621 | 27.566 | 1.00 | 48.92 | MOLA C |
| ATOM | 97 | CB | PHE | A 28 | 10.639 | 0.187 | 27.025 | 1.00 | 48.50 | MOLA C |
| ATOM | 98 | CG | PHE | A 28 | 9.996 | −0.799 | 27.987 | 1.00 | 54.11 | MOLA C |
| ATOM | 99 | CD1 | PHE | A 28 | 8.616 | −0.797 | 28.210 | 1.00 | 53.36 | MOLA C |
| ATOM | 100 | CE1 | PHE | A 28 | 8.029 | −1.735 | 29.061 | 1.00 | 48.65 | MOLA C |
| ATOM | 101 | CZ | PHE | A 28 | 8.820 | −2.704 | 29.689 | 1.00 | 40.70 | MOLA C |
| ATOM | 102 | CE2 | PHE | A 28 | 10.180 | −2.732 | 29.469 | 1.00 | 44.53 | MOLA C |
| ATOM | 103 | CD2 | PHE | A 28 | 10.770 | −1.786 | 28.610 | 1.00 | 56.83 | MOLA C |
| ATOM | 104 | C | PHE | A 28 | 11.892 | 2.308 | 26.678 | 1.00 | 48.52 | MOLA C |
| ATOM | 105 | O | PHE | A 28 | 11.573 | 3.078 | 25.770 | 1.00 | 48.35 | MOLA O |
| ATOM | 106 | N | ASN | A 29 | 13.169 | 2.017 | 26.937 | 1.00 | 48.85 | MOLA N |
| ATOM | 107 | CA | ASN | A 29 | 14.253 | 2.345 | 25.982 | 1.00 | 48.47 | MOLA C |
| ATOM | 108 | CB | ASN | A 29 | 15.223 | 3.353 | 26.551 | 1.00 | 46.09 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 109 | CG | ASN | A 29 | 15.746 | 2.920 | 27.856 | 1.00 | 39.95 | MOLA C |
| ATOM | 110 | OD1 | ASN | A 29 | 15.349 | 1.874 | 28.357 | 1.00 | 58.59 | MOLA O |
| ATOM | 111 | ND2 | ASN | A 29 | 16.606 | 3.708 | 28.448 | 1.00 | 42.77 | MOLA N |
| ATOM | 112 | C | ASN | A 29 | 15.026 | 1.069 | 25.671 | 1.00 | 50.04 | MOLA C |
| ATOM | 113 | O | ASN | A 29 | 14.761 | 0.018 | 26.264 | 1.00 | 49.87 | MOLA O |
| ATOM | 114 | N | LEU | A 30 | 16.006 | 1.163 | 24.780 | 1.00 | 49.53 | MOLA N |
| ATOM | 115 | CA | LEU | A 30 | 16.701 | −0.034 | 24.347 | 1.00 | 50.23 | MOLA C |
| ATOM | 116 | CB | LEU | A 30 | 17.758 | 0.287 | 23.309 | 1.00 | 50.24 | MOLA C |
| ATOM | 117 | CG | LEU | A 30 | 16.962 | 0.487 | 22.016 | 1.00 | 58.12 | MOLA C |
| ATOM | 118 | CD1 | LEU | A 30 | 15.960 | 1.623 | 22.191 | 1.00 | 63.47 | MOLA C |
| ATOM | 119 | CD2 | LEU | A 30 | 17.872 | 0.712 | 20.801 | 1.00 | 67.93 | MOLA C |
| ATOM | 120 | C | LEU | A 30 | 17.246 | −0.892 | 25.474 | 1.00 | 50.37 | MOLA C |
| ATOM | 121 | O | LEU | A 30 | 16.800 | −2.032 | 25.630 | 1.00 | 51.27 | MOLA O |
| ATOM | 122 | N | ALA | A 31 | 18.180 | −0.375 | 26.265 | 1.00 | 48.94 | MOLA N |
| ATOM | 123 | CA | ALA | A 31 | 18.724 | −1.181 | 27.362 | 1.00 | 50.12 | MOLA C |
| ATOM | 124 | CB | ALA | A 31 | 19.589 | −0.323 | 28.304 | 1.00 | 52.18 | MOLA C |
| ATOM | 125 | C | ALA | A 31 | 17.629 | −1.938 | 28.143 | 1.00 | 49.13 | MOLA C |
| ATOM | 126 | O | ALA | A 31 | 17.833 | −3.069 | 28.616 | 1.00 | 47.46 | MOLA O |
| ATOM | 127 | N | GLU | A 32 | 16.469 | −1.307 | 28.253 | 1.00 | 49.03 | MOLA N |
| ATOM | 128 | CA | GLU | A 32 | 15.340 | −1.898 | 28.944 | 1.00 | 50.17 | MOLA C |
| ATOM | 129 | CB | GLU | A 32 | 14.277 | −0.839 | 29.190 | 1.00 | 49.19 | MOLA C |
| ATOM | 130 | CG | GLU | A 32 | 14.682 | 0.126 | 30.294 | 1.00 | 46.85 | MOLA C |
| ATOM | 131 | CD | GLU | A 32 | 13.611 | 1.161 | 30.555 | 1.00 | 48.85 | MOLA C |
| ATOM | 132 | OE1 | GLU | A 32 | 13.075 | 1.716 | 29.566 | 1.00 | 46.08 | MOLA O |
| ATOM | 133 | OE2 | GLU | A 32 | 13.301 | 1.415 | 31.743 | 1.00 | 39.40 | MOLA O |
| ATOM | 134 | C | GLU | A 32 | 14.774 | −3.132 | 28.234 | 1.00 | 51.01 | MOLA C |
| ATOM | 135 | O | GLU | A 32 | 14.580 | −4.162 | 28.874 | 1.00 | 51.02 | MOLA O |
| ATOM | 136 | N | ARG | A 33 | 14.522 | −3.034 | 26.927 | 1.00 | 54.00 | MOLA N |
| ATOM | 137 | CA | ARG | A 33 | 14.087 | −4.191 | 26.105 | 1.00 | 56.58 | MOLA C |
| ATOM | 138 | CB | ARG | A 33 | 13.654 | −3.790 | 24.689 | 1.00 | 54.23 | MOLA C |
| ATOM | 139 | CG | ARG | A 33 | 12.620 | −2.730 | 24.557 | 1.00 | 51.14 | MOLA C |
| ATOM | 140 | CD | ARG | A 33 | 11.267 | −3.170 | 24.995 | 1.00 | 50.07 | MOLA C |
| ATOM | 141 | NE | ARG | A 33 | 10.280 | −2.365 | 24.280 | 1.00 | 47.34 | MOLA N |
| ATOM | 142 | CZ | ARG | A 33 | 9.016 | −2.206 | 24.652 | 1.00 | 39.67 | MOLA C |
| ATOM | 143 | NH1 | ARG | A 33 | 8.550 | −2.786 | 25.750 | 1.00 | 40.71 | MOLA N |
| ATOM | 144 | NH2 | ARG | A 33 | 8.216 | −1.454 | 23.917 | 1.00 | 48.89 | MOLA N |
| ATOM | 145 | C | ARG | A 33 | 15.225 | −5.183 | 25.910 | 1.00 | 59.38 | MOLA C |
| ATOM | 146 | O | ARG | A 33 | 15.025 | −6.404 | 25.969 | 1.00 | 61.15 | MOLA O |
| ATOM | 147 | N | LYS | A 34 | 16.410 | −4.636 | 25.642 | 1.00 | 60.88 | MOLA N |
| ATOM | 148 | CA | LYS | A 34 | 17.582 | −5.422 | 25.299 | 1.00 | 60.70 | MOLA C |
| ATOM | 149 | CB | LYS | A 34 | 18.770 | −4.500 | 25.051 | 1.00 | 59.84 | MOLA C |
| ATOM | 150 | CG | LYS | A 34 | 19.818 | −5.053 | 24.105 | 1.00 | 63.66 | MOLA C |
| ATOM | 151 | CD | LYS | A 34 | 20.936 | −5.764 | 24.863 | 1.00 | 65.68 | MOLA C |
| ATOM | 152 | CE | LYS | A 34 | 22.156 | −5.976 | 23.983 | 1.00 | 59.93 | MOLA C |
| ATOM | 153 | NZ | LYS | A 34 | 23.326 | −6.272 | 24.839 | 1.00 | 58.81 | MOLA N |
| ATOM | 154 | C | LYS | A 34 | 17.882 | −6.452 | 26.374 | 1.00 | 60.03 | MOLA C |
| ATOM | 155 | O | LYS | A 34 | 18.662 | −7.364 | 26.163 | 1.00 | 62.74 | MOLA O |
| ATOM | 156 | N | ALA | A 35 | 17.263 | −6.317 | 27.530 | 1.00 | 58.88 | MOLA N |
| ATOM | 157 | CA | ALA | A 35 | 17.391 | −7.353 | 28.531 | 1.00 | 59.79 | MOLA C |
| ATOM | 158 | CB | ALA | A 35 | 18.291 | −6.900 | 29.668 | 1.00 | 59.51 | MOLA C |
| ATOM | 159 | C | ALA | A 35 | 15.983 | −7.725 | 29.007 | 1.00 | 60.67 | MOLA C |
| ATOM | 160 | O | ALA | A 35 | 15.770 | −8.157 | 30.152 | 1.00 | 58.68 | MOLA O |
| ATOM | 161 | N | SER | A 36 | 15.031 | −7.546 | 28.088 | 1.00 | 61.41 | MOLA N |
| ATOM | 162 | CA | SER | A 36 | 13.621 | −7.868 | 28.299 | 1.00 | 62.96 | MOLA C |
| ATOM | 163 | CB | SER | A 36 | 13.316 | −9.326 | 27.869 | 1.00 | 65.09 | MOLA C |
| ATOM | 164 | OG | SER | A 36 | 11.954 | −9.711 | 28.104 | 1.00 | 66.82 | MOLA O |
| ATOM | 165 | C | SER | A 36 | 13.189 | −7.611 | 29.740 | 1.00 | 62.42 | MOLA C |
| ATOM | 166 | O | SER | A 36 | 12.786 | −8.529 | 30.457 | 1.00 | 63.15 | MOLA O |
| ATOM | 167 | N | ALA | A 37 | 13.281 | −6.361 | 30.173 | 1.00 | 60.74 | MOLA N |
| ATOM | 168 | CA | ALA | A 37 | 12.768 | −6.030 | 31.479 | 1.00 | 59.26 | MOLA C |
| ATOM | 169 | CB | ALA | A 37 | 13.158 | −4.623 | 31.853 | 1.00 | 59.53 | MOLA C |
| ATOM | 170 | C | ALA | A 37 | 11.247 | −6.200 | 31.362 | 1.00 | 58.34 | MOLA C |
| ATOM | 171 | O | ALA | A 37 | 10.700 | −6.172 | 30.248 | 1.00 | 57.94 | MOLA O |
| ATOM | 172 | N | HIS | A 38 | 10.568 | −6.408 | 32.488 | 1.00 | 56.62 | MOLA N |
| ATOM | 173 | CA | HIS | A 38 | 9.127 | −6.649 | 32.453 | 1.00 | 56.19 | MOLA C |
| ATOM | 174 | CB | HIS | A 38 | 8.749 | −7.864 | 33.314 | 1.00 | 56.82 | MOLA C |
| ATOM | 175 | CG | HIS | A 38 | 9.521 | −9.101 | 32.983 | 1.00 | 57.57 | MOLA C |
| ATOM | 176 | ND1 | HIS | A 38 | 9.277 | −9.850 | 31.852 | 1.00 | 60.37 | MOLA N |
| ATOM | 177 | CE1 | HIS | A 38 | 10.112 | −10.873 | 31.817 | 1.00 | 64.35 | MOLA C |
| ATOM | 178 | NE2 | HIS | A 38 | 10.889 | −10.815 | 32.884 | 1.00 | 61.85 | MOLA N |
| ATOM | 179 | CD2 | HIS | A 38 | 10.536 | −9.718 | 33.633 | 1.00 | 62.14 | MOLA C |
| ATOM | 180 | C | HIS | A 38 | 8.343 | −5.440 | 32.919 | 1.00 | 54.23 | MOLA C |
| ATOM | 181 | O | HIS | A 38 | 8.510 | −4.976 | 34.050 | 1.00 | 53.32 | MOLA O |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 182 | N | SER | A 39 | 7.470 | −4.923 | 32.071 | 1.00 | 52.05 | MOLA N |
| ATOM | 183 | CA | SER | A 39 | 6.682 | −3.815 | 32.540 | 1.00 | 52.52 | MOLA C |
| ATOM | 184 | CB | SER | A 39 | 5.600 | −3.419 | 31.561 | 1.00 | 50.94 | MOLA C |
| ATOM | 185 | OG | SER | A 39 | 4.710 | −2.553 | 32.229 | 1.00 | 54.43 | MOLA O |
| ATOM | 186 | C | SER | A 39 | 6.070 | −4.247 | 33.859 | 1.00 | 52.70 | MOLA C |
| ATOM | 187 | O | SER | A 39 | 5.555 | −5.359 | 33.986 | 1.00 | 55.01 | MOLA O |
| ATOM | 188 | N | ILE | A 40 | 6.161 | −3.392 | 34.862 | 1.00 | 51.44 | MOLA N |
| ATOM | 189 | CA | ILE | A 40 | 5.583 | −3.730 | 36.147 | 1.00 | 49.51 | MOLA C |
| ATOM | 190 | CB | ILE | A 40 | 6.657 | −3.910 | 37.215 | 1.00 | 50.19 | MOLA C |
| ATOM | 191 | CG1 | ILE | A 40 | 7.735 | −2.839 | 37.044 | 1.00 | 42.57 | MOLA C |
| ATOM | 192 | CD1 | ILE | A 40 | 8.758 | −2.922 | 38.105 | 1.00 | 39.45 | MOLA C |
| ATOM | 193 | CG2 | ILE | A 40 | 7.222 | −5.341 | 37.169 | 1.00 | 46.24 | MOLA C |
| ATOM | 194 | C | ILE | A 40 | 4.656 | −2.638 | 36.616 | 1.00 | 50.32 | MOLA C |
| ATOM | 195 | O | ILE | A 40 | 4.295 | −2.595 | 37.796 | 1.00 | 50.69 | MOLA O |
| ATOM | 196 | N | VAL | A 41 | 4.269 | −1.760 | 35.693 | 1.00 | 49.54 | MOLA N |
| ATOM | 197 | CA | VAL | A 41 | 3.480 | −0.589 | 36.022 | 1.00 | 46.39 | MOLA C |
| ATOM | 198 | CB | VAL | A 41 | 4.336 | 0.705 | 35.826 | 1.00 | 46.01 | MOLA C |
| ATOM | 199 | CG1 | VAL | A 41 | 3.539 | 1.950 | 36.135 | 1.00 | 37.82 | MOLA C |
| ATOM | 200 | CG2 | VAL | A 41 | 5.574 | 0.670 | 36.687 | 1.00 | 40.14 | MOLA C |
| ATOM | 201 | C | VAL | A 41 | 2.293 | −0.577 | 35.086 | 1.00 | 48.20 | MOLA C |
| ATOM | 202 | O | VAL | A 41 | 2.471 | −0.520 | 33.884 | 1.00 | 49.58 | MOLA O |
| ATOM | 203 | N | GLU | A 42 | 1.084 | −0.668 | 35.611 | 1.00 | 51.52 | MOLA N |
| ATOM | 204 | CA | GLU | A 42 | −0.098 | −0.526 | 34.765 | 1.00 | 54.45 | MOLA C |
| ATOM | 205 | CB | GLU | A 42 | −1.089 | −1.706 | 34.969 | 1.00 | 54.37 | MOLA C |
| ATOM | 206 | CG | GLU | A 42 | −2.403 | −1.689 | 34.078 | 1.00 | 58.48 | MOLA C |
| ATOM | 207 | CD | GLU | A 42 | −2.324 | −2.523 | 32.750 | 1.00 | 79.48 | MOLA C |
| ATOM | 208 | OE1 | GLU | A 42 | −1.863 | −3.695 | 32.781 | 1.00 | 83.88 | MOLA O |
| ATOM | 209 | OE2 | GLU | A 42 | −2.754 | −2.020 | 31.674 | 1.00 | 68.94 | MOLA O |
| ATOM | 210 | C | GLU | A 42 | −0.695 | 0.802 | 35.195 | 1.00 | 56.50 | MOLA C |
| ATOM | 211 | O | GLU | A 42 | −0.943 | 1.006 | 36.384 | 1.00 | 57.21 | MOLA O |
| ATOM | 212 | N | CYS | A 43 | −0.894 | 1.725 | 34.257 | 1.00 | 59.94 | MOLA N |
| ATOM | 213 | CA | CYS | A 43 | −1.420 | 3.063 | 34.615 | 1.00 | 62.54 | MOLA C |
| ATOM | 214 | CB | CYS | A 43 | −0.639 | 4.169 | 33.905 | 1.00 | 62.23 | MOLA C |
| ATOM | 215 | SG | CYS | A 43 | −0.933 | 4.649 | 34.659 | 1.00 | 69.01 | MOLA S |
| ATOM | 216 | C | CYS | A 43 | −2.868 | 3.248 | 34.249 | 1.00 | 62.74 | MOLA C |
| ATOM | 217 | O | CYS | A 43 | −3.264 | 2.898 | 33.149 | 1.00 | 63.55 | MOLA O |
| ATOM | 218 | N | ASP | A 44 | −3.658 | 3.820 | 35.151 | 1.00 | 63.94 | MOLA N |
| ATOM | 219 | CA | ASP | A 44 | −5.035 | 4.183 | 34.788 | 1.00 | 66.05 | MOLA C |
| ATOM | 220 | CB | ASP | A 44 | −6.092 | 3.537 | 35.696 | 1.00 | 68.12 | MOLA C |
| ATOM | 221 | CG | ASP | A 44 | −7.000 | 2.557 | 34.930 | 1.00 | 76.95 | MOLA C |
| ATOM | 222 | OD1 | ASP | A 44 | −6.918 | 2.489 | 33.670 | 1.00 | 88.54 | MOLA O |
| ATOM | 223 | OD2 | ASP | A 44 | −7.804 | 1.866 | 35.592 | 1.00 | 88.42 | MOLA O |
| ATOM | 224 | C | ASP | A 44 | −5.256 | 5.674 | 34.696 | 1.00 | 63.44 | MOLA C |
| ATOM | 225 | O | ASP | A 44 | −5.430 | 6.341 | 35.709 | 1.00 | 61.99 | MOLA O |
| ATOM | 226 | N | PRO | A 45 | −5.282 | 6.192 | 33.465 | 1.00 | 62.56 | MOLA N |
| ATOM | 227 | CA | PRO | A 45 | −5.450 | 7.610 | 33.271 | 1.00 | 63.47 | MOLA C |
| ATOM | 228 | CB | PRO | A 45 | −5.346 | 7.775 | 31.755 | 1.00 | 61.36 | MOLA C |
| ATOM | 229 | CG | PRO | A 45 | −5.716 | 6.485 | 31.206 | 1.00 | 63.16 | MOLA C |
| ATOM | 230 | CD | PRO | A 45 | −5.223 | 5.464 | 32.193 | 1.00 | 62.39 | MOLA C |
| ATOM | 231 | C | PRO | A 45 | −6.828 | 7.987 | 33.817 | 1.00 | 65.68 | MOLA C |
| ATOM | 232 | O | PRO | A 45 | −6.910 | 8.826 | 34.722 | 1.00 | 66.72 | MOLA O |
| ATOM | 233 | N | VAL | A 46 | −7.887 | 7.339 | 33.317 | 1.00 | 66.91 | MOLA N |
| ATOM | 234 | CA | VAL | A 46 | −9.236 | 7.530 | 33.865 | 1.00 | 67.23 | MOLA C |
| ATOM | 235 | CB | VAL | A 46 | −10.337 | 6.842 | 33.019 | 1.00 | 66.95 | MOLA C |
| ATOM | 236 | CG1 | VAL | A 46 | −11.390 | 6.162 | 33.918 | 1.00 | 59.15 | MOLA C |
| ATOM | 237 | CG2 | VAL | A 46 | −10.970 | 7.862 | 32.101 | 1.00 | 65.96 | MOLA C |
| ATOM | 238 | C | VAL | A 46 | −9.361 | 7.130 | 35.346 | 1.00 | 68.79 | MOLA C |
| ATOM | 239 | O | VAL | A 46 | −9.736 | 7.954 | 36.185 | 1.00 | 68.23 | MOLA O |
| ATOM | 240 | N | ARG | A 47 | −9.052 | 5.885 | 35.690 | 1.00 | 69.64 | MOLA N |
| ATOM | 241 | CA | ARG | A 47 | −9.217 | 5.522 | 37.090 | 1.00 | 70.77 | MOLA C |
| ATOM | 242 | CB | ARG | A 47 | −9.113 | 4.012 | 37.332 | 1.00 | 71.43 | MOLA C |
| ATOM | 243 | CG | ARG | A 47 | −10.430 | 3.296 | 37.065 | 1.00 | 72.96 | MOLA C |
| ATOM | 244 | CD | ARG | A 47 | −10.592 | 2.003 | 37.856 | 1.00 | 78.84 | MOLA C |
| ATOM | 245 | NE | ARG | A 47 | −10.315 | 2.134 | 39.290 | 1.00 | 82.91 | MOLA N |
| ATOM | 246 | CZ | ARG | A 47 | −11.010 | 2.884 | 40.146 | 1.00 | 83.41 | MOLA C |
| ATOM | 247 | NH1 | ARG | A 47 | −12.021 | 3.637 | 39.728 | 1.00 | 86.15 | MOLA N |
| ATOM | 248 | NH2 | ARG | A 47 | 10.674 | 2.902 | 41.429 | 1.00 | 73.39 | MOLA N |
| ATOM | 249 | C | ARG | A 47 | −8.282 | 6.320 | 37.986 | 1.00 | 70.60 | MOLA C |
| ATOM | 250 | O | ARG | A 47 | −8.221 | 6.076 | 39.192 | 1.00 | 71.12 | MOLA O |
| ATOM | 251 | N | LYS | A 48 | −7.586 | 7.287 | 37.368 | 1.00 | 70.07 | MOLA N |
| ATOM | 252 | CA | LYS | A 48 | −6.656 | 8.235 | 38.026 | 1.00 | 67.87 | MOLA C |
| ATOM | 253 | CB | LYS | A 48 | −7.426 | 9.388 | 38.677 | 1.00 | 67.99 | MOLA C |
| ATOM | 254 | CG | LYS | A 48 | −7.820 | 10.508 | 37.730 | 1.00 | 68.95 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 255 | CD | LYS | A 48 | −7.904 | 11.815 | 38.500 | 1.00 | 75.05 | MOLA C |
| ATOM | 256 | CE | LYS | A 48 | −8.474 | 11.600 | 39.905 | 1.00 | 78.24 | MOLA C |
| ATOM | 257 | NZ | LYS | A 48 | −8.056 | 12.669 | 40.853 | 1.00 | 82.36 | MOLA N |
| ATOM | 258 | C | LYS | A 48 | −5.685 | 7.652 | 39.055 | 1.00 | 66.38 | MOLA C |
| ATOM | 259 | O | LYS | A 48 | −5.448 | 8.269 | 40.108 | 1.00 | 66.91 | MOLA O |
| ATOM | 260 | N | GLU | A 49 | −5.106 | 6.494 | 38.734 | 1.00 | 64.44 | MOLA N |
| ATOM | 261 | CA | GLU | A 49 | −4.249 | 5.756 | 39.662 | 1.00 | 62.59 | MOLA C |
| ATOM | 262 | CB | GLU | A 49 | −5.117 | 4.904 | 40.572 | 1.00 | 63.37 | MOLA C |
| ATOM | 263 | CG | GLU | A 49 | −5.888 | 3.841 | 39.790 | 1.00 | 67.59 | MOLA C |
| ATOM | 264 | CD | GLU | A 49 | −6.684 | 2.924 | 40.674 | 1.00 | 74.55 | MOLA C |
| ATOM | 265 | OE1 | GLU | A 49 | −7.042 | 1.833 | 40.198 | 1.00 | 80.02 | MOLA O |
| ATOM | 266 | OE2 | GLU | A 49 | −6.938 | 3.282 | 41.844 | 1.00 | 80.68 | MOLA O |
| ATOM | 267 | C | GLU | A 49 | −3.333 | 4.826 | 38.899 | 1.00 | 60.25 | MOLA C |
| ATOM | 268 | O | GLU | A 49 | −3.665 | 4.418 | 37.782 | 1.00 | 60.12 | MOLA O |
| ATOM | 269 | N | VAL | A 50 | −2.207 | 4.470 | 39.519 | 1.00 | 58.51 | MOLA N |
| ATOM | 270 | CA | VAL | A 50 | −1.194 | 3.577 | 38.917 | 1.00 | 59.34 | MOLA C |
| ATOM | 271 | CB | VAL | A 50 | 0.114 | 4.341 | 38.535 | 1.00 | 58.65 | MOLA C |
| ATOM | 272 | CG1 | VAL | A 50 | 0.545 | 5.279 | 39.639 | 1.00 | 58.00 | MOLA C |
| ATOM | 273 | CG2 | VAL | A 50 | 1.234 | 3.377 | 38.244 | 1.00 | 55.92 | MOLA C |
| ATOM | 274 | C | VAL | A 50 | −0.852 | 2.368 | 39.813 | 1.00 | 60.90 | MOLA C |
| ATOM | 275 | O | VAL | A 50 | −0.557 | 2.515 | 41.003 | 1.00 | 62.17 | MOLA O |
| ATOM | 276 | N | SER | A 51 | −0.876 | 1.173 | 39.236 | 1.00 | 61.73 | MOLA N |
| ATOM | 277 | CA | SER | A 51 | −0.656 | −0.056 | 40.003 | 1.00 | 62.45 | MOLA C |
| ATOM | 278 | CB | SER | A 51 | −1.733 | −1.075 | 39.640 | 1.00 | 62.54 | MOLA C |
| ATOM | 279 | OG | SER | A 51 | −1.765 | −1.276 | 38.231 | 1.00 | 63.52 | MOLA O |
| ATOM | 280 | C | SER | A 51 | 0.730 | −0.670 | 39.774 | 1.00 | 62.91 | MOLA C |
| ATOM | 281 | O | SER | A 51 | 1.081 | −1.025 | 38.646 | 1.00 | 62.61 | MOLA O |
| ATOM | 282 | N | VAL | A 52 | 1.507 | −0.814 | 40.842 | 1.00 | 63.29 | MOLA N |
| ATOM | 283 | CA | VAL | A 52 | 2.851 | −1.370 | 40.712 | 1.00 | 65.93 | MOLA C |
| ATOM | 284 | CB | VAL | A 52 | 3.938 | −0.417 | 41.345 | 1.00 | 64.59 | MOLA C |
| ATOM | 285 | CG1 | VAL | A 52 | 3.920 | −0.486 | 42.846 | 1.00 | 64.79 | MOLA C |
| ATOM | 286 | CG2 | VAL | A 52 | 5.321 | −0.745 | 40.843 | 1.00 | 60.35 | MOLA C |
| ATOM | 287 | C | VAL | A 52 | 2.965 | −2.856 | 41.175 | 1.00 | 70.06 | MOLA C |
| ATOM | 288 | O | VAL | A 52 | 2.995 | −3.166 | 42.374 | 1.00 | 69.63 | MOLA O |
| ATOM | 289 | N | ARG | A 53 | 2.999 | −3.759 | 40.188 | 1.00 | 74.78 | MOLA N |
| ATOM | 290 | CA | ARG | A 53 | 3.246 | −5.206 | 40.379 | 1.00 | 77.79 | MOLA C |
| ATOM | 291 | CB | ARG | A 53 | 3.780 | −5.819 | 39.060 | 1.00 | 77.51 | MOLA C |
| ATOM | 292 | CG | ARG | A 53 | 3.813 | −7.362 | 38.958 | 1.00 | 78.04 | MOLA C |
| ATOM | 293 | CD | ARG | A 53 | 3.952 | −7.853 | 37.484 | 1.00 | 79.83 | MOLA C |
| ATOM | 294 | NE | ARG | A 53 | 3.007 | −7.184 | 36.569 | 1.00 | 85.85 | MOLA N |
| ATOM | 295 | CZ | ARG | A 53 | 1.939 | −7.737 | 35.979 | 1.00 | 74.06 | MOLA C |
| ATOM | 296 | NH1 | ARG | A 53 | 1.191 | −6.976 | 35.198 | 1.00 | 69.75 | MOLA N |
| ATOM | 297 | NH2 | ARG | A 53 | 1.611 | −9.021 | 36.145 | 1.00 | 57.09 | MOLA N |
| ATOM | 298 | C | ARG | A 53 | 4.212 | −5.454 | 41.558 | 1.00 | 78.72 | MOLA C |
| ATOM | 299 | O | ARG | A 53 | 5.436 | −5.575 | 41.387 | 1.00 | 77.82 | MOLA O |
| ATOM | 300 | N | THR | A 54 | 3.632 | −5.531 | 42.751 | 1.00 | 80.41 | MOLA N |
| ATOM | 301 | CA | THR | A 54 | 4.396 | −5.629 | 43.995 | 1.00 | 81.27 | MOLA C |
| ATOM | 302 | CB | THR | A 54 | 3.683 | −4.808 | 45.113 | 1.00 | 80.46 | MOLA C |
| ATOM | 303 | OG1 | THR | A 54 | 4.529 | −4.716 | 46.262 | 1.00 | 80.63 | MOLA O |
| ATOM | 304 | CG2 | THR | A 54 | 2.332 | −5.425 | 45.504 | 1.00 | 77.06 | MOLA C |
| ATOM | 305 | C | THR | A 54 | 4.729 | −7.083 | 44.441 | 1.00 | 83.14 | MOLA C |
| ATOM | 306 | O | THR | A 54 | 5.582 | −7.302 | 45.322 | 1.00 | 82.64 | MOLA O |
| ATOM | 307 | N | GLY | A 55 | 4.074 | −8.063 | 43.811 | 1.00 | 84.36 | MOLA N |
| ATOM | 308 | CA | GLY | A 55 | 4.288 | −9.485 | 44.106 | 1.00 | 85.55 | MOLA C |
| ATOM | 309 | C | GLY | A 55 | 5.747 | −9.873 | 44.299 | 1.00 | 87.44 | MOLA C |
| ATOM | 310 | O | GLY | A 55 | 6.064 | −10.808 | 45.052 | 1.00 | 89.08 | MOLA O |
| ATOM | 311 | N | SER | A 61 | −3.290 | −10.907 | 42.041 | 1.00 | 92.23 | MOLA N |
| ATOM | 312 | CA | SER | A 61 | −3.719 | −9.597 | 42.523 | 1.00 | 91.45 | MOLA C |
| ATOM | 313 | CB | SER | A 61 | −5.172 | −9.657 | 43.006 | 1.00 | 91.46 | MOLA C |
| ATOM | 314 | OG | SER | A 61 | −5.720 | −8.353 | 43.136 | 1.00 | 91.95 | MOLA O |
| ATOM | 315 | C | SER | A 61 | −2.788 | −9.100 | 43.632 | 1.00 | 90.99 | MOLA C |
| ATOM | 316 | O | SER | A 61 | −3.224 | −8.449 | 44.592 | 1.00 | 90.74 | MOLA O |
| ATOM | 317 | N | SER | A 62 | −1.503 | −9.427 | 43.494 | 1.00 | 90.65 | MOLA N |
| ATOM | 318 | CA | SER | A 62 | −0.478 | −8.983 | 44.436 | 1.00 | 89.65 | MOLA C |
| ATOM | 319 | CB | SER | A 62 | 0.559 | −10.072 | 44.683 | 1.00 | 89.42 | MOLA C |
| ATOM | 320 | OG | SER | A 62 | 1.343 | −9.738 | 45.811 | 1.00 | 90.40 | MOLA O |
| ATOM | 321 | C | SER | A 62 | 0.192 | −7.725 | 43.897 | 1.00 | 89.63 | MOLA C |
| ATOM | 322 | O | SER | A 62 | 1.417 | −7.661 | 43.733 | 1.00 | 90.65 | MOLA O |
| ATOM | 323 | N | ARG | A 63 | −0.642 | −6.738 | 43.592 | 1.00 | 87.56 | MOLA N |
| ATOM | 324 | CA | ARG | A 63 | −0.192 | −5.450 | 43.137 | 1.00 | 84.62 | MOLA C |
| ATOM | 325 | CB | ARG | A 63 | −0.925 | −5.041 | 41.850 | 1.00 | 84.95 | MOLA C |
| ATOM | 326 | CG | ARG | A 63 | −0.705 | −5.950 | 40.644 | 1.00 | 79.92 | MOLA C |
| ATOM | 327 | CD | ARG | A 63 | −0.960 | −5.213 | 39.326 | 1.00 | 75.75 | MOLA C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 328 | NE | ARG | A 63 | −2.378 | −4.940 | 39.065 | 1.00 | 83.76 | MOLA N |
| ATOM | 329 | CZ | ARG | A 63 | −2.841 | −4.269 | 38.001 | 1.00 | 90.05 | MOLA C |
| ATOM | 330 | NH1 | ARG | A 63 | −2.000 | −3.785 | 37.090 | 1.00 | 91.87 | MOLA N |
| ATOM | 331 | NH2 | ARG | A 63 | −4.149 | −4.074 | 37.843 | 1.00 | 85.56 | MOLA N |
| ATOM | 332 | C | ARG | A 63 | −0.488 | −4.446 | 44.251 | 1.00 | 84.45 | MOLA C |
| ATOM | 333 | O | ARG | A 63 | −1.168 | −4.762 | 45.238 | 1.00 | 84.17 | MOLA O |
| ATOM | 334 | N | LYS | A 64 | 0.056 | −3.246 | 44.095 | 1.00 | 82.90 | MOLA N |
| ATOM | 335 | CA | LYS | A 64 | −0.250 | −2.120 | 44.960 | 1.00 | 80.71 | MOLA C |
| ATOM | 336 | CB | LYS | A 64 | 1.023 | −1.649 | 45.669 | 1.00 | 79.66 | MOLA C |
| ATOM | 337 | CG | LYS | A 64 | 0.894 | −0.328 | 46.419 | 1.00 | 82.32 | MOLA C |
| ATOM | 338 | CD | LYS | A 64 | −0.360 | −0.278 | 47.305 | 1.00 | 89.95 | MOLA C |
| ATOM | 339 | CE | LYS | A 64 | −0.292 | −1.262 | 48.474 | 1.00 | 84.24 | MOLA C |
| ATOM | 340 | NZ | LYS | A 64 | −1.560 | −1.275 | 49.253 | 1.00 | 70.29 | MOLA N |
| ATOM | 341 | C | LYS | A 64 | −0.850 | −1.015 | 44.069 | 1.00 | 79.12 | MOLA C |
| ATOM | 342 | O | LYS | A 64 | −0.439 | −0.861 | 42.912 | 1.00 | 79.39 | MOLA O |
| ATOM | 343 | N | THR | A 65 | −1.839 | −0.272 | 44.569 | 1.00 | 75.90 | MOLA N |
| ATOM | 344 | CA | THR | A 65 | −2.384 | 0.825 | 43.768 | 1.00 | 72.81 | MOLA C |
| ATOM | 345 | CB | THR | A 65 | −3.855 | 0.568 | 43.301 | 1.00 | 72.33 | MOLA C |
| ATOM | 346 | OG1 | THR | A 65 | −3.959 | −0.729 | 42.700 | 1.00 | 70.33 | MOLA O |
| ATOM | 347 | CG2 | THR | A 65 | −4.281 | 1.593 | 42.258 | 1.00 | 72.92 | MOLA C |
| ATOM | 348 | C | THR | A 65 | −2.198 | 2.189 | 44.457 | 1.00 | 71.07 | MOLA C |
| ATOM | 349 | O | THR | A 65 | −2.314 | 2.307 | 45.684 | 1.00 | 71.75 | MOLA O |
| ATOM | 350 | N | TYR | A 66 | −1.837 | 3.186 | 43.647 | 1.00 | 67.88 | MOLA N |
| ATOM | 351 | CA | TYR | A 66 | −1.681 | 4.579 | 44.068 | 1.00 | 65.00 | MOLA C |
| ATOM | 352 | CB | TYR | A 66 | −0.279 | 5.115 | 43.759 | 1.00 | 62.56 | MOLA C |
| ATOM | 353 | CG | TYR | A 66 | 0.790 | 4.593 | 44.661 | 1.00 | 58.93 | MOLA C |
| ATOM | 354 | CD1 | TYR | A 66 | 1.660 | 3.581 | 44.239 | 1.00 | 54.92 | MOLA C |
| ATOM | 355 | CE1 | TYR | A 66 | 2.654 | 3.082 | 45.084 | 1.00 | 33.82 | MOLA C |
| ATOM | 356 | CZ | TYR | A 66 | 2.778 | 3.604 | 46.354 | 1.00 | 43.77 | MOLA C |
| ATOM | 357 | OH | TYR | A 66 | 3.734 | 3.128 | 47.211 | 1.00 | 47.71 | MOLA O |
| ATOM | 358 | CE2 | TYR | A 66 | 1.931 | 4.610 | 46.789 | 1.00 | 60.18 | MOLA C |
| ATOM | 359 | CD2 | TYR | A 66 | 0.936 | 5.096 | 45.942 | 1.00 | 59.38 | MOLA C |
| ATOM | 360 | C | TYR | A 66 | −2.679 | 5.421 | 43.300 | 1.00 | 64.64 | MOLA C |
| ATOM | 361 | O | TYR | A 66 | −2.970 | 5.160 | 42.130 | 1.00 | 66.09 | MOLA O |
| ATOM | 362 | N | THR | A 67 | −3.184 | 6.453 | 43.952 | 1.00 | 63.24 | MOLA N |
| ATOM | 363 | CA | THR | A 67 | −4.150 | 7.337 | 43.327 | 1.00 | 60.71 | MOLA C |
| ATOM | 364 | CB | THR | A 67 | −5.522 | 7.266 | 44.067 | 1.00 | 60.37 | MOLA C |
| ATOM | 365 | OG1 | THR | A 67 | −5.795 | 5.916 | 44.473 | 1.00 | 56.54 | MOLA O |
| ATOM | 366 | CG2 | THR | A 67 | −6.654 | 7.756 | 43.176 | 1.00 | 66.23 | MOLA C |
| ATOM | 367 | C | THR | A 67 | −3.561 | 8.758 | 43.334 | 1.00 | 57.70 | MOLA C |
| ATOM | 368 | O | THR | A 67 | −2.920 | 9.168 | 44.319 | 1.00 | 54.63 | MOLA O |
| ATOM | 369 | N | PHE | A 68 | −3.742 | 9.483 | 42.231 | 1.00 | 54.43 | MOLA N |
| ATOM | 370 | CA | PHE | A 68 | −3.237 | 10.853 | 42.139 | 1.00 | 54.53 | MOLA C |
| ATOM | 371 | CB | PHE | A 68 | −1.863 | 10.912 | 41.451 | 1.00 | 53.20 | MOLA C |
| ATOM | 372 | CG | PHE | A 68 | −0.815 | 10.052 | 42.102 | 1.00 | 51.00 | MOLA C |
| ATOM | 373 | CD1 | PHE | A 68 | −0.649 | 8.701 | 41.708 | 1.00 | 35.45 | MOLA C |
| ATOM | 374 | CE1 | PHE | A 68 | 0.333 | 7.892 | 42.307 | 1.00 | 39.18 | MOLA C |
| ATOM | 375 | CZ | PHE | A 68 | 1.170 | 8.427 | 43.323 | 1.00 | 32.97 | MOLA C |
| ATOM | 376 | CE2 | PHE | A 68 | 0.997 | 9.769 | 43.729 | 1.00 | 33.22 | MOLA C |
| ATOM | 377 | CD2 | PHE | A 68 | 0.008 | 10.581 | 43.111 | 1.00 | 26.34 | MOLA C |
| ATOM | 378 | C | PHE | A 68 | −4.221 | 11.773 | 41.409 | 1.00 | 55.29 | MOLA C |
| ATOM | 379 | O | PHE | A 68 | −5.300 | 11.329 | 40.958 | 1.00 | 54.38 | MOLA O |
| ATOM | 380 | N | ASP | A 69 | −3.834 | 13.045 | 41.290 | 1.00 | 52.87 | MOLA N |
| ATOM | 381 | CA | ASP | A 69 | −4.692 | 14.038 | 40.692 | 1.00 | 53.89 | MOLA C |
| ATOM | 382 | CB | ASP | A 69 | −4.077 | 15.406 | 40.854 | 1.00 | 54.04 | MOLA C |
| ATOM | 383 | CG | ASP | A 69 | −3.974 | 15.812 | 42.293 | 1.00 | 58.61 | MOLA C |
| ATOM | 384 | OD1 | ASP | A 69 | −4.905 | 15.483 | 43.071 | 1.00 | 65.45 | MOLA O |
| ATOM | 385 | OD2 | ASP | A 69 | −2.967 | 16.467 | 42.646 | 1.00 | 60.81 | MOLA O |
| ATOM | 386 | C | ASP | A 69 | −4.964 | 13.762 | 39.233 | 1.00 | 54.83 | MOLA C |
| ATOM | 387 | O | ASP | A 69 | −5.972 | 14.207 | 38.701 | 1.00 | 54.99 | MOLA O |
| ATOM | 388 | N | MET | A 70 | −4.042 | 13.050 | 38.593 | 1.00 | 56.97 | MOLA N |
| ATOM | 389 | CA | MET | A 70 | −4.142 | 12.600 | 37.190 | 1.00 | 58.65 | MOLA C |
| ATOM | 390 | CB | MET | A 70 | −3.872 | 13.713 | 36.177 | 1.00 | 57.88 | MOLA C |
| ATOM | 391 | CG | MET | A 70 | −4.842 | 14.874 | 36.167 | 1.00 | 61.48 | MOLA C |
| ATOM | 392 | SD | MET | A 70 | −4.121 | 16.310 | 35.315 | 1.00 | 64.25 | MOLA S |
| ATOM | 393 | CE | MET | A 70 | −5.002 | 17.651 | 36.156 | 1.00 | 60.29 | MOLA C |
| ATOM | 394 | C | MET | A 70 | −3.024 | 11.604 | 37.047 | 1.00 | 57.42 | MOLA C |
| ATOM | 395 | O | MET | A 70 | −2.125 | 11.559 | 37.905 | 1.00 | 60.16 | MOLA O |
| ATOM | 396 | N | VAL | A 71 | −3.059 | 10.813 | 35.977 | 1.00 | 53.63 | MOLA N |
| ATOM | 397 | CA | VAL | A 71 | −2.004 | 9.846 | 35.736 | 1.00 | 50.66 | MOLA C |
| ATOM | 398 | CB | VAL | A 71 | −2.364 | 8.523 | 36.334 | 1.00 | 51.34 | MOLA C |
| ATOM | 399 | CG1 | VAL | A 71 | −1.453 | 7.422 | 35.805 | 1.00 | 53.96 | MOLA C |
| ATOM | 400 | CG2 | VAL | A 71 | −2.304 | 8.627 | 37.868 | 1.00 | 51.71 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 401 | C | VAL | A 71 | −1.729 | 9.721 | 34.256 | 1.00 | 50.20 | MOLA C |
| ATOM | 402 | O | VAL | A 71 | −2.664 | 9.691 | 33.456 | 1.00 | 51.99 | MOLA O |
| ATOM | 403 | N | PHE | A 72 | −0.444 | 9.629 | 33.904 | 1.00 | 48.39 | MOLA N |
| ATOM | 404 | CA | PHE | A 72 | 0.004 | 9.791 | 32.521 | 1.00 | 46.65 | MOLA C |
| ATOM | 405 | CB | PHE | A 72 | 0.849 | 11.055 | 32.449 | 1.00 | 47.30 | MOLA C |
| ATOM | 406 | CG | PHE | A 72 | 0.050 | 12.309 | 32.545 | 1.00 | 42.59 | MOLA C |
| ATOM | 407 | CD1 | PHE | A 72 | −0.718 | 12.729 | 31.476 | 1.00 | 31.94 | MOLA C |
| ATOM | 408 | CE1 | PHE | A 72 | −1.453 | 13.849 | 31.562 | 1.00 | 27.41 | MOLA C |
| ATOM | 409 | CZ | PHE | A 72 | −1.425 | 14.610 | 32.703 | 1.00 | 21.76 | MOLA C |
| ATOM | 410 | CE2 | PHE | A 72 | −0.645 | 14.245 | 33.752 | 1.00 | 33.80 | MOLA C |
| ATOM | 411 | CD2 | PHE | A 72 | 0.088 | 13.079 | 33.679 | 1.00 | 40.21 | MOLA C |
| ATOM | 412 | C | PHE | A 72 | 0.790 | 8.658 | 31.867 | 1.00 | 46.24 | MOLA C |
| ATOM | 413 | O | PHE | A 72 | 1.998 | 8.536 | 32.054 | 1.00 | 47.90 | MOLA O |
| ATOM | 414 | N | GLY | A 73 | 0.116 | 7.878 | 31.038 | 1.00 | 45.76 | MOLA N |
| ATOM | 415 | CA | GLY | A 73 | 0.731 | 6.720 | 30.401 | 1.00 | 42.95 | MOLA C |
| ATOM | 416 | C | GLY | A 73 | 1.866 | 7.068 | 29.464 | 1.00 | 41.94 | MOLA C |
| ATOM | 417 | O | GLY | A 73 | 2.096 | 8.235 | 29.177 | 1.00 | 38.80 | MOLA O |
| ATOM | 418 | N | ALA | A 74 | 2.566 | 6.025 | 29.004 | 1.00 | 43.17 | MOLA N |
| ATOM | 419 | CA | ALA | A 74 | 3.692 | 6.113 | 28.073 | 1.00 | 41.56 | MOLA C |
| ATOM | 420 | CB | ALA | A 74 | 4.257 | 4.737 | 27.808 | 1.00 | 40.49 | MOLA C |
| ATOM | 421 | C | ALA | A 74 | 3.302 | 6.767 | 26.762 | 1.00 | 42.34 | MOLA C |
| ATOM | 422 | O | ALA | A 74 | 4.146 | 7.305 | 26.080 | 1.00 | 47.47 | MOLA O |
| ATOM | 423 | N | SER | A 75 | 2.028 | 6.699 | 26.406 | 1.00 | 42.21 | MOLA N |
| ATOM | 424 | CA | SER | A 75 | 1.476 | 7.328 | 25.200 | 1.00 | 41.05 | MOLA C |
| ATOM | 425 | CB | SER | A 75 | 0.147 | 6.646 | 24.911 | 1.00 | 41.80 | MOLA C |
| ATOM | 426 | OG | SER | A 75 | −0.698 | 6.718 | 26.076 | 1.00 | 45.62 | MOLA O |
| ATOM | 427 | C | SER | A 75 | 1.242 | 8.868 | 25.336 | 1.00 | 41.62 | MOLA C |
| ATOM | 428 | O | SER | A 75 | 0.957 | 9.558 | 24.351 | 1.00 | 42.30 | MOLA O |
| ATOM | 429 | N | THR | A 76 | 1.361 | 9.394 | 26.557 | 1.00 | 40.05 | MOLA N |
| ATOM | 430 | CA | THR | A 76 | 1.131 | 10.801 | 26.868 | 1.00 | 38.26 | MOLA C |
| ATOM | 431 | CB | THR | A 76 | 1.246 | 10.990 | 28.407 | 1.00 | 39.98 | MOLA C |
| ATOM | 432 | OG1 | THR | A 76 | 0.527 | 9.952 | 29.106 | 1.00 | 37.10 | MOLA O |
| ATOM | 433 | CG2 | THR | A 76 | 0.720 | 12.359 | 28.836 | 1.00 | 48.53 | MOLA C |
| ATOM | 434 | C | THR | A 76 | 2.071 | 11.819 | 26.153 | 1.00 | 38.50 | MOLA C |
| ATOM | 435 | O | THR | A 76 | 3.215 | 12.013 | 26.577 | 1.00 | 40.11 | MOLA O |
| ATOM | 436 | N | LYS | A 77 | 1.582 | 12.467 | 25.090 | 1.00 | 37.62 | MOLA N |
| ATOM | 437 | CA | LYS | A 77 | 2.303 | 13.542 | 24.343 | 1.00 | 36.51 | MOLA C |
| ATOM | 438 | CB | LYS | A 77 | 1.493 | 14.012 | 23.119 | 1.00 | 39.25 | MOLA C |
| ATOM | 439 | CG | LYS | A 77 | 1.453 | 13.061 | 21.906 | 1.00 | 40.06 | MOLA C |
| ATOM | 440 | CD | LYS | A 77 | 2.861 | 12.827 | 21.311 | 1.00 | 65.35 | MOLA C |
| ATOM | 441 | CE | LYS | A 77 | 2.934 | 11.600 | 20.370 | 1.00 | 58.71 | MOLA C |
| ATOM | 442 | NZ | LYS | A 77 | 2.103 | 11.766 | 19.126 | 1.00 | 66.12 | MOLA N |
| ATOM | 443 | C | LYS | A 77 | 2.637 | 14.791 | 25.167 | 1.00 | 33.47 | MOLA C |
| ATOM | 444 | O | LYS | A 77 | 2.052 | 15.016 | 26.227 | 1.00 | 33.02 | MOLA O |
| ATOM | 445 | N | GLN | A 78 | 3.579 | 15.600 | 24.673 | 1.00 | 30.73 | MOLA N |
| ATOM | 446 | CA | GLN | A 78 | 4.010 | 16.816 | 25.381 | 1.00 | 29.06 | MOLA C |
| ATOM | 447 | CB | GLN | A 78 | 5.056 | 17.566 | 24.572 | 1.00 | 27.93 | MOLA C |
| ATOM | 448 | CG | GLN | A 78 | 6.397 | 16.834 | 24.441 | 1.00 | 22.53 | MOLA C |
| ATOM | 449 | CD | GLN | A 78 | 7.059 | 16.657 | 25.807 | 1.00 | 35.07 | MOLA C |
| ATOM | 450 | OE1 | GLN | A 78 | 6.368 | 16.555 | 26.831 | 1.00 | 41.40 | MOLA O |
| ATOM | 451 | NE2 | GLN | A 78 | 8.399 | 16.645 | 25.836 | 1.00 | 12.74 | MOLA N |
| ATOM | 452 | C | GLN | A 78 | 2.797 | 17.689 | 25.595 | 1.00 | 31.71 | MOLA C |
| ATOM | 453 | O | GLN | A 78 | 2.366 | 17.920 | 26.711 | 1.00 | 34.94 | MOLA O |
| ATOM | 454 | N | ILE | A 79 | 2.215 | 18.135 | 24.498 | 1.00 | 32.28 | MOLA N |
| ATOM | 455 | CA | ILE | A 79 | 1.012 | 18.942 | 24.526 | 1.00 | 31.64 | MOLA C |
| ATOM | 456 | CB | ILE | A 79 | 0.470 | 19.077 | 23.084 | 1.00 | 33.48 | MOLA C |
| ATOM | 457 | CG1 | ILE | A 79 | −0.537 | 20.214 | 22.971 | 1.00 | 22.98 | MOLA C |
| ATOM | 458 | CD1 | ILE | A 79 | −0.471 | 20.878 | 21.642 | 1.00 | 39.14 | MOLA C |
| ATOM | 459 | CG2 | ILE | A 79 | −0.091 | 17.717 | 22.576 | 1.00 | 32.41 | MOLA C |
| ATOM | 460 | C | ILE | A 79 | −0.118 | 18.454 | 25.469 | 1.00 | 33.14 | MOLA C |
| ATOM | 461 | O | ILE | A 79 | −0.870 | 19.274 | 26.019 | 1.00 | 34.17 | MOLA O |
| ATOM | 462 | N | ASP | A 80 | −0.293 | 17.151 | 25.647 | 1.00 | 31.81 | MOLA N |
| ATOM | 463 | CA | ASP | A 80 | −1.369 | 16.742 | 26.543 | 1.00 | 35.16 | MOLA C |
| ATOM | 464 | CB | ASP | A 80 | −1.684 | 15.258 | 26.449 | 1.00 | 36.74 | MOLA C |
| ATOM | 465 | CG | ASP | A 80 | −2.087 | 14.852 | 25.042 | 1.00 | 48.30 | MOLA C |
| ATOM | 466 | OD1 | ASP | A 80 | −2.948 | 15.560 | 24.447 | 1.00 | 42.90 | MOLA O |
| ATOM | 467 | OD2 | ASP | A 80 | −1.532 | 13.842 | 24.531 | 1.00 | 58.71 | MOLA O |
| ATOM | 468 | C | ASP | A 80 | −1.001 | 17.159 | 27.950 | 1.00 | 35.58 | MOLA C |
| ATOM | 469 | O | ASP | A 80 | −1.800 | 17.826 | 28.611 | 1.00 | 37.78 | MOLA O |
| ATOM | 470 | N | VAL | A 81 | 0.214 | 16.811 | 28.381 | 1.00 | 35.11 | MOLA N |
| ATOM | 471 | CA | VAL | A 81 | 0.799 | 17.323 | 29.640 | 1.00 | 34.11 | MOLA C |
| ATOM | 472 | CB | VAL | A 81 | 2.315 | 17.128 | 29.703 | 1.00 | 31.75 | MOLA C |
| ATOM | 473 | CG1 | VAL | A 81 | 2.866 | 17.945 | 30.841 | 1.00 | 18.64 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 474 | CG2 | VAL | A 81 | 2.665 | 15.683 | 29.869 | 1.00 | 24.76 | MOLA C |
| ATOM | 475 | C | VAL | A 81 | 0.623 | 18.834 | 29.801 | 1.00 | 37.32 | MOLA C |
| ATOM | 476 | O | VAL | A 81 | 0.172 | 19.309 | 30.859 | 1.00 | 36.85 | MOLA O |
| ATOM | 477 | N | TYR | A 82 | 1.011 | 19.579 | 28.765 | 1.00 | 37.69 | MOLA N |
| ATOM | 478 | CA | TYR | A 82 | 0.832 | 21.015 | 28.786 | 1.00 | 41.95 | MOLA C |
| ATOM | 479 | CB | TYR | A 82 | 1.355 | 21.627 | 27.529 | 1.00 | 43.90 | MOLA C |
| ATOM | 480 | CG | TYR | A 82 | 1.374 | 23.104 | 27.635 | 1.00 | 40.97 | MOLA C |
| ATOM | 481 | CD1 | TYR | A 82 | 0.335 | 23.863 | 27.147 | 1.00 | 34.29 | MOLA C |
| ATOM | 482 | CE1 | TYR | A 82 | 0.367 | 25.256 | 27.229 | 1.00 | 44.06 | MOLA C |
| ATOM | 483 | CZ | TYR | A 82 | 1.456 | 25.868 | 27.837 | 1.00 | 54.46 | MOLA C |
| ATOM | 484 | OH | TYR | A 82 | 1.523 | 27.236 | 27.969 | 1.00 | 53.26 | MOLA O |
| ATOM | 485 | CE2 | TYR | A 82 | 2.493 | 25.109 | 28.336 | 1.00 | 56.67 | MOLA C |
| ATOM | 486 | CD2 | TYR | A 82 | 2.443 | 23.745 | 28.235 | 1.00 | 49.72 | MOLA C |
| ATOM | 487 | C | TYR | A 82 | −0.620 | 21.463 | 28.966 | 1.00 | 43.88 | MOLA C |
| ATOM | 488 | O | TYR | A 82 | −0.942 | 22.110 | 29.947 | 1.00 | 46.87 | MOLA O |
| ATOM | 489 | N | ARG | A 83 | −1.514 | 21.135 | 28.041 | 1.00 | 44.58 | MOLA N |
| ATOM | 490 | CA | ARG | A 83 | −2.911 | 21.487 | 28.274 | 1.00 | 42.25 | MOLA C |
| ATOM | 491 | CB | ARG | A 83 | −3.855 | 20.811 | 27.289 | 1.00 | 43.66 | MOLA C |
| ATOM | 492 | CG | ARG | A 83 | −3.750 | 21.327 | 25.867 | 1.00 | 45.82 | MOLA C |
| ATOM | 493 | CD | ARG | A 83 | −4.953 | 20.884 | 25.031 | 1.00 | 50.18 | MOLA C |
| ATOM | 494 | NE | ARG | A 83 | −4.855 | 21.380 | 23.660 | 1.00 | 56.03 | MOLA N |
| ATOM | 495 | CZ | ARG | A 83 | −4.545 | 20.630 | 22.603 | 1.00 | 68.39 | MOLA C |
| ATOM | 496 | NH1 | ARG | A 83 | −4.471 | 21.185 | 21.398 | 1.00 | 64.85 | MOLA N |
| ATOM | 497 | NH2 | ARG | A 83 | −4.322 | 19.322 | 22.740 | 1.00 | 71.57 | MOLA N |
| ATOM | 498 | C | ARG | A 83 | −3.299 | 21.074 | 29.662 | 1.00 | 39.55 | MOLA C |
| ATOM | 499 | O | ARG | A 83 | −3.831 | 21.884 | 30.385 | 1.00 | 42.58 | MOLA O |
| ATOM | 500 | N | SER | A 84 | −3.002 | 19.830 | 30.034 | 1.00 | 35.43 | MOLA N |
| ATOM | 501 | CA | SER | A 84 | −3.501 | 19.226 | 31.279 | 1.00 | 35.97 | MOLA C |
| ATOM | 502 | CB | SER | A 84 | −3.193 | 17.746 | 31.317 | 1.00 | 34.58 | MOLA C |
| ATOM | 503 | OG | SER | A 84 | −3.752 | 17.080 | 30.199 | 1.00 | 48.74 | MOLA O |
| ATOM | 504 | C | SER | A 84 | −2.925 | 19.752 | 32.552 | 1.00 | 37.49 | MOLA C |
| ATOM | 505 | O | SER | A 84 | −3.587 | 19.755 | 33.574 | 1.00 | 40.00 | MOLA O |
| ATOM | 506 | N | VAL | A 85 | −1.666 | 20.152 | 32.524 | 1.00 | 38.99 | MOLA N |
| ATOM | 507 | CA | VAL | A 85 | −1.042 | 20.678 | 33.728 | 1.00 | 36.11 | MOLA C |
| ATOM | 508 | CB | VAL | A 85 | 0.270 | 19.974 | 33.994 | 1.00 | 35.34 | MOLA C |
| ATOM | 509 | CG1 | VAL | A 85 | 0.867 | 20.467 | 35.272 | 1.00 | 31.99 | MOLA C |
| ATOM | 510 | CG2 | VAL | A 85 | 0.018 | 18.498 | 34.067 | 1.00 | 28.68 | MOLA C |
| ATOM | 511 | C | VAL | A 85 | −0.800 | 22.175 | 33.662 | 1.00 | 37.17 | MOLA C |
| ATOM | 512 | O | VAL | A 85 | −1.326 | 22.910 | 34.469 | 1.00 | 38.48 | MOLA O |
| ATOM | 513 | N | VAL | A 86 | −0.027 | 22.623 | 32.683 | 1.00 | 38.21 | MOLA N |
| ATOM | 514 | CA | VAL | A 86 | 0.414 | 24.017 | 32.610 | 1.00 | 39.70 | MOLA C |
| ATOM | 515 | CB | VAL | A 86 | 1.482 | 24.198 | 31.501 | 1.00 | 40.77 | MOLA C |
| ATOM | 516 | CG1 | VAL | A 86 | 2.076 | 25.636 | 31.512 | 1.00 | 44.86 | MOLA C |
| ATOM | 517 | CG2 | VAL | A 86 | 2.578 | 23.178 | 31.687 | 1.00 | 44.96 | MOLA C |
| ATOM | 518 | C | VAL | A 86 | −0.660 | 25.102 | 32.469 | 1.00 | 39.59 | MOLA C |
| ATOM | 519 | O | VAL | A 86 | −0.463 | 26.213 | 32.979 | 1.00 | 38.33 | MOLA O |
| ATOM | 520 | N | CYS | A 87 | −1.773 | 24.802 | 31.795 | 1.00 | 40.58 | MOLA N |
| ATOM | 521 | CA | CYS | A 87 | −2.821 | 25.822 | 31.545 | 1.00 | 41.68 | MOLA C |
| ATOM | 522 | CB | CYS | A 87 | −3.868 | 25.289 | 30.630 | 1.00 | 39.88 | MOLA C |
| ATOM | 523 | SG | CYS | A 87 | −3.288 | 25.366 | 29.007 | 1.00 | 58.99 | MOLA S |
| ATOM | 524 | C | CYS | A 87 | −3.534 | 26.346 | 32.762 | 1.00 | 41.06 | MOLA C |
| ATOM | 525 | O | CYS | A 87 | −3.503 | 27.541 | 33.042 | 1.00 | 41.73 | MOLA O |
| ATOM | 526 | N | PRO | A 88 | −4.205 | 25.461 | 33.490 | 1.00 | 39.96 | MOLA N |
| ATOM | 527 | CA | PRO | A 88 | −4.829 | 26.060 | 34.622 | 1.00 | 39.03 | MOLA C |
| ATOM | 528 | CB | PRO | A 88 | −5.148 | 24.863 | 35.511 | 1.00 | 39.01 | MOLA C |
| ATOM | 529 | CG | PRO | A 88 | −5.419 | 23.770 | 34.547 | 1.00 | 37.95 | MOLA C |
| ATOM | 530 | CD | PRO | A 88 | −4.442 | 24.011 | 33.414 | 1.00 | 40.73 | MOLA C |
| ATOM | 531 | C | PRO | A 88 | −3.805 | 26.951 | 35.292 | 1.00 | 38.64 | MOLA C |
| ATOM | 532 | O | PRO | A 88 | −4.115 | 28.074 | 35.646 | 1.00 | 43.82 | MOLA O |
| ATOM | 533 | N | ILE | A 89 | −2.577 | 26.489 | 35.424 | 1.00 | 34.95 | MOLA N |
| ATOM | 534 | CA | ILE | A 89 | −1.606 | 27.243 | 36.215 | 1.00 | 32.10 | MOLA C |
| ATOM | 535 | CB | ILE | A 89 | −0.407 | 26.361 | 36.569 | 1.00 | 31.60 | MOLA C |
| ATOM | 536 | CG1 | ILE | A 89 | −0.841 | 25.368 | 37.629 | 1.00 | 22.93 | MOLA C |
| ATOM | 537 | CD1 | ILE | A 89 | 0.193 | 24.416 | 37.953 | 1.00 | 34.44 | MOLA C |
| ATOM | 538 | CG2 | ILE | A 89 | 0.789 | 27.194 | 37.027 | 1.00 | 22.29 | MOLA C |
| ATOM | 539 | C | ILE | A 89 | −1.133 | 28.534 | 35.583 | 1.00 | 32.62 | MOLA C |
| ATOM | 540 | O | ILE | A 89 | −0.912 | 29.525 | 36.258 | 1.00 | 34.43 | MOLA O |
| ATOM | 541 | N | LEU | A 90 | −0.932 | 28.535 | 34.288 | 1.00 | 35.12 | MOLA N |
| ATOM | 542 | CA | LEU | A 90 | −0.440 | 29.749 | 33.690 | 1.00 | 37.48 | MOLA C |
| ATOM | 543 | CB | LEU | A 90 | −0.164 | 29.545 | 32.205 | 1.00 | 36.04 | MOLA C |
| ATOM | 544 | CG | LEU | A 90 | 0.187 | 30.818 | 31.452 | 1.00 | 33.67 | MOLA C |
| ATOM | 545 | CD1 | LEU | A 90 | 1.398 | 31.436 | 32.083 | 1.00 | 33.98 | MOLA C |
| ATOM | 546 | CD2 | LEU | A 90 | 0.415 | 30.532 | 29.955 | 1.00 | 32.85 | MOLA C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 547 | C | LEU | A 90 | −1.514 | 30.804 | 33.959 | 1.00 | 43.12 | MOLA C |
| ATOM | 548 | O | LEU | A 90 | −1.201 | 31.932 | 34.391 | 1.00 | 43.62 | MOLA O |
| ATOM | 549 | N | ASP | A 91 | −2.781 | 30.403 | 33.752 | 1.00 | 46.15 | MOLA N |
| ATOM | 550 | CA | ASP | A 91 | −3.954 | 31.260 | 34.030 | 1.00 | 47.09 | MOLA C |
| ATOM | 551 | CB | ASP | A 91 | −5.276 | 30.477 | 33.981 | 1.00 | 43.27 | MOLA C |
| ATOM | 552 | CG | ASP | A 91 | −5.678 | 30.094 | 32.569 | 1.00 | 48.93 | MOLA C |
| ATOM | 553 | OD1 | ASP | A 91 | −5.097 | 30.636 | 31.593 | 1.00 | 49.60 | MOLA O |
| ATOM | 554 | OD2 | ASP | A 91 | −6.572 | 29.230 | 32.426 | 1.00 | 55.58 | MOLA O |
| ATOM | 555 | C | ASP | A 91 | −3.833 | 32.023 | 35.354 | 1.00 | 48.72 | MOLA C |
| ATOM | 556 | O | ASP | A 91 | −4.284 | 33.164 | 35.441 | 1.00 | 51.78 | MOLA O |
| ATOM | 557 | N | GLU | A 92 | −3.234 | 31.412 | 36.375 | 1.00 | 47.87 | MOLA N |
| ATOM | 558 | CA | GLU | A 92 | −3.034 | 32.129 | 37.612 | 1.00 | 48.99 | MOLA C |
| ATOM | 559 | CB | GLU | A 92 | −2.542 | 31.210 | 38.730 | 1.00 | 48.60 | MOLA C |
| ATOM | 560 | CG | GLU | A 92 | −3.501 | 30.104 | 39.160 | 1.00 | 55.91 | MOLA C |
| ATOM | 561 | CD | GLU | A 92 | −4.733 | 30.603 | 39.891 | 1.00 | 71.20 | MOLA C |
| ATOM | 562 | OE1 | GLU | A 92 | −5.541 | 31.330 | 39.272 | 1.00 | 82.67 | MOLA O |
| ATOM | 563 | OE2 | GLU | A 92 | −4.909 | 30.242 | 41.074 | 1.00 | 70.69 | MOLA O |
| ATOM | 564 | C | GLU | A 92 | −2.007 | 33.214 | 37.338 | 1.00 | 49.38 | MOLA C |
| ATOM | 565 | O | GLU | A 92 | −2.331 | 34.407 | 37.275 | 1.00 | 48.76 | MOLA O |
| ATOM | 566 | N | VAL | A 93 | −0.767 | 32.784 | 37.147 | 1.00 | 49.81 | MOLA N |
| ATOM | 567 | CA | VAL | A 93 | 0.329 | 33.696 | 36.907 | 1.00 | 49.80 | MOLA C |
| ATOM | 568 | CB | VAL | A 93 | 1.462 | 32.989 | 36.153 | 1.00 | 49.16 | MOLA C |
| ATOM | 569 | CG1 | VAL | A 93 | 2.499 | 33.971 | 35.699 | 1.00 | 50.34 | MOLA C |
| ATOM | 570 | CG2 | VAL | A 93 | 2.097 | 31.916 | 37.031 | 1.00 | 50.14 | MOLA C |
| ATOM | 571 | C | VAL | A 93 | −0.169 | 34.937 | 36.159 | 1.00 | 51.49 | MOLA C |
| ATOM | 572 | O | VAL | A 93 | 0.222 | 36.054 | 36.479 | 1.00 | 51.00 | MOLA O |
| ATOM | 573 | N | ILE | A 94 | −1.052 | 34.746 | 35.182 | 1.00 | 54.11 | MOLA N |
| ATOM | 574 | CA | ILE | A 94 | −1.641 | 35.879 | 34.452 | 1.00 | 55.74 | MOLA C |
| ATOM | 575 | CB | ILE | A 94 | −2.552 | 35.433 | 33.272 | 1.00 | 55.43 | MOLA C |
| ATOM | 576 | CG1 | ILE | A 94 | −1.984 | 34.219 | 32.531 | 1.00 | 59.62 | MOLA C |
| ATOM | 577 | CD1 | ILE | A 94 | −1.204 | 34.557 | 31.262 | 1.00 | 53.03 | MOLA C |
| ATOM | 578 | CG2 | ILE | A 94 | −2.765 | 36.592 | 32.286 | 1.00 | 53.97 | MOLA C |
| ATOM | 579 | C | ILE | A 94 | −2.477 | 36.787 | 35.378 | 1.00 | 56.89 | MOLA C |
| ATOM | 580 | O | ILE | A 94 | −2.416 | 38.015 | 35.273 | 1.00 | 55.78 | MOLA O |
| ATOM | 581 | N | MET | A 95 | −3.261 | 36.190 | 36.275 | 1.00 | 56.86 | MOLA N |
| ATOM | 582 | CA | MET | A 95 | −4.112 | 36.982 | 37.137 | 1.00 | 59.87 | MOLA C |
| ATOM | 583 | CB | MET | A 95 | −5.147 | 36.109 | 37.826 | 1.00 | 57.65 | MOLA C |
| ATOM | 584 | CG | MET | A 95 | −6.085 | 35.393 | 36.858 | 1.00 | 64.70 | MOLA C |
| ATOM | 585 | SD | MET | A 95 | −7.282 | 34.310 | 37.699 | 1.00 | 75.30 | MOLA S |
| ATOM | 586 | CE | MET | A 95 | −7.586 | 32.984 | 36.495 | 1.00 | 64.04 | MOLA C |
| ATOM | 587 | C | MET | A 95 | −3.260 | 37.732 | 38.150 | 1.00 | 58.17 | MOLA C |
| ATOM | 588 | O | MET | A 95 | −3.751 | 38.605 | 38.856 | 1.00 | 60.31 | MOLA O |
| ATOM | 589 | N | GLN | A 96 | −1.975 | 37.399 | 38.218 | 1.00 | 56.67 | MOLA N |
| ATOM | 590 | CA | GLY | A 96 | −1.045 | 38.135 | 39.072 | 1.00 | 53.77 | MOLA C |
| ATOM | 591 | C | GLY | A 96 | −0.385 | 37.297 | 40.140 | 1.00 | 51.51 | MOLA C |
| ATOM | 592 | O | GLY | A 96 | 0.446 | 37.783 | 40.883 | 1.00 | 48.17 | MOLA O |
| ATOM | 593 | N | TYR | A 97 | −0.730 | 36.018 | 40.180 | 1.00 | 52.81 | MOLA N |
| ATOM | 594 | CA | TYR | A 97 | −0.281 | 35.124 | 41.251 | 1.00 | 54.09 | MOLA C |
| ATOM | 595 | CB | TYR | A 97 | −1.352 | 34.067 | 41.522 | 1.00 | 55.16 | MOLA C |
| ATOM | 596 | CG | TYR | A 97 | −2.679 | 34.717 | 41.868 | 1.00 | 56.43 | MOLA C |
| ATOM | 597 | CD1 | TYR | A 97 | −2.830 | 35.436 | 43.062 | 1.00 | 42.62 | MOLA C |
| ATOM | 598 | CE1 | TYR | A 97 | −4.030 | 36.048 | 43.390 | 1.00 | 53.02 | MOLA C |
| ATOM | 599 | CZ | TYR | A 97 | −5.110 | 35.956 | 42.523 | 1.00 | 63.26 | MOLA C |
| ATOM | 600 | OH | TYR | A 97 | −6.305 | 36.570 | 42.855 | 1.00 | 62.55 | MOLA O |
| ATOM | 601 | CE2 | TYR | A 97 | −4.991 | 35.245 | 41.320 | 1.00 | 67.21 | MOLA C |
| ATOM | 602 | CD2 | TYR | A 97 | −3.774 | 34.633 | 40.997 | 1.00 | 55.73 | MOLA C |
| ATOM | 603 | C | TYR | A 97 | 1.112 | 34.505 | 41.101 | 1.00 | 53.51 | MOLA C |
| ATOM | 604 | O | TYR | A 97 | 1.933 | 34.945 | 40.291 | 1.00 | 53.78 | MOLA O |
| ATOM | 605 | N | ASN | A 98 | 1.392 | 33.483 | 41.886 | 1.00 | 52.06 | MOLA N |
| ATOM | 606 | CA | ASN | A 98 | 2.772 | 33.069 | 41.971 | 1.00 | 53.49 | MOLA C |
| ATOM | 607 | CB | ASN | A 98 | 3.397 | 33.848 | 43.110 | 1.00 | 52.81 | MOLA C |
| ATOM | 608 | CG | ASN | A 98 | 4.808 | 34.163 | 42.859 | 1.00 | 57.14 | MOLA C |
| ATOM | 609 | OD1 | ASN | A 98 | 5.138 | 35.290 | 42.497 | 1.00 | 62.02 | MOLA O |
| ATOM | 610 | ND2 | ASN | A 98 | 5.671 | 33.169 | 43.014 | 1.00 | 65.17 | MOLA N |
| ATOM | 611 | C | ASN | A 98 | 2.964 | 31.570 | 42.178 | 1.00 | 53.30 | MOLA C |
| ATOM | 612 | O | ASN | A 98 | 2.893 | 31.091 | 43.309 | 1.00 | 54.91 | MOLA O |
| ATOM | 613 | N | CYS | A 99 | 3.229 | 30.843 | 41.092 | 1.00 | 51.06 | MOLA N |
| ATOM | 614 | CA | CYS | A 99 | 3.199 | 29.395 | 41.130 | 1.00 | 50.30 | MOLA C |
| ATOM | 615 | CB | CYS | A 99 | 2.192 | 28.927 | 40.119 | 1.00 | 50.34 | MOLA C |
| ATOM | 616 | SG | CYS | A 99 | 0.723 | 29.936 | 40.192 | 1.00 | 62.07 | MOLA S |
| ATOM | 617 | C | CYS | A 99 | 4.496 | 28.705 | 40.814 | 1.00 | 50.00 | MOLA C |
| ATOM | 618 | O | CYS | A 99 | 5.355 | 29.234 | 40.116 | 1.00 | 51.74 | MOLA O |
| ATOM | 619 | N | THR | A 100 | 4.618 | 27.477 | 41.287 | 1.00 | 48.44 | MOLA N |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 620 | CA | THR | A 100 | 5.803 | 26.719 | 40.984 | 1.00 | 45.61 | MOLA C |
| ATOM | 621 | CB | THR | A 100 | 6.673 | 26.668 | 42.233 | 1.00 | 47.07 | MOLA C |
| ATOM | 622 | OG1 | THR | A 100 | 6.545 | 27.928 | 42.913 | 1.00 | 50.20 | MOLA O |
| ATOM | 623 | CG2 | THR | A 100 | 8.132 | 26.407 | 41.886 | 1.00 | 35.79 | MOLA C |
| ATOM | 624 | C | THR | A 100 | 5.409 | 25.332 | 40.514 | 1.00 | 43.98 | MOLA C |
| ATOM | 625 | O | THR | A 100 | 4.491 | 24.737 | 41.071 | 1.00 | 44.89 | MOLA O |
| ATOM | 626 | N | ILE | A 101 | 6.062 | 24.853 | 39.454 | 1.00 | 41.05 | MOLA N |
| ATOM | 627 | CA | ILE | A 101 | 5.927 | 23.458 | 39.000 | 1.00 | 38.77 | MOLA C |
| ATOM | 628 | CB | ILE | A 101 | 5.482 | 23.370 | 37.527 | 1.00 | 37.52 | MOLA C |
| ATOM | 629 | CG1 | ILE | A 101 | 4.235 | 24.210 | 37.276 | 1.00 | 38.99 | MOLA C |
| ATOM | 630 | CD1 | ILE | A 101 | 3.450 | 23.769 | 36.014 | 1.00 | 15.62 | MOLA C |
| ATOM | 631 | CG2 | ILE | A 101 | 5.151 | 21.944 | 37.149 | 1.00 | 29.83 | MOLA C |
| ATOM | 632 | C | ILE | A 101 | 7.257 | 22.685 | 39.139 | 1.00 | 38.81 | MOLA C |
| ATOM | 633 | O | ILE | A 101 | 8.321 | 23.220 | 38.812 | 1.00 | 39.15 | MOLA O |
| ATOM | 634 | N | PHE | A 102 | 7.225 | 21.438 | 39.616 | 1.00 | 37.39 | MOLA N |
| ATOM | 635 | CA | PHE | A 102 | 8.459 | 20.624 | 39.551 | 1.00 | 35.85 | MOLA C |
| ATOM | 636 | CB | PHE | A 102 | 9.039 | 20.272 | 40.913 | 1.00 | 34.61 | MOLA C |
| ATOM | 637 | CG | PHE | A 102 | 8.634 | 21.162 | 42.032 | 1.00 | 36.45 | MOLA C |
| ATOM | 638 | CD1 | PHE | A 102 | 9.589 | 21.901 | 42.721 | 1.00 | 46.95 | MOLA C |
| ATOM | 639 | CE1 | PHE | A 102 | 9.239 | 22.712 | 43.804 | 1.00 | 37.78 | MOLA C |
| ATOM | 640 | CZ | PHE | A 102 | 7.941 | 22.762 | 44.216 | 1.00 | 31.30 | MOLA C |
| ATOM | 641 | CE2 | PHE | A 102 | 6.969 | 22.015 | 43.542 | 1.00 | 44.83 | MOLA C |
| ATOM | 642 | CD2 | PHE | A 102 | 7.325 | 21.212 | 42.460 | 1.00 | 40.93 | MOLA C |
| ATOM | 643 | C | PHE | A 102 | 8.276 | 19.279 | 38.874 | 1.00 | 34.47 | MOLA C |
| ATOM | 644 | O | PHE | A 102 | 7.174 | 18.759 | 38.760 | 1.00 | 33.56 | MOLA O |
| ATOM | 645 | N | ALA | A 103 | 9.402 | 18.708 | 38.470 | 1.00 | 35.68 | MOLA N |
| ATOM | 646 | CA | ALA | A 103 | 9.485 | 17.320 | 38.018 | 1.00 | 35.99 | MOLA C |
| ATOM | 647 | CB | ALA | A 103 | 9.977 | 17.238 | 36.630 | 1.00 | 31.85 | MOLA C |
| ATOM | 648 | C | ALA | A 103 | 10.473 | 16.635 | 38.951 | 1.00 | 38.60 | MOLA C |
| ATOM | 649 | O | ALA | A 103 | 11.543 | 17.190 | 39.247 | 1.00 | 37.70 | MOLA O |
| ATOM | 650 | N | TYR | A 104 | 10.115 | 15.445 | 39.426 | 1.00 | 39.92 | MOLA N |
| ATOM | 651 | CA | TYR | A 104 | 10.973 | 14.719 | 40.343 | 1.00 | 42.19 | MOLA C |
| ATOM | 652 | CB | TYR | A 104 | 10.481 | 14.976 | 41.767 | 1.00 | 43.62 | MOLA C |
| ATOM | 653 | CG | TYR | A 104 | 10.929 | 13.993 | 42.845 | 1.00 | 49.92 | MOLA C |
| ATOM | 654 | CD1 | TYR | A 104 | 10.397 | 12.690 | 42.904 | 1.00 | 28.93 | MOLA C |
| ATOM | 655 | CE1 | TYR | A 104 | 10.790 | 11.810 | 43.893 | 1.00 | 45.72 | MOLA C |
| ATOM | 656 | CZ | TYR | A 104 | 11.709 | 12.219 | 44.873 | 1.00 | 55.12 | MOLA C |
| ATOM | 657 | OH | TYR | A 104 | 12.098 | 11.326 | 45.868 | 1.00 | 56.15 | MOLA O |
| ATOM | 658 | CE2 | TYR | A 104 | 12.240 | 13.511 | 44.846 | 1.00 | 49.72 | MOLA C |
| ATOM | 659 | CD2 | TYR | A 104 | 11.843 | 14.388 | 43.840 | 1.00 | 50.10 | MOLA C |
| ATOM | 660 | C | TYR | A 104 | 10.937 | 13.234 | 39.995 | 1.00 | 42.13 | MOLA C |
| ATOM | 661 | O | TYR | A 104 | 9.909 | 12.744 | 39.528 | 1.00 | 43.93 | MOLA O |
| ATOM | 662 | N | GLY | A 105 | 12.051 | 12.528 | 40.206 | 1.00 | 40.20 | MOLA N |
| ATOM | 663 | CA | GLY | A 105 | 12.096 | 11.082 | 39.972 | 1.00 | 34.55 | MOLA C |
| ATOM | 664 | C | GLY | A 105 | 13.477 | 10.433 | 39.848 | 1.00 | 32.26 | MOLA C |
| ATOM | 665 | O | GLY | A 105 | 14.500 | 10.979 | 40.259 | 1.00 | 26.09 | MOLA O |
| ATOM | 666 | N | GLN | A 106 | 13.502 | 9.226 | 39.307 | 1.00 | 32.57 | MOLA N |
| ATOM | 667 | CA | GLN | A 106 | 14.768 | 8.573 | 39.048 | 1.00 | 34.08 | MOLA C |
| ATOM | 668 | CB | GLN | A 106 | 14.518 | 7.104 | 38.850 | 1.00 | 33.69 | MOLA C |
| ATOM | 669 | CG | GLN | A 106 | 15.716 | 6.338 | 38.453 | 1.00 | 28.87 | MOLA C |
| ATOM | 670 | CD | GLN | A 106 | 15.354 | 4.916 | 38.150 | 1.00 | 35.09 | MOLA C |
| ATOM | 671 | OE1 | GLN | A 106 | 14.171 | 4.559 | 38.056 | 1.00 | 37.52 | MOLA O |
| ATOM | 672 | NE2 | GLN | A 106 | 16.366 | 4.086 | 37.979 | 1.00 | 39.63 | MOLA N |
| ATOM | 673 | C | GLN | A 106 | 15.436 | 9.152 | 37.798 | 1.00 | 34.32 | MOLA C |
| ATOM | 674 | O | GLN | A 106 | 14.748 | 9.453 | 36.811 | 1.00 | 35.34 | MOLA O |
| ATOM | 675 | N | THR | A 107 | 16.752 | 9.319 | 37.811 | 1.00 | 30.02 | MOLA N |
| ATOM | 676 | CA | THR | A 107 | 17.375 | 9.800 | 36.583 | 1.00 | 32.17 | MOLA C |
| ATOM | 677 | CB | THR | A 107 | 18.904 | 9.857 | 36.645 | 1.00 | 31.21 | MOLA C |
| ATOM | 678 | OG1 | THR | A 107 | 19.308 | 11.039 | 37.342 | 1.00 | 41.15 | MOLA O |
| ATOM | 679 | CG2 | THR | A 107 | 19.458 | 9.919 | 35.223 | 1.00 | 28.05 | MOLA C |
| ATOM | 680 | C | THR | A 107 | 16.999 | 8.942 | 35.372 | 1.00 | 31.85 | MOLA C |
| ATOM | 681 | O | THR | A 107 | 17.059 | 7.703 | 35.436 | 1.00 | 33.54 | MOLA O |
| ATOM | 682 | N | GLY | A 108 | 16.634 | 9.612 | 34.280 | 1.00 | 30.52 | MOLA N |
| ATOM | 683 | CA | GLY | A 108 | 16.270 | 8.950 | 33.036 | 1.00 | 32.51 | MOLA C |
| ATOM | 684 | C | GLY | A 108 | 14.805 | 8.573 | 32.939 | 1.00 | 34.51 | MOLA C |
| ATOM | 685 | O | GLY | A 108 | 14.422 | 7.732 | 32.139 | 1.00 | 39.38 | MOLA O |
| ATOM | 686 | N | THR | A 109 | 13.967 | 9.169 | 33.761 | 1.00 | 32.91 | MOLA N |
| ATOM | 687 | CA | THR | A 109 | 12.556 | 8.914 | 33.657 | 1.00 | 33.67 | MOLA C |
| ATOM | 688 | CB | THR | A 109 | 11.992 | 8.555 | 35.009 | 1.00 | 33.34 | MOLA C |
| ATOM | 689 | OG1 | THR | A 109 | 11.584 | 9.748 | 35.684 | 1.00 | 36.18 | MOLA O |
| ATOM | 690 | CG2 | THR | A 109 | 13.067 | 7.878 | 35.822 | 1.00 | 38.09 | MOLA C |
| ATOM | 691 | C | THR | A 109 | 11.884 | 10.180 | 33.133 | 1.00 | 34.70 | MOLA C |
| ATOM | 692 | O | THR | A 109 | 10.719 | 10.448 | 33.415 | 1.00 | 35.90 | MOLA O |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 693 | N | GLY | A 110 | 12.652 | 10.992 | 32.417 | 1.00 | 34.52 | MOLA N |
| ATOM | 694 | CA | GLY | A 110 | 12.078 | 12.082 | 31.674 | 1.00 | 33.33 | MOLA C |
| ATOM | 695 | C | GLY | A 110 | 11.679 | 13.343 | 32.385 | 1.00 | 31.78 | MOLA C |
| ATOM | 696 | O | GLY | A 110 | 10.702 | 13.988 | 31.997 | 1.00 | 30.36 | MOLA O |
| ATOM | 697 | N | LYS | A 111 | 12.457 | 13.714 | 33.391 | 1.00 | 32.09 | MOLA N |
| ATOM | 698 | CA | LYS | A 111 | 12.298 | 15.005 | 34.049 | 1.00 | 30.94 | MOLA C |
| ATOM | 699 | CB | LYS | A 111 | 13.329 | 15.165 | 35.150 | 1.00 | 31.09 | MOLA C |
| ATOM | 700 | CG | LYS | A 111 | 12.935 | 14.598 | 36.492 | 1.00 | 29.98 | MOLA C |
| ATOM | 701 | CD | LYS | A 111 | 14.153 | 14.611 | 37.370 | 1.00 | 27.11 | MOLA C |
| ATOM | 702 | CE | LYS | A 111 | 14.973 | 13.358 | 37.257 | 1.00 | 32.97 | MOLA C |
| ATOM | 703 | NZ | LYS | A 111 | 14.598 | 12.490 | 38.407 | 1.00 | 32.09 | MOLA N |
| ATOM | 704 | C | LYS | A 111 | 12.537 | 16.105 | 33.046 | 1.00 | 31.61 | MOLA C |
| ATOM | 705 | O | LYS | A 111 | 11.621 | 16.870 | 32.705 | 1.00 | 32.58 | MOLA O |
| ATOM | 706 | N | THR | A 112 | 13.783 | 16.178 | 32.570 | 1.00 | 29.46 | MOLA N |
| ATOM | 707 | CA | THR | A 112 | 14.159 | 17.238 | 31.653 | 1.00 | 25.95 | MOLA C |
| ATOM | 708 | CB | THR | A 112 | 15.698 | 17.329 | 31.431 | 1.00 | 24.53 | MOLA C |
| ATOM | 709 | OG1 | THR | A 112 | 16.350 | 17.496 | 32.702 | 1.00 | 32.58 | MOLA O |
| ATOM | 710 | CG2 | THR | A 112 | 16.084 | 18.495 | 30.543 | 1.00 | 2.00 | MOLA C |
| ATOM | 711 | C | THR | A 112 | 13.357 | 17.122 | 30.359 | 1.00 | 29.83 | MOLA C |
| ATOM | 712 | O | THR | A 112 | 12.987 | 18.151 | 29.755 | 1.00 | 35.34 | MOLA O |
| ATOM | 713 | N | PHE | A 113 | 13.064 | 15.897 | 29.929 | 1.00 | 27.54 | MOLA N |
| ATOM | 714 | CA | PHE | A 113 | 12.241 | 15.740 | 28.739 | 1.00 | 27.65 | MOLA C |
| ATOM | 715 | CB | PHE | A 113 | 11.870 | 14.285 | 28.513 | 1.00 | 24.75 | MOLA C |
| ATOM | 716 | CG | PHE | A 113 | 11.004 | 14.065 | 27.318 | 1.00 | 22.45 | MOLA C |
| ATOM | 717 | CD1 | PHE | A 113 | 11.564 | 13.999 | 26.042 | 1.00 | 24.43 | MOLA C |
| ATOM | 718 | CE1 | PHE | A 113 | 10.749 | 13.810 | 24.911 | 1.00 | 27.65 | MOLA C |
| ATOM | 719 | CZ | PHE | A 113 | 9.361 | 13.660 | 25.074 | 1.00 | 17.35 | MOLA C |
| ATOM | 720 | CE2 | PHE | A 113 | 8.805 | 13.713 | 26.350 | 1.00 | 12.49 | MOLA C |
| ATOM | 721 | CD2 | PHE | A 113 | 9.622 | 13.930 | 27.458 | 1.00 | 20.05 | MOLA C |
| ATOM | 722 | C | PHE | A 113 | 10.956 | 16.566 | 28.924 | 1.00 | 30.23 | MOLA C |
| ATOM | 723 | O | PHE | A 113 | 10.586 | 17.381 | 28.073 | 1.00 | 29.41 | MOLA O |
| ATOM | 724 | N | THR | A 114 | 10.290 | 16.345 | 30.056 | 1.00 | 31.57 | MOLA N |
| ATOM | 725 | CA | THR | A 114 | 9.024 | 16.984 | 30.336 | 1.00 | 30.22 | MOLA C |
| ATOM | 726 | CB | THR | A 114 | 8.479 | 16.573 | 31.696 | 1.00 | 26.87 | MOLA C |
| ATOM | 727 | OG1 | THR | A 114 | 8.299 | 15.160 | 31.706 | 1.00 | 28.52 | MOLA O |
| ATOM | 728 | CG2 | THR | A 114 | 7.142 | 17.237 | 31.925 | 1.00 | 24.43 | MOLA C |
| ATOM | 729 | C | THR | A 114 | 9.201 | 18.467 | 30.406 | 1.00 | 32.12 | MOLA C |
| ATOM | 730 | O | THR | A 114 | 8.387 | 19.238 | 29.870 | 1.00 | 35.90 | MOLA O |
| ATOM | 731 | N | MET | A 115 | 10.259 | 18.881 | 31.085 | 1.00 | 29.83 | MOLA N |
| ATOM | 732 | CA | MET | A 115 | 10.325 | 20.267 | 31.417 | 1.00 | 26.52 | MOLA C |
| ATOM | 733 | C8 | MET | A 115 | 11.073 | 20.472 | 32.695 | 1.00 | 24.20 | MOLA C |
| ATOM | 734 | CG | MET | A 115 | 10.499 | 21.594 | 33.452 | 1.00 | 21.17 | MOLA C |
| ATOM | 735 | SD | MET | A 115 | 9.093 | 20.913 | 34.306 | 1.00 | 50.71 | MOLA S |
| ATOM | 736 | CE | MET | A 115 | 8.768 | 22.028 | 35.678 | 1.00 | 35.67 | MOLA C |
| ATOM | 737 | C | MET | A 115 | 10.905 | 21.105 | 30.305 | 1.00 | 27.47 | MOLA C |
| ATOM | 738 | O | MET | A 115 | 10.616 | 22.287 | 30.226 | 1.00 | 29.77 | MOLA O |
| ATOM | 739 | N | GLU | A 116 | 11.694 | 20.506 | 29.425 | 1.00 | 26.76 | MOLA N |
| ATOM | 740 | CA | GLU | A 116 | 12.299 | 21.287 | 28.352 | 1.00 | 26.47 | MOLA C |
| ATOM | 741 | CB | GLU | A 116 | 13.816 | 21.407 | 28.590 | 1.00 | 25.94 | MOLA C |
| ATOM | 742 | CG | GLU | A 116 | 14.237 | 21.619 | 30.072 | 1.00 | 23.10 | MOLA C |
| ATOM | 743 | CD | GLU | A 116 | 15.762 | 21.782 | 30.251 | 1.00 | 29.16 | MOLA C |
| ATOM | 744 | OE1 | GLU | A 116 | 16.206 | 22.013 | 31.408 | 1.00 | 50.08 | MOLA O |
| ATOM | 745 | OE2 | GLU | A 116 | 16.525 | 21.648 | 29.257 | 1.00 | 15.18 | MOLA O |
| ATOM | 746 | C | GLU | A 116 | 11.997 | 20.699 | 26.955 | 1.00 | 26.80 | MOLA C |
| ATOM | 747 | O | GLU | A 116 | 11.935 | 21.424 | 25.968 | 1.00 | 23.64 | MOLA O |
| ATOM | 748 | N | GLY | A 117 | 11.847 | 19.372 | 26.882 | 1.00 | 27.97 | MOLA N |
| ATOM | 749 | CA | GLY | A 117 | 11.560 | 18.684 | 25.633 | 1.00 | 28.38 | MOLA C |
| ATOM | 750 | C | GLY | A 117 | 12.744 | 18.679 | 24.700 | 1.00 | 30.59 | MOLA C |
| ATOM | 751 | O | GLY | A 117 | 13.872 | 18.848 | 25.141 | 1.00 | 29.46 | MOLA O |
| ATOM | 752 | N | GLU | A 118 | 12.499 | 18.453 | 23.410 | 1.00 | 35.46 | MOLA N |
| ATOM | 753 | CA | GLU | A 118 | 13.582 | 18.496 | 22.450 | 1.00 | 41.18 | MOLA C |
| ATOM | 754 | CB | GLU | A 118 | 14.229 | 17.145 | 22.283 | 1.00 | 41.50 | MOLA C |
| ATOM | 755 | CG | GLU | A 118 | 15.001 | 16.725 | 23.489 | 1.00 | 42.95 | MOLA C |
| ATOM | 756 | CD | GLU | A 118 | 15.189 | 15.254 | 23.507 | 1.00 | 37.17 | MOLA C |
| ATOM | 757 | OE1 | GLU | A 118 | 15.534 | 14.752 | 22.417 | 1.00 | 27.25 | MOLA O |
| ATOM | 758 | OE2 | GLU | A 118 | 14.985 | 14.618 | 24.576 | 1.00 | 37.36 | MOLA O |
| ATOM | 759 | C | GLU | A 118 | 13.167 | 19.000 | 21.114 | 1.00 | 45.41 | MOLA C |
| ATOM | 760 | O | GLU | A 118 | 11.984 | 19.076 | 20.802 | 1.00 | 46.63 | MOLA O |
| ATOM | 761 | N | ARG | A 119 | 14.196 | 19.339 | 20.348 | 1.00 | 51.78 | MOLA N |
| ATOM | 762 | CA | ARG | A 119 | 14.106 | 19.834 | 18.991 | 1.00 | 57.16 | MOLA C |
| ATOM | 763 | CB | ARG | A 119 | 15.468 | 20.416 | 18.617 | 1.00 | 55.94 | MOLA C |
| ATOM | 764 | CG | ARG | A 119 | 15.474 | 21.506 | 17.615 | 1.00 | 54.14 | MOLA C |
| ATOM | 765 | CD | ARG | A 119 | 15.014 | 22.785 | 18.260 | 1.00 | 54.59 | MOLA C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 766 | NE | ARG | A 119 | 13.642 | 23.068 | 17.887 | 1.00 | 63.36 | MOLA N |
| ATOM | 767 | CZ | ARG | A 119 | 13.307 | 23.693 | 16.764 | 1.00 | 65.54 | MOLA C |
| ATOM | 768 | NH1 | ARG | A 119 | 12.039 | 23.910 | 16.482 | 1.00 | 58.78 | MOLA N |
| ATOM | 769 | NH2 | ARG | A 119 | 14.249 | 24.091 | 15.916 | 1.00 | 72.78 | MOLA N |
| ATOM | 770 | C | ARG | A 119 | 13.871 | 18.584 | 18.159 | 1.00 | 61.53 | MOLA C |
| ATOM | 771 | O | ARG | A 119 | 14.769 | 17.726 | 18.089 | 1.00 | 62.56 | MOLA O |
| ATOM | 772 | N | SER | A 120 | 12.689 | 18.460 | 17.547 | 1.00 | 65.13 | MOLA N |
| ATOM | 773 | CA | SER | A 120 | 12.403 | 17.302 | 16.686 | 1.00 | 68.37 | MOLA C |
| ATOM | 774 | CB | SER | A 120 | 11.086 | 17.450 | 15.930 | 1.00 | 67.48 | MOLA C |
| ATOM | 775 | OG | SER | A 120 | 10.014 | 17.281 | 16.832 | 1.00 | 64.35 | MOLA O |
| ATOM | 776 | C | SER | A 120 | 13.575 | 16.988 | 15.749 | 1.00 | 72.26 | MOLA C |
| ATOM | 777 | O | SER | A 120 | 14.034 | 17.843 | 14.979 | 1.00 | 73.37 | MOLA O |
| ATOM | 778 | N | PRO | A 121 | 14.064 | 15.744 | 15.830 | 1.00 | 75.66 | MOLA N |
| ATOM | 779 | CA | PRO | A 121 | 15.306 | 15.273 | 15.207 | 1.00 | 76.09 | MOLA C |
| ATOM | 780 | CB | PRO | A 121 | 15.445 | 13.854 | 15.767 | 1.00 | 77.22 | MOLA C |
| ATOM | 781 | CG | PRO | A 121 | 14.005 | 13.424 | 16.054 | 1.00 | 77.56 | MOLA C |
| ATOM | 782 | CD | PRO | A 121 | 13.357 | 14.670 | 16.564 | 1.00 | 75.47 | MOLA C |
| ATOM | 783 | C | PRO | A 121 | 15.234 | 15.187 | 13.700 | 1.00 | 76.02 | MOLA C |
| ATOM | 784 | O | PRO | A 121 | 14.848 | 14.137 | 13.190 | 1.00 | 76.23 | MOLA O |
| ATOM | 785 | N | ASN | A 122 | 15.608 | 16.260 | 13.002 | 1.00 | 76.21 | MOLA N |
| ATOM | 786 | CA | ASN | A 122 | 15.642 | 16.279 | 11.512 | 1.00 | 78.16 | MOLA C |
| ATOM | 787 | CB | ASN | A 122 | 16.074 | 14.915 | 10.904 | 1.00 | 78.34 | MOLA C |
| ATOM | 788 | CG | ASN | A 122 | 17.587 | 14.630 | 11.066 | 1.00 | 80.48 | MOLA C |
| ATOM | 789 | OD1 | ASN | A 122 | 18.442 | 15.290 | 10.451 | 1.00 | 73.49 | MOLA O |
| ATOM | 790 | ND2 | ASN | A 122 | 17.910 | 13.624 | 11.878 | 1.00 | 78.33 | MOLA N |
| ATOM | 791 | C | ASN | A 122 | 14.368 | 16.830 | 10.822 | 1.00 | 77.82 | MOLA C |
| ATOM | 792 | O | ASN | A 122 | 14.451 | 17.451 | 9.740 | 1.00 | 77.49 | MOLA O |
| ATOM | 793 | N | GLU | A 123 | 13.203 | 16.559 | 11.424 | 1.00 | 76.89 | MOLA N |
| ATOM | 794 | CA | GLU | A 123 | 11.953 | 17.211 | 11.020 | 1.00 | 75.13 | MOLA C |
| ATOM | 795 | CB | GLU | A 123 | 10.741 | 16.601 | 11.709 | 1.00 | 74.51 | MOLA C |
| ATOM | 796 | CG | GLU | A 123 | 10.370 | 15.235 | 11.183 | 1.00 | 72.03 | MOLA C |
| ATOM | 797 | CD | GLU | A 123 | 8.878 | 15.017 | 11.182 | 1.00 | 72.82 | MOLA C |
| ATOM | 798 | OE1 | GLU | A 123 | 8.256 | 15.210 | 10.107 | 1.00 | 68.91 | MOLA O |
| ATOM | 799 | OE2 | GLU | A 123 | 8.327 | 14.690 | 12.259 | 1.00 | 71.09 | MOLA O |
| ATOM | 800 | C | GLU | A 123 | 12.158 | 18.641 | 11.453 | 1.00 | 74.23 | MOLA C |
| ATOM | 801 | O | GLU | A 123 | 12.804 | 18.890 | 12.470 | 1.00 | 75.28 | MOLA O |
| ATOM | 802 | N | GLU | A 124 | 11.667 | 19.604 | 10.698 | 1.00 | 71.92 | MOLA N |
| ATOM | 803 | CA | GLU | A 124 | 12.140 | 20.930 | 11.009 | 1.00 | 70.24 | MOLA C |
| ATOM | 804 | CB | GLU | A 124 | 13.130 | 21.401 | 9.938 | 1.00 | 70.35 | MOLA C |
| ATOM | 805 | CG | GLU | A 124 | 14.384 | 20.520 | 9.799 | 1.00 | 73.17 | MOLA C |
| ATOM | 806 | CD | GLU | A 124 | 15.330 | 20.607 | 11.003 | 1.00 | 76.81 | MOLA C |
| ATOM | 807 | OE1 | GLU | A 124 | 15.656 | 21.746 | 11.435 | 1.00 | 73.96 | MOLA O |
| ATOM | 808 | OE2 | GLU | A 124 | 15.760 | 19.533 | 11.500 | 1.00 | 68.98 | MOLA O |
| ATOM | 809 | C | GLU | A 124 | 11.058 | 21.953 | 11.223 | 1.00 | 69.24 | MOLA C |
| ATOM | 810 | O | GLU | A 124 | 11.068 | 22.991 | 10.558 | 1.00 | 71.92 | MOLA O |
| ATOM | 811 | N | TYR | A 125 | 10.137 | 21.690 | 12.150 | 1.00 | 64.93 | MOLA N |
| ATOM | 812 | CA | TYR | A 125 | 9.156 | 22.700 | 12.500 | 1.00 | 61.98 | MOLA C |
| ATOM | 813 | CB | TYR | A 125 | 8.173 | 22.168 | 13.518 | 1.00 | 60.05 | MOLA C |
| ATOM | 814 | CG | TYR | A 125 | 7.826 | 20.712 | 13.394 | 1.00 | 56.90 | MOLA C |
| ATOM | 815 | CD1 | TYR | A 125 | 6.496 | 20.289 | 13.504 | 1.00 | 40.52 | MOLA C |
| ATOM | 816 | CE1 | TYR | A 125 | 6.155 | 18.947 | 13.435 | 1.00 | 25.84 | MOLA C |
| ATOM | 817 | CZ | TYR | A 125 | 7.153 | 17.998 | 13.229 | 1.00 | 50.92 | MOLA C |
| ATOM | 818 | OH | TYR | A 125 | 6.809 | 16.646 | 13.132 | 1.00 | 53.78 | MOLA O |
| ATOM | 819 | CE2 | TYR | A 125 | 8.493 | 18.404 | 13.099 | 1.00 | 49.97 | MOLA C |
| ATOM | 820 | CD2 | TYR | A 125 | 8.815 | 19.752 | 13.183 | 1.00 | 54.54 | MOLA C |
| ATOM | 821 | C | TYR | A 125 | 9.933 | 23.811 | 13.174 | 1.00 | 61.48 | MOLA C |
| ATOM | 822 | O | TYR | A 125 | 11.087 | 23.599 | 13.559 | 1.00 | 61.50 | MOLA O |
| ATOM | 823 | N | THR | A 126 | 9.328 | 24.988 | 13.328 | 1.00 | 61.27 | MOLA N |
| ATOM | 824 | CA | THR | A 126 | 9.948 | 26.026 | 14.167 | 1.00 | 63.03 | MOLA C |
| ATOM | 825 | CB | THR | A 126 | 9.194 | 27.361 | 14.140 | 1.00 | 63.25 | MOLA C |
| ATOM | 826 | OG1 | THR | A 126 | 7.934 | 27.183 | 13.476 | 1.00 | 64.86 | MOLA O |
| ATOM | 827 | CG2 | THR | A 126 | 10.026 | 28.445 | 13.447 | 1.00 | 59.84 | MOLA C |
| ATOM | 828 | C | THR | A 126 | 9.962 | 25.558 | 15.612 | 1.00 | 63.76 | MOLA C |
| ATOM | 829 | O | THR | A 126 | 9.439 | 24.489 | 15.934 | 1.00 | 65.75 | MOLA O |
| ATOM | 830 | N | TRP | A 127 | 10.549 | 26.341 | 16.502 | 1.00 | 62.83 | MOLA N |
| ATOM | 831 | CA | TRP | A 127 | 10.511 | 25.925 | 17.882 | 1.00 | 62.57 | MOLA C |
| ATOM | 832 | CB | TRP | A 127 | 11.570 | 26.645 | 18.705 | 1.00 | 63.96 | MOLA C |
| ATOM | 833 | CG | TRP | A 127 | 11.436 | 28.119 | 18.675 | 1.00 | 66.44 | MOLA C |
| ATOM | 834 | CD1 | TRP | A 127 | 12.019 | 28.974 | 17.789 | 1.00 | 65.78 | MOLA C |
| ATOM | 835 | NE1 | TRP | A 127 | 11.664 | 30.266 | 18.087 | 1.00 | 78.27 | MOLA N |
| ATOM | 836 | CE2 | TRP | A 127 | 10.833 | 30.266 | 19.181 | 1.00 | 75.72 | MOLA C |
| ATOM | 837 | CD2 | TRP | A 127 | 10.667 | 28.928 | 19.579 | 1.00 | 68.49 | MOLA C |
| ATOM | 838 | CE3 | TRP | A 127 | 9.852 | 28.648 | 20.686 | 1.00 | 70.43 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 839 | CZ3 | TRP | A 127 | 9.232 | 29.703 | 21.348 | 1.00 | 69.09 | MOLA C |
| ATOM | 840 | CH2 | TRP | A 127 | 9.410 | 31.027 | 20.922 | 1.00 | 65.53 | MOLA C |
| ATOM | 841 | CZ2 | TRP | A 127 | 10.206 | 31.331 | 19.846 | 1.00 | 71.27 | MOLA C |
| ATOM | 842 | C | TRP | A 127 | 9.084 | 26.075 | 18.430 | 1.00 | 61.10 | MOLA C |
| ATOM | 843 | O | TRP | A 127 | 8.616 | 25.198 | 19.153 | 1.00 | 60.89 | MOLA O |
| ATOM | 844 | N | GLU | A 128 | 8.386 | 27.148 | 18.038 | 1.00 | 61.13 | MOLA N |
| ATOM | 845 | CA | GLU | A 128 | 6.980 | 27.407 | 18.442 | 1.00 | 60.92 | MOLA C |
| ATOM | 846 | CB | GLU | A 128 | 6.365 | 28.565 | 17.630 | 1.00 | 60.09 | MOLA C |
| ATOM | 847 | CG | GLU | A 128 | 6.940 | 29.959 | 17.825 | 1.00 | 63.61 | MOLA C |
| ATOM | 848 | CD | GLU | A 128 | 8.030 | 30.322 | 16.822 | 1.00 | 77.42 | MOLA C |
| ATOM | 849 | OE1 | GLU | A 128 | 8.475 | 31.490 | 16.840 | 1.00 | 85.03 | MOLA O |
| ATOM | 850 | OE2 | GLU | A 128 | 8.449 | 29.458 | 16.018 | 1.00 | 83.23 | MOLA O |
| ATOM | 851 | C | GLU | A 128 | 6.126 | 26.199 | 18.111 | 1.00 | 60.60 | MOLA C |
| ATOM | 852 | O | GLU | A 128 | 5.118 | 25.898 | 18.749 | 1.00 | 61.80 | MOLA O |
| ATOM | 853 | N | GLU | A 129 | 6.583 | 25.515 | 17.084 | 1.00 | 58.52 | MOLA N |
| ATOM | 854 | CA | GLU | A 129 | 5.818 | 24.588 | 16.319 | 1.00 | 56.41 | MOLA C |
| ATOM | 855 | CB | GLU | A 129 | 6.312 | 24.819 | 14.884 | 1.00 | 56.87 | MOLA C |
| ATOM | 856 | CG | GLU | A 129 | 5.299 | 24.706 | 13.785 | 1.00 | 64.29 | MOLA C |
| ATOM | 857 | CD | GLU | A 129 | 4.138 | 25.633 | 13.995 | 1.00 | 70.41 | MOLA C |
| ATOM | 858 | OE1 | GLU | A 129 | 3.578 | 26.102 | 12.981 | 1.00 | 69.77 | MOLA O |
| ATOM | 859 | OE2 | GLU | A 129 | 3.800 | 25.890 | 15.175 | 1.00 | 76.60 | MOLA O |
| ATOM | 860 | C | GLU | A 129 | 6.080 | 23.123 | 16.730 | 1.00 | 55.46 | MOLA C |
| ATOM | 861 | O | GLU | A 129 | 5.259 | 22.230 | 16.472 | 1.00 | 55.07 | MOLA O |
| ATOM | 862 | N | ASP | A 130 | 7.216 | 22.882 | 17.381 | 1.00 | 51.56 | MOLA N |
| ATOM | 863 | CA | ASP | A 130 | 7.730 | 21.530 | 17.547 | 1.00 | 48.19 | MOLA C |
| ATOM | 864 | CB | ASP | A 130 | 9.156 | 21.619 | 18.053 | 1.00 | 48.24 | MOLA C |
| ATOM | 865 | CG | ASP | A 130 | 9.907 | 20.347 | 17.887 | 1.00 | 43.77 | MOLA C |
| ATOM | 866 | OD1 | ASP | A 130 | 11.010 | 20.405 | 17.317 | 1.00 | 49.48 | MOLA O |
| ATOM | 867 | OD2 | ASP | A 130 | 9.410 | 19.302 | 18.327 | 1.00 | 46.43 | MOLA O |
| ATOM | 868 | C | ASP | A 130 | 6.896 | 20.749 | 18.508 | 1.00 | 47.68 | MOLA C |
| ATOM | 869 | O | ASP | A 130 | 6.603 | 21.244 | 19.577 | 1.00 | 51.23 | MOLA O |
| ATOM | 870 | N | PRO | A 131 | 6.466 | 19.536 | 18.121 | 1.00 | 47.74 | MOLA N |
| ATOM | 871 | CA | PRO | A 131 | 5.620 | 18.637 | 18.953 | 1.00 | 46.17 | MOLA C |
| ATOM | 872 | CB | PRO | A 131 | 5.259 | 17.505 | 17.993 | 1.00 | 45.49 | MOLA C |
| ATOM | 873 | CG | PRO | A 131 | 5.534 | 18.064 | 16.610 | 1.00 | 45.28 | MOLA C |
| ATOM | 874 | CD | PRO | A 131 | 6.721 | 18.959 | 16.794 | 1.00 | 46.78 | MOLA C |
| ATOM | 875 | C | PRO | A 131 | 6.316 | 18.068 | 20.194 | 1.00 | 45.47 | MOLA C |
| ATOM | 876 | O | PRO | A 131 | 5.662 | 17.941 | 21.245 | 1.00 | 45.60 | MOLA O |
| ATOM | 877 | N | LEU | A 132 | 7.607 | 17.714 | 20.054 | 1.00 | 43.25 | MOLA N |
| ATOM | 878 | CA | LEU | A 132 | 8.485 | 17.286 | 21.174 | 1.00 | 40.91 | MOLA C |
| ATOM | 879 | CB | LEU | A 132 | 9.786 | 16.719 | 20.633 | 1.00 | 37.25 | MOLA C |
| ATOM | 880 | CG | LEU | A 132 | 9.853 | 15.345 | 19.977 | 1.00 | 35.16 | MOLA C |
| ATOM | 881 | CD1 | LEU | A 132 | 11.304 | 15.080 | 19.628 | 1.00 | 24.85 | MOLA C |
| ATOM | 882 | CD2 | LEU | A 132 | 9.312 | 14.216 | 20.875 | 1.00 | 16.69 | MOLA C |
| ATOM | 883 | C | LEU | A 132 | 8.815 | 18.414 | 22.212 | 1.00 | 43.37 | MOLA C |
| ATOM | 884 | O | LEU | A 132 | 9.320 | 18.149 | 23.322 | 1.00 | 43.09 | MOLA O |
| ATOM | 885 | N | ALA | A 133 | 8.527 | 19.665 | 21.841 | 1.00 | 42.08 | MOLA N |
| ATOM | 886 | CA | ALA | A 133 | 8.669 | 20.812 | 22.735 | 1.00 | 38.53 | MOLA C |
| ATOM | 887 | CB | ALA | A 133 | 7.859 | 21.975 | 22.201 | 1.00 | 37.88 | MOLA C |
| ATOM | 888 | C | ALA | A 133 | 8.178 | 20.514 | 24.113 | 1.00 | 36.19 | MOLA C |
| ATOM | 889 | O | ALA | A 133 | 7.030 | 20.154 | 24.274 | 1.00 | 35.70 | MOLA O |
| ATOM | 890 | N | GLY | A 134 | 9.022 | 20.722 | 25.113 | 1.00 | 36.21 | MOLA N |
| ATOM | 891 | CA | GLY | A 134 | 8.573 | 20.643 | 26.524 | 1.00 | 35.75 | MOLA C |
| ATOM | 892 | C | GLY | A 134 | 7.820 | 21.868 | 27.061 | 1.00 | 33.83 | MOLA C |
| ATOM | 893 | O | GLY | A 134 | 7.604 | 22.880 | 26.359 | 1.00 | 30.19 | MOLA O |
| ATOM | 894 | N | ILE | A 135 | 7.442 | 21.768 | 28.332 | 1.00 | 32.53 | MOLA N |
| ATOM | 895 | CA | ILE | A 135 | 6.730 | 22.818 | 29.048 | 1.00 | 29.60 | MOLA C |
| ATOM | 896 | CB | ILE | A 135 | 6.606 | 22.482 | 30.499 | 1.00 | 30.81 | MOLA C |
| ATOM | 897 | CG1 | ILE | A 135 | 5.609 | 21.345 | 30.679 | 1.00 | 27.10 | MOLA C |
| ATOM | 898 | CD1 | ILE | A 135 | 5.613 | 20.812 | 32.061 | 1.00 | 13.72 | MOLA C |
| ATOM | 899 | CG2 | ILE | A 135 | 6.161 | 23.725 | 31.294 | 1.00 | 25.97 | MOLA C |
| ATOM | 900 | C | ILE | A 135 | 7.381 | 24.177 | 29.016 | 1.00 | 31.72 | MOLA C |
| ATOM | 901 | O | ILE | A 135 | 6.741 | 25.153 | 28.569 | 1.00 | 34.54 | MOLA O |
| ATOM | 902 | N | ILE | A 136 | 8.610 | 24.275 | 29.537 | 1.00 | 28.56 | MOLA N |
| ATOM | 903 | CA | ILE | A 136 | 9.349 | 25.559 | 29.483 | 1.00 | 28.11 | MOLA C |
| ATOM | 904 | CB | ILE | A 136 | 10.863 | 25.434 | 29.830 | 1.00 | 27.26 | MOLA C |
| ATOM | 905 | CG | 1ILE | A 136 | 11.009 | 25.175 | 31.324 | 1.00 | 27.40 | MOLA C |
| ATOM | 906 | CD1 | ILE | A 136 | 12.416 | 25.196 | 31.822 | 1.00 | 25.50 | MOLA C |
| ATOM | 907 | CG2 | ILE | A 136 | 11.604 | 26.731 | 29.517 | 1.00 | 24.90 | MOLA C |
| ATOM | 908 | C | ILE | A 136 | 9.127 | 26.391 | 28.186 | 1.00 | 28.33 | MOLA C |
| ATOM | 909 | O | ILE | A 136 | 8.559 | 27.489 | 28.251 | 1.00 | 30.44 | MOLA O |
| ATOM | 910 | N | PRO | A 137 | 9.532 | 25.881 | 27.011 | 1.00 | 26.84 | MOLA N |
| ATOM | 911 | CA | PRO | A 137 | 9.321 | 26.747 | 25.845 | 1.00 | 27.34 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 912 | CB | PRO | A 137 | 10.096 | 26.025 | 24.742 | 1.00 | 28.18 | MOLA C |
| ATOM | 913 | CG | PRO | A 137 | 9.952 | 24.568 | 25.072 | 1.00 | 23.64 | MOLA C |
| ATOM | 914 | CD | PRO | A 137 | 10.092 | 24.577 | 26.623 | 1.00 | 27.65 | MOLA C |
| ATOM | 915 | C | PRO | A 137 | 7.830 | 26.855 | 25.440 | 1.00 | 28.24 | MOLA C |
| ATOM | 916 | O | PRO | A 137 | 7.410 | 27.882 | 24.906 | 1.00 | 27.64 | MOLA O |
| ATOM | 917 | N | ARG | A 138 | 7.028 | 25.813 | 25.663 | 1.00 | 27.95 | MOLA N |
| ATOM | 918 | CA | ARG | A 138 | 5.618 | 25.951 | 25.321 | 1.00 | 30.50 | MOLA C |
| ATOM | 919 | CB | ARG | A 138 | 4.860 | 24.683 | 25.642 | 1.00 | 28.36 | MOLA C |
| ATOM | 920 | CG | ARG | A 138 | 5.026 | 23.677 | 24.566 | 1.00 | 26.19 | MOLA C |
| ATOM | 921 | CD | ARG | A 138 | 4.409 | 22.367 | 24.930 | 1.00 | 28.71 | MOLA C |
| ATOM | 922 | NE | ARG | A 138 | 4.787 | 21.406 | 23.918 | 1.00 | 29.74 | MOLA N |
| ATOM | 923 | CZ | ARG | A 138 | 4.000 | 20.978 | 22.939 | 1.00 | 29.03 | MOLA C |
| ATOM | 924 | NH1 | ARG | A 138 | 2.742 | 21.395 | 22.834 | 1.00 | 36.95 | MOLA N |
| ATOM | 925 | NH2 | ARG | A 138 | 4.477 | 20.093 | 22.066 | 1.00 | 51.01 | MOLA N |
| ATOM | 926 | C | ARG | A 138 | 5.022 | 27.152 | 26.073 | 1.00 | 33.14 | MOLA C |
| ATOM | 927 | O | ARG | A 138 | 4.293 | 27.988 | 25.524 | 1.00 | 34.12 | MOLA O |
| ATOM | 928 | N | THR | A 139 | 5.386 | 27.239 | 27.334 | 1.00 | 33.02 | MOLA N |
| ATOM | 929 | CA | THR | A 139 | 4.876 | 28.254 | 28.183 | 1.00 | 34.19 | MOLA C |
| ATOM | 930 | CB | THR | A 139 | 5.307 | 27.944 | 29.586 | 1.00 | 32.20 | MOLA C |
| ATOM | 931 | OG1 | THR | A 139 | 4.410 | 26.961 | 30.099 | 1.00 | 35.50 | MOLA O |
| ATOM | 932 | CG2 | THR | A 139 | 5.256 | 29.178 | 30.446 | 1.00 | 24.60 | MOLA C |
| ATOM | 933 | C | THR | A 139 | 5.328 | 29.645 | 27.757 | 1.00 | 38.01 | MOLA C |
| ATOM | 934 | O | THR | A 139 | 4.545 | 30.584 | 27.791 | 1.00 | 40.83 | MOLA O |
| ATOM | 935 | N | LEU | A 140 | 6.579 | 29.799 | 27.345 | 1.00 | 39.26 | MOLA N |
| ATOM | 936 | CA | LEU | A 140 | 7.029 | 31.129 | 26.976 | 1.00 | 38.03 | MOLA C |
| ATOM | 937 | CB | LEU | A 140 | 8.524 | 31.139 | 26.617 | 1.00 | 39.04 | MOLA C |
| ATOM | 938 | CG | LEU | A 140 | 9.472 | 31.453 | 27.787 | 1.00 | 26.91 | MOLA C |
| ATOM | 939 | CD1 | LEU | A 140 | 8.843 | 31.154 | 29.096 | 1.00 | 25.82 | MOLA C |
| ATOM | 940 | CD2 | LEU | A 140 | 10.683 | 30.644 | 27.642 | 1.00 | 27.88 | MOLA C |
| ATOM | 941 | C | LEU | A 140 | 6.132 | 31.619 | 25.859 | 1.00 | 39.51 | MOLA C |
| ATOM | 942 | O | LEU | A 140 | 5.550 | 32.709 | 25.960 | 1.00 | 38.40 | MOLA O |
| ATOM | 943 | N | HIS | A 141 | 5.980 | 30.776 | 24.831 | 1.00 | 41.16 | MOLA N |
| ATOM | 944 | CA | HIS | A 141 | 5.055 | 31.021 | 23.710 | 1.00 | 42.59 | MOLA C |
| ATOM | 945 | CB | HIS | A 141 | 4.891 | 29.747 | 22.864 | 1.00 | 40.91 | MOLA C |
| ATOM | 946 | CG | HIS | A 141 | 4.452 | 29.988 | 21.447 | 1.00 | 43.27 | MOLA C |
| ATOM | 947 | ND1 | HIS | A 141 | 3.213 | 29.609 | 20.972 | 1.00 | 42.50 | MOLA N |
| ATOM | 948 | CE1 | HIS | A 141 | 3.115 | 29.926 | 19.692 | 1.00 | 36.73 | MOLA C |
| ATOM | 949 | NE2 | HIS | A 141 | 4.247 | 30.493 | 19.313 | 1.00 | 35.42 | MOLA N |
| ATOM | 950 | CD2 | HIS | A 141 | 5.100 | 30.544 | 20.393 | 1.00 | 53.75 | MOLA C |
| ATOM | 951 | C | HIS | A 141 | 3.693 | 31.537 | 24.231 | 1.00 | 43.82 | MOLA C |
| ATOM | 952 | O | HIS | A 141 | 3.410 | 32.749 | 24.156 | 1.00 | 44.22 | MOLA O |
| ATOM | 953 | N | GLN | A 142 | 2.873 | 30.646 | 24.795 | 1.00 | 43.34 | MOLA N |
| ATOM | 954 | CA | GLN | A 142 | 1.521 | 31.046 | 25.246 | 1.00 | 44.98 | MOLA C |
| ATOM | 955 | CB | GLN | A 142 | 0.869 | 29.980 | 26.137 | 1.00 | 44.80 | MOLA C |
| ATOM | 956 | CG | GLN | A 142 | 0.769 | 28.658 | 25.446 | 1.00 | 51.72 | MOLA C |
| ATOM | 957 | CD | GLN | A 142 | 0.337 | 28.825 | 24.019 | 1.00 | 63.82 | MOLA C |
| ATOM | 958 | OE1 | GLN | A 142 | −0.850 | 29.019 | 23.752 | 1.00 | 68.04 | MOLA O |
| ATOM | 959 | NE2 | GLN | A 142 | 1.298 | 28.775 | 23.084 | 1.00 | 53.20 | MOLA N |
| ATOM | 960 | C | GLN | A 142 | 1.426 | 32.418 | 25.911 | 1.00 | 43.31 | MOLA C |
| ATOM | 961 | O | GLN | A 142 | 0.478 | 33.149 | 25.656 | 1.00 | 45.91 | MOLA O |
| ATOM | 962 | N | ILE | A 143 | 2.384 | 32.755 | 26.768 | 1.00 | 41.57 | MOLA N |
| ATOM | 963 | CA | ILE | A 143 | 2.390 | 34.057 | 27.413 | 1.00 | 39.93 | MOLA C |
| ATOM | 964 | CB | ILE | A 143 | 3.643 | 34.277 | 28.309 | 1.00 | 42.38 | MOLA C |
| ATOM | 965 | CG1 | ILE | A 143 | 3.776 | 33.193 | 29.391 | 1.00 | 38.54 | MOLA C |
| ATOM | 966 | CD1 | ILE | A 143 | 5.034 | 33.331 | 30.269 | 1.00 | 31.04 | MOLA C |
| ATOM | 967 | CG2 | ILE | A 143 | 3.560 | 35.615 | 28.992 | 1.00 | 43.86 | MOLA C |
| ATOM | 968 | C | ILE | A 143 | 2.312 | 35.110 | 26.296 | 1.00 | 41.45 | MOLA C |
| ATOM | 969 | O | ILE | A 143 | 1.287 | 35.787 | 26.119 | 1.00 | 45.15 | MOLA O |
| ATOM | 970 | N | PHE | A 144 | 3.356 | 35.228 | 25.496 | 1.00 | 36.89 | MOLA N |
| ATOM | 971 | CA | PHE | A 144 | 3.255 | 36.146 | 24.396 | 1.00 | 35.06 | MOLA C |
| ATOM | 972 | CB | PHE | A 144 | 4.453 | 36.009 | 23.515 | 1.00 | 33.81 | MOLA C |
| ATOM | 973 | CG | PHE | A 144 | 5.659 | 36.418 | 24.211 | 1.00 | 40.91 | MOLA C |
| ATOM | 974 | CD1 | PHE | A 144 | 6.021 | 37.745 | 24.243 | 1.00 | 40.00 | MOLA C |
| ATOM | 975 | CE1 | PHE | A 144 | 7.115 | 38.146 | 24.943 | 1.00 | 26.43 | MOLA C |
| ATOM | 976 | CZ | PHE | A 144 | 7.814 | 37.256 | 25.647 | 1.00 | 25.71 | MOLA C |
| ATOM | 977 | CE2 | PHE | A 144 | 7.443 | 35.925 | 25.669 | 1.00 | 31.74 | MOLA C |
| ATOM | 978 | CD2 | PHE | A 144 | 6.361 | 35.514 | 24.970 | 1.00 | 39.47 | MOLA C |
| ATOM | 979 | C | PHE | A 144 | 1.977 | 36.011 | 23.609 | 1.00 | 35.27 | MOLA C |
| ATOM | 980 | O | PHE | A 144 | 1.419 | 36.996 | 23.184 | 1.00 | 35.51 | MOLA O |
| ATOM | 981 | N | GLU | A 145 | 1.484 | 34.806 | 23.418 | 1.00 | 36.78 | MOLA N |
| ATOM | 982 | CA | GLU | A 145 | 0.257 | 34.708 | 22.662 | 1.00 | 40.04 | MOLA C |
| ATOM | 983 | CB | GLU | A 145 | −0.049 | 33.256 | 22.257 | 1.00 | 38.62 | MOLA C |
| ATOM | 984 | CG | GLU | A 145 | 1.046 | 32.615 | 21.359 | 1.00 | 48.44 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 985 | CD | GLU | A 145 | 0.839 | 32.768 | 19.820 | 1.00 | 67.68 | MOLA | C |
| ATOM | 986 | OE1 | GLU | A 145 | −0.317 | 32.632 | 19.336 | 1.00 | 77.39 | MOLA | O |
| ATOM | 987 | OE2 | GLU | A 145 | 1.849 | 32.977 | 19.090 | 1.00 | 56.92 | MOLA | O |
| ATOM | 988 | C | GLU | A 145 | −0.841 | 35.422 | 23.487 | 1.00 | 39.74 | MOLA | C |
| ATOM | 989 | O | GLU | A 145 | −1.007 | 36.624 | 23.364 | 1.00 | 43.02 | MOLA | O |
| ATOM | 990 | N | LYS | A 146 | −1.551 | 34.717 | 24.343 | 1.00 | 39.14 | MOLA | N |
| ATOM | 991 | CA | LYS | A 146 | −2.572 | 35.334 | 25.216 | 1.00 | 42.31 | MOLA | C |
| ATOM | 992 | CB | LYS | A 146 | −2.673 | 34.512 | 26.480 | 1.00 | 39.79 | MOLA | C |
| ATOM | 993 | CG | LYS | A 146 | −3.168 | 33.131 | 26.097 | 1.00 | 45.54 | MOLA | C |
| ATOM | 994 | CD | LYS | A 146 | −2.387 | 32.056 | 26.786 | 1.00 | 32.47 | MOLA | C |
| ATOM | 995 | CE | LYS | A 146 | −2.519 | 32.246 | 28.276 | 1.00 | 45.03 | MOLA | C |
| ATOM | 996 | NZ | LYS | A 146 | −3.934 | 32.591 | 28.625 | 1.00 | 38.63 | MOLA | N |
| ATOM | 997 | C | LYS | A 146 | −2.512 | 36.855 | 25.550 | 1.00 | 43.05 | MOLA | C |
| ATOM | 998 | O | LYS | A 146 | −3.481 | 37.566 | 25.297 | 1.00 | 43.15 | MOLA | O |
| ATOM | 999 | N | LEU | A 147 | −1.402 | 37.352 | 26.104 | 1.00 | 42.49 | MOLA | N |
| ATOM | 1000 | CA | LEU | A 147 | −1.288 | 38.785 | 26.423 | 1.00 | 39.93 | MOLA | C |
| ATOM | 1001 | CB | LEU | A 147 | −0.064 | 39.081 | 27.310 | 1.00 | 38.65 | MOLA | C |
| ATOM | 1002 | CG | LEU | A 147 | −0.083 | 38.293 | 28.634 | 1.00 | 39.31 | MOLA | C |
| ATOM | 1003 | CD1 | LEU | A 147 | 0.904 | 38.784 | 29.689 | 1.00 | 34.41 | MOLA | C |
| ATOM | 1004 | CD2 | LEU | A 147 | −1.477 | 38.258 | 29.248 | 1.00 | 50.05 | MOLA | C |
| ATOM | 1005 | C | LEU | A 147 | −1.325 | 39.658 | 25.156 | 1.00 | 40.42 | MOLA | C |
| ATOM | 1006 | O | LEU | A 147 | −2.083 | 40.648 | 25.092 | 1.00 | 40.15 | MOLA | O |
| ATOM | 1007 | N | THR | A 148 | −0.521 | 39.296 | 24.153 | 1.00 | 39.36 | MOLA | N |
| ATOM | 1008 | CA | THR | A 148 | −0.621 | 39.950 | 22.859 | 1.00 | 37.52 | MOLA | C |
| ATOM | 1009 | CB | THR | A 148 | 0.138 | 39.213 | 21.768 | 1.00 | 37.25 | MOLA | C |
| ATOM | 1010 | OG1 | THR | A 148 | 1.425 | 39.813 | 21.580 | 1.00 | 37.69 | MOLA | O |
| ATOM | 1011 | CG2 | THR | A 148 | −0.603 | 39.325 | 20.489 | 1.00 | 34.59 | MOLA | C |
| ATOM | 1012 | C | THR | A 148 | −2.074 | 39.939 | 22.477 | 1.00 | 37.96 | MOLA | C |
| ATOM | 1013 | O | THR | A 148 | −2.659 | 40.989 | 22.314 | 1.00 | 38.57 | MOLA | O |
| ATOM | 1014 | N | ASP | A 149 | −2.673 | 38.755 | 22.375 | 1.00 | 38.78 | MOLA | N |
| ATOM | 1015 | CA | ASP | A 149 | −4.060 | 38.648 | 21.960 | 1.00 | 39.62 | MOLA | C |
| ATOM | 1016 | CB | ASP | A 149 | −4.601 | 37.262 | 22.194 | 1.00 | 39.68 | MOLA | C |
| ATOM | 1017 | CG | ASP | A 149 | −5.980 | 37.076 | 21.589 | 1.00 | 46.58 | MOLA | C |
| ATOM | 1018 | OD1 | ASP | A 149 | −6.845 | 36.470 | 22.260 | 1.00 | 49.38 | MOLA | O |
| ATOM | 1019 | OD2 | ASP | A 149 | −6.199 | 37.540 | 20.439 | 1.00 | 59.77 | MOLA | O |
| ATOM | 1020 | C | ASP | A 149 | −5.007 | 39.627 | 22.641 | 1.00 | 42.31 | MOLA | C |
| ATOM | 1021 | O | ASP | A 149 | −5.704 | 40.369 | 21.948 | 1.00 | 48.03 | MOLA | O |
| ATOM | 1022 | N | ASN | A 150 | −5.090 | 39.643 | 23.970 | 1.00 | 40.65 | MOLA | N |
| ATOM | 1023 | CA | ASN | A 150 | −6.045 | 40.562 | 24.581 | 1.00 | 41.42 | MOLA | C |
| ATOM | 1024 | CB | ASN | A 150 | −6.777 | 39.925 | 25.761 | 1.00 | 40.13 | MOLA | C |
| ATOM | 1025 | CG | ASN | A 150 | −5.973 | 39.926 | 27.014 | 1.00 | 47.01 | MOLA | C |
| ATOM | 1026 | OD1 | ASN | A 150 | −4.739 | 39.872 | 26.982 | 1.00 | 59.61 | MOLA | O |
| ATOM | 1027 | ND2 | ASN | A 150 | −6.666 | 39.996 | 28.153 | 1.00 | 50.95 | MOLA | N |
| ATOM | 1028 | C | ASN | A 150 | −5.436 | 41.981 | 24.835 | 1.00 | 43.96 | MOLA | C |
| ATOM | 1029 | O | ASN | A 150 | −6.002 | 42.868 | 25.506 | 1.00 | 40.96 | MOLA | O |
| ATOM | 1030 | N | GLY | A 151 | −4.274 | 42.187 | 24.237 | 1.00 | 45.93 | MOLA | N |
| ATOM | 1031 | CA | GLY | A 151 | −3.746 | 43.520 | 24.107 | 1.00 | 48.24 | MOLA | C |
| ATOM | 1032 | C | GLY | A 151 | −2.861 | 43.913 | 25.244 | 1.00 | 49.62 | MOLA | C |
| ATOM | 1033 | O | GLY | A 151 | −1.832 | 44.542 | 25.024 | 1.00 | 49.64 | MOLA | O |
| ATOM | 1034 | N | THR | A 152 | −3.245 | 43.522 | 26.456 | 1.00 | 50.25 | MOLA | N |
| ATOM | 1035 | CA | THR | A 152 | −2.496 | 43.908 | 27.653 | 1.00 | 49.74 | MOLA | C |
| ATOM | 1036 | CB | THR | A 152 | −2.301 | 42.740 | 28.573 | 1.00 | 49.50 | MOLA | C |
| ATOM | 1037 | OG1 | THR | A 152 | −3.582 | 42.243 | 28.982 | 1.00 | 52.18 | MOLA | O |
| ATOM | 1038 | CG2 | THR | A 152 | −1.498 | 43.180 | 29.787 | 1.00 | 51.51 | MOLA | C |
| ATOM | 1039 | C | THR | A 152 | −1.121 | 44.482 | 27.356 | 1.00 | 49.43 | MOLA | C |
| ATOM | 1040 | O | THR | A 152 | −0.542 | 44.278 | 26.294 | 1.00 | 49.64 | MOLA | O |
| ATOM | 1041 | N | GLU | A 153 | −0.591 | 45.217 | 28.306 | 1.00 | 50.27 | MOLA | N |
| ATOM | 1042 | CA | GLU | A 153 | 0.708 | 45.801 | 28.116 | 1.00 | 52.77 | MOLA | C |
| ATOM | 1043 | CB | GLU | A 153 | 0.630 | 47.287 | 28.449 | 1.00 | 54.16 | MOLA | C |
| ATOM | 1044 | CG | GLU | A 153 | 1.929 | 48.050 | 28.349 | 1.00 | 54.39 | MOLA | C |
| ATOM | 1045 | CD | GLU | A 153 | 1.768 | 49.444 | 28.883 | 1.00 | 50.59 | MOLA | C |
| ATOM | 1046 | OE1 | GLU | A 153 | 1.984 | 50.382 | 28.106 | 1.00 | 58.28 | MOLA | O |
| ATOM | 1047 | OE2 | GLU | A 153 | 1.392 | 49.606 | 30.067 | 1.00 | 50.00 | MOLA | O |
| ATOM | 1048 | C | GLU | A 153 | 1.588 | 45.056 | 29.094 | 1.00 | 53.91 | MOLA | C |
| ATOM | 1049 | O | GLU | A 153 | 1.393 | 45.168 | 30.321 | 1.00 | 54.63 | MOLA | O |
| ATOM | 1050 | N | PHE | A 154 | 2.543 | 44.285 | 28.568 | 1.00 | 53.35 | MOLA | N |
| ATOM | 1051 | CA | PHE | A 154 | 3.338 | 43.378 | 29.421 | 1.00 | 52.36 | MOLA | C |
| ATOM | 1052 | CB | PHE | A 154 | 2.769 | 41.953 | 29.352 | 1.00 | 52.70 | MOLA | C |
| ATOM | 1053 | CG | PHE | A 154 | 2.805 | 41.335 | 27.964 | 1.00 | 56.20 | MOLA | C |
| ATOM | 1054 | CD1 | PHE | A 154 | 3.666 | 40.285 | 27.676 | 1.00 | 58.84 | MOLA | C |
| ATOM | 1055 | CE1 | PHE | A 154 | 3.697 | 39.717 | 26.407 | 1.00 | 62.87 | MOLA | C |
| ATOM | 1056 | CZ | PHE | A 154 | 2.859 | 40.197 | 25.402 | 1.00 | 62.99 | MOLA | C |
| ATOM | 1057 | CE2 | PHE | A 154 | 1.995 | 41.234 | 25.673 | 1.00 | 60.70 | MOLA | C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 1058 | CD2 | PHE | A 154 | 1.968 | 41.798 | 26.952 | 1.00 | 60.65 | MOLA C |
| ATOM | 1059 | C | PHE | A 154 | 4.823 | 43.335 | 29.113 | 1.00 | 49.85 | MOLA C |
| ATOM | 1060 | O | PHE | A 154 | 5.206 | 43.277 | 27.955 | 1.00 | 51.22 | MOLA O |
| ATOM | 1061 | N | SER | A 155 | 5.655 | 43.373 | 30.148 | 1.00 | 47.17 | MOLA N |
| ATOM | 1062 | CA | SER | A 155 | 7.081 | 43.122 | 29.978 | 1.00 | 44.48 | MOLA C |
| ATOM | 1063 | CB | SER | A 155 | 7.907 | 44.190 | 30.668 | 1.00 | 45.28 | MOLA C |
| ATOM | 1064 | OG | SER | A 155 | 7.643 | 44.194 | 32.067 | 1.00 | 48.51 | MOLA O |
| ATOM | 1065 | C | SER | A 155 | 7.397 | 41.755 | 30.587 | 1.00 | 42.64 | MOLA C |
| ATOM | 1066 | O | SER | A 155 | 6.953 | 41.433 | 31.702 | 1.00 | 43.08 | MOLA O |
| ATOM | 1067 | N | VAL | A 156 | 8.169 | 40.960 | 29.855 | 1.00 | 39.40 | MOLA N |
| ATOM | 1068 | CA | VAL | A 156 | 8.531 | 39.601 | 30.272 | 1.00 | 36.95 | MOLA C |
| ATOM | 1069 | CB | VAL | A 156 | 8.095 | 38.619 | 29.175 | 1.00 | 35.98 | MOLA C |
| ATOM | 1070 | CG1 | VAL | A 156 | 8.573 | 37.248 | 29.455 | 1.00 | 23.39 | MOLA C |
| ATOM | 1071 | CG2 | VAL | A 156 | 6.565 | 38.663 | 29.006 | 1.00 | 40.51 | MOLA C |
| ATOM | 1072 | C | VAL | A 156 | 10.038 | 39.455 | 30.481 | 1.00 | 36.70 | MOLA C |
| ATOM | 1073 | O | VAL | A 156 | 10.822 | 39.741 | 29.566 | 1.00 | 36.00 | MOLA O |
| ATOM | 1074 | N | LYS | A 157 | 10.452 | 39.025 | 31.669 | 1.00 | 36.04 | MOLA N |
| ATOM | 1075 | CA | LYS | A 157 | 11.879 | 38.819 | 31.911 | 1.00 | 40.10 | MOLA C |
| ATOM | 1076 | CB | LYS | A 157 | 12.452 | 39.920 | 32.820 | 1.00 | 41.15 | MOLA C |
| ATOM | 1077 | CG | LYS | A 157 | 12.078 | 39.818 | 34.309 | 1.00 | 43.84 | MOLA C |
| ATOM | 1078 | CD | LYS | A 157 | 12.442 | 41.108 | 35.052 | 1.00 | 44.81 | MOLA C |
| ATOM | 1079 | CE | LYS | A 157 | 12.012 | 41.062 | 36.520 | 1.00 | 51.02 | MOLA C |
| ATOM | 1080 | NZ | LYS | A 157 | 12.005 | 42.436 | 37.128 | 1.00 | 45.21 | MOLA N |
| ATOM | 1081 | C | LYS | A 157 | 12.119 | 37.446 | 32.502 | 1.00 | 39.71 | MOLA C |
| ATOM | 1082 | O | LYS | A 157 | 11.219 | 36.937 | 33.176 | 1.00 | 43.11 | MOLA O |
| ATOM | 1083 | N | VAL | A 158 | 13.305 | 36.852 | 32.285 | 1.00 | 38.05 | MOLA N |
| ATOM | 1084 | CA | VAL | A 158 | 13.582 | 35.476 | 32.813 | 1.00 | 38.44 | MOLA C |
| ATOM | 1085 | CB | VAL | A 158 | 13.315 | 34.466 | 31.743 | 1.00 | 35.61 | MOLA C |
| ATOM | 1086 | CG1 | VAL | A 158 | 11.932 | 34.669 | 31.217 | 1.00 | 38.26 | MOLA C |
| ATOM | 1087 | CG2 | VAL | A 158 | 14.304 | 34.654 | 30.645 | 1.00 | 31.90 | MOLA C |
| ATOM | 1088 | C | VAL | A 158 | 14.977 | 35.126 | 33.415 | 1.00 | 40.53 | MOLA C |
| ATOM | 1089 | O | VAL | A 158 | 16.009 | 35.559 | 32.908 | 1.00 | 42.08 | MOLA O |
| ATOM | 1090 | N | SER | A 159 | 15.005 | 34.315 | 34.473 | 1.00 | 40.72 | MOLA N |
| ATOM | 1091 | CA | SER | A 159 | 16.279 | 33.920 | 35.088 | 1.00 | 43.10 | MOLA C |
| ATOM | 1092 | CB | SER | A 159 | 16.318 | 34.438 | 36.504 | 1.00 | 43.43 | MOLA C |
| ATOM | 1093 | OG | SER | A 159. | 15.131 | 33.993 | 37.148 | 1.00 | 46.97 | MOLA O |
| ATOM | 1094 | C | SER | A 159 | 16.421 | 32.411 | 35.188 | 1.00 | 43.20 | MOLA C |
| ATOM | 1095 | O | SER | A 159 | 15.529 | 31.752 | 35.678 | 1.00 | 45.99 | MOLA O |
| ATOM | 1096 | N | LEU | A 160 | 17.542 | 31.860 | 34.767 | 1.00 | 42.19 | MOLA N |
| ATOM | 1097 | CA | LEU | A 160 | 17.766 | 30.441 | 34.953 | 1.00 | 44.35 | MOLA C |
| ATOM | 1098 | CB | LEU | A 160 | 17.873 | 29.714 | 33.624 | 1.00 | 46.01 | MOLA C |
| ATOM | 1099 | CG | LEU | A 160 | 18.458 | 28.319 | 33.817 | 1.00 | 46.96 | MOLA C |
| ATOM | 1100 | CD1 | LEU | A 160 | 17.432 | 27.424 | 34.491 | 1.00 | 45.08 | MOLA C |
| ATOM | 1101 | CD2 | LEU | A 160 | 18.885 | 27.752 | 32.502 | 1.00 | 45.00 | MOLA C |
| ATOM | 1102 | C | LEU | A 160 | 19.023 | 30.140 | 35.757 | 1.00 | 46.06 | MOLA C |
| ATOM | 1103 | O | LEU | A 160 | 20.147 | 30.499 | 35.371 | 1.00 | 46.39 | MOLA O |
| ATOM | 1104 | N | LEU | A 161 | 18.828 | 29.448 | 36.866 | 1.00 | 44.74 | MOLA N |
| ATOM | 1105 | CA | LEU | A 161 | 19.927 | 29.143 | 37.721 | 1.00 | 45.55 | MOLA C |
| ATOM | 1106 | CB | LEU | A 161 | 19.862 | 29.986 | 38.982 | 1.00 | 44.78 | MOLA C |
| ATOM | 1107 | CG | LEU | A 161 | 18.860 | 29.524 | 40.036 | 1.00 | 40.96 | MOLA C |
| ATOM | 1108 | CD1 | LEU | A 161 | 19.354 | 28.302 | 40.752 | 1.00 | 42.59 | MOLA C |
| ATOM | 1109 | CD2 | LEU | A 161 | 18.668 | 30.621 | 41.006 | 1.00 | 29.68 | MOLA C |
| ATOM | 1110 | C | LEU | A 161 | 19.884 | 27.675 | 38.076 | 1.00 | 49.54 | MOLA C |
| ATOM | 1111 | O | LEU | A 161 | 18.943 | 26.955 | 37.739 | 1.00 | 52.44 | MOLA O |
| ATOM | 1112 | N | GLU | A 162 | 20.889 | 27.253 | 38.827 | 1.00 | 50.94 | MOLA N |
| ATOM | 1113 | CA | GLU | A 162 | 21.116 | 25.858 | 39.059 | 1.00 | 49.73 | MOLA C |
| ATOM | 1114 | CB | GLU | A 162 | 22.163 | 25.455 | 38.031 | 1.00 | 49.64 | MOLA C |
| ATOM | 1115 | CG | GLU | A 162 | 22.321 | 24.004 | 37.674 | 1.00 | 50.95 | MOLA C |
| ATOM | 1116 | CD | GLU | A 162 | 23.581 | 23.839 | 36.850 | 1.00 | 62.13 | MOLA C |
| ATOM | 1117 | OE1 | GLU | A 162 | 24.010 | 22.697 | 36.562 | 1.00 | 77.52 | MOLA O |
| ATOM | 1118 | OE2 | GLU | A 162 | 24.163 | 24.888 | 36.503 | 1.00 | 58.50 | MOLA O |
| ATOM | 1119 | C | GLU | A 162 | 21.625 | 25.727 | 40.495 | 1.00 | 47.97 | MOLA C |
| ATOM | 1120 | O | GLU | A 162 | 22.282 | 26.615 | 41.008 | 1.00 | 46.53 | MOLA O |
| ATOM | 1121 | N | ILE | A 163 | 21.302 | 24.631 | 41.150 | 1.00 | 47.37 | MOLA N |
| ATOM | 1122 | CA | ILE | A 163 | 21.708 | 24.447 | 42.521 | 1.00 | 49.03 | MOLA C |
| ATOM | 1123 | CB | ILE | A 163 | 20.472 | 24.233 | 43.434 | 1.00 | 48.35 | MOLA C |
| ATOM | 1124 | CG1 | ILE | A 163 | 19.830 | 25.563 | 43.784 | 1.00 | 45.58 | MOLA C |
| ATOM | 1125 | CD1 | ILE | A 163 | 18.564 | 25.392 | 44.594 | 1.00 | 45.92 | MOLA C |
| ATOM | 1126 | CG2 | ILE | A 163 | 20.830 | 23.494 | 44.732 | 1.00 | 48.78 | MOLA C |
| ATOM | 1127 | C | ILE | A 163 | 22.590 | 23.227 | 42.617 | 1.00 | 51.67 | MOLA C |
| ATOM | 1128 | O | ILE | A 163 | 22.090 | 22.120 | 42.881 | 1.00 | 53.11 | MOLA O |
| ATOM | 1129 | N | TYR | A 164 | 23.895 | 23.392 | 42.409 | 1.00 | 53.09 | MOLA N |
| ATOM | 1130 | CA | TYR | A 164 | 24.783 | 22.237 | 42.584 | 1.00 | 54.93 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1131 | CB | TYR | A 164 | 25.820 | 22.087 | 41.456 | 1.00 | 56.40 | MOLA C |
| ATOM | 1132 | CG | TYR | A 164 | 26.724 | 20.876 | 41.663 | 1.00 | 61.65 | MOLA C |
| ATOM | 1133 | CD1 | TYR | A 164 | 27.906 | 20.988 | 42.401 | 1.00 | 66.15 | MOLA C |
| ATOM | 1134 | CE1 | TYR | A 164 | 28.732 | 19.884 | 42.620 | 1.00 | 70.93 | MOLA C |
| ATOM | 1135 | CZ | TYR | A 164 | 28.383 | 18.651 | 42.098 | 1.00 | 70.56 | MOLA C |
| ATOM | 1136 | OH | TYR | A 164 | 29.217 | 17.576 | 42.332 | 1.00 | 70.12 | MOLA O |
| ATOM | 1137 | CE2 | TYR | A 164 | 27.209 | 18.508 | 41.356 | 1.00 | 65.07 | MOLA C |
| ATOM | 1138 | CD2 | TYR | A 164 | 26.386 | 19.617 | 41.148 | 1.00 | 59.47 | MOLA C |
| ATOM | 1139 | C | TYR | A 164 | 25.458 | 22.213 | 43.957 | 1.00 | 55.14 | MOLA C |
| ATOM | 1140 | O | TYR | A 164 | 26.409 | 22.964 | 44.216 | 1.00 | 55.05 | MOLA O |
| ATOM | 1141 | N | ASN | A 165 | 24.963 | 21.351 | 44.841 | 1.00 | 55.31 | MOLA N |
| ATOM | 1142 | CA | ASN | A 165 | 25.620 | 21.178 | 46.118 | 1.00 | 54.82 | MOLA C |
| ATOM | 1143 | CB | ASN | A 165 | 27.115 | 21.058 | 45.870 | 1.00 | 53.34 | MOLA C |
| ATOM | 1144 | CG | ASN | A 165 | 27.797 | 20.187 | 46.868 | 1.00 | 56.57 | MOLA C |
| ATOM | 1145 | OD1 | ASN | A 165 | 27.150 | 19.541 | 47.703 | 1.00 | 56.19 | MOLA O |
| ATOM | 1146 | ND2 | ASN | A 165 | 29.128 | 20.141 | 46.785 | 1.00 | 64.19 | MOLA N |
| ATOM | 1147 | C | ASN | A 165 | 25.371 | 22.399 | 46.957 | 1.00 | 54.81 | MOLA C |
| ATOM | 1148 | O | ASN | A 165 | 26.305 | 22.988 | 47.500 | 1.00 | 54.56 | MOLA O |
| ATOM | 1149 | N | GLU | A 166 | 24.113 | 22.814 | 47.004 | 1.00 | 56.39 | MOLA N |
| ATOM | 1150 | CA | GLU | A 166 | 23.711 | 24.009 | 47.748 | 1.00 | 57.66 | MOLA C |
| ATOM | 1151 | CB | GLU | A 166 | 23.828 | 23.722 | 49.236 | 1.00 | 56.61 | MOLA C |
| ATOM | 1152 | CG | GLU | A 166 | 22.575 | 24.046 | 49.982 | 1.00 | 69.15 | MOLA C |
| ATOM | 1153 | CD | GLU | A 166 | 22.356 | 23.123 | 51.156 | 1.00 | 90.11 | MOLA C |
| ATOM | 1154 | OE1 | GLU | A 166 | 23.336 | 22.454 | 51.560 | 1.00 | 95.72 | MOLA O |
| ATOM | 1155 | OE2 | GLU | A 166 | 21.207 | 23.062 | 51.662 | 1.00 | 95.49 | MOLA O |
| ATOM | 1156 | C | GLU | A 166 | 24.475 | 25.306 | 47.341 | 1.00 | 57.33 | MOLA C |
| ATOM | 1157 | O | GLU | A 166 | 24.608 | 26.246 | 48.112 | 1.00 | 58.47 | MOLA O |
| ATOM | 1158 | N | GLU | A 167 | 24.976 | 25.344 | 46.116 | 1.00 | 57.02 | MOLA N |
| ATOM | 1159 | CA | GLU | A 167 | 25.630 | 26.526 | 45.574 | 1.00 | 55.44 | MOLA C |
| ATOM | 1160 | CB | GLU | A 167 | 27.097 | 26.245 | 45.261 | 1.00 | 55.11 | MOLA C |
| ATOM | 1161 | CG | GLU | A 167 | 27.975 | 26.246 | 46.506 | 1.00 | 59.42 | MOLA C |
| ATOM | 1162 | CD | GLU | A 167 | 29.231 | 25.406 | 46.322 | 1.00 | 67.51 | MOLA C |
| ATOM | 1163 | OE1 | GLU | A 167 | 30.183 | 25.879 | 45.663 | 1.00 | 41.20 | MOLA O |
| ATOM | 1164 | OE2 | GLU | A 167 | 29.260 | 24.260 | 46.842 | 1.00 | 81.16 | MOLA O |
| ATOM | 1165 | C | GLU | A 167 | 24.873 | 26.941 | 44.319 | 1.00 | 53.74 | MOLA C |
| ATOM | 1166 | O | GLU | A 167 | 24.240 | 26.109 | 43.646 | 1.00 | 55.47 | MOLA O |
| ATOM | 1167 | N | LEU | A 168 | 24.907 | 28.227 | 44.007 | 1.00 | 48.22 | MOLA N |
| ATOM | 1168 | CA | LEU | A 168 | 24.077 | 28.705 | 42.944 | 1.00 | 43.66 | MOLA C |
| ATOM | 1169 | CB | LEU | A 168 | 23.283 | 29.892 | 43.411 | 1.00 | 39.63 | MOLA C |
| ATOM | 1170 | CG | LEU | A 168 | 22.044 | 29.601 | 44.224 | 1.00 | 40.18 | MOLA C |
| ATOM | 1171 | CD1 | LEU | A 168 | 22.246 | 28.579 | 45.313 | 1.00 | 25.07 | MOLA C |
| ATOM | 1172 | CD2 | LEU | A 168 | 21.577 | 30.921 | 44.819 | 1.00 | 59.69 | MOLA C |
| ATOM | 1173 | C | LEU | A 168 | 24.928 | 29.160 | 41.832 | 1.00 | 44.61 | MOLA C |
| ATOM | 1174 | O | LEU | A 168 | 25.946 | 29.792 | 42.081 | 1.00 | 46.40 | MOLA O |
| ATOM | 1175 | N | PHE | A 169 | 24.507 | 28.856 | 40.607 | 1.00 | 44.16 | MOLA N |
| ATOM | 1176 | CA | PHE | A 169 | 25.131 | 29.418 | 39.417 | 1.00 | 46.16 | MOLA C |
| ATOM | 1177 | CB | PHE | A 169 | 25.946 | 28.349 | 38.681 | 1.00 | 43.78 | MOLA C |
| ATOM | 1178 | CG | PHE | A 169 | 26.864 | 27.565 | 39.579 | 1.00 | 45.53 | MOLA C |
| ATOM | 1179 | CD1 | PHE | A 169 | 26.354 | 26.652 | 40.501 | 1.00 | 50.25 | MOLA C |
| ATOM | 1180 | CE1 | PHE | A 169 | 27.203 | 25.927 | 41.350 | 1.00 | 40.02 | MOLA C |
| ATOM | 1181 | CZ | PHE | A 169 | 28.562 | 26.107 | 41.268 | 1.00 | 39.73 | MOLA C |
| ATOM | 1182 | CE2 | PHE | A 169 | 29.079 | 27.010 | 40.356 | 1.00 | 40.03 | MOLA C |
| ATOM | 1183 | CD2 | PHE | A 169 | 28.234 | 27.730 | 39.514 | 1.00 | 42.08 | MOLA C |
| ATOM | 1184 | C | PHE | A 169 | 24.057 | 30.071 | 38.504 | 1.00 | 49.18 | MOLA C |
| ATOM | 1185 | O | PHE | A 169 | 23.045 | 29.444 | 38.142 | 1.00 | 49.83 | MOLA O |
| ATOM | 1186 | N | ASP | A 170 | 24.255 | 31.340 | 38.165 | 1.00 | 50.05 | MOLA N |
| ATOM | 1187 | CA | ASP | A 170 | 23.364 | 31.984 | 37.211 | 1.00 | 51.63 | MOLA C |
| ATOM | 1188 | CB | ASP | A 170 | 23.458 | 33.514 | 37.271 | 1.00 | 52.38 | MOLA C |
| ATOM | 1189 | CG | ASP | A 170 | 22.993 | 34.192 | 35.987 | 1.00 | 56.43 | MOLA C |
| ATOM | 1190 | OD1 | ASP | A 170 | 22.350 | 33.545 | 35.123 | 1.00 | 60.81 | MOLA O |
| ATOM | 1191 | OD2 | ASP | A 170 | 23.280 | 35.396 | 35.850 | 1.00 | 61.75 | MOLA O |
| ATOM | 1192 | C | ASP | A 170 | 23.776 | 31.483 | 35.854 | 1.00 | 51.55 | MOLA C |
| ATOM | 1193 | O | ASP | A 170 | 24.905 | 31.729 | 35.403 | 1.00 | 50.55 | MOLA O |
| ATOM | 1194 | N | LEU | A 171 | 22.868 | 30.758 | 35.209 | 1.00 | 51.69 | MOLA N |
| ATOM | 1195 | CA | LEU | A 171 | 23.189 | 30.172 | 33.916 | 1.00 | 52.06 | MOLA C |
| ATOM | 1196 | CB | LEU | A 171 | 22.383 | 28.910 | 33.682 | 1.00 | 50.87 | MOLA C |
| ATOM | 1197 | CG | LEU | A 171 | 23.052 | 27.898 | 34.591 | 1.00 | 48.90 | MOLA C |
| ATOM | 1198 | CD1 | LEU | A 171 | 22.235 | 26.648 | 34.732 | 1.00 | 47.88 | MOLA C |
| ATOM | 1199 | CD2 | LEU | A 171 | 24.444 | 27.615 | 34.041 | 1.00 | 39.76 | MOLA C |
| ATOM | 1200 | C | LEU | A 171 | 22.999 | 31.140 | 32.792 | 1.00 | 52.86 | MOLA C |
| ATOM | 1201 | O | LEU | A 171 | 23.473 | 30.898 | 31.690 | 1.00 | 54.73 | MOLA O |
| ATOM | 1202 | N | LEU | A 172 | 22.334 | 32.252 | 33.080 | 1.00 | 53.67 | MOLA N |
| ATOM | 1203 | CA | LEU | A 172 | 22.047 | 33.235 | 32.049 | 1.00 | 53.56 | MOLA C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | | |
|---|---|---|---|---|---|---|---|---|---|---|---|
| ATOM | 1204 | CB | LEU | A 172 | 20.654 | 33.825 | 32.245 | 1.00 | 54.21 | MOLA | C |
| ATOM | 1205 | CG | LEU | A 172 | 19.473 | 33.153 | 31.553 | 1.00 | 40.42 | MOLA | C |
| ATOM | 1206 | CD1 | LEU | A 172 | 19.896 | 32.682 | 30.204 | 1.00 | 44.11 | MOLA | C |
| ATOM | 1207 | CD2 | LEU | A 172 | 19.024 | 32.021 | 32.362 | 1.00 | 47.51 | MOLA | C |
| ATOM | 1208 | C | LEU | A 172 | 23.036 | 34.375 | 31.953 | 1.00 | 56.18 | MOLA | C |
| ATOM | 1209 | O | LEU | A 172 | 22.756 | 35.333 | 31.243 | 1.00 | 55.95 | MOLA | O |
| ATOM | 1210 | N | ASN | A 173 | 24.174 | 34.284 | 32.642 | 1.00 | 59.14 | MOLA | N |
| ATOM | 1211 | CA | ASN | A 173 | 25.135 | 35.387 | 32.660 | 1.00 | 62.83 | MOLA | C |
| ATOM | 1212 | CB | ASN | A 173 | 25.614 | 35.654 | 34.070 | 1.00 | 62.50 | MOLA | C |
| ATOM | 1213 | CG | ASN | A 173 | 26.407 | 36.941 | 34.170 | 1.00 | 64.05 | MOLA | C |
| ATOM | 1214 | OD1 | ASN | A 173 | 26.918 | 37.459 | 33.162 | 1.00 | 57.68 | MOLA | O |
| ATOM | 1215 | ND2 | ASN | A 173 | 26.514 | 37.470 | 35.391 | 1.00 | 49.06 | MOLA | N |
| ATOM | 1216 | C | ASN | A 173 | 26.342 | 35.213 | 31.746 | 1.00 | 66.24 | MOLA | C |
| ATOM | 1217 | O | ASN | A 173 | 27.065 | 34.231 | 31.863 | 1.00 | 67.15 | MOLA | O |
| ATOM | 1218 | N | PRO | A 174 | 26.603 | 36.210 | 30.879 | 1.00 | 69.69 | MOLA | N |
| ATOM | 1219 | CA | PRO | A 174 | 27.618 | 36.075 | 29.823 | 1.00 | 72.56 | MOLA | C |
| ATOM | 1220 | CB | PRO | A 174 | 27.276 | 37.211 | 28.845 | 1.00 | 71.92 | MOLA | C |
| ATOM | 1221 | CG | PRO | A 174 | 26.040 | 37.887 | 29.408 | 1.00 | 70.90 | MOLA | C |
| ATOM | 1222 | CD | PRO | A 174 | 25.974 | 37.538 | 30.854 | 1.00 | 68.43 | MOLA | C |
| ATOM | 1223 | C | PRO | A 174 | 29.049 | 36.218 | 30.338 | 1.00 | 75.69 | MOLA | C |
| ATOM | 1224 | O | PRO | A 174 | 29.631 | 35.234 | 30.818 | 1.00 | 75.99 | MOLA | O |
| ATOM | 1225 | N | SER | A 175 | 29.610 | 37.423 | 30.225 | 1.00 | 78.98 | MOLA | N |
| ATOM | 1226 | CA | SER | A 175 | 30.974 | 37.694 | 30.713 | 1.00 | 82.42 | MOLA | C |
| ATOM | 1227 | CB | SER | A 175 | 31.310 | 39.203 | 30.658 | 1.00 | 82.83 | MOLA | C |
| ATOM | 1228 | OG | SER | A 175 | 30.214 | 40.018 | 31.047 | 1.00 | 81.91 | MOLA | O |
| ATOM | 1229 | C | SER | A 175 | 31.178 | 37.090 | 32.114 | 1.00 | 83.15 | MOLA | C |
| ATOM | 1230 | O | SER | A 175 | 32.309 | 36.980 | 32.620 | 1.00 | 82.53 | MOLA | O |
| ATOM | 1231 | N | SER | A 176 | 30.054 | 36.695 | 32.710 | 1.00 | 84.47 | MOLA | N |
| ATOM | 1232 | CA | SER | A 176 | 30.032 | 35.959 | 33.958 | 1.00 | 86.28 | MOLA | C |
| ATOM | 1233 | CB | SER | A 176 | 28.592 | 35.744 | 34.411 | 1.00 | 85.47 | MOLA | C |
| ATOM | 1234 | OG | SER | A 176 | 28.490 | 34.677 | 35.330 | 1.00 | 83.70 | MOLA | O |
| ATOM | 1235 | C | SER | A 176 | 30.716 | 34.607 | 33.805 | 1.00 | 88.15 | MOLA | C |
| ATOM | 1236 | O | SER | A 176 | 30.930 | 34.102 | 32.691 | 1.00 | 87.25 | MOLA | O |
| ATOM | 1237 | N | ASP | A 177 | 31.051 | 34.018 | 34.941 | 1.00 | 90.51 | MOLA | N |
| ATOM | 1238 | CA | ASP | A 177 | 31.731 | 32.750 | 34.918 | 1.00 | 92.97 | MOLA | C |
| ATOM | 1239 | CB | ASP | A 177 | 33.023 | 32.810 | 35.736 | 1.00 | 93.30 | MOLA | C |
| ATOM | 1240 | CG | ASP | A 177 | 34.122 | 31.969 | 35.132 | 1.00 | 93.08 | MOLA | C |
| ATOM | 1241 | OD1 | ASP | A 177 | 34.289 | 32.026 | 33.894 | 1.00 | 87.69 | MOLA | O |
| ATOM | 1242 | OD2 | ASP | A 177 | 34.821 | 31.265 | 35.892 | 1.00 | 94.93 | MOLA | O |
| ATOM | 1243 | C | ASP | A 177 | 30.827 | 31.657 | 35.446 | 1.00 | 94.08 | MOLA | C |
| ATOM | 1244 | O | ASP | A 177 | 29.797 | 31.913 | 36.084 | 1.00 | 94.19 | MOLA | O |
| ATOM | 1245 | N | VAL | A 178 | 31.220 | 30.428 | 35.150 | 1.00 | 94.95 | MOLA | N |
| ATOM | 1246 | CA | VAL | A 178 | 30.508 | 29.274 | 35.640 | 1.00 | 95.54 | MOLA | C |
| ATOM | 1247 | CB | VAL | A 178 | 30.603 | 28.099 | 34.658 | 1.00 | 95.44 | MOLA | C |
| ATOM | 1248 | CG1 | VAL | A 178 | 29.527 | 28.210 | 33.585 | 1.00 | 95.78 | MOLA | C |
| ATOM | 1249 | CG2 | VAL | A 178 | 32.002 | 28.028 | 34.050 | 1.00 | 95.47 | MOLA | C |
| ATOM | 1250 | C | VAL | A 178 | 31.111 | 28.876 | 36.972 | 1.00 | 95.81 | MOLA | C |
| ATOM | 1251 | O | VAL | A 178 | 30.560 | 28.021 | 37.669 | 1.00 | 97.45 | MOLA | O |
| ATOM | 1252 | N | SER | A 179 | 32.239 | 29.500 | 37.324 | 1.00 | 94.31 | MOLA | N |
| ATOM | 1253 | CA | SER | A 179 | 32.925 | 29.211 | 38.589 | 1.00 | 92.45 | MOLA | C |
| ATOM | 1254 | CB | SER | A 179 | 34.413 | 29.578 | 38.489 | 1.00 | 92.15 | MOLA | C |
| ATOM | 1255 | OG | SER | A 179 | 34.594 | 30.948 | 38.173 | 1.00 | 89.32 | MOLA | O |
| ATOM | 1256 | C | SER | A 179 | 32.261 | 29.932 | 39.771 | 1.00 | 91.48 | MOLA | C |
| ATOM | 1257 | O | SER | A 179 | 32.609 | 29.714 | 40.944 | 1.00 | 91.81 | MOLA | O |
| ATOM | 1258 | N | GLU | A 180 | 31.261 | 30.747 | 39.446 | 1.00 | 89.58 | MOLA | N |
| ATOM | 1259 | CA | GLU | A 180 | 30.690 | 31.699 | 40.389 | 1.00 | 87.43 | MOLA | C |
| ATOM | 1260 | CB | GLU | A 180 | 30.176 | 32.914 | 39.608 | 1.00 | 87.83 | MOLA | C |
| ATOM | 1261 | CG | GLU | A 180 | 30.368 | 34.256 | 40.292 | 1.00 | 87.37 | MOLA | C |
| ATOM | 1262 | CD | GLU | A 180 | 31.691 | 34.896 | 39.926 | 1.00 | 80.62 | MOLA | C |
| ATOM | 1263 | OE1 | GLU | A 180 | 32.039 | 35.928 | 40.544 | 1.00 | 71.04 | MOLA | O |
| ATOM | 1264 | OE2 | GLU | A 180 | 32.372 | 34.363 | 39.018 | 1.00 | 77.11 | MOLA | O |
| ATOM | 1265 | C | GLU | A 180 | 29.546 | 31.156 | 41.226 | 1.00 | 85.42 | MOLA | C |
| ATOM | 1266 | O | GLU | A 180 | 28.501 | 30.799 | 40.680 | 1.00 | 84.50 | MOLA | O |
| ATOM | 1267 | N | ARG | A 181 | 29.743 | 31.083 | 42.543 | 1.00 | 83.53 | MOLA | N |
| ATOM | 1268 | CA | ARG | A 181 | 28.602 | 30.917 | 43.423 | 1.00 | 83.08 | MOLA | C |
| ATOM | 1269 | CB | ARG | A 181 | 28.994 | 30.757 | 44.910 | 1.00 | 84.25 | MOLA | C |
| ATOM | 1270 | CG | ARG | A 181 | 29.264 | 29.322 | 45.491 | 1.00 | 90.67 | MOLA | C |
| ATOM | 1271 | CD | ARG | A 181 | 30.756 | 29.104 | 45.961 | 1.00 | 102.59 | MOLA | C |
| ATOM | 1272 | NE | ARG | A 181 | 30.893 | 28.321 | 47.210 | 1.00 | 96.38 | MOLA | N |
| ATOM | 1273 | CZ | ARG | A 181 | 32.049 | 28.046 | 47.831 | 1.00 | 88.58 | MOLA | C |
| ATOM | 1274 | NH1 | ARG | A 181 | 33.203 | 28.465 | 47.332 | 1.00 | 83.57 | MOLA | N |
| ATOM | 1275 | NH2 | ARG | A 181 | 32.057 | 27.338 | 48.958 | 1.00 | 83.56 | MOLA | N |
| ATOM | 1276 | C | ARG | A 181 | 27.849 | 32.241 | 43.233 | 1.00 | 80.42 | MOLA | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1277 | O | ARG | A 181 | 28.397 | 33.186 | 42.663 | 1.00 | 78.55 | MOLA O |
| ATOM | 1278 | N | LEU | A 182 | 26.594 | 32.294 | 43.678 | 1.00 | 78.36 | MOLA N |
| ATOM | 1279 | CA | LEU | A 182 | 25.832 | 33.547 | 43.752 | 1.00 | 75.76 | MOLA C |
| ATOM | 1280 | CB | LEU | A 182 | 24.690 | 33.605 | 42.741 | 1.00 | 74.91 | MOLA C |
| ATOM | 1281 | CG | LEU | A 182 | 25.080 | 34.291 | 41.436 | 1.00 | 70.76 | MOLA C |
| ATOM | 1282 | CD1 | LEU | A 182 | 23.879 | 34.463 | 40.551 | 1.00 | 52.74 | MOLA C |
| ATOM | 1283 | CD2 | LEU | A 182 | 25.706 | 35.648 | 41.735 | 1.00 | 79.24 | MOLA C |
| ATOM | 1284 | C | LEU | A 182 | 25.302 | 33.717 | 45.161 | 1.00 | 75.42 | MOLA C |
| ATOM | 1285 | O | LEU | A 182 | 25.035 | 32.735 | 45.851 | 1.00 | 75.70 | MOLA O |
| ATOM | 1286 | N | GLN | A 183 | 25.140 | 34.956 | 45.600 | 1.00 | 74.54 | MOLA N |
| ATOM | 1287 | CA | GLN | A 183 | 24.821 | 35.155 | 47.001 | 1.00 | 73.37 | MOLA C |
| ATOM | 1288 | CB | GLN | A 183 | 25.690 | 36.262 | 47.606 | 1.00 | 74.32 | MOLA C |
| ATOM | 1289 | CG | GLN | A 183 | 27.004 | 35.700 | 48.167 | 1.00 | 72.43 | MOLA C |
| ATOM | 1290 | CD | GLN | A 183 | 26.762 | 34.616 | 49.242 | 1.00 | 70.85 | MOLA C |
| ATOM | 1291 | OE1 | GLN | A 183 | 26.521 | 33.428 | 48.947 | 1.00 | 31.15 | MOLA O |
| ATOM | 1292 | NE2 | GLN | A 183 | 26.827 | 35.035 | 50.502 | 1.00 | 83.81 | MOLA N |
| ATOM | 1293 | C | GLN | A 183 | 23.342 | 35.271 | 47.363 | 1.00 | 72.88 | MOLA C |
| ATOM | 1294 | O | GLN | A 183 | 22.515 | 35.745 | 46.581 | 1.00 | 72.49 | MOLA O |
| ATOM | 1295 | N | MET | A 184 | 23.031 | 34.798 | 48.565 | 1.00 | 72.25 | MOLA N |
| ATOM | 1296 | CA | MET | A 184 | 21.662 | 34.711 | 49.021 | 1.00 | 72.27 | MOLA C |
| ATOM | 1297 | CB | MET | A 184 | 21.257 | 33.248 | 49.106 | 1.00 | 72.19 | MOLA C |
| ATOM | 1298 | CG | MET | A 184 | 19.839 | 32.989 | 48.685 | 1.00 | 71.54 | MOLA C |
| ATOM | 1299 | SD | MET | A 184 | 19.382 | 31.261 | 48.875 | 1.00 | 73.99 | MOLA S |
| ATOM | 1300 | CE | MET | A 184 | 18.495 | 31.267 | 50.446 | 1.00 | 62.87 | MOLA C |
| ATOM | 1301 | C | MET | A 184 | 21.483 | 35.365 | 50.386 | 1.00 | 73.15 | MOLA C |
| ATOM | 1302 | O | MET | A 184 | 21.915 | 34.814 | 51.410 | 1.00 | 73.26 | MOLA O |
| ATOM | 1303 | N | PHE | A 185 | 20.840 | 36.539 | 50.380 | 1.00 | 74.07 | MOLA N |
| ATOM | 1304 | CA | PHE | A 185 | 20.531 | 37.329 | 51.582 | 1.00 | 73.27 | MOLA C |
| ATOM | 1305 | CB | PHE | A 185 | 21.025 | 38.776 | 51.425 | 1.00 | 73.43 | MOLA C |
| ATOM | 1306 | CG | PHE | A 185 | 22.468 | 38.901 | 50.970 | 1.00 | 71.06 | MOLA C |
| ATOM | 1307 | CD1 | PHE | A 185 | 22.779 | 39.064 | 49.629 | 1.00 | 78.36 | MOLA C |
| ATOM | 1308 | CE1 | PHE | A 185 | 24.106 | 39.185 | 49.212 | 1.00 | 81.94 | MOLA C |
| ATOM | 1309 | CZ | PHE | A 185 | 25.137 | 39.159 | 50.141 | 1.00 | 73.18 | MOLA C |
| ATOM | 1310 | CE2 | PHE | A 185 | 24.838 | 39.009 | 51.469 | 1.00 | 72.60 | MOLA C |
| ATOM | 1311 | CD2 | PHE | A 185 | 23.504 | 38.880 | 51.883 | 1.00 | 64.20 | MOLA C |
| ATOM | 1312 | C | PHE | A 185 | 19.023 | 37.337 | 51.755 | 1.00 | 72.87 | MOLA C |
| ATOM | 1313 | O | PHE | A 185 | 18.297 | 37.376 | 50.758 | 1.00 | 71.98 | MOLA O |
| ATOM | 1314 | N | ASP | A 186 | 18.539 | 37.299 | 52.994 | 1.00 | 73.55 | MOLA N |
| ATOM | 1315 | CA | ASP | A 186 | 17.097 | 37.353 | 53.199 | 1.00 | 75.57 | MOLA C |
| ATOM | 1316 | CB | ASP | A 186 | 16.711 | 37.120 | 54.665 | 1.00 | 76.28 | MOLA C |
| ATOM | 1317 | CG | ASP | A 186 | 15.226 | 36.668 | 54.844 | 1.00 | 82.20 | MOLA C |
| ATOM | 1318 | OD1 | ASP | A 186 | 14.292 | 37.252 | 54.222 | 1.00 | 84.62 | MOLA O |
| ATOM | 1319 | OD2 | ASP | A 186 | 14.996 | 35.725 | 55.643 | 1.00 | 85.45 | MOLA O |
| ATOM | 1320 | C | ASP | A 186 | 16.595 | 38.702 | 52.672 | 1.00 | 76.70 | MOLA C |
| ATOM | 1321 | O | ASP | A 186 | 17.397 | 39.592 | 52.358 | 1.00 | 77.33 | MOLA O |
| ATOM | 1322 | N | ASP | A 187 | 15.274 | 38.852 | 52.571 | 1.00 | 77.19 | MOLA N |
| ATOM | 1323 | CA | ASP | A 187 | 14.676 | 39.999 | 51.888 | 1.00 | 75.86 | MOLA C |
| ATOM | 1324 | CB | ASP | A 187 | 13.673 | 39.506 | 50.853 | 1.00 | 76.72 | MOLA C |
| ATOM | 1325 | CG | ASP | A 187 | 13.028 | 40.629 | 50.096 | 1.00 | 78.04 | MOLA C |
| ATOM | 1326 | OD1 | ASP | A 187 | 11.894 | 40.417 | 49.618 | 1.00 | 83.63 | MOLA O |
| ATOM | 1327 | OD2 | ASP | A 187 | 13.648 | 41.715 | 49.979 | 1.00 | 79.26 | MOLA O |
| ATOM | 1328 | C | ASP | A 187 | 14.004 | 41.014 | 52.801 | 1.00 | 74.92 | MOLA C |
| ATOM | 1329 | O | ASP | A 187 | 12.983 | 40.709 | 53.436 | 1.00 | 73.06 | MOLA O |
| ATOM | 1330 | N | PRO | A 188 | 14.582 | 42.234 | 52.847 | 1.00 | 74.31 | MOLA N |
| ATOM | 1331 | CA | PRO | A 188 | 14.145 | 43.391 | 53.611 | 1.00 | 73.29 | MOLA C |
| ATOM | 1332 | CB | PRO | A 188 | 15.189 | 44.451 | 53.250 | 1.00 | 73.49 | MOLA C |
| ATOM | 1333 | CG | PRO | A 188 | 16.403 | 43.662 | 52.905 | 1.00 | 72.66 | MOLA C |
| ATOM | 1334 | CD | PRO | A 188 | 15.821 | 42.536 | 52.109 | 1.00 | 74.34 | MOLA C |
| ATOM | 1335 | C | PRO | A 188 | 12.741 | 43.857 | 53.242 | 1.00 | 72.90 | MOLA C |
| ATOM | 1336 | O | PRO | A 188 | 11.952 | 44.127 | 54.136 | 1.00 | 72.66 | MOLA O |
| ATOM | 1337 | N | ARG | A 189 | 12.426 | 43.953 | 51.954 | 1.00 | 73.39 | MOLA N |
| ATOM | 1338 | CA | ARG | A 189 | 11.057 | 44.291 | 51.532 | 1.00 | 74.79 | MOLA C |
| ATOM | 1339 | CB | ARG | A 189 | 10.979 | 44.563 | 50.018 | 1.00 | 75.31 | MOLA C |
| ATOM | 1340 | CG | ARG | A 189 | 11.368 | 45.991 | 49.566 | 1.00 | 77.83 | MOLA C |
| ATOM | 1341 | CD | ARG | A 189 | 11.308 | 46.158 | 48.023 | 1.00 | 78.39 | MOLA C |
| ATOM | 1342 | NE | ARG | A 189 | 10.015 | 45.784 | 47.421 | 1.00 | 88.24 | MOLA N |
| ATOM | 1343 | CZ | ARG | A 189 | 9.759 | 45.749 | 46.106 | 1.00 | 88.02 | MOLA C |
| ATOM | 1344 | NH1 | ARG | A 189 | 10.698 | 46.068 | 45.212 | 1.00 | 78.95 | MOLA N |
| ATOM | 1345 | NH2 | ARG | A 189 | 8.549 | 45.396 | 45.676 | 1.00 | 83.96 | MOLA N |
| ATOM | 1346 | C | ARG | A 189 | 10.033 | 43.213 | 51.925 | 1.00 | 74.29 | MOLA C |
| ATOM | 1347 | O | ARG | A 189 | 8.897 | 43.532 | 52.275 | 1.00 | 73.04 | MOLA O |
| ATOM | 1348 | N | ASN | A 190 | 10.443 | 41.944 | 51.893 | 1.00 | 75.57 | MOLA N |
| ATOM | 1349 | CA | ASN | A 190 | 9.508 | 40.836 | 52.119 | 1.00 | 77.09 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1350 | CB | ASN | A 190 | 9.143 | 40.185 | 50.773 | 1.00 | 77.27 | MOLA C |
| ATOM | 1351 | CG | ASN | A 190 | 8.067 | 39.095 | 50.894 | 1.00 | 81.63 | MOLA C |
| ATOM | 1352 | OD1 | ASN | A 190 | 7.475 | 38.863 | 51.959 | 1.00 | 89.21 | MOLA O |
| ATOM | 1353 | ND2 | ASN | A 190 | 7.809 | 38.426 | 49.779 | 1.00 | 83.54 | MOLA N |
| ATOM | 1354 | C | ASN | A 190 | 9.946 | 39.753 | 53.112 | 1.00 | 77.30 | MOLA C |
| ATOM | 1355 | O | ASN | A 190 | 11.144 | 39.455 | 53.261 | 1.00 | 76.92 | MOLA O |
| ATOM | 1356 | N | LYS | A 191 | 8.933 | 39.194 | 53.788 | 1.00 | 77.35 | MOLA N |
| ATOM | 1357 | CA | LYS | A 191 | 9.053 | 37.996 | 54.628 | 1.00 | 76.57 | MOLA C |
| ATOM | 1358 | CB | LYS | A 191 | 7.699 | 37.664 | 55.302 | 1.00 | 76.87 | MOLA C |
| ATOM | 1359 | CG | LYS | A 191 | 7.546 | 38.098 | 56.772 | 1.00 | 76.75 | MOLA C |
| ATOM | 1360 | CD | LYS | A 191 | 6.218 | 37.607 | 57.381 | 1.00 | 74.62 | MOLA C |
| ATOM | 1361 | CE | LYS | A 191 | 6.089 | 37.959 | 58.865 | 1.00 | 67.85 | MOLA C |
| ATOM | 1362 | NZ | LYS | A 191 | 6.109 | 39.439 | 59.119 | 1.00 | 53.57 | MOLA N |
| ATOM | 1363 | C | LYS | A 191 | 9.502 | 36.792 | 53.784 | 1.00 | 74.98 | MOLA C |
| ATOM | 1364 | O | LYS | A 191 | 10.708 | 36.499 | 53.670 | 1.00 | 74.95 | MOLA O |
| ATOM | 1365 | N | ARG | A 192 | 8.516 | 36.115 | 53.189 | 1.00 | 72.00 | MOLA N |
| ATOM | 1366 | CA | ARG | A 192 | 8.748 | 34.932 | 52.358 | 1.00 | 68.77 | MOLA C |
| ATOM | 1367 | CB | ARG | A 192 | 7.436 | 34.440 | 51.721 | 1.00 | 67.44 | MOLA C |
| ATOM | 1368 | CG | ARG | A 192 | 6.334 | 35.487 | 51.611 | 1.00 | 72.69 | MOLA C |
| ATOM | 1369 | CD | ARG | A 192 | 5.502 | 35.329 | 50.307 | 1.00 | 85.88 | MOLA C |
| ATOM | 1370 | NE | ARG | A 192 | 4.626 | 34.150 | 50.275 | 1.00 | 90.51 | MOLA N |
| ATOM | 1371 | CZ | ARG | A 192 | 3.718 | 33.908 | 49.327 | 1.00 | 93.90 | MOLA C |
| ATOM | 1372 | NH1 | ARG | A 192 | 3.553 | 34.756 | 48.315 | 1.00 | 89.15 | MOLA N |
| ATOM | 1373 | NH2 | ARG | A 192 | 2.966 | 32.814 | 49.391 | 1.00 | 94.40 | MOLA N |
| ATOM | 1374 | C | ARG | A 192 | 9.897 | 35.064 | 51.324 | 1.00 | 66.37 | MOLA C |
| ATOM | 1375 | O | ARG | A 192 | 10.739 | 34.183 | 51.221 | 1.00 | 67.56 | MOLA O |
| ATOM | 1376 | N | GLY | A 193 | 9.959 | 36.171 | 50.595 | 1.00 | 63.27 | MOLA N |
| ATOM | 1377 | CA | GLY | A 193 | 11.010 | 36.368 | 49.594 | 1.00 | 59.32 | MOLA C |
| ATOM | 1378 | C | GLY | A 193 | 12.454 | 36.304 | 50.068 | 1.00 | 56.48 | MOLA C |
| ATOM | 1379 | O | GLY | A 193 | 12.730 | 36.165 | 51.264 | 1.00 | 54.89 | MOLA O |
| ATOM | 1380 | N | VAL | A 194 | 13.360 | 36.443 | 49.097 | 1.00 | 54.99 | MOLA N |
| ATOM | 1381 | CA | VAL | A 194 | 14.809 | 36.275 | 49.239 | 1.00 | 52.73 | MOLA C |
| ATOM | 1382 | CB | VAL | A 194 | 15.197 | 34.800 | 49.097 | 1.00 | 52.77 | MOLA C |
| ATOM | 1383 | CG1 | VAL | A 194 | 16.591 | 34.658 | 48.488 | 1.00 | 52.56 | MOLA C |
| ATOM | 1384 | CG2 | VAL | A 194 | 15.063 | 34.048 | 50.430 | 1.00 | 49.66 | MOLA C |
| ATOM | 1385 | C | VAL | A 194 | 15.451 | 36.960 | 48.056 | 1.00 | 53.25 | MOLA C |
| ATOM | 1386 | O | VAL | A 194 | 14.791 | 37.140 | 47.042 | 1.00 | 53.67 | MOLA O |
| ATOM | 1387 | N | ILE | A 195 | 16.732 | 37.322 | 48.145 | 1.00 | 53.84 | MOLA N |
| ATOM | 1388 | CA | ILE | A 195 | 17.409 | 37.963 | 46.995 | 1.00 | 53.01 | MOLA C |
| ATOM | 1389 | CB | ILE | A 195 | 17.794 | 39.447 | 47.251 | 1.00 | 54.44 | MOLA C |
| ATOM | 1390 | CG1 | ILE | A 195 | 16.563 | 40.360 | 47.370 | 1.00 | 48.69 | MOLA C |
| ATOM | 1391 | CD1 | ILE | A 195 | 16.890 | 41.747 | 47.930 | 1.00 | 49.87 | MOLA C |
| ATOM | 1392 | CG2 | ILE | A 195 | 18.713 | 39.936 | 46.125 | 1.00 | 55.61 | MOLA C |
| ATOM | 1393 | C | ILE | A 195 | 18.692 | 37.271 | 46.579 | 1.00 | 53.20 | MOLA C |
| ATOM | 1394 | O | ILE | A 195 | 19.528 | 36.940 | 47.412 | 1.00 | 54.09 | MOLA O |
| ATOM | 1395 | N | ILE | A 196 | 18.866 | 37.093 | 45.280 | 1.00 | 52.61 | MOLA N |
| ATOM | 1396 | CA | ILE | A 196 | 20.088 | 36.500 | 44.783 | 1.00 | 53.05 | MOLA C |
| ATOM | 1397 | CB | ILE | A 196 | 19.816 | 35.372 | 43.781 | 1.00 | 53.52 | MOLA C |
| ATOM | 1398 | CG1 | ILE | A 196 | 18.828 | 34.380 | 44.377 | 1.00 | 50.39 | MOLA C |
| ATOM | 1399 | CD1 | ILE | A 196 | 18.806 | 33.090 | 43.620 | 1.00 | 54.73 | MOLA C |
| ATOM | 1400 | CG2 | ILE | A 196 | 21.109 | 34.630 | 43.419 | 1.00 | 54.68 | MOLA C |
| ATOM | 1401 | C | ILE | A 196 | 20.950 | 37.603 | 44.197 | 1.00 | 52.96 | MOLA C |
| ATOM | 1402 | O | ILE | A 196 | 20.811 | 37.993 | 43.045 | 1.00 | 50.62 | MOLA O |
| ATOM | 1403 | N | LYS | A 197 | 21.829 | 38.113 | 45.042 | 1.00 | 55.27 | MOLA N |
| ATOM | 1404 | CA | LYS | A 197 | 22.688 | 39.218 | 44.692 | 1.00 | 58.50 | MOLA C |
| ATOM | 1405 | CB | LYS | A 197 | 23.674 | 39.520 | 45.841 | 1.00 | 59.17 | MOLA C |
| ATOM | 1406 | CG | LYS | A 197 | 23.937 | 41.029 | 46.125 | 1.00 | 59.84 | MOLA C |
| ATOM | 1407 | CD | LYS | A 197 | 23.281 | 41.559 | 47.449 | 1.00 | 54.71 | MOLA C |
| ATOM | 1408 | CE | LYS | A 197 | 21.796 | 41.974 | 47.322 | 1.00 | 61.26 | MOLA C |
| ATOM | 1409 | NZ | LYS | A 197 | 21.189 | 42.521 | 48.592 | 1.00 | 53.96 | MOLA N |
| ATOM | 1410 | C | LYS | A 197 | 23.4463 | 8.857 | 43.423 | 1.00 | 60.34 | MOLA C |
| ATOM | 1411 | O | LYS | A 197 | 24.4173 | 8.083 | 43.459 | 1.00 | 61.73 | MOLA O |
| ATOM | 1412 | N | GLY | A 198 | 22.9863 | 9.399 | 42.296 | 1.00 | 60.79 | MOLA N |
| ATOM | 1413 | CA | GLY | A 198 | 23.6873 | 9.215 | 41.027 | 1.00 | 60.10 | MOLA C |
| ATOM | 1414 | C | GLY | A 198 | 22.906 | 38.544 | 39.912 | 1.00 | 59.98 | MOLA C |
| ATOM | 1415 | O | GLY | A 198 | 23.202 | 38.776 | 38.732 | 1.00 | 61.27 | MOLA O |
| ATOM | 1416 | N | LEU | A 199 | 21.903 | 37.737 | 40.282 | 1.00 | 58.12 | MOLA N |
| ATOM | 1417 | CA | LEU | A 199 | 21.137 | 36.900 | 39.339 | 1.00 | 56.15 | MOLA C |
| ATOM | 1418 | CB | LEU | A 199 | 19.988 | 36.187 | 40.049 | 1.00 | 55.40 | MOLA C |
| ATOM | 1419 | CG | LEU | A 199 | 19.200 | 35.245 | 39.128 | 1.00 | 49.26 | MOLA C |
| ATOM | 1420 | CD1 | LEU | A 199 | 20.141 | 34.381 | 38.273 | 1.00 | 38.96 | MOLA C |
| ATOM | 1421 | CD2 | LEU | A 199 | 18.255 | 34.403 | 39.947 | 1.00 | 22.80 | MOLA C |
| ATOM | 1422 | C | LEU | A 199 | 20.586 | 37.567 | 38.076 | 1.00 | 56.93 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1423 | O | LEU | A 199 | 19.569 | 38.263 | 38.128 | 1.00 | 57.26 | MOLA O |
| ATOM | 1424 | N | GLU | A 200 | 21.240 | 37.300 | 36.946 | 1.00 | 56.38 | MOLA N |
| ATOM | 1425 | CA | GLU | A 200 | 20.817 | 37.817 | 35.664 | 1.00 | 56.40 | MOLA C |
| ATOM | 1426 | CB | GLU | A 200 | 21.674 | 37.233 | 34.561 | 1.00 | 56.68 | MOLA C |
| ATOM | 1427 | CG | GLU | A 200 | 21.645 | 38.049 | 33.299 | 1.00 | 58.71 | MOLA C |
| ATOM | 1428 | CD | GLU | A 200 | 22.436 | 39.332 | 33.435 | 1.00 | 59.80 | MOLA C |
| ATOM | 1429 | OE1 | GLU | A 200 | 22.600 | 39.833 | 34.567 | 1.00 | 67.10 | MOLA O |
| ATOM | 1430 | OE2 | GLU | A 200 | 22.898 | 39.843 | 32.400 | 1.00 | 62.18 | MOLA O |
| ATOM | 1431 | C | GLU | A 200 | 19.365 | 37.465 | 35.393 | 1.00 | 57.01 | MOLA C |
| ATOM | 1432 | O | GLU | A 200 | 18.910 | 36.363 | 35.706 | 1.00 | 58.18 | MOLA O |
| ATOM | 1433 | N | GLU | A 201 | 18.646 | 38.405 | 34.795 | 1.00 | 57.40 | MOLA N |
| ATOM | 1434 | CA | GLU | A 201 | 17.227 | 38.235 | 34.528 | 1.00 | 57.79 | MOLA C |
| ATOM | 1435 | CB | GLU | A 201 | 16.385 | 38.997 | 35.562 | 1.00 | 57.18 | MOLA C |
| ATOM | 1436 | CG | GLU | A 201 | 16.386 | 38.482 | 37.012 | 1.00 | 56.96 | MOLA C |
| ATOM | 1437 | CD | GLU | A 201 | 15.493 | 39.342 | 37.911 | 1.00 | 57.11 | MOLA C |
| ATOM | 1438 | OE1 | GLU | A 201 | 15.517 | 40.575 | 37.738 | 1.00 | 63.52 | MOLA O |
| ATOM | 1439 | OE2 | GLU | A 201 | 14.764 | 38.813 | 38.776 | 1.00 | 39.62 | MOLA O |
| ATOM | 1440 | C | GLU | A 201 | 16.923 | 38.811 | 33.157 | 1.00 | 58.76 | MOLA C |
| ATOM | 1441 | O | GLU | A 201 | 16.332 | 39.888 | 33.060 | 1.00 | 61.76 | MOLA O |
| ATOM | 1442 | N | ILE | A 202 | 17.290 | 38.118 | 32.088 | 1.00 | 56.79 | MOLA N |
| ATOM | 1443 | CA | ILE | A 202 | 17.114 | 38.733 | 30.786 | 1.00 | 56.72 | MOLA C |
| ATOM | 1444 | CB | ILE | A 202 | 17.680 | 37.881 | 29.670 | 1.00 | 56.66 | MOLA C |
| ATOM | 1445 | CG1 | ILE | A 202 | 19.091 | 37.421 | 30.037 | 1.00 | 57.03 | MOLA C |
| ATOM | 1446 | CD1 | ILE | A 202 | 19.645 | 36.360 | 29.130 | 1.00 | 44.59 | MOLA C |
| ATOM | 1447 | CG2 | ILE | A 202 | 17.699 | 38.675 | 28.376 | 1.00 | 59.05 | MOLA C |
| ATOM | 1448 | C | ILE | A 202 | 15.663 | 39.108 | 30.497 | 1.00 | 57.36 | MOLA C |
| ATOM | 1449 | O | ILE | A 202 | 14.738 | 38.443 | 30.964 | 1.00 | 57.87 | MOLA O |
| ATOM | 1450 | N | THR | A 203 | 15.487 | 40.199 | 29.753 | 1.00 | 57.48 | MOLA N |
| ATOM | 1451 | CA | THR | A 203 | 14.177 | 40.636 | 29.292 | 1.00 | 56.80 | MOLA C |
| ATOM | 1452 | CB | THR | A 203 | 14.112 | 42.170 | 29.130 | 1.00 | 56.65 | MOLA C |
| ATOM | 1453 | OG1 | THR | A 203 | 13.626 | 42.745 | 30.345 | 1.00 | 53.59 | MOLA O |
| ATOM | 1454 | CG2 | THR | A 203 | 13.171 | 42.570 | 27.976 | 1.00 | 46.33 | MOLA C |
| ATOM | 1455 | C | THR | A 203 | 13.886 | 39.980 | 27.956 | 1.00 | 59.13 | MOLA C |
| ATOM | 1456 | O | THR | A 203 | 14.789 | 39.875 | 27.111 | 1.00 | 58.72 | MOLA O |
| ATOM | 1457 | N | VAL | A 204 | 12.636 | 39.536 | 27.779 | 1.00 | 60.00 | MOLA N |
| ATOM | 1458 | CA | VAL | A 204 | 12.188 | 38.884 | 26.543 | 1.00 | 61.06 | MOLA C |
| ATOM | 1459 | CB | VAL | A 204 | 11.387 | 37.611 | 26.802 | 1.00 | 59.23 | MOLA C |
| ATOM | 1460 | CG1 | VAL | A 204 | 11.266 | 36.839 | 25.534 | 1.00 | 55.83 | MOLA C |
| ATOM | 1461 | CG2 | VAL | A 204 | 12.059 | 36.761 | 27.825 | 1.00 | 63.34 | MOLA C |
| ATOM | 1462 | C | VAL | A 204 | 11.251 | 39.806 | 25.821 | 1.00 | 63.66 | MOLA C |
| ATOM | 1463 | O | VAL | A 204 | 10.062 | 39.880 | 26.159 | 1.00 | 64.25 | MOLA O |
| ATOM | 1464 | N | HIS | A 205 | 11.773 | 40.503 | 24.817 | 1.00 | 65.26 | MOLA N |
| ATOM | 1465 | CA | HIS | A 205 | 11.005 | 41.569 | 24.173 | 1.00 | 65.81 | MOLA C |
| ATOM | 1466 | CB | HIS | A 205 | 11.945 | 42.522 | 23.428 | 1.00 | 65.96 | MOLA C |
| ATOM | 1467 | CG | HIS | A 205 | 13.012 | 43.109 | 24.305 | 1.00 | 65.23 | MOLA C |
| ATOM | 1468 | ND1 | HIS | A 205 | 14.167 | 42.430 | 24.629 | 1.00 | 62.38 | MOLA N |
| ATOM | 1469 | CE1 | HIS | A 205 | 14.916 | 43.180 | 25.417 | 1.00 | 62.41 | MOLA C |
| ATOM | 1470 | NE2 | HIS | A 205 | 14.282 | 44.319 | 25.626 | 1.00 | 65.89 | MOLA N |
| ATOM | 1471 | CD2 | HIS | A 205 | 13.087 | 44.298 | 24.944 | 1.00 | 64.74 | MOLA C |
| ATOM | 1472 | C | HIS | A 205 | 9.861 | 41.041 | 23.305 | 1.00 | 66.80 | MOLA C |
| ATOM | 1473 | O | HIS | A 205 | 8.759 | 41.597 | 23.336 | 1.00 | 67.76 | MOLA O |
| ATOM | 1474 | N | ASN | A 206 | 10.122 | 39.949 | 22.584 | 1.00 | 66.76 | MOLA N |
| ATOM | 1475 | CA | ASN | A 206 | 9.155 | 39.261 | 21.720 | 1.00 | 66.55 | MOLA C |
| ATOM | 1476 | CB | ASN | A 206 | 9.459 | 39.623 | 20.280 | 1.00 | 66.43 | MOLA C |
| ATOM | 1477 | CG | ASN | A 206 | 10.946 | 39.449 | 19.939 | 1.00 | 73.57 | MOLA C |
| ATOM | 1478 | OD1 | ASN | A 206 | 11.796 | 39.365 | 20.835 | 1.00 | 83.93 | MOLA O |
| ATOM | 1479 | ND2 | ASN | A 206 | 11.262 | 39.393 | 18.647 | 1.00 | 75.10 | MOLA N |
| ATOM | 1480 | C | ASN | A 206 | 9.381 | 37.769 | 21.887 | 1.00 | 66.71 | MOLA C |
| ATOM | 1481 | O | ASN | A 206 | 10.263 | 37.374 | 22.636 | 1.00 | 67.83 | MOLA O |
| ATOM | 1482 | N | LYS | A 207 | 8.625 | 36.911 | 21.219 | 1.00 | 65.79 | MOLA N |
| ATOM | 1483 | CA | LYS | A 207 | 9.114 | 35.544 | 21.154 | 1.00 | 65.95 | MOLA C |
| ATOM | 1484 | CB | LYS | A 207 | 8.121 | 34.623 | 20.499 | 1.00 | 64.57 | MOLA C |
| ATOM | 1485 | CG | LYS | A 207 | 6.828 | 34.521 | 21.222 | 1.00 | 66.67 | MOLA C |
| ATOM | 1486 | CD | LYS | A 207 | 5.851 | 33.745 | 20.368 | 1.00 | 78.97 | MOLA C |
| ATOM | 1487 | CE | LYS | A 207 | 5.670 | 34.406 | 18.991 | 1.00 | 79.00 | MOLA C |
| ATOM | 1488 | NZ | LYS | A 207 | 6.974 | 34.629 | 18.292 | 1.00 | 80.22 | MOLA N |
| ATOM | 1489 | C | LYS | A 207 | 10.333 | 35.660 | 20.268 | 1.00 | 66.93 | MOLA C |
| ATOM | 1490 | O | LYS | A 207 | 10.704 | 36.766 | 19.910 | 1.00 | 67.75 | MOLA O |
| ATOM | 1491 | N | ASP | A 208 | 10.947 | 34.541 | 19.893 | 1.00 | 69.31 | MOLA N |
| ATOM | 1492 | CA | ASP | A 208 | 12.087 | 34.535 | 18.948 | 1.00 | 71.07 | MOLA C |
| ATOM | 1493 | CB | ASP | A 208 | 11.835 | 35.443 | 17.746 | 1.00 | 71.90 | MOLA C |
| ATOM | 1494 | CG | ASP | A 208 | 10.755 | 34.920 | 16.844 | 1.00 | 79.56 | MOLA C |
| ATOM | 1495 | OD1 | ASP | A 208 | 9.779 | 35.671 | 16.622 | 1.00 | 82.68 | MOLA O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1496 | OD2 | ASP | A 208 | 10.872 | 33.759 | 16.378 | 1.00 | 88.98 | MOLA O |
| ATOM | 1497 | C | ASP | A 208 | 13.383 | 34.968 | 19.579 | 1.00 | 70.75 | MOLA C |
| ATOM | 1498 | O | ASP | A 208 | 14.454 | 34.481 | 19.222 | 1.00 | 72.29 | MOLA O |
| ATOM | 1499 | N | GLU | A 209 | 13.289 | 35.941 | 20.470 | 1.00 | 69.71 | MOLA N |
| ATOM | 1500 | CA | GLU | A 209 | 14.427 | 36.328 | 21.264 | 1.00 | 67.75 | MOLA C |
| ATOM | 1501 | CB | GLU | A 209 | 14.218 | 37.736 | 21.818 | 1.00 | 68.26 | MOLA C |
| ATOM | 1502 | CG | GLU | A 209 | 15.390 | 38.284 | 22.603 | 1.00 | 75.22 | MOLA C |
| ATOM | 1503 | CD | GLU | A 209 | 15.036 | 39.555 | 23.346 | 1.00 | 84.21 | MOLA C |
| ATOM | 1504 | OE1 | GLU | A 209 | 14.194 | 40.328 | 22.827 | 1.00 | 75.22 | MOLA O |
| ATOM | 1505 | OE2 | GLU | A 209 | 15.605 | 39.773 | 24.444 | 1.00 | 94.29 | MOLA O |
| ATOM | 1506 | C | GLU | A 209 | 14.533 | 35.260 | 22.367 | 1.00 | 63.94 | MOLA C |
| ATOM | 1507 | O | GLU | A 209 | 15.609 | 35.048 | 22.952 | 1.00 | 63.72 | MOLA O |
| ATOM | 1508 | N | VAL | A 210 | 13.405 | 34.584 | 22.619 | 1.00 | 58.87 | MOLA N |
| ATOM | 1509 | CA | VAL | A 210 | 13.349 | 33.458 | 23.559 | 1.00 | 54.30 | MOLA C |
| ATOM | 1510 | CB | VAL | A 210 | 11.916 | 32.912 | 23.771 | 1.00 | 52.71 | MOLA C |
| ATOM | 1511 | CG1 | VAL | A 210 | 11.030 | 33.340 | 22.654 | 1.00 | 55.14 | MOLA C |
| ATOM | 1512 | CG2 | VAL | A 210 | 11.928 | 31.384 | 23.935 | 1.00 | 45.57 | MOLA C |
| ATOM | 1513 | C | VAL | A 210 | 14.266 | 32.336 | 23.121 | 1.00 | 52.18 | MOLA C |
| ATOM | 1514 | O | VAL | A 210 | 15.200 | 31.974 | 23.831 | 1.00 | 50.81 | MOLA O |
| ATOM | 1515 | N | TYR | A 211 | 14.022 | 31.798 | 21.941 | 1.00 | 51.26 | MOLA N |
| ATOM | 1516 | CA | TYR | A 211 | 14.861 | 30.716 | 21.491 | 1.00 | 50.18 | MOLA C |
| ATOM | 1517 | CB | TYR | A 211 | 14.584 | 30.363 | 20.040 | 1.00 | 48.21 | MOLA C |
| ATOM | 1518 | CG | TYR | A 211 | 15.377 | 29.175 | 19.582 | 1.00 | 46.75 | MOLA C |
| ATOM | 1519 | CD1 | TYR | A 211 | 16.662 | 29.341 | 19.035 | 1.00 | 49.00 | MOLA C |
| ATOM | 1520 | CE1 | TYR | A 211 | 17.420 | 28.237 | 18.607 | 1.00 | 53.26 | MOLA C |
| ATOM | 1521 | CZ | TYR | A 211 | 16.897 | 26.948 | 18.736 | 1.00 | 53.12 | MOLA C |
| ATOM | 1522 | OH | TYR | A 211 | 17.664 | 25.871 | 18.325 | 1.00 | 53.01 | MOLA O |
| ATOM | 1523 | CE2 | TYR | A 211 | 15.619 | 26.755 | 19.278 | 1.00 | 48.74 | MOLA C |
| ATOM | 1524 | CD2 | TYR | A 211 | 14.864 | 27.873 | 19.700 | 1.00 | 41.83 | MOLA C |
| ATOM | 1525 | C | TYR | A 211 | 16.374 | 30.928 | 21.774 | 1.00 | 51.58 | MOLA C |
| ATOM | 1526 | O | TYR | A 211 | 17.044 | 29.970 | 22.178 | 1.00 | 52.38 | MOLA O |
| ATOM | 1527 | N | GLN | A 212 | 16.930 | 32.139 | 21.625 | 1.00 | 51.92 | MOLA N |
| ATOM | 1528 | CA | GLN | A 212 | 18.376 | 32.276 | 21.919 | 1.00 | 51.34 | MOLA C |
| ATOM | 1529 | CB | GLN | A 212 | 18.931 | 33.662 | 21.709 | 1.00 | 50.64 | MOLA C |
| ATOM | 1530 | CG | GLN | A 212 | 19.341 | 33.943 | 20.332 | 1.00 | 51.72 | MOLA C |
| ATOM | 1531 | CD | GLN | A 212 | 18.201 | 34.505 | 19.610 | 1.00 | 62.20 | MOLA C |
| ATOM | 1532 | OE1 | GLN | A 212 | 17.067 | 34.436 | 20.099 | 1.00 | 72.97 | MOLA O |
| ATOM | 1533 | NE2 | GLN | A 212 | 18.459 | 35.102 | 18.448 | 1.00 | 74.08 | MOLA N |
| ATOM | 1534 | C | GLN | A 212 | 18.661 | 31.930 | 23.341 | 1.00 | 52.52 | MOLA C |
| ATOM | 1535 | O | GLN | A 212 | 19.446 | 31.041 | 23.624 | 1.00 | 55.89 | MOLA O |
| ATOM | 1536 | N | ILE | A 213 | 18.047 | 32.673 | 24.245 | 1.00 | 52.40 | MOLA N |
| ATOM | 1537 | CA | ILE | A 213 | 18.164 | 32.391 | 25.662 | 1.00 | 51.15 | MOLA C |
| ATOM | 1538 | CB | ILE | A 213 | 16.990 | 33.032 | 26.410 | 1.00 | 52.30 | MOLA C |
| ATOM | 1539 | CG1 | ILE | A 213 | 17.462 | 34.315 | 27.096 | 1.00 | 58.58 | MOLA C |
| ATOM | 1540 | CD1 | ILE | A 213 | 16.351 | 35.356 | 27.325 | 1.00 | 75.32 | MOLA C |
| ATOM | 1541 | CG2 | ILE | A 213 | 16.393 | 32.076 | 27.422 | 1.00 | 55.87 | MOLA C |
| ATOM | 1542 | C | ILE | A 213 | 18.237 | 30.888 | 25.918 | 1.00 | 47.80 | MOLA C |
| ATOM | 1543 | O | ILE | A 213 | 19.219 | 30.404 | 26.471 | 1.00 | 46.00 | MOLA O |
| ATOM | 1544 | N | LEU | A 214 | 17.215 | 30.154 | 25.480 | 1.00 | 45.71 | MOLA N |
| ATOM | 1545 | CA | LEU | A 214 | 17.157 | 28.713 | 25.720 | 1.00 | 42.79 | MOLA C |
| ATOM | 1546 | CB | LEU | A 214 | 15.894 | 28.080 | 25.121 | 1.00 | 41.71 | MOLA C |
| ATOM | 1547 | CG | LEU | A 214 | 14.639 | 28.685 | 25.788 | 1.00 | 37.56 | MOLA C |
| ATOM | 1548 | CD1 | LEU | A 214 | 13.381 | 27.846 | 25.652 | 1.00 | 15.00 | MOLA C |
| ATOM | 1549 | CD2 | LEU | A 214 | 14.909 | 28.899 | 27.245 | 1.00 | 28.22 | MOLA C |
| ATOM | 1550 | C | LEU | A 214 | 18.437 | 28.033 | 25.272 | 1.00 | 42.75 | MOLA C |
| ATOM | 1551 | O | LEU | A 214 | 18.900 | 27.119 | 25.946 | 1.00 | 42.76 | MOLA O |
| ATOM | 1552 | N | GLU | A 215 | 19.032 | 28.495 | 24.169 | 1.00 | 42.10 | MOLA N |
| ATOM | 1553 | CA | GLU | A 215 | 20.367 | 28.012 | 23.768 | 1.00 | 42.47 | MOLA C |
| ATOM | 1554 | CB | GLU | A 215 | 20.760 | 28.532 | 22.415 | 1.00 | 40.29 | MOLA C |
| ATOM | 1555 | CG | GLU | A 215 | 20.485 | 27.587 | 21.302 | 1.00 | 48.53 | MOLA C |
| ATOM | 1556 | CD | GLU | A 215 | 20.799 | 28.214 | 19.976 | 1.00 | 62.44 | MOLA C |
| ATOM | 1557 | OE1 | GLU | A 215 | 20.386 | 29.388 | 19.782 | 1.00 | 71.58 | MOLA O |
| ATOM | 1558 | OE2 | GLU | A 215 | 21.455 | 27.542 | 19.143 | 1.00 | 65.51 | MOLA O |
| ATOM | 1559 | C | GLU | A 215 | 21.428 | 28.443 | 24.750 | 1.00 | 43.21 | MOLA C |
| ATOM | 1560 | O | GLU | A 215 | 21.986 | 27.618 | 25.448 | 1.00 | 43.70 | MOLA O |
| ATOM | 1561 | N | LYS | A 216 | 21.686 | 29.746 | 24.800 | 1.00 | 45.78 | MOLA N |
| ATOM | 1562 | CA | LYS | A 216 | 22.623 | 30.345 | 25.754 | 1.00 | 49.55 | MOLA C |
| ATOM | 1563 | CB | LYS | A 216 | 22.211 | 31.790 | 26.101 | 1.00 | 51.47 | MOLA C |
| ATOM | 1564 | CG | LYS | A 216 | 22.550 | 32.912 | 25.085 | 1.00 | 56.78 | MOLA C |
| ATOM | 1565 | CD | LYS | A 216 | 22.395 | 34.316 | 25.760 | 1.00 | 55.05 | MOLA C |
| ATOM | 1566 | CE | LYS | A 216 | 22.915 | 35.476 | 24.881 | 1.00 | 61.58 | MOLA C |
| ATOM | 1567 | NZ | LYS | A 216 | 22.176 | 35.685 | 23.585 | 1.00 | 71.01 | MOLA N |
| ATOM | 1568 | C | LYS | A 216 | 22.701 | 29.540 | 27.055 | 1.00 | 48.38 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1569 | O | LYS | A 216 | 23.800 | 29.127 | 27.488 | 1.00 | 48.55 | MOLA O |
| ATOM | 1570 | N | GLY | A 217 | 21.527 | 29.346 | 27.671 | 1.00 | 46.21 | MOLA N |
| ATOM | 1571 | CA | GLY | A 217 | 21.388 | 28.597 | 28.917 | 1.00 | 43.66 | MOLA C |
| ATOM | 1572 | C | GLY | A 217 | 22.008 | 27.227 | 28.764 | 1.00 | 43.18 | MOLA C |
| ATOM | 1573 | O | GLY | A 217 | 23.059 | 26.939 | 29.344 | 1.00 | 40.67 | MOLA O |
| ATOM | 1574 | N | ALA | A 218 | 21.374 | 26.401 | 27.937 | 1.00 | 43.23 | MOLA N |
| ATOM | 1575 | CA | ALA | A 218 | 21.852 | 25.058 | 27.689 | 1.00 | 43.19 | MOLA C |
| ATOM | 1576 | CB | ALA | A 218 | 21.235 | 24.492 | 26.434 | 1.00 | 43.91 | MOLA C |
| ATOM | 1577 | C | ALA | A 218 | 23.357 | 25.090 | 27.570 | 1.00 | 43.73 | MOLA C |
| ATOM | 1578 | O | ALA | A 218 | 24.040 | 24.294 | 28.204 | 1.00 | 46.28 | MOLA O |
| ATOM | 1579 | N | ALA | A 219 | 23.876 | 26.018 | 26.774 | 1.00 | 42.36 | MOLA N |
| ATOM | 1580 | CA | ALA | A 219 | 25.316 | 26.141 | 26.581 | 1.00 | 41.91 | MOLA C |
| ATOM | 1581 | CB | ALA | A 219 | 25.639 | 27.268 | 25.639 | 1.00 | 40.46 | MOLA C |
| ATOM | 1582 | CA | LA | A 219 | 26.010 | 26.351 | 27.917 | 1.00 | 43.49 | MOLA C |
| ATOM | 1583 | O | ALA | A 219 | 26.871 | 25.557 | 28.308 | 1.00 | 44.41 | MOLA O |
| ATOM | 1584 | N | LYS | A 220 | 25.633 | 27.398 | 28.639 | 1.00 | 44.19 | MOLA N |
| ATOM | 1585 | CA | LYS | A 220 | 26.309 | 27.654 | 29.897 | 1.00 | 45.36 | MOLA C |
| ATOM | 1586 | CB | LYS | A 220 | 25.838 | 28.975 | 30.526 | 1.00 | 46.26 | MOLA C |
| ATOM | 1587 | CG | LYS | A 220 | 26.829 | 29.515 | 31.581 | 1.00 | 57.07 | MOLA C |
| ATOM | 1588 | CD | LYS | A 220 | 26.805 | 31.039 | 31.813 | 1.00 | 51.86 | MOLA C |
| ATOM | 1589 | CE | LYS | A 220 | 27.352 | 31.347 | 33.232 | 1.00 | 64.64 | MOLA C |
| ATOM | 1590 | NZ | LYS | A 220 | 27.574 | 32.795 | 33.575 | 1.00 | 59.41 | MOLA N |
| ATOM | 1591 | C | LYS | A 220 | 26.156 | 26.447 | 30.833 | 1.00 | 42.25 | MOLA C |
| ATOM | 1592 | O | LYS | A 220 | 27.050 | 26.120 | 31.605 | 1.00 | 40.39 | MOLA O |
| ATOM | 1593 | N | ARG | A 221 | 25.026 | 25.762 | 30.717 | 1.00 | 42.67 | MOLA N |
| ATOM | 1594 | CA | ARG | A 221 | 24.742 | 24.545 | 31.476 | 1.00 | 43.12 | MOLA C |
| ATOM | 1595 | CB | ARG | A 221 | 23.486 | 23.903 | 30.912 | 1.00 | 42.23 | MOLA C |
| ATOM | 1596 | CG | ARG | A 221 | 23.086 | 22.641 | 31.627 | 1.00 | 48.01 | MOLA C |
| ATOM | 1597 | CD | ARG | A 221 | 21.879 | 22.921 | 32.447 | 1.00 | 44.15 | MOLA C |
| ATOM | 1598 | NE | ARG | A 221 | 20.799 | 23.240 | 31.523 | 1.00 | 52.54 | MOLA N |
| ATOM | 1599 | CZ | ARG | A 221 | 19.556 | 23.465 | 31.899 | 1.00 | 46.98 | MOLA C |
| ATOM | 1600 | NH1 | ARG | A 221 | 19.242 | 23.414 | 33.190 | 1.00 | 45.06 | MOLA N |
| ATOM | 1601 | NH2 | ARG | A 221 | 18.642 | 23.728 | 30.985 | 1.00 | 51.88 | MOLA N |
| ATOM | 1602 | C | ARG | A 221 | 25.847 | 23.528 | 31.299 | 1.00 | 44.97 | MOLA C |
| ATOM | 1603 | O | ARG | A 221 | 26.387 | 22.989 | 32.261 | 1.00 | 43.68 | MOLA O |
| ATOM | 1604 | N | THR | A 222 | 26.110 | 23.244 | 30.022 | 1.00 | 47.71 | MOLA N |
| ATOM | 1605 | CA | THR | A 222 | 27.150 | 22.354 | 29.565 | 1.00 | 48.26 | MOLA C |
| ATOM | 1606 | CB | THR | A 222 | 27.259 | 22.426 | 28.049 | 1.00 | 47.88 | MOLA C |
| ATOM | 1607 | OG1 | THR | A 222 | 26.083 | 21.830 | 27.490 | 1.00 | 47.71 | MOLA O |
| ATOM | 1608 | CG2 | THR | A 222 | 28.485 | 21.681 | 27.549 | 1.00 | 48.98 | MOLA C |
| ATOM | 1609 | C | THR | A 222 | 28.427 | 22.783 | 30.212 | 1.00 | 50.20 | MOLA C |
| ATOM | 1610 | O | THR | A 222 | 28.943 | 22.071 | 31.069 | 1.00 | 51.35 | MOLA O |
| ATOM | 1611 | N | THR | A 223 | 28.910 | 23.959 | 29.816 | 1.00 | 52.61 | MOLA N |
| ATOM | 1612 | CA | THR | A 223 | 30.069 | 24.600 | 30.444 | 1.00 | 55.52 | MOLA C |
| ATOM | 1613 | CB | THR | A 223 | 30.126 | 26.123 | 30.105 | 1.00 | 57.16 | MOLA C |
| ATOM | 1614 | OG1 | THR | A 223 | 30.159 | 26.310 | 28.673 | 1.00 | 59.33 | MOLA O |
| ATOM | 1615 | CG2 | THR | A 223 | 31.356 | 26.783 | 30.729 | 1.00 | 56.06 | MOLA C |
| ATOM | 1616 | C | THR | A 223 | 30.066 | 24.370 | 31.966 | 1.00 | 56.50 | MOLA C |
| ATOM | 1617 | O | THR | A 223 | 31.112 | 24.143 | 32.576 | 1.00 | 55.53 | MOLA O |
| ATOM | 1618 | N | ALA | A 224 | 28.882 | 24.402 | 32.575 | 1.00 | 58.42 | MOLA N |
| ATOM | 1619 | CA | ALA | A 224 | 28.757 | 24.035 | 33.983 | 1.00 | 58.84 | MOLA C |
| ATOM | 1620 | CB | ALA | A 224 | 27.346 | 24.257 | 34.494 | 1.00 | 59.54 | MOLA C |
| ATOM | 1621 | C | ALA | A 224 | 29.135 | 22.582 | 34.135 | 1.00 | 58.56 | MOLA C |
| ATOM | 1622 | O | ALA | A 224 | 30.158 | 22.267 | 34.722 | 1.00 | 60.97 | MOLA O |
| ATOM | 1623 | N | ALA | A 225 | 28.323 | 21.701 | 33.573 | 1.00 | 58.13 | MOLA N |
| ATOM | 1624 | CA | ALA | A 225 | 28.530 | 20.274 | 33.737 | 1.00 | 59.04 | MOLA C |
| ATOM | 1625 | CB | ALA | A 225 | 27.628 | 19.501 | 32.793 | 1.00 | 58.62 | MOLA C |
| ATOM | 1626 | C | ALA | A 225 | 30.009 | 19.850 | 33.590 | 1.00 | 61.12 | MOLA C |
| ATOM | 1627 | O | ALA | A 225 | 30.504 | 19.009 | 34.365 | 1.00 | 60.71 | MOLA O |
| ATOM | 1628 | N | THR | A 226 | 30.723 | 20.429 | 32.624 | 1.00 | 61.54 | MOLA N |
| ATOM | 1629 | CA | THR | A 226 | 32.146 | 20.126 | 32.486 | 1.00 | 63.47 | MOLA C |
| ATOM | 1630 | CB | THR | A 226 | 32.697 | 20.601 | 31.184 | 1.00 | 61.53 | MOLA C |
| ATOM | 1631 | OG1 | THR | A 226 | 31.803 | 20.208 | 30.141 | 1.00 | 66.84 | MOLA O |
| ATOM | 1632 | CG2 | THR | A 226 | 34.063 | 19.979 | 30.958 | 1.00 | 61.82 | MOLA C |
| ATOM | 1633 | C | THR | A 226 | 32.994 | 20.723 | 33.622 | 1.00 | 67.47 | MOLA C |
| ATOM | 1634 | O | THR | A 226 | 32.871 | 20.287 | 34.777 | 1.00 | 70.78 | MOLA O |
| ATOM | 1635 | N | LEU | A 227 | 33.831 | 21.723 | 33.315 | 1.00 | 67.66 | MOLA N |
| ATOM | 1636 | CA | LEU | A 227 | 34.812 | 22.251 | 34.291 | 1.00 | 66.20 | MOLA C |
| ATOM | 1637 | CB | LEU | A 227 | 35.290 | 23.667 | 33.940 | 1.00 | 66.60 | MOLA C |
| ATOM | 1638 | CG | LEU | A 227 | 35.551 | 24.244 | 32.540 | 1.00 | 65.56 | MOLA C |
| ATOM | 1639 | CD1 | LEU | A 227 | 36.860 | 25.035 | 32.654 | 1.00 | 72.12 | MOLA C |
| ATOM | 1640 | CD2 | LEU | A 227 | 35.641 | 23.211 | 31.420 | 1.00 | 34.58 | MOLA C |
| ATOM | 1641 | C | LEU | A 227 | 34.355 | 22.221 | 35.759 | 1.00 | 66.07 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1642 | O | LEU | A 227 | 35.129 | 21.875 | 36.655 | 1.00 | 67.76 | MOLA O |
| ATOM | 1643 | N | MET | A 228 | 33.112 | 22.585 | 36.027 | 1.00 | 64.56 | MOLA N |
| ATOM | 1644 | CA | MET | A 228 | 32.656 | 22.567 | 37.410 | 1.00 | 63.34 | MOLA C |
| ATOM | 1645 | CB | MET | A 228 | 31.511 | 23.557 | 37.623 | 1.00 | 64.01 | MOLA C |
| ATOM | 1646 | CG | MET | A 228 | 31.948 | 24.957 | 38.002 | 1.00 | 66.85 | MOLA C |
| ATOM | 1647 | SD | MET | A 228 | 33.528 | 25.426 | 37.277 | 1.00 | 71.44 | MOLA S |
| ATOM | 1648 | CE | MET | A 228 | 34.651 | 25.076 | 38.647 | 1.00 | 73.15 | MOLA C |
| ATOM | 1649 | C | MET | A 228 | 32.224 | 21.190 | 37.839 | 1.00 | 60.99 | MOLA C |
| ATOM | 1650 | O | MET | A 228 | 32.348 | 20.854 | 39.018 | 1.00 | 62.12 | MOLA O |
| ATOM | 1651 | N | ASN | A 229 | 31.729 | 20.407 | 36.877 | 1.00 | 57.33 | MOLA N |
| ATOM | 1652 | CA | ASN | A 229 | 31.148 | 19.070 | 37.103 | 1.00 | 55.33 | MOLA C |
| ATOM | 1653 | CB | ASN | A 229 | 31.966 | 18.190 | 38.051 | 1.00 | 54.06 | MOLA C |
| ATOM | 1654 | CG | ASN | A 229 | 33.335 | 17.805 | 37.508 | 1.00 | 52.31 | MOLA C |
| ATOM | 1655 | OD1 | ASN | A 229 | 33.646 | 17.911 | 36.306 | 1.00 | 30.68 | MOLA O |
| ATOM | 1656 | ND2 | ASN | A 229 | 34.174 | 17.331 | 38.420 | 1.00 | 59.45 | MOLA N |
| ATOM | 1657 | C | ASN | A 229 | 29.775 | 19.193 | 37.697 | 1.00 | 54.89 | MOLA C |
| ATOM | 1658 | O | ASN | A 229 | 29.403 | 18.420 | 38.575 | 1.00 | 55.30 | MOLA O |
| ATOM | 1659 | N | ALA | A 230 | 29.023 | 20.184 | 37.261 | 1.00 | 54.90 | MOLA N |
| ATOM | 1660 | CA | ALA | A 230 | 27.657 | 20.285 | 37.730 | 1.00 | 56.83 | MOLA C |
| ATOM | 1661 | CB | ALA | A 230 | 27.101 | 21.693 | 37.467 | 1.00 | 59.38 | MOLA C |
| ATOM | 1662 | C | ALA | A 230 | 26.847 | 19.225 | 36.989 | 1.00 | 55.45 | MOLA C |
| ATOM | 1663 | O | ALA | A 230 | 25.988 | 19.538 | 36.162 | 1.00 | 56.85 | MOLA O |
| ATOM | 1664 | N | TYR | A 231 | 27.128 | 17.957 | 37.247 | 1.00 | 53.13 | MOLA N |
| ATOM | 1665 | CA | TYR | A 231 | 26.459 | 16.952 | 36.441 | 1.00 | 48.28 | MOLA C |
| ATOM | 1666 | CB | TYR | A 231 | 26.730 | 15.528 | 36.930 | 1.00 | 48.80 | MOLA C |
| ATOM | 1667 | CG | TYR | A 231 | 28.191 | 15.188 | 36.875 | 1.00 | 41.10 | MOLA C |
| ATOM | 1668 | CD1 | TYR | A 231 | 28.895 | 15.237 | 35.671 | 1.00 | 41.92 | MOLA C |
| ATOM | 1669 | CE1 | TYR | A 231 | 30.248 | 14.950 | 35.629 | 1.00 | 52.66 | MOLA C |
| ATOM | 1670 | CZ | TYR | A 231 | 30.902 | 14.608 | 36.816 | 1.00 | 52.92 | MOLA C |
| ATOM | 1671 | OH | TYR | A 231 | 32.240 | 14.308 | 36.848 | 1.00 | 44.91 | MOLA O |
| ATOM | 1672 | CE2 | TYR | A 231 | 30.208 | 14.558 | 38.006 | 1.00 | 53.39 | MOLA C |
| ATOM | 1673 | CD2 | TYR | A 231 | 28.868 | 14.851 | 38.025 | 1.00 | 37.28 | MOLA C |
| ATOM | 1674 | C | TYR | A 231 | 25.007 | 17.292 | 36.518 | 1.00 | 45.49 | MOLA C |
| ATOM | 1675 | O | TYR | A 231 | 24.467 | 17.477 | 37.617 | 1.00 | 45.30 | MOLA O |
| ATOM | 1676 | N | SER | A 232 | 24.391 | 17.439 | 35.355 | 1.00 | 39.34 | MOLA N |
| ATOM | 1677 | CA | SER | A 232 | 22.965 | 17.656 | 35.321 | 1.00 | 38.72 | MOLA C |
| ATOM | 1678 | CB | SER | A 232 | 22.433 | 17.563 | 33.898 | 1.00 | 38.02 | MOLA C |
| ATOM | 1679 | OG | SER | A 232 | 23.438 | 17.068 | 33.038 | 1.00 | 45.94 | MOLA O |
| ATOM | 1680 | C | SER | A 232 | 22.222 | 16.707 | 36.252 | 1.00 | 36.89 | MOLA C |
| ATOM | 1681 | O | SER | A 232 | 21.475 | 17.145 | 37.118 | 1.00 | 39.02 | MOLA O |
| ATOM | 1682 | N | SER | A 233 | 22.454 | 15.411 | 36.106 | 1.00 | 36.05 | MOLA N |
| ATOM | 1683 | CA | SER | A 233 | 21.729 | 14.432 | 36.895 | 1.00 | 35.00 | MOLA C |
| ATOM | 1684 | CB | SER | A 233 | 22.400 | 13.077 | 36.784 | 1.00 | 35.43 | MOLA C |
| ATOM | 1685 | OG | SER | A 233 | 23.723 | 13.124 | 37.329 | 1.00 | 52.54 | MOLA O |
| ATOM | 1686 | C | SER | A 233 | 21.673 | 14.851 | 38.342 | 1.00 | 32.12 | MOLA C |
| ATOM | 1687 | O | SER | A 233 | 20.752 | 14.504 | 39.070 | 1.00 | 31.73 | MOLA O |
| ATOM | 1688 | N | ARG | A 234 | 22.648 | 15.654 | 38.725 | 1.00 | 33.30 | MOLA N |
| ATOM | 1689 | CA | ARG | A 234 | 22.944 | 15.907 | 40.134 | 1.00 | 37.39 | MOLA C |
| ATOM | 1690 | CB | ARG | A 234 | 24.444 | 15.661 | 40.401 | 1.00 | 36.48 | MOLA C |
| ATOM | 1691 | CG | ARG | A 234 | 24.894 | 14.241 | 40.041 | 1.00 | 46.24 | MOLA C |
| ATOM | 1692 | CD | ARG | A 234 | 26.359 | 13.898 | 40.390 | 1.00 | 43.68 | MOLA C |
| ATOM | 1693 | NE | ARG | A 234 | 26.563 | 12.459 | 40.251 | 1.00 | 56.94 | MOLA N |
| ATOM | 1694 | CZ | ARG | A 234 | 26.351 | 11.578 | 41.234 | 1.00 | 58.11 | MOLA C |
| ATOM | 1695 | NH1 | ARG | A 234 | 25.970 | 11.991 | 42.436 | 1.00 | 48.12 | MOLA N |
| ATOM | 1696 | NH2 | ARG | A 234 | 26.530 | 10.280 | 41.023 | 1.00 | 52.29 | MOLA N |
| ATOM | 1697 | C | ARG | A 234 | 22.502 | 17.262 | 40.701 | 1.00 | 34.82 | MOLA C |
| ATOM | 1698 | O | ARG | A 234 | 22.448 | 17.418 | 41.907 | 1.00 | 32.44 | MOLA O |
| ATOM | 1699 | N | SER | A 235 | 22.181 | 18.224 | 39.839 | 1.00 | 35.51 | MOLA N |
| ATOM | 1700 | CA | SER | A 235 | 21.733 | 19.548 | 40.297 | 1.00 | 35.58 | MOLA C |
| ATOM | 1701 | CB | SER | A 235 | 22.602 | 20.668 | 39.716 | 1.00 | 34.08 | MOLA C |
| ATOM | 1702 | OG | SER | A 235 | 22.646 | 20.601 | 38.311 | 1.00 | 35.26 | MOLA O |
| ATOM | 1703 | C | SER | A 235 | 20.260 | 19.849 | 40.028 | 1.00 | 35.70 | MOLA C |
| ATOM | 1704 | O | SER | A 235 | 19.558 | 19.085 | 39.357 | 1.00 | 36.24 | MOLA O |
| ATOM | 1705 | N | HIS | A 236 | 19.816 | 20.973 | 40.582 | 1.00 | 36.60 | MOLA N |
| ATOM | 1706 | CA | HIS | A 236 | 18.458 | 21.442 | 40.448 | 1.00 | 39.31 | MOLA C |
| ATOM | 1707 | CB | HIS | A 236 | 17.933 | 21.999 | 41.753 | 1.00 | 38.49 | MOLA C |
| ATOM | 1708 | CG | HIS | A 236 | 17.768 | 20.979 | 42.837 | 1.00 | 45.76 | MOLA C |
| ATOM | 1709 | ND1 | HIS | A 236 | 16.837 | 19.964 | 42.771 | 1.00 | 53.75 | MOLA N |
| ATOM | 1710 | CE1 | HIS | A 236 | 16.889 | 19.246 | 43.880 | 1.00 | 50.54 | MOLA C |
| ATOM | 1711 | NE2 | HIS | A 236 | 17.817 | 19.761 | 44.667 | 1.00 | 49.11 | MOLA N |
| ATOM | 1712 | CD2 | HIS | A 236 | 18.375 | 20.853 | 44.042 | 1.00 | 49.64 | MOLA C |
| ATOM | 1713 | C | HIS | A 236 | 18.461 | 22.556 | 39.454 | 1.00 | 41.28 | MOLA C |
| ATOM | 1714 | O | HIS | A 236 | 19.284 | 23.474 | 39.543 | 1.00 | 42.92 | MOLA O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 1715 | N | SER | A 237 | 17.541 | 22.473 | 38.494 | 1.00 | 43.48 | MOLA | N |
| ATOM | 1716 | CA | SER | A 237 | 17.411 | 23.516 | 37.501 | 1.00 | 43.56 | MOLA | C |
| ATOM | 1717 | CB | SER | A 237 | 17.469 | 22.977 | 36.093 | 1.00 | 42.41 | MOLA | C |
| ATOM | 1718 | OG | SER | A 237 | 17.627 | 24.079 | 35.222 | 1.00 | 46.38 | MOLA | O |
| ATOM | 1719 | C | SER | A 237 | 16.127 | 24.289 | 37.733 | 1.00 | 43.86 | MOLA | C |
| ATOM | 1720 | O | SER | A 237 | 15.017 | 23.705 | 37.733 | 1.00 | 45.28 | MOLA | O |
| ATOM | 1721 | N | VAL | A 238 | 16.299 | 25.600 | 37.954 | 1.00 | 40.56 | MOLA | N |
| ATOM | 1722 | CA | VAL | A 238 | 15.194 | 26.469 | 38.310 | 1.00 | 36.80 | MOLA | C |
| ATOM | 1723 | CB | VAL | A 238 | 15.399 | 27.122 | 39.635 | 1.00 | 36.20 | MOLA | C |
| ATOM | 1724 | CG1 | VAL | A 238 | 14.055 | 27.313 | 40.281 | 1.00 | 32.63 | MOLA | C |
| ATOM | 1725 | CG2 | VAL | A 238 | 16.238 | 26.235 | 40.504 | 1.00 | 40.18 | MOLA | C |
| ATOM | 1726 | C | VAL | A 238 | 15.086 | 27.561 | 37.319 | 1.00 | 35.49 | MOLA | C |
| ATOM | 1727 | O | VAL | A 238 | 15.845 | 28.528 | 37.365 | 1.00 | 36.32 | MOLA | O |
| ATOM | 1728 | N | PHE | A 239 | 14.138 | 27.383 | 36.414 | 1.00 | 33.53 | MOLA | N |
| ATOM | 1729 | CA | PHE | A 239 | 13.878 | 28.348 | 35.393 | 1.00 | 34.51 | MOLA | C |
| ATOM | 1730 | CB | PHE | A 239 | 13.568 | 27.657 | 34.080 | 1.00 | 32.29 | MOLA | C |
| ATOM | 1731 | CG | PHE | A 239 | 13.399 | 28.621 | 32.948 | 1.00 | 36.81 | MOLA | C |
| ATOM | 1732 | CD1 | PHE | A 239 | 12.216 | 29.379 | 32.834 | 1.00 | 31.95 | MOLA | C |
| ATOM | 1733 | CE1 | PHE | A 239 | 12.058 | 30.299 | 31.783 | 1.00 | 42.09 | MOLA | C |
| ATOM | 1734 | CZ | PHE | A 239 | 13.123 | 30.500 | 30.841 | 1.00 | 38.40 | MOLA | C |
| ATOM | 1735 | CE2 | PHE | A 239 | 14.314 | 29.754 | 30.970 | 1.00 | 22.92 | MOLA | C |
| ATOM | 1736 | CD2 | PHE | A 239 | 14.444 | 28.830 | 32.028 | 1.00 | 20.56 | MOLA | C |
| ATOM | 1737 | C | PHE | A 239 | 12.694 | 29.225 | 35.799 | 1.00 | 37.17 | MOLA | C |
| ATOM | 1738 | O | PHE | A 239 | 11.560 | 28.720 | 35.946 | 1.00 | 38.32 | MOLA | O |
| ATOM | 1739 | N | SER | A 240 | 12.949 | 30.526 | 35.963 | 1.00 | 36.63 | MOLA | N |
| ATOM | 1740 | CA | SER | A 240 | 11.916 | 31.446 | 36.474 | 1.00 | 38.69 | MOLA | C |
| ATOM | 1741 | CB | SER | A 240 | 12.322 | 32.066 | 37.814 | 1.00 | 37.90 | MOLA | C |
| ATOM | 1742 | OG | SER | A 240 | 11.795 | 31.309 | 38.895 | 1.00 | 40.95 | MOLA | O |
| ATOM | 1743 | C | SER | A 240 | 11.507 | 32.533 | 35.512 | 1.00 | 37.76 | MOLA | C |
| ATOM | 1744 | O | SER | A 240 | 12.349 | 33.231 | 34.929 | 1.00 | 40.65 | MOLA | O |
| ATOM | 1745 | N | VAL | A 241 | 10.205 | 32.695 | 35.364 | 1.00 | 36.07 | MOLA | N |
| ATOM | 1746 | CA | VAL | A 241 | 9.718 | 33.673 | 34.411 | 1.00 | 38.52 | MOLA | C |
| ATOM | 1747 | CB | VAL | A 241 | 9.078 | 32.995 | 33.234 | 1.00 | 38.47 | MOLA | C |
| ATOM | 1748 | CG1 | VAL | A 241 | 7.756 | 32.370 | 33.681 | 1.00 | 40.20 | MOLA | C |
| ATOM | 1749 | CG2 | VAL | A 241 | 8.896 | 33.991 | 32.090 | 1.00 | 36.83 | MOLA | C |
| ATOM | 1750 | C | VAL | A 241 | 8.718 | 34.603 | 35.075 | 1.00 | 40.02 | MOLA | C |
| ATOM | 1751 | O | VAL | A 241 | 7.754 | 34.178 | 35.690 | 1.00 | 41.08 | MOLA | O |
| ATOM | 1752 | N | THR | A 242 | 8.971 | 35.885 | 34.947 | 1.00 | 42.18 | MOLA | N |
| ATOM | 1753 | CA | THR | A 242 | 8.242 | 36.862 | 35.690 | 1.00 | 45.09 | MOLA | C |
| ATOM | 1754 | CB | THR | A 242 | 9.230 | 37.655 | 36.535 | 1.00 | 45.00 | MOLA | C |
| ATOM | 1755 | OG1 | THR | A 242 | 10.493 | 36.973 | 36.523 | 1.00 | 50.62 | MOLA | O |
| ATOM | 1756 | CG2 | THR | A 242 | 8.732 | 37.792 | 37.955 | 1.00 | 42.82 | MOLA | C |
| ATOM | 1757 | C | THR | A 242 | 7.605 | 37.788 | 34.680 | 1.00 | 47.28 | MOLA | C |
| ATOM | 1758 | O | THR | A 242 | 8.278 | 38.309 | 33.760 | 1.00 | 47.86 | MOLA | O |
| ATOM | 1759 | N | ILE | A 243 | 6.305 | 37.990 | 34.812 | 1.00 | 47.93 | MOLA | N |
| ATOM | 1760 | CA | ILE | A 243 | 5.671 | 38.894 | 33.863 | 1.00 | 51.27 | MOLA | C |
| ATOM | 1761 | CB | ILE | A 243 | 5.042 | 38.132 | 32.627 | 1.00 | 51.73 | MOLA | C |
| ATOM | 1762 | CG1 | ILE | A 243 | 4.384 | 39.123 | 31.669 | 1.00 | 56.20 | MOLA | C |
| ATOM | 1763 | CD1 | ILE | A 243 | 2.974 | 39.532 | 32.083 | 1.00 | 66.74 | MOLA | C |
| ATOM | 1764 | CG2 | ILE | A 243 | 4.060 | 36.994 | 33.039 | 1.00 | 47.93 | MOLA | C |
| ATOM | 1765 | C | ILE | A 243 | 4.772 | 39.984 | 34.489 | 1.00 | 52.55 | MOLA | C |
| ATOM | 1766 | O | ILE | A 243 | 3.796 | 39.686 | 35.200 | 1.00 | 51.67 | MOLA | O |
| ATOM | 1767 | N | HIS | A 244 | 5.160 | 41.244 | 34.236 | 1.00 | 53.16 | MOLA | N |
| ATOM | 1768 | CA | HIS | A 244 | 4.399 | 42.427 | 34.663 | 1.00 | 53.77 | MOLA | C |
| ATOM | 1769 | CB | HIS | A 244 | 5.301 | 43.657 | 34.894 | 1.00 | 54.17 | MOLA | C |
| ATOM | 1770 | CG | HIS | A 244 | 6.665 | 43.353 | 35.450 | 1.00 | 61.03 | MOLA | C |
| ATOM | 1771 | ND1 | HIS | A 244 | 7.437 | 42.290 | 35.020 | 1.00 | 69.65 | MOLA | N |
| ATOM | 1772 | CE1 | HIS | A 244 | 8.601 | 42.310 | 35.647 | 1.00 | 66.02 | MOLA | C |
| ATOM | 1773 | NE2 | HIS | A 244 | 8.623 | 43.359 | 36.453 | 1.00 | 59.88 | MOLA | N |
| ATOM | 1774 | CD2 | HIS | A 244 | 7.430 | 44.035 | 36.340 | 1.00 | 58.36 | MOLA | C |
| ATOM | 1775 | C | HIS | A 244 | 3.366 | 42.783 | 33.580 | 1.00 | 52.17 | MOLA | C |
| ATOM | 1776 | O | HIS | A 244 | 3.708 | 42.978 | 32.400 | 1.00 | 49.97 | MOLA | O |
| ATOM | 1777 | N | MET | A 245 | 2.110 | 42.887 | 34.000 | 1.00 | 51.26 | MOLA | N |
| ATOM | 1778 | CA | MET | A 245 | 0.998 | 43.181 | 33.100 | 1.00 | 50.78 | MOLA | C |
| ATOM | 1779 | CB | MET | A 245 | 0.096 | 41.967 | 32.993 | 1.00 | 49.99 | MOLA | C |
| ATOM | 1780 | CG | MET | A 245 | 0.770 | 40.703 | 32.691 | 1.00 | 45.65 | MOLA | C |
| ATOM | 1781 | SD | MET | A 245 | −0.253 | 39.444 | 33.426 | 1.00 | 46.13 | MOLA | S |
| ATOM | 1782 | CE | MET | A 245 | 0.472 | 39.367 | 35.047 | 1.00 | 49.69 | MOLA | C |
| ATOM | 1783 | C | MET | A 245 | 0.111 | 44.280 | 33.644 | 1.00 | 51.92 | MOLA | C |
| ATOM | 1784 | O | MET | A 245 | −0.118 | 44.336 | 34.849 | 1.00 | 53.76 | MOLA | O |
| ATOM | 1785 | N | LYS | A 246 | −0.438 | 45.108 | 32.759 | 1.00 | 52.63 | MOLA | N |
| ATOM | 1786 | CA | LYS | A 246 | −1.422 | 46.137 | 33.145 | 1.00 | 53.85 | MOLA | C |
| ATOM | 1787 | CB | LYS | A 246 | −0.752 | 47.495 | 33.367 | 1.00 | 52.63 | MOLA | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1788 | CG | LYS | A 246 | −1.584 | 48.707 | 32.942 | 1.00 | 53.46 | MOLA C |
| ATOM | 1789 | CD | LYS | A 246 | −0.742 | 49.987 | 33.002 | 1.00 | 56.29 | MOLA C |
| ATOM | 1790 | CE | LYS | A 246 | −1.435 | 51.159 | 32.338 | 1.00 | 57.30 | MOLA C |
| ATOM | 1791 | NZ | LYS | A 246 | −0.680 | 52.424 | 32.586 | 1.00 | 48.24 | MOLA N |
| ATOM | 1792 | C | LYS | A 246 | −2.538 | 46.251 | 32.114 | 1.00 | 54.38 | MOLA C |
| ATOM | 1793 | O | LYS | A 246 | −2.370 | 46.873 | 31.076 | 1.00 | 55.96 | MOLA O |
| ATOM | 1794 | N | GLU | A 247 | −3.666 | 45.619 | 32.398 | 1.00 | 55.38 | MOLA N |
| ATOM | 1795 | CA | GLU | A 247 | −4.838 | 45.711 | 31.553 | 1.00 | 57.54 | MOLA C |
| ATOM | 1796 | CB | GLU | A 247 | −5.860 | 44.664 | 31.983 | 1.00 | 58.27 | MOLA C |
| ATOM | 1797 | CG | GLU | A 247 | −5.877 | 43.339 | 31.255 | 1.00 | 58.74 | MOLA C |
| ATOM | 1798 | CD | GLU | A 247 | −7.000 | 42.474 | 31.793 | 1.00 | 62.04 | MOLA C |
| ATOM | 1799 | OE1 | GLU | A 247 | −7.64 | 541.737 | 30.998 | 1.00 | 65.34 | MOLA O |
| ATOM | 1800 | OE2 | GLU | A 247 | −7.253 | 42.571 | 33.024 | 1.00 | 53.42 | MOLA O |
| ATOM | 1801 | C | GLU | A 247 | −5.507 | 47.048 | 31.776 | 1.00 | 59.06 | MOLA C |
| ATOM | 1802 | O | GLU | A 247 | −5.599 | 47.501 | 32.927 | 1.00 | 60.68 | MOLA O |
| ATOM | 1803 | N | THR | A 248 | −6.011 | 47.671 | 30.706 | 1.00 | 58.89 | MOLA N |
| ATOM | 1804 | CA | THR | A 248 | −6.853 | 48.868 | 30.865 | 1.00 | 56.07 | MOLA C |
| ATOM | 1805 | CB | THR | A 248 | −6.102 | 50.131 | 30.494 | 1.00 | 55.12 | MOLA C |
| ATOM | 1806 | OG1 | THR | A 248 | −4.811 | 50.101 | 31.107 | 1.00 | 51.15 | MOLA O |
| ATOM | 1807 | CG2 | THR | A 248 | −6.857 | 51.331 | 31.000 | 1.00 | 56.33 | MOLA C |
| ATOM | 1808 | C | THR | A 248 | −8.159 | 48.763 | 30.071 | 1.00 | 55.49 | MOLA C |
| ATOM | 1809 | O | THR | A 248 | −8.150 | 48.358 | 28.921 | 1.00 | 56.44 | MOLA O |
| ATOM | 1810 | N | THR | A 249 | −9.269 | 49.123 | 30.700 | 1.00 | 55.63 | MOLA N |
| ATOM | 1811 | CA | THR | A 249 | −10.598 | 49.015 | 30.099 | 1.00 | 56.83 | MOLA C |
| ATOM | 1812 | CB | THR | A 249 | −11.372 | 47.802 | 30.694 | 1.00 | 57.49 | MOLA C |
| ATOM | 1813 | OG1 | THR | A 249 | −10.699 | 46.579 | 30.373 | 1.00 | 59.11 | MOLA O |
| ATOM | 1814 | CG2 | THR | A 249 | −12.809 | 47.747 | 30.169 | 1.00 | 55.23 | MOLA C |
| ATOM | 1815 | C | THR | A 249 | −11.442 | 50.268 | 30.369 | 1.00 | 57.00 | MOLA C |
| ATOM | 1816 | O | THR | A 249 | −11.618 | 50.648 | 31.526 | 1.00 | 56.88 | MOLA O |
| ATOM | 1817 | N | ILE | A 250 | −11.972 | 50.888 | 29.314 | 1.00 | 57.13 | MOLA N |
| ATOM | 1818 | CA | ILE | A 250 | −12.880 | 52.039 | 29.444 | 1.00 | 57.93 | MOLA C |
| ATOM | 1819 | CB | ILE | A 250 | −13.264 | 52.644 | 28.059 | 1.00 | 58.23 | MOLA C |
| ATOM | 1820 | CG1 | ILE | A 250 | −12.063 | 53.275 | 27.363 | 1.00 | 55.93 | MOLA C |
| ATOM | 1821 | CD1 | ILE | A 250 | −12.331 | 53.596 | 25.906 | 1.00 | 57.90 | MOLA C |
| ATOM | 1822 | CG2 | ILE | A 250 | −14.371 | 53.676 | 28.209 | 1.00 | 54.05 | MOLA C |
| ATOM | 1823 | C | ILE | A 250 | −14.174 | 51.600 | 30.129 | 1.00 | 58.42 | MOLA C |
| ATOM | 1824 | O | ILE | A 250 | −14.823 | 50.655 | 29.674 | 1.00 | 55.55 | MOLA O |
| ATOM | 1825 | N | ASP | A 251 | −14.544 | 52.315 | 31.197 | 1.00 | 60.87 | MOLA N |
| ATOM | 1826 | CA | ASP | A 251 | −15.697 | 51.987 | 32.051 | 1.00 | 64.26 | MOLA C |
| ATOM | 1827 | CB | ASP | A 251 | −17.006 | 51.882 | 31.253 | 1.00 | 64.94 | MOLA C |
| ATOM | 1828 | CG | ASP | A 251 | −17.247 | 53.071 | 30.342 | 1.00 | 66.20 | MOLA C |
| ATOM | 1829 | OD1 | ASP | A 251 | −16.918 | 54.214 | 30.738 | 1.00 | 67.60 | MOLA O |
| ATOM | 1830 | OD2 | ASP | A 251 | −17.775 | 52.843 | 29.227 | 1.00 | 59.69 | MOLA O |
| ATOM | 1831 | C | ASP | A 251 | −15.454 | 50.665 | 32.783 | 1.00 | 66.50 | MOLA C |
| ATOM | 1832 | O | ASP | A 251 | −16.301 | 49.768 | 32.752 | 1.00 | 66.07 | MOLA O |
| ATOM | 1833 | N | GLY | A 252 | −14.289 | 50.545 | 33.422 | 1.00 | 68.33 | MOLA N |
| ATOM | 1834 | CA | GLY | A 252 | −13.923 | 49.337 | 34.162 | 1.00 | 69.39 | MOLA C |
| ATOM | 1835 | C | GLY | A 252 | −12.743 | 49.505 | 35.118 | 1.00 | 70.80 | MOLA C |
| ATOM | 1836 | O | GLY | A 252 | −12.376 | 50.632 | 35.473 | 1.00 | 70.75 | MOLA O |
| ATOM | 1837 | N | GLU | A 253 | −12.162 | 48.375 | 35.542 | 1.00 | 70.92 | MOLA N |
| ATOM | 1838 | CA | GLU | A 253 | −10.988 | 48.353 | 36.421 | 1.00 | 69.87 | MOLA C |
| ATOM | 1839 | CB | GLU | A 253 | −10.942 | 47.039 | 37.217 | 1.00 | 71.12 | MOLA C |
| ATOM | 1840 | CG | GLU | A 253 | −12.186 | 46.769 | 38.066 | 1.00 | 72.96 | MOLA C |
| ATOM | 1841 | CD | GLU | A 253 | −12.473 | 47.890 | 39.058 | 1.00 | 83.35 | MOLA C |
| ATOM | 1842 | OE1 | GLU | A 253 | −12.124 | 49.057 | 38.769 | 1.00 | 81.25 | MOLA O |
| ATOM | 1843 | OE2 | GLU | A 253 | −13.055 | 47.606 | 40.128 | 1.00 | 92.10 | MOLA O |
| ATOM | 1844 | C | GLU | A 253 | −9.704 | 48.538 | 35.603 | 1.00 | 67.79 | MOLA C |
| ATOM | 1845 | O | GLU | A 253 | −9.578 | 47.985 | 34.500 | 1.00 | 66.77 | MOLA O |
| ATOM | 1846 | N | GLU | A 254 | −8.781 | 49.345 | 36.125 | 1.00 | 65.40 | MOLA N |
| ATOM | 1847 | CA | GLU | A 254 | −7.505 | 49.575 | 35.454 | 1.00 | 63.82 | MOLA C |
| ATOM | 1848 | CB | GLU | A 254 | −7.179 | 51.070 | 35.363 | 1.00 | 63.29 | MOLA C |
| ATOM | 1849 | CG | GLU | A 254 | −6.011 | 51.444 | 34.423 | 1.00 | 64.77 | MOLA C |
| ATOM | 1850 | CD | GLU | A 254 | −4.667 | 51.688 | 35.139 | 1.00 | 75.26 | MOLA C |
| ATOM | 1851 | OE1 | GLU | A 254. | −3.824 | 52.438 | 34.587 | 1.00 | 77.90 | MOLA O |
| ATOM | 1852 | OE2 | GLU | A 254 | −4.446 | 51.152 | 36.251 | 1.00 | 73.62 | MOLA O |
| ATOM | 1853 | C | GLU | A 254 | −6.445 | 48.796 | 36.226 | 1.00 | 63.74 | MOLA C |
| ATOM | 1854 | O | GLU | A 254 | −5.664 | 49.362 | 36.997 | 1.00 | 63.20 | MOLA O |
| ATOM | 1855 | N | LEU | A 255 | −6.449 | 47.480 | 35.997 | 1.00 | 62.71 | MOLA N |
| ATOM | 1856 | CA | LEU | A 255 | −5.611 | 46.500 | 36.699 | 1.00 | 59.86 | MOLA C |
| ATOM | 1857 | CB | LEU | A 255 | −6.174 | 45.099 | 36.410 | 1.00 | 57.15 | MOLA C |
| ATOM | 1858 | CG | LEU | A 255 | −7.671 | 45.065 | 36.779 | 1.00 | 57.51 | MOLA C |
| ATOM | 1859 | CD1 | LEU | A 255 | −-8.528 | 44.378 | 35.710 | 1.00 | 59.03 | MOLA C |
| ATOM | 1860 | CD2 | LEU | A 255 | −7.982 | 44.507 | 38.218 | 1.00 | 42.30 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 1861 | C | LEU | A 255 | −4.080 | 46.586 | 36.427 | 1.00 | 59.03 | MOLA C |
| ATOM | 1862 | O | LEU | A 255 | −3.645 | 46.868 | 35.298 | 1.00 | 57.31 | MOLA O |
| ATOM | 1863 | N | VAL | A 256 | −3.293 | 46.401 | 37.496 | 1.00 | 57.05 | MOLA N |
| ATOM | 1864 | CA | VAL | A 256 | −1.832 | 46.263 | 37.424 | 1.00 | 54.68 | MOLA C |
| ATOM | 1865 | CB | VAL | A 256 | −1.078 | 47.474 | 37.990 | 1.00 | 54.75 | MOLA C |
| ATOM | 1866 | CG1 | VAL | A 256 | 0.228 | 47.011 | 38.682 | 1.00 | 55.18 | MOLA C |
| ATOM | 1867 | CG2 | VAL | A 256 | −0.769 | 48.453 | 36.904 | 1.00 | 51.92 | MOLA C |
| ATOM | 1868 | C | VAL | A 256 | −1.392 | 45.042 | 38.229 | 1.00 | 53.42 | MOLA C |
| ATOM | 1869 | O | VAL | A 256 | −1.639 | 44.976 | 39.439 | 1.00 | 53.32 | MOLA O |
| ATOM | 1870 | N | LYS | A 257 | −0.722 | 44.093 | 37.570 | 1.00 | 50.51 | MOLA N |
| ATOM | 1871 | CA | LYS | A 257 | −0.322 | 42.841 | 38.223 | 1.00 | 47.39 | MOLA C |
| ATOM | 1872 | CB | LYS | A 257 | −1.360 | 41.749 | 37.931 | 1.00 | 46.45 | MOLA C |
| ATOM | 1873 | CG | LYS | A 257 | −2.227 | 42.099 | 36.741 | 1.00 | 45.74 | MOLA C |
| ATOM | 1874 | CD | LYS | A 257 | −3.622 | 41.508 | 36.851 | 1.00 | 44.06 | MOLA C |
| ATOM | 1875 | CE | LYS | A 257 | −3.750 | 40.283 | 36.001 | 1.00 | 42.30 | MOLA C |
| ATOM | 1876 | NZ | LYS | A 257 | −3.243 | 40.650 | 34.655 | 1.00 | 38.17 | MOLA N |
| ATOM | 1877 | C | LYS | A 257 | 1.082 | 42.353 | 37.907 | 1.00 | 45.33 | MOLA C |
| ATOM | 1878 | O | LYS | A 257 | 1.593 | 42.542 | 36.814 | 1.00 | 45.91 | MOLA O |
| ATOM | 1879 | N | ILE | A 258 | 1.717 | 41.758 | 38.900 | 1.00 | 44.06 | MOLA N |
| ATOM | 1880 | CA | ILE | A 258 | 2.941 | 41.027 | 38.658 | 1.00 | 44.78 | MOLA C |
| ATOM | 1881 | CB | ILE | A 258 | 4.090 | 41.470 | 39.579 | 1.00 | 45.83 | MOLA C |
| ATOM | 1882 | CG1 | ILE | A 258 | 4.337 | 42.969 | 39.479 | 1.00 | 45.39 | MOLA C |
| ATOM | 1883 | CD1 | ILE | A 258 | 5.312 | 43.346 | 38.364 | 1.00 | 36.31 | MOLA C |
| ATOM | 1884 | CG2 | ILE | A 258 | 5.362 | 40.793 | 39.169 | 1.00 | 46.51 | MOLA C |
| ATOM | 1885 | C | ILE | A 258 | 2.635 | 39.540 | 38.875 | 1.00 | 43.51 | MOLA C |
| ATOM | 1886 | O | ILE | A 258 | 1.984 | 39.155 | 39.843 | 1.00 | 39.41 | MOLA O |
| ATOM | 1887 | N | GLY | A 259 | 3.097 | 38.724 | 37.933 | 1.00 | 45.19 | MOLA N |
| ATOM | 1888 | CA | GLY | A 259 | 2.888 | 37.267 | 37.940 | 1.00 | 43.06 | MOLA C |
| ATOM | 1889 | C | GLY | A 259 | 4.206 | 36.543 | 37.740 | 1.00 | 41.28 | MOLA C |
| ATOM | 1890 | O | GLY | A 259 | 5.101 | 37.027 | 37.036 | 1.00 | 39.68 | MOLA O |
| ATOM | 1891 | N | LYS | A 260 | 4.328 | 35.379 | 38.364 | 1.00 | 42.03 | MOLA N |
| ATOM | 1892 | CA | LYS | A 260 | 5.600 | 34.653 | 38.364 | 1.00 | 42.50 | MOLA C |
| ATOM | 1893 | CB | LYS | A 260 | 6.449 | 35.079 | 39.559 | 1.00 | 42.20 | MOLA C |
| ATOM | 1894 | CG | LYS | A 260 | 7.864 | 34.578 | 39.474 | 1.00 | 46.74 | MOLA C |
| ATOM | 1895 | CD | LYS | A 260 | 8.651 | 34.818 | 40.749 | 1.00 | 47.73 | MOLA C |
| ATOM | 1896 | CE | LYS | A 260 | 10.122 | 34.600 | 40.460 | 1.00 | 41.34 | MOLA C |
| ATOM | 1897 | NZ | LYS | A 260 | 10.947 | 34.861 | 41.653 | 1.00 | 47.03 | MOLA N |
| ATOM | 1898 | C | LYS | A 260 | 5.450 | 33.141 | 38.407 | 1.00 | 41.66 | MOLA C |
| ATOM | 1899 | O | LYS | A 260 | 4.747 | 32.588 | 39.260 | 1.00 | 42.91 | MOLA O |
| ATOM | 1900 | N | LEU | A 261 | 6.142 | 32.473 | 37.495 | 1.00 | 40.07 | MOLA N |
| ATOM | 1901 | CA | LEU | A 261 | 6.133 | 31.014 | 37.445 | 1.00 | 36.78 | MOLA C |
| ATOM | 1902 | CB | LEU | A 261 | 5.508 | 30.519 | 36.136 | 1.00 | 36.14 | MOLA C |
| ATOM | 1903 | CG | LEU | A 261 | 5.329 | 29.035 | 35.855 | 1.00 | 28.06 | MOLA C |
| ATOM | 1904 | CD1 | LEU | A 261 | 4.104 | 28.525 | 36.534 | 1.00 | 30.53 | MOLA C |
| ATOM | 1905 | CD2 | LEU | A 261 | 5.191 | 28.806 | 34.357 | 1.00 | 31.77 | MOLA C |
| ATOM | 1906 | C | LEU | A 261 | 7.556 | 30.564 | 37.513 | 1.00 | 37.52 | MOLA C |
| ATOM | 1907 | O | LEU | A 261 | 8.416 | 31.100 | 36.781 | 1.00 | 36.70 | MOLA O |
| ATOM | 1908 | N | ASN | A 262 | 7.803 | 29.626 | 38.430 | 1.00 | 38.96 | MOLA N |
| ATOM | 1909 | CA | ASN | A 262 | 9.068 | 28.857 | 38.504 | 1.00 | 39.16 | MOLA C |
| ATOM | 1910 | CB | ASN | A 262 | 9.669 | 28.850 | 39.917 | 1.00 | 38.37 | MOLA C |
| ATOM | 1911 | CG | ASN | A 262 | 9.220 | 30.017 | 40.757 | 1.00 | 41.76 | MOLA C |
| ATOM | 1912 | OD1 | ASN | A 262 | 8.335 | 29.873 | 41.618 | 1.00 | 36.02 | MOLA O |
| ATOM | 1913 | ND2 | ASN | A 262 | 9.818 | 31.191 | 40.514 | 1.00 | 36.44 | MOLA N |
| ATOM | 1914 | C | ASN | A 262 | 8.795 | 27.392 | 38.097 | 1.00 | 38.69 | MOLA C |
| ATOM | 1915 | O | ASN | A 262 | 8.015 | 26.673 | 38.731 | 1.00 | 39.95 | MOLA O |
| ATOM | 1916 | N | LEU | A 263 | 9.437 | 26.953 | 37.036 | 1.00 | 36.80 | MOLA N |
| ATOM | 1917 | CA | LEU | A 263 | 9.377 | 25.574 | 36.634 | 1.00 | 33.68 | MOLA C |
| ATOM | 1918 | CB | LEU | A 263 | 9.322 | 25.582 | 35.131 | 1.00 | 33.93 | MOLA C |
| ATOM | 1919 | CG | LEU | A 263 | 8.346 | 26.666 | 34.698 | 1.00 | 24.47 | MOLA C |
| ATOM | 1920 | CD1 | LEU | A 263 | 8.796 | 27.394 | 33.423 | 1.00 | 13.99 | MOLA C |
| ATOM | 1921 | CD2 | LEU | A 263 | 7.043 | 26.014 | 34.461 | 1.00 | 21.52 | MOLA C |
| ATOM | 1922 | C | LEU | A 263 | 10.660 | 24.874 | 37.127 | 1.00 | 33.64 | MOLA C |
| ATOM | 1923 | O | LEU | A 263 | 11.767 | 25.311 | 36.817 | 1.00 | 33.67 | MOLA O |
| ATOM | 1924 | N | VAL | A 264 | 10.527 | 23.784 | 37.881 | 1.00 | 34.38 | MOLA N |
| ATOM | 1925 | CA | VAL | A 264 | 11.715 | 23.175 | 38.518 | 1.00 | 33.24 | MOLA C |
| ATOM | 1926 | CB | VAL | A 264 | 11.680 | 23.388 | 40.040 | 1.00 | 32.52 | MOLA C |
| ATOM | 1927 | CG1 | VAL | A 264 | 12.944 | 22.884 | 40.649 | 1.00 | 29.22 | MOLA C |
| ATOM | 1928 | CG2 | VAL | A 264 | 11.519 | 24.846 | 40.343 | 1.00 | 28.08 | MOLA C |
| ATOM | 1929 | C | VAL | A 264 | 12.006 | 21.695 | 38.223 | 1.00 | 33.21 | MOLA C |
| ATOM | 1930 | O | VAL | A 264 | 11.204 | 20.810 | 38.542 | 1.00 | 31.44 | MOLA O. |
| ATOM | 1931 | N | ASP | A 265 | 13.183 | 21.475 | 37.627 | 1.00 | 34.60 | MOLA N |
| ATOM | 1932 | CA | ASP | A 265 | 13.764 | 20.166 | 37.280 | 1.00 | 32.76 | MOLA C |
| ATOM | 1933 | CB | ASP | A 265 | 14.686 | 20.347 | 36.091 | 1.00 | 33.82 | MOLA C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 1934 | CG | ASP | A 265 | 14.775 | 19.117 | 35.200 | 1.00 | 36.48 | MOLA C |
| ATOM | 1935 | OD1 | ASP | A 265 | 14.742 | 17.974 | 35.710 | 1.00 | 53.03 | MOLA O |
| ATOM | 1936 | OD2 | ASP | A 265 | 14.883 | 19.314 | 33.971 | 1.00 | 31.07 | MOLA O |
| ATOM | 1937 | C | ASP | A 265 | 14.640 | 19.710 | 38.407 | 1.00 | 34.10 | MOLA C |
| ATOM | 1938 | O | ASP | A 265 | 15.757 | 20.190 | 38.561 | 1.00 | 33.83 | MOLA O |
| ATOM | 1939 | N | LEU | A 266 | 14.162 | 18.766 | 39.197 | 1.00 | 36.05 | MOLA N |
| ATOM | 1940 | CA | LEU | A 266 | 14.910 | 18.333 | 40.357 | 1.00 | 37.44 | MOLA C |
| ATOM | 1941 | CB | LEU | A 266 | 13.957 | 17.582 | 41.264 | 1.00 | 35.28 | MOLA C |
| ATOM | 1942 | CG | LEU | A 266 | 13.015 | 18.577 | 41.908 | 1.00 | 36.50 | MOLA C |
| ATOM | 1943 | CD1 | LEU | A 266 | 12.175 | 17.931 | 43.024 | 1.00 | 25.63 | MOLA C |
| ATOM | 1944 | CD2 | LEU | A 266 | 13.859 | 19.712 | 42.433 | 1.00 | 25.08 | MOLA C |
| ATOM | 1945 | C | LEU | A 266 | 16.135 | 17.454 | 40.060 | 1.00 | 38.78 | MOLA C |
| ATOM | 1946 | O | LEU | A 266 | 16.142 | 16.734 | 39.084 | 1.00 | 40.83 | MOLA O |
| ATOM | 1947 | N | ALA | A 267 | 17.173 | 17.515 | 40.892 | 1.00 | 40.14 | MOLA N |
| ATOM | 1948 | CA | ALA | A 267 | 18.235 | 16.497 | 40.839 | 1.00 | 40.99 | MOLA C |
| ATOM | 1949 | CB | ALA | A 267 | 19.246 | 16.687 | 41.977 | 1.00 | 41.25 | MOLA C |
| ATOM | 1950 | C | ALA | A 267 | 17.540 | 15.146 | 40.973 | 1.00 | 40.63 | MOLA C |
| ATOM | 1951 | O | ALA | A 267 | 16.465 | 15.083 | 41.579 | 1.00 | 42.63 | MOLA O |
| ATOM | 1952 | N | GLY | A 268 | 18.138 | 14.072 | 40.433 | 1.00 | 39.77 | MOLA N |
| ATOM | 1953 | CA | GLY | A 268 | 17.488 | 12.750 | 40.403 | 1.00 | 32.98 | MOLA C |
| ATOM | 1954 | C | GLY | A 268 | 17.261 | 12.243 | 41.801 | 1.00 | 30.19 | MOLA C |
| ATOM | 1955 | O | GLY | A 268 | 17.995 | 12.615 | 42.688 | 1.00 | 32.98 | MOLA O |
| ATOM | 1956 | N | SER | A 269 | 16.262 | 11.395 | 42.016 | 1.00 | 28.80 | MOLA N |
| ATOM | 1957 | CA | SER | A 269 | 15.954 | 10.930 | 43.372 | 1.00 | 28.42 | MOLA C |
| ATOM | 1958 | CB | SER | A 269 | 14.456 | 10.782 | 43.558 | 1.00 | 25.13 | MOLA C |
| ATOM | 1959 | OG | SER | A 269 | 13.890 | 10.345 | 42.349 | 1.00 | 29.66 | MOLA O |
| ATOM | 1960 | C | SER | A 269 | 16.672 | 9.649 | 43.798 | 1.00 | 30.93 | MOLA C |
| ATOM | 1961 | O | SER | A 269 | 16.579 | 9.217 | 44.967 | 1.00 | 33.98 | MOLA O |
| ATOM | 1962 | N | GLU | A 270 | 17.383 | 9.012 | 42.888 | 1.00 | 29.83 | MOLA N |
| ATOM | 1963 | CA | GLU | A 270 | 18.144 | 7.867 | 43.341 | 1.00 | 31.68 | MOLA C |
| ATOM | 1964 | CB | GLU | A 270 | 19.010 | 7.278 | 42.232 | 1.00 | 30.94 | MOLA C |
| ATOM | 1965 | CG | GLU | A 270 | 19.883 | 8.305 | 41.525 | 1.00 | 36.36 | MOLA C |
| ATOM | 1966 | CD | GLU | A 270 | 19.141 | 9.075 | 40.433 | 1.00 | 43.98 | MOLA C |
| ATOM | 1967 | OE1 | GLU | A 270 | 17.920 | 8.834 | 40.219 | 1.00 | 38.26 | MOLA O |
| ATOM | 1968 | OE2 | GLU | A 270 | 19.797 | 9.911 | 39.773 | 1.00 | 44.10 | MOLA O |
| ATOM | 1969 | C | GLU | A 270 | 19.013 | 8.328 | 44.502 | 1.00 | 29.85 | MOLA C |
| ATOM | 1970 | O | GLU | A 270 | 19.591 | 7.503 | 45.198 | 1.00 | 30.15 | MOLA O |
| ATOM | 1971 | N | ALA | A 285 | 26.203 | 14.893 | 47.833 | 1.00 | 70.75 | MOLA N |
| ATOM | 1972 | CA | ALA | A 285 | 24.803 | 14.563 | 47.561 | 1.00 | 69.96 | MOLA C |
| ATOM | 1973 | CB | ALA | A 285 | 24.718 | 13.383 | 46.594 | 1.00 | 67.70 | MOLA C |
| ATOM | 1974 | C | ALA | A 285 | 23.964 | 14.302 | 48.840 | 1.00 | 71.36 | MOLA C |
| ATOM | 1975 | O | ALA | A 285 | 22.808 | 13.862 | 48.740 | 1.00 | 72.37 | MOLA O |
| ATOM | 1976 | N | GLY | A 286 | 24.538 | 14.570 | 50.026 | 1.00 | 71.08 | MOLA N |
| ATOM | 1977 | CA | GLY | A 286 | 23.830 | 14.392 | 51.304 | 1.00 | 68.75 | MOLA C |
| ATOM | 1978 | C | GLY | A 286 | 22.810 | 15.503 | 51.378 | 1.00 | 68.50 | MOLA C |
| ATOM | 1979 | O | GLY | A 286 | 21.697 | 15.337 | 51.884 | 1.00 | 68.19 | MOLA O |
| ATOM | 1980 | N | ASN | A 287 | 23.209 | 16.647 | 50.838 | 1.00 | 67.70 | MOLA N |
| ATOM | 1981 | CA | ASN | A 287 | 22.349 | 17.817 | 50.747 | 1.00 | 68.21 | MOLA C |
| ATOM | 1982 | CB | ASN | A 287 | 23.192 | 19.005 | 50.319 | 1.00 | 67.99 | MOLA C |
| ATOM | 1983 | CG | ASN | A 287 | 24.311 | 18.588 | 49.405 | 1.00 | 69.18 | MOLA C |
| ATOM | 1984 | OD1 | ASN | A 287 | 24.140 | 18.515 | 48.191 | 1.00 | 77.95 | MOLA O |
| ATOM | 1985 | ND2 | ASN | A 287 | 25.461 | 18.271 | 49.985 | 1.00 | 63.70 | MOLA N |
| ATOM | 1986 | C | ASN | A 287 | 21.206 | 17.585 | 49.771 | 1.00 | 67.94 | MOLA C |
| ATOM | 1987 | O | ASN | A 287 | 20.076 | 17.994 | 50.027 | 1.00 | 68.64 | MOLA O |
| ATOM | 1988 | N | ILE | A 288 | 21.500 | 16.916 | 48.656 | 1.00 | 67.68 | MOLA N |
| ATOM | 1989 | CA | ILE | A 288 | 20.468 | 16.551 | 47.674 | 1.00 | 66.46 | MOLA C |
| ATOM | 1990 | CB | ILE | A 288 | 21.034 | 15.766 | 46.457 | 1.00 | 66.23 | MOLA C |
| ATOM | 1991 | CG1 | ILE | A 288 | 21.996 | 16.634 | 45.646 | 1.00 | 69.98 | MOLA C |
| ATOM | 1992 | CD1 | ILE | A 288 | 22.411 | 15.999 | 44.340 | 1.00 | 65.53 | MOLA C |
| ATOM | 1993 | CG2 | ILE | A 288 | 19.921 | 15.308 | 45.534 | 1.00 | 63.59 | MOLA C |
| ATOM | 1994 | C | ILE | A 288 | 19.315 | 15.768 | 48.318 | 1.00 | 66.42 | MOLA C |
| ATOM | 1995 | O | ILE | A 288 | 18.170 | 16.215 | 48.261 | 1.00 | 67.10 | MOLA O |
| ATOM | 1996 | N | ASN | A 289 | 19.592 | 14.621 | 48.941 | 1.00 | 65.53 | MOLA N |
| ATOM | 1997 | CA | ASN | A 289 | 18.491 | 13.864 | 49.542 | 1.00 | 65.47 | MOLA C |
| ATOM | 1998 | CB | ASN | A 289 | 18.907 | 12.450 | 50.003 | 1.00 | 66.61 | MOLA C |
| ATOM | 1999 | CG | ASN | A 289 | 19.499 | 12.417 | 51.431 | 1.00 | 68.50 | MOLA C |
| ATOM | 2000 | OD1 | ASN | A 289 | 20.693 | 12.698 | 51.651 | 1.00 | 54.07 | MOLA O |
| ATOM | 2001 | ND2 | ASN | A 289 | 18.663 | 12.023 | 52.399 | 1.00 | 67.62 | MOLA N |
| ATOM | 2002 | C | ASN | A 289 | 17.822 | 14.674 | 50.659 | 1.00 | 64.61 | MOLA C |
| ATOM | 2003 | O | ASN | A 289 | 16.678 | 14.401 | 51.037 | 1.00 | 63.92 | MOLA O |
| ATOM | 2004 | N | GLN | A 290 | 18.544 | 15.678 | 51.164 | 1.00 | 62.53 | MOLA N |
| ATOM | 2005 | CA | GLN | A 290 | 18.003 | 16.570 | 52.174 | 1.00 | 61.67 | MOLA C |
| ATOM | 2006 | CB | GLN | A 290 | 19.107 | 17.348 | 52.895 | 1.00 | 62.94 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2007 | CG | GLN | A 290 | 18.585 | 18.209 | 54.056 | 1.00 | 70.00 | MOLA C |
| ATOM | 2008 | CD | GLN | A 290 | 17.676 | 17.425 | 55.033 | 1.00 | 89.18 | MOLA C |
| ATOM | 2009 | OE1 | GLN | A 290 | 18.039 | 16.348 | 55.519 | 1.00 | 93.13 | MOLA O |
| ATOM | 2010 | NE2 | GLN | A 290 | 16.497 | 17.981 | 55.327 | 1.00 | 92.21 | MOLA N |
| ATOM | 2011 | C | GLN | A 290 | 16.998 | 17.532 | 51.551 | 1.00 | 59.72 | MOLA C |
| ATOM | 2012 | O | GLN | A 290 | 15.921 | 17.757 | 52.115 | 1.00 | 59.81 | MOLA O |
| ATOM | 2013 | N | SER | A 291 | 17.346 | 18.092 | 50.394 | 1.00 | 55.62 | MOLA N |
| ATOM | 2014 | CA | SER | A 291 | 16.443 | 18.985 | 49.694 | 1.00 | 54.03 | MOLA C |
| ATOM | 2015 | CB | SER | A 291 | 17.060 | 19.427 | 48.367 | 1.00 | 55.65 | MOLA C |
| ATOM | 2016 | OG | SER | A 291 | 18.458 | 19.643 | 48.463 | 1.00 | 51.60 | MOLA O |
| ATOM | 2017 | C | SER | A 291 | 15.170 | 18.211 | 49.396 | 1.00 | 52.89 | MOLA C |
| ATOM | 2018 | O | SER | A 291 | 14.105 | 18.449 | 49.969 | 1.00 | 51.31 | MOLA O |
| ATOM | 2019 | N | LEU | A 292 | 15.316 | 17.253 | 48.494 | 1.00 | 52.96 | MOLA N |
| ATOM | 2020 | CA | LEU | A 292 | 14.215 | 16.418 | 48.055 | 1.00 | 52.58 | MOLA C |
| ATOM | 2021 | CB | LEU | A 292 | 14.722 | 15.216 | 47.248 | 1.00 | 53.97 | MOLA C |
| ATOM | 2022 | CG | LEU | A 292 | 15.608 | 15.550 | 46.030 | 1.00 | 55.05 | MOLA C |
| ATOM | 2023 | CD1 | LEU | A 292 | 16.025 | 14.307 | 45.266 | 1.00 | 60.32 | MOLA C |
| ATOM | 2024 | CD2 | LEU | A 292 | 14.896 | 16.497 | 45.082 | 1.00 | 62.29 | MOLA C |
| ATOM | 2025 | C | LEU | A 292 | 13.465 | 15.987 | 49.279 | 1.00 | 52.17 | MOLA C |
| ATOM | 2026 | O | LEU | A 292 | 12.236 | 15.973 | 49.288 | 1.00 | 51.55 | MOLA O |
| ATOM | 2027 | N | LEU | A 293 | 14.206 | 15.648 | 50.329 | 1.00 | 52.31 | MOLA N |
| ATOM | 2028 | CA | LEU | A 293 | 13.546 | 15.366 | 51.584 | 1.00 | 51.46 | MOLA C |
| ATOM | 2029 | CB | LEU | A 293 | 14.507 | 14.841 | 52.645 | 1.00 | 51.49 | MOLA C |
| ATOM | 2030 | CG | LEU | A 293 | 14.230 | 13.378 | 52.992 | 1.00 | 52.60 | MOLA C |
| ATOM | 2031 | CD1 | LEU | A 293 | 12.708 | 13.241 | 53.244 | 1.00 | 53.75 | MOLA C |
| ATOM | 2032 | CD2 | LEU | A 293 | 14.715 | 12.393 | 51.933 | 1.00 | 35.26 | MOLA C |
| ATOM | 2033 | C | LEU | A 293 | 12.838 | 16.629 | 52.023 | 1.00 | 50.55 | MOLA C |
| ATOM | 2034 | O | LEU | A 293 | 11.608 | 16.715 | 51.884 | 1.00 | 49.36 | MOLA O |
| ATOM | 2035 | N | THR | A 294 | 13.613 | 17.618 | 52.483 | 1.00 | 49.65 | MOLA N |
| ATOM | 2036 | CA | THR | A 294 | 13.057 | 18.895 | 52.993 | 1.00 | 50.77 | MOLA C |
| ATOM | 2037 | CB | THR | A 294 | 14.115 | 20.040 | 53.088 | 1.00 | 52.08 | MOLA C |
| ATOM | 2038 | OG1 | THR | A 294 | 15.018 | 19.773 | 54.174 | 1.00 | 57.37 | MOLA O |
| ATOM | 2039 | CG2 | THR | A 294 | 13.457 | 21.389 | 53.334 | 1.00 | 45.65 | MOLA C |
| ATOM | 2040 | C | THR | A 294 | 11.882 | 19.335 | 52.150 | 1.00 | 49.62 | MOLA C |
| ATOM | 2041 | O | THR | A 294 | 10.758 | 19.446 | 52.657 | 1.00 | 48.88 | MOLA O |
| ATOM | 2042 | N | LEU | A 295 | 12.135 | 19.553 | 50.864 | 1.00 | 48.11 | MOLA N |
| ATOM | 2043 | CA | LEU | A 295 | 11.056 | 19.879 | 49.945 | 1.00 | 48.22 | MOLA C |
| ATOM | 2044 | CB | LEU | A 295 | 11.432 | 19.561 | 48.486 | 1.00 | 48.53 | MOLA C |
| ATOM | 2045 | CG | LEU | A 295 | 10.266 | 19.562 | 47.472 | 1.00 | 47.92 | MOLA C |
| ATOM | 2046 | CD1 | LEU | A 295 | 9.195 | 20.575 | 47.860 | 1.00 | 30.65 | MOLA C |
| ATOM | 2047 | CD2 | LEU | A 295 | 10.737 | 19.780 | 46.021 | 1.00 | 46.01 | MOLA C |
| ATOM | 2048 | C | LEU | A 295 | 9.794 | 19.130 | 50.307 | 1.00 | 48.64 | MOLA C |
| ATOM | 2049 | O | LEU | A 295 | 8.810 | 19.746 | 50.699 | 1.00 | 50.29 | MOLA O |
| ATOM | 2050 | N | GLY | A 296 | 9.844 | 17.801 | 50.179 | 1.00 | 48.63 | MOLA N |
| ATOM | 2051 | CA | GLY | A 296 | 8.693 | 16.925 | 50.366 | 1.00 | 46.64 | MOLA C |
| ATOM | 2052 | C | GLY | A 296 | 7.944 | 17.223 | 51.627 | 1.00 | 47.63 | MOLA C |
| ATOM | 2053 | O | GLY | A 296 | 6.741 | 17.358 | 51.597 | 1.00 | 48.24 | MOLA O |
| ATOM | 2054 | N | ARG | A 297 | 8.658 | 17.328 | 52.744 | 1.00 | 50.49 | MOLA N |
| ATOM | 2055 | CA | ARG | A 297 | 8.030 | 17.694 | 54.025 | 1.00 | 53.17 | MOLA C |
| ATOM | 2056 | CB | ARG | A 297 | 9.053 | 17.694 | 55.164 | 1.00 | 53.86 | MOLA C |
| ATOM | 2057 | CG | ARG | A 297 | 9.798 | 16.337 | 55.272 | 1.00 | 55.93 | MOLA C |
| ATOM | 2058 | CD | ARG | A 297 | 10.373 | 16.059 | 56.657 | 1.00 | 60.20 | MOLA C |
| ATOM | 2059 | NE | ARG | A 297 | 11.197 | 17.155 | 57.152 | 1.00 | 73.44 | MOLA N |
| ATOM | 2060 | CZ | ARG | A 297 | 10.833 | 17.984 | 58.130 | 1.00 | 81.04 | MOLA C |
| ATOM | 2061 | NH1 | ARG | A 297 | 9.658 | 17.831 | 58.735 | 1.00 | 73.19 | MOLA N |
| ATOM | 2062 | NH2 | ARG | A 297 | 11.651 | 18.966 | 58.513 | 1.00 | 85.99 | MOLA N |
| ATOM | 2063 | C | ARG | A 297 | 7.308 | 19.034 | 53.865 | 1.00 | 53.47 | MOLA C |
| ATOM | 2064 | O | ARG | A 297 | 6.078 | 19.079 | 53.929 | 1.00 | 56.62 | MOLA O |
| ATOM | 2065 | N | VAL | A 298 | 8.072 | 20.096 | 53.614 | 1.00 | 51.35 | MOLA N |
| ATOM | 2066 | CA | VAL | A 298 | 7.537 | 21.374 | 53.124 | 1.00 | 49.99 | MOLA C |
| ATOM | 2067 | CB | VAL | A 298 | 8.570 | 22.094 | 52.175 | 1.00 | 49.82 | MOLA C |
| ATOM | 2068 | CG1 | VAL | A 298 | 7.930 | 23.267 | 51.457 | 1.00 | 48.61 | MOLA C |
| ATOM | 2069 | CG2 | VAL | A 298 | 9.814 | 22.556 | 52.921 | 1.00 | 43.24 | MOLA C |
| ATOM | 2070 | C | VAL | A 298 | 6.216 | 21.200 | 52.341 | 1.00 | 51.34 | MOLA C |
| ATOM | 2071 | O | VAL | A 298 | 5.189 | 21.832 | 52.651 | 1.00 | 52.55 | MOLA O |
| ATOM | 2072 | N | ILE | A 299 | 6.234 | 20.364 | 51.310 | 1.00 | 50.11 | MOLA N |
| ATOM | 2073 | CA | ILE | A 299 | 5.006 | 20.130 | 50.564 | 1.00 | 50.11 | MOLA C |
| ATOM | 2074 | CB | ILE | A 299 | 5.195 | 19.189 | 49.380 | 1.00 | 49.71 | MOLA C |
| ATOM | 2075 | CG1 | ILE | A 299 | 6.156 | 19.801 | 48.369 | 1.00 | 47.04 | MOLA C |
| ATOM | 2076 | CD1 | ILE | A 299 | 5.920 | 21.269 | 48.146 | 1.00 | 45.62 | MOLA C |
| ATOM | 2077 | CG2 | ILE | A 299 | 3.855 | 18.887 | 48.773 | 1.00 | 38.48 | MOLA C |
| ATOM | 2078 | C | ILE | A 299 | 4.005 | 19.439 | 51.444 | 1.00 | 51.80 | MOLA C |
| ATOM | 2079 | O | ILE | A 299 | 2.869 | 19.906 | 51.598 | 1.00 | 52.42 | MOLA O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2080 | N | THR | A 300 | 4.435 | 18.315 | 52.013 | 1.00 | 52.00 | MOLA N |
| ATOM | 2081 | CA | THR | A 300 | 3.536 | 17.498 | 52.809 | 1.00 | 54.89 | MOLA C |
| ATOM | 2082 | CB | THR | A 300 | 4.265 | 16.321 | 53.518 | 1.00 | 55.64 | MOLA C |
| ATOM | 2083 | OG1 | THR | A 300 | 4.431 | 15.238 | 52.587 | 1.00 | 55.91 | MOLA O |
| ATOM | 2084 | CG2 | THR | A 300 | 3.451 | 15.813 | 54.693 | 1.00 | 56.56 | MOLA C |
| ATOM | 2085 | C | THR | A 300 | 2.790 | 18.436 | 53.753 | 1.00 | 54.17 | MOLA C |
| ATOM | 2086 | O | THR | A 300 | 1.567 | 18.290 | 53.947 | 1.00 | 52.35 | MOLA O |
| ATOM | 2087 | N | ALA | A 301 | 3.537 | 19.419 | 54.266 | 1.00 | 51.20 | MOLA N |
| ATOM | 2088 | CA | ALA | A 301 | 2.994 | 20.521 | 55.032 | 1.00 | 52.41 | MOLA C |
| ATOM | 2089 | CB | ALA | A 301 | 4.077 | 21.549 | 55.311 | 1.00 | 53.14 | MOLA C |
| ATOM | 2090 | C | ALA | A 301 | 1.827 | 21.197 | 54.318 | 1.00 | 53.82 | MOLA C |
| ATOM | 2091 | O | ALA | A 301 | 0.674 | 20.965 | 54.662 | 1.00 | 55.49 | MOLA O |
| ATOM | 2092 | N | LEU | A 302 | 2.124 | 22.031 | 53.326 | 1.00 | 53.76 | MOLA N |
| ATOM | 2093 | CA | LEU | A 302 | 1.093 | 22.806 | 52.653 | 1.00 | 54.83 | MOLA C |
| ATOM | 2094 | CB | LEU | A 302 | 1.633 | 23.400 | 51.368 | 1.00 | 55.31 | MOLA C |
| ATOM | 2095 | CG | LEU | A 302 | 3.104 | 23.821 | 51.406 | 1.00 | 64.21 | MOLA C |
| ATOM | 2096 | CD1 | LEU | A 302 | 3.429 | 24.718 | 50.218 | 1.00 | 64.61 | MOLA C |
| ATOM | 2097 | CD2 | LEU | A 302 | 3.446 | 24.530 | 52.715 | 1.00 | 77.53 | MOLA C |
| ATOM | 2098 | C | LEU | A 302 | −0.127 | 21.958 | 52.348 | 1.00 | 55.95 | MOLA C |
| ATOM | 2099 | O | LEU | A 302 | −1.250 | 22.445 | 52.334 | 1.00 | 53.42 | MOLA O |
| ATOM | 2100 | N | VAL | A 303 | 0.091 | 20.678 | 52.091 | 1.00 | 59.68 | MOLA N |
| ATOM | 2101 | CA | VAL | A 303 | −1.031 | 19.779 | 51.898 | 1.00 | 62.89 | MOLA C |
| ATOM | 2102 | CB | VAL | A 303 | −0.559 | 18.336 | 51.617 | 1.00 | 63.36 | MOLA C |
| ATOM | 2103 | CG1 | VAL | A 303 | −1.717 | 17.470 | 51.119 | 1.00 | 62.02 | MOLA C |
| ATOM | 2104 | CG2 | VAL | A 303 | 0.575 | 18.340 | 50.616 | 1.00 | 64.24 | MOLA C |
| ATOM | 2105 | C | VAL | A 303 | −1.844 | 19.783 | 53.187 | 1.00 | 64.79 | MOLA C |
| ATOM | 2106 | O | VAL | A 303 | −3.032 | 20.125 | 53.187 | 1.00 | 63.44 | MOLA O |
| ATOM | 2107 | N | GLU | A 304 | −1.156 | 19.462 | 54.285 | 1.00 | 68.15 | MOLA N |
| ATOM | 2108 | CA | GLU | A 304 | −1.764 | 19.168 | 55.591 | 1.00 | 72.58 | MOLA C |
| ATOM | 2109 | CB | GLU | A 304 | −0.765 | 18.416 | 56.481 | 1.00 | 72.86 | MOLA C |
| ATOM | 2110 | CG | GLU | A 304 | −0.702 | 16.955 | 56.123 | 1.00 | 75.09 | MOLA C |
| ATOM | 2111 | CD | GLU | A 304 | −2.043 | 16.480 | 55.598 | 1.00 | 84.67 | MOLA C |
| ATOM | 2112 | OE1 | GLU | A 304 | −3.027 | 16.459 | 56.380 | 1.00 | 83.26 | MOLA O |
| ATOM | 2113 | OE2 | GLU | A 304 | −2.113 | 16.161 | 54.387 | 1.00 | 87.75 | MOLA O |
| ATOM | 2114 | C | GLU | A 304 | −2.495 | 20.254 | 56.398 | 1.00 | 76.14 | MOLA C |
| ATOM | 2115 | O | GLU | A 304 | −3.319 | 19.924 | 57.273 | 1.00 | 77.94 | MOLA O |
| ATOM | 2116 | N | ARG | A 305 | −2.220 | 21.529 | 56.101 | 1.00 | 77.88 | MOLA N |
| ATOM | 2117 | CA | ARG | A 305 | −2.918 | 22.661 | 56.725 | 1.00 | 77.95 | MOLA C |
| ATOM | 2118 | CB | ARG | A 305 | −4.411 | 22.352 | 56.974 | 1.00 | 78.80 | MOLA C |
| ATOM | 2119 | CG | ARG | A 305 | −5.194 | 21.528 | 55.901 | 1.00 | 83.88 | MOLA C |
| ATOM | 2120 | CD | ARG | A 305 | −5.189 | 22.167 | 54.515 | 1.00 | 97.61 | MOLA C |
| ATOM | 2121 | NE | ARG | A 305 | −4.952 | 23.607 | 54.598 | 1.00 | 107.00 | MOLA N |
| ATOM | 2122 | CZ | ARG | A 305 | −5.779 | 24.472 | 55.178 | 1.00 | 112.51 | MOLA C |
| ATOM | 2123 | NH1 | ARG | A 305 | −5.473 | 25.763 | 55.206 | 1.00 | 116.80 | MOLA N |
| ATOM | 2124 | NH2 | ARG | A 305 | −6.906 | 24.047 | 55.742 | 1.00 | 111.07 | MOLA N |
| ATOM | 2125 | C | ARG | A 305 | −2.268 | 22.972 | 58.057 | 1.00 | 77.43 | MOLA C |
| ATOM | 2126 | O | ARG | A 305 | −2.871 | 23.619 | 58.911 | 1.00 | 78.06 | MOLA O |
| ATOM | 2127 | N | THR | A 306 | −1.044 | 22.500 | 58.238 | 1.00 | 75.87 | MOLA N |
| ATOM | 2128 | CA | THR | A 306 | −0.379 | 22.625 | 59.523 | 1.00 | 76.85 | MOLA C |
| ATOM | 2129 | CB | THR | A 306 | 0.522 | 21.419 | 59.772 | 1.00 | 77.13 | MOLA C |
| ATOM | 2130 | OG1 | THR | A 306 | 1.672 | 21.500 | 58.925 | 1.00 | 82.26 | MOLA O |
| ATOM | 2131 | CG2 | THR | A 306 | −0.236 | 20.128 | 59.473 | 1.00 | 79.52 | MOLA C |
| ATOM | 2132 | C | THR | A 306 | 0.391 | 23.946 | 59.645 | 1.00 | 75.90 | MOLA C |
| ATOM | 2133 | O | THR | A 306 | 0.445 | 24.708 | 58.683 | 1.00 | 76.59 | MOLA O |
| ATOM | 2134 | N | PRO | A 307 | 0.964 | 24.232 | 60.836 | 1.00 | 74.68 | MOLA N |
| ATOM | 2135 | CA | PRO | A 307 | 1.566 | 25.533 | 61.145 | 1.00 | 73.61 | MOLA C |
| ATOM | 2136 | CB | PRO | A 307 | 1.146 | 25.748 | 62.612 | 1.00 | 73.56 | MOLA C |
| ATOM | 2137 | CG | PRO | A 307 | 0.894 | 24.347 | 63.173 | 1.00 | 72.56 | MOLA C |
| ATOM | 2138 | CD | PRO | A 307 | 1.013 | 23.357 | 62.017 | 1.00 | 75.12 | MOLA C |
| ATOM | 2139 | C | PRO | A 307 | 3.090 | 25.676 | 61.040 | 1.00 | 72.56 | MOLA C |
| ATOM | 2140 | O | PRO | A 307 | 3.610 | 26.769 | 61.273 | 1.00 | 70.70 | MOLA O |
| ATOM | 2141 | N | HIS | A 308 | 3.798 | 24.599 | 60.724 | 1.00 | 72.82 | MOLA N |
| ATOM | 2142 | CA | HIS | A 308 | 5.265 | 24.655 | 60.607 | 1.00 | 72.27 | MOLA C |
| ATOM | 2143 | CB | HIS | A 308 | 5.901 | 23.763 | 61.699 | 1.00 | 74.08 | MOLA C |
| ATOM | 2144 | CG | HIS | A 308 | 7.334 | 23.370 | 61.438 | 1.00 | 84.04 | MOLA C |
| ATOM | 2145 | ND1 | HIS | A 308 | 7.687 | 22.150 | 60.890 | 1.00 | 90.78 | MOLA N |
| ATOM | 2146 | CE1 | HIS | A 308 | 9.005 | 22.076 | 60.791 | 1.00 | 93.63 | MOLA C |
| ATOM | 2147 | NE2 | HIS | A 308 | 9.522 | 23.200 | 61.259 | 1.00 | 94.06 | MOLA N |
| ATOM | 2148 | CD2 | HIS | A 308 | 8.501 | 24.023 | 61.675 | 1.00 | 90.23 | MOLA C |
| ATOM | 2149 | C | HIS | A 308 | 5.737 | 24.251 | 59.196 | 1.00 | 69.02 | MOLA C |
| ATOM | 2150 | O | HIS | A 308 | 5.614 | 23.077 | 58.812 | 1.00 | 68.29 | MOLA O |
| ATOM | 2151 | N | VAL | A 309 | 6.254 | 25.206 | 58.417 | 1.00 | 64.75 | MOLA N |
| ATOM | 2152 | CA | VAL | A 309 | 6.771 | 24.872 | 57.070 | 1.00 | 63.45 | MOLA C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 2153 | CB | VAL | A 309 | 5.897 | 25.452 | 55.902 | 1.00 | 63.88 | MOLA | C |
| ATOM | 2154 | CG1 | VAL | A 309 | 6.539 | 25.168 | 54.558 | 1.00 | 64.59 | MOLA | C |
| ATOM | 2155 | CG2 | VAL | A 309 | 4.482 | 24.860 | 55.924 | 1.00 | 64.04 | MOLA | C |
| ATOM | 2156 | C | VAL | A 309 | 8.269 | 25.198 | 56.911 | 1.00 | 61.72 | MOLA | C |
| ATOM | 2157 | O | VAL | A 309 | 8.671 | 26.360 | 56.855 | 1.00 | 61.81 | MOLA | O |
| ATOM | 2158 | N | PRO | A 310 | 9.110 | 24.163 | 56.854 | 1.00 | 59.90 | MOLA | N |
| ATOM | 2159 | CA | PRO | A 310 | 10.534 | 24.439 | 56.899 | 1.00 | 59.69 | MOLA | C |
| ATOM | 2160 | CB | PRO | A 310 | 11.161 | 23.045 | 57.053 | 1.00 | 58.54 | MOLA | C |
| ATOM | 2161 | CG | PRO | A 310 | 10.025 | 22.154 | 57.503 | 1.00 | 60.37 | MOLA | C |
| ATOM | 2162 | CD | PRO | A 310 | 8.835 | 22.723 | 56.793 | 1.00 | 58.96 | MOLA | C |
| ATOM | 2163 | C | PRO | A 310 | 11.039 | 25.097 | 55.643 | 1.00 | 59.35 | MOLA | C |
| ATOM | 2164 | O | PRO | A 310 | 11.801 | 24.492 | 54.912 | 1.00 | 61.64 | MOLA | O |
| ATOM | 2165 | N | TYR | A 311 | 10.633 | 26.326 | 55.382 | 1.00 | 58.16 | MOLA | N |
| ATOM | 2166 | CA | TYR | A 311 | 11.168 | 26.991 | 54.209 | 1.00 | 59.57 | MOLA | C |
| ATOM | 2167 | CB | TYR | A 311 | 10.494 | 28.336 | 53.935 | 1.00 | 58.64 | MOLA | C |
| ATOM | 2168 | CG | TYR | A 311 | 9.136 | 28.151 | 53.354 | 1.00 | 58.83 | MOLA | C |
| ATOM | 2169 | CD1 | TYR | A 311 | 7.992 | 28.368 | 54.119 | 1.00 | 56.56 | MOLA | C |
| ATOM | 2170 | CE1 | TYR | A 311 | 6.738 | 28.170 | 53.591 | 1.00 | 53.67 | MOLA | C |
| ATOM | 2171 | CZ | TYR | A 311 | 6.612 | 27.738 | 52.287 | 1.00 | 59.68 | MOLA | C |
| ATOM | 2172 | OH | TYR | A 311 | 5.364 | 27.529 | 51.741 | 1.00 | 63.86 | MOLA | O |
| ATOM | 2173 | CE2 | TYR | A 311 | 7.735 | 27.502 | 51.518 | 1.00 | 61.31 | MOLA | C |
| ATOM | 2174 | CD2 | TYR | A 311 | 8.987 | 27.699 | 52.056 | 1.00 | 51.14 | MOLA | C |
| ATOM | 2175 | C | TYR | A 311 | 12.664 | 27.159 | 54.338 | 1.00 | 61.28 | MOLA | C |
| ATOM | 2176 | O | TYR | A 311 | 13.402 | 26.655 | 53.497 | 1.00 | 61.92 | MOLA | O |
| ATOM | 2177 | N | ARG | A 312 | 13.106 | 27.870 | 55.384 | 1.00 | 63.47 | MOLA | N |
| ATOM | 2178 | CA | ARG | A 312 | 14.540 | 28.129 | 55.578 | 1.00 | 64.41 | MOLA | C |
| ATOM | 2179 | CB | ARG | A 312 | 14.872 | 29.128 | 56.722 | 1.00 | 64.98 | MOLA | C |
| ATOM | 2180 | CG | ARG | A 312 | 13.823 | 29.322 | 57.810 | 1.00 | 71.90 | MOLA | C |
| ATOM | 2181 | CD | ARG | A 312 | 13.252 | 30.741 | 57.755 | 1.00 | 82.57 | MOLA | C |
| ATOM | 2182 | NE | ARG | A 312 | 11.792 | 30.770 | 57.821 | 1.00 | 90.81 | MOLA | N |
| ATOM | 2183 | CZ | ARG | A 312 | 10.998 | 29.694 | 57.866 | 1.00 | 97.17 | MOLA | C |
| ATOM | 2184 | NH1 | ARG | A 312 | 11.503 | 28.459 | 57.877 | 1.00 | 89.64 | MOLA | N |
| ATOM | 2185 | NH2 | ARG | A 312 | 9.679 | 29.855 | 57.907 | 1.00 | 97.91 | MOLA | N |
| ATOM | 2186 | C | ARG | A 312 | 15.349 | 26.858 | 55.743 | 1.00 | 62.83 | MOLA | C |
| ATOM | 2187 | O | ARG | A 312 | 16.563 | 26.917 | 55.623 | 1.00 | 60.88 | MOLA | O |
| ATOM | 2188 | N | GLU | A 313 | 14.689 | 25.722 | 55.985 | 1.00 | 63.16 | MOLA | N |
| ATOM | 2189 | CA | GLU | A 313 | 15.421 | 24.449 | 56.176 | 1.00 | 64.85 | MOLA | C |
| ATOM | 2190 | CB | GLU | A 313 | 14.518 | 23.338 | 56.718 | 1.00 | 63.81 | MOLA | C |
| ATOM | 2191 | CG | GLU | A 313 | 14.458 | 23.304 | 58.232 | 1.00 | 65.51 | MOLA | C |
| ATOM | 2192 | CD | GLU | A 313 | 14.111 | 21.925 | 58.772 | 1.00 | 73.08 | MOLA | C |
| ATOM | 2193 | OE1 | GLU | A 313 | 15.029 | 21.274 | 59.339 | 1.00 | 63.05 | MOLA | O |
| ATOM | 2194 | OE2 | GLU | A 313 | 12.936 | 21.489 | 58.606 | 1.00 | 67.66 | MOLA | O |
| ATOM | 2195 | C | GLU | A 313 | 16.334 | 23.952 | 55.009 | 1.00 | 65.45 | MOLA | C |
| ATOM | 2196 | O | GLU | A 313 | 17.337 | 23.276 | 55.258 | 1.00 | 66.60 | MOLA | O |
| ATOM | 2197 | N | SER | A 314 | 16.012 | 24.281 | 53.757 | 1.00 | 64.88 | MOLA | N |
| ATOM | 2198 | CA | SER | A 314 | 16.959 | 24.011 | 52.662 | 1.00 | 62.67 | MOLA | C |
| ATOM | 2199 | CB | SER | A 314 | 16.534 | 22.817 | 51.804 | 1.00 | 63.85 | MOLA | C |
| ATOM | 2200 | OG | SER | A 314 | 15.737 | 23.252 | 50.705 | 1.00 | 59.04 | MOLA | O |
| ATOM | 2201 | C | SER | A 314 | 17.040 | 25.226 | 51.769 | 1.00 | 60.80 | MOLA | C |
| ATOM | 2202 | O | SER | A 314 | 16.085 | 26.012 | 51.693 | 1.00 | 56.79 | MOLA | O |
| ATOM | 2203 | N | LYS | A 315 | 18.170 | 25.366 | 51.079 | 1.00 | 59.76 | MOLA | N |
| ATOM | 2204 | CA | LYS | A 315 | 18.304 | 26.432 | 50.100 | 1.00 | 60.13 | MOLA | C |
| ATOM | 2205 | CB | LYS | A 315 | 19.685 | 26.445 | 49.464 | 1.00 | 60.69 | MOLA | C |
| ATOM | 2206 | CG | LYS | A 315 | 20.670 | 27.314 | 50.199 | 1.00 | 61.59 | MOLA | C |
| ATOM | 2207 | CD | LYS | A 315 | 21.807 | 27.724 | 49.303 | 1.00 | 54.08 | MOLA | C |
| ATOM | 2208 | CE | LYS | A 315 | 22.903 | 28.378 | 50.132 | 1.00 | 72.37 | MOLA | C |
| ATOM | 2209 | NZ | LYS | A 315 | 24.128 | 28.684 | 49.341 | 1.00 | 72.77 | MOLA | N |
| ATOM | 2210 | C | LYS | A 315 | 17.225 | 26.348 | 49.018 | 1.00 | 60.38 | MOLA | C |
| ATOM | 2211 | O | LYS | A 315 | 16.700 | 27.390 | 48.587 | 1.00 | 61.71 | MOLA | O |
| ATOM | 2212 | N | LEU | A 316 | 16.899 | 25.120 | 48.588 | 1.00 | 57.06 | MOLA | N |
| ATOM | 2213 | CA | LEU | A 316 | 15.800 | 24.899 | 47.642 | 1.00 | 53.20 | MOLA | C |
| ATOM | 2214 | CB | LEU | A 316 | 15.710 | 23.428 | 47.204 | 1.00 | 53.47 | MOLA | C |
| ATOM | 2215 | CG | LEU | A 316 | 14.565 | 23.097 | 46.22S | 1.00 | 43.13 | MOLA | C |
| ATOM | 2216 | CD1 | LEU | A 316 | 14.760 | 23.820 | 44.963 | 1.00 | 30.51 | MOLA | C |
| ATOM | 2217 | CD2 | LEU | A 316 | 14.486 | 21.632 | 45.925 | 1.00 | 48.98 | MOLA | C |
| ATOM | 2218 | C | LEU | A 316 | 14.424 | 25.419 | 48.151 | 1.00 | 53.86 | MOLA | C |
| ATOM | 2219 | O | LEU | A 316 | 13.858 | 26.332 | 47.558 | 1.00 | 53.03 | MOLA | O |
| ATOM | 2220 | N | THR | A 317 | 13.868 | 24.835 | 49.213 | 1.00 | 53.38 | MOLA | N |
| ATOM | 2221 | CA | THR | A 317 | 12.606 | 25.352 | 49.723 | 1.00 | 51.55 | MOLA | C |
| ATOM | 2222 | CB | THR | A 317 | 12.222 | 24.761 | 51.061 | 1.00 | 50.27 | MOLA | C |
| ATOM | 2223 | OG1 | THR | A 317 | 13.380 | 24.180 | 51.662 | 1.00 | 57.10 | MOLA | O |
| ATOM | 2224 | CG2 | THR | A 317 | 11.207 | 23.704 | 50.873 | 1.00 | 44.52 | MOLA | C |
| ATOM | 2225 | C | THR | A 317 | 12.736 | 26.844 | 49.882 | 1.00 | 53.42 | MOLA | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2226 | O | THR | A 317 | 11.814 | 27.586 | 49.544 | 1.00 | 54.72 | MOLA O |
| ATOM | 2227 | N | ARG | A 318 | 13.898 | 27.294 | 50.359 | 1.00 | 55.04 | MOLA N |
| ATOM | 2228 | CA | ARG | A 318 | 14.127 | 28.746 | 50.591 | 1.00 | 55.20 | MOLA C |
| ATOM | 2229 | CB | ARG | A 318 | 15.504 | 28.998 | 51.221 | 1.00 | 54.49 | MOLA C |
| ATOM | 2230 | CG | ARG | A 318 | 15.735 | 30.414 | 51.705 | 1.00 | 65.49 | MOLA C |
| ATOM | 2231 | CD | ARG | A 318 | 14.585 | 30.946 | 52.594 | 1.00 | 96.21 | MOLA C |
| ATOM | 2232 | NE | ARG | A 318 | 14.763 | 32.355 | 52.971 | 1.00 | 106.15 | MOLA N |
| ATOM | 2233 | CZ | ARG | A 318 | 15.251 | 32.777 | 54.138 | 1.00 | 114.42 | MOLA C |
| ATOM | 2234 | NH1 | ARG | A 318 | 15.607 | 31.915 | 55.085 | 1.00 | 118.70 | MOLA N |
| ATOM | 2235 | NH2 | ARG | A 318 | 15.375 | 34.074 | 54.363 | 1.00 | 117.89 | MOLA N |
| ATOM | 2236 | C | ARG | A 318 | 13.881 | 29.633 | 49.351 | 1.00 | 52.18 | MOLA C |
| ATOM | 2237 | O | ARG | A 318 | 12.900 | 30.369 | 49.307 | 1.00 | 52.00 | MOLA O |
| ATOM | 2238 | N | ILE | A 319 | 14.755 | 29.557 | 48.352 | 1.00 | 50.10 | MOLA N |
| ATOM | 2239 | CA | ILE | A 319 | 14.546 | 30.282 | 47.102 | 1.00 | 47.53 | MOLA C |
| ATOM | 2240 | CB | ILE | A 319 | 15.432 | 29.707 | 45.991 | 1.00 | 45.53 | MOLA C |
| ATOM | 2241 | CG1 | ILE | A 319 | 16.886 | 29.693 | 46.429 | 1.00 | 45.51 | MOLA C |
| ATOM | 2242 | CD1 | ILE | A 319 | 17.838 | 29.181 | 45.359 | 1.00 | 49.13 | MOLA C |
| ATOM | 2243 | CG2 | ILE | A 319 | 15.286 | 30.516 | 44.721 | 1.00 | 43.99 | MOLA C |
| ATOM | 2244 | C | ILE | A 319 | 13.090 | 30.177 | 46.638 | 1.00 | 47.74 | MOLA C |
| ATOM | 2245 | O | ILE | A 319 | 12.575 | 31.067 | 45.985 | 1.00 | 46.12 | MOLA O |
| ATOM | 2246 | N | LEU | A 320 | 12.428 | 29.085 | 46.995 | 1.00 | 50.59 | MOLA N |
| ATOM | 2247 | CA | LEU | A 320 | 11.095 | 28.787 | 46.485 | 1.00 | 53.97 | MOLA C |
| ATOM | 2248 | CB | LEU | A 320 | 10.970 | 27.298 | 46.211 | 1.00 | 53.01 | MOLA C |
| ATOM | 2249 | CG | LEU | A 320 | 11.597 | 26.904 | 44.884 | 1.00 | 47.58 | MOLA C |
| ATOM | 2250 | CD1 | LEU | A 320 | 11.168 | 25.484 | 44.528 | 1.00 | 55.21 | MOLA C |
| ATOM | 2251 | CD2 | LEU | A 320 | 11.137 | 27.850 | 43.827 | 1.00 | 23.27 | MOLA C |
| ATOM | 2252 | C | LEU | A 320 | 9.928 | 29.256 | 47.350 | 1.00 | 57.73 | MOLA C |
| ATOM | 2253 | O | LEU | A 320 | 8.886 | 29.658 | 46.812 | 1.00 | 59.26 | MOLA O |
| ATOM | 2254 | N | GLN | A 321 | 10.110 | 29.171 | 48.672 | 1.00 | 60.20 | MOLA N |
| ATOM | 2255 | CA | GLN | A 321 | 9.184 | 29.700 | 49.703 | 1.00 | 61.61 | MOLA C |
| ATOM | 2256 | CB | GLN | A 321 | 9.986 | 30.454 | 50.764 | 1.00 | 62.55 | MOLA C |
| ATOM | 2257 | CG | GLN | A 321 | 9.125 | 31.280 | 51.695 | 1.00 | 56.25 | MOLA C |
| ATOM | 2258 | CD | GLN | A 321 | 9.767 | 31.449 | 53.049 | 1.00 | 54.08 | MOLA C |
| ATOM | 2259 | OE1 | GLN | A 321 | 10.974 | 31.666 | 53.154 | 1.00 | 58.49 | MOLA O |
| ATOM | 2260 | NE2 | GLN | A 321 | 8.966 | 31.337 | 54.097 | 1.00 | 48.56 | MOLA N |
| ATOM | 2261 | C | GLN | A 321 | 8.130 | 30.660 | 49.212 | 1.00 | 62.42 | MOLA C |
| ATOM | 2262 | O | GLN | A 321 | 6.927 | 30.478 | 49.441 | 1.00 | 60.85 | MOLA O |
| ATOM | 2263 | N | ASP | A 322 | 8.638 | 31.717 | 48.588 | 1.00 | 63.64 | MOLA N |
| ATOM | 2264 | CA | ASP | A 322 | 7.851 | 32.742 | 47.945 | 1.00 | 65.38 | MOLA C |
| ATOM | 2265 | CB | ASP | A 322 | 8.710 | 33.444 | 46.908 | 1.00 | 66.20 | MOLA C |
| ATOM | 2266 | CG | ASP | A 322 | 8.300 | 34.862 | 46.719 | 1.00 | 68.49 | MOLA C |
| ATOM | 2267 | OD1 | ASP | A 322 | 9.108 | 35.650 | 46.179 | 1.00 | 74.53 | MOLA O |
| ATOM | 2268 | OD2 | ASP | A 322 | 7.166 | 35.187 | 47.145 | 1.00 | 71.33 | MOLA O |
| ATOM | 2269 | C | ASP | A 322 | 6.599 | 32.212 | 47.269 | 1.00 | 65.34 | MOLA C |
| ATOM | 2270 | O | ASP | A 322 | 5.498 | 32.401 | 47.777 | 1.00 | 65.96 | MOLA O |
| ATOM | 2271 | N | SER | A 323 | 6.764 | 31.567 | 46.117 | 1.00 | 64.95 | MOLA N |
| ATOM | 2272 | CA | SER | A 323 | 5.608 | 31.009 | 45.405 | 1.00 | 65.77 | MOLA C |
| ATOM | 2273 | CB | SER | A 323 | 5.963 | 30.597 | 43.968 | 1.00 | 65.50 | MOLA C |
| ATOM | 2274 | OG | SER | A 323 | 7.331 | 30.245 | 43.841 | 1.00 | 70.25 | MOLA O |
| ATOM | 2275 | C | SER | A 323 | 4.845 | 29.892 | 46.154 | 1.00 | 64.97 | MOLA C |
| ATOM | 2276 | O | SER | A 323 | 3.614 | 29.889 | 46.157 | 1.00 | 64.40 | MOLA O |
| ATOM | 2277 | N | LEU | A 324 | 5.547 | 28.973 | 46.815 | 1.00 | 64.70 | MOLA N |
| ATOM | 2278 | CA | LEU | A 324 | 4.849 | 27.888 | 47.511 | 1.00 | 65.09 | MOLA C |
| ATOM | 2279 | CB | LEU | A 324 | 5.809 | 27.019 | 48.314 | 1.00 | 63.30 | MOLA C |
| ATOM | 2280 | CG | LEU | A 324 | 7.114 | 26.417 | 47.801 | 1.00 | 61.65 | MOLA C |
| ATOM | 2281 | CD1 | LEU | A 324 | 7.071 | 24.903 | 48.085 | 1.00 | 46.78 | MOLA C |
| ATOM | 2282 | CD2 | LEU | A 324 | 7.350 | 26.648 | 46.339 | 1.00 | 59.96 | MOLA C |
| ATOM | 2283 | C | LEU | A 324 | 3.768 | 28.417 | 48.459 | 1.00 | 67.43 | MOLA C |
| ATOM | 2284 | O | LEU | A 324 | 2.779 | 27.739 | 48.729 | 1.00 | 67.20 | MOLA O |
| ATOM | 2285 | N | GLY | A 325 | 3.984 | 29.643 | 48.939 | 1.00 | 70.64 | MOLA N |
| ATOM | 2286 | CA | GLY | A 325 | 3.183 | 30.326 | 49.972 | 1.00 | 72.23 | MOLA C |
| ATOM | 2287 | C | GLY | A 325 | 1.702 | 30.071 | 50.238 | 1.00 | 73.29 | MOLA C |
| ATOM | 2288 | O | GLY | A 325 | 1.356 | 29.442 | 51.245 | 1.00 | 72.44 | MOLA O |
| ATOM | 2289 | N | GLY | A 326 | 0.821 | 30.584 | 49.377 | 1.00 | 73.92 | MOLA N |
| ATOM | 2290 | CA | GLY | A 326 | −0.618 | 30.530 | 49.673 | 1.00 | 74.52 | MOLA C |
| ATOM | 2291 | C | GLY | A 326 | −1.601 | 30.345 | 48.530 | 1.00 | 74.81 | MOLA C |
| ATOM | 2292 | O | GLY | A 326 | −1.853 | 29.215 | 48.101 | 1.00 | 75.94 | MOLA O |
| ATOM | 2293 | N | ARG | A 327 | −2.168 | 31.453 | 48.048 | 1.00 | 73.55 | MOLA N |
| ATOM | 2294 | CA | ARG | A 327 | −3.199 | 31.436 | 46.986 | 1.00 | 72.51 | MOLA C |
| ATOM | 2295 | CB | ARG | A 327 | −3.935 | 32.801 | 46.937 | 1.00 | 73.95 | MOLA C |
| ATOM | 2296 | CG | ARG | A 327 | −5.493 | 32.743 | 47.026 | 1.00 | 76.64 | MOLA C |
| ATOM | 2297 | CD | ARG | A 327 | −6.248 | 32.867 | 45.681 | 1.00 | 88.88 | MOLA C |
| ATOM | 2298 | NE | ARG | A 327 | −5.810 | 31.915 | 44.651 | 1.00 | 92.59 | MOLA N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2299 | CZ | ARG | A 327 | −6.194 | 30.639 | 44.561 | 1.00 | 83.85 | MOLA C |
| ATOM | 2300 | NH1 | ARG | A 327 | −5.720 | 29.889 | 43.575 | 1.00 | 83.19 | MOLA N |
| ATOM | 2301 | NH2 | ARG | A 327 | −7.035 | 30.106 | 45.444 | 1.00 | 69.88 | MOLA N |
| ATOM | 2302 | C | ARG | A 327 | −2.548 | 31.083 | 45.636 | 1.00 | 69.85 | MOLA C |
| ATOM | 2303 | O | ARG | A 327 | −2.873 | 31.656 | 44.586 | 1.00 | 69.17 | MOLA O |
| ATOM | 2304 | N | THR | A 328 | −1.634 | 30.115 | 45.693 | 1.00 | 66.10 | MOLA N |
| ATOM | 2305 | CA | THR | A 328 | −0.811 | 29.715 | 44.572 | 1.00 | 63.02 | MOLA C |
| ATOM | 2306 | CB | THR | A 328 | 0.672 | 29.812 | 44.955 | 1.00 | 62.92 | MOLA C |
| ATOM | 2307 | OG1 | THR | A 328 | 1.474 | 29.153 | 43.971 | 1.00 | 65.52 | MOLA O |
| ATOM | 2308 | CG2 | THR | A 328 | 0.917 | 29.127 | 46.293 | 1.00 | 67.95 | MOLA C |
| ATOM | 2309 | C | THR | A 328 | −1.103 | 28.275 | 44.184 | 1.00 | 60.25 | MOLA C |
| ATOM | 2310 | O | THR | A 328 | −1.426 | 27.458 | 45.042 | 1.00 | 59.32 | MOLA O |
| ATOM | 2311 | N | ARG | A 329 | −0.989 | 27.973 | 42.891 | 1.00 | 58.49 | MOLA N |
| ATOM | 2312 | CA | ARG | A 329 | −1.102 | 26.598 | 42.413 | 1.00 | 57.27 | MOLA C |
| ATOM | 2313 | CB | ARG | A 329 | −1.667 | 26.531 | 41.012 | 1.00 | 57.36 | MOLA C |
| ATOM | 2314 | CG | ARG | A 329 | −2.910 | 27.348 | 40.803 | 1.00 | 59.50 | MOLA C |
| ATOM | 2315 | CD | ARG | A 329 | −4.069 | 26.845 | 41.619 | 1.00 | 64.56 | MOLA C |
| ATOM | 2316 | NE | ARG | A 329 | −5.280 | 26.999 | 40.835 | 1.00 | 69.32 | MOLA N |
| ATOM | 2317 | CZ | ARG | A 329 | −5.707 | 26.076 | 39.984 | 1.00 | 72.39 | MOLA C |
| ATOM | 2318 | NH1 | ARG | A 329 | −5.021 | 24.939 | 39.846 | 1.00 | 61.92 | MOLA N |
| ATOM | 2319 | NH2 | ARG | A 329 | −6.819 | 26.283 | 39.286 | 1.00 | 77.77 | MOLA N |
| ATOM | 2320 | C | ARG | A 329 | 0.280 | 26.025 | 42.378 | 1.00 | 56.10 | MOLA C |
| ATOM | 2321 | O | ARG | A 329 | 1.254 | 26.714 | 42.056 | 1.00 | 57.36 | MOLA O |
| ATOM | 2322 | N | THR | A 330 | 0.385 | 24.756 | 42.715 | 1.00 | 53.31 | MOLA N |
| ATOM | 2323 | CA | THR | A 330 | 1.692 | 24.151 | 42.755 | 1.00 | 49.95 | MOLA C |
| ATOM | 2324 | CB | THR | A 330 | 2.306 | 24.234 | 44.144 | 1.00 | 49.52 | MOLA C |
| ATOM | 2325 | OG1 | THR | A 330 | 2.604 | 25.609 | 44.430 | 1.00 | 54.14 | MOLA O |
| ATOM | 2326 | CG2 | THR | A 330 | 3.573 | 23.428 | 44.224 | 1.00 | 44.57 | MOLA C |
| ATOM | 2327 | C | THR | A 330 | 1.497 | 22.745 | 42.304 | 1.00 | 49.03 | MOLA C |
| ATOM | 2328 | O | THR | A 330 | 0.518 | 22.091 | 42.686 | 1.00 | 49.16 | MOLA O |
| ATOM | 2329 | N | SER | A 331 | 2.403 | 22.308 | 41.436 | 1.00 | 47.08 | MOLA N |
| ATOM | 2330 | CA | SER | A 331 | 2.286 | 20.999 | 40.866 | 1.00 | 44.47 | MOLA C |
| ATOM | 2331 | CB | SER | A 331 | 1.686 | 21.087 | 39.489 | 1.00 | 43.99 | MOLA C |
| ATOM | 2332 | OG | SER | A 331 | 0.894 | 19.947 | 39.272 | 1.00 | 47.39 | MOLA O |
| ATOM | 2333 | C | SER | A 331 | 3.599 | 20.266 | 40.817 | 1.00 | 42.92 | MOLA C |
| ATOM | 2334 | O | SER | A 331 | 4.658 | 20.835 | 40.559 | 1.00 | 44.24 | MOLA O |
| ATOM | 2335 | N | ILE | A 332 | 3.500 | 18.980 | 41.080 | 1.00 | 40.95 | MOLA N |
| ATOM | 2336 | CA | ILE | A 332 | 4.632 | 18.120 | 41.139 | 1.00 | 38.84 | MOLA C |
| ATOM | 2337 | CB | ILE | A 332 | 4.698 | 17.464 | 42.503 | 1.00 | 40.24 | MOLA C |
| ATOM | 2338 | CG1 | ILE | A 332 | 4.407 | 18.503 | 43.590 | 1.00 | 45.19 | MOLA C |
| ATOM | 2339 | CD1 | ILE | A 332 | 4.037 | 17.885 | 44.957 | 1.00 | 38.84 | MOLA C |
| ATOM | 2340 | CG2 | ILE | A 332 | 6.044 | 16.721 | 42.712 | 1.00 | 35.24 | MOLA C |
| ATOM | 2341 | C | ILE | A 332 | 4.344 | 17.022 | 40.180 | 1.00 | 37.62 | MOLA C |
| ATOM | 2342 | O | ILE | A 332 | 3.362 | 16.287 | 40.341 | 1.00 | 36.71 | MOLA O |
| ATOM | 2343 | N | ILE | A 333 | 5.203 | 16.908 | 39.182 | 1.00 | 36.70 | MOLA N |
| ATOM | 2344 | CA | ILE | A 333 | 5.087 | 15.850 | 38.205 | 1.00 | 35.60 | MOLA C |
| ATOM | 2345 | CB | ILE | A 333 | 5.335 | 16.379 | 36.798 | 1.00 | 35.26 | MOLA C |
| ATOM | 2346 | CG1 | ILE | A 333 | 4.340 | 17.501 | 36.490 | 1.00 | 39.33 | MOLA C |
| ATOM | 2347 | CD1 | ILE | A 333 | 4.418 | 18.032 | 35.084 | 1.00 | 31.28 | MOLA C |
| ATOM | 2348 | CG2 | ILE | A 333 | 5.167 | 15.295 | 35.785 | 1.00 | 25.60 | MOLA C |
| ATOM | 2349 | C | ILE | A 333 | 6.116 | 14.810 | 38.495 | 1.00 | 35.99 | MOLA C |
| ATOM | 2350 | O | ILE | A 333 | 7.262 | 14.973 | 38.101 | 1.00 | 37.62 | MOLA O |
| ATOM | 2351 | N | ALA | A 334 | 5.719 | 13.758 | 39.212 | 1.00 | 37.84 | MOLA N |
| ATOM | 2352 | CA | ALA | A 334 | 6.603 | 12.596 | 39.465 | 1.00 | 38.55 | MOLA C |
| ATOM | 2353 | CB | ALA | A 334 | 5.979 | 11.666 | 40.472 | 1.00 | 36.54 | MOLA C |
| ATOM | 2354 | C | ALA | A 334 | 6.847 | 11.842 | 38.165 | 1.00 | 38.60 | MOLA C |
| ATOM | 2355 | O | ALA | A 334 | 5.880 | 11.411 | 37.540 | 1.00 | 41.20 | MOLA O |
| ATOM | 2356 | N | THR | A 335 | 8.112 | 11.698 | 37.745 | 1.00 | 37.58 | MOLA N |
| ATOM | 2357 | CA | THR | A 335 | 8.447 | 10.911 | 36.534 | 1.00 | 36.82 | MOLA C |
| ATOM | 2358 | CB | THR | A 335 | 9.407 | 11.688 | 35.530 | 1.00 | 40.56 | MOLA C |
| ATOM | 2359 | OG1 | THR | A 335 | 10.609 | 12.125 | 36.180 | 1.00 | 42.44 | MOLA O |
| ATOM | 2360 | CG2 | THR | A 335 | 8.712 | 12.910 | 34.858 | 1.00 | 28.64 | MOLA C |
| ATOM | 2361 | C | THR | A 335 | 8.939 | 9.466 | 36.841 | 1.00 | 36.73 | MOLA C |
| ATOM | 2362 | O | THR | A 335 | 9.828 | 9.256 | 37.663 | 1.00 | 37.36 | MOLA O |
| ATOM | 2363 | N | ILE | A 336 | 8.324 | 8.463 | 36.210 | 1.00 | 37.02 | MOLA N |
| ATOM | 2364 | CA | ILE | A 336 | 8.704 | 7.032 | 36.418 | 1.00 | 33.54 | MOLA C |
| ATOM | 2365 | CB | ILE | A 336 | 7.677 | 6.285 | 37.304 | 1.00 | 31.05 | MOLA C |
| ATOM | 2366 | CG1 | ILE | A 336 | 6.272 | 6.378 | 36.712 | 1.00 | 34.95 | MOLA C |
| ATOM | 2367 | CD1 | ILE | A 336 | 5.282 | 5.274 | 37.189 | 1.00 | 28.34 | MOLA C |
| ATOM | 2368 | CG2 | ILE | A 336 | 7.665 | 6.825 | 38.709 | 1.00 | 25.33 | MOLA C |
| ATOM | 2369 | C | ILE | A 336 | 8.980 | 6.176 | 35.130 | 1.00 | 35.05 | MOLA C |
| ATOM | 2370 | O | ILE | A 336 | 8.439 | 6.456 | 34.040 | 1.00 | 35.47 | MOLA O |
| ATOM | 2371 | N | SER | A 337 | 9.848 | 5.160 | 35.270 | 1.00 | 36.25 | MOLA N |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2372 | CA | SER | A 337 | 10.098 | 4.116 | 34.228 | 1.00 | 35.37 | MOLA C |
| ATOM | 2373 | CB | SER | A 337 | 11.563 | 3.643 | 34.247 | 1.00 | 35.19 | MOLA C |
| ATOM | 2374 | OG | SER | A 337 | 11.712 | 2.351 | 33.661 | 1.00 | 28.06 | MOLA O |
| ATOM | 2375 | C | SER | A 337 | 9.192 | 2.911 | 34.469 | 1.00 | 35.48 | MOLA C |
| ATOM | 2376 | O | SER | A 337 | 8.909 | 2.593 | 35.627 | 1.00 | 37.66 | MOLA O |
| ATOM | 2377 | N | PRO | A 338 | 8.733 | 2.230 | 33.402 | 1.00 | 35.21 | MOLA N |
| ATOM | 2378 | CA | PRO | A 338 | 7.841 | 1.102 | 33.715 | 1.00 | 38.17 | MOLA C |
| ATOM | 2379 | CB | PRO | A 338 | 6.947 | 1.019 | 32.481 | 1.00 | 37.03 | MOLA C |
| ATOM | 2380 | CG | PRO | A 338 | 7.825 | 1.584 | 31.329 | 1.00 | 34.75 | MOLA C |
| ATOM | 2381 | CD | PRO | A 338 | 8.933 | 2.404 | 31.952 | 1.00 | 34.79 | MOLA C |
| ATOM | 2382 | C | PRO | A 338 | 8.570 | −0.241 | 33.975 | 1.00 | 41.46 | MOLA C |
| ATOM | 2383 | O | PRO | A 338 | 7.931 | −1.218 | 34.409 | 1.00 | 45.38 | MOLA O |
| ATOM | 2384 | N | ALA | A 339 | 9.893 | −0.269 | 33.772 | 1.00 | 40.58 | MOLA N |
| ATOM | 2385 | CA | ALA | A 339 | 10.686 | −1.513 | 33.819 | 1.00 | 40.44 | MOLA C |
| ATOM | 2386 | CB | ALA | A 339 | 12.023 | −1.306 | 33.102 | 1.00 | 41.01 | MOLA C |
| ATOM | 2387 | C | ALA | A 339 | 10.933 | −2.097 | 35.213 | 1.00 | 39.74 | MOLA C |
| ATOM | 2388 | O | ALA | A 339 | 10.947 | −1.374 | 36.194 | 1.00 | 39.91 | MOLA O |
| ATOM | 2389 | N | SER | A 340 | 11.168 | −3.404 | 35.268 | 1.00 | 37.62 | MOLA N |
| ATOM | 2390 | CA | SER | A 340 | 11.421 | −4.099 | 36.509 | 1.00 | 37.87 | MOLA C |
| ATOM | 2391 | CB | SER | A 340 | 11.316 | −5.630 | 36.304 | 1.00 | 40.91 | MOLA C |
| ATOM | 2392 | OG | SER | A 340 | 12.281 | −6.153 | 35.383 | 1.00 | 42.09 | MOLA O |
| ATOM | 2393 | C | SER | A 340 | 12.823 | −3.716 | 36.916 | 1.00 | 37.10 | MOLA C |
| ATOM | 2394 | O | SER | A 340 | 13.210 | −3.731 | 38.098 | 1.00 | 36.28 | MOLA O |
| ATOM | 2395 | N | LEU | A 341 | 13.600 | −3.360 | 35.913 | 1.00 | 36.19 | MOLA N |
| ATOM | 2396 | CA | LEU | A 341 | 14.976 | −3.002 | 36.166 | 1.00 | 36.04 | MOLA C |
| ATOM | 2397 | CB | LEU | A 341 | 15.657 | −2.711 | 34.833 | 1.00 | 34.10 | MOLA C |
| ATOM | 2398 | CG | LEU | A 341 | 17.105 | −3.061 | 34.470 | 1.00 | 33.75 | MOLA C |
| ATOM | 2399 | CD1 | LEU | A 341 | 17.807 | −4.108 | 35.369 | 1.00 | 33.23 | MOLA C |
| ATOM | 2400 | CD2 | LEU | A 341 | 17.096 | −3.475 | 32.999 | 1.00 | 22.19 | MOLA C |
| ATOM | 2401 | C | LEU | A 341 | 15.075 | −1.848 | 37.187 | 1.00 | 37.25 | MOLA C |
| ATOM | 2402 | O | LEU | A 341 | 16.088 | −1.717 | 37.873 | 1.00 | 37.74 | MOLA O |
| ATOM | 2403 | N | ASN | A 342 | 14.004 | −1.057 | 37.330 | 1.00 | 38.91 | MOLA N |
| ATOM | 2404 | CA | ASN | A 342 | 13.954 | 0.023 | 38.331 | 1.00 | 39.52 | MOLA C |
| ATOM | 2405 | CB | ASN | A 342 | 13.939 | 1.375 | 37.653 | 1.00 | 35.78 | MOLA C |
| ATOM | 2406 | CG | ASN | A 342 | 14.852 | 1.429 | 36.477 | 1.00 | 37.08 | MOLA C |
| ATOM | 2407 | OD1 | ASN | A 342 | 14.409 | 1.687 | 35.345 | 1.00 | 34.28 | MOLA O |
| ATOM | 2408 | ND2 | ASN | A 342 | 16.148 | 1.169 | 36.716 | 1.00 | 27.36 | MOLA N |
| ATOM | 2409 | C | ASN | A 342 | 12.752 | −0.036 | 39.276 | 1.00 | 42.31 | MOLA C |
| ATOM | 2410 | O | ASN | A 342 | 12.354 | 0.985 | 39.889 | 1.00 | 45.43 | MOLA O |
| ATOM | 2411 | N | LEU | A 343 | 12.173 | −1.211 | 39.415 | 1.00 | 40.90 | MOLA N |
| ATOM | 2412 | CA | LEU | A 343 | 11.038 | −1.341 | 40.288 | 1.00 | 45.52 | MOLA C |
| ATOM | 2413 | CB | LEU | A 343 | 10.706 | −2.829 | 40.455 | 1.00 | 47.34 | MOLA C |
| ATOM | 2414 | CG | LEU | A 343 | 9.766 | −3.313 | 41.558 | 1.00 | 46.56 | MOLA C |
| ATOM | 2415 | CD1 | LEU | A 343 | 10.460 | −3.188 | 42.934 | 1.00 | 38.71 | MOLA C |
| ATOM | 2416 | CD2 | LEU | A 343 | 8.421 | −2.578 | 41.496 | 1.00 | 43.57 | MOLA C |
| ATOM | 2417 | C | LEU | A 343 | 11.319 | −0.639 | 41.630 | 1.00 | 48.16 | MOLA C |
| ATOM | 2418 | O | LEU | A 343 | 10.451 | 0.031 | 42.207 | 1.00 | 49.81 | MOLA O |
| ATOM | 2419 | N | GLU | A 344 | 12.535 | −0.795 | 42.129 | 1.00 | 49.90 | MOLA N |
| ATOM | 2420 | CA | GLU | A 344 | 12.953 | −0.058 | 43.302 | 1.00 | 52.85 | MOLA C |
| ATOM | 2421 | CB | GLU | A 344 | 14.485 | −0.042 | 43.403 | 1.00 | 53.05 | MOLA C |
| ATOM | 2422 | CG | GLU | A 344 | 15.083 | −1.287 | 43.981 | 1.00 | 58.09 | MOLA C |
| ATOM | 2423 | CD | GLU | A 344 | 14.475 | −1.598 | 45.325 | 1.00 | 70.30 | MOLA C |
| ATOM | 2424 | OE1 | GLU | A 344 | 13.557 | −2.453 | 45.381 | 1.00 | 69.94 | MOLA O |
| ATOM | 2425 | OE2 | GLU | A 344 | 14.885 | −0.951 | 46.315 | 1.00 | 76.54 | MOLA O |
| ATOM | 2426 | C | GLU | A 344 | 12.475 | 1.381 | 43.211 | 1.00 | 53.28 | MOLA C |
| ATOM | 2427 | O | GLU | A 344 | 11.350 | 1.716 | 43.581 | 1.00 | 51.84 | MOLA O |
| ATOM | 2428 | N | GLU | A 345 | 13.367 | 2.207 | 42.673 | 1.00 | 55.13 | MOLA N |
| ATOM | 2429 | CA | GLU | A 345 | 13.212 | 3.647 | 42.599 | 1.00 | 55.92 | MOLA C |
| ATOM | 2430 | CB | GLU | A 345 | 14.264 | 4.228 | 41.654 | 1.00 | 57.39 | MOLA C |
| ATOM | 2431 | CG | GLU | A 345 | 15.676 | 4.154 | 42.205 | 1.00 | 58.77 | MOLA C |
| ATOM | 2432 | CD | GLU | A 345 | 15.883 | 5.063 | 43.414 | 1.00 | 66.69 | MOLA C |
| ATOM | 2433 | OE1 | GLU | A 345 | 15.261 | 6.159 | 43.476 | 1.00 | 66.02 | MOLA O |
| ATOM | 2434 | OE2 | GLU | A 345 | 16.691 | 4.680 | 44.291 | 1.00 | 67.30 | MOLA O |
| ATOM | 2435 | C | GLU | A 345 | 11.827 | 4.061 | 42.165 | 1.00 | 55.47 | MOLA C |
| ATOM | 2436 | O | GLU | A 345 | 11.394 | 5.168 | 42.483 | 1.00 | 55.18 | MOLA O |
| ATOM | 2437 | N | THR | A 346 | 11.129 | 3.180 | 41.448 | 1.00 | 53.76 | MOLA N |
| ATOM | 2438 | CA | THR | A 346 | 9.751 | 3.481 | 41.080 | 1.00 | 53.09 | MOLA C |
| ATOM | 2439 | CB | THR | A 346 | 9.188 | 2.513 | 40.015 | 1.00 | 52.35 | MOLA C |
| ATOM | 2440 | OG1 | THR | A 346 | 9.822 | 2.755 | 38.754 | 1.00 | 54.63 | MOLA O |
| ATOM | 2441 | CG2 | THR | A 346 | 7.714 | 2.748 | 39.825 | 1.00 | 54.95 | MOLA C |
| ATOM | 2442 | C | THR | A 346 | 8.824 | 3.560 | 42.313 | 1.00 | 52.00 | MOLA C |
| ATOM | 2443 | O | THR | A 346 | 7.845 | 4.304 | 42.334 | 1.00 | 53.13 | MOLA O |
| ATOM | 2444 | N | LEU | A 347 | 9.127 | 2.812 | 43.354 | 1.00 | 50.47 | MOLA N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 2445 | CA | LEU | A 347 | 8.273 | 2.881 | 44.518 | 1.00 | 49.25 | MOLA C |
| ATOM | 2446 | CB | LEU | A 347 | 8.450 | 1.638 | 45.385 | 1.00 | 50.00 | MOLA C |
| ATOM | 2447 | CG | LEU | A 347 | 8.471 | 0.319 | 44.618 | 1.00 | 51.98 | MOLA C |
| ATOM | 2448 | CD1 | LEU | A 347 | 8.576 | −0.854 | 45.578 | 1.00 | 56.89 | MOLA C |
| ATOM | 2449 | CD2 | LEU | A 347 | 7.227 | 0.192 | 43.765 | 1.00 | 60.64 | MOLA C |
| ATOM | 2450 | C | LEU | A 347 | 8.676 | 4.115 | 45.286 | 1.00 | 48.34 | MOLA C |
| ATOM | 2451 | O | LEU | A 347 | 7.831 | 4.851 | 45.809 | 1.00 | 49.00 | MOLA O |
| ATOM | 2452 | N | SER | A 348 | 9.989 | 4.330 | 45.339 | 1.00 | 46.83 | MOLA N |
| ATOM | 2453 | CA | SER | A 348 | 10.574 | 5.427 | 46.085 | 1.00 | 45.05 | MOLA C |
| ATOM | 2454 | CB | SER | A 348 | 12.076 | 5.447 | 45.904 | 1.00 | 42.95 | MOLA C |
| ATOM | 2455 | OG | SER | A 348 | 12.633 | 6.468 | 46.702 | 1.00 | 46.40 | MOLA O |
| ATOM | 2456 | C | SER | A 348 | 9.990 | 6.730 | 45.593 | 1.00 | 44.93 | MOLA C |
| ATOM | 2457 | O | SER | A 348 | 9.700 | 7.623 | 46.375 | 1.00 | 46.54 | MOLA O |
| ATOM | 2458 | N | THR | A 349 | 9.821 | 6.825 | 44.286 | 1.00 | 43.68 | MOLA N |
| ATOM | 2459 | CA | THR | A 349 | 9.234 | 7.989 | 43.685 | 1.00 | 42.05 | MOLA C |
| ATOM | 2460 | CB | THR | A 349 | 9.600 | 8.021 | 42.210 | 1.00 | 40.72 | MOLA C |
| ATOM | 2461 | OG1 | THR | A 349 | 10.912 | 8.579 | 42.090 | 1.00 | 46.66 | MOLA O |
| ATOM | 2462 | CG2 | THR | A 349 | 8.657 | 8.846 | 41.406 | 1.00 | 28.87 | MOLA C |
| ATOM | 2463 | C | THR | A 349 | 7.728 | 7.959 | 43.973 | 1.00 | 44.91 | MOLA C |
| ATOM | 2464 | O | THR | A 349 | 7.165 | 8.944 | 44.464 | 1.00 | 46.53 | MOLA O |
| ATOM | 2465 | N | LEU | A 350 | 7.088 | 6.815 | 43.727 | 1.00 | 45.51 | MOLA N |
| ATOM | 2466 | CA | LEU | A 350 | 5.660 | 6.645 | 44.027 | 1.00 | 44.55 | MOLA C |
| ATOM | 2467 | CB | LEU | A 350 | 5.179 | 5.290 | 43.557 | 1.00 | 42.71 | MOLA C |
| ATOM | 2468 | CG | LEU | A 350 | 4.900 | 5.278 | 42.067 | 1.00 | 40.10 | MOLA C |
| ATOM | 2469 | CD1 | LEU | A 350 | 4.466 | 3.891 | 41.562 | 1.00 | 41.17 | MOLA C |
| ATOM | 2470 | CD2 | LEU | A 350 | 3.817 | 6.292 | 41.800 | 1.00 | 45.52 | MOLA C |
| ATOM | 2471 | C | LEU | A 350 | 5.359 | 6.814 | 45.513 | 1.00 | 47.42 | MOLA C |
| ATOM | 2472 | O | LEU | A 350 | 4.266 | 7.241 | 45.898 | 1.00 | 47.37 | MOLA O |
| ATOM | 2473 | N | GLU | A 351 | 6.329 | 6.467 | 46.354 | 1.00 | 48.60 | MOLA N |
| ATOM | 2474 | CA | GLU | A 351 | 6.184 | 6.720 | 47.767 | 1.00 | 49.63 | MOLA C |
| ATOM | 2475 | CB | GLU | A 351 | 7.301 | 6.027 | 48.556 | 1.00 | 49.31 | MOLA C |
| ATOM | 2476 | CG | GLU | A 351 | 7.137 | 4.513 | 48.697 | 1.00 | 55.26 | MOLA C |
| ATOM | 2477 | CD | GLU | A 351 | 5.753 | 4.119 | 49.248 | 1.00 | 72.74 | MOLA C |
| ATOM | 2478 | OE1 | GLU | A 351 | 5.068 | 4.958 | 49.883 | 1.00 | 75.89 | MOLA O |
| ATOM | 2479 | OE2 | GLU | A 351 | 5.336 | 2.964 | 49.032 | 1.00 | 68.84 | MOLA O |
| ATOM | 2480 | C | GLU | A 351 | 6.223 | 8.240 | 47.954 | 1.00 | 49.90 | MOLA C |
| ATOM | 2481 | O | GLU | A 351 | 5.239 | 8.871 | 48.350 | 1.00 | 48.91 | MOLA O |
| ATOM | 2482 | N | TYR | A 352 | 7.372 | 8.804 | 47.601 | 1.00 | 50.00 | MOLA N |
| ATOM | 2483 | CA | TYR | A 352 | 7.670 | 10.200 | 47.784 | 1.00 | 49.21 | MOLA C |
| ATOM | 2484 | CB | TYR | A 352 | 8.815 | 10.613 | 46.870 | 1.00 | 49.79 | MOLA C |
| ATOM | 2485 | CG | TYR | A 352 | 9.277 | 12.034 | 47.088 | 1.00 | 49.85 | MOLA C |
| ATOM | 2486 | CD1 | TYR | A 352 | 8.728 | 13.093 | 46.355 | 1.00 | 55.64 | MOLA C |
| ATOM | 2487 | CE1 | TYR | A 352 | 9.163 | 14.398 | 46.548 | 1.00 | 52.24 | MOLA C |
| ATOM | 2488 | CZ | TYR | A 352 | 10.152 | 14.648 | 47.507 | 1.00 | 55.09 | MOLA C |
| ATOM | 2489 | OH | TYR | A 352 | 10.600 | 15.933 | 47.749 | 1.00 | 43.30 | MOLA O |
| ATOM | 2490 | CE2 | TYR | A 352 | 10.703 | 13.606 | 48.241 | 1.00 | 50.19 | MOLA C |
| ATOM | 2491 | CD2 | TYR | A 352 | 10.265 | 12.317 | 48.027 | 1.00 | 44.94 | MOLA C |
| ATOM | 2492 | C | TYR | A 352 | 6.481 | 11.027 | 47.451 | 1.00 | 49.13 | MOLA C |
| ATOM | 2493 | O | TYR | A 352 | 6.151 | 11.944 | 48.173 | 1.00 | 48.74 | MOLA O |
| ATOM | 2494 | N | ALA | A 353 | 5.850 | 10.705 | 46.334 | 1.00 | 51.26 | MOLA N |
| ATOM | 2495 | CA | ALA | A 353 | 4.678 | 11.451 | 45.859 | 1.00 | 53.73 | MOLA C |
| ATOM | 2496 | CB | ALA | A 353 | 4.425 | 11.138 | 44.393 | 1.00 | 54.84 | MOLA C |
| ATOM | 2497 | C | ALA | A 353 | 3.405 | 11.196 | 46.678 | 1.00 | 53.67 | MOLA C |
| ATOM | 2498 | O | ALA | A 353 | 2.779 | 12.118 | 47.193 | 1.00 | 51.57 | MOLA O |
| ATOM | 2499 | N | HIS | A 354 | 3.019 | 9.934 | 46.788 | 1.00 | 55.53 | MOLA N |
| ATOM | 2500 | CA | HIS | A 354 | 1.875 | 9.611 | 47.601 | 1.00 | 55.41 | MOLA C |
| ATOM | 2501 | CB | HIS | A 354 | 1.750 | 8.120 | 47.813 | 1.00 | 56.57 | MOLA C |
| ATOM | 2502 | CG | HIS | A 354 | 0.711 | 7.782 | 48.820 | 1.00 | 57.03 | MOLA C |
| ATOM | 2503 | ND1 | HIS | A 354 | −0.625 | 7.684 | 48.495 | 1.00 | 65.19 | MOLA N |
| ATOM | 2504 | CE1 | HIS | A 354 | −1.319 | 7.430 | 49.588 | 1.00 | 69.72 | MOLA C |
| ATOM | 2505 | NE2 | HIS | A 354 | −0.482 | 7.385 | 50.611 | 1.00 | 68.04 | MOLA N |
| ATOM | 2506 | CD2 | HIS | A 354 | 0.794 | 7.609 | 50.158 | 1.00 | 48.09 | MOLA C |
| ATOM | 2507 | C | HIS | A 354 | 2.000 | 10.253 | 48.957 | 1.00 | 54.87 | MOLA C |
| ATOM | 2508 | O | HIS | A 354 | 1.006 | 10.513 | 49.623 | 1.00 | 55.26 | MOLA O |
| ATOM | 2509 | N | ARG | A 355 | 3.231 | 10.491 | 49.379 | 1.00 | 55.89 | MOLA N |
| ATOM | 2510 | CA | ARG | A 355 | 3.461 | 11.116 | 50.671 | 1.00 | 57.11 | MOLA C |
| ATOM | 2511 | CB | ARG | A 355 | 4.815 | 10.721 | 51.236 | 1.00 | 55.82 | MOLA C |
| ATOM | 2512 | CG | ARG | A 355 | 5.310 | 11.693 | 52.287 | 1.00 | 57.66 | MOLA C |
| ATOM | 2513 | CD | ARG | A 355 | 6.033 | 10.951 | 53.348 | 1.00 | 62.43 | MOLA C |
| ATOM | 2514 | NE | ARG | A 355 | 6.785 | 9.869 | 52.738 | 1.00 | 61.41 | MOLA N |
| ATOM | 2515 | CZ | ARG | A 355 | 8.010 | 10.009 | 52.252 | 1.00 | 55.34 | MOLA C |
| ATOM | 2516 | NH1 | ARG | A 355 | 8.623 | 11.185 | 52.321 | 1.00 | 50.19 | MOLA N |
| ATOM | 2517 | NH2 | ARG | A 355 | 8.621 | 8.968 | 51.713 | 1.00 | 52.50 | MOLA N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | | |
|---|---|---|---|---|---|---|---|---|---|---|---|
| ATOM | 2518 | C | ARG | A 355 | 3.322 | 12.636 | 50.653 | 1.00 | 58.42 | MOLA | C |
| ATOM | 2519 | O | ARG | A 355 | 3.030 | 13.259 | 51.686 | 1.00 | 60.78 | MOLA | O |
| ATOM | 2520 | N | ALA | A 356 | 3.538 | 13.246 | 49.494 | 1.00 | 57.81 | MOLA | N |
| ATOM | 2521 | CA | ALA | A 356 | 3.399 | 14.692 | 49.400 | 1.00 | 56.34 | MOLA | C |
| ATOM | 2522 | CB | ALA | A 356 | 3.883 | 15.187 | 48.066 | 1.00 | 55.02 | MOLA | C |
| ATOM | 2523 | C | ALA | A 356 | 1.938 | 15.058 | 49.610 | 1.00 | 55.71 | MOLA | C |
| ATOM | 2524 | O | ALA | A 356 | 1.622 | 16.008 | 50.326 | 1.00 | 54.96 | MOLA | O |
| ATOM | 2525 | N | LYS | A 357 | 1.049 | 14.279 | 49.006 | 1.00 | 55.47 | MOLA | N |
| ATOM | 2526 | CA | LYS | A 357 | −0.375 | 14.556 | 49.103 | 1.00 | 57.60 | MOLA | C |
| ATOM | 2527 | CB | LYS | A 357 | −0.777 | 15.635 | 48.099 | 1.00 | 57.01 | MOLA | C |
| ATOM | 2528 | CG | LYS | A 357 | −2.256 | 15.874 | 47.964 | 1.00 | 55.50 | MOLA | C |
| ATOM | 2529 | CD | LYS | A 357 | −2.576 | 16.393 | 46.544 | 1.00 | 58.35 | MOLA | C |
| ATOM | 2530 | CE | LYS | A 357 | −4.018 | 16.115 | 46.136 | 1.00 | 60.09 | MOLA | C |
| ATOM | 2531 | NZ | LYS | A 357 | −4.352 | 16.679 | 44.812 | 1.00 | 66.54 | MOLA | N |
| ATOM | 2532 | C | LYS | A 357 | −1.186 | 13.281 | 48.931 | 1.00 | 59.16 | MOLA | C |
| ATOM | 2533 | O | LYS | A 357 | −1.596 | 12.905 | 47.830 | 1.00 | 57.93 | MOLA | O |
| ATOM | 2534 | N | ASN | A 358 | −1.399 | 12.618 | 50.059 | 1.00 | 62.51 | MOLA | N |
| ATOM | 2535 | CA | ASN | A 358 | −2.152 | 11.385 | 50.116 | 1.00 | 64.97 | MOLA | C |
| ATOM | 2536 | CB | ASN | A 358 | −2.030 | 10.806 | 51.530 | 1.00 | 64.44 | MOLA | C |
| ATOM | 2537 | CG | ASN | A 358 | −3.088 | 9.771 | 51.831 | 1.00 | 66.77 | MOLA | C |
| ATOM | 2538 | OD1 | ASN | A 358 | −3.491 | 9.011 | 50.951 | 1.00 | 73.15 | MOLA | O |
| ATOM | 2539 | ND2 | ASN | A 358 | −3.545 | 9.727 | 53.086 | 1.00 | 62.82 | MOLA | N |
| ATOM | 2540 | C | ASN | A 358 | −3.631 | 11.538 | 49.729 | 1.00 | 67.04 | MOLA | C |
| ATOM | 2541 | O | ASN | A 358 | −4.352 | 12.349 | 50.323 | 1.00 | 68.00 | MOLA | O |
| ATOM | 2542 | N | ILE | A 359 | −4.055 | 10.803 | 48.696 | 1.00 | 68.18 | MOLA | N |
| ATOM | 2543 | CA | ILE | A 359 | −5.477 | 10.540 | 48.477 | 1.00 | 69.52 | MOLA | C |
| ATOM | 2544 | CB | ILE | A 359 | −5.997 | 10.786 | 47.043 | 1.00 | 69.03 | MOLA | C |
| ATOM | 2545 | CG1 | ILE | A 359 | −5.099 | 11.733 | 46.240 | 1.00 | 72.16 | MOLA | C |
| ATOM | 2546 | CD1 | ILE | A 359 | −5.567 | 11.902 | 44.775 | 1.00 | 69.02 | MOLA | C |
| ATOM | 2547 | CG2 | ILE | A 359 | −7.500 | 11.216 | 47.076 | 1.00 | 68.13 | MOLA | C |
| ATOM | 2548 | C | ILE | A 359 | −5.653 | 9.048 | 48.711 | 1.00 | 70.93 | MOLA | C |
| ATOM | 2549 | O | ILE | A 359 | −4.676 | 8.292 | 48.658 | 1.00 | 71.34 | MOLA | O |
| ATOM | 2550 | N | LEU | A 360 | −6.897 | 8.624 | 48.947 | 1.00 | 72.34 | MOLA | N |
| ATOM | 2551 | CA | LEU | A 360 | −7.215 | 7.211 | 49.151 | 1.00 | 71.59 | MOLA | C |
| ATOM | 2552 | CB | LEU | A 360 | −8.453 | 7.012 | 50.047 | 1.00 | 70.74 | MOLA | C |
| ATOM | 2553 | CG | LEU | A 360 | −8.541 | 7.422 | 51.508 | 1.00 | 62.91 | MOLA | C |
| ATOM | 2554 | CD1 | LEU | A 360 | −7.234 | 7.078 | 52.256 | 1.00 | 31.33 | MOLA | C |
| ATOM | 2555 | CD2 | LEU | A 360 | −8.914 | 8.908 | 51.586 | 1.00 | 62.18 | MOLA | C |
| ATOM | 2556 | C | LEU | A 360 | −7.527 | 6.513 | 47.848 | 1.00 | 73.27 | MOLA | C |
| ATOM | 2557 | O | LEU | A 360 | −8.222 | 7.054 | 46.976 | 1.00 | 72.72 | MOLA | O |
| ATOM | 2558 | N | ASN | A 361 | −7.035 | 5.288 | 47.734 | 1.00 | 74.56 | MOLA | N |
| ATOM | 2559 | CA | ASN | A 361 | −7.528 | 4.416 | 46.709 | 1.00 | 76.50 | MOLA | C |
| ATOM | 2560 | CB | ASN | A 361 | −6.918 | 3.020 | 46.867 | 1.00 | 76.34 | MOLA | C |
| ATOM | 2561 | CG | ASN | A 361 | −5.454 | 2.981 | 46.489 | 1.00 | 75.23 | MOLA | C |
| ATOM | 2562 | OD1 | ASN | A 361 | −5.108 | 3.023 | 45.302 | 1.00 | 74.44 | MOLA | O |
| ATOM | 2563 | ND2 | ASN | A 361 | −4.581 | 2.897 | 47.495 | 1.00 | 62.68 | MOLA | N |
| ATOM | 2564 | C | ASN | A 361 | −9.049 | 4.379 | 46.879 | 1.00 | 77.89 | MOLA | C |
| ATOM | 2565 | O | ASN | A 361 | −9.562 | 4.208 | 47.991 | 1.00 | 77.24 | MOLA | O |
| ATOM | 2566 | N | LYS | A 362 | −9.762 | 4.589 | 45.782 | 1.00 | 80.60 | MOLA | N |
| ATOM | 2567 | CA | LYS | A 362 | −11.218 | 4.549 | 45.795 | 1.00 | 83.61 | MOLA | C |
| ATOM | 2568 | CB | LYS | A 362 | −11.794 | 5.226 | 44.538 | 1.00 | 83.44 | MOLA | C |
| ATOM | 2569 | CG | LYS | A 362 | −11.459 | 6.698 | 44.349 | 1.00 | 81.17 | MOLA | C |
| ATOM | 2570 | CD | LYS | A 362 | −12.654 | 7.437 | 43.774 | 1.00 | 71.20 | MOLA | C |
| ATOM | 2571 | CE | LYS | A 362 | −13.804 | 7.381 | 44.784 | 1.00 | 72.07 | MOLA | C |
| ATOM | 2572 | NZ | LYS | A 362 | −14.848 | 8.408 | 44.579 | 1.00 | 61.80 | MOLA | N |
| ATOM | 2573 | C | LYS | A 362 | −11.760 | 3.121 | 45.835 | 1.00 | 86.40 | MOLA | C |
| ATOM | 2574 | O | LYS | A 362 | −11.067 | 2.167 | 45.464 | 1.00 | 85.91 | MOLA | O |
| ATOM | 2575 | N | PRO | A 363 | −13.006 | 2.966 | 46.313 | 1.00 | 89.59 | MOLA | N |
| ATOM | 2576 | CA | PRO | A 363 | −13.717 | 1.723 | 46.033 | 1.00 | 91.20 | MOLA | C |
| ATOM | 2577 | CB | PRO | A 363 | −14.700 | 1.600 | 47.206 | 1.00 | 91.35 | MOLA | C |
| ATOM | 2578 | CG | PRO | A 363 | −14.853 | 3.013 | 47.778 | 1.00 | 89.38 | MOLA | C |
| ATOM | 2579 | CD | PRO | A 363 | −13.794 | 3.898 | 47.148 | 1.00 | 89.66 | MOLA | C |
| ATOM | 2580 | C | PRO | A 363 | −14.455 | 1.872 | 44.691 | 1.00 | 93.09 | MOLA | C |
| ATOM | 2581 | O | PRO | A 363 | −15.415 | 2.644 | 44.594 | 1.00 | 93.47 | MOLA | O |
| ATOM | 2582 | N | GLU | A 364 | −13.982 | 1.169 | 43.663 | 1.00 | 94.94 | MOLA | N |
| ATOM | 2583 | CA | GLU | A 364 | −14.586 | 1.187 | 42.319 | 1.00 | 97.13 | MOLA | C |
| ATOM | 2584 | CB | GLU | A 364 | −14.009 | 0.046 | 41.472 | 1.00 | 97.14 | MOLA | C |
| ATOM | 2585 | CG | GLU | A 364 | −12.529 | −0.227 | 41.674 | 1.00 | 98.55 | MOLA | C |
| ATOM | 2586 | CD | GLU | A 364 | −12.225 | −0.939 | 42.987 | 1.00 | 98.82 | MOLA | C |
| ATOM | 2587 | OE1 | GLU | A 364 | −11.260 | −1.719 | 43.023 | 1.00 | 98.10 | MOLA | O |
| ATOM | 2588 | OE2 | GLU | A 364 | −12.943 | −0.732 | 43.986 | 1.00 | 102.58 | MOLA | O |
| ATOM | 2589 | C | GLU | A 364 | −16.120 | 1.056 | 42.344 | 1.00 | 98.73 | MOLA | C |
| ATOM | 2590 | O | GLU | A 364 | −16.687 | 0.555 | 43.324 | 1.00 | 99.55 | MOLA | O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2591 | N | VAL | A 365 | −16.787 | 1.498 | 41.269 | 1.00 | 99.92 | MOLA N |
| ATOM | 2592 | CA | VAL | A 365 | −18.259 | 1.390 | 41.164 | 1.00 | 100.66 | MOLA C |
| ATOM | 2593 | CB | VAL | A 365 | −18.885 | 2.265 | 40.007 | 1.00 | 100.98 | MOLA C |
| ATOM | 2594 | CG1 | VAL | A 365 | −18.353 | 1.863 | 38.626 | 1.00 | 98.65 | MOLA C |
| ATOM | 2595 | CG2 | VAL | A 365 | −20.414 | 2.182 | 40.036 | 1.00 | 99.03 | MOLA C |
| ATOM | 2596 | C | VAL | A 365 | −18.711 | −0.071 | 41.043 | 1.00 | 101.08 | MOLA C |
| ATOM | 2597 | O | VAL | A 365 | −19.759 | −0.448 | 41.584 | 1.00 | 101.34 | MOLA O |
| ATOM | 2598 | OXT | VAL | A 365 | −18.032 | −0.896 | 40.418 | 1.00 | 100.86 | MOLA O |
| ATOM | 2627 | N | GLY | B 16 | 49.852 | −16.828 | 48.575 | 1.00 | 67.44 | MOLB N |
| ATOM | 2628 | CA | GLY | B 16 | 48.362 | −16.717 | 48.661 | 1.00 | 68.00 | MOLB C |
| ATOM | 2629 | C | GLY | B 16 | 47.686 | −16.512 | 47.315 | 1.00 | 67.73 | MOLB C |
| ATOM | 2630 | O | GLY | B 16 | 46.879 | −15.587 | 47.136 | 1.00 | 68.16 | MOLB O |
| ATOM | 2631 | N | LYS | B 17 | 47.983 | −17.409 | 46.383 | 1.00 | 66.62 | MOLB N |
| ATOM | 2632 | CA | LYS | B 17 | 47.542 | −17.271 | 44.996 | 1.00 | 66.62 | MOLB C |
| ATOM | 2633 | CB | LYS | B 17 | 48.708 | −17.619 | 44.043 | 1.00 | 68.23 | MOLB C |
| ATOM | 2634 | CG | LYS | B 17 | 49.877 | −18.413 | 44.708 | 1.00 | 73.19 | MOLB C |
| ATOM | 2635 | CD | LYS | B 17 | 49.566 | −19.903 | 44.981 | 1.00 | 79.14 | MOLB C |
| ATOM | 2636 | CE | LYS | B 17 | 50.221 | −20.833 | 43.956 | 1.00 | 76.91 | MOLB C |
| ATOM | 2637 | NZ | LYS | B 17 | 49.935 | −20.444 | 42.541 | 1.00 | 75.15 | MOLB N |
| ATOM | 2638 | C | LYS | B 17 | 46.270 | −18.021 | 44.580 | 1.00 | 64.48 | MOLB C |
| ATOM | 2639 | O | LYS | B 17 | 45.854 | −17.904 | 43.428 | 1.00 | 63.40 | MOLB O |
| ATOM | 2640 | N | ASN | B 18 | 45.651 | −18.776 | 45.490 | 1.00 | 62.11 | MOLB N |
| ATOM | 2641 | CA | ASN | B 18 | 44.501 | −19.618 | 45.105 | 1.00 | 60.45 | MOLB C |
| ATOM | 2642 | CB | ASN | B 18 | 44.203 | −20.700 | 46.139 | 1.00 | 61.32 | MOLB C |
| ATOM | 2643 | CG | ASN | B 18 | 45.341 | −21.677 | 46.302 | 1.00 | 70.23 | MOLB C |
| ATOM | 2644 | OD1 | ASN | B 18 | 45.129 | −22.832 | 46.706 | 1.00 | 85.28 | MOLB O |
| ATOM | 2645 | ND2 | ASN | B 18 | 46.566 | −21.226 | 45.991 | 1.00 | 72.98 | MOLB N |
| ATOM | 2646 | C | ASN | B 18 | 43.247 | −18.835 | 44.867 | 1.00 | 56.63 | MOLB C |
| ATOM | 2647 | O | ASN | B 18 | 42.259 | −19.370 | 44.373 | 1.00 | 56.50 | MOLB O |
| ATOM | 2648 | N | ILE | B 19 | 43.286 | −17.571 | 45.254 | 1.00 | 53.45 | MOLB N |
| ATOM | 2649 | CA | ILE | B 19 | 42.154 | −16.690 | 45.065 | 1.00 | 51.75 | MOLB C |
| ATOM | 2650 | CB | ILE | B 19 | 41.520 | −16.296 | 46.394 | 1.00 | 50.63 | MOLB C |
| ATOM | 2651 | CG1 | ILE | B 19 | 41.239 | −17.537 | 47.250 | 1.00 | 51.81 | MOLB C |
| ATOM | 2652 | CD1 | ILE | B 19 | 42.429 | −18.041 | 48.071 | 1.00 | 50.95 | MOLB C |
| ATOM | 2653 | CG2 | ILE | B 19 | 40.261 | −15.492 | 46.143 | 1.00 | 50.50 | MOLB C |
| ATOM | 2654 | C | ILE | B 19 | 42.602 | −15.415 | 44.372 | 1.00 | 51.48 | MOLB C |
| ATOM | 2655 | O | ILE | B 19 | 43.388 | −14.639 | 44.939 | 1.00 | 52.52 | MOLB O |
| ATOM | 2656 | N | GLN | B 20 | 42.120 | −15.202 | 43.149 | 1.00 | 48.27 | MOLB N |
| ATOM | 2657 | CA | GLN | B 20 | 42.483 | −14.007 | 42.409 | 1.00 | 46.07 | MOLB C |
| ATOM | 2658 | CB | GLN | B 20 | 42.827 | −14.309 | 40.937 | 1.00 | 47.87 | MOLB C |
| ATOM | 2659 | CG | GLN | B 20 | 44.104 | −15.169 | 40.702 | 1.00 | 54.26 | MOLB C |
| ATOM | 2660 | CD | GLN | B 20 | 45.378 | −14.606 | 41.364 | 1.00 | 58.06 | MOLB C |
| ATOM | 2661 | OE1 | GLN | B 20 | 46.428 | −14.520 | 40.737 | 1.00 | 47.76 | MOLB O |
| ATOM | 2662 | NE2 | GLN | B 20 | 45.276 | −14.224 | 42.633 | 1.00 | 66.38 | MOLB N |
| ATOM | 2663 | C | GLN | B 20 | 41.294 | −13.113 | 42.453 | 1.00 | 42.72 | MOLB C |
| ATOM | 2664 | O | GLN | B 20 | 40.161 | −13.607 | 42.425 | 1.00 | 43.93 | MOLB O |
| ATOM | 2665 | N | VAL | B 21 | 41.554 | −11.810 | 42.556 | 1.00 | 38.10 | MOLB N |
| ATOM | 2666 | CA | VAL | B 21 | 40.531 | −10.788 | 42.363 | 1.00 | 33.42 | MOLB C |
| ATOM | 2667 | CB | VAL | B 21 | 40.312 | −9.954 | 43.588 | 1.00 | 32.56 | MOLB C |
| ATOM | 2668 | CG1 | VAL | B 21 | 39.265 | −8.927 | 43.290 | 1.00 | 33.13 | MOLB C |
| ATOM | 2669 | CG2 | VAL | B 21 | 39.821 | −10.827 | 44.692 | 1.00 | 30.11 | MOLB C |
| ATOM | 2670 | C | VAL | B 21 | 40.881 | −9.874 | 41.194 | 1.00 | 31.27 | MOLB C |
| ATOM | 2671 | O | VAL | B 21 | 41.956 | −9.268 | 41.146 | 1.00 | 32.61 | MOLB O |
| ATOM | 2672 | N | VAL | B 22 | 39.981 | −9.793 | 40.230 | 1.00 | 28.90 | MOLB N |
| ATOM | 2673 | CA | VAL | B 22 | 40.227 | −8.942 | 39.082 | 1.00 | 27.60 | MOLB C |
| ATOM | 2674 | CB | VAL | B 22 | 40.484 | −9.767 | 37.869 | 1.00 | 25.94 | MOLB C |
| ATOM | 2675 | CG1 | VAL | B 22 | 41.525 | −10.739 | 38.215 | 1.00 | 25.88 | MOLB C |
| ATOM | 2676 | CG2 | VAL | B 22 | 39.233 | −10.515 | 37.501 | 1.00 | 26.29 | MOLB C |
| ATOM | 2677 | C | VAL | B 22 | 39.005 | −8.098 | 38.860 | 1.00 | 25.65 | MOLB C |
| ATOM | 2678 | O | VAL | B 22 | 37.927 | −8.444 | 39.354 | 1.00 | 24.96 | MOLB O |
| ATOM | 2679 | N | VAL | B 23 | 39.190 | −7.034 | 38.085 | 1.00 | 23.80 | MOLB N |
| ATOM | 2680 | CA | VAL | B 23 | 38.189 | −5.997 | 37.823 | 1.00 | 24.70 | MOLB C |
| ATOM | 2681 | CB | VAL | B 23 | 38.758 | −4.610 | 38.255 | 1.00 | 26.05 | MOLB C |
| ATOM | 2682 | CG1 | VAL | B 23 | 38.123 | −3.478 | 37.458 | 1.00 | 18.88 | MOLB C |
| ATOM | 2683 | CG2 | VAL | B 23 | 38.629 | −4.382 | 39.805 | 1.00 | 28.41 | MOLB C |
| ATOM | 2684 | C | VAL | B 23 | 37.861 | −5.841 | 36.347 | 1.00 | 23.97 | MOLB C |
| ATOM | 2685 | O | VAL | B 23 | 38.776 | −5.584 | 35.551 | 1.00 | 23.73 | MOLB O |
| ATOM | 2686 | N | ARG | B 24 | 36.590 | −5.952 | 35.946 | 1.00 | 22.36 | MOLB N |
| ATOM | 2687 | CA | ARG | B 24 | 36.306 | −5.658 | 34.530 | 1.00 | 22.78 | MOLB C |
| ATOM | 2688 | CB | ARG | B 24 | 35.635 | −6.808 | 33.818 | 1.00 | 20.50 | MOLB~C |
| ATOM | 2689 | CG | ARG | B 24 | 35.712 | −6.687 | 32.277 | 1.00 | 19.71 | MOLB C |
| ATOM | 2690 | CD | ARG | B 24 | 34.608 | −7.535 | 31.605 | 1.00 | 29.94 | MOLB C |
| ATOM | 2691 | NE | ARG | B 24 | 34.915 | −7.879 | 30.219 | 1.00 | 27.31 | MOLB N |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2692 | CZ | ARG | B 24 | 34.031 | −8.275 | 29.306 | 1.00 | 29.72 | MOLB C |
| ATOM | 2693 | NH1 | ARG | B 24 | 32.750 | −8.352 | 29.601 | 1.00 | 46.30 | MOLB N |
| ATOM | 2694 | NH2 | ARG | B 24 | 34.426 | −8.564 | 28.075 | 1.00 | 37.50 | MOLB N |
| ATOM | 2695 | C | ARG | B 24 | 35.445 | −4.433 | 34.336 | 1.00 | 26.95 | MOLB C |
| ATOM | 2696 | O | ARG | B 24 | 34.229 | −4.485 | 34.545 | 1.00 | 31.03 | MOLB O |
| ATOM | 2697 | N | CYS | B 25 | 36.049 | −3.331 | 33.920 | 1.00 | 28.05 | MOLB N |
| ATOM | 2698 | CA | CYS | B 25 | 35.255 | −2.153 | 33.613 | 1.00 | 29.45 | MOLB C |
| ATOM | 2699 | CB | CYS | B 25 | 36.101 | −0.877 | 33.772 | 1.00 | 32.05 | MOLB C |
| ATOM | 2700 | SG | CYS | B 25 | 35.284 | 0.750 | 33.486 | 1.00 | 36.49 | MOLB S |
| ATOM | 2701 | C | CYS | B 25 | 34.696 | −2.274 | 32.176 | 1.00 | 29.65 | MOLB C |
| ATOM | 2702 | O | CYS | B 25 | 35.361 | −2.826 | 31.275 | 1.00 | 27.30 | MOLB O |
| ATOM | 2703 | N | ARG | B 26 | 33.472 | −1.763 | 31.988 | 1.00 | 29.26 | MOLB N |
| ATOM | 2704 | CA | ARG | B 26 | 32.772 | −1.768 | 30.703 | 1.00 | 27.40 | MOLB C |
| ATOM | 2705 | CB | ARG | B 26 | 31.348 | −2.259 | 30.872 | 1.00 | 25.59 | MOLB C |
| ATOM | 2706 | CG | ARG | B 26 | 30.505 | −1.504 | 31.883 | 1.00 | 24.85 | MOLB C |
| ATOM | 2707 | CD | ARG | B 26 | 29.122 | −1.343 | 31.276 | 1.00 | 34.12 | MOLB C |
| ATOM | 2708 | NE | ARG | B 26 | 28.126 | −0.720 | 32.145 | 1.00 | 34.06 | MOLB N |
| ATOM | 2709 | CZ | ARG | B 26 | 27.939 | 0.593 | 32.259 | 1.00 | 27.37 | MOLB C |
| ATOM | 2710 | NH1 | ARG | B 26 | 28.693 | 1.435 | 31.590 | 1.00 | 34.94 | MOLB N |
| ATOM | 2711 | NH2 | ARG | B 26 | 27.003 | 1.067 | 33.058 | 1.00 | 26.97 | MOLB N |
| ATOM | 2712 | C | ARG | B 26 | 32.718 | −0.379 | 30.099 | 1.00 | 31.22 | MOLB C |
| ATOM | 2713 | O | ARG | B 26 | 32.950 | 0.607 | 30.789 | 1.00 | 33.06 | MOLB O |
| ATOM | 2714 | N | PRO | B 27 | 32.465 | −0.301 | 28.784 | 1.00 | 33.52 | MOLB N |
| ATOM | 2715 | CA | PRO | B 27 | 32.256 | 0.965 | 28.109 | 1.00 | 32.43 | MOLB C |
| ATOM | 2716 | CB | PRO | B 27 | 31.975 | 0.536 | 26.673 | 1.00 | 28.16 | MOLB C |
| ATOM | 2717 | CG | PRO | B 27 | 32.692 | −0.763 | 26.542 | 1.00 | 33.76 | MOLB C |
| ATOM | 2718 | CD | PRO | B 27 | 32.443 | −1.435 | 27.832 | 1.00 | 34.27 | MOLB C |
| ATOM | 2719 | C | PRO | B 27 | 31.053 | 1.729 | 28.659 | 1.00 | 36.37 | MOLB C |
| ATOM | 2720 | O | PRO | B 27 | 30.283 | 1.173 | 29.446 | 1.00 | 35.98 | MOLB O |
| ATOM | 2721 | N | PHE | B 28 | 30.934 | 3.005 | 28.258 | 1.00 | 39.39 | MOLB N |
| ATOM | 2722 | CA | PHE | B 28 | 29.783 | 3.858 | 28.534 | 1.00 | 39.95 | MOLB C |
| ATOM | 2723 | CB | PHE | B 28 | 30.044 | 5.246 | 27.958 | 1.00 | 42.91 | MOLB C |
| ATOM | 2724 | CG | PHE | B 28 | 30.702 | 6.187 | 28.905 | 1.00 | 40.70 | MOLB C |
| ATOM | 2725 | CD1 | PHE | B 28 | 32.050 | 6.059 | 29.198 | 1.00 | 29.93 | MOLB C |
| ATOM | 2726 | CE1 | PHE | B 28 | 32.658 | 6.928 | 30.086 | 1.00 | 34.51 | MOLB C |
| ATOM | 2727 | CZ | PHE | B 28 | 31.906 | 7.945 | 30.682 | 1.00 | 43.73 | MOLB C |
| ATOM | 2728 | CE2 | PHE | B 28 | 30.547 | 8.082 | 30.398 | 1.00 | 25.40 | MOLB C |
| ATOM | 2729 | CD2 | PHE | B 28 | 29.958 | 7.208 | 29.506 | 1.00 | 34.41 | MOLB C |
| ATOM | 2730 | C | PHE | B 28 | 28.594 | 3.277 | 27.804 | 1.00 | 39.54 | MOLB C |
| ATOM | 2731 | O | PHE | B 28 | 28.774 | 2.379 | 26.997 | 1.00 | 37.28 | MOLB O |
| ATOM | 2732 | N | ASN | B 29 | 27.393 | 3.804 | 28.062 | 1.00 | 39.86 | MOLB N |
| ATOM | 2733 | CA | ASN | B 29 | 26.161 | 3.362 | 27.372 | 1.00 | 39.28 | MOLB C |
| ATOM | 2734 | CB | ASN | B 29 | 25.441 | 2.351 | 28.243 | 1.00 | 35.94 | MOLB C |
| ATOM | 2735 | CG | ASN | B 29 | 24.982 | 2.953 | 29.533 | 1.00 | 34.89 | MOLB C |
| ATOM | 2736 | OD1 | ASN | B 29 | 24.485 | 4.068 | 29.555 | 1.00 | 56.35 | MOLB O |
| ATOM | 2737 | ND2 | ASN | B 29 | 25.157 | 2.245 | 30.616 | 1.00 | 38.82 | MOLB N |
| ATOM | 2738 | C | ASN | B 29 | 25.232 | 4.574 | 27.034 | 1.00 | 42.73 | MOLB C |
| ATOM | 2739 | O | ASN | B 29 | 25.391 | 5.665 | 27.610 | 1.00 | 42.78 | MOLB O |
| ATOM | 2740 | N | LEU | B 30 | 24.268 | 4.402 | 26.123 | 1.00 | 42.32 | MOLB N |
| ATOM | 2741 | CA | LEU | B 30 | 23.444 | 5.532 | 25.673 | 1.00 | 43.06 | MOLB C |
| ATOM | 2742 | CB | LEU | B 30 | 22.245 | 5.043 | 24.852 | 1.00 | 42.00 | MOLB C |
| ATOM | 2743 | CG | LEU | B 30 | 22.787 | 3.787 | 24.111 | 1.00 | 59.69 | MOLB C |
| ATOM | 2744 | CD1 | LEU | B 30 | 21.807 | 2.571 | 23.981 | 1.00 | 64.76 | MOLB C |
| ATOM | 2745 | CD2 | LEU | B 30 | 23.457 | 4.121 | 22.743 | 1.00 | 70.18 | MOLB C |
| ATOM | 2746 | C | LEU | B 30 | 22.999 | 6.403 | 26.853 | 1.00 | 41.35 | MOLB C |
| ATOM | 2747 | O | LEU | B 30 | 22.884 | 7.616 | 26.714 | 1.00 | 40.90 | MOLB O |
| ATOM | 2748 | N | ALA | B 31 | 22.767 | 5.804 | 28.016 | 1.00 | 38.13 | MOLB N |
| ATOM | 2749 | CA | ALA | B 31 | 22.288 | 6.580 | 29.154 | 1.00 | 37.09 | MOLB C |
| ATOM | 2750 | CB | ALA | B 31 | 21.616 | 5.672 | 30.203 | 1.00 | 33.64 | MOLB C |
| ATOM | 2751 | C | ALA | B 31 | 23.413 | 7.439 | 29.778 | 1.00 | 39.08 | MOLB C |
| ATOM | 2752 | O | ALA | B 31 | 23.285 | 8.665 | 29.979 | 1.00 | 39.11 | MOLB O |
| ATOM | 2753 | N | GLU | B 32 | 24.534 | 6.811 | 30.076 | 1.00 | 38.01 | MOLB N |
| ATOM | 2754 | CA | GLU | B 32 | 25.604 | 7.585 | 30.647 | 1.00 | 39.16 | MOLB C |
| ATOM | 2755 | CB | GLU | B 32 | 26.708 | 6.651 | 31.145 | 1.00 | 41.01 | MOLB C |
| ATOM | 2756 | CG | GLU | B 32 | 26.179 | 5.447 | 32.008 | 1.00 | 37.13 | MOLB C |
| ATOM | 2757 | CD | GLU | B 32 | 27.244 | 4.365 | 32.225 | 1.00 | 40.72 | MOLB C |
| ATOM | 2758 | OE1 | GLU | B 32 | 27.800 | 3.839 | 31.217 | 1.00 | 46.16 | MOLB O |
| ATOM | 2759 | OE2 | GLU | B 32 | 27.528 | 4.048 | 33.400 | 1.00 | 29.76 | MOLB O |
| ATOM | 2760 | C | GLU | B 32 | 26.074 | 8.690 | 29.664 | 1.00 | 39.35 | MOLB C |
| ATOM | 2761 | O | GLU | B 32 | 26.286 | 9.831 | 30.074 | 1.00 | 40.42 | MOLB O |
| ATOM | 2762 | N | ARG | B 33 | 26.188 | 8.368 | 28.378 | 1.00 | 39.87 | MOLB N |
| ATOM | 2763 | CA | ARG | B 33 | 26.428 | 9.384 | 27.348 | 1.00 | 42.32 | MOLB C |
| ATOM | 2764 | CB | ARG | B 33 | 26.538 | 8.762 | 25.954 | 1.00 | 38.68 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2765 | CG | ARG | B 33 | 27.741 | 7.869 | 25.713 | 1.00 | 47.84 | MOLB C |
| ATOM | 2766 | CD | ARG | B 33 | 29.052 | 8.628 | 25.723 | 1.00 | 38.67 | MOLB C |
| ATOM | 2767 | NE | ARG | B 33 | 30.173 | 7.702 | 25.768 | 1.00 | 41.22 | MOLB N |
| ATOM | 2768 | CZ | ARG | B 33 | 31.425 | 8.063 | 26.031 | 1.00 | 51.35 | MOLB C |
| ATOM | 2769 | NH1 | ARG | B 33 | 31.741 | 9.334 | 26.255 | 1.00 | 36.01 | MOLB N |
| ATOM | 2770 | NH2 | ARG | B 33 | 32.374 | 7.149 | 26.059 | 1.00 | 55.68 | MOLB N |
| ATOM | 2771 | C | ARG | B 33 | 25.287 | 10.419 | 27.291 | 1.00 | 45.45 | MOLB C |
| ATOM | 2772 | O | ARG | B 33 | 25.527 | 11.624 | 27.115 | 1.00 | 44.61 | MOLB O |
| ATOM | 2773 | N | LYS | B 34 | 24.050 | 9.931 | 27.417 | 1.00 | 47.40 | MOLB N |
| ATOM | 2774 | CA | LYS | B 34 | 22.847 | 10.743 | 27.217 | 1.00 | 47.67 | MOLB C |
| ATOM | 2775 | CB | LYS | B 34 | 21.602 | 9.833 | 27.174 | 1.00 | 47.53 | MOLB C |
| ATOM | 2776 | CG | LYS | B 34 | 20.517 | 10.109 | 26.110 | 1.00 | 49.52 | MOLB C |
| ATOM | 2777 | CD | LYS | B 34 | 19.761 | 8.795 | 25.709 | 1.00 | 47.73 | MOLB C |
| ATOM | 2778 | CE | LYS | B 34 | 19.436 | 7.903 | 26.970 | 1.00 | 68.68 | MOLB C |
| ATOM | 2779 | NZ | LYS | B 34 | 19.128 | 6.414 | 26.812 | 1.00 | 53.10 | MOLB N |
| ATOM | 2780 | C | LYS | B 34 | 22.789 | 11.732 | 28.369 | 1.00 | 47.18 | MOLB C |
| ATOM | 2781 | O | LYS | B 34 | 22.288 | 12.842 | 28.216 | 1.00 | 47.27 | MOLB O |
| ATOM | 2782 | N | ALA | B 35 | 23.326 | 11.337 | 29.521 | 1.00 | 47.62 | MOLB N |
| ATOM | 2783 | CA | ALA | B 35 | 23.392 | 12.242 | 30.683 | 1.00 | 48.63 | MOLB C |
| ATOM | 2784 | CB | ALA | B 35 | 23.019 | 11.511 | 31.969 | 1.00 | 48.66 | MOLB C |
| ATOM | 2785 | C | ALA | B 35 | 24.795 | 12.850 | 30.773 | 1.00 | 48.63 | MOLB C |
| ATOM | 2786 | O | ALA | B 35 | 25.181 | 13.498 | 31.759 | 1.00 | 44.96 | MOLB O |
| ATOM | 2787 | N | SER | B 36 | 25.548 | 12.632 | 29.702 | 1.00 | 49.44 | MOLB N |
| ATOM | 2788 | CA | SER | B 36 | 26.922 | 13.069 | 29.623 | 1.00 | 49.83 | MOLB C |
| ATOM | 2789 | CB | SER | B 36 | 27.028 | 14.454 | 28.981 | 1.00 | 50.54 | MOLB C |
| ATOM | 2790 | OG | SER | B 36 | 25.974 | 15.274 | 29.424 | 1.00 | 54.05 | MOLB O |
| ATOM | 2791 | C | SER | B 36 | 27.557 | 13.093 | 30.989 | 1.00 | 48.50 | MOLB C |
| ATOM | 2792 | O | SER | B 36 | 27.878 | 14.175 | 31.475 | 1.00 | 48.31 | MOLB O |
| ATOM | 2793 | N | ALA | B 37 | 27.716 | 11.911 | 31.604 | 1.00 | 45.51 | MOLB N |
| ATOM | 2794 | CA | ALA | B 37 | 28.514 | 11.777 | 32.816 | 1.00 | 42.20 | MOLB C |
| ATOM | 2795 | CB | ALA | B 37 | 28.181 | 10.514 | 33.492 | 1.00 | 38.70 | MOLB C |
| ATOM | 2796 | C | ALA | B 37 | 29.948 | 11.762 | 32.295 | 1.00 | 43.11 | MOLB C |
| ATOM | 2797 | O | ALA | B 37 | 30.134 | 11.565 | 31.094 | 1.00 | 45.99 | MOLB O |
| ATOM | 2798 | N | HIS | B 38 | 30.963 | 11.989 | 33.130 | 1.00 | 40.78 | MOLB N |
| ATOM | 2799 | CA | HIS | B 38 | 32.338 | 11.838 | 32.632 | 1.00 | 38.39 | MOLB C |
| ATOM | 2800 | CB | HIS | B 38 | 33.294 | 12.858 | 33.231 | 1.00 | 39.55 | MOLB C |
| ATOM | 2801 | CG | HIS | B 38 | 32.839 | 14.270 | 33.127 | 1.00 | 44.07 | MOLB C |
| ATOM | 2802 | ND1 | HIS | B 38 | 32.618 | 14.895 | 31.920 | 1.00 | 49.71 | MOLB N |
| ATOM | 2803 | CE1 | HIS | B 38 | 32.238 | 16.141 | 32.141 | 1.00 | 56.57 | MOLB C |
| ATOM | 2804 | NE2 | HIS | B 38 | 32.224 | 16.352 | 33.445 | 1.00 | 56.96 | MOLB N |
| ATOM | 2805 | CD2 | HIS | B 38 | 32.610 | 15.199 | 34.083 | 1.00 | 51.54 | MOLB C |
| ATOM | 2806 | C | HIS | B 38 | 32.905 | 10.474 | 32.994 | 1.00 | 38.30 | MOLB C |
| ATOM | 2807 | O | HIS | B 38 | 32.422 | 9.798 | 33.908 | 1.00 | 40.40 | MOLB O |
| ATOM | 2808 | N | SER | B 39 | 33.959 | 10.076 | 32.295 | 1.00 | 37.44 | MOLB N |
| ATOM | 2809 | CA | SER | B 39 | 34.665 | 8.860 | 32.635 | 1.00 | 37.23 | MOLB C |
| ATOM | 2810 | CB | SER | B 39 | 35.718 | 8.530 | 31.598 | 1.00 | 37.79 | MOLB C |
| ATOM | 2811 | OG | SER | B 39 | 36.670 | 7.655 | 32.173 | 1.00 | 35.18 | MOLB O |
| ATOM | 2812 | C | SER | B 39 | 35.388 | 9.091 | 33.921 | 1.00 | 37.59 | MOLB C |
| ATOM | 2813 | O | SER | B 39 | 36.132 | 10.060 | 34.040 | 1.00 | 41.37 | MOLB O |
| ATOM | 2814 | N | ILE | B 40 | 35.224 | 8.209 | 34.891 | 1.00 | 34.87 | MOLB N |
| ATOM | 2815 | CA | ILE | B 40 | 35.952 | 8.443 | 36.125 | 1.00 | 30.82 | MOLB C |
| ATOM | 2816 | CB | ILE | B 40 | 35.107 | 9.212 | 37.157 | 1.00 | 27.24 | MOLB C |
| ATOM | 2817 | CG1 | ILE | B 40 | 33.798 | 8.503 | 37.404 | 1.00 | 22.21 | MOLB C |
| ATOM | 2818 | CD1 | ILE | B 40 | 33.498 | 8.433 | 38.844 | 1.00 | 18.59 | MOLB C |
| ATOM | 2819 | CG2 | ILE | B 40 | 34.794 | 10.557 | 36.645 | 1.00 | 22.87 | MOLB C |
| ATOM | 2820 | C | ILE | B 40 | 36.521 | 7.176 | 36.716 | 1.00 | 31.51 | MOLB C |
| ATOM | 2821 | O | ILE | B 40 | 36.260 | 6.900 | 37.894 | 1.00 | 32.67 | MOLB O |
| ATOM | 2822 | N | VAL | B 41 | 37.308 | 6.454 | 35.891 | 1.00 | 27.58 | MOLB N |
| ATOM | 2823 | CA | VAL | B 41 | 37.929 | 5.162 | 36.178 | 1.00 | 24.89 | MOLB C |
| ATOM | 2824 | CB | VAL | B 41 | 36.970 | 3.964 | 35.931 | 1.00 | 22.25 | MOLB C |
| ATOM | 2825 | CG1 | VAL | B 41 | 37.635 | 2.623 | 36.291 | 1.00 | 21.12 | MOLB C |
| ATOM | 2826 | CG2 | VAL | B 41 | 35.701 | 4.098 | 36.683 | 1.00 | 23.43 | MOLB C |
| ATOM | 2827 | C | VAL | B 41 | 39.005 | 4.958 | 35.135 | 1.00 | 30.52 | MOLB C |
| ATOM | 2828 | O | VAL | B 41 | 38.718 | 4.892 | 33.952 | 1.00 | 30.07 | MOLB O |
| ATOM | 2829 | N | GLU | B 42 | 40.254 | 4.810 | 35.524 | 1.00 | 36.76 | MOLB N |
| ATOM | 2830 | CA | GLU | B 42 | 41.255 | 4.537 | 34.505 | 1.00 | 39.80 | MOLB C |
| ATOM | 2831 | CB | GLU | B 42 | 42.214 | 5.752 | 34.401 | 1.00 | 41.54 | MOLB C |
| ATOM | 2832 | CG | GLU | B 42 | 43.504 | 5.624 | 33.543 | 1.00 | 51.98 | MOLB C |
| ATOM | 2833 | CD | GLU | B 42 | 44.788 | 5.470 | 34.392 | 1.00 | 74.51 | MOLB C |
| ATOM | 2834 | OE1 | GLU | B 42 | 45.094 | 6.381 | 35.208 | 1.00 | 70.48 | MOLB O |
| ATOM | 2835 | OE2 | GLU | B 42 | 45.496 | 4.443 | 34.230 | 1.00 | 87.71 | MOLB O |
| ATOM | 2836 | C | GLU | B 42 | 41.852 | 3.139 | 34.820 | 1.00 | 41.19 | MOLB C |
| ATOM | 2837 | O | GLU | B 42 | 41.738 | 2.673 | 35.964 | 1.00 | 41.75 | MOLB O |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 2838 | N | CYS | B 43 | 42.396 | 2.426 | 33.827 | 1.00 | 41.79 | MOLB N |
| ATOM | 2839 | CA | CYS | B 43 | 42.785 | 1.023 | 34.080 | 1.00 | 43.13 | MOLB C |
| ATOM | 2840 | CB | CYS | B 43 | 41.778 | 0.053 | 33.477 | 1.00 | 42.51 | MOLB C |
| ATOM | 2841 | SG | CYS | B 43 | 40.388 | −0.291 | 34.546 | 1.00 | 53.97 | MOLB S |
| ATOM | 2842 | C | CYS | B 43 | 44.176 | 0.602 | 33.655 | 1.00 | 43.17 | MOLB C |
| ATOM | 2843 | O | CYS | B 43 | 44.395 | 0.162 | 32.539 | 1.00 | 42.87 | MOLB O |
| ATOM | 2844 | N | ASP | B 44 | 45.103 | 0.685 | 34.590 | 1.00 | 43.81 | MOLB N |
| ATOM | 2845 | CA | ASP | B 44 | 46.464 | 0.282 | 34.347 | 1.00 | 43.28 | MOLB C |
| ATOM | 2846 | CB | ASP | B 44 | 47.368 | 1.005 | 35.339 | 1.00 | 45.34 | MOLB C |
| ATOM | 2847 | CG | ASP | B 44 | 48.726 | 1.295 | 34.769 | 1.00 | 49.67 | MOLB C |
| ATOM | 2848 | OD1 | ASP | B 44 | 49.458 | 0.324 | 34.395 | 1.00 | 43.56 | MOLB O |
| ATOM | 2849 | OD2 | ASP | B 44 | 49.034 | 2.511 | 34.709 | 1.00 | 58.91 | MOLB O |
| ATOM | 2850 | C | ASP | B 44 | 46.657 | −1.226 | 34.501 | 1.00 | 40.55 | MOLB C |
| ATOM | 2851 | O | ASP | B 44 | 46.668 | −1.737 | 35.619 | 1.00 | 35.88 | MOLB O |
| ATOM | 2852 | N | PRO | B 45 | 46.783 | −1.946 | 33.377 | 1.00 | 40.99 | MOLB N |
| ATOM | 2853 | CA | PRO | B 45 | 47.091 | −3.361 | 33.423 | 1.00 | 42.69 | MOLB C |
| ATOM | 2854 | CB | PRO | B 45 | 46.494 | −3.895 | 32.115 | 1.00 | 41.37 | MOLB C |
| ATOM | 2855 | CG | PRO | B 45 | 45.858 | −2.721 | 31.437 | 1.00 | 39.08 | MOLB C |
| ATOM | 2856 | CD | PRO | B 45 | 46.552 | −1.526 | 31.997 | 1.00 | 40.95 | MOLB C |
| ATOM | 2857 | C | PRO | B 45 | 48.586 | −3.636 | 33.459 | 1.00 | 45.48 | MOLB C |
| ATOM | 2858 | O | PRO | B 45 | 48.980 | −4.789 | 33.491 | 1.00 | 46.72 | MOLB O |
| ATOM | 2859 | N | VAL | B 46 | 49.423 | −2.602 | 33.441 | 1.00 | 48.79 | MOLB N |
| ATOM | 2860 | CA | VAL | B 46 | 50.848 | −2.844 | 33.628 | 1.00 | 50.77 | MOLB C |
| ATOM | 2861 | CB | VAL | B 46 | 51.730 | −1.643 | 33.275 | 1.00 | 52.48 | MOLB C |
| ATOM | 2862 | CG1 | VAL | B 46 | 53.195 | −2.122 | 33.099 | 1.00 | 55.74 | MOLB C |
| ATOM | 2863 | CG2 | VAL | B 46 | 51.200 | −0.869 | 32.048 | 1.00 | 55.62 | MOLB C |
| ATOM | 2864 | C | VAL | B 46 | 51.043 | −3.009 | 35.112 | 1.00 | 49.88 | MOLB C |
| ATOM | 2865 | O | VAL | B 46 | 51.495 | −4.049 | 35.592 | 1.00 | 50.88 | MOLB O |
| ATOM | 2866 | N | ARG | B 47 | 50.709 | −1.931 | 35.820 | 1.004 | 7.46 | MOLB N |
| ATOM | 2867 | CA | ARG | B 47 | 50.840 | −1.841 | 37.256 | 1.00 | 45.24 | MOLB C |
| ATOM | 2868 | CB | ARG | B 47 | 51.188 | −0.399 | 37.665 | 1.00 | 44.70 | MOLB C |
| ATOM | 2869 | CG | ARG | B 47 | 50.179 | 0.657 | 37.220 | 1.00 | 47.75 | MOLB C |
| ATOM | 2870 | CD | ARG | B 47 | 50.651 | 2.117 | 37.426 | 1.00 | 50.43 | MOLB C |
| ATOM | 2871 | NE | ARG | B 47 | 50.831 | 2.499 | 38.834 | 1.00 | 50.16 | MOLB N |
| ATOM | 2872 | CZ | ARG | B 47 | 51.974 | 2.331 | 39.498 | 1.00 | 45.10 | MOLB C |
| ATOM | 2873 | NH1 | ARG | B 47 | 53.005 | 1.780 | 38.877 | 1.00 | 23.22 | MOLB N |
| ATOM | 2874 | NH2 | ARG | B 47 | 52.089 | 2.695 | 40.772 | 1.00 | 36.33 | MOLB N |
| ATOM | 2875 | C | ARG | B 47 | 49.543 | −2.299 | 37.880 | 1.00 | 42.95 | MOLB C |
| ATOM | 2876 | O | ARG | B 47 | 49.203 | −1.919 | 38.983 | 1.00 | 43.70 | MOLB 0 |
| ATOM | 2877 | N | LYS | B 48 | 48.806 | −3.104 | 37.137 | 1.00 | 42.37 | MOLB N |
| ATOM | 2878 | CA | LYS | B 48 | 47.572 | −3.741 | 37.611 | 1.00 | 43.58 | MOLB C |
| ATOM | 2879 | CB | LYS | B 48 | 47.903 | −5.145 | 38.174 | 1.00 | 42.11 | MOLB C |
| ATOM | 2880 | CG | LYS | B 48 | 48.776 | −5.976 | 37.194 | 1.00 | 47.76 | MOLB C |
| ATOM | 2881 | CD | LYS | B 48 | 48.829 | −7.486 | 37.459 | 1.00 | 49.64 | MOLB C |
| ATOM | 2882 | CE | LYS | B 48 | 49.426 | −7.836 | 38.815 | 1.00 | 64.15 | MOLB C |
| ATOM | 2883 | NZ | LYS | B 48 | 48.478 | −7.534 | 39.930 | 1.00 | 69.47 | MOLB N |
| ATOM | 2884 | C | LYS | B 48 | 46.700 | −2.922 | 38.581 | 1.00 | 40.68 | MOLB C |
| ATOM | 2885 | O | LYS | B 48 | 46.380 | −3.377 | 39.656 | 1.00 | 41.26 | MOLB O |
| ATOM | 2886 | N | GLU | B 49 | 46.290 | −1.724 | 38.188 | 1.00 | 40.42 | MOLB N |
| ATOM | 2887 | CA | GLU | B 49 | 45.467 | −0.901 | 39.067 | 1.00 | 39.71 | MOLB C |
| ATOM | 2888 | CB | GLU | B 49 | 46.265 | 0.257 | 39.660 | 1.00 | 39.12 | MOLB C |
| ATOM | 2889 | CG | GLU | B 49 | 47.694 | −0.046 | 40.074 | 1.00 | 46.55 | MOLB C |
| ATOM | 2890 | CD | GLU | B 49 | 48.536 | 1.218 | 40.318 | 1.00 | 42.69 | MOLB C |
| ATOM | 2891 | OE1 | GLU | B 49 | 49.522 | 1.135 | 41.078 | 1.00 | 49.15 | MOLB O |
| ATOM | 2892 | OE2 | GLU | B 49 | 48.211 | 2.287 | 39.764 | 1.00 | 42.57 | MOLB O |
| ATOM | 2893 | C | GLU | B 49 | 44.282 | −0.277 | 38.365 | 1.00 | 38.63 | MOLB C |
| ATOM | 2894 | O | GLU | B 49 | 44.308 | 0.045 | 37.176 | 1.00 | 36.79 | MOLB O |
| ATOM | 2895 | N | VAL | B 50 | 43.245 | −0.057 | 39.144 | 1.00 | 38.50 | MOLB N |
| ATOM | 2896 | CA | VAL | B 50 | 42.112 | 0.685 | 38.680 | 1.00 | 40.06 | MOLB C |
| ATOM | 2897 | CB | VAL | B 50 | 40.831 | −0.132 | 38.853 | 1.00 | 39.58 | MOLB C |
| ATOM | 2898 | CG1 | VAL | B 50 | 40.828 | −0.785 | 40.207 | 1.00 | 45.33 | MOLB C |
| ATOM | 2899 | CG2 | VAL | B 50 | 39.604 | 0.743 | 38.703 | 1.00 | 40.41 | MOLB C |
| ATOM | 2900 | C | VAL | B 50 | 42.099 | 1.844 | 39.627 | 1.00 | 39.46 | MOLB C |
| ATOM | 2901 | O | VAL | B 50 | 42.558 | 1.685 | 40.758 | 1.00 | 38.74 | MOLB O |
| ATOM | 2902 | N | SER | B 51 | 41.622 | 3.008 | 39.182 | 1.00 | 41.44 | MOLB N |
| ATOM | 2903 | CA | SER | B 51 | 41.466 | 4.183 | 40.098 | 1.00 | 44.61 | MOLB C |
| ATOM | 2904 | CB | SER | B 51 | 42.761 | 4.977 | 40.253 | 1.00 | 43.47 | MOLB C |
| ATOM | 2905 | OG | SER | B 51 | 42.986 | 5.789 | 39.121 | 1.00 | 50.34 | MOLB O |
| ATOM | 2906 | C | SER | B 51 | 40.343 | 5.130 | 39.690 | 1.00 | 43.14 | MOLB C |
| ATOM | 2907 | O | SER | B 51 | 40.150 | 5.410 | 38.509 | 1.00 | 43.99 | MOLB O |
| ATOM | 2908 | N | VAL | B 52 | 39.598 | 5.611 | 40.670 | 1.00 | 42.43 | MOLB N |
| ATOM | 2909 | CA | VAL | B 52 | 38.466 | 6.456 | 40.359 | 1.00 | 44.07 | MOLB C |
| ATOM | 2910 | CB | VAL | B 52 | 37.137 | 5.929 | 40.990 | 1.00 | 44.92 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 2911 | CG1 | VAL | B 52 | 37.272 | 4.450 | 41.468 | 1.00 | 45.35 | MOLB | C |
| ATOM | 2912 | CG2 | VAL | B 52 | 36.679 | 6.805 | 42.119 | 1.00 | 43.21 | MOLB | C |
| ATOM | 2913 | C | VAL | B 52 | 38.731 | 7.917 | 40.755 | 1.00 | 45.26 | MOLB | C |
| ATOM | 2914 | O | VAL | B 52 | 39.331 | 8.195 | 41.801 | 1.00 | 45.52 | MOLB | O |
| ATOM | 2915 | N | ARG | B 53 | 38.304 | 8.838 | 39.893 | 1.00 | 44.11 | MOLB | N |
| ATOM | 2916 | CA | ARG | B 53 | 38.396 | 10.271 | 40.150 | 1.00 | 44.32 | MOLB | C |
| ATOM | 2917 | CB | ARG | B 53 | 38.518 | 11.016 | 38.812 | 1.00 | 43.45 | MOLB | C |
| ATOM | 2918 | CG | ARG | B 53 | 38.447 | 12.551 | 38.901 | 1.00 | 53.47 | MOLB | C |
| ATOM | 2919 | CD | ARG | B 53 | 37.546 | 13.170 | 37.783 | 1.00 | 60.68 | MOLB | C |
| ATOM | 2920 | NE | ARG | B 53 | 38.034 | 13.105 | 36.379 | 1.00 | 70.66 | MOLB | N |
| ATOM | 2921 | CZ | ARG | B 53 | 39.043 | 12.372 | 35.879 | 1.00 | 52.89 | MOLB | C |
| ATOM | 2922 | NH1 | ARG | B 53 | 39.309 | 12.482 | 34.582 | 1.00 | 32.02 | MOLB | N |
| ATOM | 2923 | NH2 | ARG | B 53 | 39.778 | 11.547 | 36.638 | 1.00 | 28.77 | MOLB | N |
| ATOM | 2924 | C | ARG | B 53 | 37.174 | 10.749 | 40.979 | 1.00 | 42.68 | MOLB | C |
| ATOM | 2925 | O | ARG | B 53 | 36.048 | 10.361 | 40.729 | 1.00 | 38.54 | MOLB | O |
| ATOM | 2926 | N | THR | B 54 | 37.359 | 11.634 | 41.942 | 1.00 | 44.91 | MOLB | N |
| ATOM | 2927 | CA | THR | B 54 | 36.227 | 11.827 | 42.824 | 1.00 | 46.57 | MOLB | C |
| ATOM | 2928 | CB | THR | B 54 | 36.408 | 10.831 | 43.954 | 1.00 | 45.18 | MOLB | C |
| ATOM | 2929 | OG1 | THR | B 54 | 35.676 | 11.270 | 45.105 | 1.00 | 52.74 | MOLB | O |
| ATOM | 2930 | CG2 | THR | B 54 | 37.880 | 10.702 | 44.258 | 1.00 | 38.83 | MOLB | C |
| ATOM | 2931 | C | THR | B 54 | 35.744 | 13.220 | 43.356 | 1.00 | 47.50 | MOLB | C |
| ATOM | 2932 | O | THR | B 54 | 34.838 | 13.264 | 44.197 | 1.00 | 47.74 | MOLB | O |
| ATOM | 2933 | N | GLY | B 55 | 36.258 | 14.334 | 42.832 | 1.00 | 47.91 | MOLB | N |
| ATOM | 2934 | CA | GLY | B 55 | 35.955 | 15.675 | 43.400 | 1.00 | 47.46 | MOLB | C |
| ATOM | 2935 | C | GLY | B 55 | 34.776 | 16.475 | 42.853 | 1.00 | 48.56 | MOLB | C |
| ATOM | 2936 | O | GLY | B 55 | 34.626 | 17.682 | 43.128 | 1.00 | 47.26 | MOLB | O |
| ATOM | 2937 | N | SER | B 61 | 40.607 | 17.351 | 41.587 | 1.00 | 65.30 | MOLB | N |
| ATOM | 2938 | CA | SER | B 61 | 40.859 | 16.259 | 40.642 | 1.00 | 66.58 | MOLB | C |
| ATOM | 2939 | CB | SER | B 61 | 41.629 | 16.748 | 39.416 | 1.00 | 67.98 | MOLB | C |
| ATOM | 2940 | OG | SER | B 61 | 43.028 | 16.666 | 39.650 | 1.00 | 66.55 | MOLB | O |
| ATOM | 2941 | C | SER | B 61 | 41.646 | 15.131 | 41.302 | 1.00 | 65.61 | MOLB | C |
| ATOM | 2942 | O | SER | B 61 | 42.605 | 14.591 | 40.726 | 1.00 | 64.06 | MOLB | O |
| ATOM | 2943 | N | SER | B 62 | 41.220 | 14.783 | 42.509 | 1.00 | 63.42 | MOLB | N |
| ATOM | 2944 | CA | SER | B 62 | 41.811 | 13.706 | 43.270 | 1.00 | 63.00 | MOLB | C |
| ATOM | 2945 | CB | SER | B 62 | 41.324 | 13.839 | 44.705 | 1.00 | 63.98 | MOLB | C |
| ATOM | 2946 | OG | SER | B 62 | 40.964 | 15.189 | 44.958 | 1.00 | 63.89 | MOLB | O |
| ATOM | 2947 | C | SER | B 62 | 41.404 | 12.336 | 42.709 | 1.00 | 61.72 | MOLB | C |
| ATOM | 2948 | O | SER | B 62 | 40.553 | 12.259 | 41.821 | 1.00 | 60.65 | MOLB | O |
| ATOM | 2949 | N | ARG | B 63 | 42.015 | 11.272 | 43.239 | 1.00 | 60.30 | MOLB | N |
| ATOM | 2950 | CA | ARG | B 63 | 41.699 | 9.883 | 42.884 | 1.00 | 59.96 | MOLB | C |
| ATOM | 2951 | CB | ARG | B 63 | 42.624 | 9.348 | 41.773 | 1.00 | 59.24 | MOLB | C |
| ATOM | 2952 | CG | ARG | B 63 | 42.748 | 10.191 | 40.468 | 1.00 | 69.71 | MOLB | C |
| ATOM | 2953 | CD | ARG | B 63 | 41.708 | 9.830 | 39.366 | 1.00 | 88.13 | MOLB | C |
| ATOM | 2954 | NE | ARG | B 63 | 42.245 | 9.078 | 38.219 | 1.00 | 89.04 | MOLB | N |
| ATOM | 2955 | CZ | ARG | B 63 | 41.507 | 8.376 | 37.350 | 1.00 | 90.85 | MOLB | C |
| ATOM | 2956 | NH1 | ARG | B 63 | 40.185 | 8.282 | 37.484 | 1.00 | 90.46 | MOLB | N |
| ATOM | 2957 | NH2 | ARG | B 63 | 42.093 | 7.747 | 36.343 | 1.00 | 88.42 | MOLB | N |
| ATOM | 2958 | C | ARG | B 63 | 41.884 | 8.982 | 44.111 | 1.00 | 59.65 | MOLB | C |
| ATOM | 2959 | O | ARG | B 63 | 42.673 | 9.278 | 45.011 | 1.00 | 62.43 | MOLB | O |
| ATOM | 2960 | N | LYS | B 64 | 41.159 | 7.876 | 44.157 | 1.00 | 57.77 | MOLB | N |
| ATOM | 2961 | CA | LYS | B 64 | 41.438 | 6.842 | 45.142 | 1.00 | 55.50 | MOLB | C |
| ATOM | 2962 | CB | LYS | B 64 | 40.191 | 6.523 | 45.985 | 1.00 | 56.16 | MOLB | C |
| ATOM | 2963 | CG | LYS | B 64 | 40.473 | 6.113 | 47.451 | 1.00 | 58.15 | MOLB | C |
| ATOM | 2964 | CD | LYS | B 64 | 40.992 | 4.665 | 47.578 | 1.00 | 65.76 | MOLB | C |
| ATOM | 2965 | CE | LYS | B 64 | 41.559 | 4.338 | 48.966 | 1.00 | 57.99 | MOLB | C |
| ATOM | 2966 | NZ | LYS | B 64 | 43.035 | 4.559 | 49.017 | 1.00 | 70.80 | MOLB | N |
| ATOM | 2967 | C | LYS | B 64 | 41.898 | 5.647 | 44.301 | 1.00 | 53.22 | MOLB | C |
| ATOM | 2968 | O | LYS | B 64 | 41.261 | 5.309 | 43.310 | 1.00 | 54.33 | MOLB | O |
| ATOM | 2969 | N | THR | B 65 | 43.024 | 5.038 | 44.646 | 1.00 | 51.38 | MOLB | N |
| ATOM | 2970 | CA | THR | B 65 | 43.549 | 3.941 | 43.829 | 1.00 | 48.28 | MOLB | C |
| ATOM | 2971 | CB | THR | B 65 | 44.957 | 4.254 | 43.283 | 1.00 | 47.72 | MOLB | C |
| ATOM | 2972 | OG1 | THR | B 65 | 44.867 | 5.395 | 42.432 | 1.00 | 46.44 | MOLB | O |
| ATOM | 2973 | CG2 | THR | B 65 | 45.518 | 3.111 | 42.474 | 1.00 | 34.71 | MOLB | C |
| ATOM | 2974 | C | THR | B 65 | 43.543 | 2.628 | 44.565 | 1.00 | 48.20 | MOLB | C |
| ATOM | 2975 | O | THR | B 65 | 43.769 | 2.569 | 45.767 | 1.00 | 49.90 | MOLB | O |
| ATOM | 2976 | N | TYR | B 66 | 43.269 | 1.577 | 43.814 | 1.00 | 46.91 | MOLB | N |
| ATOM | 2977 | CA | TYR | B 66 | 43.248 | 0.226 | 44.330 | 1.00 | 46.29 | MOLB | C |
| ATOM | 2978 | CB | TYR | B 66 | 41.842 | −0.345 | 44.154 | 1.00 | 44.34 | MOLB | C |
| ATOM | 2979 | CG | TYR | B 66 | 40.827 | 0.384 | 44.973 | 1.00 | 41.75 | MOLB | C |
| ATOM | 2980 | CD1 | TYR | B 66 | 40.096 | 1.453 | 44.446 | 1.00 | 33.68 | MOLB | C |
| ATOM | 2981 | CE1 | TYR | B 66 | 39.167 | 2.116 | 45.209 | 1.00 | 21.51 | MOLB | C |
| ATOM | 2982 | CZ | TYR | B 66 | 38.990 | 1.715 | 46.526 | 1.00 | 32.53 | MOLB | C |
| ATOM | 2983 | OH | TYR | B 66 | 38.105 | 2.324 | 47.359 | 1.00 | 33.30 | MOLB | O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 2984 | CE2 | TYR | B 66 | 39.701 | 0.668 | 47.063 | 1.00 | 43.15 | MOLB C |
| ATOM | 2985 | CD2 | TYR | B 66 | 40.608 | 0.013 | 46.289 | 1.00 | 46.02 | MOLB C |
| ATOM | 2986 | C | TYR | B 66 | 44.221 | −0.633 | 43.545 | 1.00 | 46.63 | MOLB C |
| ATOM | 2987 | O | TYR | B 66 | 44.642 | −0.276 | 42.444 | 1.00 | 48.62 | MOLB O |
| ATOM | 2988 | N | THR | B 67 | 44.561 | −1.787 | 44.088 | 1.00 | 46.24 | MOLB N |
| ATOM | 2989 | CA | THR | B 67 | 45.347 | −2.737 | 43.316 | 1.00 | 44.87 | MOLB C |
| ATOM | 2990 | CB | THR | B 67 | 46.703 | −2.940 | 43.977 | 1.00 | 45.22 | MOLB C |
| ATOM | 2991 | OG1 | THR | B 67 | 47.221 | −1.656 | 44.341 | 1.00 | 51.06 | MOLB O |
| ATOM | 2992 | CG2 | THR | B 67 | 47.687 | −3.624 | 43.022 | 1.00 | 48.59 | MOLB C |
| ATOM | 2993 | C | THR | B 67 | 44.590 | −4.060 | 43.171 | 1.00 | 41.23 | MOLB C |
| ATOM | 2994 | O | THR | B 67 | 43.797 | −4.425 | 44.040 | 1.00 | 41.71 | MOLB O |
| ATOM | 2995 | N | PHE | B 68 | 44.798 | −4.767 | 42.070 | 1.00 | 37.22 | MOLB N |
| ATOM | 2996 | CA | PHE | B 68 | 44.165 | −6.078 | 41.920 | 1.00 | 34.71 | MOLB C |
| ATOM | 2997 | CB | PHE | B 68 | 42.751 | −5.962 | 41.321 | 1.00 | 32.75 | MOLB C |
| ATOM | 2998 | CG | PHE | B 68 | 41.815 | −5.233 | 42.210 | 1.00 | 26.70 | MOLB C |
| ATOM | 2999 | CD1 | PHE | B 68 | 41.567 | −3.888 | 42.023 | 1.00 | 34.16 | MOLB C |
| ATOM | 3000 | CE1 | PHE | B 68 | 40.738 | −3.178 | 42.907 | 1.00 | 28.22 | MOLB C |
| ATOM | 3001 | CZ | PHE | B 68 | 40.164 | −3.814 | 43.975 | 1.00 | 19.92 | MOLB C |
| ATOM | 3002 | CE2 | PHE | B 68 | 40.424 | −5.156 | 44.196 | 1.00 | 30.84 | MOLB C |
| ATOM | 3003 | CD2 | PHE | B 68 | 41.268 | −5.857 | 43.317 | 1.00 | 34.23 | MOLB C |
| ATOM | 3004 | C | PHE | B 68 | 45.047 | −7.072 | 41.176 | 1.00 | 34.37 | MOLB C |
| ATOM | 3005 | O | PHE | B 68 | 46.131 | −6.713 | 40.685 | 1.00 | 33.37 | MOLB O |
| ATOM | 3006 | N | ASP | B 69 | 44.593 | −8.320 | 41.124 | 1.00 | 32.58 | MOLB N |
| ATOM | 3007 | CA | ASP | B 69 | 45.378 | −9.352 | 40.505 | 1.00 | 33.59 | MOLB C |
| ATOM | 3008 | CB | ASP | B 69 | 44.776 | −10.723 | 40.794 | 1.00 | 33.43 | MOLB C |
| ATOM | 3009 | CG | ASP | B 69 | 44.966 | −11.138 | 42.251 | 1.00 | 37.59 | MOLB C |
| ATOM | 3010 | OD1 | ASP | B 69 | 46.126 | −11.118 | 42.726 | 1.00 | 39.95 | MOLB O |
| ATOM | 3011 | OD2 | ASP | B 69 | 43.968 | −11.465 | 42.924 | 1.00 | 32.36 | MOLB O |
| ATOM | 3012 | C | ASP | B 69 | 45.460 | −9.043 | 39.036 | 1.00 | 34.70 | MOLB C |
| ATOM | 3013 | O | ASP | B 69 | 46.498 | −9.223 | 38.429 | 1.00 | 34.35 | MOLB O |
| ATOM | 3014 | N | MET | B 70 | 44.357 | −8.536 | 38.491 | 1.00 | 38.63 | MOLB N |
| ATOM | 3015 | CA | MET | B 70 | 44.256 | −8.088 | 37.097 | 1.00 | 42.29 | MOLB C |
| ATOM | 3016 | CB | MET | B 70 | 43.829 | −9.215 | 36.173 | 1.00 | 41.08 | MOLB C |
| ATOM | 3017 | CG | MET | B 70 | 44.985 | −9.878 | 35.472 | 1.00 | 53.93 | MOLB C |
| ATOM | 3018 | SD | MET | B 70 | 44.621 | −11.521 | 34.807 | 1.00 | 56.46 | MOLB S |
| ATOM | 3019 | CE | MET | B 70 | 46.059 | −11.684 | 33.696 | 1.00 | 58.97 | MOLB C |
| ATOM | 3020 | C | MET | B 70 | 43.224 | −7.004 | 36.990 | 1.00 | 40.16 | MOLB C |
| ATOM | 3021 | O | MET | B 70 | 42.281 | −6.935 | 37.794 | 1.00 | 41.12 | MOLB O |
| ATOM | 3022 | N | VAL | B 71 | 43.394 | −6.165 | 35.980 | 1.00 | 36.98 | MOLB N |
| ATOM | 3023 | CA | VAL | B 71 | 42.475 | −5.092 | 35.755 | 1.00 | 34.68 | MOLB C |
| ATOM | 3024 | CB | VAL | B 71 | 43.106 | −3.781 | 36.090 | 1.00 | 34.67 | MOLB C |
| ATOM | 3025 | CG1 | VAL | B 71 | 42.025 | −2.696 | 36.061 | 1.00 | 44.30 | MOLB C |
| ATOM | 3026 | CG2 | VAL | B 71 | 43.802 | −3.834 | 37.429 | 1.00 | 30.24 | MOLB C |
| ATOM | 3027 | C | VAL | B 71 | 42.111 | −5.032 | 34.278 | 1.00 | 34.38 | MOLB C |
| ATOM | 3028 | O | VAL | B 71 | 43.065 | −4.792 | 33.488 | 1.00 | 35.41 | MOLB O |
| ATOM | 3029 | N | PHE | B 72 | 40.915 | −5.255 | 33.903 | 1.00 | 33.74 | MOLB N |
| ATOM | 3030 | CA | PHE | B 72 | 40.520 | −5.244 | 32.508 | 1.00 | 30.90 | MOLB C |
| ATOM | 3031 | CB | PHE | B 72 | 39.660 | −6.472 | 32.173 | 1.00 | 32.91 | MOLB C |
| ATOM | 3032 | CG | PHE | B 72 | 40.347 | −7.767 | 32.424 | 1.00 | 25.57 | MOLB C |
| ATOM | 3033 | CD1 | PHE | B 72 | 41.172 | −8.327 | 31.449 | 1.00 | 17.97 | MOLB C |
| ATOM | 3034 | CE1 | PHE | B 72 | 41.864 | −9.536 | 31.701 | 1.00 | 17.19 | MOLB C |
| ATOM | 3035 | CZ | PHE | B 72 | 41.693 | −10.197 | 32.940 | 1.00 | 21.92 | MOLB C |
| ATOM | 3036 | CE2 | PHE | B 72 | 40.852 | −9.641 | 33.911 | 1.00 | 15.60 | MOLB C |
| ATOM | 3037 | CD2 | PHE | B 72 | 40.194 | −8.420 | 33.645 | 1.00 | 17.87 | MOLB C |
| ATOM | 3038 | C | PHE | B 72 | 39.748 | −3.982 | 32.257 | 1.00 | 31.27 | MOLB C |
| ATOM | 3039 | O | PHE | B 72 | 38.810 | −3.663 | 32.996 | 1.00 | 33.66 | MOLB O |
| ATOM | 3040 | N | GLY | B 73 | 40.147 | −3.269 | 31.210 | 1.00 | 31.90 | MOLB N |
| ATOM | 3041 | CA | GLY | B 73 | 39.566 | −1.980 | 30.838 | 1.00 | 31.46 | MOLB C |
| ATOM | 3042 | C | GLY | B 73 | 38.395 | −2.198 | 29.912 | 1.00 | 31.27 | MOLB C |
| ATOM | 3043 | O | GLY | B 73 | 38.168 | −3.337 | 29.495 | 1.00 | 33.41 | MOLB O |
| ATOM | 3044 | N | ALA | B 74 | 37.681 | −1.116 | 29.584 | 1.00 | 27.93 | MOLB N |
| ATOM | 3045 | CA | ALA | B 74 | 36.433 | −1.158 | 28.820 | 1.00 | 29.81 | MOLB C |
| ATOM | 3046 | CB | ALA | B 74 | 35.736 | 0.215 | 28.834 | 1.00 | 31.26 | MOLB C |
| ATOM | 3047 | C | ALA | B 74 | 36.610 | −1.597 | 27.395 | 1.00 | 32.05 | MOLB C |
| ATOM | 3048 | O | ALA | B 74 | 35.636 | −1.693 | 26.647 | 1.00 | 35.23 | MOLB O |
| ATOM | 3049 | N | SER | B 75 | 37.845 | −1.819 | 26.991 | 1.00 | 32.15 | MOLB N |
| ATOM | 3050 | CA | SER | B 75 | 38.078 | −2.294 | 25.659 | 1.00 | 33.53 | MOLB C |
| ATOM | 3051 | CB | SER | B 75 | 39.281 | −1.582 | 25.051 | 1.00 | 35.37 | MOLB C |
| ATOM | 3052 | OG | SER | B 75 | 40.491 | −2.288 | 25.330 | 1.00 | 34.81 | MOLB O |
| ATOM | 3053 | C | SER | B 75 | 38.373 | −3.788 | 25.671 | 1.00 | 34.71 | MOLB C |
| ATOM | 3054 | O | SER | B 75 | 38.721 | −4.343 | 24.640 | 1.00 | 34.40 | MOLB O |
| ATOM | 3055 | N | THR | B 76 | 38.256 | −4.438 | 26.826 | 1.00 | 35.95 | MOLB N |
| ATOM | 3056 | CA | THR | B 76 | 38.724 | −5.821 | 26.967 | 1.00 | 37.09 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3057 | CB | THR | B 76 | 38.869 | −6.198 | 28.429 | 1.00 | 37.65 | MOLB C |
| ATOM | 3058 | OG1 | THR | B 76 | 40.187 | −5.849 | 28.879 | 1.00 | 51.20 | MOLB O |
| ATOM | 3059 | CG2 | THR | B 76 | 38.691 | −7.675 | 28.586 | 1.00 | 37.80 | MOLB C |
| ATOM | 3060 | C | THR | B 76 | 37.764 | −6.789 | 26.364 | 1.00 | 35.91 | MOLB C |
| ATOM | 3061 | O | THR | B 76 | 36.627 | −6.883 | 26.823 | 1.00 | 37.76 | MOLB O |
| ATOM | 3062 | N | LYS | B 77 | 38.201 | −7.522 | 25.349 | 1.00 | 35.09 | MOLB N |
| ATOM | 3063 | CA | LYS | B 77 | 37.269 | −8.420 | 24.650 | 1.00 | 34.50 | MOLB C |
| ATOM | 3064 | CB | LYS | B 77 | 37.648 | −8.539 | 23.182 | 1.00 | 33.99 | MOLB C |
| ATOM | 3065 | CG | LYS | B 77 | 37.241 | −7.299 | 22.433 | 1.00 | 39.05 | MOLB C |
| ATOM | 3066 | CD | LYS | B 77 | 35.672 | −7.120 | 22.478 | 1.00 | 64.56 | MOLB C |
| ATOM | 3067 | CE | LYS | B 77 | 35.176 | −5.666 | 22.799 | 1.00 | 47.59 | MOLB C |
| ATOM | 3068 | NZ | LYS | B 77 | 36.054 | −4.614 | 22.205 | 1.00 | 29.34 | MOLB N |
| ATOM | 3069 | C | LYS | B 77 | 37.158 | −9.784 | 25.329 | 1.00 | 33.18 | MOLB C |
| ATOM | 3070 | O | LYS | B 77 | 38.179 | −10.312 | 25.778 | 1.00 | 35.10 | MOLB O |
| ATOM | 3071 | N | GLN | B 78 | 35.922 | −10.308 | 25.431 | 1.00 | 29.23 | MOLB N |
| ATOM | 3072 | CA | GLN | B 78 | 35.576 | −11.598 | 26.108 | 1.00 | 24.35 | MOLB C |
| ATOM | 3073 | CB | GLN | B 78 | 34.276 | −12.208 | 25.553 | 1.00 | 24.38 | MOLB C |
| ATOM | 3074 | CG | GLN | B 78 | 33.056 | −11.329 | 25.420 | 1.00 | 14.79 | MOLB C |
| ATOM | 3075 | CD | GLN | B 78 | 32.148 | −11.346 | 26.644 | 1.00 | 24.95 | MOLB C |
| ATOM | 3076 | OE1 | GLN | B 78 | 32.593 | −11.167 | 27.783 | 1.00 | 24.27 | MOLB O |
| ATOM | 3077 | NE2 | GLN | B 78 | 30.854 | −11.539 | 26.405 | 1.00 | 18.34 | MOLB N |
| ATOM | 3078 | C | GLN | B 78 | 36.687 | −12.667 | 25.992 | 1.00 | 21.84 | MOLB C |
| ATOM | 3079 | O | GLN | B 78 | 37.240 | −13.109 | 26.974 | 1.00 | 16.95 | MOLB O |
| ATOM | 3080 | N | ILE | B 79 | 37.014 | −13.075 | 24.781 | 1.00 | 22.27 | MOLB N |
| ATOM | 3081 | CA | ILE | B 79 | 38.185 | −13.910 | 24.630 | 1.00 | 27.26 | MOLB C |
| ATOM | 3082 | CB | ILE | B 79 | 38.732 | −13.893 | 23.209 | 1.00 | 27.34 | MOLB C |
| ATOM | 3083 | CG1 | ILE | B 79 | 39.821 | −14.954 | 23.073 | 1.00 | 27.72 | MOLB C |
| ATOM | 3084 | CD1 | ILE | B 79 | 39.630 | −15.790 | 21.836 | 1.00 | 37.97 | MOLB C |
| ATOM | 3085 | CG2 | ILE | B 79 | 39.279 | −12.543 | 22.904 | 1.00 | 27.47 | MOLB C |
| ATOM | 3086 | C | ILE | B 79 | 39.320 | −13.558 | 25.609 | 1.00 | 28.85 | MOLB C |
| ATOM | 3087 | O | ILE | B 79 | 39.766 | −14.430 | 26.340 | 1.00 | 32.92 | MOLB O |
| ATOM | 3088 | N | ASP | B 80 | 39.787 | −12.311 | 25.630 | 1.00 | 29.46 | MOLB N |
| ATOM | 3089 | CA | ASP | B 80 | 40.871 | −11.906 | 26.540 | 1.00 | 30.66 | MOLB C |
| ATOM | 3090 | CB | ASP | B 80 | 41.038 | −10.381 | 26.565 | 1.00 | 31.37 | MOLB C |
| ATOM | 3091 | CG | ASP | B 80 | 41.502 | −9.846 | 25.274 | 1.00 | 32.98 | MOLB C |
| ATOM | 3092 | OD1 | ASP | B 80 | 41.079 | −8.730 | 24.902 | 1.00 | 42.96 | MOLB O |
| ATOM | 3093 | OD2 | ASP | B 80 | 42.257 | −10.585 | 24.615 | 1.00 | 35.17 | MOLB O |
| ATOM | 3094 | C | ASP | B 80 | 40.582 | −12.341 | 27.957 | 1.00 | 31.43 | MOLB C |
| ATOM | 3095 | O | ASP | B 80 | 41.477 | −12.762 | 28.681 | 1.00 | 35.97 | MOLB O |
| ATOM | 3096 | N | VAL | B 81 | 39.329 | −12.179 | 28.362 | 1.00 | 30.48 | MOLB N |
| ATOM | 3097 | CA | VAL | B 81 | 38.901 | −12.474 | 29.713 | 1.00 | 28.74 | MOLB C |
| ATOM | 3098 | CB | VAL | B 81 | 37.430 | −12.078 | 29.920 | 1.00 | 28.55 | MOLB C |
| ATOM | 3099 | CG1 | VAL | B 81 | 36.852 | −12.803 | 31.114 | 1.00 | 30.84 | MOLB C |
| ATOM | 3100 | CG2 | VAL | B 81 | 37.296 | −10.592 | 30.074 | 1.00 | 15.66 | MOLB C |
| ATOM | 3101 | C | VAL | B 81 | 39.028 | −13.958 | 29.954 | 1.00 | 28.81 | MOLB C |
| ATOM | 3102 | O | VAL | B 81 | 39.672 | −14.368 | 30.906 | 1.00 | 29.75 | MOLB O |
| ATOM | 3103 | N | TYR | B 82 | 38.403 | −14.749 | 29.086 | 1.00 | 28.23 | MOLB N |
| ATOM | 3104 | CA | TYR | B 82 | 38.470 | −16.187 | 29.184 | 1.00 | 29.02 | MOLB C |
| ATOM | 3105 | CB | TYR | B 82 | 37.924 | −16.834 | 27.944 | 1.00 | 29.82 | MOLB C |
| ATOM | 3106 | CG | TYR | B 82 | 37.981 | −18.316 | 28.064 | 1.00 | 31.25 | MOLB C |
| ATOM | 3107 | CD1 | TYR | B 82 | 39.108 | −19.037 | 27.643 | 1.00 | 35.38 | MOLB C |
| ATOM | 3108 | CE1 | TYR | B 82 | 39.153 | −20.453 | 27.757 | 1.00 | 35.07 | MOLB C |
| ATOM | 3109 | CZ | TYR | B 82 | 38.058 | −21.119 | 28.319 | 1.00 | 40.31 | MOLB C |
| ATOM | 3110 | OH | TYR | B 82 | 38.041 | −22.484 | 28.464 | 1.00 | 41.48 | MOLB O |
| ATOM | 3111 | CE2 | TYR | B 82 | 36.950 | −20.401 | 28.762 | 1.00 | 47.96 | MOLB C |
| ATOM | 3112 | CD2 | TYR | B 82 | 36.922 | −19.011 | 28.631 | 1.00 | 37.76 | MOLB C |
| ATOM | 3113 | C | TYR | B 82 | 39.900 | −16.636 | 29.332 | 1.00 | 28.66 | MOLB C |
| ATOM | 3114 | O | TYR | B 82 | 40.244 | −17.301 | 30.303 | 1.00 | 27.71 | MOLB O |
| ATOM | 3115 | N | ARG | B 83 | 40.731 | −16.259 | 28.364 | 1.00 | 27.60 | MOLB N |
| ATOM | 3116 | CA | ARG | B 83 | 42.158 | −16.541 | 28.412 | 1.00 | 27.29 | MOLB C |
| ATOM | 3117 | CB | ARG | B 83 | 42.902 | −15.677 | 27.417 | 1.00 | 26.39 | MOLB C |
| ATOM | 3118 | CG | ARG | B 83 | 42.681 | −16.053 | 25.954 | 1.00 | 35.92 | MOLB C |
| ATOM | 3119 | CD | ARG | B 83 | 43.692 | −15.324 | 25.058 | 1.00 | 62.57 | MOLB C |
| ATOM | 3120 | NE | ARG | B 83 | 43.412 | −15.486 | 23.626 | 1.00 | 79.08 | MOLB N |
| ATOM | 3121 | CZ | ARG | B 83 | 43.927 | −14.710 | 22.670 | 1.00 | 78.53 | MOLB C |
| ATOM | 3122 | NH1 | ARG | B 83 | 43.620 | −14.921 | 21.397 | 1.00 | 76.20 | MOLB N |
| ATOM | 3123 | NH2 | ARG | B 83 | 44.741 | −13.710 | 22.983 | 1.00 | 75.71 | MOLB N |
| ATOM | 3124 | C | ARG | B 83 | 42.799 | −16.341 | 29.779 | 1.00 | 28.32 | MOLB C |
| ATOM | 3125 | O | ARG | B 83 | 43.506 | −17.223 | 30.269 | 1.00 | 29.49 | MOLB O |
| ATOM | 3126 | N | SER | B 84 | 42.569 | −15.195 | 30.398 | 1.00 | 28.96 | MOLB N |
| ATOM | 3127 | CA | SER | B 84 | 43.327 | −14.830 | 31.607 | 1.00 | 34.07 | MOLB C |
| ATOM | 3128 | CB | SER | B 84 | 43.377 | −13.308 | 31.758 | 1.00 | 33.43 | MOLB C |
| ATOM | 3129 | OG | SER | B 84 | 44.071 | −12.712 | 30.670 | 1.00 | 44.90 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 3130 | C | SER | B 84 | 42.784 | −15.414 | 32.908 | 1.00 | 36.22 | MOLB | C |
| ATOM | 3131 | O | SER | B 84 | 43.528 | −15.939 | 33.746 | 1.00 | 38.28 | MOLB | O |
| ATOM | 3132 | N | VAL | B 85 | 41.475 | −15.296 | 33.073 | 1.00 | 34.24 | MOLB | N |
| ATOM | 3133 | CA | VAL | B 85 | 40.802 | −15.738 | 34.259 | 1.00 | 29.34 | MOLB | C |
| ATOM | 3134 | CB | VAL | B 85 | 39.550 | −14.940 | 34.347 | 1.00 | 27.33 | MOLB | C |
| ATOM | 3135 | CG1 | VAL | B 85 | 38.759 | −15.257 | 35.590 | 1.00 | 21.44 | MOLB | C |
| ATOM | 3136 | CG2 | VAL | B 85 | 39.963 | −13.508 | 34.317 | 1.00 | 27.06 | MOLB | C |
| ATOM | 3137 | C | VAL | B 85 | 40.526 | −17.245 | 34.219 | 1.00 | 30.19 | MOLB | C |
| ATOM | 3138 | O | VAL | B 85 | 40.806 | −17.966 | 35.181 | 1.00 | 28.88 | MOLB | O |
| ATOM | 3139 | N | VAL | B 86 | 40.035 | −17.738 | 33.098 | 1.00 | 29.88 | MOLB | N |
| ATOM | 3140 | CA | VAL | B 86 | 39.609 | −19.142 | 33.044 | 1.00 | 32.18 | MOLB | C |
| ATOM | 3141 | CB | VAL | B 86 | 38.365 | −19.291 | 32.163 | 1.00 | 30.02 | MOLB | C |
| ATOM | 3142 | CG1 | VAL | B 86 | 37.737 | −20.614 | 32.408 | 1.00 | 27.64 | MOLB | C |
| ATOM | 3143 | CG2 | VAL | B 86 | 37.412 | −18.169 | 32.480 | 1.00 | 29.82 | MOLB | C |
| ATOM | 3144 | C | VAL | B 86 | 40.710 | −20.184 | 32.650 | 1.00 | 34.07 | MOLB | C |
| ATOM | 3145 | O | VAL | B 86 | 40.972 | −21.138 | 33.402 | 1.00 | 36.00 | MOLB | O |
| ATOM | 3146 | N | CYS | B 87 | 41.365 | −20.039 | 31.509 | 1.00 | 31.78 | MOLB | N |
| ATOM | 3147 | CA | CYS | B 87 | 42.391 | −21.029 | 31.215 | 1.00 | 33.74 | MOLB | C |
| ATOM | 3148 | CB | CYS | B 87 | 43.384 | −20.501 | 30.241 | 1.00 | 32.01 | MOLB | C |
| ATOM | 3149 | SG | CYS | B 87 | 42.495 | −20.517 | 28.779 | 1.00 | 40.51 | MOLB | S |
| ATOM | 3150 | C | CYS | B 87 | 43.092 | −21.613 | 32.426 | 1.00 | 32.24 | MOLB | C |
| ATOM | 3151 | O | CYS | B 87 | 43.054 | −22.817 | 32.624 | 1.00 | 31.73 | MOLB | O |
| ATOM | 3152 | N | PRO | B 88 | 43.705 | −20.766 | 33.252 | 1.00 | 30.99 | MOLB | N |
| ATOM | 3153 | CA | PRO | B 88 | 44.345 | −21.296 | 34.438 | 1.00 | 32.18 | MOLB | C |
| ATOM | 3154 | CB | PRO | B 88 | 44.662 | −20.036 | 35.232 | 1.00 | 30.09 | MOLB | C |
| ATOM | 3155 | CG | PRO | B 88 | 44.897 | −19.055 | 34.208 | 1.00 | 28.11 | MOLB | C |
| ATOM | 3156 | CD | PRO | B 88 | 43.844 | −19.308 | 33.183 | 1.00 | 30.04 | MOLB | C |
| ATOM | 3157 | C | PRO | B 88 | 43.443 | −22.221 | 35.264 | 1.00 | 33.26 | MOLB | C |
| ATOM | 3158 | O | PRO | B 88 | 43.886 | −23.310 | 35.707 | 1.00 | 34.79 | MOLB | O |
| ATOM | 3159 | N | ILE | B 89 | 42.197 | −21.786 | 35.448 | 1.00 | 31.64 | MOLB | N |
| ATOM | 3160 | CA | ILE | B 89 | 41.217 | −22.491 | 36.268 | 1.00 | 30.76 | MOLB | C |
| ATOM | 3161 | CB | ILE | B 89 | 40.104 | −21.538 | 36.707 | 1.00 | 30.20 | MOLB | C |
| ATOM | 3162 | CG1 | ILE | B 89 | 40.603 | −20.696 | 37.885 | 1.00 | 28.89 | MOLB | C |
| ATOM | 3163 | CD1 | ILE | B 89 | 40.182 | −19.237 | 37.845 | 1.00 | 31.02 | MOLB | C |
| ATOM | 3164 | CG2 | ILE | B 89 | 38.835 | −22.303 | 37.073 | 1.00 | 32.13 | MOLB | C |
| ATOM | 3165 | C | ILE | B 89 | 40.622 | −23.713 | 35.601 | 1.00 | 32.52 | MOLB | C |
| ATOM | 3166 | O | ILE | B 89 | 40.270 | −24.661 | 36.283 | 1.00 | 33.63 | MOLB | O |
| ATOM | 3167 | N | LEU | B 90 | 40.503 | −23.715 | 34.277 | 1.00 | 34.32 | MOLB | N |
| ATOM | 3168 | CA | LEU | B 90 | 39.959 | −24.900 | 33.628 | 1.00 | 34.99 | MOLB | C |
| ATOM | 3169 | CB | LEU | B 90 | 39.620 | −24.657 | 32.160 | 1.00 | 34.87 | MOLB | C |
| ATOM | 3170 | CG | LEU | B 90 | 38.899 | −25.787 | 31.422 | 1.00 | 34.70 | MOLB | C |
| ATOM | 3171 | CD1 | LEU | B 90 | 37.924 | −26.516 | 32.343 | 1.00 | 32.96 | MOLB | C |
| ATOM | 3172 | CD2 | LEU | B 90 | 38.194 | −25.275 | 30.153 | 1.00 | 28.41 | MOLB | C |
| ATOM | 3173 | C | LEU | B 90 | 41.005 | −25.977 | 33.814 | 1.00 | 38.29 | MOLB | C |
| ATOM | 3174 | O | LEU | B 90 | 40.667 | −27.077 | 34.225 | 1.00 | 40.46 | MOLB | O |
| ATOM | 3175 | N | ASP | B 91 | 42.272 | −25.629 | 33.553 | 1.00 | 40.44 | MOLB | N |
| ATOM | 3176 | CA | ASP | B 91 | 43.427 | −26.473 | 33.838 | 1.00 | 41.58 | MOLB | C |
| ATOM | 3177 | CB | ASP | B 91 | 44.704 | −25.622 | 34.007 | 1.00 | 42.28 | MOLB | C |
| ATOM | 3178 | CG | ASP | B 91 | 45.333 | −25.161 | 32.682 | 1.00 | 46.33 | MOLB | C |
| ATOM | 3179 | OD1 | ASP | B 91 | 44.865 | −25.579 | 31.594 | 1.00 | 42.95 | MOLB | O |
| ATOM | 3180 | OD2 | ASP | B 91 | 46.310 | −24.354 | 32.749 | 1.00 | 49.75 | MOLB | O |
| ATOM | 3181 | C | ASP | B 91 | 43.198 | −27.236 | 35.152 | 1.00 | 43.48 | MOLB | C |
| ATOM | 3182 | O | ASP | B 91 | 43.149 | −28.478 | 35.174 | 1.00 | 45.27 | MOLB | O |
| ATOM | 3183 | N | GLU | B 92 | 43.041 | −26.500 | 36.251 | 1.00 | 41.83 | MOLB | N |
| ATOM | 3184 | CA | GLU | B 92 | 42.934 | −27.152 | 37.554 | 1.00 | 43.41 | MOLB | C |
| ATOM | 3185 | CB | GLU | B 92 | 43.013 | −26.119 | 38.693 | 1.00 | 43.93 | MOLB | C |
| ATOM | 3186 | CG | GLU | B 92 | 44.428 | −25.612 | 39.004 | 1.00 | 53.61 | MOLB | C |
| ATOM | 3187 | CD | GLU | B 92 | 45.113 | −26.387 | 40.135 | 1.00 | 79.69 | MOLB | C |
| ATOM | 3188 | OE1 | GLU | B 92 | 46.240 | −26.889 | 39.915 | 1.00 | 82.77 | MOLB | O |
| ATOM | 3189 | OE2 | GLU | B 92 | 44.523 | −26.493 | 41.243 | 1.00 | 85.92 | MOLB | O |
| ATOM | 3190 | C | GLU | B 92 | 41.692 | −28.032 | 37.709 | 1.00 | 41.60 | MOLB | C |
| ATOM | 3191 | O | GLU | B 92 | 41.664 | −28.923 | 38.553 | 1.00 | 42.69 | MOLB | O |
| ATOM | 3192 | N | VAL | B 93 | 40.670 | −27.791 | 36.904 | 1.00 | 39.85 | MOLB | N |
| ATOM | 3193 | CA | VAL | B 93 | 39.453 | −28.555 | 37.035 | 1.00 | 42.07 | MOLB | C |
| ATOM | 3194 | CB | VAL | B 93 | 38.251 | −27.806 | 36.439 | 1.00 | 41.88 | MOLB | C |
| ATOM | 3195 | CG1 | VAL | B 93 | 37.090 | −28.755 | 36.163 | 1.00 | 45.95 | MOLB | C |
| ATOM | 3196 | CG2 | VAL | B 93 | 37.810 | −26.680 | 37.366 | 1.00 | 43.27 | MOLB | C |
| ATOM | 3197 | C | VAL | B 93 | 39.651 | −29.873 | 36.324 | 1.00 | 44.48 | MOLB | C |
| ATOM | 3198 | O | VAL | B 93 | 38.920 | −30.828 | 36.546 | 1.00 | 45.15 | MOLB | O |
| ATOM | 3199 | N | ILE | B 94 | 40.668 | −29.922 | 35.476 | 1.00 | 45.58 | MOLB | N |
| ATOM | 3200 | CA | ILE | B 94 | 40.886 | −31.077 | 34.627 | 1.00 | 45.02 | MOLB | C |
| ATOM | 3201 | CB | ILE | B 94 | 41.385 | −30.620 | 33.200 | 1.00 | 45.46 | MOLB | C |
| ATOM | 3202 | CG1 | ILE | B 94 | 40.220 | −29.937 | 32.482 | 1.00 | 40.73 | MOLB | C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 3203 | CD1 | ILE | B 94 | 40.533 | −29.287 | 31.178 | 1.00 | 24.95 | MOLB C |
| ATOM | 3204 | CG2 | ILE | B 94 | 41.877 | −31.785 | 32.321 | 1.00 | 41.37 | MOLB C |
| ATOM | 3205 | C | ILE | B 94 | 41.780 | −32.069 | 35.360 | 1.00 | 46.81 | MOLB C |
| ATOM | 3206 | O | ILE | B 94 | 41.694 | −33.284 | 35.148 | 1.00 | 46.50 | MOLB O |
| ATOM | 3207 | N | MET | B 95 | 42.602 | −31.552 | 36.267 | 1.00 | 47.65 | MOLB N |
| ATOM | 3208 | CA | MET | B 95 | 43.458 | −32.416 | 37.046 | 1.00 | 49.23 | MOLB C |
| ATOM | 3209 | CB | MET | B 95 | 44.683 | −31.691 | 37.487 | 1.00 | 47.24 | MOLB C |
| ATOM | 3210 | CG | MET | B 95 | 45.443 | −31.147 | 36.332 | 1.00 | 52.45 | MOLB C |
| ATOM | 3211 | SD | MET | B 95 | 46.500 | −29.931 | 37.064 | 1.00 | 67.20 | MOLB S |
| ATOM | 3212 | CE | MET | B 95 | 46.459 | −28.663 | 35.789 | 1.00 | 79.53 | MOLB C |
| ATOM | 3213 | C | MET | B 95 | 42.736 | −32.917 | 38.249 | 1.00 | 48.29 | MOLB C |
| ATOM | 3214 | O | MET | B 95 | 43.379 | −33.459 | 39.152 | 1.00 | 47.89 | MOLB O |
| ATOM | 3215 | N | GLY | B 96 | 41.405 | −32.728 | 38.256 | 1.00 | 49.27 | MOLB N |
| ATOM | 3216 | CA | GLY | B 96 | 40.503 | −33.307 | 39.277 | 1.00 | 47.34 | MOLB C |
| ATOM | 3217 | C | GLY | B 96 | 39.894 | −32.385 | 40.331 | 1.00 | 46.62 | MOLB C |
| ATOM | 3218 | O | GLY | B 96 | 38.877 | −32.726 | 40.948 | 1.00 | 45.34 | MOLB O |
| ATOM | 3219 | N | TYR | B 97 | 40.500 | −31.218 | 40.536 | 1.00 | 45.63 | MOLB N |
| ATOM | 3220 | CA | TYR | B 97 | 40.026 | −30.266 | 41.552 | 1.00 | 46.47 | MOLB C |
| ATOM | 3221 | CB | TYR | B 97 | 41.058 | −29.150 | 41.759 | 1.00 | 48.03 | MOLB C |
| ATOM | 3222 | CG | TYR | B 97 | 42.432 | −29.715 | 42.070 | 1.00 | 53.57 | MOLB C |
| ATOM | 3223 | CD1 | TYR | B 97 | 42.651 | −30.447 | 43.238 | 1.00 | 42.64 | MOLB C |
| ATOM | 3224 | CE1 | TYR | B 97 | 43.886 | −30.983 | 43.527 | 1.00 | 44.08 | MOLB C |
| ATOM | 3225 | CZ | TYR | B 97 | 44.928 | −30.814 | 42.652 | 1.00 | 51.93 | MOLB C |
| ATOM | 3226 | OH | TYR | B 97 | 46.131 | −31.373 | 42.962 | 1.00 | 58.59 | MOLB O |
| ATOM | 3227 | CE2 | TYR | B 97 | 44.762 | −30.097 | 41.476 | 1.00 | 63.26 | MOLB C |
| ATOM | 3228 | CD2 | TYR | B 97 | 43.501 | −29.552 | 41.185 | 1.00 | 61.24 | MOLB C |
| ATOM | 3229 | C | TYR | B 97 | 38.629 | −29.685 | 41.322 | 1.00 | 44.62 | MOLB C |
| ATOM | 3230 | O | TYR | B 97 | 37.908 | −30.048 | 40.404 | 1.00 | 43.14 | MOLB O |
| ATOM | 3231 | N | ASN | B 98 | 38.236 | −28.787 | 42.196 | 1.00 | 45.53 | MOLB N |
| ATOM | 3232 | CA | ASN | B 98 | 36.904 | −28.240 | 42.106 | 1.00 | 47.08 | MOLB C |
| ATOM | 3233 | CB | ASN | B 98 | 35.999 | −28.981 | 43.080 | 1.00 | 47.31 | MOLB C |
| ATOM | 3234 | CG | ASN | B 98 | 34.543 | −28.738 | 42.803 | 1.00 | 57.33 | MOLB C |
| ATOM | 3235 | OD1 | ASN | B 98 | 33.853 | −9.638 | 42.313 | 1.00 | 72.08 | MOLB O |
| ATOM | 3236 | ND2 | ASN | B 98 | 34.063 | −27.513 | 43.076 | 1.00 | 50.02 | MOLB N |
| ATOM | 3237 | C | ASN | B 98 | 36.968 | −26.763 | 42.436 | 1.00 | 44.63 | MOLB C |
| ATOM | 3238 | O | ASN | B 98 | 37.347 | −26.434 | 43.559 | 1.00 | 44.14 | MOLB O |
| ATOM | 3239 | N | CYS | B 99 | 36.627 | −25.897 | 41.465 | 1.00 | 43.79 | MOLB N |
| ATOM | 3240 | CA | CYS | B 99 | 36.832 | −24.449 | 41.581 | 1.00 | 43.53 | MOLB C |
| ATOM | 3241 | CB | CYS | B 99 | 37.982 | −23.988 | 40.695 | 1.00 | 45.27 | MOLB C |
| ATOM | 3242 | SG | CYS | B 99 | 39.440 | −25.039 | 40.600 | 1.00 | 52.30 | MOLB S |
| ATOM | 3243 | C | CYS | B 99 | 35.657 | −23.633 | 41.148 | 1.00 | 42.61 | MOLB C |
| ATOM | 3244 | O | CYS | B 99 | 34.913 | −24.016 | 40.265 | 1.00 | 43.81 | MOLB O |
| ATOM | 3245 | N | THR | B 100 | 35.571 | −22.437 | 41.706 | 1.00 | 42.55 | MOLB N |
| ATOM | 3246 | CA | THR | B 100 | 34.463 | −21.537 | 41.455 | 1.00 | 41.70 | MOLB C |
| ATOM | 3247 | CB | THR | B 100 | 33.810 | −21.167 | 42.785 | 1.00 | 42.85 | MOLB C |
| ATOM | 3248 | OG1 | THR | B 100 | 33.842 | −22.290 | 43.681 | 1.00 | 49.02 | MOLB O |
| ATOM | 3249 | CG2 | THR | B 100 | 32.383 | −20.683 | 42.578 | 1.00 | 43.34 | MOLB C |
| ATOM | 3250 | C | THR | B 100 | 34.930 | −20.213 | 40.889 | 1.00 | 40.07 | MOLB C |
| ATOM | 3251 | O | THR | B 100 | 35.985 | −19.711 | 41.263 | 1.00 | 40.56 | MOLB O |
| ATOM | 3252 | N | ILE | B 101 | 34.111 | −19.621 | 40.028 | 1.00 | 38.63 | MOLB N |
| ATOM | 3253 | CA | ILE | B 101 | 34.374 | −18.280 | 39.495 | 1.00 | 36.87 | MOLB C |
| ATOM | 3254 | CB | ILE | B 101 | 34.557 | −18.347 | 37.980 | 1.00 | 36.83 | MOLB C |
| ATOM | 3255 | CG1 | ILE | B 101 | 35.846 | −19.073 | 37.628 | 1.00 | 37.69 | MOLB C |
| ATOM | 3256 | CD1 | ILE | B 101 | 36.105 | −19.058 | 36.160 | 1.00 | 23.60 | MOLB C |
| ATOM | 3257 | CG2 | ILE | B 101 | 34.588 | −16.970 | 37.384 | 1.00 | 27.00 | MOLB C |
| ATOM | 3258 | C | ILE | B 101 | 33.216 | −17.286 | 39.781 | 1.00 | 37.32 | MOLB C |
| ATOM | 3259 | O | ILE | B 101 | 32.039 | −17.566 | 39.432 | 1.00 | 40.34 | MOLB O |
| ATOM | 3260 | N | PHE | B 102 | 33.531 | −16.128 | 40.363 | 1.00 | 30.80 | MOLB N |
| ATOM | 3261 | CA | PHE | B 102 | 32.482 | −15.158 | 40.683 | 1.00 | 33.70 | MOLB C |
| ATOM | 3262 | CB | PHE | B 102 | 32.636 | −14.714 | 42.132 | 1.00 | 36.42 | MOLB C |
| ATOM | 3263 | CG | PHE | B 102 | 32.431 | −15.810 | 43.139 | 1.00 | 38.64 | MOLB C |
| ATOM | 3264 | CD1 | PHE | B 102 | 31.169 | −16.358 | 43.338 | 1.00 | 50.44 | MOLB C |
| ATOM | 3265 | CE1 | PHE | B 102 | 30.978 | −17.360 | 44.280 | 1.00 | 48.67 | MOLB C |
| ATOM | 3266 | CZ | PHE | B 102 | 32.045 | −17.802 | 45.043 | 1.00 | 41.77 | MOLB C |
| ATOM | 3267 | CE2 | PHE | B 102 | 33.312 | −17.250 | 44.858 | 1.00 | 37.14 | MOLB C |
| ATOM | 3268 | CD2 | PHE | B 102 | 33.491 | −16.253 | 43.926 | 1.00 | 28.39 | MOLB C |
| ATOM | 3269 | C | PHE | B 102 | 32.307 | −13.881 | 39.814 | 1.00 | 32.27 | MOLB C |
| ATOM | 3270 | O | PHE | B 102 | 33.273 | −13.254 | 39.400 | 1.00 | 32.35 | MOLB O |
| ATOM | 3271 | N | ALA | B 103 | 31.061 | −13.494 | 39.558 | 1.00 | 32.54 | MOLB N |
| ATOM | 3272 | CA | ALA | B 103 | 30.785 | −12.175 | 38.966 | 1.00 | 35.29 | MOLB C |
| ATOM | 3273 | CB | ALA | B 103 | 29.874 | −12.254 | 37.742 | 1.00 | 34.09 | MOLB C |
| ATOM | 3274 | C | ALA | B 103 | 30.113 | −11.359 | 40.029 | 1.00 | 36.02 | MOLB C |
| ATOM | 3275 | O | ALA | B 103 | 29.022 | −11.706 | 40.469 | 1.00 | 37.15 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3276 | N | TYR | B 104 | 30.740 | −10.270 | 40.448 | 1.00 | 36.99 | MOLB N |
| ATOM | 3277 | CA | TYR | B 104 | 30.153 | −9.488 | 41.524 | 1.00 | 36.91 | MOLB C |
| ATOM | 3278 | CB | TYR | B 104 | 30.964 | −9.650 | 42.827 | 1.00 | 35.96 | MOLB C |
| ATOM | 3279 | CG | TYR | B 104 | 30.508 | −8.691 | 43.932 | 1.00 | 41.69 | MOLB C |
| ATOM | 3280 | CD1 | TYR | B 104 | 30.974 | −7.377 | 43.975 | 1.00 | 39.41 | MOLB C |
| ATOM | 3281 | CE1 | TYR | B 104 | 30.571 | −6.507 | 44.962 | 1.00 | 43.83 | MOLB C |
| ATOM | 3282 | CZ | TYR | B 104 | 29.678 | −6.927 | 45.919 | 1.00 | 46.95 | MOLB C |
| ATOM | 3283 | OH | TYR | B 104 | 29.281 | −6.045 | 46.914 | 1.00 | 41.45 | MOLB O |
| ATOM | 3284 | CE2 | TYR | B 104 | 29.195 | −8.224 | 45.891 | 1.00 | 43.12 | MOLB C |
| ATOM | 3285 | CD2 | TYR | B 104 | 29.598 | −9.088 | 44.906 | 1.00 | 33.59 | MOLB C |
| ATOM | 3286 | C | TYR | B 104 | 30.042 | −8.022 | 41.163 | 1.00 | 35.76 | MOLB C |
| ATOM | 3287 | O | TYR | B 104 | 31.003 | −7.431 | 40.661 | 1.00 | 35.64 | MOLB O |
| ATOM | 3288 | N | GLY | B 105 | 28.883 | −7.431 | 41.438 | 1.00 | 34.41 | MOLB N |
| ATOM | 3289 | CA | GLY | B 105 | 28.757 | −5.989 | 41.271 | 1.00 | 32.19 | MOLB C |
| ATOM | 3290 | C | GLY | B 105 | 27.400 | −5.415 | 40.923 | 1.00 | 33.34 | MOLB C |
| ATOM | 3291 | O | GLY | B 105 | 26.416 | −6.127 | 40.746 | 1.00 | 32.90 | MOLB O |
| ATOM | 3292 | N | GLN | B 106 | 27.372 | −4.089 | 40.819 | 1.00 | 36.55 | MOLB N |
| ATOM | 3293 | CA | GLN | B 106 | 26.160 | −3.317 | 40.497 | 1.00 | 36.25 | MOLB C |
| ATOM | 3294 | CB | GLN | B 106 | 26.538 | −1.880 | 40.229 | 1.00 | 34.19 | MOLB C |
| ATOM | 3295 | CG | GLN | B 106 | 25.403 | −1.055 | 39.731 | 1.00 | 40.44 | MOLB C |
| ATOM | 3296 | CD | GLN | B 106 | 25.867 | 0.306 | 39.279 | 1.00 | 53.67 | MOLB C |
| ATOM | 3297 | OE1 | GLN | B 106 | 25.314 | 1.313 | 39.714 | 1.00 | 57.46 | MOLB O |
| ATOM | 3298 | NE2 | GLN | B 106 | 26.907 | 0.354 | 38.421 | 1.00 | 38.64 | MOLB N |
| ATOM | 3299 | C | GLN | B 106 | 25.440 | −3.851 | 39.282 | 1.00 | 34.41 | MOLB C |
| ATOM | 3300 | O | GLN | B 106 | 26.089 | −4.249 | 38.325 | 1.00 | 36.44 | MOLB O |
| ATOM | 3301 | N | THR | B 107 | 24.112 | −3.850 | 39.313 | 1.00 | 31.59 | MOLB N |
| ATOM | 3302 | CA | THR | B 107 | 23.343 | −4.301 | 38.176 | 1.00 | 33.47 | MOLB C |
| ATOM | 3303 | CB | THR | B 107 | 21.881 | −4.079 | 38.404 | 1.00 | 32.91 | MOLB C |
| ATOM | 3304 | OG1 | THR | B 107 | 21.475 | −4.749 | 39.613 | 1.00 | 38.50 | MOLB O |
| ATOM | 3305 | CG2 | THR | B 107 | 21.099 | −4.607 | 37.225 | 1.00 | 35.23 | MOLB C |
| ATOM | 3306 | C | THR | B 107 | 23.736 | −3.482 | 36.961 | 1.00 | 34.87 | MOLB C |
| ATOM | 3307 | O | THR | B 107 | 24.007 | −2.288 | 37.104 | 1.00 | 39.33 | MOLB O |
| ATOM | 3308 | N | GLY | B 108 | 23.803 | −4.114 | 35.784 | 1.00 | 34.63 | MOLB N |
| ATOM | 3309 | CA | GLY | B 108 | 24.118 | −3.419 | 34.517 | 1.00 | 33.39 | MOLB C |
| ATOM | 3310 | C | GLY | B 108 | 25.567 | −3.000 | 34.288 | 1.00 | 34.03 | MOLB C |
| ATOM | 3311 | O | GLY | B 108 | 25.850 | −1.998 | 33.618 | 1.00 | 33.82 | MOLB O |
| ATOM | 3312 | N | THR | B 109 | 26.498 | −3.750 | 34.854 | 1.00 | 32.36 | MOLB N |
| ATOM | 3313 | CA | THR | B 109 | 27.893 | −3.462 | 34.627 | 1.00 | 32.64 | MOLB C |
| ATOM | 3314 | CB | THR | B 109 | 28.591 | −3.250 | 35.928 | 1.00 | 32.33 | MOLB C |
| ATOM | 3315 | OG1 | THR | B 109 | 28.400 | −4.422 | 36.734 | 1.00 | 35.94 | MOLB O |
| ATOM | 3316 | CG2 | THR | B 109 | 27.988 | −2.073 | 36.613 | 1.00 | 28.36 | MOLB C |
| ATOM | 3317 | C | THR | B 109 | 28.498 | −4.656 | 33.897 | 1.00 | 33.68 | MOLB C |
| ATOM | 3318 | O | THR | B 109 | 29.630 | −4.615 | 33.411 | 1.00 | 34.16 | MOLB O |
| ATOM | 3319 | N | GLY | B 110 | 27.737 | −5.741 | 33.851 | 1.00 | 34.63 | MOLB N |
| ATOM | 3320 | CA | GLY | B 110 | 28.050 | −6.836 | 32.947 | 1.00 | 33.65 | MOLB C |
| ATOM | 3321 | C | GLY | B 110 | 28.384 | −8.173 | 33.541 | 1.00 | 32.09 | MOLB C |
| ATOM | 3322 | O | GLY | B 110 | 29.130 | −8.935 | 32.928 | 1.00 | 34.44 | MOLB 0 |
| ATOM | 3323 | N | LYS | B 111 | 27.856 | −8.470 | 34.722 | 1.00 | 29.15 | MOLB N |
| ATOM | 3324 | CA | LYS | B 111 | 28.076 | −9.779 | 35.290 | 1.00 | 28.18 | MOLB C |
| ATOM | 3325 | CB | LYS | B 111 | 27.313 | −9.937 | 36.610 | 1.00 | 26.45 | MOLB C |
| ATOM | 3326 | CG | LYS | B 111 | 27.872 | −9.088 | 37.758 | 1.00 | 26.83 | MOLB C |
| ATOM | 3327 | CD | LYS | B 111 | 26.842 | −8.765 | 38.868 | 1.00 | 25.26 | MOLB C |
| ATOM | 3328 | CE | LYS | B 111 | 25.654 | −7.958 | 38.302 | 1.00 | 41.09 | MOLB C |
| ATOM | 3329 | NZ | LYS | B 111 | 24.729 | −7.394 | 39.340 | 1.00 | 40.15 | MOLB N |
| ATOM | 3330 | C | LYS | B 111 | 27.633 | −10.805 | 34.223 | 1.00 | 30.47 | MOLB C |
| ATOM | 3331 | O | LYS | B 111 | 28.389 | −11.728 | 33.863 | 1.00 | 28.31 | MOLB O |
| ATOM | 3332 | N | THR | B 112 | 26.432 | −10.601 | 33.668 | 1.00 | 30.50 | MOLB N |
| ATOM | 3333 | CA | THR | B 112 | 25.854 | −11.602 | 32.780 | 1.00 | 28.84 | MOLB C |
| ATOM | 3334 | CB | THR | B 112 | 24.323 | −11.550 | 32.742 | 1.00 | 28.08 | MOLB C |
| ATOM | 3335 | OG1 | THR | B 112 | 23.824 | −11.192 | 34.032 | 1.00 | 32.67 | MOLB O |
| ATOM | 3336 | CG2 | THR | B 112 | 23.781 | −12.893 | 32.417 | 1.00 | 22.16 | MOLB C |
| ATOM | 3337 | C | THR | B 112 | 26.469 | −11.490 | 31.395 | 1.00 | 30.58 | MOLB C |
| ATOM | 3338 | O | THR | B 112 | 26.633 | −12.502 | 30.678 | 1.00 | 30.97 | MOLB O |
| ATOM | 3339 | N | PHE | B 113 | 26.846 | −10.274 | 31.005 | 1.00 | 29.79 | MOLB N |
| ATOM | 3340 | CA | PHE | B 113 | 27.606 | −10.175 | 29.775 | 1.00 | 28.45 | MOLB C |
| ATOM | 3341 | CB | PHE | B 113 | 28.193 | −8.803 | 29.587 | 1.00 | 26.72 | MOLB C |
| ATOM | 3342 | CG | PHE | B 113 | 28.904 | −8.636 | 28.276 | 1.00 | 23.11 | MOLB C |
| ATOM | 3343 | CD1 | PHE | B 113 | 28.226 | −8.879 | 27.066 | 1.00 | 11.70 | MOLB C |
| ATOM | 3344 | CE1 | PHE | B 113 | 28.854 | −8.670 | 25.838 | 1.00 | 18.54 | MOLB C |
| ATOM | 3345 | CZ | PHE | B 113 | 30.204 | −8.228 | 25.791 | 1.00 | 17.33 | MOLB C |
| ATOM | 3346 | CE2 | PHE | B 113 | 30.905 | −8.007 | 26.995 | 1.00 | 21.24 | MOLB C |
| ATOM | 3347 | CD2 | PHE | B 113 | 30.229 | −8.185 | 28.236 | 1.00 | 20.70 | MOLB C |
| ATOM | 3348 | C | PHE | B 113 | 28.789 | −11.106 | 29.899 | 1.00 | 30.10 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 3349 | O | PHE | B | 113 | 29.034 | −11.934 | 29.027 | 1.00 | 32.98 | MOLB O |
| ATOM | 3350 | N | THR | B | 114 | 29.520 | −10.958 | 31.004 | 1.00 | 27.99 | MOLB N |
| ATOM | 3351 | CA | THR | B | 114 | 30.836 | −11.544 | 31.113 | 1.00 | 25.38 | MOLB C |
| ATOM | 3352 | CB | THR | B | 114 | 31.556 | −11.082 | 32.364 | 1.00 | 21.59 | MOLB C |
| ATOM | 3353 | OG1 | THR | B | 114 | 32.016 | −9.745 | 32.179 | 1.00 | 29.10 | MOLB O |
| ATOM | 3354 | CG2 | THR | B | 114 | 32.745 | −11.960 | 32.631 | 1.00 | 17.30 | MOLB C |
| ATOM | 3355 | C | THR | B | 114 | 30.670 | −13.015 | 31.235 | 1.00 | 27.50 | MOLB C |
| ATOM | 3356 | O | THR | B | 114 | 31.558 | −13.783 | 30.805 | 1.00 | 28.60 | MOLB O |
| ATOM | 3357 | N | MET | B | 115 | 29.534 | −13.415 | 31.810 | 1.00 | 25.33 | MOLB N |
| ATOM | 3358 | CA | MET | B | 115 | 29.400 | −14.804 | 32.214 | 1.00 | 25.24 | MOLB C |
| ATOM | 3359 | CB | MET | B | 115 | 28.830 | −14.920 | 33.594 | 1.00 | 22.85 | MOLB C |
| ATOM | 3360 | CG | MET | B | 115 | 29.326 | −16.134 | 34.297 | 1.00 | 21.29 | MOLB C |
| ATOM | 3361 | SD | MET | B | 115 | 30.556 | −15.642 | 35.482 | 1.00 | 46.07 | MOLB S |
| ATOM | 3362 | CE | MET | B | 115 | 31.204 | −17.212 | 36.043 | 1.00 | 24.67 | MOLB C |
| ATOM | 3363 | C | MET | B | 115 | 28.593 | −15.675 | 31.281 | 1.00 | 27.44 | MOLB C |
| ATOM | 3364 | O | MET | B | 115 | 28.623 | −16.889 | 31.412 | 1.00 | 30.04 | MOLB O |
| ATOM | 3365 | N | GLU | B | 116 | 27.890 | −15.071 | 30.333 | 1.00 | 27.95 | MOLB N |
| ATOM | 3366 | CA | GLU | B | 116 | 27.124 | −15.846 | 29.387 | 1.00 | 26.21 | MOLB C |
| ATOM | 3367 | CB | GLU | B | 116 | 25.648 | −15.797 | 29.737 | 1.00 | 25.71 | MOLB C |
| ATOM | 3368 | CG | GLU | B | 116 | 25.385 | −16.065 | 31.191 | 1.00 | 19.05 | MOLB C |
| ATOM | 3369 | CD | GLU | B | 116 | 23.919 | −16.252 | 31.469 | 1.00 | 25.43 | MOLB C |
| ATOM | 3370 | OE1 | GLU | B | 116 | 23.586 | −16.730 | 32.584 | 1.00 | 15.86 | MOLB O |
| ATOM | 3371 | OE2 | GLU | B | 116 | 23.104 | −15.934 | 30.566 | 1.00 | 32.21 | MOLB O |
| ATOM | 3372 | C | GLU | B | 116 | 27.328 | −15.284 | 28.032 | 1.00 | 28.51 | MOLB C |
| ATOM | 3373 | O | GLU | B | 116 | 27.498 | −16.001 | 27.063 | 1.00 | 28.73 | MOLB O |
| ATOM | 3374 | N | GLY | B | 117 | 27.313 | −13.967 | 27.947 | 1.00 | 32.64 | MOLB N |
| ATOM | 3375 | CA | GLY | B | 117 | 27.570 | −13.346 | 26.660 | 1.00 | 33.61 | MOLB C |
| ATOM | 3376 | C | GLY | B | 117 | 26.260 | −13.091 | 25.977 | 1.00 | 34.68 | MOLB C |
| ATOM | 3377 | O | GLY | B | 117 | 25.216 | −12.899 | 26.634 | 1.00 | 33.29 | MOLB O |
| ATOM | 3378 | N | GLU | B | 118 | 26.333 | −13.086 | 24.658 | 1.00 | 35.32 | MOLB N |
| ATOM | 3379 | CA | GLU | B | 118 | 25.218 | −12.792 | 23.813 | 1.00 | 38.20 | MOLB C |
| ATOM | 3380 | CB | GLU | B | 118 | 24.962 | −11.290 | 23.745 | 1.00 | 38.55 | MOLB C |
| ATOM | 3381 | CG | GLU | B | 118 | 24.180 | −10.696 | 24.876 | 1.00 | 45.82 | MOLB C |
| ATOM | 3382 | CD | GLU | B | 118 | 24.620 | −9.278 | 25.177 | 1.00 | 56.54 | MOLB C |
| ATOM | 3383 | OE1 | GLU | B | 118 | 25.628 | −8.854 | 24.581 | 1.00 | 52.56 | MOLB O |
| ATOM | 3384 | OE2 | GLU | B | 118 | 23.979 | −8.606 | 26.023 | 1.00 | 58.82 | MOLB O |
| ATOM | 3385 | C | GLU | B | 118 | 25.738 | −13.195 | 22.481 | 1.00 | 41.11 | MOLB C |
| ATOM | 3386 | O | GLU | B | 118 | 26.949 | −13.181 | 22.250 | 1.00 | 38.14 | MOLB O |
| ATOM | 3387 | N | ARG | B | 119 | 24.812 | −13.538 | 21.597 | 1.00 | 46.16 | MOLB N |
| ATOM | 3388 | CA | ARG | B | 119 | 25.133 | −13.944 | 20.260 | 1.00 | 50.42 | MOLB C |
| ATOM | 3389 | CB | ARG | B | 119 | 23.922 | −14.693 | 19.731 | 1.00 | 50.93 | MOLB C |
| ATOM | 3390 | CG | ARG | B | 119 | 24.220 | −15.682 | 18.664 | 1.00 | 53.80 | MOLB C |
| ATOM | 3391 | CD | ARG | B | 119 | 24.597 | −17.030 | 19.207 | 1.00 | 51.44 | MOLB,C |
| ATOM | 3392 | NE | ARG | B | 119 | 25.456 | −17.672 | 18.221 | 1.00 | 61.07 | MOLB N |
| ATOM | 3393 | CZ | ARG | B | 119 | 25.060 | −18.022 | 17.000 | 1.00 | 57.17 | MOLB C |
| ATOM | 3394 | NH1 | ARG | B | 119 | 23.814 | −17.801 | 16.626 | 1.00 | 48.40 | MOLB N |
| ATOM | 3395 | NH2 | ARG | B | 119 | 25.907 | −18.589 | 16.148 | 1.00 | 62.26 | MOLB N |
| ATOM | 3396 | C | ARG | B | 119 | 25.365 | −12.624 | 19.534 | 1.00 | 53.87 | MOLB C |
| ATOM | 3397 | O | ARG | B | 119 | 24.923 | −11.591 | 20.020 | 1.00 | 55.25 | MOLB O |
| ATOM | 3398 | N | SER | B | 120 | 26.076 | −12.600 | 18.412 | 1.00 | 59.02 | MOLB N |
| ATOM | 3399 | CA | SER | B | 120 | 26.169 | −11.320 | 17.670 | 1.00 | 64.21 | MOLB C |
| ATOM | 3400 | CB | SER | B | 120 | 27.595 | −11.002 | 17.169 | 1.00 | 63.65 | MOLB C |
| ATOM | 3401 | OG | SER | B | 120 | 28.384 | −12.161 | 17.020 | 1.00 | 67.38 | MOLB O |
| ATOM | 3402 | C | SER | B | 120 | 25.073 | −11.142 | 16.586 | 1.00 | 68.02 | MOLB C |
| ATOM | 3403 | O | SER | B | 120 | 24.590 | −12.123 | 16.015 | 1.00 | 68.00 | MOLB O |
| ATOM | 3404 | N | PRO | B | 121 | 24.693 | −9.880 | 16.293 | 1.00 | 72.49 | MOLB N |
| ATOM | 3405 | CA | PRO | B | 121 | 23.500 | −9.573 | 15.499 | 1.00 | 75.18 | MOLB C |
| ATOM | 3406 | CB | PRO | B | 121 | 23.200 | −8.136 | 15.904 | 1.00 | 74.88 | MOLB C |
| ATOM | 3407 | CG | PRO | B | 121 | 24.575 | −7.535 | 16.081 | 1.00 | 73.79 | MOLB C |
| ATOM | 3408 | CD | PRO | B | 121 | 25.440 | −8.650 | 16.641 | 1.00 | 72.68 | MOLB C |
| ATOM | 3409 | C | PRO | B | 121 | 23.807 | −9.601 | 14.013 | 1.00 | 79.48 | MOLB C |
| ATOM | 3410 | O | PRO | B | 121 | 24.816 | −9.004 | 13.588 | 1.00 | 81.27 | MOLB O |
| ATOM | 3411 | N | ASN | B | 122 | 22.935 | −10.246 | 13.230 | 1.00 | 81.76 | MOLB N |
| ATOM | 3412 | CA | ASN | B | 122 | 23.173 | −10.454 | 11.793 | 1.00 | 84.21 | MOLB C |
| ATOM | 3413 | CB | ASN | B | 122 | 23.634 | −9.169 | 11.070 | 1.00 | 84.09 | MOLB C |
| ATOM | 3414 | CG | ASN | B | 122 | 22.620 | −8.051 | 11.137 | 1.00 | 89.61 | MOLB C |
| ATOM | 3415 | OD1 | ASN | B | 122 | 21.417 | −8.296 | 11.179 | 1.00 | 94.75 | MOLB O |
| ATOM | 3416 | ND2 | ASN | B | 122 | 23.104 | −6.805 | 11.127 | 1.00 | 97.28 | MOLB N |
| ATOM | 3417 | C | ASN | B | 122 | 24.248 | −11.518 | 11.607 | 1.00 | 84.17 | MOLB C |
| ATOM | 3418 | O | ASN | B | 122 | 23.940 | −12.681 | 11.361 | 1.00 | 84.85 | MOLB O |
| ATOM | 3419 | N | GLU | B | 123 | 25.509 | −11.091 | 11.743 | 1.00 | 83.87 | MOLB N |
| ATOM | 3420 | CA | GLU | B | 123 | 26.688 | −11.934 | 11.546 | 1.00 | 81.37 | MOLB C |
| ATOM | 3421 | CB | GLU | B | 123 | 27.900 | −11.336 | 12.227 | 1.00 | 80.95 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3422 | CG | GLU | B 123 | 29.141 | −11.474 | 11.414 | 1.00 | 76.70 | MOLB C |
| ATOM | 3423 | CD | GLU | B 123 | 29.933 | −10.208 | 11.476 | 1.00 | 72.98 | MOLB C |
| ATOM | 3424 | OE1 | GLU | B 123 | 30.859 | −10.042 | 10.656 | 1.00 | 76.98 | MOLB O |
| ATOM | 3425 | OE2 | GLU | B 123 | 29.599 | −9.366 | 12.341 | 1.00 | 63.79 | MOLB O |
| ATOM | 3426 | C | GLU | B 123 | 26.405 | −13.291 | 12.103 | 1.00 | 80.68 | MOLB C |
| ATOM | 3427 | O | GLU | B 123 | 25.898 | −13.437 | 13.220 | 1.00 | 80.28 | MOLB O |
| ATOM | 3428 | N | GLU | B 124 | 26.713 | −14.296 | 11.314 | 1.00 | 78.81 | MOLB N |
| ATOM | 3429 | CA | GLU | B 124 | 26.228 | −15.593 | 11.677 | 1.00 | 78.49 | MOLB C |
| ATOM | 3430 | CB | GLU | B 124 | 25.345 | −16.169 | 10.555 | 1.00 | 78.85 | MOLB C |
| ATOM | 3431 | CG | GLU | B 124 | 24.076 | −15.334 | 10.274 | 1.00 | 77.55 | MOLB C |
| ATOM | 3432 | CD | GLU | B 124 | 23.135 | −15.222 | 11.490 | 1.00 | 77.96 | MOLB C |
| ATOM | 3433 | OE1 | GLU | B 124 | 22.635 | −16.262 | 11.985 | 1.00 | 63.40 | MOLB O |
| ATOM | 3434 | OE2 | GLU | B 124 | 22.870 | −14.084 | 11.939 | 1.00 | 85.89 | MOLB O |
| ATOM | 3435 | C | GLU | B 124 | 27.354 | −16.525 | 12.061 | 1.00 | 77.53 | MOLB C |
| ATOM | 3436 | O | GLU | B 124 | 27.320 | −17.708 | 11.690 | 1.00 | 80.31 | MOLB O |
| ATOM | 3437 | N | TYR | B 125 | 28.347 | −16.007 | 12.795 | 1.00 | 71.96 | MOLB N |
| ATOM | 3438 | CA | TYR | B 125 | 29.376 | −16.880 | 13.324 | 1.00 | 67.42 | MOLB C |
| ATOM | 3439 | CB | TYR | B 125 | 30.196 | −16.231 | 14.438 | 1.00 | 66.78 | MOLB C |
| ATOM | 3440 | CG | TYR | B 125 | 30.888 | −14.904 | 14.199 | 1.00 | 62.26 | MOLB C |
| ATOM | 3441 | CD1 | TYR | B 125 | 32.201 | −14.849 | 13.725 | 1.00 | 47.20 | MOLB C |
| ATOM | 3442 | CE1 | TYR | B 125 | 32.858 | −13.620 | 13.563 | 1.00 | 46.24 | MOLB C |
| ATOM | 3443 | CZ | TYR | B 125 | 32.192 | −12.440 | 13.897 | 1.00 | 57.86 | MOLB C |
| ATOM | 3444 | OH | TYR | B 125 | 32.809 | −11.208 | 13.734 | 1.00 | 63.21 | MOLB O |
| ATOM | 3445 | CE2 | TYR | B 125 | 30.890 | −12.484 | 14.388 | 1.00 | 49.92 | MOLB C |
| ATOM | 3446 | CD2 | TYR | B 125 | 30.260 | −13.701 | 14.548 | 1.00 | 58.90 | MOLB C |
| ATOM | 3447 | C | TYR | B 125 | 28.635 | −18.035 | 13.984 | 1.00 | 66.32 | MOLB C |
| ATOM | 3448 | O | TYR | B 125 | 27.664 | −17.815 | 14.719 | 1.00 | 64.44 | MOLB O |
| ATOM | 3449 | N | THR | B 126 | 29.071 | −19.264 | 13.731 | 1.00 | 65.93 | MOLB N |
| ATOM | 3450 | CA | THR | B 126 | 28.532 | −20.383 | 14.490 | 1.00 | 65.91 | MOLB C |
| ATOM | 3451 | CB | THR | B 126 | 29.124 | −21.727 | 14.054 | 1.00 | 66.50 | MOLB C |
| ATOM | 3452 | OG1 | THR | B 126 | 30.544 | −21.707 | 14.235 | 1.00 | 67.13 | MOLB O |
| ATOM | 3453 | CG2 | THR | B 126 | 28.814 | −21.993 | 12.585 | 1.00 | 65.19 | MOLB C |
| ATOM | 3454 | C | THR | B 126 | 28.859 | −20.096 | 15.955 | 1.00 | 65.47 | MOLB C |
| ATOM | 3455 | O | THR | B 126 | 29.884 | −19.469 | 16.267 | 1.00 | 65.66 | MOLB O |
| ATOM | 3456 | N | TRP | B 127 | 27.988 | −20.533 | 16.855 | 1.00 | 63.92 | MOLB N |
| ATOM | 3457 | CA | TRP | B 127 | 28.140 | −20.169 | 18.254 | 1.00 | 61.26 | MOLB C |
| ATOM | 3458 | CB | TRP | B 127 | 26.958 | −20.667 | 19.057 | 1.00 | 60.98 | MOLB C |
| ATOM | 3459 | CG | TRP | B 127 | 26.857 | −22.114 | 19.038 | 1.00 | 59.88 | MOLB C |
| ATOM | 3460 | CD1 | TRP | B 127 | 26.148 | −22.869 | 18.158 | 1.00 | 60.20 | MOLB C |
| ATOM | 3461 | NE1 | TRP | B 127 | 26.303 | −24.205 | 18.459 | 1.00 | 68.96 | MOLB N |
| ATOM | 3462 | CE2 | TRP | B 127 | 27.131 | −24.329 | 19.546 | 1.00 | 71.10 | MOLB C |
| ATOM | 3463 | CD2 | TRP | B 127 | 27.502 | −23.028 | 19.940 | 1.00 | 68.75 | MOLB C |
| ATOM | 3464 | CE3 | TRP | B 127 | 28.355 | −22.872 | 21.048 | 1.00 | 65.43 | MOLB C |
| ATOM | 3465 | CZ3 | TRP | B 127 | 28.808 | −24.014 | 21.720 | 1.00 | 65.00 | MOLB C |
| ATOM | 3466 | CH2 | TRP | B 127 | 28.423 | −25.294 | 21.303 | 1.00 | 65.85 | MOLB C |
| ATOM | 3467 | CZ2 | TRP | B 127 | 27.584 | −25.475 | 20.224 | 1.00 | 71.03 | MOLB C |
| ATOM | 3468 | C | TRP | B 127 | 29.454 | −20.662 | 18.849 | 1.00 | 61.04 | MOLB C |
| ATOM | 3469 | O | TRP | B 127 | 29.901 | −20.158 | 19.879 | 1.00 | 62.31 | MOLB O |
| ATOM | 3470 | N | GLU | B 128 | 30.076 | −21.646 | 18.207 | 1.00 | 59.38 | MOLB N |
| ATOM | 3471 | CA | GLU | B 128 | 31.370 | −22.122 | 18.664 | 1.00 | 57.92 | MOLB C |
| ATOM | 3472 | CB | GLU | B 128 | 31.878 | −23.287 | 17.807 | 1.00 | 59.35 | MOLB C |
| ATOM | 3473 | CG | GLU | B 128 | 31.686 | −24.664 | 18.411 | 1.00 | 60.85 | MOLB C |
| ATOM | 3474 | CD | GLU | B 128 | 30.463 | −25.336 | 17.904 | 1.00 | 70.17 | MOLB C |
| ATOM | 3475 | OE1 | GLU | B 128 | 30.097 | −25.076 | 16.740 | 1.00 | 77.40 | MOLB O |
| ATOM | 3476 | OE2 | GLU | B 128 | 29.879 | −26.140 | 18.655 | 1.00 | 78.85 | MOLB O |
| ATOM | 3477 | C | GLU | B 128 | 32.387 | −21.005 | 18.588 | 1.00 | 56.04 | MOLB C |
| ATOM | 3478 | O | GLU | B 128 | 33.349 | −20.976 | 19.380 | 1.00 | 54.87 | MOLB O |
| ATOM | 3479 | N | GLU | B 129 | 32.135 | −20.080 | 17.655 | 1.00 | 53.66 | MOLB N |
| ATOM | 3480 | CA | GLU | B 129 | 33.118 | −19.093 | 17.213 | 1.00 | 52.66 | MOLB C |
| ATOM | 3481 | CB | GLU | B 129 | 33.380 | −19.277 | 15.716 | 1.00 | 52.84 | MOLB C |
| ATOM | 3482 | CG | GLU | B 129 | 33.948 | −20.613 | 15.350 | 1.00 | 61.07 | MOLB C |
| ATOM | 3483 | CD | GLU | B 129 | 34.958 | −21.087 | 16.379 | 1.00 | 82.66 | MOLB C |
| ATOM | 3484 | OE1 | GLU | B 129 | 35.807 | −20.263 | 16.813 | 1.00 | 81.37 | MOLB O |
| ATOM | 3485 | OE2 | GLU | B 129 | 34.890 | −22.281 | 16.764 | 1.00 | 91.10 | MOLB O |
| ATOM | 3486 | C | GLU | B 129 | 32.740 | −17.640 | 17.403 | 1.00 | 52.40 | MOLB C |
| ATOM | 3487 | O | GLU | B 129 | 33.396 | −16.761 | 16.823 | 1.00 | 52.55 | MOLB O |
| ATOM | 3488 | N | ASP | B 130 | 31.699 | −17.373 | 18.189 | 1.00 | 50.11 | MOLB N |
| ATOM | 3489 | CA | ASP | B 130 | 31.200 | −16.007 | 18.351 | 1.00 | 46.96 | MOLB C |
| ATOM | 3490 | CB | ASP | B 130 | 29.721 | −16.085 | 18.674 | 1.00 | 47.27 | MOLB C |
| ATOM | 3491 | CG | ASP | B 130 | 29.078 | −14.739 | 18.766 | 1.00 | 50.49 | MOLB C |
| ATOM | 3492 | OD1 | ASP | B 130 | 27.852 | −14.666 | 18.530 | 1.00 | 55.03 | MOLB O |
| ATOM | 3493 | OD2 | ASP | B 130 | 29.792 | −13.756 | 19.071 | 1.00 | 63.82 | MOLB O |
| ATOM | 3494 | C | ASP | B 130 | 31.929 | −15.196 | 19.433 | 1.00 | 44.52 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3495 | O | ASP | B 130 | 31.816 | −15.515 | 20.603 | 1.00 | 45.81 | MOLB O |
| ATOM | 3496 | N | PRO | B 131 | 32.647 | −14.121 | 19.048 | 1.00 | 42.74 | MOLB N |
| ATOM | 3497 | CA | PRO | B 131 | 33.450 | −13.277 | 19.955 | 1.00 | 42.24 | MOLB C |
| ATOM | 3498 | CB | PRO | B 131 | 33.912 | −12.126 | 19.055 | 1.00 | 41.37 | MOLB C |
| ATOM | 3499 | CG | PRO | B 131 | 33.069 | −12.197 | 17.855 | 1.00 | 38.76 | MOLB C |
| ATOM | 3500 | CD | PRO | B 131 | 32.724 | −13.621 | 17.670 | 1.00 | 43.14 | MOLB C |
| ATOM | 3501 | C | PRO | B 131 | 32.703 | −12.708 | 21.172 | 1.00 | 42.75 | MOLB C |
| ATOM | 3502 | O | PRO | B 131 | 33.340 | −12.426 | 22.208 | 1.00 | 43.86 | MOLB O |
| ATOM | 3503 | N | LEU | B 132 | 31.377 | −12.551 | 21.049 | 1.00 | 40.75 | MOLB N |
| ATOM | 3504 | CA | LEU | B 132 | 30.522 | −12.082 | 22.153 | 1.00 | 36.33 | MOLB C |
| ATOM | 3505 | CB | LEU | B 132 | 29.297 | −11.320 | 21.612 | 1.00 | 35.10 | MOLB C |
| ATOM | 3506 | CG | LEU | B 132 | 29.609 | −10.031 | 20.862 | 1.00 | 36.04 | MOLB C |
| ATOM | 3507 | CD1 | LEU | B 132 | 28.363 | −9.427 | 20.240 | 1.00 | 26.18 | MOLB C |
| ATOM | 3508 | CD2 | LEU | B 132 | 30.310 | −9.033 | 21.779 | 1.00 | 19.11 | MOLB C |
| ATOM | 3509 | C | LEU | B 132 | 30.069 | −13.208 | 23.115 | 1.00 | 33.81 | MOLB C |
| ATOM | 3510 | O | LEU | B 132 | 29.377 | −12.943 | 24.114 | 1.00 | 36.58 | MOLB O |
| ATOM | 3511 | N | ALA | B 133 | 30.434 | −14.454 | 22.847 | 1.00 | 26.82 | MOLB N |
| ATOM | 3512 | CA | ALA | B 133 | 30.019 | −15.505 | 23.771 | 1.00 | 25.64 | MOLB C |
| ATOM | 3513 | CB | ALA | B 133 | 30.394 | −16.847 | 23.239 | 1.00 | 26.67 | MOLB C |
| ATOM | 3514 | C | ALA | B 133 | 30.668 | −15.239 | 25.132 | 1.00 | 25.68 | MOLB C |
| ATOM | 3515 | O | ALA | B 133 | 31.587 | −14.445 | 25.225 | 1.00 | 25.17 | MOLB O |
| ATOM | 3516 | N | GLY | B 134 | 30.212 | −15.893 | 26.189 | 1.00 | 26.36 | MOLB N |
| ATOM | 3517 | CA | GLY | B 134 | 30.694 | −15.547 | 27.547 | 1.00 | 28.24 | MOLB C |
| ATOM | 3518 | C | GLY | B 134 | 31.532 | −16.644 | 28.187 | 1.00 | 27.61 | MOLB C |
| ATOM | 3519 | O | GLY | B 134 | 31.984 | −17.542 | 27.499 | 1.00 | 28.93 | MOLB O |
| ATOM | 3520 | N | ILE | B 135 | 31.729 | −16.628 | 29.496 | 1.00 | 25.42 | MOLB N |
| ATOM | 3521 | CA | ILE | B 135 | 32.530 | −17.686 | 30.028 | 1.00 | 25.81 | MOLB C |
| ATOM | 3522 | CB | ILE | B 135 | 32.878 | −17.464 | 31.430 | 1.00 | 25.82 | MOLB C |
| ATOM | 3523 | CG1 | ILE | a 135 | 33.692 | −16.178 | 31.523 | 1.00 | 17.83 | MOLB C |
| ATOM | 3524 | CD1 | ILE | B 135 | 34.143 | −15.793 | 32.903 | 1.00 | 5.51 | MOLB C |
| ATOM | 3525 | CG2 | ILE | B 135 | 33.658 | −18.743 | 31.890 | 1.00 | 25.64 | MOLB C |
| ATOM | 3526 | C | ILE | B 135 | 31.897 | −19.074 | 29.979 | 1.00 | 30.04 | MOLE C |
| ATOM | 3527 | O | ILE | B 135 | 32.595 | −20.061 | 29.779 | 1.00 | 31.09 | MOLB O |
| ATOM | 3528 | N | ILE | B 136 | 30.584 | −19.136 | 30.203 | 1.00 | 32.57 | MOLB N |
| ATOM | 3529 | CA | ILE | B 136 | 29.830 | −20.392 | 30.233 | 1.00 | 32.89 | MOLE C |
| ATOM | 3530 | CB | ILE | B 136 | 28.394 | −20.143 | 30.730 | 1.00 | 34.66 | MOLB C |
| ATOM | 3531 | CG1 | ILE | B 136 | 28.407 | −20.116 | 32.259 | 1.00 | 29.86 | MOLB C |
| ATOM | 3532 | CD1 | ILE | B 136 | 27.309 | −19.317 | 32.826 | 1.00 | 27.20 | MOLE C |
| ATOM | 3533 | CG2 | ILE | B 136 | 27.410 | −21.233 | 30.246 | 1.00 | 37.99 | MOLE C |
| ATOM | 3534 | C | ILE | B 136 | 29.873 | −21.183 | 28.929 | 1.00 | 34.47 | MOLE C |
| ATOM | 3535 | O | ILE | B 136 | 30.264 | −22.347 | 28.927 | 1.00 | 35.70 | MOLB O |
| ATOM | 3536 | N | PRO | B 137 | 29.465 | −20.576 | 27.810 | 1.00 | 35.57 | MOLB N |
| ATOM | 3537 | CA | PRO | B 137 | 29.642 | −21.312 | 26.545 | 1.00 | 36.93 | MOLB C |
| ATOM | 3538 | CB | PRO | B 137 | 28.908 | −20.437 | 25.535 | 1.00 | 38.34 | MOLB C |
| ATOM | 3539 | CG | PRO | B 137 | 29.032 | −19.033 | 26.124 | 1.00 | 35.28 | MOLB C |
| ATOM | 3540 | CD | PRO | B 137 | 28.806 | −19.273 | 27.608 | 1.00 | 33.20 | MOLB C |
| ATOM | 3541 | C | PRO | B 137 | 31.103 | −21.460 | 26.075 | 1.00 | 39.29 | MOLB C |
| ATOM | 3542 | O | PRO | B 137 | 31.380 | −22.302 | 25.226 | 1.00 | 42.00 | MOLB O |
| ATOM | 3543 | N | ARG | B 138 | 32.033 | −-20.632 | 26.539 | 1.00 | 38.02 | MOLB N |
| ATOM | 3544 | CA | ARG | B 138 | 33.389 | −20.811 | 26.031 | 1.00 | 36.73 | MOLB C |
| ATOM | 3545 | CB | ARG | B 138 | 34.285 | −19.592 | 26.231 | 1.00 | 36.29 | MOLB C |
| ATOM | 3546 | CG | ARG | B 138 | 34.124 | −18.569 | 25.162 | 1.00 | 32.82 | MOLB C |
| ATOM | 3547 | CD | ARG | B 138 | 34.858 | −17.290 | 25.494 | 1.00 | 25.97 | MOLB C |
| ATOM | 3548 | NE | ARG | B 138 | 34.269 | −16.256 | 24.662 | 1.00 | 26.69 | MOLB N |
| ATOM | 3549 | CZ | ARG | B 138 | 34.761 | −15.873 | 23.491 | 1.00 | 34.61 | MOLB C |
| ATOM | 3550 | NH1 | ARG | B 138 | 35.903 | −16.406 | 23.039 | 1.00 | 25.69 | MOLB N |
| ATOM | 3551 | NH2 | ARG | B 138 | 34.122 | −14.935 | 22.795 | 1.00 | 25.55 | MOLB N |
| ATOM | 3552 | C | ARG | B 138 | 33.987 | −21.983 | 26.747 | 1.00 | 36.41 | MOLB C |
| ATOM | 3553 | O | ARG | B 138 | 34.809 | −22.701 | 26.181 | 1.00 | 39.13 | MOLB O |
| ATOM | 3554 | N | THR | B 139 | 33.595 | −22.167 | 27.994 | 1.00 | 32.60 | MOLB N |
| ATOM | 3555 | CA | THR | B 139 | 34.129 | −23.263 | 28.736 | 1.00 | 35.38 | MOLB C |
| ATOM | 3556 | CB | THR | B 139 | 33.694 | −23.204 | 30.220 | 1.00 | 35.63 | MOLB C |
| ATOM | 3557 | OG1 | THR | B 139 | 33.977 | −21.902 | 30.763 | 1.00 | 39.02 | MOLB O |
| ATOM | 3558 | CG2 | THR | B 139 | 34.429 | −24.248 | 31.042 | 1.00 | 34.83 | MOLB C |
| ATOM | 3559 | C | THR | B 139 | 33.639 | −24.546 | 28.027 | 1.00 | 37.76 | MOLB C |
| ATOM | 3560 | O | THR | B 139 | 34.445 | −25.334 | 27.495 | 1.00 | 34.86 | MOLB O |
| ATOM | 3561 | N | LEU | B 140 | 32.318 | −24.707 | 27.948 | 1.00 | 38.24 | MOLB N |
| ATOM | 3562 | CA | LEU | B 140 | 31.742 | −25.906 | 27.368 | 1.00 | 38.35 | MOLB C |
| ATOM | 3563 | CB | LEU | B 140 | 30.261 | −25.732 | 27.135 | 1.00 | 38.01 | MOLB C |
| ATOM | 3564 | CG | LEU | B 140 | 29.484 | −26.127 | 28.395 | 1.00 | 40.57 | MOLB C |
| ATOM | 3565 | CD1 | LEU | B 140 | 30.364 | −26.422 | 29.601 | 1.00 | 40.76 | MOLB C |
| ATOM | 3566 | CD2 | LEU | B 140 | 28.468 | −25.061 | 28.721 | 1.00 | 42.56 | MOLB C |
| ATOM | 3567 | C | LEU | B 140 | 32.450 | −26.348 | 26.109 | 1.00 | 40.00 | MOLB C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 3568 | O | LEU | B 140 | 32.881 | −27.500 | 26.030 | 1.00 | 41.92 | MOLB O |
| ATOM | 3569 | N | HIS | B 141 | 32.595 | −25.443 | 25.139 | 1.00 | 40.60 | MOLB N |
| ATOM | 3570 | CA | HIS | B 141 | 33.328 | −25.757 | 23.905 | 1.00 | 41.50 | MOLB C |
| ATOM | 3571 | CB | HIS | B 141 | 33.252 | −24.593 | 22.883 | 1.00 | 41.98 | MOLB C |
| ATOM | 3572 | CG | HIS | B 141 | 33.967 | −24.854 | 21.583 | 1.00 | 47.20 | MOLB C |
| ATOM | 3573 | ND1 | HIS | B 141 | 35.178 | −24.267 | 21.263 | 1.00 | 55.42 | MOLB N |
| ATOM | 3574 | CE1 | HIS | B 141 | 35.574 | −24.681 | 20.072 | 1.00 | 40.26 | MOLB C |
| ATOM | 3575 | NE2 | HIS | B 141 | 34.663 | −25.518 | 19.606 | 1.00 | 63.53 | MOLB N |
| ATOM | 3576 | CD2 | HIS | B 141 | 33.652 | −25.648 | 20.532 | 1.00 | 58.17 | MOLB C |
| ATOM | 3577 | C | HIS | B 141 | 34.773 | −26.228 | 24.225 | 1.00 | 41.46 | MOLB C |
| ATOM | 3578 | O | HIS | B 141 | 35.141 | −27.332 | 23.844 | 1.00 | 41.45 | MOLB O |
| ATOM | 3579 | N | GLN | B 142 | 35.569 | −25.431 | 24.954 | 1.00 | 41.06 | MOLB N |
| ATOM | 3580 | CA | GLN | B 142 | 36.947 | −25.850 | 25.319 | 1.00 | 39.08 | MOLB C |
| ATOM | 3581 | CB | GLN | B 142 | 37.681 | −24.825 | 26.208 | 1.00 | 37.14 | MOLB C |
| ATOM | 3582 | CG | GLN | B 142 | 37.851 | −23.481 | 25.580 | 1.00 | 37.87 | MOLB C |
| ATOM | 3583 | CD | GLN | B 142 | 38.188 | −23.600 | 24.129 | 1.00 | 51.87 | MOLB C |
| ATOM | 3584 | OE1 | GLN | B 142 | 39.241 | −24.106 | 23.776 | 1.00 | 53.36 | MOLB O |
| ATOM | 3585 | NE2 | GLN | B 142 | 37.278 | −23.156 | 23.266 | 1.00 | 65.95 | MOLB N |
| ATOM | 3586 | C | GLN | B 142 | 37.007 | −27.191 | 26.033 | 1.00 | 38.72 | MOLB C |
| ATOM | 3587 | O | GLN | B 142 | 38.008 | −27.893 | 25.933 | 1.00 | 40.97 | MOLB O |
| ATOM | 3588 | N | ILE | B 143 | 35.976 | −27.542 | 26.791 | 1.00 | 35.30 | MOLB N |
| ATOM | 3589 | CA | ILE | B 143 | 36.078 | −28.766 | 27.547 | 1.00 | 34.23 | MOLB C |
| ATOM | 3590 | CB | ILE | B 143 | 35.007 | −28.907 | 28.630 | 1.00 | 34.67 | MOLB C |
| ATOM | 3591 | CG1 | ILE | B 143 | 35.395 | −28.117 | 29.876 | 1.00 | 34.97 | MOLB C |
| ATOM | 3592 | CD1 | ILE | B 143 | 34.231 | −28.076 | 30.879 | 1.00 | 17.55 | MOLB C |
| ATOM | 3593 | CG2 | ILE | B 143 | 34.840 | −30.374 | 29.045 | 1.00 | 33.87 | MOLB C |
| ATOM | 3594 | C | ILE | B 143 | 36.002 | −29.931 | 26.594 | 1.00 | 34.38 | MOLB C |
| ATOM | 3595 | O | ILE | B 143 | 36.757 | −30.880 | 26.733 | 1.00 | 35.62 | MOLB O |
| ATOM | 3596 | N | PHE | B 144 | 35.099 | −29.887 | 25.632 | 1.00 | 32.65 | MOLB N |
| ATOM | 3597 | CA | PHE | B 144 | 35.074 | −30.974 | 24.714 | 1.00 | 33.12 | MOLB C |
| ATOM | 3598 | CB | PHE | B 144 | 33.836 | −30.915 | 23.865 | 1.00 | 32.17 | MOLB C |
| ATOM | 3599 | CG | PHE | B 144 | 32.614 | −31.264 | 24.635 | 1.00 | 29.43 | MOLB C |
| ATOM | 3600 | CD1 | PHE | B 144 | 32.284 | −32.577 | 24.850 | 1.00 | 30.82 | MOLB C |
| ATOM | 3601 | CE1 | PHE | B 144 | 31.180 | −32.921 | 25.579 | 1.00 | 40.54 | MOLB C |
| ATOM | 3602 | CZ | PHE | B 144 | 30.385 | −31.943 | 26.131 | 1.00 | 41.74 | MOLB C |
| ATOM | 3603 | CE2 | PHE | B 144 | 30.717 | −30.616 | 25.938 | 1.00 | 46.32 | MOLB C |
| ATOM | 3604 | CD2 | PHE | B 144 | 31.844 | −30.287 | 25.207 | 1.00 | 35.32 | MOLB C |
| ATOM | 3605 | C | PHE | B 144 | 36.369 | −30.860 | 23.968 | 1.00 | 35.99 | MOLB C |
| ATOM | 3606 | O | PHE | B 144 | 37.255 | −31.701 | 24.095 | 1.00 | 40.81 | MOLB O |
| ATOM | 3607 | N | GLU | B 145 | 36.519 | −29.783 | 23.241 | 1.00 | 37.17 | MOLB N |
| ATOM | 3608 | CA | GLU | B 145 | 37.812 | −29.405 | 22.726 | 1.00 | 39.90 | MOLB C |
| ATOM | 3609 | CB | GLU | B 145 | 37.994 | −27.903 | 22.953 | 1.00 | 42.23 | MOLB C |
| ATOM | 3610 | CG | GLU | B 145 | 39.259 | −27.318 | 22.356 | 1.00 | 50.63 | MOLB C |
| ATOM | 3611 | CD | GLU | B 145 | 39.088 | −27.056 | 20.889 | 1.00 | 52.12 | MOLB C |
| ATOM | 3612 | OE1 | GLU | B 145 | 37.977 | −27.320 | 20.369 | 1.00 | 57.42 | MOLB O |
| ATOM | 3613 | OE2 | GLU | B 145 | 40.052 | −26.575 | 20.272 | 1.00 | 49.35 | MOLB O |
| ATOM | 3614 | C | GLU | B 145 | 38.988 | −30.147 | 23.387 | 1.00 | 39.02 | MOLB C |
| ATOM | 3615 | O | GLU | B 145 | 39.606 | −31.003 | 22.767 | 1.00 | 41.55 | MOLB O |
| ATOM | 3616 | N | LYS | B 146 | 39.294 | −29.832 | 24.640 | 1.00 | 37.50 | MOLB N |
| ATOM | 3617 | CA | LYS | B 146 | 40.535 | −30.318 | 25.238 | 1.00 | 38.50 | MOLB C |
| ATOM | 3618 | CB | LYS | B 146 | 40.929 | −29.462 | 26.430 | 1.00 | 37.75 | MOLB C |
| ATOM | 3619 | CG | LYS | B 146 | 41.125 | −28.000 | 26.074 | 1.00 | 39.56 | MOLB C |
| ATOM | 3620 | CD | LYS | B 146 | 41.399 | −27.163 | 27.309 | 1.00 | 28.87 | MOLB C |
| ATOM | 3621 | CE | LYS | B 146 | 42.836 | −27.243 | 27.734 | 1.00 | 36.55 | MOLB C |
| ATOM | 3622 | NZ | LYS | B 146 | 42.909 | −26.922 | 29.183 | 1.00 | 48.85 | MOLB N |
| ATOM | 3623 | C | LYS | B 146 | 40.565 | −31.799 | 25.622 | 1.00 | 38.05 | MOLB C |
| ATOM | 3624 | O | LYS | B 146 | 41.598 | −32.460 | 25.501 | 1.00 | 37.38 | MOLB O |
| ATOM | 3625 | N | LEU | B 147 | 39.448 | −32.332 | 26.081 | 1.00 | 36.72 | MOLB N |
| ATOM | 3626 | CA | LEU | B 147 | 39.459 | −33.731 | 26.487 | 1.00 | 36.11 | MOLB C |
| ATOM | 3627 | CB | LEU | B 147 | 38.275 | −34.050 | 27.409 | 1.00 | 33.23 | MOLB C |
| ATOM | 3628 | CG | LEU | B 147 | 38.550 | −33.201 | 28.677 | 1.00 | 32.18 | MOLB C |
| ATOM | 3629 | CD1 | LEU | B 147 | 37.685 | −33.480 | 29.916 | 1.00 | 26.76 | MOLB C |
| ATOM | 3630 | CD2 | LEU | B 147 | 40.012 | −33.340 | 29.068 | 1.00 | 40.29 | MOLB C |
| ATOM | 3631 | C | LEU | B 147 | 39.606 | −34.623 | 25.248 | 1.00 | 37.08 | MOLB C |
| ATOM | 3632 | O | LEU | B 147 | 40.408 | −35.568 | 25.222 | 1.00 | 36.75 | MOLB O |
| ATOM | 3633 | N | THR | B 148 | 38.903 | −34.262 | 24.192 | 1.00 | 35.45 | MOLB N |
| ATOM | 3634 | CA | THR | B 148 | 39.103 | −34.919 | 22.938 | 1.00 | 34.63 | MOLB C |
| ATOM | 3635 | CB | THR | B 148 | 38.247 | −34.265 | 21.899 | 1.00 | 35.93 | MOLB C |
| ATOM | 3636 | OG1 | THR | B 148 | 36.866 | −34.553 | 22.189 | 1.00 | 34.50 | MOLB O |
| ATOM | 3637 | CG2 | THR | B 148 | 38.630 | −34.789 | 20.519 | 1.00 | 35.17 | MOLB C |
| ATOM | 3638 | C | THR | B 148 | 40.560 | −34.899 | 22.459 | 1.00 | 36.55 | MOLB C |
| ATOM | 3639 | O | THR | B 148 | 41.137 | −35.918 | 22.123 | 1.00 | 38.41 | MOLB O |
| ATOM | 3640 | N | ASP | B 149 | 41.194 | −33.743 | 22.415 | 1.00 | 39.26 | MOLB N |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 3641 | CA | ASP | B 149 | 42.555 | −33.760 | 21.908 | 1.00 | 37.91 | MOLB | C |
| ATOM | 3642 | CB | ASP | B 149 | 43.099 | −32.350 | 21.697 | 1.00 | 35.23 | MOLB | C |
| ATOM | 3643 | CG | ASP | B 149 | 42.550 | −31.700 | 20.418 | 1.00 | 46.16 | MOLB | C |
| ATOM | 3644 | OD1 | ASP | B 149 | 42.133 | −32.451 | 19.500 | 1.00 | 63.28 | MOLB | O |
| ATOM | 3645 | OD2 | ASP | B 149 | 42.536 | −30.443 | 20.304 | 1.00 | 52.08 | MOLB | O |
| ATOM | 3646 | C | ASP | B 149 | 43.458 | −34.628 | 22.775 | 1.00 | 37.46 | MOLB | C |
| ATOM | 3647 | O | ASP | B 149 | 44.361 | −35.256 | 22.281 | 1.00 | 40.19 | MOLB | O |
| ATOM | 3648 | N | ASN | B 150 | 43.216 | −34.718 | 24.063 | 1.00 | 38.46 | MOLB | N |
| ATOM | 3649 | CA | ASN | B 150 | 44.181 | −35.470 | 24.848 | 1.00 | 41.39 | MOLB | C |
| ATOM | 3650 | CB | ASN | B 150 | 44.429 | −34.827 | 26.222 | 1.00 | 39.15 | MOLB | C |
| ATOM | 3651 | CG | ASN | B 150 | 43.777 | −35.601 | 27.365 | 1.00 | 51.22 | MOLB | C |
| ATOM | 3652 | OD1 | ASN | B 150 | 43.603 | −35.074 | 28.477 | 1.00 | 65.69 | MOLB | O |
| ATOM | 3653 | ND2 | ASN | B 150 | 43.445 | −36.871 | 27.113 | 1.00 | 54.56 | MOLB | N |
| ATOM | 3654 | C | ASN | B 150 | 43.841 | −36.975 | 24.924 | 1.00 | 42.32 | MOLB | C |
| ATOM | 3655 | O | ASN | B 150 | 44.591 | −37.769 | 25.517 | 1.00 | 41.69 | MOLB | 0 |
| ATOM | 3656 | N | GLY | B 151 | 42.719 | −37.349 | 24.299 | 1.00 | 43.44 | MOLB | N |
| ATOM | 3657 | CA | GLY | B 151 | 42.238 | −38.735 | 24.261 | 1.00 | 41.55 | MOLB | C |
| ATOM | 3658 | C | GLY | B 151 | 41.648 | −39.263 | 25.563 | 1.00 | 43.65 | MOLB | C |
| ATOM | 3659 | O | GLY | B 151 | 41.602 | −40.465 | 25.796 | 1.00 | 46.46 | MOLB | O |
| ATOM | 3660 | N | THR | B 152 | 41.180 | −38.398 | 26.440 | 1.00 | 42.46 | MOLB | N |
| ATOM | 3661 | CA | THR | B 152 | 40.585 | −38.919 | 27.649 | 1.00 | 40.78 | MOLB | C |
| ATOM | 3662 | CB | THR | B 152 | 40.572 | −37.889 | 28.772 | 1.00 | 41.18 | MOLB | C |
| ATOM | 3663 | OG1 | THR | B 152 | 41.925 | −37.596 | 29.162 | 1.00 | 48.17 | MOLB | O |
| ATOM | 3664 | CG2 | THR | B 152 | 39.828 | −38.445 | 29.967 | 1.00 | 47.58 | MOLB | C |
| ATOM | 3665 | C | THR | B 152 | 39.180 | −39.425 | 27.406 | 1.00 | 38.24 | MOLB | C |
| ATOM | 3666 | O | THR | B 152 | 38.575 | −39.182 | 26.357 | 1.00 | 35.80 | MOLB | O |
| ATOM | 3667 | N | GLU | B 153 | 38.701 | −40.188 | 28.373 | 1.00 | 38.39 | MOLB | N |
| ATOM | 3668 | CA | GLU | B 153 | 37.337 | −40.645 | 28.376 | 1.00 | 41.65 | MOLB | C |
| ATOM | 3669 | CB | GLU | B 153 | 37.231 | −42.164 | 28.481 | 1.00 | 40.13 | MOLB | C |
| ATOM | 3670 | CG | GLU | B 153 | 38.104 | −42.778 | 29.546 | 1.00 | 47.45 | MOLB | C |
| ATOM | 3671 | CD | GLU | B 153 | 37.815 | −44.248 | 29.704 | 1.00 | 68.98 | MOLB | C |
| ATOM | 3672 | OE1 | GLU | B 153 | 38.715 | −45.083 | 29.429 | 1.00 | 74.79 | MOLB | O |
| ATOM | 3673 | OE2 | GLU | B 153 | 36.662 | −44.563 | 30.069 | 1.00 | 75.09 | MOLB | O |
| ATOM | 3674 | C | GLU | B 153 | 36.653 | −39.945 | 29.536 | 1.00 | 42.64 | MOLB | C |
| ATOM | 3675 | O | GLU | B 153 | 36.957 | −40.186 | 30.708 | 1.00 | 44.77 | MOLB | O |
| ATOM | 3676 | N | PHE | B 154 | 35.746 | −39.042 | 29.176 | 1.00 | 42.76 | MOLB | N |
| ATOM | 3677 | CA | PHE | B 154 | 35.037 | −38.202 | 30.116 | 1.00 | 38.91 | MOLB | C |
| ATOM | 3678 | CB | PHE | B 154 | 35.599 | −36.788 | 29.989 | 1.00 | 40.51 | MOLB | C |
| ATOM | 3679 | CG | PHE | B 154 | 35.463 | −36.200 | 28.589 | 1.00 | 44.98 | MOLB | C |
| ATOM | 3680 | CD1 | PHE | B 154 | 34.688 | −35.049 | 28.365 | 1.00 | 37.24 | MOLB | C |
| ATOM | 3681 | CE1 | PHE | B 154 | 34.531 | −34.520 | 27.070 | 1.00 | 28.76 | MOLB | C |
| ATOM | 3682 | CZ | PHE | B 154 | 35.159 | −35.134 | 26.004 | 1.00 | 41.17 | MOLB | C |
| ATOM | 3683 | CE2 | PHE | B 154 | 35.933 | −36.288 | 26.217 | 1.00 | 37.75 | MOLB | C |
| ATOM | 3684 | CD2 | PHE | B 154 | 36.078 | −36.815 | 27.496 | 1.00 | 28.31 | MOLB | C |
| ATOM | 3685 | C | PHE | B 154 | 33.598 | −38.177 | 29.709 | 1.00 | 35.01 | MOLB | C |
| ATOM | 3686 | O | PHE | B 154 | 33.287 | −38.348 | 28.547 | 1.00 | 31.30 | MOLB | O |
| ATOM | 3687 | N | SER | B 155 | 32.703 | −37.991 | 30.655 | 1.00 | 38.59 | MOLB | N |
| ATOM | 3688 | CA | SER | B 155 | 31.352 | −37.563 | 30.262 | 1.00 | 43.18 | MOLB | C |
| ATOM | 3689 | CB | SER | B 155 | 30.252 | −38.538 | 30.692 | 1.00 | 41.61 | MOLB | C |
| ATOM | 3690 | OG | SER | B 155 | 29.992 | −38.424 | 32.084 | 1.00 | 47.77 | MOLB | O |
| ATOM | 3691 | C | SER | B 155 | 31.146 | −36.203 | 30.910 | 1.00 | 42.88 | MOLB | C |
| ATOM | 3692 | O | SER | 8 155 | 31.692 | −35.938 | 31.984 | 1.00 | 43.83 | MOLB | O |
| ATOM | 3693 | N | VAL | B 156 | 30.372 | −35.342 | 30.268 | 1.00 | 43.67 | MOLB | N |
| ATOM | 3694 | CA | VAL | B 156 | 30.088 | −34.037 | 30.867 | 1.00 | 43.63 | MOLB | C |
| ATOM | 3695 | CB | VAL | B 156 | 30.406 | −32.902 | 29.893 | 1.00 | 44.05 | MOLB | C |
| ATOM | 3696 | CG1 | VAL | B 156 | 29.802 | −31.608 | 30.413 | 1.00 | 40.05 | MOLB | C |
| ATOM | 3697 | CG2 | VAL | B 156 | 31.925 | −32.774 | 29.688 | 1.00 | 38.25 | MOLB | C |
| ATOM | 3698 | C | VAL | B 156 | 28.651 | −33.853 | 31.336 | 1.00 | 44.06 | MOLB | C |
| ATOM | 3699 | O | VAL | B 156 | 27.707 | −33.979 | 30.553 | 1.00 | 42.14 | MOLB | O |
| ATOM | 3700 | N | LYS | B 157 | 28.489 | −33.531 | 32.610 | 1.00 | 47.28 | MOLB | N |
| ATOM | 3701 | CA | LYS | B 157 | 27.159 | −33.142 | 33.129 | 1.00 | 52.43 | MOLB | C |
| ATOM | 3702 | CB | LYS | B 157 | 26.550 | −34.240 | 34.029 | 1.00 | 52.88 | MOLB | C |
| ATOM | 3703 | CG | LYS | B 157 | 27.532 | −34.933 | 34.995 | 1.00 | 58.76 | MOLB | C |
| ATOM | 3704 | CD | LYS | B 157 | 27.110 | −36.383 | 35.326 | 1.00 | 58.17 | MOLB | C |
| ATOM | 3705 | CE | LYS | B 157 | 28.190 | −37.090 | 36.168 | 1.00 | 65.38 | MOLB | C |
| ATOM | 3706 | NZ | LYS | B 157 | 27.757 | −38.399 | 36.749 | 1.00 | 54.58 | MOLB | N |
| ATOM | 3707 | C | LYS | B 157 | 27.157 | −31.734 | 33.797 | 1.00 | 52.26 | MOLB | C |
| ATOM | 3708 | O | LYS | B 157 | 28.192 | −31.261 | 34.303 | 1.00 | 52.48 | MOLB | O |
| ATOM | 3709 | N | VAL | B 158 | 25.997 | −31.071 | 33.780 | 1.00 | 51.66 | MOLB | N |
| ATOM | 3710 | CA | VAL | B 158 | 25.887 | −29.687 | 34.237 | 1.00 | 50.25 | MOLB | C |
| ATOM | 3711 | CB | VAL | B 158 | 25.863 | −28.747 | 33.047 | 1.00 | 50.40 | MOLB | C |
| ATOM | 3712 | CG1 | VAL | B 158 | 27.077 | −28.974 | 32.153 | 1.00 | 52.05 | MOLB | C |
| ATOM | 3713 | CG2 | VAL | B 158 | 24.572 | −28.965 | 32.267 | 1.00 | 41.75 | MOLB | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3714 | C | VAL | B 158 | 24.580 | −29.388 | 34.927 | 1.00 | 51.24 | MOLB C |
| ATOM | 3715 | O | VAL | B 158 | 23.521 | −29.832 | 34.488 | 1.00 | 51.26 | MOLB O |
| ATOM | 3716 | N | SER | B 159 | 24.630 | −28.579 | 35.970 | 1.00 | 50.49 | MOLB N |
| ATOM | 3717 | CA | SER | B 159 | 23.399 | −28.125 | 36.550 | 1.00 | 50.41 | MOLB C |
| ATOM | 3718 | CB | SER | B 159 | 23.244 | −28.735 | 37.923 | 1.00 | 51.01 | MOLB C |
| ATOM | 3719 | OG | SER | B 159 | 24.334 | −28.366 | 38.743 | 1.00 | 51.68 | MOLB O |
| ATOM | 3720 | C | SER | B 159 | 23.365 | −26.604 | 36.656 | 1.00 | 51.18 | MOLB C |
| ATOM | 3721 | O | SER | B 159 | 24.319 | −25.991 | 37.122 | 1.00 | 50.81 | MOLB O |
| ATOM | 3722 | N | LEU | B 160 | 22.257 | −26.005 | 36.220 | 1.00 | 51.46 | MOLB N |
| ATOM | 3723 | CA | LEU | B 160 | 21.991 | −24.583 | 36.440 | 1.00 | 49.76 | MOLB C |
| ATOM | 3724 | CB | LEU | B 160 | 21.643 | −23.860 | 35.130 | 1.00 | 51.32 | MOLB C |
| ATOM | 3725 | CG | LEU | B 160 | 20.987 | −22.458 | 35.268 | 1.00 | 47.59 | MOLB C |
| ATOM | 3726 | CD1 | LEU | B 160 | 21.926 | −21.441 | 35.920 | 1.00 | 52.75 | MOLB C |
| ATOM | 3727 | CD2 | LEU | B 160 | 20.506 | −21.922 | 33.949 | 1.00 | 42.39 | MOLB C |
| ATOM | 3728 | C | LEU | B 160 | 20.835 | −24.388 | 37.402 | 1.00 | 51.28 | MOLB C |
| ATOM | 3729 | O | LEU | B 160 | 19.751 | −24.889 | 37.152 | 1.00 | 54.80 | MOLB O |
| ATOM | 3730 | N | LEU | B 161 | 21.036 | −23.609 | 38.461 | 1.00 | 51.60 | MOLB N |
| ATOM | 3731 | CA | LEU | B 161 | 19.984 | −23.359 | 39.454 | 1.00 | 52.20 | MOLB C |
| ATOM | 3732 | CB | LEU | B 161 | 20.184 | −24.305 | 40.624 | 1.00 | 51.77 | MOLB C |
| ATOM | 3733 | CG | LEU | B 161 | 21.536 | −24.015 | 41.287 | 1.00 | 48.15 | MOLB C |
| ATOM | 3734 | CD1 | LEU | B 161 | 21.445 | −24.159 | 42.784 | 1.00 | 35.27 | MOLB C |
| ATOM | 3735 | CD2 | LEU | B 161 | 22.694 | −24.848 | 40.675 | 1.00 | 55.28 | MOLB C |
| ATOM | 3736 | C | LEU | B 161 | 20.033 | −21.927 | 40.014 | 1.00 | 54.46 | MOLB C |
| ATOM | 3737 | O | LEU | B 161 | 21.089 | −21.497 | 40.502 | 1.00 | 55.36 | MOLB O |
| ATOM | 3738 | N | GLU | B 162 | 18.898 | −21.215 | 39.976 | 1.00 | 54.88 | MOLB N |
| ATOM | 3739 | CA | GLU | B 162 | 18.775 | −19.830 | 40.483 | 1.00 | 54.81 | MOLB C |
| ATOM | 3740 | CB | GLU | B 162 | 17.575 | −19.156 | 39.810 | 1.00 | 53.11 | MOLB C |
| ATOM | 3741 | CG | GLU | B 162 | 17.669 | −17.638 | 39.563 | 1.00 | 57.85 | MOLB C |
| ATOM | 3742 | CD | GLU | B 162 | 16.288 | −16.977 | 39.214 | 1.00 | 59.59 | MOLB C |
| ATOM | 3743 | OE1 | GLU | B 162 | 16.137 | −16.416 | 38.099 | 1.00 | 56.46 | MOLB O |
| ATOM | 3744 | OE2 | GLU | B 162 | 15.354 | −17.018 | 40.060 | 1.00 | 64.97 | MOLB O |
| ATOM | 3745 | C | GLU | B 162 | 18.594 | −19.845 | 42.012 | 1.00 | 53.48 | MOLB C |
| ATOM | 3746 | O | GLU | B 162 | 18.129 | −20.836 | 42.551 | 1.00 | 53.08 | MOLB O |
| ATOM | 3747 | N | ILE | B 163 | 19.024 | −18.781 | 42.698 | 1.00 | 53.84 | MOLB N |
| ATOM | 3748 | CA | ILE | B 163 | 18.765 | −18.569 | 44.134 | 1.00 | 53.98 | MOLB C |
| ATOM | 3749 | CB | ILE | B 163 | 19.988 | −18.334 | 45.003 | 1.00 | 52.45 | MOLB C |
| ATOM | 3750 | CG1 | ILE | B 163 | 20.733 | −19.609 | 45.337 | 1.00 | 52.27 | MOLB C |
| ATOM | 3751 | CD1 | ILE | B 163 | 21.985 | −19.330 | 46.171 | 1.00 | 38.63 | MOLB C |
| ATOM | 3752 | CG2 | ILE | B 163 | 19.549 | −17.716 | 46.323 | 1.00 | 45.81 | MOLB C |
| ATOM | 3753 | C | ILE | B 163 | 18.117 | −17.222 | 44.234 | 1.00 | 57.58 | MOLB C |
| ATOM | 3754 | O | ILE | B 163 | 18.684 | −16.222 | 43.814 | 1.00 | 56.89 | MOLB O |
| ATOM | 3755 | N | TYR | B 164 | 16.952 | −17.187 | 44.848 | 1.00 | 62.52 | MOLB N |
| ATOM | 3756 | CA | TYR | B 164 | 16.201 | −15.965 | 44.944 | 1.00 | 65.92 | MOLB C |
| ATOM | 3757 | CB | TYR | B 164 | 15.135 | −15.937 | 43.858 | 1.00 | 66.14 | MOLB C |
| ATOM | 3758 | CG | TYR | B 164 | 14.253 | −14.729 | 43.919 | 1.00 | 66.32 | MOLB C |
| ATOM | 3759 | CD1 | TYR | B 164 | 13.471 | −14.472 | 45.033 | 1.00 | 72.10 | MOLB C |
| ATOM | 3760 | CE1 | TYR | B 164 | 12.659 | −13.360 | 45.089 | 1.00 | 77.58 | MOLB C |
| ATOM | 3761 | CZ | TYR | B 164 | 12.614 | −12.503 | 44.010 | 1.00 | 73.11 | MOLB C |
| ATOM | 3762 | OH | TYR | B 164 | 11.810 | −11.398 | 44.046 | 1.00 | 73.88 | MOLB O |
| ATOM | 3763 | CE2 | TYR | B 164 | 13.376 | −12.741 | 42.895 | 1.00 | 73.21 | MOLB C |
| ATOM | 3764 | CD2 | TYR | B 164 | 14.188 | −13.850 | 42.855 | 1.00 | 72.53 | MOLB C |
| ATOM | 3765 | C | TYR | B 164 | 15.550 | −15.906 | 46.306 | 1.00 | 67.92 | MOLB C |
| ATOM | 3766 | O | TYR | B 164 | 14.636 | −16.676 | 46.603 | 1.00 | 68.81 | MOLB O |
| ATOM | 3767 | N | ASN | B 165 | 16.023 | −14.995 | 47.141 | 1.00 | 70.07 | MOLB N |
| ATOM | 3768 | CA | ASN | B 165 | 15.408 | −14.825 | 48.426 | 1.00 | 72.38 | MOLB C |
| ATOM | 3769 | CB | ASN | B 165 | 13.957 | −14.428 | 48.213 | 1.00 | 72.96 | MOLB C |
| ATOM | 3770 | CG | ASN | B 165 | 13.354 | −13.797 | 49.424 | 1.00 | 78.21 | MOLB C |
| ATOM | 3771 | OD1 | ASN | B 165 | 13.967 | −13.774 | 50.498 | 1.00 | 82.63 | MOLB O |
| ATOM | 3772 | ND2 | ASN | B 165 | 12.141 | −13.269 | 49.269 | 1.00 | 84.85 | MOLB N |
| ATOM | 3773 | C | ASN | B 165 | 15.491 | −16.146 | 49.170 | 1.00 | 72.68 | MOLB C |
| ATOM | 3774 | O | ASN | B 165 | 14.486 | −16.825 | 49.356 | 1.00 | 72.45 | MOLB O |
| ATOM | 3775 | N | GLU | B 166 | 16.713 | −16.494 | 49.568 | 1.00 | 74.77 | MOLB N |
| ATOM | 3776 | CA | GLU | B 166 | 17.066 | −17.781 | 50.206 | 1.00 | 76.79 | MOLB C |
| ATOM | 3777 | CB | GLU | B 166 | 17.157 | −17.627 | 51.737 | 1.00 | 77.06 | MOLB C |
| ATOM | 3778 | CG | GLU | B 166 | 18.410 | −16.843 | 52.203 | 1.00 | 85.88 | MOLB C |
| ATOM | 3779 | CD | GLU | B 166 | 19.670 | −17.736 | 52.342 | 1.00 | 102.90 | MOLB C |
| ATOM | 3780 | OE1 | GLU | B 166 | 19.616 | −18.700 | 53.147 | 1.00 | 106.69 | MOLB O |
| ATOM | 3781 | OE2 | GLU | B 166 | 20.717 | −17.467 | 51.679 | 1.00 | 103.65 | MOLB O |
| ATOM | 3782 | C | GLU | B 166 | 16.225 | −19.008 | 49.764 | 1.00 | 76.40 | MOLB C |
| ATOM | 3783 | O | GLU | B 166 | 16.119 | −20.011 | 50.476 | 1.00 | 76.32 | MOLB O |
| ATOM | 3784 | N | GLU | B 167 | 15.673 | −18.917 | 48.558 | 1.00 | 76.77 | MOLB N |
| ATOM | 3785 | CA | GLU | B 167 | 14.820 | −19.947 | 47.980 | 1.00 | 76.89 | MOLB C |
| ATOM | 3786 | CB | GLU | B 167 | 13.509 | −19.293 | 47.579 | 1.00 | 76.12 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 3787 | CG | GLU | B 167 | 12.275 | −19.962 | 48.093 | 1.00 | 77.96 | MOLB | C |
| ATOM | 3788 | CO | GLU | B 167 | 11.036 | −19.270 | 47.591 | 1.00 | 83.71 | MOLB | C |
| ATOM | 3789 | OE1 | GLU | B 167 | 11.183 | −18.208 | 46.936 | 1.00 | 79.49 | MOLB | O |
| ATOM | 3790 | OE2 | GLU | B 167 | 9.923 | −19.789 | 47.842 | 1.00 | 89.63 | MOLB | O |
| ATOM | 3791 | C | GLU | B 167 | 15.543 | −20.456 | 46.734 | 1.00 | 76.52 | MOLB | C |
| ATOM | 3792 | O | GLU | B 167 | 16.131 | −19.649 | 46.011 | 1.00 | 77.86 | MOLB | O |
| ATOM | 3793 | N | LEU | B 168 | 15.510 | −21.767 | 46.466 | 1.00 | 74.31 | MOLB | N |
| ATOM | 3794 | CA | LEU | B 168 | 16.292 | −22.328 | 45.343 | 1.00 | 70.89 | MOLB | C |
| ATOM | 3795 | CB | LEU | B 168 | 17.245 | −23.411 | 45.841 | 1.00 | 69.59 | MOLB | C |
| ATOM | 3796 | CG | LEU | B 168 | 18.087 | −22.973 | 47.038 | 1.00 | 70.28 | MOLB | C |
| ATOM | 3797 | CD1 | LEU | B 168 | 17.161 | −22.843 | 48.250 | 1.00 | 67.74 | MOLB | C |
| ATOM | 3798 | CD2 | LEU | B 168 | 19.244 | −23.944 | 47.314 | 1.00 | 61.95 | MOLB | C |
| ATOM | 3799 | C | LEU | B 168 | 15.442 | −22.869 | 44.209 | 1.00 | 70.00 | MOLB | C |
| ATOM | 3800 | O | LEU | B 168 | 14.429 | −23.506 | 44.460 | 1.00 | 72.14 | MOLB | O |
| ATOM | 3801 | N | PHE | B 169 | 15.855 | −22.638 | 42.963 | 1.00 | 68.08 | MOLB | N |
| ATOM | 3802 | CA | PHE | B 169 | 15.066 | −23.103 | 41.818 | 1.00 | 66.35 | MOLB | C |
| ATOM | 3803 | CB | PHE | B 169 | 14.194 | −21.967 | 41.276 | 1.00 | 65.86 | MOLB | C |
| ATOM | 3804 | CG | PHE | B 169 | 13.569 | −21.105 | 42.342 | 1.00 | 66.40 | MOLB | C |
| ATOM | 3805 | CD1 | PHE | B 169 | 13.744 | −19.730 | 42.327 | 1.00 | 68.96 | MOLB | C |
| ATOM | 3806 | CE1 | PHE | B 169 | 13.174 | −18.928 | 43.299 | 1.00 | 63.30 | MOLB | C |
| ATOM | 3807 | CZ | PHE | B 169 | 12.423 | −19.494 | 44.297 | 1.00 | 67.14 | MOLB | C |
| ATOM | 3808 | CE2 | PHE | B 169 | 12.242 | −20.862 | 44.328 | 1.00 | 69.52 | MOLB | C |
| ATOM | 3809 | CD2 | PHE | B 169 | 12.808 | −21.660 | 43.355 | 1.00 | 67.41 | MOLB | C |
| ATOM | 3810 | C | PHE | B 169 | 15.872 | −23.733 | 40.663 | 1.00 | 66.27 | MOLB | C |
| ATOM | 3811 | O | PHE | B 169 | 16.818 | −23.126 | 40.147 | 1.00 | 67.57 | MOLB | O |
| ATOM | 3812 | N | ASP | B 170 | 15.486 | −24.942 | 40.245 | 1.00 | 65.17 | MOLB | N |
| ATOM | 3813 | CA | ASP | B 170 | 16.131 | −25.608 | 39.098 | 1.00 | 63.55 | MOLB | C |
| ATOM | 3814 | CB | ASP | B 170 | 16.006 | −27.136 | 39.180 | 1.00 | 62.65 | MOLB | C |
| ATOM | 3815 | CG | ASP | B 170 | 16.672 | −27.837 | 38.005 | 1.00 | 67.94 | MOLB | C |
| ATOM | 3816 | OD1 | ASP | B 170 | 16.353 | −27.525 | 36.835 | 1.00 | 65.57 | MOLB | O |
| ATOM | 3817 | OD2 | ASP | B 170 | 17.526 | −28.710 | 38.256 | 1.00 | 81.68 | MOLB | O |
| ATOM | 3818 | C | ASP | B 170 | 15.597 | −25.086 | 37.749 | 1.00 | 61.09 | MOLB | C |
| ATOM | 3819 | O | ASP | B 170 | 14.386 | −25.018 | 37.533 | 1.00 | 59.31 | MOLB | O |
| ATOM | 3820 | N | LEU | B 171 | 16.515 | −24.749 | 36.840 | 1.00 | 59.42 | MOLB | N |
| ATOM | 3821 | CA | LEU | B 171 | 16.140 | −24.096 | 35.596 | 1.00 | 55.78 | MOLB | C |
| ATOM | 3822 | CB | LEU | B 171 | 16.910 | −22.787 | 35.444 | 1.00 | 53.93 | MOLB | C |
| ATOM | 3823 | CG | LEU | B 171 | 16.701 | −21.780 | 36.600 | 1.00 | 50.11 | MOLB | C |
| ATOM | 3824 | CD1 | LEU | B 171 | 17.480 | −20.487 | 36.410 | 1.00 | 31.35 | MOLB | C |
| ATOM | 3825 | CD2 | LEU | B 171 | 15.240 | −21.430 | 36.821 | 1.00 | 40.59 | MOLB | C |
| ATOM | 3826 | C | LEU | B 171 | 16.230 | −24.966 | 34.341 | 1.00 | 57.01 | MOLB | C |
| ATOM | 3827 | O | LEU | B 171 | 15.501 | −24.688 | 33.376 | 1.00 | 55.70 | MOLB | O |
| ATOM | 3828 | N | LEU | B 172 | 17.082 | −26.011 | 34.355 | 1.00 | 57.52 | MOLB | N |
| ATOM | 3829 | CA | LEU | B 172 | 17.217 | −26.954 | 33.199 | 1.00 | 57.21 | MOLB | C |
| ATOM | 3830 | CB | LEU | B 172 | 18.593 | −27.637 | 33.137 | 1.00 | 57.78 | MOLB | C |
| ATOM | 3831 | CG | LEU | B 172 | 19.949 | −26.940 | 33.131 | 1.00 | 55.16 | MOLB | C |
| ATOM | 3832 | CD1 | LEU | B 172 | 19.734 | −25.457 | 32.985 | 1.00 | 53.59 | MOLB | C |
| ATOM | 3833 | CD2 | LEU | B 172 | 20.725 | −27.264 | 34.400 | 1.00 | 48.41 | MOLB | C |
| ATOM | 3834 | C | LEU | B 172 | 16.161 | −28.068 | 33.146 | 1.00 | 57.52 | MOLB | C |
| ATOM | 3835 | O | LEU | B 172 | 15.827 | −28.581 | 32.062 | 1.00 | 55.91 | MOLB | O |
| ATOM | 3836 | N | ASN | B 173 | 15.697 | −28.468 | 34.330 | 1.00 | 58.38 | MOLB | N |
| ATOM | 3837 | CA | ASN | B 173 | 14.646 | −29.465 | 34.508 | 1.00 | 58.78 | MOLB | C |
| ATOM | 3838 | CB | ASN | B 173 | 14.451 | −29.681 | 36.006 | 1.00 | 59.65 | MOLB | C |
| ATOM | 3839 | CG | ASN | B 173 | 13.091 | −30.243 | 36.355 | 1.00 | 59.53 | MOLB | C |
| ATOM | 3840 | OD1 | ASN | B 173 | 12.843 | −30.583 | 37.516 | 1.00 | 52.87 | MOLB | O |
| ATOM | 3841 | ND2 | ASN | B 173 | 12.201 | −30.337 | 35.364 | 1.00 | 36.75 | MOLB | N |
| ATOM | 3842 | C | ASN | B 173 | 13.332 | −29.066 | 33.815 | 1.00 | 58.76 | MOLB | C |
| ATOM | 3843 | O | ASN | B 173 | 12.653 | −28.146 | 34.260 | 1.00 | 55.73 | MOLB | O |
| ATOM | 3844 | N | PRO | B 174 | 12.944 | −29.815 | 32.762 | 1.00 | 61.14 | MOLB | N |
| ATOM | 3845 | CA | PRO | B 174 | 11.891 | −29.417 | 31.822 | 1.00 | 63.02 | MOLB | C |
| ATOM | 3846 | CB | PRO | B 174 | 12.137 | −30.345 | 30.628 | 1.00 | 62.43 | MOLB | C |
| ATOM | 3847 | CG | PRO | B 174 | 12.694 | −31.597 | 31.230 | 1.00 | 59.01 | MOLB | C |
| ATOM | 3848 | CD | PRO | B 174 | 13.445 | −31.179 | 32.480 | 1.00 | 61.20 | MOLB | C |
| ATOM | 3849 | C | PRO | B 174 | 10.520 | −29.685 | 32.414 | 1.00 | 66.20 | MOLB | C |
| ATOM | 3850 | O | PRO | B 174 | 9.687 | −28.778 | 32.531 | 1.00 | 64.85 | MOLB | O |
| ATOM | 3851 | N | SER | B 175 | 10.327 | −30.954 | 32.768 | 1.00 | 70.64 | MOLB | N |
| ATOM | 3852 | CA | SER | B 175 | 9.183 | −31.457 | 33.503 | 1.00 | 73.84 | MOLB | C |
| ATOM | 3853 | CB | SER | B 175 | 9.534 | −32.859 | 34.015 | 1.00 | 73.50 | MOLB | C |
| ATOM | 3854 | OG | SER | B 175 | 9.121 | −33.051 | 35.354 | 1.00 | 69.51 | MOLB | O |
| ATOM | 3855 | C | SER | B 175 | 8.780 | −30.561 | 34.673 | 1.00 | 77.21 | MOLB | C |
| ATOM | 3856 | O | SER | B 175 | 7.602 | −30.497 | 35.024 | 1.00 | 78.02 | MOLB | O |
| ATOM | 3857 | N | SER | B 176 | 9.753 | −29.859 | 35.255 | 1.00 | 80.82 | MOLB | N |
| ATOM | 3858 | CA | SER | B 176 | 9.531 | −29.079 | 36.482 | 1.00 | 84.68 | MOLB | C |
| ATOM | 3859 | CB | SER | B 176 | 10.856 | −28.813 | 37.217 | 1.00 | 85.57 | MOLB | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 3860 | OG | SER | B 176 | 10.641 | −28.313 | 38.536 | 1.00 | 85.60 | MOLB O |
| ATOM | 3861 | C | SER | B 176 | 8.779 | −27.761 | 36.328 | 1.00 | 86.84 | MOLB C |
| ATOM | 3862 | O | SER | B 176 | 9.094 | −26.924 | 35.466 | 1.00 | 86.32 | MOLB O |
| ATOM | 3863 | N | ASP | B 177 | 7.803 | −27.593 | 37.217 | 1.00 | 89.11 | MOLB N |
| ATOM | 3864 | CA | ASP | B 177 | 7.021 | −26.381 | 37.342 | 1.00 | 91.49 | MOLB C |
| ATOM | 3865 | CB | ASP | B 177 | 5.654 | −26.741 | 37.908 | 1.00 | 91.61 | MOLB C |
| ATOM | 3866 | CG | ASP | B 177 | 4.609 | −25.710 | 37.587 | 1.00 | 94.42 | MOLB C |
| ATOM | 3867 | OD1 | ASP | B 177 | 4.583 | −25.266 | 36.417 | 1.00 | 97.57 | MOLB O |
| ATOM | 3868 | OD2 | ASP | B 177 | 3.816 | −25.354 | 38.492 | 1.00 | 93.57 | MOLB O |
| ATOM | 3869 | C | ASP | B 177 | 7.745 | −25.459 | 38.320 | 1.00 | 92.89 | MOLB C |
| ATOM | 3870 | O | ASP | B 177 | 7.876 | −25.805 | 39.496 | 1.00 | 93.93 | MOLB O |
| ATOM | 3871 | N | VAL | B 178 | 8.202 | −24.295 | 37.845 | 1.00 | 93.75 | MOLB N |
| ATOM | 3872 | CA | VAL | B 178 | 9.034 | −23.355 | 38.648 | 1.00 | 94.37 | MOLB C |
| ATOM | 3873 | CB | VAL | B 178 | 9.198 | −21.956 | 37.971 | 1.00 | 94.50 | MOLB C |
| ATOM | 3874 | CG1 | VAL | B 178 | 10.190 | −22.017 | 36.811 | 1.00 | 95.47 | MOLB C |
| ATOM | 3875 | CG2 | VAL | B 178 | 7.830 | −21.372 | 37.552 | 1.00 | 94.87 | MOLB C |
| ATOM | 3876 | C | VAL | B 178 | 8.631 | −23.093 | 40.107 | 1.00 | 94.18 | MOLB C |
| ATOM | 3877 | O | VAL | B 178 | 9.513 | −22.883 | 40.955 | 1.00 | 93.98 | MOLB O |
| ATOM | 3878 | N | SER | B 179 | 7.322 | −23.088 | 40.389 | 1.00 | 94.19 | MOLB N |
| ATOM | 3879 | CA | SER | B 179 | 6.795 | −22.830 | 41.751 | 1.00 | 93.64 | MOLB C |
| ATOM | 3880 | CB | SER | B 179 | 5.264 | −23.035 | 41.815 | 1.00 | 93.53 | MOLB C |
| ATOM | 3881 | OG | SER | B 179 | 4.883 | −24.383 | 41.584 | 1.00 | 90.92 | MOLB O |
| ATOM | 3882 | C | SER | B 179 | 7.510 | −23.640 | 42.853 | 1.00 | 93.17 | MOLB C |
| ATOM | 3883 | O | SER | B 179 | 7.430 | −23.296 | 44.038 | 1.00 | 93.35 | MOLB O |
| ATOM | 3884 | N | GLU | B 180 | 8.219 | −24.691 | 42.428 | 1.00 | 91.00 | MOLB N |
| ATOM | 3885 | CA | GLU | B 180 | 8.953 | −25.605 | 43.289 | 1.00 | 88.81 | MOLB C |
| ATOM | 3886 | CB | GLU | B 180 | 9.308 | −26.854 | 42.499 | 1.00 | 88.42 | MOLB C |
| ATOM | 3887 | CG | GLU | B 180 | 8.185 | −27.814 | 42.210 | 1.00 | 87.93 | MOLB C |
| ATOM | 3888 | CD | GLU | B 180 | 8.737 | −29.113 | 41.675 | 1.00 | 84.29 | MOLB C |
| ATOM | 3889 | OE1 | GLU | B 180 | 7.945 | −29.977 | 41.233 | 1.00 | 71.81 | MOLB O |
| ATOM | 3890 | OE2 | GLU | B 180 | 9.984 | −29.257 | 41.697 | 1.00 | 82.04 | MOLB O |
| ATOM | 3891 | C | GLU | B 180 | 10.274 | −25.084 | 43.812 | 1.00 | 88.40 | MOLB C |
| ATOM | 3892 | O | GLU | B 180 | 11.155 | −24.720 | 43.033 | 1.00 | 89.14 | MOLB O |
| ATOM | 3893 | N | ARG | B 181 | 10.422 | −25.083 | 45.130 | 1.00 | 87.55 | MOLB N |
| ATOM | 3894 | CA | ARG | B 181 | 11.722 | −24.888 | 45.745 | 1.00 | 88.23 | MOLB C |
| ATOM | 3895 | CB | ARG | B 181 | 11.602 | −24.266 | 47.137 | 1.00 | 88.81 | MOLB C |
| ATOM | 3896 | CG | ARG | B 181 | 11.459 | −22.764 | 47.184 | 1.00 | 92.38 | MOLB C |
| ATOM | 3897 | CD | ARG | B 181 | 10.186 | −22.286 | 46.496 | 1.00 | 102.07 | MOLB C |
| ATOM | 3898 | NE | ARG | B 181 | 8.987 | −22.947 | 47.000 | 1.00 | 106.12 | MOLB N |
| ATOM | 3899 | CZ | ARG | B 181 | 7.749 | −22.551 | 46.727 | 1.00 | 107.67 | MOLB C |
| ATOM | 3900 | NH1 | ARG | B 181 | 7.544 | −21.485 | 45.960 | 1.00 | 104.43 | MOLB N |
| ATOM | 3901 | NH2 | ARG | B 181 | 6.717 | −23.222 | 47.221 | 1.00 | 109.20 | MOLB N |
| ATOM | 3902 | C | ARG | B 181 | 12.305 | −26.270 | 45.912 | 1.00 | 87.59 | MOLB C |
| ATOM | 3903 | O | ARG | B 181 | 11.664 | −27.137 | 46.487 | 1.00 | 88.60 | MOLB O |
| ATOM | 3904 | N | LEU | B 182 | 13.508 | −26.505 | 45.416 | 1.00 | 86.82 | MOLB N |
| ATOM | 3905 | CA | LEU | B 182 | 14.128 | −27.788 | 45.693 | 1.00 | 85.41 | MOLB C |
| ATOM | 3906 | CB | LEU | B 182 | 15.114 | −28.208 | 44.588 | 1.00 | 85.23 | MOLB C |
| ATOM | 3907 | CG | LEU | B 182 | 14.646 | −28.102 | 43.108 | 1.00 | 82.23 | MOLB C |
| ATOM | 3908 | CD1 | LEU | B 182 | 15.114 | −29.296 | 42.295 | 1.00 | 66.93 | MOLB C |
| ATOM | 3909 | CD2 | LEU | B 182 | 13.127 | −27.968 | 42.919 | 1.00 | 77.18 | MOLB C |
| ATOM | 3910 | C | LEU | B 182 | 14.745 | −27.624 | 47.084 | 1.00 | 85.34 | MOLB C |
| ATOM | 3911 | O | LEU | B 182 | 14.967 | −26.489 | 47.518 | 1.00 | 84.06 | MOLB O |
| ATOM | 3912 | N | GLN | B 183 | 14.975 | −28.740 | 47.787 | 1.00 | 85.90 | MOLB N |
| ATOM | 3913 | CA | GLN | B 183 | 15.355 | −28.743 | 49.223 | 1.00 | 85.91 | MOLB C |
| ATOM | 3914 | CB | GLN | B 183 | 14.578 | −29.855 | 49.940 | 1.00 | 86.99 | MOLB C |
| ATOM | 3915 | CG | GLN | B 183 | 13.359 | −30.445 | 49.172 | 1.00 | 92.21 | MOLB C |
| ATOM | 3916 | CD | GLN | B 183 | 12.013 | −29.763 | 49.477 | 1.00 | 105.57 | MOLB C |
| ATOM | 3917 | OE1 | GLN | B 183 | 10.945 | −30.376 | 49.322 | 1.00 | 108.46 | MOLB O |
| ATOM | 3918 | NE2 | GLN | B 183 | 12.060 | −28.504 | 49.911 | 1.00 | 105.70 | MOLB N |
| ATOM | 3919 | C | GLN | B 183 | 16.861 | −28.962 | 49.469 | 1.00 | 84.50 | MOLB C |
| ATOM | 3920 | O | GLN | B 183 | 17.524 | −29.579 | 48.639 | 1.00 | 85.57 | MOLB O |
| ATOM | 3921 | N | MET | B 184 | 17.392 | −28.526 | 50.615 | 1.00 | 83.24 | MOLB N |
| ATOM | 3922 | CA | MET | B 184 | 18.853 | −28.611 | 50.874 | 1.00 | 83.96 | MOLB C |
| ATOM | 3923 | CB | MET | B 184 | 19.403 | −27.185 | 51.042 | 1.00 | 83.44 | MOLB C |
| ATOM | 3924 | CG | MET | B 184 | 20.928 | −27.072 | 51.127 | 1.00 | 87.19 | MOLB C |
| ATOM | 3925 | SD | MET | B 184 | 21.562 | −25.384 | 51.391 | 1.00 | 87.11 | MOLB S |
| ATOM | 3926 | CE | MET | B 184 | 20.886 | −24.990 | 53.012 | 1.00 | 86.82 | MOLB C |
| ATOM | 3927 | C | MET | B 184 | 19.336 | −29.529 | 52.039 | 1.00 | 82.78 | MOLB C |
| ATOM | 3928 | O | MET | B 184 | 19.062 | −29.250 | 53.203 | 1.00 | 81.95 | MOLB O |
| ATOM | 3929 | N | PHE | B 185 | 20.085 | −30.592 | 51.717 | 1.00 | 84.06 | MOLB N |
| ATOM | 3930 | CA | PHE | B 185 | 20.603 | −31.580 | 52.715 | 1.00 | 85.88 | MOLB C |
| ATOM | 3931 | CB | PHE | B 185 | 20.144 | −33.013 | 52.378 | 1.00 | 86.47 | MOLB C |
| ATOM | 3932 | CG | PHE | B 185 | 18.661 | −33.261 | 52.508 | 1.00 | 90.65 | MOLB C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 3933 | CD1 | PHE | B 185 | 17.904 | −33.609 | 51.383 | 1.00 | 97.52 | MOLB C |
| ATOM | 3934 | CE1 | PHE | B 185 | 16.531 | −33.867 | 51.483 | 1.00 | 98.73 | MOLB C |
| ATOM | 3935 | CZ | PHE | B 185 | 15.905 | −33.796 | 52.724 | 1.00 | 97.00 | MOLB C |
| ATOM | 3936 | CE2 | PHE | B 185 | 16.654 | −33.464 | 53.866 | 1.00 | 97.82 | MOLB C |
| ATOM | 3937 | CD2 | PHE | B 185 | 18.028 | −33.206 | 53.752 | 1.00 | 96.49 | MOLB C |
| ATOM | 3938 | C | PHE | B 18S | 22.146 | −31.682 | 52.841 | 1.00 | 86.47 | MOLB C |
| ATOM | 3939 | O | PHE | B 185 | 22.830 | −31.904 | 51.835 | 1.00 | 85.56 | MOLB O |
| ATOM | 3940 | N | ASP | B 186 | 22.685 | −31.585 | 54.064 | 1.00 | 86.89 | MOLB N |
| ATOM | 3941 | CA | ASP | B 186 | 24.120 | −31.850 | 54.305 | 1.00 | 88.24 | MOLB C |
| ATOM | 3942 | CB | ASP | B 186 | 24.523 | −31.467 | 55.727 | 1.00 | 87.88 | MOLB C |
| ATOM | 3943 | CG | ASP | B 186 | 24.800 | −29.992 | 55.880 | 1.00 | 86.63 | MOLB C |
| ATOM | 3944 | OD1 | ASP | B 186 | 24.845 | −29.525 | 57.037 | 1.00 | 76.38 | MOLB O |
| ATOM | 3945 | OD2 | ASP | B 186 | 24.982 | −29.301 | 54.853 | 1.00 | 88.77 | MOLB O |
| ATOM | 3946 | C | ASP | B 186 | 24.422 | −33.330 | 54.083 | 1.00 | 89.39 | MOLB C |
| ATOM | 3947 | O | ASP | B 186 | 23.828 | −34.184 | 54.732 | 1.00 | 89.91 | MOLB O |
| ATOM | 3948 | N | ASP | B 187 | 25.360 | −33.643 | 53.197 | 1.00 | 91.17 | MOLB N |
| ATOM | 3949 | CA | ASP | B 187 | 25.525 | −35.040 | 52.754 | 1.00 | 93.33 | MOLB C |
| ATOM | 3950 | CB | ASP | B 187 | 26.153 | −35.130 | 51.342 | 1.00 | 94.17 | MOLB C |
| ATOM | 3951 | CG | ASP | B 187 | 27.636 | −34.760 | 51.313 | 1.00 | 92.19 | MOLB C |
| ATOM | 3952 | OD1 | ASP | B 187 | 28.010 | −33.714 | 51.883 | 1.00 | 84.97 | MOLB O |
| ATOM | 3953 | OD2 | ASP | B 187 | 28.420 | −35.508 | 50.686 | 1.00 | 90.91 | MOLB O |
| ATOM | 3954 | C | ASP | B 187 | 26.247 | −35.998 | 53.699 | 1.00 | 94.82 | MOLB C |
| ATOM | 3955 | O | ASP | B 187 | 27.211 | 35.618 | 54.372 | 1.00 | 95.52 | MOLB O |
| ATOM | 3956 | N | PRO | B 188 | 25.763 | −37.256 | 53.743 | 1.00 | 96.09 | MOLB N |
| ATOM | 3957 | CA | PRO | B 188 | 26.407 | −38.364 | 54.456 | 1.00 | 96.50 | MOLB C |
| ATOM | 3958 | CB | PRO | B 188 | 25.454 | −39.547 | 54.205 | 1.00 | 96.58 | MOLB C |
| ATOM | 3959 | CG | PRO | B 188 | 24.659 | −39.162 | 52.988 | 1.00 | 96.92 | MOLB C |
| ATOM | 3960 | CD | PRO | B 188 | 24.501 | −37.678 | 53.104 | 1.00 | 96.24 | MOLB C |
| ATOM | 3961 | C | PRO | B 188 | 27.807 | −38.680 | 53.904 | 1.00 | 96.22 | MOLB C |
| ATOM | 3962 | O | PRO | B 188 | 28.780 | −38.671 | 54.658 | 1.00 | 96.08 | MOLB O |
| ATOM | 3963 | N | ARG | B 189 | 27.897 | −38.943 | 52.601 | 1.00 | 95.88 | MOLB N |
| ATOM | 3964 | CA | ARG | B 189 | 29.158 | −39.311 | 51.956 | 1.00 | 95.97 | MOLB C |
| ATOM | 3965 | CB | ARG | B 189 | 28.922 | −39.623 | 50.470 | 1.00 | 96.23 | MOLB C |
| ATOM | 3966 | CG | ARG | B 189 | 28.058 | −40.872 | 50.228 | 1.00 | 94.40 | MOLB C |
| ATOM | 3967 | CD | ARG | B 189 | 27.615 | −41.021 | 48.765 | 1.00 | 95.19 | MOLB C |
| ATOM | 3968 | NE | ARG | B 189 | 28.739 | −41.107 | 47.823 | 1.00 | 102.74 | MOLB N |
| ATOM | 3969 | CZ | ARG | B 189 | 28.621 | −41.238 | 46.497 | 1.00 | 103.41 | MOLB C |
| ATOM | 3970 | NH1 | ARG | B 189 | 27.424 | −41.304 | 45.920 | 1.00 | 103.98 | MOLB N |
| ATOM | 3971 | NH2 | ARG | B 189 | 29.709 | −41.304 | 45.738 | 1.00 | 99.67 | MOLB N |
| ATOM | 3972 | C | ARG | B 189 | 30.314 | −38.301 | 52.164 | 1.00 | 96.65 | MOLB C |
| ATOM | 3973 | O | ARG | B 189 | 31.435 | −38.710 | 52.472 | 1.00 | 97.49 | MOLB O |
| ATOM | 3974 | N | ASN | B 190 | 30.047 | −37.000 | 52.011 | 1.00 | 96.96 | MOLB N |
| ATOM | 3975 | CA | ASN | B 190 | 31.068 | −35.955 | 52.242 | 1.00 | 96.62 | MOLB C |
| ATOM | 3976 | CB | ASN | B 190 | 31.452 | −35.253 | 50.930 | 1.00 | 96.47 | MOLB C |
| ATOM | 3977 | CG | ASN | B 190 | 32.446 | −34.106 | 51.138 | 1.00 | 98.50 | MOLB C |
| ATOM | 3978 | OD1 | ASN | B 190 | 33.098 | −34.003 | 52.181 | 1.00 | 100.50 | MOLB O |
| ATOM | 3979 | ND2 | ASN | B 190 | 32.561 | −33.239 | 50.137 | 1.00 | 100.42 | MOLB N |
| ATOM | 3980 | C | ASN | B 190 | 30.656 | −34.908 | 53.287 | 1.00 | 95.84 | MOLB C |
| ATOM | 3981 | O | ASN | B 190 | 29.503 | −34.490 | 53.335 | 1.00 | 95.93 | MOLB O |
| ATOM | 3982 | N | LYS | B 191 | 31.606 | −34.489 | 54.118 | 1.00 | 95.01 | MOLB N |
| ATOM | 3983 | CA | LYS | B 191 | 31.356 | −33.461 | 55.136 | 1.00 | 94.17 | MOLB C |
| ATOM | 3984 | CB | LYS | B 191 | 32.541 | −33.368 | 56.098 | 1.00 | 94.67 | MOLB C |
| ATOM | 3985 | CG | LYS | B 191 | 32.282 | −33.880 | 57.497 | 1.00 | 95.40 | MOLB C |
| ATOM | 3986 | CD | LYS | B 191 | 32.866 | −32.877 | 58.498 | 1.00 | 98.45 | MOLB C |
| ATOM | 3987 | CE | LYS | B 191 | 31.874 | −31.744 | 58.836 | 1.00 | 97.70 | MOLB C |
| ATOM | 3988 | NZ | LYS | B 191 | 30.937 | −31.326 | 57.738 | 1.00 | 94.81 | MOLB N |
| ATOM | 3989 | C | LYS | B 191 | 31.090 | −32.056 | 54.572 | 1.00 | 92.82 | MOLB C |
| ATOM | 3990 | O | LYS | B 191 | 30.027 | −31.461 | 54.810 | 1.00 | 92.75 | MOLB O |
| ATOM | 3991 | N | ARG | B 192 | 32.078 | −31.534 | 53.842 | 1.00 | 90.20 | MOLB N |
| ATOM | 3992 | CA | ARG | B 192 | 32.060 | −30.166 | 53.312 | 1.00 | 86.66 | MOLB C |
| ATOM | 3993 | CB | ARG | B 192 | 33.465 | −29.809 | 52.832 | 1.00 | 86.01 | MOLB C |
| ATOM | 3994 | CG | ARG | B 192 | 34.577 | −30.367 | 53.716 | 1.00 | 83.00 | MOLB C |
| ATOM | 3995 | CD | ARG | B 192 | 35.884 | −30.481 | 52.934 | 1.00 | 90.88 | MOLB C |
| ATOM | 3996 | NE | ARG | B 192 | 36.303 | −29.213 | 52.314 | 1.00 | 95.92 | MOLB N |
| ATOM | 3997 | CZ | ARG | B 192 | 36.083 | −28.860 | 51.041 | 1.00 | 92.27 | MOLB C |
| ATOM | 3998 | NH1 | ARG | B 192 | 35.438 | −29.673 | 50.205 | 1.00 | 89.10 | MOLB N |
| ATOM | 3999 | NH2 | ARG | B 192 | 36.513 | −27.680 | 50.601 | 1.00 | 84.83 | MOLB N |
| ATOM | 4000 | C | ARG | B 192 | 31.022 | −29.955 | 52.182 | 1.00 | 84.50 | MOLB C |
| ATOM | 4OD1 | O | ARG | B 192 | 30.748 | −28.818 | 51.763 | 1.00 | 83.26 | MOLB O |
| ATOM | 4002 | N | GLY | B 193 | 30.450 | −31.063 | 51.708 | 1.00 | 81.05 | MOLB N |
| ATOM | 4003 | CA | GLY | B 193 | 29.473 | −31.051 | 50.624 | 1.00 | 76.17 | MOLB C |
| ATOM | 4004 | C | GLY | B 193 | 28.083 | −30.735 | 51.120 | 1.00 | 71.71 | MOLB C |
| ATOM | 4005 | O | GLY | B 193 | 27.908 | −30.314 | 52.273 | 1.00 | 69.93 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4006 | N | VAL | B 194 | 27.105 | −30.959 | 50.243 | 1.00 | 68.12 | MOLB N |
| ATOM | 4007 | CA | VAL | B 194 | 25.708 | −30.600 | 50.482 | 1.00 | 65.56 | MOLB C |
| ATOM | 4008 | CB | VAL | B 194 | 25.549 | −29.064 | 50.682 | 1.00 | 65.72 | MOLB C |
| ATOM | 4009 | CG1 | VAL | B 194 | 24.296 | −28.531 | 49.985 | 1.00 | 62.99 | MOLB C |
| ATOM | 4010 | CG2 | VAL | B 194 | 25.573 | −28.687 | 52.172 | 1.00 | 63.92 | MOLB C |
| ATOM | 4011 | C | VAL | B 194 | 24.852 | −31.054 | 49.297 | 1.00 | 64.74 | MOLB C |
| ATOM | 4012 | O | VAL | B 194 | 25.170 | −30.747 | 48.158 | 1.00 | 62.88 | MOLB O |
| ATOM | 4013 | N | ILE | B 195 | 23.765 | −31.776 | 49.568 | 1.00 | 64.45 | MOLB N |
| ATOM | 4014 | CA | ILE | B 195 | 22.903 | −32.300 | 48.504 | 1.00 | 65.26 | MOLB C |
| ATOM | 4015 | CB | ILE | B 195 | 22.469 | −33.800 | 48.771 | 1.00 | 66.52 | MOLB C |
| ATOM | 4016 | CG1 | ILE | B 195 | 23.687 | −34.720 | 48.992 | 1.00 | 71.27 | MOLB C |
| ATOM | 4017 | CD1 | ILE | B 195 | 23.348 | −36.110 | 49.583 | 1.00 | 66.28 | MOLB C |
| ATOM | 4018 | CG2 | ILE | B 195 | 21.585 | −34.356 | 47.638 | 1.00 | 64.07 | MOLB C |
| ATOM | 4019 | C | ILE | B 195 | 21.657 | −31.444 | 48.266 | 1.00 | 64.63 | MOLB C |
| ATOM | 4020 | O | ILE | B 195 | 20.934 | −31.089 | 49.198 | 1.00 | 61.97 | MOLB O |
| ATOM | 4021 | N | ILE | B 196 | 21.416 | −31.112 | 47.006 | 1.00 | 66.24 | MOLB N |
| ATOM | 4022 | CA | ILE | B 196 | 20.162 | −30.466 | 46.634 | 1.00 | 70.02 | MOLB C |
| ATOM | 4023 | CB | ILE | B 196 | 20.381 | −29.197 | 45.761 | 1.00 | 70.09 | MOLB C |
| ATOM | 4024 | CG1 | ILE | B 196 | 21.336 | −28.227 | 46.469 | 1.00 | 68.96 | MOLB C |
| ATOM | 4025 | CD1 | ILE | B 196 | 21.536 | −26.908 | 45.735 | 1.00 | 71.81 | MOLB C |
| ATOM | 4026 | CG2 | ILE | B 196 | 19.039 | −28.535 | 45.406 | 1.00 | 68.52 | MOLB C |
| ATOM | 4027 | C | ILE | B 196 | 19.269 | −31.493 | 45.927 | 1.00 | 71.46 | MOLB C |
| ATOM | 4028 | O | ILE | B 196 | 19.266 | −31.613 | 44.697 | 1.00 | 73.19 | MOLB O |
| ATOM | 4029 | N | LYS | B 197 | 18.527 | −32.251 | 46.721 | 1.00 | 72.04 | MOLB N |
| ATOM | 4030 | CA | LYS | B 197 | 17.662 | −33.284 | 46.177 | 1.00 | 71.88 | MOLB C |
| ATOM | 4031 | CB | LYS | B 197 | 16.905 | −34.012 | 47.319 | 1.00 | 72.79 | MOLB C |
| ATOM | 4032 | CG | LYS | B 197 | 15.742 | −34.934 | 46.866 | 1.00 | 79.36 | MOLB C |
| ATOM | 4033 | CD | LYS | B 197 | 15.251 | −35.923 | 47.944 | 1.00 | 73.10 | MOLB C |
| ATOM | 4034 | CE | LYS | B 197 | 15.815 | −37.316 | 47.711 | 1.00 | 66.32 | MOLB C |
| ATOM | 4035 | NZ | LYS | B 197 | 17.303 | −37.267 | 47.643 | 1.00 | 73.12 | MOLB N |
| ATOM | 4036 | C | LYS | B 197 | 16.721 | −32.681 | 45.126 | 1.00 | 68.98 | MOLB C |
| ATOM | 4037 | O | LYS | B 197 | 16.105 | −31.630 | 45.351 | 1.00 | 69.24 | MOLB O |
| ATOM | 4038 | N | GLY | B 198 | 16.657 | −33.335 | 43.968 | 1.00 | 66.08 | MOLB N |
| ATOM | 4039 | CA | GLY | B 198 | 15.714 | −32.962 | 42.913 | 1.00 | 64.14 | MOLB C |
| ATOM | 4040 | C | GLY | B 198 | 16.350 | −32.332 | 41.691 | 1.00 | 62.01 | MOLB C |
| ATOM | 4041 | O | GLY | B 198 | 15.874 | −32.523 | 40.568 | 1.00 | 61.57 | MOLB O |
| ATOM | 4042 | N | LEU | B 199 | 17.445 | −31.605 | 41.924 | 1.00 | 60.16 | MOLB N |
| ATOM | 4043 | CA | LEU | B 199 | 18.116 | −30.749 | 40.912 | 1.00 | 58.59 | MOLB C |
| ATOM | 4044 | CB | LEU | B 199 | 19.177 | −29.850 | 41.609 | 1.00 | 59.51 | MOLB C |
| ATOM | 4045 | CG | LEU | B 199 | 20.531 | −29.320 | 41.098 | 1.00 | 58.48 | MOLB C |
| ATOM | 4046 | CD1 | LEU | B 199 | 20.494 | −28.703 | 39.730 | 1.00 | 52.75 | MOLB C |
| ATOM | 4047 | CD2 | LEU | B 199 | 21.062 | −28.321 | 42.103 | 1.00 | 55.82 | MOLB C |
| ATOM | 4048 | C | LEU | B 199 | 18.636 | −31.439 | 39.632 | 1.00 | 56.76 | MOLB C |
| ATOM | 4049 | O | LEU | B 199 | 19.538 | −32.274 | 39.662 | 1.00 | 56.09 | MOLB O |
| ATOM | 4050 | N | GLU | B 200 | 18.050 | −31.055 | 38.508 | 1.00 | 54.72 | MOLB N |
| ATOM | 4051 | CA | GLU | B 200 | 18.381 | −31.635 | 37.222 | 1.00 | 55.91 | MOLB C |
| ATOM | 4052 | CB | GLU | B 200 | 17.692 | −30.821 | 36.121 | 1.00 | 55.43 | MOLB C |
| ATOM | 4053 | CG | GLU | B 200 | 17.380 | −31.574 | 34.847 | 1.00 | 59.41 | MOLB C |
| ATOM | 4054 | CD | GLU | B 200 | 16.333 | −32.660 | 35.055 | 1.00 | 66.80 | MOLB C |
| ATOM | 4055 | OE1 | GLU | B 200 | 16.572 | −33.570 | 35.877 | 1.00 | 59.03 | MOLB O |
| ATOM | 4056 | OE2 | GLU | B 200 | 15.277 | −32.614 | 34.382 | 1.00 | 71.33 | MOLB O |
| ATOM | 4057 | C | GLU | B 200 | 19.898 | −31.697 | 36.975 | 1.00 | 55.71 | MOLB C |
| ATOM | 4058 | O | GLU | B 200 | 20.617 | −30.721 | 37.190 | 1.00 | 56.34 | MOLB O |
| ATOM | 4059 | N | GLU | B 201 | 20.389 | −32.853 | 36.546 | 1.00 | 54.62 | MOLB N |
| ATOM | 4060 | CA | GLU | B 201 | 21.767 | −32.938 | 36.094 | 1.00 | 55.18 | MOLB C |
| ATOM | 4061 | CB | GLU | B 201 | 22.586 | −33.844 | 36.987 | 1.00 | 53.64 | MOLB C |
| ATOM | 4062 | CG | GLU | B 201 | 23.163 | −33.154 | 38.186 | 1.00 | 54.76 | MOLB C |
| ATOM | 4063 | CD | GLU | B 201 | 23.894 | −34.116 | 39.078 | 1.00 | 53.91 | MOLB C |
| ATOM | 4064 | OE1 | GLU | B 201 | 23.873 | −35.334 | 38.806 | 1.00 | 52.23 | MOLB O |
| ATOM | 4065 | OE2 | GLU | B 201 | 24.497 | −33.652 | 40.057 | 1.00 | 65.31 | MOLB O |
| ATOM | 4066 | C | GLU | B 201 | 21.853 | −33.428 | 34.652 | 1.00 | 57.82 | MOLB C |
| ATOM | 4067 | O | GLU | B 201 | 22.203 | −34.588 | 34.408 | 1.00 | 60.65 | MOLB O |
| ATOM | 4068 | N | ILE | B 202 | 21.525 | −32.557 | 33.696 | 1.00 | 57.13 | MOLB N |
| ATOM | 4069 | CA | ILE | B 202 | 21.597 | −32.917 | 32.283 | 1.00 | 55.98 | MOLB C |
| ATOM | 4070 | CB | ILE | B 202 | 21.100 | −31.785 | 31.422 | 1.00 | 53.94 | MOLB C |
| ATOM | 4071 | CG | 1ILE | B 202 | 19.575 | −31.861 | 31.294 | 1.00 | 53.73 | MOLB C |
| ATOM | 4072 | CD1 | ILE | B 202 | 18.882 | −30.524 | 30.965 | 1.00 | 22.57 | MOLB C |
| ATOM | 4073 | CG2 | ILE | B 202 | 21.747 | −31.863 | 30.080 | 1.00 | 52.73 | MOLB C |
| ATOM | 4074 | C | ILE | B 202 | 23.016 | −33.309 | 31.838 | 1.00 | 58.15 | MOLB C |
| ATOM | 4075 | O | ILE | B 202 | 23.999 | −32.626 | 32.142 | 1.00 | 59.98 | MOLB O |
| ATOM | 4076 | N | THR | B 203 | 23.118 | −34.426 | 31.128 | 1.00 | 59.12 | MOLB N |
| ATOM | 4077 | CA | THR | B 203 | 24.400 | −34.880 | 30.610 | 1.00 | 58.93 | MOLB C |
| ATOM | 4078 | CB | THR | B 203 | 24.424 | −36.416 | 30.391 | 1.00 | 58.71 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4079 | OG1 | THR | B 203 | 24.235 | −37.096 | 31.645 | 1.00 | 54.66 | MOLB O |
| ATOM | 4080 | CG2 | THR | 8 203 | 25.748 | −36.851 | 29.759 | 1.00 | 55.01 | MOLB C |
| ATOM | 4081 | C | THR | B 203 | 24.616 | −34.198 | 29.279 | 1.00 | 60.53 | MOLB C |
| ATOM | 4082 | O | THR | B 203 | 23.652 | −33.978 | 28.540 | 1.00 | 61.11 | MOLB O |
| ATOM | 4083 | N | VAL | B 204 | 25.866 | −33.857 | 28.966 | 1.00 | 61.07 | MOLB N |
| ATOM | 4084 | CA | VAL | B 204 | 26.173 | −33.233 | 27.680 | 1.00 | 61.17 | MOLB C |
| ATOM | 4085 | CB | VAL | B 204 | 26.988 | −31.934 | 27.834 | 1.00 | 63.53 | MOLB C |
| ATOM | 4086 | CG1 | VAL | B 204 | 27.078 | −31.200 | 26.484 | 1.00 | 62.55 | MOLB C |
| ATOM | 4087 | CG2 | VAL | B 204 | 26.389 | −31.027 | 28.923 | 1.00 | 64.46 | MOLB C |
| ATOM | 4088 | C | VAL | B 204 | 26.992 | −34.182 | 26.861 | 1.00 | 59.00 | MOLB C |
| ATOM | 4089 | O | VAL | B 204 | 28.193 | −34.286 | 27.065 | 1.00 | 58.44 | MOLB 0 |
| ATOM | 4090 | N | HIS | B 205 | 26.346 | −34.860 | 25.923 | 1.00 | 59.37 | MOLB N |
| ATOM | 4091 | CA | HIS | B 205 | 27.019 | −35.912 | 25.156 | 1.00 | 60.00 | MOLB C |
| ATOM | 4092 | CB | HIS | B 205 | 25.992 | −36.789 | 24.443 | 1.00 | 59.06 | MOLB C |
| ATOM | 4093 | CG | HIS | B 205 | 24.971 | −37.367 | 25.372 | 1.00 | 63.91 | MOLB C |
| ATOM | 4094 | ND1 | HIS | B 205 | 23.664 | −36.927 | 25.414 | 1.00 | 72.75 | MOLB N |
| ATOM | 4095 | CE1 | HIS | B 205 | 23.OD1 | −37.604 | 26.336 | 1.00 | 71.66 | MOLB C |
| ATOM | 4096 | NE2 | HIS | B 205 | 23.836 | −38.455 | 26.905 | 1.00 | 74.42 | MOLB N |
| ATOM | 4097 | CD2 | HIS | B 205 | 25.077 | −38.319 | 26.329 | 1.00 | 69.87 | MOLB C |
| ATOM | 4098 | C | HIS | B 205 | 28.065 | −35.354 | 24.200 | 1.00 | 58.73 | MOLB C |
| ATOM | 4099 | O | HIS | B 205 | 29.116 | −35.946 | 24.005 | 1.00 | 59.68 | MOLB O |
| ATOM | 4100 | N | ASN | B 206 | 27.792 | −34.190 | 23.637 | 1.00 | 57.85 | MOLB N |
| ATOM | 4101 | CA | ASN | B 206 | 28.735 | −33.550 | 22.743 | 1.00 | 57.42 | MOLB C |
| ATOM | 4102 | CB | ASN | B 206 | 28.466 | −34.027 | 21.313 | 1.00 | 57.09 | MOLB C |
| ATOM | 4103 | CG | ASN | B 206 | 26.996 | −33.817 | 20.878 | 1.00 | 59.56 | MOLB C |
| ATOM | 4104 | OD1 | ASN | B 206 | 26.489 | −32.691 | 20.841 | 1.00 | 76.04 | MOLB O |
| ATOM | 4105 | ND2 | ASN | B 206 | 26.324 | −34.905 | 20.527 | 1.00 | 61.34 | MOLB N |
| ATOM | 4106 | C | ASN | B 206 | 28.644 | −32.023 | 22.790 | 1.00 | 57.90 | MOLB C |
| ATOM | 4107 | O | ASN | B 206 | 27.628 | −31.447 | 23.227 | 1.00 | 54.95 | MOLB O |
| ATOM | 4108 | N | LYS | B 207 | 29.707 | −31.363 | 22.334 | 1.00 | 59.58 | MOLB N |
| ATOM | 4109 | CA | LYS | B 207 | 29.591 | −29.941 | 22.005 | 1.00 | 59.83 | MOLB C |
| ATOM | 4110 | CB | LYS | B 207 | 30.918 | −29.374 | 21.480 | 1.00 | 58.28 | MOLB C |
| ATOM | 4111 | CG | LYS | B 207 | 31.294 | −29.855 | 20.109 | 1.00 | 52.59 | MOLB C |
| ATOM | 4112 | CD | LYS | B 207 | 32.283 | −28.930 | 19.474 | 1.00 | 64.71 | MOLB C |
| ATOM | 4113 | CE | LYS | B 207 | 32.213 | −29.033 | 17.961 | 1.00 | 70.65 | MOLB C |
| ATOM | 4114 | NZ | LYS | B 207 | 32.885 | −27.868 | 17.312 | 1.00 | 78.20 | MOLB N |
| ATOM | 4115 | C | LYS | B 207 | 28.483 | −29.892 | 20.937 | 1.00 | 60.16 | MOLB C |
| ATOM | 4116 | O | LYS | B 207 | 28.310 | −30.851 | 20.195 | 1.00 | 61.57 | MOLB O |
| ATOM | 4117 | N | ASP | B 208 | 27.735 | −28.802 | 20.846 | 1.00 | 60.47 | MOLB N |
| ATOM | 4118 | CA | ASP | B 208 | 26.568 | −28.753 | 19.958 | 1.00 | 62.12 | MOLB C |
| ATOM | 4119 | CB | ASP | B 208 | 26.545 | −29.912 | 18.937 | 1.00 | 62.10 | MOLB C |
| ATOM | 4120 | CG | ASP | B 208 | 27.441 | −29.663 | 17.719 | 1.00 | 66.53 | MOLB C |
| ATOM | 4121 | OD1 | ASP | B 208 | 28.256 | −28.703 | 17.754 | 1.00 | 71.15 | MOLB O |
| ATOM | 4122 | OD2 | ASP | B 208 | 27.326 | −30.437 | 16.730 | 1.00 | 62.54 | MOLB O |
| ATOM | 4123 | C | ASP | B 208 | 25.354 | −28.861 | 20.852 | 1.00 | 62.21 | MOLB C |
| ATOM | 4124 | O | ASP | B 208 | 24.754 | −27.841 | 21.232 | 1.00 | 61.53 | MOLB O |
| ATOM | 4125 | N | GLU | B 209 | 25.008 | −30.107 | 21.191 | 1.00 | 60.89 | MOLB N |
| ATOM | 4126 | CA | GLU | B 209 | 23.924 | −30.390 | 22.113 | 1.00 | 59.86 | MOLB C |
| ATOM | 4127 | CB | GLU | 8 209 | 24.128 | −31.759 | 22.763 | 1.00 | 59.90 | MOLB C |
| ATOM | 4128 | CG | GLU | B 209 | 23.087 | −32.090 | 23.846 | 1.00 | 62.75 | MOLB C |
| ATOM | 4129 | CD | GLU | B 209 | 23.180 | −33.516 | 24.360 | 1.00 | 63.74 | MOLB C |
| ATOM | 4130 | OE1 | GLU | B 209 | 23.571 | −34.420 | 23.584 | 1.00 | 75.49 | MOLB O |
| ATOM | 4131 | OE2 | GLU | B 209 | 22.854 | −33.733 | 25.546 | 1.00 | 69.99 | MOLB O |
| ATOM | 4132 | C | GLU | B 209 | 23.846 | −29.315 | 23.193 | 1.00 | 57.77 | MOLB C |
| ATOM | 4133 | O | GLU | B 209 | 22.845 | −29.196 | 23.911 | 1.00 | 58.69 | MOLB O |
| ATOM | 4134 | N | VAL | B 210 | 24.911 | −28.528 | 23.304 | 1.00 | 54.60 | MOLB N |
| ATOM | 4135 | CA | VAL | B 210 | 24.979 | −27.492 | 24.324 | 1.00 | 50.37 | MOLB C |
| ATOM | 4136 | CB | VAL | B 210 | 26.455 | −26.976 | 24.551 | 1.00 | 50.31 | MOLB C |
| ATOM | 4137 | CG1 | VAL | B 210 | 27.411 | −27.560 | 23.527 | 1.00 | 41.74 | MOLB C |
| ATOM | 4138 | CG2 | VAL | B 210 | 26.537 | −25.427 | 24.621 | 1.00 | 39.92 | MOLB C |
| ATOM | 4139 | C | VAL | B 210 | 23.981 | −26.360 | 24.077 | 1.00 | 51.71 | MOLB C |
| ATOM | 4140 | O | VAL | B 210 | 23.295 | −25.944 | 25.OD1 | 1.00 | 52.59 | MOLB O |
| ATOM | 4141 | N | TYR | B 211 | 23.867 | −25.896 | 22.834 | 1.00 | 50.28 | MOLB N |
| ATOM | 4142 | CA | TYR | B 211 | 23.098 | −24.676 | 22.559 | 1.00 | 48.99 | MOLB C |
| ATOM | 4143 | CB | TYR | B 211 | 23.103 | −24.350 | 21.073 | 1.00 | 48.83 | MOLB C |
| ATOM | 4144 | CG | TYR | B 211 | 22.775 | −22.914 | 20.795 | 1.00 | 53.57 | MOLB C |
| ATOM | 4145 | CD1 | TYR | B 211 | 21.581 | −22.554 | 20.161 | 1.00 | 67.17 | MOLB C |
| ATOM | 4146 | CE1 | TYR | B 211 | 21.269 | −21.214 | 19.895 | 1.00 | 65.00 | MOLB C |
| ATOM | 4147 | CZ | TYR | B 211 | 22.160 | −20.220 | 20.279 | 1.00 | 66.05 | MOLB C |
| ATOM | 4148 | OH | TYR | B 211 | 21.879 | −18.879 | 20.039 | 1.00 | 62.46 | MOLB O |
| ATOM | 4149 | CE2 | TYR | B 211 | 23.353 | −20.567 | 20.914 | 1.00 | 68.05 | MOLB C |
| ATOM | 4150 | CD2 | TYR | B 211 | 23.647 | −21.905 | 21.171 | 1.00 | 54.11 | MOLB C |
| ATOM | 4151 | C | TYR | B 211 | 21.678 | −24.696 | 23.100 | 1.00 | 47.82 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4152 | O | TYR | B 211 | 21.281 | −23.794 | 23.835 | 1.00 | 46.80 | MOLB O |
| ATOM | 4153 | N | GLN | B 212 | 20.925 | −25.730 | 22.741 | 1.00 | 48.24 | MOLB N |
| ATOM | 4154 | CA | GLN | B 212 | 19.551 | −25.888 | 23.198 | 1.00 | 48.96 | MOLB C |
| ATOM | 4155 | CB | GLN | B 212 | 18.905 | −27.161 | 22.642 | 1.00 | 49.90 | MOLB C |
| ATOM | 4156 | CG | GLN | B 212 | 19.628 | −27.806 | 21.446 | 1.00 | 59.05 | MOLB C |
| ATOM | 4157 | CD | GLN | B 212 | 20.775 | −28.731 | 21.878 | 1.00 | 65.17 | MOLB C |
| ATOM | 4158 | OE1 | GLN | B 212 | 21.863 | −28.737 | 21.277 | 1.00 | 58.17 | MOLB O |
| ATOM | 4159 | NE2 | GLN | B 212 | 20.536 | −29.504 | 22.935 | 1.00 | 66.39 | MOLB N |
| ATOM | 4160 | C | GLN | B 212 | 19.559 | −25.960 | 24.717 | 1.00 | 48.11 | MOLB C |
| ATOM | 4161 | O | GLN | B 212 | 18.720 | −25.370 | 25.390 | 1.00 | 47.51 | MOLB O |
| ATOM | 4162 | N | ILE | B 213 | 20.509 | −26.686 | 25.279 | 1.00 | 47.45 | MOLB N |
| ATOM | 4163 | CA | ILE | B 213 | 20.547 | −26.725 | 26.721 | 1.00 | 47.12 | MOLB C |
| ATOM | 4164 | CB | ILE | B 213 | 21.803 | −27.409 | 27.246 | 1.00 | 47.81 | MOLB C |
| ATOM | 4165 | CG1 | ILE | B 213 | 21.939 | −28.819 | 26.666 | 1.00 | 47.91 | MOLB C |
| ATOM | 4166 | CD1 | ILE | B 213 | 23.060 | −29.630 | 27.331 | 1.00 | 42.63 | MOLB C |
| ATOM | 4167 | CG2 | ILE | B 213 | 21.810 | −27.410 | 28.779 | 1.00 | 46.33 | MOLB C |
| ATOM | 4168 | C | ILE | B 213 | 20.501 | −25.288 | 27.238 | 1.00 | 47.69 | MOLB C |
| ATOM | 4169 | O | ILE | B 213 | 19.742 | −24.977 | 28.148 | 1.00 | 49.77 | MOLB 0 |
| ATOM | 4170 | N | LEU | B 214 | 21.305 | −24.405 | 26.649 | 1.00 | 47.21 | MOLB N |
| ATOM | 4171 | CA | LEU | B 214 | 21.375 | −23.035 | 27.142 | 1.00 | 45.34 | MOLB C |
| ATOM | 4172 | CB | LEU | B 214 | 22.594 | −22.271 | 26.605 | 1.00 | 44.85 | MOLB C |
| ATOM | 4173 | CG | LEU | B 214 | 24.015 | −22.615 | 27.051 | 1.00 | 34.59 | MOLB C |
| ATOM | 4174 | CD1 | LEU | B 214 | 25.066 | −21.940 | 26.152 | 1.00 | 26.68 | MOLB C |
| ATOM | 4175 | CD2 | LEU | B 214 | 24.244 | −22.255 | 28.482 | 1.00 | 34.21 | MOLB C |
| ATOM | 4176 | C | LEU | B 214 | 20.086 | −22.297 | 26.821 | 1.00 | 46.03 | MOLB C |
| ATOM | 4177 | O | LEU | B 214 | 19.693 | −21.399 | 27.575 | 1.00 | 44.99 | MOLB O |
| ATOM | 4178 | N | GLU | B 215 | 19.433 | −22.668 | 25.715 | 1.00 | 46.27 | MOLB N |
| ATOM | 4179 | CA | GLU | B 215 | 18.102 | −22.101 | 25.408 | 1.00 | 47.96 | MOLB C |
| ATOM | 4180 | CB | GLU | B 215 | 17.566 | −22.561 | 24.049 | 1.00 | 45.42 | MOLB C |
| ATOM | 4181 | CG | GLU | B 215 | 18.272 | −21.889 | 22.886 | 1.00 | 52.17 | MOLB C |
| ATOM | 4182 | CD | GLU | B 215 | 18.239 | −22.689 | 21.593 | 1.00 | 68.73 | MOLB C |
| ATOM | 4183 | OE1 | GLU | B 215 | 17.985 | −23.917 | 21.633 | 1.00 | 71.33 | MOLB O |
| ATOM | 4184 | OE2 | GLU | B 215 | 18.494 | −22.084 | 20.527 | 1.00 | 77.67 | MOLB O |
| ATOM | 4185 | C | GLU | B 215 | 17.139 | −22.450 | 26.535 | 1.00 | 47.80 | MOLB C |
| ATOM | 4186 | O | GLU | B 215 | 16.610 | −21.568 | 27.204 | 1.00 | 47.51 | MOLB O |
| ATOM | 4187 | N | LYS | B 216 | 16.960 | −23.742 | 26.765 | 1.00 | 49.47 | MOLB N |
| ATOM | 4188 | CA | LYS | B 216 | 16.131 | −24.211 | 27.854 | 1.00 | 52.75 | MOLB C |
| ATOM | 4189 | CB | LYS | B 216 | 16.422 | −25.693 | 28.163 | 1.00 | 53.47 | MOLB C |
| ATOM | 4190 | CG | LYS | B 216 | 16.024 | −26.697 | 27.061 | 1.00 | 56.75 | MOLB C |
| ATOM | 4191 | CD | LYS | B 216 | 16.340 | −28.146 | 27.500 | 1.00 | 57.59 | MOLB C |
| ATOM | 4192 | CE | LYS | B 216 | 16.021 | −29.179 | 26.405 | 1.00 | 59.05 | MOLB C |
| ATOM | 4193 | NZ | LYS | B 216 | 16.775 | −28.923 | 25.163 | 1.00 | 54.12 | MOLB N |
| ATOM | 4194 | C | LYS | B 216 | 16.398 | −23.359 | 29.093 | 1.00 | 51.47 | MOLB C |
| ATOM | 4195 | O | LYS | B 216 | 15.477 | −22.869 | 29.752 | 1.00 | 51.46 | MOLB O |
| ATOM | 4196 | N | GLY | B 217 | 17.676 | 2−3.182 | 29.391 | 1.00 | 49.81 | MOLB N |
| ATOM | 4197 | CA | GLY | B 217 | 18.080 | −22.465 | 30.581 | 1.00 | 49.73 | MOLB C |
| ATOM | 4198 | C | GLY | B 217 | 17.565 | −21.052 | 30.629 | 1.00 | 49.46 | MOLB C |
| ATOM | 4199 | O | GLY | B 217 | 16.801 | −20.693 | 31.513 | 1.00 | 50.81 | MOLB O |
| ATOM | 4200 | N | ALA | B 218 | 17.976 | −20.236 | 29.674 | 1.00 | 49.68 | MOLB N |
| ATOM | 4201 | CA | ALA | B 218 | 17.518 | −18.856 | 29.666 | 1.00 | 49.27 | MOLB C |
| ATOM | 4202 | CB | ALA | B 218 | 18.287 | −18.025 | 28.610 | 1.00 | 49.20 | MOLB C |
| ATOM | 4203 | C | ALA | B 218 | 15.996 | −18.784 | 29.456 | 1.00 | 47.83 | MOLB C |
| ATOM | 4204 | O | ALA | B 218 | 15.350 | −17.854 | 29.951 | 1.00 | 47.83 | MOLB O |
| ATOM | 4205 | N | ALA | B 219 | 15.434 | −19.769 | 28.747 | 1.00 | 46.32 | MOLB N |
| ATOM | 4206 | CA | ALA | B 219 | 13.998 | −19.774 | 28.436 | 1.00 | 46.32 | MOLB C |
| ATOM | 4207 | CB | ALA | B 219 | 13.664 | −20.844 | 27.432 | 1.00 | 43.25 | MOLB C |
| ATOM | 4208 | C | ALA | B 219 | 13.165 | −19.921 | 29.712 | 1.00 | 47.87 | MOLB C |
| ATOM | 4209 | O | ALA | B 219 | 12.212 | −19.168 | 29.955 | 1.00 | 48.20 | MOLB O |
| ATOM | 4210 | N | LYS | B 220 | 13.559 | −20.866 | 30.550 | 1.00 | 49.44 | MOLB N |
| ATOM | 4211 | CA | LYS | B 220 | 12.931 | −21.018 | 31.839 | 1.00 | 50.52 | MOLB C |
| ATOM | 4212 | CB | LYS | B 220 | 13.255 | −22.391 | 32.431 | 1.00 | 52.01 | MOLB C |
| ATOM | 4213 | CG | LYS | B 220 | 12.344 | −22.844 | 33.593 | 1.00 | 54.20 | MOLB C |
| ATOM | 4214 | CD | LYS | B 220 | 12.497 | −24.347 | 33.837 | 1.00 | 51.38 | MOLB C |
| ATOM | 4215 | CE | LYS | B 220 | 11.999 | −24.740 | 35.214 | 1.00 | 58.65 | MOLB C |
| ATOM | 4216 | NZ | LYS | B 220 | 12.106 | −26.213 | 35.455 | 1.00 | 72.13 | MOLB N |
| ATOM | 4217 | C | LYS | B 220 | 13.360 | −19.915 | 32.781 | 1.00 | 51.01 | MOLB C |
| ATOM | 4218 | O | LYS | B 220 | 12.656 | −19.622 | 33.722 | 1.00 | 52.79 | MOLB O |
| ATOM | 4219 | N | ARG | B 221 | 14.507 | −19.286 | 32.554 | 1.00 | 54.47 | MOLB N |
| ATOM | 4220 | CA | ARG | B 221 | 14.917 | −18.211 | 33.478 | 1.00 | 57.43 | MOLB C |
| ATOM | 4221 | CB | ARG | B 221 | 16.351 | −17.721 | 33.253 | 1.00 | 57.92 | MOLB C |
| ATOM | 4222 | CG | ARG | B 221 | 16.719 | −16.581 | 34.230 | 1.00 | 60.38 | MOLB C |
| ATOM | 4223 | CD | ARG | B 221 | 18.209 | −16.347 | 34.344 | 1.00 | 61.71 | MOLB C |
| ATOM | 4224 | NE | ARG | B 221 | 18.885 | −16.465 | 33.053 | 1.00 | 66.55 | MOLB N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 4225 | CZ | ARG | B 221 | 19.974 | −17.193 | 32.847 | 1.00 | 65.92 | MOLB C |
| ATOM | 4226 | NH1 | ARG | B 221 | 20.514 | −17.847 | 33.866 | 1.00 | 68.24 | MOLB N |
| ATOM | 4227 | NH2 | ARG | B 221 | 20.537 | −17.244 | 31.637 | 1.00 | 60.78 | MOLB N |
| ATOM | 4228 | C | ARG | B 221 | 13.958 | −17.033 | 33.427 | 1.00 | 58.89 | MOLB C |
| ATOM | 4229 | O | ARG | B 221 | 13.664 | −16.417 | 34.442 | 1.00 | 58.70 | MOLB O |
| ATOM | 4230 | N | THR | B 222 | 13.478 | −16.724 | 32.233 | 1.00 | 60.98 | MOLB N |
| ATOM | 4231 | CA | THR | B 222 | 12.524 | −15.656 | 32.058 | 1.00 | 62.58 | MOLB C |
| ATOM | 4232 | CB | THR | B 222 | 12.318 | −15.404 | 30.596 | 1.00 | 62.43 | MOLB C |
| ATOM | 4233 | OG1 | THR | B 222 | 11.993 | −16.653 | 29.970 | 1.00 | 67.21 | MOLB O |
| ATOM | 4234 | CG2 | THR | B 222 | 13.594 | −14.824 | 29.977 | 1.00 | 62.70 | MOLB C |
| ATOM | 4235 | C | THR | B 222 | 11.194 | −16.064 | 32.669 | 1.00 | 63.48 | MOLB C |
| ATOM | 4236 | O | THR | B 222 | 10.597 | −15.295 | 33.430 | 1.00 | 64.31 | MOLB O |
| ATOM | 4237 | N | THR | B 223 | 10.748 | −17.276 | 32.333 | 1.00 | 63.42 | MOLB N |
| ATOM | 4238 | CA | THR | B 223 | 9.494 | −17.838 | 32.846 | 1.00 | 64.93 | MOLB C |
| ATOM | 4239 | CB | THR | B 223 | 9.464 | −19.378 | 32.705 | 1.00 | 65.80 | MOLB C |
| ATOM | 4240 | OG1 | THR | B 223 | 9.391 | −19.753 | 31.321 | 1.00 | 67.26 | MOLB O |
| ATOM | 4241 | CG2 | THR | B 223 | 8.277 | −19.961 | 33.461 | 1.00 | 65.69 | MOLB C |
| ATOM | 4242 | C | THR | B 223 | 9.278 | −17.531 | 34.319 | 1.00 | 65.51 | MOLB C |
| ATOM | 4243 | O | THR | B 223 | 8.147 | −17.326 | 34.753 | 1.00 | 66.13 | MOLB O |
| ATOM | 4244 | N | ALA | B 224 | 10.374 | −17.513 | 35.075 | 1.00 | 65.91 | MOLB N |
| ATOM | 4245 | CA | ALA | B 224 | 10.352 | −17.316 | 36.527 | 1.00 | 67.50 | MOLB C |
| ATOM | 4246 | CB | ALA | B 224 | 11.527 | −18.067 | 37.179 | 1.00 | 67.50 | MOLB C |
| ATOM | 4247 | C | ALA | B 224 | 10.381 | −15.848 | 36.934 | 1.00 | 67.84 | MOLB C |
| ATOM | 4248 | O | ALA | B 224 | 10.082 | −15.492 | 38.069 | 1.00 | 66.11 | MOLB O |
| ATOM | 4249 | N | ALA | B 225 | 10.776 | −14.993 | 36.009 | 1.00 | 70.17 | MOLB N |
| ATOM | 4250 | CA | ALA | B 225 | 10.808 | −13.583 | 36.303 | 1.00 | 72.35 | MOLB C |
| ATOM | 4251 | CB | ALA | B 225 | 11.590 | −12.845 | 35.237 | 1.00 | 72.49 | MOLB C |
| ATOM | 4252 | C | ALA | B 225 | 9.361 | −13.088 | 36.386 | 1.00 | 74.19 | MOLB C |
| ATOM | 4253 | O | ALA | B 225 | 8.992 | −12.371 | 37.315 | 1.00 | 74.44 | MOLB O |
| ATOM | 4254 | N | THR | B 226 | 8.542 | −13.502 | 35.423 | 1.00 | 75.09 | MOLB N |
| ATOM | 4255 | CA | THR | B 226 | 7.139 | −13.136 | 35.402 | 1.00 | 75.63 | MOLB C |
| ATOM | 4256 | CB | THR | B 226 | 6.471 | −13.505 | 34.058 | 1.00 | 76.48 | MOLB C |
| ATOM | 4257 | OG1 | THR | B 226 | 7.412 | −13.367 | 32.983 | 1.00 | 80.19 | MOLB O |
| ATOM | 4258 | CG2 | THR | B 226 | 5.212 | −12.642 | 33.815 | 1.00 | 74.81 | MOLB C |
| ATOM | 4259 | C | THR | B 226 | 6.362 | −13.912 | 36.451 | 1.00 | 75.19 | MOLB C |
| ATOM | 4260 | O | THR | B 226 | 5.845 | −13.336 | 37.402 | 1.00 | 74.98 | MOLB O |
| ATOM | 4261 | N | LEU | B 227 | 6.301 | −15.229 | 36.267 | 1.00 | 74.01 | MOLB N |
| ATOM | 4262 | CA | LEU | B 227 | 5.349 | −16.060 | 36.991 | 1.00 | 73.57 | MOLB C |
| ATOM | 4263 | CB | LEU | B 227 | 5.103 | −17.370 | 36.243 | 1.00 | 72.43 | MOLB C |
| ATOM | 4264 | CG | LEU | B 227 | 4.671 | −17.194 | 34.781 | 1.00 | 77.05 | MOLB C |
| ATOM | 4265 | CD1 | LEU | B 227 | 4.393 | −18.538 | 34.101 | 1.00 | 78.86 | MOLB C |
| ATOM | 4266 | CD2 | LEU | B 227 | 3.461 | −16.259 | 34.653 | 1.00 | 83.44 | MOLB C |
| ATOM | 4267 | C | LEU | B 227 | 5.716 | −16.338 | 38.433 | 1.00 | 73.98 | MOLB C |
| ATOM | 4268 | O | LEU | B 227 | 5.092 | −17.196 | 39.076 | 1.00 | 74.37 | MOLB O |
| ATOM | 4269 | N | MET | B 228 | 6.701 | −15.598 | 38.945 | 1.00 | 73.32 | MOLB N |
| ATOM | 4270 | CA | MET | B 228 | 7.178 | −15.779 | 40.323 | 1.00 | 73.80 | MOLB C |
| ATOM | 4271 | CB | MET | B 228 | 7.893 | −17.126 | 40.446 | 1.00 | 72.03 | MOLB C |
| ATOM | 4272 | CG | MET | B 228 | 7.942 | −17.661 | 41.860 | 1.00 | 77.10 | MOLB C |
| ATOM | 4273 | SD | MET | B 228 | 7.468 | −19.390 | 41.871 | 1.00 | 82.79 | MOLB S |
| ATOM | 4274 | CE | MET | B 228 | 5.744 | −19.268 | 41.371 | 1.00 | 85.41 | MOLB C |
| ATOM | 4275 | C | MET | B 228 | 8.051 | −14.614 | 40.846 | 1.00 | 71.18 | MOLB C |
| ATOM | 4276 | O | MET | B 228 | 8.626 | −14.685 | 41.941 | 1.00 | 70.00 | MOLB O |
| ATOM | 4277 | N | ASN | B 229 | 8.102 | −13.542 | 40.050 | 1.00 | 70.64 | MOLB N |
| ATOM | 4278 | CA | ASN | B 229 | 8.819 | −12.287 | 40.341 | 1.00 | 68.29 | MOLB C |
| ATOM | 4279 | CB | ASN | B 229 | 8.065 | −11.405 | 41.349 | 1.00 | 68.85 | MOLB C |
| ATOM | 4280 | CG | ASN | B 229 | 6.926 | −10.605 | 40.695 | 1.00 | 74.53 | MOLB C |
| ATOM | 4281 | OD1 | ASN | B 229 | 7.042 | −10.128 | 39.553 | 1.00 | 78.04 | MOLB O |
| ATOM | 4282 | ND2 | ASN | B 229 | 5.817 | −10.456 | 41.424 | 1.00 | 83.34 | MOLB N |
| ATOM | 4283 | C | ASN | B 229 | 10.259 | −12.452 | 40.737 | 1.00 | 66.57 | MOLB C |
| ATOM | 4284 | O | ASN | B 229 | 10.782 | −11.690 | 41.553 | 1.00 | 65.89 | MOLB O |
| ATOM | 4285 | N | ALA | B 230 | 10.894 | −13.463 | 40.155 | 1.00 | 65.53 | MOLB N |
| ATOM | 4286 | CA | ALA | B 230 | 12.325 | −13.641 | 40.317 | 1.00 | 63.22 | MOLB C |
| ATOM | 4287 | CB | ALA | B 230 | 12.708 | −15.094 | 40.179 | 1.00 | 63.05 | MOLB C |
| ATOM | 4288 | C | ALA | B 230 | 12.945 | −12.803 | 39.216 | 1.00 | 61.83 | MOLB C |
| ATOM | 4289 | O | ALA | 8 230 | 13.120 | −13.275 | 38.085 | 1.00 | 62.78 | MOLB O |
| ATOM | 4290 | N | TYR | B 231 | 13.187 | −11.528 | 39.516 | 1.00 | 59.35 | MOLB N |
| ATOM | 4291 | CA | TYR | B 231 | 13.820 | −10.659 | 38.537 | 1.00 | 56.71 | MOLB C |
| ATOM | 4292 | CB | TYR | B 231 | 13.486 | −9.165 | 38.728 | 1.00 | 57.11 | MOLB C |
| ATOM | 4293 | CG | TYR | B 231 | 12.051 | −8.932 | 38.343 | 1.00 | 55.59 | MOLB C |
| ATOM | 4294 | CD1 | TYR | B 231 | 11.629 | −9.180 | 37.034 | 1.00 | 57.32 | MOLB C |
| ATOM | 4295 | CE1 | TYR | B 231 | 10.303 | −9.023 | 36.650 | 1.00 | 57.09 | MOLB C |
| ATOM | 4296 | CZ | TYR | B 231 | 9.364 | −8.622 | 37.590 | 1.00 | 63.54 | MOLB C |
| ATOM | 4297 | OH | TYR | B 231 | 8.043 | −8.474 | 37.191 | 1.00 | 62.15 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4298 | CE2 | TYR | B 231 | 9.757 | −8.377 | 38.914 | 1.00 | 55.96 | MOLB C |
| ATOM | 4299 | CD2 | TYR | B 231 | 11.102 | −8.544 | 39.280 | 1.00 | 50.71 | MOLB C |
| ATOM | 4300 | C | TYR | B 231 | 15.298 | −11.030 | 38.496 | 1.00 | 56.36 | MOLB C |
| ATOM | 4301 | O | TYR | B 231 | 15.980 | −11.214 | 9.520 | 1.00 | 54.97 | MOLB O |
| ATOM | 4302 | N | SER | B 232 | 15.742 | −11.214 | 37.269 | 1.00 | 55.76 | MOLB N |
| ATOM | 4303 | CA | SER | B 232 | 17.034 | −11.776 | 36.951 | 1.00 | 55.44 | MOLB C |
| ATOM | 4304 | CB | SER | B 232 | 17.049 | −11.934 | 35.435 | 1.00 | 55.58 | MOLB C |
| ATOM | 4305 | OG | SER | B 232 | 15.675 | −12.070 | 34.997 | 1.00 | 48.43 | MOLB O |
| ATOM | 4306 | C | SER | B 232 | 18.211 | −10.955 | 37.530 | 1.00 | 55.44 | MOLB C |
| ATOM | 4307 | O | SER | B 232 | 19.303 | −11.462 | 37.698 | 1.00 | 57.04 | MOLB O |
| ATOM | 4308 | N | SER | B 233 | 17.947 | −9.712 | 37.907 | 1.00 | 55.64 | MOLB N |
| ATOM | 4309 | CA | SER | B 233 | 18.926 | −8.827 | 38.544 | 1.00 | 55.64 | MOLB C |
| ATOM | 4310 | CB | SER | B 233 | 18.521 | −7.406 | 38.221 | 1.00 | 55.19 | MOLB C |
| ATOM | 4311 | OG | SER | B 233 | 17.720 | −7.425 | 37.053 | 1.00 | 61.38 | MOLB O |
| ATOM | 4312 | C | SER | B 233 | 19.046 | −8.939 | 40.080 | 1.00 | 55.42 | MOLB C |
| ATOM | 4313 | O | SER | B 233 | 19.887 | −8.264 | 40.675 | 1.00 | 54.93 | MOLB O |
| ATOM | 4314 | N | ARG | B 234 | 18.216 | −9.772 | 40.716 | 1.00 | 55.12 | MOLB N |
| ATOM | 4315 | CA | ARG | B 234 | 18.201 | −9.890 | 42.184 | 1.00 | 55.38 | MOLB C |
| ATOM | 4316 | CB | ARG | B 234 | 16.929 | −9.247 | 42.778 | 1.00 | 56.91 | MOLB C |
| ATOM | 4317 | CG | ARG | B 234 | 16.437 | −7.977 | 42.035 | 1.00 | 62.45 | MOLB C |
| ATOM | 4318 | CD | ARG | B 234 | 15.308 | −7.187 | 42.764 | 1.00 | 58.99 | MOLB C |
| ATOM | 4319 | NE | ARG | B 234 | 14.776 | −6.099 | 41.919 | 1.00 | 74.13 | MOLB N |
| ATOM | 4320 | CZ | ARG | B 234 | 15.383 | −4.925 | 41.675 | 1.00 | 78.89 | MOLB C |
| ATOM | 4321 | NH1 | ARG | B 234 | 16.567 | −4.640 | 42.215 | 1.00 | 77.12 | MOLB N |
| ATOM | 4322 | NH2 | ARG | B 234 | 14.802 | −4.021 | 40.881 | 1.00 | 72.78 | MOLB N |
| ATOM | 4323 | C | ARG | B 234 | 18.325 | −11.344 | 42.655 | 1.00 | 53.13 | MOLB C |
| ATOM | 4324 | O | ARG | B 234 | 18.092 | −11.660 | 43.834 | 1.00 | 51.41 | MOLB O |
| ATOM | 4325 | N | SER | B 235 | 18.697 | −12.220 | 41.724 | 1.00 | 51.84 | MOLB N |
| ATOM | 4326 | CA | SER | B 235 | 18.836 | −13.657 | 42.002 | 1.00 | 50.56 | MOLB C |
| ATOM | 4327 | CB | SER | B 235 | 18.048 | −14.488 | 40.990 | 1.00 | 48.02 | MOLB C |
| ATOM | 4328 | OG | SER | B 235 | 16.973 | −13.760 | 40.423 | 1.00 | 56.59 | MOLB O |
| ATOM | 4329 | C | SER | B 235 | 20.292 | −14.068 | 41.877 | 1.00 | 49.75 | MOLB C |
| ATOM | 4330 | O | SER | B 235 | 20.932 | −13.739 | 40.869 | 1.00 | 50.93 | MOLB O |
| ATOM | 4331 | N | HIS | B 236 | 20.829 | −14.774 | 42.872 | 1.00 | 47.33 | MOLB N |
| ATOM | 4332 | CA | HIS | B 236 | 22.162 | −15.292 | 42.723 | 1.00 | 47.67 | MOLB C |
| ATOM | 4333 | CB | HIS | B 236 | 22.636 | −15.949 | 43.981 | 1.00 | 46.25 | MOLB C |
| ATOM | 4334 | CG | HIS | B 236 | 22.911 | −14.979 | 45.071 | 1.00 | 48.32 | MOLB C |
| ATOM | 4335 | ND1 | HIS | B 236 | 23.465 | −13.743 | 44.829 | 1.00 | 53.07 | MOLB N |
| ATOM | 4336 | CE1 | HIS | B 236 | 23.615 | −13.105 | 45.974 | 1.00 | 58.11 | MOLB C |
| ATOM | 4337 | NE2 | HIS | B 236 | 23.182 | −13.884 | 46.949 | 1.00 | 55.52 | MOLB N |
| ATOM | 4338 | CD2 | HIS | B 236 | 22.745 | −15.067 | 46.411 | 1.00 | 53.16 | MOLB C |
| ATOM | 4339 | C | HIS | B 236 | 22.077 | −16.312 | 41.636 | 1.00 | 49.93 | MOLB C |
| ATOM | 4340 | O | HIS | B 236 | 20.982 | −16.730 | 41.260 | 1.00 | 51.43 | MOLB O |
| ATOM | 4341 | N | SER | B 237 | 23.209 | −16.727 | 41.096 | 1.00 | 50.14 | MOLB N |
| ATOM | 4342 | CA | SER | B 237 | 23.095 | −17.697 | 40.014 | 1.00 | 50.48 | MOLB C |
| ATOM | 4343 | CB | SER | B 237 | 22.787 | −17.019 | 38.667 | 1.00 | 48.69 | MOLB C |
| ATOM | 4344 | OG | SER | B 237 | 22.442 | −17.997 | 37.707 | 1.00 | 44.36 | MOLB O |
| ATOM | 4345 | C | SER | B 237 | 24.286 | −18.655 | 39.923 | 1.00 | 49.62 | MOLB C |
| ATOM | 4346 | O | SER | B 237 | 25.465 | −18.246 | 39.969 | 1.00 | 49.37 | MOLB O |
| ATOM | 4347 | N | VAL | B 238 | 23.941 | −19.931 | 39.780 | 1.00 | 46.99 | MOLB N |
| ATOM | 4348 | CA | VAL | B 238 | 24.918 | −20.984 | 39.858 | 1.00 | 44.43 | MOLB C |
| ATOM | 4349 | CB | VAL | B 238 | 24.817 | −21.736 | 41.197 | 1.00 | 44.14 | MOLB C |
| ATOM | 4350 | CG1 | VAL | B 238 | 25.543 | −23.044 | 41.109 | 1.00 | 44.27 | MOLB C |
| ATOM | 4351 | CG2 | VAL | B 238 | 25.400 | −20.890 | 42.316 | 1.00 | 35.86 | MOLB C |
| ATOM | 4352 | C | VAL | B 238 | 24.821 | −21.971 | 38.724 | 1.00 | 43.86 | MOLB C |
| ATOM | 4353 | O | VAL | B 238 | 23.853 | −22.736 | 38.632 | 1.00 | 44.42 | MOLB O |
| ATOM | 4354 | N | PHE | B 239 | 25.846 | −21.920 | 37.869 | 1.00 | 42.42 | MOLB N |
| ATOM | 4355 | CA | PHE | B 239 | 26.085 | −22.898 | 36.833 | 1.00 | 39.50 | MOLB C |
| ATOM | 4356 | CB | PHE | B 239 | 26.422 | −22.214 | 35.536 | 1.00 | 38.22 | MOLB C |
| ATOM | 4357 | CG | PHE | B 239 | 26.100 | −23.030 | 34.313 | 1.00 | 39.92 | MOLB C |
| ATOM | 4358 | CD1 | PHE | B 239 | 27.037 | −23.928 | 33.779 | 1.00 | 24.67 | MOLB C |
| ATOM | 4359 | CE1 | PHE | B 239 | 26.727 | −24.668 | 32.611 | 1.00 | 22.06 | MOLB C |
| ATOM | 4360 | CZ | PHE | B 239 | 25.466 | −24.518 | 31.981 | 1.00 | 29.73 | MOLB C |
| ATOM | 4361 | CE2 | PHE | B 239 | 24.535 | −23.627 | 32.508 | 1.00 | 34.34 | MOLB C |
| ATOM | 4362 | CD2 | PHE | B 239 | 24.863 | −22.879 | 33.670 | 1.00 | 35.48 | MOLB C |
| ATOM | 4363 | C | PHE | B 239 | 27.234 | −23.793 | 37.311 | 1.00 | 40.16 | MOLB C |
| ATOM | 4364 | O | PHE | B 239 | 28.283 | −23.336 | 37.820 | 1.00 | 38.19 | MOLB O |
| ATOM | 4365 | N | SER | B 240 | 27.000 | −25.093 | 37.197 | 1.00 | 41.30 | MOLB N |
| ATOM | 4366 | CA | SER | B 240 | 27.948 | −26.066 | 37.690 | 1.00 | 41.82 | MOLB C |
| ATOM | 4367 | CB | SER | B 240 | 27.414 | −26.755 | 38.924 | 1.00 | 40.33 | MOLB C |
| ATOM | 4368 | OG | SER | B 240 | 27.287 | −25.815 | 39.968 | 1.00 | 46.46 | MOLB O |
| ATOM | 4369 | C | SER | B 240 | 28.141 | −27.097 | 36.653 | 1.00 | 42.50 | MOLB C |
| ATOM | 4370 | O | SER | B 240 | 27.163 | −27.690 | 36.159 | 1.00 | 43.98 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 4371 | N | VAL | B | 241 | 29.396 | −27.300 | 36.288 | 1.00 | 40.97 | MOLB N |
| ATOM | 4372 | CA | VAL | B | 241 | 29.686 | −28.463 | 35.497 | 1.00 | 41.60 | MOLB C |
| ATOM | 4373 | CB | VAL | B | 241 | 30.184 | −28.144 | 34.079 | 1.00 | 40.21 | MOLB C |
| ATOM | 4374 | CG1 | VAL | B | 241 | 30.711 | −26.750 | 33.997 | 1.00 | 37.95 | MOLB C |
| ATOM | 4375 | CG2 | VAL | B | 241 | 31.214 | −29.174 | 33.654 | 1.00 | 36.33 | MOLB C |
| ATOM | 4376 | C | VAL | B | 241 | 30.592 | −29.416 | 36.280 | 1.00 | 44.52 | MOLB C |
| ATOM | 4377 | O | VAL | B | 241 | 31.437 | −29.009 | 37.089 | 1.00 | 44.55 | MOLB O |
| ATOM | 4378 | N | THR | B | 242 | 30.334 | −30.701 | 36.095 | 1.00 | 46.58 | MOLB N |
| ATOM | 4379 | CA | THR | B | 242 | 31.124 | −31.721 | 36.725 | 1.00 | 46.28 | MOLB C |
| ATOM | 4380 | CB | THR | B | 242 | 30.332 | −32.464 | 37.802 | 1.00 | 45.07 | MOLB C |
| ATOM | 4381 | OG1 | THR | B | 242 | 30.154 | −31.605 | 38.932 | 1.00 | 51.95 | MOLB O |
| ATOM | 4382 | CG2 | THR | B | 242 | 31.093 | −33.659 | 38.279 | 1.00 | 43.79 | MOLB C |
| ATOM | 4383 | C | THR | B | 242 | 31.419 | −32.640 | 35.600 | 1.00 | 47.28 | MOLB C |
| ATOM | 4384 | O | THR | B | 242 | 30.528 | −32.976 | 34.803 | 1.00 | 47.09 | MOLB O |
| ATOM | 4385 | N | ILE | B | 243 | 32.675 | −33.037 | 35.510 | 1.00 | 48.93 | MOLB N |
| ATOM | 4386 | CA | ILE | B | 243 | 33.073 | −33.955 | 34.453 | 1.00 | 50.83 | MOLB C |
| ATOM | 4387 | CB | ILE | B | 243 | 33.662 | −33.190 | 33.242 | 1.00 | 50.38 | MOLB C |
| ATOM | 4388 | CG1 | ILE | B | 243 | 34.730 | −34.020 | 32.537 | 1.00 | 54.78 | MOLB C |
| ATOM | 4389 | CD1 | ILE | B | 243 | 36.154 | −33.617 | 32.931 | 1.00 | 59.96 | MOLB C |
| ATOM | 4390 | CG2 | ILE | B | 243 | 34.313 | −31.856 | 33.685 | 1.00 | 47.03 | MOLB C |
| ATOM | 4391 | C | ILE | B | 243 | 34.006 | −35.066 | 34.959 | 1.00 | 51.33 | MOLB C |
| ATOM | 4392 | O | ILE | B | 243 | 35.108 | −34.793 | 35.470 | 1.00 | 50.45 | MOLB O |
| ATOM | 4393 | N | HIS | B | 244 | 33.539 | −36.310 | 34.827 | 1.00 | 51.82 | MOLB N |
| ATOM | 4394 | CA | HIS | B | 244 | 34.335 | −37.480 | 35.209 | 1.00 | 52.54 | MOLB C |
| ATOM | 4395 | CB | HIS | B | 244 | 33.442 | −38.674 | 35.611 | 1.00 | 51.30 | MOLB C |
| ATOM | 4396 | CG | HIS | B | 244 | 32.599 | −38.426 | 36.825 | 1.00 | 53.46 | MOLB C |
| ATOM | 4397 | ND1 | HIS | B | 244 | 31.238 | −38.201 | 36.758 | 1.00 | 60.51 | MOLB N |
| ATOM | 4398 | CE1 | HIS | B | 244 | 30.762 | −38.012 | 37.979 | 1.00 | 55.30 | MOLB C |
| ATOM | 4399 | NE2 | HIS | B | 244 | 31.766 | −38.102 | 38.835 | 1.00 | 56.24 | MOLB N |
| ATOM | 4400 | CD2 | HIS | B | 244 | 32.926 | −38.358 | 38.139 | 1.00 | 54.55 | MOLB C |
| ATOM | 4401 | C | HIS | B | 244 | 35.241 | −37.836 | 34.034 | 1.00 | 52.24 | MOLB C |
| ATOM | 4402 | O | HIS | B | 244 | 34.759 | −38.072 | 32.922 | 1.00 | 51.05 | MOLB O |
| ATOM | 4403 | N | MET | B | 245 | 36.547 | −37.848 | 34.291 | 1.00 | 53.22 | MOLB N |
| ATOM | 4404 | CA | MET | B | 245 | 37.557 | −38.154 | 33.279 | 1.00 | 54.08 | MOLB C |
| ATOM | 4405 | CB | MET | B | 245 | 38.585 | −37.032 | 33.190 | 1.00 | 54.14 | MOLB C |
| ATOM | 4406 | CG | MET | B | 245 | 38.059 | −35.648 | 32.957 | 1.00 | 48.68 | MOLB C |
| ATOM | 4407 | SD | MET | B | 245 | 39.322 | −34.422 | 33.408 | 1.00 | 49.14 | MOLB S |
| ATOM | 4408 | CE | MET | B | 245 | 38.919 | −33.982 | 35.086 | 1.00 | 28.03 | MOLB C |
| ATOM | 4409 | C | MET | B | 245 | 38.325 | −39.398 | 33.693 | 1.00 | 58.06 | MOLB C |
| ATOM | 4410 | O | MET | B | 245. | 38.070 | −39.948 | 34.758 | 1.00 | 58.77 | MOLB O |
| ATOM | 4411 | N | LYS | B | 246 | 39.286 | −39.804 | 32.855 | 1.00 | 61.26 | MOLB N |
| ATOM | 4412 | CA | LYS | B | 246 | 40.219 | −40.913 | 33.134 | 1.00 | 63.13 | MOLB C |
| ATOM | 4413 | CB | LYS | B | 246 | 39.485 | −42.247 | 33.320 | 1.00 | 61.64 | MOLB C |
| ATOM | 4414 | CG | LYS | B | 246 | 40.453 | −43.417 | 33.217 | 1.00 | 69.56 | MOLB C |
| ATOM | 4415 | CD | LYS | B | 246 | 40.217 | −44.493 | 34.256 | 1.00 | 76.83 | MOLB C |
| ATOM | 4416 | CE | LYS | B | 246 | 39.137 | −45.472 | 33.830 | 1.00 | 78.32 | MOLB C |
| ATOM | 4417 | NZ | LYS | B | 246 | 39.026 | −46.582 | 34.818 | 1.00 | 75.95 | MOLB N |
| ATOM | 4418 | C | LYS | B | 246 | 41.369 | −41.082 | 32.099 | 1.00 | 63.70 | MOLB C |
| ATOM | 4419 | O | LYS | B | 246 | 41.257 | −41.879 | 31.155 | 1.00 | 61.56 | MOLB O |
| ATOM | 4420 | N | GLU | B | 247 | 42.464 | −40.338 | 32.295 | 1.00 | 65.03 | MOLB N |
| ATOM | 4421 | CA | GLU | B | 247 | 43.671 | −40.462 | 31.458 | 1.00 | 65.94 | MOLB C |
| ATOM | 4422 | CB | GLU | B | 247 | 44.685 | −39.344 | 31.752 | 1.00 | 65.91 | MOLB C |
| ATOM | 4423 | CG | GLU | B | 247 | 44.689 | −38.152 | 30.765 | 1.00 | 65.67 | MOLB C |
| ATOM | 4424 | CD | GLU | B | 247 | 45.872 | −37.176 | 30.993 | 1.00 | 65.78 | MOLB C |
| ATOM | 4425 | OE1 | GLU | B | 247 | 46.734 | −37.007 | 30.076 | 1.00 | 44.86 | MOLB O |
| ATOM | 4426 | OE2 | GLU | B | 247 | 45.937 | −36.577 | 32.098 | 1.00 | 66.96 | MOLB O |
| ATOM | 4427 | C | GLU | B | 247 | 44.342 | −41.811 | 31.682 | 1.00 | 67.47 | MOLB C |
| ATOM | 4428 | O | GLU | B | 247 | 44.512 | −42.228 | 32.830 | 1.00 | 66.80 | MOLB O |
| ATOM | 4429 | N | THR | B | 248 | 44.723 | −42.473 | 30.580 | 1.00 | 69.32 | MOLB N |
| ATOM | 4430 | CA | THR | B | 248 | 45.387 | −43.792 | 30.586 | 1.00 | 70.04 | MOLB C |
| ATOM | 4431 | CB | THR | B | 248 | 44.401 | −44.922 | 30.142 | 1.00 | 68.14 | MOLB C |
| ATOM | 4432 | OG1 | THR | B | 248 | 43.146 | −44.804 | 30.833 | 1.00 | 64.72 | MOLB O |
| ATOM | 4433 | CG2 | THR | B | 248 | 44.987 | −46.268 | 30.433 | 1.00 | 66.12 | MOLB C |
| ATOM | 4434 | C | THR | B | 248 | 46.618 | −43.794 | 29.647 | 1.00 | 71.64 | MOLB C |
| ATOM | 4435 | O | THR | B | 248 | 46.474 | −43.473 | 28.465 | 1.00 | 71.63 | MOLB O |
| ATOM | 4436 | N | THR | B | 249 | 47.811 | −44.144 | 30.161 | 1.00 | 74.50 | MOLB N |
| ATOM | 4437 | CA | THR | B | 249 | 49.078 | −44.221 | 29.349 | 1.00 | 75.89 | MOLB C |
| ATOM | 4438 | CB | THR | B | 249 | 50.131 | −43.100 | 29.749 | 1.00 | 76.11 | MOLB C |
| ATOM | 4439 | OG1 | THR | B | 249 | 49.841 | −41.877 | 29.062 | 1.00 | 77.04 | MOLB O |
| ATOM | 4440 | CG2 | THR | B | 249 | 51.549 | −43.487 | 29.385 | 1.00 | 74.94 | MOLB C |
| ATOM | 4441 | C | THR | B | 249 | 49.757 | −45.630 | 29.310 | 1.00 | 79.53 | MOLB C |
| ATOM | 4442 | O | THR | B | 249 | 49.320 | −46.573 | 29.990 | 1.00 | 79.79 | MOLB O |
| ATOM | 4443 | N | ILE | B | 250 | 50.805 | −45.769 | 28.490 | 1.00 | 82.70 | MOLB N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 4444 | CA | ILE | B 250 | 51.585 | −47.011 | 28.428 | 1.00 | 85.91 | MOLB C |
| ATOM | 4445 | CB | ILE | B 250 | 51.999 | −47.401 | 26.979 | 1.00 | 86.18 | MOLB C |
| ATOM | 4446 | CG | 1ILE | B 250 | 50.871 | −47.168 | 25.972 | 1.00 | 86.07 | MOLB C |
| ATOM | 4447 | CD1 | ILE | B 250 | 51.259 | −47.511 | 24.530 | 1.00 | 83.95 | MOLB C |
| ATOM | 4448 | CG2 | ILE | B 250 | 52.432 | −48.867 | 26.930 | 1.00 | 89.81 | MOLB C |
| ATOM | 4449 | C | ILE | B 250 | 52.854 | −46.868 | 29.291 | 1.00 | 88.10 | MOLB C |
| ATOM | 4450 | O | ILE | B 250 | 53.613 | −45.897 | 29.129 | 1.00 | 88.29 | MOLB O |
| ATOM | 4451 | N | ASP | B 251 | 53.084 | −47.842 | 30.184 | 1.00 | 90.34 | MOLB N |
| ATOM | 4452 | CA | ASP | B 251 | 54.178 | −47.790 | 31.182 | 1.00 | 91.10 | MOLB C |
| ATOM | 4453 | CB | ASP | B 251 | 55.533 | −48.235 | 30.595 | 1.00 | 91.61 | MOLB C |
| ATOM | 4454 | CG | ASP | B 251 | 55.527 | −49.696 | 30.115 | 1.00 | 92.69 | MOLB C |
| ATOM | 4455 | OD1 | ASP | B 251 | 55.072 | −50.606 | 30.854 | 1.00 | 81.98 | MOLB O |
| ATOM | 4456 | OD2 | ASP | B 251 | 56.000 | −49.930 | 28.982 | 1.00 | 99.24 | MOLB O |
| ATOM | 4457 | C | ASP | B 251 | 54.258 | −46.378 | 31.745 | 1.00 | 90.66 | MOLB C |
| ATOM | 4458 | O | ASP | B 251 | 55.281 | −45.702 | 31.622 | 1.00 | 89.77 | MOLB O |
| ATOM | 4459 | N | GLY | B 252 | 53.138 | −45.965 | 32.341 | 1.00 | 91.72 | MOLB N |
| ATOM | 4460 | CA | GLY | B 252 | 52.892 | −44.610 | 32.852 | 1.00 | 92.97 | MOLB C |
| ATOM | 4461 | C | GLY | B 252 | 51.587 | −44.586 | 33.656 | 1.00 | 93.85 | MOLB C |
| ATOM | 4462 | O | GLY | B 252 | 50.650 | −45.339 | 33.351 | 1.00 | 95.12 | MOLB O |
| ATOM | 4463 | N | GLU | B 253 | 51.517 | −43.697 | 34.654 | 1.00 | 93.44 | MOLB N |
| ATOM | 4464 | CA | GLU | B 253 | 50.458 | −43.682 | 35.705 | 1.00 | 91.66 | MOLB C |
| ATOM | 4465 | CB | GLU | B 253 | 50.847 | −42.667 | 36.803 | 1.00 | 92.15 | MOLB C |
| ATOM | 4466 | CG | GLU | B 253 | 50.385 | −43.028 | 38.215 | 1.00 | 92.35 | MOLB C |
| ATOM | 4467 | CD | GLU | B 253 | 51.420 | −42.671 | 39.278 | 1.00 | 90.53 | MOLB C |
| ATOM | 4468 | OE1 | GLU | B 253 | 52.617 | −42.538 | 38.930 | 1.00 | 90.07 | MOLB O |
| ATOM | 4469 | OE2 | GLU | B 253 | 51.040 | −42.540 | 40.462 | 1.00 | 85.20 | MOLB O |
| ATOM | 4470 | C | GLU | B 253 | 48.985 | −43.481 | 35.261 | 1.00 | 89.36 | MOLB C |
| ATOM | 4471 | O | GLU | B 253 | 48.609 | −42.395 | 34.810 | 1.00 | 91.02 | MOLB O |
| ATOM | 4472 | N | GLU | B 254 | 48.179 | −44.543 | 35.413 | 1.00 | 85.53 | MOLB N |
| ATOM | 4473 | CA | GLU | B 254 | 46.726 | −44.581 | 35.126 | 1.00 | 80.40 | MOLB C |
| ATOM | 4474 | CB | GLU | B 254 | 46.218 | −46.020 | 35.382 | 1.00 | 80.45 | MOLB C |
| ATOM | 4475 | CG | GLU | B 254 | 45.158 | −46.582 | 34.419 | 1.00 | 79.68 | MOLB C |
| ATOM | 4476 | CD | GLU | B 254 | 43.705 | −46.404 | 34.894 | 1.00 | 80.00 | MOLB C |
| ATOM | 4477 | OE1 | GLU | B 254 | 42.796 | −46.553 | 34.052 | 1.00 | 83.84 | MOLB O |
| ATOM | 4478 | OE2 | GLU | B 254 | 43.457 | −46.129 | 36.091 | 1.00 | 68.99 | MOLB O |
| ATOM | 4479 | C | GLU | B 254 | 46.016 | −43.572 | 36.047 | 1.00 | 76.48 | MOLB C |
| ATOM | 4480 | O | GLU | B 254 | 46.441 | −43.398 | 37.187 | 1.00 | 76.71 | MOLB O |
| ATOM | 4481 | N | LEU | B 255 | 44.961 | −42.897 | 35.579 | 1.00 | 72.17 | MOLB N |
| ATOM | 4482 | CA | LEU | B 255 | 44.296 | −41.854 | 36.402 | 1.00 | 68.29 | MOLB C |
| ATOM | 4483 | CB | LEU | B 255 | 44.987 | −40.476 | 36.178 | 1.00 | 68.99 | MOLB C |
| ATOM | 4484 | CG | LEU | B 255 | 46.387 | −40.111 | 36.750 | 1.00 | 64.71 | MOLB C |
| ATOM | 4485 | CD1 | LEU | B 255 | 47.324 | −39.526 | 35.687 | 1.00 | 65.79 | MOLB C |
| ATOM | 4486 | CD2 | LEU | B 255 | 46.350 | −39.189 | 37.975 | 1.00 | 46.37 | MOLB C |
| ATOM | 4487 | C | LEU | B 255 | 42.754 | −41.731 | 36.220 | 1.00 | 65.76 | MOLB C |
| ATOM | 4488 | O | LEU | B 255 | 42.253 | −41.654 | 35.098 | 1.00 | 65.12 | MOLB O |
| ATOM | 4489 | N | VAL | B 256 | 42.009 | −41.726 | 37.330 | 1.00 | 62.90 | MOLB N |
| ATOM | 4490 | CA | VAL | B 256 | 40.561 | −41.415 | 37.302 | 1.00 | 59.51 | MOLB C |
| ATOM | 4491 | CB | VAL | B 256 | 39.674 | −42.530 | 37.885 | 1.00 | 58.81 | MOLB C |
| ATOM | 4492 | CG1 | VAL | B 256 | 38.177 | −42.148 | 37.768 | 1.00 | 58.41 | MOLB C |
| ATOM | 4493 | CG2 | VAL | B 256 | 39.952 | −43.836 | 37.207 | 1.00 | 59.79 | MOLB C |
| ATOM | 4494 | C | VAL | B 256 | 40.317 | −40.169 | 38.142 | 1.00 | 56.96 | MOLB C |
| ATOM | 4495 | O | VAL | B 256 | 40.776 | −40.100 | 39.282 | 1.00 | 57.63 | MOLB O |
| ATOM | 4496 | N | LYS | B 257 | 39.606 | −39.183 | 37.599 | 1.00 | 53.69 | MOLB N |
| ATOM | 4497 | CA | LYS | B 257 | 39.394 | −37.928 | 38.339 | 1.00 | 47.69 | MOLB C |
| ATOM | 4498 | CB | LYS | B 257 | 40.565 | −36.952 | 38.149 | 1.00 | 45.68 | MOLB C |
| ATOM | 4499 | CG | LYS | B 257 | 41.010 | −36.797 | 36.728 | 1.00 | 38.23 | MOLB C |
| ATOM | 4500 | CD | LYS | B 257 | 42.320 | −37.500 | 36.540 | 1.00 | 55.36 | MOLB C |
| ATOM | 4501 | CE | LYS | B 257 | 43.491 | −36.554 | 36.716 | 1.00 | 62.27 | MOLB C |
| ATOM | 4502 | NZ | LYS | B 257 | 43.571 | −35.580 | 35.571 | 1.00 | 59.18 | MOLB N |
| ATOM | 4503 | C | LYS | B 257 | 38.087 | −37.215 | 38.052 | 1.00 | 44.35 | MOLB C |
| ATOM | 4504 | O | LYS | B 257 | 37.470 | −37.367 | 36.998 | 1.00 | 41.97 | MOLB O |
| ATOM | 4505 | N | ILE | B 258 | 37.679 | −36.425 | 39.024 | 1.00 | 43.71 | MOLB N |
| ATOM | 4506 | CA | ILE | B 258 | 36.498 | −35.600 | 38.855 | 1.00 | 45.03 | MOLB C |
| ATOM | 4507 | CB | ILE | B 258 | 35.384 | −35.991 | 39.827 | 1.00 | 43.87 | MOLB C |
| ATOM | 4508 | CG1 | ILE | B 258 | 35.200 | −37.518 | 39.856 | 1.00 | 49.53 | MOLB C |
| ATOM | 4509 | CD1 | ILE | B 258 | 34.355 | −38.055 | 41.042 | 1.00 | 43.17 | MOLB C |
| ATOM | 4510 | CG2 | ILE | B 258 | 34.126 | −35.334 | 39.413 | 1.00 | 46.61 | MOLB C |
| ATOM | 4511 | C | ILE | B 258 | 36.821 | −34.094 | 38.959 | 1.00 | 44.18 | MOLB C |
| ATOM | 4512 | O | ILE | B 258 | 37.614 | −33.643 | 39.787 | 1.00 | 44.25 | MOLB O |
| ATOM | 4513 | N | GLY | B 259 | 36.212 | −33.331 | 38.069 | 1.00 | 42.97 | MOLB N |
| ATOM | 4514 | CA | GLY | B 259 | 36.388 | −31.908 | 38.038 | 1.00 | 40.27 | MOLB C |
| ATOM | 4515 | C | GLY | B 259 | 35.017 | −31.280 | 38.062 | 1.00 | 41.00 | MOLB C |
| ATOM | 4516 | O | GLY | B 259 | 34.050 | −31.793 | 37.460 | 1.00 | 41.00 | MOLB O |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 4517 | N | LYS | B 260 | 34.932 | −30.174 | 38.786 | 1.00 | 40.87 | MOLB N |
| ATOM | 4518 | CA | LYS | B 260 | 33.712 | −29.429 | 38.886 | 1.00 | 41.36 | MOLB C |
| ATOM | 4519 | CB | LYS | B 260 | 33.005 | −29.769 | 40.200 | 1.00 | 41.11 | MOLB C |
| ATOM | 4520 | CG | LYS | B 260 | 31.557 | −29.330 | 40.260 | 1.00 | 42.32 | MOLB C |
| ATOM | 4521 | CD | LYS | B 260 | 30.913 | −29.854 | 41.514 | 1.00 | 53.95 | MOLB C |
| ATOM | 4522 | CE | LYS | B 260 | 29.561 | −29.214 | 41.741 | 1.00 | 59.83 | MOLB C |
| ATOM | 4523 | NZ | LYS | B 260 | 29.177 | −29.270 | 43.189 | 1.00 | 60.27 | MOLB N |
| ATOM | 4524 | C | LYS | B 260 | 34.072 | −27.948 | 38.777 | 1.00 | 41.30 | MOLB C |
| ATOM | 4525 | O | LYS | B 260 | 35.196 | −27.544 | 39.056 | 1.00 | 42.24 | MOLB O |
| ATOM | 4526 | N | LEU | B 261 | 33.121 | −27.145 | 38.336 | 1.00 | 40.43 | MOLB N |
| ATOM | 4527 | CA | LEU | B 261 | 33.349 | −25.742 | 38.163 | 1.00 | 40.06 | MOLB C |
| ATOM | 4528 | CB | LEU | B 261 | 33.896 | −25.449 | 36.770 | 1.00 | 37.56 | MOLB C |
| ATOM | 4529 | CG | LEU | B 261 | 34.022 | −23.973 | 36.335 | 1.00 | 38.86 | MOLB C |
| ATOM | 4530 | CD1 | LEU | B 261 | 35.083 | −23.186 | 37.096 | 1.00 | 35.22 | MOLB C |
| ATOM | 4531 | CD2 | LEU | B 261 | 34.283 | −23.849 | 34.830 | 1.00 | 42.09 | MOLB C |
| ATOM | 4532 | C | LEU | B 261 | 32.015 | −25.057 | 38.365 | 1.00 | 42.71 | MOLB C |
| ATOM | 4533 | O | LEU | B 261 | 30.981 | −25.456 | 37.770 | 1.00 | 43.26 | MOLB O |
| ATOM | 4534 | N | ASN | B 262 | 32.034 | −24.034 | 39.218 | 1.00 | 42.07 | MOLB N |
| ATOM | 4535 | CA | ASN | B 262 | 30.822 | −23.302 | 39.507 | 1.00 | 41.06 | MOLB C |
| ATOM | 4536 | CB | ASN | B 262 | 30.457 | −23.426 | 41.007 | 1.00 | 41.09 | MOLB C |
| ATOM | 4537 | CG | ASN | B 262 | 30.231 | −24.905 | 41.450 | 1.00 | 44.17 | MOLB C |
| ATOM | 4538 | OD1 | ASN | B 262 | 30.826 | −25.380 | 42.424 | 1.00 | 50.35 | MOLB O |
| ATOM | 4539 | ND2 | ASN | B 262 | 29.385 | −25.625 | 40.720 | 1.00 | 47.58 | MOLB N |
| ATOM | 4540 | C | ASN | B 262 | 30.896 | −21.855 | 38.978 | 1.00 | 39.65 | MOLB C |
| ATOM | 4541 | O | ASN | B 262 | 31.743 | −21.008 | 39.378 | 1.00 | 37.89 | MOLB O |
| ATOM | 4542 | N | LEU | B 263 | 30.008 | −21.587 | 38.036 | 1.00 | 37.01 | MOLB N |
| ATOM | 4543 | CA | LEU | B 263 | 29.990 | −20.282 | 37.420 | 1.00 | 35.58 | MOLB C |
| ATOM | 4544 | CB | LEU | B 263 | 29.885 | −20.432 | 35.899 | 1.00 | 32.61 | MOLB C |
| ATOM | 4545 | CG | LEU | B 263 | 31.133 | −21.246 | 35.475 | 1.00 | 32.07 | MOLB C |
| ATOM | 4546 | CD1 | LEU | B 263 | 31.263 | −21.637 | 34.013 | 1.00 | 26.51 | MOLB C |
| ATOM | 4547 | CD2 | LEU | B 263 | 32.306 | −20.460 | 35.837 | 1.00 | 2.00 | MOLB C |
| ATOM | 4548 | C | LEU | B 263 | 28.942 | −19.359 | 38.075 | 1.00 | 37.25 | MOLB C |
| ATOM | 4549 | O | LEU | B 263 | 27.745 | −19.459 | 37.816 | 1.00 | 37.98 | MOLB O |
| ATOM | 4550 | N | VAL | B 264 | 29.417 | −18.456 | 38.935 | 1.00 | 38.49 | MOLB N |
| ATOM | 4551 | CA | VAL | B 264 | 28.503 | −17.683 | 39.758 | 1.00 | 39.13 | MOLB C |
| ATOM | 4552 | CB | VAL | B 264 | 28.831 | −17.827 | 41.274 | 1.00 | 40.11 | MOLB C |
| ATOM | 4553 | CG1 | VAL | B 264 | 27.566 | −17.651 | 42.102 | 1.00 | 37.07 | MOLB C |
| ATOM | 4554 | CG2 | VAL | B 264 | 29.407 | −19.182 | 41.566 | 1.00 | 38.90 | MOLB C |
| ATOM | 4555 | C | VAL | B 264 | 28.321 | −16.205 | 39.352 | 1.00 | 39.38 | MOLB C |
| ATOM | 4556 | O | VAL | B 264 | 29.192 | −15.337 | 39.560 | 1.00 | 36.77 | MOLB O |
| ATOM | 4557 | N | ASP | B 265 | 27.163 | −15.960 | 38.756 | 1.00 | 38.33 | MOLB N |
| ATOM | 4558 | CA | ASP | B 265 | 26.705 | −14.643 | 38.410 | 1.00 | 38.54 | MOLB C |
| ATOM | 4559 | CB | ASP | B 265 | 25.705 | −14.757 | 37.239 | 1.00 | 39.37 | MOLB C |
| ATOM | 4560 | CG | ASP | B 265 | 25.135 | −13.402 | 36.776 | 1.00 | 39.46 | MOLB C |
| ATOM | 4561 | OD1 | ASP | B 265 | 25.277 | −12.432 | 37.544 | 1.00 | 42.24 | MOLB O |
| ATOM | 4562 | OD2 | ASP | B 265 | 24.552 | −13.305 | 35.647 | 1.00 | 21.82 | MOLB O |
| ATOM | 4563 | C | ASP | B 265 | 26.001 | −14.229 | 39.677 | 1.00 | 40.91 | MOLB C |
| ATOM | 4564 | O | ASP | B 265 | 24.793 | −14.430 | 39.797 | 1.00 | 43.04 | MOLB O |
| ATOM | 4565 | N | LEU | B 266 | 26.739 | −13.719 | 40.663 | 1.00 | 41.29 | MOLB N |
| ATOM | 4566 | CA | LEU | B 266 | 26.111 | −13.277 | 41.906 | 1.00 | 41.52 | MOLB C |
| ATOM | 4567 | CB | LEU | B 266 | 27.087 | −12.526 | 42.770 | 1.00 | 39.53 | MOLB C |
| ATOM | 4568 | CG | LEU | B 266 | 28.300 | −13.269 | 43.300 | 1.00 | 41.82 | MOLB C |
| ATOM | 4569 | CD1 | LEU | B 266 | 29.033 | −12.298 | 44.217 | 1.00 | 38.99 | MOLB C |
| ATOM | 4570 | CD2 | LEU | B 266 | 27.926 | −14.568 | 44.038 | 1.00 | 34.70 | MOLB C |
| ATOM | 4571 | C | LEU | B 266 | 24.987 | −12.358 | 41.504 | 1.00 | 43.84 | MOLB C |
| ATOM | 4572 | O | LEU | B 266 | 24.641 | −12.320 | 40.345 | 1.00 | 46.90 | MOLB O |
| ATOM | 4573 | N | ALA | B 267 | 24.413 | −11.593 | 42.417 | 1.00 | 45.73 | MOLB N |
| ATOM | 4574 | CA | ALA | B 267 | 23.322 | −10.724 | 41.995 | 1.00 | 47.76 | MOLB C |
| ATOM | 4575 | CB | ALA | B 267 | 21.990 | −11.422 | 42.194 | 1.00 | 49.23 | MOLB C |
| ATOM | 4576 | C | ALA | B 267 | 23.312 | −9.386 | 42.696 | 1.00 | 48.03 | MOLB C |
| ATOM | 4577 | O | ALA | B 267 | 23.537 | −9.331 | 43.881 | 1.00 | 48.68 | MOLB O |
| ATOM | 4578 | N | GLY | B 268 | 23.038 | −8.329 | 41.937 | 1.00 | 48.27 | MOLB N |
| ATOM | 4579 | CA | GLY | B 268 | 22.933 | −6.951 | 42.425 | 1.00 | 49.09 | MOLB C |
| ATOM | 4580 | C | GLY | B 268 | 23.641 | −6.503 | 43.694 | 1.00 | 48.95 | MOLB C |
| ATOM | 4581 | O | GLY | B 268 | 23.150 | −6.741 | 44.802 | 1.00 | 50.29 | MOLB O |
| ATOM | 4582 | N | SER | B 269 | 24.761 | −5.798 | 43.556 | 1.00 | 47.79 | MOLB N |
| ATOM | 4583 | CA | SER | B 269 | 25.448 | −5.304 | 44.741 | 1.00 | 47.50 | MOLB C |
| ATOM | 4584 | CB | SER | B 269 | 26.961 | −5.438 | 44.583 | 1.00 | 46.35 | MOLB C |
| ATOM | 4585 | OG | SER | B 269 | 27.390 | −4.837 | 43.391 | 1.00 | 39.19 | MOLB O |
| ATOM | 4586 | C | SER | B 269 | 25.048 | −3.868 | 45.089 | 1.00 | 49.66 | MOLB C |
| ATOM | 4587 | O | SER | B 269 | 25.898 | −3.041 | 45.414 | 1.00 | 52.16 | MOLB O |
| ATOM | 4588 | N | GLU | B 270 | 23.751 | −3.574 | 45.036 | 1.00 | 51.09 | MOLB N |
| ATOM | 4589 | CA | GLU | B 270 | 23.241 | −2.222 | 45.334 | 1.00 | 51.46 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4590 | CB | GLU | B 270 | 23.215 | −1.362 | 44.047 | 1.00 | 50.02 | MOLB C |
| ATOM | 4591 | CG | GLU | B 270 | 22.062 | −1.607 | 43.039 | 1.00 | 42.69 | MOLB C |
| ATOM | 4592 | CD | GLU | B 270 | 22.139 | −2.954 | 42.294 | 1.00 | 60.05 | MOLB C |
| ATOM | 4593 | OE1 | GLU | B 270 | 23.182 | −3.652 | 42.402 | 1.00 | 63.95 | MOLB O |
| ATOM | 4594 | OE2 | GLU | B 270 | 21.152 | −3.316 | 41.596 | 1.00 | 50.98 | MOLB O |
| ATOM | 4595 | C | GLU | B 270 | 21.848 | −2.249 | 46.024 | 1.00 | 54.87 | MOLB C |
| ATOM | 4596 | O | GLU | B 270 | 21.713 | −2.090 | 47.255 | 1.00 | 56.23 | MOLB O |
| ATOM | 4597 | N | ALA | B 285 | 15.653 | −9.281 | 49.296 | 1.00 | 63.72 | MOLB N |
| ATOM | 4598 | CA | ALA | B 285 | 16.264 | −7.982 | 49.575 | 1.00 | 65.75 | MOLB C |
| ATOM | 4599 | CB | ALA | B 285 | 15.187 | −6.887 | 49.701 | 1.00 | 64.37 | MOLB C |
| ATOM | 4600 | C | ALA | B 285 | 17.176 | −8.013 | 50.821 | 1.00 | 67.53 | MOLB C |
| ATOM | 4601 | O | ALA | B 285 | 18.410 | −8.073 | 50.697 | 1.00 | 67.41 | MOLB O |
| ATOM | 4602 | N | GLY | B 286 | 16.584 | −7.961 | 52.014 | 1.00 | 67.92 | MOLB N |
| ATOM | 4603 | CA | GLY | B 286 | 17.385 | −8.068 | 53.224 | 1.00 | 69.42 | MOLB C |
| ATOM | 4604 | C | GLY | B 286 | 18.272 | −9.295 | 53.064 | 1.00 | 70.24 | MOLB C |
| ATOM | 4605 | O | GLY | B 286 | 19.489 | −9.248 | 53.270 | 1.00 | 69.05 | MOLB O |
| ATOM | 4606 | N | ASN | B 287 | 17.641 | −10.393 | 52.658 | 1.00 | 70.50 | MOLB N |
| ATOM | 4607 | CA | ASN | B 287 | 18.326 | −11.652 | 52.438 | 1.00 | 69.22 | MOLB C |
| ATOM | 4608 | CB | ASN | B 287 | 17.320 | −12.808 | 52.481 | 1.00 | 68.96 | MOLB C |
| ATOM | 4609 | CG | ASN | B 287 | 16.146 | −12.590 | 51.545 | 1.00 | 67.48 | MOLB C |
| ATOM | 4610 | OD1 | ASN | B 287 | 14.992 | −12.625 | 51.967 | 1.00 | 66.14 | MOLB O |
| ATOM | 4611 | ND2 | ASN | B 287 | 16.436 | −12.337 | 50.272 | 1.00 | 54.27 | MOLB N |
| ATOM | 4612 | C | ASN | B 287 | 19.173 | −11.704 | 51.158 | 1.00 | 68.97 | MOLB C |
| ATOM | 4613 | O | ASN | B 287 | 19.832 | −12.709 | 50.914 | 1.00 | 71.72 | MOLB O |
| ATOM | 4614 | N | ILE | B 288 | 19.149 | −10.659 | 50.330 | 1.00 | 67.19 | MOLB N |
| ATOM | 4615 | CA | ILE | B 288 | 20.106 | −10.581 | 49.213 | 1.00 | 65.76 | MOLB C |
| ATOM | 4616 | CB | ILE | B 288 | 19.524 | −9.891 | 47.921 | 1.00 | 66.51 | MOLB C |
| ATOM | 4617 | CG1 | ILE | B 288 | 19.387 | −10.890 | 46.757 | 1.00 | 68.92 | MOLB C |
| ATOM | 4618 | CD1 | ILE | B 288 | 18.789 | −12.267 | 47.094 | 1.00 | 63.25 | MOLB C |
| ATOM | 4619 | CG2 | ILE | B 288 | 20.445 | −8.818 | 47.391 | 1.00 | 64.15 | MOLB C |
| ATOM | 4620 | C | ILE | B 288 | 21.384 | −9.937 | 49.739 | 1.00 | 64.18 | MOLB C |
| ATOM | 4621 | O | ILE | B 288 | 22.403 | −10.600 | 49.934 | 1.00 | 63.54 | MOLB O |
| ATOM | 4622 | N | ASN | B 289 | 21.306 | −8.654 | 50.036 | 1.00 | 63.62 | MOLB N |
| ATOM | 4623 | CA | ASN | B 289 | 22.461 | −7.933 | 50.561 | 1.00 | 64.71 | MOLB C |
| ATOM | 4624 | CB | ASN | B 289 | 22.059 | −6.520 | 51.039 | 1.00 | 64.70 | MOLB C |
| ATOM | 4625 | CG | ASN | B 289 | 20.551 | −6.393 | 51.366 | 1.00 | 72.32 | MOLB C |
| ATOM | 4626 | OD1 | ASN | B 289 | 20.050 | −6.918 | 52.377 | 1.00 | 72.49 | MOLB O |
| ATOM | 4627 | ND2 | ASN | B 289 | 19.835 | −5.665 | 50.511 | 1.00 | 76.47 | MOLB N |
| ATOM | 4628 | C | ASN | B 289 | 23.223 | −8.686 | 51.646 | 1.00 | 63.78 | MOLB C |
| ATOM | 4629 | O | ASN | B 289 | 24.377 | −8.379 | 51.937 | 1.00 | 64.48 | MOLB O |
| ATOM | 4630 | N | GLN | B 290 | 22.585 | −9.686 | 52.239 | 1.00 | 63.60 | MOLB N |
| ATOM | 4631 | CA | GLN | B 290 | 23.204 | −10.416 | 53.350 | 1.00 | 62.25 | MOLB C |
| ATOM | 4632 | CB | GLN | B 290 | 22.118 | −10.975 | 54.300 | 1.00 | 63.49 | MOLB C |
| ATOM | 4633 | CG | GLN | B 290 | 22.525 | −12.142 | 55.210 | 1.00 | 65.46 | MOLB C |
| ATOM | 4634 | CD | GLN | B 290 | 23.724 | −11.826 | 56.079 | 1.00 | 72.79 | MOLB C |
| ATOM | 4635 | OE1 | GLN | B 290 | 24.141 | −10.670 | 56.186 | 1.00 | 81.97 | MOLB O |
| ATOM | 4636 | NE2 | GLN | B 290 | 24.292 | −12.856 | 56.703 | 1.00 | 65.57 | MOLB N |
| ATOM | 4637 | C | GLN | B 290 | 24.132 | −11.503 | 52.807 | 1.00 | 59.35 | MOLB C |
| ATOM | 4638 | O | GLN | B 290 | 25.279 | −11.667 | 53.276 | 1.00 | 58.12 | MOLB O |
| ATOM | 4639 | N | SER | B 291 | 23.632 | −12.218 | 51.799 | 1.00 | 53.42 | MOLB N |
| ATOM | 4640 | CA | SER | B 291 | 24.386 | −13.285 | 51.189 | 1.00 | 48.35 | MOLB C |
| ATOM | 4641 | CB | SER | B 291 | 23.725 | −13.678 | 49.880 | 1.00 | 47.56 | MOLB C |
| ATOM | 4642 | OG | SER | B 291 | 22.340 | −13.385 | 49.907 | 1.00 | 39.75 | MOLB O |
| ATOM | 4643 | C | SER | B 291 | 25.749 | −12.732 | 50.885 | 1.00 | 47.92 | MOLB C |
| ATOM | 4644 | O | SER | B 291 | 26.780 | −13.264 | 51.305 | 1.00 | 43.98 | MOLB O |
| ATOM | 4645 | N | LEU | B 292 | 25.731 | −11.622 | 50.156 | 1.00 | 49.15 | MOLB N |
| ATOM | 4646 | CA | LEU | B 292 | 26.943 | −11.067 | 49.632 | 1.00 | 50.62 | MOLB C |
| ATOM | 4647 | CB | LEU | B 292 | 26.684 | −9.790 | 48.842 | 1.00 | 50.96 | MOLB C |
| ATOM | 4648 | CG | LEU | B 292 | 25.841 | −9.810 | 47.566 | 1.00 | 52.50 | MOLB C |
| ATOM | 4649 | CD1 | LEU | B 292 | 25.686 | −8.377 | 47.050 | 1.00 | 46.36 | MOLB C |
| ATOM | 4650 | CD2 | LEU | B 292 | 26.453 | −10.692 | 46.506 | 1.00 | 51.24 | MOLB C |
| ATOM | 4651 | C | LEU | B 292 | 27.874 | −10.787 | 50.781 | 1.00 | 51.83 | MOLB C |
| ATOM | 4652 | O | LEU | B 292 | 29.029 | −11.212 | 50.762 | 1.00 | 55.28 | MOLB O |
| ATOM | 4653 | N | LEU | B 293 | 27.387 | −10.094 | 51.799 | 1.00 | 49.87 | MOLB N |
| ATOM | 4654 | CA | LEU | B 293 | 28.300 | −9.689 | 52.848 | 1.00 | 48.03 | MOLB C |
| ATOM | 4655 | CB | LEU | B 293 | 27.556 | −8.917 | 53.922 | 1.00 | 49.93 | MOLB C |
| ATOM | 4656 | CG | LEU | B 293 | 27.282 | −7.468 | 53.500 | 1.00 | 54.31 | MOLB C |
| ATOM | 4657 | CD1 | LEU | B 293 | 28.566 | −6.760 | 53.073 | 1.00 | 54.31 | MOLB C |
| ATOM | 4658 | CD2 | LEU | B 293 | 26.289 | −7.450 | 52.377 | 1.00 | 60.21 | MOLB C |
| ATOM | 4659 | C | LEU | B 293 | 29.016 | −10.892 | 53.426 | 1.00 | 46.07 | MOLB C |
| ATOM | 4660 | O | LEU | B 293 | 30.209 | −10.840 | 53.738 | 1.00 | 43.98 | MOLB O |
| ATOM | 4661 | N | THR | B 294 | 28.265 | −11.983 | 53.515 | 1.00 | 45.05 | MOLB N |
| ATOM | 4662 | CA | THR | B 294 | 28.715 | −13.232 | 54.086 | 1.00 | 45.06 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4663 | CB | THR | B 294 | 27.539 | −14.245 | 54.098 | 1.00 | 46.49 | MOLB C |
| ATOM | 4664 | OG1 | THR | B 294 | 26.482 | −13.749 | 54.946 | 1.00 | 45.91 | MOLB O |
| ATOM | 4665 | CG2 | THR | B 294 | 27.997 | −15.652 | 54.548 | 1.00 | 40.47 | MOLB C |
| ATOM | 4666 | C | THR | B 294 | 29.866 | −13.791 | 53.267 | 1.00 | 46.72 | MOLB C |
| ATOM | 4667 | O | THR | B 294 | 30.943 | −14.086 | 53.801 | 1.00 | 46.57 | MOLB O |
| ATOM | 4668 | N | LEU | B 295 | 29.606 | −13.923 | 51.965 | 1.00 | 46.86 | MOLB N |
| ATOM | 4669 | CA | LEU | B 295 | 30.558 | −14.428 | 50.981 | 1.00 | 44.95 | MOLB C |
| ATOM | 4670 | CB | LEU | B 295 | 29.975 | −14.260 | 49.559 | 1.00 | 45.85 | MOLB C |
| ATOM | 4671 | CG | LEU | B 295 | 30.931 | −14.233 | 48.351 | 1.00 | 40.49 | MOLB C |
| ATOM | 4672 | CD1 | LEU | B 295 | 31.779 | −15.469 | 48.334 | 1.00 | 42.76 | MOLB C |
| ATOM | 4673 | CD2 | LEU | B 295 | 30.214 | −14.117 | 47.018 | 1.00 | 42.09 | MOLB C |
| ATOM | 4674 | C | LEU | B 295 | 31.862 | −13.679 | 51.088 | 1.00 | 45.51 | MOLB C |
| ATOM | 4675 | O | LEU | B 295 | 32.948 | −14.280 | 51.142 | 1.00 | 44.35 | MOLB O |
| ATOM | 4676 | N | GLY | B 296 | 31.733 | −12.358 | 51.100 | 1.00 | 45.07 | MOLB N |
| ATOM | 4677 | CA | GLY | B 296 | 32.875 | −11.480 | 51.163 | 1.00 | 48.05 | MOLB C |
| ATOM | 4678 | C | GLY | B 296 | 33.695 | −11.791 | 52.387 | 1.00 | 50.31 | MOLB C |
| ATOM | 4679 | O | GLY | B 296 | 34.929 | −11.828 | 52.327 | 1.00 | 50.90 | MOLB O |
| ATOM | 4680 | N | ARG | B 297 | 33.007 | −12.029 | 53.501 | 1.00 | 51.37 | MOLB N |
| ATOM | 4681 | CA | ARG | B 297 | 33.684 | −12.361 | 54.748 | 1.00 | 51.65 | MOLB C |
| ATOM | 4682 | CB | ARG | B 297 | 32.701 | −12.224 | 55.911 | 1.00 | 51.22 | MOLB C |
| ATOM | 4683 | CG | ARG | B 297 | 33.277 | −11.523 | 57.167 | 1.00 | 56.41 | MOLB C |
| ATOM | 4684 | CD | ARG | B 297 | 32.155 | −11.077 | 58.130 | 1.00 | 56.68 | MOLB C |
| ATOM | 4685 | NE | ARG | B 297 | 31.069 | −12.068 | 58.220 | 1.00 | 68.03 | MOLB N |
| ATOM | 4686 | CZ | ARG | B 297 | 30.844 | −12.870 | 59.261 | 1.00 | 64.33 | MOLB C |
| ATOM | 4687 | NH1 | ARG | B 297 | 31.612 | −12.807 | 60.349 | 1.00 | 72.60 | MOLB N |
| ATOM | 4688 | NH2 | ARG | B 297 | 29.840 | −13.732 | 59.217 | 1.00 | 54.14 | MOLB N |
| ATOM | 4689 | C | ARG | B 297 | 34.351 | −13.763 | 54.663 | 1.00 | 49.77 | MOLB C |
| ATOM | 4690 | O | ARG | B 297 | 35.452 | −13.965 | 55.193 | 1.00 | 48.62 | MOLB O |
| ATOM | 4691 | N | VAL | B 298 | 33.701 | −14.692 | 53.950 | 1.00 | 47.23 | MOLB N |
| ATOM | 4692 | CA | VAL | B 298 | 34.206 | −16.058 | 53.693 | 1.00 | 45.84 | MOLB C |
| ATOM | 4693 | CB | VAL | B 298 | 33.161 | −16.878 | 52.892 | 1.00 | 44.76 | MOLB C |
| ATOM | 4694 | CG1 | VAL | B 298 | 33.642 | −18.274 | 52.677 | 1.00 | 30.22 | MOLB C |
| ATOM | 4695 | CG2 | VAL | B 298 | 31.819 | −16.892 | 53.595 | 1.00 | 47.95 | MOLB C |
| ATOM | 4696 | C | VAL | B 298 | 35.530 | −16.111 | 52.888 | 1.00 | 49.28 | MOLB C |
| ATOM | 4697 | O | VAL | B 298 | 36.411 | −16.961 | 53.123 | 1.00 | 45.83 | MOLB O |
| ATOM | 4698 | N | ILE | B 299 | 35.630 | −15.229 | 51.896 | 1.00 | 51.79 | MOLB N |
| ATOM | 4699 | CA | ILE | B 299 | 36.808 | −15.156 | 51.063 | 1.00 | 53.27 | MOLB C |
| ATOM | 4700 | CB | ILE | B 299 | 36.595 | −14.246 | 49.831 | 1.00 | 54.12 | MOLB C |
| ATOM | 4701 | CG1 | ILE | B 299 | 35.265 | −14.555 | 49.131 | 1.00 | 53.29 | MOLB C |
| ATOM | 4702 | CD1 | ILE | B 299 | 35.025 | −15.986 | 48.910 | 1.00 | 41.54 | MOLB C |
| ATOM | 4703 | CG2 | ILE | B 299 | 37.771 | −14.324 | 48.870 | 1.00 | 49.51 | MOLB C |
| ATOM | 4704 | C | ILE | B 299 | 37.876 | −14.542 | 51.929 | 1.00 | 56.03 | MOLB C |
| ATOM | 4705 | O | ILE | B 299 | 38.872 | −15.185 | 52.227 | 1.00 | 58.45 | MOLB O |
| ATOM | 4706 | N | THR | B 300 | 37.644 | −13.306 | 52.369 | 1.00 | 57.68 | MOLB N |
| ATOM | 4707 | CA | THR | B 300 | 38.627 | −12.581 | 53.163 | 1.00 | 56.97 | MOLB C |
| ATOM | 4708 | CB | THR | B 300 | 38.032 | −11.376 | 53.896 | 1.00 | 54.92 | MOLB C |
| ATOM | 4709 | OG1 | THR | B 300 | 37.193 | −10.628 | 53.009 | 1.00 | 52.88 | MOLB O |
| ATOM | 4710 | CG2 | THR | B 300 | 39.155 | −10.489 | 54.385 | 1.00 | 52.94 | MOLB C |
| ATOM | 4711 | C | THR | B 300 | 39.172 | −13.540 | 54.192 | 1.00 | 58.51 | MOLB C |
| ATOM | 4712 | O | THR | B 300 | 40.287 | −13.383 | 54.684 | 1.00 | 58.29 | MOLB O |
| ATOM | 4713 | N | ALA | B 301 | 38.353 | −14.538 | 54.507 | 1.00 | 59.85 | MOLB N |
| ATOM | 4714 | CA | ALA | B 301 | 38.717 | −15.538 | 55.480 | 1.00 | 60.75 | MOLB C |
| ATOM | 4715 | CB | ALA | B 301 | 37.477 | −16.293 | 55.951 | 1.00 | 61.00 | MOLB C |
| ATOM | 4716 | C | ALA | B 301 | 39.692 | −16.464 | 54.792 | 1.00 | 61.48 | MOLB C |
| ATOM | 4717 | O | ALA | B 301 | 40.821 | −16.663 | 55.268 | 1.00 | 64.10 | MOLB O |
| ATOM | 4718 | N | LEU | B 302 | 39.263 | −17.024 | 53.662 | 1.00 | 59.43 | MOLB N |
| ATOM | 4719 | CA | LEU | B 302 | 40.145 | −17.860 | 52.882 | 1.00 | 57.50 | MOLB C |
| ATOM | 4720 | CB | LEU | B 302 | 39.482 | −18.253 | 51.569 | 1.00 | 55.63 | MOLB C |
| ATOM | 4721 | CG | LEU | B 302 | 38.477 | −19.371 | 51.854 | 1.00 | 54.36 | MOLB C |
| ATOM | 4722 | CD1 | LEU | B 302 | 37.167 | −19.277 | 51.074 | 1.00 | 54.98 | MOLB C |
| ATOM | 4723 | CD2 | LEU | B 302 | 39.131 | −20.694 | 51.617 | 1.00 | 51.91 | MOLB C |
| ATOM | 4724 | C | LEU | B 302 | 41.462 | −17.107 | 52.693 | 1.00 | 58.00 | MOLB C |
| ATOM | 4725 | O | LEU | B 302 | 42.497 | −17.533 | 53.184 | 1.00 | 56.77 | MOLB O |
| ATOM | 4726 | N | VAL | B 303 | 41.410 | −15.947 | 52.060 | 1.00 | 59.24 | MOLB N |
| ATOM | 4727 | CA | VAL | B 303 | 42.627 | −15.200 | 51.805 | 1.00 | 61.07 | MOLB C |
| ATOM | 4728 | CB | VAL | B 303 | 42.362 | −13.793 | 51.296 | 1.00 | 61.25 | MOLB C |
| ATOM | 4729 | CG1 | VAL | B 303 | 43.572 | −13.309 | 50.487 | 1.00 | 58.40 | MOLB C |
| ATOM | 4730 | CG2 | VAL | B 303 | 41.085 | −13.757 | 50.464 | 1.00 | 60.79 | MOLB C |
| ATOM | 4731 | C | VAL | B 303 | 43.463 | −15.053 | 53.048 | 1.00 | 63.16 | MOLB C |
| ATOM | 4732 | O | VAL | B 303 | 44.669 | −15.267 | 52.995 | 1.00 | 63.46 | MOLB O |
| ATOM | 4733 | N | GLU | B 304 | 42.828 | −14.673 | 54.157 | 1.00 | 66.24 | MOLB N |
| ATOM | 4734 | CA | GLU | B 304 | 43.549 | −14.427 | 55.424 | 1.00 | 68.63 | MOLB C |
| ATOM | 4735 | CB | GLU | B 304 | 42.833 | −13.373 | 56.300 | 1.00 | 67.69 | MOLB C |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 4736 | CG | GLU | B 304 | 42.630 | −12.007 | 55.620 | 1.00 | 68.70 | MOLB C |
| ATOM | 4737 | CD | GLU | B 304 | 43.913 | −11.461 | 55.000 | 1.00 | 77.56 | MOLB C |
| ATOM | 4738 | OE1 | GLU | B 304 | 44.909 | −11.298 | 55.740 | 1.00 | 81.32 | MOLB O |
| ATOM | 4739 | OE2 | GLU | B 304 | 43.936 | −11.197 | 53.772 | 1.00 | 75.06 | MOLB O |
| ATOM | 4740 | C | GLU | B 304 | 43.866 | −15.709 | 56.215 | 1.00 | 70.97 | MOLB C |
| ATOM | 4741 | O | GLU | B 304 | 45.014 | −15.898 | 56.661 | 1.00 | 71.20 | MOLB O |
| ATOM | 4742 | N | ARG | B 305 | 42.873 | −16.591 | 56.388 | 1.00 | 71.84 | MOLB N |
| ATOM | 4743 | CA | ARG | B 305 | 43.152 | −17.829 | 57.089 | 1.00 | 72.79 | MOLB C |
| ATOM | 4744 | CB | ARG | B 305 | 44.619 | −17.764 | 57.469 | 1.00 | 71.93 | MOLB C |
| ATOM | 4745 | CG | ARG | B 305 | 45.304 | −19.016 | 57.841 | 1.00 | 80.90 | MOLB C |
| ATOM | 4746 | CD | ARG | B 305 | 46.780 | −18.740 | 57.595 | 1.00 | 102.40 | MOLB C |
| ATOM | 4747 | NE | ARG | B 305 | 47.613 | −18.892 | 58.789 | 1.00 | 115.90 | MOLB N |
| ATOM | 4748 | CZ | ARG | B 305 | 48.700 | −18.157 | 59.035 | 1.00 | 121.37 | MOLB C |
| ATOM | 4749 | NH1 | ARG | B 305 | 49.080 | −17.215 | 58.173 | 1.00 | 118.66 | MOLB N |
| ATOM | 4750 | NH2 | ARG | B 305 | 49.405 | −18.354 | 60.147 | 1.00 | 124.27 | MOLB N |
| ATOM | 4751 | C | ARG | B 305 | 42.293 | −18.060 | 58.342 | 1.00 | 72.47 | MOLB C |
| ATOM | 4752 | O | ARG | B 305 | 42.448 | −19.081 | 59.001 | 1.00 | 70.46 | MOLB O |
| ATOM | 4753 | N | THR | B 306 | 41.379 | −17.133 | 58.649 | 1.00 | 74.73 | MOLB N |
| ATOM | 4754 | CA | THR | B 306 | 40.546 | −17.190 | 59.890 | 1.00 | 77.24 | MOLB C |
| ATOM | 4755 | CB | THR | B 306 | 39.708 | −15.890 | 60.124 | 1.00 | 77.31 | MOLB C |
| ATOM | 4756 | OG1 | THR | B 306. | 38.734 | −15.750 | 59.088 | 1.00 | 83.26 | MOLB O |
| ATOM | 4757 | CG2 | THR | B 306 | 40.594 | −14.645 | 60.148 | 1.00 | 79.12 | MOLB C |
| ATOM | 4758 | C | THR | B 306 | 39.609 | −18.409 | 59.997 | 1.00 | 77.73 | MOLB C |
| ATOM | 4759 | O | THR | B 306 | 38.473 | −18.381 | 59.499 | 1.00 | 76.74 | MOLB O |
| ATOM | 4760 | N | PRO | B 307 | 40.067 | −19.457 | 60.714 | 1.00 | 77.79 | MOLB N |
| ATOM | 4761 | CA | PRO | B 307 | 39.464 | −20.780 | 60.690 | 1.00 | 76.46 | MOLB C |
| ATOM | 4762 | CB | PRO | B 307 | 40.125 | −21.482 | 61.876 | 1.00 | 76.89 | MOLB C |
| ATOM | 4763 | CG | PRO | B 307 | 41.446 | −20.829 | 61.993 | 1.00 | 76.95 | MOLB C |
| ATOM | 4764 | CD | PRO | B 307 | 41.200 | −19.395 | 61.662 | 1.00 | 78.27 | MOLB C |
| ATOM | 4765 | C | PRO | B 307 | 37.941 | −20.781 | 60.822 | 1.00 | 76.22 | MOLB C |
| ATOM | 4766 | O | PRO | B 307 | 37.310 | −21.811 | 60.570 | 1.00 | 77.74 | MOLB 0 |
| ATOM | 4767 | N | HIS | B 308 | 37.340 | −19.668 | 61.225 | 1.00 | 73.98 | MOLB N |
| ATOM | 4768 | CA | HIS | B 308 | 35.889 | −19.605 | 61.146 | 1.00 | 72.41 | MOLB C |
| ATOM | 4769 | CB | HIS | B 308 | 35.252 | −18.754 | 62.248 | 1.00 | 70.75 | MOLB C |
| ATOM | 4770 | CG | HIS | B 308 | 33.754 | −18.832 | 62.272 | 1.00 | 80.21 | MOLB C |
| ATOM | 4771 | ND1 | HIS | B 308 | 32.941 | −17.732 | 62.076 | 1.00 | 96.12 | MOLB N |
| ATOM | 4772 | CE1 | HIS | B 308 | 31.672 | −18.102 | 62.144 | 1.00 | 100.94 | MOLB C |
| ATOM | 4773 | NE2 | HIS | B 308 | 31.629 | −19.404 | 62.373 | 1.00 | 102.46 | MOLB N |
| ATOM | 4774 | CD2 | HIS | B 308 | 32.917 | −19.886 | 62.452 | 1.00 | 95.49 | MOLB C |
| ATOM | 4775 | C | HIS | B 308 | 35.569 | −19.086 | 59.741 | 1.00 | 70.27 | MOLB C |
| ATOM | 4776 | O | HIS | B 308 | 35.804 | −17.922 | 59.411 | 1.00 | 70.53 | MOLB O |
| ATOM | 4777 | N | VAL | B 309 | 35.081 | −19.977 | 58.894 | 1.00 | 66.73 | MOLB N |
| ATOM | 4778 | CA | VAL | B 309 | 34.762 | −19.595 | 57.544 | 1.00 | 63.72 | MOLB C |
| ATOM | 4779 | CB | VAL | B 309 | 35.701 | −20.297 | 56.467 | 1.00 | 63.45 | MOLB C |
| ATOM | 4780 | CG1 | VAL | B 309 | 37.118 | −19.747 | 56.543 | 1.00 | 58.55 | MOLB C |
| ATOM | 4781 | CG2 | VAL | B 309 | 35.770 | −21.792 | 56.670 | 1.00 | 65.56 | MOLB C |
| ATOM | 4782 | C | VAL | B 309 | 33.251 | −19.771 | 57.376 | 1.00 | 62.02 | MOLB C |
| ATOM | 4783 | O | VAL | B 309 | 32.769 | −20.802 | 56.930 | 1.00 | 62.31 | MOLB O |
| ATOM | 4784 | N | PRO | B 310 | 32.497 | −18.740 | 57.770 | 1.00 | 61.56 | MOLB N |
| ATOM | 4785 | CA | PRO | B 310 | 31.032 | −18.615 | 57.808 | 1.00 | 60.86 | MOLB C |
| ATOM | 4786 | CB | PRO | B 310 | 30.822 | −17.102 | 57.796 | 1.00 | 61.31 | MOLB C |
| ATOM | 4787 | CG | PRO | B 310 | 32.029 | −16.549 | 58.488 | 1.00 | 60.74 | MOLB C |
| ATOM | 4788 | CD | PRO | B 310 | 33.167 | −17.516 | 58.248 | 1.00 | 61.42 | MOLB C |
| ATOM | 4789 | C | PRO | B 310 | 30.248 | −19.249 | 56.650 | 1.00 | 60.05 | MOLB C |
| ATOM | 4790 | O | PRO | B 310 | 29.303 | −18.644 | 56.135 | 1.00 | 59.87 | MOLB O |
| ATOM | 4791 | N | TYR | B 311 | 30.592 | −20.464 | 56.259 | 1.00 | 59.09 | MOLB N |
| ATOM | 4792 | CA | TYR | B 311 | 29.839 | −21.071 | 55.200 | 1.00 | 61.53 | MOLB C |
| ATOM | 4793 | CB | TYR | B 311 | 30.317 | −22.481 | 54.932 | 1.00 | 62.62 | MOLB C |
| ATOM | 4794 | CG | TYR | B 311 | 31.676 | −22.487 | 54.354 | 1.00 | 62.25 | MOLB C |
| ATOM | 4795 | CD1 | TYR | B 311 | 32.766 | −22.713 | 55.159 | 1.00 | 59.97 | MOLB C |
| ATOM | 4796 | CE1 | TYR | B 311 | 34.031 | −22.699 | 54.657 | 1.00 | 66.27 | MOLB C |
| ATOM | 4797 | CZ | TYR | B 311 | 34.236 | −22.437 | 53.331 | 1.00 | 66.50 | MOLB C |
| ATOM | 4798 | OH | TYR | B 311 | 35.535 | −22.434 | 52.880 | 1.00 | 68.95 | MOLB O |
| ATOM | 4799 | CE2 | TYR | B 311 | 33.162 | −22.195 | 52.489 | 1.00 | 66.44 | MOLB C |
| ATOM | 4800 | CD2 | TYR | B 311 | 31.883 | −22.215 | 53.008 | 1.00 | 61.87 | MOLB C |
| ATOM | 4801 | C | TYR | B 311 | 28.401 | −21.118 | 55.599 | 1.00 | 63.96 | MOLB C |
| ATOM | 4802 | O | TYR | B 311 | 27.518 | −20.876 | 54.776 | 1.00 | 63.88 | MOLB O |
| ATOM | 4803 | N | ARG | B 312 | 28.182 | −21.429 | 56.877 | 1.00 | 66.62 | MOLB N |
| ATOM | 4804 | CA | ARG | B 312 | 26.847 | −21.676 | 57.416 | 1.00 | 69.28 | MOLB C |
| ATOM | 4805 | CB | ARG | B 312 | 26.925 | −22.242 | 58.834 | 1.00 | 70.69 | MOLB C |
| ATOM | 4806 | CG | ARG | B 312 | 27.124 | −23.749 | 58.911 | 1.00 | 75.96 | MOLB C |
| ATOM | 4807 | CD | ARG | B 312 | 25.900 | −24.501 | 58.404 | 1.00 | 86.20 | MOLB C |
| ATOM | 4808 | NE | ARG | B 312 | 26.025 | −25.942 | 58.619 | 1.00 | 91.60 | MOLB N |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 4809 | CZ | ARG | B 312 | 26.618 | −26.787 | 57.774 | 1.00 | 99.88 | MOLB | C |
| ATOM | 4810 | NH1 | ARG | B 312 | 27.154 | −26.349 | 56.636 | 1.00 | 101.44 | MOLB | N |
| ATOM | 4811 | NH2 | ARG | B 312 | 26.679 | −28.079 | 58.072 | 1.00 | 103.43 | MOLB | N |
| ATOM | 4812 | C | ARG | B 312 | 25.915 | −20.473 | 57.392 | 1.00 | 69.79 | MOLB | C |
| ATOM | 4813 | O | ARG | B 312 | 24.691 | −20.645 | 57.327 | 1.00 | 71.58 | MOLB | O |
| ATOM | 4814 | N | GLU | B 313 | 26.482 | −19.266 | 57.431 | 1.00 | 68.76 | MOLB | N |
| ATOM | 4815 | CA | GLU | B 313 | 25.674 | −18.038 | 57.403 | 1.00 | 67.10 | MOLB | C |
| ATOM | 4816 | CB | GLU | B 313 | 26.486 | −16.851 | 57.953 | 1.00 | 66.61 | MOLB | C |
| ATOM | 4817 | CG | GLU | B 313 | 26.903 | −16.964 | 59.416 | 1.00 | 62.05 | MOLB | C |
| ATOM | 4818 | CD | GLU | B 313 | 28.041 | −16.014 | 59.764 | 1.00 | 65.19 | MOLB | C |
| ATOM | 4819 | OE1 | GLU | B 313 | 28.144 | −14.962 | 59.101 | 1.00 | 70.14 | MOLB | O |
| ATOM | 4820 | OE2 | GLU | B 313 | 28.838 | −16.309 | 60.687 | 1.00 | 44.94 | MOLB | O |
| ATOM | 4821 | C | GLU | B 313 | 25.083 | −17.690 | 56.015 | 1.00 | 67.03 | MOLB | C |
| ATOM | 4822 | O | GLU | B 313 | 25.131 | −16.535 | 55.608 | 1.00 | 69.13 | MOLB | O |
| ATOM | 4823 | N | SER | B 314 | 24.538 | −18.675 | 55.290 | 1.00 | 65.81 | MOLB | N |
| ATOM | 4824 | CA | SER | B 314 | 23.844 | −18.428 | 53.993 | 1.00 | 64.12 | MOLB | C |
| ATOM | 4825 | CB | SER | B 314 | 24.440 | −17.219 | 53.253 | 1.00 | 64.73 | MOLB | C |
| ATOM | 4826 | OG | SER | B 314 | 25.810 | −17.424 | 52.949 | 1.00 | 64.54 | MOLB | O |
| ATOM | 4827 | C | SER | B 314 | 23.771 | −19.639 | 53.042 | 1.00 | 61.66 | MOLB | C |
| ATOM | 4828 | O | SER | B 314 | 24.744 | −20.365 | 52.843 | 1.00 | 60.18 | MOLB | O |
| ATOM | 4829 | N | LYS | B 315 | 22.620 | −19.846 | 52.430 | 1.00 | 59.43 | MOLB | N |
| ATOM | 4830 | CA | LYS | B 315 | 22.511 | −20.988 | 51.563 | 1.00 | 59.26 | MOLB | C |
| ATOM | 4831 | CB | LYS | B 315 | 21.145 | −21.040 | 50.898 | 1.00 | 60.24 | MOLB | C |
| ATOM | 4832 | CG | LYS | B 315 | 19.969 | −21.311 | 51.825 | 1.00 | 60.49 | MOLB | C |
| ATOM | 4833 | CD | LYS | B 315 | 18.748 | −21.803 | 51.023 | 1.00 | 59.59 | MOLB | C |
| ATOM | 4834 | CE | LYS | B 315 | 17.447 | −21.667 | 51.811 | 1.00 | 52.27 | MOLB | C |
| ATOM | 4835 | NZ | LYS | B 315 | 17.650 | −22.024 | 53.249 | 1.00 | 66.11 | MOLB | N |
| ATOM | 4836 | C | LYS | B 315 | 23.600 | −20.903 | 50.503 | 1.00 | 59.83 | MOLB | C |
| ATOM | 4837 | O | LYS | B 315 | 24.154 | −21.920 | 50.084 | 1.00 | 62.75 | MOLB | O |
| ATOM | 4838 | N | LEU | B 316 | 23.901 | −19.679 | 50.075 | 1.00 | 57.78 | MOLB | N |
| ATOM | 4839 | CA | LEU | B 316 | 24.930 | −19.424 | 49.068 | 1.00 | 52.96 | MOLB | C |
| ATOM | 4840 | CB | LEU | B 316 | 25.141 | −17.916 | 48.890 | 1.00 | 51.76 | MOLB | C |
| ATOM | 4841 | CG | LEU | B 316 | 26.044 | −17.557 | 47.710 | 1.00 | 43.52 | MOLB | C |
| ATOM | 4842 | CD1 | LEU | B 316 | 25.290 | −17.835 | 46.416 | 1.00 | 38.66 | MOLB | C |
| ATOM | 4843 | CD2 | LEU | B 316 | 26.490 | −16.124 | 47.748 | 1.00 | 37.79 | MOLB | C |
| ATOM | 4844 | C | LEU | B 316 | 26.258 | −20.084 | 49.424 | 1.00 | 52.25 | MOLB | C |
| ATOM | 4845 | O | LEU | B 316 | 26.635 | −21.086 | 48.841 | 1.00 | 49.91 | MOLB | O |
| ATOM | 4846 | N | THR | B 317 | 26.974 | −19.507 | 50.383 | 1.00 | 53.94 | MOLB | N |
| ATOM | 4847 | CA | THR | B 317 | 28.238 | −20.086 | 50.819 | 1.00 | 54.84 | MOLB | C |
| ATOM | 4848 | CB | THR | B 317 | 28.741 | −19.438 | 52.107 | 1.00 | 54.31 | MOLB | C |
| ATOM | 4849 | OG1 | THR | B 317 | 27.640 | −18.813 | 52.770 | 1.00 | 55.23 | MOLB | O |
| ATOM | 4850 | CG2 | THR | B 317 | 29.798 | −18.408 | 51.800 | 1.00 | 52.04 | MOLB | C |
| ATOM | 4851 | C | THR | B 317 | 28.126 | −21.581 | 51.070 | 1.00 | 56.52 | MOLB | C |
| ATOM | 4852 | O | THR | B 317 | 28.978 | −22.353 | 50.643 | 1.00 | 54.90 | MOLB | O |
| ATOM | 4853 | N | ARG | B 318 | 27.073 | −21.981 | 51.775 | 1.00 | 59.43 | MOLB | N |
| ATOM | 4854 | CA | ARG | B 318 | 26.896 | −23.382 | 52.129 | 1.00 | 62.73 | MOLB | C |
| ATOM | 4855 | CB | ARG | B 318 | 25.606 | −23.610 | 52.930 | 1.00 | 63.68 | MOLB | C |
| ATOM | 4856 | CG | ARG | B 318 | 25.437 | −25.058 | 53.457 | 1.00 | 71.17 | MOLB | C |
| ATOM | 4857 | CD | ARG | B 318 | 24.291 | −25.156 | 54.477 | 1.00 | 71.67 | MOLB | C |
| ATOM | 4858 | NE | ARG | B 318 | 23.666 | −26.480 | 54.510 | 1.00 | 99.98 | MOLB | N |
| ATOM | 4859 | CZ | ARG | B 318 | 22.598 | −26.784 | 55.245 | 1.00 | 106.95 | MOLB | C |
| ATOM | 4860 | NH1 | ARG | B 318 | 22.040 | −25.857 | 56.018 | 1.00 | 108.52 | MOLB | N |
| ATOM | 4861 | NH2 | ARG | B 318 | 22.087 | −28.012 | 55.209 | 1.00 | 110.65 | MOLB | N |
| ATOM | 4862 | C | ARG | B 318 | 26.924 | −24.254 | 50.886 | 1.00 | 58.66 | MOLB | C |
| ATOM | 4863 | O | ARG | B 318 | 27.548 | −25.330 | 50.882 | 1.00 | 59.16 | MOLB | O |
| ATOM | 4864 | N | ILE | B 319 | 26.263 | −23.788 | 49.835 | 1.00 | 53.90 | MOLB | N |
| ATOM | 4865 | CA | ILE | B 319 | 26.270 | −24.531 | 48.596 | 1.00 | 51.44 | MOLB | C |
| ATOM | 4866 | CB | ILE | B 319 | 25.236 | −24.006 | 47.620 | 1.00 | 49.97 | MOLB | C |
| ATOM | 4867 | CG1 | ILE | B 319 | 23.848 | −24.237 | 48.199 | 1.00 | 47.18 | MOLB | C |
| ATOM | 4868 | CD1 | ILE | B 319 | 22.736 | −24.140 | 47.158 | 1.00 | 56.58 | MOLB | C |
| ATOM | 4869 | CG2 | ILE | B 319 | 25.384 | −24.676 | 46.239 | 1.00 | 44.75 | MOLB | C |
| ATOM | 4870 | C | ILE | B 319 | 27.662 | −24.624 | 47.932 | 1.00 | 53.25 | MOLB | C |
| ATOM | 4871 | O | ILE | B 319 | 27.994 | −25.660 | 47.334 | 1.00 | 54.78 | MOLB | O |
| ATOM | 4872 | N | LEU | B 320 | 28.478 | −23.572 | 48.041 | 1.00 | 51.77 | MOLB | N |
| ATOM | 4873 | CA | LEU | B 320 | 29.780 | −23.576 | 47.355 | 1.00 | 51.71 | MOLB | C |
| ATOM | 4874 | CB | LEU | B 320 | 30.175 | −22.173 | 46.912 | 1.00 | 49.66 | MOLB | C |
| ATOM | 4875 | CG | LEU | B 320 | 29.029 | −21.450 | 46.206 | 1.00 | 51.29 | MOLB | C |
| ATOM | 4876 | CD1 | LEU | B 320 | 29.355 | −19.996 | 45.928 | 1.00 | 54.63 | MOLB | C |
| ATOM | 4877 | CD2 | LEU | B 320 | 28.646 | −22.169 | 44.924 | 1.00 | 41.50 | MOLB | C |
| ATOM | 4878 | C | LEU | B 320 | 30.864 | −24.148 | 48.232 | 1.00 | 53.95 | MOLB | C |
| ATOM | 4879 | O | LEU | B 320 | 31.997 | −24.319 | 47.791 | 1.00 | 54.76 | MOLB | O |
| ATOM | 4880 | N | GLN | B 321 | 30.510 | −24.430 | 49.481 | 1.00 | 56.68 | MOLB | N |
| ATOM | 4881 | CA | GLN | B 321 | 31.445 | −24.956 | 50.459 | 1.00 | 58.89 | MOLB | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4882 | CB | GLN | B 321 | 30.704 | −25.821 | 51.469 | 1.00 | 58.48 | MOLB C |
| ATOM | 4883 | CG | GLN | B 321 | 30.156 | −25.068 | 52.637 | 1.00 | 61.16 | MOLB C |
| ATOM | 4884 | CD | GLN | B 321 | 30.341 | −25.830 | 53.932 | 1.00 | 65.95 | MOLB C |
| ATOM | 4885 | OE1 | GLN | B 321 | 29.364 | −26.274 | 54.550 | 1.00 | 79.40 | MOLB O |
| ATOM | 4886 | NE2 | GLN | B 321 | 31.601 | −26.005 | 54.344 | 1.00 | 51.23 | MOLB N |
| ATOM | 4887 | C | GLN | B 321 | 32.483 | −25.816 | 49.786 | 1.00 | 61.28 | MOLB C |
| ATOM | 4888 | O | GLN | B 321 | 33.690 | −25.539 | 49.809 | 1.00 | 59.77 | MOLB O |
| ATOM | 4889 | N | ASP | B 322 | 31.962 | −26.881 | 49.198 | 1.00 | 65.05 | MOLB N |
| ATOM | 4890 | CA | ASP | B 322 | 32.734 | −27.864 | 48.525 | 1.00 | 67.70 | MOLB C |
| ATOM | 4891 | CB | ASP | B 322 | 31.772 | −28.731 | 47.718 | 1.00 | 68.02 | MOLB C |
| ATOM | 4892 | CG | ASP | B 322 | 32.150 | −30.189 | 47.743 | 1.00 | 74.15 | MOLB C |
| ATOM | 4893 | OD1 | ASP | B 322 | 31.293 | −31.021 | 47.372 | 1.00 | 78.70 | MOLB O |
| ATOM | 4894 | OD2 | ASP | B 322 | 33.295 | −30.502 | 48.153 | 1.00 | 80.64 | MOLB O |
| ATOM | 4895 | C | ASP | B 322 | 33.706 | −27.121 | 47.623 | 1.00 | 69.31 | MOLB C |
| ATOM | 4896 | O | ASP | B 322 | 34.906 | −27.041 | 47.907 | 1.00 | 70.41 | MOLB O |
| ATOM | 4897 | N | SER | B 323 | 33.158 | −26.540 | 46.556 | 1.00 | 71.44 | MOLB N |
| ATOM | 4898 | CA | SER | B 323 | 33.917 | −25.813 | 45.519 | 1.00 | 72.13 | MOLB C |
| ATOM | 4899 | CB | SER | B 323 | 32.923 | −25.324 | 44.443 | 1.00 | 71.81 | MOLB C |
| ATOM | 4900 | OG | SER | B 323 | 33.578 | −24.720 | 43.337 | 1.00 | 73.31 | MOLB O |
| ATOM | 4901 | C | SER | B 323 | 34.822 | −24.641 | 46.009 | 1.00 | 71.08 | MOLB C |
| ATOM | 4902 | O | SER | B 323 | 35.383 | −23.895 | 45.194 | 1.00 | 70.64 | MOLB O |
| ATOM | 4903 | N | LEU | B 324 | 34.987 | −24.496 | 47.323 | 1.00 | 70.35 | MOLB N |
| ATOM | 4904 | CA | LEU | B 324 | 35.684 | −23.326 | 47.874 | 1.00 | 68.33 | MOLB C |
| ATOM | 4905 | CB | LEU | B 324 | 34.727 | −22.490 | 48.717 | 1.00 | 66.18 | MOLB C |
| ATOM | 4906 | CG | LEU | B 324 | 34.107 | −21.408 | 47.848 | 1.00 | 62.98 | MOLB C |
| ATOM | 4907 | CD1 | LEU | B 324 | 32.989 | −20.637 | 48.557 | 1.00 | 48.25 | MOLB C |
| ATOM | 4908 | CD2 | LEU | B 324 | 35.225 | −20.485 | 47.372 | 1.00 | 51.33 | MOLB C |
| ATOM | 4909 | C | LEU | B 324 | 36.982 | −23.543 | 48.638 | 1.00 | 68.90 | MOLB C |
| ATOM | 4910 | O | LEU | B 324 | 38.066 | −23.259 | 48.116 | 1.00 | 69.05 | MOLB O |
| ATOM | 4911 | N | GLY | B 325 | 36.869 | −24.042 | 49.868 | 1.00 | 69.28 | MOLB N |
| ATOM | 4912 | CA | GLY | B 325 | 38.022 | −24.144 | 50.759 | 1.00 | 70.75 | MOLB C |
| ATOM | 4913 | C | GLY | B 325 | 38.862 | −25.419 | 50.812 | 1.00 | 72.65 | MOLB C |
| ATOM | 4914 | O | GLY | B 325 | 39.220 | −25.877 | 51.905 | 1.00 | 72.82 | MOLB O |
| ATOM | 4915 | N | GLY | B 326 | 39.191 | −25.999 | 49.657 | 1.00 | 72.33 | MOLB N |
| ATOM | 4916 | CA | GLY | B 326 | 40.158 | −27.104 | 49.623 | 1.00 | 71.76 | MOLB C |
| ATOM | 4917 | C | GLY | B 326 | 41.459 | −26.566 | 49.040 | 1.00 | 71.35 | MOLB C |
| ATOM | 4918 | O | GLY | B 326 | 41.832 | −25.412 | 49.287 | 1.00 | 69.80 | MOLB O |
| ATOM | 4919 | N | ARG | B 327 | 42.180 | −27.397 | 48.289 | 1.00 | 71.28 | MOLB N |
| ATOM | 4920 | CA | ARG | B 327 | 43.211 | −26.841 | 47.406 | 1.00 | 70.41 | MOLB C |
| ATOM | 4921 | CB | ARG | B 327 | 44.512 | −27.659 | 47.349 | 1.00 | 70.25 | MOLB C |
| ATOM | 4922 | CG | ARG | B 327 | 45.752 | −26.798 | 47.011 | 1.00 | 73.64 | MOLB C |
| ATOM | 4923 | CD | ARG | B 327 | 46.214 | −26.879 | 45.534 | 1.00 | 79.64 | MOLB C |
| ATOM | 4924 | NE | ARG | B 327 | 45.261 | −26.332 | 44.566 | 1.00 | 83.78 | MOLB N |
| ATOM | 4925 | CZ | ARG | B 327 | 45.382 | −25.152 | 43.960 | 1.00 | 87.63 | MOLB C |
| ATOM | 4926 | NH1 | ARG | B 327 | 44.455 | −24.757 | 43.096 | 1.00 | 87.66 | MOLB N |
| ATOM | 4927 | NH2 | ARG | B 327 | 46.422 | −24.365 | 44.209 | 1.00 | 86.69 | MOLB N |
| ATOM | 4928 | C | ARG | B 327 | 42.483 | −26.699 | 46.057 | 1.00 | 67.78 | MOLB C |
| ATOM | 4929 | O | ARG | B 327 | 42.373 | −27.639 | 45.244 | 1.00 | 65.99 | MOLB O |
| ATOM | 4930 | N | THR | B 328 | 41.939 | −25.497 | 45.888 | 1.00 | 63.14 | MOLB N |
| ATOM | 4931 | CA | THR | B 328 | 41.070 | −25.177 | 44.807 | 1.00 | 58.11 | MOLB C |
| ATOM | 4932 | CB | THR | B 328 | 39.664 | −25.033 | 45.307 | 1.00 | 57.10 | MOLB C |
| ATOM | 4933 | OG1 | THR | B 328 | 38.802 | −24.966 | 44.183 | 1.00 | 56.50 | MOLB O |
| ATOM | 4934 | CG2 | THR | B 328 | 39.515 | −23.745 | 46.122 | 1.00 | 55.90 | MOLB C |
| ATOM | 4935 | C | THR | B 328 | 41.488 | −23.824 | 44.328 | 1.00 | 56.92 | MOLB C |
| ATOM | 4936 | O | THR | B 328 | 42.470 | −23.270 | 44.821 | 1.00 | 59.13 | MOLB O |
| ATOM | 4937 | N | ARG | B 329 | 40.742 | −23.290 | 43.366 | 1.00 | 53.70 | MOLB N |
| ATOM | 4938 | CA | ARG | B 329 | 40.972 | −21.943 | 42.873 | 1.00 | 47.34 | MOLB C |
| ATOM | 4939 | CB | ARG | B 329 | 41.686 | −21.941 | 41.538 | 1.00 | 46.54 | MOLB C |
| ATOM | 4940 | CG | ARG | B 329 | 43.108 | −22.233 | 41.713 | 1.00 | 46.64 | MOLB C |
| ATOM | 4941 | CD | ARG | B 329 | 43.922 | −21.943 | 40.509 | 1.00 | 50.16 | MOLB C |
| ATOM | 4942 | NE | ARG | B 329 | 45.256 | −22.439 | 40.804 | 1.00 | 65.70 | MOLB N |
| ATOM | 4943 | CZ | ARG | B 329 | 46.294 | −22.351 | 39.987 | 1.00 | 77.32 | MOLB C |
| ATOM | 4944 | NH1 | ARG | B 329 | 46.155 | −21.770 | 38.801 | 1.00 | 81.71 | MOLB N |
| ATOM | 4945 | NH2 | ARG | B 329 | 47.469 | −22.848 | 40.363 | 1.00 | 80.67 | MOLB N |
| ATOM | 4946 | C | ARG | B 329 | 39.667 | −21.238 | 42.746 | 1.00 | 45.59 | MOLB C |
| ATOM | 4947 | O | ARG | B 329 | 38.617 | −21.850 | 42.471 | 1.00 | 46.30 | MOLB O |
| ATOM | 4948 | N | THR | B 330 | 39.752 | −19.930 | 42.909 | 1.00 | 41.77 | MOLB N |
| ATOM | 4949 | CA | THR | B 330 | 38.583 | −19.117 | 43.009 | 1.00 | 40.70 | MOLB C |
| ATOM | 4950 | CB | THR | B 330 | 38.108 | −19.148 | 44.471 | 1.00 | 42.71 | MOLB C |
| ATOM | 4951 | OG1 | THR | B 330 | 37.541 | −20.441 | 44.747 | 1.00 | 49.75 | MOLB O |
| ATOM | 4952 | CG2 | THR | B 330 | 37.088 | −18.056 | 44.769 | 1.00 | 46.81 | MOLB C |
| ATOM | 4953 | C | THR | B 330 | 38.934 | −17.721 | 42.571 | 1.00 | 37.28 | MOLB C |
| ATOM | 4954 | O | THR | B 330 | 39.981 | −17.171 | 42.934 | 1.00 | 37.40 | MOLB O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 4955 | N | SER | B 331 | 38.079 | −17.136 | 41.760 | 1.00 | 33.74 | MOLB N |
| ATOM | 4956 | CA | SER | B 331 | 38.353 | −15.791 | 41.365 | 1.00 | 32.60 | MOLB C |
| ATOM | 4957 | CB | SER | B 331 | 38.993 | −15.771 | 39.998 | 1.00 | 34.24 | MOLB C |
| ATOM | 4958 | OG | SER | B 331 | 38.011 | −16.075 | 39.035 | 1.00 | 41.16 | MOLB O |
| ATOM | 4959 | C | SER | B 331 | 37.065 | −15.040 | 41.314 | 1.00 | 31.04 | MOLB C |
| ATOM | 4960 | O | SER | B 331 | 36.021 | −15.604 | 41.028 | 1.00 | 26.90 | MOLB O |
| ATOM | 4961 | N | ILE | B 332 | 37.141 | −13.753 | 41.617 | 1.00 | 33.19 | MOLB N |
| ATOM | 4962 | CA | ILE | B 332 | 35.990 | −12.910 | 41.453 | 1.00 | 32.67 | MOLB C |
| ATOM | 4963 | CB | ILE | B 332 | 35.629 | −12.110 | 42.684 | 1.00 | 32.55 | MOLB C |
| ATOM | 4964 | CG1 | ILE | B 332 | 35.959 | −12.836 | 43.981 | 1.00 | 33.79 | MOLB C |
| ATOM | 4965 | CD1 | ILE | B 332 | 35.422 | −12.055 | 45.208 | 1.00 | 26.39 | MOLB C |
| ATOM | 4966 | CG2 | ILE | B 332 | 34.165 | −11.782 | 42.640 | 1.00 | 34.95 | MOLB C |
| ATOM | 4967 | C | ILE | B 332 | 36.313 | −11.887 | 40.413 | 1.00 | 33.15 | MOLB C |
| ATOM | 4968 | O | ILE | B 332 | 37.371 | −11.233 | 40.433 | 1.00 | 35.19 | MOLB O |
| ATOM | 4969 | N | ILE | B 333 | 35.392 | −11.746 | 39.491 | 1.00 | 31.59 | MOLB N |
| ATOM | 4970 | CA | ILE | B 333 | 35.494 | −10.694 | 38.538 | 1.00 | 32.04 | MOLB C |
| ATOM | 4971 | CB | ILE | B 333 | 34.967 | −11.188 | 37.187 | 1.00 | 32.70 | MOLB C |
| ATOM | 4972 | CG1 | ILE | B 333 | 35.728 | −12.444 | 36.741 | 1.00 | 33.38 | MOLB C |
| ATOM | 4973 | CD1 | ILE | B 333 | 35.346 | −12.993 | 35.341 | 1.00 | 29.04 | MOLB C |
| ATOM | 4974 | CG2 | ILE | B 333 | 35.096 | −10.120 | 36.160 | 1.00 | 36.05 | MOLB C |
| ATOM | 4975 | C | ILE | B 333 | 34.628 | −9.563 | 39.091 | 1.00 | 31.26 | MOLB C |
| ATOM | 4976 | O | ILE | B 333 | 33.398 | −9.620 | 39.006 | 1.00 | 32.98 | MOLB O |
| ATOM | 4977 | N | ALA | B 334 | 35.246 | −8.574 | 39.721 | 1.00 | 29.61 | MOLB N |
| ATOM | 4978 | CA | ALA | B 334 | 34.491 | −7.385 | 40.171 | 1.00 | 29.39 | MOLB C |
| ATOM | 4979 | CB | ALA | B 334 | 35.259 | −6.606 | 41.199 | 1.00 | 26.13 | MOLB C |
| ATOM | 4980 | C | ALA | B 334 | 34.275 | −6.509 | 38.976 | 1.00 | 29.52 | MOLB C |
| ATOM | 4981 | O | ALA | B 334 | 35.282 | −6.013 | 38.411 | 1.00 | 32.61 | MOLB O |
| ATOM | 4982 | N | THR | B 335 | 33.005 | −6.288 | 38.603 | 1.00 | 26.43 | MOLB N |
| ATOM | 4983 | CA | THR | B 335 | 32.658 | −5.468 | 37.413 | 1.00 | 27.19 | MOLB C |
| ATOM | 4984 | CB | THR | B 335 | 31.424 | −6.013 | 36.691 | 1.00 | 28.59 | MOLB C |
| ATOM | 4985 | OG1 | THR | B 335 | 30.268 | −5.853 | 37.540 | 1.00 | 29.16 | MOLB O |
| ATOM | 4986 | CG2 | THR | B 335 | 31.613 | −7.500 | 36.261 | 1.00 | 17.08 | MOLB C |
| ATOM | 4987 | C | THR | B 335 | 32.254 | −4.047 | 37.747 | 1.00 | 30.28 | MOLB C |
| ATOM | 4988 | O | THR | B 335 | 31.591 | −3.824 | 38.759 | 1.00 | 33.53 | MOLB O |
| ATOM | 4989 | N | ILE | B 336 | 32.584 | −3.078 | 36.894 | 1.00 | 31.54 | MOLB N |
| ATOM | 4990 | CA | ILE | B 336 | 32.101 | −1.675 | 37.114 | 1.00 | 30.58 | MOLB C |
| ATOM | 4991 | CB | ILE | B 336 | 33.157 | −0.829 | 37.797 | 1.00 | 27.50 | MOLB C |
| ATOM | 4992 | CG1 | ILE | B 336 | 34.499 | −1.006 | 37.080 | 1.00 | 37.03 | MOLB C |
| ATOM | 4993 | CD1 | ILE | B 336 | 35.698 | −0.436 | 37.809 | 1.00 | 26.47 | MOLB C |
| ATOM | 4994 | CG2 | ILE | B 336 | 33.271 | −1.224 | 39.192 | 1.00 | 26.13 | MOLB C |
| ATOM | 4995 | C | ILE | B 336 | 31.716 | −0.870 | 35.877 | 1.00 | 30.77 | MOLB C |
| ATOM | 4996 | O | ILE | B 336 | 32.136 | −1.198 | 34.768 | 1.00 | 33.80 | MOLB O |
| ATOM | 4997 | N | SER | B 337 | 30.932 | −0.196 | 36.081 | 1.00 | 30.75 | MOLB N |
| ATOM | 4998 | CA | SER | B 337 | 30.712 | −1.235 | 35.046 | 1.00 | 29.66 | MOLB C |
| ATOM | 4999 | CB | SER | B 337 | 29.353 | −1.904 | 35.228 | 1.00 | 27.14 | MOLB C |
| ATOM | 5000 | OG | SER | B 337 | 29.429 | −3.322 | 35.075 | 1.00 | 31.71 | MOLB O |
| ATOM | 5001 | C | SER | B 337 | 31.863 | −2.274 | 35.076 | 1.00 | 29.01 | MOLB C |
| ATOM | 5002 | O | SER | B 337 | 32.492 | −2.457 | 36.116 | 1.00 | 31.75 | MOLB O |
| ATOM | 5003 | N | PRO | B 338 | 32.168 | −2.943 | 33.947 | 1.00 | 26.46 | MOLB N |
| ATOM | 5004 | CA | PRO | B 338 | 33.297 | −3.828 | 34.124 | 1.00 | 25.55 | MOLB C |
| ATOM | 5005 | CB | PRO | B 338 | 34.042 | 3.686 | 32.790 | 1.00 | 23.88 | MOLB C |
| ATOM | 5006 | CG | PRO | B 338 | 33.003 | 3.211 | 31.798 | 1.00 | 24.13 | MOLB C |
| ATOM | 5007 | CD | PRO | B 338 | 31.707 | 2.969 | 32.556 | 1.00 | 24.88 | MOLB C |
| ATOM | 5008 | C | PRO | B 338 | 32.927 | 5.286 | 34.349 | 1.00 | 25.28 | MOLB C |
| ATOM | 5009 | O | PRO | B 338 | 33.807 | 6.135 | 34.161 | 1.00 | 23.65 | MOLB O |
| ATOM | 5010 | N | ALA | B 339 | 31.699 | 5.557 | 34.838 | 1.00 | 25.67 | MOLB N |
| ATOM | 5011 | CA | ALA | B 339 | 31.076 | 6.895 | 34.760 | 1.00 | 25.49 | MOLB C |
| ATOM | 5012 | CB | ALA | B 339 | 29.865 | 6.746 | 33.925 | 1.00 | 22.75 | MOLB C |
| ATOM | 5013 | C | ALA | B 339 | 30.677 | 7.654 | 36.041 | 1.00 | 28.63 | MOLB C |
| ATOM | 5014 | O | ALA | B 339 | 30.449 | 7.049 | 37.060 | 1.00 | 31.46 | MOLB O |
| ATOM | 5015 | N | SER | B 340 | 30.557 | 8.985 | 35.960 | 1.00 | 31.96 | MOLB N |
| ATOM | 5016 | CA | SER | B 340 | 29.830 | 9.844 | 36.962 | 1.00 | 35.53 | MOLB C |
| ATOM | 5017 | CB | SER | B 340 | 29.423 | 11.248 | 36.368 | 1.00 | 41.32 | MOLB C |
| ATOM | 5018 | OG | SER | B 340 | 28.262 | 11.888 | 37.015 | 1.00 | 33.38 | MOLB O |
| ATOM | 5019 | C | SER | B 340 | 28.566 | 9.321 | 37.650 | 1.00 | 36.16 | MOLB C |
| ATOM | 5020 | O | SER | B 340 | 28.430 | 9.495 | 38.846 | 1.00 | 35.80 | MOLB O |
| ATOM | 5021 | N | LEU | B 341 | 27.593 | 8.794 | 36.922 | 1.00 | 36.59 | MOLB N |
| ATOM | 5022 | CA | LEU | B 341 | 26.348 | 8.402 | 37.622 | 1.00 | 39.85 | MOLB C |
| ATOM | 5023 | CB | LEU | B 341 | 25.314 | 7.816 | 36.682 | 1.00 | 38.02 | MOLB C |
| ATOM | 5024 | CG | LEU | B 341 | 24.422 | 8.731 | 35.889 | 1.00 | 36.73 | MOLB C |
| ATOM | 5025 | CD1 | LEU | B 341 | 25.173 | 9.154 | 34.669 | 1.00 | 39.74 | MOLB C |
| ATOM | 5026 | CD2 | LEU | B 341 | 23.178 | 7.954 | 35.494 | 1.00 | 41.23 | MOLB C |
| ATOM | 5027 | C | LEU | B 341 | 26.548 | 7.364 | 38.704 | 1.00 | 42.05 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 5028 | O | LEU | B 341 | 25.808 | 7.314 | 39.696 | 1.00 | 44.81 | MOLB O |
| ATOM | 5029 | N | ASN | B 342 | 27.554 | 6.531 | 38.513 | 1.00 | 43.57 | MOLB N |
| ATOM | 5030 | CA | ASN | B 342 | 27.678 | 5.343 | 39.321 | 1.00 | 45.79 | MOLB C |
| ATOM | 5031 | CB | ASN | B 342 | 27.554 | 4.130 | 38.425 | 1.00 | 43.05 | MOLB C |
| ATOM | 5032 | CG | ASN | B 342 | 26.307 | 4.180 | 37.610 | 1.00 | 45.85 | MOLB C |
| ATOM | 5033 | OD1 | ASN | B 342 | 26.307 | 3.845 | 36.430 | 1.00 | 50.27 | MOLB O |
| ATOM | 5034 | ND2 | ASN | B 342 | 25.230 | 4.659 | 38.221 | 1.00 | 40.03 | MOLB N |
| ATOM | 5035 | C | ASN | B 342 | 28.949 | 5.289 | 40.111 | 1.00 | 48.01 | MOLB C |
| ATOM | 5036 | O | ASN | B 342 | 29.482 | 4.202 | 40.377 | 1.00 | 50.70 | MOLB O |
| ATOM | 5037 | N | LEU | B 343 | 29.429 | 6.467 | 40.492 | 1.00 | 46.93 | MOLB N |
| ATOM | 5038 | CA | LEU | B 343 | 30.604 | 6.556 | 41.339 | 1.00 | 46.29 | MOLB C |
| ATOM | 5039 | CB | LEU | B 343 | 31.170 | 7.968 | 41.269 | 1.00 | 45.64 | MOLB C |
| ATOM | 5040 | CG | LEU | B 343 | 31.909 | 8.794 | 42.306 | 1.00 | 42.72 | MOLB C |
| ATOM | 5041 | CD1 | LEU | B 343 | 32.074 | 8.126 | 43.624 | 1.00 | 41.80 | MOLB C |
| ATOM | 5042 | CD2 | LEU | B 343 | 33.234 | 9.197 | 41.688 | 1.00 | 42.35 | MOLB C |
| ATOM | 5043 | C | LEU | B 343 | 30.182 | 6.116 | 42.715 | 1.00 | 45.62 | MOLB C |
| ATOM | 5044 | O | LEU | B 343 | 30.955 | 5.555 | 43.463 | 1.00 | 44.39 | MOLB O |
| ATOM | 5045 | N | GLU | B 344 | 28.913 | 6.340 | 43.010 | 1.00 | 49.32 | MOLB N |
| ATOM | 5046 | CA | GLU | B 344 | 28.294 | 5.817 | 44.223 | 1.00 | 51.17 | MOLB C |
| ATOM | 5047 | CB | GLU | B 344 | 26.748 | 5.796 | 44.064 | 1.00 | 53.60 | MOLB C |
| ATOM | 5048 | CG | GLU | B 344 | 25.911 | 7.048 | 44.361 | 1.00 | 57.99 | MOLB C |
| ATOM | 5049 | CD | GLU | B 344 | 26.629 | 8.346 | 44.082 | 1.00 | 62.48 | MOLB C |
| ATOM | 5050 | OE1 | GLU | B 344 | 26.417 | 8.938 | 43.003 | 1.00 | 71.07 | MOLB O |
| ATOM | 5051 | OE2 | GLU | B 344 | 27.399 | 8.777 | 44.957 | 1.00 | 56.55 | MOLB O |
| ATOM | 5052 | C | GLU | B 344 | 28.717 | 4.360 | 44.377 | 1.00 | 47.67 | MOLB C |
| ATOM | 5053 | O | GLU | B 344 | 29.474 | 3.990 | 45.265 | 1.00 | 43.31 | MOLB O |
| ATOM | 5054 | N | GLU | B 345 | 28.214 | 3.569 | 43.441 | 1.00 | 46.51 | MOLB N |
| ATOM | 5055 | CA | GLU | B 345 | 28.167 | 2.134 | 43.543 | 1.00 | 48.54 | MOLB C |
| ATOM | 5056 | CB | GLU | B 345 | 27.037 | 1.635 | 42.628 | 1.00 | 48.80 | MOLB C |
| ATOM | 5057 | CG | GLU | B 345 | 26.173 | 0.475 | 43.158 | 1.00 | 60.64 | MOLB C |
| ATOM | 5058 | CD | GLU | B 345 | 25.950 | 0.475 | 44.684 | 1.00 | 77.23 | MOLB C |
| ATOM | 5059 | OE1 | GLU | B 345 | 24.778 | 0.372 | 45.121 | 1.00 | 77.18 | MOLB O |
| ATOM | 5060 | OE2 | GLU | B 345 | 26.949 | 0.545 | 45.445 | 1.00 | 82.42 | MOLB O |
| ATOM | 5061 | C | GLU | B 345 | 29.508 | 1.487 | 43.210 | 1.00 | 47.17 | MOLB C |
| ATOM | 5062 | O | GLU | B 345 | 29.900 | 0.494 | 43.850 | 1.00 | 45.75 | MOLB O |
| ATOM | 5063 | N | THR | B 346 | 30.208 | 2.064 | 42.225 | 1.00 | 45.23 | MOLB N |
| ATOM | 5064 | CA | THR | B 346 | 31.526 | 1.569 | 41.830 | 1.00 | 42.20 | MOLB C |
| ATOM | 5065 | CB | THR | B 346 | 32.245 | 2.482 | 40.839 | 1.00 | 41.06 | MOLB C |
| ATOM | 5066 | OG1 | THR | B 346 | 31.696 | 2.309 | 39.522 | 1.00 | 43.02 | MOLB O |
| ATOM | 5067 | CG2 | THR | B 346 | 33.672 | 2.099 | 40.193 | 1.00 | 22.56 | MOLB C |
| ATOM | 5068 | C | THR | B 346 | 32.423 | 1.441 | 43.046 | 1.00 | 43.91 | MOLB C |
| ATOM | 5069 | O | THR | B 346 | 32.973 | 0.372 | 43.319 | 1.00 | 46.70 | MOLB O |
| ATOM | 5070 | N | LEU | B 347 | 32.564 | 2.527 | 43.787 | 1.00 | 41.50 | MOLB N |
| ATOM | 5071 | CA | LEU | B 347 | 33.419 | 2.497 | 44.951 | 1.00 | 40.71 | MOLB C |
| ATOM | 5072 | CB | LEU | B 347 | 33.423 | 3.844 | 45.679 | 1.00 | 39.74 | MOLB C |
| ATOM | 5073 | CG | LEU | B 347 | 34.480 | 4.726 | 44.996 | 1.00 | 44.29 | MOLB C |
| ATOM | 5074 | CD1 | LEU | B 347 | 34.049 | 5.116 | 43.584 | 1.00 | 47.31 | MOLB C |
| ATOM | 5075 | CD2 | LEU | B 347 | 34.821 | 5.957 | 45.805 | 1.00 | 44.79 | MOLB C |
| ATOM | 5076 | C | LEU | B 347 | 33.043 | 1.352 | 45.858 | 1.00 | 39.80 | MOLB C |
| ATOM | 5077 | O | LEU | B 347 | 33.883 | 0.555 | 46.216 | 1.00 | 41.67 | MOLB O |
| ATOM | 5078 | N | SER | B 348 | 31.771 | 1.243 | 46.200 | 1.00 | 39.45 | MOLB N |
| ATOM | 5079 | CA | SER | B 348 | 31.311 | 0.168 | 47.067 | 1.00 | 37.83 | MOLB C |
| ATOM | 5080 | CB | SER | B 348 | 29.789 | 0.323 | 47.248 | 1.00 | 35.96 | MOLB C |
| ATOM | 5081 | OG | SER | B 348 | 29.041 | −0.854 | 47.003 | 1.00 | 41.39 | MOLB O |
| ATOM | 5082 | C | SER | B 348 | 31.762 | −1.188 | 46.475 | 1.00 | 37.53 | MOLB C |
| ATOM | 5083 | O | SER | B 348 | 32.406 | −2.027 | 47.141 | 1.00 | 36.47 | MOLB O |
| ATOM | 5084 | N | THR | B 349 | 31.467 | −1.366 | 45.194 | 1.00 | 34.75 | MOLB N |
| ATOM | 5085 | CA | THR | B 349 | 31.870 | −2.558 | 44.496 | 1.00 | 31.42 | MOLB C |
| ATOM | 5086 | CB | THR | B 349 | 31.516 | −2.419 | 43.022 | 1.00 | 30.21 | MOLB C |
| ATOM | 5087 | OG1 | THR | B 349 | 30.107 | −2.609 | 42.839 | 1.00 | 40.70 | MOLB O |
| ATOM | 5088 | CG2 | THR | B 349 | 32.210 | −3.422 | 42.249 | 1.00 | 8.00 | MOLB C |
| ATOM | 5089 | C | THR | B 349 | 33.375 | −2.824 | 44.665 | 1.00 | 33.62 | MOLB C |
| ATOM | 5090 | O | THR | B 349 | 33.792 | −3.969 | 44.774 | 1.00 | 34.61 | MOLB O |
| ATOM | 5091 | N | LEU | B 350 | 34.177 | −1.760 | 44.677 | 1.00 | 34.01 | MOLB N |
| ATOM | 5092 | CA | LEU | B 350 | 35.628 | −1.858 | 44.680 | 1.00 | 35.63 | MOLB C |
| ATOM | 5093 | CB | LEU | B 350 | 36.219 | −0.549 | 44.201 | 1.00 | 33.07 | MOLB C |
| ATOM | 5094 | CG | LEU | B 350 | 36.207 | −0.424 | 42.710 | 1.00 | 31.26 | MOLB C |
| ATOM | 5095 | CD1 | LEU | B 350 | 36.909 | 0.865 | 42.283 | 1.00 | 28.77 | MOLB C |
| ATOM | 5096 | CD2 | LEU | B 350 | 36.923 | −1.647 | 42.214 | 1.00 | 27.19 | MOLB C |
| ATOM | 5097 | C | LEU | B 350 | 36.170 | −2.119 | 46.069 | 1.00 | 40.60 | MOLB C |
| ATOM | 5098 | O | LEU | B 350 | 37.086 | −2.925 | 46.273 | 1.00 | 43.51 | MOLB O |
| ATOM | 5099 | N | GLU | B 351 | 35.638 | −1.359 | 47.016 | 1.00 | 43.47 | MOLB N |
| ATOM | 5100 | CA | GLU | B 351 | 35.952 | −1.494 | 48.422 | 1.00 | 44.15 | MOLB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | | |
|---|---|---|---|---|---|---|---|---|---|---|---|
| ATOM | 5101 | CB | GLU | B 351 | 35.039 | −0.564 | 49.239 | 1.00 | 45.06 | MOLB | C |
| ATOM | 5102 | CG | GLU | B 351 | 35.245 | 0.900 | 48.965 | 1.00 | 39.30 | MOLB | C |
| ATOM | 5103 | CD | GLU | B 351 | 36.512 | 1.426 | 49.616 | 1.00 | 51.46 | MOLB | C |
| ATOM | 5104 | OE1 | GLU | B 351 | 36.578 | 2.654 | 49.862 | 1.00 | 72.83 | MOLB | O |
| ATOM | 5105 | OE2 | GLU | B 351 | 37.437 | 0.630 | 49.899 | 1.00 | 42.91 | MOLB | O |
| ATOM | 5106 | C | GLU | B 351 | 35.667 | −2.938 | 48.787 | 1.00 | 44.62 | MOLB | C |
| ATOM | 5107 | O | GLU | B 351 | 36.473 | −3.603 | 49.457 | 1.00 | 45.71 | MOLB | O |
| ATOM | 5108 | N | TYR | B 352 | 34.507 | −3.398 | 48.316 | 1.00 | 44.28 | MOLB | N |
| ATOM | 5109 | CA | TYR | B 352 | 34.044 | −4.733 | 48.554 | 1.00 | 45.06 | MOLB | C |
| ATOM | 5110 | CB | TYR | B 352 | 32.797 | −4.986 | 47.747 | 1.00 | 45.20 | MOLB | C |
| ATOM | 5111 | CG | TYR | B 352 | 32.374 | −6.398 | 47.915 | 1.00 | 48.41 | MOLB | C |
| ATOM | 5112 | CD1 | TYR | B 352 | 33.009 | −7.412 | 47.219 | 1.00 | 54.47 | MOLB | C |
| ATOM | 5113 | CE1 | TYR | B 352 | 32.646 | −8.744 | 47.390 | 1.00 | 56.97 | MOLB | C |
| ATOM | 5114 | CZ | TYR | B 352 | 31.653 | −9.059 | 48.274 | 1.00 | 54.29 | MOLB | C |
| ATOM | 5115 | OH | TYR | B 352 | 31.280 | −10.367 | 48.436 | 1.00 | 49.62 | MOLB | O |
| ATOM | 5116 | CE2 | TYR | B 352 | 31.024 | −8.062 | 49.006 | 1.00 | 65.16 | MOLB | C |
| ATOM | 5117 | CD2 | TYR | B 352 | 31.391 | −6.741 | 48.831 | 1.00 | 55.67 | MOLB | C |
| ATOM | 5118 | C | TYR | B 352 | 35.097 | −5.756 | 48.153 | 1.00 | 46.03 | MOLB | C |
| ATOM | 5119 | O | TYR | B 352 | 35.422 | −6.678 | 48.904 | 1.00 | 47.81 | MOLB | O |
| ATOM | 5120 | N | ALA | B 353 | 35.625 | −5.589 | 46.953 | 1.00 | 45.49 | MOLB | N |
| ATOM | 5121 | CA | ALA | B 353 | 36.673 | −6.449 | 46.476 | 1.00 | 46.56 | MOLB | C |
| ATOM | 5122 | CB | ALA | B 353 | 36.893 | −6.187 | 45.028 | 1.00 | 46.70 | MOLB | C |
| ATOM | 5123 | C | ALA | B 353 | 37.984 | −6.261 | 47.263 | 1.00 | 48.74 | MOLB | C |
| ATOM | 5124 | O | ALA | B 353 | 38.783 | −7.192 | 47.383 | 1.00 | 49.22 | MOLB | O |
| ATOM | 5125 | N | HIS | B 354 | 38.210 | −5.059 | 47.783 | 1.00 | 49.44 | MOLB | N |
| ATOM | 5126 | CA | HIS | B 354 | 39.438 | −4.768 | 48.507 | 1.00 | 50.72 | MOLB | C |
| ATOM | 5127 | CB | HIS | B 354 | 39.618 | −3.281 | 48.657 | 1.00 | 50.88 | MOLB | C |
| ATOM | 5128 | CG | HIS | B 354 | 40.984 | −2.908 | 49.114 | 1.00 | 52.09 | MOLB | C |
| ATOM | 5129 | ND1 | HIS | B 354 | 42.095 | −3.059 | 48.314 | 1.00 | 55.29 | MOLB | N |
| ATOM | 5130 | CE1 | HIS | B 354 | 43.165 | −2.646 | 48.968 | 1.00 | 53.98 | MOLB | C |
| ATOM | 5131 | NE2 | HIS | B 354 | 42.787 | −2.248 | 50.170 | 1.00 | 48.61 | MOLB | N |
| ATOM | 5132 | CD2 | HIS | B 354 | 41.427 | −2.402 | 50.286 | 1.00 | 50.50 | MOLB | C |
| ATOM | 5133 | C | HIS | B 354 | 39.371 | −5.378 | 49.889 | 1.00 | 51.82 | MOLB | C |
| ATOM | 5134 | O | HIS | B 354 | 40.377 | −5.599 | 50.555 | 1.00 | 49.33 | MOLB | O |
| ATOM | 5135 | N | ARG | B 355 | 38.150 | −5.616 | 50.331 | 1.00 | 52.90 | MOLB | N |
| ATOM | 5136 | CA | ARG | B 355 | 37.936 | −6.302 | 51.574 | 1.00 | 53.40 | MOLB | C |
| ATOM | 5137 | CB | ARG | B 355 | 36.477 | −6.098 | 51.992 | 1.00 | 54.89 | MOLB | C |
| ATOM | 5138 | CG | ARG | B 355 | 36.038 | −6.691 | 53.314 | 1.00 | 52.64 | MOLB | C |
| ATOM | 5139 | CD | ARG | B 355 | 35.082 | −5.738 | 54.028 | 1.00 | 44.91 | MOLB | C |
| ATOM | 5140 | NE | ARG | B 355 | 34.484 | −4.712 | 53.161 | 1.00 | 41.47 | MOLB | N |
| ATOM | 5141 | CZ | ARG | B 355 | 33.284 | −4.794 | 52.582 | 1.00 | 43.10 | MOLB | C |
| ATOM | 5142 | NH1 | ARG | B 355 | 32.508 | −5.874 | 52.749 | 1.00 | 35.23 | MOLB | N |
| ATOM | 5143 | NH2 | ARG | B 355 | 32.852 | −3.780 | 51.831 | 1.00 | 38.88 | MOLB | N |
| ATOM | 5144 | C | ARG | B 355 | 38.279 | −7.748 | 51.214 | 1.00 | 52.85 | MOLB | C |
| ATOM | 5145 | O | ARG | B 355 | 39.414 | −8.178 | 51.395 | 1.00 | 51.37 | MOLB | O |
| ATOM | 5146 | N | ALA | B 356 | 37.315 | −8.461 | 50.633 | 1.00 | 52.29 | MOLB | N |
| ATOM | 5147 | CA | ALA | B 356 | 37.531 | −9.812 | 50.105 | 1.00 | 49.62 | MOLB | C |
| ATOM | 5148 | CB | ALA | B 356 | 36.883 | −9.953 | 48.734 | 1.00 | 48.80 | MOLB | C |
| ATOM | 5149 | C | ALA | B 356 | 38.999 | −10.223 | 50.051 | 1.00 | 47.36 | MOLB | C |
| ATOM | 5150 | O | ALA | B 356 | 39.333 | −11.302 | 50.535 | 1.00 | 47.67 | MOLB | O |
| ATOM | 5151 | N | LYS | B 357 | 39.849 | −9.370 | 49.466 | 1.00 | 44.76 | MOLB | N |
| ATOM | 5152 | CA | LYS | B 357 | 41.304 | −9.597 | 49.353 | 1.00 | 43.01 | MOLB | C |
| ATOM | 5153 | CB | LYS | B 357 | 41.646 | −10.474 | 48.158 | 1.00 | 43.73 | MOLB | C |
| ATOM | 5154 | CG | LYS | B 357 | 43.136 | −10.445 | 47.782 | 1.00 | 45.47 | MOLB | C |
| ATOM | 5155 | CD | LYS | B 357 | 43.504 | −11.482 | 46.725 | 1.00 | 38.04 | MOLB | C |
| ATOM | 5156 | CE | LYS | B 357 | 45.010 | −11.679 | 46.644 | 1.00 | 50.37 | MOLB | C |
| ATOM | 5157 | NZ | LYS | B 357 | 45.442 | −12.673 | 45.585 | 1.00 | 57.29 | MOLB | N |
| ATOM | 5158 | C | LYS | B 357 | 42.062 | −8.289 | 49.203 | 1.00 | 44.43 | MOLB | C |
| ATOM | 5159 | O | LYS | B 357 | 42.081 | −7.669 | 48.141 | 1.00 | 42.50 | MOLB | O |
| ATOM | 5160 | N | ASN | B 358 | 42.728 | −7.880 | 50.268 | 1.00 | 46.92 | MOLB | N |
| ATOM | 5161 | CA | ASN | B 358 | 43.346 | −6.576 | 50.265 | 1.00 | 47.40 | MOLB | C |
| ATOM | 5162 | CB | ASN | B 358 | 43.371 | −5.974 | 51.668 | 1.00 | 48.14 | MOLB | C |
| ATOM | 5163 | CG | ASN | B 358 | 44.133 | −4.660 | 51.705 | 1.00 | 50.17 | MOLB | C |
| ATOM | 5164 | OD1 | ASN | B 358 | 44.549 | −4.151 | 50.659 | 1.00 | 48.13 | MOLB | O |
| ATOM | 5165 | ND2 | ASN | B 358 | 44.328 | −4.109 | 52.899 | 1.00 | 43.83 | MOLB | N |
| ATOM | 5166 | C | ASN | B 358 | 44.740 | −6.596 | 49.719 | 1.00 | 47.84 | MOLB | C |
| ATOM | 5167 | O | ASN | B 358 | 45.654 | −7.077 | 50.383 | 1.00 | 47.82 | MOLB | O |
| ATOM | 5168 | N | ILE | B 359 | 44.920 | −6.064 | 48.517 | 1.00 | 47.93 | MOLB | N |
| ATOM | 5169 | CA | ILE | B 359 | 46.262 | −6.020 | 47.953 | 1.00 | 46.77 | MOLB | C |
| ATOM | 5170 | CB | ILE | B 359 | 46.280 | −6.417 | 46.488 | 1.00 | 46.55 | MOLB | C |
| ATOM | 5171 | CG1 | ILE | B 359 | 45.711 | −7.830 | 46.331 | 1.00 | 41.09 | MOLB | C |
| ATOM | 5172 | CD1 | ILE | B 359 | 45.753 | −8.366 | 44.896 | 1.00 | 33.71 | MOLB | C |
| ATOM | 5173 | CG2 | ILE | B 359 | 47.691 | −6.260 | 45.937 | 1.00 | 37.83 | MOLB | C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 5174 | C | ILE | B 359 | 46.826 | −4.626 | 48.089 | 1.00 | 48.49 | MOLB C |
| ATOM | 5175 | O | ILE | B 359 | 46.224 | −3.654 | 47.604 | 1.00 | 50.41 | MOLB O |
| ATOM | 5176 | N | LEU | B 360 | 47.983 | −4.536 | 48.736 | 1.00 | 47.80 | MOLB N |
| ATOM | 5177 | CA | LEU | B 360 | 48.616 | −3.265 | 49.027 | 1.00 | 47.91 | MOLB C |
| ATOM | 5178 | CB | LEU | B 360 | 49.906 | −3.477 | 49.815 | 1.00 | 46.94 | MOLB C |
| ATOM | 5179 | CG | LEU | B 360 | 49.885 | −3.904 | 51.293 | 1.00 | 54.92 | MOLB C |
| ATOM | 5180 | CD1 | LEU | B 360 | 48.722 | −3.236 | 52.032 | 1.00 | 65.10 | MOLB C |
| ATOM | 5181 | CD2 | LEU | B 360 | 49.844 | −5.438 | 51.497 | 1.00 | 67.85 | MOLB C |
| ATOM | 5182 | C | LEU | B 360 | 48.971 | −2.577 | 47.754 | 1.00 | 48.54 | MOLB C |
| ATOM | 5183 | O | LEU | B 360 | 49.604 | −3.177 | 46.916 | 1.00 | 49.98 | MOLB O |
| ATOM | 5184 | N | ASN | B 361 | 48.581 | −1.317 | 47.605 | 1.00 | 52.22 | MOLB N |
| ATOM | 5185 | CA | ASN | B 361 | 49.004 | −0.526 | 46.438 | 1.00 | 55.81 | MOLB C |
| ATOM | 5186 | CB | ASN | B 361 | 48.352 | 0.874 | 46.417 | 1.00 | 55.09 | MOLB C |
| ATOM | 5187 | CG | ASN | B 361 | 46.898 | 0.881 | 45.874 | 1.00 | 59.94 | MOLB C |
| ATOM | 5188 | OD1 | ASN | B 361 | 46.242 | −0.164 | 45.724 | 1.00 | 73.20 | MOLB O |
| ATOM | 5189 | ND2 | ASN | B 361 | 46.388 | 2.090 | 45.600 | 1.00 | 53.54 | MOLB N |
| ATOM | 5190 | C | ASN | B 361 | 50.521 | −0.370 | 46.443 | 1.00 | 56.89 | MOLB C |
| ATOM | 5191 | O | ASN | B 361 | 51.076 | 0.101 | 47.417 | 1.00 | 54.66 | MOLB O |
| ATOM | 5192 | N | LYS | B 362 | 51.183 | −0.796 | 45.366 | 1.00 | 61.86 | MOLB N |
| ATOM | 5193 | CA | LYS | B 362 | 52.637 | −0.626 | 45.200 | 1.00 | 65.51 | MOLB C |
| ATOM | 5194 | CB | LYS | B 362 | 53.079 | −0.982 | 43.774 | 1.00 | 64.69 | MOLB C |
| ATOM | 5195 | CG | LYS | B 362 | 52.958 | −2.440 | 43.331 | 1.00 | 67.95 | MOLB C |
| ATOM | 5196 | CD | LYS | B 362 | 52.782 | −2.458 | 41.791 | 1.00 | 79.52 | MOLB C |
| ATOM | 5197 | CE | LYS | B 362 | 53.246 | −3.753 | 41.131 | 1.00 | 80.48 | MOLB C |
| ATOM | 5198 | NZ | LYS | B 362 | 52.295 | −4.878 | 41.383 | 1.00 | 87.76 | MOLB N |
| ATOM | 5199 | C | LYS | B 362 | 53.023 | 0.830 | 45.438 | 1.00 | 68.21 | MOLB C |
| ATOM | 5200 | O | LYS | B 362 | 52.161 | 1.709 | 45.427 | 1.00 | 67.79 | MOLB O |
| ATOM | 5201 | N | PRO | B 363 | 54.328 | 1.094 | 45.657 | 1.00 | 71.61 | MOLB N |
| ATOM | 5202 | CA | PRO | B 363 | 54.792 | 2.477 | 45.679 | 1.00 | 71.99 | MOLB C |
| ATOM | 5203 | CB | PRO | B 363 | 56.183 | 2.366 | 46.294 | 1.00 | 71.22 | MOLB C |
| ATOM | 5204 | CG | PRO | B 363 | 56.660 | 1.004 | 45.899 | 1.00 | 71.09 | MOLB C |
| ATOM | 5205 | CD | PRO | B 363 | 55.430 | 0.135 | 45.892 | 1.00 | 72.66 | MOLB C |
| ATOM | 5206 | C | PRO | B 363 | 54.888 | 2.932 | 44.235 | 1.00 | 73.09 | MOLB C |
| ATOM | 5207 | O | PRO | B 363 | 55.720 | 2.423 | 43.485 | 1.00 | 73.41 | MOLB O |
| ATOM | 5208 | N | GLU | B 364 | 54.021 | 3.850 | 43.838 | 1.00 | 74.15 | MOLB N |
| ATOM | 5209 | CA | GLU | B 364 | 53.986 | 4.289 | 42.463 | 1.00 | 77.22 | MOLB C |
| ATOM | 5210 | CB | GLU | B 364 | 52.993 | 5.418 | 42.329 | 1.00 | 76.72 | MOLB C |
| ATOM | 5211 | CG | GLU | B 364 | 53.245 | 6.517 | 43.325 | 1.00 | 80.63 | MOLB C |
| ATOM | 5212 | CD | GLU | B 364 | 52.850 | 7.869 | 42.778 | 1.00 | 97.30 | MOLB C |
| ATOM | 5213 | OE1 | GLU | B 364 | 52.484 | 8.752 | 43.583 | 1.00 | 101.01 | MOLB O |
| ATOM | 5214 | OE2 | GLU | B 364 | 52.901 | 8.047 | 41.537 | 1.00 | 100.96 | MOLB O |
| ATOM | 5215 | C | GLU | B 364 | 55.353 | 4.767 | 41.973 | 1.00 | 79.85 | MOLB C |
| ATOM | 5216 | O | GLU | B 364 | 56.363 | 4.074 | 42.146 | 1.00 | 81.35 | MOLB O |
| ATOM | 5217 | N | VAL | B 365 | 55.354 | 5.938 | 41.324 | 1.00 | 80.89 | MOLB N |
| ATOM | 5218 | CA | VAL | B 365 | 56.556 | 6.676 | 40.877 | 1.00 | 80.42 | MOLB C |
| ATOM | 5219 | CB | VAL | B 365 | 57.736 | 5.762 | 40.328 | 1.00 | 80.96 | MOLB C |
| ATOM | 5220 | CG1 | VAL | B 365 | 57.343 | 5.003 | 39.050 | 1.00 | 77.37 | MOLB C |
| ATOM | 5221 | CG2 | VAL | B 365 | 59.041 | 6.576 | 40.128 | 1.00 | 80.03 | MOLB C |
| ATOM | 5222 | C | VAL | B 365 | 56.090 | 7.729 | 39.860 | 1.00 | 80.91 | MOLB C |
| ATOM | 5223 | O | VAL | B 365 | 56.353 | 8.933 | 39.989 | 1.00 | 80.89 | MOLB O |
| ATOM | 5224 | OXT | VAL | B 365 | 55.388 | 7.400 | 38.900 | 1.00 | 80.48 | MOLB O |
| ATOM | 2599 | MG | MG | A3001 | 17.5581 | 5.429 | 33.763 | 1.00 | 39.37 | COFAMG |
| ATOM | 2600 | O2A | ADP | A4001 | 16.541 | 13.381 | 29.888 | 1.00 | 37.09 | COFA O |
| ATOM | 2601 | PA | ADP | A4001 | 15.361 | 12.676 | 30.501 | 1.00 | 36.53 | COFA P |
| ATOM | 2602 | O1A | ADP | A4001 | 14.112 | 13.443 | 30.782 | 1.00 | 41.83 | COFA O |
| ATOM | 2603 | O3A | ADP | A4001 | 15.766 | 12.018 | 31.927 | 1.00 | 23.99 | COFA O |
| ATOM | 2604 | PB | ADP | A4001 | 15.766 | 12.874 | 33.291 | 1.00 | 28.78 | COFA P |
| ATOM | 2605 | O3B | ADP | A4001 | 17.085 | 12.523 | 33.921 | 1.00 | 34.66 | COFA O |
| ATOM | 2606 | O2B | ADP | A4001 | 15.639 | 14.355 | 32.961 | 1.00 | 35.57 | COFA O |
| ATOM | 2607 | O1B | ADP | A4001 | 14.600 | 12.362 | 34.049 | 1.00 | 25.36 | COFA O |
| ATOM | 2608 | O5* | ADP | A4001 | 15.013 | 11.440 | 29.522 | 1.00 | 38.09 | COFA O |
| ATOM | 2609 | C5* | ADP | A4001 | 16.110 | 10.640 | 29.062 | 1.00 | 38.19 | COFA C |
| ATOM | 2610 | C4* | ADP | A4001 | 15.892 | 10.070 | 27.666 | 1.00 | 21.34 | COFA C |
| ATOM | 2611 | C3* | ADP | A4001 | 15.882 | 11.172 | 26.631 | 1.00 | 23.23 | COFA C |
| ATOM | 2612 | O3* | ADP | A4001 | 16.482 | 10.695 | 25.427 | 1.00 | 26.55 | COFA O |
| ATOM | 2613 | C2* | ADP | A4001 | 14.393 | 11.436 | 26.495 | 1.00 | 20.15 | COFA C |
| ATOM | 2614 | O2* | ADP | A4001 | 13.957 | 12.124 | 25.310 | 1.00 | 34.17 | COFA O |
| ATOM | 2615 | C1* | ADP | A4001 | 13.807 | 10.054 | 26.640 | 1.00 | 24.67 | COFA C |
| ATOM | 2616 | O4* | ADP | A4001 | 14.595 | 9.474 | 27.667 | 1.00 | 23.81 | COFA O |
| ATOM | 2617 | N9 | ADP | A4001 | 12.484 | 10.129 | 27.245 | 1.00 | 33.30 | COFA N |
| ATOM | 2618 | C4 | ADP | A4001 | 11.340 | 10.155 | 26.588 | 1.00 | 25.15 | COFA C |
| ATOM | 2619 | C5 | ADP | A4001 | 10.292 | 10.242 | 27.617 | 1.00 | 31.74 | COFA C |
| ATOM | 2620 | N7 | ADP | A4001 | 10.916 | 10.287 | 28.817 | 1.00 | 33.08 | COFA N |

TABLE 10-continued

Novel Eg5 ligand binding site/compound 3 X-ray coordinates.
Complete coordinates of the entire motor domain of Eg5
Table 10 discloses residues 16-55, 61-270, 285-365, 16-55,
61-270, and 285-365 of SEQ ID NO: 1, respectively, in order
of appearance

| | | | | | | | | | | |
|---|---|---|---|---|---|---|---|---|---|---|
| ATOM | 2621 | C8 | ADP | A4001 | 12.250 | 10.200 | 28.571 | 1.00 | 29.19 | COFA C |
| ATOM | 2622 | N3 | ADP | A4001 | 10.998 | 10.110 | 25.294 | 1.00 | 21.72 | COFA N |
| ATOM | 2623 | C2 | ADP | A4001 | 9.672 | 10.143 | 24.964 | 1.00 | 29.43 | COFA C |
| ATOM | 2624 | N1 | ADP | A4001 | 8.641 | 10.214 | 25.832 | 1.00 | 19.63 | COFA N |
| ATOM | 2625 | C6 | ADP | A4001 | 8.882 | 10.261 | 27.162 | 1.00 | 29.55 | COFA C |
| ATOM | 2626 | N6 | ADP | A4001 | 7.899 | 10.350 | 28.082 | 1.00 | 27.36 | COFA N |
| ATOM | 5225 | MG | MG | B3002 | 22.607 | −9.836 | 34.508 | 1.00 | 23.91 | COFBMG |
| ATOM | 5226 | O2A | ADP | B4002 | 23.168 | −7.372 | 31.776 | 1.00 | 38.29 | MOLB O |
| ATOM | 5227 | PA | ADP | B4002 | 24.642 | −7.027 | 31.758 | 1.00 | 32.35 | MOLB P |
| ATOM | 5228 | O1A | ADP | B4002 | 25.764 | −8.037 | 31.583 | 1.00 | 48.71 | MOLB O |
| ATOM | 5229 | O3A | ADP | B4002 | 24.926 | −6.337 | 33.175 | 1.00 | 17.73 | MOLB O |
| ATOM | 5230 | PB | ADP | B4002 | 24.442 | −7.228 | 34.395 | 1.00 | 35.86 | MOLB P |
| ATOM | 5231 | O3B | ADP | B4002 | 22.952 | −6.933 | 34.419 | 1.00 | 51.22 | MOLB O |
| ATOM | 5232 | O2B | ADP | B4002 | 24.814 | −8.609 | 33.892 | 1.00 | 35.53 | MOLB O |
| ATOM | 5233 | O1B | ADP | B4002 | 25.152 | −6.756 | 35.664 | 1.00 | 13.25 | MOLB O |
| ATOM | 5234 | O5* | ADP | B4002 | 24.870 | −5.913 | 30.642 | 1.00 | 43.17 | MOLB O |
| ATOM | 5235 | C5* | ADP | B4002 | 23.888 | −4.913 | 30.361 | 1.00 | 41.82 | MOLB C |
| ATOM | 5236 | C4* | ADP | B4002 | 24.381 | −4.244 | 29.085 | 1.00 | 42.98 | MOLB C |
| ATOM | 5237 | C3* | ADP | B4002 | 24.301 | −5.175 | 27.885 | 1.00 | 41.85 | MOLB C |
| ATOM | 5238 | O3* | ADP | B4002 | 23.817 | −4.378 | 26.804 | 1.00 | 44.59 | MOLB O |
| ATOM | 5239 | C2* | ADP | B4002 | 25.717 | −5.629 | 27.577 | 1.00 | 36.47 | MOLB C |
| ATOM | 5240 | O2* | ADP | B4002 | 25.924 | −5.687 | 26.160 | 1.00 | 43.50 | MOLB O |
| ATOM | 5241 | C1* | ADP | B4002 | 26.503 | −4.470 | 28.125 | 1.00 | 27.81 | MOLB C |
| ATOM | 5242 | O4* | ADP | B4002 | 25.770 | −3.948 | 29.236 | 1.00 | 36.44 | MOLB O |
| ATOM | 5243 | N9 | ADP | B4002 | 27.893 | −4.739 | 28.526 | 1.00 | 29.77 | MOLB N |
| ATOM | 5244 | C4 | ADP | B4002 | 28.922 | −4.667 | 27.671 | 1.00 | 22.14 | MOLB C |
| ATOM | 5245 | C5 | ADP | B4002 | 30.127 | −4.959 | 28.468 | 1.00 | 19.70 | MOLB C |
| ATOM | 5246 | N7 | ADP | B4002 | 29.725 | −5.145 | 29.743 | 1.00 | 26.67 | MOLB N |
| ATOM | 5247 | C8 | ADP | B4002 | 28.353 | −5.025 | 29.770 | 1.00 | 25.47 | MOLB C |
| ATOM | 5248 | N3 | ADP | B4002 | 29.040 | −4.434 | 26.341 | 1.00 | 18.65 | MOLB N |
| ATOM | 5249 | C2 | ADP | B4002 | 30.250 | −4.418 | 25.755 | 1.00 | 23.48 | MOLB C |
| ATOM | 5250 | N1 | ADP | B4002 | 31.400 | −4.655 | 26.430 | 1.00 | 26.40 | MOLB N |
| ATOM | 5251 | C6 | ADP | B4002 | 31.408 | −4.944 | 27.753 | 1.00 | 20.09 | MOLB C |
| ATOM | 5252 | N6 | ADP | B4002 | 32.550 | −5.192 | 28.429 | 1.00 | 28.46 | MOLB N |
| ATOM | 5253 | O13 | LIG | A1001 | 16.160 | 20.711 | 21.719 | 1.00 | 65.10 | LIGA O |
| ATOM | 5254 | C12 | LIG | A1001 | 17.064 | 20.485 | 22.504 | 1.00 | 53.25 | LIGA C |
| ATOM | 5255 | C14 | LIG | A1001 | 17.582 | 19.078 | 22.664 | 1.00 | 58.39 | LIGA C |
| ATOM | 5256 | N31 | LIG | A1001 | 18.081 | 18.343 | 23.701 | 1.00 | 59.53 | LIGA N |
| ATOM | 5257 | N33 | LIG | A1001 | 18.386 | 17.082 | 23.143 | 1.00 | 45.65 | LIGA N |
| ATOM | 5258 | C37 | LIG | A1001 | 18.933 | 16.045 | 24.039 | 1.00 | 32.46 | LIGA C |
| ATOM | 5259 | C35 | LIG | A1001 | 18.067 | 17.126 | 21.873 | 1.00 | 43.92 | LIGA C |
| ATOM | 5260 | C38 | LIG | A1001 | 18.241 | 15.997 | 20.936 | 1.00 | 50.09 | LIGA C |
| ATOM | 5261 | C36 | LIG | A1001 | 17.578 | 18.316 | 21.567 | 1.00 | 54.47 | LIGA C |
| ATOM | 5262 | N11 | LIG | A1001 | 17.567 | 21.498 | 23.203 | 1.00 | 46.47 | LIGA N |
| ATOM | 5263 | C15 | LIG | A1001 | 18.625 | 21.389 | 24.203 | 1.00 | 46.94 | LIGA C |
| ATOM | 5264 | C16 | LIG | A1001 | 17.927 | 21.351 | 25.558 | 1.00 | 33.87 | LIGA C |
| ATOM | 5265 | C17 | LIG | A1001 | 17.651 | 19.935 | 26.024 | 1.00 | 27.45 | LIGA C |
| ATOM | 5266 | N18 | LIG | A1001 | 17.422 | 20.013 | 27.452 | 1.00 | 30.80 | LIGA N |
| ATOM | 5267 | C10 | LIG | A1001 | 17.013 | 22.847 | 22.971 | 1.00 | 37.95 | LIGA C |
| ATOM | 5268 | C19 | LIG | A1001 | 18.024 | 23.869 | 22.453 | 1.00 | 33.41 | LIGA C |
| ATOM | 5269 | C20 | LIG | A1001 | 17.309 | 25.214 | 22.415 | 1.00 | 33.08 | LIGA C |
| ATOM | 5270 | C21 | LIG | A1001 | 18.438 | 23.469 | 21.045 | 1.00 | 32.59 | LIGA C |
| ATOM | 5271 | C | LIG | A1001 | 19.225 | 23.970 | 23.276 | 1.00 | 33.65 | LIGA C |
| ATOM | 5272 | C9 | LIG | A1001 | 16.294 | 23.337 | 24.179 | 1.00 | 49.51 | LIGA C |
| ATOM | 5273 | N22 | LIG | A1001 | 14.992 | 23.098 | 24.435 | 1.00 | 56.25 | LIGA N |
| ATOM | 5274 | C23 | LIG | A1001 | 14.100 | 22.294 | 23.573 | 1.00 | 39.37 | LIGA C |
| ATOM | 5275 | C24 | LIG | A1001 | 13.066 | 23.055 | 22.783 | 1.00 | 50.24 | LIGA C |
| ATOM | 5276 | C26 | LIG | A1001 | 12.065 | 22.368 | 22.199 | 1.00 | 50.24 | LIGA C |
| ATOM | 5277 | C27 | LIG | A1001 | 11.166 | 23.076 | 21.509 | 1.00 | 49.99 | LIGA C |
| ATOM | 5278 | C28 | LIG | A1001 | 11.319 | 24.404 | 21.445 | 1.00 | 40.15 | LIGA C |
| ATOM | 5279 | C29 | LIG | A1001 | 12.306 | 24.944 | 22.022 | 1.00 | 40.43 | LIGA C |
| ATOM | 5280 | C30 | LIG | A1001 | 13.121 | 24.318 | 22.646 | 1.00 | 50.70 | LIGA C |
| ATOM | 5281 | C25 | LIG | A1001 | 14.694 | 23.662 | 25.628 | 1.00 | 49.02 | LIGA C |
| ATOM | 5282 | C2 | LIG | A1001 | 15.848 | 24.282 | 26.110 | 1.00 | 41.53 | LIGA C |
| ATOM | 5283 | N8 | LIG | A1001 | 16.820 | 24.067 | 25.195 | 1.00 | 48.45 | LIGA N |
| ATOM | 5284 | C1 | LIG | A1001 | 16.017 | 25.035 | 27.391 | 1.00 | 32.60 | LIGA C |
| ATOM | 5285 | C3 | LIG | A1001 | 15.161 | 24.866 | 28.416 | 1.00 | 34.30 | LIGA C |
| ATOM | 5286 | C4 | LIG | A1001 | 15.424 | 25.466 | 29.587 | 1.00 | 29.32 | LIGA C |
| ATOM | 5287 | C5 | LIG | A1001 | 16.538 | 26.195 | 29.677 | 1.00 | 22.03 | LIGA C |
| ATOM | 5288 | C6 | LIG | A1001 | 17.286 | 26.269 | 28.652 | 1.00 | 42.31 | LIGA C |
| ATOM | 5289 | C7 | LIG | A1001 | 17.052 | 25.730 | 27.601 | 1.00 | 43.54 | LIGA C |
| ATOM | 5290 | O13 | LIG | B1002 | 22.604 | −14.538 | 22.821 | 1.00 | 63.41 | LIGB O |
| ATOM | 5291 | C12 | LIG | B1002 | 22.008 | −14.347 | 23.883 | 1.00 | 47.61 | LIGB C |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 5292 | C14 | LIG | B1002 | 21.547 | −12.974 | 24.249 | 1.00 | 53.32 | LIGB C |
| ATOM | 5293 | N31 | LIG | B1002 | 20.986 | −12.477 | 25.383 | 1.00 | 53.98 | LIGB N |
| ATOM | 5294 | N33 | LIG | B1002 | 20.789 | −11.117 | 25.129 | 1.00 | 45.98 | LIGB N |
| ATOM | 5295 | C37 | LIG | B1002 | 20.153 | −10.380 | 26.258 | 1.00 | 45.10 | LIGB C |
| ATOM | 5296 | C35 | LIG | B1002 | 21.232 | −10.886 | 23.884 | 1.00 | 32.35 | LIGB C |
| ATOM | 5297 | C38 | LIG | B1002 | 21.228 | −9.592 | 23.168 | 1.00 | 40.28 | LIGB C |
| ATOM | 5298 | C36 | LIG | B1002 | 21.699 | −11.993 | 23.344 | 1.00 | 39.29 | LIGB C |
| ATOM | 5299 | N11 | LIG | B1002 | 21.741 | −15.332 | 24.729 | 1.00 | 32.27 | LIGB N |
| ATOM | 5300 | C15 | LIG | B1002 | 21.047 | −15.241 | 26.016 | 1.00 | 39.OS | LIGB C |
| ATOM | 5301 | C16 | LIG | B1002 | 22.061 | −14.947 | 27.124 | 1.00 | 28.17 | LIGB C |
| ATOM | 5302 | C17 | LIG | B1002 | 21.470 | −13.948 | 28.122 | 1.00 | 33.89 | LIGB C |
| ATOM | 5303 | N18 | LIG | B1002 | 22.281 | −13.792 | 29.322 | 1.00 | 26.21 | LIGB N |
| ATOM | 5304 | C10 | LIG | B1002 | 22.148 | −16.702 | 24.386 | 1.00 | 44.82 | LIGB C |
| ATOM | 5305 | C19 | LIG | B1002 | 20.997 | −17.629 | 23.937 | 1.00 | 42.23 | LIGB C |
| ATOM | 5306 | C20 | LIG | B1002 | 21.596 | −19.001 | 23.619 | 1.00 | 33.33 | LIGB C |
| ATOM | 5307 | C21 | LIG | B1002 | 20.340 | −17.109 | 22.664 | 1.00 | 44.23 | LIGB C |
| ATOM | 5308 | C | LIG | B1002 | 19.953 | −17.739 | 24.954 | 1.00 | 40.10 | LIGB C |
| ATOM | 5309 | C9 | LIG | B1002 | 22.887 | −17.262 | 25.540 | 1.00 | 50.20 | LIGB C |
| ATOM | 5310 | N22 | LIG | B1002 | 24.208 | −17.156 | 25.730 | 1.00 | 57.19 | LIGB N |
| ATOM | 5311 | C23 | LIG | B1002 | 25.169 | −16.461 | 24.853 | 1.00 | 52.96 | LIGB C |
| ATOM | 5312 | C24 | LIG | B1002 | 25.887 | −17.332 | 23.852 | 1.00 | 49.16 | LIGB C |
| ATOM | 5313 | C26 | LIG | B1002 | 26.685 | −16.741 | 22.940 | 1.00 | 56.74 | LIGB C |
| ATOM | 5314 | C27 | LIG | B1002 | 27.302 | −17.538 | 22.055 | 1.00 | 60.39 | LIGB C |
| ATOM | 5315 | C28 | LIG | B1002 | 27.086 | −18.858 | 22.153 | 1.00 | 49.57 | LIGB C |
| ATOM | 5316 | C29 | LIG | B1002 | 26.318 | −19.307 | 23.065 | 1.00 | 39.13 | LIGB C |
| ATOM | 5317 | C30 | LIG | B1002 | 25.760 | −18.597 | 23.855 | 1.00 | 46.03 | LIGB C |
| ATOM | 5318 | C25 | LIG | B1002 | 24.502 | −17.753 | 26.893 | 1.00 | 56.54 | LIGB C |
| ATOM | 5319 | C2 | LIG | B1002 | 23.323 | −18.247 | 27.428 | 1.00 | 58.86 | LIGB C |
| ATOM | 5320 | N8 | LIG | B1002 | 22.333 | −17.928 | 26.576 | 1.00 | 52.78 | LIGB N |
| ATOM | 5321 | C1 | LIG | B1002 | 23.173 | −19.007 | 28.706 | 1.00 | 52.58 | LIGB C |
| ATOM | 5322 | C3 | LIG | B1002 | 24.227 | −9.145 | 29.536 | 1.00 | 46.53 | LIGB C |
| ATOM | 5323 | C4 | LIG | B1002 | 23.995 | −19.695 | 30.716 | 1.00 | 46.47 | LIGB C |
| ATOM | 5324 | C5 | LIG | B1002 | 22.737 | −20.057 | 30.981 | 1.00 | 43.93 | LIGB C |
| ATOM | 5325 | C6 | LIG | B1002 | 21.830 | −19.873 | 30.124 | 1.00 | 44.58 | LIGB C |
| ATOM | 5326 | C7 | LIG | B1002 | 22.028 | −19.388 | 29.060 | 1.00 | 40.92 | LIGB C |
| ATOM | 5327 | O | HOH | w 1 | 33.668 | −8.251 | 24.408 | 1.00 | 26.28 | WATR O |
| ATOM | 5328 | O | HOH | w 2 | 26.295 | 12.653 | 37.429 | 1.00 | 30.48 | WATR O |
| ATOM | 5329 | O | HOH | w 3 | 44.204 | −33.562 | 43.028 | 1.00 | 40.37 | WATR O |
| ATOM | 5330 | O | HOH | w 4 | 37.657 | 17.669 | 41.588 | 1.00 | 41.74 | WATR O |
| ATOM | 5331 | O | HOH | w 5 | 22.434 | 20.451 | 45.128 | 1.00 | 38.93 | WATR O |
| ATOM | 5332 | O | HOH | w 6 | 19.620 | −28.063 | 36.680 | 1.00 | 49.24 | WATR O |
| ATOM | 5333 | O | HOH | w 7 | 33.904 | 20.345 | 42.211 | 1.00 | 37.49 | WATR O |
| ATOM | 5334 | O | HOH | w 8 | 19.947 | −16.105 | 49.074 | 1.00 | 40.14 | WATR O |
| ATOM | 5335 | O | HOH | w 9 | 40.291 | 16.144 | 37.463 | 1.00 | 51.03 | WATR O |
| ATOM | 5336 | O | HOH | w 10 | 5.362 | 13.149 | 23.149 | 1.00 | 47.22 | WATR O |
| ATOM | 5337 | O | HOH | w 11 | 27.156 | −30.597 | 36.748 | 1.00 | 53.39 | WATR O |
| ATOM | 5338 | O | HOH | w 12 | 22.537 | 2.815 | 27.241 | 1.00 | 50.37 | WATR O |
| ATOM | 5339 | O | HOH | w 13 | 49.968 | −1.615 | 42.212 | 1.00 | 57.82 | WATR O |
| ATOM | 5340 | O | HOH | w 14 | −0.984 | 41.019 | 40.645 | 1.00 | 53.83 | WATR O |
| ATOM | 5341 | O | HOH | w 15 | 20.439 | 10.346 | 46.115 | 1.00 | 46.64 | WATR O |
| ATOM | 5342 | O | HOH | w 16 | 36.680 | 21.645 | 39.653 | 1.00 | 51.05 | WATR O |
| ATOM | 5343 | O | HOH | w 17 | 4.812 | 20.439 | 27.341 | 1.00 | 65.65 | WATR O |
| ATOM | 5344 | O | HOH | w 18 | 21.544 | −10.521 | 39.451 | 1.00 | 50.79 | WATR O |
| ATOM | 5345 | O | HOH | w 19 | 13.569 | −6.603 | 52.655 | 1.00 | 66.55 | WATR O |
| ATOM | 5346 | O | HOH | w 20 | −4.353 | 40.229 | 30.901 | 1.00 | 41.11 | WATR O |
| ATOM | 5347 | O | HOH | w 21 | 24.163 | −10.125 | 36.403 | 1.00 | 45.36 | WATR O |
| ATOM | 5348 | O | HOH | w 22 | 31.830 | −8.550 | 8.414 | 1.00 | 50.08 | WATR O |
| ATOM | 5349 | O | HOH | w 23 | 13.185 | 7.800 | 43.222 | 1.00 | 48.51 | WATR O |
| ATOM | 5350 | O | HOH | w 24 | 27.984 | −13.020 | 57.548 | 1.00 | 42.47 | WATR O |
| ATOM | 5351 | O | HOH | w 25 | 16.185 | 15.832 | 35.437 | 1.00 | 41.93 | WATR O |
| ATOM | 5352 | O | HOH | w 26 | 36.501 | −44.850 | 34.822 | 1.00 | 49.66 | WATR O |
| ATOM | 5353 | O | HOH | w 27 | −10.202 | 2.186 | 34.948 | 1.00 | 53.52 | WATR O |
| ATOM | 5354 | O | HOH | w 28 | 22.168 | −16.961 | 49.852 | 1.00 | 50.83 | WATR O |
| ATOM | 5355 | O | HOH | w 29 | 19.474 | 33.794 | 34.932 | 1.00 | 68.49 | WATR O |
| ATOM | 5356 | O | HOH | w 30 | 15.088 | −6.782 | 35.549 | 1.00 | 45.53 | WATR O |
| ATOM | 5357 | O | HOH | w 31 | 29.919 | −2.124 | 40.128 | 1.00 | 43.45 | WATR O |
| ATOM | 5358 | O | HOH | w 32 | −19.778 | 54.145 | 32.102 | 1.00 | 41.67 | WATR O |
| ATOM | 5359 | O | HOH | w 33 | 38.356 | 19.655 | 40.206 | 1.00 | 48.73 | WATR O |
| ATOM | 5360 | O | HOH | w 34 | 13.982 | 36.459 | 17.990 | 1.00 | 54.13 | WATR O |
| ATOM | 5361 | O | HOH | w 35 | 20.471 | −31.764 | 24.503 | 1.00 | 61.58 | WATR O |
| ATOM | 5362 | O | HOH | w 36 | 13.267 | 27.087 | 16.089 | 1.00 | 57.35 | WATR O |
| ATOM | 5363 | O | HOH | w 37 | 2.520 | 20.824 | 19.690 | 1.00 | 66.00 | WATR O |
| ATOM | 5364 | O | HOH | w 38 | 8.564 | 10.621 | 31.039 | 1.00 | 47.56 | WATR O |

TABLE 10-continued

Novel Eg5 ligand binding site/compound 3 X-ray coordinates. Complete coordinates of the entire motor domain of Eg5 Table 10 discloses residues 16-55, 61-270, 285-365, 16-55, 61-270, and 285-365 of SEQ ID NO: 1, respectively, in order of appearance

| | | | | | | | | | | |
|---|---|---|---|---|---|---|---|---|---|---|
| ATOM | 5365 | O | HOH | w 39 | 35.667 | −28.195 | 19.791 | 1.00 | 57.36 | WATR O |
| ATOM | 5366 | O | HOH | w 40 | 27.510 | 12.888 | 26.302 | 1.00 | 53.58 | WATR O |
| ATOM | 5367 | O | HOH | w 41 | 11.241 | 7.582 | 39.392 | 1.00 | 56.48 | WATR O |
| ATOM | 5368 | O | HOH | w 42 | 38.363 | −28.053 | 45.152 | 1.00 | 68.88 | WATR O |
| ATOM | 5369 | O | HOH | w 43 | 18.854 | -33.664 | 33.748 | 1.00 | 62.07 | WATR O |
| ATOM | 5370 | O | HOH | w 44 | 38.480 | 16.843 | 39.562 | 1.00 | 58.64 | WATR O |
| ATOM | 5371 | O | HOH | w 45 | 18.201 | 3.083 | 25.990 | 1.00 | 59.43 | WATR O |
| ATOM | 5372 | O | HOH | w 46 | −6.731 | 25.466 | 44.053 | 1.00 | 61.06 | WATR O |
| ATOM | 5373 | O | HOH | w 47 | 26.085 | 3.743 | 42.533 | 1.00 | 54.72 | WATR O |
| ATOM | 5374 | O | HOH | w 48 | 7.256 | 14.803 | 53.463 | 1.00 | 60.29 | WATR O |
| ATOM | 5375 | O | HOH | w 49 | 34.834 | −10.207 | 23.401 | 1.00 | 66.83 | WATR O |
| ATOM | 5376 | O | HOH | w 50 | 57.422 | −1.107 | 44.225 | 1.00 | 58.36 | WATR O |
| ATOM | 5377 | O | HOH | w 51 | 17.943 | 15.180 | 31.290 | 1.00 | 40.69 | WATR O |
| ATOM | 5378 | O | HOH | w 52 | 14.102 | 23.329 | 34.859 | 1.00 | 49.29 | WATR O |
| ATOM | 5379 | O | HOH | w 53 | 17.945 | 41.462 | 29.046 | 1.00 | 70.90 | WATR O |
| ATOM | 5380 | O | HOH | w 54 | 24.130 | −6.316 | 53.651 | 1.00 | 70.17 | WATR O |
| ATOM | 5381 | O | HOH | w 55 | 46.003 | −20.907 | 31.923 | 1.00 | 61.97 | WATR O |
| ATOM | 5382 | O | HOH | w 56 | 40.435 | −22.914 | 49.838 | 1.00 | 69.05 | WATR O |
| ATOM | 5383 | O | HOH | w 57 | 41.471 | 19.733 | 39.306 | 1.00 | 56.35 | WATR O |
| ATOM | 5384 | O | HOH | w 58 | 15.145 | 4.938 | 34.548 | 1.00 | 47.05 | WATR O |
| ATOM | 5385 | O | HOH | w 59 | 46.524 | −6.603 | 34.568 | 1.00 | 60.26 | WATR O |
| ATOM | 5386 | O | HOH | w 60 | 21.016 | 0.927 | 25.882 | 1.00 | 73.65 | WATR O |
| ATOM | 5387 | O | HOH | w 61 | 3.022 | 16.302 | 21.543 | 1.00 | 69.14 | WATR O |
| ATOM | 5388 | O | HOH | w 62 | −4.656 | 38.768 | 43.041 | 1.00 | 68.04 | WATR O |
| ATOM | 5389 | O | HOH | w 63 | −17.014 | 54.034 | 26.955 | 1.00 | 84.94 | WATR O |
| ATOM | 5390 | O | HOH | w 64 | 2.944 | 37.252 | 20.275 | 1.00 | 62.66 | WATR O |
| ATOM | 5391 | O | HOH | w 65 | 18.693 | 22.305 | 48.628 | 1.00 | 61.31 | WATR O |
| ATOM | 5392 | O | HOH | w 66 | 22.264 | −1.881 | 27.421 | 1.00 | 55.70 | WATR O |
| ATOM | 5393 | O | HOH | w 67 | 40.304 | −23.518 | 28.216 | 1.00 | 52.15 | WATR O |
| ATOM | 5394 | O | HOH | w 68 | 9.604 | 44.635 | 34.681 | 1.00 | 66.25 | WATR O |
| ATOM | 5395 | O | HOH | w 69 | 36.634 | −19.656 | 23.590 | 1.00 | 57.74 | WATR O |
| ATOM | 5396 | O | HOH | w 70 | 18.947 | −14.699 | 47.372 | 1.00 | 76.08 | WATR O |
| ATOM | 5397 | O | HOH | w 71 | −7.366 | 33.805 | 42.369 | 1.00 | 74.51 | WATR O |
| ATOM | 5398 | O | HOH | w 72 | −7.917 | 4.953 | 33.848 | 1.00 | 88.61 | WATR O |
| ATOM | 5399 | O | HOH | w 73 | 35.919 | −16.004 | 19.199 | 1.00 | 58.39 | WATR O |
| ATOM | 5400 | O | HOH | w 74 | 40.641 | −−17.893 | 40.511 | 1.00 | 72.82 | WATR O |
| ATOM | 5401 | O | HOH | w 75 | −15.210 | 46.684 | 41.370 | 1.00 | 68.96 | WATR O |
| ATOM | 5402 | O | HOH | w 76 | −0.867 | 10.367 | 47.113 | 1.00 | 61.43 | WATR O |
| ATOM | 5403 | O | HOH | w 77 | 12.274 | 35.637 | 37.467 | 1.00 | 67.34 | WATR O |
| ATOM | 5404 | O | HOH | w 78 | 1.691 | 26.324 | 46.846 | 1.00 | 68.30 | WATR O |
| ATOM | 5405 | O | HOH | w 79 | −0.057 | −11.150 | 47.984 | 1.00 | 60.92 | WATR O |
| ATOM | 5406 | O | HOH | w 80 | 31.710 | 10.971 | 36.393 | 1.00 | 74.55 | WATR O |
| ATOM | 5407 | O | HOH | w 81 | 21.576 | −36.573 | 38.668 | 1.00 | 60.12 | WATR O |
| ATOM | 5408 | O | HOH | w 82 | 25.109 | −22.648 | 55.690 | 1.00 | 74.55 | WATR O |
| ATOM | 5409 | O | HOH | w 83 | 34.970 | −8.596 | 51.680 | 1.00 | 67.60 | WATR O |
| ATOM | 5410 | O | HOH | w 84 | 4.818 | 36.497 | 17.708 | 1.00 | 74.35 | WATR O |
| ATOM | 5411 | O | HOH | w 85 | 15.308 | −35.598 | 35.558 | 1.00 | 52.09 | WATR O |
| ATOM | 5412 | O | HOH | w 86 | 21.525 | 39.536 | 29.904 | 1.00 | 53.20 | WATR O |
| ATOM | 5413 | O | HOH | w 87 | 44.751 | −29.908 | 32.936 | 1.00 | 60.47 | WATR O |
| ATOM | 5414 | O | HOH | w 88 | 39.247 | 17.259 | 43.115 | 1.00 | 54.71 | WATR O |
| ATOM | 5415 | O | HOH | w 89 | −9.260 | 22.858 | 46.193 | 1.00 | 83.21 | WATR O |
| ATOM | 5416 | O | HOH | w 90 | 9.541 | −10.014 | 29.106 | 1.00 | 62.46 | WATR O |
| ATOM | 5417 | O | HOH | w 91 | 17.265 | 23.892 | 11.409 | 1.00 | 60.44 | WATR O |
| ATOM | 5418 | O | HOH | w 92 | 13.958 | −24.011 | 26.326. | 1.00 | 64.04 | WATR O |
| ATOM | 5419 | O | HOH | w 93 | 27.182 | 16.485 | 49.037 | 1.00 | 61.35 | WATR O |
| ATOM | 5420 | O | HOH | w 94 | −8.640 | 45.830 | 32.280 | 1.00 | 52.26 | WATR O |
| ATOM | 5421 | O | HOH | w 95 | 41.761 | −20.271 | 57.359 | 1.00 | 61.03 | WATR O |
| ATOM | 5422 | O | HOH | w 96 | 5.727 | −27.002 | 43.068 | 1.00 | 73.80 | WATR O |
| ATOM | 5423 | O | HOH | W 97 | 24.225 | −26.212 | 59.758 | 1.00 | 61.87 | WATR O |
| ATOM | 5424 | O | HOH | w 98 | 45.371 | −33.833 | 34.821 | 1.00 | 76.42 | WATR O |
| ATOM | 5425 | O | HOH | w 99 | 28.234 | 30.672 | 37.990 | 1.00 | 68.82 | WATR O |
| ATOM | 5426 | O | HOH | w 100 | 32.779 | 26.299 | 27.102 | 1.00 | 57.44 | WATR O |

What is claimed is:

1. A method for identifying an Eg5 binding ligand, the method comprising:

(a) generating a three dimensional structure of an Eg5 protein using the atomic coordinates as set forth in Table 4 or Table 10 for all of the amino acids listed in Table 3 with a Root Mean Square Deviation (RMSD) for all heavy atoms being less than 2.5 Å, wherein said Eg5 is a kinesin-like motor protein that is localized to a mitotic spindle characterized by a motor domain having about 350 amino acid residues;

(b) identifying a pharmacophore of a compound capable of binding with the said three dimensional structure of said Eg5 protein wherein said pharmacophore is:

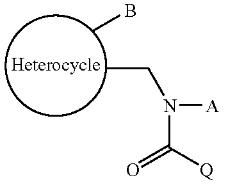

wherein B is benzyl, A is 3-aminopropyl, and Q is a group having a molecular moiety and wherein said pharmacophore binds at B and Q groups to the three dimensional structure of said Eg5 protein;

(c) designing an Eg5 binding ligand with the based on said pharmacophore;

(d) synthesizing said ligand; and (e) contacting said ligand with said Eg5 protein to determine an ability of said ligand to modify Eg5 activity thereby identifying said Eg5 binding ligand.

2. The method of claim 1 wherein the compound is selected from the group consisting of N-(3-aminopropyl)-N-[(3-benzyl-4-oxo-4H-pyrido[1,2a]pyrimidin-2-yl)(cyclopropyl)methyl]-4-chlorobenzamide (1), N-(3-aminopropyl)-N-[(1R)-1-(1-benzyl-4-phenyl-1H-imidazol-2-yl)-2-methylpropyl]-4-methylbenzamide (2), N-(3-aminopropyl)-N-[(1R)-1-(1-benzyl-4-phenyl-1H-imidazol-2-yl)-2,2-dimethylpropyl]-1,5-dimethyl-1H-pyrazol-3-carboxamide (3), N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide (4), N-(3-aminopropyl)-N-[(1R)-1-(1-benzyl-1H-benzimidazol-2-yl)-2-methylpropyl]-4-chlorobenzamide (5), and N-(3-aminopropyl)-N-[(1R)-1-(1-benzyl-5-bromo-1H-benzimidazol-2-yl)-2-methylpropyl]-4-methylbenzamide (6).

3. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-[(3-benzyl-4-oxo-4H-pyrido[1,2a]pyrimidin-2-yl)(cyclopropyl)methyl]-4-chlorobenzamide wherein said co-crystal complex has unit cell dimensions a=−80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-[(3-benzyl-4-oxo-4H-pyrido[1,2a]pyrimidin-2-yl)(cyclopropyl)methyl]-4-chlorobenzamide using atomic coordinates as set forth in Table 4 or Table 10 for all of the amino acids listed in Table 3;

(c) identifying a pharmacophore of said N-(3-aminopropyl)-N-[(3-benzyl-4-oxo-4H-pyrido[1,2a]pyrimidin-2-yl)(cyclopropyl)methyl]-4-chlorobenzamide capable of binding with said Eg5 protein wherein said pharmacophore is:

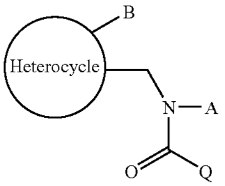

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

4. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-[(1R)-1-(1-benzyl-4-phenyl-1H-imidazol-2-yl)-2-methylpropyl]-4-methylbenzamide wherein said co-crystal complex has unit cell dimensions a=80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-[(1R)-1-(1-benzyl-4-phenyl-1H-imidazol-2-yl)-2-methylpropyl]-4-methylbenzamide using atomic coordinates as set forth in Table 4 or Table 10 for all of the amino acids listed in Table 3;

(c) identifying a pharmacophore of said N-(3-aminopropyl)-N-[(1R)-1-(1-benzyl-4-phenyl-1H-imidazol-2-yl)-2-methylpropyl]-4-methylbenzamide capable of binding with said Eg5 protein wherein said pharmacophore is:

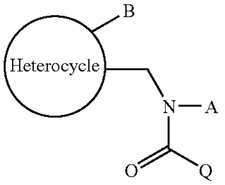

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

5. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-[(1R)-1-(1-benzyl-4-phenyl-1H-imidazol-2-yl)-2,2-dimethylpropyl]-1,5-dimethyl-1H-pyrazol-3-carboxamide wherein said co-crystal complex has unit cell dimensions a=80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-[(1R)-1-(1-benzyl-4-phenyl-1H-imidazol-2-yl)-2,2-dimethylpropyl]-1,5-dimethyl-1H-pyrazol-3-carboxamide using atomic coordinates as set forth in Table 4 or Table 10 for all of the amino acids listed in Table 3;

(c) identifying a pharmacophore of said N-(3-aminopropyl)-N-[(1R)-1-(1-benzyl-4-phenyl-1H-imidazol-2-yl)-2,2-dimethylpropyl]-1,5-dimethyl-1H-pyrazol-3-carboxamide capable of binding with said Eg5 protein wherein said pharmacophore is:

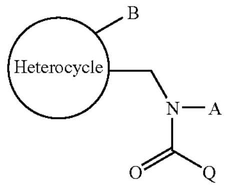

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

6. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide wherein said co-crystal complex has unit cell dimensions a=80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide using atomic coordinates as set forth in Table 4 or Table 10 for all of the amino acids listed in Table 3;

(c) identifying a pharmacophore of said N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide capable of binding with said Eg5 protein wherein said pharmacophore is:

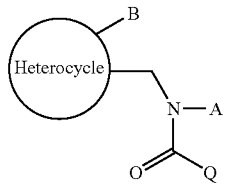

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

7. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-[(1R)-1-(1-benzyl-1H-benzimidazol-2-yl)-2-methylpropyl]-4-chlorobenzamide wherein said co-crystal complex has unit cell dimensions a=80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-[(1R)-1-(1-benzyl-1H-benzimidazol-2-yl)-2-methylpropyl]-4-chlorobenzamide using atomic coordinates as set forth in Table 4 or Table 10 for all of the amino acids listed in Table 3;

(c) identifying a pharmacophore of said N-(3-aminopropyl)-N-[(1R)-1-(1-benzyl-1H-benzimidazol-2-yl)-2-methylpropyl]-4-chlorobenzamide capable of binding with said Eg5 protein wherein said pharmacophore is:

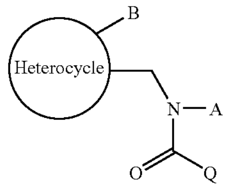

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

8. A method for identifying an Eg5 binding ligand, the method comprising:

(a) crystallizing an X-ray diffraction quality co-crystal complex of an Eg5 protein as set forth in SEQ ID NO: 1 with N-(3-aminopropyl)-N-[(1R)-1-(1-benzyl-5-bromo-1H-benzimidazol-2-yl)-2-methylpropyl]-4-methylbenzamide wherein said co-crystal complex has unit cell dimensions a=80.5 Å, b=94.7 Å, c=107.365 Å, alpha=beta=gamma=90°, and space group $P2_12_12_1$ wherein said Eg5 is a kinesin-like motor protein that is localized to a mitotic spindle characterized by a motor domain having about 350 amino acid residues;

(b) determining atomic coordinates from said X-ray diffraction quality co-crystal complex of said Eg5 protein with said N-(3-aminopropyl)-N-[(1R)-1-(1-benzyl-5-bromo-1H-benzimidazol-2-yl)-2-methylpropyl]-4-methylbenzamide using atomic coordinates as set forth in Table 4 or Table 10 for all of the amino acids listed in Table 3;

(c) identifying a pharmacophore of said N-(3-aminopropyl)-N-[(1R)-1-(1-benzyl-5-bromo-1H-benzimidazol-2-yl)-2-methylpropyl]-4-methylbenzamide capable of binding with said Eg5 protein wherein said pharmacophore is:

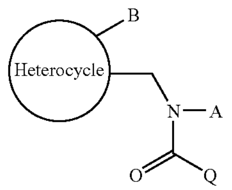

wherein B is benzyl, A is 3-aminopropyl, and Q is a group having a molecular moiety and wherein said pharmacophore binds at B and Q groups to the three dimensional structure of said Eg5 protein; and (d) designing an Eg5 binding ligand based on said pharmacophore;

(e) synthesizing said ligand; and (f) contacting said ligand with said Eg5 protein to determine an ability of said ligand to modify Eg5 activity.

* * * * *